US012558356B2

(12) United States Patent
Shokat et al.

(10) Patent No.: US 12,558,356 B2
(45) Date of Patent: Feb. 24, 2026

(54) IMMUNOPHILIN BINDING AGENTS AND USES THEREOF

(71) Applicant: The Regents of the University of California, Oakland, CA (US)

(72) Inventors: Kevan M. Shokat, San Francisco, CA (US); Ziyang Zhang, San Francisco, CA (US); William A. Weiss, San Francisco, CA (US); QiWen Fan, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/957,502

(22) Filed: Nov. 22, 2024

(65) Prior Publication Data

US 2025/0108052 A1 Apr. 3, 2025

Related U.S. Application Data

(62) Division of application No. 17/427,039, filed as application No. PCT/US2020/017012 on Feb. 6, 2020.

(60) Provisional application No. 62/802,668, filed on Feb. 7, 2019.

(51) Int. Cl.
*A61K 31/506* (2006.01)
*A61K 31/444* (2006.01)
*A61K 31/496* (2006.01)
*A61K 31/517* (2006.01)

(52) U.S. Cl.
CPC .......... *A61K 31/506* (2013.01); *A61K 31/444* (2013.01); *A61K 31/496* (2013.01); *A61K 31/517* (2013.01)

(58) Field of Classification Search
CPC .. A61K 31/506; A61K 31/444; A61K 31/496; A61K 31/517
See application file for complete search history.

(56) References Cited

U.S. PATENT DOCUMENTS

| | | | |
|---|---|---|---|
| 3,929,992 | A | 12/1975 | Sehgal et al. |
| 4,316,885 | A | 2/1982 | Rakhit |
| 4,650,803 | A | 3/1987 | Stella et al. |
| 5,023,263 | A | 6/1991 | Von Burg |
| 5,023,264 | A | 6/1991 | Caufield et al. |
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,130,307 | A | 7/1992 | Failli et al. |
| 5,151,413 | A | 9/1992 | Caufield et al. |
| 5,162,333 | A | 11/1992 | Failli et al. |
| 5,177,203 | A | 1/1993 | Failli et al. |
| 5,221,670 | A | 6/1993 | Caufield |
| 5,233,036 | A | 8/1993 | Hughes |
| 5,252,579 | A | 10/1993 | Skotnicki et al. |
| 5,256,790 | A | 10/1993 | Nelson |
| 5,258,389 | A | 11/1993 | Goulet et al. |
| 5,260,300 | A | 11/1993 | Goulet et al. |
| 5,262,423 | A | 11/1993 | Kao |
| 5,302,584 | A | 4/1994 | Kao et al. |
| 5,362,718 | A | 11/1994 | Skotnicki et al. |
| 5,373,014 | A | 12/1994 | Failli et al. |
| 5,378,836 | A | 1/1995 | Kao et al. |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,411,967 | A | 5/1995 | Kao et al. |
| 5,463,048 | A | 10/1995 | Skotnicki et al. |
| 5,480,988 | A | 1/1996 | Failli et al. |
| 5,480,989 | A | 1/1996 | Kao et al. |
| 5,489,680 | A | 2/1996 | Failli et al. |
| 5,491,231 | A | 2/1996 | Nelson et al. |
| 5,504,091 | A | 4/1996 | Molnar-Kimber et al. |
| 5,563,145 | A | 10/1996 | Failli et al. |
| 5,665,772 | A | 9/1997 | Cottens et al. |
| 5,780,462 | A | 7/1998 | Lee et al. |
| 6,277,983 | B1 | 8/2001 | Shaw et al. |
| 6,358,969 | B1 | 3/2002 | Shelley et al. |
| 6,887,842 | B1 | 5/2005 | Briesewitz et al. |
| 6,921,531 | B2 | 7/2005 | Briesewitz et al. |
| 7,390,784 | B2 | 6/2008 | Briesewitz et al. |

(Continued)

FOREIGN PATENT DOCUMENTS

| | | | | |
|---|---|---|---|---|
| EP | 0184162 A2 * | 11/1986 | .......... | C07D 498/18 |
| WO | WO 1991004025 A1 * | 4/1991 | ............ | A61K 31/33 |

(Continued)

OTHER PUBLICATIONS

Bonner, J. M.; et al. "Diverse structures, functions and uses of FK506 binding proteins" 2017, Cellular Signalling, vol. 38, pp. 97-105. (Year: 2017).*
Bierer, B. E.; et al. "Probing Inmunmosuppressant Action with a Nonnatural Immunophilin Ligand" 1990, Science, vol. 250, pp. 556-559. (Year: 1990).*
Tanaka, et al. "Structure of FK506: A Novel Immunosuppressant Isolated from Streptomyces" 1987, Journal of the American Chemical Society, vol. 109, pp. 5031-5033. (Year: 1987).*
Nambu, M.; et al. "A calcineurin antifungal strategy with analogs of FK506" 2017, Bioorganic Medicinal Chemistry Letters, vol. 27, pp. 2465-2471 (with Supporting Information). (Year: 2017).*
Marinec, P. S.; et al. "Synthesis of orthogonally reactive FK506 derivatives via olefin cross metathesis" Bioorganic and Medicinal Chemistry 2009, vol. 17, pp. 5763-5768. (Year: 2009).*

(Continued)

*Primary Examiner* — Eric Olson
*Assistant Examiner* — Benjamin M Brandsen
(74) *Attorney, Agent, or Firm* — Mintz, Levin, Cohn, Ferris, Glovsky and Popeo, P.C.

(57) ABSTRACT

Described herein, inter alia, are immunophilin binding compounds and methods of treating CNS diseases, including co-administering outside the CNS of a subject an anti-CNS disease drug and a compound described herein.

9 Claims, 69 Drawing Sheets

Specification includes a Sequence Listing.

(56) References Cited

U.S. PATENT DOCUMENTS

| | | | | |
|---|---|---|---|---|
| 7,498,025 | B1 | 3/2009 | Briesewitz et al. | |
| 7,696,165 | B2 | 4/2010 | Molino | |
| 8,044,099 | B2 | 10/2011 | Briesewitz et al. | |
| 9,260,484 | B2 | 2/2016 | Briesewitz et al. | |
| 9,956,207 | B2 | 5/2018 | Covel et al. | |
| 10,117,945 | B2 | 11/2018 | Shokat et al. | |
| 10,568,872 | B2 | 2/2020 | Covel et al. | |
| 10,646,577 | B2 | 5/2020 | Shokat et al. | |
| 11,000,514 | B2 | 5/2021 | Covel et al. | |
| 11,452,780 | B2 | 9/2022 | Shokat et al. | |
| 2004/0110666 | A1 | 6/2004 | Or et al. | |
| 2004/0157768 | A1 | 8/2004 | Or et al. | |
| 2005/0209146 | A1 | 9/2005 | Briesewitz et al. | |
| 2005/0209173 | A1 | 9/2005 | Graef et al. | |
| 2005/0209265 | A1 | 9/2005 | Briesewitz et al. | |
| 2006/0069015 | A1 | 3/2006 | Molino et al. | |
| 2006/0074015 | A1 | 4/2006 | Molino et al. | |
| 2007/0054348 | A1 | 3/2007 | Gestwicki et al. | |
| 2008/0306098 | A1 | 12/2008 | Mutz et al. | |
| 2009/0054334 | A1 | 2/2009 | Mutz et al. | |
| 2014/0200186 | A1 | 7/2014 | Briesewitz et al. | |
| 2016/0176916 | A1* | 6/2016 | Bradner | A61K 47/54 546/187 |
| 2016/0331730 | A1* | 11/2016 | Covel | A61K 31/425 |
| 2016/0333054 | A1 | 11/2016 | Briesewitz et al. | |
| 2017/0246305 | A1* | 8/2017 | Shokat | A61P 35/00 |
| 2022/0193242 | A1 | 6/2022 | Shokat et al. | |
| 2022/0251108 | A1* | 8/2022 | Liu | A61K 31/675 |
| 2023/0063768 | A1 | 3/2023 | Shokat et al. | |
| 2025/0092383 | A1* | 3/2025 | Basu | C12N 15/1082 |

FOREIGN PATENT DOCUMENTS

| | | | | |
|---|---|---|---|---|
| WO | WO-92/05179 | A1 | 4/1992 | |
| WO | WO-93/11130 | A1 | 6/1993 | |
| WO | WO-94/02136 | A1 | 2/1994 | |
| WO | WO-94/02485 | A1 | 2/1994 | |
| WO | WO-94/09010 | A1 | 4/1994 | |
| WO | WO-95/14023 | A1 | 5/1995 | |
| WO | WO-95/16691 | A1 | 6/1995 | |
| WO | WO-96/41807 | A1 | 12/1996 | |
| WO | WO-2004/082629 | A2 | 9/2004 | |
| WO | WO-2004/082629 | A3 | 9/2004 | |
| WO | WO-2006/095185 | A1 | 9/2006 | |
| WO | WO-2007/053792 | A2 | 5/2007 | |
| WO | WO-2007/053792 | A3 | 5/2007 | |
| WO | WO-2007/112345 | A2 | 10/2007 | |
| WO | WO-2007/112345 | A3 | 10/2007 | |
| WO | WO-2007/112345 | A8 | 10/2007 | |
| WO | WO-2007/112352 | A2 | 10/2007 | |
| WO | WO-2007/112352 | A3 | 10/2007 | |
| WO | WO-2007/112357 | A2 | 10/2007 | |
| WO | WO-2007/112357 | A3 | 10/2007 | |
| WO | WO-2008013569 | A2 * | 1/2008 | B01J 19/0046 |
| WO | WO-2009/055042 | A1 | 4/2009 | |
| WO | WO-2010/065110 | A3 | 6/2010 | |
| WO | WO-2010065110 | A2 * | 6/2010 | A61K 31/397 |
| WO | WO-2010/077317 | A2 | 7/2010 | |
| WO | WO-2010/077317 | A3 | 7/2010 | |
| WO | WO-2010/132852 | A2 | 11/2010 | |
| WO | WO-2010/132852 | A3 | 11/2010 | |
| WO | WO-2011/130317 | A2 | 10/2011 | |
| WO | WO-2011/130317 | A3 | 10/2011 | |
| WO | WO-2012/047762 | A2 | 4/2012 | |
| WO | WO-2012/047762 | A3 | 4/2012 | |
| WO | WO-2012/079172 | A1 | 6/2012 | |
| WO | WO-2013/030208 | A1 | 3/2013 | |
| WO | WO-2013/181339 | A2 | 12/2013 | |
| WO | WO-2013/181339 | A3 | 12/2013 | |
| WO | WO-2014/037260 | A1 | 3/2014 | |
| WO | WO-2015/057511 | A1 | 4/2015 | |
| WO | WO-2015/106283 | A1 | 7/2015 | |
| WO | WO-2016/040806 | A1 | 3/2016 | |
| WO | WO-2016/112321 | A1 | 7/2016 | |
| WO | WO-2016/160362 | A1 | 10/2016 | |
| WO | WO-2017/136708 | A1 | 8/2017 | |
| WO | WO-2018/148508 | A1 | 8/2018 | |
| WO | WO-2020/154455 | A1 | 7/2020 | |
| WO | WO-2020/163598 | A1 | 8/2020 | |

OTHER PUBLICATIONS

Choi, W.H. et al. (Oct. 2013). “Extremely delayed brain metastasis from renal cell carcinoma,” *Brain Tumor Res Treat* 1(2):99-102.

Gabathuler, R. (2010). “Approaches to Transport Therapeutic Drugs Across the Blood-Brain Barrier to Treat Brain Diseases,” *Neurobiol Dis* 37(1):48-57.

Grzmil, M. et al. (Jul. 2013). “Overcoming resistance to rapalogs in gliomas by combinatory therapies,” *Biochim Biophys Acta* 1834(7):1371-1380.

Hainsworth, J.D. et al. (Apr. 2012). “Phase II study of concurrent radiation therapy, temozolomide, and bevacizumab followed by bevacizumab/everolimus as first-line treatment for patients with glioblastoma,” *Clin Adv Hematol Oncol* 10(4):240-246.

Kallen, J. et al. (1998). “X-ray structures and analysis of 11 cyclosporin derivatives complexed with cyclophilin A,” *J Mol Biol* 283(2):435-449.

Luan, F.L. et al. (May 27, 2002). “Rapamycin blocks tumor progression: unlinking immunosuppression from antitumor efficacy,” *Transplantation* 73(10):1565-1572.

Palmer, A.M. (2010). “The role of the blood-CNS barrier in CNS disorders and their treatment,” *Neurobiol Dis* 37(1):3-12.

Peluffo, H. et al. (Mar.-Apr. 2015). “BBB-targeting, protein-based nanomedicines for drug and nucleic acid delivery to the CNS,” *Biotechnol Adv* 33(2):277-287.

Rodrik-Outmezguine, V.S. et al. (Jun. 9, 2016). “Overcoming mTOR resistance mutations with a new-generation mTOR inhibitor,” *Nature* 534(7606):272-276.

Álvarez-García, O. et al. (Sep. 2010). “Rapamycin induces growth retardation by disrupting angiogenesis in the growth plate,” *Kidney Int* 78(6):561-568.

Bierer, B.E. et al. (Oct. 26, 1990). “Probing immunosuppressant action with a nonnatural immunophilin ligand,” *Science* 250(4980):556-559.

Bos, P.H. et al. (Dec. 19, 2019). “Development of MAP4 Kinase Inhibitors as Motor Neuron-Protecting Agents,” *Cell Chem Biol* 26(12):1703-1715.e37.

Braun, P.D. et al. (Jun. 25, 2003). “A bifunctional molecule that displays context-dependent cellular activity,” *J Am Chem Soc* 125(25):7575-7580.

Briesewitz, R. et al. (Mar. 2, 1999). “Affinity modulation of small-molecule ligands by borrowing endogenous protein surfaces,” *PNAS USA* 96(5):1953-1958.

Carry, J.-C. et al. Semisynthetic Di- and Tri-Functionalized Non-Immunosuppressive Cyclosporin A Derivatives as Potential Anti-HIV 1 Drugs. *Synlett* 2:316-320.

Drachman, J.G. et al. (2013). “Antibody-drug conjugates: the chemistry behind empowering antibodies to fight cancer,” *Hematology Am Soc Hematol Educ Program* 2013:306-310.

Dunyak, B.M. et al. (Nov. 20, 2015). “Selective Targeting of Cells via Bispecific Molecules That Exploit Coexpression of Two Intracellular Proteins,” *ACS Chem Biol* 10(11):2441-2447.

Estrada, A.A. et al. (Nov. 26, 2012). “Discovery of highly potent, selective, and brain-penetrable leucine-rich repeat kinase 2 (LRRK2) small molecule inhibitors,” *J Med Chem* 55(22):9416-9433.

Fan, Q.W. et al. (Mar. 2017). “A Kinase Inhibitor Targeted to mTORC1 Drives Regression in Glioblastoma,” *Cancer Cell* 31(3):424-435.

Fan, Q.W et al. (Jan. 1, 2018). “Inhibiting 4EBP1 in Glioblastoma,” *Clin Cancer Res* 24(1):14-21.

Flygare, J.A. et al. (Jan. 2013). “Antibody-drug conjugates for the treatment of cancer,” *Chem Biol Drug Des* 81(1):113-121.

Galat, A. (Sep. 2013). “Functional diversity and pharmacological profiles of the FKBPs and their complexes with small natural ligands,” *Cell Mol Life Sci* 70(18):3243-3275.

(56) References Cited

OTHER PUBLICATIONS

Gestwicki, J.E. et al. (Oct. 29, 2004). "Harnessing chaperones to generate small-molecule inhibitors of amyloid beta aggregation," *Science* 306(5697):865-869.
Gold, B.G. (Oct. 2000). "Neuroimmunophilin ligands: evaluation of their therapeutic potential for the treatment of neurological disorders," *Expert Opinion on Investigational Drugs* 9(10):2331-2342.
González, D. et al. (Jun. 2011). "Growth of kidney-transplanted pediatric patients treated with sirolimus," *Pediatr Nephrol* 26(6):961-966.
Guo, Z.-F. et al. (2014). "Facile functionalization of FK506 for biological studies by the thiol-ene 'click' reaction," *RSC Adv* 4:11400-11403.
Guo, Z. et al. (Mar. 2019). "Rapamycin-inspired macrocycles with new target specificity," *Nat Chem* 11(3):254-263.
Harmsen, S. et al. (2012). "Kinase Inhibitor Conjugates," *Current Pharmaceutical Design* 18:2891-2900.
Holt, D. A. et al. (1993). "Design, synthesis, and kinetic evaluation of high-affinity FKBP ligands and the X-ray crystal structures of their complexes with FKBP12," *J. Am Chem. Soc.* 115:9925-9938.
International Search Report mailed Jun. 12, 2020, for PCT Application No. PCT/US2020/017012, filed Feb. 6, 2020, 5 pages.
International Search Report mailed Jun. 23, 2020, for PCT Application No. PCT/US2020/017017, filed Feb. 6, 2020, 5 pages.
Juvvadi, P.R. et al. (Sep. 19, 2019). "Harnessing calcineurin-FK506-FKBP12 crystal structures from invasive fungal pathogens to develop antifungal agents," *Nature Communications* 10(1):4275.
Klettner, A. et al. (Jun. 2003). "FK506 and its analogs—therapeutic potential for neurological disorders," *Curr Drug Targets CNS Neurol Disord* 2(3):153-162.
Ko, S.Y. et al. (Nov. 1992). "Conformation of cyclosporin A in polar solvents," *Int J Pept Protein Res* 40(5):380-382.
Marinec, P.S. et al. (Jun. 2008). "Bifunctional molecules evade cytochrome P450 metabolism by forming protective complexes with FK506-binding protein," *Mol. BioSyst.* 4(6):571-578.
Marinec, P.S. et al. (Feb. 3, 2009). "FK506-binding protein (FKBP) partitions a modified HIV protease inhibitor into blood cells and prolongs its lifetime in vivo," *PNAS USA* 106(5):1336-1341.
Marinec, P.S. et al. Aug. 15, 2009). "Synthesis of orthogonally reactive FK506 derivatives via olefin cross metathesis," *Bioorg Med Chem* 17(16):5763-5768.
Nambu, M. et al. (Jun. 1, 2017). "A calcineurin antifungal strategy with analogs of FK506," *Bioorg Med Chem Lett* 27(11):2465-2471.
Paprica, P.A. et al. (Jan-Feb. 1992). "Preparation of novel cyclosporin A derivatives," *Bioconjug Chem* 3(1):32-36.
Park, S.B. et al. (1989). "A Semi-Synthetic Approach to Olefinic Analogs of Amino Acid One (MeBMT) in Cyclosporin A," *Tetrahedron Letters* 30(32):4215-4218.
Piggott, A.M. et al. (Oct. 1, 2009). "Rapid isolation of novel FK506 binding proteins from multiple organisms using gDNA and cDNA T7 phage display," *Bioorg Med Chem* 17(19):6841-6850.
Registry 1054668-19-7, entered STN Sep. 29, 2008, 1 page.
Rutaganira, F.U. et al. (Mar. 10, 2016). "Design and Structural Characterization of Potent and Selective Inhibitors of Phosphatidylinositol 4 Kinase IIIβ," *J Med Chem* 59(5):1830-1839.
Sellmyer, M.A. et al. (May 15, 2007). "Engineering small molecule specificity in nearly identical cellular environments," *Bioorg Med Chem Lett* 17(10):2703-2705.
Siu, M. et al. (Sep. 27, 2018). "Dual Leucine Zipper Kinase Inhibitors for the Treatment of Neurodegeneration," *J Med Chem* 61(18):8078-8087.
Wang, Y. et al. (Aug. 19, 2019). "One-step Heck Reaction Generates Nonimmunosuppressive FK506 Analogs for Pharmacological BMP Activation," *ACS Med Chem Lett* 10(9):1279-1283.
Wassarman, D.R. et al. (Sep. 20, 2022). "Tissue-restricted inhibition of mTOR using chemical genetics," *PNAS USA* 119(38):e2204083119.
Winter, G.E. et al. (Jun. 19, 2015). "Drug Development. Phthalimide conjugation as a strategy for in vivo target protein degradation," *Science* 348(6241):1376-1381.
Written Opinion mailed Jun. 12, 2020, for PCT Application No. PCT/US2020/017012, filed Feb. 6, 2020, 6 pages.
Written Opinion mailed Jun. 23, 2020, for PCT Application No. PCT/US2020/017017, filed Feb. 6, 2020, 4 pages.
Wu, X. et al. (Sep. 12, 2011). "Creating diverse target-binding surfaces on FKBP12: synthesis and evaluation of a rapamycin analogue library," *ACS Comb Sci* 13(5):486-495.
Zhang, Z. et al. (Nov. 4, 2019). "Bifunctional Small-Molecule Ligands of K-Ras Induce Its Association with Immunophilin Proteins," *Angew Chem Int Ed* 58(45):16314-16319.
Zhang, Z. et al. (Sep. 22, 2022). "Brain-restricted mTOR inhibition with binary pharmacology," *Nature* 609:822-828.
Kavanagh, M.E. et al. (Jul. 1, 2013). "The development of CNS-active LRRK2 inhibitors using property-directed optimization," *Bioorg Med Chem Lett* 23(13):3690-3696.
Ayral-Kaloustian, S. et al. (Jan. 14, 2010). "Hybrid inhibitors of phosphatidylinositol 3-kinase (PI3K) and the mammalian target of rapamycin (mTOR): design, synthesis, and superior antitumor activity of novel wortmannin-rapamycin conjugates," *J Med Chem* 53(1):452-459.
Cai, J. et al. (2024). "Effect and Mechanism of Rapamycin on Cognitive Deficits in Animal Models of Alzheimer's Disease: A Systematic Review and Meta-analysis of Preclinical Studies," *J Alzheimer's Dis* 99(1):53-84.
Cassano, T. et al. (Jan. 2019). "Early intrathecal infusion of everolimus restores cognitive function and mood in a murine model of Alzheimer's disease," *Exp Neurol* 311:88-105.
Cihan, Y.B. (Jul. 1, 2019). "Lapatinib? or Radiotherapy? In Cranial Metastasis of Breast Cancer," *Eur J Breast Health* 15(3):205-206.
French, J.A. et al. (Oct. 29, 2016). "Adjunctive everolimus therapy for treatment-resistant focal-onset seizures associated with tuberous sclerosis (EXIST-3): a phase 3, randomised, double-blind, placebo-controlled study," *Lancet* 388(10056):2153-2163.
Hou, S.-J. et al. (Oct. 2, 2023). "Rapamycin Responds to Alzheimer's Disease: A Potential Translational Therapy," *Clin Interv Aging* 18:1629-1639.
Jhanwar-Uniyal, M. (2017). "Mighty RapaLink-1 Vanquishes Undruggable Mutant mTOR in Glioblastoma," *Translational Cancer Research* 6(Suppl 7):S1143-S1148.
Kaeberlein, M. et al. (Jan. 23, 2019). "Rapamycin and Alzheimer's disease: Time for a clinical trial?" *Sci Transl Med* 111(476):doi:10.1126/scitranslmed.aar4289.
Lin, A.-L. et al. (Jun. 2020). "APOE genotype-dependent pharmacogenetic responses to rapamycin for preventing Alzheimer's disease," *Neurobiol Dis* 139:104834.
Manzoni, C. et al. (Oct. 12, 2016). "mTOR independent regulation of macroautophagy by Leucine Rich Repeat Kinase 2 via Beclin-1," *Sci Rep* 6:35106.
Mukherjee, S. et al. (2009). "A Comprehensive Review of Immunosuppression Used for Liver Transplantation," *J Transplant* 2009:701464.
Porkka, K. et al. (Aug. 15, 2008). "Dasatinib crosses the blood-brain barrier and is an efficient therapy for central nervous system Philadelphia chromosome-positive leukemia," *Blood* 112(4):1005-1012.
Taymans, J.-M. et al. (Jul. 1, 2023). "Perspective on the current state of the LRRK2 field," *NPJ Parkinsons Dis* 9(1):104.
Terceiro, L.E.L. et al. (Jul. 27, 2023). "Navigating the Blood-Brain Barrier: Challenges and Therapeutic Strategies in Breast Cancer Brain Metastases," *Int J Mol Sci* 24(15):12034.
Xie, P.-L. et al. (May 30, 2024). "Pharmacological mTOR inhibitors in ameliorating Alzheimer's disease: current review and perspectives," *Front Pharmacol* 15:1366061.
Zhu, Z. et al. (Feb. 8, 2019). "Balancing mTOR Signaling and Autophagy in the Treatment of Parkinson's Disease," *Int J Mol Sci* 20(3):728.

* cited by examiner

RapaLink-1

SLF
non-toxic
Kd(FKBP12) = 0.2 ~ 20 nM (reported)

FK506
immunosuppresant
Kd(FKBP12) = 0.4 nM (reported)

FIG. 13A
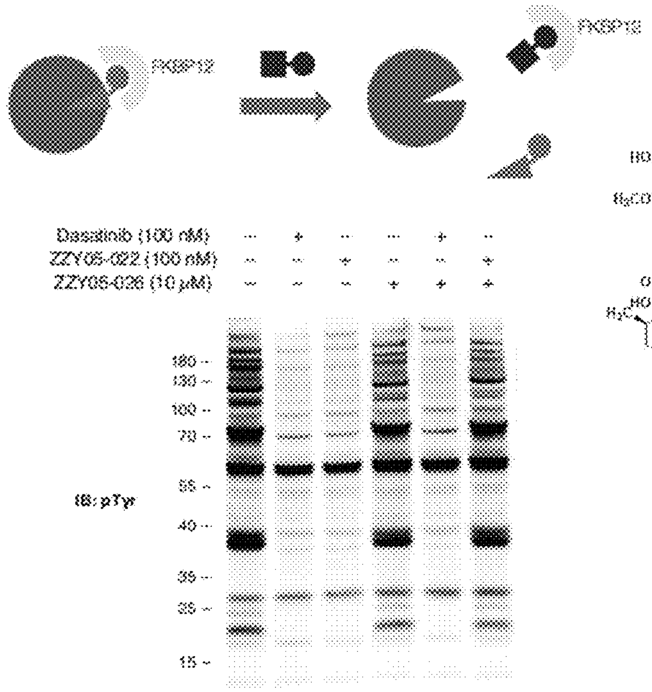
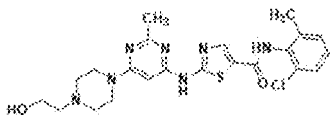
Dasatinib
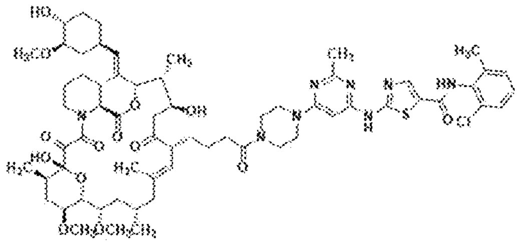
ZZY05-022
(FK506-Dasatinib)
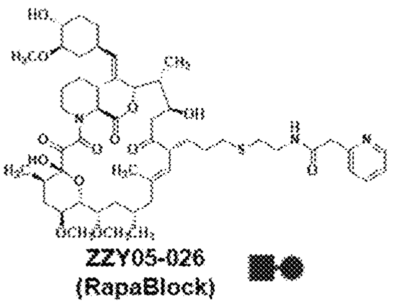
ZZY05-026
(RapaBlock)
FIG. 13B
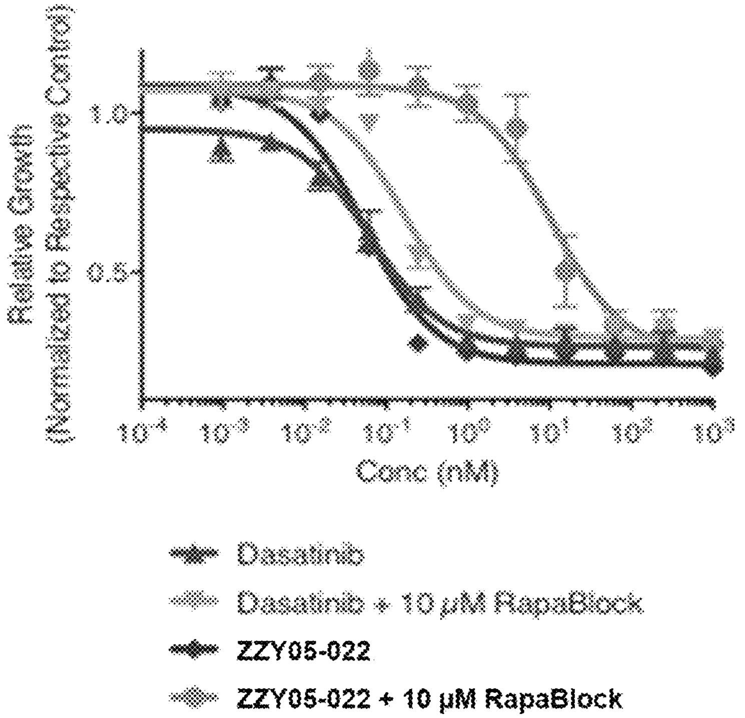

FIG. 14A
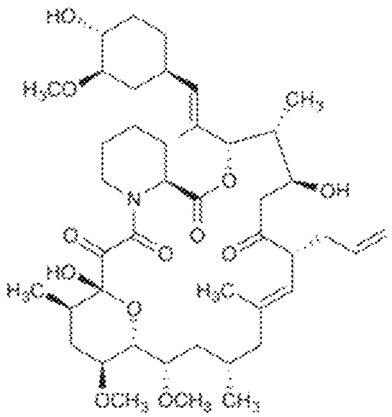
FK506
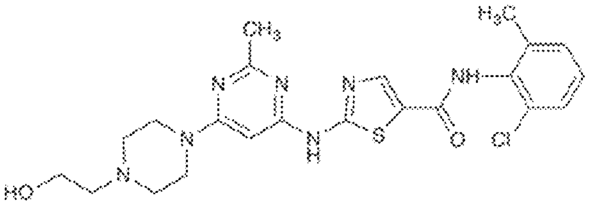
Dasatinib
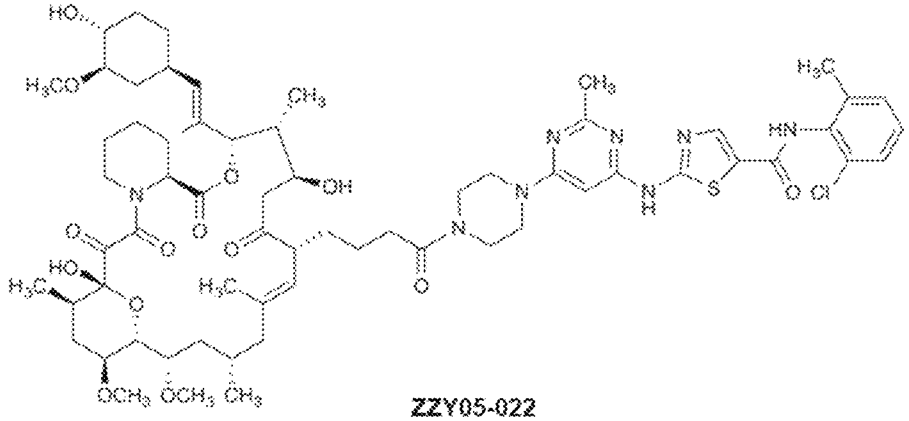
ZZY05-022
(FK506-Dasatinib)

| Kinase | Average Inhibition [Dasatinib] | Average Inhibition [05-022] |
| --- | --- | --- |
| ABL1 | 100 | 100 |
| YES1 | 100 | 97 |
| GAK | 100 | 98 |
| BLK | 100 | 100 |
| SIK2 | 100 | 100 |
| ABL2 | 100 | 100 |
| SRC | 100 | 100 |
| CSK | 94 | 90 |
| LCK | 92 | 86 |

FIG. 17A
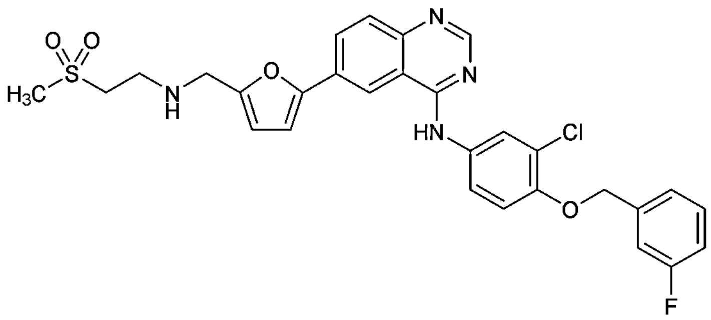
Lapatinib
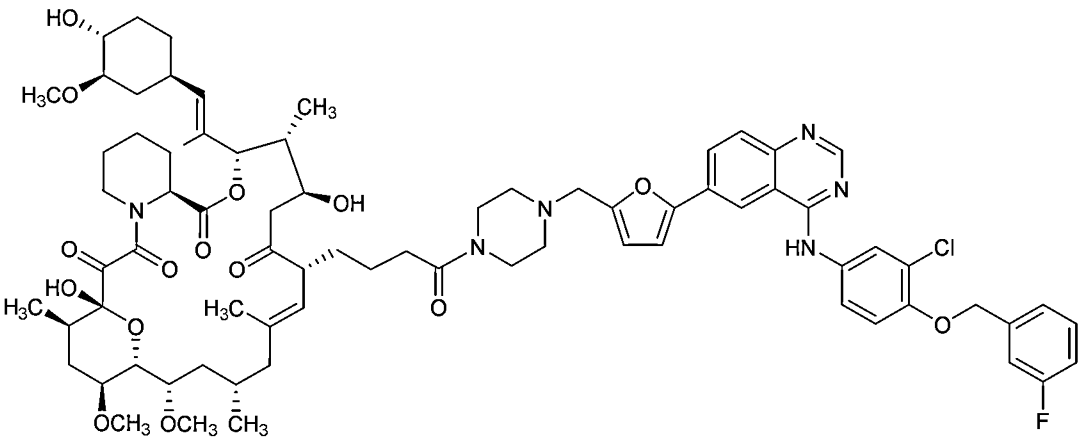
08-047
(FK506-Lapatinib)

FIG. 17D
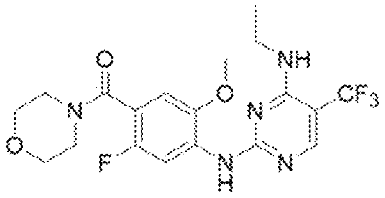
GNE7915
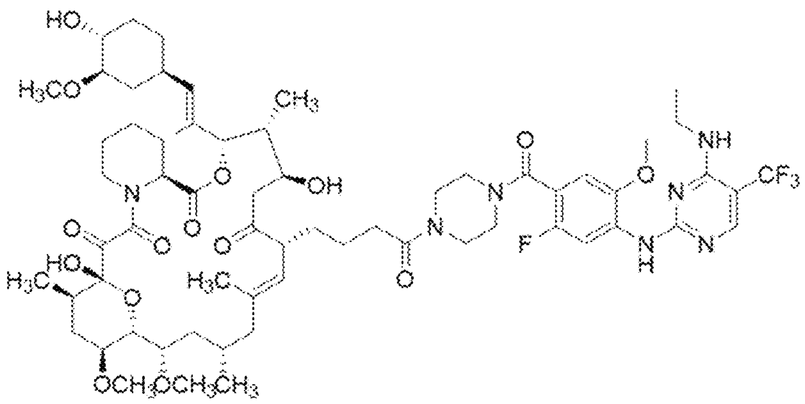
08-074
(FK506-GNE7915)
FIG. 17E
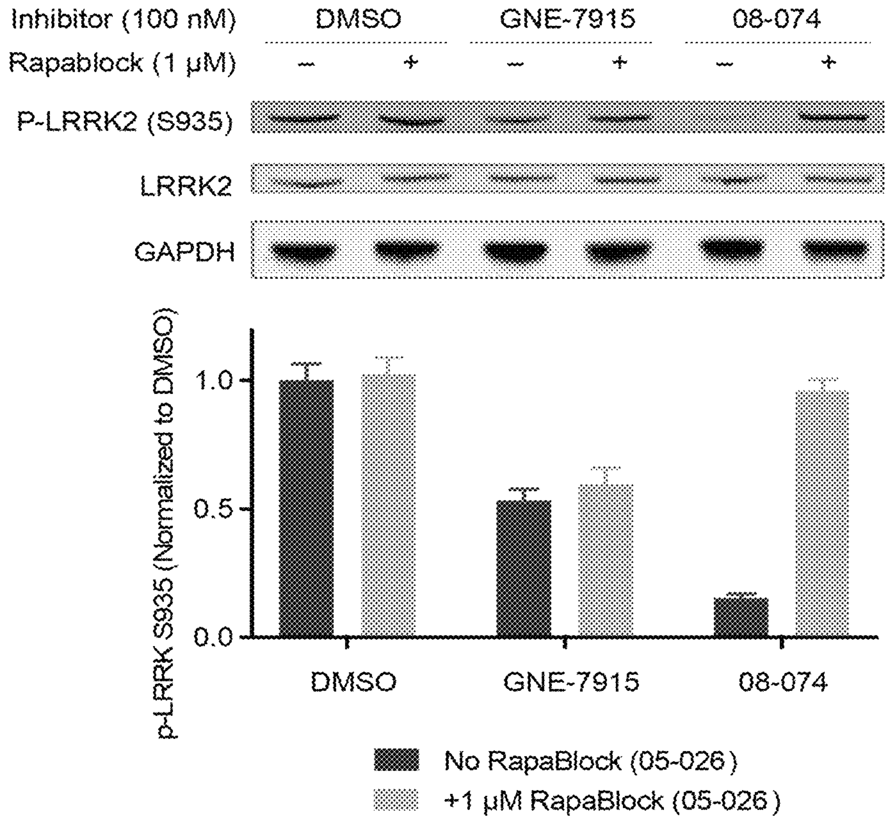

FIG. 19A
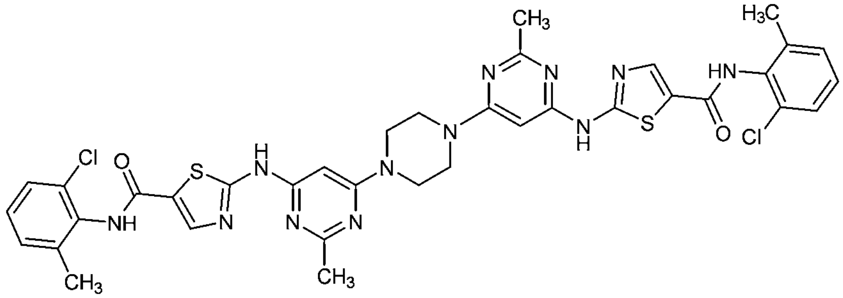
Dasa Dimer 0
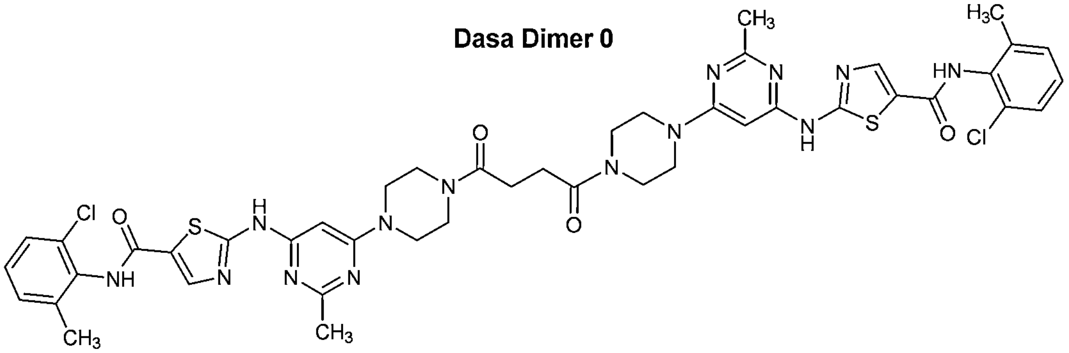
Dasa Dimer 4
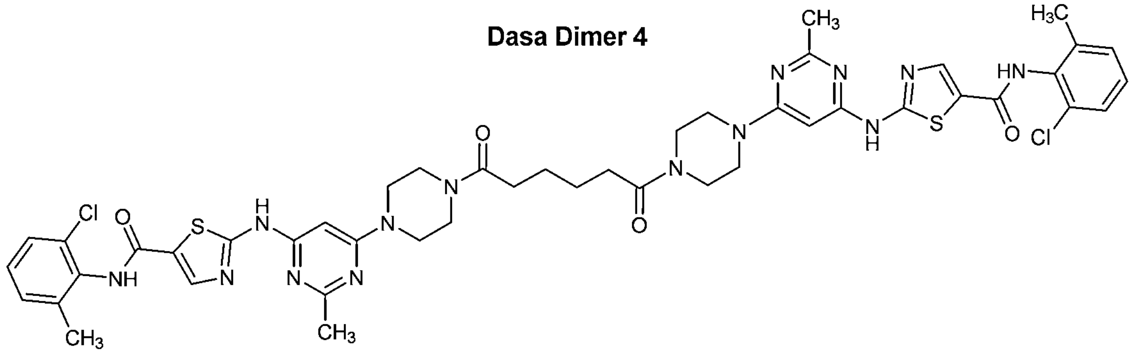
Dasa Dimer 6

| Gene Name | Average Inhibition [Dasatinib] | Average Inhibition [05-022] |
|---|---|---|
| ABL1 | 100 | 100 |
| YES1 | 100 | 97 |
| GAK | 100 | 98 |
| BLK | 100 | 100 |
| SIK2 | 100 | 100 |
| ABL2 | 100 | 100 |
| SRC | 100 | 100 |
| CSK | 94 | 90 |
| LCK | 92 | 86 |

FIG. 21C

Immunophilin-dependent Kinase Inhibitors
+Immunophilin "Blocker"

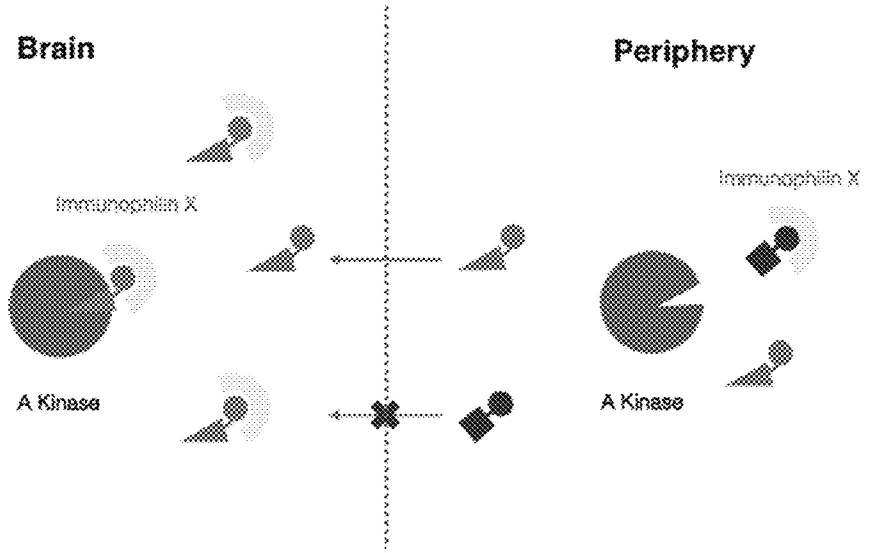

*FKBP12 is highly expressed in the brain.

FIG. 22

TABLE 1 Distribution of [$^3$H]FK506 binding sites in brain and peripheral tissues

| Tissue | Membrane | Soluble |
|---|---|---|
| Cortex | 24.5 ± 2.2 | 17.5 ± 1.0 |
| Cerebellum | 4.0 ± 0.3 | 9.6 ± 0.7 |
| Striatum | 45.8 ± 3.9 | 33.8 ± 2.5 |
| Hippocampus | 34.7 ± 1.5 | 42.6 ± 3.2 |
| Brainstem | 5.9 ± 0.6 | 9.7 ± 0.4 |
| Hypothalamus | 10.3 ± 0.9 | 7.5 ± 0.5 |
| Midbrain | 12.8 ± 1.0 | 29.9 ± 1.0 |
| Pituitary | * | 11.3 ± 1.2 |
| Thymus | 1.8 ± 0.2 | 3.1 ± 0.4 |
| Spleen | 1.4 ± 0.2 | 2.0 ± 0.1 |
| Heart | * | 3.6 ± 0.4 |
| Kidney | 0.5 ± 0.02 | 3.4 ± 0.4 |
| Liver | * | 3.7 ± 0.5 |
| Lung | 0.7 ± 0.04 | 2.6 ± 0.3 |

[$^3$H]FK506 bound is expressed as pmol per mg protein. Regions of rat brain were dissected, homogenized at 100 mg ml$^{-1}$ wet weight in 50 mM Tris-HCl, pH 7.4, 1 mM sodium EDTA, 100 μg ml$^{-1}$ phenylmethylsul- Steiner, J. P. *et al.* High brain densities of the immunophilin FKBP colocalized with calcineurin. *Nature* 358, 584–587 (1992).

FIG. 24
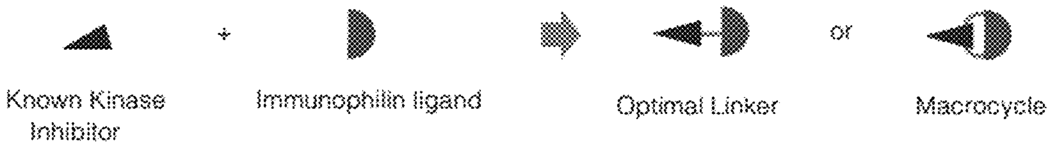
FIG. 25
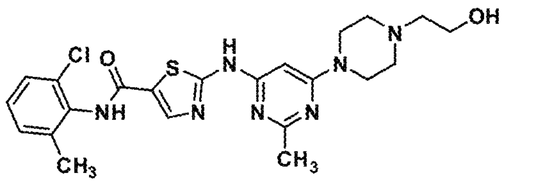
Dasatinib
Src family kinase, Abl
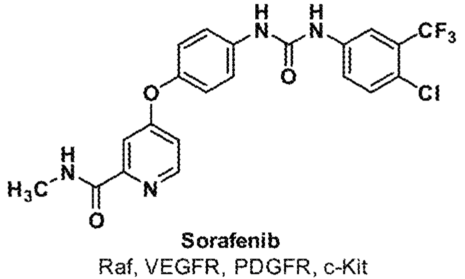
Sorafenib
Raf, VEGFR, PDGFR, c-Kit
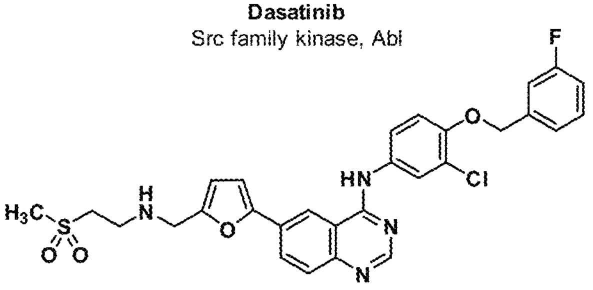
Lapatinib
EGFR, HER2
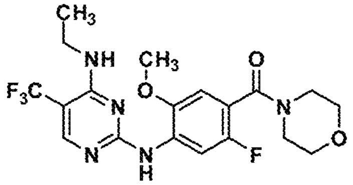
GNE-7915
LRRK2

FIG. 27
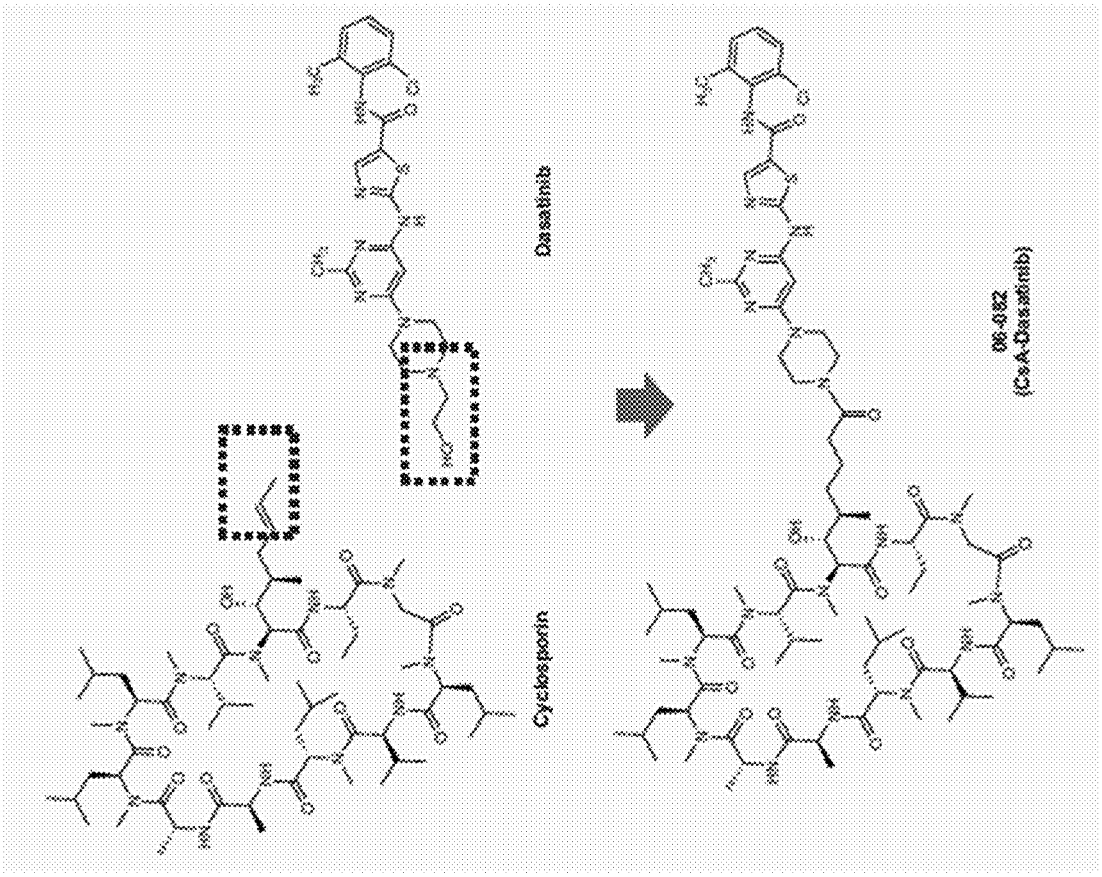
Cyclosporin
Dasatinib
06-032
(CsA-Dasatinib)
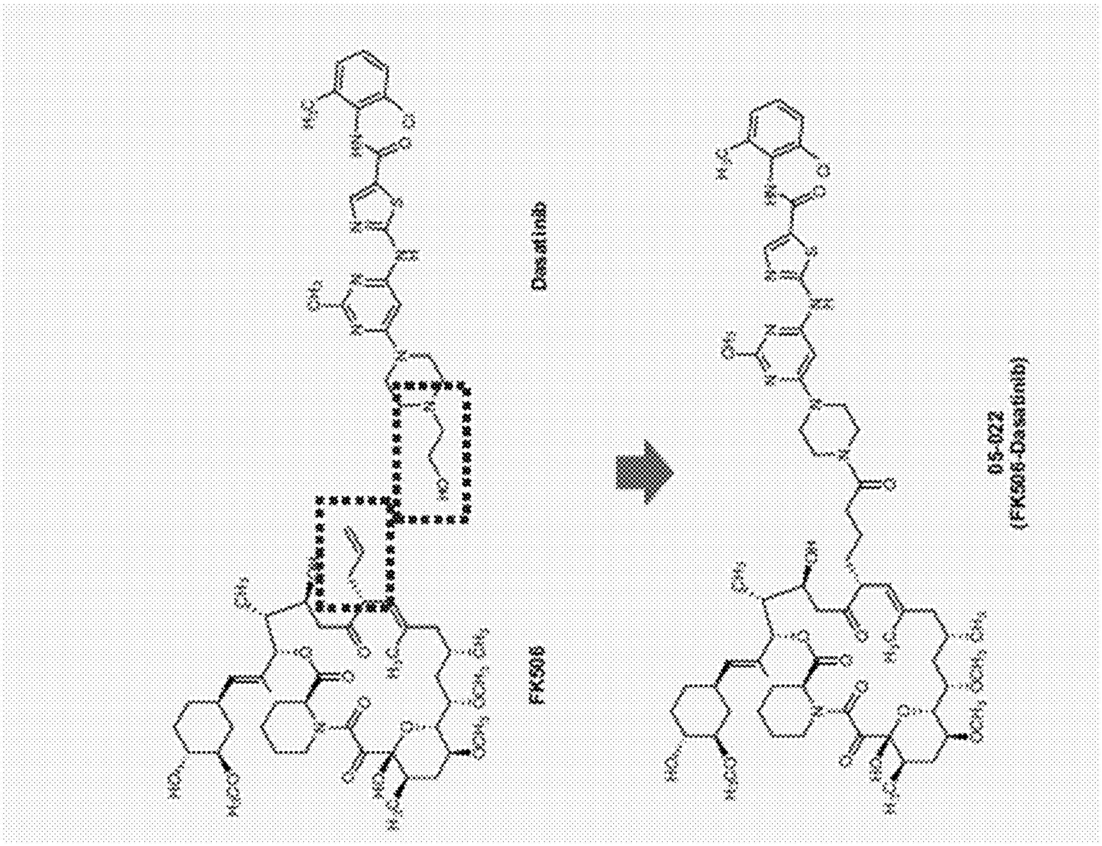
FK506
Dasatinib
05-022
(FK506-Dasatinib)

FIG. 28
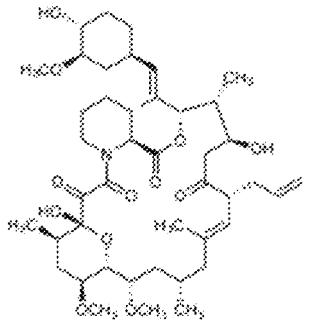
$K_d$ (FKBP12)
0.6 nM
FK506
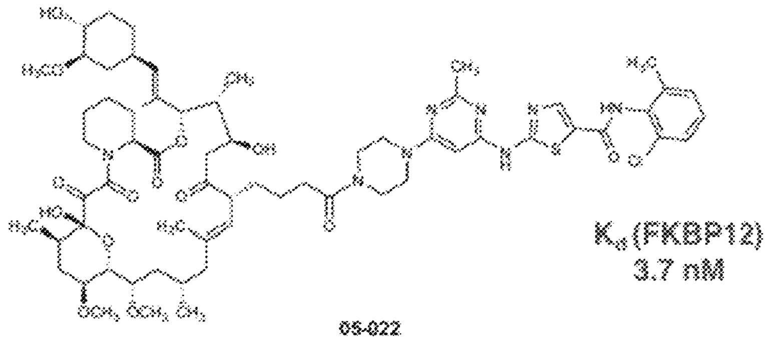
$K_d$ (FKBP12)
3.7 nM
05-022
(FK506-Dasatinib)
Src Kinase Assay
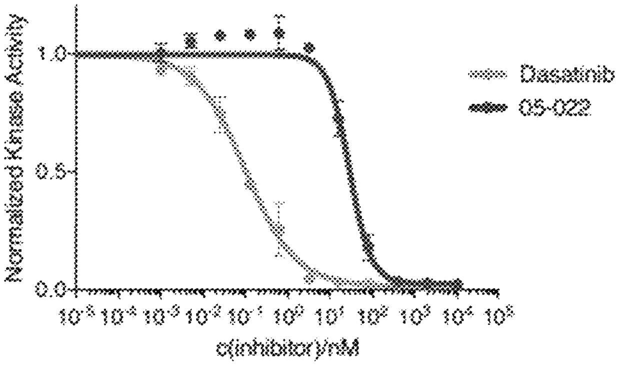
FKBP12 Fluorescence Polarization Assay:
1 nM FKBP12, 0.5 nM Rapa-FITC, x nM ligand, 20 mM HEPES 8.0, 0.01% Triton X-100, 5% DMSO. Average of triplicate.
Src Kinase Assay:
0.4 ng/μL kinase, 125 μM ATP, 0.4 μg/μL Poly $E_4Y_1$, 60 min, 23 °C. Average of triplicate.

| Kinase | Inhibition% 10 nM 05-022 + 10 µM FKBP12 | Inhibition% 10 nM Dasatinib + 10 µM FKBP12 | Difference |
|---|---|---|---|
| EPHB2 | 100 | 101 | -1 |
| YES1 | 99 | 100 | -1 |
| FGR | 99 | 102 | -3 |
| SRC | 98 | 101 | -3 |
| PEAK1 | 97 | 96 | 1 |
| EPHB4 | 96 | 98 | -2 |
| ABL1 | 95 | 100 | -5 |
| EPHA5 | 94 | 99 | -5 |
| EPHA8 | 93 | 101 | -8 |
| BLK | 93 | 99 | -6 |
| FYN | 90 | 101 | -11 |
| EPHB1 | 90 | 100 | -10 |
| BTK | 90 | 98 | -8 |
| BMX | 89 | 98 | -9 |
| LCK | 86 | 98 | -12 |
| HCK | 86 | 100 | -14 |
| EPHA2 | 79 | 99 | -20 |
| EPHA4 | 76 | 99 | -23 |
| EPHA3 | 58 | 102 | -44 |
| SNF1LK2 | 46 | 93 | -47 |
| EPHB3 | 42 | 85 | -43 |
| TXK | 37 | 76 | -39 |
| EPHA1 | 37 | 76 | -39 |
| CSK | 37 | 61 | -24 |
| RIPK2 | 30 | 87 | -57 |
| SIK1 | 26 | 87 | -61 |
| DDR1 | 13 | 74 | -61 |

Au-Yeung BB, Deindl S, Hsu LY, Palacios EH, Levin SE, Kuriyan J, Weiss A 2009. The structure, regulation, and function of ZAP-70. Immunol Rev 228:41–57

Au-Yeung BB, Deindl S, Hsu LY, Palacios EH, Levin SE, Kuriyan J, Weiss A 2009. The structure, regulation, and function of ZAP-70. Immunol Rev 228:41–57

FIG. 38
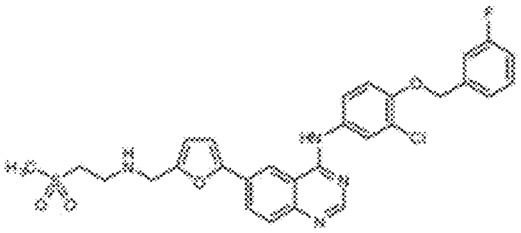
Lapatinib
Lapatinib
Erlotinib
Gefitinib
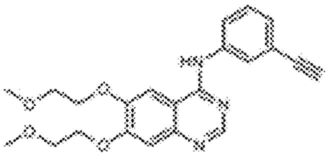
Erlotinib
Focused optimization of
- Attachment point
- Linker chemistry
~20 compounds
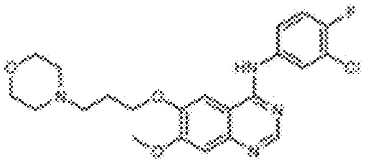
Gefitinib
FK-Lap (ZZY-08-047)
FK-Erlo (ZZY-08-068)
FK-Gefi (ZZY-08-069)

- The decreased potency may be due to low FKBP12 expression in these cells.
- In brain tumors which express large amounts of FKBP12, we may see improved pharmacology.
- Should try a glioma cell line or try overexpressing FKBP in these cells.

FIG. 41
It is active at concentrations where GNE-7915 was sub-efficacious.
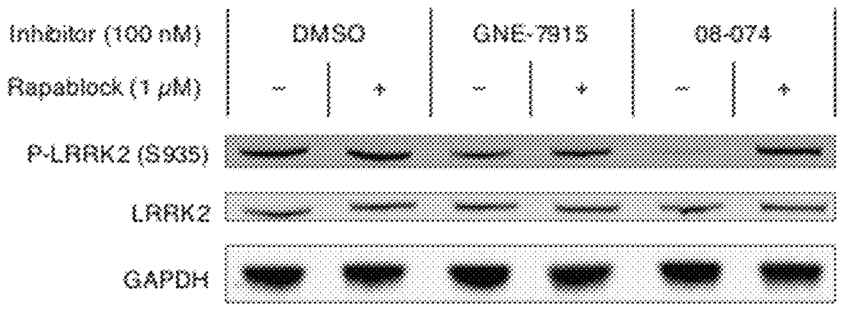
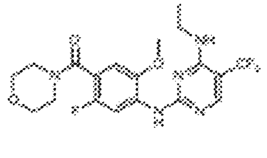
GNE-7915
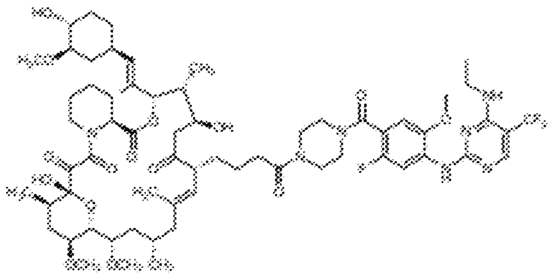
08-074
(FK506-GNE7915)
The degree of inhibition can be quantified with a sandwich TR-FRET assay
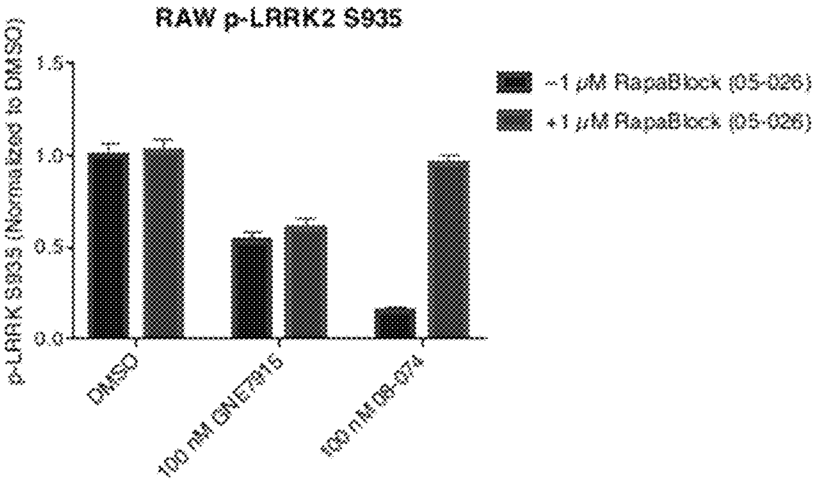

Dose-Response confirms potent inhibition of p-LRRK2

| IC50 (nM) | 3T3 | RAW264.7 |
|---|---|---|
| GNE-7915 | 75.6±10.2 | 81.3±12.2 |
| ZZY08-074 | 8.51±0.71 | 6.47±0.64 |

FIG. 43
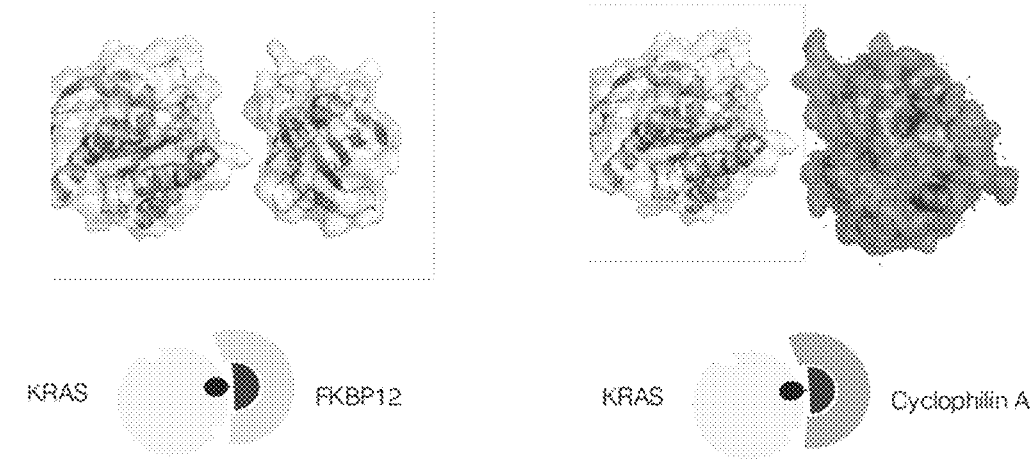
FIG. 44
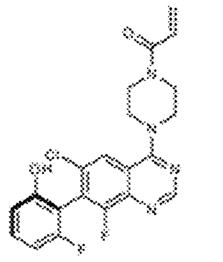
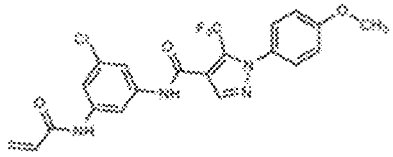
KRAS (G12C) inhibitor
GDP-state specific
$K_i$ > 64 μM (~1 mM)
$k_{inact}$ > 0.066 $s^{-1}$
KRAS (M72C) inhibitor
Binds both GDP- and GTP-state
$K_i$ ~ 300 μM
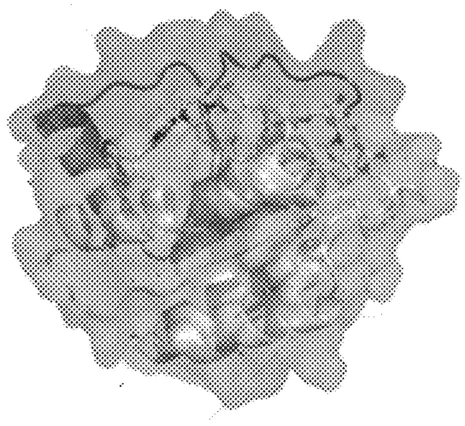
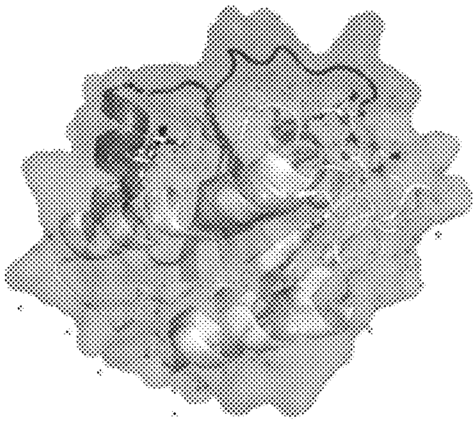

FIG. 46
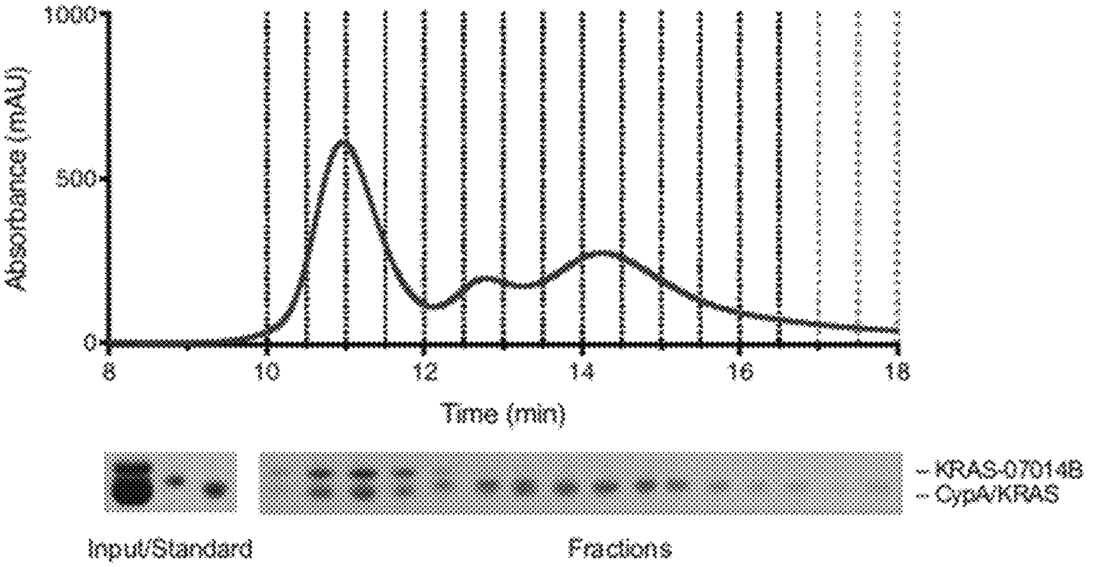
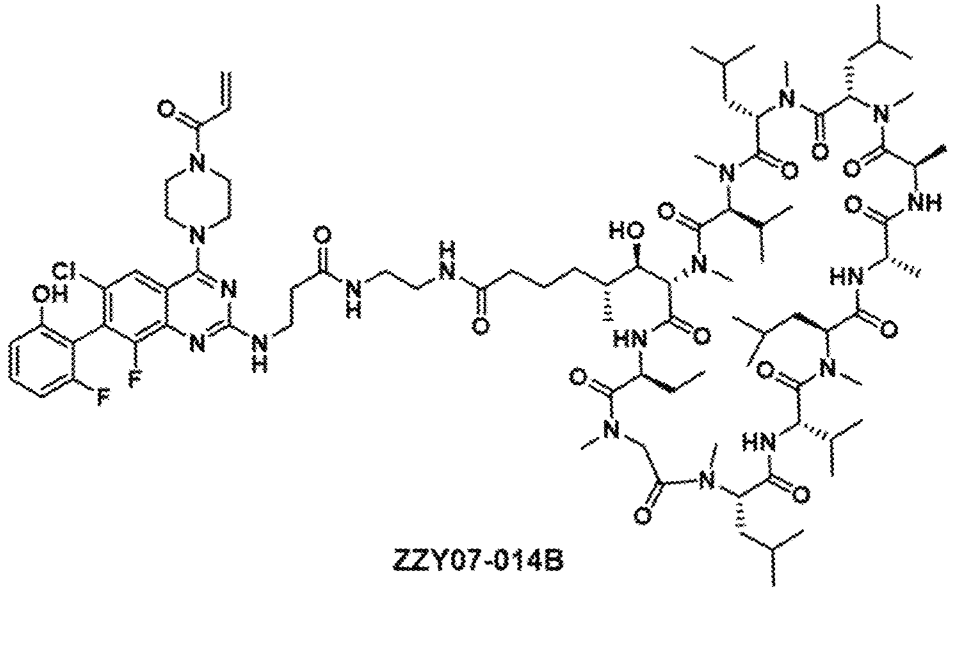
ZZY07-014B

This likely indicates a first melting event of CypA, then a second melting event of labeled KRAS at a higher temperature.
Not shown: CypA and KRAS alone both melt at 50 °C.

CypA Set

FIG. 53
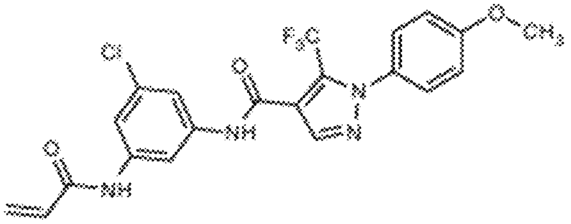
KRAS (M72C) inhibitor
Binds both GDP- and GTP-state
$K_i$ ~ 300 μM
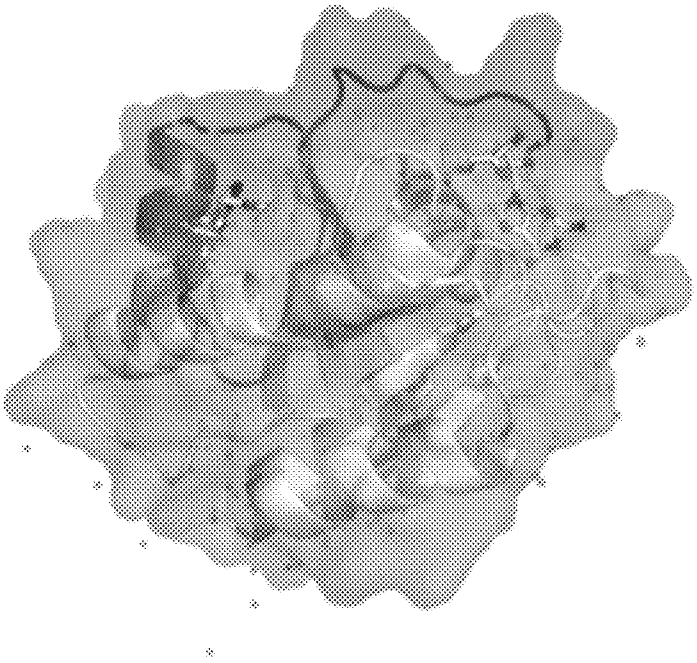

FIG. 55
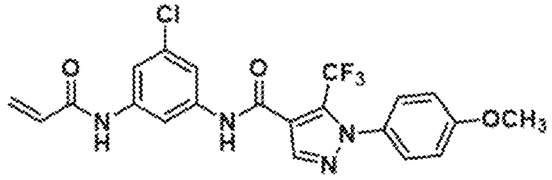
06-031
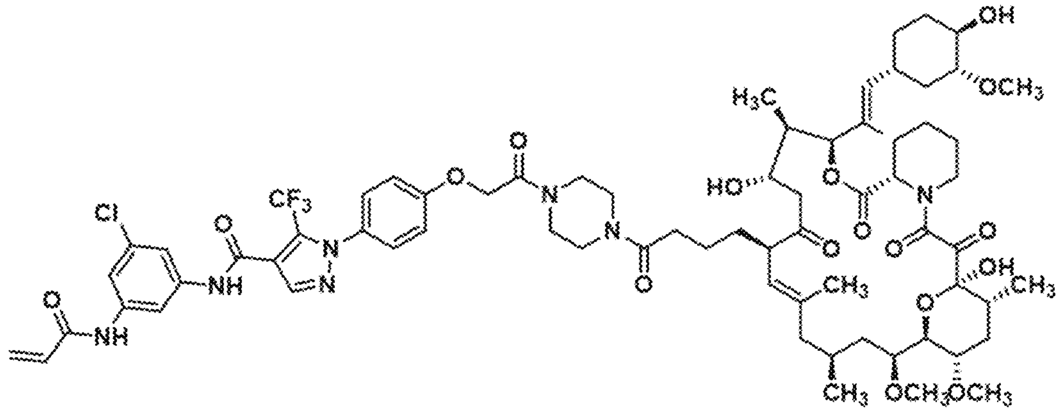
06-057

FIG. 58
To avoid complications of a bead-based assay that involves extensive washing, a homogeneous TR-FRET assay was used here.
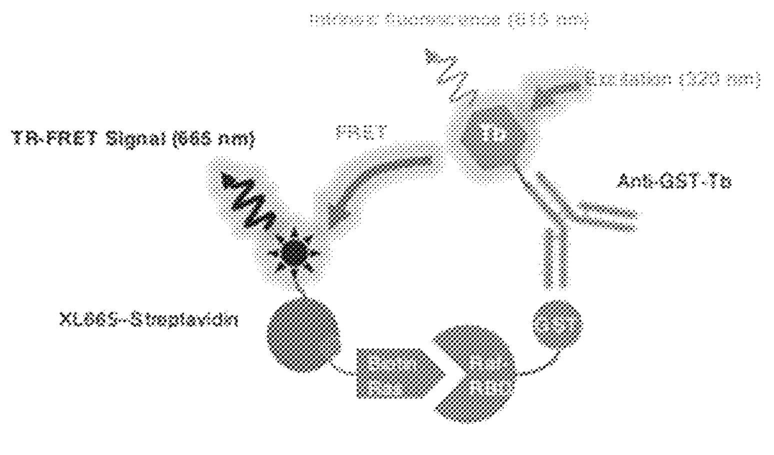
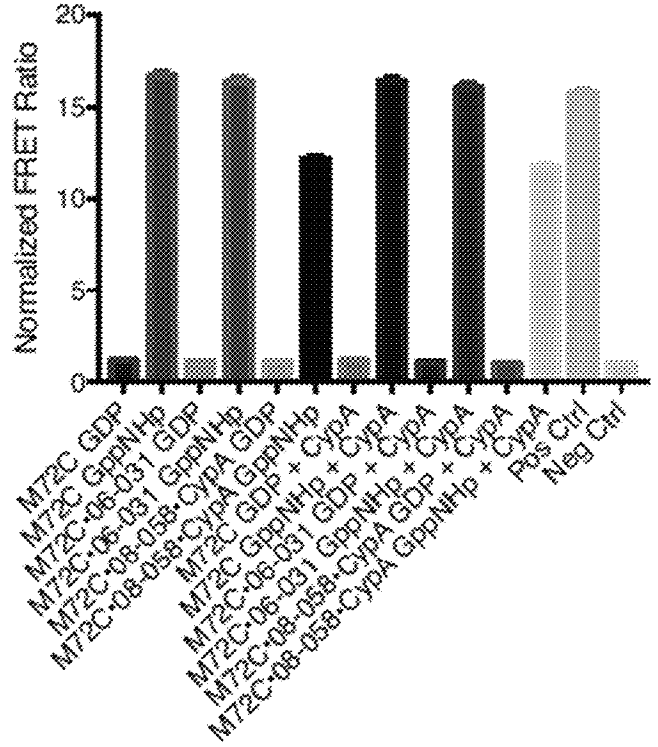

FIG. 60
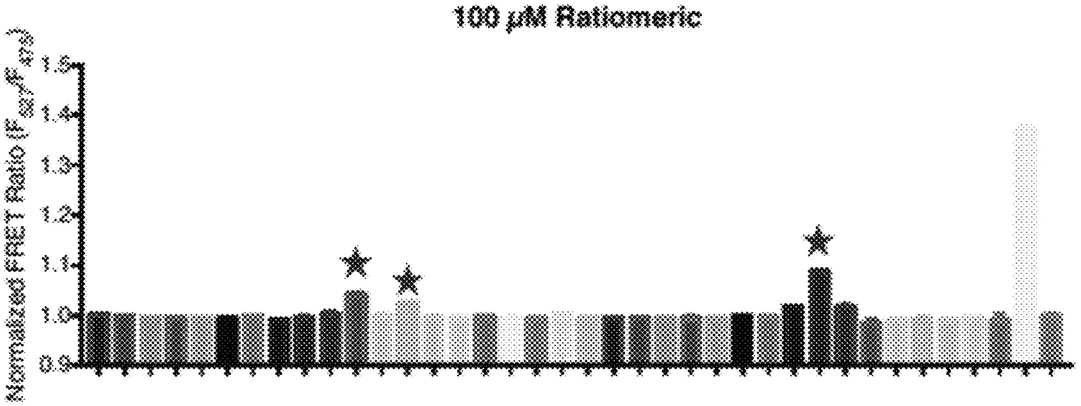
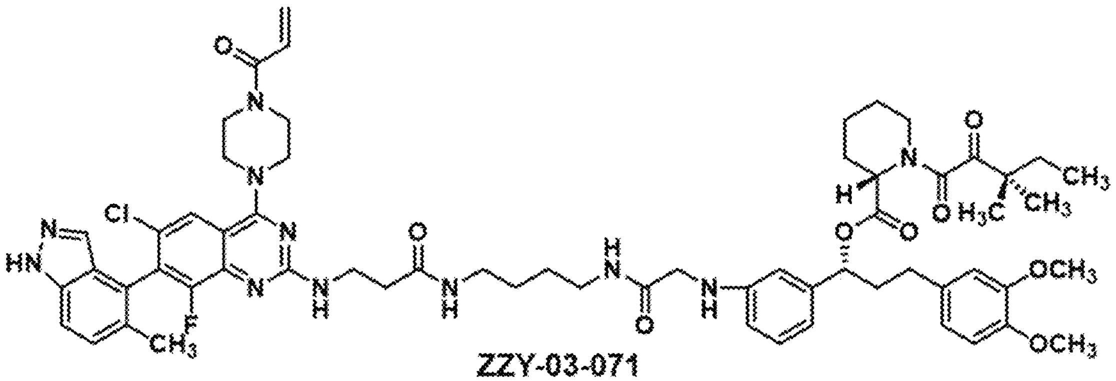
ZZY-03-071

FIG. 63
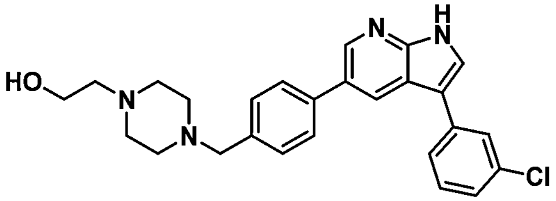
HGK inhibitor 12k
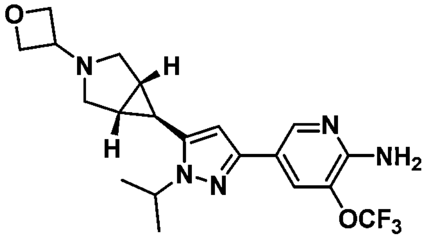
DLK inhibitor 8
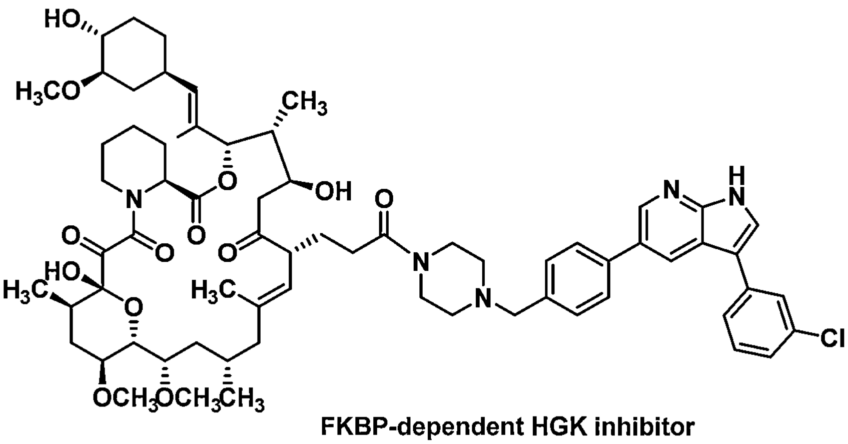
FKBP-dependent HGK inhibitor
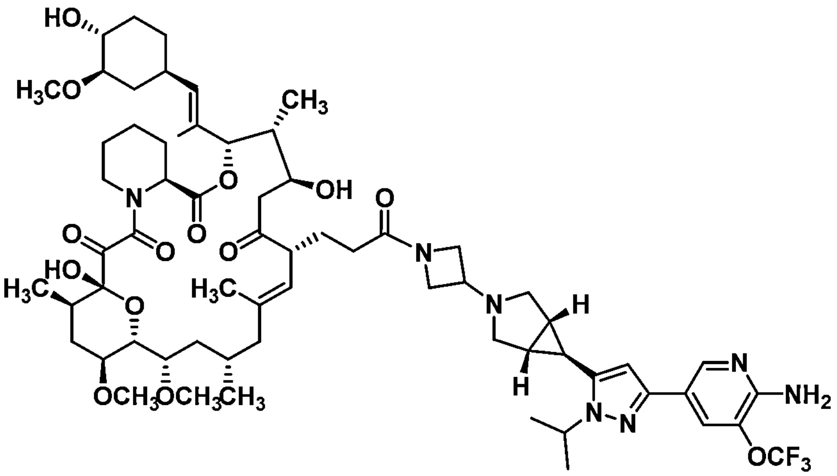
FKBP-dependent DLK inhibitor

FIG. 64
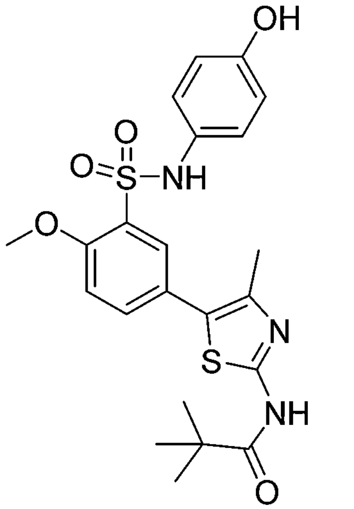
PI4K inhibitor of interest
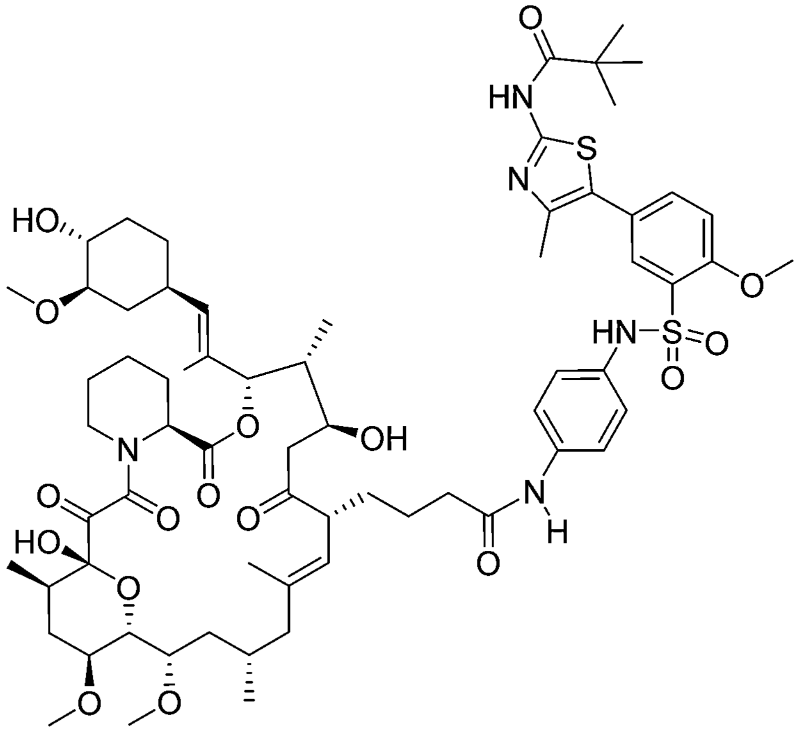
example of an FKBP-dependent PI4K inhibitor

IMMUNOPHILIN BINDING AGENTS AND USES THEREOF

CROSS-REFERENCES TO RELATED APPLICATIONS

This application is a divisional of U.S. application Ser. No. 17/427,039, filed Jul. 29, 2021, which is the national stage filing under 35 U.S.C. § 371 of International Application No. PCT/US2020/017012 filed Feb. 6, 2020, which claims the benefit of U.S. Provisional Application No. 62/802,668, filed Feb. 7, 2019, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. U19 AI109622 and R01 CA221969 awarded by the National Institutes of Health. The government has certain rights in the invention.

REFERENCE TO AN ELECTRONIC SEQUENCE LISTING

The contents of the electronic sequence listing (048536-636D01US_Sequence_Listing_ST26.xml; Size: 33,074 bytes; and Date of Creation: Nov. 21, 2024) is hereby incorporated by reference in its entirety.

BACKGROUND mTOR is a protein kinase that plays a central role in regulating cell growth and proliferation, and is estimated to be overactivated in 30% of cancers. Therapeutic agents targeting mTOR have been widely pursued as potential therapies for cancer, as well as neurological disorders such as epilepsy. However, the success of these therapies is often hampered by insufficient amount of drug that can cross the blood-brain barrier. Even when this condition is met, the application of these drugs is sometimes confounded by the toxicity caused by system-wide inhibition of mTOR (e.g., immunosuppression, hyperglycemia, mucocytis in particular is a class specific effect of all mTOR inhibitors). Disclosed herein, inter alia, are solutions to these and other problems in the art.

BRIEF SUMMARY

In an aspect is provided a compound having the formula: $A^B$-$L^{B1}$-$R^{B1}$, or a pharmaceutically acceptable salt thereof.

$A^B$ is an immunophilin-binding moiety.

$L^{B1}$-$R^{B1}$ is a polar moiety.

$L^{B1}$ is a bond, covalent linker, or bioconjugate linker.

$R^{B1}$ is hydrogen, halogen, $-CX^{B1}_3$, $-CHX^{B1}_2$, $-CH_2X^{B1}$, $-OCX^{B1}_3$, $-OCH_2X^{B1}$, $-OCHX^{B1}_2$, —CN, $-SO_{nB1}R^{B1D}$, $-SO_{vB1}NR^{B1A}R^{B1B}$, $-NHC(O)NR^{B1A}R^{B1B}$, $-N(O)_{mB1}$, $-NR^{B1A}R^{B1B}$, $-C(O)R^{B1C}$, $-C(O)OR^{B1C}$, $-C(O)NR^{B1A}R^{B1B}$, $-OR^{B1D}$, $-NR^{B1A}SO_2R^{B1D}$, $-NR^{B1A}C(O)R^{B1C}$, $-NR^{B1A}C(O)OR^{B1C}$, $-NR^{B1A}OR^{B1C}$, $-NR^{B1A}O(NR^{B1C})R^{B1D}$, $-NR^{B1A}C(NR^{B1C})NR^{B1A}R^{B1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{B1A}$, $R^{B1B}$, $R^{B1C}$, and $R^{B1D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHC(NH)H, $-NHC(NH)NH_2$, —NHOH, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl.

nB1 is independently an integer from 0 to 4.

mB1 and vB1 are independently 1 or 2.

$X^{B1}$ is independently —F, —Cl, —Br, or —I.

When $L^{B1}$ is a bond, $R^{B1}$ is not H.

Subsequent to administration to a subject, the concentration of the compound in circulating blood of the subject is greater than the concentration of the compound in the CNS of the subject.

In an aspect is provided a pharmaceutical composition including a compound described herein and a pharmaceutically acceptable excipient.

In an aspect is provided a method of treating a CNS disease in a subject in need of such treatment, including co-administering outside the CNS of the subject an anti-CNS disease drug and a compound described herein.

BRIEF DESCRIPTION OF THE DRAWINGS

FIG. 1A: RapaLink-1 suppresses growth of glioblastoma PDX in mice (Fan, Q. et al., 2017, Cancer Cell 31(3): 424-435). FIG. 1B: Structure of RapaLink-1.

FIGS. 13A-13B. FK506-Dasatinib is a programmable kinase inhibitor whose activity can be attenuated by a competing FKBP ligand (RapaBlock). FIG. 13A: RapaBlock (ZZY05-026) reverses the inhibition of phosphotyrosine signaling by FK506-dasatinib but not that by dasatinib. FIG. 13B: Dasatinib and FK506-dasatinib both inhibit the growth of K562 cells at sub-nanomolar concentration, and the activity of the latter is diminished by RapaBlock.

FIGS. 14A-14D. Design and biochemical characterization of a bispecific kinase inhibitor. FIG. 14A: Structures of FK506, dasatinib, and FK506-dasatinib. FIG. 14B: Dose-dependent inhibition of Src, Csk and DDR2 by dasatinib and FK506-dasatinib in the absence or presence of supplemented 10 μM recombinant FKBP12 protein. Data is the average of two replicates. FIG. 14C: Profiling of dasatinib and FK506-dasatinib against a panel of 485 purified kinases (SelectScreen™) in the presence of FKBP12. Each dot on the scatter plot represent one kinase colored by the extent of their inhibition by dasatinib. FIG. 14D: Schematic illustration of FK506, dasatinib, FK506-dasatinib and FKBP-presented FK506-dasatinib.

FIG. 15A: A mixture of recombinant Src kinase domain and FKBP12 (1:1.5 molar ratio) was incubated with buffer, dasatinib or FK506-dasatinib for 1 h and analyzed by size exclusion chromatography (Superdex 75 10/300). Fractions of 0.5 mL were collected and analyzed by SDS-PAGE. Coomassie-stained gel image of fractions from the FK506-dasatinib-treated sample is shown. FIG. 15B: Thermal denaturation curves of a 1:1 mixture of Src kinase domain and FKBP12 treated with buffer, dasatinib, or FK506-dasatinib. FIG. 15C: Immunoprecipitation of HA-FKBP12 from Jurkat cell lysate (1 mg/mL) treated with DMSO, 1 μM FK506 or 1 μM FK506-dasatinib.

FIGS. 16A and 16C: FK506-Dasatinib potently inhibits TCR signaling, whereas dasatinib dimers failed to show cellular activity. FIG. 16B: Profiling of intracellular kinase inhibition by dasatinib and FK506-dasatinib using the chemoproteomic probe XO44. Each dot in the scatter plot represents one kinase captured by XO44, and kinases that show statistically significant inhibition ($p<0.05$, comparing to DMSO-treated samples, Student's t-test) in both dasatinib and FK506-dasatinib-treated samples are colored blue. FIG. 16D: Jurkat cells were treated with dasatinib or FK506-dasatinib for 1 h and the drug-containing media were removed and replaced with fresh media. The phosphotyrosine levels were monitored by Western blot at various time points over 24 h.

FIGS. 17A-17F. A general approach to construct FKBP-dependent, programmable kinase inhibitors. FIGS. 17A-17C: Structures of lapatinib and FK506-lapatinib, their effects on HER2 signaling and the growth inhibition of SK-BR-3 cells by these compounds. FIGS. 17D-17F: Structures of GNE7915 and FK506-GNE7915 and their inhibition of LRRK2 autophosphorylation.

FIGS. 19A-19B. The structure of three dasatinib homodimers (FIG. 19A). Dasatinib homodimers are ineffective at inhibiting Src family kinases (FIG. 19B).

FIGS. 21A-21C. Immunophilin-dependent kinase inhibitors.

FIG. 22. Immunophilin-dependent kinase inhibitors: Distribution of [$^3$H]FK506 binding sites in brain and peripheral tissues.

FIG. 23A: Improvement in potency and blocking protein-protein interactions. FIG. 23B: Possible increase in selectivity and greater intracellular retention. FIG. 23C: Tissue-specific effects.

FIG. 24. Proof of concept approach.

FIG. 25. Selected kinase inhibitors.

FIG. 27. Design of chimeric kinase inhibitors.

FIG. 28. FK506-dasatinib hybrid maintains potent FKBP12 binding but attenuated kinase inhibition.

FIG. 30A: A scatter plot comparing inhibitory activity of dasatinib and ZZY05-022. FIG. 30B: Percent inhibition of dasatinib and ZZY05-022 against various kinases.

FIG. 38. Generation of FKBP-dependent EGFR inhibitors through multiple rounds of chemical evolution.

FIG. 41. FK506-GNE7915 hybrid potently inhibits LRRK2 phosphorylation.

FIG. 43. Dimerizing KRAS and immunophilins.

FIG. 44. KRAS Inhibitors.

FIG. 46. $KRAS^{G12C}$, once labeled with ZZY07-014B, forms a stable 1:1 complex with CypA.

FIG. 53. The M72C inhibitor scaffold offers a handle to tackle the GTP state.

FIG. 55. Molecules built on the M72C inhibitor scaffold (e.g., 06-031, 06-027, 07-026, 06-057, 07-015, 07-025, and 08-058) display similar dependence on immunophilins.

FIG. 58. Independent Ras•Raf binding TR-FRET assay confirm no significant inhibition of Raf binding.

FIG. 60. Data from a screen of a limited SLF analog library. SLF analogs listed from left to right: SLF, Rapa, FK506, 01-025, 01-038, 01-040, 01-041, 01-043, 01-044, 01-059, 01-065, 01-060A, 01-060B, 01-070, 01-072, 01-083, 02-014, 02-032, 02-033, 02-055, 02-096, 03-022, 03-084, 03-077, 03-083, 03-087, 03-091, 03-048, 03-071, 03-088, 03-025, 03-026, 02-075, 04-059, DMSO, DMSO, Pos Ctrl, Neg Ctrl. Assay conditions: 0.6 μM KRAS(G12C)-ECFP, 1.0 μM EYFP-FKBP, 100 μM Compound, 10 mM HEPES 8.0, 0.05% Tween-20, 1% DMSO, 23° C., 4 h incubation.

FIG. 63. Additional brain targets and inhibitors. HGK inhibitor 12k (Bos et al. Cell Chem. Bio 2019), DLK inhibitor 8 (Siu et al. J. Med. Chem. 2018), FKBP-dependent HGK inhibitor, and FKBP-dependent DLK inhibitor.

FIG. 64. PI4K inhibitor of interest (Rutanganira, et al. *J. Med. Chem.*, 2016, 59 (5), 1830-1839) and an example of an FKBP-dependent PI4K inhibitor.

DETAILED DESCRIPTION

I. Definitions

Figure 1A:
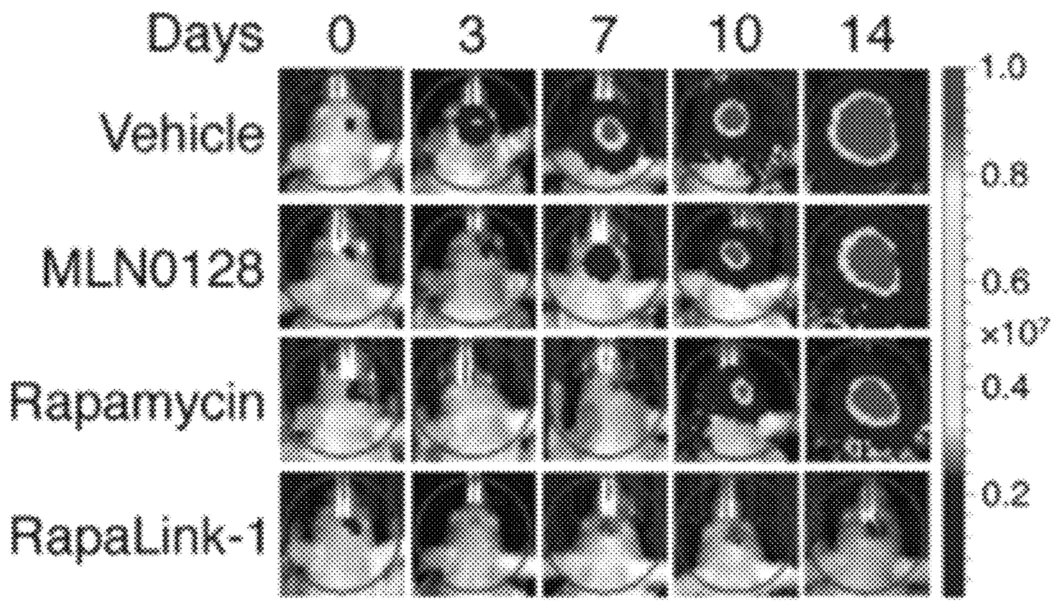
FIGS. 1A-1B. mTOR inhibition is an attractive therapeutic strategy for glioblastoma.
Figure 1B:
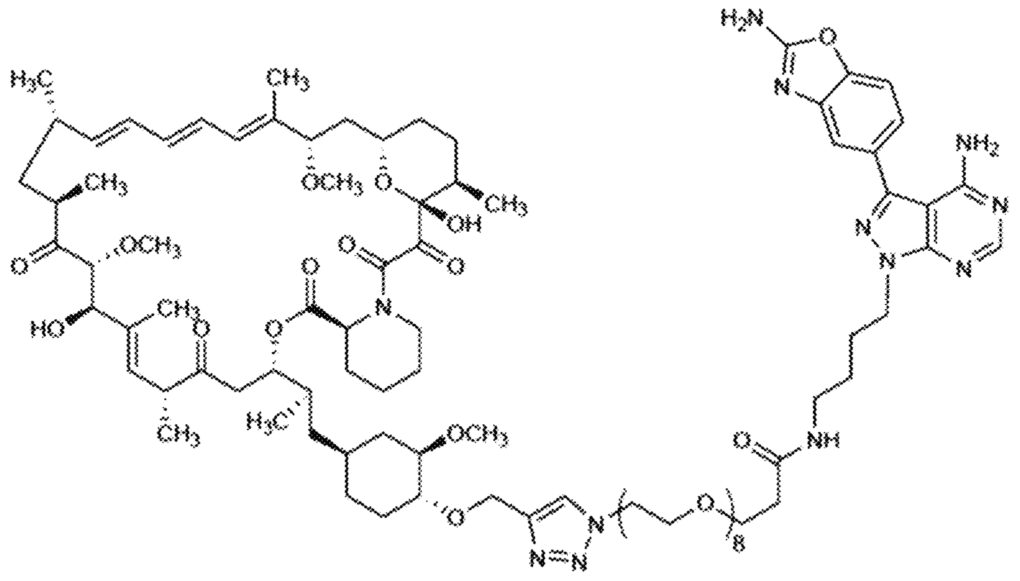
Figure 2:
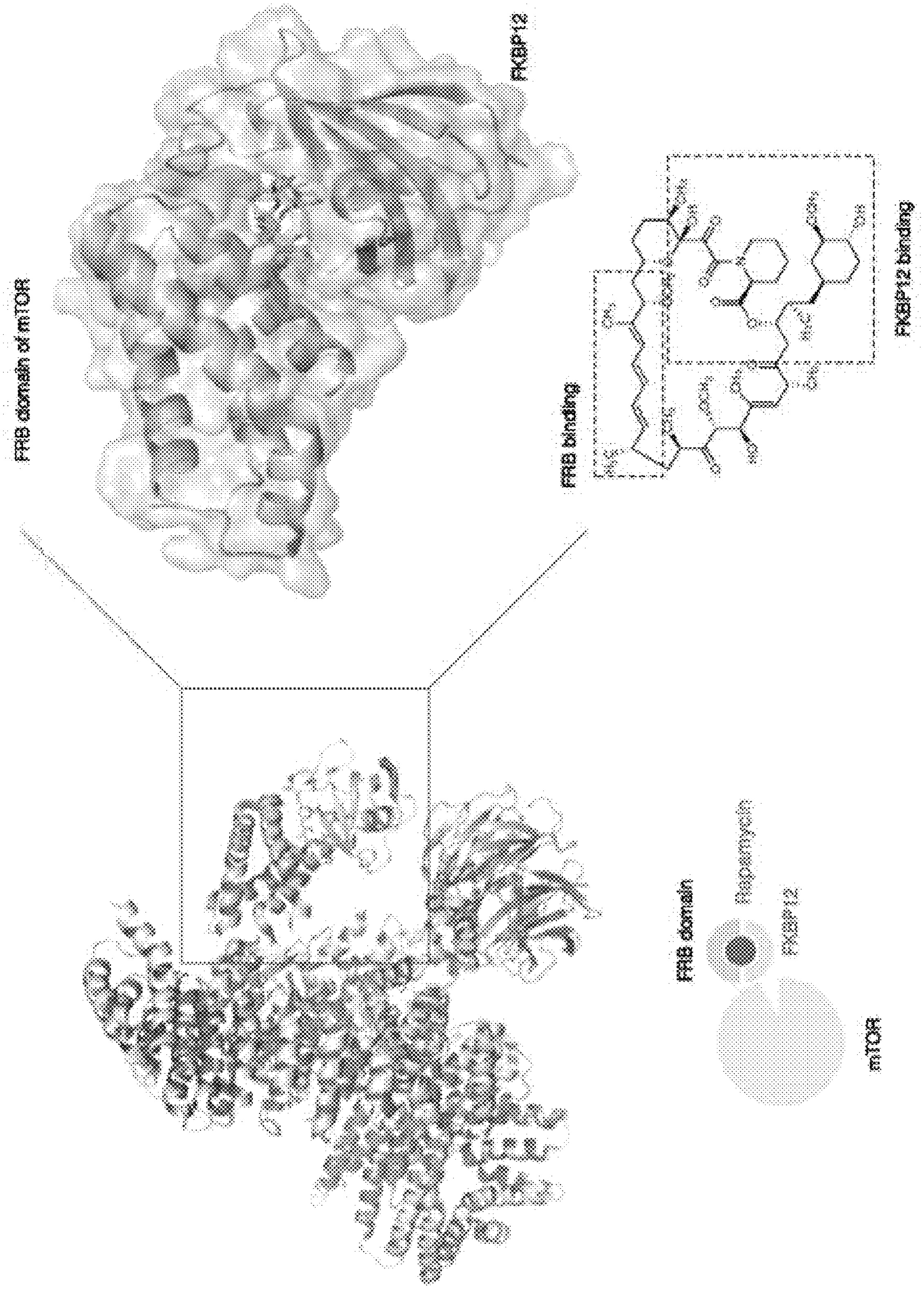
FIG. 2. Rapamycin binds FKBP to inhibit mTORC1.
Figure 3:
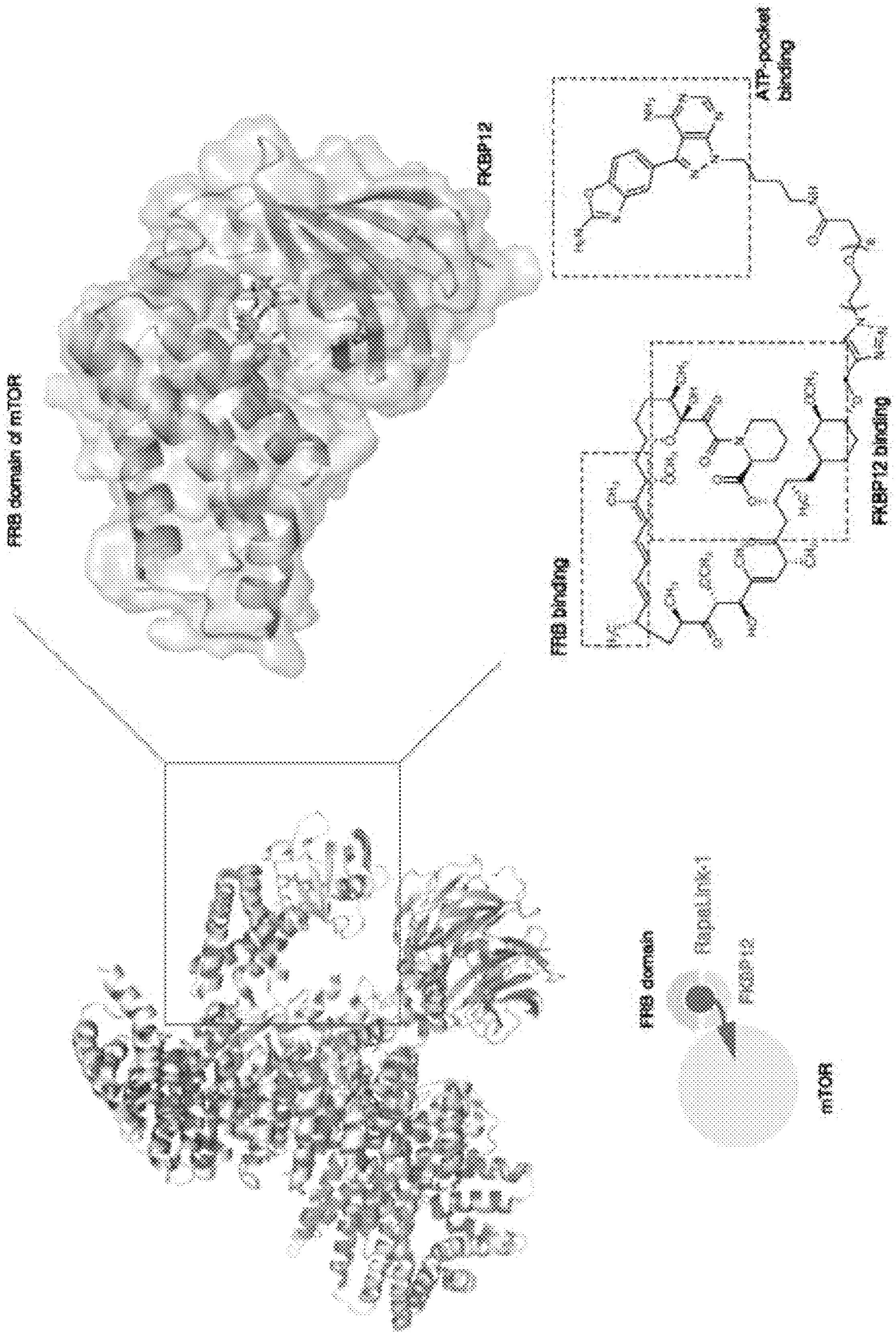
FIG. 3. RapaLink-1 binds FKBP to inhibit mTORC1.
Figure 4:
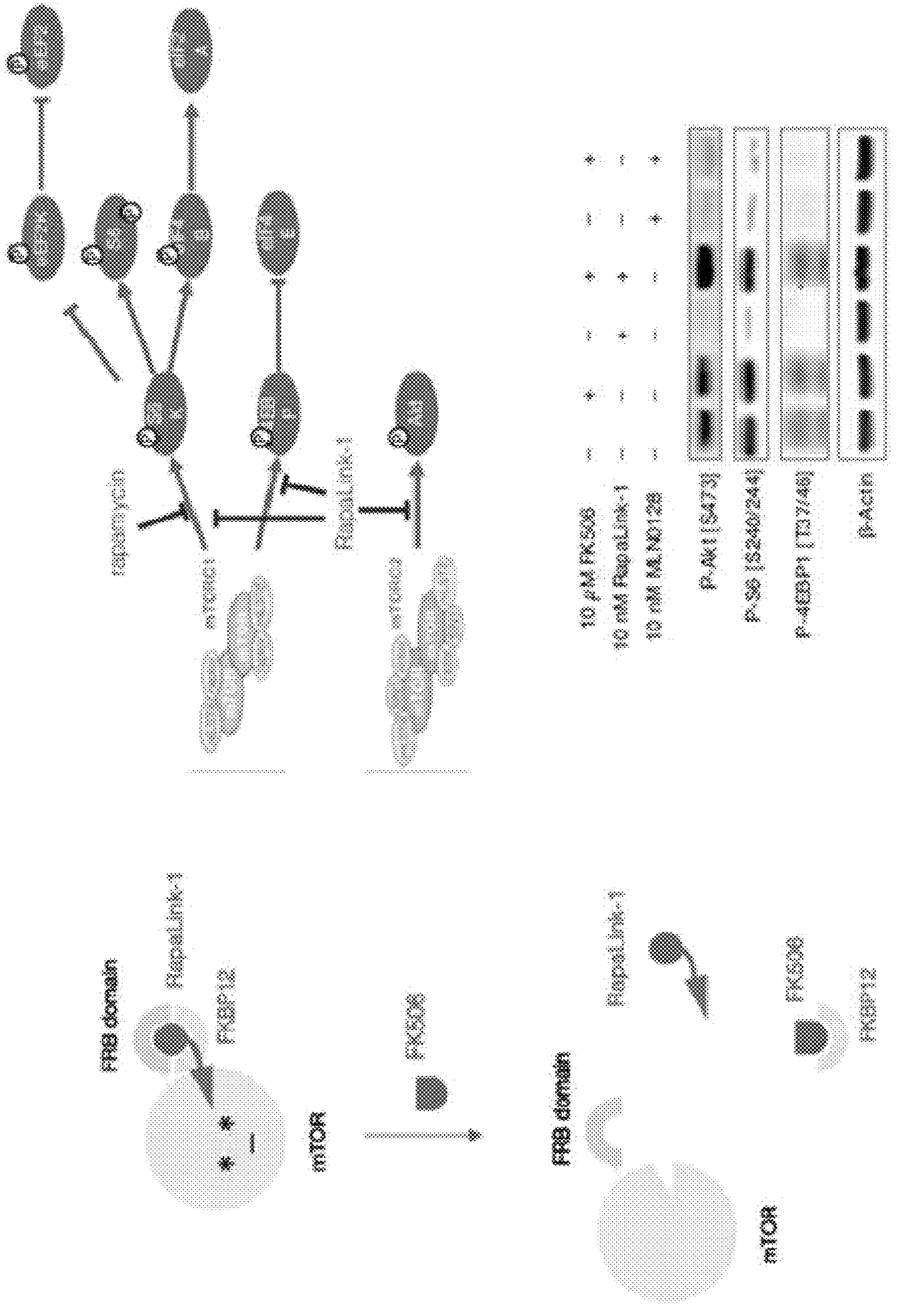
FIG. 4. FKBP is essential for the function of Rapamycin/RapaLink-1. MCF7 cells dosed at 50% confluency, 37° C., 24 h.
Figure 5A:
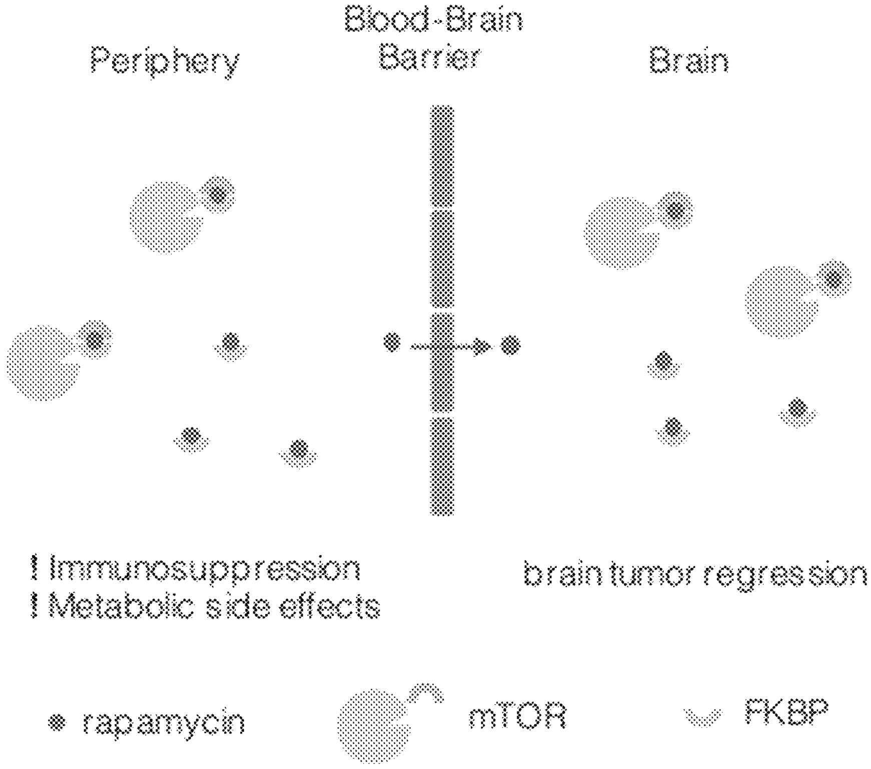
FIGS. 5A-5B. Concentrating rapamycin/Rapalink-1 in the brain.
Figure 5B:
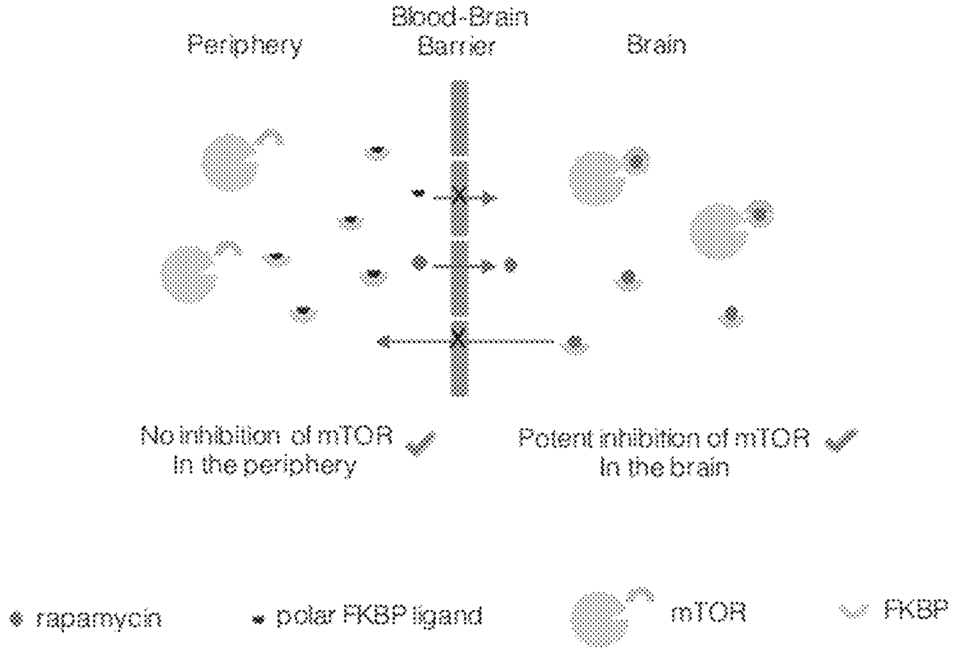
Figure 6:
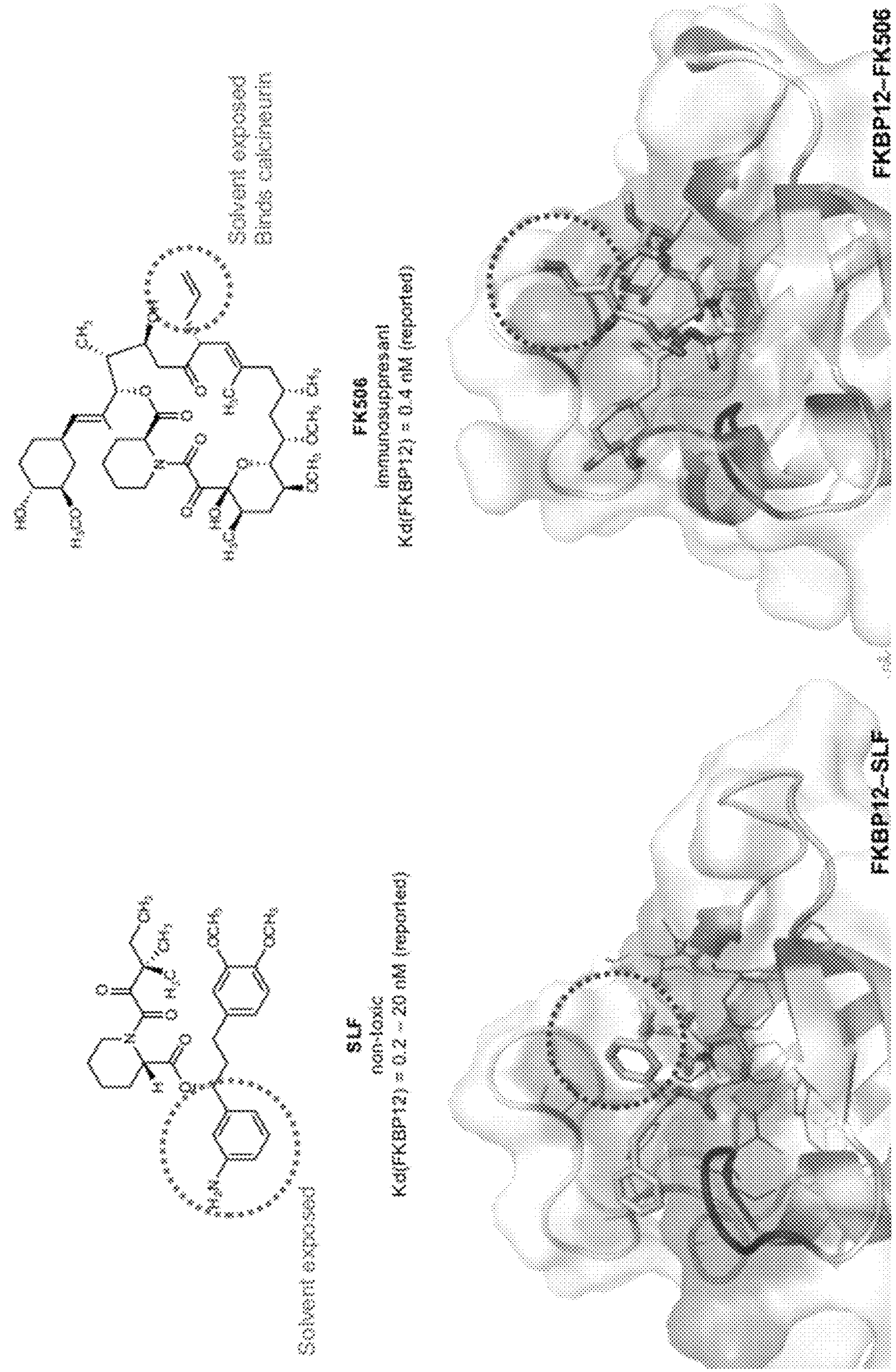
FIG. 6. Building polar components onto existing high-affinity FKBP ligand scaffolds.
Figure 7:
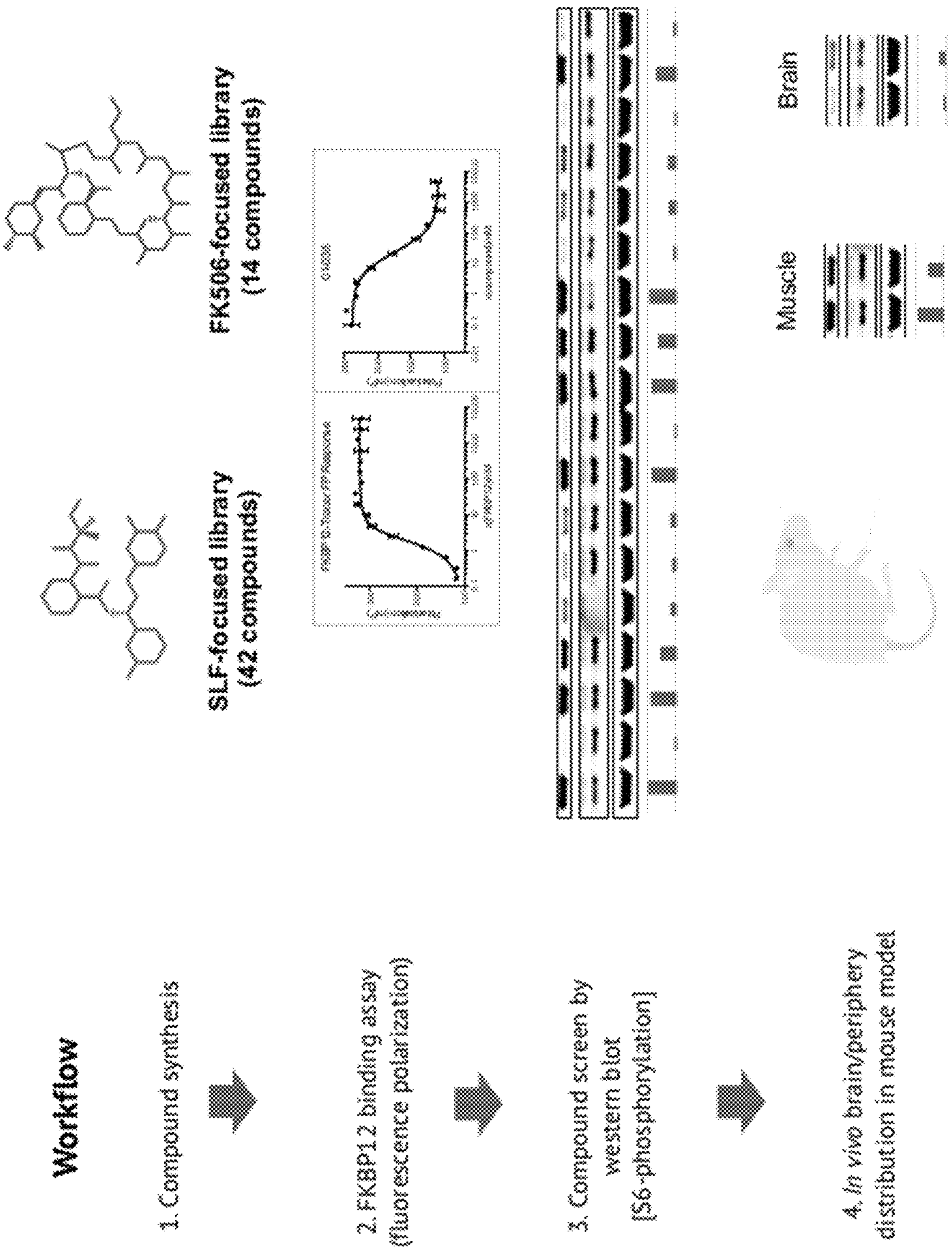
FIG. 7. Building a focused, non-BBB permeable FKBP ligand library.
Figure 8:
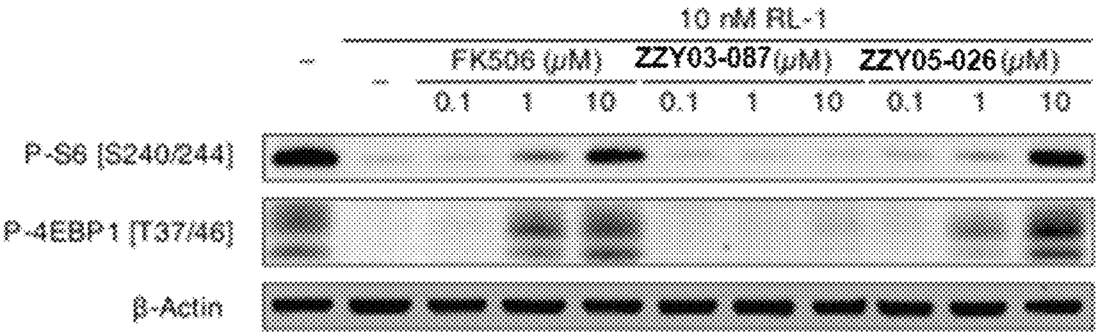
FIG. 8. FK506-derived compounds block RapaLink-1 function in cell culture. MCF7 cells, 24 h treatment. P-AKT and total protein blots are omitted for clarity.
Figure 9:
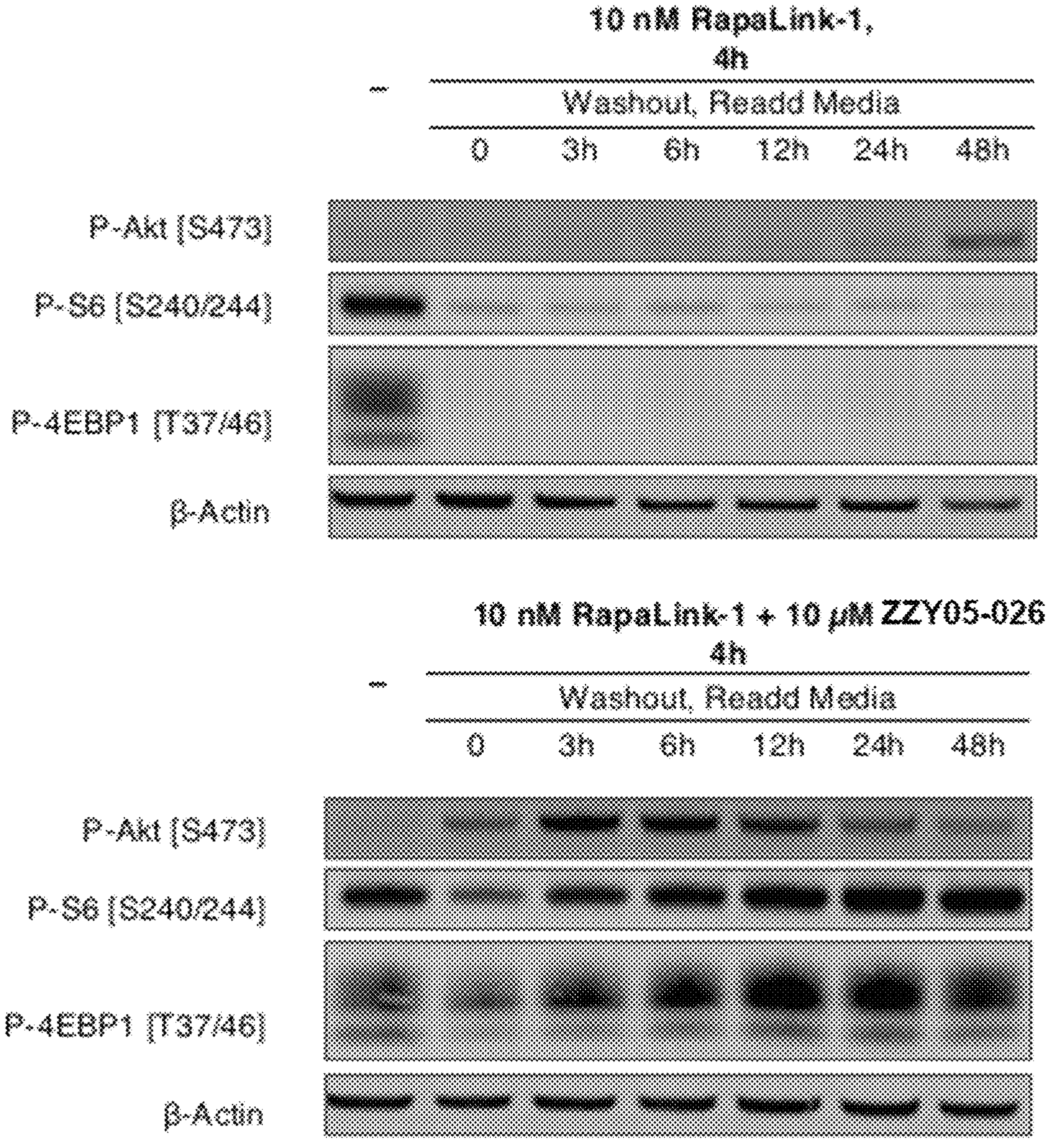
FIG. 9. The protective effects of 05-026 are durable even after washout. MCF7 cells, 24 h treatment. Total protein blots are omitted for clarity.
Figure 10:
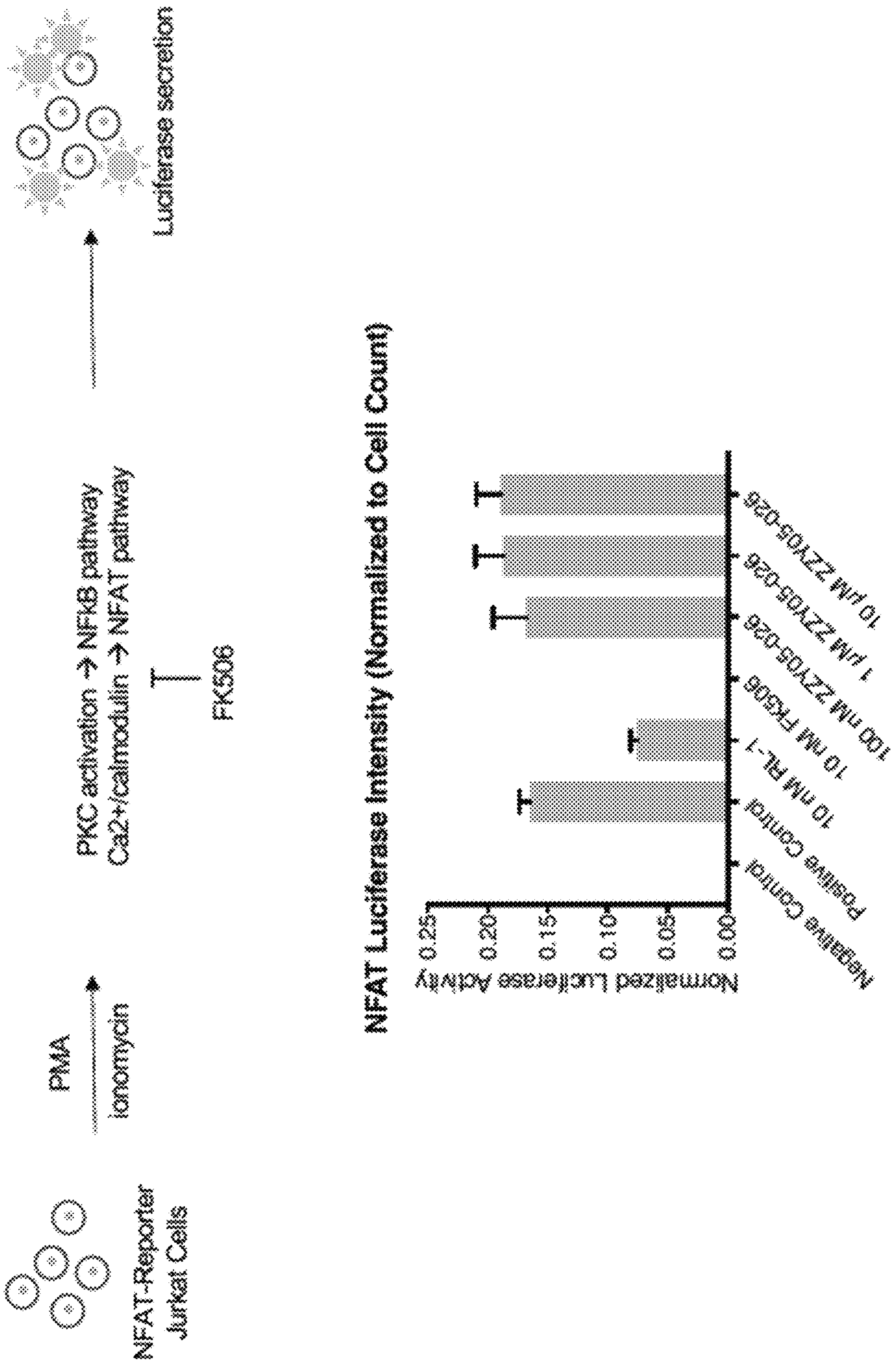
FIG. 10. ZZY05-026 is not immunosuppressive at up to 10 μM. Jurkat cells stably expressing a secreted luciferase (Invivogen) under NFAT promoter was stimulated with PMA (10 ng/mL) and ionomycin (1 μg/mL) in the presence of drugs for 16 h. Positive control: PMA/ionomycin+DMSO. Negative control: DMSO only.
Figure 11:
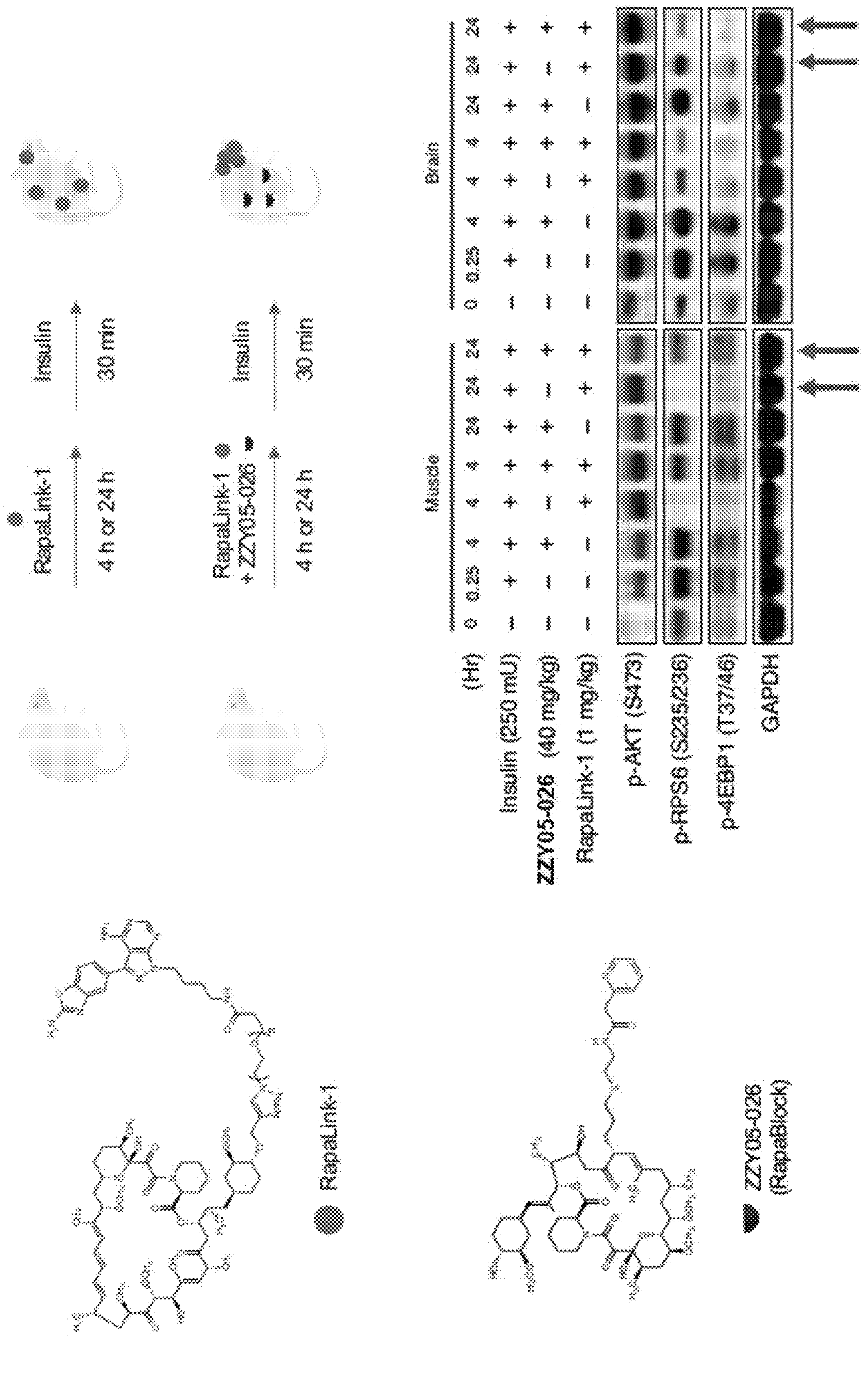
FIG. 11. ZZY05-026 protects mouse peripheral tissue from RapaLink-1.
Figure 12:
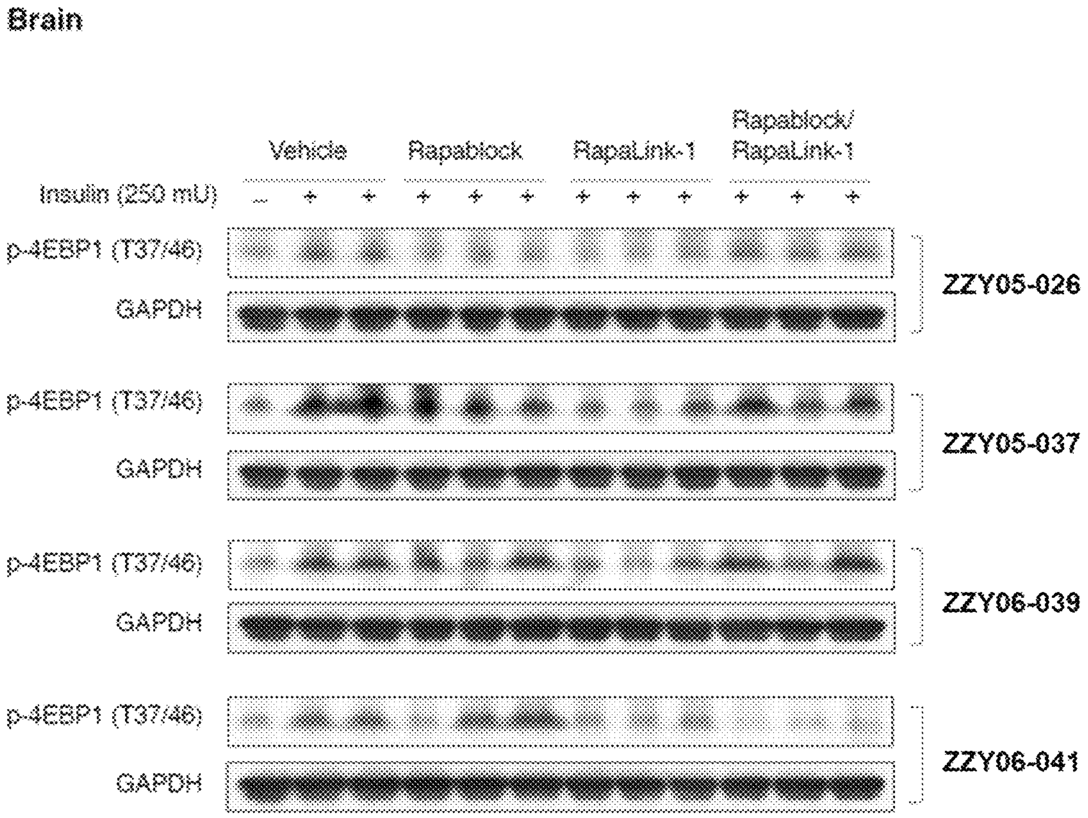
FIG. 12. Evaluation of RapaBlock molecules in augmenting the mTOR inhibitory activity of RapaLink-1 in brain tissues. All animal experiments were conducted using protocols approved by University of California, San Francisco's Institutional Animal Care and Use Committee (IACUC). BALB/Cnu/nu mice were treated with i.p. injection of vehicle (20% DMSO, 40% PEG-300, and 40% PBS [v/v], daily), RapaLink-1 (1 mg/kg), RapaBlock (40 mg/kg), or RapaLink-1+RapaBlock combination (1 mg/kg+40 mg/kg). After 4 or 24 h, mice were treated by i.p. injection of 250 mU insulin or saline, then euthanized 15 min later. Skeletal muscle and brain of each mouse were lysed, and analyzed by western blotting.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-S-CH_2-CH_2$, $-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $-O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5- yl, 1,2,3,4-tetrahydropyrido[4,3-g]isoquinolin-2-yl, 12H-benzo[b]phenoxazin-12-yl, and dodecahydro-1H-carbazol-9-yl.

The terms “halo” or “halogen,” by themselves or as part of another substituent, mean, unless otherwise stated, a fluorine, chlorine, bromine, or iodine atom. Additionally, terms such as “haloalkyl” are meant to include monohaloalkyl and polyhaloalkyl. For example, the term “halo($C_1$-$C_4$) alkyl” includes, but is not limited to, fluoromethyl, difluoromethyl, trifluoromethyl, 2,2,2-trifluoroethyl, 4-chlorobutyl, 3-bromopropyl, and the like.

The term “acyl” means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term “aryl” means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term “heteroaryl” refers to aryl groups (or rings) that contain at least one heteroatom such as N, O, or S, wherein the nitrogen and sulfur atoms are optionally oxidized, and the nitrogen atom(s) are optionally quaternized. Thus, the term “heteroaryl” includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An “arylene” and a “heteroarylene,” alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol denotes the point of attachment of a chemical moiety to the remainder of a molecule or chemical formula.

The term “oxo,” as used herein, means an oxygen that is double bonded to a carbon atom.

The term “alkylarylene” as an arylene moiety covalently bonded to an alkylene moiety (also referred to herein as an alkylene linker). In embodiments, the alkylarylene group has the formula:

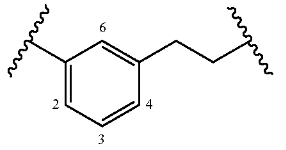

or

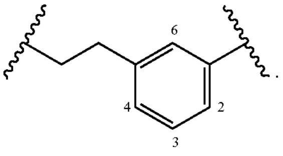

An alkylarylene moiety may be substituted (e.g., with a substituent group) on the alkylene moiety or the arylene linker (e.g., at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$, $—SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”)

includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R"', —OC(O)R', —C(O)R', —$CO_2$R', —CONR'R", —OC(O)NR'R", —NR"C(O)R', —NR'—C(O)NR"R"', —NR"C$(O)_2$R', —NR—C(NR'R"R"')=NR"", —NR—C(NR'R")=NR"', —S(O)R', —$S(O)_2$R', —$S(O)_2$NR'R", —$NRSO_2$R', —NR'NR"R"', —ONR'R", —NR'C(O) NR"NR"'R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', halogen, —SiR'R"R"', —OC(O)R', —C(O)R', —$CO_2$R', —CONR'R", —OC(O)NR'R", —NR"C(O)R', —NR'—C(O)NR"R"', —NR"C$(O)_2$R', —NR—C(NR'R"R"')=NR"", —NR—C(NR'R")=NR"', —S(O)R', —$S(O)_2$R', —$S(O)_2$NR'R", —$NRSO_2$R', —NR'NR"R"', —ONR'R", —NR'C(O) NR"NR"'R"", —CN, —$NO_2$, —R', —$N_3$, —CH$(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C"R"R"')_d$—, where s and d are independently integers of from 0 to 3, and X is —O—, —NR'—, —S—, —S(O)—, —$S(O)_2$—, or —$S(O)_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group,"

wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refer to the resulting association between atoms or molecules of bioconjugate reactive groups or bioconjugate reactive moieties. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.;

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g., phosphines) to form, for example, phosphate diester bonds;

(n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and/or appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154\text{-}1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, 18F, $^{32}P$, $^{33}P$, $^{45}Ti$, $^{47}Sc$, $^{52}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154\text{-}1581}Gd$, $^{161}Tb$ $^{166}Dy$, $^{166}Ho$, $^{169}Er$, $^{175}Lu$, $^{177}Lu$, $^{186}Re$, $^{188}Re$, $^{189}Re$, $^{194}I$ $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Compounds or functional moieties are "polar" when there are opposing charges (i.e., having partial positive and partial negative charges) from polar bonds arranged asymmetrically. The polarity of a molecule can be measured, for example, by its partition coefficient, P, defined as the ratio of the concentrations of a solute between two immiscible solvents. When one of the solvents is water, the c log P value is a measure of lipophilicity or hydrophobicity. In embodiments, the compound has a c log P of about 5. In embodiments, the compound has a c log P of less than 5. Polarity can also be measured, for example, by ts topological polar surface area (PSA), which is the surface sum over all polar atoms, primarily oxygen and nitrogen, also including their attached hydrogen atoms. Molecules with a PSA of greater than 140 Å tend to be poor at permeating cell membranes. In embodiments, for molecules to penetrate the blood-brain barrier, a PSA less than 90 Å is usually necessary. In embodiments, the compound described herein has a PSA between 90 Å and 140 Å. In embodiments, the compound described herein has a PSA between 100 Å and 140 Å.

A polypeptide, or a cell is "recombinant" when it is artificial or engineered, or derived from or contains an artificial or engineered protein or nucleic acid (e.g., nonnatural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Co-administer" is meant that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease. In embodiments, treating is preventing. In embodiments, treating does not include preventing. In embodiments, the treating or treatment is no prophylactic treatment.

An "effective amount" is an amount sufficient for a compound to accomplish a stated purpose relative to the absence of the compound (e.g., achieve the effect for which it is administered, treat a disease, reduce enzyme activity, increase enzyme activity, reduce signaling pathway, reduce one or more symptoms of a disease or condition. An example of an "effective amount" is an amount sufficient to contribute to the treatment, prevention, or reduction of a symptom or symptoms of a disease, which could also be referred to as a "therapeutically effective amount" when referred to in this context. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g., signaling pathway) of a protein in the absence of a compound as described herein (including embodiments, examples, figures, or Tables).

"Contacting" is used in accordance with its plain ordinary meaning and refers to the process of allowing at least two distinct species (e.g., chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a cellular component (e.g., protein, ion, lipid, nucleic acid, nucleotide, amino acid, protein, particle, organelle, cellular compartment, microorganism, virus, lipid droplet, vesicle, small molecule, protein complex, protein aggregate, or macromolecule). In some embodiments contacting includes allowing a compound described herein to interact with a cellular component (e.g., protein, ion, lipid, nucleic acid, nucleotide, amino acid, protein, particle, virus, lipid droplet, organelle, cellular compartment, microorganism, vesicle, small molecule, protein complex, protein aggregate, or macromolecule) that is involved in a signaling pathway.

As defined herein, the term "inhibition," "inhibit," "inhibiting" and the like in reference to a cellular component-inhibitor interaction means negatively affecting (e.g., decreasing) the activity or function of the cellular component (e.g., decreasing the signaling pathway stimulated by a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)), relative to the activity or function of the cellular component in the absence of the inhibitor. In some embodiments inhibition refers to reduction of a disease or symptoms of disease. In some embodiments, inhibition refers to a reduction in the activity of a signal transduction pathway or signaling pathway (e.g., reduction of a pathway involving the cellular component). Thus, inhibition includes, at least in part, partially or totally blocking stimulation, decreasing, preventing, or delaying activation, or inactivating, desensitizing, or down-regulating the signaling pathway or enzymatic activity or the amount of a cellular component.

The term "modulator" refers to a composition that increases or decreases the level of a target molecule or the function of a target molecule or the physical state of the target of the molecule (e.g., a target may be a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)) relative to the absence of the composition.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g., caused by) a cellular component (e.g., protein, ion, lipid, nucleic acid, nucleotide, amino acid, protein, particle, organelle, cellular compartment, microorganism, vesicle, small molecule, protein complex, protein aggregate, or macromolecule).

As used herein, the term "cancer" refers to all types of cancer, neoplasm or malignant tumors found in mammals (e.g., humans), including leukemia, lymphoma, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "neurodegenerative disease" or "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis (ALS), Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes *dorsalis*.

"Anti-neurodegenerative disease agent" is used in accordance with its plain ordinary meaning and refers to a composition (e.g., compound, drug, antagonist, inhibitor, modulator) capable of inhibiting neurodegeneration. In some embodiments, an anti-neurodegenerative disease agent is an agent identified herein having utility in methods of treating a neurodegenerative disease. In some embodiments, an anti-neurodegenerative disease agent is an agent approved by the FDA or similar regulatory agency of a country other than the USA, for treating a neurodegenerative disease. Examples of anti-neurodegenerative disease agents include, but are not limited to, galantamine, rivastigmine, donepezil, memantine, imatinib, tamibarotene, bexarotene, carmustine, thalidomide, sildenafil, trazodone, clioquinol, nilvadipine, levodopa, pramipexole, repinirole, rotigotine, apomorphine, selegiline, rasagiline, safinamide, amantadine, milotinib, zonisamide, selegiline, methylphenidate, salbutamol, exenatide, tetrabenazine, tiapride, clozapine, olanzapine, risperidone, quetiapine, memantine, mitoxantrone, cyclophosphamide, cladribine, amiloride, ibudilast, mastinib, dolutegravir, abacavir, lamivudine, retigabine, and tamoxifen.

The term "central nervous system" or "CNS" is used with its plain ordinary meaning and refers to the part of the nervous system consisting of the brain and spinal cord. The "blood-brain barrier (BBB)" is a highly selective semipermeable border that separates the circulating blood from the brain and extracellular fluid in the CNS. The BBB allows passage of water, some gases, and lipid-soluble molecules by passive diffusion, as well as selective transport of molecules that are crucial to neural function. In embodiments, the brain/periphery distribution is measured in an in vivo mouse model.

"Anti-CNS disease drug" is used in accordance with its plain ordinary meaning and refers to a drug capable of inhibiting a CNS disease. In embodiments, a CNS disease is a neurodegenerative disease. In some embodiments, an anti-CNS disease drug is a drug identified herein having utility in methods of treating a CNS disease. In some embodiments, an anti-CNS disease drug is a drug approved by the FDA or similar regulatory agency of a country other than the USA, for treating a CNS disease. Examples of anti-CNS disease drugs include, but are not limited to, sirolimus, temsirolimus, everolimus, dactolisib, GSK2126458, XL765, AZD8055, INK128/MLN0128, OSI027, and RapaLinks. In embodiments, an anti-CNS disease drug is an anti-neurodegenerative disease drug. In embodiments, an anti-CNS disease drug is an anti-cancer agent.

As used herein, the term "metabolic disease" or "metabolic disorder" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

The term "cellular component associated disease" (e.g., the cellular component may be a protein, ion, lipid, nucleic acid, nucleotide, amino acid, protein, particle, organelle, cellular compartment, microorganism, virus, vesicle, small molecule, protein complex, protein aggregate, or macromolecule; the disease may be a neurodegenerative disease, cancer, a metabolic disease, autoimmune disease, inflammatory disease, or infectious disease) (also referred to herein as "cellular component related disease") refers to a disease caused by the cellular component. Other diseases that are associated with aberrant activity or level of the cellular component are well known in the art and determining such diseases are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compounds described herein can be used in combination with one another, with other active agents known to be useful in treating a disease associated with cells expressing a disease associated cellular component, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In therapeutic use for the treatment of a disease, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer, a neurodegenerative disease, a metabolic disease, an autoimmune disease, an inflammatory disease, or an infectious disease, or with adjunctive agents that may not be effective alone, but may contribute to the efficacy of the active agent.

The term "associated" or "associated with" in the context of a substance or substance activity or function associated with a disease (e.g., a protein associated disease, disease associated with a cellular component) means that the disease (e.g., neurodegenerative disease, cancer) is caused by (in whole or in part), or a symptom of the disease is caused by (in whole or in part) the substance or substance activity or function or the disease or a symptom of the disease may be treated by modulating (e.g., inhibiting or activating) the substance (e.g., cellular component). For example, a neurodegenerative disease associated with a protein aggregate may be a neurodegenerative disease that results (entirely or partially) from aberrant protein aggregation or a neurodegenerative disease wherein a particular symptom of the disease is caused (entirely or partially) by aberrant protein aggregation. As used herein, what is described as being associated with a disease, if a causative agent, could be a target for treatment of the disease. For example, a neurodegenerative disease associated with aberrant protein aggregation or a protein aggregate associated neurodegenerative disease, may be treated with a protein aggregate modulator or protein aggregate targeted autophagy degrader, in the instance where increased protein aggregation causes the neurodegenerative disease.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

"Anti-cancer agent" is used in accordance with its plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. In embodiments, an anti-cancer agent is an agent with antineoplastic properties that has not (e.g., yet) been approved by the FDA or similar regulatory agency of a country other than the USA, for treating cancer. Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine;

titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds comprising the taxane skeleton, Erbulozole (i.e., R-55104), Dolastatin 10 (i.e., DLS-10 and NSC-376128), Mivobulin isethionate (i.e., as CI-980), Vincristine, NSC-639829, Discodermolide (i.e., as NVP-XX-A-296), ABT-751 (Abbott, i.e., E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e., LU-103793 and NSC-D-669356), Epothilones (e.g., Epothilone A, Epothilone B, Epothilone C (i.e., desoxyepothilone A or dEpoA), Epothilone D (i.e., KOS-862, dEpoB, and desoxyepothilone B), Epothilone E, Epothilone F, Epothilone B N-oxide, Epothilone A N-oxide, 16-aza-epothilone B, 21-aminoepothilone B (i.e., BMS-310705), 21-hydroxyepothilone D (i.e., Desoxyepothilone F and dEpoF), 26-fluoroepothilone, Auristatin PE (i.e., NSC-654663), Soblidotin (i.e., TZT-1027), LS-4559-P (Pharmacia, i.e., LS-4577), LS-4578 (Pharmacia, i.e., LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e., TLX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e., LY-355703), AC-7739 (Ajinomoto, i.e., AVE-8063A and CS-39.HCl), AC-7700 (Ajinomoto, i.e., AVE-8062, AVE-8062A, CS-39-L-Ser-.HCl, and RPR-258062A), Vitilevuamide, Tubulysin A, Canadensol, Centaureidin (i.e., NSC-106969), T-138067 (Tularik, i.e., T-67, TL-138067 and TI-138067), COBRA-1 (Parker Hughes Institute, i.e., DDE-261 and WHI-261), H10 (Kansas State University), H16 (Kansas State University), Oncocidin A1 (i.e., BTO-956 and DIME), DDE-313 (Parker Hughes Institute), Fijianolide B, Laulimalide, SPA-2 (Parker Hughes Institute), SPA-1 (Parker Hughes Institute, i.e., SPIKET-P), 3-IAABU (Cytoskeleton/Mt. Sinai School of Medicine, i.e., MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e., MF-191), TMPN (Arizona State University), Vanadocene acetylacetonate, T-138026 (Tularik), Monsatrol, lnanocine (i.e., NSC-698666), 3-IAABE (Cytoskeleton/Mt. Sinai School of Medicine), A-204197 (Abbott), T-607 (Tuiarik, i.e., T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e., NSCL-96F037), D-68838 (Asta Medica), D-68836 (Asta Medica), Myoseverin B, D-43411 (Zentaris, i.e., D-81862), A-289099 (Abbott), A-318315 (Abbott), HTI-286 (i.e., SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. A moiety of an anti-cancer agent is a monovalent anti-cancer agent (e.g., a monovalent form of an agent listed above).

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent," "electrophilic chemical moiety," or "electrophilic moiety" refers to an electron-poor chemical group, substituent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue and may be referred to as a "covalent cysteine modifier moiety" or "covalent cysteine modifier substituent." The covalent bond formed between the electrophilic substituent and the sulfhydryl group of the cysteine may be a reversible or irreversible bond. In some embodiments, the electrophilic substituent of the compound is capable of reacting with a lysine residue. In some embodiments, the electrophilic substituent of the compound is capable of reacting with a serine residue. In some embodiments, the electrophilic substituent of the compound is capable of reacting with a methionine residue.

"Nucleophilic" as used herein refers to a chemical group that is capable of donating electron density.

An amino acid residue in a protein "corresponds" to a given residue when it occupies the same essential structural position within the protein as the given residue. Instead of a primary sequence alignment, a three dimensional structural alignment can also be used, e.g., where the structure of the selected protein is aligned for maximum correspondence with the human protein and the overall structures compared. In this case, an amino acid that occupies the same essential position as a specified amino acid in the structural model is said to correspond to the specified residue.

The term "isolated," when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide," and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "protein complex" is used in accordance with its plain ordinary meaning and refers to a protein which is associated with an additional substance (e.g., another protein, protein subunit, or a compound). Protein complexes typically have defined quaternary structure. The association between the protein and the additional substance may be a covalent bond. In embodiments, the association between the protein and the additional substance (e.g., compound) is via non-covalent interactions. In embodiments, a protein complex refers to a group of two or more polypeptide chains. Proteins in a protein complex are linked by non-covalent protein-protein interactions. A non-limiting example of a protein complex is the proteasome.

The term "protein aggregate" is used in accordance with its plain ordinary meaning and refers to an aberrant collection or accumulation of proteins (e.g., misfolded proteins). Protein aggregates are often associated with diseases (e.g., amyloidosis). Typically, when a protein misfolds as a result of a change in the amino acid sequence or a change in the native environment which disrupts normal non-covalent interactions, and the misfolded protein is not corrected or degraded, the unfolded/misfolded protein may aggregate. There are three main types of protein aggregates that may form: amorphous aggregates, oligomers, and amyloid fibrils. In embodiments, protein aggregates are termed aggresomes. In embodiments, the protein aggregate TDP43, HTT, APP, SNCA, or MAPT. In embodiments, the protein aggregate includes the protein Beta amyloid, Amyloid precursor protein, IAPP, Alpha-synuclein, PrPSc, PrPSc, Huntingtin, Calcitonin, Atrial natriuretic factor, Apolipoprotein A1, Serum amyloid A, Medin, Prolactin, Transthyretin, Lysozyme, Beta-2 microglobulin, Gelsolin, Keratoepithelin, Beta amyloid, Cystatin, Immunoglobulin light chain AL, TDP43, or S-IBM.

The term "vesicle" is used in accordance with its plain ordinary meaning and refers to a small membrane enclosed compartment within a cell. Vesicles are typically involved in transport, buoyancy control, or enzyme storage within a cell. Some vesicles, for example a lysosome, may include enzymes, proteins, polysaccharides, lipids, nucleic acids, or organelles within the compartment. Vesicles are typically formed within cells as a result of exocytosis or phagocytosis, however some vesicles are formed at the Golgi complex and transported to the cell membrane. Vesicles may be unilamellar or multilamellar.

The term "small molecule" is used in accordance with its well understood meaning and refers to a low molecular weight organic compound that may regulate a biological process. In embodiments, the small molecule is a compound that weighs less than 900 daltons. In embodiments, the small molecule weighs less than 800 daltons. In embodiments, the small molecule weighs less than 700 daltons. In embodiments, the small molecule weighs less than 600 daltons. In embodiments, the small molecule weighs less than 500 daltons. In embodiments, the small molecule weighs less than 450 daltons. In embodiments, the small molecule weighs less than 400 daltons.

The term "pseudokinase" is used in accordance with its well understood meaning in Biology and Chemistry and refers to proteins that are variants of kinases (e.g., having similar or identical protein structures or folds) that are catalytically deficient in kinase enzymatic activity.

The term "GTPase" is used in accordance with its well understood meaning in Biology and Chemistry and refers to hydrolase enzymes capable of binding and hydrolyzing GTP.

The term "histone modifying enzyme" is used in accordance with its well understood meaning in Biology and Chemistry and refers to proteins that are capable of modifying histones at one or more of various sites. In embodiments a histone modifying enzyme is an enzyme capable of acetylation, methylation, demethylation, phosphorylation, ubiquitination, sumoylation, ADP-ribosylation, deamination, and/or proline isomerization; all of one or more histone proteins. In embodiments, the histone modifying enzyme is a histone deacetylase, histone methyltransferase, or histone acetyltransferase. In embodiments, the histone modifying enzyme is SETD3.

The terms "virus" or "virus particle" are used according to its plain ordinary meaning within Virology and refers to a virion including the viral genome (e.g., DNA, RNA, single strand, double strand), viral capsid and associated proteins, and in the case of enveloped viruses (e.g., herpesvirus), an envelope including lipids and optionally components of host cell membranes, and/or viral proteins.

The term "viral disease" is an infection that occurs when an organisms's body is invaded by pathogenic viruses and infectious virus particles attach to and enter susceptible cells.

The term "kinase inhibitor" refers to an agent (e.g., small molecule, nucleic acid, protein, or antibody) that can reduce the activity or level of a kinase.

The term "pseudokinase inhibitor" refers to an agent (e.g., small molecule, nucleic acid, protein, or antibody) that can reduce the activity or level of a pseudokinase.

The term "GTPase inhibitor" refers to an agent (e.g., small molecule, nucleic acid, protein, or antibody) that can reduce the activity or level of a GTPase.

The term "histone modifying enzyme inhibitor" refers to an agent (e.g., small molecule, nucleic acid, protein, or antibody) that can reduce the activity or level of a histone modifying enzyme.

The term "monovalent anti-viral agent" refers to a monovalent form of an agent (e.g., small molecule, nucleic acid, protein, or antibody) that can reduce the activity or level of a virus (e.g., in a subject or patient).

The term "mTOR" refers to the protein "mechanistic target of rapamycin (serine/threonine kinase)" or "mammalian target of rapamycin." The term "mTOR" may refer to the nucleotide sequence or protein sequence of human mTOR (e.g., Entrez 2475, Uniprot P42345, RefSeq NM_004958, or RefSeq NP_004949). The term "mTOR" includes both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ refers to a nucleotide sequence or protein of a mutant mTOR wherein the Y numbered amino acid of mTOR that normally has an X amino acid in the wildtype, instead has a Z amino acid in the mutant. In embodiments, an mTOR is the human mTOR. In embodiments, the mTOR has the following amino acid sequence:

```
                                        (SEQ ID NO: 1)
MLGTGPAAATTAATTSSNVSVLQQFASGLKSRNEETRAKAAKELQHYVTM

ELREMSQEESTRFYDQLNHHIFELVSSSDANERKGGILAIASLIGVEGGN
```

-continued

ATRIGRFANYLRNLLPSNDPVVMEMASKAIGRLAMAGDTFTAEYVEFEVK
RALEWLGADRNEGRRHAAVLVLRELAISVPTFFFQQVQPFFDNIFVAVWD
PKQAIREGAVAALRACLILTTQREPKEMQKPQWYRHTFEEAEKGFDETLA
KEKGMNRDDRIHGALLILNELVRISSMEGERLREEMEEITQQQLVHDKYC
KDLMGFGTKPRHITPFTSFQAVQPQQSNALVGLLGYSSHQGLMGFGTSPS
PAKSTLVESRCCRDLMEEKFDQVCQWVLKCRNSKNSLIQMTILNLLPRLA
AFRPSAFTDTQYLQDTMNHVLSCVKKEKERTAAFQALGLLSVAVRSEFKV
YLPRVLDIIRAALPPKDFAHKRQKAMQVDATVFTCISMLARAMGPGIQQD
IKELLEPMLAVGLSPALTAVLYDLSRQIPQLKKDIQDGLLKMLSLVLMHK
PLRHPGMPKGLAHQLASPGLTTLPEASDVGSITLALRTLGSFEFEGHSLT
QFVRHCADHFLNSEHKEIRMEAARTCSRLLTPSIHLISGHAHVVSQTAVQ
VVADVLSKLLVVGITDPDPDIRYCVLASLDERFDAHLAQAENLQALFVAL
NDQVFEIRELAICTVGRLSSMNPAFVMPFLRKMLIQILTELEHSGIGRIK
EQSARMLGHLVSNAPRLIRPYMEPILKALILKLKDPDPDPNPGVINNVLA
TIGELAQVSGLEMRKWVDELFIIIMDMLQDSSLLAKRQVALWTLGQLVAS
TGYVVEPYRKYPTLLEVLLNFLKTEQNQGTRREAIRVLGLLGALDPYKHK
VNIGMIDQSRDASAVSLSESKSSQDSSDYSTSEMLVNMGNLPLDEFYPAV
SMVALMRIFRDQSLSHHHTMVVQAITFIFKSLGLKCVQFLPQVMPTFLNV
IRVCDGAIREFLFQQLGMLVSFVKSHIRPYMDEIVTLMREFWVMNTSIQS
TIILLIEQIVVALGGEFKLYLPQLIPHMLRVFMHDNSPGRIVSIKLLAAI
QLFGANLDDYLHLLLPPIVKLFDAPEAPLPSRKAALETVDRLTESLDFTD
YASRIIHPIVRTLDQSPELRSTAMDTLSSLVFQLGKKYQIFIPMVNKVLV
RHRINHQRYDVLICRIVKGYTLADEEEDPLIYQHRMLRSGQGDALASGPV
ETGPMKKLHVSTINLQKAWGAARRVSKDDWLEWLRRLSLELLKDSSSPSL
RSCWALAQAYNPMARDLFNAAFVSCWSELNEDQQDELIRSIELALTSQDI
AEVTQTLLNLAEFMEHSDKGPLPLRDDNGIVLLGERAAKCRAYAKALHYK
ELEFQKGPTPAILESLISINNKLQQPEAAAGVLEYAMKHFGELEIQATWY
EKLHEWEDALVAYDKKMDTNKDDPELMLGRMRCLEALGEWGQLHQQCCEK
WTLVNDETQAKMARMAAAAAWGLGQWDSMEEYTCMIPRDTHDGAFYRAVL
ALHQDLFSLAQQCIDKARDLLDAELTAMAGESYSRAYGAMVSCHMLSELE
EVIQYKLVPERREIIRQIWWERLQGCQRIVEDWQKILMVRSLVVSPHEDM
RTWLKYASLCGKSGRLALAHKTLVLLLGVDPSRQLDHPLPTVHPQVTYAY
MKNMWKSARKIDAFQHMQHFVQTMQQQAQHAIATEDQQHKQELHKLMARC
FLKLGEWQLNLQGINESTIPKVLQYYSAATEHDRSWYKAWHAWAVMNFEA
VLHYKHQNQARDEKKKLRHASGANITNATTAATTAATATTTASTEGSNSE
SEAESTENSPTPSPLQKKVTEDLSKTLLMYTVPAVQGFFRSISLSRGNNL
QDTLRVLTLWFDYGHWPDVNEALVEGVKAIQIDTWLQVIPQLIARIDTPR
PLVGRLIHQLLTDIGRYHPQALIYPLTVASKSTTTARHNAANKILKNMCE
HSNTLVQQAMMVSEELIRVAILWHEMWHEGLEEASRLYFGERNVKGMFEV
LEPLHAMMERGPQTLKETSFNQAYGRDLMEAQEWCRKYMKSGNVKDLTQA
WDLYYHVFRRISKQLPQLTSLELQYVSPKLLMCRDLELAVPGTYDPNQPI

-continued

IRIQSIAPSLQVITSKQRPRKLTLMGSNGHEFVFLLKGHEDLRQDERVMQ
LFGLVNTLLANDPTSLRKNLSIQRYAVIPLSTNSGLIGWVPHCDTLHALI
RDYREKKKILLNIEHRIMLRMAPDYDHLTLMQKVEVFEHAVNNTAGDDLA
KLLWLKSPSSEVWFDRRTNYTRSLAVMSMVGYILGLGDRHPSNLMLDRLS
GKILHIDFGDCFEVAMTREKFPEKIPFRLTRMLTNAMEVTGLDGNYRITC
HTVMEVLREHKDSVMAVLEAFVYDPLLNWRLMDTNTKGNKRSRTRTDSYS
AGQSVEILDGVELGEPAHKKTGTTVPESIHSFIGDGLVKPEALNKKAIQI
INRVRDKLTGRDFSHDDTLDVPTQVELLIKQATSHENLCQCYIGWCPFW.

The term "mTORC1" refers to the protein complex including mTOR and Raptor (regulatory-associated protein of mTOR). mTORC1 may also include MLST8 (mammalian lethal with SEC13 protein 8), PRAS40, and/or DEPTOR. mTORC1 may function as a nutrient/energy/redox sensor and regulator of protein synthesis. The term "mTORC1 pathway" or "mTORC1 signal transduction pathway" refers to a cellular pathway including mTORC1. An mTORC1 pathway includes the pathway components upstream and downstream from mTORC1. An mTORC1 pathway is a signaling pathway that is modulated by modulation of mTORC1 activity. In embodiments, an mTORC1 pathway is a signaling pathway that is modulated by modulation of mTORC1 activity but not by modulation of mTORC2 activity. In embodiments, an mTORC1 pathway is a signaling pathway that is modulated to a greater extent by modulation of mTORC1 activity than by modulation of mTORC2 activity.

The term "mTORC2" refers to the protein complex including mTOR and RICTOR (rapamycin-insensitive companion of mTOR). mTORC2 may also include GβL, mSIN1 (mammalian stress-activated protein kinase interacting protein 1), Protor 1/2, DEPTOR, TTI1, and/or TEL2. mTORC2 may regulate cellular metabolism and the cytoskeleton. The term "mTORC2 pathway" or "mTORC2 signal transduction pathway" refers to a cellular pathway including mTORC2. An mTORC2 pathway includes the pathway components upstream and downstream from mTORC2. An mTORC2 pathway is a signaling pathway that is modulated by modulation of mTORC2 activity. In embodiments, an mTORC2 pathway is a signaling pathway that is modulated by modulation of mTORC2 activity but not by modulation of mTORC1 activity. In embodiments, an mTORC2 pathway is a signaling pathway that is modulated to a greater extent by modulation of mTORC2 activity than by modulation of mTORC1 activity.

The term "active site mTOR inhibitor" refers to a compound that inhibits the activity of mTOR (e.g., kinase activity) and binds to the active site of mTOR (e.g., the ATP binding site, overlapping with the ATP binding site, blocking access by ATP to the ATP binding site of mTOR). Examples of active site mTOR inhibitors include, but are not limited to, INK128, PP242, PP121, MLN0128, AZD8055, AZD2014, NVP-BEZ235, BGT226, SF1126, Torin 1, Torin 2, WYE 687, WYE 687 salt (e.g., hydrochloride), PF04691502, PI-103, CC-223, OSI-027, XL388, KU-0063794, GDC-0349, and PKI-587. In embodiments, an active site mTOR inhibitor is an asTORi.

The term "rapamycin analog" or "rapalog" refer to analogs or derivatives (e.g., prodrugs) of rapamycin. Examples of rapamycin analogs include, but are not limited to, deforolimus (AP23573, MK-8669, ridaforolimus), temsirolimus (CCI-779), ABT478, and everolimus (RAD001). In embodiments, rapamycin analogs include esters, ethers, amides, carbonates, carbamates, sulfonates, oximes, hydrazones, or hydroxyamines of rapamycin. In embodiments, rapamycin analogs include rapamycins in which functional groups on rapamycin have been modified, (e.g., through reduction or oxidation, replacement with a nucleophile). In embodiments, rapamycin analogs include a metabolite of rapamycin (e.g., a desmethylrapamycin derivative or a linear rapamycin (e.g., secorapamycin, as described in U.S. Pat. No. 5,252, 579). In embodiments, rapamycin analogs include O-desmethylrapamycin, desmethylrapamycin, or desmethoxyrapamycin (for example, as described in WO 2006/095185, U.S. Pat. No. 6,358,969). In embodiments, rapamycin analogs include ester derivatives or ether derivatives of rapamycin, including alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. Nos. 5,118,678; 5,411,967; 5,480,989; 5,480,988; 5,489,680); amino carbamate esters (U.S. Pat. No. 5,463,048); silyl ethers (U.S. Pat. No. 5,120,842); aminoesters (U.S. Pat. No. 5,130,307); acetals; aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385, 910); amino alkanoic esters (U.S. Pat. No. 5,389,639); phosphorylcarbamate esters (U.S. Pat. No. 5,391,730); hindered N-oxide esters (U.S. Pat. No. 5,491,231); biotin esters (U.S. Pat. No. 5,504,091); O-alkyl ethers (U.S. Pat. No. 5,665,772); and PEG esters (U.S. Pat. No. 5,780,462); all of rapamycin. In embodiments, rapamycin analogs include ester, oxime, hydrazone, ether, or hydroxylamine derivatives of rapamycin, including those described in U.S. Pat. Nos. 5,256,790, 5,373,014, 5,378,836, 5,023,264, 5,563,145, and 5,023,263. In embodiments, rapamycin analogs include rapamycin 42-ester with 3-hydroxy-2-(hydroxymethyl)-2-methylpropionic acid (U.S. Pat. No. 5,362,718), 42-Q-(2-hydroxy)ethyl rapamycin (U.S. Pat. No. 5,665,772), and 42-epi-tetrazolyl rapamycin, or those described in U.S. Pat. Nos. 3,929,992, 5,362,718, and 6,277,983 (e.g., position 42 corresponding to position 40 shown in Example tables). In embodiments, rapamycin analogs include a substituted rapamycin e.g., a 40-O-substituted rapamycin e.g., as described in U.S. Pat. No. 5,258,389, WO 94/09010, WO 92/05179, U.S. Pat. Nos. 5,118,677, 5,118,678, 5,100,883, 5,151,413, 5,120,842, WO 93/11130, WO 94/02136, WO 94/02485 or WO 95/14023. In embodiments, rapamycin analogs include a 16-O-substituted rapamycin e.g., as disclosed in WO 94/02136, WO 95/16691 or WO 96/41807. In embodiments, rapamycin analogs include a 32-hydrogenated rapamycin e.g., as described in WO 96/41807 or U.S. Pat. No. 5,256,790. In embodiments, rapamycin analogs include 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-O-(2-hydroxyethyl)-rapamycin or 40-O-(2-hydroxyethyl)-rapamycin. In embodiments, rapamycin analogs include 40-O-(2-hydroxyethyl)-rapamycin, 40-[3-hydroxy-2-(hydroxymethyl)-2-methylpropanoate]-rapamycin (also called CCI779), 40-epi-(tetrazolyl)-rapamycin (also called ABT578), 32-deoxorapamycin, 16-pent-2-ynyloxy-32(S)-dihydro rapamycin, or TAFA-93. The publications, patents, and applications described above are incorporated by reference in their entireties for all purposes.

The term "FKBP" refers to a protein peptidyl-prolyl cis-trans isomerase. For non-limiting examples of FKBP, see Cell Mol Life Sci. 2013 September; 70(18):3243-75. In embodiments, "FKBP" refers to "FKBP-12" or "FKBP 12" or "FKBP1A". In embodiments, "FKBP" refers to the human protein. Included in the term "FKBP" is the wildtype and mutant forms of the protein. In embodiments, "FKBP" refers to the wildtype human protein. In embodiments, "FKBP" refers to the wildtype human nucleic acid. In embodiments, the FKBP is a mutant FKBP. In embodiments, the mutant FKBP is associated with a disease that is not associated with wildtype FKBP. In embodiments, the FKBP includes at least one amino acid mutation (e.g., 1, 2,3,4, 5,6,7, 8,9, 10, 11, 12, 13, 14, 15, 16, 17, 18, 19, 20, 21, 22, 23, 24, 25, 26, 27, 28, 29, or 30 mutations) compared to wildtype FKBP. In embodiments, FKBP refers to human ATP, AIPL1, FKBP1A, FKBP1B, FKBP2, FKBP3, FKBP5, FKBP6, FKBP7, FKBP8, FKBP9, FKBP9L, FKBP10, FKBP11, FKBP14, FKBP15, FKBP52, FKBP51, or LOC541473.

The term "FKBP-12" or "FKBP 12" or "FKBP1A" refers to the protein "peptidyl-prolyl cis-trans isomerase FKBP1A." In embodiments, "FKBP-12" or "FKBP 12" or "FKBP1A" refers to the human protein. Included in the term "FKBP-12" or "FKBP 12" or "FKBP1A" are the wildtype and mutant forms of the protein. In embodiments, "FKBP-12" or "FKBP 12" or "FKBP1A" refers to the protein associated with Entrez Gene 2280, OMIM 186945, UniProt P62942, and/or RefSeq (protein) NP_000792. In embodiments, the reference numbers immediately above refer to the protein, and associated nucleic acids, known as of the date of filing of this application. In embodiments, "FKBP-12" or "FKBP 12" or "FKBP1A" refers to the wildtype human protein. In embodiments, "FKBP-12" or "FKBP 12" or "FKBP1A" refers to the wildtype human nucleic acid. In embodiments, the FKBP-12 is a mutant FKBP-12. In embodiments, the mutant FKBP-12 is associated with a disease that is not associated with wildtype FKBP-12. In embodiments, the FKBP-12 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype FKBP-12. In embodiments, the FKBP-12 has the protein sequence corresponding to RefSeq NP_000792.1. In embodiments, the FKBP-12 has the protein sequence corresponding to RefSeq NM_000801.5.

The term "calcineurin" refers to a protein, which is a calcium and calmodulin dependent serine/threonine protein phosphatase, also known as a protein phosphatase 3, and calcium-dependent serine-threonine phosphatase. Calcineurin is a heterodimer of a 61-kD calmodulin-binding catalytic subunit, calcineurin A and a 19-kD Ca2+-binding regulatory subunit, calcineurin B. There are three isozymes of the catalytic subunit, each encoded by a separate gene (PPP3CA, PPP3CB, and PPP3CC) and two isoforms of the regulatory, also encoded by separate genes (PPP3R1, PPP3R2).

The term "immunophilins" refers to cytosolic peptidyl-prolyl isomerases that catalyze the interconversion between the cis and trans isomers of peptide bonds containing the amino acid proline. Immunophilins can be classified into two main families: "cyclosporin-binding cyclophilins" and "FK506-binding proteins." Immunophilins act as receptors for immunosuppressive drugs, such as cyclosporin and tacrolimus (or FK506), which inhibit the prolyl isomerase activity of immunophilins. In embodiments, the compound described herein is an immunophilin-binding compound. In embodiments, the compound includes an immunophilin-binding moiety.

The term "cyclophilin" refers to a family of proteins that bind to cyclosporin, which is an immunosuppressant usually used to suppress rejection after internal organ transplants. Cyclophilins have peptidyl prolyl isomerase activity. In embodiments, the compound described herein is a cyclophilin-binding compound. In embodiments, the compound includes a cyclophilin-binding moiety.

The term "FK506-binding protein" or "FKBP" refers to a family of proteins that have peptidyl prolyl isomerase activity. FKBP12 is notable in humans for binding tacrolimus (or FK506), which is an immunosuppressant used in treating subjects after organ transplant as well as subjects suffering from autoimmune disorders. Both the FKBP-FK506 complex and the cyclosporin-cyclophilin complex inhibit calcineurin, thus blocking signal transduction in the T-lymphocyte transduction pathway.

The term "EGFR" or "ErbB-1" or "HER1" refers to the protein "Epidermal growth factor receptor". In embodiments, "EGFR" or "ErbB-1" or "HER1" refers to the human protein. Included in the term "EGFR" or "ErbB-1" or "HER1" are the wildtype and mutant forms of the protein. In embodiments, "EGFR" or "ErbB-1" or "HER1" refers to the protein associated with Entrez Gene 1956, OMIM 131550, UniProt P00533, and/or RefSeq (protein) NP_005219, RefSeq (protein) NP_958439, RefSeq (protein) NP_958440, or RefSeq (protein) NP_958441. In embodiments, the reference numbers immediately above refer to the protein, and associated nucleic acids, known as of the date of filing of this application. In embodiments, "EGFR" or "ErbB-1" or "HER1" refers to the wildtype human protein. In embodiments, "EGFR" or "ErbB-1" or "HER1" refers to the wildtype human nucleic acid. In embodiments, the EGFR is a mutant EGFR. In embodiments, the mutant EGFR is associated with a disease that is not associated with wildtype EGFR. In embodiments, the mutant EGFR is associated with cancer. In embodiments, the EGFR includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype EGFR. In embodiments, the EGFR has the protein sequence corresponding to RefSeq NP_005219.2. In embodiments, the EGFR has the protein sequence corresponding to RefSeq NM_005219.2. In embodiments, the EGFR has the following amino acid sequence:

```
                                      (SEQ ID NO: 2)
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE
```

-continued

```
ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFMRRRHIVRKRTLRRLLQERELVEPLTPSGEAPN

QALLRILKETEFKKIKVLGSGAFGTVYKGLWIPEGEKVKIPVAIKELREA

TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDGIPASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNST

FDSPAHWAQKGSHQISLDNPDYQQDFFPKEAKPNGIFKGSTAENAEYLRV

APQSSEFIGA.
```

The term "HER2" or "ErbB-2" or "ERBB2" refers to the protein "human epidermal growth factor receptor 2". In embodiments, "HER2" or "ErbB-2" or "ERBB2" refers to the protein "receptor tyrosine-protein kinase erbB-2". In embodiments, "HER2" or "ErbB-2" or "ERBB2" refers to the human protein. Included in the term "HER2" or "ErbB-2" or "ERBB2" are the wildtype and mutant forms of the protein. In embodiments, "HER2" or "ErbB-2" or "ERBB2" refers to the protein associated with Entrez Gene 2064, OMIM 164870, UniProt P04626, and/or RefSeq (protein) NP_004439. In embodiments, the reference numbers immediately above refer to the protein, and associated nucleic acids, known as of the date of filing of this application. In embodiments, "HER2" or "ErbB-2" or "ERBB2" refers to the wildtype human protein. In embodiments, "HER2" or "ErbB-2" or "ERBB2" refers to the wildtype human nucleic acid. In embodiments, the HER2 protein is a mutant HER2 protein. In embodiments, the mutant HER2 protein is associated with a disease that is not associated with wildtype HER-2. In embodiments, the mutant HER-2 is associated with cancer. In embodiments, the mutant HER-2 is associated with breast cancer. In embodiments, the HER-2 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype HER-2. In embodiments, the HER-2 protein has the protein sequence corresponding to RefSeq NP_004439.2. In embodiments, the HER-2 protein has the protein sequence corresponding to RefSeq NM_004448.3. In embodiments, the HER2 has the following amino acid sequence:

```
                                      (SEQ ID NO: 3)
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK
```

-continued

```
GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV.
```

The term "LRRK" or "LRKK2" or "dardarin" refers to the protein "Leucine-rich repeat kinase 2". In embodiments, "LRRK" or "LRKK2" or "dardarin" refers to the human protein. Included in the term "LRRK" or "LRKK2" or "dardarin" are the wildtype and mutant forms of the protein. In embodiments, "LRRK" or "LRKK2" or "dardarin" refers to the protein associated with Entrez Gene 120892, OMIM 609007, UniProt Q5S007, and/or RefSeq (protein) NP_940980. In embodiments, the reference numbers immediately above refer to the protein, and associated nucleic acids, known as of the date of filing of this application. In embodiments, "LRRK" or "LRKK2" or "dardarin" refers to the wildtype human protein. In embodiments, "LRRK" or "LRKK2" or "dardarin" refers to the wildtype human nucleic acid. In embodiments, the LRKK2 is a mutant LRKK2 protein. In embodiments, the mutant LRKK2 is associated with a disease that is not associated with wildtype LRKK2. In embodiments, the LRKK2 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype LRKK2. In embodiments, the LRKK2 protein has the protein sequence corresponding to RefSeq NP_940980.3. In embodiments, the LRKK2 protein has the protein sequence corresponding to RefSeq NM_198578.3. In embodiments, the LRRK2 has the following amino acid sequence:

```
                                         (SEQ ID NO: 4)
MASGSCQGCEEDEETLKKLIVRLNNVQEGKQIETLVQILEDLLVFTYSER

ASKLFQGKNIHVPLLIVLDSYMRVASVQQVGWSLLCKLIEVCPGTMQSLM

GPQDVGNDWEVLGVHQLILKMLTVHNASVNLSVIGLKTLDLLLTSGKITL

LILDEESDIFMLIFDAMHSFPANDEVQKLGCKALHVLFERVSEEQLTEFV

ENKDYMILLSALTNFKDEEEIVLHVLHCLHSLAIPCNNVEVLMSGNVRCY

NIVVEAMKAFPMSERIQEVSCCLLHRLTLGNFFNILVLNEVHEFVVKAVQ

QYPENAALQISALSCLALLTETIFLNQDLEEKNENQENDDEGEEDKLFWL

EACYKALTWHRKNKHVQEAACWALNNLLMYQNSLHEKIGDEDGHFPAHRE

VMLSMLMHSSSKEVFQASANALSTLLEQNVNFRKILLSKGIHLNVLELMQ

KHIHSPEVAESGCKMLNHLFEGSNTSLDIMAAVVPKILTVMKRHETSLPV

QLEALRAILHFIVPGMPEESREDTEFHHKLNMVKKQCFKNDIHKLVLAAL

NRFIGNPGIQKCGLKVISSIVHFPDALEMLSLEGAMDSVLHTLQMYPDDQ

EIQCLGLSLIGYLITKKNVFIGTGHLLAKILVSSLYRFKDVAEIQTKGFQ

TILAILKLSASFSKLLVHHSFDLVIFHQMSSNIMEQKDQQFLNLCCKCFA

KVAMDDYLKNVMLERACDQNNSIMVECLLLLGADANQAKEGSSLICQVCE

KESSPKLVELLLNSGSREQDVRKALTISIGKGDSQIISLLLRRLALDVAN

NSICLGGFCIGKVEPSWLGPLFPDKTSNLRKQTNIASTLARMVIRYQMKS

AVEEGTASGSDGNFSEDVLSKFDEWTFIPDSSMDSVFAQSDDLDSEGSEG

SFLVKKKSNSISVGEFYRDAVLQRCSPNLQRHSNSLGPIFDHEDLLKRKR

KILSSDDSLRSSKLQSHMRHSDSISSLASEREYITSLDLSANELRDIDAL

SQKCCISVHLEHLEKLELHQNALTSFPQQLCETLKSLTHLDLHSNKFTSF

PSYLLKMSCIANLDVSRNDIGPSVVLDPTVKCPTLKQFNLSYNQLSFVPE

NLTDVVEKLEQLILEGNKISGICSPLRLKELKILNLSKNHISSLSENFLE

ACPKVESFSARMNFLAAMPFLPPSMTILKLSQNKFSCIPEAILNLPHLRS

LDMSSNDIQYLPGPAHWKSLNLRELLFSHNQISILDLSEKAYLWSRVEKL

HLSHNKLKEIPPEIGCLENLTSLDVSYNLELRSFPNEMGKLSKIWDLPLD

ELHLNFDFKHIGCKAKDIIRFLQQRLKKAVPYNRMKLMIVGNTGSGKTTL

LQQLMKTKKSDLGMQSATVGIDVKDWPIQIRDKRKRDLVLNVWDFAGREE

FYSTHPHFMTQRALYLAVYDLSKGQAEVDAMKPWLFNIKARASSSPVILV

GTHLDVSDEKQRKACMSKITKELLNKRGFPAIRDYHFVNATEESDALAKL

RKTIINESLNFKIRDQLVVGQLIPDCYVELEKIILSERKNVPIEFPVIDR

KRLLQLVRENQLQLDENELPHAVHFLNESGVLLHFQDPALQLSDLYFVEP

KWLCKIMAQILTVKVEGCPKHPKGIISRRDVEKFLSKKRKFPKNYMSQYF

KLLEKFQIALPIGEEYLLVPSSLSDHRPVIELPHCENSEIIIRLYEMPYF

PMGFWSRLINRLLEISPYMLSGRERALRPNRMYWRQGIYLNWSPEAYCLV

GSEVLDNHPESFLKITVPSCRKGCILLGQVVDHIDSLMEEWFPGLLEIDI

CGEGETLLKKWALYSFNDGEEHQKILLDDLMKKAEEGDLLVNPDQPRLTI

PISQIAPDLILADLPRNIMLNNDELEFEQAPEFLLGDGSFGSVYRAAYEG

EEVAVKIFNKHTSLRLLRQELVVLCHLHHPSLISLLAAGIRPRMLVMELA

SKGSLDRLLQQDKASLTRTLQHRIALHVADGLRYLHSAMITYRDLKPHNV
```

-continued

LLFTLYPNAAIIAKIADYGIAQYCCRMGIKTSEGTPGFRAPEVARGNVIY

NQQADVYSFGLLLYDILTTGGRIVEGLKFPNEFDELEIQGKLPDPVKEYG

CAPWPMVEKLIKQCLKENPQERPTSAQVFDILNSAELVCLTRRILLPKNV

IVECMVATHHNSRNASIWLGCGHTDRGQLSFLDLNTEGYTSEEVADSRIL

CLALVHLPVEKESWIVSGTQSGTLLVINTEDGKKRHTLEKMTDSVTCLYC

NSFSKQSKQKNFLLVGTADGKLAIFEDKTVKLKGAAPLKILNIGNVSTPL

MCLSESTNSTERNVMWGGCGTKIFSFSNDFTIQKLIETRTSQLFSYAAFS

DSNIITVVVDTALYIAKQNSPVVEVWDKKTEKLCGLIDCVHFLREVMVKE

NKESKHKMSYSGRVKTLCLQKNTALWIGTGGGHILLLDLSTRRLIRVIYN

FCNSVRVMMTAQLGSLKNVMLVLGYNRKNTEGTQKQKEIQSCLTVWDINL

PHEVQNLEKHIEVRKELAEKMRRTSVE.

The term “KRAS” or “K-Ras” or “Ki-ras” refers to the protein “Kirsten Rat Sarcoma”. In embodiments, “KRAS” or “K-Ras” or “Ki-ras” refers to the human protein. Included in the term “KRAS” or “K-Ras” or “Ki-ras” are the wildtype and mutant forms of the protein. In embodiments, “KRAS” or “K-Ras” or “Ki-ras” refers to the protein associated with Entrez Gene 3845, OMIM 190070, UniProt P01116, and/or RefSeq (protein) NP_004976, RefSeq (protein) NP_004976.2, or RefSeq (protein) NP_203524. In embodiments, the reference numbers immediately above refer to the protein, and associated nucleic acids, known as of the date of filing of this application. In embodiments, “KRAS” or “K-Ras” or “Ki-ras” refers to the wildtype human protein. In embodiments, “KRAS” or “K-Ras” or “Ki-ras” refers to the wildtype human nucleic acid. In embodiments, the KRAS is a mutant KRAS protein. In embodiments, the mutant KRAS is associated with a disease that is not associated with wildtype KRAS. In embodiments, the KRAS includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype KRAS. In embodiments, the KRAS protein has the protein sequence corresponding to RefSeq NP_004976.2. In embodiments, the KRAS protein has the protein sequence corresponding to RefSeq NM_004985.4. In embodiments, the KRAS has the following amino acid sequence:

(SEQ ID NO: 5)

MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

RVEDAFYTLVREIRQYRLKKISKEEKTPGCVKIKKCIIM.

In embodiments, the KRAS has the following amino acid sequence:

(SEQ ID NO: 6)

MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEKMSKDGKKKKKKSKTKCVIM.

The term “PI4KA” or “PI4K-ALPHA” refers to the protein “Phosphatidylinositol 4-kinase alpha”. In embodiments, “PI4KA” or “PI4K-ALPHA” refers to the human protein. Included in the term “PI4KA” or “PI4K-ALPHA” are the wildtype and mutant forms of the protein. In embodiments, “PI4KA” refers to PI4KIIIβ. In embodiments, “PI4KA” or “PI4K-ALPHA” refers to the protein associated with Entrez Gene 5297, UniProt P42356, and/or RefSeq (protein) NP_477352. In embodiments, the reference numbers immediately above refer to the protein, and associated nucleic acids, known as of the date of filing of this application. In embodiments, “PI4KA” or “PI4K-ALPHA” refers to the wildtype human protein. In embodiments, “PI4KA” or “PI4K-ALPHA” refers to the wildtype human nucleic acid. In embodiments, the PI4KA is a mutant PI4KA protein. In embodiments, the mutant PI4KA is associated with a disease that is not associated with wildtype PI4KA. In embodiments, the PI4KA includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype PI4KA. In embodiments, the PI4KA protein has the protein sequence corresponding to RefSeq NP_477352.3. In embodiments, the PI4KA protein has the protein sequence corresponding to RefSeq NM_058004.3. In embodiments, the PI4KA has the following amino acid sequence:

(SEQ ID NO: 7)

MAAAPARGGGGGGGGGGGGCSGSGSSASRGFYFNTVLSLARSLAVQRPASL

EKVQKLLCMCPVDFHGIFQLDERRRDAVIALGIFLIESDLQHKDCVVPYL

LRLLKGLPKVYWVEESTARKGRGALPVAESFSFCLVTLLSDVAYRDPSLR

DEILEVLLQVLHVLLGMCQALEIQDKEYLCKYAIPCLIGISRAFGRYSNM

EESLLSKLFPKIPPHSLRVLEELEGVRRRSFNDFRSILPSNLLTVCQEGT

LKRKTSSVSSISQVSPERGMPPPSSPGGSAFHYFEASCLPDGTALEPEYY

FSTISSSFSVSPLFNGVTYKEFNIPLEMLRELLNLVKKIVEEAVLKSLDA

IVASVMEANPSADLYYTSFSDPLYLTMFKMLRDTLYYMKDLPTSFVKEIH

DFVLEQFNTSQGELQKILHDADRIHNELSPLKLRCQANAACVDLMVWAVK

DEQGAENLCIKLSEKLQSKTSSKVIIAHLPLLICCLQGLGRLCERFPVVV

HSVTPSLRDFLVIPSPVLVKLYKYHSQYHTVAGNDIKISVTNEHSESTLN

VMSGKKSQPSMYEQLRDIAIDNICRCLKAGLTVDPVIVEAFLASLSNRLY

ISQESDKDAHLIPDHTIRALGHIAVALRDTPKVMEPILQILQQKFCQPPS

PLDVLIIDQLGCLVITGNQYIYQEVWNLFQQISVKASSVVYSATKDYKDH

GYRHCSLAVINALANIAANIQDEHLVDELLMNLLELFVQLGLEGKRASER

ASEKGPALKASSSAGNLGVLIPVIAVLTRRLPPIKEAKPRLQKLFRDFWL

YSVLMGFAVEGSGLWPEEWYEGVCEIATKSPLLTFPSKEPLRSVLQYNSA

MKNDTVTPAELSELRSTIINLLDPPPEVSALINKLDFAMSTYLLSVYRLE

YMRVLRSTDPDRFQVMFCYFEDKAIQKDKSGMMQCVIAVADKVFDAFLNM

MADKAKTKENEEELERHAQFLLVNFNHIHKRIRRVADKYLSGLVDKFPHL

LWSGTVLKTMLDILQTLSLSLSADIHKDQPYYDIPDAPYRITVPDTYEAR

ESIVKDFAARCGMILQEAMKWAPTVTKSHLQEYLNKHQNWVSGLSQHTGL

AMATESILHFAGYNKQNTTLGATQLSERPACVKKDYSNFMASLNLRNRYA

GEVYGMIRFSGTTGQMSDLNKMMVQDLHSALDRSHPQHYTQAMFKLTAML

ISSKDCDPQLLHHLCWGPLRMFNEHGMETALACWEWLLAGKDGVEVPFMR

-continued

EMAGAWHMTVEQKFGLFSAEIKEADPLAASEASQPKPCPPEVTPHYIWID

FLVQRFEIAKYCSSDQVEIFSSLLQRSMSLNIGGAKGSMNRHVAAIGPRF

KLLTLGLSLLHADVVPNATIRNVLREKIYSTAFDYFSCPPKFPTQGEKRL

REDISIMIKFWTAMFSDKKYLTASQLVPPDNQDTRSNLDITVGSRQQATQ

GWINTYPLSSGMSTISKKSGMSKKTNRGSQLHKYYMKRRTLLLSLLATEI

ERLITWYNPLSAPELELDQAGENSVANWRSKYISLSEKQWKDNVNLAWSI

SPYLAVQLPARFKNTEAIGNEVTRLVRLDPGAVSDVPEAIKFLVTWHTID

ADAPELSHVLCWAPTDPPTGLSYFSSMYPPHPLTAQYGVKVLRSFPPDAI

LFYIPQIVQALRYDKMGYVREYILWAASKSQLLAHQFIWNMKTNIYLDEE

GHQKDPDIGDLLDQLVEEITGSLSGPAKDFYQREFDFFNKITNVSAIIKP

YPKGDERKKACLSALSEVKVQPGCYLPSNPEAIVLDIDYKSGTPMQSAAK

APYLAKFKVKRCGVSELEKEGLRCRSDSEDECSTQEADGQKISWQAAIFK

VGDDCRQDMLALQIIDLFKNIFQLVGLDLFVFPYRVVATAPGCGVIECIP

DCTSRDQLGRQTDFGMYDYFTRQYGDESTLAFQQARYNFIRSMAAYSLLL

FLLQIKDRHNGNIMLDKKGHIIHIDFGFMFESSPGGNLGWEPDIKLTDEM

VMIMGGKMEATPFKWFMEMCVRGYLAVRPYMDAVVSLVTLMLDTGLPCFR

GQTIKLLKHRFSPNMTEREAANFIMKVIQSCFLSNRSRTYDMIQYYQNDI

PY.

The term “PIP5K” or “PI4P5K” or “PI5K” refers to the protein “Phosphatidylinositol 4-phosphate 5-kinase”. In embodiments, “PIP5K” or “PI4P5K” or “PI5K” refers to the human protein. Included in the term “PIP5K” or “PI4P5K” or “PI5K” are the wildtype and mutant forms of the protein. In embodiments, “PIP5K” or “PI4P5K” or “PI5K” refers to the protein associated with UniProt Q99755, and/or RefSeq (protein) NP_001129110. In embodiments, the reference numbers immediately above refer to the protein, and associated nucleic acids, known as of the date of filing of this application. In embodiments, “PIP5K” refers to “PIP5K1A.” In embodiments, “PIP5K” or “PI4P5K” or “PI5K” refers to the wildtype human protein. In embodiments, “PIP5K” or “PI4P5K” or “PI5K” refers to the wildtype human nucleic acid. In embodiments, the PIP5K is a mutant PIP5K protein. In embodiments, the mutant PIP5K is associated with a disease that is not associated with wildtype PIP5K. In embodiments, the PIP5K includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype PIP5K. In embodiments, the PIP5K protein has the protein sequence corresponding to RefSeq NP_001129110.1. In embodiments, the PIP5K protein has the protein sequence corresponding to RefSeq NM_001135638.2. In embodiments, the PIP5K has the following amino acid sequence:

(SEQ ID NO: 8)

MASASSGPSSSVGFSSFDPAVPSCTLSSAASGIKRPMASEVLEARQDSYI

SLVPYASGMPIKKIGHRSVDSSGETTYKKTTSSALKGAIQLGITHTVGSL

STKPERDVLMQDFYVVESIFFPSEGSNLTPAHHYNDFRFKTYAPVAFRYF

RELFGIRPDDYLYSLCSEPLIELCSSGASGSLFYVSSDDEFIIKTVQHKE

-continued

AEFLQKLLPGYYMNLNQNPRTLLPKFYGLYCVQAGGKNIRIVVMNNLLPR

SVKMHIKYDLKGSTYKRRASQKEREKPLPTFKDLDFLQDIPDGLFLDADM

YNALCKTLQRDCLVLQSFKIMDYSLLMSIHNIDHAQREPLSSETQYSVDT

RRPAPQKALYSTAMESIQGEARRGGTMETDDHMGGIPARNSKGERLLLYI

GIIDILQSYRFVKKLEHSWKALVHDGDTVSVHRPGFYAERFQRFMCNTVF

KKIPLKPSPSKKFRSGSSFSRRAGSSGNSCITYQPSVSGEHKAQVTTKAE

VEPGVHLGRPDVLPQTPPLEEISEGSPIPDPSFSPLVGETLQMLTTSTTL

EKLEVAESEFTH.

The term “SETD3” refers to the protein “SET domain containing 3 protein”. In embodiments, the term “SETD3” refers to the protein “Su(var)3-9, Enhancer of Zeste, Trithorax domain containing Histone-lysine N-methyltransferase”. In embodiments, “SETD3” refers to the human protein. Included in the term “SETD3” are the wildtype and mutant forms of the protein. In embodiments, “SETD3” refers to the protein associated with Entrez Gene 84193, UniProt Q86TU7, and/or RefSeq (protein) NP_115609. In embodiments, the reference numbers immediately above refer to the protein, and associated nucleic acids, known as of the date of filing of this application. In embodiments, “SETD3” refers to the wildtype human protein. In embodiments, “SETD3” refers to the wildtype human nucleic acid. In embodiments, the SETD3 is a mutant SETD3 protein. In embodiments, the mutant SETD3 is associated with a disease that is not associated with wildtype SETD3. In embodiments, the SETD3 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype SETD3. In embodiments, the SETD3 protein has the protein sequence corresponding to RefSeq NP_115609.2. In embodiments, the SETD3 protein has the protein sequence corresponding to RefSeq NM_032233.3. In embodiments, the SETD3 has the following amino acid sequence:

(SEQ ID NO: 9)

MGKKSRVKTQKSGTGATATVSPKEILNLTSELLQKCSSPAPGPGKEWEEY

VQIRTLVEKIRKKQKGLSVTFDGKREDYFPDLMKWASENGASVEGFEMVN

FKEEGFGLRATRDIKAEELFLWVPRKLLMTVESAKNSVLGPLYSQDRILQ

AMGNIALAFHLLCERASPNSFWQPYIQTLPSEYDTPLYFEEDEVRYLQST

QAIHDVFSQYKNTARQYAYFYKVIQTHPHANKLPLKDSFTYEDYRWAVSS

VMTRQNQIPTEDGSRVTLALIPLWDMCNHTNGLITTGYNLEDDRCECVAL

QDFRAGEQIYIFYGTRSNAEFVIHSGFFFDNNSHDRVKIKLGVSKSDRLY

AMKAEVLARAGIPTSSVFALHFTEPPISAQLLAFLRVFCMTEEELKEHLL

GDSAIDRIFTLGNSEFPVSWDNEVKLWTFLEDRASLLLKTYKTTIEEDKS

VLKNHDLSVRAKMAIKLRLGEKEILEKAVKSAAVNREYYRQQMEEKAPLP

KYEESNLGLLESSVGDSRLPLVLRNLEEEAGVQDALNIREAISKAKATEN

GLVNGENSIPNGTRSENESLNQESKRAVEDAKGSSSDSTAGVKE.

The term “TRRAP” refers to the protein “Transformation/transcription domain-associated protein”. In embodiments, “TRRAP” refers to the human protein. Included in the term “TRRAP” are the wildtype and mutant forms of the protein. In embodiments, “TRRAP” refers to the protein associated with Entrez Gene 8295, UniProt Q9Y4A5, and/or RefSeq (protein) NP_001231509. In embodiments, the reference numbers immediately above refer to the protein, and associated nucleic acids, known as of the date of filing of this application. In embodiments, "TRRAP" refers to the wildtype human protein. In embodiments, "TRRAP" refers to the wildtype human nucleic acid. In embodiments, the TRRAP is a mutant TRRAP protein. In embodiments, the mutant TRRAP is associated with a disease that is not associated with wildtype TRRAP. In embodiments, the TRRAP includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype TRRAP. In embodiments, the TRRAP protein has the protein sequence corresponding to RefSeq NP_001231509.1. In embodiments, the TRRAP protein has the protein sequence corresponding to RefSeq NM_001244580.1. In embodiments, the TRRAP has the following amino acid sequence:

(SEQ ID NO: 10)

MAFVATQGATVVDQTTLMKKYLQFVAALTDVNTPDETKLKMMQEVSENFE

NVTSSPQYSTFLEHIIPRFLTFLQDGEVQFLQEKPAQQLRKLVLEIIHRI

PTNEHLRPHTKNVLSVMFRFLETENEENVLICLRIIIELHKQFRPPITQE

IHHFLDFVKQIYKELPKVVNRYFENPQVIPENTVPPPEMVGMITTIAVKV

NPEREDSETRTHSIIPRGSLSLKVLAELPIIVVLMYQLYKLNIHNVVAEF

VPLIMNTIAIQVSAQARQHKLYNKELYADFIAAQIKTLSFLAYIIRIYQE

LVTKYSQQMVKGMLQLLSNCPAETAHLRKELLIAAKHILTTELRNQFIPC

MDKLFDESILIGSGYTARETLRPLAYSTLADLVHHVRQHLPLSDLSLAVQ

LFAKNIDDESLPSSIQTMSCKLLLNLVDCIRSKSEQESGNGRDVLMRMLE

VFVLKFHTIARYQLSAIFKKCKPQSELGAVEAALPGVPTAPAAPGPAPSP

APVPAPPPPPPPPPPATPVTPAPVPPFEKQGEKDKEDKQTFQVTDCRSLV

KTLVCGVKTITWGITSCKAPGEAQFIPNKQLQPKETQIYIKLVKYAMQAL

DIYQVQIAGNGQTYIRVANCQTVRMKEEKEVLEHFAGVFTMMNPLTFKEI

FQTTVPYMVERISKNYALQIVANSFLANPTTSALFATILVEYLLDRLPEM

GSNVELSNLYLKLFKLVFGSVSLFAAENEQMLKPHLHKIVNSSMELAQTA

KEPYNYFLLLRALFRSIGGGSHDLLYQEFLPLLPNLLQGLNMLQSGLHKQ

HMKDLFVELCLTVPVRLSSLLPYLPMLMDPLVSALNGSQTLVSQGLRTLE

LCVDNLQPDFLYDHIQPVRAELMQALWRTLRNPADSISHVAYRVLGKFGG

SNRKMLKESQKLHYVVTEVQGPSITVEFSDCKASLQLPMEKAIETALDCL

KSANTEPYYRRQAWEVIKCFLVAMMSLEDNKHALYQLLAHPNFTEKTIPN

VIISHRYKAQDTPARKTFEQALTGAFMSAVIKDLRPSALPFVASLIRHYT

MVAVAQQCGPFLLPCYQVGSQPSTAMFHSEENGSKGMDPLVLIDAIAICM

AYEEKELCKIGEVALAVIFDVASIILGSKERACQLPLFSYIVERLCACCY

EQAWYAKLGGVVSIKFLMERLPLTWVLQNQQTFLKALLFVMMDLTGEVSN

GAVAMAKTTLEQLLMRCATPLKDEERAEEIVAAQEKSFHHVTHDLVREVT

SPNSTVRKQAMHSLQVLAQVTGKSVTVIMEPHKEVLQDMVPPKKHLLRHQ

PANAQIGLMEGNTFCTTLQPRLFTMDLNVVEHKVFYTELLNLCEAEDSAL

TKLPCYKSLPSLVPLRIAALNALAACNYLPQSREKIIAALFKALNSTNSE

-continued

LQEAGEACMRKFLEGATIEVDQIHTHMRPLLMMLGDYRSLTLNVVNRLTS

VTRLFPNSFNDKFCDQMMQHLRKWMEVVVITHKGGQRSDGNESISECGRC

PLSPFCQFEEMKICSAIINLFHLIPAAPQTLVKPLLEVVMKTERAMLIEA

GSPFREPLIKFLTRHPSQTVELFMMEATLNDPQWSRMFMSFLKHKDARPL

RDVLAANPNRFITLLLPGGAQTAVRPGSPSTSTMRLDLQFQAIKIISIIV

KNDDSWLASQHSLVSQLRRVWVSENFQERHRKENMAATNWKEPKLLAYCL

LNYCKRNYGDIELLFQLLRAFTGRFLCNMTFLKEYMEEEIPKNYSIAQKR

ALFFRFVDFNDPNFGDELKAKVLQHILNPAFLYSFEKGEGEQLLGPPNPE

GDNPESITSVFITKVLDPEKQADMLDSLRIYLLQYATLLVEHAPHHIHDN

NKNRNSKLRRLMTFAWPCLLSKACVDPACKYSGHLLLAHIIAKFAIHKKI

VLQVFHSLLKAHAMEARAIVRQAMAILTPAVPARMEDGHQMLTHWTRKII

VEEGHTVPQLVHILHLIVQHFKVYYPVRHHLVQHMVSAMQRLGFTPSVTI

EQRRLAVDLSEVVIKWELQRIKDQQPDSDMDPNSSGEGVNSVSSSIKRGL

SVDSAQEVKRFRTATGAISAVFGRSQSLPGADSLLAKPIDKQHTDTVVNF

LIRVACQVNDNTNTAGSPGEVLSRRCVNLLKTALRPDMWPKSELKLQWFD

KLLMTVEQPNQVNYGNICTGLEVLSFLLTVLQSPAILSSFKPLQRGIAAC

MTCGNTKVLRAVHSLLSRLMSIFPTEPSTSSVASKYEELECLYAAVGKVI

YEGLTNYEKATNANPSQLFGTLMILKSACSNNPSYIDRLISVFMRSLQKM

VREHLNPQAASGSTEATSGTSELVMLSLELVKTRLAVMSMEMRKNFIQAI

LTSLIEKSPDAKILRAVVKIVEEWVKNNSPMAANQTPTLREKSILLVKMM

TYIEKRFPEDLELNAQFLDLVNYVYRDETLSGSELTAKLEPAFLSGLRCA

QPLIRAKFFEVFDNSMKRRVYERLLYVTCSQNWEAMGNHFWIKQCIELLL

AVCEKSTPIGTSCQGAMLPSITNVINLADSHDRAAFAMVTHVKQEPRERE

NSESKEEDVEIDIELAPGDQTSTPKTKELSEKDIGNQLHMLTNRHDKFLD

TLREVKTGALLSAFVQLCHISTTLAEKTWVQLFPRLWKILSDRQQHALAG

EISPFLCSGSHQVQRDCQPSALNCFVEAMSQCVPPIPIRPCVLKYLGKTH

NLWFRSTLMLEHQAFEKGLSLQIKPKQTTEFYEQESITPPQQEILDSLAE

LYSLLQEEDMWAGLWQKRCKYSETATAIAYEQHGFFEQAQESYEKAMDKA

KKEHERSNASPAIFPEYQLWEDHWIRCSKELNQWEALTEYGQSKGHINPY

LVLECAWRVSNWTAMKEALVQVEVSCPKEMAWKVNMYRGYLAICHPEEQQ

LSFIERLVEMASSLAIREWRRLPHVVSHVHTPLLQAAQQIIELQEAAQIN

AGLQPTNLGRNNSLHDMKTVVKTWRNRLPIVSDDLSHWSSIFMWRQHHYQ

GKPTWSGMHSSSIVTAYENSSQHDPSSNNAMLGVHASASAIIQYGKIARK

QGLVNVALDILSRIHTIPTVPIVDCFQKIRQQVKCYLQLAGVMGKNECMQ

GLEVIESTNLKYFTKEMTAEFYALKGMFLAQINKSEEANKAFSAAVQMHD

VLVKAWAMWGDYLENIFVKERQLHLGVSAITCYLHACRHQNESKSRKYLA

KVLWLLSFDDDKNTLADAVDKYCIGVPPIQWLAWIPQLLTCLVGSEGKLL

LNLISQVGRVYPQAVYFPIRTLYLTLKIEQRERYKSDPGPIRATAPMWRC

SRIMHMQRELHPTLLSSLEGIVDQMVWFRENWHEEVLRQLQQGLAKCYSV

AFEKSGAVSDAKITPHTLNFVKKLVSTFGVGLENVSNVSTMFSSAASESL

-continued

ARRAQATAQDPVFQKLKGQFTTDFDFSVPGSMKLHNLISKLKKWIKILEA KTKQLPKFFLIEEKCRFLSNFSAQTAEVEIPGEFLMPKPTHYYIKIARFM PRVEIVQKHNTAARRLYIRGHNGKIYPYLVMNDACLTESRREERVLQLLR LLNPCLEKRKETTKRHLFFTVPRVVAVSPQMRLVEDNPSSLSLVEIYKQR CAKKGIEHDNPISRYYDRLATVQARGTQASHQVLRDILKEVQSNMVPRSM LKEWALHTFPNATDYWTFRKMFTIQLALIGFAEFVLHLNRLNPEMLQIAQ DTGKLNVAYFRFDINDATGDLDANRPVPFRLTPNISEFLTTIGVSGPLTA SMIAVARCFAQPNFKVDGILKTVLRDEIIAWHKKTQEDTSSPLSAAGQPE NMDSQQLVSLVQKAVTAIMTRLHNLAQFEGGESKVNTLVAAANSLDNLCR MDPAWHPWL.

The term "MAP4K" or "mitogen-activated protein kinase kinase kinase kinase" refers to the family of serine/threonine kinases involved in cellular signal transduction. In embodiments, MAP4K is MAP4K1 or hematopoietic progenitor kinase 1 (HPK1). In embodiments, MAP4K is MAP4K2 or germinal center kinase (GCK). In embodiments, MAP4K is MAP4K3 or germinal center kinase-like kinase (GLK). In embodiments, MAP4K is MAP4K4 or hepatocyte progenitor kinase-like/germinal center kinase-like kinase (HGK). In embodiments, MAP4K is MAP4K5 or kinase homologous to SPS1/STE20 (KHS). In embodiments, MAP4K is MAP4K6 or misshapen-like kinase 1 (MINK).

The term "hepatocyte progenitor kinase-like/germinal center kinase-like kinase" or "HGK" or "MAP4K4" is encoded by the MAP4K4 gene. The term "HGK" may refer to the nucleotide sequence or protein sequence of human HGK (e.g., Entrez 9448, Uniprot 095819, RefSeq NM_00124559.1, RefSeq NM_001242560, RefSeq NM_004834.4, RefSeq NM_145686.3, RefSeq NM_145687.3, RefSeq NP_001229488.1, RefSeq NP_001229489, RefSeq NP_004825.3, RefSeq NP_663719.2, or RefSeq NP_663720.1). The term "HGK" includes both the wild-type form of the nucleotide sequences or proteins as well as any mutants thereof. In some embodiments, "HGK" is wild-type HGK. In some embodiments, "HGK" is one or more mutant forms. The term "HGK" XYZ refers to a nucleotide sequence or protein of a mutant HGK wherein the Y numbered amino acid of HGK that normally has an X amino acid in the wildtype, instead has a Z amino acid in the mutant. In embodiments, an HGK is the human HGK. In embodiments, the HGK has the following amino acid sequence:

(SEQ ID NO: 11)

MANDSPAKSLVDIDLSSLRDPAGIFELVEVVGNGTYGQVYKGRHVKTGQL AAIKVMDVTEDEEEEIKLEINMLKKYSHHRNIATYYGAFIKKSPPGHDDQ LWLVMEFCGAGSITDLVKNTKGNTLKEDWIAYISREILRGLAHLHIHHVI HRDIKGQNVLLTENAEVKLVDFGVSAQLDRTVGRRNTFIGTPYWMAPEVI ACDENPDATYDYRSDLWSCGITAIEMAEGAPPLCDMHPMRALFLIPRNPP PRLKSKKWSKKFFSFIEGCLVKNYMQRPSTEQLLKHPFIRDQPNERQVRI QLKDHIDRTRKKRGEKDETEYEYSGSEEEEEEVPEQEGEPSSIVNVPGES TLRRDFLRLQQENKERSEALRRQQLLQEQQLREQEEYKRQLLAERQKRIE QQKEQRRRLEEQQRREREARRQQEREQRRREQEEKRRLEELERRRKEEEE

-continued

RRRAEEEKRRVEREQEYIRRQLEEEQRHLEVLQQQLLQEQAMLLECRWRE MEEHRQAERLQRQLQQEQAYLLSLQHDHRRPHPQHSQQPPPPQQERSKPS FHAPEPKAHYEPADRAREVEDRFRKTNHSSPEAQSKQTGRVLEPPVPSRS ESFSNGNSESVHPALQRPAEPQVPVRTTSRSPVLSRRDSPLQGSGQQNSQ AGQRNSTSIEPRLLWERVEKLVPRPGSGSSSGSSNSGSQPGSHPGSQSGS GERFRVRSSSKSEGSPSQRLENAVKKPEDKKEVFRPLKPADLTALAKELR AVEDVRPPHKVTDYSSSSEESGTTDEEDDDVEQEGADESTSGPEDTRAAS SLNLSNGETESVKTMIVHDDVESEPAMTPSKEGTLIVRQTQSASSTLQKH KSSSSFTPFIDPRLLQISPSSGTTVTSVVGFSCDGMRPEAIRQDPTRKGS VVNVNPTNTRPQSDTPEIRKYKKRFNSEILCAALWGVNLLVGTESGLMLL DRSGQGKVYPLINRRRFQQMDVLEGLNVLVTISGKKDKLRVYYLSWLRNK ILHNDPEVEKKQGWTTVGDLEGCVHYKVVKYERIKFLVIALKSSVEVYAW APKPYHKFMAFKSFGELVHKPLLVDLTVEEGQRLKVIYGSCAGFHAVDVD SGSVYDIYLPTHIQCSIKPHAIIILPNTDGMELLVCYEDEGVYVNTYGRI TKDVVLQWGEMPTSVAYIRSNQTMGWGEKAIEIRSVETGHLDGVFMHKRA QRLKFLCERNDKVFFASVRSGGSSQVYFMTLGRTSLLSW.

The term "MAP3K" or "mitogen-activated protein kinase kinase kinase" refers to the family of serine/threonine-specific protein kinases. In embodiments, MAP3K is MAP3K12 or dual leucine zipper bearing kinase (DLK).

The term "dual leucine zipper bearing kinase" or "DLK" or "MAP3K12" is encoded by the MAP3K12 gene. The term "DLK" may refer to the nucleotide sequence or protein sequence of human DLK (e.g., Entrez 7786, Uniprot Q12852, RefSeq NM_001193511.1, RefSeq NM_006301.3, RefSeq NP_001180440.1, or RefSeq NP_006292.3). The term "DLK" includes both the wild-type form of the nucleotide sequences or proteins as well as any mutants thereof. In some embodiments, "DLK" is wild-type DLK. In some embodiments, "DLK" is one or more mutant forms. The term "DLK" XYZ refers to a nucleotide sequence or protein of a mutant DLK wherein the Y numbered amino acid of DLK that normally has an X amino acid in the wildtype, instead has a Z amino acid in the mutant. In embodiments, an DLK is the human DLK. In embodiments, the DLK has the following amino acid sequence:

(SEQ ID NO: 12)

MACLHETRTPSPSFGGFVSTLSEASMRKLDPDTSDCTPEKDLTPTHVLQL HEQDAGGPGGAAGSPESRASRVRADEVRLQCQSGSGFLEGLFGCLRPVWT MIGKAYSTEHKQQQEDLWEVPFEEILDLQWVGSGAQGAVFLGRFHGEEVA VKKVRDLKETDIKHLRKLKHPNIITFKGVCTQAPCYCILMEFCAQGQLYE VLRAGRPVTPSLLVDWSMGIAGGMNYLHLHKIIHRDLKSPNMLITYDDVV KISDFGTSKELSDKSTKMSFAGTVAWMAPEVIRNEPVSEKVDIWSFGVVL WELLTGEIPYKDVDSSAIIWGVGSNSLHLPVPSSCPDGFKILLRQCWNSK PRNRPSFRQILLHLDIASADVLSTPQETYFKSQAEWREEVKLHFEKIKSE GTCLHRLEEELVMRRREELRHALDIREHYERKLERANNLYMELNALMLQL ELKERELLRREQALERRCPGLLKPHPSRGLLHGNTMEKLIKKRNVPQKLS

-continued

PHSKRPDILKTESLLPKLDAALSGVGLPGCPKGPPSPGRSRRGKTRHRKA
SAKGSCGDLPGLRTAVPPHEPGGPGSPGGLGGGPSAWEACPPALRGLHHD
LLLRKMSSSSPDLLSAALGSRGRGATGGAGDPGSPPPARGDTPPSEGSAP
GSTSPDSPGGAKGEPPPPVGPGEGVGLLGTGREGTSGRGGSRAGSQHLTP
AALLYRAAVTRSQKRGISSEEEEGEVDSEVELTSSQRWPQSLNMRQSLST
FSSENPSDGEEGTASEPSPSGTPEVGSTNTDERPDERSDDMCSQGSEIPL
DPPPSEVIPGPEPSSLPIPHQELLRERGPPNSEDSDCDSTELDNSNSVDA
LRPPASLPP.

An "immunophilin blocking agent" is an agent (e.g., compound, small molecule, nucleic acid, or protein) capable of inhibiting or reducing contact between an immunophilin binding compound described herein and an immunophilin wherein the immunophilin blocking agent is deficient in biological activity (e.g., not capable of inhibiting an immune response or T cell activity, reduced or lacking binding to calcineurin) not associated with blocking binding to immunophilin of a separate immunophilin binding compound (e.g., compound described herein).

II. Compounds

In an aspect is provided a compound having the formula: $A^{B}$-$L^{B1}$-$R^{B1}$, or a pharmaceutically acceptable salt thereof.

$A^{B}$ is an immunophilin-binding moiety.

$L^{B1}$-$R^{B1}$ is a polar moiety.

$L^{B1}$ is a bond, covalent linker, or bioconjugate linker.

$R^{B1}$ is hydrogen, halogen, $—CX^{B1}_3$, $—CHX^{B1}_2$, $—CH_2X^{B1}$, $—OCX^{B1}_3$, $—OCH_2X^{B1}$, $—OCHX^{B1}_2$, —CN, $—SO_{nB1}R^{B1D}$, $—SO_{vB1}NR^{B1A}R^{B1B}$, $—NHC(O)NR^{B1A}R^{B1B}$, $—N(O)_{mB1}$, $—NR^{B1A}R^{B1B}$, $—C(O)R^{B1C}$, $—C(O)OR^{B1C}$, $—C(O)NR^{B1A}R^{B1B}$, $—OR^{B1D}$, $—NR^{B1A}SO_2R^{B1D}$, $—NR^{B1A}C(O)R^{B1C}$, $—NR^{B1A}C(O)OR^{B1C}$, $—NR^{B1A}OR^{B1C}$, $—NR^{B1A}C(NR^{B1C})R^{B1D}$, $—NR^{B1}DC(NR^{B1C})NR^{B1A}R^{B1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{B1A}$, $R^{B1B}$, $R^{B1C}$, and $R^{B1D}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl.

nB1 is independently an integer from 0 to 4.

mB1 and vB1 are independently 1 or 2.

$X^{B1}$ is independently —F, —Cl, —Br, or —I.

When $L^{B1}$ is a bond, $R^{B1}$ is not H.

Subsequent to administration to a subject, the concentration of the compound in circulating blood of the subject is greater than the concentration of the compound in the CNS of the subject.

In embodiments, the compound has the formula:

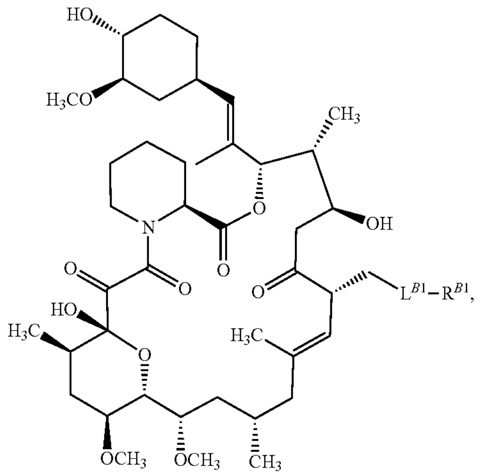

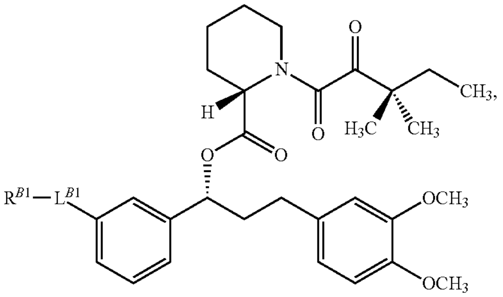

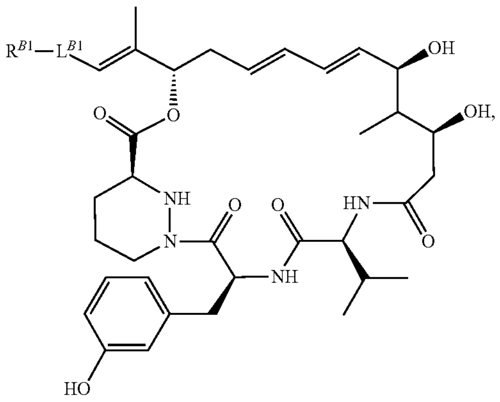

-continued
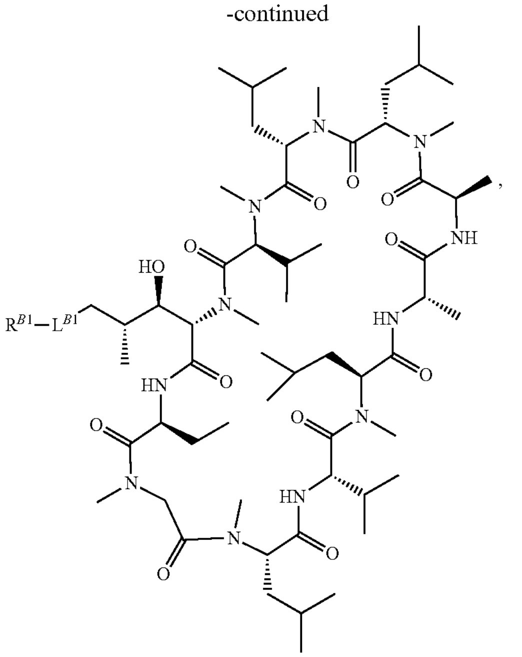
or
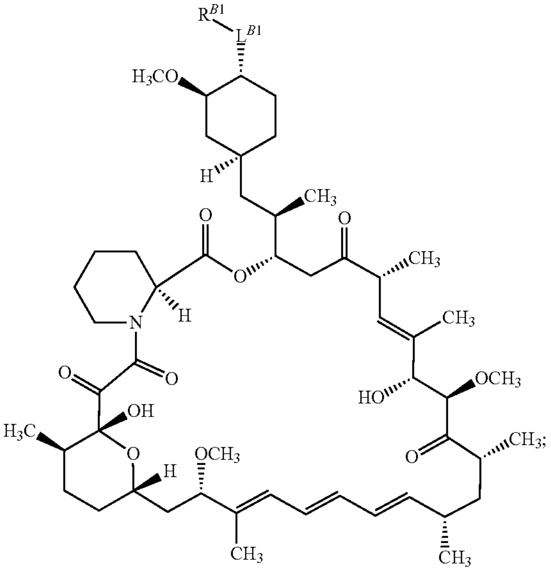
or an analog thereof. In embodiments, the compound has the formula
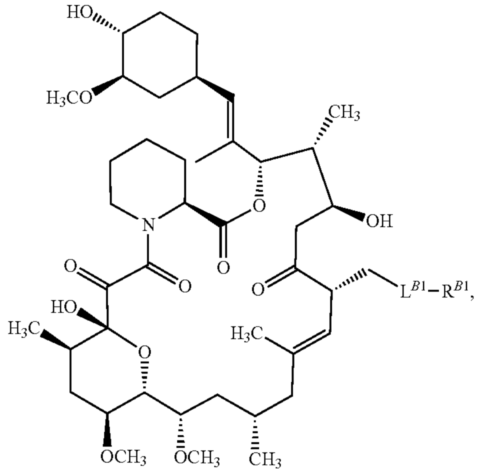
or an analog thereof. In embodiments, the compound has the formula
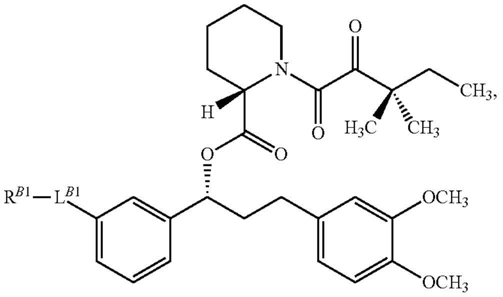
or an analog thereof. In embodiments, the compound has the formula
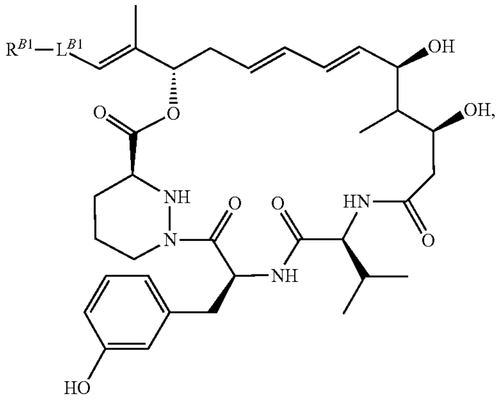
or an analog thereof. In embodiments, the compound has the formula

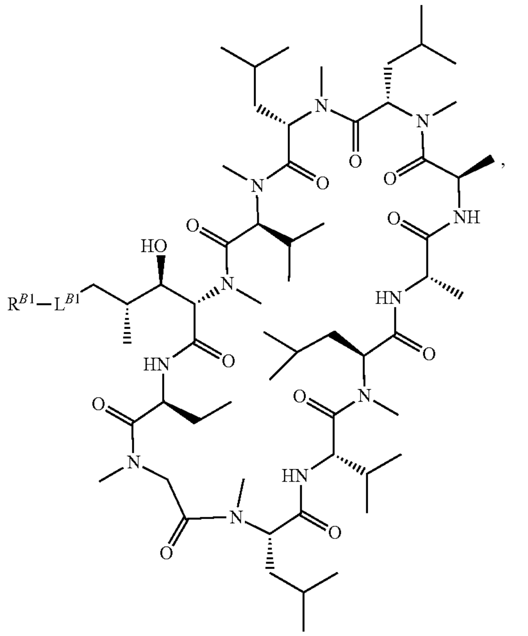
or an analog thereof. In embodiments, the compound has the formula
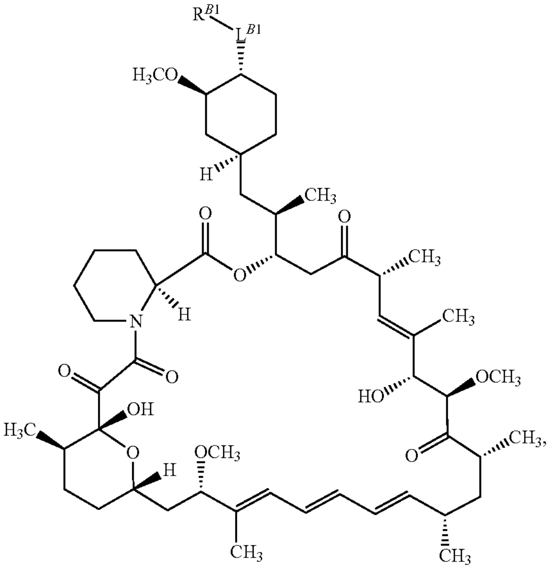
or an analog thereof. In embodiments, the compound has the formula
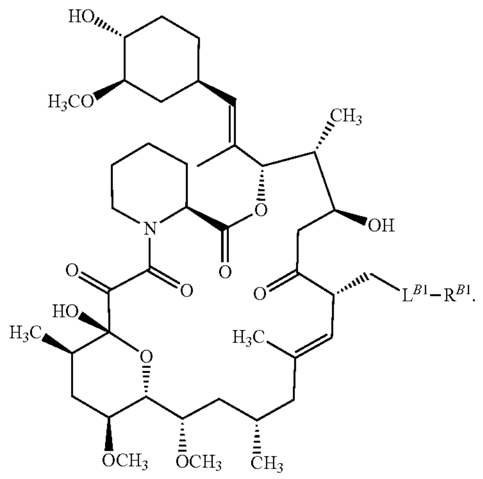
In embodiments, the compound has the formula
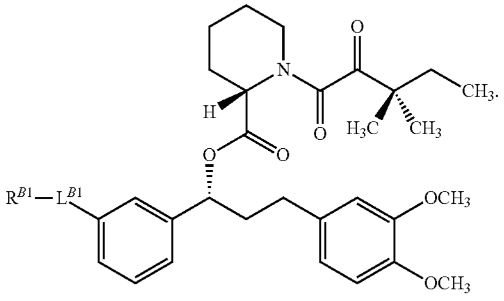
In embodiments, the compound has the formula
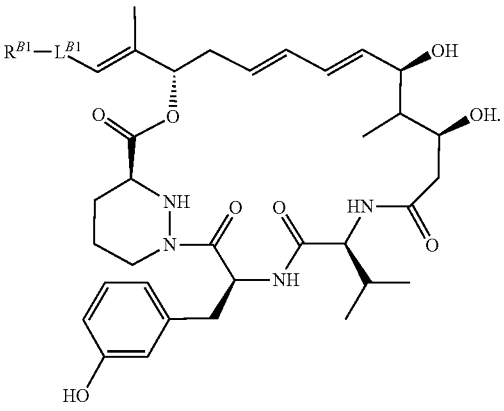

In embodiments, the compound has the formula
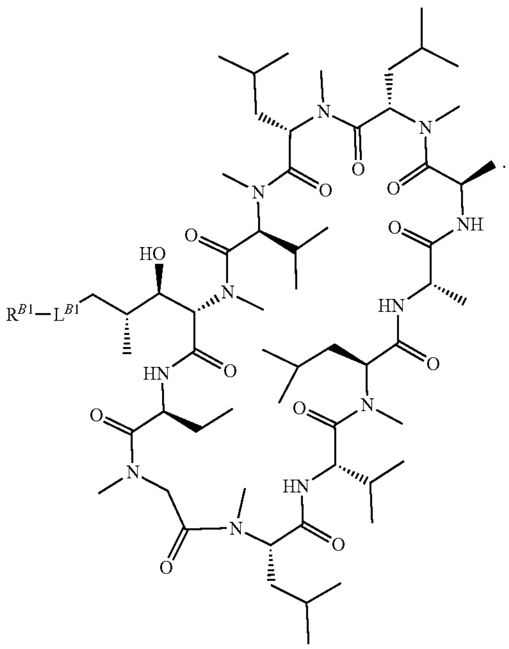
In embodiments, the compound has the formula
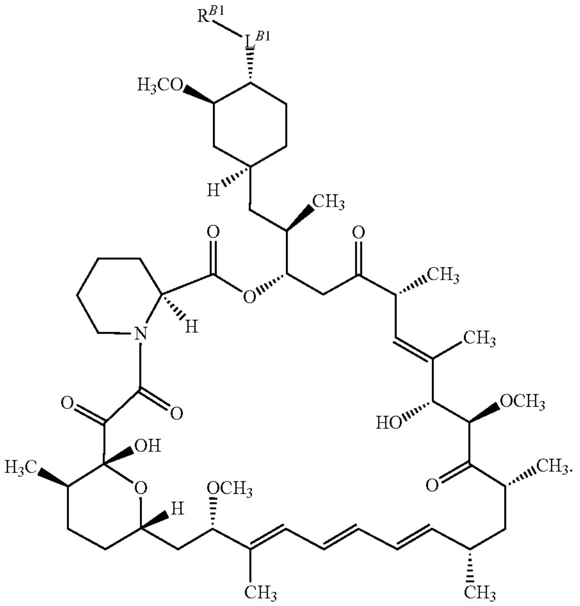
In embodiments, the compound has the formula
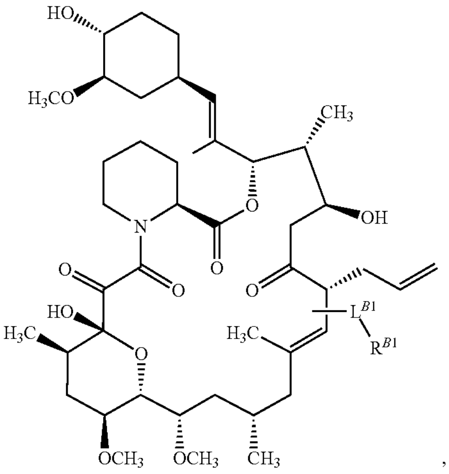
,
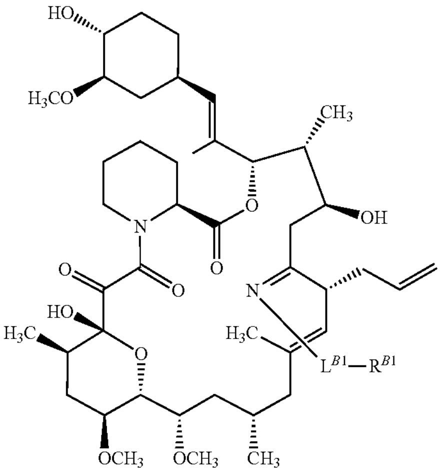
, -continued
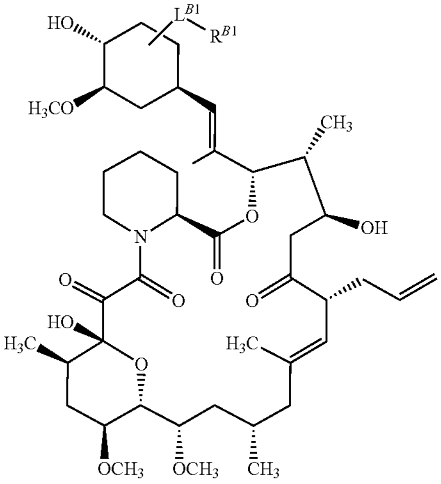
,
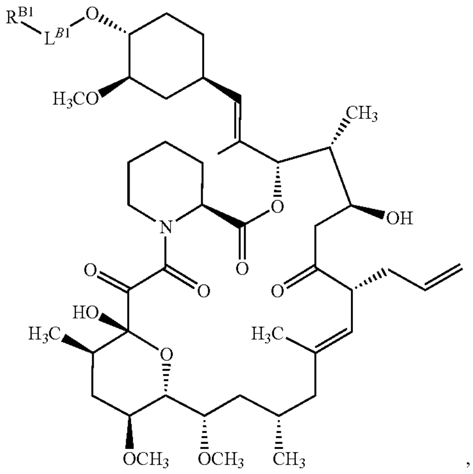
,
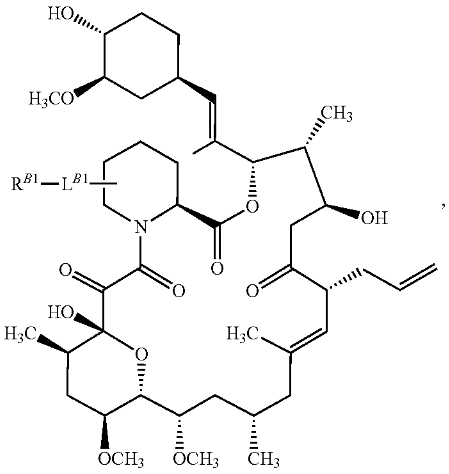
,
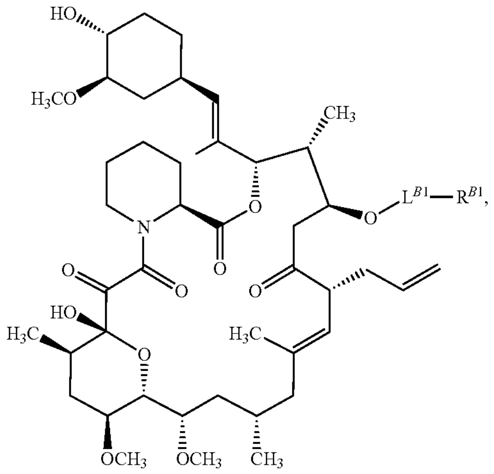
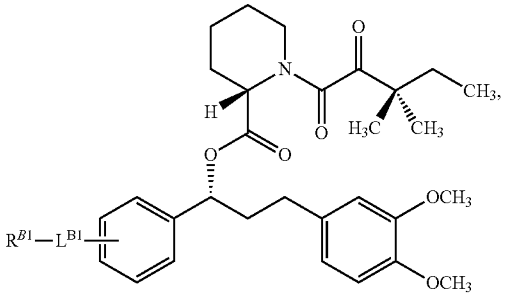
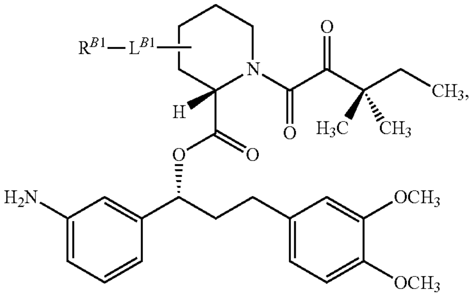
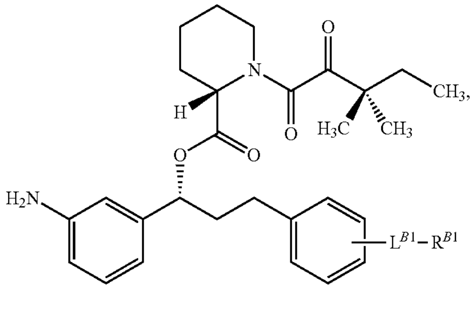

-continued
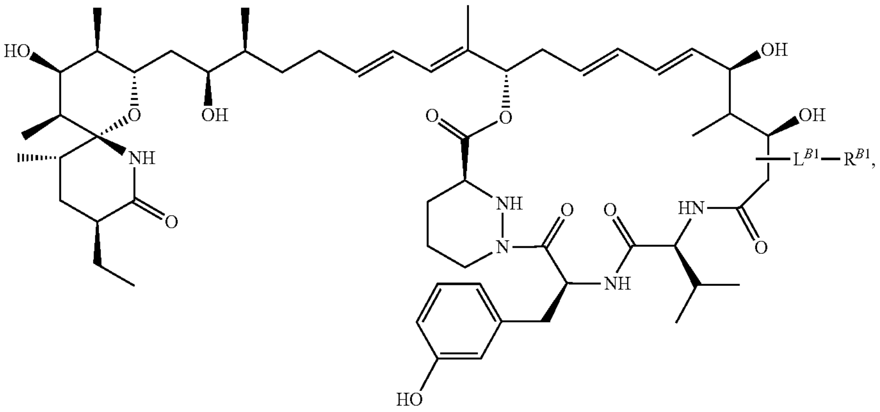
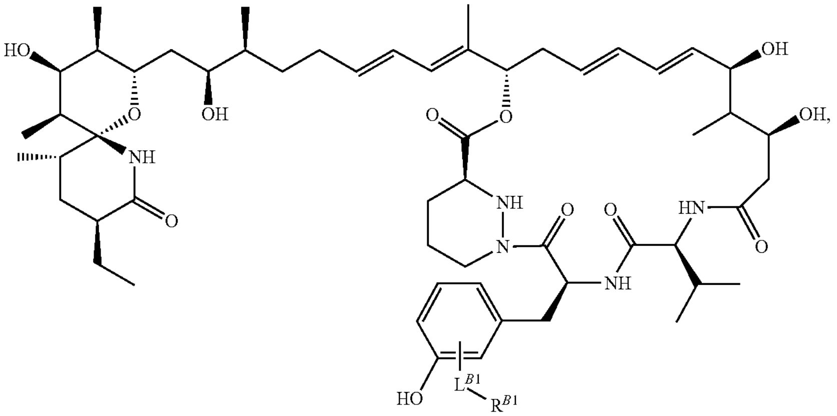
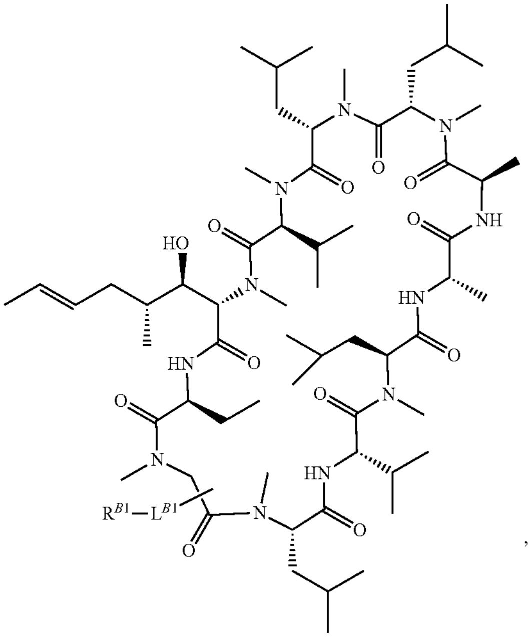
,
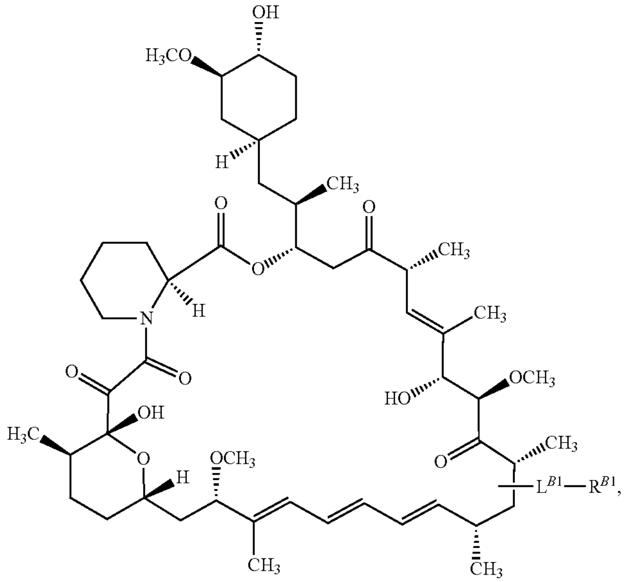

-continued
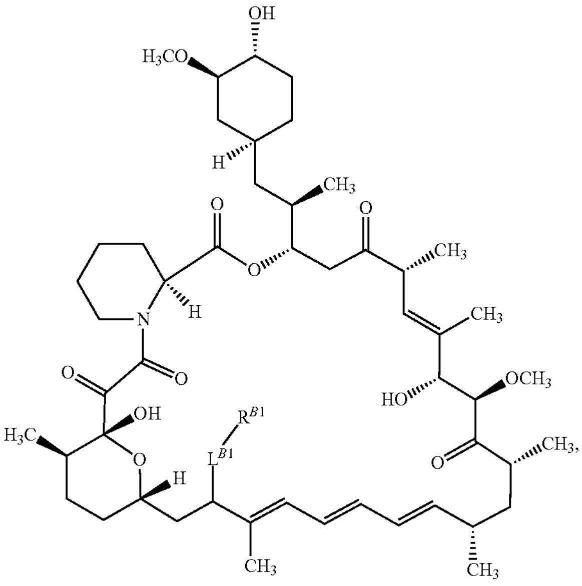
,
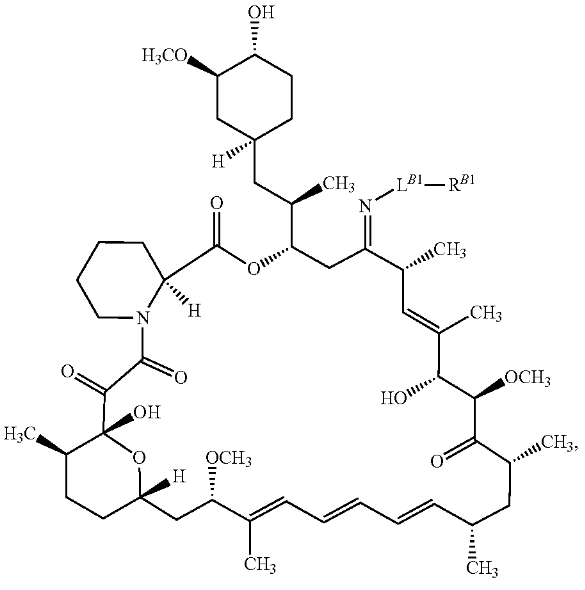
, or

-continued
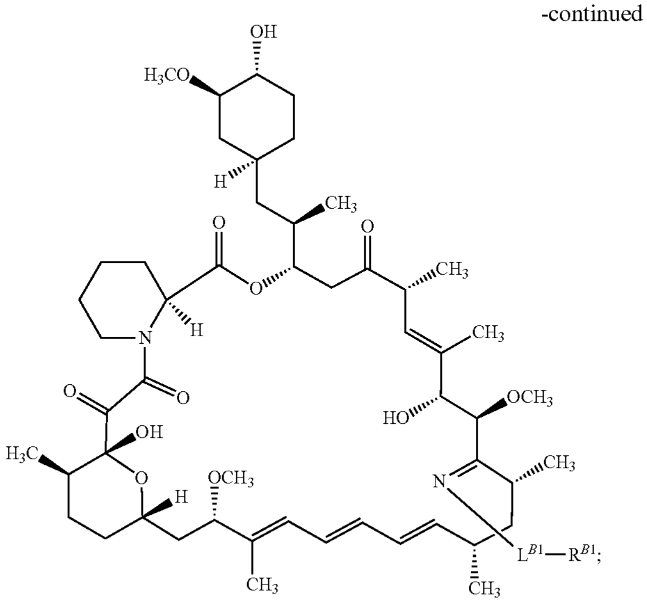
or an analog thereof. In embodiments, the compound has the formula
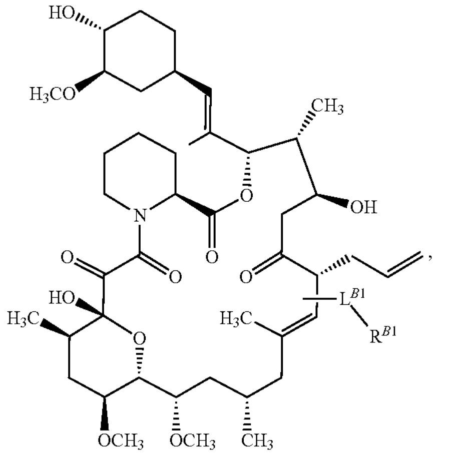
or an analog thereof. In embodiments, the compound has the formula
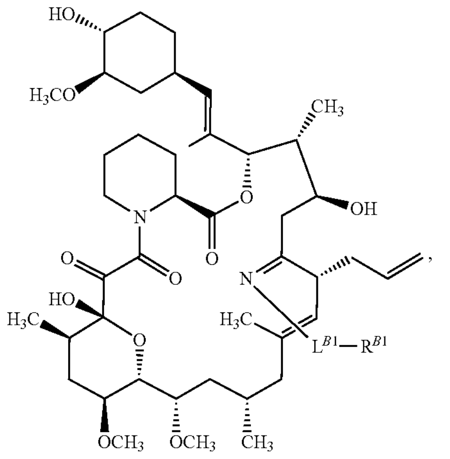
or an analog thereof. In embodiments, the compound has the formula
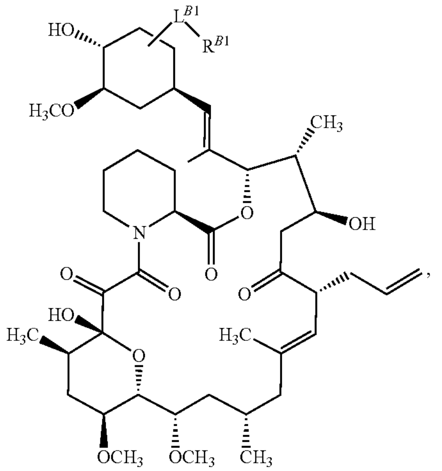
or an analog thereof. In embodiments, the compound has the formula

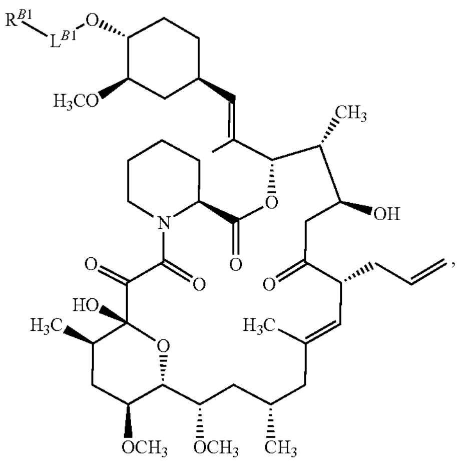

or an analog thereof. In embodiments, the compound has the formula

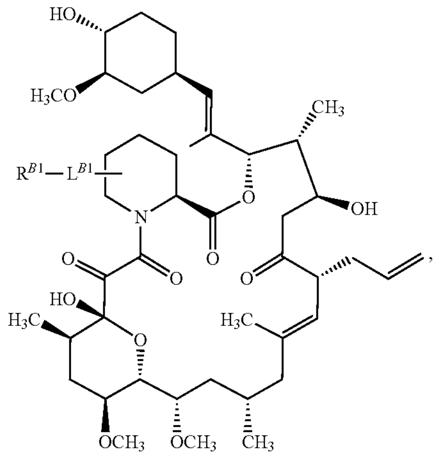

or an analog thereof. In embodiments, the compound has the formula

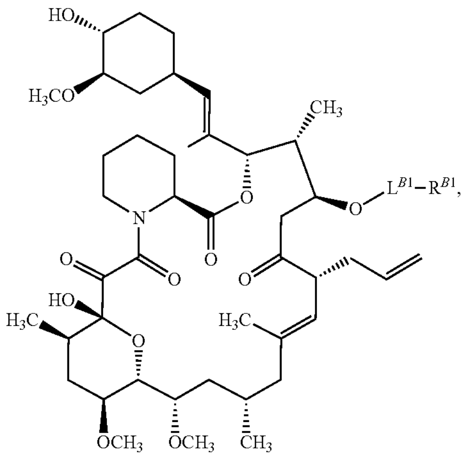

or an analog thereof. In embodiments, the compound has the formula

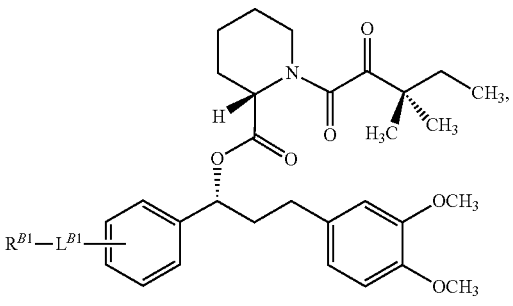

or an analog thereof. In embodiments, the compound has the formula

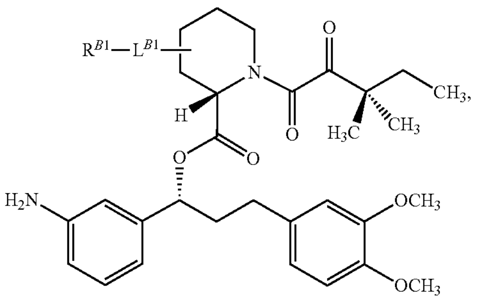

or an analog thereof. In embodiments, the compound has the formula

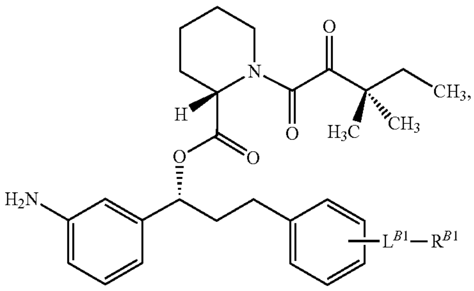

or an analog thereof. In embodiments, the compound has the formula

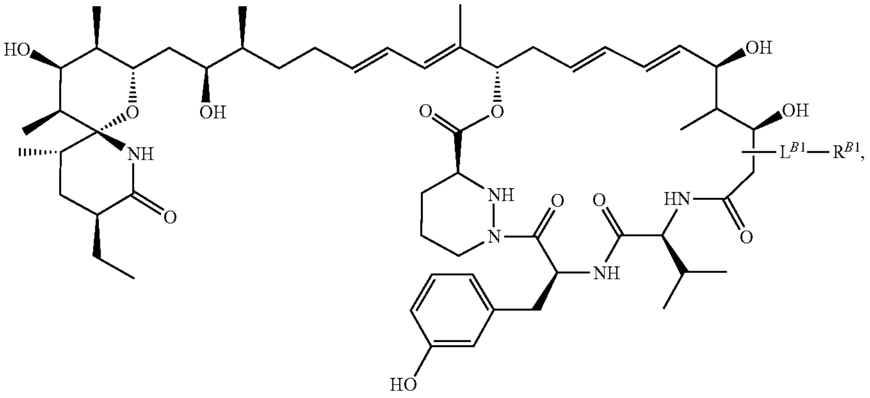
or an analog thereof. In embodiments, the compound has the formula
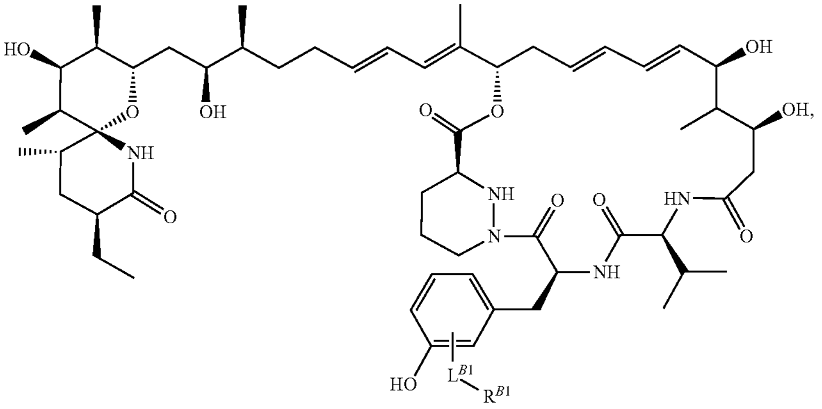
or an analog thereof. In embodiments, the compound has the formula
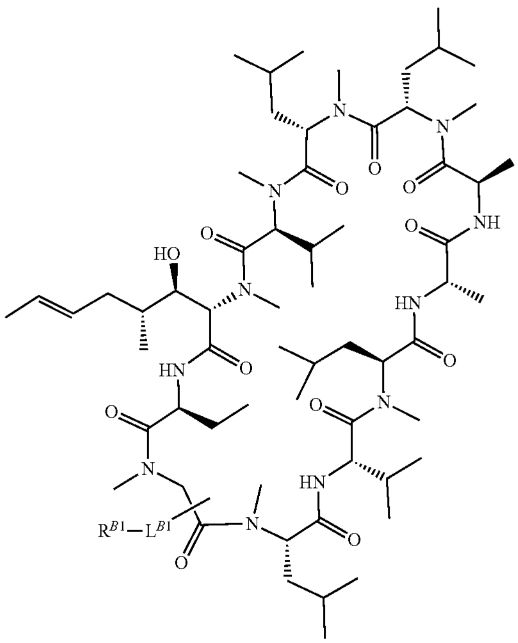
or an analog thereof. In embodiments, the compound has the formula
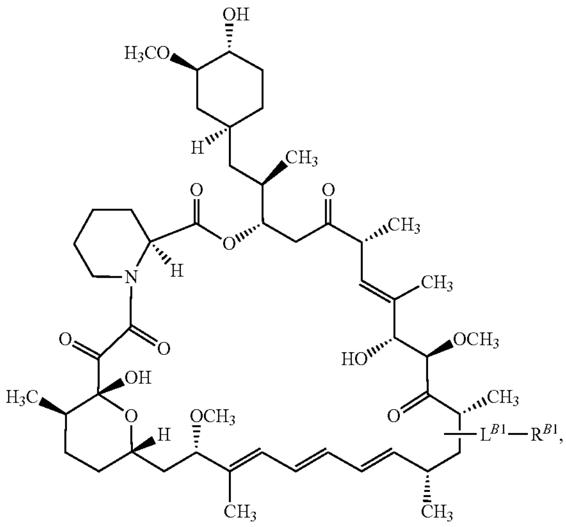
or an analog thereof. In embodiments, the compound has the formula

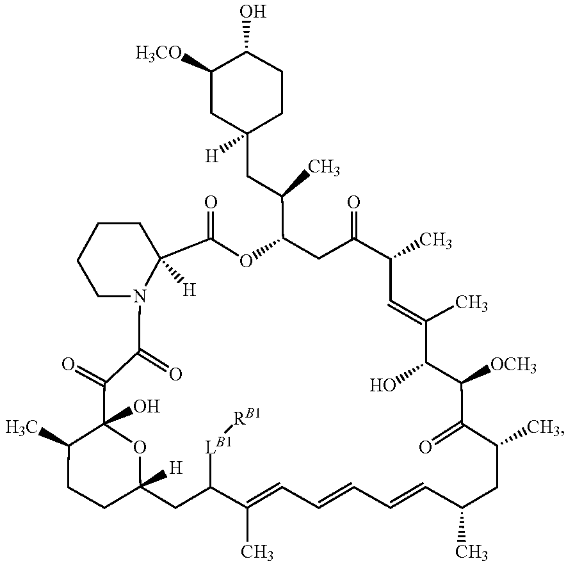
or an analog thereof. In embodiments, the compound has the formula
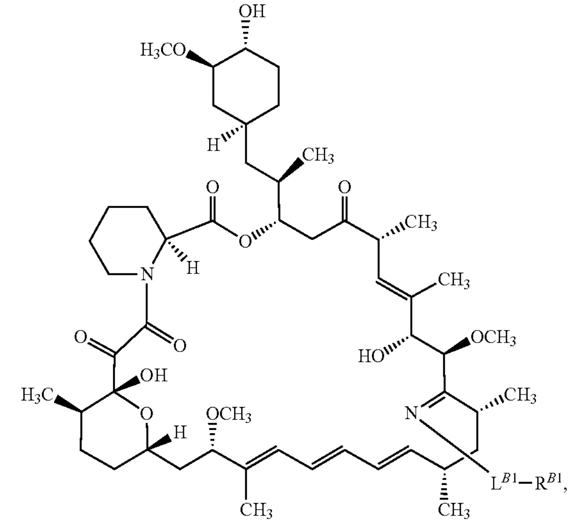
or an analog thereof. In embodiments, the compound has the formula
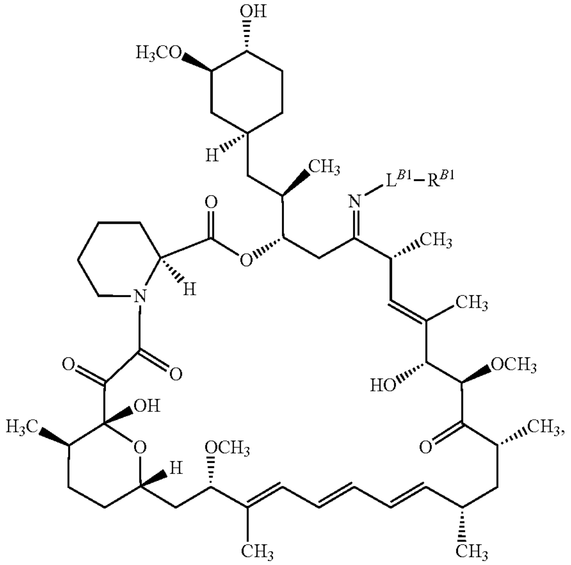
or an analog thereof. In embodiments, the compound has the formula
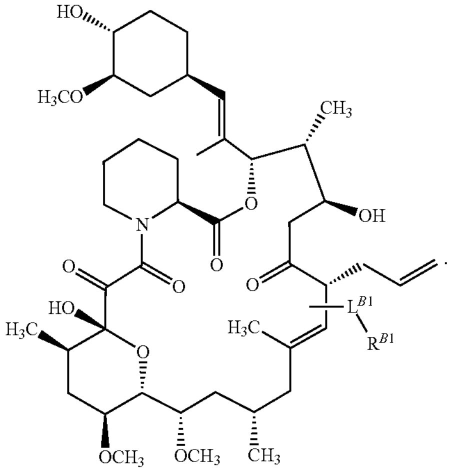
In embodiments, the compound has the formula
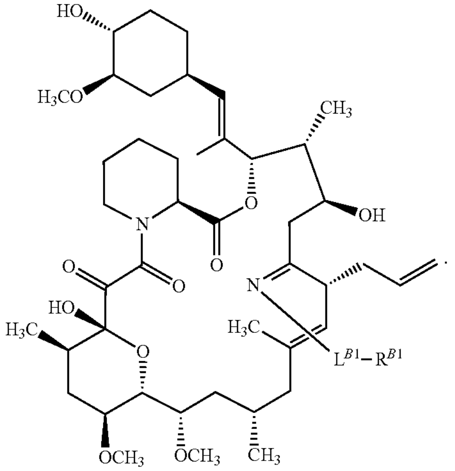

In embodiments, the compound has the formula
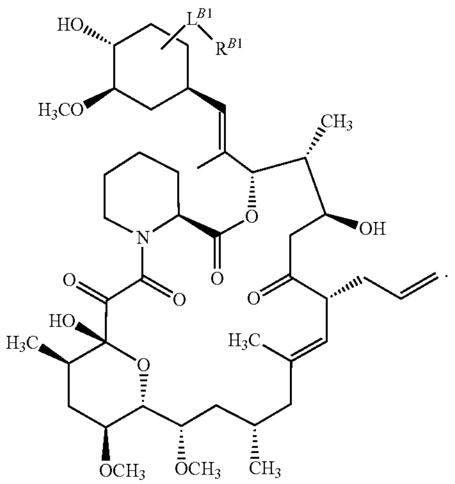
In embodiments, the compound has the formula
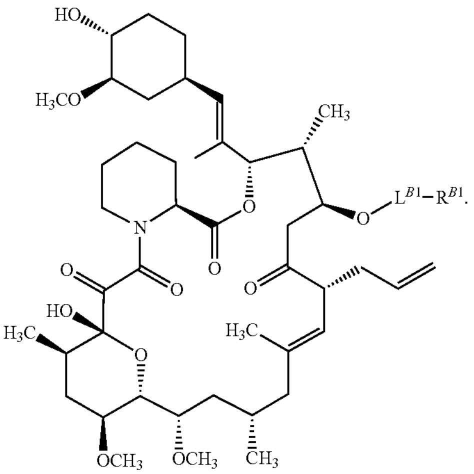
In embodiments, the compound has the formula
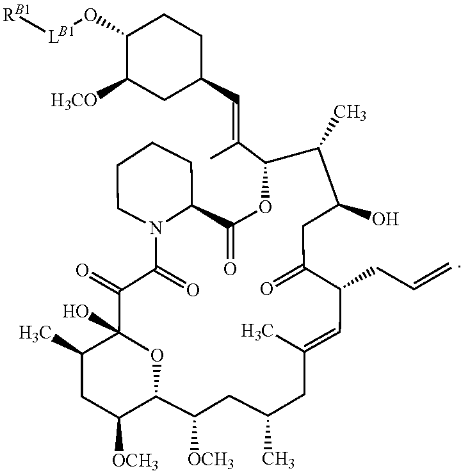
In embodiments, the compound has the formula
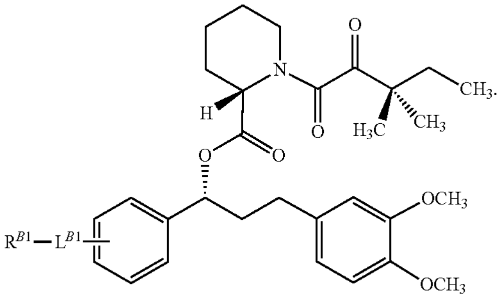
In embodiments, the compound has the formula
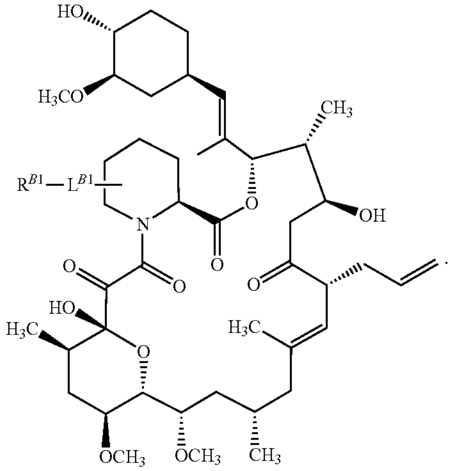
In embodiments, the compound has the formula
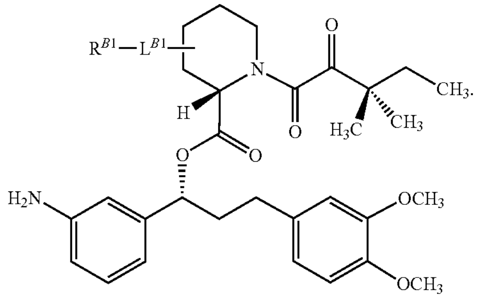

In embodiments, the compound has the formula
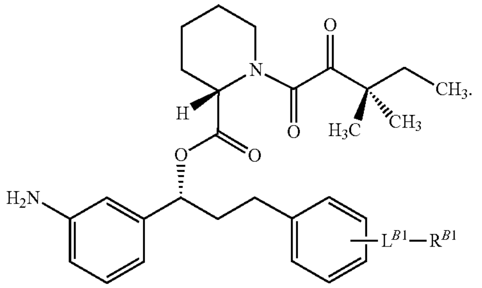
In embodiments, the compound has the formula
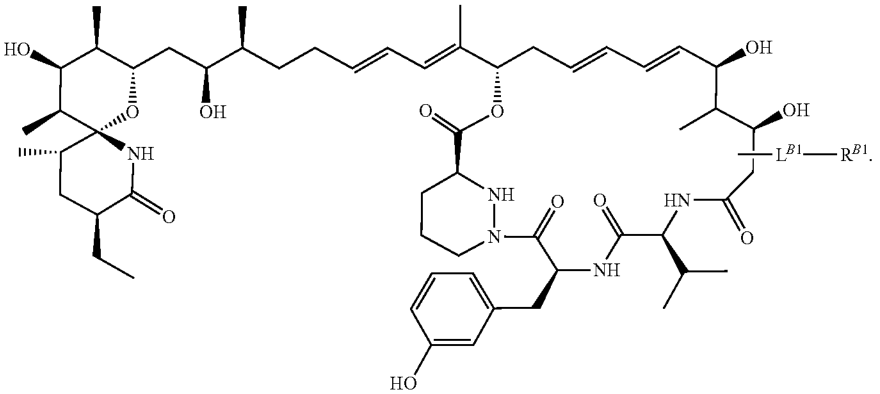
In embodiments, the compound has the formula
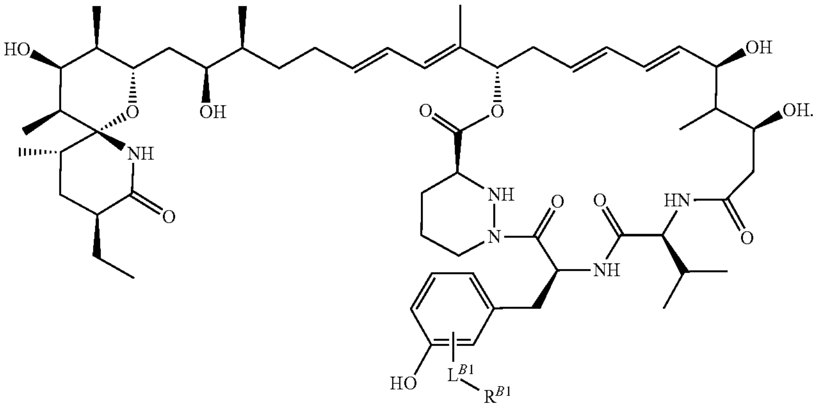

In embodiments, the compound has the formula
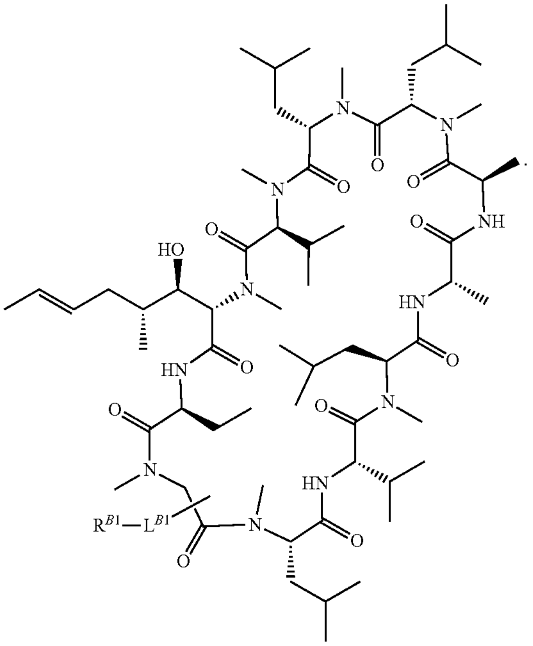
In embodiments, the compound has the formula
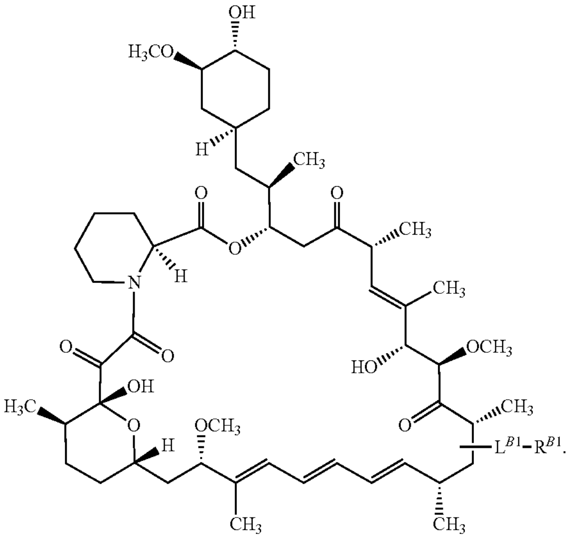
In embodiments the compound has the formula
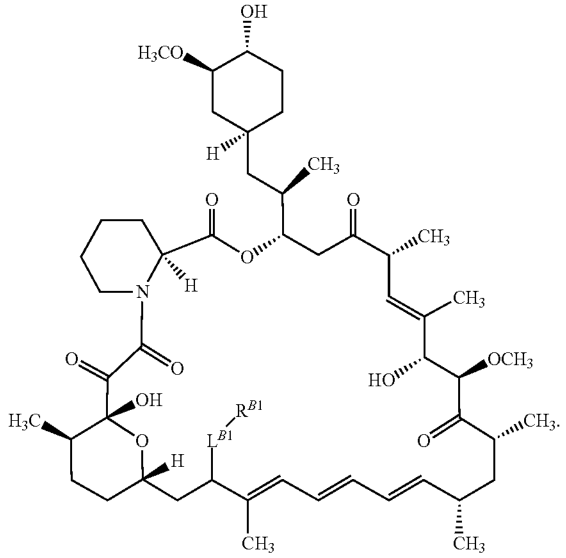
In embodiments, the compound has the formula
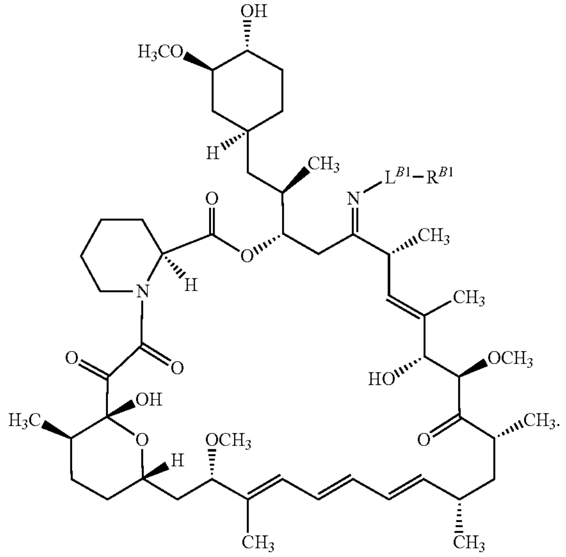

In embodiments, the compound has the formula

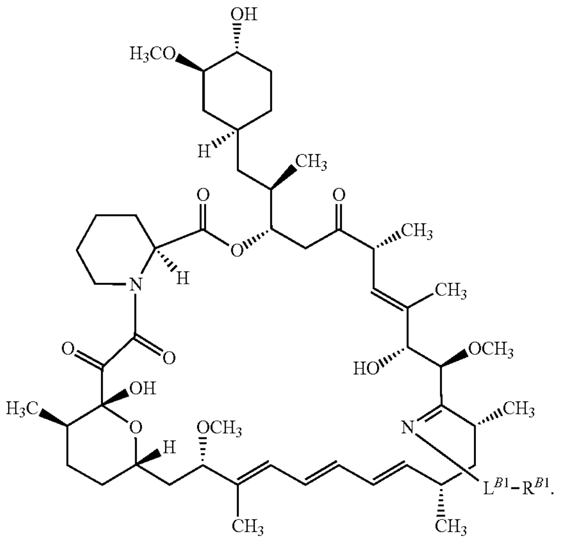

In embodiments, $A^B$ is a cyclophilin-binding moiety or an FKBP-binding moiety. In embodiments, $A^B$ is a cyclophilin-binding moiety. In embodiments, $A^B$ is a cyclophilin-binding moiety or an FKBP-binding moiety. In embodiments, $A^B$ is a cyclophilin-binding moiety. In embodiments, $A^B$ is an FKBP-binding moiety. In embodiments, the FKBP is FKBP12. In embodiments, the FKBP-binding moiety is an FK506 moiety, or an analog thereof.

In embodiments, the immunophilin-binding moiety is

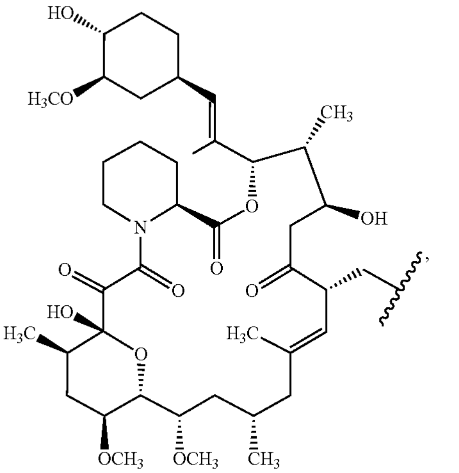

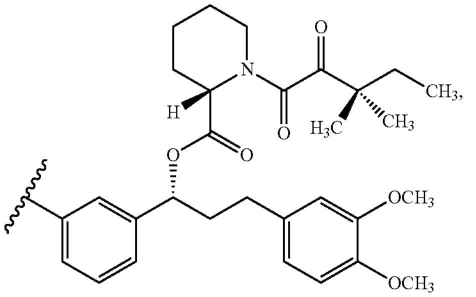

-continued

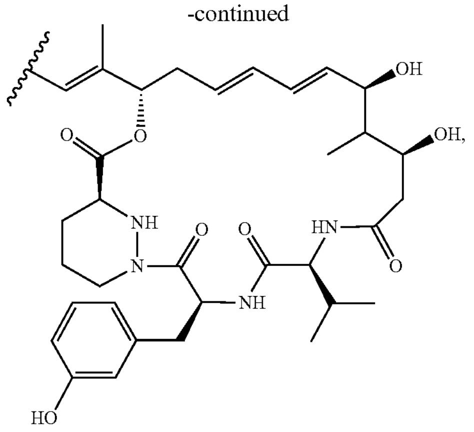

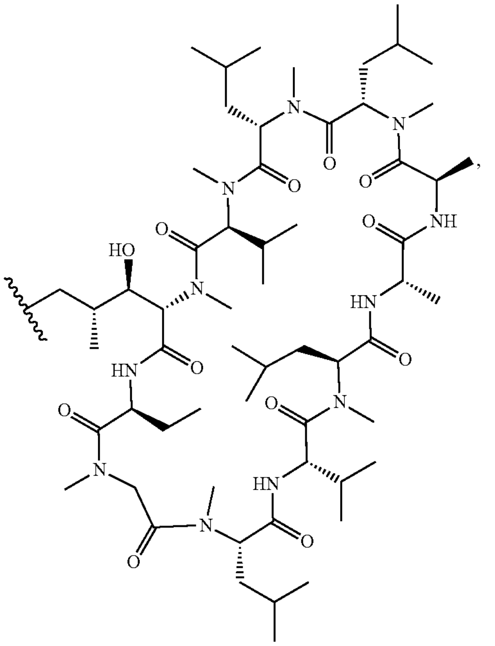

or

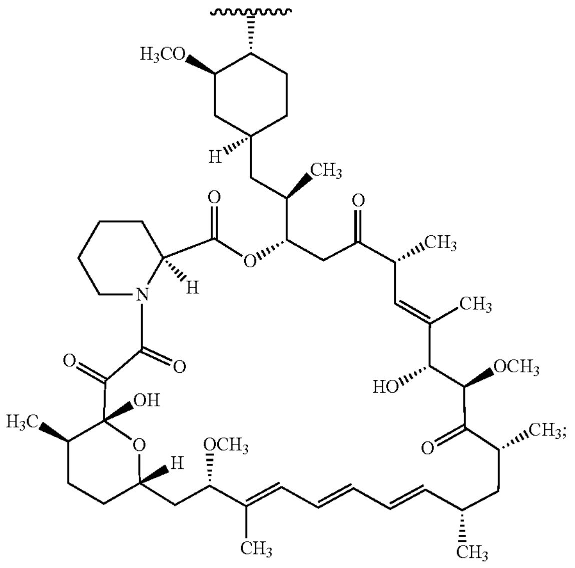 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or an analog thereof. In embodiments, the immunophilin-binding moiety is

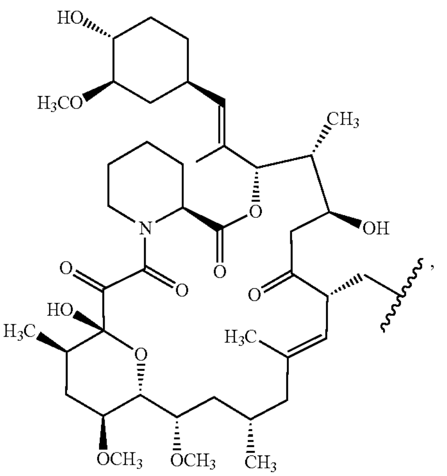 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof. In embodiments, the immunophilin-binding moiety is

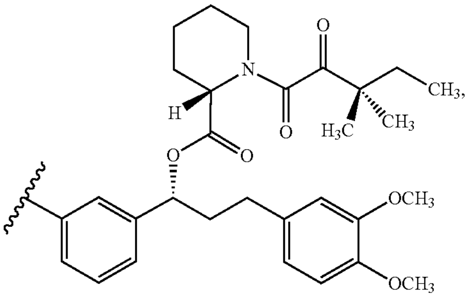

or an analog thereof. In embodiments, the immunophilin-binding moiety is

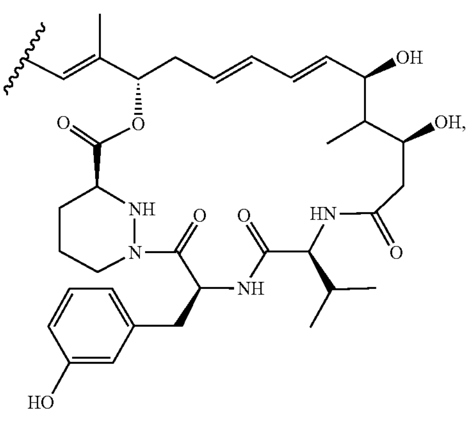 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]

or an analog thereof. In embodiments, the immunophilin-binding moiety is

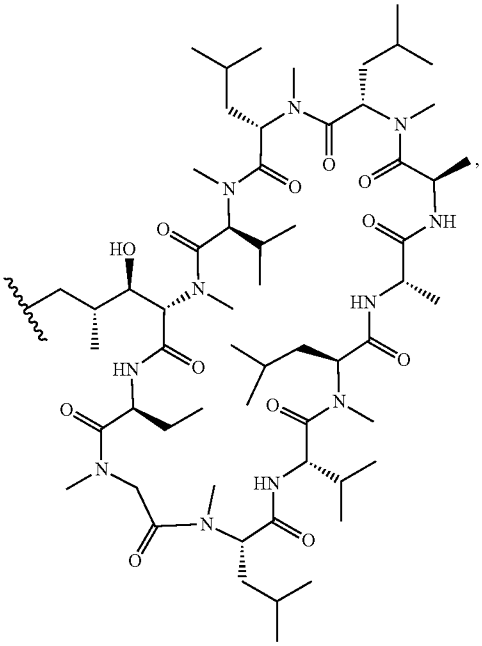 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

or an analog thereof. In embodiments, the immunophilin-binding moiety is

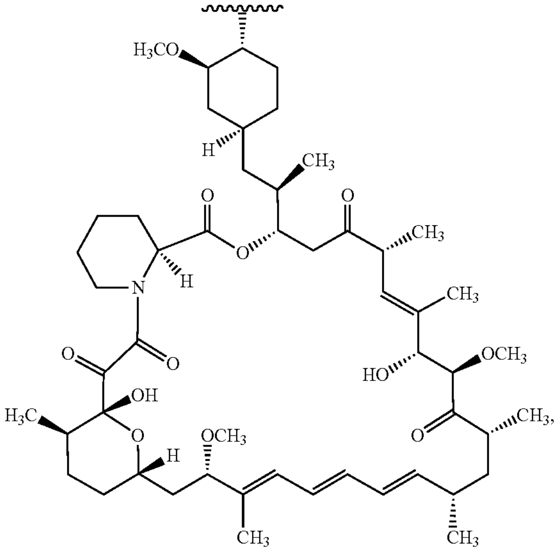 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or an analog thereof. In embodiments, the immunophilin-binding moiety is

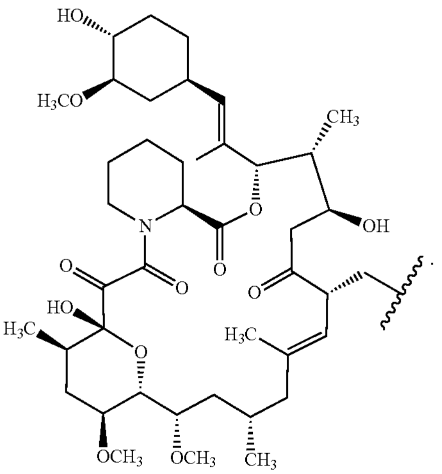 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
In embodiments, the immunophilin-binding moiety is
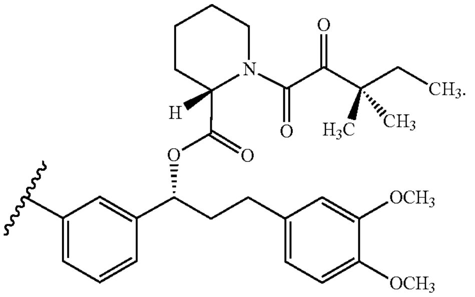
In embodiments, the immunophilin-binding moiety is
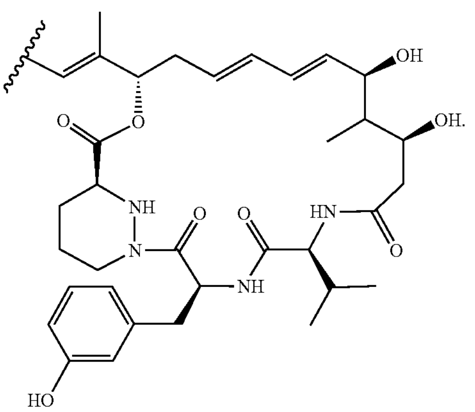 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
In embodiments, the immunophilin-binding moiety is
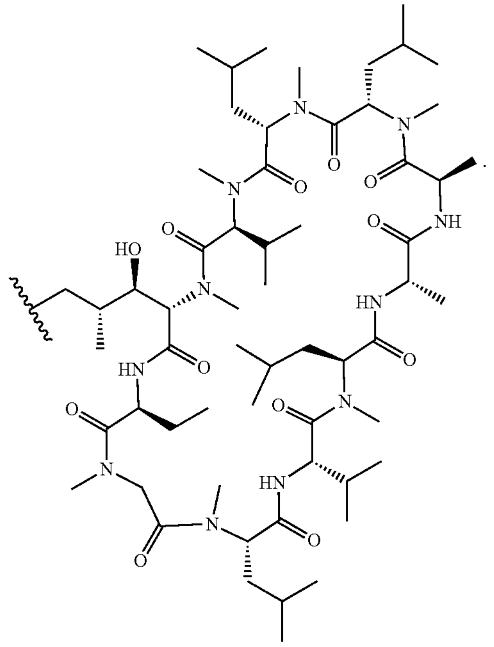 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
In embodiments, the immunophilin-binding moiety is
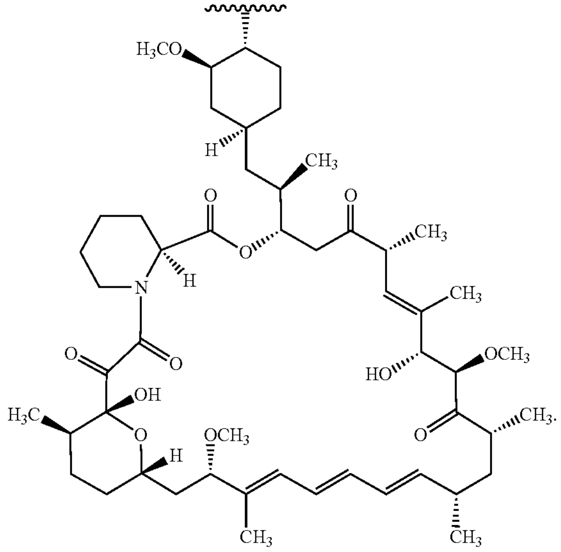 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
In embodiments, the immunophilin-binding moiety is
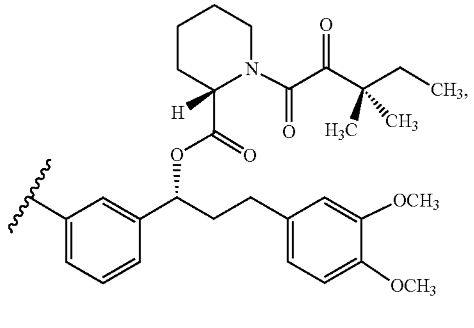

-continued
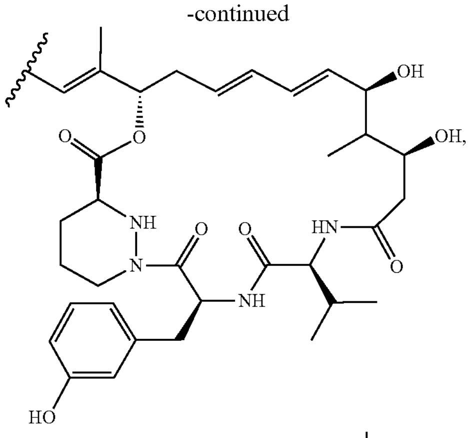
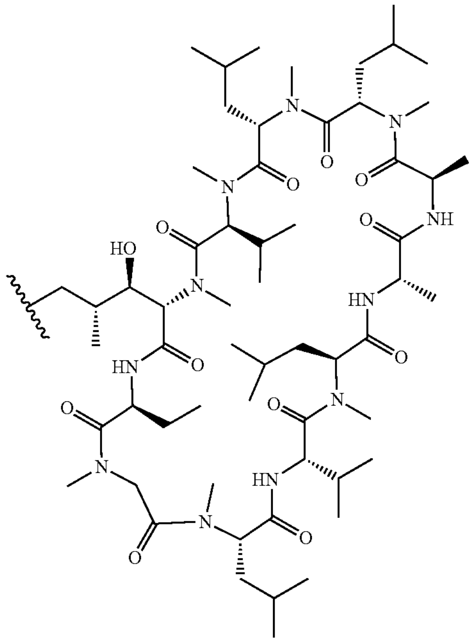
, or
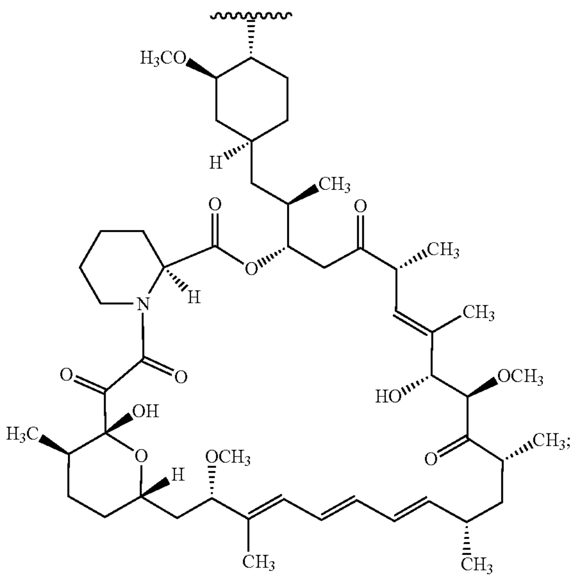 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
or an analog thereof.
In embodiments, the FKBP-binding moiety is
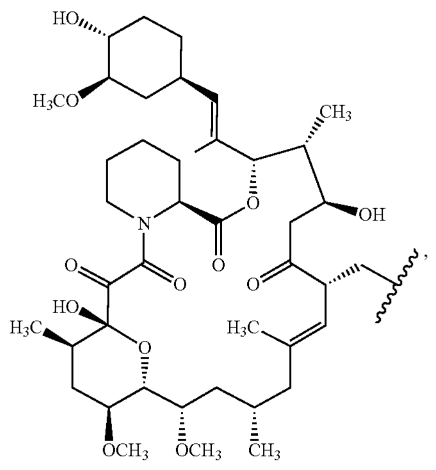 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
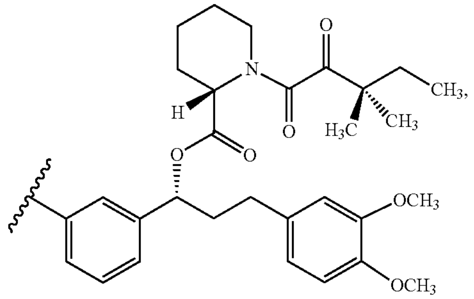
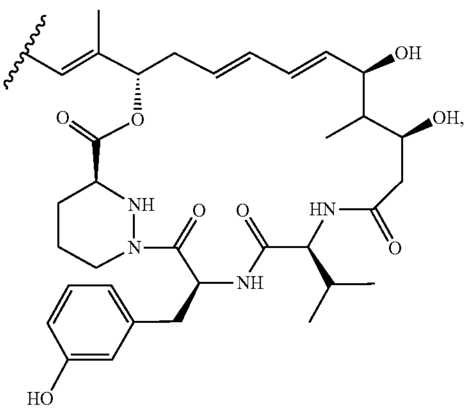
or -continued
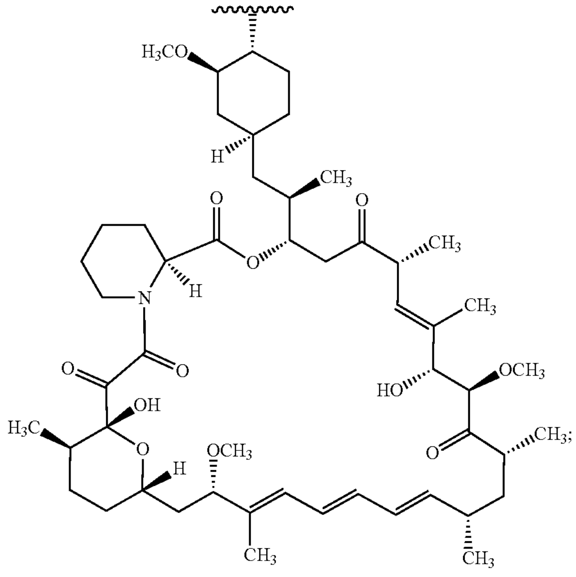
or an analog thereof. In embodiments, the FKBP-binding moiety is
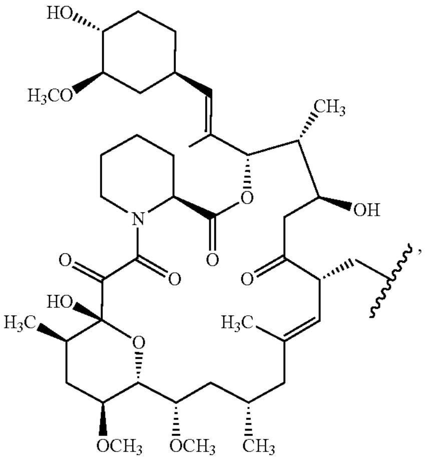
or an analog thereof. In embodiments, the FKBP-binding moiety is
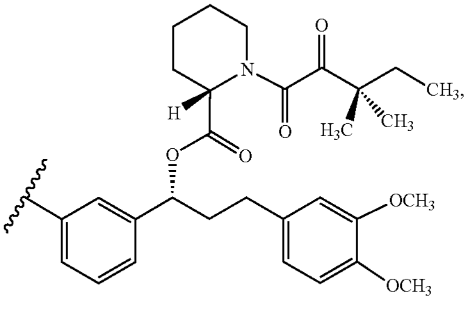
or an analog thereof. In embodiments, the FKBP-binding moiety is
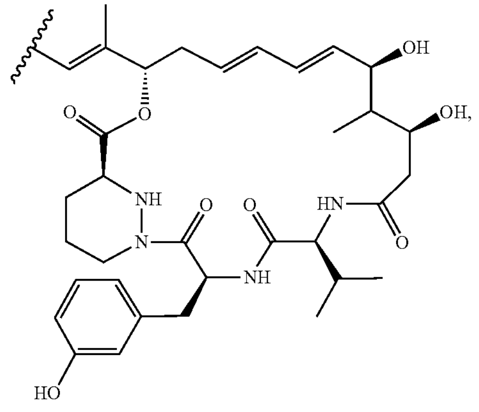 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
or an analog thereof. In embodiments, the FKBP-binding moiety is
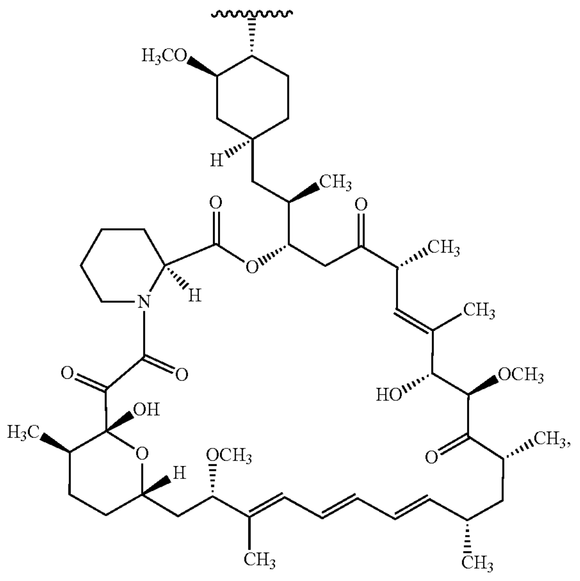 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
or an analog thereof.

In embodiments, the cyclophilin-binding moiety is
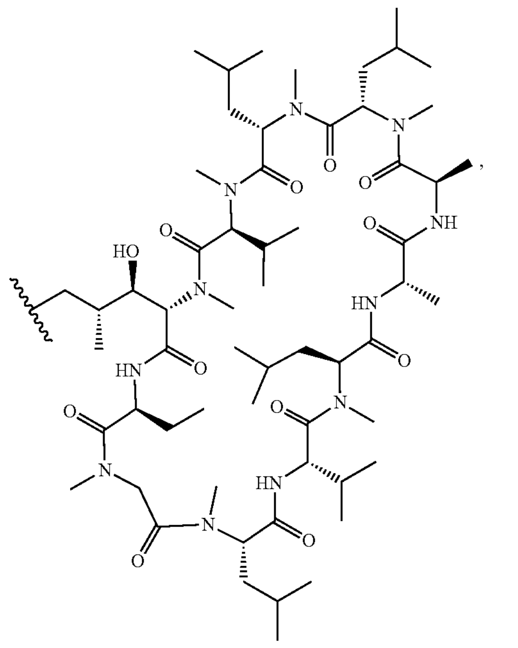 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
or an analog thereof.
In embodiments, the immunophilin-binding moiety is
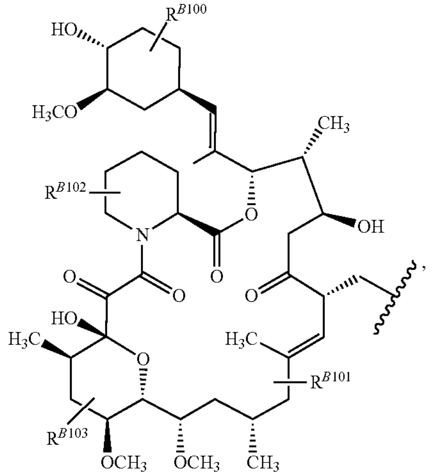
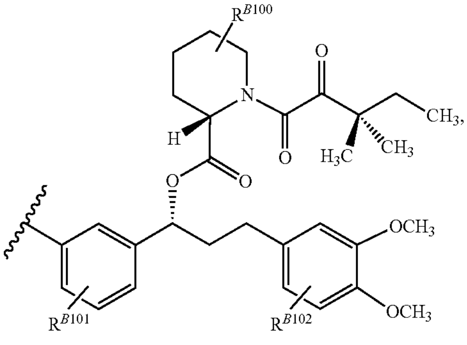
-continued
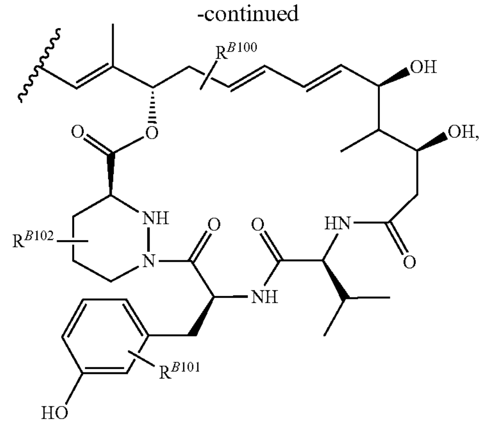
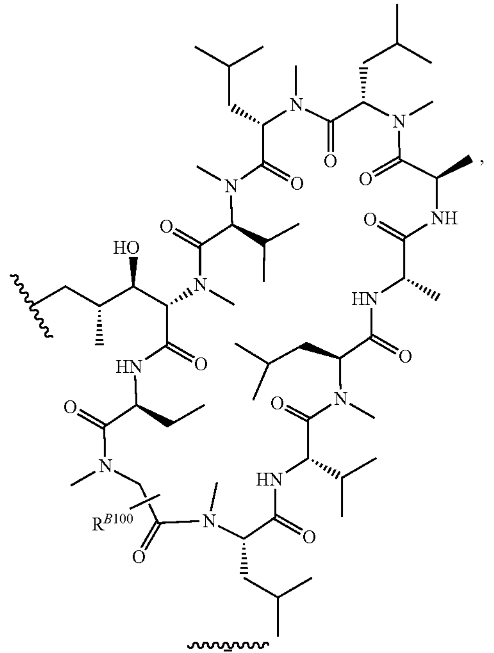
or
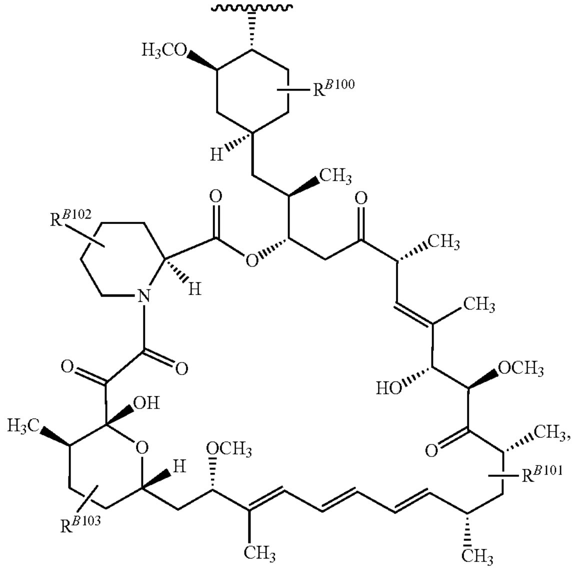
wherein $R^{B100}$, $R^{B101}$, $R^{B102}$, and $R^{B103}$ are as described herein and may be bonded to any atom in the ring ($R^{B100}$, $R^{B11}$, $R^{B102}$, and $R^{B103}$ are floating substituents). In embodiments, the immunophilin-binding moiety is

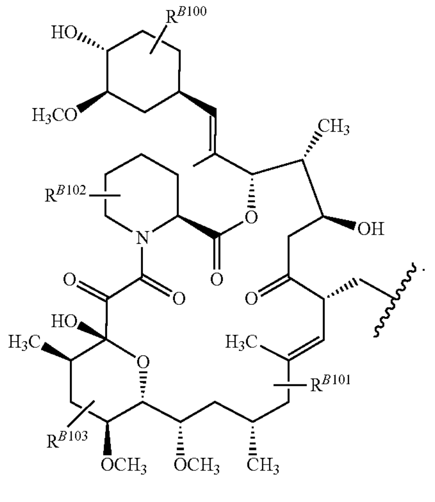

$R^{B100}$, $R^{B101}$, and $R^{B102}$ are as described herein. In embodiments, the immunophilin-binding moiety is

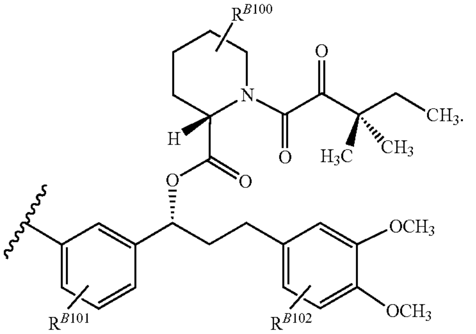

$R^{B100}$, $R^{B101}$, and $R^{B102}$ are as described herein. In embodiments, the immunophilin-binding moiety is

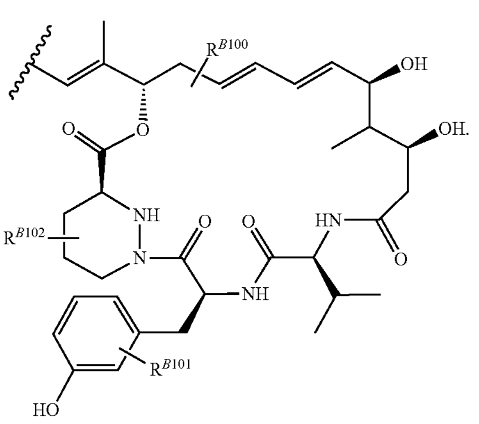

$R^{B100}$, $R^{B101}$, and $R^{B102}$ are as described herein. In embodiments, the immunophilin-binding moiety is

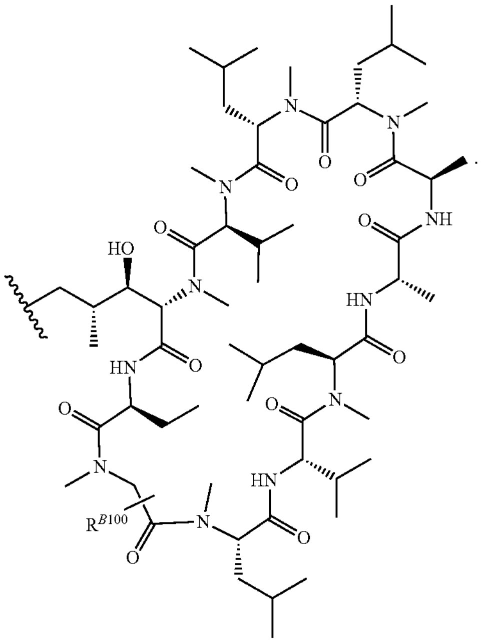

$R^{B100}$ is as described herein. In embodiments, the immunophilin-binding moiety is

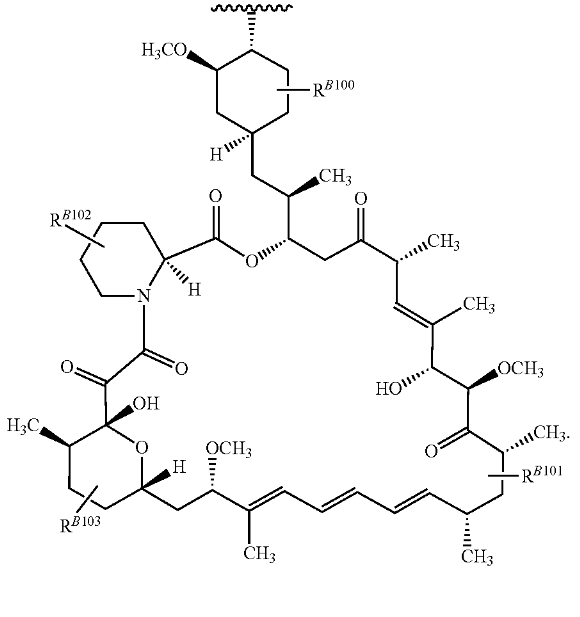

$R^{B100}$, $R^{B101}$, $R^{B102}$, and $R^{B103}$ are as described herein.

In embodiments, the immunophilin-binding moiety is not

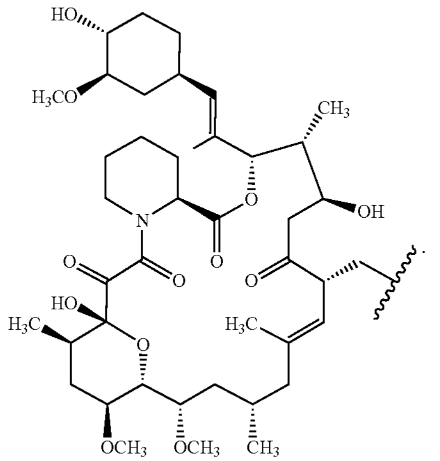 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

$R^{B100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B100}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B100}$ is substituted with a plurality of groups selected from substituent groups, size-limited substituent groups, and lower substituent groups; each substituent group, size-limited substituent group, and/or lower substituent group may optionally be different. In embodiments, when $R^{B100}$ is substituted, it is substituted with at least one substituent group. In embodiments, when $R^{B100}$ is substituted, it is substituted with at least one size-limited substituent group. In embodiments, when $R^{B100}$ is substituted, it is substituted with at least one lower substituent group.

In embodiments, $R^{B100}$ is independently hydrogen. In embodiments, $R^{B100}$ is independently halogen. In embodiments, $R^{B100}$ is independently —$CCl_3$. In embodiments, $R^{B100}$ is independently —$CBr_3$. In embodiments, $R^{B100}$ is independently —$CF_3$. In embodiments, $R^{B100}$ is independently —$CI_3$. In embodiments, $R^{B100}$ is independently —$CH_2Cl$. In embodiments, $R^{B100}$ is independently —$CH_2Br$. In embodiments, $R^{B100}$ is independently —$CH_2F$. In embodiments, $R^{B100}$ is independently —$CH_2I$. In embodiments, $R^{B100}$ is independently —$CHCl_2$. In embodiments, $R^{B100}$ is independently —$CHBr_2$. In embodiments, $R^{B100}$ is independently —$CHF_2$. In embodiments, $R^{B100}$ is independently —$CHI_2$. In embodiments, $R^{B100}$ is independently —CN. In embodiments, $R^{B100}$ is independently —OH. In embodiments, $R^{B100}$ is independently —$NH_2$. In embodiments, $R^{B100}$ is independently —COOH. In embodiments, $R^{B100}$ is independently —$CONH_2$. In embodiments, $R^{B100}$ is independently —$NO_2$. In embodiments, $R^{B100}$ is independently —SH. In embodiments, $R^{B100}$ is independently —$SO_3H$. In embodiments, $R^{B100}$ is independently —$SO_4H$. In embodiments, $R^{B100}$ is independently —$SO_2NH_2$. In embodiments, $R^{B100}$ is independently —$NHNH_2$. In embodiments, $R^{B100}$ is independently —$ONH_2$. In embodiments, $R^{B100}$ independently —NHC(O)$NHNH_2$. In embodiments, $R^{B100}$ is independently —NHC(O)$NH_2$. In embodiments, $R^{B100}$ is independently —$NHSO_2H$. In embodiments, $R^{B100}$ is independently —NHC(O)H. In embodiments, $R^{B100}$ is independently —NHC(O)OH. In embodiments, $R^{B100}$ is independently —NHC(NH)H. In embodiments, $R^{B100}$ is independently —NHC(NH)$NH_2$. In embodiments, $R^{B100}$ is independently —NHOH. In embodiments, $R^{B100}$ is independently —$OCCl_3$. In embodiments, $R^{B100}$ is independently —$OCBr_3$. In embodiments, $R^{B100}$ is independently —$OCF_3$. In embodiments, $R^{B100}$ is independently —$OCI_3$. In embodiments, $R^{B100}$ is independently —$OCH_2Cl$. In embodiments, $R^{B100}$ is independently —$OCH_2Br$. In embodiments, $R^{B100}$ is independently —$OCH_2F$. In embodiments, $R^{B0}$ is independently —$OCH_2I$. In embodiments, $R^{B100}$ is independently —$OCHCl_2$. In embodiments, $R^{B100}$ is independently —$OCHBr_2$. In embodiments, $R^{B100}$ is independently —$OCHF_2$. In embodiments, $R^{B100}$ is independently —$OCHI_2$. In embodiments, $R^{B100}$ is independently —$N_3$. In embodiments, $R^{B100}$ is independently substituted or unsubstituted alkyl (e.g., $C_1$-$C_8$, $C_1$-$C_6$, $C_1$-$C_4$, or $C_1$-$C_2$). In embodiments, $R^{B100}$ is independently substituted alkyl (e.g., $C_1$-$C_8$, $C_1$-$C_6$, $C_1$-$C_4$, or $C_1$-$C_2$). In embodiments, $R^{B100}$ is independently unsubstituted alkyl (e.g., $C_1$-$C_8$, $C_1$-$C_6$, $C_1$-$C_4$, or $C_1$-$C_2$). In embodiments, $R^{B100}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B100}$ is independently substituted heteroalkyl (e.g., 2 to 8 membered, 2 to 6 membered, 4 to 6 membered, 2 to 3 membered, or 4 to 5 membered). In embodiments, $R^{B100}$ is independently unsubstituted heteroalkyl (e.g., 2 to 8 membered, 2 to 6 membered, 4 to 6 membered, 2 to 3 membered, or 4 to 5 membered). In embodiments, $R^{B100}$ is independently substituted or unsubstituted cycloalkyl (e.g., $C_3$-$C_8$, $C_3$-$C_6$, $C_4$-$C_6$, or $C_5$-$C_6$). In embodiments, $R^{B100}$ is independently substituted cycloalkyl (e.g., $C_3$-$C_8$, $C_3$-$C_6$, $C_4$-$C_6$, or $C_5$-$C_6$). In embodiments, $R^{B100}$ is independently unsubstituted cycloalkyl (e.g., $C_3$-$C_8$, $C_3$-$C_6$, $C_4$-$C_6$, or $C_5$-$C_6$). In embodiments, $R^{B100}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B100}$ is independently substituted heterocycloalkyl (e.g., 3 to 8 membered, 3 to 6 membered, 4 to 6 membered, 4 to 5 membered, or 5 to 6 membered). In embodiments, $R^{B100}$ is independently unsubstituted heterocycloalkyl (e.g., 3 to 8 membered, 3 to 6 membered, 4 to 6 membered, 4 to 5 membered, or 5 to 6 membered). In embodiments, $R^{B100}$ is independently substituted or unsubstituted aryl (e.g., $C_6$-$C_{10}$ or phenyl). In embodiments, $R^{B100}$ is independently substituted aryl (e.g., $C_6$-$C_{10}$ or phenyl). In embodiments, $R^{B100}$ is independently unsubstituted aryl (e.g., $C_6$-$C_{10}$ or phenyl). In embodiments, $R^{B100}$ is independently substituted or unsubstituted heteroaryl (e.g., 5 to 10 membered, 5 to 9 membered, or 5 to 6 membered). In embodiments, $R^{B100}$ is independently substituted heteroaryl (e.g., 5 to 10 membered, 5 to 9 membered, or 5 to 6 membered). In embodiments, $R^{B100}$ is independently unsubstituted heteroaryl (e.g., 5 to 10 membered, 5 to 9 membered, or 5 to 6 membered).

$R^{B101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B101}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B101}$ is substituted with a plurality of groups selected from substituent groups, size-limited substituent groups, and lower substituent groups; each substituent group, size-limited substituent group, and/or lower substituent group may optionally be different. In embodiments, when $R^{B101}$ is substituted, it is substituted with at least one substituent group. In embodiments, when $R^{B101}$ is substituted, it is substituted with at least one size-limited substituent group. In embodiments, when $R^{B101}$ is substituted, it is substituted with at least one lower substituent group.

In embodiments, $R^{B101}$ is independently hydrogen. In embodiments, $R^{B101}$ is independently halogen. In embodiments, $R^{B101}$ is independently —$CCl_3$. In embodiments, $R^{B101}$ is independently —$CBr_3$. In embodiments, $R^{B101}$ is independently —$CF_3$. In embodiments, $R^{B101}$ is independently —$CI_3$. In embodiments, $R^{B101}$ is independently —$CH_2Cl$. In embodiments, $R^{B101}$ is independently —$CH_2Br$. In embodiments, $R^{B101}$ is independently —$CH_2F$. In embodiments, $R^{B101}$ is independently —$CH_2I$. In embodiments, $R^{B101}$ is independently —$CHCl_2$. In embodiments, $R^{B101}$ is independently —$CHBr_2$. In embodiments, $R^{B101}$ is independently —$CHF_2$. In embodiments, $R^{B101}$ is independently —$CHI_2$. In embodiments, $R^{B101}$ is independently —CN. In embodiments, $R^{B101}$ is independently —OH. In embodiments, $R^{B101}$ is independently —$NH_2$. In embodiments, $R^{B101}$ is independently —COOH. In embodiments, $R^{B101}$ is independently —$CONH_2$. In embodiments, $R^{B101}$ is independently —$NO_2$. In embodiments, $R^{B101}$ is independently —SH. In embodiments, $R^{B101}$ is independently —$SO_3H$. In embodiments, $R^{B101}$ is independently —$SO_4H$. In embodiments, $R^{B101}$ is independently —$SO_2NH_2$. In embodiments, $R^{B101}$ is independently —$NHNH_2$. In embodiments, $R^{B101}$ is independently —$ONH_2$. In embodiments, $R^{B101}$ independently —NHC(O)$NHNH_2$. In embodiments, $R^{B101}$ is independently —NHC(O)$NH_2$. In embodiments, $R^{B101}$ is independently —$NHSO_2H$. In embodiments, $R^{B101}$ is independently —NHC(O)H. In embodiments, $R^{B101}$ is independently —NHC(O)OH. In embodiments, $R^{B101}$ is independently —NHC(NH)H. In embodiments, $R^{B101}$ is independently —NHC(NH)$NH_2$. In embodiments, $R^{B101}$ is independently —NHOH. In embodiments, $R^{B101}$ is independently —$OCCl_3$. In embodiments, $R^{B101}$ is independently —$OCBr_3$. In embodiments, $R^{B101}$ is independently —$OCF_3$. In embodiments, $R^{B101}$ is independently —$OCI_3$. In embodiments, $R^{B101}$ is independently —$OCH_2Cl$. In embodiments, $R^{B101}$ is independently —$OCH_2Br$. In embodiments, $R^{B101}$ is independently —$OCH_2F$. In embodiments, $R^{B101}$ is independently —$OCH_2I$. In embodiments, $R^{B101}$ is independently —$OCHCl_2$. In embodiments, $R^{B101}$ is independently —$OCHBr_2$. In embodiments, $R^{B101}$ is independently —$OCHF_2$. In embodiments, $R^{B101}$ is independently —$OCHI_2$. In embodiments, $R^{B101}$ is independently —$N_3$. In embodiments, $R^{B101}$ is independently substituted or unsubstituted alkyl (e.g., $C_1$-$C_8$, $C_1$-$C_6$, $C_1$-$C_4$, or $C_1$-$C_2$). In embodiments, $R^{B101}$ is independently substituted alkyl (e.g., $C_1$-$C_8$, $C_1$-$C_6$, $C_1$-$C_4$, or $C_1$-$C_2$). In embodiments, $R^{B101}$ is independently unsubstituted alkyl (e.g., $C_1$-$C_8$, $C_1$-$C_6$, $C_1$-$C_4$, or $C_1$-$C_2$). In embodiments, $R^{B101}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B101}$ is independently substituted heteroalkyl (e.g., 2 to 8 membered, 2 to 6 membered, 4 to 6 membered, 2 to 3 membered, or 4 to 5 membered). In embodiments, $R^{B101}$ is independently unsubstituted heteroalkyl (e.g., 2 to 8 membered, 2 to 6 membered, 4 to 6 membered, 2 to 3 membered, or 4 to 5 membered). In embodiments, $R^{B101}$ is independently substituted or unsubstituted cycloalkyl (e.g., $C_3$-$C_8$, $C_3$-$C_6$, $C_4$-$C_6$, or $C_5$-$C_6$). In embodiments, $R^{B101}$ is independently substituted cycloalkyl (e.g., $C_3$-$C_8$, $C_3$-$C_6$, $C_4$-$C_6$, or $C_5$-$C_6$). In embodiments, $R^{B101}$ is independently unsubstituted cycloalkyl (e.g., $C_3$-$C_8$, $C_3$-$C_6$, $C_4$-$C_6$, or $C_5$-$C_6$). In embodiments, $R^{B101}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B101}$ is independently substituted heterocycloalkyl (e.g., 3 to 8 membered, 3 to 6 membered, 4 to 6 membered, 4 to 5 membered, or 5 to 6 membered). In embodiments, $R^{B101}$ is independently unsubstituted heterocycloalkyl (e.g., 3 to 8 membered, 3 to 6 membered, 4 to 6 membered, 4 to 5 membered, or 5 to 6 membered). In embodiments, $R^{B101}$ is independently substituted or unsubstituted aryl (e.g., $C_6$-$C_{10}$ or phenyl). In embodiments, $R^{B101}$ is independently substituted aryl (e.g., $C_6$-$C_{10}$ or phenyl). In embodiments, $R^{B101}$ is independently unsubstituted aryl (e.g., $C_6$-$C_{10}$ or phenyl). In embodiments, $R^{B101}$ is independently substituted or unsubstituted heteroaryl (e.g., 5 to 10 membered, 5 to 9 membered, or 5 to 6 membered). In embodiments, $R^{B101}$ is independently substituted heteroaryl (e.g., 5 to 10 membered, 5 to 9 membered, or 5 to 6 membered). In embodiments, $R^{B101}$ is independently unsubstituted heteroaryl (e.g., 5 to 10 membered, 5 to 9 membered, or 5 to 6 membered).

$R^{B102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B102}$ is substituted with a plurality of groups selected from substituent groups, size-limited substituent groups, and lower substituent groups; each substituent group, size-limited substituent group, and/or lower substituent group may optionally be different. In embodiments, when $R^{B102}$ is substituted, it is substituted with at least one substituent group. In embodiments, when $R^{B102}$ is substituted, it is substituted with at least one size-limited substituent group. In embodiments, when $R^{B102}$ is substituted, it is substituted with at least one lower substituent group.

In embodiments, $R^{B102}$ is independently hydrogen. In embodiments, $R^{B102}$ is independently halogen. In embodiments, $R^{B102}$ is independently —$CCl_3$. In embodiments, $R^{B102}$ is independently —$CBr_3$. In embodiments, $R^{B102}$ is independently —$CF_3$. In embodiments, $R^{B102}$ is independently —$CI_3$. In embodiments, $R^{B102}$ is independently —$CH_2Cl$. In embodiments, $R^{B102}$ is independently —$CH_2Br$. In embodiments, $R^{B102}$ is independently —$CH_2F$. In embodiments, $R^{B102}$ is independently —$CH_2I$. In embodiments, $R^{B102}$ is independently —$CHCl_2$. In embodiments, $R^{B102}$ is independently —$CHBr_2$. In embodiments, $R^{B102}$ is independently —$CHF_2$. In embodiments, $R^{B102}$ is independently —$CHI_2$. In embodiments, $R^{B102}$ is independently —CN. In embodiments, $R^{B102}$ is independently —OH. In embodiments, $R^{B102}$ is independently —$NH_2$. In embodiments, $R^{B102}$ is independently —COOH. In embodiments, $R^{B102}$ is independently —$CONH_2$. In embodiments, $R^{B102}$ is independently —$NO_2$. In embodiments, $R^{B102}$ is independently —SH. In embodiments, $R^{B102}$ is independently —$SO_3H$. In embodiments, $R^{B102}$ is independently —$SO_4H$. In embodiments, $R^{B102}$ is independently —$SO_2NH_2$. In embodiments, $R^{B102}$ is independently —$NHNH_2$. In embodiments, $R^{B102}$ is independently —$ONH_2$. In embodiments, $R^{B102}$ independently —NHC(O)$NHNH_2$. In embodiments, $R^{B102}$ is independently —NHC(O)$NH_2$. In embodiments, $R^{B102}$ is independently —$NHSO_2H$. In embodiments, $R^{B102}$ is independently —NHC(O)H. In embodiments, $R^{B102}$ is independently —NHC(O)OH. In embodiments, $R^{B102}$ is independently —NHC(NH)H. In embodiments, $R^{B102}$ is independently —NHC(NH)$NH_2$. In embodiments, $R^{B102}$ is independently —NHOH. In embodiments, $R^{B102}$ is independently —$OCCl_3$. In embodiments, $R^{B102}$ is independently —$OCBr_3$. In embodiments, $R^{B102}$ is independently —$OCF_3$. In embodiments, $R^{B102}$ is independently —$OCI_3$. In embodiments, $R^{B102}$ is independently —$OCH_2Cl$. In embodiments, $R^{B102}$ is independently —$OCH_2Br$. In embodiments, $R^{B102}$ is independently —$OCH_2F$. In embodiments, $R^{B102}$ is independently —$OCH_2I$. In embodiments, $R^{B102}$ is independently —$OCHCl_2$. In embodiments, $R^{B102}$ is independently —$OCHBr_2$. In embodiments, $R^{B1020}$ is independently —$OCHF_2$. In embodiments, $R^{B102}$ is independently —$OCHI_2$. In embodiments, $R^{B102}$ is independently —$N_3$. In embodiments, $R^{B102}$ is independently substituted or unsubstituted alkyl (e.g., $C_1$-$C_8$, $C_1$-$C_6$, $C_1$-$C_4$, or $C_1$-$C_2$). In embodiments, $R^{B102}$ is independently substituted alkyl (e.g., $C_1$-$C_8$, $C_1$-$C_6$, $C_1$-$C_4$, or $C_1$-$C_2$). In embodiments, $R^{B102}$ is independently unsubstituted alkyl (e.g., $C_1$-$C_8$, $C_1$-$C_6$, $C_1$-$C_4$, or $C_1$-$C_2$). In embodiments, $R^{B102}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B102}$ is independently substituted heteroalkyl (e.g., 2 to 8 membered, 2 to 6 membered, 4 to 6 membered, 2 to 3 membered, or 4 to 5 membered). In embodiments, $R^{B102}$ is independently unsubstituted heteroalkyl (e.g., 2 to 8 membered, 2 to 6 membered, 4 to 6 membered, 2 to 3 membered, or 4 to 5 membered). In embodiments, $R^{B102}$ is independently substituted or unsubstituted cycloalkyl (e.g., $C_3$-$C_8$, $C_3$-$C_6$, $C_4$-$C_6$, or $C_5$-$C_6$). In embodiments, $R^{B102}$ is independently substituted cycloalkyl (e.g., $C_3$-$C_8$, $C_3$-$C_6$, $C_4$-$C_6$, or $C_5$-$C_6$). In embodiments, $R^{B102}$ is independently unsubstituted cycloalkyl (e.g., $C_3$-$C_8$, $C_3$-$C_6$, $C_4$-$C_6$, or $C_5$-$C_6$). In embodiments, $R^{B102}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B102}$ is independently substituted heterocycloalkyl (e.g., 3 to 8 membered, 3 to 6 membered, 4 to 6 membered, 4 to 5 membered, or 5 to 6 membered). In embodiments, $R^{B102}$ is independently unsubstituted heterocycloalkyl (e.g., 3 to 8 membered, 3 to 6 membered, 4 to 6 membered, 4 to 5 membered, or 5 to 6 membered). In embodiments, $R^{B102}$ is independently substituted or unsubstituted aryl (e.g., $C_6$-$C_{10}$ or phenyl). In embodiments, $R^{B102}$ is independently substituted aryl (e.g., $C_6$-$C_{10}$ or phenyl). In embodiments, $R^{B102}$ is independently unsubstituted aryl (e.g., $C_6$-$C_{10}$ or phenyl). In embodiments, $R^{B102}$ is independently substituted or unsubstituted heteroaryl (e.g., 5 to 10 membered, 5 to 9 membered, or 5 to 6 membered). In embodiments, $R^{B102}$ is independently substituted heteroaryl (e.g., 5 to 10 membered, 5 to 9 membered, or 5 to 6 membered). In embodiments, $R^{B102}$ is independently unsubstituted heteroaryl (e.g., 5 to 10 membered, 5 to 9 membered, or 5 to 6 membered).

$R^{B103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B103}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B103}$ is substituted with a plurality of groups selected from substituent groups, size-limited substituent groups, and lower substituent groups; each substituent group, size-limited substituent group, and/or lower substituent group may optionally be different. In embodiments, when $R^{B103}$ is substituted, it is substituted with at least one substituent group. In embodiments, when $R^{B103}$ is substituted, it is substituted with at least one size-limited substituent group. In embodiments, when $R^{B103}$ is substituted, it is substituted with at least one lower substituent group.

In embodiments, $R^{B103}$ is independently hydrogen. In embodiments, $R^{B103}$ is independently halogen. In embodiments, $R^{B103}$ is independently $—CCl_3$. In embodiments, $R^{B103}$ is independently $—CBr_3$. In embodiments, $R^{B103}$ is independently $—CF_3$. In embodiments, $R^{B103}$ is independently $—CI_3$. In embodiments, $R^{B103}$ is independently $—CH_2Cl$. In embodiments, $R^{B103}$ is independently $—CH_2Br$. In embodiments, $R^{B103}$ is independently $—CH_2F$. In embodiments, $R^{B103}$ is independently $—CH_2I$. In embodiments, $R^{B103}$ is independently $—CHCl_2$. In embodiments, $R^{B103}$ is independently $—CHBr_2$. In embodiments, $R^{B103}$ is independently $—CHF_2$. In embodiments, $R^{B103}$ is independently $—CHI_2$. In embodiments, $R^{B103}$ is independently —CN. In embodiments, $R^{B103}$ is independently —OH. In embodiments, $R^{B103}$ is independently $—NH_2$. In embodiments, $R^{B103}$ is independently —COOH. In embodiments, $R^{B103}$ is independently $—CONH_2$. In embodiments, $R^{B103}$ is independently $—NO_2$. In embodiments, $R^{B103}$ is independently —SH. In embodiments, $R^{B103}$ is independently $—SO_3H$. In embodiments, $R^{B103}$ is independently $—SO_4H$. In embodiments, $R^{B103}$ is independently $—SO_2NH_2$. In embodiments, $R^{B103}$ is independently $—NHNH_2$. In embodiments, $R^{B103}$ is independently $—ONH_2$. In embodiments, $R^{B103}$ independently $—NHC(O)NHNH_2$. In embodiments, $R^{B103}$ is independently $—NHC(O)NH_2$. In embodiments, $R^{B103}$ is independently $—NHSO_2H$. In embodiments, $R^{B103}$ is independently —NHC(O)H. In embodiments, $R^{B103}$ is independently —NHC(O)OH. In embodiments, $R^{B103}$ is independently —NHC(NH)H. In embodiments, $R^{B103}$ is independently $—NHC(NH)NH_2$. In embodiments, $R^{B103}$ is independently —NHOH. In embodiments, $R^{B103}$ is independently $—OCCl_3$. In embodiments, $R^{B103}$ is independently $—OCBr_3$. In embodiments, $R^{B103}$ is independently $—OCF_3$. In embodiments, $R^{B103}$ is independently $—OCI_3$. In embodiments, $R^{B103}$ is independently $—OCH_2Cl$. In embodiments, $R^{B103}$ is independently $—OCH_2Br$. In embodiments, $R^{B103}$ is independently $—OCH_2F$. In embodiments, $R^{B103}$ is independently $—OCH_2I$. In embodiments, $R^{B103}$ is independently $—OCHCl_2$. In embodiments, $R^{B103}$ is independently $—OCHBr_2$. In embodiments, $R^{B1030}$ is independently $—OCHF_2$. In embodiments, $R^{B103}$ is independently $—OCHI_2$. In embodiments, $R^{B103}$ is independently $—N_3$. In embodiments, $R^{B103}$ is independently substituted or unsubstituted alkyl (e.g., $C_1$-$C_8$, $C_1$-$C_6$, $C_1$-$C_4$, or $C_1$-$C_2$). In embodiments, $R^{B103}$ is independently substituted alkyl (e.g., $C_1$-$C_8$, $C_1$-$C_6$, $C_1$-$C_4$, or $C_1$-$C_2$). In embodiments, $R^{B103}$ is independently unsubstituted alkyl (e.g., $C_1$-$C_8$, $C_1$-$C_6$, $C_1$-$C_4$, or $C_1$-$C_2$). In embodiments, $R^{B103}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B103}$ is independently substituted heteroalkyl (e.g., 2 to 8 membered, 2 to 6 membered, 4 to 6 membered, 2 to 3 membered, or 4 to 5 membered). In embodiments, $R^{B103}$ is independently unsubstituted heteroalkyl (e.g., 2 to 8 membered, 2 to 6 membered, 4 to 6 membered, 2 to 3 membered, or 4 to 5 membered). In embodiments, $R^{B103}$ is independently substituted or unsubstituted cycloalkyl (e.g., $C_3$-$C_8$, $C_3$-$C_6$, $C_4$-$C_6$, or $C_5$-$C_6$). In embodiments, $R^{B103}$ is independently substituted cycloalkyl (e.g., $C_3$-$C_8$, $C_3$-$C_6$, $C_4$-$C_6$, or $C_5$-$C_6$). In embodiments, $R^{B103}$ is independently unsubstituted cycloalkyl (e.g., $C_3$-$C_8$, $C_3$-$C_6$, $C_4$-$C_6$, or $C_5$-$C_6$). In embodiments, $R^{B103}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B103}$ is independently substituted heterocycloalkyl (e.g., 3 to 8 membered, 3 to 6 membered, 4 to 6 membered, 4 to 5 membered, or 5 to 6 membered). In embodiments, $R^{B103}$ is independently unsubstituted heterocycloalkyl (e.g., 3 to 8 membered, 3 to 6 membered, 4 to 6 membered, 4 to 5 membered, or 5 to 6 membered). In embodiments, $R^{B103}$ is independently substituted or unsubstituted aryl (e.g., $C_6$-$C_{10}$ or phenyl). In embodiments, $R^{B103}$ is independently substituted aryl (e.g., $C_6$-$C_{10}$ or phenyl). In embodiments, $R^{B103}$ is independently unsubstituted aryl (e.g., $C_6$-$C_{10}$ or phenyl). In embodiments, $R^{B103}$ is independently substituted or unsubstituted heteroaryl (e.g., 5 to 10 membered, 5 to 9 membered, or 5 to 6 membered). In embodiments, $R^{B103}$ is independently substituted heteroaryl (e.g., 5 to 10 membered, 5 to 9 membered, or 5 to 6 membered). In embodiments, $R^{B103}$ is independently unsubstituted heteroaryl (e.g., 5 to 10 membered, 5 to 9 membered, or 5 to 6 membered).

In embodiments, $L^{B1}$ is a bond or covalent linker.

In embodiments, $L^{B1}$ is $L^{B2}$-$L^{B3}$-$L^{B4}$-$L^{B5}$-$L^{B6}$.

In embodiments, $L^{B1}$ is $L^{B2}$-$L^{B3}$-$L^{B4}$.

$L^{B2}$ is a bond, $—S(O)_2—$, $—N(R^{B2})—$, —O—, —S—, —C(O)—, $—C(O)N(R^{B2})—$, $—N(R^{B2})C(O)—$, $—N(R^{B2})C(O)NH—$, $—NHC(O)N(R^{B2})—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B3}$ is a bond, $—S(O)_2—$, $—N(R^{B3})—$, —O—, —S—, —C(O)—, $—C(O)N(R^{B3})—$, $—N(R^{B3})C(O)—$, $—N(R^{B3})C(O)NH—$, $—NHC(O)N(R^{B3})—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B4}$ is a bond, $—S(O)_2—$, $—N(R^{B4})—$, —O—, —S—, —C(O)—, $—C(O)N(R^{B4})—$, $—N(R^{B4})C(O)—$, $—N(R^{B4})C(O)NH—$, $—NHC(O)N(R^{B4})—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B5}$ is a bond, $—S(O)_2—$, $—N(R^{B5})—$, —O—, —S—, —C(O)—, $—C(O)N(R^{B5})—$, $—N(R^{B5})C(O)—$, $—N(R^{B5})C(O)NH—$, $—NHC(O)N(R^{B5})—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B6}$ is a bond, $—S(O)_2—$, $—N(R^{B6})—$, —O—, —S—, —C(O)—, $—C(O)N(R^{B6})—$, $—N(R^{B6})C(O)—$, $—N(R^{B6})C(O)NH—$, $—NHC(O)N(R^{B6})—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

In embodiments, $L^{B2}$ is a bond, $—S(O)_2—$, $—N(R^{B2})—$, —O—, —S—, —C(O)—, $—C(O)N(R^{B2})—$, $—N(R^{B2})C(O)—$, $—N(R^{B2})C(O)NH—$, —NHC $(O)N(R^{B2})—$, —C(O)

O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B3}$ is a bond, —S(O)$_2$—, —N($R^{B3}$)—, —O—, —S—, —C(O)—, —C(O)N($R^{B3}$)—, —N($R^{B3}$)C(O)—, —N($R^{B3}$)C(O)NH—, —NH(O)N($R^{B3}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B4}$ is a bond, —S(O)$_2$—, —N($R^{B4}$)—, —O—, —S—, —C(O)—, —C(O)N($R^{B4}$)—, —N($R^{B4}$)C(O)—, —N($R^{B4}$)C(O)NH—, —NH(O)N($R^{B4}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B5}$ is a bond, —S(O)$_2$—, —N($R^{B5}$)—, —O—, —S—, —C(O)—, —C(O)N($R^{B5}$)—, —N($R^{B5}$)C(O)—, —N($R^{B5}$)C(O)NH—, —NH(O)N($R^{B5}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B6}$ is a bond, —S(O)$_2$—, —N($R^{B6}$)—, —O—, —S—, —C(O)—, —C(O)N($R^{B6}$)—, —N($R^{B6}$)C(O)—, —N($R^{B6}$)C(O)NH—, —NH(O)N($R^{B6}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^{B2}$, $R^{B3}$, $R^{B4}$, $R^{B5}$, and $R^{B6}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B2}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B2}$ is substituted with a plurality of groups selected from substituent groups, size-limited substituent groups, and lower substituent groups; each substituent group, size-limited substituent group, and/or lower substituent group may optionally be different. In embodiments, when $L^{B2}$ is substituted, it is substituted with at least one substituent group. In embodiments, when $L^{B2}$ is substituted, it is substituted with at least one size-limited substituent group. In embodiments, when $L^{B2}$ is substituted, it is substituted with at least one lower substituent group.

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted or unsubstituted $C_1$-$C_6$ alkylene, or substituted or unsubstituted 2 to 6 membered heteroalkylene.

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, $R^{B2}$-substituted or unsubstituted alkylene, $R^{B2}$-substituted or unsubstituted heteroalkylene, $R^{B2}$-substituted or unsubstituted cycloalkylene, $R^{B2}$-substituted or unsubstituted heterocycloalkylene, $R^{B2}$-substituted or unsubstituted arylene, or $R^{B2}$-substituted or unsubstituted heteroarylene.

In embodiments, $R^{B2}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B2}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B2}$ is substituted with a plurality of groups selected from substituent groups, size-limited substituent groups, and lower substituent groups; each substituent group, size-limited substituent group, and/or lower substituent group may optionally be different. In embodiments, when $R^{B2}$ is substituted, it is substituted with at least one substituent group. In embodiments, when $R^{B2}$ is substituted, it is substituted with at least one size-limited substituent group. In embodiments, when $R^{B2}$ is substituted, it is substituted with at least one lower substituent group.

In embodiments, $R^{B2}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, $R^{B20}$-substituted or unsubstituted alkyl, $R^{B20}$-substituted or unsubstituted heteroalkyl, $R^{B20}$-substituted or unsubstituted cycloalkyl, $R^{B20}$-substituted or unsubstituted heterocycloalkyl, $R^{B20}$-substituted or unsubstituted aryl, or $R^{B20}$-substituted or unsubstituted heteroaryl.

$R^{B20}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B20}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B3}$ is a bond, —$S(O)_2$—, —N($R^{B3}$)—, —O—, —S—, —C(O)—, —C(O)N($R^{B3}$)—, —N($R^{B3}$)C(O)—, —N($R^{B3}$)C(O)NH—, —NHC(O)N($R^{B3}$)—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{B3}$ is a bond, —$S(O)_2$—, —N($R^{B3}$)—, —O—, —S—, —C(O)—, —C(O)N($R^{B3}$)—, —N($R^{B3}$)C(O)—, —N($R^{B3}$)C(O)NH—, —NHC(O)N($R^{B3}$)—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B3}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B3}$ is substituted with a plurality of groups selected from substituent groups, size-limited substituent groups, and lower substituent groups; each substituent group, size-limited substituent group, and/or lower substituent group may optionally be different. In embodiments, when $L^{B3}$ is substituted, it is substituted with at least one substituent group. In embodiments, when $L^{B3}$ is substituted, it is substituted with at least one size-limited substituent group. In embodiments, when $L^{B3}$ is substituted, it is substituted with at least one lower substituent group.

In embodiments, $L^{B3}$ is a bond, —S(O)$_2$—, —N($R^{B3}$)—, —O—, —S—, —C(O)—, —C(O)N($R^{B3}$)—, —N($R^{B3}$)C(O)—, —N($R^{B3}$)C(O)NH—, —NHC(O)N($R^{B3}$)—, —C(O)O—, —OC(O)—, substituted or unsubstituted $C_1$-$C_6$ alkylene, or substituted or unsubstituted 2 to 6 membered heteroalkylene.

In embodiments, $L^{B3}$ is a bond, —S(O)$_2$—, —N($R^{B3}$)—, —O—, —S—, —C(O)—, —C(O)N($R^{B3}$)—, —N($R^{B3}$)C(O)—, —N($R^{B3}$)C(O)NH—, —NHC(O)N($R^{B3}$)—, —C(O)O—, —OC(O)—, $R^{B3}$-substituted or unsubstituted alkylene, $R^{B3}$-substituted or unsubstituted heteroalkylene, $R^{B3}$-substituted or unsubstituted cycloalkylene, $R^{B3}$-substituted or unsubstituted heterocycloalkylene, $R^{B3}$-substituted or unsubstituted arylene, or $R^{B3}$-substituted or unsubstituted heteroarylene.

In embodiments, $R^{B3}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B3}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B3}$ is substituted with a plurality of groups selected from substituent groups, size-limited substituent groups, and lower substituent groups; each substituent group, size-limited substituent group, and/or lower substituent group may optionally be different. In embodiments, when $R^{B3}$ is substituted, it is substituted with at least one substituent group. In embodiments, when $R^{B3}$ is substituted, it is substituted with at least one size-limited substituent group. In embodiments, when $R^{B3}$ is substituted, it is substituted with at least one lower substituent group.

In embodiments, $R^{B3}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, $R^{B30}$-substituted or unsubstituted alkyl, $R^{B30}$-substituted or unsubstituted heteroalkyl, $R^{B30}$-substituted or unsubstituted cycloalkyl, $R^{B30}$-substituted or unsubstituted heterocycloalkyl, $R^{B30}$-substituted or unsubstituted aryl, or $R^{B30}$-substituted or unsubstituted heteroaryl.

$R^{B30}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B30}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B4}$ is a bond, —S(O)$_2$—, —N($R^{B4}$)—, —O—, —S—, —C(O)—, —C(O)N($R^{B4}$)—, —N($R^{B4}$)C(O)—, —N($R^{B4}$)C(O)NH—, —NHC(O)N($R^{B4}$)—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B4}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B4}$ is substituted with a plurality of groups selected from substituent groups, size-limited substituent groups, and lower substituent groups; each substituent group, size-limited substituent group, and/or lower substituent group may optionally be different. In embodiments, when $L^{B4}$ is substituted, it is substituted with at least one substituent group. In embodiments, when $L^{B4}$ is substituted, it is substituted with at least one size-limited substituent group. In embodiments, when $L^{B4}$ is substituted, it is substituted with at least one lower substituent group.

In embodiments, $L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted $C_1$-$C_6$ alkylene, or substituted or unsubstituted 2 to 6 membered heteroalkylene.

In embodiments, $L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, $R^{B4}$-substituted or unsubstituted alkylene, $R^{B4}$-substituted or unsubstituted heteroalkylene, $R^{B4}$-substituted or unsubstituted cycloalkylene, $R^{B4}$-substituted or unsubstituted heterocycloalkylene, $R^{B4}$-substituted or unsubstituted arylene, or $R^{B4}$-substituted or unsubstituted heteroarylene.

In embodiments, $R^{B4}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B4}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B4}$ is substituted with a plurality of groups selected from substituent groups, size-limited substituent groups, and lower substituent groups; each substituent group, size-limited substituent group, and/or lower substituent group may optionally be different. In embodiments, when $R^{B4}$ is substituted, it is substituted with at least one substituent group. In embodiments, when $R^{B4}$ is substituted, it is substituted with at least one size-limited substituent group. In embodiments, when $R^{B4}$ is substituted, it is substituted with at least one lower substituent group.

In embodiments, $R^{B4}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, $R^{B40}$-substituted or unsubstituted alkyl, $R^{B40}$-substituted or unsubstituted heteroalkyl, $R^{B40}$-substituted or unsubstituted cycloalkyl, $R^{B40}$-substituted or unsubstituted heterocycloalkyl, $R^{B40}$-substituted or unsubstituted aryl, or $R^{B40}$-substituted or unsubstituted heteroaryl.

$R^{B40}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B40}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B5}$ is a bond, $—S(O)_2—$, $—N(R^{B5})—$, —O—, —S—, —C(O)—, $—C(O)N(R^{B5})—$, $—N(R^{B5})C(O)—$, $—N(R^{B5})C(O)NH—$, $—NHC(O)N(R^{B5})—$, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B5}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B5}$ is substituted with a plurality of groups selected from substituent groups, size-limited substituent groups, and lower substituent groups; each substituent group, size-limited substituent group, and/or lower substituent group may optionally be different. In embodiments, when $L^{B5}$ is substituted, it is substituted with at least one substituent group. In embodiments, when $L^{B5}$ is substituted, it is substituted with at least one size-limited substituent group. In embodiments, when $L^{B5}$ is substituted, it is substituted with at least one lower substituent group.

In embodiments, $L^{B5}$ is a bond, $—S(O)_2—$, $—N(R^{B5})—$, —O—, —S—, —C(O)—, $—C(O)N(R^{B5})—$, $—N(R^{B5})C(O)—$, $—N(R^{B5})C(O)NH—$, $—NHC(O)N(R^{B5})—$, —C(O)O—, —OC(O)—, substituted or unsubstituted $C_1$-$C_6$ alkylene, or substituted or unsubstituted 2 to 6 membered heteroalkylene.

In embodiments, $L^{B5}$ is a bond, $—S(O)_2—$, $—N(R^{B5})—$, —O—, —S—, —C(O)—, $—C(O)N(R^{B5})—$, $—N(R^{B5})C(O)—$, $—N(R^{B5})C(O)NH—$, $—NHC(O)N(R^{B5})—$, —C(O)O—, —OC(O)—, $R^{B5}$-substituted or unsubstituted alkylene, $R^{B5}$-substituted or unsubstituted heteroalkylene, $R^{B5}$-substituted or unsubstituted cycloalkylene, $R^{B5}$-substituted or unsubstituted heterocycloalkylene, $R^{B5}$-substituted or unsubstituted arylene, or $R^{B5}$-substituted or unsubstituted heteroarylene.

In embodiments, $R^{B5}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B5}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B5}$ is substituted with a plurality of groups selected from substituent groups, size-limited substituent groups, and lower substituent groups; each substituent group, size-limited substituent group, and/or lower substituent group may optionally be different. In embodiments, when $R^{B5}$ is substituted, it is substituted with at least one substituent group. In embodiments, when $R^{B5}$ is substituted, it is substituted with at least one size-limited substituent group. In embodiments, when $R^{B5}$ is substituted, it is substituted with at least one lower substituent group.

In embodiments, $R^{B5}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, $R^{B50}$-substituted or unsubstituted alkyl, $R^{B50}$-substituted or unsubstituted heteroalkyl, $R^{B50}$-substituted or unsubstituted cycloalkyl, $R^{B50}$-substituted or unsubstituted heterocycloalkyl, $R^{B50}$-substituted or unsubstituted aryl, or $R^{B50}$-substituted or unsubstituted heteroaryl.

$R^{B50}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B50}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —CH 12, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B6}$ is a bond, —$S(O)_2$—, —N($R^{B6}$)—, —O—, —S—, —C(O)—, —C(O)N($R^{B6}$)—, —N($R^{B6}$)C(O)—, —N($R^{B6}$)C(O)NH—, —NHC(O)N($R^{B6}$)—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B6}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B6}$ is substituted with a plurality of groups selected from substituent groups, size-limited substituent groups, and lower substituent groups; each substituent group, size-limited substituent group, and/or lower substituent group may optionally be different. In embodiments, when $L^{B6}$ is substituted, it is substituted with at least one substituent group. In embodiments, when $L^{B6}$ is substituted, it is substituted with at least one size-limited substituent group. In embodiments, when $L^{B6}$ is substituted, it is substituted with at least one lower substituent group.

In embodiments, $L^{B6}$ is a bond, —$S(O)_2$—, —N($R^{B6}$)—, —O—, —S—, —C(O)—, —C(O)N($R^{B6}$)—, —N($R^{B6}$)C(O)—, —N($R^{B6}$)C(O)NH—, —NHC(O)N($R^{B6}$)—, —C(O)O—, —OC(O)—, substituted or unsubstituted $C_1$-$C_6$ alkylene, or substituted or unsubstituted 2 to 6 membered heteroalkylene.

In embodiments, $L^{B6}$ is a bond, —$S(O)_2$—, —N($R^{B6}$)—, —O—, —S—, —C(O)—, —C(O)N($R^{B6}$)—, —N($R^{B6}$)C(O)—, —N($R^{B6}$)C(O)NH—, —NHC(O)N($R^{B6}$)—, —C(O)O—, —OC(O)—, $R^{B6}$-substituted or unsubstituted alkylene, $R^{B6}$-substituted or unsubstituted heteroalkylene, $R^{B6}$-substituted or unsubstituted cycloalkylene, $R^{B6}$-substituted or unsubstituted heterocycloalkylene, $R^{B6}$-substituted or unsubstituted arylene, or $R^{B6}$-substituted or unsubstituted heteroarylene.

In embodiments, $R^{B6}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B6}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B6}$ is substituted with a plurality of groups selected from substituent groups, size-limited substituent groups, and lower substituent groups; each substituent group, size-limited substituent group, and/or lower substituent group may optionally be different. In embodiments, when $R^{B6}$ is substituted, it is substituted with at least one substituent group. In embodiments, when $R^{B6}$ is substituted, it is substituted with at least one size-limited substituent group. In embodiments, when $R^{B6}$ is substituted, it is substituted with at least one lower substituent group.

In embodiments, $R^{B6}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, $R^{B60}$-substituted or unsubstituted alkyl, $R^{B60}$-substituted or unsubstituted heteroalkyl, $R^{B60}$-substituted or unsubstituted cycloalkyl, $R^{B60}$-substituted or unsubstituted heterocycloalkyl, $R^{B60}$-substituted or unsubstituted aryl, or $R^{B60}$-substituted or unsubstituted heteroaryl.

$R^{B600}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B60}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B1}$ is

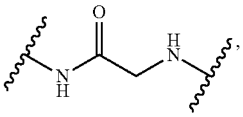,
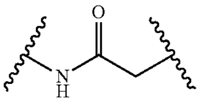,
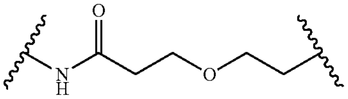,
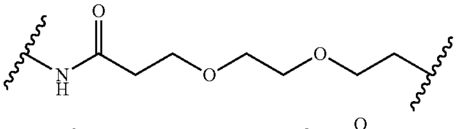,
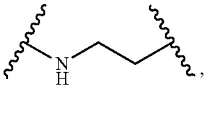,
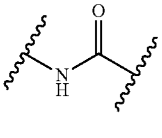,

-continued

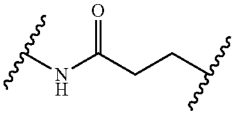,
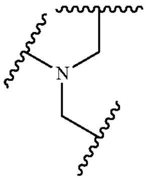,
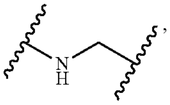,
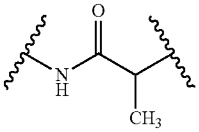,
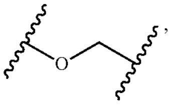,
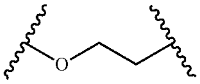,
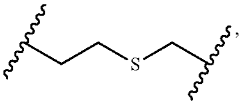,
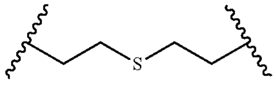,
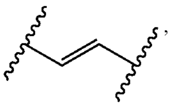,
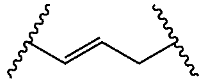,
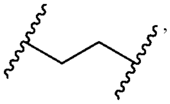,
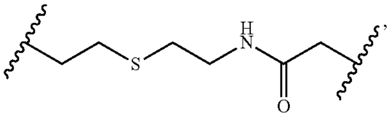,
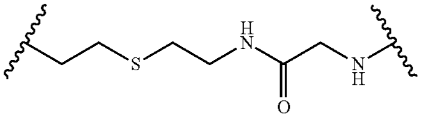,
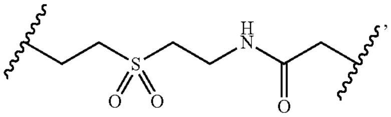, or
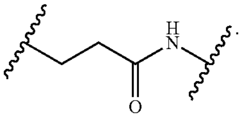.

In embodiments, $R^{B1}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B1}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1}$ is substituted with a plurality of groups selected from substituent groups, size-limited substituent groups, and lower substituent groups; each substituent group, size-limited substituent group, and/or lower substituent group may optionally be different. In embodiments, when $R^{B1}$ is substituted, it is substituted with at least one substituent group. In embodiments, when $R^{B1}$ is substituted, it is substituted with at least one size-limited substituent group. In embodiments, when $R^{B1}$ is substituted, it is substituted with at least one lower substituent group.

In embodiments, $R^{B1}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted $C_1$-$C_4$ alkyl, substituted or unsubstituted 2 to 4 membered heteroalkyl, or substituted or unsubstituted 5 to 6 membered heteroaryl.

In embodiments, $R^{B1}$ is substituted or unsubstituted pyridyl. In embodiments, $R^{B1}$ is unsubstituted pyridyl or pyridyl N-oxide. In embodiments, $R^{B1}$ is unsubstituted pyridyl. In embodiments, $R^{B1}$ is pyridyl N-oxide.

In embodiments, $R^{B1}$ is independently hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$N_3$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^{B1}$ is independently hydrogen, halogen, —$CX^{B1}_3$, —$CHX^{B1}_2$, —$CH_2X^{B1}$, —OH, —$NH_2$, —SH, —$OCX^{B1}_3$, —$OCHX^{B1}_2$, —$OCH_2X^{B1}$, —$CH_3$, —$CH_2CH_3$, —$OCH_3$, —$OCH_2CH_3$, —$SCH_3$, or —$SCH_2CH_3$, or —$N_3$. In embodiments, $R^{B1}$ is independently hydrogen, halogen, —$CF_3$, —$CHF_2$, —$CH_2F$, —OH, —$NH_2$, —SH, —$OCF_3$, —$OCHF_2$, —$OCH_2F$, —$CH_3$, —$CH_2CH_3$, —$OCH_3$, —$OCH_2CH_3$, —$SCH_3$, or —$SCH_2CH_3$, or —$N_3$. In embodiments, $R^{B1}$ is substituted or unsubstituted $C_1$-$C_6$ alkyl. In embodiments, $R^{B1}$ is substituted or unsubstituted 2 to 6 membered heteroalkyl. In embodiments, $R^{B1}$ is substituted or unsubstituted $C_3$-$C_8$ cycloalkyl. In embodiments, $R^{B1}$ is substituted or unsubstituted 3 to 8 membered heterocycloalkyl. In embodiments, $R^{B1}$ is substituted or unsubstituted phenyl. In embodiments, $R^{B1}$ is substituted or unsubstituted 5 to 6 membered heteroaryl. In embodiments, $R^{B1}$ is substituted or unsubstituted pyridyl. In embodiments, $R^{B1}$ is independently hydrogen. In embodiments, $R^{B1}$ is independently halogen. In embodiments, $R^{B1}$ is independently —$CX^{B1}_3$. In embodiments, $R^{B1}$ is independently —$CHX^{B1}_2$. In embodiments, $R^{B1}$ is independently —$CH_2X^{B1}$. In embodiments, $R^{B1}$ is independently —$OCX^{B1}_3$. In embodiments, $R^{B1}$ is independently —$OCH_2X^{B1}$. In embodiments, $R^{B1}$ is independently —$OCHX^{B1}_2$. In embodiments, $R^{B1}$ is independently —$OCH_2X^{B1}$. In embodiments, $R^{B1}$ is independently —CN. In embodiments, $R^{B1}$ is independently —$SO_{nB1}R^{B1D}$. In embodiments, $R^{B1}$ is independently —$SR^{B1D}$. In embodiments, $R^{B1}$ is independently —$SO_{vB1}NR^{B1A}R^{B1B}$. In embodiments, $R^{B1}$ is independently —NHC(O)$NR^{B1A}R^{B1B}$. In embodiments, $R^{B1}$ is independently —$NR^{B1A}C(NR^{B1C})R^{B1D}$. In embodiments, $R^{B1}$ is independently —$NR^{B1A}C(NR^{B1C})NR^{B1A}R^{B1B}$. In embodiments, $R^{B1}$ is independently —$N(O)_{mB1}$. In embodiments, $R^{B1}$ is independently —$NR^{B1A}R^{B1B}$. In embodiments, $R^{B1}$ is independently —$C(O)R^{B1C}$. In embodiments, $R^{B1}$ is independently —$C(O)OR^{B1C}$. In embodiments, $R^{B1}$ is independently —$C(O)NR^{B1A}R^{B1B}$. In embodiments, $R^{B1}$ is independently —$OR^{B1D}$. In embodiments, $R^{B1}$ is independently —$NR^{B1A}SO_2R^{B1D}$ In embodiments, $R^{B1}$ is independently —$NR^{B1A}C(O)R^{B1C}$. In embodiments, $R^{B1}$ is independently —$NR^{B1A}C(O)OR^{B1C}$. In embodiments, $R^{B1}$ is independently —$NR^{B1A}OR^{B1C}$. In embodiments, $R^{B1}$ is independently —OH. In embodiments, $R^{B1}$ is independently —$NH_2$. In embodiments, $R^{B1}$ is independently —COOH. In embodiments, $R^{B1}$ is independently —$CONH_2$. In embodiments, $R^{B1}$ is independently —$NO_2$. In embodiments, $R^{B1}$ is independently —SH. In embodiments, $R^{B1}$ is independently —$CF_3$. In embodiments, $R^{B1}$ is independently —$CHF_2$. In embodiments, $R^{B1}$ is independently —$CH_2F$. In embodiments, $R^{B1}$ is independently —$OCF_3$. In embodiments, $R^{B1}$ is independently —$OCH_2F$. In embodiments, $R^{B1}$ is independently —$OCHF_2$. In embodiments, $R^{B1}$ is independently —$OCH_3$. In embodiments, $R^{B1}$ is independently —$OCH_2CH_3$. In embodiments, $R^{B1}$ is independently —$OCH_2CH_2CH_3$. In embodiments, $R^{B1}$ is independently —$OCH(CH_3)_2$. In embodiments, $R^{B1}$ is independently —$OC(CH_3)_3$. In embodiments, $R^{B1}$ is independently —$N(CH_3)_3^+$. In embodiments, $R^{B1}$ is independently —$SCH_3$. In embodiments, $R^{B1}$ is independently —$SCH_2CH_3$. In embodiments, $R^{B1}$ is independently —$SCH_2CH_2CH_3$. In embodiments, $R^{B1}$ is independently —$SCH(CH_3)_2$. In embodiments, $R^{B1}$ is independently —$SC(CH_3)_3$. In embodiments, $R^{B1}$ is independently —$N_3$. In embodiments, $R^{B1}$ is independently —$CH_3$. In embodiments, $R^{B1}$ is independently —$CH_2CH_3$. In embodiments, $R^{B1}$ is independently —$CH_2CH_2CH_3$. In embodiments, $R^{B1}$ is independently —$CH(CH_3)_2$. In embodiments, $R^{B1}$ is independently —$C(CH_3)_3$. In embodiments, $R^{B1}$ is independently —F. In embodiments, $R^{B1}$ is independently —Cl. In embodiments, $R^{B1}$ is independently —Br. In embodiments, $R^{B1}$ is independently —I. $X^{B1}$ is independently —F, —Cl, —Br, or —I.

In embodiments, $R^{B1A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1A}$ is substituted with a plurality of groups selected from substituent groups, size-limited substituent groups, and lower substituent groups; each substituent group, size-limited substituent group, and/or lower substituent group may optionally be different. In embodiments, when $R^{B1A}$ is substituted, it is substituted with at least one substituent group. In embodiments, when $R^{B1A}$ is substituted, it is substituted with at least one size-limited substituent group. In embodiments, when $R^{B1A}$ is substituted, it is substituted with at least one lower substituent group.

In embodiments, $R^{B1A}$ is independently hydrogen. In embodiments, $R^{B1A}$ is independently —$CX^{B1A}_3$. In embodiments, $R^{B1A}$ is independently —$CHX^{B1A}_2$. In embodiments, $R^{B1A}$ is independently —$CH_2X^{B1A}$. In embodiments, $R^{B1A}$ is independently —$OCX^{B1A}_3$. In embodiments, $R^{B1A}$ is independently —$OCHX^{B1A}_2$. In embodiments, $R^{B1A}$ is independently —$OCH_2X^{B1A}$. In embodiments, $R^{B1A}$ is independently —OH. In embodiments, $R^{B1A}$ is independently —CN. In embodiments, $R^{B1A}$ is independently —COOH. In embodiments, $R^{B1A}$ is independently —$CONH_2$. $X^{B1A}$ is independently —F, —Cl, —Br, or —I.

In embodiments, $R^{B1A}$ is independently substituted or unsubstituted alkyl (e.g., $C_1$-$C_8$, $C_1$-$C_6$, $C_1$-$C_4$, or $C_1$-$C_2$). In embodiments, $R^{B1A}$ is independently substituted alkyl (e.g., $C_1$-$C_8$, $C_1$-$C_6$, $C_1$-$C_4$, or $C_1$-$C_2$). In embodiments, $R^{B1A}$ is independently unsubstituted alkyl (e.g., $C_1$-$C_8$, $C_1$-$C_6$, $C_1$-$C_4$, or $C_1$-$C_2$). In embodiments, $R^{B1A}$ is independently unsubstituted methyl. In embodiments, $R^{B1A}$ is independently unsubstituted ethyl. In embodiments, $R^{B1A}$ is independently unsubstituted propyl. In embodiments, $R^{B1A}$ is independently unsubstituted isopropyl. In embodiments, $R^{B1A}$ is independently unsubstituted tert-butyl. In embodiments, $R^{B1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1A}$ is independently substituted heteroalkyl (e.g., 2 to 8 membered, 2 to 6 membered, 4 to 6 membered, 2 to 3 membered, or 4 to 5 membered). In embodiments, $R^{B1A}$ is independently unsubstituted heteroalkyl (e.g., 2 to 8 membered, 2 to 6 membered, 4 to 6 membered, 2 to 3 membered, or 4 to 5 membered). In embodiments, $R^{B1A}$ is independently substituted or unsubstituted cycloalkyl (e.g., $C_3$-$C_8$, $C_3$-$C_6$, $C_4$-$C_6$, or $C_5$-$C_6$). In embodiments, $R^{B1A}$ is independently substituted cycloalkyl (e.g., $C_3$-$C_8$, $C_3$-$C_6$, $C_4$-$C_6$, or $C_5$-$C_6$). In embodiments, $R^{B1A}$ is independently unsubstituted cycloalkyl (e.g., $C_3$-$C_8$, $C_3$-$C_6$, $C_4$-$C_6$, or $C_5$-$C_6$). In embodiments, $R^{B1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1A}$ is independently substituted heterocycloalkyl (e.g., 3 to 8 membered, 3 to 6 membered, 4 to 6 membered, 4 to 5 membered, or 5 to 6 membered). In embodiments, $R^{B1A}$ is independently unsubstituted heterocycloalkyl (e.g., 3 to 8 membered, 3 to 6 membered, 4 to 6 membered, 4 to 5 membered, or 5 to 6 membered). In embodiments, $R^{B1A}$ is independently substituted or unsubstituted aryl (e.g., $C_6$-$C_{10}$ or phenyl). In embodiments, $R^{B1A}$ is independently substituted aryl (e.g., $C_6$-$C_{10}$ or phenyl). In embodiments, $R^{B1A}$ is independently unsubstituted aryl (e.g., $C_6$-$C_{10}$ or phenyl). In embodiments, $R^{B1A}$ is independently substituted or unsubstituted heteroaryl (e.g., 5 to 10 membered, 5 to 9 membered, or 5 to 6 membered). In embodiments, $R^{B1A}$ is independently substituted heteroaryl (e.g., 5 to 10 membered, 5 to 9 membered, or 5 to 6 membered). In embodiments, $R^{B1A}$ is independently pyridyl N-oxide. In embodiments, $R^{B1A}$ is independently unsubstituted heteroaryl (e.g., 5 to 10 membered, 5 to 9 membered, or 5 to 6 membered). In embodiments, $R^{B1A}$ is independently unsubstituted pyridyl.

In embodiments, $R^{B1B}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$HC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1B}$ is substituted with a plurality of groups selected from substituent groups, size-limited substituent groups, and lower substituent groups; each substituent group, size-limited substituent group, and/or lower substituent group may optionally be different. In embodiments, when $R^{B1B}$ is substituted, it is substituted with at least one substituent group. In embodiments, when $R^{B1B}$ is substituted, it is substituted with at least one size-limited substituent group. In embodiments, when $R^{B1B}$ is substituted, it is substituted with at least one lower substituent group.

In embodiments, $R^{B1B}$ is independently hydrogen. In embodiments, $R^{B1B}$ is independently —$CX^{B1B}_3$. In embodiments, $R^{B1B}$ is independently —$CHX^{B1B}_2$. In embodiments, $R^{B1B}$ is independently —$CH_2X^{B1B}$. In embodiments, $R^{B1B}$ is independently —$OCX^{B1B}_3$. In embodiments, $R^{B1B}$ is independently —$OCHX^{B1B}_2$. In embodiments, $R^{B1B}$ is independently —$OCH_2X^{B1B}$. In embodiments, $R^{B1B}$ is independently —OH. In embodiments, $R^{B1B}$ is independently —CN. In embodiments, $R^{B1B}$ is independently —COOH. In embodiments, $R^{B1B}$ is independently —$CONH_2$. $X^{B1B}$ is independently —F, —Cl, —Br, or —I.

In embodiments, $R^{B1B}$ is independently substituted or unsubstituted alkyl (e.g., $C_1$-$C_8$, $C_1$-$C_6$, $C_1$-$C_4$, or $C_1$-$C_2$). In embodiments, $R^{B1B}$ is independently substituted alkyl (e.g., $C_1$-$C_8$, $C_1$-$C_6$, $C_1$-$C_4$, or $C_1$-$C_2$). In embodiments, $R^{B1B}$ is independently unsubstituted alkyl (e.g., $C_1$-$C_8$, $C_1$-$C_6$, $C_1$-$C_4$, or $C_1$-$C_2$). In embodiments, $R^{B1B}$ is independently unsubstituted methyl. In embodiments, $R^{B1B}$ is independently unsubstituted ethyl. In embodiments, $R^{B1B}$ is independently unsubstituted propyl. In embodiments, $R^{B1B}$ is independently unsubstituted isopropyl. In embodiments, $R^{B1B}$ is independently unsubstituted tert-butyl. In embodiments, $R^{B1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1B}$ is independently substituted heteroalkyl (e.g., 2 to 8 membered, 2 to 6 membered, 4 to 6 membered, 2 to 3 membered, or 4 to 5 membered). In embodiments, $R^{B1B}$ is independently unsubstituted heteroalkyl (e.g., 2 to 8 membered, 2 to 6 membered, 4 to 6 membered, 2 to 3 membered, or 4 to 5 membered). In embodiments, $R^{B1B}$ is independently substituted or unsubstituted cycloalkyl (e.g., $C_3$-$C_8$, $C_3$-$C_6$, $C_4$-$C_6$, or $C_5$-$C_6$). In embodiments, $R^{B1B}$ is independently substituted cycloalkyl (e.g., $C_3$-$C_8$, $C_3$-$C_6$, $C_4$-$C_6$, or $C_5$-$C_6$). In embodiments, $R^{B1B}$ is independently unsubstituted cycloalkyl (e.g., $C_3$-$C_8$, $C_3$-$C_6$, $C_4$-$C_6$, or $C_5$-$C_6$). In embodiments, $R^{B1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1B}$ is independently substituted heterocycloalkyl (e.g., 3 to 8 membered, 3 to 6 membered, 4 to 6 membered, 4 to 5 membered, or 5 to 6 membered). In embodiments, $R^{B1B}$ is independently unsubstituted heterocycloalkyl (e.g., 3 to 8 membered, 3 to 6 membered, 4 to 6 membered, 4 to 5 membered, or 5 to 6 membered). In embodiments, $R^{B1B}$ is independently substituted or unsubstituted aryl (e.g., $C_6$-$C_{10}$ or phenyl). In embodiments, $R^{B1B}$ is independently substituted aryl (e.g., $C_6$-$C_{10}$ or phenyl). In embodiments, $R^{B1B}$ is independently unsubstituted aryl (e.g., $C_6$-$C_{10}$ or phenyl). In embodiments, $R^{B1B}$ is independently substituted or unsubstituted heteroaryl (e.g., 5 to 10 membered, 5 to 9 membered, or 5 to 6 membered). In embodiments, $R^{B1B}$ is independently substituted heteroaryl (e.g., 5 to 10 membered, 5 to 9 membered, or 5 to 6 membered). In embodiments, $R^{B1B}$ is independently pyridyl N-oxide. In embodiments, $R^{B1B}$ is independently unsubstituted heteroaryl (e.g., 5 to 10 membered, 5 to 9 membered, or 5 to 6 membered). In embodiments, $R^{B1B}$ is independently unsubstituted pyridyl.

In embodiments, $R^{B1A}$ and $R^{B1B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{B1A}$ and $R^{B1B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{B1A}$ and $R^{B1B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{B1A}$ and $R^{B1B}$ substituents bonded to the same nitrogen atom is substituted, it is substituted with at least one substituent group. In embodiments, when the moiety formed by joining $R^{B1A}$ and $R^{B1B}$ substituents bonded to the same nitrogen atom is substituted, it is substituted with at least one size-limited substituent group. In embodiments, when the moiety formed by joining $R^{B1A}$ and $R^{B1B}$ substituents bonded to the same nitrogen atom is substituted, it is substituted with at least one lower substituent group.

In embodiments, $R^{B1A}$ and $R^{B1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{B1A}$ and $R^{B1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form a substituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form an unsubstituted heteroaryl (e.g., 5 to 10 membered, 5 to 9 membered, or 5 to 6 membered).

In embodiments, $R^{B1C}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1C}$ is substituted with a plurality of groups selected from substituent groups, size-limited substituent groups, and lower substituent groups; each substituent group, size-limited substituent group, and/or lower substituent group may optionally be different. In embodiments, when $R^{B1C}$ is substituted, it is substituted with at least one substituent group. In embodiments, when $R^{B1C}$ is substituted, it is substituted with at least one size-limited substituent group. In embodiments, when $R^{B1C}$ is substituted, it is substituted with at least one lower substituent group.

In embodiments, $R^{B1C}$ is independently hydrogen. In embodiments, $R^{B1C}$ is independently $—CX^{B1C}_3$. In embodiments, $R^{B1C}$ is independently $—CHX^{B1C}_2$. In embodiments, $R^{B1C}$ is independently $—CH_2X^{B1C}$. In embodiments, $R^{B1C}$ is independently $—OCX^{B1C}_3$. In embodiments, $R^{B1C}$ is independently $—OCHX^{B1C}_2$. In embodiments, $R^{B1C}$ is independently $—OCH_2X^{B1C}$. In embodiments, $R^{B1C}$ is independently —OH. In embodiments, $R^{B1C}$ is independently —CN. In embodiments, $R^{B1C}$ is independently —COOH. In embodiments, $R^{B1C}$ is independently $—CONH_2$. In embodiments, $X^{B1C}$ is independently —F, —Cl, —Br, or —I.

In embodiments, $R^{B1C}$ is independently substituted or unsubstituted alkyl (e.g., $C_1$-$C_8$, $C_1$-$C_6$, $C_1$-$C_4$, or $C_1$-$C_2$). In embodiments, $R^{B1C}$ is independently substituted alkyl (e.g., $C_1$-$C_8$, $C_1$-$C_6$, $C_1$-$C_4$, or $C_1$-$C_2$). In embodiments, $R^{B1C}$ is independently unsubstituted alkyl (e.g., $C_1$-$C_8$, $C_1$-$C_6$, $C_1$-$C_4$, or $C_1$-$C_2$). In embodiments, $R^{B1C}$ is independently unsubstituted methyl. In embodiments, $R^{B1C}$ is independently unsubstituted ethyl. In embodiments, $R^{B1C}$ is independently unsubstituted propyl. In embodiments, $R^{B1C}$ is independently unsubstituted isopropyl. In embodiments, $R^{B1C}$ is independently unsubstituted tert-butyl. In embodiments, $R^{B1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted heteroalkyl (e.g., 2 to 8 membered, 2 to 6 membered, 4 to 6 membered, 2 to 3 membered, or 4 to 5 membered). In embodiments, $R^{B1C}$ is independently unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted or unsubstituted cycloalkyl (e.g., $C_3$-$C_8$, $C_3$-$C_6$, $C_4$-$C_6$, or $C_5$-$C_6$). In embodiments, $R^{B1C}$ is independently substituted cycloalkyl (e.g., $C_3$-$C_8$, $C_3$-$C_6$, $C_4$-$C_6$, or $C_5$-$C_6$). In embodiments, $R^{B1C}$ is independently unsubstituted cycloalkyl (e.g., $C_3$-$C_8$, $C_3$-$C_6$, $C_4$-$C_6$, or $C_5$-$C_6$). In embodiments, $R^{B1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted heterocycloalkyl (e.g., 3 to 8 membered, 3 to 6 membered, 4 to 6 membered, 4 to 5 membered, or 5 to 6 membered). In embodiments, $R^{B1C}$ is independently unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted or unsubstituted aryl (e.g., $C_6$-$C_{10}$ or phenyl). In embodiments, $R^{B1C}$ is independently substituted aryl (e.g., $C_6$-$C_{10}$ or phenyl). In embodiments, $R^{B1C}$ is independently unsubstituted aryl (e.g., $C_6$-$C_{10}$ or phenyl). In embodiments, $R^{B1C}$ is independently substituted or unsubstituted heteroaryl (e.g., 5 to 10 membered, 5 to 9 membered, or 5 to 6 membered). In embodiments, $R^{B1C}$ is independently substituted heteroaryl (e.g., 5 to 10 membered, 5 to 9 membered, or 5 to 6 membered). In embodiments, $R^{B1C}$ is independently pyridyl N-oxide. In embodiments, RBC is independently unsubstituted heteroaryl (e.g., 5 to 10 membered, 5 to 9 membered, or 5 to 6 membered). In embodiments, $R^{B1C}$ is independently unsubstituted pyridyl.

In embodiments, $R^{B1D}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1D}$ is substituted with a plurality of groups selected from substituent groups, size-limited substituent groups, and lower substituent groups; each substituent group, size-limited substituent group, and/or lower substituent group may optionally be different. In embodiments, when $R^{B1D}$ is substituted, it is substituted with at least one substituent group. In embodiments, when $R^{B1D}$ is substituted, it is substituted with at least one size-limited substituent group. In embodiments, when $R^{B1D}$ is substituted, it is substituted with at least one lower substituent group.

In embodiments, $R^{B1D}$ is independently hydrogen. In embodiments, $R^{B1D}$ is independently —$CX^{B1D}_3$. In embodiments, $R^{B1D}$ is independently —$CHX^{B1D}_2$. In embodiments, $R^{B1D}$ is independently —$CH_2X^{B1D}$. In embodiments, $R^{B1D}$ is independently —$OCX^{B1D}_3$. In embodiments, $R^{B1D}$ is independently —$OCHX^{B1D}_2$. In embodiments, $R^{B1D}$ is independently —$OCH_2X^{B1D}$. In embodiments, $R^{B1D}$ is independently —OH. In embodiments, $R^{B1D}$ is independently —CN. In embodiments, $R^{B1D}$ is independently —COOH. In embodiments, $R^{B1D}$ is independently —$CONH_2$. In embodiments, $X^{B1D}$ is independently —F, —Cl, —Br, or —I.

In embodiments, $R^{B1D}$ is independently substituted or unsubstituted alkyl (e.g., $C_1$-$C_8$, $C_1$-$C_6$, $C_1$-$C_4$, or $C_1$-$C_2$). In embodiments, $R^{B1D}$ is independently substituted alkyl (e.g., $C_1$-$C_8$, $C_1$-$C_6$, $C_1$-$C_4$, or $C_1$-$C_2$). In embodiments, $R^{B1D}$ is independently unsubstituted alkyl (e.g., $C_1$-$C_8$, $C_1$-$C_6$, $C_1$-$C_4$, or $C_1$-$C_2$). In embodiments, $R^{B1D}$ is independently unsubstituted methyl. In embodiments, $R^{1D}$ is independently unsubstituted ethyl. In embodiments, $R^{B1D}$ is independently unsubstituted propyl. In embodiments, $R^{B1D}$ is independently unsubstituted isopropyl. In embodiments, $R^{B1D}$ is independently unsubstituted tert-butyl. In embodiments, $R^{B1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1D}$ is independently substituted heteroalkyl (e.g., 2 to 8 membered, 2 to 6 membered, 4 to 6 membered, 2 to 3 membered, or 4 to 5 membered). In embodiments, $R^{B1D}$ is independently unsubstituted heteroalkyl (e.g., 2 to 8 membered, 2 to 6 membered, 4 to 6 membered, 2 to 3 membered, or 4 to 5 membered). In embodiments, $R^{B1D}$ is independently substituted or unsubstituted cycloalkyl (e.g., $C_3$-$C_8$, $C_3$-$C_6$, $C_4$-$C_6$, or $C_5$-$C_6$). In embodiments, $R^{B1D}$ is independently substituted cycloalkyl (e.g., $C_3$-$C_8$, $C_3$-$C_6$, $C_4$-$C_6$, or $C_5$-$C_6$). In embodiments, $R^{B1D}$ is independently unsubstituted cycloalkyl (e.g., $C_3$-$C_8$, $C_3$-$C_6$, $C_4$-$C_6$, or $C_5$-$C_6$). In embodiments, $R^{B1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1D}$ is independently substituted heterocycloalkyl (e.g., 3 to 8 membered, 3 to 6 membered, 4 to 6 membered, 4 to 5 membered, or 5 to 6 membered). In embodiments, $R^{B1D}$ is independently unsubstituted heterocycloalkyl (e.g., 3 to 8 membered, 3 to 6 membered, 4 to 6 membered, 4 to 5 membered, or 5 to 6 membered). In embodiments, $R^{B1D}$ is independently substituted or unsubstituted aryl (e.g., $C_6$-$C_{10}$ or phenyl). In embodiments, $R^{B1D}$ is independently substituted aryl (e.g., $C_6$-$C_{10}$ or phenyl). In embodiments, $R^{B1D}$ is independently unsubstituted aryl (e.g., $C_6$-$C_{10}$ or phenyl). In embodiments, $R^{B1D}$ is independently substituted or unsubstituted heteroaryl (e.g., 5 to 10 membered, 5 to 9 membered, or 5 to 6 membered). In embodiments, $R^{B1D}$ is independently substituted heteroaryl (e.g., 5 to 10 membered, 5 to 9 membered, or 5 to 6 membered). In embodiments, $R^{B1D}$ is independently pyridyl N-oxide. In embodiments, $R^{B1D}$ is independently unsubstituted heteroaryl (e.g., 5 to 10 membered, 5 to 9 membered, or 5 to 6 membered). In embodiments, $R^{B1D}$ is independently unsubstituted pyridyl.

In embodiments, $R^{B1}$ is independently hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —NHC(NH)H, —NHC(NH)$NH_2$, —$NHSO_2H$, —NHC(O)H, —NHC(O)OH, —NHOH, —$N_3$, $R^{B10}$-substituted or unsubstituted alkyl (e.g., $C_1$-$C_8$, $C_1$-$C_6$, $C_1$-$C_4$, or $C_1$-$C_2$), $R^{B10}$-substituted or unsubstituted heteroalkyl (e.g., 2 to 8 membered, 2 to 6 membered, 4 to 6 membered, 2 to 3 membered, or 4 to 5 membered), $R^{B10}$-substituted or unsubstituted cycloalkyl (e.g., $C_3$-$C_8$, $C_3$-$C_6$, $C_4$-$C_6$, or $C_5$-$C_6$), $R^{B10}$-substituted or unsubstituted heterocycloalkyl (e.g., 3 to 8 membered, 3 to 6 membered, 4 to 6 membered, 4 to 5 membered, or 5 to 6 membered), $R^{B10}$-substituted or unsubstituted aryl (e.g., $C_6$-$C_{10}$ or phenyl), or $R^{B10}$-substituted or unsubstituted heteroaryl (e.g., 5 to 10 membered, 5 to 9 membered, or 5 to 6 membered). In embodiments, $R^{B1}$ is independently hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —NHC(NH)H, —NHC(NH)$NH_2$, —$NHSO_2H$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{B1}$ is independently —F, —Cl, —Br, or —I. In embodiments, $R^{B1}$ is independently —COOH. In embodiments, $R^{B1}$ is independently unsubstituted pyridyl. In embodiments, $R^{B1}$ is independently pyridyl N-oxide. In embodiments, $R^{B1}$ is independently $R^{B10}$-substituted pyridyl N-oxide. In embodiments, $R^{B1}$ is independently unsubstituted pyridyl N-oxide. In embodiments, $R^{B1}$ is independently $R^{B10}$-substituted pyridin-2-yl N-oxide. In embodiments, $R^{B1}$ is independently unsubstituted pyridin-2-yl N-oxide. In embodiments, $R^{B1}$ is independently $R^{B10}$-substituted pyridin-3-yl N-oxide. In embodiments, $R^{B1}$ is independently unsubstituted pyridin-3-yl N-oxide. In embodiments, $R^{B1}$ is independently $R^{B10}$-substituted pyridin-4-yl N-oxide. In embodiments, $R^{B1}$ is independently unsubstituted pyridin-4-yl N-oxide.

$R^{B10}$ is oxo, halogen, $-CX^{B10}_3$, $-CHX^{B10}_2$, $-CH_2X^{B10}$, $-OCX^{B10}_3$, $-OCH_2X^{B10}$, $-OCHX^{B10}_2$, $-CN$, $-SO_{nB10}R^{B10D}$, $-SO_{vB10}NR^{B10A}R^{B10B}$, $-NHC(O)NR^{B10A}R^{B10B}$, $-NR^{B1A}C(NR^{B10C})R^{B10D}$, $-NR^{B10D}C(NR^{B10C})NR^{B10A}R^{B10B}$, $-N(O)_{mB10}$, $-NR^{B10A}R^{B10B}$, $-C(O)R^{B10C}$, $-C(O)OR^{B10C}$, $-C(O)NR^{B10A}R^{B10B}$, $-OR^{B10D}$, $-NR^{B10A}SO_2R^{B10D}$, $-NR^{B10A}C(O)R^{B10C}$, $-NR^{B10A}C(O)OR^{B10C}$, $-NR^{B10A}OR^{B10C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B10A}$, $R^{B10B}$, $R^{B10C}$, and $R^{B10D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B10A}$ and $R^{B10B}$ substituents bonded to the same nitrogen atom may be joined to form a substituted or unsubstituted heterocycloalkyl or substituted or unsubstituted heteroaryl; nB10 is independently an integer from 0 to 4; mB10 and v10 are independently 1 or 2; and $X^{B10}$ is independently $-F$, $-Cl$, $-Br$, or $-I$.

In embodiments, $R^{B10}$ is halogen, $-CX^{B10}_3$, $-CHX^{B10}_2$, $-CH_2X^{B10}$, $-OCX^{B10}_3$, $-OCH_2X^{B10}$, $-OCHX^{B10}_2$, $-CN$, $-SO_{nB10}R^{B10D}$, $-SO_{vB10}NR^{B10A}R^{B10B}$, $-NHC(O)NR^{B10A}R^{B10B}$, $-NR^{B1A}C(NR^{B10C})R^{B10D}$, $-NR^{B1A}C(NR^{B10C})NR^{B10A}R^{B10B}$, $-N(O)_{mB10}$, $-NR^{B10A}R^{B10B}$, $-C(O)R^{B10C}$, $-C(O)OR^{B10C}$, $-C(O)NR^{B10A}R^{B10B}$, $-OR^{B10D}$, $-NR^{10A}SO_2R^{B10D}$, $-NR^{B10A}C(O)R^{B10C}$, $-NR^{B10A}C(O)OR^{B10C}$, $-NR^{B10A}OR^{B10C}$, $-N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10}$ is substituted with a plurality of groups selected from substituent groups, size-limited substituent groups, and lower substituent groups; each substituent group, size-limited substituent group, and/or lower substituent group may optionally be different. In embodiments, when $R^{B10}$ is substituted, it is substituted with at least one substituent group. In embodiments, when $R^{B10}$ is substituted, it is substituted with at least one size-limited substituent group. In embodiments, when $R^{B10}$ is substituted, it is substituted with at least one lower substituent group.

In embodiments, $R^{B10}$ is halogen, $-CX^{B10}_3$, $-CHX^{B10}_2$, $-CH_2X^{B10}$, $-OCX^{B10}_3$, $-OCH_2X^{B10}$, $-OCHX^{B10}_2$, $-CN$, $-SO_{nB10}R^{B10D}$, $-SO_{vB10}NR^{B10A}R^{B10B}$, $-NHC(O)NR^{B10A}R^{B10B}$, $-NR^{B10A}C(NR^{B10C})R^{B10D}$, $-NR^{B10A}C(NR^{B10C})NR^{B10A}R^{B10B}$, $-N(O)_{mB10}$, $-NR^{B10A}R^{B10B}$, $-C(O)R^{B10C}$, $-C(O)OR^{B10C}$, $-C(O)NR^{B10A}R^{B10B}$, $-OR^{B10D}$, $-NR^{B10A}SO_2R^{B10D}$, $-NR^{B10A}C(O)R^{B10C}$, $-NR^{B10A}C(O)OR^{B10C}$, $-NR^{B10A}OR^{B10C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B10A}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group;

wherein if the substituted $R^{B10A}$ is substituted with a plurality of groups selected from substituent groups, size-limited substituent groups, and lower substituent groups; each substituent group, size-limited substituent group, and/or lower substituent group may optionally be different. In embodiments, when $R^{B10A}$ is substituted, it is substituted with at least one substituent group. In embodiments, when $R^{B10A}$ is substituted, it is substituted with at least one size-limited substituent group. In embodiments, when $R^{B10A}$ is substituted, it is substituted with at least one lower substituent group.

In embodiments, $R^{B10B}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10B}$ is substituted with a plurality of groups selected from substituent groups, size-limited substituent groups, and lower substituent groups; each substituent group, size-limited substituent group, and/or lower substituent group may optionally be different. In embodiments, when $R^{B10B}$ is substituted, it is substituted with at least one substituent group. In embodiments, when $R^{B10B}$ is substituted, it is substituted with at least one size-limited substituent group. In embodiments, when $R^{B10B}$ is substituted, it is substituted with at least one lower substituent group.

In embodiments, $R^{B10A}$ and $R^{B10B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{B10A}$ and $R^{B10B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{B10A}$ and $R^{B1}$0B substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{B10A}$ and $R^{B10B}$ substituents bonded to the same nitrogen atom is substituted, it is substituted with at least one substituent group. In embodiments, when the moiety formed by joining $R^{B10A}$ and $R^{B10B}$ substituents bonded to the same nitrogen atom is substituted, it is substituted with at least one size-limited substituent group. In embodiments, when the moiety formed by joining $R^{B10A}$ and $R^{B10}$B substituents bonded to the same nitrogen atom is substituted, it is substituted with at least one lower substituent group.

In embodiments, $R^{B10C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10C}$ is substituted with a plurality of groups selected from substituent groups, size-limited substituent groups, and lower substituent groups; each substituent group, size-limited substituent group, and/or lower substituent group may optionally be different. In embodiments, when $R^{B10C}$ is substituted, it is substituted with at least one substituent group. In embodiments, when $R^{B10C}$ is substituted, it is substituted with at least one size-limited substituent group. In embodiments, when $R^{B10C}$ is substituted, it is substituted with at least one lower substituent group.

In embodiments, $R^{B10D}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10D}$ is substituted with a plurality of groups selected from substituent groups, size-limited substituent groups, and lower substituent groups; each substituent group, size-limited substituent group, and/or lower substituent group may optionally be different. In embodiments, when $R^{B10D}$ is substituted, it is substituted with at least one substituent group. In embodiments, when $R^{B10D}$ is substituted, it is substituted with at least one size-limited substituent group. In embodiments, when $R^{B10D}$ is substituted, it is substituted with at least one lower substituent group.

In embodiments, $R^{B10}$ is independently oxo, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, —OH, $—NH_2$, —C OOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, —NHC(NH)H, $—NHC(NH)NH_2$, $—NHSO_2H$, —NHC(O)H, —NHC(O)OH, —NHOH, $—N_3$, $R^{B11}$-substituted or unsubstituted alkyl (e.g., $C_1$-$C_8$, $C_1$-$C_6$, $C_1$-$C_4$, or $C_1$-$C_2$), $R^{B11}$-substituted or unsubstituted heteroalkyl (e.g., 2 to 8 membered, 2 to 6 membered, 4 to 6 membered, 2 to 3 membered, or 4 to 5 membered), $R^{B11}$-substituted or unsubstituted cycloalkyl (e.g., $C_3$-$C_8$, $C_3$-$C_6$, $C_4$-$C_6$, or $C_5$-$C_6$), $R^{B11}$-substituted or unsubstituted heterocycloalkyl (e.g., 3 to 8 membered, 3 to 6 membered, 4 to 6 membered, 4 to 5 membered, or 5 to 6 membered), $R^{B11}$-substituted or unsubstituted aryl (e.g., $C_6$-$C_{10}$ or phenyl), or $R^{B11}$-substituted or unsubstituted heteroaryl (e.g., 5 to 10 membered, 5 to 9 membered, or 5 to 6 membered). $X^{B10}$ is independently —F, —Cl, —Br, or —I. In embodiments, $R^{B10}$ is independently substituted or unsubstituted $C_1$-$C_4$ alkyl. In embodiments, $R^{B10}$ is independently unsubstituted methyl. In embodiments, $R^{B10}$ is independently —COOH. In embodiments, $R^{B10}$ is independently unsubstituted pyridyl. In embodiments, $R^{B10}$ is independently pyridyl N-oxide. In embodiments, $R^{B10}$ is independently $R^{B11}$-substituted pyridin-2-yl N-oxide. In embodiments, $R^{B10}$ is independently unsubstituted pyridin-2-yl N-oxide. In embodiments, $R^{B10}$ is independently $R^{B11}$-substituted pyridin-3-yl N-oxide. In embodiments, $R^{B10}$ is independently unsubstituted pyridin-3-yl N-oxide. In embodiments, $R^{B10}$ is independently $R^{B11}$-substituted pyridin-4-yl N-oxide. In embodiments, $R^{B10}$ is independently unsubstituted pyridin-4-yl N-oxide.

$R^{B11}$ is independently oxo, halogen, $—CX^{B11}_3$, $—CHX^{B11}_2$, $—CH_2X^{B11}$, $—OCX^{B11}_3$, $—OCH_2X^{B11}$, $—OCHX^{B11}_2$, —CN, —OH, $—NH_2$, —C OOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, —NHC(NH)H, $—NHC(NH)NH_2$, $—NHSO_2H$, —NHC(O)H, —NHC(O)OH, —NHOH, $—N_3$, $R^{B12}$-substituted or unsubstituted alkyl (e.g., $C_1$-$C_8$, $C_1$-$C_6$, $C_1$-$C_4$, or $C_1$-$C_2$), $R^{B12}$-substituted or unsubstituted heteroalkyl (e.g., 2 to 8 membered, 2 to 6 membered, 4 to 6 membered, 2 to 3 membered, or 4 to 5 membered), $R^{B12}$-substituted or unsubstituted cycloalkyl (e.g., $C_3$-$C_8$, $C_3$-$C_6$, $C_4$-$C_6$, or $C_5$-$C_6$), $R^{B12}$-substituted or unsubstituted heterocycloalkyl (e.g., 3 to 8 membered, 3 to 6 membered, 4 to 6 membered, 4 to 5 membered, or 5 to 6 membered), $R^{B12}$-substituted or unsubstituted aryl (e.g., $C_6$-$C_{10}$ or phenyl), or $R^{B12}$-substituted or unsubstituted heteroaryl (e.g., 5 to 10 membered, 5 to 9 membered, or 5 to 6 membered). $X^{B11}$ is independently —F, —Cl, —Br, or —I. In embodiments, $R^{B11}$ is independently substituted or unsubstituted $C_1$-$C_4$ alkyl. In embodiments, $R^{B11}$ is independently unsubstituted methyl. In embodiments, $R^{B11}$ is independently —COOH. In embodiments, $R^{B11}$ is independently unsubstituted pyridyl. In embodiments, $R^{B11}$ is independently pyridyl N-oxide. In embodiments, $R^{B11}$ is independently $R^{B12}$-substituted pyridin-2-yl N-oxide. In embodiments, $R^{B11}$ is independently unsubstituted pyridin-2-yl N-oxide. In embodiments, $R^{B11}$ is independently $R^{B12}$-substituted pyridin-3-yl N-oxide. In embodiments, $R^{B11}$ is independently unsubstituted pyridin-3-yl N-oxide. In embodiments, $R^{B11}$ is independently $R^{B12}$-substituted pyridin-4-yl N-oxide. In embodiments, $R^{B11}$ is independently unsubstituted pyridin-4-yl N-oxide.

$R^{B12}$ is independently oxo, halogen, $—CX^{B123}$, $—CHX^{B122}$, $—CH_2X^{B12}$, $—OCX^{B12}_3$, $—OCH_2X^{B12}$, $—OCHX^{B122}$, —CN, —OH, $—NH_2$, —C OOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, —NHC(NH)H, $—NHC(NH)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), or unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{B12}$ is independently —F, —Cl, —Br, or —I. In embodiments, $R^{B12}$ is independently unsubstituted methyl. In embodiments, $R^{B12}$ is independently —COOH. In embodiments, $R^{B12}$ is independently unsubstituted pyridyl. In embodiments, $R^{B12}$ is independently —O.

In embodiments, nB1 is 0. In embodiments, nB1 is 1. In embodiments, nB1 is 2. In embodiments, nB1 is 3. In embodiments, nB1 is 4. In embodiments, mB1 is 1. In embodiments, mB1 is 2. In embodiments, vB1 is 1. In embodiments, vB1 is 2. In embodiments, $X^{B1}$ is independently —F. In embodiments, $X^{B1}$ is independently —Cl. In embodiments, $X^{B1}$ is independently —Br. In embodiments, $X^{B1}$ is independently —I.

In embodiments, nB10 is 0. In embodiments, nB10 is 1. In embodiments, nB10 is 2. In embodiments, nB10 is 3. In embodiments, nB10 is 4. In embodiments, mB10 is 1. In embodiments, mB10 is 2. In embodiments, vB10 is 1. In embodiments, vB10 is 2. In embodiments, $X^{B10}$ is independently —F. In embodiments, $X^{B10}$ is independently —Cl. In embodiments, $X^{B10}$ is independently —Br. In embodiments, $X^{B10}$ is independently —I.

In embodiments, $X^{B11}$ is independently —F. In embodiments, $X^{B11}$ is independently —Cl. In embodiments, $X^{B11}$ is independently —Br. In embodiments, $X^{B11}$ is independently —I.

In embodiments, $X^{B12}$ is independently —F. In embodiments, $X^{B12}$ is independently —Cl. In embodiments, $X^{B12}$ is independently —Br. In embodiments, $X^{B12}$ is independently —I.

In embodiments, $R^{B1}$ is halogen, $—NR^{B1A}R^{B1B}$, $—N_3$, $—SR^{B1D}$,

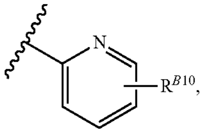, 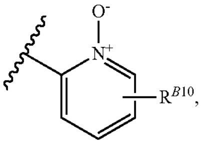,

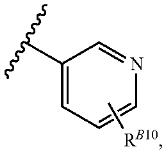, 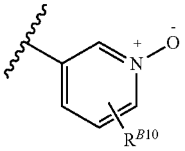,

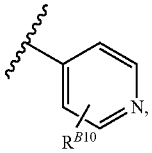, 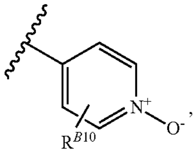,

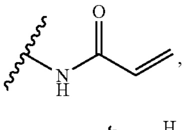, 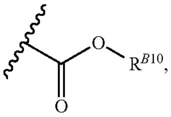, 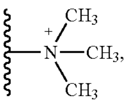,

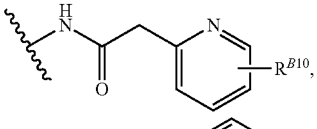,

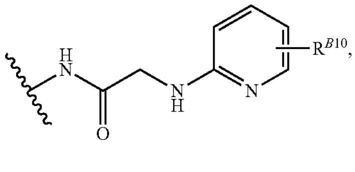,

-continued

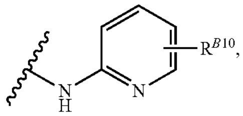, 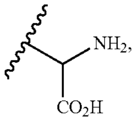,

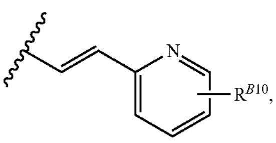, 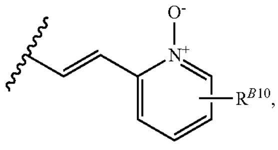,

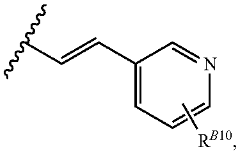, 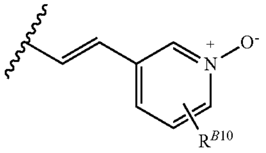,

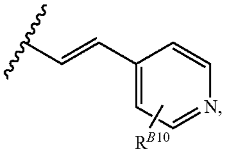 or 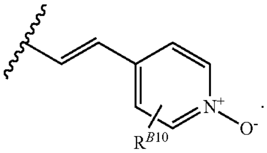.

$R^{B1A}$, $R^{B1B}$, $R^{B1D}$, and $R^{B10}$ are as described herein, including in embodiments.

In embodiments, $R^{B1}$ is —Cl, $—NH_2$, $—N_3$, —SH, $—N(CH_3)_3^+$,

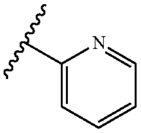, 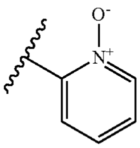,

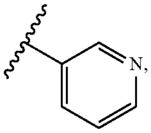, 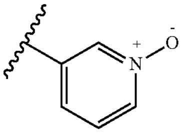,

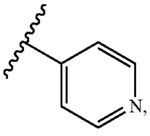, 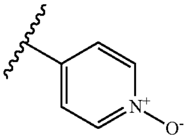,

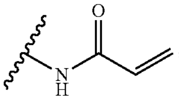, 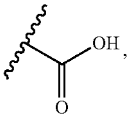, ,

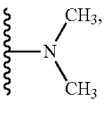, 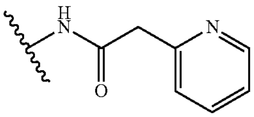,

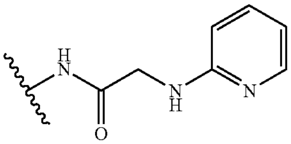,

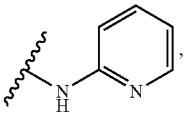, 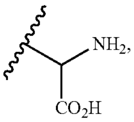

-continued
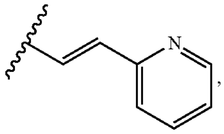
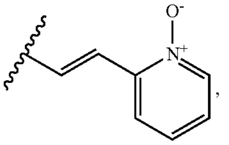
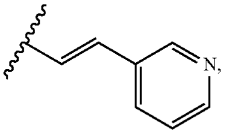
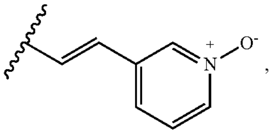
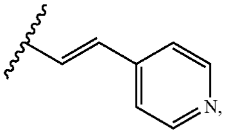
or
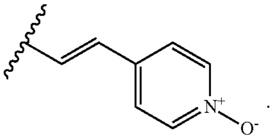
In embodiments, $L^{B1}$-$R^{B1}$ is
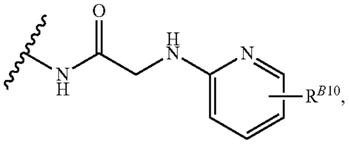
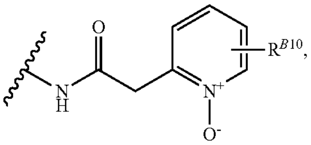
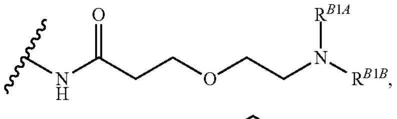
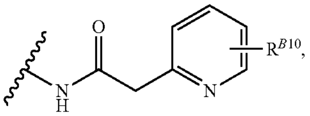
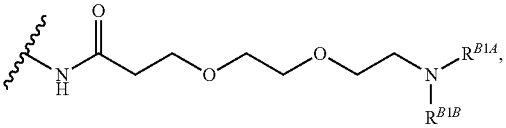
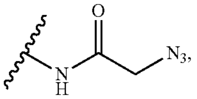
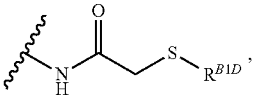
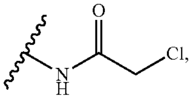
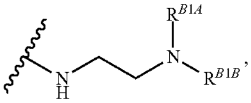
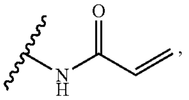
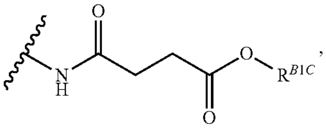
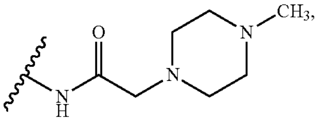
-continued
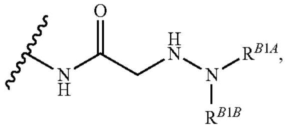
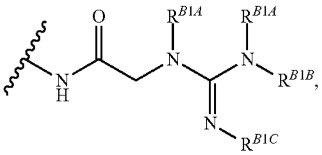
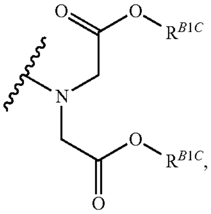
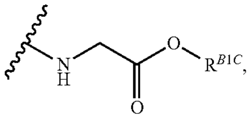
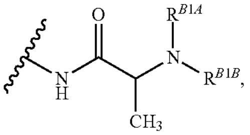
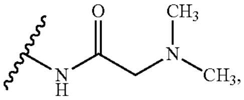
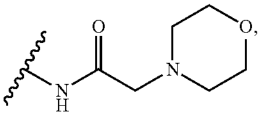
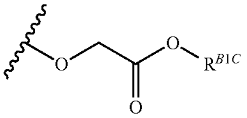
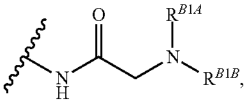
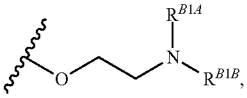
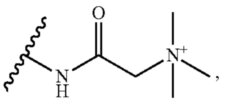
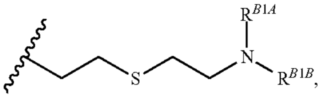
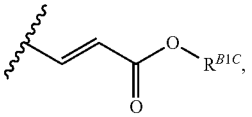
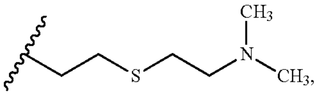
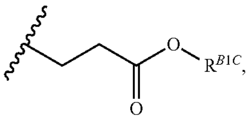
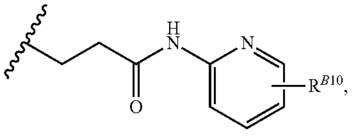
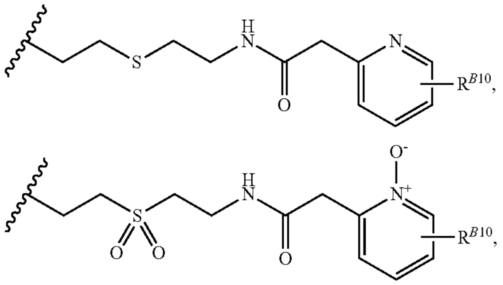

-continued
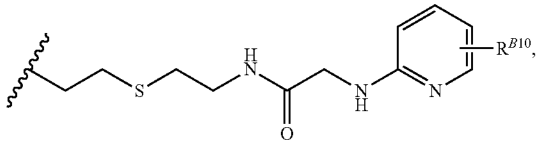
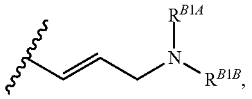
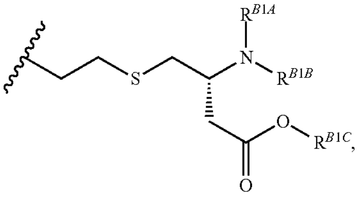
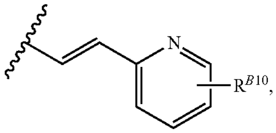
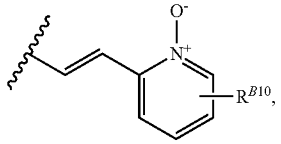
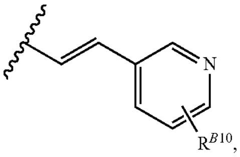
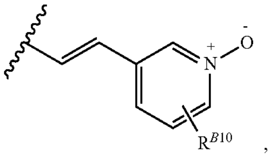
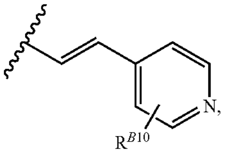
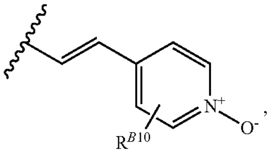
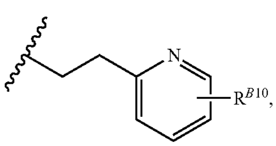
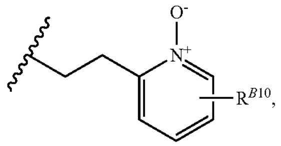
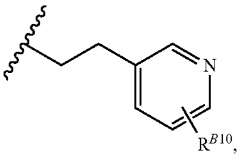
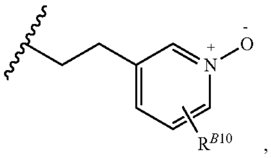
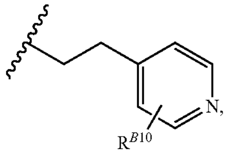
or
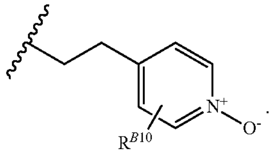
$R^{B1A}$, $R^{B1B}$, $R^{B1D}$, and $R^{B10}$ are as described herein, including in embodiments.
In embodiments, $L^{B1}$-$R^{B1}$ is
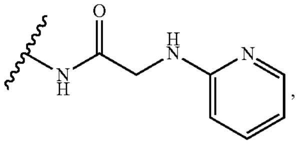
-continued
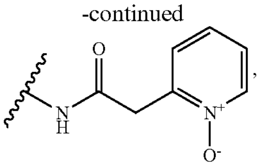
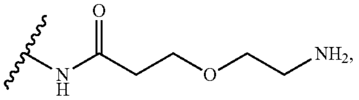
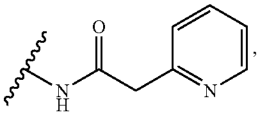
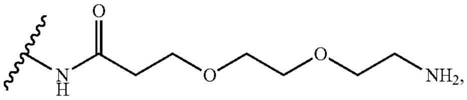
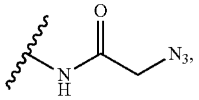
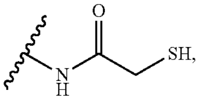
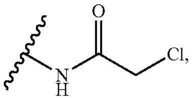
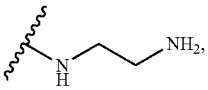
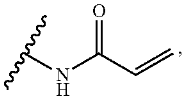
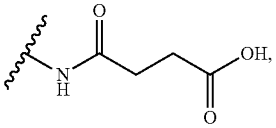
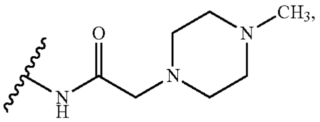
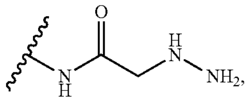
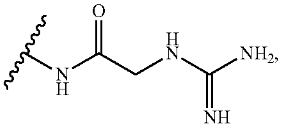
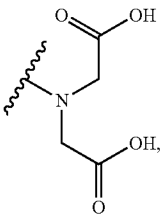
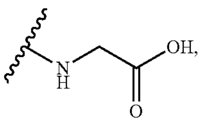
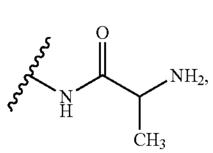
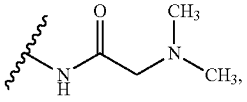
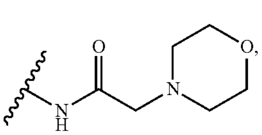
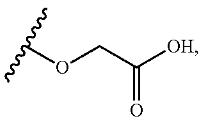
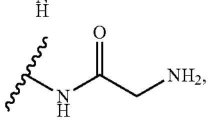
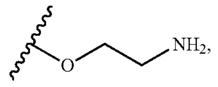

-continued
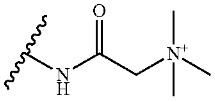,
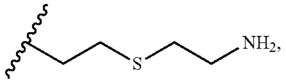,
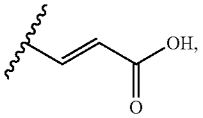,
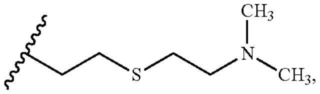,
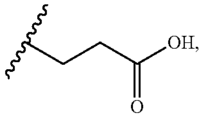,
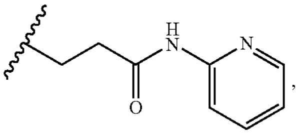,
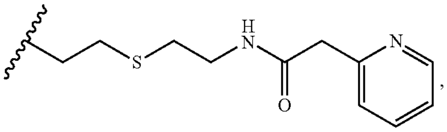,
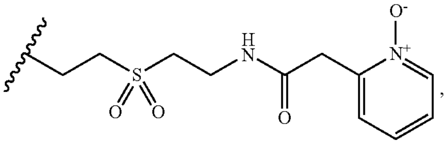,
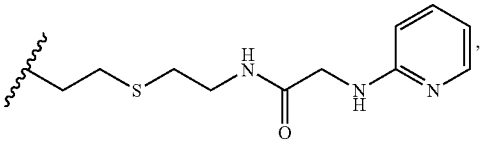,
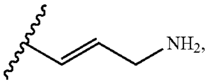,
-continued
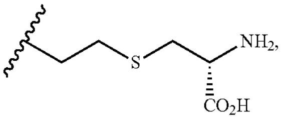,
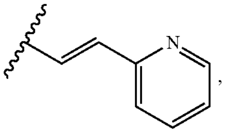,
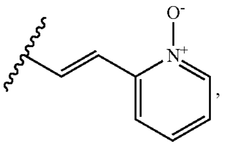,
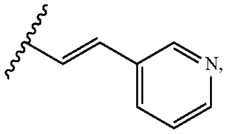,
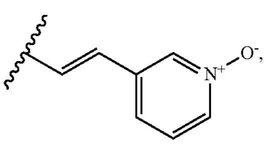,
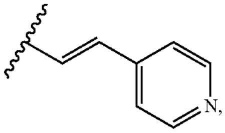,
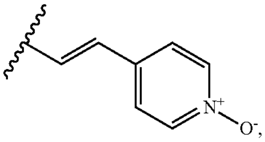,
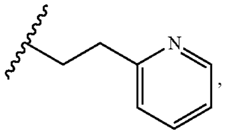,
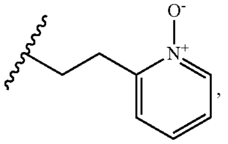,
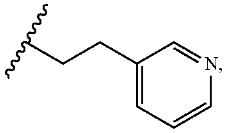,
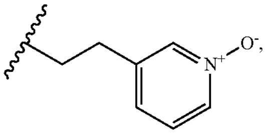,
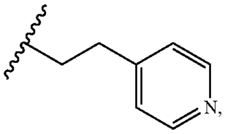, or
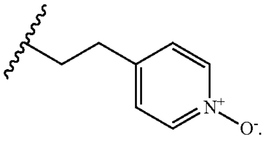.
In embodiments, the compound is not
(FK506, (I))
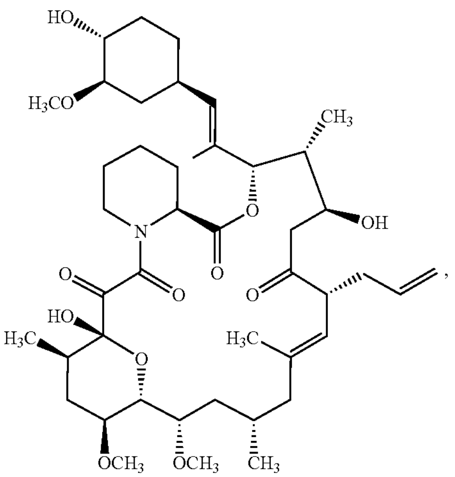,
(SLF, (II))
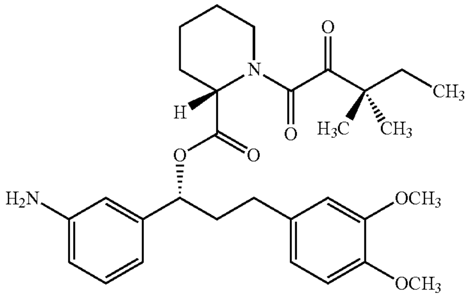, -continued
(Sanglefehrin A (III))
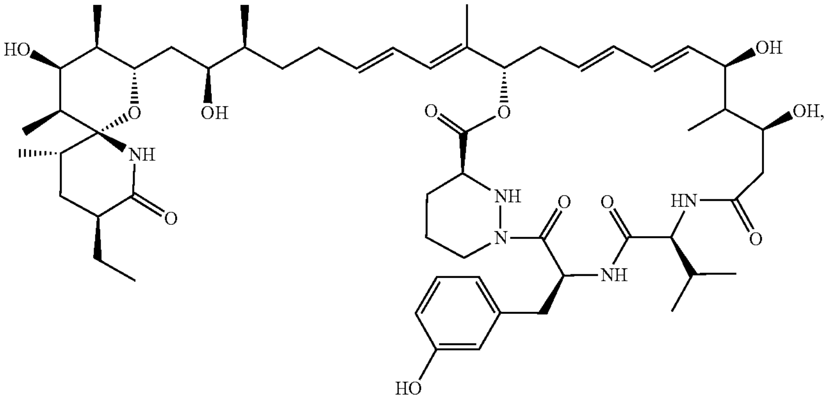
(Cyclosporin A (IV))
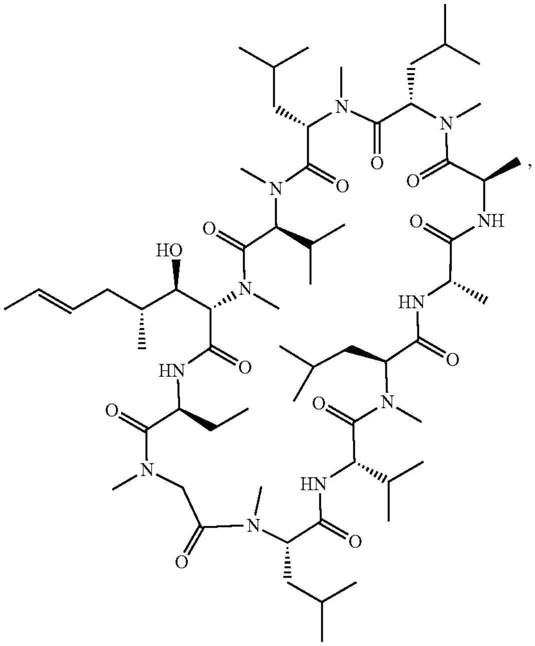
, or
(Rapamycin (V))
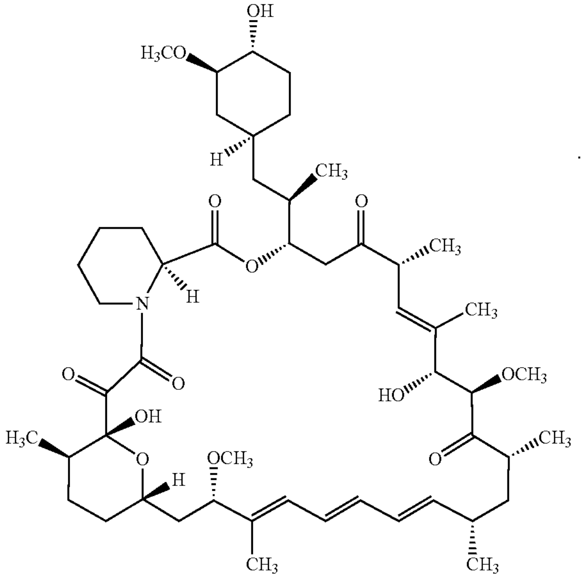
.
In embodiments, the compound is not
(FK506, (I))
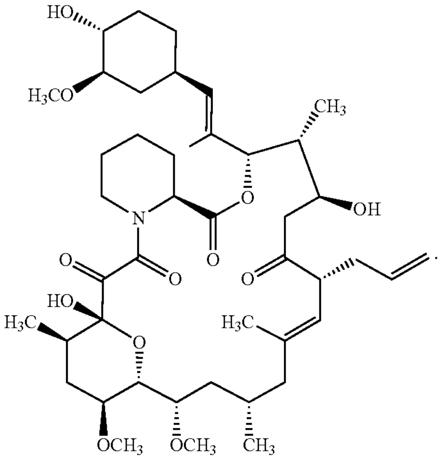
.
In embodiments, the compound is not
(SLF, (II))
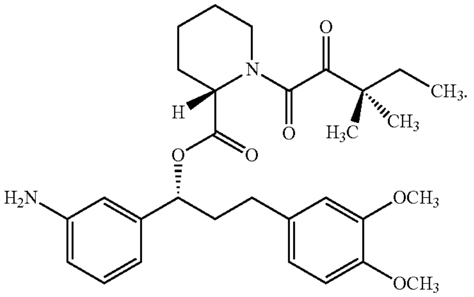
.

In embodiments, the compound is not
(Sanglefehrin A (III))
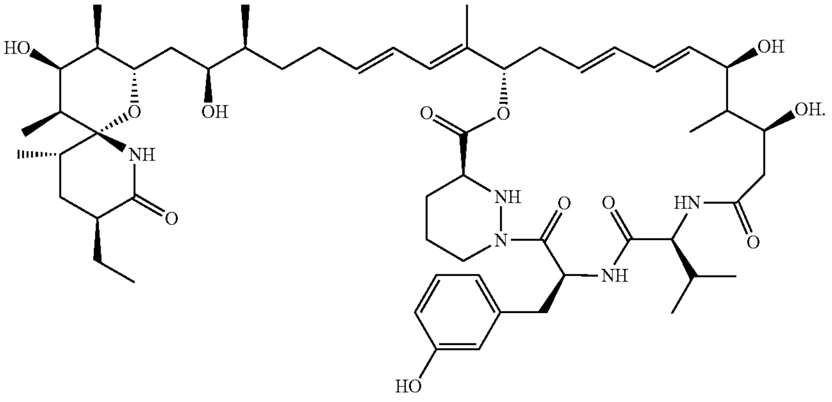
In embodiments, the compound is not
(Cyclosporin A (IV))
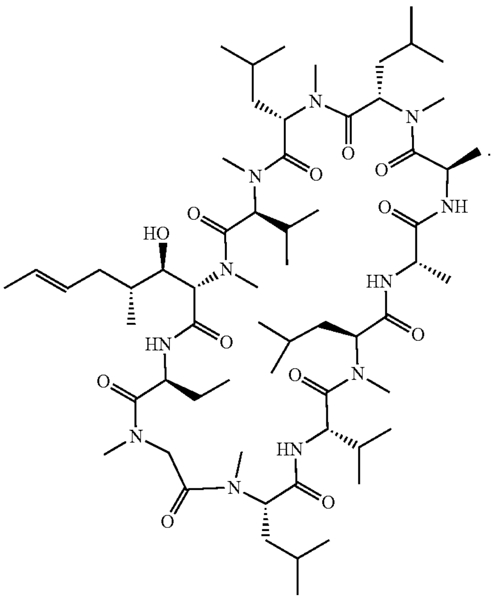
In embodiments, the compound is not
(Rapamycin (V))
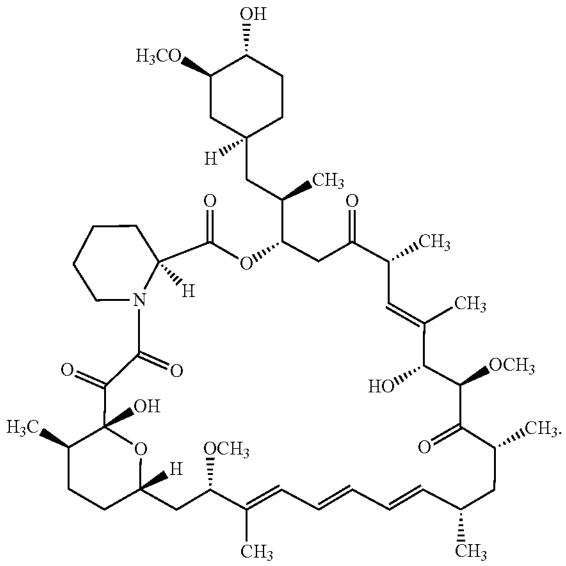
In embodiments, the compound is not
(SLF, (II))
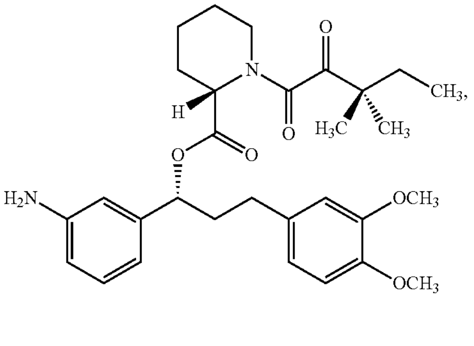

-continued (Sanglefehrin A (III))

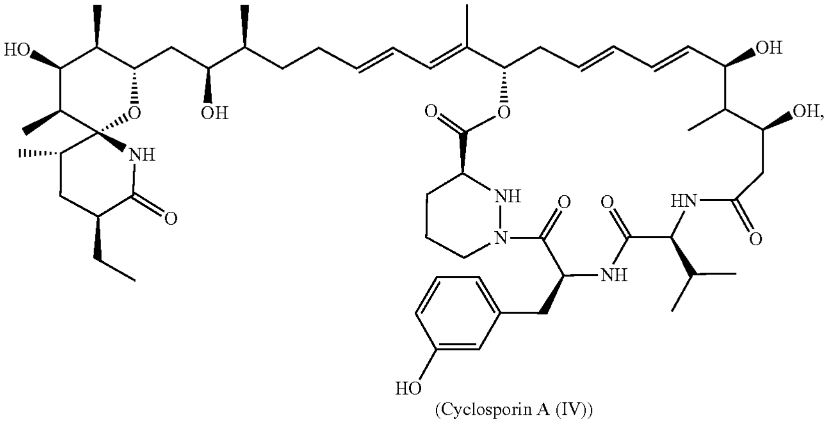

(Cyclosporin A (IV))

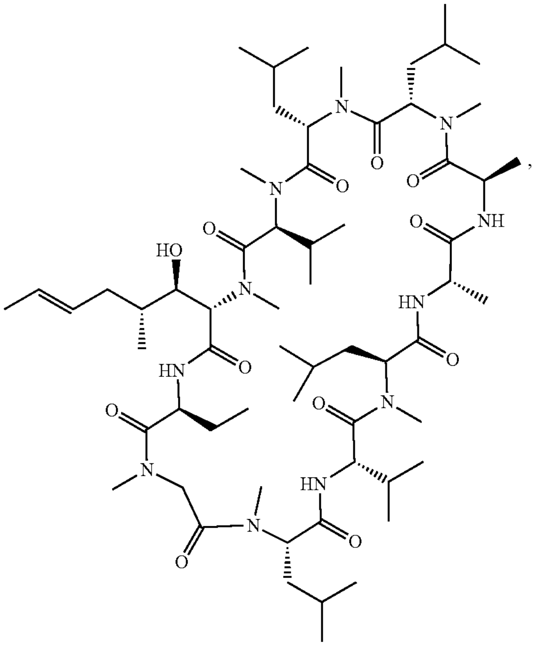

, or (Rapamycin (V))

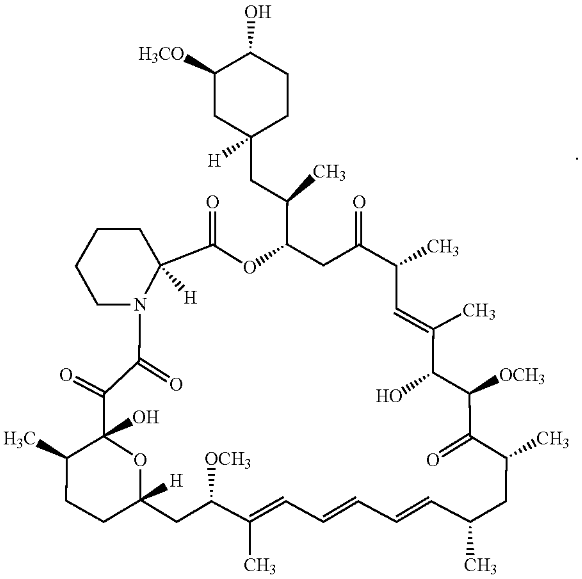

.

In embodiments, $A^B$ is an immunophilin-binding moiety having the formula

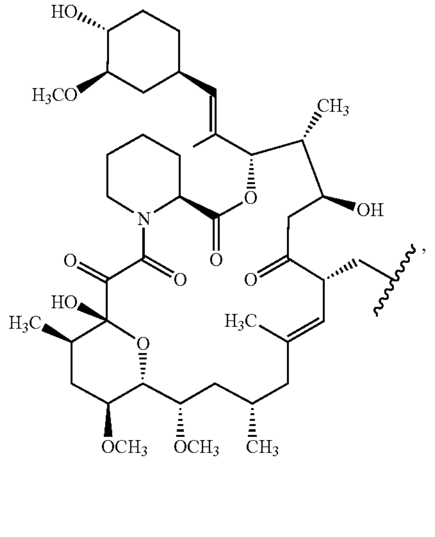 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof, $L^{B1}$ is $L^{B2}$-$L^{B3}$-$L^{B4}$; $L^{B2}$ is —$S(O)_2$—, —$N(R^{B2})$—, —O—, —S—, —$C(O)N(R^{B2})$—, —$N(R^{B2})C(O)$—, —$N(R^{B2})C(O)NH$—, —$NHC(O)N(R^{B2})$—, —C(O)O—, —OC(O)—; $L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{B2}$ $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —ONH$_2$, —NHC(O)NHNH$_2$, —NHC(O)NH$_2$, —NHSO$_2$H, —NHC(O)H, —NHC(O)OH, —NHC(NH)H, —NHC(NH)NH$_2$, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —$NHC(O)NR^{B1A}R^{B1B}$, —$N(O)_{mB1}$, —$NR^{B1A}R^{B1B}$, —$C(O)R^{B1C}$, —$C(O)OR^{B1C}$, —$C(O)NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B1C}$, —$NR^{B1A}OR^{B1C}$, —$NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$, $R^{B1B}$, $R^{B1C}$ and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl; nB1 is independently an integer from 0 to 4; mB1 and vB1 are independently 1 or 2; and $X^{B1}$ is independently —F, —Cl, —Br, or —I.

In embodiments, $L^{B1}$ is

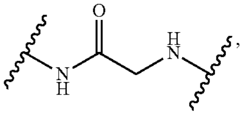, 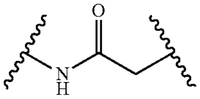,

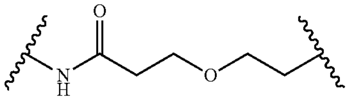,

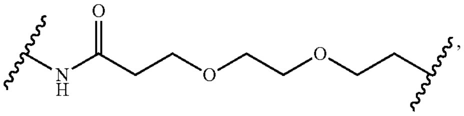,

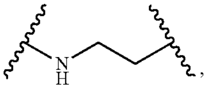, 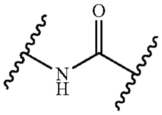,

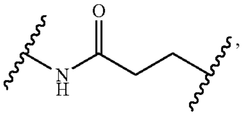, 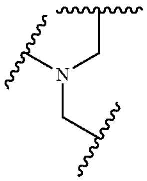,

-continued

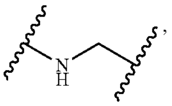, 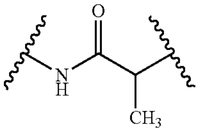,

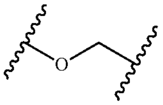, or 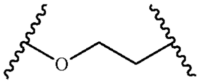.

In embodiments, $L^{B1}$-$R^{B1}$ is

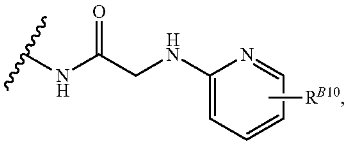,

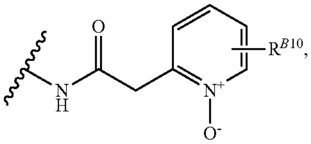,

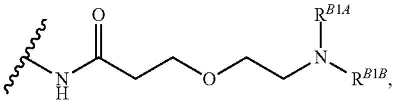,

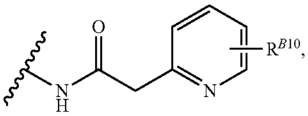,

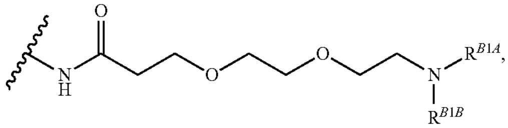,

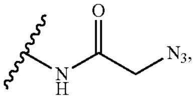, 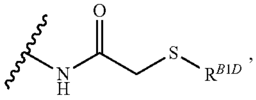,

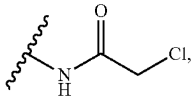, 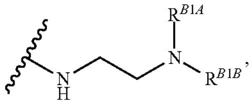,

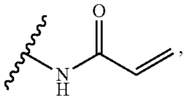, 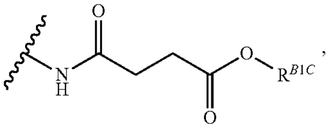,

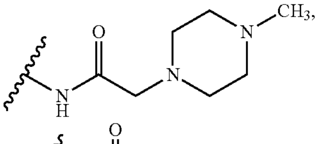,

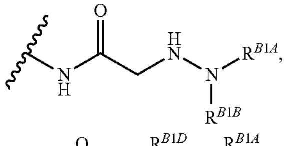,

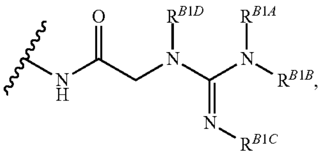,

-continued
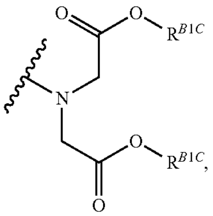
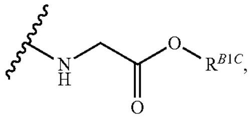,
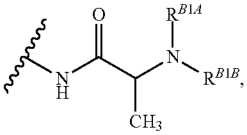
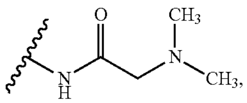
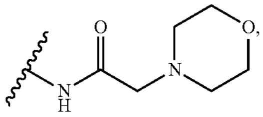
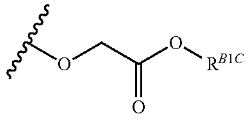,
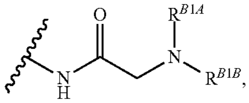
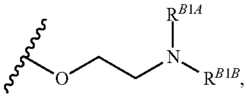
or
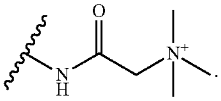
$R^{B1A}$, $R^{B1B}$, $R^{B1D}$, and $R^{B10}$ are as described herein, including in embodiments.
In embodiments, $L^{B1}$-$R^{B1}$ is
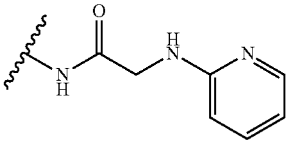,
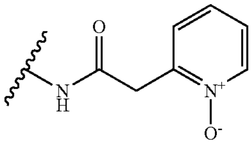,
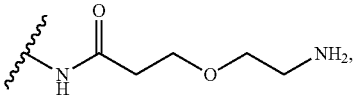
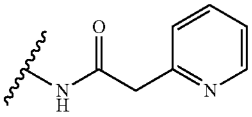,
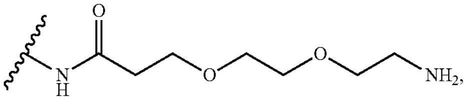
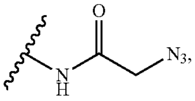
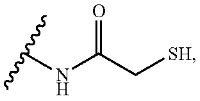
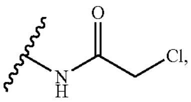
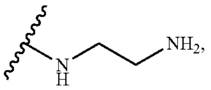
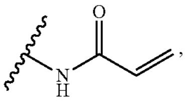,
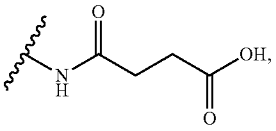
-continued
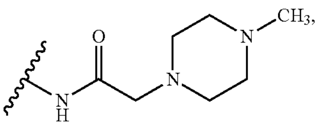
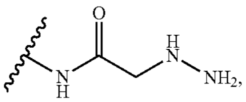
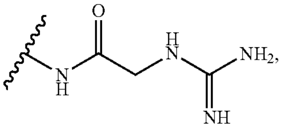
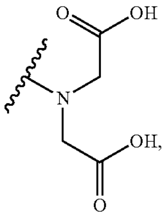
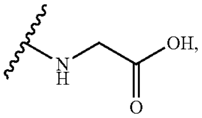
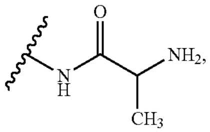
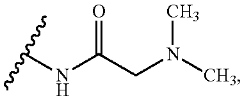
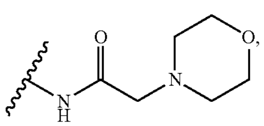
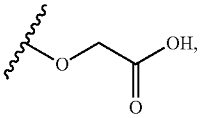
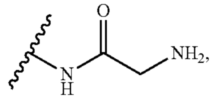
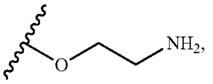
or
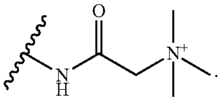
In embodiments, $A^{B}$ is an immunophilin-binding moiety having the formula
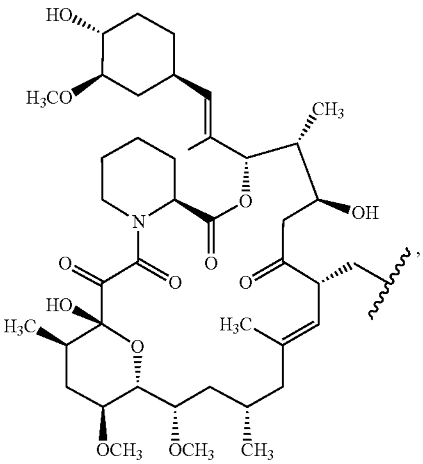 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof; $L^{B1}$ is

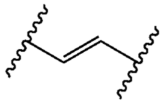
or
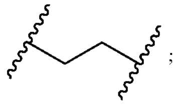
;

$R^{B1}$ is substituted or unsubstituted heteroaryl. In embodiments, $R^{B1}$ is independently substituted or unsubstituted heteroaryl (e.g., 5 to 10 membered, 5 to 9 membered, or 5 to 6 membered). In embodiments, $R^{B1}$ is independently substituted heteroaryl (e.g., 5 to 10 membered, 5 to 9 membered, or 5 to 6 membered). In embodiments, $R^{B1}$ is substituted or unsubstituted pyridyl. In embodiments, $R^{B1}$ is independently pyridyl N-oxide. In embodiments, $R^{B1}$ is independently unsubstituted heteroaryl (e.g., 5 to 10 membered, 5 to 9 membered, or 5 to 6 membered). In embodiments, $R^{B1}$ is independently unsubstituted pyridyl. In embodiments, $R^{B1}$ is independently $R^{B10}$-substituted pyridyl N-oxide. In embodiments, $R^{B1}$ is independently unsubstituted pyridyl N-oxide. In embodiments, $R^{B1}$ is independently $R^{B10}$-substituted pyridin-2-yl N-oxide. In embodiments, $R^{B1}$ is independently unsubstituted pyridin-2-yl N-oxide. In embodiments, $R^{B1}$ is independently $R^{B10}$-substituted pyridin-3-yl N-oxide. In embodiments, $R^{B1}$ is independently unsubstituted pyridin-3-yl N-oxide. In embodiments, $R^{B1}$ is independently $R^{B10}$-substituted pyridin-4-yl N-oxide. In embodiments, $R^{B1}$ is independently unsubstituted pyridin-4-yl N-oxide.

In embodiments, $A^{B}$ is an immunophilin-binding moiety having the formula

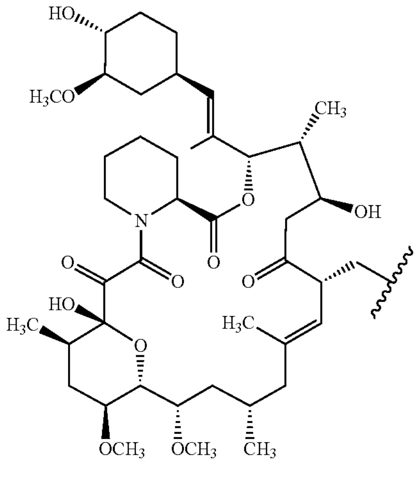
, or an analog thereof; $L^{B1}$ is

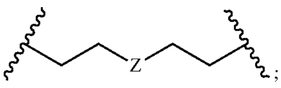
;

Z is —S— or —$SO_2$—; $R^{B1}$ is —$NR^{B1A}R^{B1B}$ or —NHC(O)$CH_2R^{B1C}$.

In embodiments, $R^{B1A}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B1A}$ is independently —$CX^{B1A}_3$. In embodiments, $R^{B1A}$ is independently —$CHX^{B1A}_2$. In embodiments, $R^{B1A}$ is independently —$CH_2X^{B1A}$. In embodiments, $R^{B1A}$ is independently —$OCX^{B1A}_3$. In embodiments, $R^{B1A}$ is independently —$OCHX^{B1A}_2$. In embodiments, $R^{B1A}$ is independently —$OCH_2X^{B1A}$. In embodiments, $R^{B1A}$ is independently —OH. In embodiments, $R^{B1A}$ is independently —CN. In embodiments, $R^{B1A}$ is independently —COOH. In embodiments, $R^{B1A}$ is independently —$CONH_2$. In embodiments, $X^{B1A}$ is independently —F, —Cl, —Br, or —I.

In embodiments, $R^{B1B}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B1B}$ is independently —$CX^{B1B}_3$. In embodiments, $R^{B1B}$ is independently —$CHX^{B1B}_2$. In embodiments, $R^{B1B}$ is independently —$CH_2X^{B1B}$. In embodiments, $R^{B1B}$ is independently —$OCX^{B1B}_3$. In embodiments, $R^{B1B}$ is independently —$OCHX^{B1B}_2$. In embodiments, $R^{B1B}$ is independently —$OCH_2X^{B1B}$. In embodiments, $R^{B1B}$ is independently —OH. In embodiments, $R^{B1B}$ is independently —CN. In embodiments, $R^{B1B}$ is independently —COOH. In embodiments, $R^{B1B}$ is independently —$CONH_2$. In embodiments, $X^{B1B}$ is independently —F, —Cl, —Br, or —I.

In embodiments, $R^{B1A}$ and $R^{B1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{B1A}$ and $R^{B1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form a substituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form an unsubstituted heteroaryl (e.g., 5 to 10 membered, 5 to 9 membered, or 5 to 6 membered).

In embodiments, $R^{B1C}$ is substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted heteroalkyl (e.g., 2 to 8 membered, 2 to 6 membered, 4 to 6 membered, 2 to 3 membered, or 4 to 5 membered). In embodiments, $R^{B1C}$ is independently unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted or unsubstituted cycloalkyl (e.g., $C_3$-$C_8$, $C_3$-$C_6$, $C_4$-$C_6$, or $C_5$-$C_6$). In embodiments, $R^{B1C}$ is independently substituted cycloalkyl (e.g., $C_3$-$C_8$, $C_3$-$C_6$, $C_4$-$C_6$, or $C_5$-$C_6$). In embodiments, $R^{B1C}$ is independently unsubstituted cycloalkyl (e.g., $C_3$-$C_8$, $C_3$-$C_6$, $C_4$-$C_6$, or $C_5$-$C_6$). In embodiments, $R^{B1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted heterocycloalkyl (e.g., 3 to 8 membered, 3 to 6 membered, 4 to 6 membered, 4 to 5 membered, or 5 to 6 membered). In embodiments, $R^{B1C}$ is independently unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted or unsubstituted aryl (e.g., $C_6$-$C_{10}$ or phenyl). In embodiments, $R^{B1C}$ is independently substituted aryl (e.g., $C_6$-$C_{10}$ or phenyl). In embodiments, $R^{B1C}$ is independently unsubstituted aryl (e.g., $C_6$-$C_{10}$ or phenyl). In embodiments, $R^{B1C}$ is independently substituted or unsubstituted heteroaryl (e.g., 5 to 10 membered, 5 to 9 membered, or 5 to 6 membered). In embodiments, $R^{B1C}$ is independently substituted heteroaryl (e.g., 5 to 10 membered, 5 to 9 membered, or 5 to 6 membered). In embodiments, $R^{B1C}$ is independently pyridyl N-oxide. In embodiments, RBC is independently unsubstituted heteroaryl (e.g., 5 to 10 membered, 5 to 9 membered, or 5 to 6 membered). In embodiments, $R^{B1C}$ is independently unsubstituted pyridyl.

In embodiments, the compound is

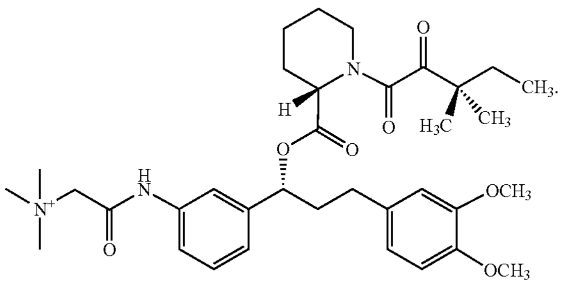

In embodiments, the compound is

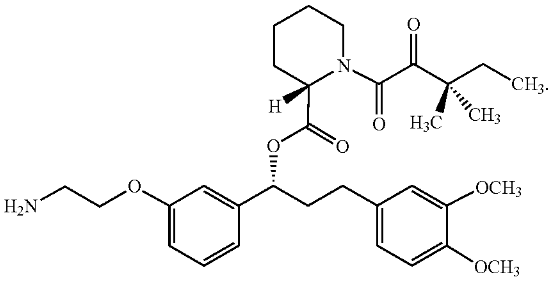

In embodiments, the compound is

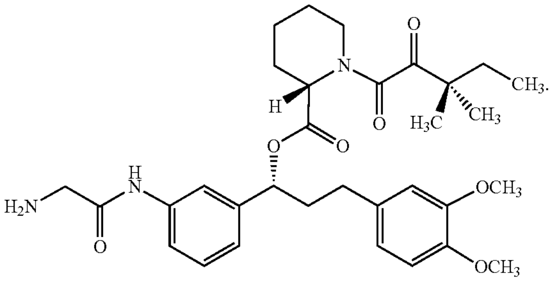

In embodiments, the compound is

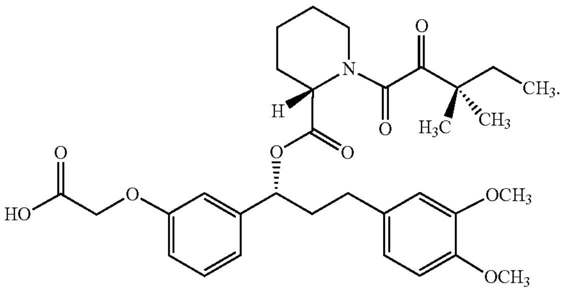

In embodiments, the compound is

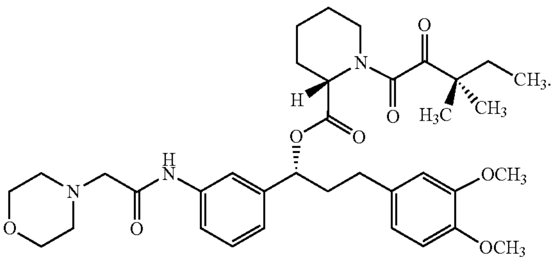

In embodiments, the compound is
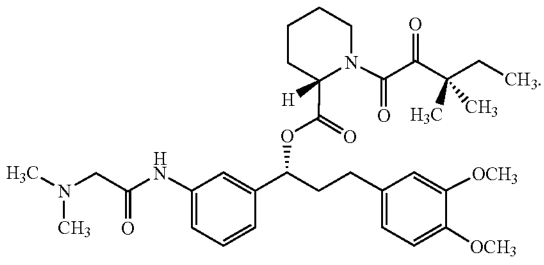
In embodiments, the compound is
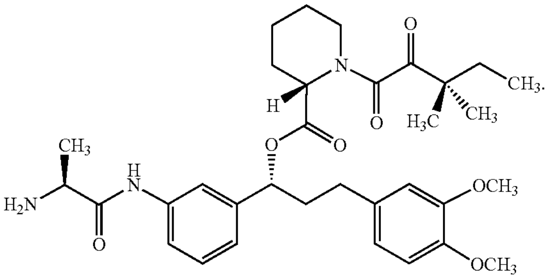
In embodiments, the compound is
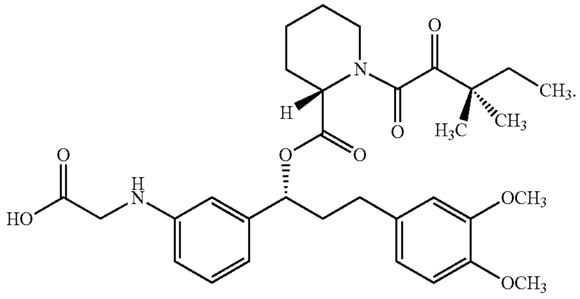
In embodiments, the compound is
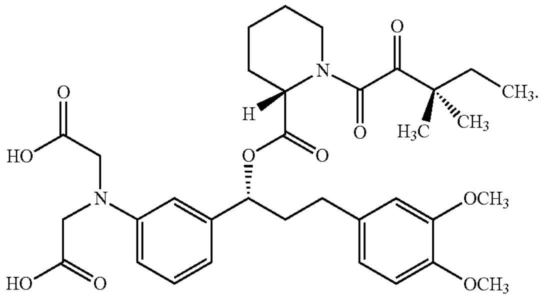
In embodiments, the compound is
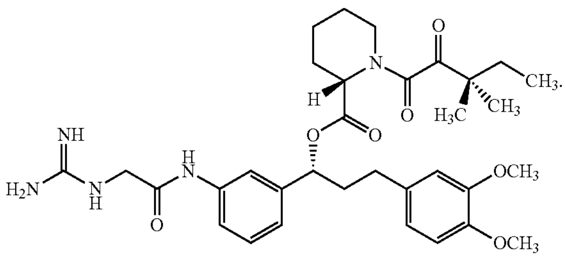
In embodiments, the compound is
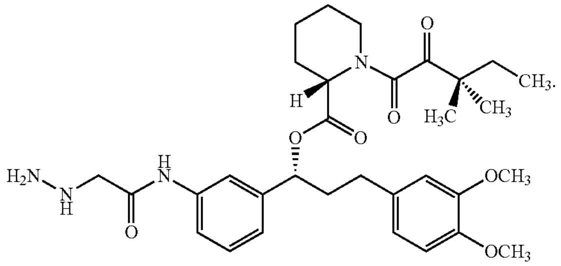
In embodiments, the compound is
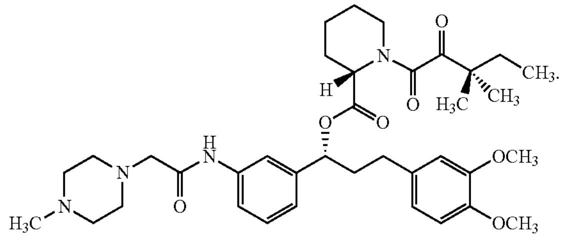
In embodiments, the compound is
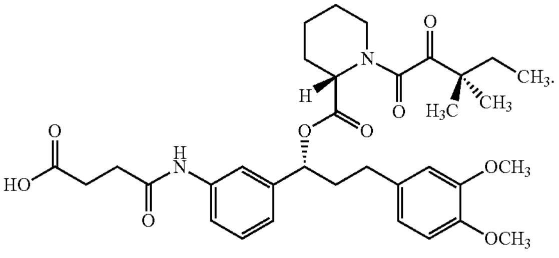

In embodiments, the compound is
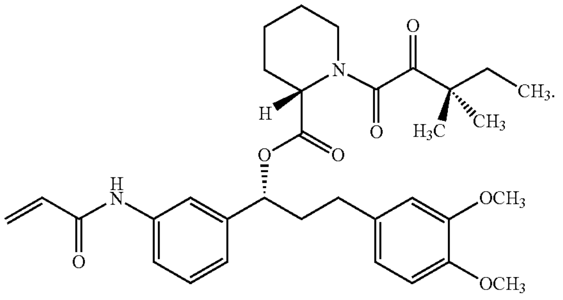
In embodiments, the compound is
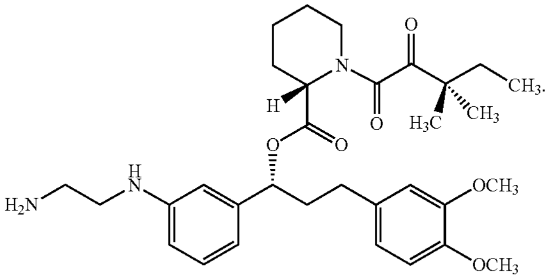
In embodiments, the compound is
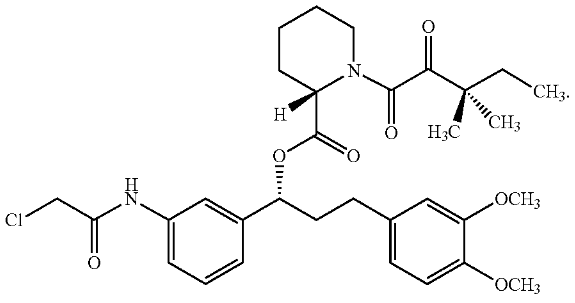
In embodiments, the compound is
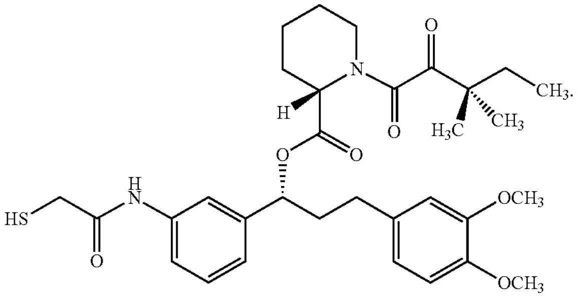
In embodiments, the compound is
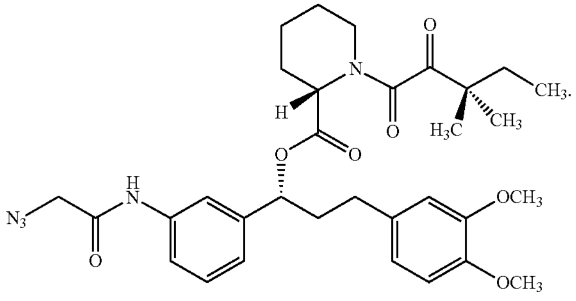
In embodiments, the compound is
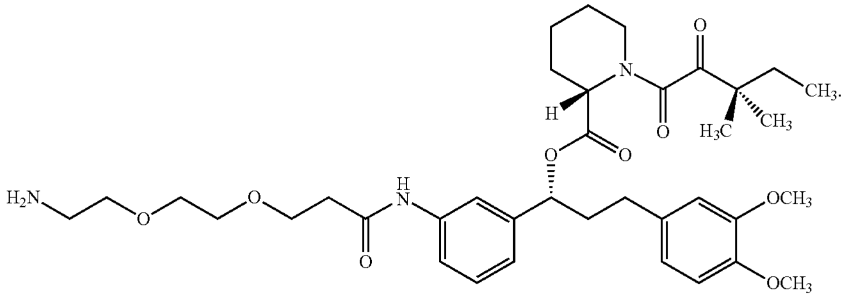
In embodiments, the compound is
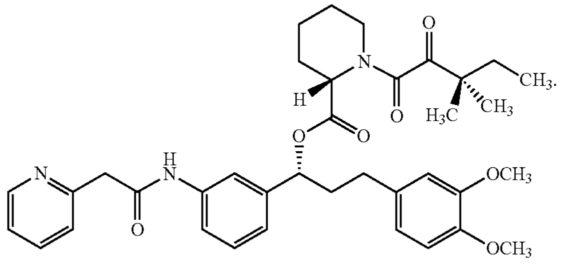

In embodiments, the compound is
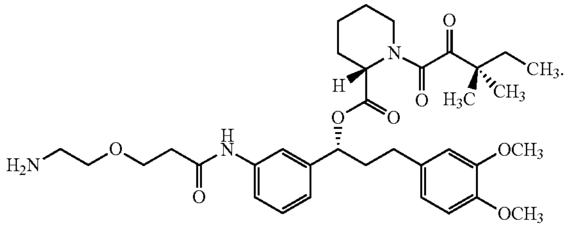
In embodiments, the compound is
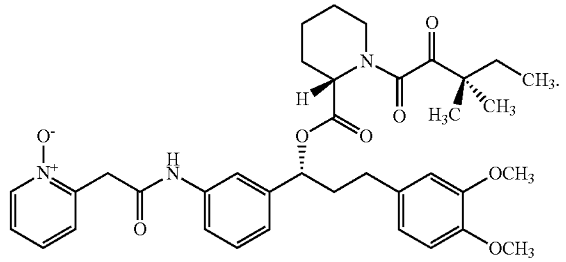
In embodiments, the compound is
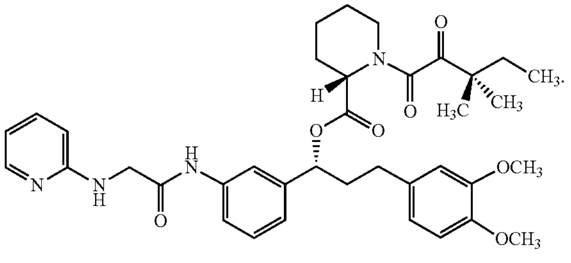
In embodiments, the compound is
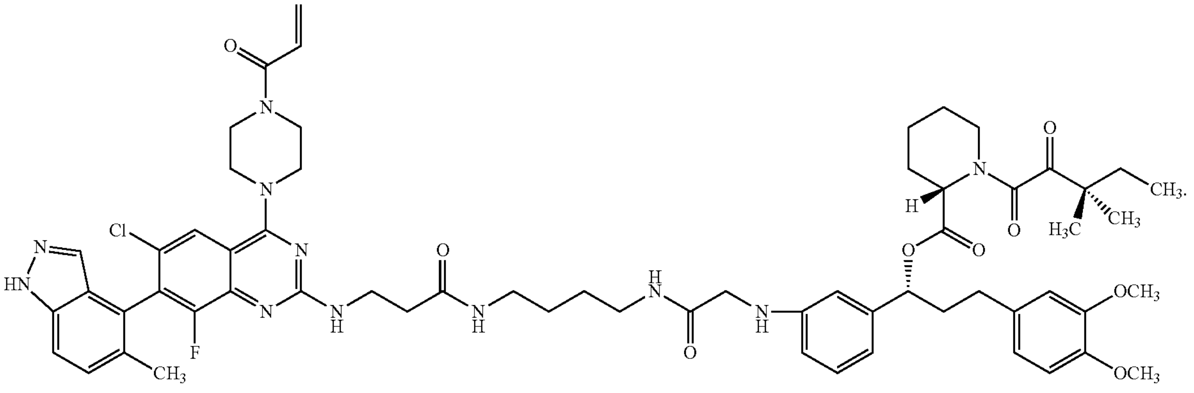
In embodiments, the compound is
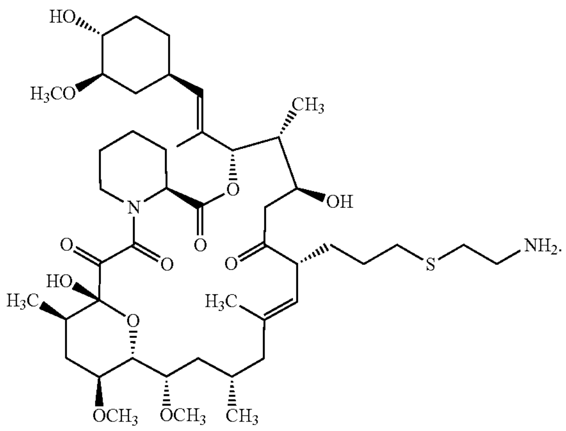 [SMILES: CO[C@H]1C[C@@H](C)C/C(C)=C/[C@@H](CCCSCCN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
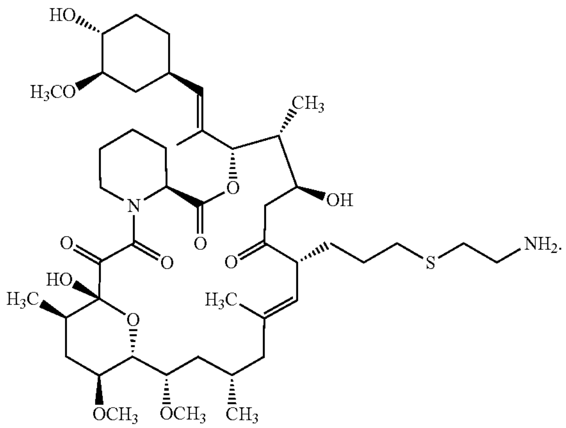 [SMILES: CO[C@H]1C[C@@H](C)C/C(C)=C/[C@@H](CCCSCCN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is
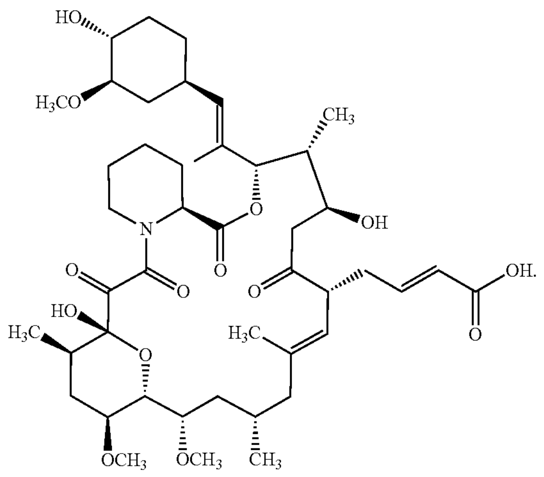 [SMILES: CO[C@H]1C[C@@H](C)C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
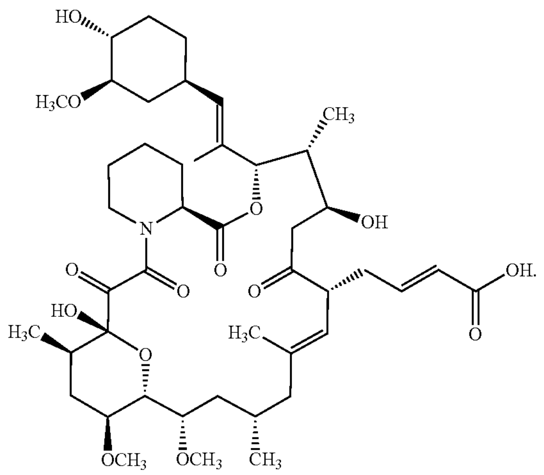 [SMILES: CO[C@H]1C[C@@H](C)C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
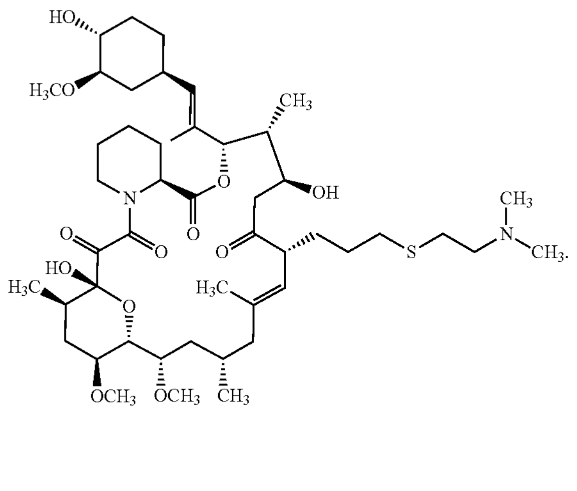 [SMILES: CO[C@H]1C[C@@H](C)C/C(C)=C/[C@@H](CCCSCCN(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
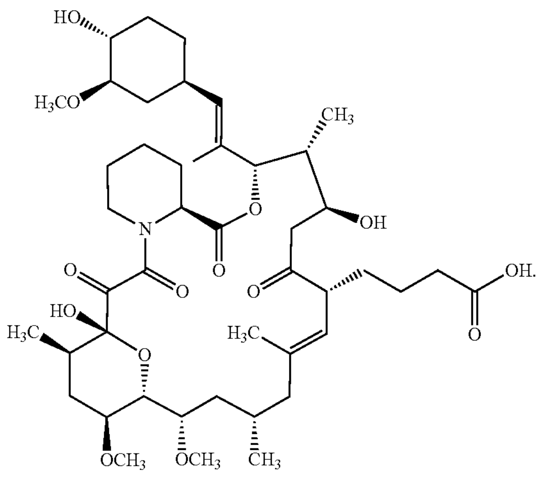 [SMILES: CO[C@H]1C[C@@H](C)C/C(C)=C/[C@@H](CCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
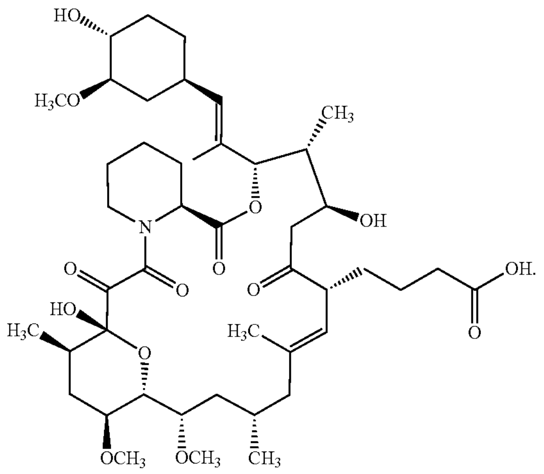 [SMILES: CO[C@H]1C[C@@H](C)C/C(C)=C/[C@@H](CCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is
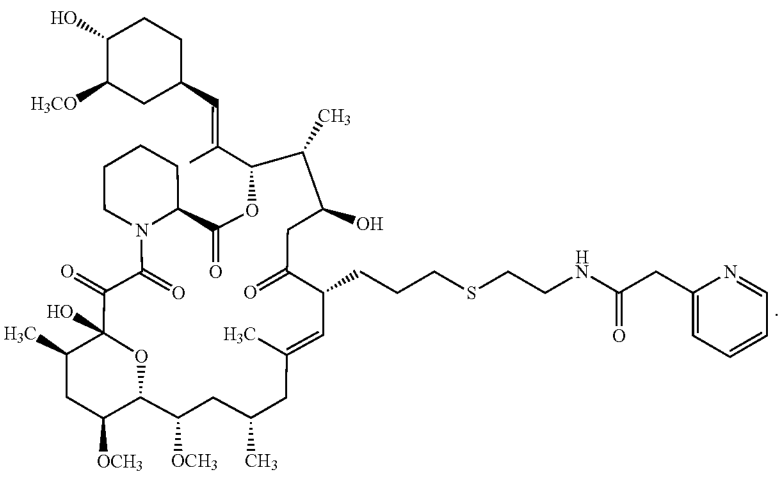 [SMILES: CO[C@H]1C[C@@H](C)C/C(C)=C/[C@@H](CCCSCCNC(=O)Cc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
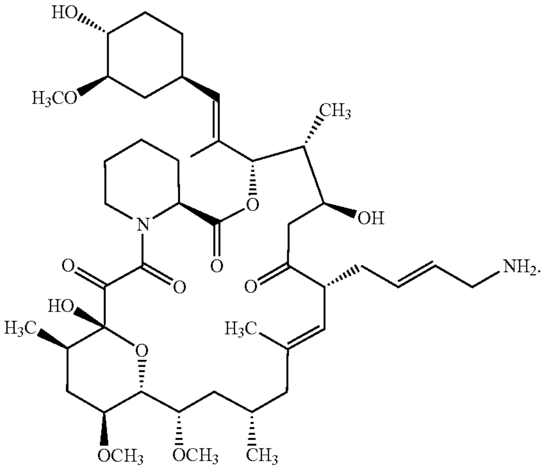 [SMILES: CO[C@H]1C[C@@H](C)C/C(C)=C/[C@@H](C/C=C/CN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
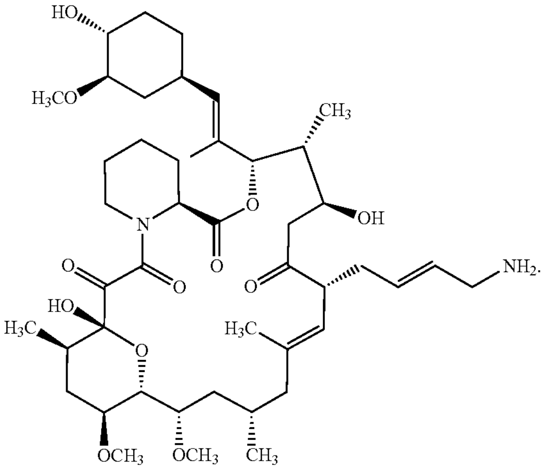 [SMILES: CO[C@H]1C[C@@H](C)C/C(C)=C/[C@@H](C/C=C/CN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
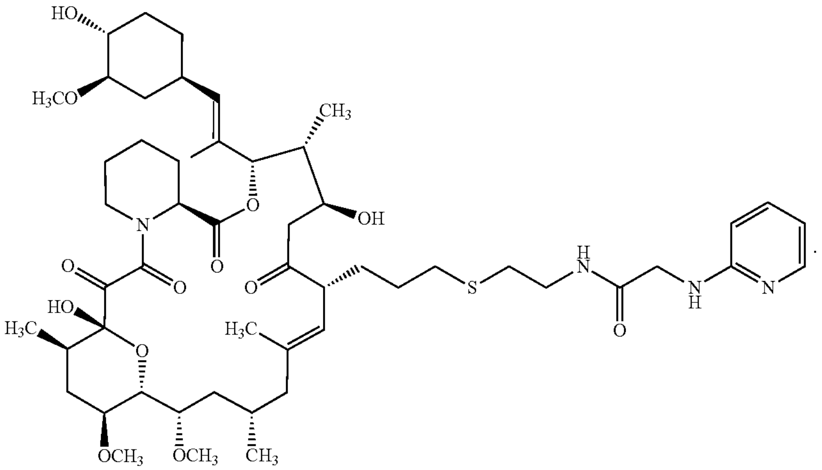 [SMILES: CO[C@H]1C[C@@H](C)C/C(C)=C/[C@@H](CCCSCCNC(=O)CNc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is
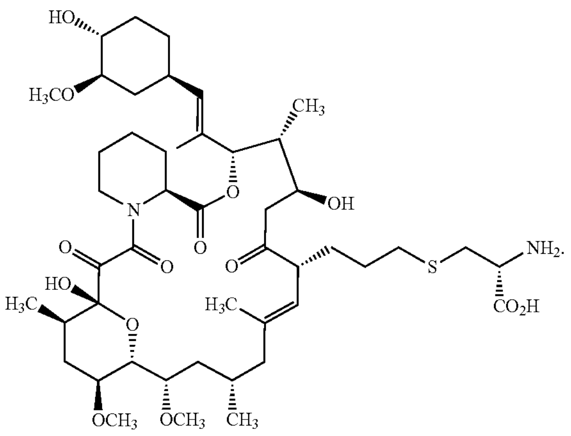 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
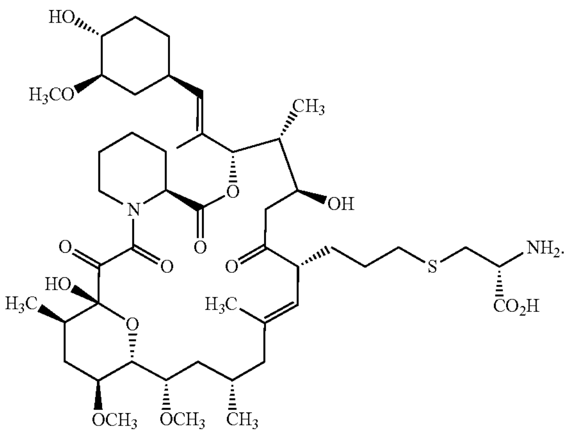 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
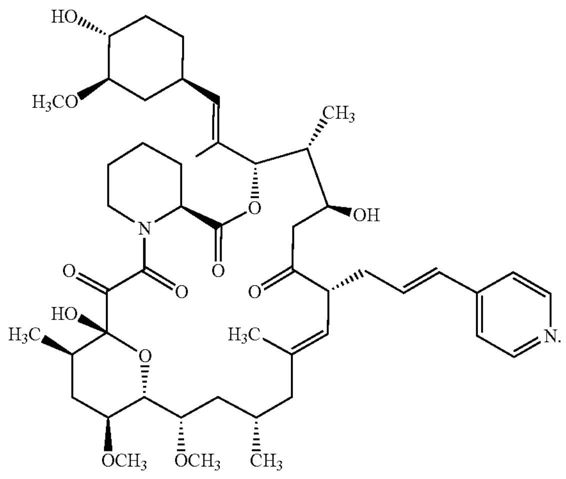 [SMILES: CO[C@H]1C[C@@H](C)C/C(C)=C/[C@@H](C/C=C/c2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
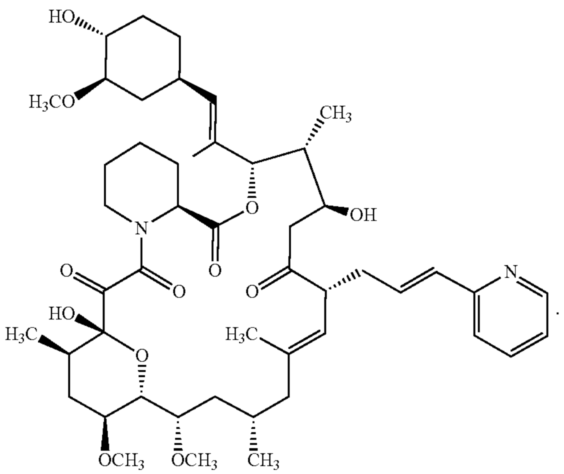
In embodiments, the compound is
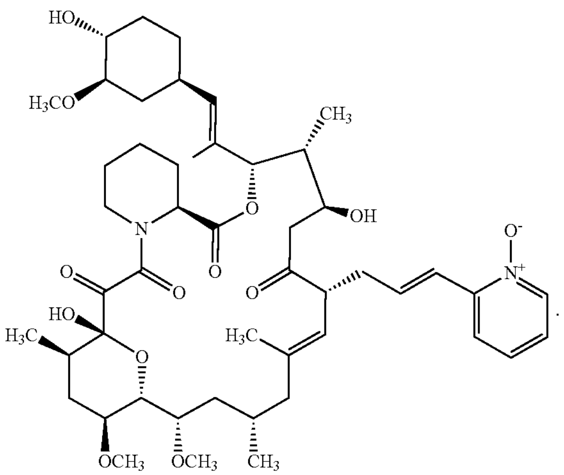 [SMILES: CO[C@H]1C[C@@H](C)C/C(C)=C/[C@@H](C/C=C/c2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
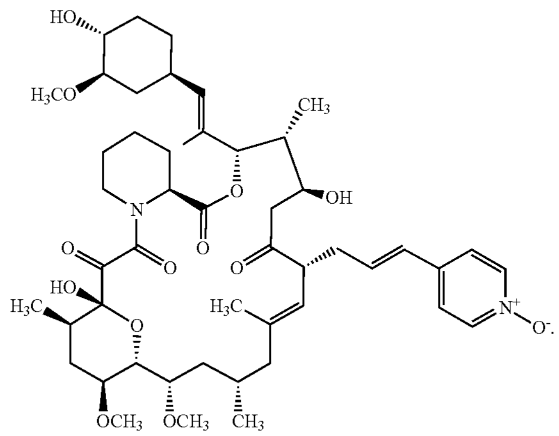

In embodiments, the compound is
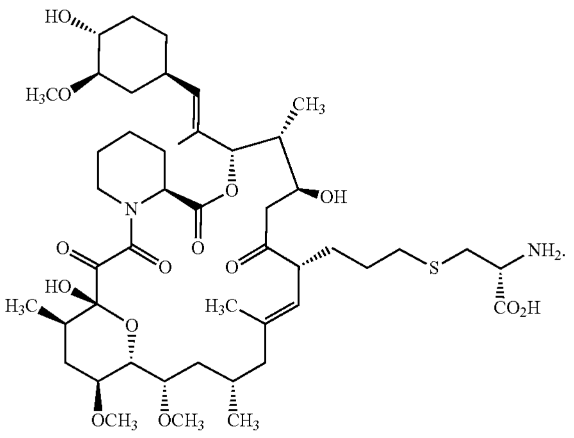 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
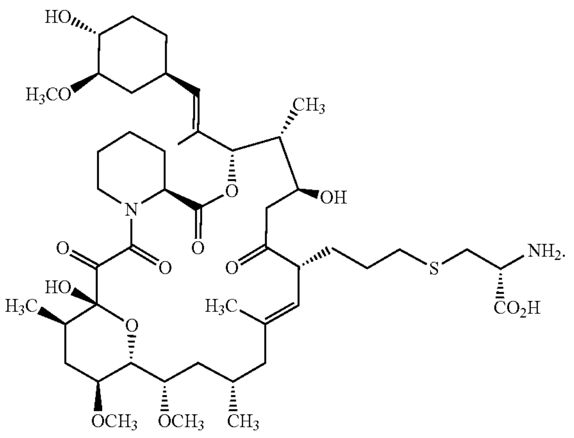 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
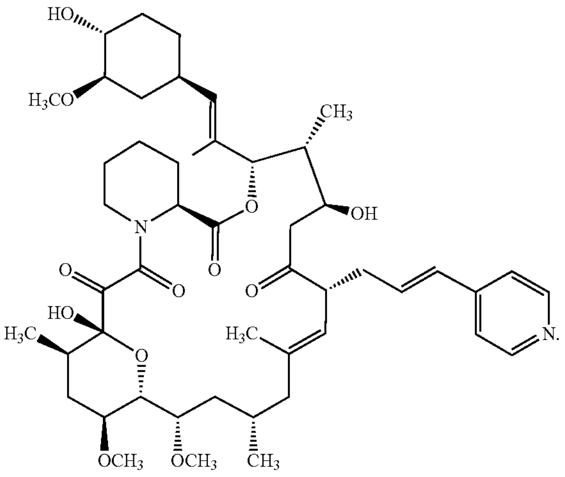
In embodiments, the compound is
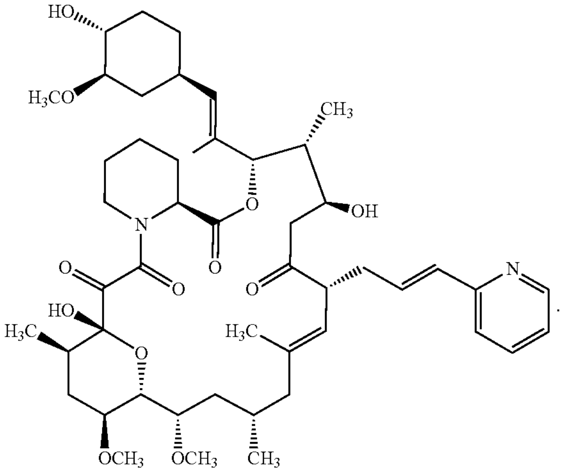
In embodiments, the compound is
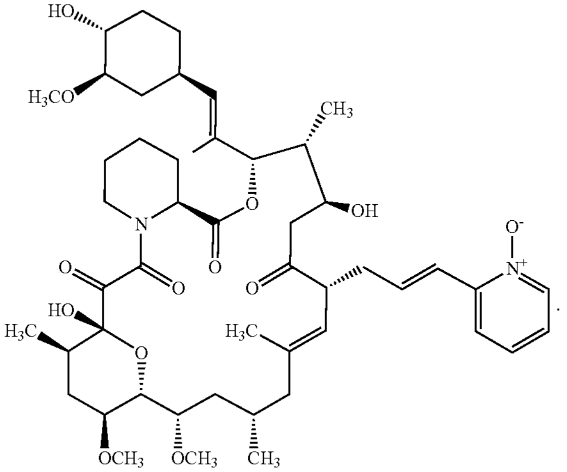
In embodiments, the compound is
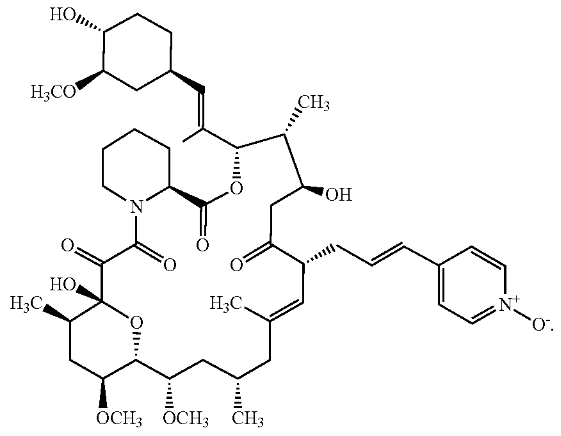

In embodiments, the compound is
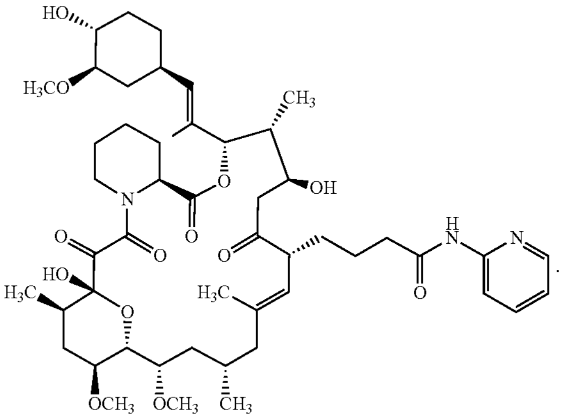 [SMILES: CO[C@H]1C[C@@H](C)C/C(C)=C/[C@@H](CCCC(=O)Nc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
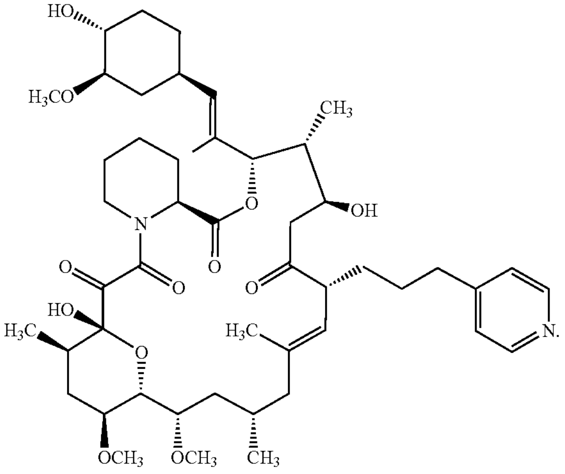
In embodiments, the compound is
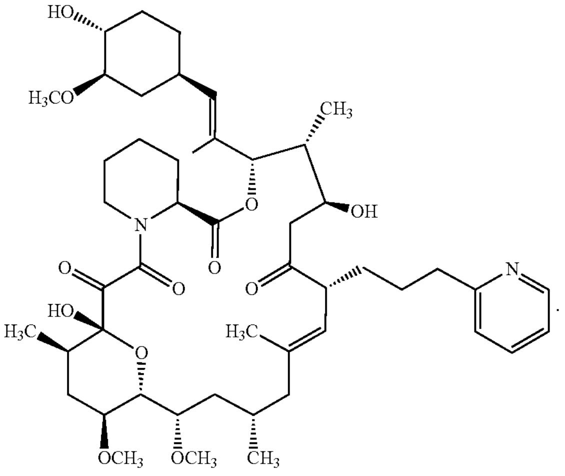
In embodiments, the compound is
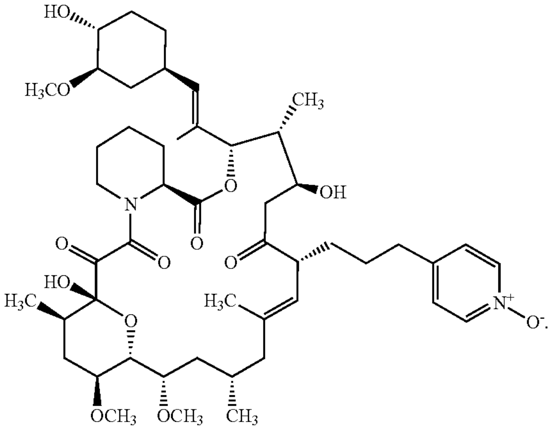
In embodiments, the compound is
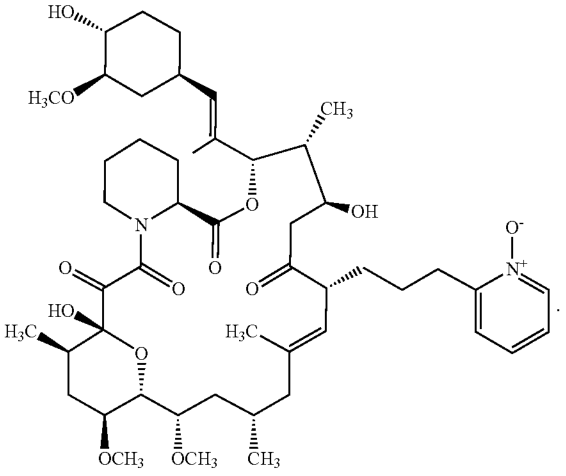

In embodiments, the compound is

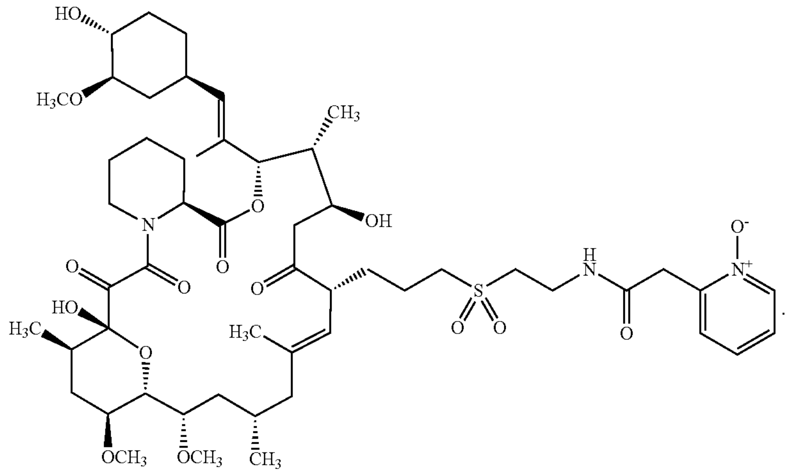 [SMILES: CO[C@H]1C[C@@H](C)C/C(C)=C/[C@@H](CCCS(=O)(=O)CCNC(=O)Cc2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is a compound described herein.

III. Pharmaceutical Compositions

In an aspect is provided a pharmaceutical composition including a compound described herein and a pharmaceutically acceptable excipient.

In embodiments, the pharmaceutical composition includes both a compound (e.g., as described herein) and a second agent (e.g., an anti-CNS disease drug as described herein). In embodiments, a first pharmaceutical composition includes the compound (e.g., as described herein), and a second pharmaceutical composition includes a second agent (e.g., an anti-CNS disease drug as described herein), and both the first and second pharmaceutical compositions are intended to be co-administered.

In embodiments, the pharmaceutical composition includes an effective amount of the compound. In embodiments, the pharmaceutical composition includes a therapeutically effective amount of the compound. In embodiments, the pharmaceutical composition includes an anti-CNS disease drug. In embodiments of the pharmaceutical compositions, the pharmaceutical composition includes an anti-CNS disease drug in a therapeutically effective amount.

In embodiments, the anti-CNS disease drug includes a monovalent active site mTOR inhibitor covalently bound to a monovalent rapamycin or a monovalent rapamycin analog.

In embodiments, the anti-CNS disease drug includes a divalent linker that binds the monovalent active site mTOR inhibitor (active site mTOR inhibitor moiety) to the monovalent rapamycin (rapamycin moiety) or the monovalent rapamycin analog (rapamycin analog moiety). In embodiments, the divalent linker may be bonded to rapamycin or a rapamycin analog at a position capable of being modified to include a linker. For example, a linker may be bonded to rapamycin or a rapamycin analog at position 10, 16, 27, 28, 39, or 40, among others (as indicated in figure immediately below). In embodiments, a linker is bonded to position 10 of rapamycin or a rapamycin analog. In embodiments, a linker is bonded to position 16 of rapamycin or a rapamycin analog. In embodiments, a linker is bonded to position 27 of rapamycin or a rapamycin analog. In embodiments, a linker is bonded to position 28 of rapamycin or a rapamycin analog. In embodiments, a linker is bonded to position 39 of rapamycin or a rapamycin analog. In embodiments, a linker is bonded to position 40 of rapamycin or a rapamycin analog.

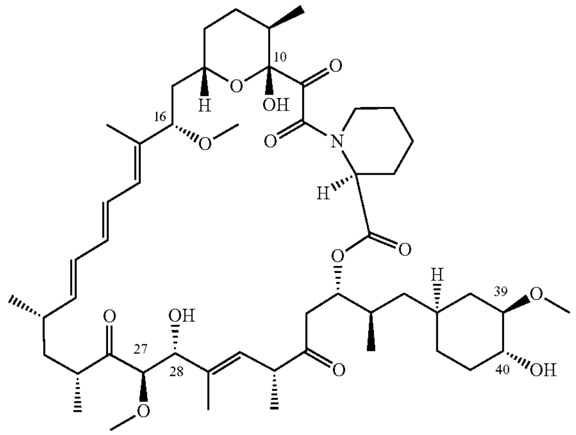

In embodiments, the divalent linker is at least about or about 5 Å in length (e.g., at least about or about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Å in length). In embodiments, the divalent linker is at least about or about the length of 5 methylene groups (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the divalent linker is at least about or about the length of 11 methylene groups (e.g., at least about or about 11, 12, 13, 14, 15, 16, 17, 18, 19, 20, 21, 22, 23,24,25,26,27,28,29,30,31,32,33,34,35,36,37,38,39,40,41, 42,43,44,45,46,47,48, 49, or 50 methylene groups). In embodiments, the divalent linker is at least about or about the length of 27 methylene groups (e.g., 27, 28, 29, 30, 31, 32, 33, 34, 35, 36, 37, 38, 39, 40, 41, 42, 43, 44, 45, 46, 47, 48, 49, or 50 methylene groups).

The specified length of a linker is the through space distance between the ends of the linker (i.e., the ends or termini that are connected to the two parts of the molecule connected by the linker) wherein the length of the linker is measured when the linker is fully extended and wherein the linker termini are the furthest apart they may naturally exist in solution (i.e., the longest distance between the ends of the linker wherein the linker adopts allowable conformations, bond lengths, and bond angles following the principles of Chemistry), (e.g., without adopting non-natural bond lengths, non-allowed or non-preferred bond angles, or high energy non-preferred or non-natural interactions of different components of the linker). In embodiments, the linker length is measured when included in a compound as described herein (e.g., aspect, embodiment, example, figures, table, or claim). It will be understood that a linker may adopt a through space distance (e.g., in solution, when bound to mTORC1, when bound to mTOR) that is less than the fully extended conformation used to define the linker length.

In embodiments, the linker is a hydrolysable linker (e.g., in solution). In embodiments, the linker is a non-hydrolysable linker (e.g., in solution). In embodiments, the linker may be cleaved by an enzyme (e.g., hydrolase, protease, cytochrome). In embodiments, the linker is not cleavable by an enzyme (e.g., under normal cellular conditions). In embodiments, the linker is a polyethylene glycol linker. In embodiments, the linker is hydrophilic. In embodiments, the linker is hydrophobic. In embodiments, the linker includes a disulfide bond. In embodiments, the linker includes a hydrazone bond. In embodiments, the linker includes an ester. In embodiments, the linker includes a sulfonyl. In embodiments, the linker includes a thioether. In embodiments, the linker includes a phosphinate. In embodiments, the linker includes an alkyloxime bond. In embodiments, the linker includes one or more amino acids. In embodiments, the linker consists of amino acids. In embodiments, the linker includes an amino acid analog. In embodiments, the linker includes an amino acid mimetic. In embodiments, the linker is a linker known in the art for use in linking antibodies to agents (e.g., antibody drug conjugates). In embodiments, the linker is a linker as described in Bioconjugate Techniques (Second Edition) by Greg T. Hermanson (2008), which is herein incorporated by referenced in its entirety for all purposes. In embodiments, the linker is a linker as described in Flygare J. A., Pillow T. H., Aristoff P., Antibody-drug conjugates for the treatment of cancer, Chemical Biology and Drug Design, 2013 January; 81(1):113-21, which is herein incorporated by referenced in its entirety for all purposes. In embodiments, the linker is a linker as described in Drachman J. G., Senter P. D., Antibody-drug conjugates: the chemistry behind empowering antibodies to fight cancer, Hematology Am Soc Hematol Educ Program, 2013; 2013: 306-10, which is herein incorporated by referenced in its entirety for all purposes.

In embodiments, the anti-CNS disease drug includes a divalent linker covalently bound to the monovalent active site mTOR inhibitor and the monovalent rapamycin or monovalent rapamycin analog. In embodiments, the anti-CNS disease drug includes a divalent linker covalently bound directly to the monovalent active site mTOR inhibitor and directly to the monovalent rapamycin or monovalent rapamycin analog.

In embodiments, the anti-CNS disease drug has the formula:

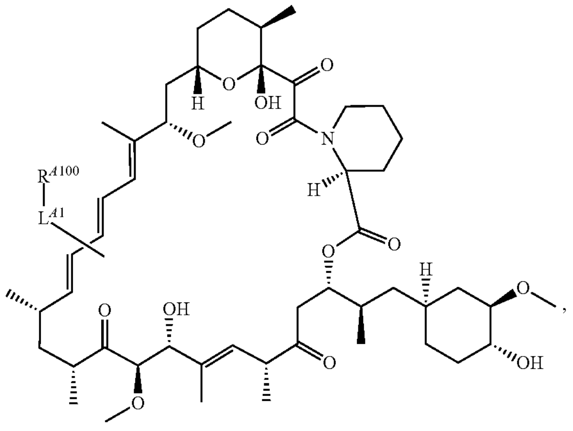

wherein $L^{A1}$ is as described herein and may be bonded to any atom in the ring ($L^{A1}$ is a floating substituent) and $R^{A100}$ is a monovalent active site mTOR inhibitor.

In embodiments, the anti-CNS disease drug has the formula:

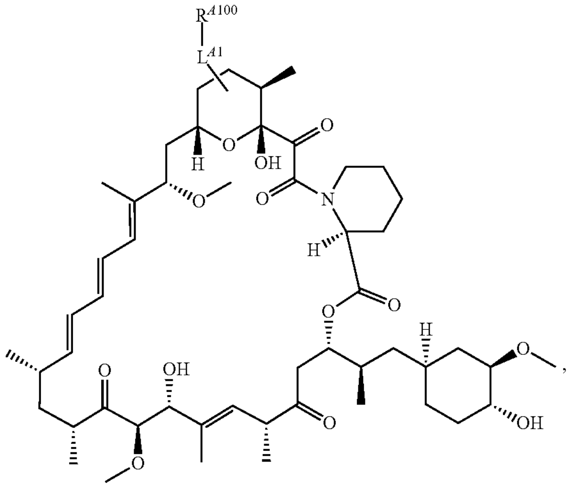

wherein $L^{A1}$ is as described herein and may be bonded to any atom in the ring ($L^{A1}$ is a floating substituent) and $R^{A100}$ is a monovalent active site mTOR inhibitor.

In embodiments, the anti-CNS disease drug has the formula:

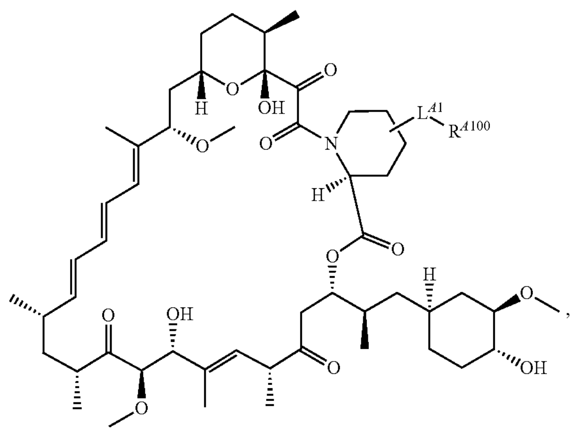

wherein $L^{A1}$ is as described herein and may be bonded to any atom in the ring ($L^{A1}$ is a floating substituent) and $R^{A100}$ is a monovalent active site mTOR inhibitor.

In embodiments, the anti-CNS disease drug has the formula:

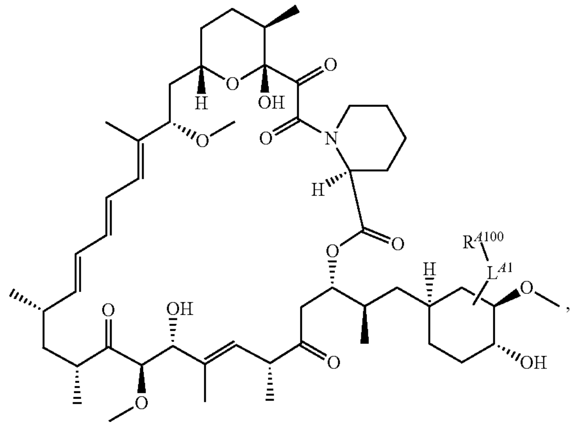

wherein $L^{A1}$ is as described herein and may be bonded to any atom in the ring ($L^{A1}$ is a floating substituent) and $R^{A100}$ is a monovalent active site mTOR inhibitor.

$R^{A100}$ is a monovalent active site mTOR inhibitor. In embodiments, $R^{A100}$ is

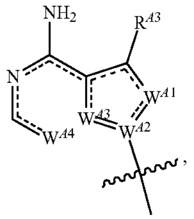

wherein $W^{A1}$, $W^{A2}$, $W^{A3}$, $W^{A4}$, and $R^{A3}$ are as described herein. In embodiments, $R^{A100}$ is

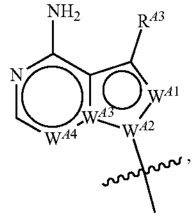

wherein $W^{A1}$, $W^{A2}$, $W^{A3}$, $W^{A4}$, and $R^{A3}$ are as described herein. In embodiments, $R^{A100}$ is

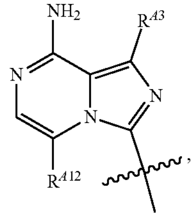

wherein $R^{A3}$ and $R^{A12}$ are as described herein. In embodiments, $R^{A100}$ is

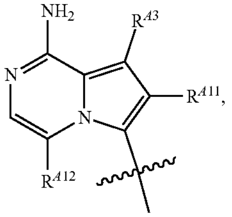

wherein $R^{A3}$, $R^{A11}$, and $R^{A12}$ are as described herein. In embodiments, $R^{A100}$ is

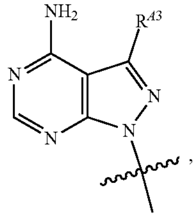

wherein $R^{A3}$ is as described herein. In embodiments, $R^{A100}$ is

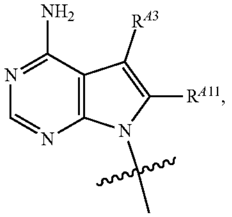

wherein $R^{A3}$ and $R^{A11}$ are as described herein. In embodiments, $R^{A100}$ is

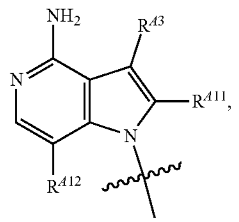

wherein $R^{A3}$, $R^{A12}$, and $R^{A12}$ are as described herein. In embodiments, $R^{A100}$ is

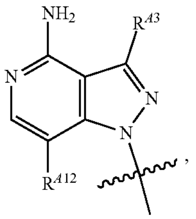

wherein $R^{A3}$ and $R^{A12}$ are as described herein.

In embodiments, the anti-CNS disease drug has the formula:

(VI)

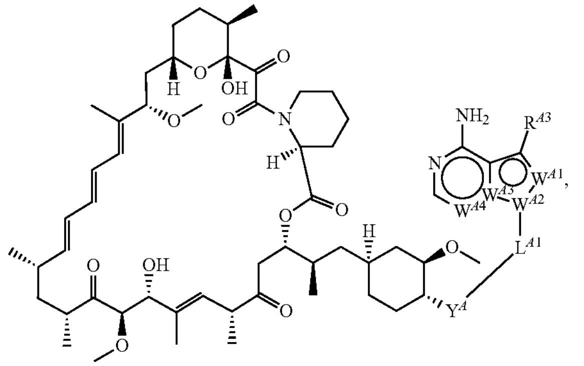

wherein $W^{A1}$, $W^{A2}$, $W^{A3}$, $W^{A4}$, $L^{A1}$, $Y^{A}$, and $R^{A3}$ are as described herein.

In embodiments, the anti-CNS disease drug has the formula:

(VIa)

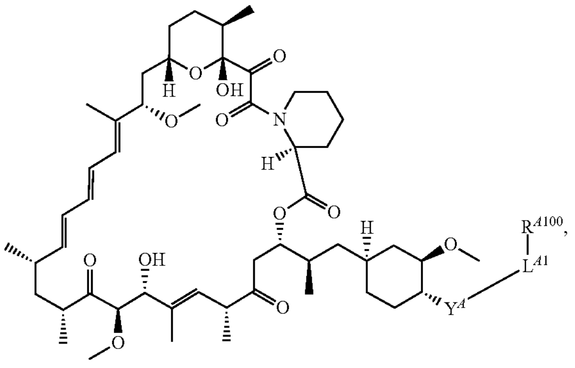

wherein $L^{A1}$, $Y^{A}$, and $R^{A100}$ are as described herein.

In embodiments, the anti-CNS disease drug has the formula:

(VIb)

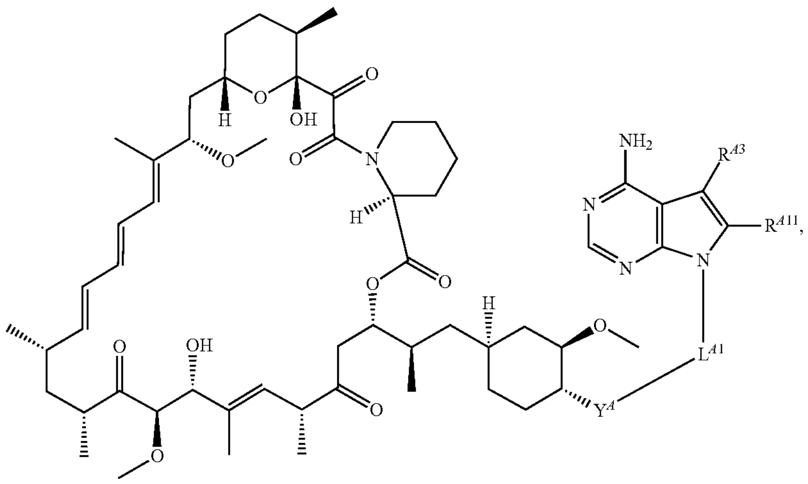

wherein $L^{A1}$, $Y^{A}$, $R^{A3}$, and $R^{A11}$ are as described herein.

In embodiments, the anti-CNS disease drug has the formula:

(VIc)

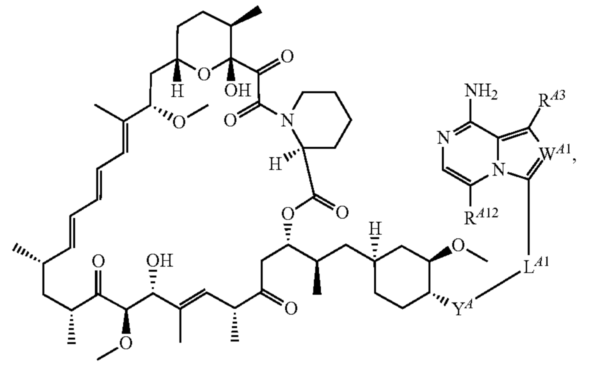

wherein $L^{A1}$, $Y^A$, $R^{A3}$, $W^{A1}$, and $R^{A12}$ are as described herein.

In embodiments, the anti-CNS disease drug has the formula:

(VId)

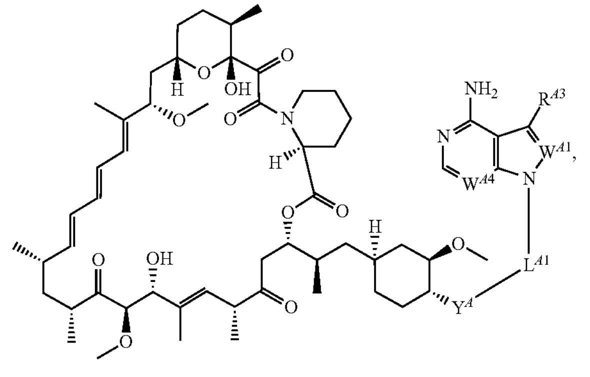

wherein $L^{A1}$, $Y^A$, $R^{A3}$, $W^{A1}$, and $W^{A4}$ are as described herein.

$L^{A1}$ is a divalent linker as described herein. $W^{A1}$ is N or $CR^{A11}$. $W^{A2}$ is N and $W^{A3}$ is C or, alternatively, $W^{A2}$ is C and $W^{A3}$ is N. $W^{A4}$ is N or $CR^{A12}$. $Y^A$ is O or $NR^{A13}$, $R^{A3}$ is hydrogen, oxo, halogen, $—CX^{A}_3$, —CN, $—SO_2Cl$, $—SO_{nA}R^{A10}$, $—SO_{vA}NR^{A7}R^{A8}$, $—NHNH_2—ONR^{A7}R^{A8}$, $—NHC(O)NHNH_2$, $—NHC(O)NR^{A7}R^{A8}$, $—N(O)_{mA}$, $—NR^{A7}R^{A8}$, $—C(O)R^{A9}$, $—C(O)OR^{A9}$, $—C(O)NR^{A7}R^{A8}$, $—OR^{A10}$, $—NR^{A7}SO_2R^{A10}$, $—NR^{A7}C(O)R^{A9}$, $—NR^{A7}C(O)OR^{A9}$, $—NR^{A7}OR^{A9}$, $—OCX^{A3}$, $—OCHX^{A2}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{A7}$, $R^{A8}$, $R^{A9}$, $R^{A10}$, $R^{A11}$, $R^{A12}$, and $R^{A13}$ are independently hydrogen, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{A7}$ and $R^{A8}$ substituents bonded to the same nitrogen atom may optionally be joined to form a substituted or unsubstituted heterocycloalkyl or substituted or unsubstituted heteroaryl. The variables mA and vA are independently 1 or 2. The variable nA is independently an integer from 0 to 4. The variable $X^A$ is independently —Cl, —Br, —I, or —F. In embodiments, $L^{A1}$ is a divalent linker including one or more amino acids. In embodiments, $L^{A1}$ is a divalent linker consisting of amino acids (i.e., a peptidyl linker). In embodiments, $L^{A1}$ is a divalent linker (e.g., a peptidyl linker) including an amino acid analog. In embodiments, $L^{A1}$ is a divalent linker (e.g., a peptidyl linker) including an amino acid mimetic. In embodiments, $L^{A1}$ is a divalent linker consisting of amino acid analogs (also referred to herein as a peptidyl analog linker). In embodiments, $L^{A1}$ is a divalent linker consisting of amino acid mimetics (also referred to herein as a peptidyl mimetic linker).

In embodiments, the anti-CNS disease drug has the formula:

(VII)

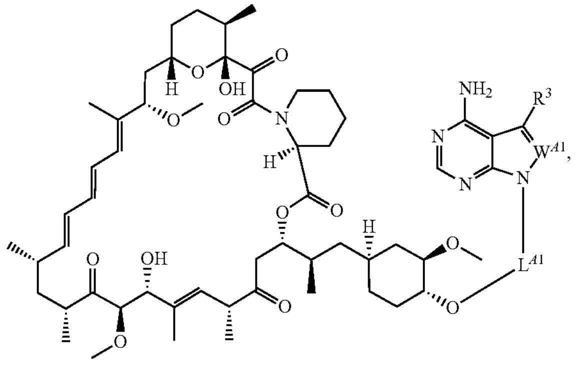

wherein $W^{A1}$ is N or CH. In embodiments, $W^{A1}$ is N. In embodiments, $W^{A1}$ is CH.

In embodiments, the anti-CNS disease drug has the formula:

(VIII)

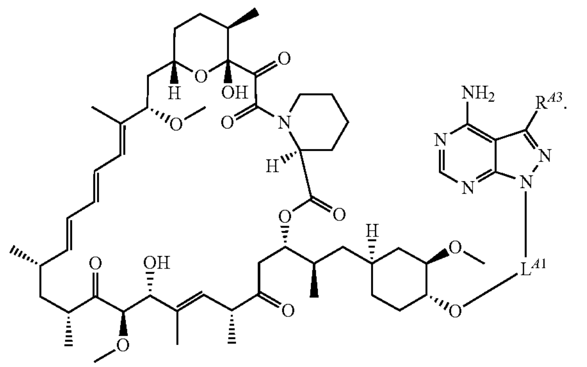

In embodiments, $R^{A3}$ is hydrogen, oxo, halogen, $—CX^{A3}$, —CN, $—SO_2Cl$, $—SO_{nA}R^{A10}$, $—SO_{vA}NR^{A7}R^{A8}$, $—NHNH_2$, $—ONR^{A7}R^{A8}$, $—NHC(O)NHNH_2$, $—NHC(O)NR^{A7}R^{A8}$, $—N(O)_{mA}$, $—NR^{A7}R^{A8}$, $—C(O)R^{A9}$, $—C(O)OR^{A9}$, $—C(O)NR^{A7}R^{A8}$, $—OR^{A10}$, $—NR^{A7}SO_2R^{A10}$, —$NR^{A7}C(O)R^{A9}$, —$NR^{A7}C(O)OR^{A9}$, —$NR^{A7}OR^{A9}$, —$OCX^{A3}$, —$OCHX^{A2}$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A3}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A3}$ is substituted with a plurality of groups selected from substituent groups, size-limited substituent groups, and lower substituent groups; each substituent group, size-limited substituent group, and/or lower substituent group may optionally be different. In embodiments, when $R^{A3}$ is substituted, it is substituted with at least one substituent group. In embodiments, when $R^{A3}$ is substituted, it is substituted with at least one size-limited substituent group. In embodiments, when $R^{A3}$ is substituted, it is substituted with at least one lower substituent group.

In embodiments, $R^{A3}$ is

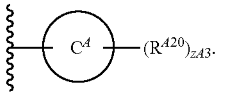

$R^{A20}$ is as described herein. Ring $C^A$ is an aryl (e.g., phenyl, diphenyl, or fused ring aryl) or a heteroaryl (e.g., monocyclic heteroaryl or fused ring heteroaryl). Ring $C^A$ may be any of the aryl or heteroaryl rings in the embodiments of $R^{A3}$ described herein (e.g., benzoxazolyl, indolyl, phenyl, or naphthyl). The symbol zA3 is an integer from 0 to 7. In embodiments, zA3 is 0. In embodiments, zA3 is 1. In embodiments, zA3 is 2. In embodiments, zA3 is 3. In embodiments, zA3 is 4. In embodiments, zA3 is 5. In embodiments, zA3 is 6. In embodiments, zA3 is 7.

In embodiments, Ring $C^A$ is an aryl (e.g., $C_6$-$C_{10}$ or phenyl) or a heteroaryl (e.g., 5 to 10 membered, 5 to 9 membered, or 5 to 6 membered).

In embodiments, $R^{A3}$ is independently substituted benzoxazolyl, substituted pyrimidinyl, substituted thiophenyl, substituted furanyl, substituted indolyl, substituted benzoxadiazolyl, substituted benzodioxolyl, substituted benzodioxanyl, substituted thianaphthanyl, substituted pyrrolopyridinyl, substituted indazolyl, substituted quinolinyl, substituted quinoxalinyl, substituted pyridopyrazinyl, substituted quinazolinonyl, substituted benzoisoxazolyl, substituted imidazopyridinyl, substituted benzofuranyl, substituted benzothiophenyl, substituted phenyl, substituted naphthyl, substituted biphenyl, substituted pyrrolyl, substituted pyrazolyl, substituted imidazolyl, substituted pyrazinyl, substituted oxazolyl, substituted isoxazolyl, substituted thiazolyl, substituted furylthienyl, substituted pyridyl, substituted pyrimidyl, substituted benzothiazolyl, substituted purinyl, substituted benzimidazolyl, substituted isoquinolyl, substituted thiadiazolyl, substituted oxadiazolyl, substituted pyrrolyl, substituted diazolyl, substituted triazolyl, substituted tetrazolyl, substituted benzothiadiazolyl, substituted isothiazolyl, substituted pyrazolopyrimidinyl, substituted pyrrolopyrimidinyl, substituted benzotriazolyl, or substituted quinolyl. In embodiments, $R^3$ is independently substituted benzoxazolyl.

In some embodiments of the anti-CNS disease drugs provided herein, $R^{A3}$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{A20}$-substituted or unsubstituted alkyl, $R^{A20}$-substituted or unsubstituted heteroalkyl, $R^{A20}$-substituted or unsubstituted cycloalkyl, $R^{A20}$-substituted or unsubstituted heterocycloalkyl, $R^{A20}$-substituted or unsubstituted aryl, or $R^{A20}$-substituted or unsubstituted heteroaryl.

In some embodiments, $R^{A3}$ is substituted with one or more substituents independently selected from halogen, —$CF_3$, —OH, and —$NH_2$. In some embodiments, $R^{A20}$ is substituted heteroaryl, such as benzoxazolyl or benzothiazolyl. In some embodiments, $R^{A3}$ is heteroaryl, such as benzoxazolyl or benzothiazolyl, substituted with one or more substituents independently selected from halogen, —$CF_3$, —OH, and —$NH_2$.

In embodiments, $R^{A3}$ is independently $R^{A20}$-substituted benzoxazolyl, $R^{A20}$-substituted pyrimidinyl, $R^{A20}$-substituted thiophenyl, $R^{A20}$-substituted furanyl, $R^{A20}$-substituted indolyl, $R^{A20}$-substituted benzoxadiazolyl, $R^{A20}$-substituted benzodioxolyl, $R^{A20}$-substituted benzodioxanyl, $R^{A20}$-substituted thianaphthanyl, $R^{A20}$-substituted pyrrolopyridinyl, $R^{A20}$-substituted indazolyl, $R^{A20}$-substituted quinolinyl, $R^{A20}$-substituted quinoxalinyl, $R^{A20}$-substituted pyridopyrazinyl, $R^{A20}$-substituted quinazolinonyl, $R^{A20}$-substituted benzoisoxazolyl, $R^{A20}$-substituted imidazopyridinyl, $R^{A20}$-substituted benzofuranyl, $R^{A20}$-substituted benzothiophenyl, $R^{A20}$-substituted phenyl, $R^{A20}$-substituted naphthyl, $R^{A20}$-substituted biphenyl, $R^{A20}$-substituted pyrrolyl, $R^{A20}$-substituted pyrazolyl, $R^{A20}$-substituted imidazolyl, $R^{A20}$-substituted pyrazinyl, $R^{A20}$-substituted oxazolyl, $R^{A20}$-substituted isoxazolyl, $R^{A20}$-substituted thiazolyl, $R^{A20}$-substituted furylthienyl, $R^{A20}$-substituted pyridyl, $R^{A20}$-substituted pyrimidyl, $R^{A20}$-substituted benzothiazolyl, $R^{A20}$-substituted purinyl, $R^{A20}$-substituted benzimidazolyl, $R^{A20}$-substituted isoquinolyl, $R^{A20}$-substituted thiadiazolyl, $R^{A20}$-substituted oxadiazolyl, $R^{A20}$-substituted pyrrolyl, $R^{A20}$-substituted diazolyl, $R^{A20}$-substituted triazolyl, $R^{A20}$-substituted tetrazolyl, $R^{A20}$-substituted benzothiadiazolyl, $R^{A20}$-substituted isothiazolyl, $R^{A20}$-substituted pyrazolopyrimidinyl, $R^{A20}$-substituted pyrrolopyrimidinyl, $R^{A20}$-substituted benzotriazolyl, or $R^{A20}$-substituted quinolyl. In embodiments, $R^{A3}$ is independently $R^{A20}$-substituted benzoxazolyl.

$R^{A20}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{A21}$-substituted or unsubstituted alkyl, $R^{A21}$-substituted or unsubstituted heteroalkyl, $R^{A21}$-substituted or unsubstituted cycloalkyl, $R^{A2}$-substituted or unsubstituted heterocycloalkyl, $R^{A2}$-substituted or unsubstituted aryl, or $R^{A21}$-substituted or unsubstituted heteroaryl.

In embodiments, $R^{A20}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A21}$-substituted or unsubstituted alkyl (e.g., $C_1$-$C_8$, $C_1$-$C_6$, $C_1$-$C_4$, or $C_1$-$C_2$), $R^{A21}$-substituted or unsubstituted heteroalkyl (e.g., 2 to 8 membered, 2 to 6 membered, 4 to 6 membered, 2 to 3 membered, or 4 to 5 membered), $R^{A21}$-substituted or unsubstituted cycloalkyl (e.g., $C_3$-$C_8$, $C_3$-$C_6$, $C_4$-$C_6$, or $C_5$-$C_6$), $R^{A21}$-substituted or unsubstituted heterocycloalkyl (e.g., 3 to 8 membered, 3 to 6 membered, 4 to 6 membered, 4 to 5 membered, or 5 to 6 membered), $R^{A21}$-substituted or unsubstituted aryl (e.g., $C_6$-$C_{10}$ or phenyl), or $R^{A21}$-substituted or unsubstituted heteroaryl (e.g., 5 to 10 membered, 5 to 9 membered, or 5 to 6 membered).

$R^{A21}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A22}$-substituted or unsubstituted alkyl, $R^{A22}$-substituted or unsubstituted heteroalkyl, $R^{A22}$-substituted or unsubstituted cycloalkyl, $R^{A22}$-substituted or unsubstituted heterocycloalkyl, $R^{A22}$-substituted or unsubstituted aryl, or $R^{A22}$-substituted or unsubstituted heteroaryl.

In embodiments, $R^{A21}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A22}$-substituted or unsubstituted alkyl (e.g., $C_1$-$C_8$, $C_1$-$C_6$, $C_1$-$C_4$, or $C_1$-$C_2$), $R^{A22}$-substituted or unsubstituted heteroalkyl (e.g., 2 to 8 membered, 2 to 6 membered, 4 to 6 membered, 2 to 3 membered, or 4 to 5 membered), $R^{A22}$-substituted or unsubstituted cycloalkyl (e.g., $C_3$-$C_8$, $C_3$-$C_6$, $C_4$-$C_6$, or $C_5$-$C_6$), $R^{A22}$-substituted or unsubstituted heterocycloalkyl (e.g., 3 to 8 membered, 3 to 6 membered, 4 to 6 membered, 4 to 5 membered, or 5 to 6 membered), $R^{A22}$-substituted or unsubstituted aryl (e.g., $C_6$-$C_{10}$ or phenyl), or $R^{A22}$-substituted or unsubstituted heteroaryl (e.g., 5 to 10 membered, 5 to 9 membered, or 5 to 6 membered).

$R^{A22}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A22}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A7}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A7}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A7}$ is substituted with a plurality of groups selected from substituent groups, size-limited substituent groups, and lower substituent groups; each substituent group, size-limited substituent group, and/or lower substituent group may optionally be different. In embodiments, when $R^{A7}$ is substituted, it is substituted with at least one substituent group. In embodiments, when $R^{A7}$ is substituted, it is substituted with at least one size-limited substituent group. In embodiments, when $R^{A7}$ is substituted, it is substituted with at least one lower substituent group.

In embodiments, $R^{A7}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A38}$-substituted or unsubstituted alkyl, $R^{A38}$-substituted or unsubstituted heteroalkyl, $R^{A38}$-substituted or unsubstituted cycloalkyl, $R^{A38}$-substituted or unsubstituted heterocycloalkyl, $R^{A38}$-substituted or unsubstituted aryl, or $R^{A38}$-substituted or unsubstituted heteroaryl.

In embodiments, $R^{A7}$ is independently hydrogen, —$CF_3$, —CN, —COOH, —$CONH_2$, $R^{A38}$-substituted or unsubstituted alkyl, $R^{A38}$-substituted or unsubstituted heteroalkyl, $R^{A38}$-substituted or unsubstituted cycloalkyl, $R^{A38}$-substituted or unsubstituted heterocycloalkyl, $R^{A38}$-substituted or unsubstituted aryl, or $R^{A38}$-substituted or unsubstituted heteroaryl. In embodiments, $R^{A7}$ is independently $R^{A38}$-substituted or unsubstituted $C_1$-$C_4$ alkyl, $R^{A38}$-substituted or unsubstituted 2 to 4 membered heteroalkyl, $R^{A38}$-substituted or unsubstituted $C_3$-$C_6$ cycloalkyl, $R^{A38}$-substituted or unsubstituted 3 to 6 membered heterocycloalkyl, $R^{A38}$-substituted or unsubstituted phenyl, or $R^{A38}$-substituted or unsubstituted 5 to 6 membered heteroaryl. In embodiments, $R^{A7}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A7}$ is independently an unsubstituted $C_1$-$C_4$ alkyl. In embodiments, $R^{A7}$ is independently an unsubstituted methyl. In embodiments, $R^{A7}$ is independently an unsubstituted ethyl. In embodiments, $R^{A7}$ is independently an unsubstituted isopropyl. In embodiments, $R^{A7}$ is independently an unsubstituted tert-butyl. In embodiments, $R^{A7}$ is independently hydrogen.

$R^{A38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{A39}$-substituted or unsubstituted alkyl, $R^{A39}$-substituted or unsubstituted heteroalkyl, $R^{A39}$-substituted or unsubstituted cycloalkyl, $R^{A39}$-substituted or unsubstituted heterocycloalkyl, $R^{19}$-substituted or unsubstituted aryl, or $R^{A39}$-substituted or unsubstituted heteroaryl.

In embodiments, $R^{A38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{A39}$-substituted or unsubstituted alkyl (e.g., $C_1$-$C_8$, $C_1$-$C_6$, $C_1$-$C_4$, or $C_1$-$C_2$), $R^{A39}$-substituted or unsubstituted heteroalkyl (e.g., 2 to 8 membered, 2 to 6 membered, 4 to 6 membered, 2 to 3 membered, or 4 to 5 membered), $R^{A39}$-substituted or unsubstituted cycloalkyl (e.g., $C_3$-$C_8$, $C_3$-$C_6$, $C_4$-$C_6$, or $C_5$-$C_6$), $R^{A39}$-substituted or unsubstituted heterocycloalkyl (e.g., 3 to 8 membered, 3 to 6 membered, 4 to 6 membered, 4 to 5 membered, or 5 to 6 membered), $R^{A39}$-substituted or unsubstituted aryl (e.g., $C_6$-$C_{10}$ or phenyl), or $R^{A39}$-substituted or unsubstituted heteroaryl (e.g., 5 to 10 membered, 5 to 9 membered, or 5 to 6 membered).

$R^{A39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{A40}$-substituted or unsubstituted alkyl, $R^{A40}$-substituted or unsubstituted heteroalkyl, $R^{A40}$-substituted or unsubstituted cycloalkyl, $R^{A40}$-substituted or unsubstituted heterocycloalkyl, $R^{A40}$-substituted or unsubstituted aryl, or $R^{A40}$-substituted or unsubstituted heteroaryl.

In embodiments, $R^{A39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{A40}$-substituted or unsubstituted alkyl (e.g., $C_1$-$C_8$, $C_1$-$C_6$, $C_1$-$C_4$, or $C_1$-$C_2$), $R^{A40}$-substituted or unsubstituted heteroalkyl (e.g., 2 to 8 membered, 2 to 6 membered, 4 to 6 membered, 2 to 3 membered, or 4 to 5 membered), $R^{A40}$-substituted or unsubstituted cycloalkyl (e.g., $C_3$-$C_8$, $C_3$-$C_6$, $C_4$-$C_6$, or $C_5$-$C_6$), $R^{A40}$-substituted or unsubstituted heterocycloalkyl (e.g., 3 to 8 membered, 3 to 6 membered, 4 to 6 membered, 4 to 5 membered, or 5 to 6 membered), $R^{A40}$-substituted or unsubstituted aryl (e.g., $C_6$-$C_{10}$ or phenyl), or $R^{A40}$-substituted or unsubstituted heteroaryl (e.g., 5 to 10 membered, 5 to 9 membered, or 5 to 6 membered).

$R^{A40}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A40}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A8}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A8}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A8}$ is substituted with a plurality of groups selected from substituent groups, size-limited substituent groups, and lower substituent groups; each substituent group, size-limited substituent group, and/or lower substituent group may optionally be different. In embodiments, when $R^{A8}$ is substituted, it is substituted with at least one substituent group. In embodiments, when $R^{A8}$ is substituted, it is substituted with at least one size-limited substituent group. In embodiments, when $R^{A8}$ is substituted, it is substituted with at least one lower substituent group.

In embodiments, $R^{A7}$ and $R^{A8}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{A7}$ and $R^{A8}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{A7}$ and $R^{A8}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{A7}$ and $R^{A8}$ substituents bonded to the same nitrogen atom is substituted, it is substituted with at least one substituent group. In embodiments, when the moiety formed by joining $R^{A7}$ and $R^{A8}$ substituents bonded to the same nitrogen atom is substituted, it is substituted with at least one size-limited substituent group. In embodiments, when the moiety formed by joining $R^{A7}$ and $R^{A8}$ substituents bonded to the same nitrogen atom is substituted, it is substituted with at least one lower substituent group.

In embodiments, $R^{A8}$ is independently hydrogen, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, $R^{A41}$-substituted or unsubstituted alkyl, $R^{A41}$-substituted or unsubstituted heteroalkyl, $R^{A41}$-substituted or unsubstituted cycloalkyl, $R^{A41}$-substituted or unsubstituted heterocycloalkyl, $R^{A41}$-substituted or unsubstituted aryl, or $R^{A41}$-substituted or unsubstituted heteroaryl.

In embodiments, $R^{A8}$ is independently hydrogen, $-CF_3$, $-CN$, $-COOH$, $-CONH_2$, $R^{A41}$-substituted or unsubstituted alkyl, $R^{A41}$-substituted or unsubstituted heteroalkyl, $R^{A41}$-substituted or unsubstituted cycloalkyl, $R^{A41}$-substituted or unsubstituted heterocycloalkyl, $R^{A41}$-substituted or unsubstituted aryl, or $R^{A41}$-substituted or unsubstituted heteroaryl. In embodiments, $R^{A8}$ is independently an $R^{A41}$-substituted or unsubstituted $C_1$-$C_4$ alkyl, $R^{A41}$-substituted or unsubstituted 2 to 4 membered heteroalkyl, $R^{A41}$-substituted or unsubstituted $C_3$-$C_6$ cycloalkyl, $R^{A41}$-substituted or unsubstituted 3 to 6 membered heterocycloalkyl, $R^{A41}$-substituted or unsubstituted phenyl, or $R^{A41}$-substituted or unsubstituted 5 to 6 membered heteroaryl. In embodiments, $R^{A8}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A8}$ is independently an unsubstituted $C_1$-$C_4$ alkyl. In embodiments, $R^{A8}$ is independently an unsubstituted methyl. In embodiments, $R^{A8}$ is independently an unsubstituted ethyl. In embodiments, $R^{A8}$ is independently an unsubstituted isopropyl. In embodiments, $R^{A8}$ is independently an unsubstituted tert-butyl. In embodiments, $R^{A8}$ is independently hydrogen.

$R^{A41}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, $-S(O)_2CHCH_2$, $-NHS(O)_2CHCH_2$, $R^{A42}$-substituted or unsubstituted alkyl, $R^{A42}$-substituted or unsubstituted heteroalkyl, $R^{A42}$-substituted or unsubstituted cycloalkyl, $R^{A42}$-substituted or unsubstituted heterocycloalkyl, $R^{A42}$-substituted or unsubstituted aryl, or $R^{A42}$-substituted or unsubstituted heteroaryl.

In embodiments, $R^{A41}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, $-S(O)_2CHCH_2$, $-NHS(O)_2CHCH_2$, $R^{A42}$-substituted or unsubstituted alkyl (e.g., $C_1$-$C_8$, $C_1$-$C_6$, $C_1$-$C_4$, or $C_1$-$C_2$), $R^{A42}$-substituted or unsubstituted heteroalkyl (e.g., 2 to 8 membered, 2 to 6 membered, 4 to 6 membered, 2 to 3 membered, or 4 to 5 membered), $R^{A42}$-substituted or unsubstituted cycloalkyl (e.g., $C_3$-$C_8$, $C_3$-$C_6$, $C_4$-$C_6$, or $C_5$-$C_6$), $R^{A42}$-substituted or unsubstituted heterocycloalkyl (e.g., 3 to 8 membered, 3 to 6 membered, 4 to 6 membered, 4 to 5 membered, or 5 to 6 membered), $R^{A42}$-substituted or unsubstituted aryl (e.g., $C_6$-$C_{10}$ or phenyl), or $R^{A42}$-substituted or unsubstituted heteroaryl (e.g., 5 to 10 membered, 5 to 9 membered, or 5 to 6 membered).

$R^{A42}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, $-S(O)_2CHCH_2$, $-NHS(O)_2CHCH_2$, $R^{A43}$-substituted or unsubstituted alkyl, $R^{A43}$-substituted or unsubstituted heteroalkyl, $R^{A43}$-substituted or unsubstituted cycloalkyl, $R^{A43}$-substituted or unsubstituted heterocycloalkyl, $R^{A43}$-substituted or unsubstituted aryl, or $R^{A43}$-substituted or unsubstituted heteroaryl.

In embodiments, $R^{A42}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, $-S(O)_2CHCH_2$, $-NHS(O)_2CHCH_2$, $R^{A43}$-substituted or unsubstituted alkyl (e.g., $C_1$-$C_8$, $C_1$-$C_6$, $C_1$-$C_4$, or $C_1$-$C_2$), $R^{A43}$-substituted or unsubstituted heteroalkyl (e.g., 2 to 8 membered, 2 to 6 membered, 4 to 6 membered, 2 to 3 membered, or 4 to 5 membered), $R^{A43}$-substituted or unsubstituted cycloalkyl (e.g., $C_3$-$C_8$, $C_3$-$C_6$, $C_4$-$C_6$, or $C_5$-$C_6$), $R^{A43}$-substituted or unsubstituted heterocycloalkyl (e.g., 3 to 8 membered, 3 to 6 membered, 4 to 6 membered, 4 to 5 membered, or 5 to 6 membered), $R^{A43}$-substituted or unsubstituted aryl (e.g., $C_6$-$C_{10}$ or phenyl), or $R^{A43}$-substituted or unsubstituted heteroaryl (e.g., 5 to 10 membered, 5 to 9 membered, or 5 to 6 membered).

$R^{A43}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, $-S(O)_2CHCH_2$, $-NHS(O)_2CHCH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A43}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A9}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A9}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A9}$ is substituted with a plurality of groups selected from substituent groups, size-limited substituent groups, and lower substituent groups; each substituent group, size-limited substituent group, and/or lower substituent group may optionally be different. In embodiments, when $R^{A9}$ is substituted, it is substituted with at least one substituent group. In embodiments, when $R^{A9}$ is substituted, it is substituted with at least one size-limited substituent group. In embodiments, when $R^{A9}$ is substituted, it is substituted with at least one lower substituent group.

In embodiments, $R^{A9}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A44}$-substituted or unsubstituted alkyl, $R^{A44}$-substituted or unsubstituted heteroalkyl, $R^{A44}$-substituted or unsubstituted cycloalkyl, $R^{A44}$-substituted or unsubstituted heterocycloalkyl, $R^{A44}$-substituted or unsubstituted aryl, or $R^{A44}$-substituted or unsubstituted heteroaryl.

In embodiments, $R^{A9}$ is independently hydrogen, —$CF_3$, —CN, —COOH, —$CONH_2$, $R^{A44}$-substituted or unsubstituted alkyl, $R^{A44}$-substituted or unsubstituted heteroalkyl, $R^{A44}$-substituted or unsubstituted cycloalkyl, $R^{A44}$-substituted or unsubstituted heterocycloalkyl, $R^{A44}$-substituted or unsubstituted aryl, or $R^{A44}$-substituted or unsubstituted heteroaryl. In embodiments, $R^{A9}$ is independently an $R^{A44}$-substituted or unsubstituted $C_1$-$C_4$ alkyl, $R^{A44}$-substituted or unsubstituted 2 to 4 membered heteroalkyl, $R^{A44}$-substituted or unsubstituted $C_3$-$C_6$ cycloalkyl, $R^{A44}$-substituted or unsubstituted 3 to 6 membered heterocycloalkyl, $R^{A44}$-substituted or unsubstituted phenyl, or $R^{A44}$-substituted or unsubstituted 5 to 6 membered heteroaryl. In embodiments, $R^{A9}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A9}$ is independently an unsubstituted $C_1$-$C_4$ alkyl. In embodiments, $R^{A9}$ is independently an unsubstituted methyl. In embodiments, $R^{A9}$ is independently an unsubstituted ethyl. In embodiments, $R^{A9}$ is independently an unsubstituted isopropyl. In embodiments, $R^{A9}$ is independently an unsubstituted tert-butyl. In embodiments, $R^{A9}$ is independently hydrogen.

$R^{A44}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A45}$-substituted or unsubstituted alkyl, $R^{A45}$-substituted or unsubstituted heteroalkyl, $R^{A45}$-substituted or unsubstituted cycloalkyl, $R^{A45}$-substituted or unsubstituted heterocycloalkyl, $R^{A45}$-substituted or unsubstituted aryl, or $R^{A45}$-substituted or unsubstituted heteroaryl.

In embodiments, $R^{A44}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A45}$-substituted or unsubstituted alkyl (e.g., $C_1$-$C_8$, $C_1$-$C_6$, $C_1$-$C_4$, or $C_1$-$C_2$), $R^{A45}$-substituted or unsubstituted heteroalkyl (e.g., 2 to 8 membered, 2 to 6 membered, 4 to 6 membered, 2 to 3 membered, or 4 to 5 membered), $R^{A45}$-substituted or unsubstituted cycloalkyl (e.g., $C_3$-$C_8$, $C_3$-$C_6$, $C_4$-$C_6$, or $C_5$-$C_6$), $R^{A45}$-substituted or unsubstituted heterocycloalkyl (e.g., 3 to 8 membered, 3 to 6 membered, 4 to 6 membered, 4 to 5 membered, or 5 to 6 membered), $R^{A45}$-substituted or unsubstituted aryl (e.g., $C_6$-$C_{10}$ or phenyl), or $R^{A45}$-substituted or unsubstituted heteroaryl (e.g., 5 to 10 membered, 5 to 9 membered, or 5 to 6 membered).

$R^{A45}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A46}$-substituted or unsubstituted alkyl, $R^{A46}$-substituted or unsubstituted heteroalkyl, $R^{A46}$-substituted or unsubstituted cycloalkyl, $R^{A46}$-substituted or unsubstituted heterocycloalkyl, $R^{A46}$-substituted or unsubstituted aryl, or $R^{A46}$-substituted or unsubstituted heteroaryl.

In embodiments, $R^{A45}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A46}$-substituted or unsubstituted alkyl (e.g., $C_1$-$C_8$, $C_1$-$C_6$, $C_1$-$C_4$, or $C_1$-$C_2$), $R^{A46}$-substituted or unsubstituted heteroalkyl (e.g., 2 to 8 membered, 2 to 6 membered, 4 to 6 membered, 2 to 3 membered, or 4 to 5 membered), $R^{A46}$-substituted or unsubstituted cycloalkyl (e.g., $C_3$-$C_8$, $C_3$-$C_6$, $C_4$-$C_6$, or $C_5$-$C_6$), $R^{A46}$-substituted or unsubstituted heterocycloalkyl (e.g., 3 to 8 membered, 3 to 6 membered, 4 to 6 membered, 4 to 5 membered, or 5 to 6 membered), $R^{A46}$-substituted or unsubstituted aryl (e.g., $C_6$-$C_{10}$ or phenyl), or $R^{A46}$-substituted or unsubstituted heteroaryl (e.g., 5 to 10 membered, 5 to 9 membered, or 5 to 6 membered).

$R^{A46}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A46}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A10}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A10}$ is substituted with a plurality of groups selected from substituent groups, size-limited substituent groups, and lower substituent groups; each substituent group, size-limited substituent group, and/or lower substituent group may optionally be different. In embodiments, when $R^{A10}$ is substituted, it is substituted with at least one substituent group. In embodiments, when $R^{A10}$ is substituted, it is substituted with at least one size-limited substituent group. In embodiments, when $R^{A10}$ is substituted, it is substituted with at least one lower substituent group.

In embodiments, $R^{A10}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A47}$-substituted or unsubstituted alkyl, $R^{A47}$-substituted or unsubstituted heteroalkyl, $R^{A47}$-substituted or unsubstituted cycloalkyl, $R^{A47}$-substituted or unsubstituted heterocycloalkyl, $R^{A47}$-substituted or unsubstituted aryl, or $R^{A47}$-substituted or unsubstituted heteroaryl.

In embodiments, $R^{A10}$ is independently hydrogen, —$CF_3$, —CN, —COOH, —$CONH_2$, $R^{A47}$-substituted or unsubstituted alkyl, $R^{A47}$-substituted or unsubstituted heteroalkyl, $R^{A47}$-substituted or unsubstituted cycloalkyl, $R^{A47}$-substituted or unsubstituted heterocycloalkyl, $R^{A47}$-substituted or unsubstituted aryl, or $R^{A47}$-substituted or unsubstituted heteroaryl. In embodiments, $R^{A10}$ is independently an $R^{A47}$-substituted or unsubstituted $C_1$-$C_4$ alkyl, $R^{A47}$-substituted or unsubstituted 2 to 4 membered heteroalkyl, $R^{A47}$-substituted or unsubstituted $C_3$-$C_6$ cycloalkyl, $R^{A47}$-substituted or unsubstituted 3 to 6 membered heterocycloalkyl, $R^{A47}$-substituted or unsubstituted phenyl, or $R^{A47}$-substituted or unsubstituted 5 to 6 membered heteroaryl. In embodiments, $R^{A10}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A10}$ is independently an unsubstituted $C_1$-$C_4$ alkyl. In embodiments, $R^{A10}$ is independently an unsubstituted methyl. In embodiments, $R^{A10}$ is independently an unsubstituted ethyl. In embodiments, $R^{A0}$ is independently an unsubstituted isopropyl. In embodiments, $R^{A10}$ is independently an unsubstituted tert-butyl. In embodiments, $R^{A10}$ is independently hydrogen.

$R^{A47}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A48}$-substituted or unsubstituted alkyl, $R^{A48}$-substituted or unsubstituted heteroalkyl, $R^{A48}$-substituted or unsubstituted cycloalkyl, $R^{A48}$-substituted or unsubstituted heterocycloalkyl, $R^{A48}$-substituted or unsubstituted aryl, or $R^{A48}$-substituted or unsubstituted heteroaryl.

In embodiments, $R^{A47}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A48}$-substituted or unsubstituted alkyl (e.g., $C_1$-$C_8$, $C_1$-$C_6$, $C_1$-$C_4$, or $C_1$-$C_2$), $R^{A48}$-substituted or unsubstituted heteroalkyl (e.g., 2 to 8 membered, 2 to 6 membered, 4 to 6 membered, 2 to 3 membered, or 4 to 5 membered), $R^{A48}$-substituted or unsubstituted cycloalkyl (e.g., $C_3$-$C_8$, $C_3$-$C_6$, $C_4$-$C_6$, or $C_5$-$C_6$), $R^{A48}$-substituted or unsubstituted heterocycloalkyl (e.g., 3 to 8 membered, 3 to 6 membered, 4 to 6 membered, 4 to 5 membered, or 5 to 6 membered), $R^{A48}$-substituted or unsubstituted aryl (e.g., $C_6$-$C_{10}$ or phenyl), or $R^{A48}$-substituted or unsubstituted heteroaryl (e.g., 5 to 10 membered, 5 to 9 membered, or 5 to 6 membered).

$R^{A48}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A49}$-substituted or unsubstituted alkyl, $R^{A49}$-substituted or unsubstituted heteroalkyl, $R^{A49}$-substituted or unsubstituted cycloalkyl, $R^{A49}$-substituted or unsubstituted heterocycloalkyl, $R^{A49}$-substituted or unsubstituted aryl, or $R^{A49}$-substituted or unsubstituted heteroaryl.

In embodiments, $R^{A48}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A49}$-substituted or unsubstituted alkyl (e.g., $C_1$-$C_8$, $C_1$-$C_6$, $C_1$-$C_4$, or $C_1$-$C_2$), $R^{A49}$-substituted or unsubstituted heteroalkyl (e.g., 2 to 8 membered, 2 to 6 membered, 4 to 6 membered, 2 to 3 membered, or 4 to 5 membered), $R^{A49}$-substituted or unsubstituted cycloalkyl (e.g., $C_3$-$C_8$, $C_3$-$C_6$, $C_4$-$C_6$, or $C_5$-$C_6$), $R^{A49}$-substituted or unsubstituted heterocycloalkyl (e.g., 3 to 8 membered, 3 to 6 membered, 4 to 6 membered, 4 to 5 membered, or 5 to 6 membered), $R^{A49}$-substituted or unsubstituted aryl (e.g., $C_6$-$C_{10}$ or phenyl), or $R^{A49}$-substituted or unsubstituted heteroaryl (e.g., 5 to 10 membered, 5 to 9 membered, or 5 to 6 membered).

$R^{A49}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A49}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A11}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A11}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A11}$ is substituted with a plurality of groups selected from substituent groups, size-limited substituent groups, and lower substituent groups; each substituent group, size-limited substituent group, and/or lower substituent group may optionally be different. In embodiments, when $R^{A11}$ is substituted, it is substituted with at least one substituent group. In embodiments, when $R^{A11}$ is substituted, it is substituted with at least one size-limited substituent group. In embodiments, when $R^{A11}$ is substituted, it is substituted with at least one lower substituent group.

In embodiments, $R^{A11}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A50}$-substituted or unsubstituted alkyl, $R^{A50}$-substituted or unsubstituted heteroalkyl, $R^{A50}$-substituted or unsubstituted cycloalkyl, $R^{A50}$-substituted or unsubstituted heterocycloalkyl, $R^{A50}$-substituted or unsubstituted aryl, or $R^{A50}$-substituted or unsubstituted heteroaryl.

In embodiments, $R^{A11}$ is independently hydrogen, —$CF_3$, —CN, —COOH, —$CONH_2$, $R^{A50}$-substituted or unsubstituted alkyl, $R^{A50}$-substituted or unsubstituted heteroalkyl, $R^{A50}$-substituted or unsubstituted cycloalkyl, $R^{A50}$-substituted or unsubstituted heterocycloalkyl, $R^{A50}$-substituted or unsubstituted aryl, or $R^{A50}$-substituted or unsubstituted heteroaryl. In embodiments, $R^{A11}$ is independently an $R^{A50}$-substituted or unsubstituted $C_1$-$C_4$ alkyl, $R^{A50}$-substituted or unsubstituted 2 to 4 membered heteroalkyl, $R^{A50}$-substituted or unsubstituted $C_3$-$C_6$ cycloalkyl, $R^{A50}$-substituted or unsubstituted 3 to 6 membered heterocycloalkyl, $R^{A50}$-substituted or unsubstituted phenyl, or $R^{A50}$-substituted or unsubstituted 5 to 6 membered heteroaryl. In embodiments, $R^{A11}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A11}$ is independently an unsubstituted $C_1$-$C_4$ alkyl. In embodiments, $R^{A11}$ is independently an unsubstituted methyl. In embodiments, $R^{A11}$ is independently an unsubstituted ethyl. In embodiments, $R^{A11}$ is independently an unsubstituted isopropyl. In embodiments, $R^{A11}$ is independently an unsubstituted tert-butyl. In embodiments, $R^{A11}$ is independently hydrogen. In embodiments, $R^{A11}$ is independently an $R^{A50}$-substituted or unsubstituted $C_1$-$C_4$ alkyl. In embodiments, $R^{A11}$ is independently an $R^{A50}$-substituted or unsubstituted 2 to 4 membered heteroalkyl. In embodiments, $R^{A11}$ is independently an $R^{A50}$-substituted or unsubstituted $C_3$-$C_6$ cycloalkyl. In embodiments, $R^{A11}$ is independently an $R^{A50}$-substituted or unsubstituted 3 to 6 membered heterocycloalkyl. In embodiments, $R^{A11}$ is independently an $R^{A50}$-substituted or unsubstituted phenyl. In embodiments, $R^{A11}$ is independently an $R^{A50}$-substituted or unsubstituted 5 to 6 membered heteroaryl. In embodiments, $R^{A11}$ is independently an unsubstituted $C_1$-$C_4$ alkyl. In embodiments, $R^{A11}$ is independently an unsubstituted 2 to 4 membered heteroalkyl. In embodiments, $R^{A11}$ is independently an unsubstituted $C_3$-$C_6$ cycloalkyl. In embodiments, $R^{A11}$ is independently an unsubstituted 3 to 6 membered heterocycloalkyl. In embodiments, $R^{A11}$ is independently an unsubstituted phenyl. In embodiments, $R^{A11}$ is independently an unsubstituted 5 to 6 membered heteroaryl.

$R^{A50}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A51}$-substituted or unsubstituted alkyl, $R^{A51}$-substituted or unsubstituted heteroalkyl, $R^{A51}$-substituted or unsubstituted cycloalkyl, $R^{A51}$-substituted or unsubstituted heterocycloalkyl, $R^{A51}$-substituted or unsubstituted aryl, or $R^{A51}$-substituted or unsubstituted heteroaryl.

In embodiments, $R^{A50}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A51}$-substituted or unsubstituted alkyl (e.g., $C_1$-$C_8$, $C_1$-$C_6$, $C_1$-$C_4$, or $C_1$-$C_2$), $R^{A51}$-substituted or unsubstituted heteroalkyl (e.g., 2 to 8 membered, 2 to 6 membered, 4 to 6 membered, 2 to 3 membered, or 4 to 5 membered), $R^{A51}$-substituted or unsubstituted cycloalkyl (e.g., $C_3$-$C_8$, $C_3$-$C_6$, $C_4$-$C_6$, or $C_5$-$C_6$), $R^{A51}$-substituted or unsubstituted heterocycloalkyl (e.g., 3 to 8 membered, 3 to 6 membered, 4 to 6 membered, 4 to 5 membered, or 5 to 6 membered), $R^{A51}$-substituted or unsubstituted aryl (e.g., $C_6$-$C_{10}$ or phenyl), or $R^{A51}$-substituted or unsubstituted heteroaryl (e.g., 5 to 10 membered, 5 to 9 membered, or 5 to 6 membered).

$R^{A51}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A52}$-substituted or unsubstituted alkyl, $R^{A52}$-substituted or unsubstituted heteroalkyl, $R^{A52}$-substituted or unsubstituted cycloalkyl, $R^{A52}$-substituted or unsubstituted heterocycloalkyl, $R^{A52}$-substituted or unsubstituted aryl, or $R^{A52}$-substituted or unsubstituted heteroaryl.

In embodiments, $R^{A51}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A52}$-substituted or unsubstituted alkyl (e.g., $C_1$-$C_8$, $C_1$-$C_6$, $C_1$-$C_4$, or $C_1$-$C_2$), $R^{A52}$-substituted or unsubstituted heteroalkyl (e.g., 2 to 8 membered, 2 to 6 membered, 4 to 6 membered, 2 to 3 membered, or 4 to 5 membered), $R^{A52}$-substituted or unsubstituted cycloalkyl (e.g., $C_3$-$C_8$, $C_3$-$C_6$, $C_4$-$C_6$, or $C_5$-$C_6$), $R^{A52}$-substituted or unsubstituted heterocycloalkyl (e.g., 3 to 8 membered, 3 to 6 membered, 4 to 6 membered, 4 to 5 membered, or 5 to 6 membered), $R^{A52}$-substituted or unsubstituted aryl (e.g., $C_6$-$C_{10}$ or phenyl), or $R^{A52}$-substituted or unsubstituted heteroaryl (e.g., 5 to 10 membered, 5 to 9 membered, or 5 to 6 membered).

$R^{A52}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A52}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A12}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A12}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A12}$ is substituted with a plurality of groups selected from substituent groups, size-limited substituent groups, and lower substituent groups; each substituent group, size-limited substituent group, and/or lower substituent group may optionally be different. In embodiments, when $R^{A12}$ is substituted, it is substituted with at least one substituent group. In embodiments, when $R^{A12}$ is substituted, it is substituted with at least one size-limited substituent group. In embodiments, when $R^{A12}$ is substituted, it is substituted with at least one lower substituent group.

In embodiments, $R^{A12}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A53}$-substituted or unsubstituted alkyl, $R^{A53}$-substituted or unsubstituted heteroalkyl, $R^{A53}$-substituted or unsubstituted cycloalkyl, $R^{A53}$-substituted or unsubstituted heterocycloalkyl, $R^{A53}$-substituted or unsubstituted aryl, or $R^{A53}$-substituted or unsubstituted heteroaryl.

In embodiments, $R^{A12}$ is independently hydrogen, —$CF_3$, —CN, —COOH, —$CONH_2$, $R^{A53}$-substituted or unsubstituted alkyl, $R^{A53}$-substituted or unsubstituted heteroalkyl, $R^{A53}$-substituted or unsubstituted cycloalkyl, $R^{A53}$-substituted or unsubstituted heterocycloalkyl, $R^{A53}$-substituted or unsubstituted aryl, or $R^{A53}$-substituted or unsubstituted heteroaryl. In embodiments, $R^{A12}$ is independently an $R^{A53}$-substituted or unsubstituted $C_1$-$C_4$ alkyl, $R^{A53}$-substituted or unsubstituted 2 to 4 membered heteroalkyl, $R^{A53}$-substituted or unsubstituted $C_3$-$C_6$ cycloalkyl, $R^{A53}$-substituted or unsubstituted 3 to 6 membered heterocycloalkyl, $R^{A53}$-substituted or unsubstituted phenyl, or $R^{A53}$-substituted or unsubstituted 5 to 6 membered heteroaryl. In embodiments, $R^{A12}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A12}$ is independently an unsubstituted $C_1$-$C_4$ alkyl. In embodiments, $R^{A12}$ is independently an unsubstituted methyl. In embodiments, $R^{A12}$ is independently an unsubstituted ethyl. In embodiments, $R^{A12}$ is independently an unsubstituted isopropyl. In embodiments, $R^{A12}$ is independently an unsubstituted tert-butyl. In embodiments, $R^{A12}$ is independently hydrogen. In embodiments, $R^{A12}$ is independently an $R^{A53}$-substituted or unsubstituted $C_1$-$C_4$ alkyl. In embodiments, $R^{A12}$ is independently an $R^{A53}$-substituted or unsubstituted 2 to 4 membered heteroalkyl. In embodiments, $R^{A12}$ is independently an $R^{A53}$-substituted or unsubstituted $C_3$-$C_6$ cycloalkyl. In embodiments, $R^{A12}$ is independently an $R^{A53}$-substituted or unsubstituted 3 to 6 membered heterocycloalkyl. In embodiments, $R^{A12}$ is independently an $R^{A53}$-substituted or unsubstituted phenyl. In embodiments, $R^{A12}$ is independently an $R^{A53}$-substituted or unsubstituted 5 to 6 membered heteroaryl. In embodiments, $R^{A12}$ is independently an unsubstituted $C_1$-$C_4$ alkyl. In embodiments, $R^{A12}$ is independently an unsubstituted 2 to 4 membered heteroalkyl. In embodiments, $R^{A12}$ is independently an unsubstituted $C_3$-$C_6$ cycloalkyl. In embodiments, $R^{A12}$ is independently an unsubstituted 3 to 6 membered heterocycloalkyl. In embodiments, $R^{A12}$ is independently an unsubstituted phenyl. In embodiments, $R^{A12}$ is independently an unsubstituted 5 to 6 membered heteroaryl.

$R^{A53}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, $R^{A54}$-substituted or unsubstituted alkyl, $R^{A54}$-substituted or unsubstituted heteroalkyl, $R^{A54}$-substituted or unsubstituted cycloalkyl, $R^{A54}$-substituted or unsubstituted heterocycloalkyl, $R^{A54}$-substituted or unsubstituted aryl, or $R^{A54}$-substituted or unsubstituted heteroaryl.

In embodiments, $R^{A53}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, $R^{A54}$-substituted or unsubstituted alkyl (e.g., $C_1$-$C_8$, $C_1$-$C_6$, $C_1$-$C_4$, or $C_1$-$C_2$), $R^{A54}$-substituted or unsubstituted heteroalkyl (e.g., 2 to 8 membered, 2 to 6 membered, 4 to 6 membered, 2 to 3 membered, or 4 to 5 membered), $R^{A54}$-substituted or unsubstituted cycloalkyl (e.g., $C_3$-$C_8$, $C_3$-$C_6$, $C_4$-$C_6$, or $C_5$-$C_6$), $R^{A54}$-substituted or unsubstituted heterocycloalkyl (e.g., 3 to 8 membered, 3 to 6 membered, 4 to 6 membered, 4 to 5 membered, or 5 to 6 membered), $R^{A54}$-substituted or unsubstituted aryl (e.g., $C_6$-$C_{10}$ or phenyl), or $R^{A54}$-substituted or unsubstituted heteroaryl (e.g., 5 to 10 membered, 5 to 9 membered, or 5 to 6 membered).

$R^{A54}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A55}$-substituted or unsubstituted alkyl, $R^{A55}$-substituted or unsubstituted heteroalkyl, $R^{A55}$-substituted or unsubstituted cycloalkyl, $R^{A55}$-substituted or unsubstituted heterocycloalkyl, $R^{A55}$-substituted or unsubstituted aryl, or $R^{A55}$-substituted or unsubstituted heteroaryl.

In embodiments, $R^{A54}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A55}$-substituted or unsubstituted alkyl (e.g., $C_1$-$C_8$, $C_1$-$C_6$, $C_1$-$C_4$, or $C_1$-$C_2$), $R^{A55}$-substituted or unsubstituted heteroalkyl (e.g., 2 to 8 membered, 2 to 6 membered, 4 to 6 membered, 2 to 3 membered, or 4 to 5 membered), $R^{A55}$-substituted or unsubstituted cycloalkyl (e.g., $C_3$-$C_8$, $C_3$-$C_6$, $C_4$-$C_6$, or $C_5$-$C_6$), $R^{A55}$-substituted or unsubstituted heterocycloalkyl (e.g., 3 to 8 membered, 3 to 6 membered, 4 to 6 membered, 4 to 5 membered, or 5 to 6 membered), $R^{A55}$-substituted or unsubstituted aryl (e.g., $C_6$-$C_{10}$ or phenyl), or $R^{A55}$-substituted or unsubstituted heteroaryl (e.g., 5 to 10 membered, 5 to 9 membered, or 5 to 6 membered).

$R^{A55}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A55}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A13}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A13}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A13}$ is substituted with a plurality of groups selected from substituent groups, size-limited substituent groups, and lower substituent groups; each substituent group, size-limited substituent group, and/or lower substituent group may optionally be different. In embodiments, when $R^{A13}$ is substituted, it is substituted with at least one substituent group. In embodiments, when $R^{A13}$ is substituted, it is substituted with at least one size-limited substituent group. In embodiments, when $R^{A13}$ is substituted, it is substituted with at least one lower substituent group.

In embodiments, $R^{A13}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A56}$-substituted or unsubstituted alkyl, $R^{A56}$-substituted or unsubstituted heteroalkyl, $R^{A56}$-substituted or unsubstituted cycloalkyl, $R^{A56}$-substituted or unsubstituted heterocycloalkyl, $R^{A56}$-substituted or unsubstituted aryl, or $R^{A56}$-substituted or unsubstituted heteroaryl.

In embodiments, $R^{A13}$ is independently hydrogen, —$CF_3$, —CN, —COOH, —$CONH_2$, $R^{A56}$-substituted or unsubstituted alkyl, $R^{A56}$-substituted or unsubstituted heteroalkyl, $R^{A56}$-substituted or unsubstituted cycloalkyl, $R^{A56}$-substituted or unsubstituted heterocycloalkyl, $R^{A56}$-substituted or unsubstituted aryl, or $R^{A56}$-substituted or unsubstituted heteroaryl. In embodiments, $R^{A13}$ is independently an $R^{A56}$-substituted or unsubstituted $C_1$-$C_4$ alkyl, $R^{A56}$-substituted or unsubstituted 2 to 4 membered heteroalkyl, $R^{A56}$-substituted or unsubstituted $C_3$-$C_6$ cycloalkyl, $R^{A56}$-substituted or unsubstituted 3 to 6 membered heterocycloalkyl, $R^{A56}$-substituted or unsubstituted phenyl, or $R^{A56}$-substituted or unsubstituted 5 to 6 membered heteroaryl. In embodiments, $R^{A13}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A13}$ is independently an unsubstituted $C_1$-$C_4$ alkyl. In embodiments, $R^{A13}$ is independently an unsubstituted methyl. In embodiments, $R^{A13}$ is independently an unsubstituted ethyl. In embodiments, $R^{A13}$ is independently an unsubstituted isopropyl. In embodiments, $R^{A13}$ is independently an unsubstituted tert-butyl. In embodiments, $R^{A13}$ is independently hydrogen. In embodiments, $R^{A13}$ is independently an $R^{A56}$-substituted or unsubstituted $C_1$-$C_4$ alkyl. In embodiments, $R^{A13}$ is independently an $R^{A56}$-substituted or unsubstituted 2 to 4 membered heteroalkyl. In embodiments, $R^{A13}$ is independently an $R^{A56}$-substituted or unsubstituted $C_3$-$C_6$ cycloalkyl. In embodiments, $R^{A13}$ is independently an $R^{A56}$-substituted or unsubstituted 3 to 6 membered heterocycloalkyl. In embodiments, $R^{A13}$ is independently an $R^{A56}$-substituted or unsubstituted phenyl. In embodiments, $R^{A13}$ is independently an $R^{A56}$-substituted or unsubstituted 5 to 6 membered heteroaryl. In embodiments, $R^{A13}$ is independently an unsubstituted $C_1$-$C_4$ alkyl. In embodiments, $R^{A13}$ is independently an unsubstituted 2 to 4 membered heteroalkyl. In embodiments, $R^{A13}$ is independently an unsubstituted $C_3$-$C_6$ cycloalkyl. In embodiments, $R^{A13}$ is independently an unsubstituted 3 to 6 membered heterocycloalkyl. In embodiments, $R^{A13}$ is independently an unsubstituted phenyl. In embodiments, $R^{A13}$ is independently an unsubstituted 5 to 6 membered heteroaryl.

$R^{A56}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A57}$-substituted or unsubstituted alkyl, $R^{A57}$-substituted or unsubstituted heteroalkyl, $R^{A57}$-substituted or unsubstituted cycloalkyl, $R^{A57}$-substituted or unsubstituted heterocycloalkyl, $R^{A57}$-substituted or unsubstituted aryl, or $R^{A57}$-substituted or unsubstituted heteroaryl.

In embodiments, $R^{A56}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A57}$-substituted or unsubstituted alkyl (e.g., $C_1$-$C_8$, $C_1$-$C_6$, $C_1$-$C_4$, or $C_1$-$C_2$), $R^{A57}$-substituted or unsubstituted heteroalkyl (e.g., 2 to 8 membered, 2 to 6 membered, 4 to 6 membered, 2 to 3 membered, or 4 to 5 membered), $R^{A57}$-substituted or unsubstituted cycloalkyl (e.g., $C_3$-$C_8$, $C_3$-$C_6$, $C_4$-$C_6$, or $C_5$-$C_6$), $R^{A57}$-substituted or unsubstituted heterocycloalkyl (e.g., 3 to 8 membered, 3 to 6 membered, 4 to 6 membered, 4 to 5 membered, or 5 to 6 membered), $R^{A57}$-substituted or unsubstituted aryl (e.g., $C_6$-$C_{10}$ or phenyl), or $R^{A57}$-substituted or unsubstituted heteroaryl (e.g., 5 to 10 membered, 5 to 9 membered, or 5 to 6 membered).

$R^{A57}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A458}$-substituted or unsubstituted alkyl, $R^{A458}$-substituted or unsubstituted heteroalkyl, $R^{A458}$-substituted or unsubstituted cycloalkyl, $R^{A458}$-substituted or unsubstituted heterocycloalkyl, $R^{A458}$-substituted or unsubstituted aryl, or $R^{A458}$-substituted or unsubstituted heteroaryl.

In embodiments, $R^{A457}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A458}$-substituted or unsubstituted alkyl (e.g., $C_1$-$C_8$, $C_1$-$C_6$, $C_1$-$C_4$, or $C_1$-$C_2$), $R^{A458}$-substituted or unsubstituted heteroalkyl (e.g., 2 to 8 membered, 2 to 6 membered, 4 to 6 membered, 2 to 3 membered, or 4 to 5 membered), $R^{A458}$-substituted or unsubstituted cycloalkyl (e.g., $C_3$-$C_8$, $C_3$-$C_6$, $C_4$-$C_6$, or $C_5$-$C_6$), $R^{A458}$-substituted or unsubstituted heterocycloalkyl (e.g., 3 to 8 membered, 3 to 6 membered, 4 to 6 membered, 4 to 5 membered, or 5 to 6 membered), $R^{A458}$-substituted or unsubstituted aryl (e.g., $C_6$-$C_{10}$ or phenyl), or $R^{A458}$-substituted or unsubstituted heteroaryl (e.g., 5 to 10 membered, 5 to 9 membered, or 5 to 6 membered).

$R^{A458}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, or unsubstituted heteroalkyl, unsubstituted cycloalkyl, unsubstituted heterocycloalkyl, unsubstituted aryl, or unsubstituted heteroaryl.

In embodiments, $R^{A458}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{A1}$ is a bond, —NH—, —$NR^{A423}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A1}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A1}$ is substituted with a plurality of groups selected from substituent groups, size-limited substituent groups, and lower substituent groups; each substituent group, size-limited substituent group, and/or lower substituent group may optionally be different. In embodiments, when $L^{A1}$ is substituted, it is substituted with at least one substituent group. In embodiments, when $L^{A1}$ is substituted, it is substituted with at least one size-limited substituent group. In embodiments, when $L^{A1}$ is substituted, it is substituted with at least one lower substituent group.

In embodiments, $L^{A1}$ is a bond, —NH—, —$NR^{A423}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A1}$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A1}$ is $L^{A2}$-$L^{A3}$-$L^{A4}$-$L^{A5}$ $L^{A2}$ is connected directly to a monovalent rapamycin or a monovalent rapamycin analog. $L^{A2}$ is a bond, —NH—, —$NR^{A426}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^{A3}$ is a bond, —NH—, —$NR^{A429}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^{A4}$ is a bond, —NH—, —$NR^{A432}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^{A5}$ is a bond, —NH—, —$NR^{A435}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A2}$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A3}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A4}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A5}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A1}$ is a divalent linker including one or more amino acids. In embodiments, $L^{A1}$ is a divalent linker consisting of amino acids. In embodiments, $L^{A1}$ is a divalent linker including an amino acid analog. In embodiments, $L^{A1}$ is a divalent linker including an amino acid mimetic. In embodiments, $L^{A1}$ is a divalent linker consisting of amino acid analogs. In embodiments, $L^{A1}$ is a divalent linker consisting of amino acid mimetics.

In embodiments, $L^{A2}$ is a bond, —NH—, —$NR^{A26}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A}$ is substituted with a plurality of groups selected from substituent groups, size-limited substituent groups, and lower substituent groups; each substituent group, size-limited substituent group, and/or lower substituent group may optionally be different. In embodiments, when $L^{A}$ is substituted, it is substituted with at least one substituent group. In embodiments, when $L^{A2}$ is substituted, it is substituted with at least one size-limited substituent group. In embodiments, when $L^{A2}$ is substituted, it is substituted with at least one lower substituent group.

In embodiments, $L^{A2}$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A2}$ is substituted or unsubstituted 3 to 8 membered heteroalkylene. In embodiments, $L^{A2}$ is —$CH_2CH_2OCH_2$—. In embodiments, $L^{A2}$ is unsubstituted 3 to 8 membered heteroalkylene. In embodiments, $L^{A2}$ is unsubstituted 3 to 6 membered heteroalkylene. In embodiments, $L^{A2}$ is unsubstituted 3 to 5 membered heteroalkylene. In embodiments, $L^{A}$ is a divalent linker including one or more amino acids. In embodiments, $L^{A2}$ is a divalent linker consisting of amino acids. In embodiments, $L^{A2}$ is a divalent linker including an amino acid analog. In embodiments, $L^{A2}$ is a divalent linker including an amino acid mimetic. In embodiments, $L^{A2}$ is a divalent linker consisting of amino acid analogs. In embodiments, $L^{A2}$ is a divalent linker consisting of amino acid mimetics.

In embodiments, $L^{A3}$ is a bond, —NH—, —$NR^{A29}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A3}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A3}$ is substituted with a plurality of groups selected from substituent groups, size-limited substituent groups, and lower substituent groups; each substituent group, size-limited substituent group, and/or lower substituent group may optionally be different. In embodiments, when $L^{A3}$ is substituted, it is substituted with at least one substituent group. In embodiments, when $L^{A3}$ is substituted, it is substituted with at least one size-limited substituent group. In embodiments, when $L^{A3}$ is substituted, it is substituted with at least one lower substituent group.

In embodiments, $L^{A3}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A3}$ is a substituted or unsubstituted 5 to 10 membered heteroarylene. In embodiments, $L^{A3}$ is a bond. In embodiments, $L^{A3}$ is a substituted or unsubstituted 5 to 6 membered heteroarylene. In embodiments, $L^{A3}$ is unsubstituted 5 to 6 membered heteroarylene. In embodiments, $L^{A3}$ is unsubstituted divalent triazole. In embodiments, $L^{A3}$ is unsubstituted divalent 1H-1,2,3-triazole. In embodiments, $L^{A3}$ is unsubstituted divalent 2H-1,2,3-triazole. In embodiments, $L^{A3}$ is a divalent linker including one or more amino acids. In embodiments, $L^{A3}$ is a divalent linker consisting of amino acids. In embodiments, $L^{A3}$ is a divalent linker including an amino acid analog. In embodiments, $L^{A3}$ is a divalent linker including an amino acid mimetic. In embodiments, $L^{A3}$ is a divalent linker consisting of amino acid analogs. In embodiments, $L^{A3}$ is a divalent linker consisting of amino acid mimetics.

In embodiments, $L^{A4}$ is a bond, —NH—, —$NR^{A32}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A4}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A4}$ is substituted with a plurality of groups selected from substituent groups, size-limited substituent groups, and lower substituent groups; each substituent group, size-limited substituent group, and/or lower substituent group may optionally be different. In embodiments, when $L^{A4}$ is substituted, it is substituted with at least one substituent group. In embodiments, when $L^{A4}$ is substituted, it is substituted with at least one size-limited substituent group. In embodiments, when $L^{A4}$ is substituted, it is substituted with at least one lower substituent group.

In embodiments, $L^{A4}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A4}$ is a substituted or unsubstituted 2 to 12 membered heteroalkylene. In embodiments, $L^{A4}$ is a substituted or unsubstituted 2 to 32 membered heteroalkylene. In embodiments, $L^{A4}$ is a bond. In embodiments, $L^{A4}$ is a divalent linker including one or more amino acids. In embodiments, $L^{A4}$ is a divalent linker consisting of amino acids. In embodiments, $L^{A4}$ is a divalent linker including an amino acid analog. In embodiments, $L^{A4}$ is a divalent linker including an amino acid mimetic. In embodiments, $L^{A4}$ is a divalent linker consisting of amino acid analogs. In embodiments, $L^{A4}$ is a divalent linker consisting of amino acid mimetics.

In embodiments, $L^{A5}$ is a bond, —NH—, —$NR^{A35}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A5}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A5}$ is substituted with a plurality of groups selected from substituent groups, size-limited substituent groups, and lower substituent groups; each substituent group, size-limited substituent group, and/or lower substituent group may optionally be different. In embodiments, when $L^{A5}$ is substituted, it is substituted with at least one substituent group. In embodiments, when $L^{A5}$ is substituted, it is substituted with at least one size-limited substituent group. In embodiments, when $L^{A5}$ is substituted, it is substituted with at least one lower substituent group.

In embodiments, $L^{A5}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A5}$ is a substituted or unsubstituted 2 to 12 membered heteroalkylene. In embodiments, $L^{A5}$ is a substituted or unsubstituted 2 to 32 membered heteroalkylene. In embodiments, $L^{A5}$ is a bond. In embodiments, $L^{A5}$ is a divalent linker including one or more amino acids. In embodiments, $L^{A5}$ is a divalent linker consisting of amino acids. In embodiments, $L^{A5}$ is a divalent linker including an amino acid analog. In embodiments, $L^{A5}$ is a divalent linker including an amino acid mimetic. In embodiments, $L^{A5}$ is a divalent linker consisting of amino acid analogs. In embodiments, $L^{A5}$ is a divalent linker consisting of amino acid mimetics.

In embodiments, $L^{A5}$ is a divalent oligomer of ethylene oxide. In embodiments, $L^{A5}$ is a divalent polyethylene glycol. In embodiments, $L^{A5}$ is a divalent oligomer of ethylene oxide having 2 to 30 linear atoms (carbon and oxygen) between the two termini connecting to the remainder of the compound. In embodiments, $L^{A5}$ is a —$(CH_2)_4C(O)NH$—. In embodiments, $L^{A5}$ is a 2 to 8 membered substituted heteroalkylene. In embodiments, $L^{A5}$ is a 3 to 6 membered substituted heteroalkylene. In embodiments, $L^{A5}$ is a 5 to 6 membered substituted heteroalkylene. In embodiments, $L^{A5}$ is a 5 to 7 membered oxo substituted heteroalkylene. In embodiments, $L^{A5}$ is an unsubstituted $C_1$-$C_6$ alkylene.

In embodiments, $L^{A4}$ is a divalent oligomer of ethylene oxide. In embodiments, $L^{A4}$ is a divalent polyethylene glycol. In embodiments, $L^{A4}$ is a divalent oligomer of ethylene oxide having 2 to 30 linear atoms (carbon and oxygen)

between the two termini connecting to the remainder of the compound. In embodiments, $L^{A4}$ is —$(CH_2CH_2O)_{eA}$ $CH_2CH_2$— and eA is an integer from 1 to 16. In embodiments, $L^{A4}$ is —$(CH_2CH_2O)_{eA}CH_2$— and eA is an integer from 1 to 16. In embodiments, $L^{A4}$ is —$(CH_2CH_2O)_{eA}$— and eA is an integer from 1 to 16. In embodiments, eA is an integer from 2 to 15. In embodiments, eA is an integer from 3 to 14. In embodiments, eA is an integer from 4 to 12. In embodiments, eA is an integer from 5 to 10. In embodiments, eA is an integer from 5 to 8. In embodiments, eA is an integer from 6 to 7.

In embodiments, the linker is formed by a conjugation or bioconjugation reaction combining a first reactant moiety covalently bonded to the rapamycin or rapamycin analog and a second reactant moiety covalently bonded to the active site mTOR inhibitor. In such embodiments, the anti-CNS disease drug formed by such conjugation or bioconjugation reaction (including compounds as described herein) may be referred to as a conjugate.

In some embodiments, $L^{A1}$ is $L^{A2}$-$L^{A3}$-$L^{A4}$-$L^{AS}$; $L^{A2}$ is —$CH_2CH_2OCH_2$—; $L^{A3}$ is 5 to 10 membered heteroarylene; $L^{A4}$ is —$(CH_2CH_2O)_{eA}$—; eA is an integer from 2 to 8; $L^{A5}$ is —$CH_2CH_2C(O)NH(CH_2)_{eA10}$—; and eA10 is an integer from 1 to 6. In some embodiments, $L^{A1}$ is $L^{A2}$-$L^{A3}$-$L^{A4}$-$L^{A5}$; $L^{A2}$ is 2 to 8 membered heteroalkylene comprising at least one NH or O; $L^{A3}$ is 5 to 10 membered heteroarylene; $L^{A4}$ is —$[(CH_2)_{eA11}O]_{eA12}$—; eA11 is an integer from 1 to 3; eA12 is an integer from 1 to 8; $L^{A5}$ is —$CH_2CH_2C(O)NH(CH_2)_{eA}10$; and eA10 is an integer from 1 to 6. In some embodiments, $L^{A1}$ is $L^{A2}$-$L^{A3}$-$L^{A4}$-$L^{A5}$; $L^{A2}$ is —$CH_2CH_2OCH_2$—; $L^{A3}$ is 5 membered heteroarylene; $L^{A4}$ is —$(CH_2CH_2O)_{eA}$—; eA is an integer from 4 to 8; and $L^{A5}$ is —$CH_2CH_2C(O)NH(CH_2)_4$. In some embodiments, $L^{A1}$ is $L^{A2}$-$L^{A3}$-$L^{A4}$-$L^{A}$; $L^{A2}$ is —$CH_2CH_2OCH_2$—; $L^{A3}$ is triazolylene; $L^{A4}$ is —$(CH_2CH_2O)_{eA}$—; eA is an integer from 4 to 8; and $L^{A5}$ is —$CH_2CH_2C(O)NH(CH_2)_4$. In some embodiments, $L^{A1}$ is $L^{A2}$-$L^{A3}$-$L^{A4}$-$L^{A5}$; $L^{A2}$ is —$CH_2CH_2OCH_2$—; $L^{A3}$ is 5 to 10 membered heteroarylene; $L^{A4}$ is —$(CH_2)_{eA}$—; eA is an integer from 2 to 8; and $L^{A5}$ is a bond.

$R^{A23}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A24}$-substituted or unsubstituted alkyl, $R^{A24}$-substituted or unsubstituted heteroalkyl, $R^{A24}$-substituted or unsubstituted cycloalkyl, $R^{A24}$-substituted or unsubstituted heterocycloalkyl, $R^{A24}$-substituted or unsubstituted aryl, or $R^{A24}$-substituted or unsubstituted heteroaryl.

In embodiments, $R^{A23}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A24}$-substituted or unsubstituted alkyl (e.g., $C_1$-$C_8$, $C_1$-$C_6$, $C_1$-$C_4$, or $C_1$-$C_2$), $R^{A24}$-substituted or unsubstituted heteroalkyl (e.g., 2 to 8 membered, 2 to 6 membered, 4 to 6 membered, 2 to 3 membered, or 4 to 5 membered), $R^{A24}$-substituted or unsubstituted cycloalkyl (e.g., $C_3$-$C_8$, $C_3$-$C_6$, $C_4$-$C_6$, or $C_5$-$C_6$), $R^{A24}$-substituted or unsubstituted heterocycloalkyl (e.g., 3 to 8 membered, 3 to 6 membered, 4 to 6 membered, 4 to 5 membered, or 5 to 6 membered), $R^{A24}$-substituted or unsubstituted aryl (e.g., $C_6$-$C_{10}$ or phenyl), or $R^{A24}$-substituted or unsubstituted heteroaryl (e.g., 5 to 10 membered, 5 to 9 membered, or 5 to 6 membered).

$R^{A24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A25}$-substituted or unsubstituted alkyl, $R^{A25}$-substituted or unsubstituted heteroalkyl, $R^{A25}$-substituted or unsubstituted cycloalkyl, $R^{A25}$-substituted or unsubstituted heterocycloalkyl, $R^{A25}$-substituted or unsubstituted aryl, or $R^{A25}$-substituted or unsubstituted heteroaryl.

In embodiments, $R^{A24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A25}$-substituted or unsubstituted alkyl (e.g., $C_1$-$C_8$, $C_1$-$C_6$, $C_1$-$C_4$, or $C_1$-$C_2$), $R^{A25}$-substituted or unsubstituted heteroalkyl (e.g., 2 to 8 membered, 2 to 6 membered, 4 to 6 membered, 2 to 3 membered, or 4 to 5 membered), $R^{A25}$-substituted or unsubstituted cycloalkyl (e.g., $C_3$-$C_8$, $C_3$-$C_6$, $C_4$-$C_6$, or $C_5$-$C_6$), $R^{A25}$-substituted or unsubstituted heterocycloalkyl (e.g., 3 to 8 membered, 3 to 6 membered, 4 to 6 membered, 4 to 5 membered, or 5 to 6 membered), $R^{A5}$-substituted or unsubstituted aryl (e.g., $C_6$-$C_{10}$ or phenyl), or $R^{A25}$-substituted or unsubstituted heteroaryl (e.g., 5 to 10 membered, 5 to 9 membered, or 5 to 6 membered).

$R^{A25}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A25}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the anti-CNS disease drugs provided herein, $L^{A2}$ is independently a bond, $R^{A26}$-substituted or unsubstituted alkylene, $R^{A26}$-substituted or unsubstituted heteroalkylene, $R^{A26}$-substituted or unsubstituted cycloalkylene, $R^{A26}$-substituted or unsubstituted heterocycloalkylene, $R^{A26}$-substituted or unsubstituted arylene, or $R^{A26}$-substituted or unsubstituted heteroarylene.

$R^{A26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A27}$-substituted or unsubstituted alkyl, $R^{A27}$-substituted or unsubstituted heteroalkyl, $R^{A27}$-substituted or unsubstituted cycloalkyl, $R^{A27}$-substituted or unsubstituted heterocycloalkyl, $R^{A27}$-substituted or unsubstituted aryl, or $R^{A27}$-substituted or unsubstituted heteroaryl.

In embodiments, $R^{A26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A27}$-substituted or unsubstituted alkyl (e.g., $C_1$-$C_8$, $C_1$-$C_6$, $C_1$-$C_4$, or $C_1$-$C_2$), $R^{A27}$-substituted or unsubstituted heteroalkyl (e.g., 2 to 8 membered, 2 to 6 membered, 4 to 6 membered, 2 to 3 membered, or 4 to 5 membered), $R^{A27}$-substituted or unsubstituted cycloalkyl (e.g., $C_3$-$C_8$, $C_3$-$C_6$, $C_4$-$C_6$, or $C_5$-$C_6$), $R^{A27}$-substituted or unsubstituted heterocycloalkyl (e.g., 3 to 8 membered, 3 to 6 membered, 4 to 6 membered, 4 to 5 membered, or 5 to 6 membered), $R^{A27}$-substituted or unsubstituted aryl (e.g., $C_6$-$C_{10}$ or phenyl), or $R^{A27}$-substituted or unsubstituted heteroaryl (e.g., 5 to 10 membered, 5 to 9 membered, or 5 to 6 membered)

$R^{A27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A28}$-substituted or unsubstituted alkyl, $R^{A28}$-substituted or unsubstituted heteroalkyl, $R^{A28}$-substituted or unsubstituted cycloalkyl, $R^{A28}$-substituted or unsubstituted heterocycloalkyl, $R^{A28}$-substituted or unsubstituted aryl, or $R^{A28}$-substituted or unsubstituted heteroaryl.

In embodiments, $R^{A27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A28}$-substituted or unsubstituted alkyl (e.g., $C_1$-$C_8$, $C_1$-$C_6$, $C_1$-$C_4$, or $C_1$-$C_2$), $R^{A28}$-substituted or unsubstituted heteroalkyl (e.g., 2 to 8 membered, 2 to 6 membered, 4 to 6 membered, 2 to 3 membered, or 4 to 5 membered), $R^{A28}$-substituted or unsubstituted cycloalkyl (e.g., $C_3$-$C_8$, $C_3$-$C_6$, $C_4$-$C_6$, or $C_5$-$C_6$), $R^{A28}$-substituted or unsubstituted heterocycloalkyl (e.g., 3 to 8 membered, 3 to 6 membered, 4 to 6 membered, 4 to 5 membered, or 5 to 6 membered), $R^{A28}$-substituted or unsubstituted aryl (e.g., $C_6$-$C_{10}$ or phenyl), or $R^{A28}$-substituted or unsubstituted heteroaryl (e.g., 5 to 10 membered, 5 to 9 membered, or 5 to 6 membered)

$R^{A28}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A28}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the compounds provided herein, $L^{A3}$ is independently a bond, $R^{A29}$-substituted or unsubstituted alkylene, $R^{A29}$-substituted or unsubstituted heteroalkylene, $R^{A29}$-substituted or unsubstituted cycloalkylene, $R^{A29}$-substituted or unsubstituted heterocycloalkylene, $R^{A29}$-substituted or unsubstituted arylene, or $R^{A29}$-substituted or unsubstituted heteroarylene.

$R^{A29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A30}$-substituted or unsubstituted alkyl, $R^{A30}$-substituted or unsubstituted heteroalkyl, $R^{A30}$-substituted or unsubstituted cycloalkyl, $R^{A30}$-substituted or unsubstituted heterocycloalkyl, $R^{A30}$-substituted or unsubstituted aryl, or $R^{A30}$-substituted or unsubstituted heteroaryl.

In embodiments, $R^{A29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A30}$-substituted or unsubstituted alkyl (e.g., $C_1$-$C_8$, $C_1$-$C_6$, $C_1$-$C_4$, or $C_1$-$C_2$), $R^{A}$—O-substituted or unsubstituted heteroalkyl (e.g., 2 to 8 membered, 2 to 6 membered, 4 to 6 membered, 2 to 3 membered, or 4 to 5 membered), $R^{A30}$-substituted or unsubstituted cycloalkyl (e.g., $C_3$-$C_8$, $C_3$-$C_6$, $C_4$-$C_6$, or $C_5$-$C_6$), $R^{A30}$-substituted or unsubstituted heterocycloalkyl (e.g., 3 to 8 membered, 3 to 6 membered, 4 to 6 membered, 4 to 5 membered, or 5 to 6 membered), $R^{A30}$-substituted or unsubstituted aryl (e.g., $C_6$-$C_{10}$ or phenyl), or $R^{A30}$-substituted or unsubstituted heteroaryl (e.g., 5 to 10 membered, 5 to 9 membered, or 5 to 6 membered).

$R^{A30}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A31}$-substituted or unsubstituted alkyl, $R^{A31}$-substituted or unsubstituted heteroalkyl, $R^{A31}$-substituted or unsubstituted cycloalkyl, $R^{A31}$-substituted or unsubstituted heterocycloalkyl, $R^{A31}$-substituted or unsubstituted aryl, or $R^{A31}$-substituted or unsubstituted heteroaryl.

In embodiments, $R^{A30}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A31}$-substituted or unsubstituted alkyl (e.g., $C_1$-$C_8$, $C_1$-$C_6$, $C_1$-$C_4$, or $C_1$-$C_2$), $R^{A31}$-substituted or unsubstituted heteroalkyl (e.g., 2 to 8 membered, 2 to 6 membered, 4 to 6 membered, 2 to 3 membered, or 4 to 5 membered), $R^{A31}$-substituted or unsubstituted cycloalkyl (e.g., $C_3$-$C_8$, $C_3$-$C_6$, $C_4$-$C_6$, or $C_5$-$C_6$), $R^{A31}$-substituted or unsubstituted heterocycloalkyl (e.g., 3 to 8 membered, 3 to 6 membered, 4 to 6 membered, 4 to 5 membered, or 5 to 6 membered), $R^{A31}$-substituted or unsubstituted aryl (e.g., $C_6$-$C_{10}$ or phenyl), or $R^{A31}$-substituted or unsubstituted heteroaryl (e.g., 5 to 10 membered, 5 to 9 membered, or 5 to 6 membered).

$R^{A31}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A31}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the compounds provided herein, $L^{A4}$ is independently a bond, $R^{A32}$-substituted or unsubstituted alkylene, $R^{A32}$-substituted or unsubstituted heteroalkylene, $R^{A32}$-substituted or unsubstituted cycloalkylene, $R^{A32}$-substituted or unsubstituted heterocycloalkylene, $R^{A32}$-substituted or unsubstituted arylene, or $R^{A32}$-substituted or unsubstituted heteroarylene.

$R^{A32}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCF_2$, $R^{A13}$-substituted or unsubstituted alkyl, $R^{A3}$-substituted or unsubstituted heteroalkyl, $R^{A33}$-substituted or unsubstituted cycloalkyl, $R^{A33}$-substituted or unsubstituted heterocycloalkyl, $R^{A33}$-substituted or unsubstituted aryl, or $R^{A33}$-substituted or unsubstituted heteroaryl.

In embodiments, $R^{A32}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCF_2$, $R^{A13}$-substituted or unsubstituted alkyl (e.g., $C_1$-$C_8$, $C_1$-$C_6$, $C_1$-$C_4$, or $C_1$-$C_2$), $R^{A58}$-substituted or unsubstituted heteroalkyl (e.g., 2 to 8 membered, 2 to 6 membered, 4 to 6 membered, 2 to 3 membered, or 4 to 5 membered), $R^{A33}$-substituted or unsubstituted cycloalkyl (e.g., $C_3$-$C_8$, $C_3$-$C_6$, $C_4$-$C_6$, or $C_5$-$C_6$), $R^{A33}$-substituted or unsubstituted heterocycloalkyl (e.g., 3 to 8 membered, 3 to 6 membered, 4 to 6 membered, 4 to 5 membered, or 5 to 6 membered), $R^{A3}$-substituted or unsubstituted aryl (e.g., $C_6$-$C_{10}$ or phenyl), or $R^{A33}$-substituted or unsubstituted heteroaryl (e.g., 5 to 10 membered, 5 to 9 membered, or 5 to 6 membered).

$R^{A33}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A34}$-substituted or unsubstituted alkyl, $R^{A34}$-substituted or unsubstituted heteroalkyl, $R^{A34}$-substituted or unsubstituted cycloalkyl, $R^{A34}$-substituted or unsubstituted heterocycloalkyl, $R^{A34}$-substituted or unsubstituted aryl, or $R^{A34}$-substituted or unsubstituted heteroaryl.

In embodiments, $R^{A33}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A34}$-substituted or unsubstituted alkyl (e.g., $C_1$-$C_8$, $C_1$-$C_6$, $C_1$-$C_4$, or $C_1$-$C_2$), $R^{A34}$-substituted or unsubstituted heteroalkyl (e.g., 2 to 8 membered, 2 to 6 membered, 4 to 6 membered, 2 to 3 membered, or 4 to 5 membered), $R^{A34}$-substituted or unsubstituted cycloalkyl (e.g., $C_3$-$C_8$, $C_3$-$C_6$, $C_4$-$C_6$, or $C_5$-$C_6$), $R^{A34}$-substituted or unsubstituted heterocycloalkyl (e.g., 3 to 8 membered, 3 to 6 membered, 4 to 6 membered, 4 to 5 membered, or 5 to 6 membered), $R^{A14}$-substituted or unsubstituted aryl (e.g., $C_6$-$C_{10}$ or phenyl), or $R^{A34}$-substituted or unsubstituted heteroaryl (e.g., 5 to 10 membered, 5 to 9 membered, or 5 to 6 membered).

$R^{A34}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A34}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the compounds provided herein, $L^{A5}$ is independently a bond, $R^{A35}$-substituted or unsubstituted alkylene, $R^{A35}$-substituted or unsubstituted heteroalkylene, $R^{A35}$-substituted or unsubstituted cycloalkylene, $R^{A35}$-substituted or unsubstituted heterocycloalkylene, $R^{A35}$-substituted or unsubstituted arylene, or $R^{A35}$-substituted or unsubstituted heteroarylene.

$R^{A35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCF_2$, $R^{A16}$-substituted or unsubstituted alkyl, $R^{A16}$-substituted or unsubstituted heteroalkyl, $R^{A36}$-substituted or unsubstituted cycloalkyl, $R^{A36}$-substituted or unsubstituted heterocycloalkyl, $R^{A36}$-substituted or unsubstituted aryl, or $R^{A36}$-substituted or unsubstituted heteroaryl.

In embodiments, $R^{A35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCF_2$, $R^{A16}$-substituted or unsubstituted alkyl (e.g., $C_1$-$C_8$, $C_1$-$C_6$, $C_1$-$C_4$, or $C_1$-$C_2$), $R^{A36}$-substituted or unsubstituted heteroalkyl (e.g., 2 to 8 membered, 2 to 6 membered, 4 to 6 membered, 2 to 3 membered, or 4 to 5 membered), $R^{A36}$-substituted or unsubstituted cycloalkyl (e.g., $C_3$-$C_8$, $C_3$-$C_6$, $C_4$-$C_6$, or $C_5$-$C_6$), $R^{A36}$-substituted or unsubstituted heterocycloalkyl (e.g., 3 to 8 membered, 3 to 6 membered, 4 to 6 membered, 4 to 5 membered, or 5 to 6 membered), $R^{A36}$-substituted or unsubstituted aryl (e.g., $C_6$-$C_{10}$ or phenyl), or $R^{A36}$-substituted or unsubstituted heteroaryl (e.g., 5 to 10 membered, 5 to 9 membered, or 5 to 6 membered).

$R^{A36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A37}$-substituted or unsubstituted alkyl, $R^{A37}$-substituted or unsubstituted heteroalkyl, $R^{A37}$-substituted or unsubstituted cycloalkyl, $R^{A37}$-substituted or unsubstituted heterocycloalkyl, $R^{A37}$-substituted or unsubstituted aryl, or $R^{A37}$-substituted or unsubstituted heteroaryl.

In embodiments, $R^{A36}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A37}$-substituted or unsubstituted alkyl (e.g., $C_1$-$C_8$, $C_1$-$C_6$, $C_1$-$C_4$, or $C_1$-$C_2$), $R^{A37}$-substituted or unsubstituted heteroalkyl (e.g., 2 to 8 membered, 2 to 6 membered, 4 to 6 membered, 2 to 3 membered, or 4 to 5 membered), $R^{A37}$-substituted or unsubstituted cycloalkyl (e.g., $C_3$-$C_8$, $C_3$-$C_6$, $C_4$-$C_6$, or $C_5$-$C_6$), $R^{A37}$-substituted or unsubstituted heterocycloalkyl (e.g., 3 to 8 membered, 3 to 6 membered, 4 to 6 membered, 4 to 5 membered, or 5 to 6 membered), $R^{A17}$-substituted or unsubstituted aryl (e.g., $C_6$-$C_{10}$ or phenyl), or $R^{A37}$-substituted or unsubstituted heteroaryl (e.g., 5 to 10 membered, 5 to 9 membered, or 5 to 6 membered).

$R^{A37}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A37}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, the anti-CNS disease drug competes with rapamycin for binding to mTORC1. In embodiments, the anti-CNS disease drug binds an overlapping region of mTORC1 with the binding region of rapamycin. In embodiments, the anti-CNS disease drug competes with ATP for binding to mTOR. In embodiments, the anti-CNS disease drug competes with ATP for binding to mTORC1. In embodiments, the anti-CNS disease drug competes with rapamycin and ATP for binding to mTORC1.

In embodiments, the anti-CNS disease drug is an mTORC1 specific inhibitor. In embodiments, the anti-CNS disease drug has a slow off-rate from mTORC1. In embodiments, the anti-CNS disease drug has an off-rate of slower than 0.1 per minute. In embodiments, the anti-CNS disease drug has an off-rate of slower than 0.01 per minute. In embodiments, the anti-CNS disease drug has an off-rate of slower than 0.001 per minute. In embodiments, the anti-CNS disease drug has an off-rate of slower than 0.0001 per minute. In embodiments, the anti-CNS disease drug mTORC1 complex has a half-life of at least 10 minutes. In embodiments, the anti-CNS disease drug-mTORC1 complex has a half-life of at least 100 minutes. In embodiments, the anti-CNS disease drug mTORC1 complex has a half-life of at least 300 minutes. In embodiments, the anti-CNS disease drug-mTORC1 complex has a half-life of at least 1000 minutes. In embodiments, the anti-CNS disease drug mTORC1 complex has a half-life of at least 3000 minutes. In embodiments, the anti-CNS disease drug mTORC1 complex has a half-life of at least 10000 minutes.

In embodiments, the anti-CNS disease drug is

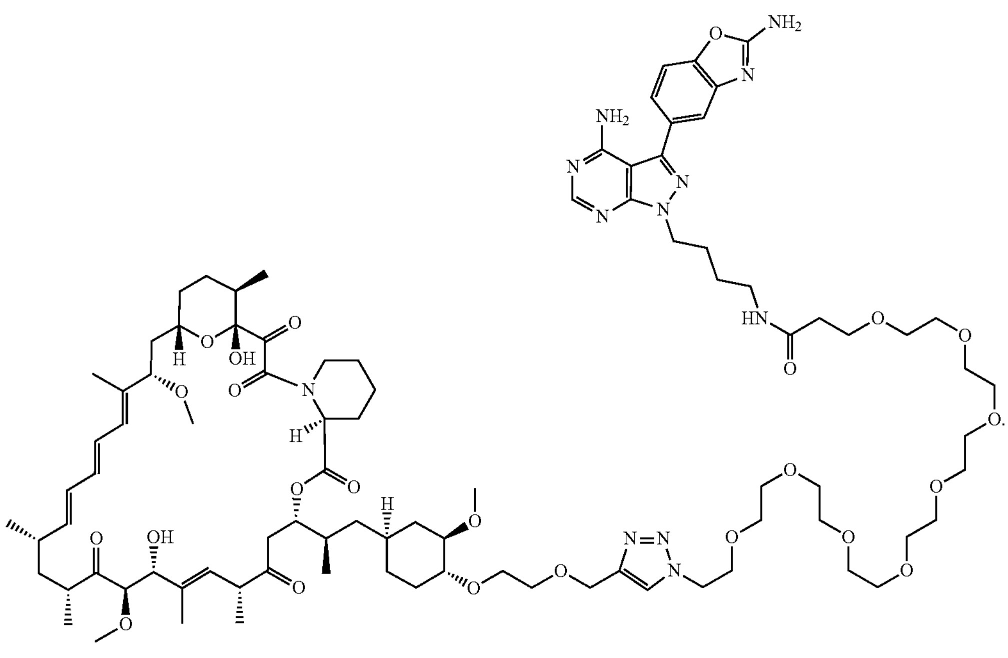 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

In embodiments, the anti-CNS disease drug is
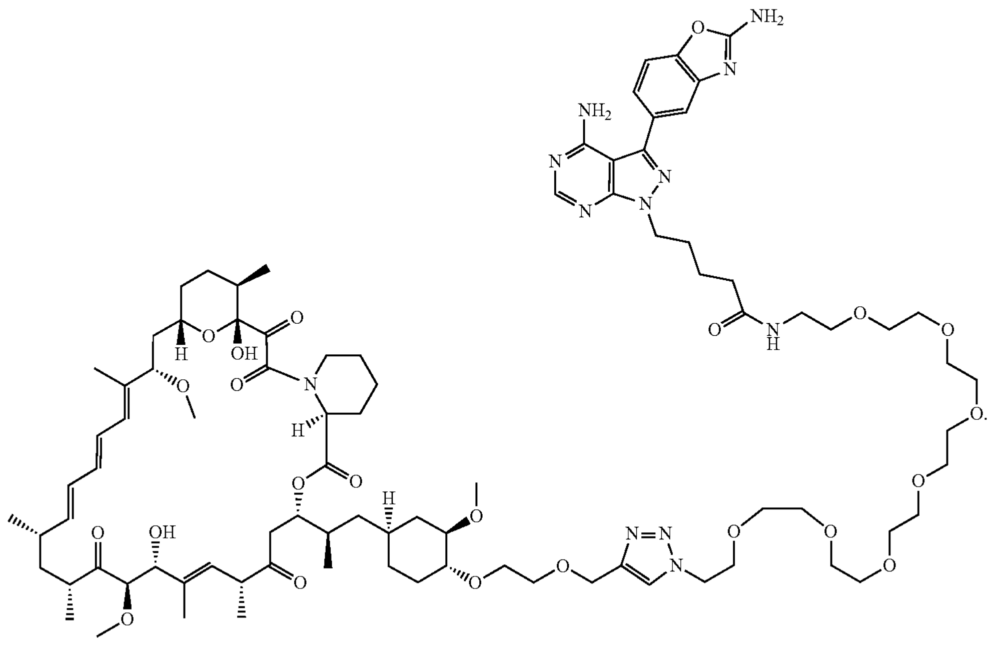 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCNC(=O)CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]
In embodiments, the anti-CNS disease drug is
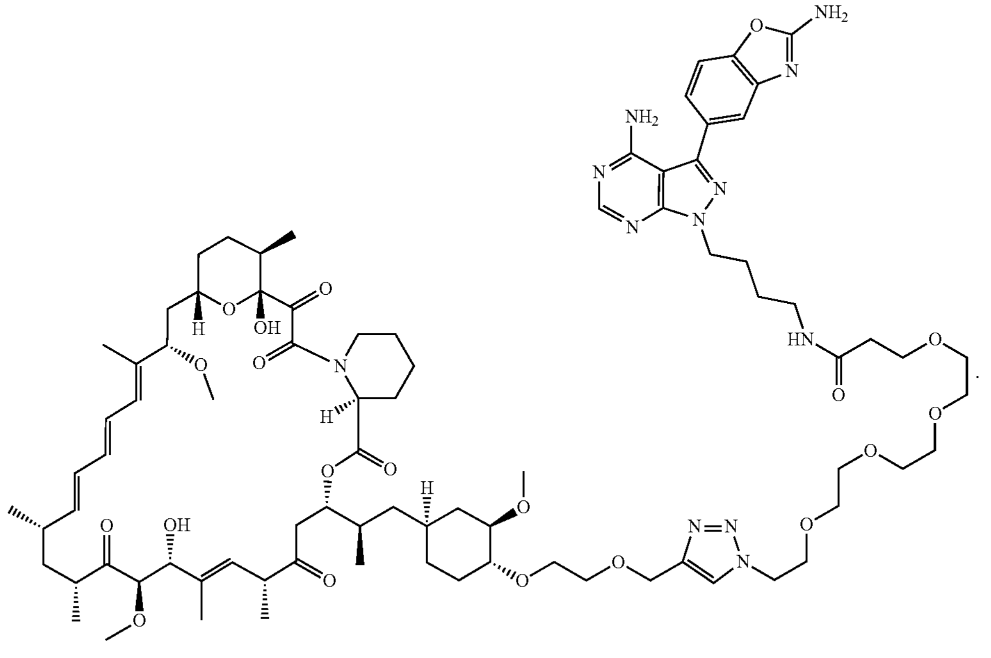 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

In embodiments, the anti-CNS disease drug is

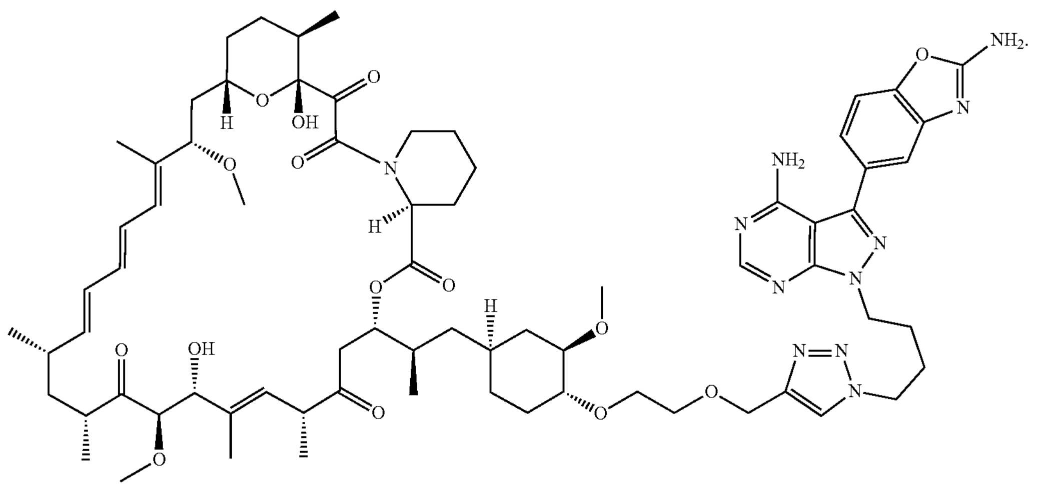 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

In embodiments, the anti-CNS disease drug is M-1071. In embodiments, the anti-CNS disease drug is M-1111. In embodiments, the anti-CNS disease drug is M-3059. In embodiments, the anti-CNS disease drug is M-1115. In embodiments, the anti-CNS disease drug is not M-1115. In embodiments, the anti-CNS disease drug is E1010. In embodiments, the anti-CNS disease drug is E1035.

In embodiments, the active site mTOR inhibitor is a monovalent MLN0128.

In embodiments, the active site mTOR inhibitor is

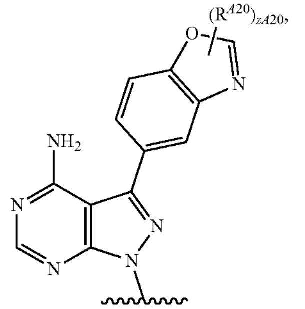

wherein $R^{A20}$ is as described herein, including in embodiments. In embodiments, zA20 is an integer from 0 to 4. In embodiments, zA20 is 0. In embodiments, zA20 is 1. In embodiments, zA20 is 2. In embodiments, zA20 is 3. In embodiments, zA20 is 4. In embodiments, the active site mTOR inhibitor is

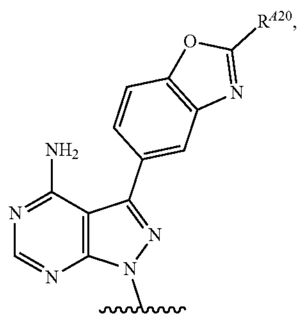

wherein $R^{A20}$ is as described herein, including in embodiments. In embodiments, the active site mTOR inhibitor is

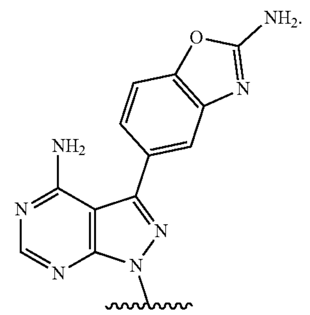 [SMILES: *n1nc(-c2ccc3oc(N)nc3c2)c2c(N)ncnc21]

In embodiments, the active site mTOR inhibitor is

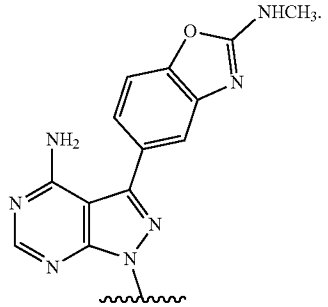 [SMILES: *n1nc(-c2ccc3oc(NC)nc3c2)c2c(N)ncnc21]

In embodiments, the active site mTOR inhibitor is

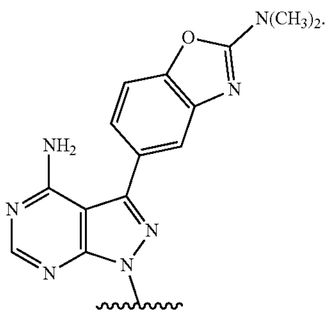 [SMILES: *n1nc(-c2ccc3oc(N(C)C)nc3c2)c2c(N)ncnc21]

In embodiments, the active site mTOR inhibitor is

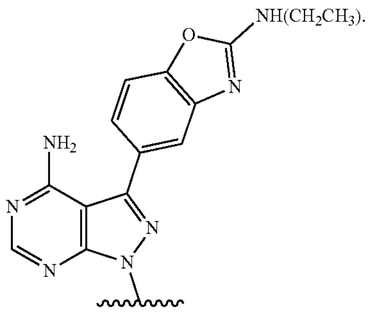

In embodiments, the active site mTOR inhibitor is

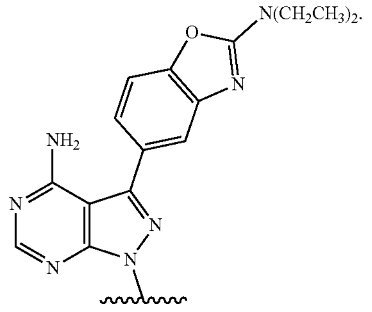

In embodiments, the active site mTOR inhibitor is

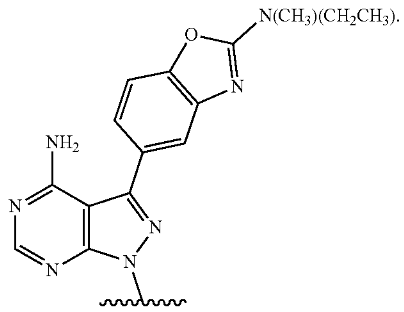

In embodiments, the active site mTOR inhibitor

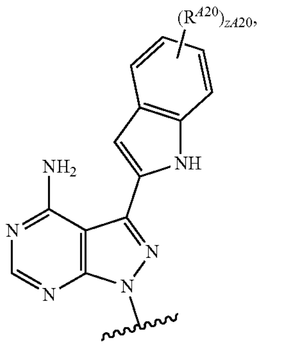

wherein $R^{A20}$ is as described herein, including in embodiments. zA20 is an integer from 0 to 5. In embodiments, zA20 is 0. In embodiments, zA20 is 1. In embodiments, zA20 is 2. In embodiments, zA20 is 3. In embodiments, zA20 is 4. In embodiments, zA20 is 5. In embodiments, the active site mTOR inhibitor is

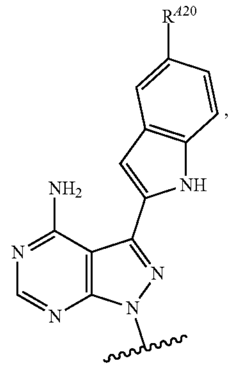

wherein $R^{A20}$ is as described herein. In embodiments, the active site mTOR inhibitor is

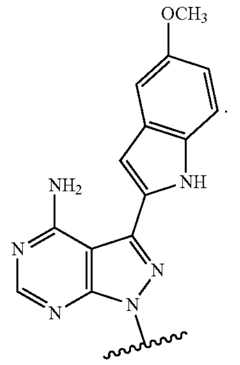 [SMILES: *n1nc(-c2cc3cc(OC)ccc3[nH]2)c2c(N)ncnc21]

In embodiments, the active site mTOR inhibitor is

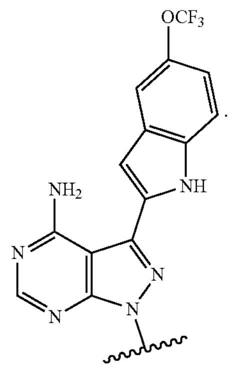 [SMILES: *n1nc(-c2cc3cc(OC(F)(F)F)ccc3[nH]2)c2c(N)ncnc21]

In embodiments, the active site mTOR inhibitor is

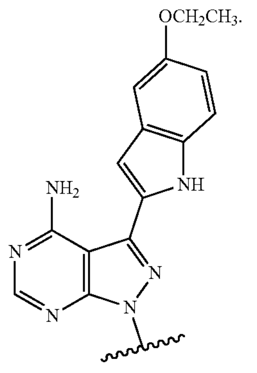 [SMILES: *n1nc(-c2cc3cc(OCC)ccc3[nH]2)c2c(N)ncnc21]

In embodiments, the active site mTOR inhibitor is

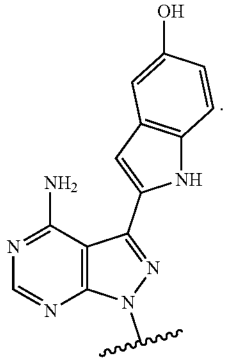 [SMILES: *n1nc(-c2cc3cc(O)ccc3[nH]2)c2c(N)ncnc21]

In embodiments, the active site mTOR inhibitor (e.g., asTORi) has a weaker binding affinity for mTOR than MLN0128. In embodiments, the active site mTOR inhibitor has a binding affinity that results in preferential binding to mTORC1 over mTORC2 that is greater than the same compound wherein the active site mTOR inhibitor is MLN0128. In embodiments, the active site mTOR inhibitor has a binding affinity that results in preferential binding to mTORC1 over mTORC2 that is greater than the same compound wherein the active site mTOR inhibitor is PP242. In embodiments, the active site mTOR inhibitor has a binding affinity that results in preferential binding to mTORC1 over mTORC2 that is greater than the same compound wherein the active site mTOR inhibitor is PP242 wherein the —OH substituent on the indoyly moiety is replaced with an unsubstituted methoxy moiety. Without being limited by mechanism, the compound may include an active site mTOR inhibitor that results in a preferential binding of the compound to mTORC1 over mTORC2 of at least 1.1-fold (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold). Without being limited by mechanism, the compound may include an active site mTOR inhibitor that results in a preferential inhibition of mTORC1 over mTORC2 by the compound of at least 1.1-fold (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold).

In embodiments, the anti-CNS disease drug is included in a drug-eluting stent.

In embodiments, the anti-CNS disease drug has the formula: A-$L^1$-$R^1$; A is an immunophilin-binding moiety; $L^1$ is a bond or a covalent linker; and $R^1$ is a monovalent kinase inhibitor, a monovalent pseudokinase inhibitor, a monovalent GTPase inhibitor, a monovalent histone-modifying enzyme inhibitor, or monovalent anti-viral agent.

In embodiments, the anti-CNS disease drug is

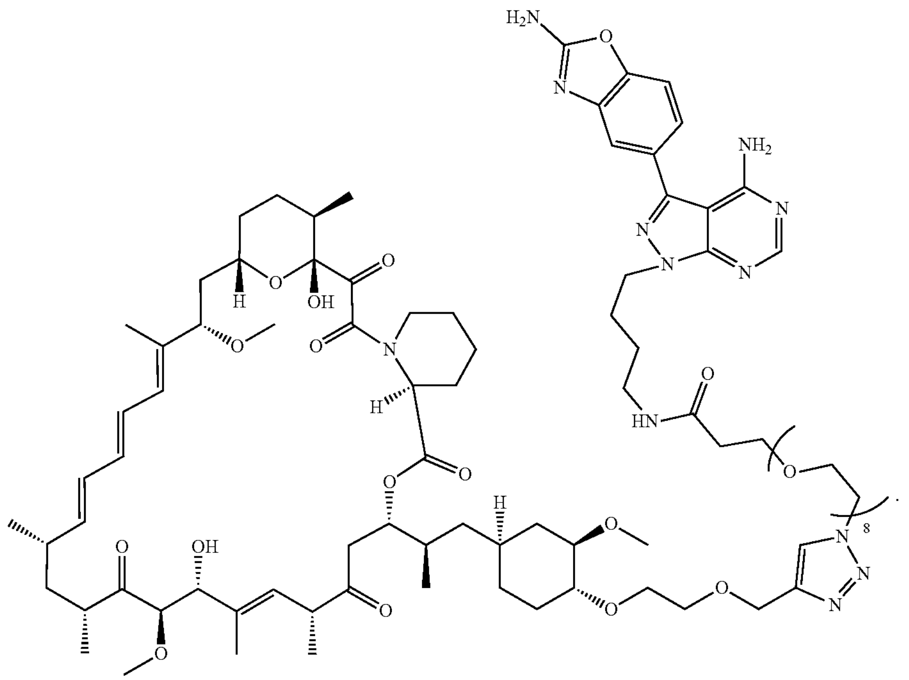

In embodiments, the anti-CNS disease drug is not

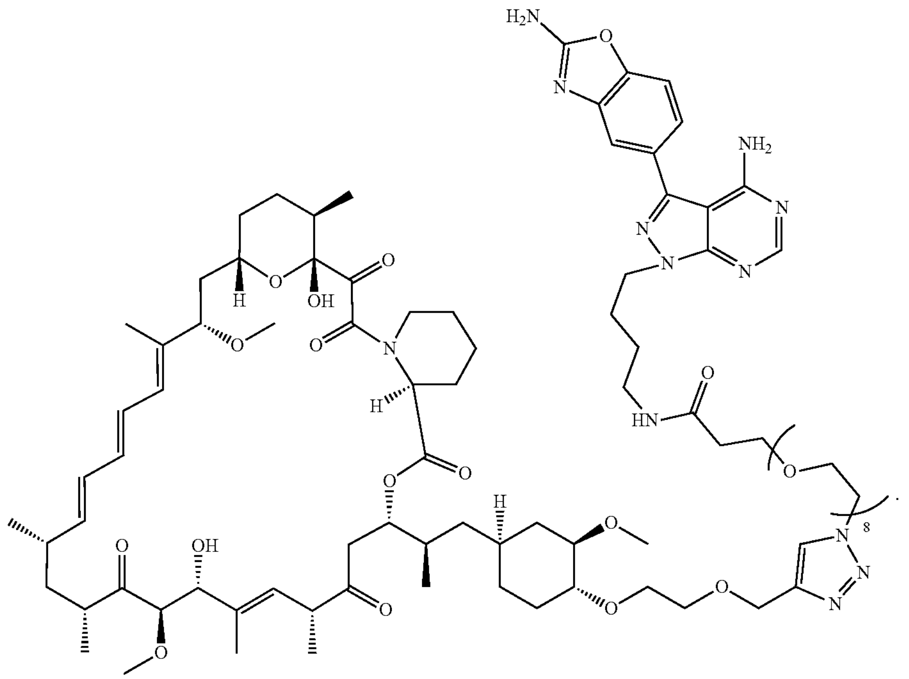

In embodiments, the immunophilin-binding moiety is a cyclophilin-binding moiety or an FKBP-binding moiety. In embodiments, the immunophilin-binding moiety is
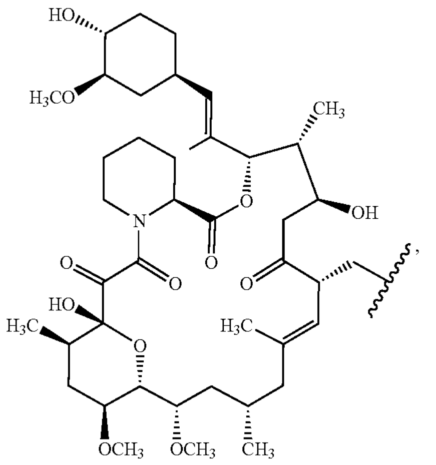
,
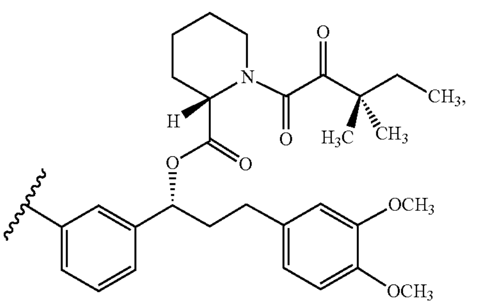
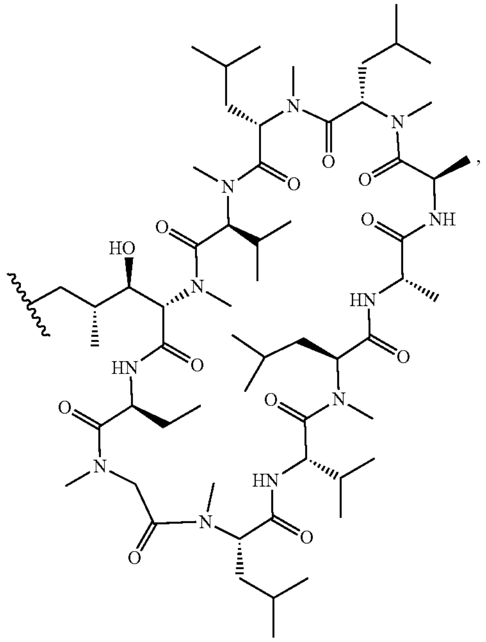
,
-continued
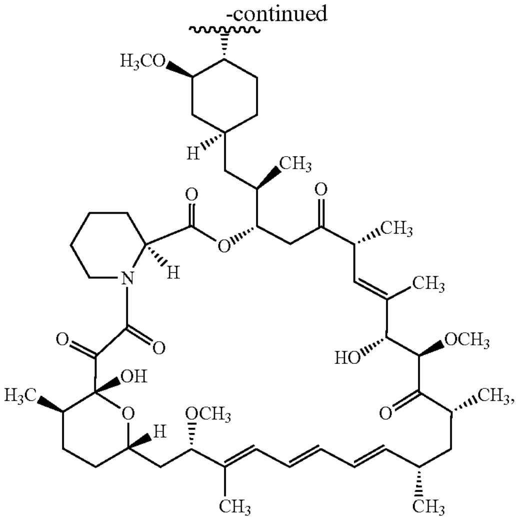
or
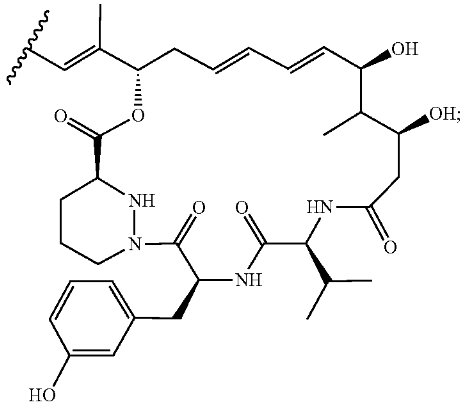
or an analog thereof.
In embodiments, the immunophilin-binding moiety is
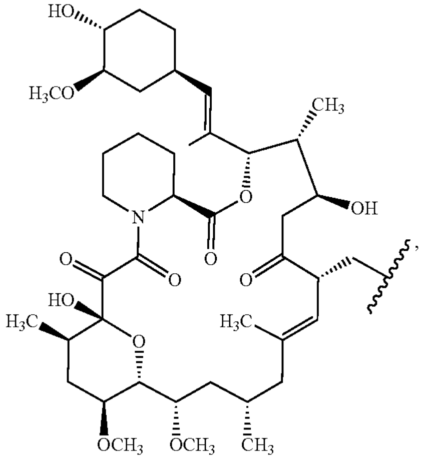 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
,
or an analog thereof.

In embodiments, the immunophilin-binding moiety is
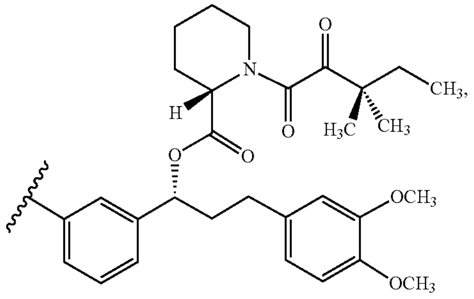
or an analog thereof.
In embodiments, the immunophilin-binding moiety is
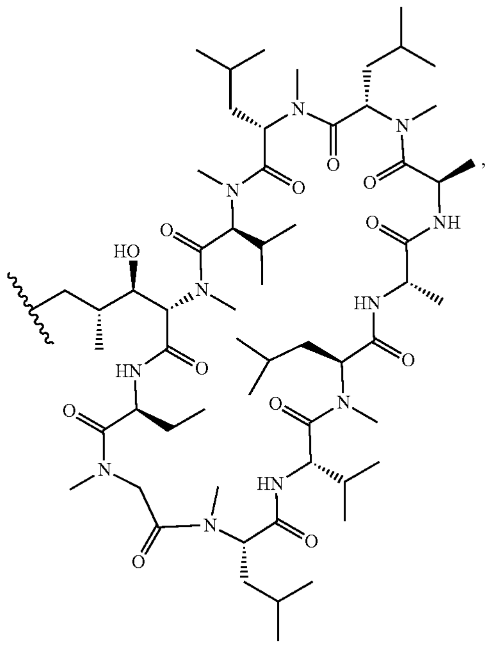 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
or an analog thereof.
In embodiments, the immunophilin-binding moiety is
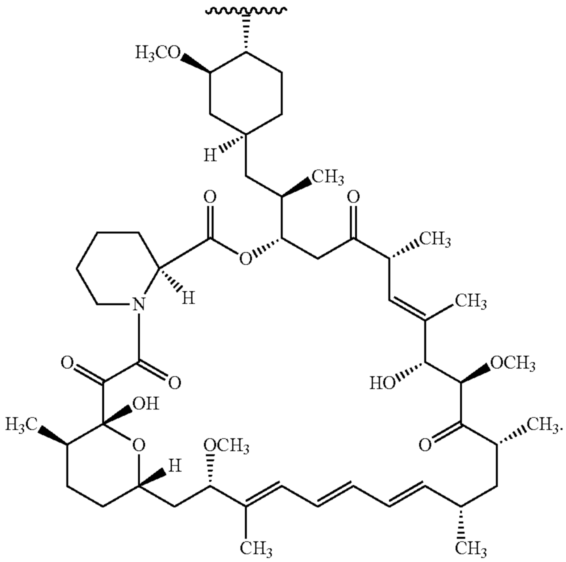 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
or an analog thereof.
In embodiments, the immunophilin-binding moiety is
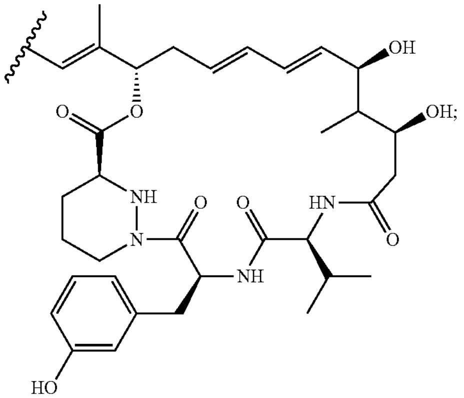 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
or an analog thereof.
In embodiments, the immunophilin-binding moiety is
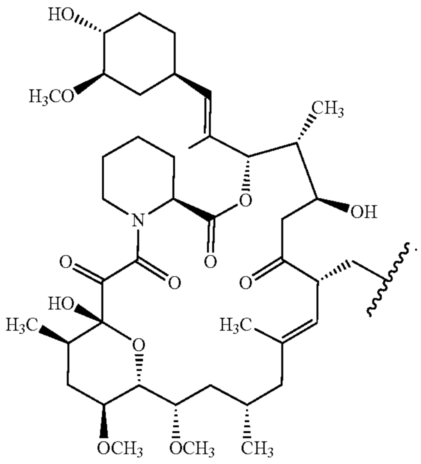 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

In embodiments, the immunophilin-binding moiety is
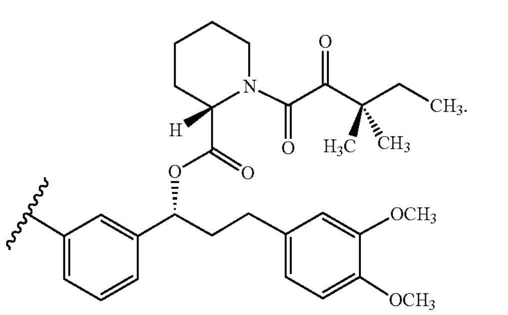
In embodiments, the immunophilin-binding moiety is
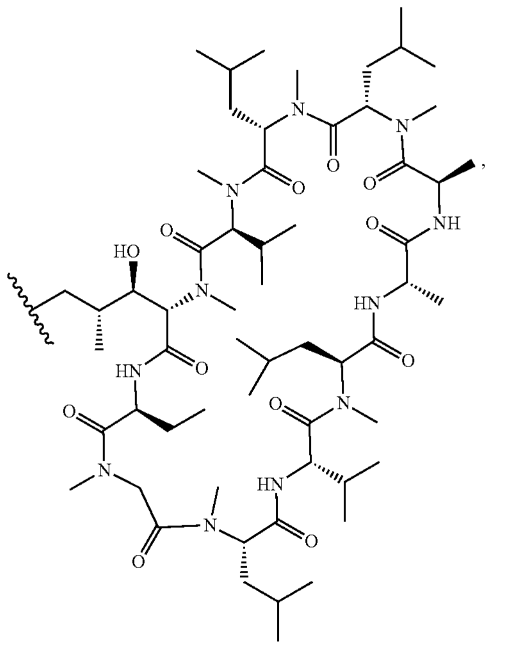 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
In embodiments, the immunophilin-binding moiety is
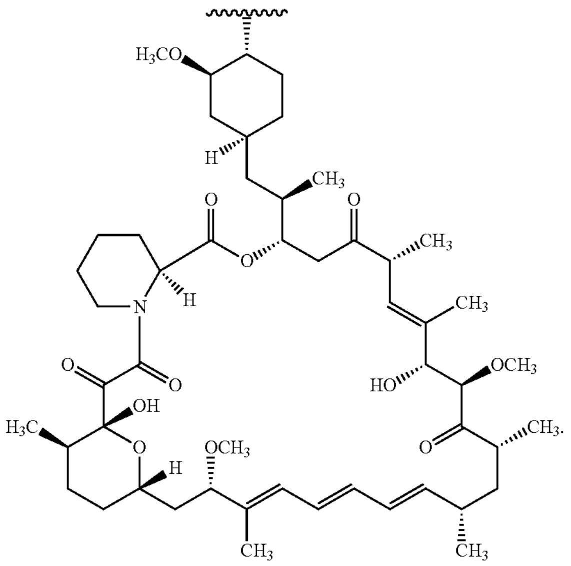 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
In embodiments, the immunophilin-binding moiety is
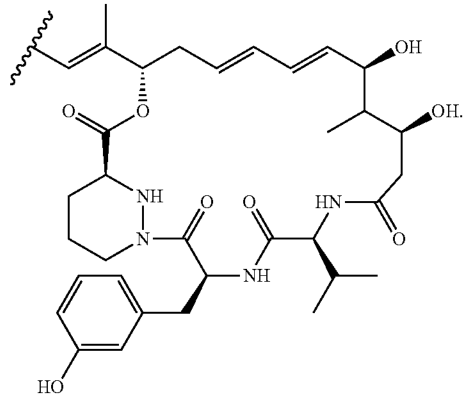 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
In embodiments, the immunophilin-binding moiety is
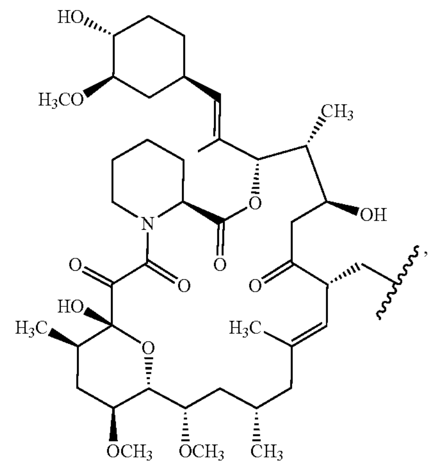
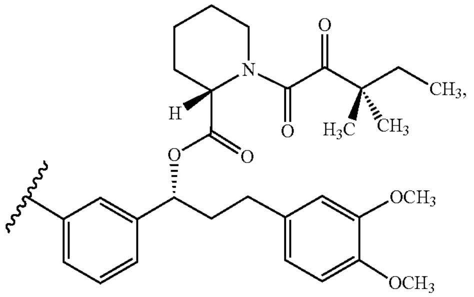

-continued
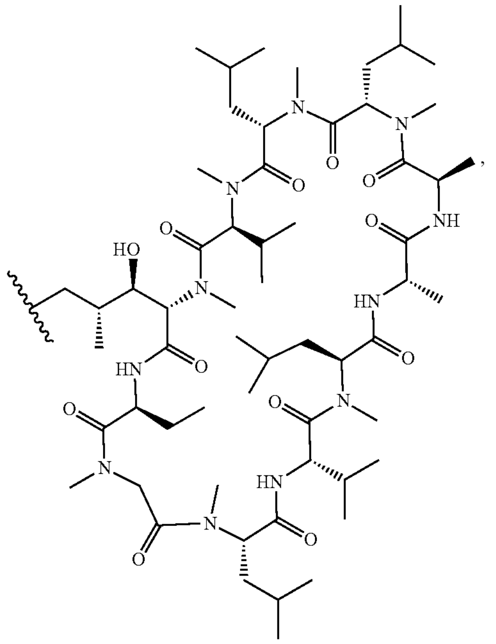
or
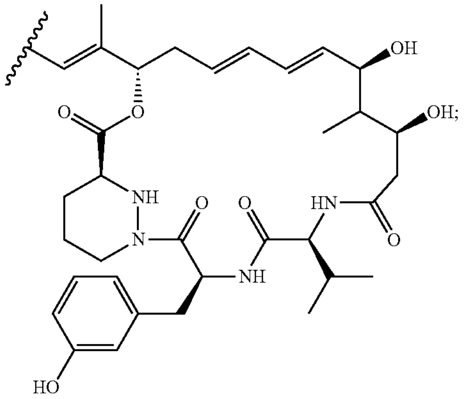
or an analog thereof.
In embodiments, the immunophilin-binding moiety is
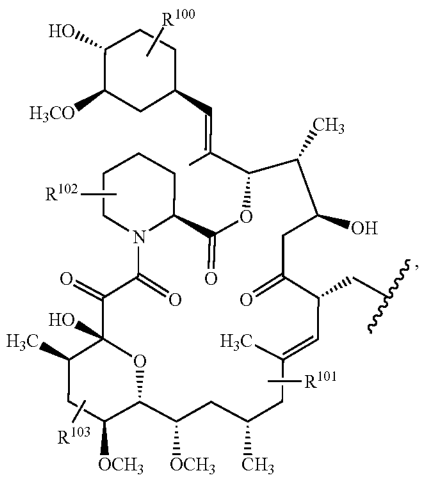
-continued
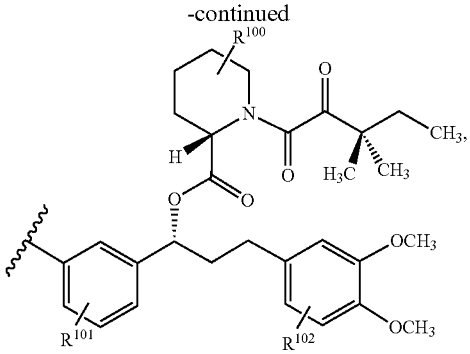
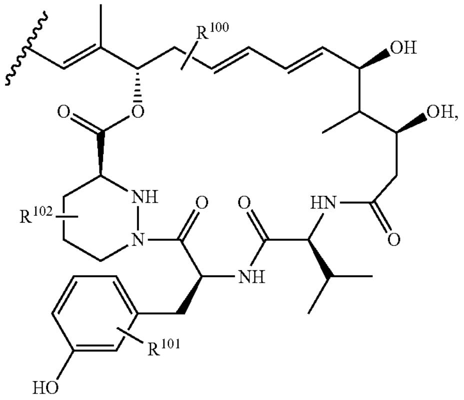
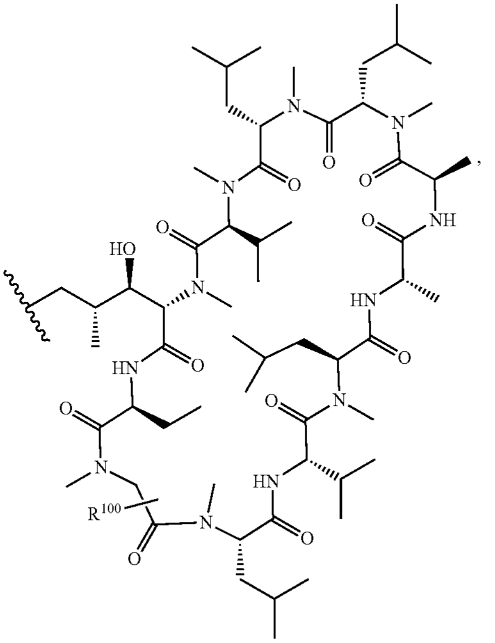
or -continued

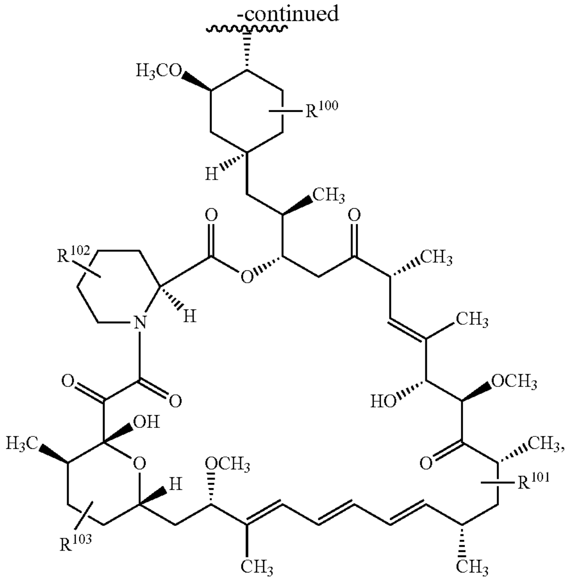

wherein $R^{100}$, $R^{101}$, $R^{102}$, and $R^{103}$ are as described herein and may be bonded to any atom in the ring ($R^{100}$, $R^{101}$, $R^{102}$, and $R^{103}$ are floating substituents). In embodiments, the immunophilin-binding moiety is

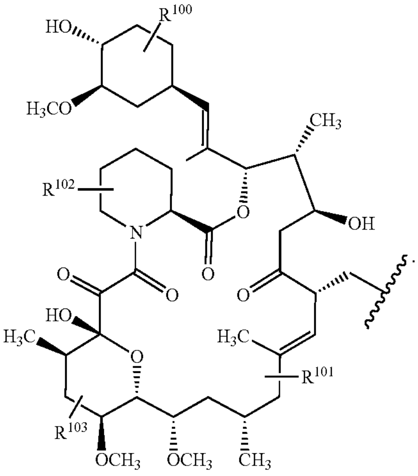

$R^{100}$, $R^{101}$, $R^{102}$, and $R^{103}$ are as described herein. In embodiments, the immunophilin-binding moiety is

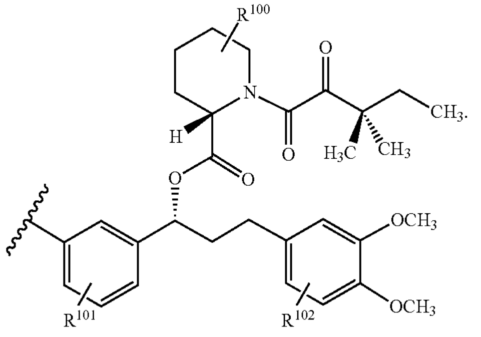

$R^{100}$, $R^{101}$, and $R^{102}$ are as described herein. In embodiments, the immunophilin-binding moiety is

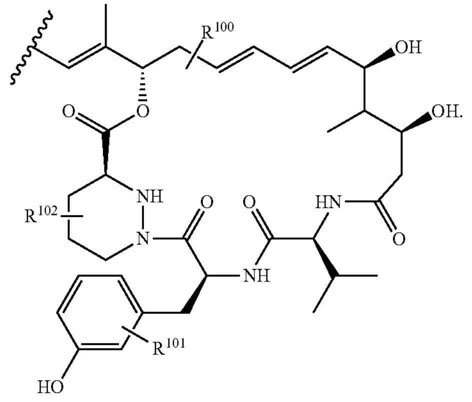

$R^{100}$, $R^{101}$, and $R^{102}$ are as described herein. In embodiments, the immunophilin-binding moiety is

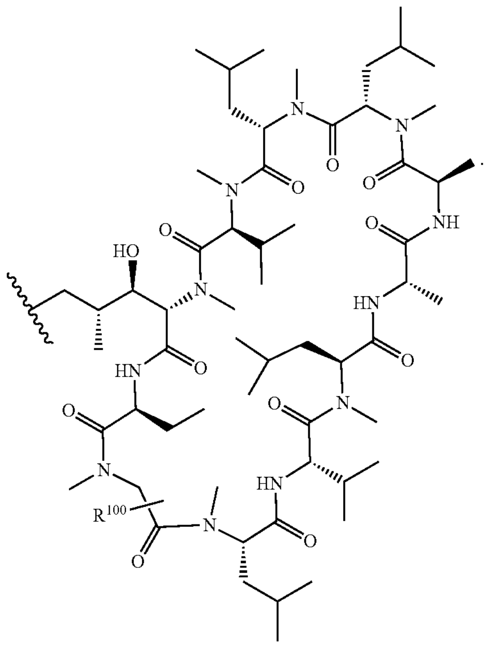

$R^{100}$ is as described herein. In embodiments, the immunophilin-binding moiety is

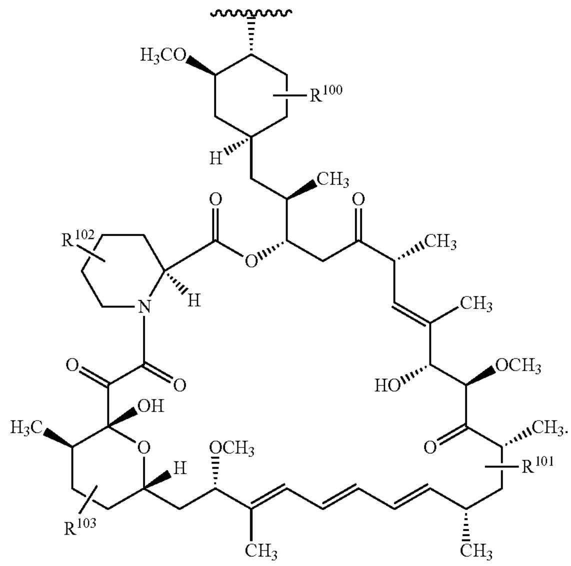

$R^{100}$, $R^{101}$, $R^{102}$, and $R^{103}$ are as described herein.

$R^{100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{100}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{100}$ is substituted with a plurality of groups selected from substituent groups, size-limited substituent groups, and lower substituent groups; each substituent group, size-limited substituent group, and/or lower substituent group may optionally be different. In embodiments, when $R^{100}$ is substituted, it is substituted with at least one substituent group. In embodiments, when $R^{100}$ is substituted, it is substituted with at least one size-limited substituent group. In embodiments, when $R^{100}$ is substituted, it is substituted with at least one lower substituent group.

In embodiments, $R^{100}$ is independently hydrogen. In embodiments, $R^{100}$ is independently halogen. In embodiments, $R^{100}$ is independently —$CCl_3$. In embodiments, $R^{100}$ is independently —$CBr_3$. In embodiments, $R^{100}$ is independently —$CF_3$. In embodiments, $R^{100}$ is independently —$CI_3$. In embodiments, $R^{100}$ is independently —$CH_2Cl$. In embodiments, $R^{100}$ is independently —$CH_2Br$. In embodiments, $R^{100}$ is independently —$CH_2F$. In embodiments, $R^{100}$ is independently —$CH_2I$. In embodiments, $R^{100}$ is independently —$CHCl_2$. In embodiments, $R^{100}$ is independently —$CHBr_2$. In embodiments, $R^{100}$ is independently —$CHF_2$. In embodiments, $R^{100}$ is independently —$CHI_2$. In embodiments, $R^{100}$ is independently —CN. In embodiments, $R^{100}$ is independently —OH. In embodiments, $R^{100}$ is independently —$NH_2$. In embodiments, $R^{100}$ is independently —COOH. In embodiments, $R^{100}$ is independently —$CONH_2$. In embodiments, $R^{100}$ is independently —$NO_2$. In embodiments, $R^{100}$ is independently —SH. In embodiments, $R^{100}$ is independently —$SO_3H$. In embodiments, $R^{100}$ is independently —$SO_4H$. In embodiments, $R^{100}$ is independently —$SO_2NH_2$. In embodiments, $R^{100}$ is independently —$NHNH_2$. In embodiments, $R^{100}$ is independently —$ONH_2$. In embodiments, $R^{100}$ is independently —NHC(O)$NHNH_2$. In embodiments, $R^{100}$ is independently —NHC(O)$NH_2$. In embodiments, $R^{100}$ is independently —$NHSO_2H$. In embodiments, $R^{100}$ is independently —NHC(O)H. In embodiments, $R^{100}$ is independently —NHC(O)OH. In embodiments, $R^{100}$ is independently —NHC(NH)H. In embodiments, $R^{100}$ is independently —NHC(NH)$NH_2$. In embodiments, $R^{100}$ is independently —NHOH. In embodiments, $R^{100}$ is independently —$OCCl_3$. In embodiments, $R^{100}$ is independently —$OCBr_3$. In embodiments, $R^{100}$ is independently —$OCF_3$. In embodiments, $R^{100}$ is independently —$OCI_3$. In embodiments, $R^{100}$ is independently —$OCH_2Cl$. In embodiments, $R^{100}$ is independently —$OCH_2Br$. In embodiments, $R^{100}$ is independently —$OCH_2F$. In embodiments, $R^{100}$ is independently —$OCH_2I$. In embodiments, $R^{100}$ is independently —$OCHCl_2$. In embodiments, $R^{100}$ is independently —$OCHBr_2$. In embodiments, $R^{100}$ is independently —$OCHF_2$. In embodiments, $R^{100}$ is independently —$OCHI_2$. In embodiments, $R^{100}$ is independently —$N_3$. In embodiments, $R^{100}$ is independently substituted or unsubstituted alkyl (e.g., $C_1$-$C_8$, $C_1$-$C_6$, $C_1$-$C_4$, or $C_1$-$C_2$). In embodiments, $R^{100}$ is independently substituted alkyl (e.g., $C_1$-$C_8$, $C_1$-$C_6$, $C_1$-$C_4$, or $C_1$-$C_2$). In embodiments, $R^{100}$ is independently unsubstituted alkyl (e.g., $C_1$-$C_8$, $C_1$-$C_6$, $C_1$-$C_4$, or $C_1$-$C_2$). In embodiments, $R^{100}$ is independently substituted or unsubstituted heteroalkyl (e.g., 2 to 8 membered, 2 to 6 membered, 4 to 6 membered, 2 to 3 membered, or 4 to 5 membered). In embodiments, $R^{100}$ is independently substituted heteroalkyl (e.g., 2 to 8 membered, 2 to 6 membered, 4 to 6 membered, 2 to 3 membered, or 4 to 5 membered). In embodiments, $R^{100}$ is independently unsubstituted heteroalkyl (e.g., 2 to 8 membered, 2 to 6 membered, 4 to 6 membered, 2 to 3 membered, or 4 to 5 membered). In embodiments, $R^{100}$ is independently substituted or unsubstituted cycloalkyl (e.g., $C_3$-$C_8$, $C_3$-$C_6$, $C_4$-$C_6$, or $C_5$-$C_6$). In embodiments, $R^{100}$ is independently substituted cycloalkyl (e.g., $C_3$-$C_8$, $C_3$-$C_6$, $C_4$-$C_6$, or $C_5$-$C_6$). In embodiments, $R^{100}$ is independently unsubstituted cycloalkyl (e.g., $C_3$-$C_8$, $C_3$-$C_6$, $C_4$-$C_6$, or $C_5$-$C_6$). In embodiments, $R^{100}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{100}$ is independently substituted heterocycloalkyl (e.g., 3 to 8 membered, 3 to 6 membered, 4 to 6 membered, 4 to 5 membered, or 5 to 6 membered). In embodiments, $R^{100}$ is independently unsubstituted heterocycloalkyl (e.g., 3 to 8 membered, 3 to 6 membered, 4 to 6 membered, 4 to 5 membered, or 5 to 6 membered). In embodiments, $R^{100}$ is independently substituted or unsubstituted aryl (e.g., $C_6$-$C_{10}$ or phenyl). In embodiments, $R^{100}$ is independently substituted aryl (e.g., $C_6$-$C_{10}$ or phenyl). In embodiments, $R^{100}$ is independently unsubstituted aryl (e.g., $C_6$-$C_{10}$ or phenyl). In embodiments, $R^{100}$ is independently substituted or unsubstituted heteroaryl (e.g., 5 to 10 membered, 5 to 9 membered, or 5 to 6 membered). In embodiments, $R^{100}$ is independently substituted heteroaryl (e.g., 5 to 10 membered, 5 to 9 membered, or 5 to 6 membered). In embodiments, $R^{100}$ is independently unsubstituted heteroaryl (e.g., 5 to 10 membered, 5 to 9 membered, or 5 to 6 membered).

$R^{101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{101}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{101}$ is substituted with a plurality of groups selected from substituent groups, size-limited substituent groups, and lower substituent groups; each substituent group, size-limited substituent group, and/or lower substituent group may optionally be different. In embodiments, when $R^{101}$ is substituted, it is substituted with at least one substituent group. In embodiments, when $R^{101}$ is substituted, it is substituted with at least one size-limited substituent group. In embodiments, when $R^{101}$ is substituted, it is substituted with at least one lower substituent group.

In embodiments, $R^{101}$ is independently hydrogen. In embodiments, $R^{101}$ is independently halogen. In embodiments, $R^{101}$ is independently —$CCl_3$. In embodiments, $R^{101}$ is independently —$CBr_3$. In embodiments, $R^{101}$ is independently —$CF_3$. In embodiments, $R^{101}$ is independently —$CI_3$. In embodiments, $R^{101}$ is independently —$CH_2Cl$. In embodiments, $R^{101}$ is independently —$CH_2Br$. In embodiments, $R^{101}$ is independently —$CH_2F$. In embodiments, $R^{101}$ is independently —$CH_2I$. In embodiments, $R^{101}$ is independently —$CHCl_2$. In embodiments, $R^{101}$ is independently —$CHBr_2$. In embodiments, $R^{101}$ is independently —$CHF_2$. In embodiments, $R^{101}$ is independently —$CHI_2$. In embodiments, $R^{101}$ is independently —CN. In embodiments, $R^{101}$ is independently —OH. In embodiments, $R^{101}$ is independently —$NH_2$. In embodiments, $R^{101}$ is independently —COOH. In embodiments, $R^{101}$ is independently —$CONH_2$. In embodiments, $R^{101}$ is independently —$NO_2$. In embodiments, $R^{101}$ is independently —SH. In embodiments, $R^{101}$ is independently —$SO_3H$. In embodiments, $R^{101}$ is independently —$SO_4H$. In embodiments, $R^{101}$ is independently —$SO_2NH_2$. In embodiments, $R^{101}$ is independently —$NHNH_2$. In embodiments, $R^{101}$ is independently —$ONH_2$. In embodiments, $R^{101}$ is independently —NHC(O)$NHNH_2$. In embodiments, $R^{101}$ is independently —NHC(O)$NH_2$. In embodiments, $R^{101}$ is independently —$NHSO_2H$. In embodiments, $R^{101}$ is independently —NHC (O)H. In embodiments, $R^{101}$ is independently —NHC(O)

OH. In embodiments, $R^{101}$ is independently —NHC(NH)H. In embodiments, $R^{101}$ is independently —NHC(NH)$NH_2$. In embodiments, $R^{101}$ is independently —NHOH. In embodiments, $R^{101}$ is independently —$OCCl_3$. In embodiments, $R^{101}$ is independently —$OCBr_3$. In embodiments, $R^{101}$ is independently —$OCF_3$. In embodiments, $R^{101}$ is independently —$OCI_3$. In embodiments, $R^{101}$ is independently —$OCH_2Cl$. In embodiments, $R^{101}$ is independently —$OCH_2Br$. In embodiments, $R^{101}$ is independently —$OCH_2F$. In embodiments, $R^{101}$ is independently —$OCH_2I$. In embodiments, $R^{101}$ is independently —$OCHCl_2$. In embodiments, $R^{101}$ is independently —$OCHBr_2$. In embodiments, $R^{101}$ is independently —$OCHF_2$. In embodiments, $R^{101}$ is independently —$OCHI_2$. In embodiments, $R^{101}$ is independently —$N_3$. In embodiments, $R^{101}$ is independently substituted or unsubstituted alkyl (e.g., $C_1$-$C_8$, $C_1$-$C_6$, $C_1$-$C_4$, or $C_1$-$C_2$). In embodiments, $R^{101}$ is independently substituted alkyl (e.g., $C_1$-$C_8$, $C_1$-$C_6$, $C_1$-$C_4$, or $C_1$-$C_2$). In embodiments, $R^{101}$ is independently unsubstituted alkyl (e.g., $C_1$-$C_8$, $C_1$-$C_6$, $C_1$-$C_4$, or $C_1$-$C_2$). In embodiments, $R^{101}$ is independently substituted or unsubstituted heteroalkyl (e.g., 2 to 8 membered, 2 to 6 membered, 4 to 6 membered, 2 to 3 membered, or 4 to 5 membered). In embodiments, $R^{101}$ is independently substituted heteroalkyl (e.g., 2 to 8 membered, 2 to 6 membered, 4 to 6 membered, 2 to 3 membered, or 4 to 5 membered). In embodiments, $R^{101}$ is independently unsubstituted heteroalkyl (e.g., 2 to 8 membered, 2 to 6 membered, 4 to 6 membered, 2 to 3 membered, or 4 to 5 membered). In embodiments, $R^{101}$ is independently substituted or unsubstituted cycloalkyl (e.g., $C_3$-$C_8$, $C_3$-$C_6$, $C_4$-$C_6$, or $C_5$-$C_6$). In embodiments, $R^{101}$ is independently substituted cycloalkyl (e.g., $C_3$-$C_8$, $C_3$-$C_6$, $C_4$-$C_6$, or $C_5$-$C_6$). In embodiments, $R^{101}$ is independently unsubstituted cycloalkyl (e.g., $C_3$-$C_8$, $C_3$-$C_6$, $C_4$-$C_6$, or $C_5$-$C_6$). In embodiments, $R^{101}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{101}$ is independently substituted heterocycloalkyl (e.g., 3 to 8 membered, 3 to 6 membered, 4 to 6 membered, 4 to 5 membered, or 5 to 6 membered). In embodiments, $R^{101}$ is independently unsubstituted heterocycloalkyl (e.g., 3 to 8 membered, 3 to 6 membered, 4 to 6 membered, 4 to 5 membered, or 5 to 6 membered). In embodiments, $R^{101}$ is independently substituted or unsubstituted aryl (e.g., $C_6$-$C_{10}$ or phenyl). In embodiments, $R^{101}$ is independently substituted aryl (e.g., $C_6$-$C_{10}$ or phenyl). In embodiments, $R^{101}$ is independently unsubstituted aryl (e.g., $C_6$-$C_{10}$ or phenyl). In embodiments, $R^{101}$ is independently substituted or unsubstituted heteroaryl (e.g., 5 to 10 membered, 5 to 9 membered, or 5 to 6 membered). In embodiments, $R^{101}$ is independently substituted heteroaryl (e.g., 5 to 10 membered, 5 to 9 membered, or 5 to 6 membered). In embodiments, $R^{101}$ is independently unsubstituted heteroaryl (e.g., 5 to 10 membered, 5 to 9 membered, or 5 to 6 membered).

$R^{102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102}$ is substituted with a plurality of groups selected from substituent groups, size-limited substituent groups, and lower substituent groups; each substituent group, size-limited substituent group, and/or lower substituent group may optionally be different. In embodiments, when $R^{102}$ is substituted, it is substituted with at least one substituent group. In embodiments, when $R^{102}$ is substituted, it is substituted with at least one size-limited substituent group. In embodiments, when $R^{102}$ is substituted, it is substituted with at least one lower substituent group.

In embodiments, $R^{102}$ is independently hydrogen. In embodiments, $R^{102}$ is independently halogen. In embodiments, $R^{102}$ is independently —$CCl_3$. In embodiments, $R^{102}$ is independently —$CBr_3$. In embodiments, $R^{102}$ is independently —$CF_3$. In embodiments, $R^{102}$ is independently —$CI_3$. In embodiments, $R^{102}$ is independently —$CH_2Cl$. In embodiments, $R^{102}$ is independently —$CH_2Br$. In embodiments, $R^{102}$ is independently —$CH_2F$. In embodiments, $R^{102}$ is independently —$CH_2I$. In embodiments, $R^{102}$ is independently —$CHCl_2$. In embodiments, $R^{102}$ is independently —$CHBr_2$. In embodiments, $R^{102}$ is independently —$CHF_2$. In embodiments, $R^{102}$ is independently —$CHI_2$. In embodiments, $R^{102}$ is independently —CN. In embodiments, $R^{102}$ is independently —OH. In embodiments, $R^{102}$ is independently —$NH_2$. In embodiments, $R^{102}$ is independently —COOH. In embodiments, $R^{102}$ is independently —$CONH_2$. In embodiments, $R^{102}$ is independently —$NO_2$. In embodiments, $R^{102}$ is independently —SH. In embodiments, $R^{102}$ is independently —$SO_3H$. In embodiments, $R^{102}$ is independently —$SO_4H$. In embodiments, $R^{102}$ is independently —$SO_2NH_2$. In embodiments, $R^{102}$ is independently —$NHNH_2$. In embodiments, $R^{102}$ is independently —$ONH_2$. In embodiments, $R^{102}$ is independently —$NHC(O)NHNH_2$. In embodiments, $R^{102}$ is independently —$NHC(O)NH_2$. In embodiments, $R^{102}$ is independently —$NHSO_2H$. In embodiments, $R^{102}$ is independently —NHC(O)H. In embodiments, $R^{102}$ is independently —NHC(O)OH. In embodiments, $R^{102}$ is independently —NHC(NH)H. In embodiments, $R^{102}$ is independently —$NHC(NH)NH_2$. In embodiments, $R^{102}$ is independently —NHOH. In embodiments, $R^{102}$ is independently —$OCCl_3$. In embodiments, $R^{102}$ is independently —$OCBr_3$. In embodiments, $R^{102}$ is independently —$OCF_3$. In embodiments, $R^{102}$ is independently —$OCI_3$. In embodiments, $R^{102}$ is independently —$OCH_2Cl$. In embodiments, $R^{102}$ is independently —$OCH_2Br$. In embodiments, $R^{102}$ is independently —$OCH_2F$. In embodiments, $R^{102}$ is independently —$OCH_2I$. In embodiments, $R^{102}$ is independently —$OCHCl_2$. In embodiments, $R^{102}$ is independently —$OCHBr_2$. In embodiments, $R^{102}$ is independently —$OCHF_2$. In embodiments, $R^{102}$ is independently —$OCHI_2$. In embodiments, $R^{12}$ is independently —$N_3$. In embodiments, $R^{102}$ is independently substituted or unsubstituted alkyl (e.g., $C_1$-$C_8$, $C_1$-$C_6$, $C_1$-$C_4$, or $C_1$-$C_2$). In embodiments, $R^{102}$ is independently substituted alkyl (e.g., $C_1$-$C_8$, $C_1$-$C_6$, $C_1$-$C_4$, or $C_1$-$C_2$). In embodiments, $R^{102}$ is independently unsubstituted alkyl (e.g., $C_1$-$C_8$, $C_1$-$C_6$, $C_1$-$C_4$, or $C_1$-$C_2$). In embodiments, $R^{102}$ is independently substituted or unsubstituted heteroalkyl (e.g., 2 to 8 membered, 2 to 6 membered, 4 to 6 membered, 2 to 3 membered, or 4 to 5 membered). In embodiments, $R^{102}$ is independently substituted heteroalkyl (e.g., 2 to 8 membered, 2 to 6 membered, 4 to 6 membered, 2 to 3 membered, or 4 to 5 membered). In embodiments, $R^{102}$ is independently unsubstituted heteroalkyl (e.g., 2 to 8 membered, 2 to 6 membered, 4 to 6 membered, 2 to 3 membered, or 4 to 5 membered). In embodiments, $R^{102}$ is independently substituted or unsubstituted cycloalkyl (e.g., $C_3$-$C_8$, $C_3$-$C_6$, $C_4$-$C_6$, or $C_5$-$C_6$). In embodiments, $R^{102}$ is independently substituted cycloalkyl (e.g., $C_3$-$C_8$, $C_3$-$C_6$, $C_4$-$C_6$, or $C_5$-$C_6$). In embodiments, $R^{102}$ is independently unsubstituted cycloalkyl (e.g., $C_3$-$C_8$, $C_3$-$C_6$, $C_4$-$C_6$, or $C_5$-$C_6$). In embodiments, $R^{102}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{102}$ is independently substituted heterocycloalkyl (e.g., 3 to 8 membered, 3 to 6 membered, 4 to 6 membered, 4 to 5 membered, or 5 to 6 membered). In embodiments, $R^{102}$ is independently unsubstituted heterocycloalkyl (e.g., 3 to 8 membered, 3 to 6 membered, 4 to 6 membered, 4 to 5 membered, or 5 to 6 membered). In embodiments, $R^{102}$ is independently substituted or unsubstituted aryl (e.g., $C_6$-$C_{10}$ or phenyl). In embodiments, $R^{102}$ is independently substituted aryl (e.g., $C_6$-$C_{10}$ or phenyl). In embodiments, $R^{102}$ is independently unsubstituted aryl (e.g., $C_6$-$C_{10}$ or phenyl). In embodiments, $R^{102}$ is independently substituted or unsubstituted heteroaryl (e.g., 5 to 10 membered, 5 to 9 membered, or 5 to 6 membered). In embodiments, $R^{102}$ is independently substituted heteroaryl (e.g., 5 to 10 membered, 5 to 9 membered, or 5 to 6 membered). In embodiments, $R^{102}$ is independently unsubstituted heteroaryl (e.g., 5 to 10 membered, 5 to 9 membered, or 5 to 6 membered).

$R^{103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{103}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{103}$ is substituted with a plurality of groups selected from substituent groups, size-limited substituent groups, and lower substituent groups; each substituent group, size-limited substituent group, and/or lower substituent group may optionally be different. In embodiments, when $R^{103}$ is substituted, it is substituted with at least one substituent group. In embodiments, when $R^{103}$ is substituted, it is substituted with at least one size-limited substituent group. In embodiments, when $R^{103}$ is substituted, it is substituted with at least one lower substituent group.

In embodiments, $R^{103}$ is independently hydrogen. In embodiments, $R^{103}$ is independently halogen. In embodiments, $R^{103}$ is independently —$CCl_3$. In embodiments, $R^{103}$ is independently —$CBr_3$. In embodiments, $R^{103}$ is independently —$CF_3$. In embodiments, $R^{103}$ is independently —$CI_3$. In embodiments, $R^{103}$ is independently —$CH_2Cl$. In embodiments, $R^{103}$ is independently —$CH_2Br$. In embodiments, $R^{103}$ is independently —$CH_2F$. In embodiments, $R^{103}$ is independently —$CH_2I$. In embodiments, $R^{103}$ is independently —$CHCl_2$. In embodiments, $R^{103}$ is independently —$CHBr_2$. In embodiments, $R^{103}$ is independently —$CHF_2$. In embodiments, $R^{103}$ is independently —$CHI_2$. In embodiments, $R^{103}$ is independently —CN. In embodiments, $R^{103}$ is independently —OH. In embodiments, $R^{103}$ is independently —$NH_2$. In embodiments, $R^{103}$ is independently —COOH. In embodiments, $R^{103}$ is independently —$CONH_2$. In embodiments, $R^{103}$ is independently —$NO_2$. In embodiments, $R^{103}$ is independently —SH. In embodiments, $R^{103}$ is independently —$SO_3H$. In embodiments, $R^{103}$ is independently —$SO_4H$. In embodiments, $R^{103}$ is independently —$SO_2NH_2$. In embodiments, $R^{103}$ is independently —$NHNH_2$. In embodiments, $R^{103}$ is independently —$ONH_2$. In embodiments, $R^{103}$ is independently —$NHC(O)NHNH_2$. In embodiments, $R^{103}$ is independently —$NHC(O)NH_2$. In embodiments, $R^{103}$ is independently —$NHSO_2H$. In embodiments, $R^{103}$ is independently —NHC(O)H. In embodiments, $R^{103}$ is independently —NHC(O)OH. In embodiments, $R^{103}$ is independently —NHC(NH)H. In embodiments, $R^{103}$ is independently —$NHC(NH)NH_2$. In embodiments, $R^{103}$ is independently —NHOH. In embodiments, $R^{103}$ is independently —$OCCl_3$. In embodiments, $R^{103}$ is independently —$OCBr_3$. In embodiments, $R^{103}$ is independently —$OCF_3$. In embodiments, $R^{103}$ is independently —$OCI_3$. In embodiments, $R^{103}$ is independently —$OCH_2Cl$. In embodiments, $R^{103}$ is independently —$OCH_2Br$. In embodiments, $R^{103}$ is independently —$OCH_2F$. In embodiments, $R^{103}$ is independently —$OCH_2I$. In embodiments, $R^{103}$ is independently —$OCHCl_2$. In embodiments, $R^{103}$ is independently —$OCHBr_2$. In embodiments, $R^{103}$ is independently —$OCHF_2$. In embodiments, $R^{103}$ is independently —$OCHI_2$. In embodiments, $R^{103}$ is independently —$N_3$. In embodiments, $R^{103}$ is independently substituted or unsubstituted alkyl (e.g., $C_1$-$C_8$, $C_1$-$C_6$, $C_1$-$C_4$, or $C_1$-$C_2$). In embodiments, $R^{103}$ is independently substituted alkyl (e.g., $C_1$-$C_8$, $C_1$-$C_6$, $C_1$-$C_4$, or $C_1$-$C_2$). In embodiments, $R^{103}$ is independently unsubstituted alkyl (e.g., $C_1$-$C_8$, $C_1$-$C_6$, $C_1$-$C_4$, or $C_1$-$C_2$). In embodiments, $R^{103}$ is independently substituted or unsubstituted heteroalkyl (e.g., 2 to 8 membered, 2 to 6 membered, 4 to 6 membered, 2 to 3 membered, or 4 to 5 membered). In embodiments, $R^{103}$ is independently substituted heteroalkyl (e.g., 2 to 8 membered, 2 to 6 membered, 4 to 6 membered, 2 to 3 membered, or 4 to 5 membered). In embodiments, $R^{103}$ is independently unsubstituted heteroalkyl (e.g., 2 to 8 membered, 2 to 6 membered, 4 to 6 membered, 2 to 3 membered, or 4 to 5 membered). In embodiments, $R^{103}$ is independently substituted or unsubstituted cycloalkyl (e.g., $C_3$-$C_8$, $C_3$-$C_6$, $C_4$-$C_6$, or $C_5$-$C_6$). In embodiments, $R^{103}$ is independently substituted cycloalkyl (e.g., $C_3$-$C_8$, $C_3$-$C_6$, $C_4$-$C_6$, or $C_5$-$C_6$). In embodiments, $R^{103}$ is independently unsubstituted cycloalkyl (e.g., $C_3$-$C_8$, $C_3$-$C_6$, $C_4$-$C_6$, or $C_5$-$C_6$). In embodiments, $R^{103}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{103}$ is independently substituted heterocycloalkyl (e.g., 3 to 8 membered, 3 to 6 membered, 4 to 6 membered, 4 to 5 membered, or 5 to 6 membered). In embodiments, $R^{103}$ is independently unsubstituted heterocycloalkyl (e.g., 3 to 8 membered, 3 to 6 membered, 4 to 6 membered, 4 to 5 membered, or 5 to 6 membered). In embodiments, $R^{103}$ is independently substituted or unsubstituted aryl (e.g., $C_6$-$C_{10}$ or phenyl). In embodiments, $R^{103}$ is independently substituted aryl (e.g., $C_6$-$C_{10}$ or phenyl). In embodiments, $R^{103}$ is independently unsubstituted aryl (e.g., $C_6$-$C_{10}$ or phenyl). In embodiments, $R^{103}$ is independently substituted or unsubstituted heteroaryl (e.g., 5 to 10 membered, 5 to 9 membered, or 5 to 6 membered). In embodiments, $R^{103}$ is independently substituted heteroaryl (e.g., 5 to 10 membered, 5 to 9 membered, or 5 to 6 membered). In embodiments, $R^{103}$ is independently unsubstituted heteroaryl (e.g., 5 to 10 membered, 5 to 9 membered, or 5 to 6 membered).

In embodiments, $L^1$ is $L^2$-$L^3$-$L^4$-$L^5$-$L^6$.

$L^2$ is connected directly to the moiety of an immunophilin-binding compound.

$L^2$ is a bond, —$S(O)_2$—, —$N(R^2)$—, —O—, —S—, —C(O)—, —$C(O)N(R^2)$—, —$N(R^2)C(O)$—, —$N(R^2)C(O)NH$—, —NHC(O) $N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —NHC(O) $N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —NHC(O) $N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —NHC(O) $N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —NHC(O) $N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$R^2$, $R^3$, $R^4$, $R^5$, and $R^6$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^2$ is —$S(O)_2$—, —$N(R^2)$—, —O—, —S—, —C(O)—, —C(O)$N(R^2)$—, —$N(R^2)$C(O)—, —$N(R^2)$C(O)NH—, —NHC(O)$N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^2$ is a bond, —$S(O)_2$—, —$N(R^2)$—, —O—, —S—, —C(O)—, —C(O)$N(R^2)$—, —$N(R^2)$C(O)—, —$N(R^2)$C(O)NH—, —NHC(O) $N(R^2)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^2$ is —$S(O)_2$—, —$N(R^2)$—, —O—, —S—, —C(O)—, —C(O)$N(R^2)$—, —$N(R^2)$C(O)—, —$N(R^2)$C(O)NH—, —NHC(O)$N(R^2)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^2$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^2$ is substituted with a plurality of groups selected from substituent groups, size-limited substituent groups, and lower substituent groups; each substituent group, size-limited substituent group, and/or lower substituent group may optionally be different. In embodiments, when $L^2$ is substituted, it is substituted with at least one substituent group. In embodiments, when $L^2$ is substituted, it is substituted with at least one size-limited substituent group. In embodiments, when $L^2$ is substituted, it is substituted with at least one lower substituent group.

In embodiments, $L^2$ is —$S(O)_2$—, —$N(R^{26})$—, —O—, —S—, —C(O)—, —C(O)$N(R^{26})$—, —$N(R^{26})$C(O)—, —$N(R^{26})$C(O)NH—, —NHC(O)$N(R^{26})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^2$ is —$S(O)_2$—, —$N(R^{26})$—, —O—, —S—, —C(O)—, —C(O)$N(R^{26})$—, —$N(R^{26})$C(O)—, —$N(R^{26})$C(O)NH—, —NHC(O)$N(R^{26})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^3$ is a bond, —$S(O)_2$—, —$N(R^3)$—, —O—, —S—, —C(O)—, —C(O)$N(R^3)$—, —$N(R^3)$C(O)—, —$N(R^3)$C(O)NH—, —NHC(O) $N(R^3)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^3$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^3$ is substituted with a plurality of groups selected from substituent groups, size-limited substituent groups, and lower substituent groups; each substituent group, size-limited substituent group, and/or lower substituent group may optionally be different. In embodiments, when $L^3$ is substituted, it is substituted with at least one substituent group. In embodiments, when $L^3$ is substituted, it is substituted with at least one size-limited substituent group. In embodiments, when $L^3$ is substituted, it is substituted with at least one lower substituent group.

In embodiments, $L^3$ is a bond, —$S(O)_2$—, —$N(R^{29})$—, —O—, —S—, —C(O)—, —$C(O)N(R^{29})$—, —$N(R^{29})C(O)$—, —$N(R^{29})C(O)NH$—, —$NHC(O)N(R^{29})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^3$ is a bond, —$S(O)_2$—, —$N(R^{29})$—, —O—, —S—, —C(O)—, —$C(O)N(R^{29})$—, —$N(R^{29})C(O)$—, —$N(R^{29})C(O)NH$—, —$NHC(O)N(R^{29})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —NHC(O) $N(R^4)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^4$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^4$ is substituted with a plurality of groups selected from substituent groups, size-limited substituent groups, and lower substituent groups; each substituent group, size-limited substituent group, and/or lower substituent group may optionally be different. In embodiments, when $L^4$ is substituted, it is substituted with at least one substituent group. In embodiments, when $L^4$ is substituted, it is substituted with at least one size-limited substituent group. In embodiments, when $L^4$ is substituted, it is substituted with at least one lower substituent group.

In embodiments, $L^4$ is a bond, —$S(O)_2$—, —$N(R^{32})$—, —O—, —S—, —C(O)—, —$C(O)N(R^{32})$—, —$N(R^{32})C(O)$—, —$N(R^{32})C(O)NH$—, —$NHC(O)N(R^{32})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^4$ is a bond, —$S(O)_2$—, —$N(R^{32})$—, —O—, —S—, —C(O)—, —$C(O)N(R^{32})$—, —$N(R^{32})C(O)$—, —$N(R^{32})C(O)NH$—, —$NHC(O)N(R^{32})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^5$ is a bond, —S(O)$_2$—, —N($R^5$)—, —O—, —S—, —C(O)—, —C(O)N($R^5$)—, —N($R^5$)C (O)—, —N($R^5$)C(O)NH—, —NHC(O) N($R^5$)—, —C(O) O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^5$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^5$ is substituted with a plurality of groups selected from substituent groups, size-limited substituent groups, and lower substituent groups; each substituent group, size-limited substituent group, and/or lower substituent group may optionally be different. In embodiments, when $L^5$ is substituted, it is substituted with at least one substituent group. In embodiments, when $L^5$ is substituted, it is substituted with at least one size-limited substituent group. In embodiments, when $L^5$ is substituted, it is substituted with at least one lower substituent group.

In embodiments, $L^5$ is a bond, —S(O)$_2$—, —N($R^{35}$)—, —O—, —S—, —C(O)—, —C(O)N($R^{35}$)—, —N($R^{35}$)C (O)—, —N($R^{35}$)C(O)NH—, —NHC(O)N($R^{35}$)—, —C(O) O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^5$ is a bond, —S(O)$_2$—, —N($R^{35}$)—, —O—, —S—, —C(O)—, —C(O)N($R^{35}$)—, —N($R^{35}$)C (O)—, —N($R^{35}$)C(O)NH—, —NHC(O)N($R^{35}$)—, —C(O) O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^6$ is a bond, —S(O)$_2$—, —N($R^6$)—, —O—, —S—, —C(O)—, —C(O)N($R^6$)—, —N($R^6$)C (O)—, —N($R^6$)C(O)NH—, —NHC(O) N($R^6$)—, —C(O) O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^6$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^6$ is substituted with a plurality of groups selected from substituent groups, size-limited substituent groups, and lower substituent groups; each substituent group, size-limited substituent group, and/or lower substituent group may optionally be different. In embodiments, when $L^6$ is substituted, it is substituted with at least one substituent group. In embodiments, when $L^6$ is substituted, it is substituted with at least one size-limited substituent group. In embodiments, when $L^6$ is substituted, it is substituted with at least one lower substituent group.

In embodiments, $L^6$ is a bond, —S(O)$_2$—, —N($R^{38}$)—, —O—, —S—, —C(O)—, —C(O)N($R^{38}$)—, —N($R^{38}$)C (O)—, —N($R^{38}$)C(O)NH—, —NHC(O)N($R^{38}$)—, —C(O) O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^6$ is a bond, —$S(O)_2$—, —$N(R^{38})$—, —O—, —S—, —C(O)—, —$C(O)N(R^{38})$—, —$N(R^{38})C(O)$—, —$N(R^{38})C(O)NH$—, —$NHC(O)N(R^{38})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —NHC(O) $N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —NHC(O) $N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —NHC(O) $N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —NHC(O) $N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^3$, $L^4$, $L^5$, and $L^6$ are a bond.

In embodiments, $L^2$ is a substituted or unsubstituted alkylene, substituted or unsubstituted heteroalkylene, substituted or unsubstituted cycloalkylene, or substituted or unsubstituted heterocycloalkylene; $L^3$ is a bond, substituted or unsubstituted alkylene, substituted or unsubstituted heteroalkylene, substituted or unsubstituted cycloalkylene, or substituted or unsubstituted heterocycloalkylene; $L^4$ is a bond, substituted or unsubstituted alkylene, or substituted or unsubstituted heteroalkylene; $L^5$ is a bond; and $L^6$ is a bond.

In embodiments, $L^2$ is a substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^3$ is a bond, substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^4$ is a bond, substituted or unsubstituted alkylene, substituted or unsubstituted heteroalkylene, or bioconjugate linker.

In embodiments, $L^5$ is a bond.

In embodiments, $L^6$ is a bond.

In embodiments, $L^2$ is a substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^3$ is a bond, substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^4$ is a bond, substituted or unsubstituted alkylene, substituted or unsubstituted heteroalkylene, or bioconjugate linker.

In embodiments, $L^2$ is a substituted or unsubstituted alkylene, substituted or unsubstituted heteroalkylene, substituted or unsubstituted cycloalkylene, or substituted or unsubstituted heterocycloalkylene.

In embodiments, $L^3$ is a bond, substituted or unsubstituted alkylene, substituted or unsubstituted heteroalkylene, substituted or unsubstituted cycloalkylene, or substituted or unsubstituted heterocycloalkylene.

In embodiments, $L^4$ is a bond, substituted or unsubstituted alkylene, or substituted or unsubstituted heteroalkylene.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or a bioconjugate linker; $L^3$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, an unsubstituted 5 to 6 membered heterocycloalkylene, or a bioconjugate linker; $L^4$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or a bioconjugate linker; $L^5$ is a bond; and $L^6$ is a bond.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, or an oxo-substituted 3 to 17 membered heteroalkylene; $L^3$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or an unsubstituted 5 to 6 membered heterocycloalkylene; $L^4$ is a bond, an unsubstituted $C_3$-$C_7$ alkylene, an oxo-substituted $C_3$-$C_{10}$ alkylene, an unsubstituted 3 to 17 membered heteroalkylene, or an oxo-substituted 3 to 17 membered heteroalkylene; $L^5$ is a bond; and $L^6$ is a bond.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or a bioconjugate linker.

In embodiments, $L^3$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, an unsubstituted 5 to 6 membered heterocycloalkylene, or a bioconjugate linker.

In embodiments, $L^4$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or a bioconjugate linker.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, or an oxo-substituted 3 to 17 membered heteroalkylene.

In embodiments, $L^3$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or an unsubstituted 5 to 6 membered heterocycloalkylene.

In embodiments, $L^4$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

In embodiments, $L^1$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene; or a bioconjugate linker.

In embodiments, $L^1$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

In embodiments, $L^1$ is

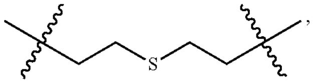

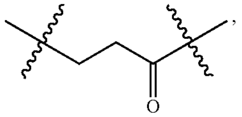

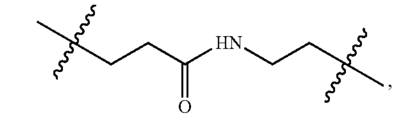

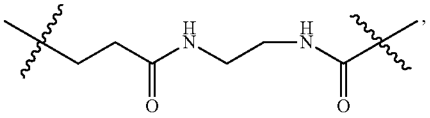

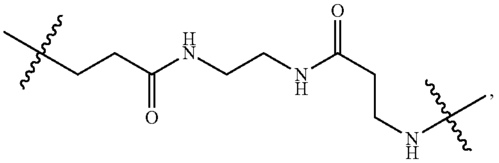

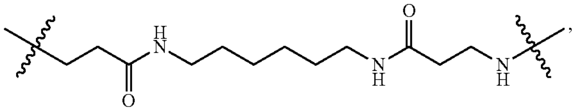

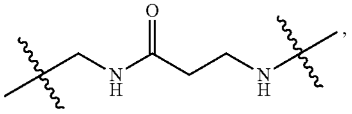

-continued

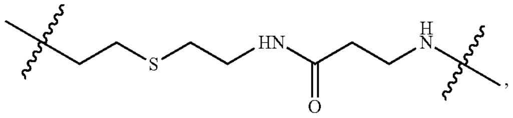

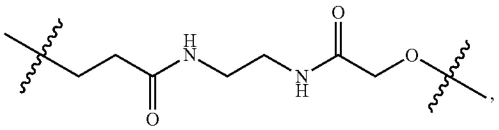

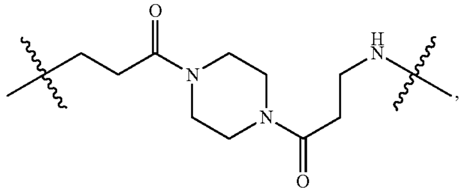

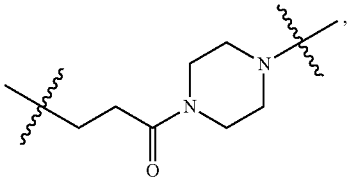

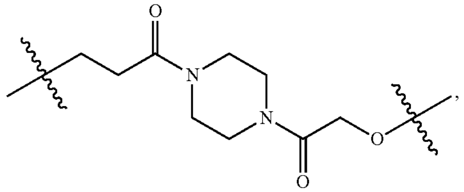

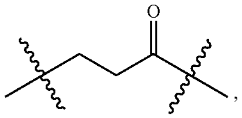

or

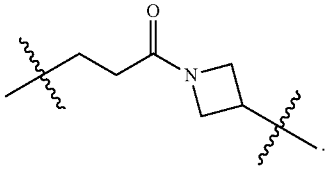

In embodiments, $L^1$ is a bond. In embodiments, $L^1$ is a substituted or unsubstituted alkylene or substituted or unsubstituted heteroalkylene.

In embodiments, $L^1$ is

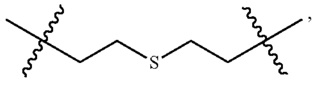

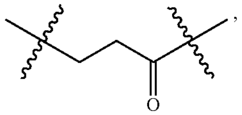

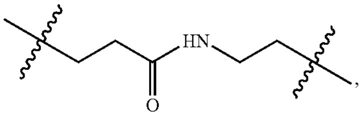

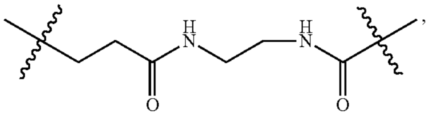

-continued

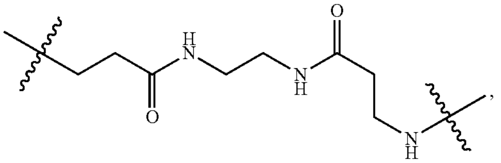

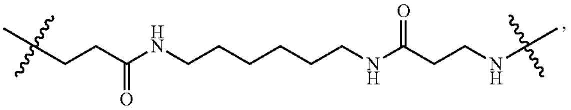

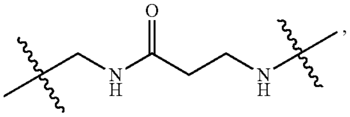

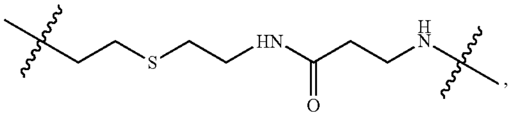

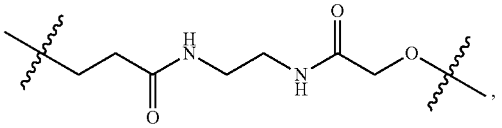

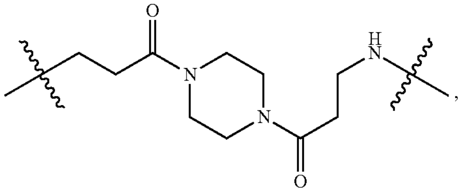

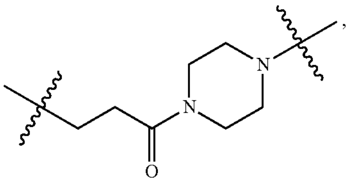

or

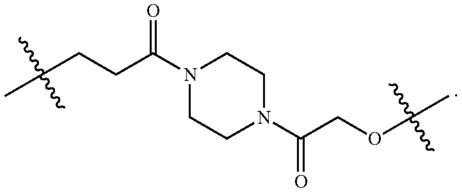

In embodiments, $L^1$ is a bond. In embodiments, $L^1$ is a substituted or unsubstituted alkylene or substituted or unsubstituted heteroalkylene.

In embodiments, $R^1$ is a monovalent kinase inhibitor, a monovalent pseudokinase inhibitor, a monovalent GTPase inhibitor, or a monovalent histone-modifying enzyme inhibitor.

In embodiments, $R^1$ is a monovalent kinase inhibitor.

In embodiments, the kinase is not mTOR.

In embodiments, the monovalent kinase inhibitor is a monovalent Src kinase inhibitor.

In embodiments, the monovalent Src kinase inhibitor is a monovalent dasatinib or monovalent dasatinib derivative.

In embodiments, the monovalent dasatinib derivative has the formula:

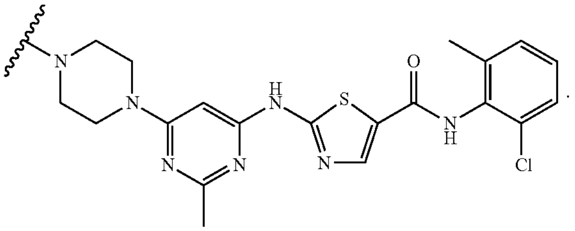 [SMILES: *N1CCN(c2cc(Nc3ncc(C(=O)Nc4c(C)cccc4Cl)s3)nc(C)n2)CC1]

In embodiments, the monovalent kinase inhibitor is a monovalent Raf inhibitor, VEGFR inhibitor, PDGFR inhibitor, or c-Kit inhibitor.

In embodiments, the monovalent Raf inhibitor, VEGFR inhibitor, PDGFR inhibitor, or c-Kit inhibitor is a monovalent sorafenib or monovalent sorafenib derivative.

In embodiments, the monovalent sorafenib derivative has the formula:

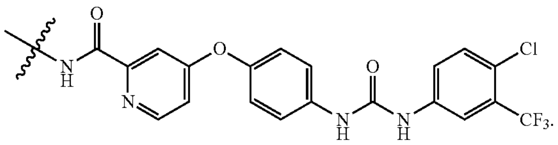 [SMILES: *NC(=O)c1cc(Oc2ccc(NC(=O)Nc3ccc(Cl)c(C(F)(F)F)c3)cc2)ccn1]

In embodiments, the monovalent kinase inhibitor is a monovalent EGFR inhibitor.

In embodiments, the monovalent EGFR inhibitor is a monovalent lapatinib, monovalent lapatinib derivative, monovalent erlotinib, monovalent erlotinib derivative, monovalent gefitinib, or monovalent gefitinib derivative.

In embodiments, the monovalent EGFR inhibitor has the formula:

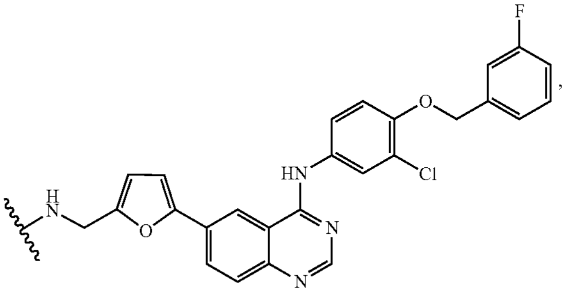

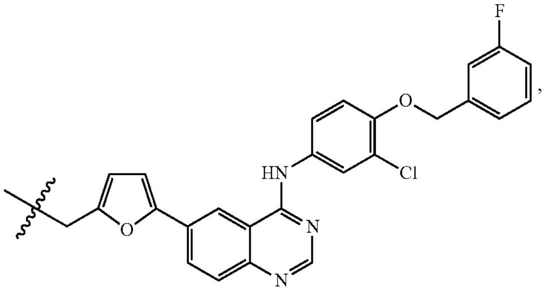

-continued

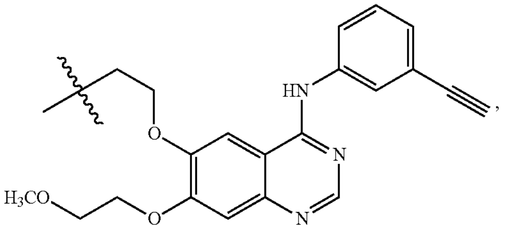

or

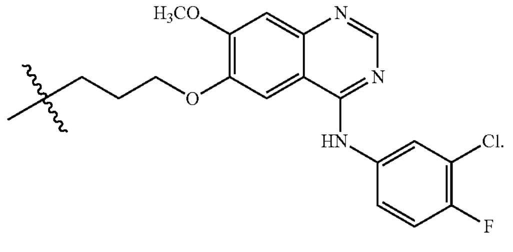

In embodiments, the monovalent kinase inhibitor is a monovalent LRRK2 inhibitor.

In embodiments, the monovalent LRRK2 inhibitor is a monovalent GNE-7915 or monovalent GNE-7915 derivative.

In embodiments, the monovalent GNE-7915 derivative has the formula:

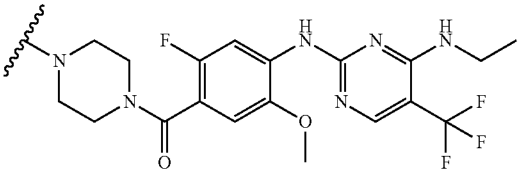

or

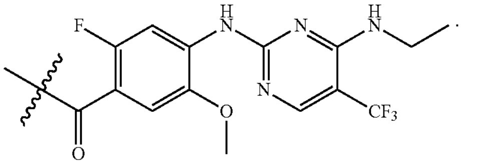

In embodiments, $R^1$ is a monovalent KRAS inhibitor.

In embodiments, the monovalent KRAS inhibitor is a monovalent KRAS G12C inhibitor or a monovalent KRAS M72C inhibitor. In embodiments, the monovalent KRAS inhibitor is a monovalent KRAS G12C inhibitor. In embodiments, the monovalent KRAS inhibitor has the formula:

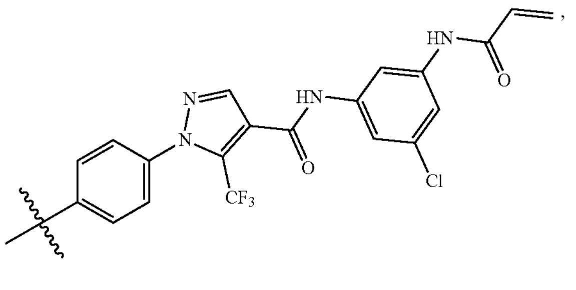

-continued

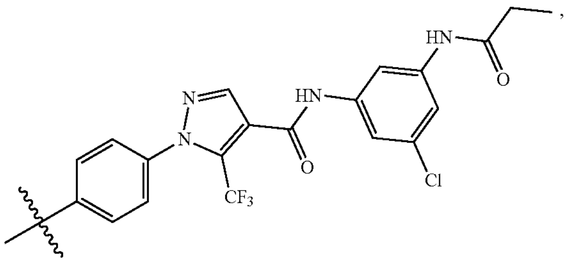

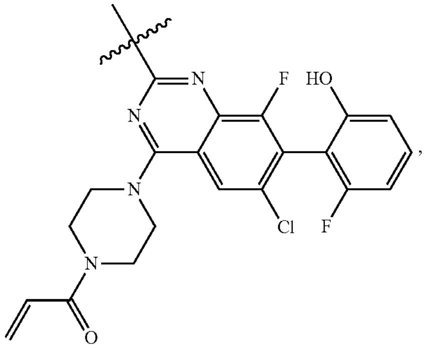

or

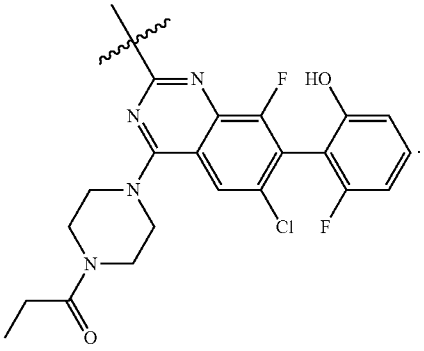

In embodiments, $R^1$ is a monovalent PI4K inhibitor.

In embodiments, the monovalent PI4K inhibitor has the formula:

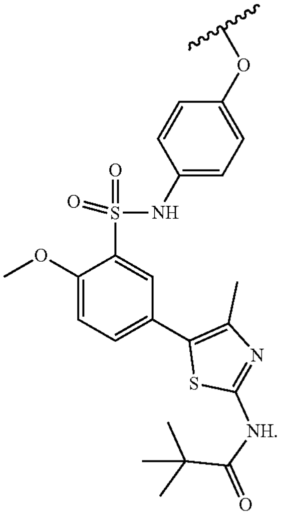 [SMILES: *Oc1ccc(NS(=O)(=O)c2cc(-c3sc(NC(=O)C(C)(C)C)nc3C)ccc2OC)cc1]

In embodiments, the monovalent PI4K inhibitor has the formula:

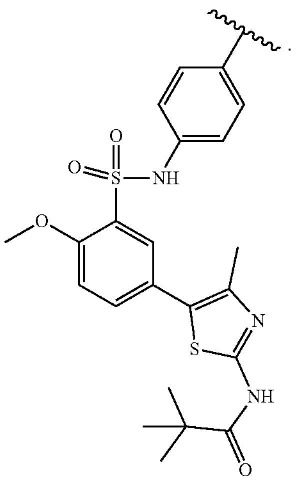 [SMILES: *c1ccc(NS(=O)(=O)c2cc(-c3sc(NC(=O)C(C)(C)C)nc3C)ccc2OC)cc1]

In embodiments, the monovalent PI4K inhibitor has the formula:

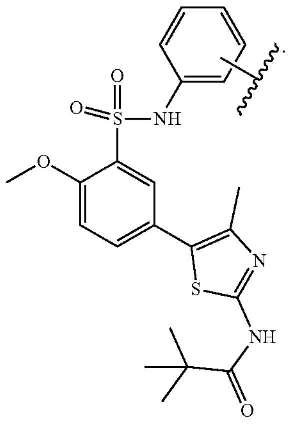

In embodiments, the monovalent PI4K inhibitor has the formula:

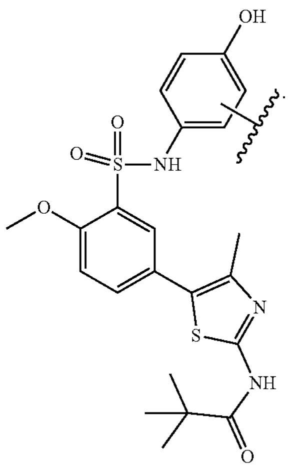

In embodiments, the monovalent PI4K inhibitor has the formula:

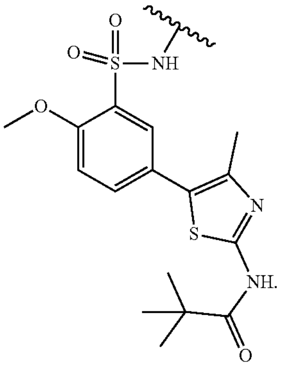 [SMILES: *NS(=O)(=O)c1cc(-c2sc(NC(=O)C(C)(C)C)nc2C)ccc1OC]

In embodiments, the monovalent PI4K inhibitor has the formula:

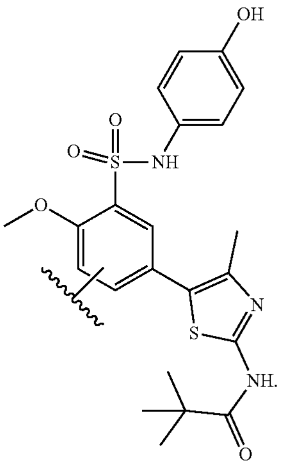

In embodiments, the monovalent kinase inhibitor is a monovalent MAP4K inhibitor. In embodiments, the monovalent MAP4K inhibitor is a monovalent HGK inhibitor. In embodiments, the monovalent HGK inhibitor has the formula:

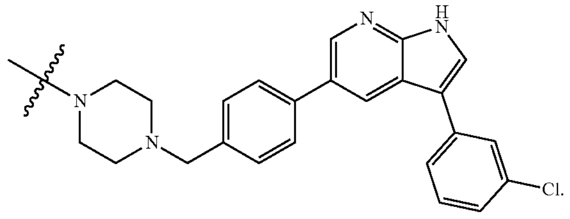 [SMILES: *N1CCN(Cc2ccc(-c3cnc4[nH]cc(-c5cccc(Cl)c5)c4c3)cc2)CC1]

In embodiments, the monovalent kinase inhibitor is a monovalent MAP3K inhibitor. In embodiments, the monovalent MAP3K inhibitor is a monovalent DLK inhibitor. In embodiments, the monovalent DLK inhibitor has the formula:

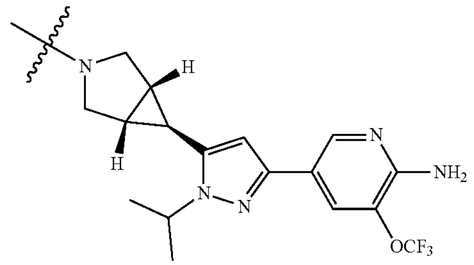

or

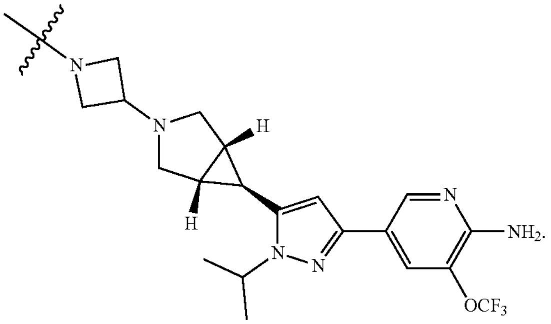

In embodiments, the monovalent DLK inhibitor has the formula

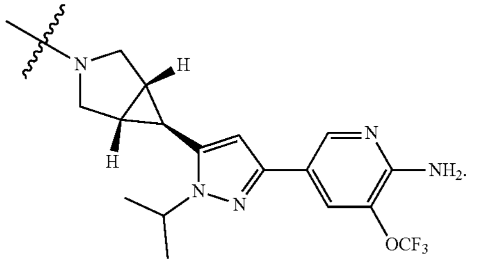 [SMILES: *N1C[C@@H]2[C@H](C1)[C@H]2c1cc(-c2cnc(N)c(OC(F)(F)F)c2)nn1C(C)C]

In embodiments, the monovalent DLK inhibitor has the formula

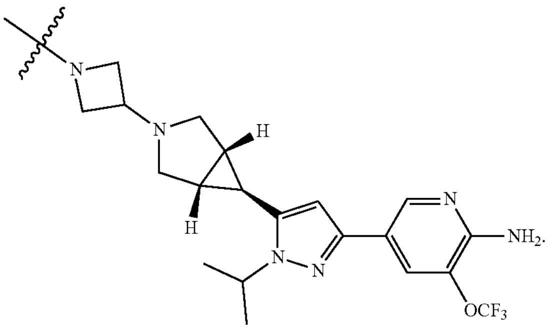 [SMILES: *N1CC(N2C[C@@H]3[C@H](C2)[C@H]3c2cc(-c3cnc(N)c(OC(F)(F)F)c3)nn2C(C)C)C1]

In embodiments, the compound is not a calcineurin inhibitor.

In one aspect is provided a pharmaceutical composition including a pharmaceutically acceptable excipient and a compound as provided herein, including embodiments thereof.

In embodiments, the covalent linker is at least or about 1.5 Å in length (e.g., at least or about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Å in length). In embodiments, the covalent linker is at least or about the length of 1 methylene groups (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is at least or about the length of 5 methylene groups (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is at least or about the length of 11 methylene groups (e.g., at least or about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is at least or about the length of 27 methylene groups (e.g., 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is from about 5 to 54 Å in length. In embodiments, the covalent linker is from about 6 to 54 Å in length. In embodiments, the covalent linker is from about 7 to 54 Å in length. In embodiments, the covalent linker is from about 9 to 54 Å in length. In embodiments, the covalent linker is from about 11 to 54 Å in length. In embodiments, the covalent linker is from about 13 to 54 Å in length. In embodiments, the covalent linker is from about 15 to 54 Å in length. In embodiments, the covalent linker is from about 20 to 54 Å in length. In embodiments, the covalent linker is from about 24 to 54 Å in length. In embodiments, the covalent linker is from about 28 to 54 Å in length. In embodiments, the covalent linker is from about 5 to 50 Å in length. In embodiments, the covalent linker is from about 5 to 46 Å in length. In embodiments, the covalent linker is from about 5 to 42 Å in length. In embodiments, the covalent linker is from about 5 to 38 Å in length. In embodiments, the covalent linker is from about 5 to 34 Å in length. In embodiments, the covalent linker is from about 5 to 30 Å in length. In embodiments, the covalent linker is from about 5 to 26 Å in length. In embodiments, the covalent linker is from about 5 to 22 Å in length. In embodiments, the covalent linker is from about 5 to 39 Å in length. In embodiments, the covalent linker is from about 7 to 37 Å in length. In embodiments, the covalent linker is from about 9 to 35 Å in length. In embodiments, the covalent linker is from about 11 to 33 Å in length. In embodiments, the covalent linker is from about 13 to 31 Å in length. In embodiments, the covalent linker is from about 15 to 29 Å in length. In embodiments, the covalent linker is from about 15 to 25 Å in length. In embodiments, the covalent linker is from about 15 to 23 Å in length. In embodiments, the covalent linker is at least or about 32 Å in length (e.g., at least or about 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Ain length). In embodiments, the covalent linker is at least or about the length of 27 methylene groups.

In embodiments, the covalent linker is from about 32 to 54 Å in length. In embodiments, the covalent linker is from about 33 to 53 Å in length. In embodiments, the covalent linker is from about 34 to 52 Å in length. In embodiments, the covalent linker is from about 35 to 51 Å in length. In embodiments, the covalent linker is from about 36 to 50 Å in length. In embodiments, the covalent linker is from about 37 to 49 Å in length. In embodiments, the covalent linker is from about 38 to 48 Å in length. In embodiments, the covalent linker is from about 39 to 47 Å in length. In embodiments, the covalent linker is from about 40 to 46 Å in length. In embodiments, the covalent linker is from about 41 to 45 Å in length. In embodiments, the covalent linker is from about 42 to 44 Å in length. In embodiments, the covalent linker is from about 32 to 52 Å in length. In embodiments, the covalent linker is from about 32 to 50 Å in length. In embodiments, the covalent linker is from about 32 to 48 Å in length. In embodiments, the covalent linker is from about 32 to 46 Å in length. In embodiments, the covalent linker is from about 32 to 44 Å in length. In embodiments, the covalent linker is from about 32 to 42 Å in length. In embodiments, the covalent linker is from about 32 to 40 Å in length. In embodiments, the covalent linker is from about 32 to 38 Å in length. In embodiments, the covalent linker is from about 32 to 36 Å in length. In embodiments, the covalent linker is from about 34 to 54 Å in length. In embodiments, the covalent linker is from about 36 to 54 Å in length. In embodiments, the covalent linker is from about 38 to 54 Å in length. In embodiments, the covalent linker is from about 40 to 54 Å in length. In embodiments, the covalent linker is from about 42 to 54 Å in length. In embodiments, the covalent linker is from about 44 to 54 Å in length. In embodiments, the covalent linker is from about 46 to 54 Å in length. In embodiments, the covalent linker is from about 48 to 54 Å in length. In embodiments, the covalent linker is from about 50 to 54 Å in length.

The specified length of a linker is the through space distance between the ends of the linker (i.e., the ends or termini that are connected to the two parts of the molecule connected by the linker) wherein the length of the linker is measured when the linker is fully extended and wherein the linker termini are the furthest apart they may naturally exist in solution (i.e., the longest distance between the ends of the linker wherein the linker adopts allowable conformations, bond lengths, and bond angles following the principles of Chemistry), (e.g., without adopting non-natural bond lengths, non-allowed or non-preferred bond angles, or high energy non-preferred or non-natural interactions of different components of the linker). In embodiments, the linker length is measured when included in a compound as described herein (e.g., aspect, embodiment, example, figures, table, claim). It will be understood that a linker may adopt a through space distance that is less than the fully extended conformation used to define the linker length.

In embodiments, the linker is a hydrolysable linker (e.g., in solution). In embodiments, the linker is a non-hydrolysable linker (e.g., in solution). In embodiments, the linker may be cleaved by an enzyme (e.g., hydrolase, protease, cytochrome). In embodiments, the linker is not cleavable by an enzyme (e.g., under normal cellular conditions). In embodiments, the linker is a polyethylene glycol linker. In embodiments, the linker is hydrophilic. In embodiments, the linker is hydrophobic. In embodiments, the linker includes a disulfide bond. In embodiments, the linker includes a hydrazone bond. In embodiments, the linker includes an ester. In embodiments, the linker includes a sulfonyl. In embodiments, the linker includes a thioether. In embodiments, the linker includes a phosphinate. In embodiments, the linker includes an alkyloxime bond. In embodiments, the linker includes one or more amino acids. In embodiments, the linker consists of amino acids. In embodiments, the linker includes an amino acid analog. In embodiments, the linker includes an amino acid mimetic. In embodiments, the linker is a linker known in the art for use in linking antibodies to agents (e.g., antibody drug conjugates). In embodiments, the linker is a linker as described in Bioconjugate Techniques (Second Edition) by Greg T. Hermanson (2008), which is herein incorporated by reference in its entirety for all purposes. In embodiments, the linker is a linker as described in Flygare J A, Pillow T H, Aristoff P., Antibody-drug conjugates for the treatment of cancer. Chemical Biology and Drug Design. 2013 January; 81(1):113-21, which is herein incorporated by reference in its entirety for all purposes. In embodiments, the linker is a linker as described in Drachman J G, Senter P D., Antibody-drug conjugates: the chemistry behind empowering antibodies to fight cancer. Hematology Am Soc Hematol Educ Program. 2013; 2013:306-10, which is herein incorporated by reference in its entirety for all purposes.

In embodiments, the anti-CNS disease drug has the formula:

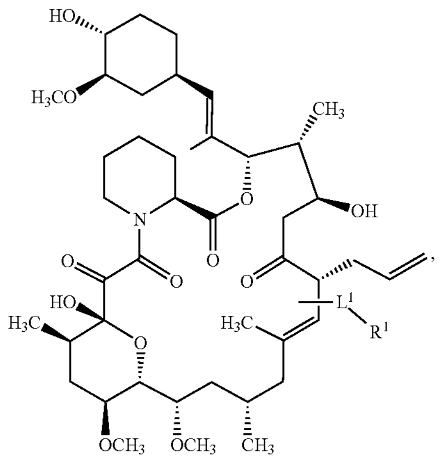

wherein $L^1$ is as described herein and may be bonded to any atom in the ring ($L^1$ is a floating substituent) and $R^1$ is as described herein.

In embodiments, the anti-CNS disease drug has the formula:

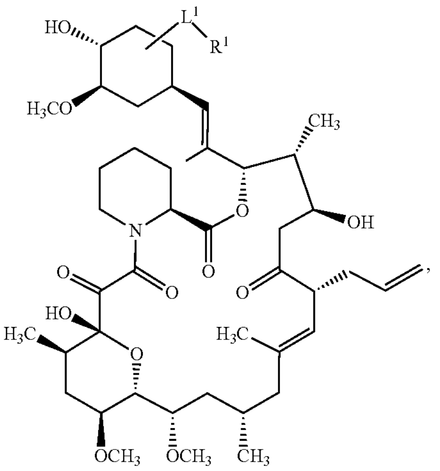

wherein $L^1$ is as described herein and may be bonded to any atom in the ring ($L^1$ is a floating substituent) and $R^1$ is as described herein.

In embodiments, the anti-CNS disease drug has the formula:

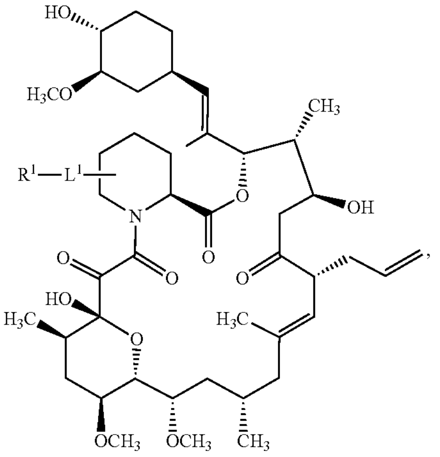

wherein $L^1$ is as described herein and may be bonded to any atom in the ring ($L^1$ is a floating substituent) and $R^1$ is as described herein.

In embodiments, the anti-CNS disease drug has the formula:

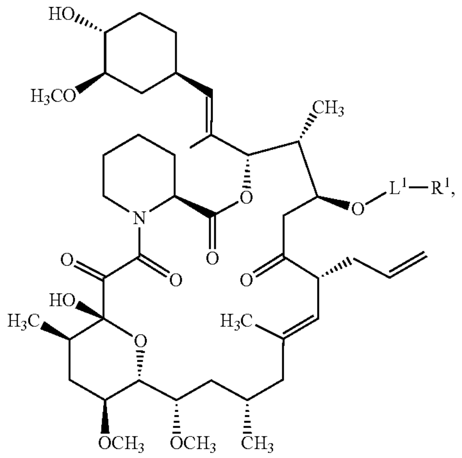

wherein $L^1$ is as described herein and $R^1$ is as described herein.

In embodiments, the anti-CNS disease drug has the formula:

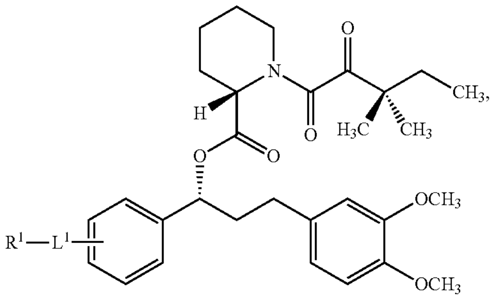

wherein $L^1$ is as described herein and may be bonded to any atom in the ring ($L^1$ is a floating substituent) and $R^1$ is as described herein.

In embodiments, the anti-CNS disease drug has the formula:

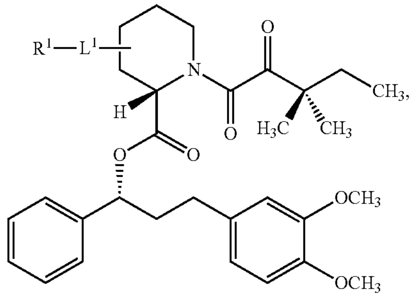

wherein $L^1$ is as described herein and may be bonded to any atom in the ring ($L^1$ is a floating substituent) and $R^1$ is as described herein.

In embodiments, the anti-CNS disease drug has the formula:

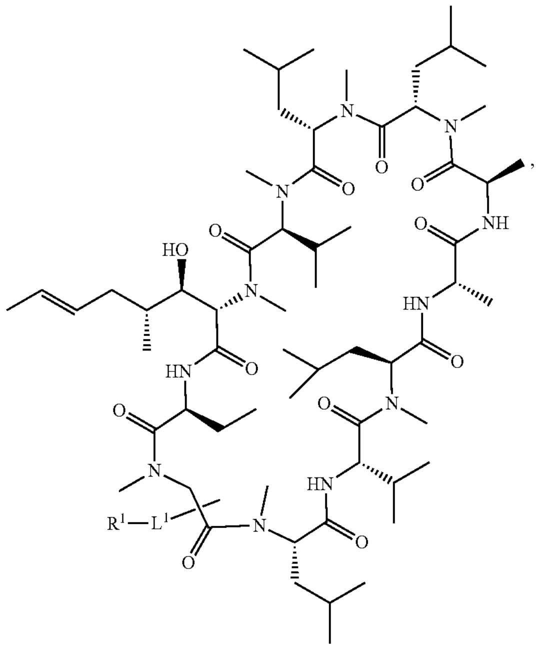

wherein $L^1$ is as described herein and may be bonded to any atom in the ring ($L^1$ is a floating substituent) and $R^1$ is as described herein.

In embodiments, the anti-CNS disease drug has the formula:

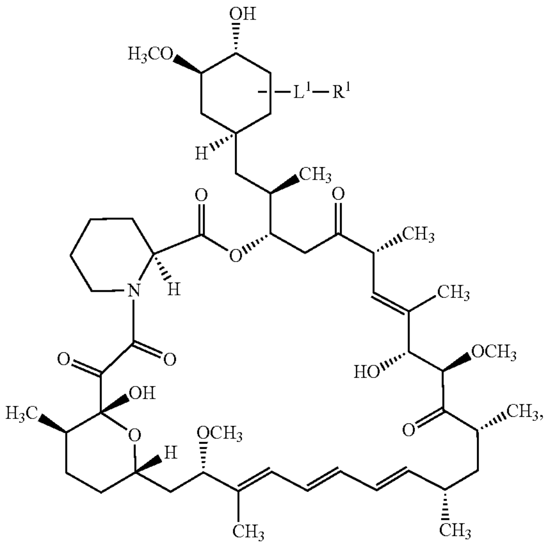

wherein $L^1$ is as described herein and may be bonded to any atom in the ring ($L^1$ is a floating substituent) and $R^1$ is as described herein.

In embodiments, the anti-CNS disease drug has the formula:

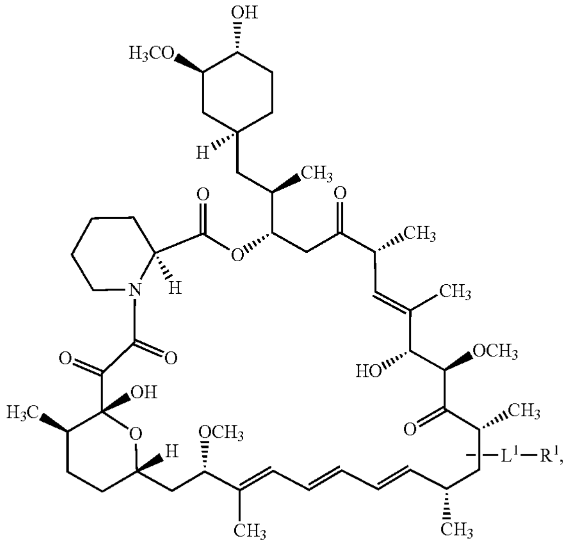

wherein $L^1$ is as described herein and may be bonded to any atom in the ring ($L^1$ is a floating substituent) and $R^1$ is as described herein.

In embodiments, the anti-CNS disease drug has the formula:

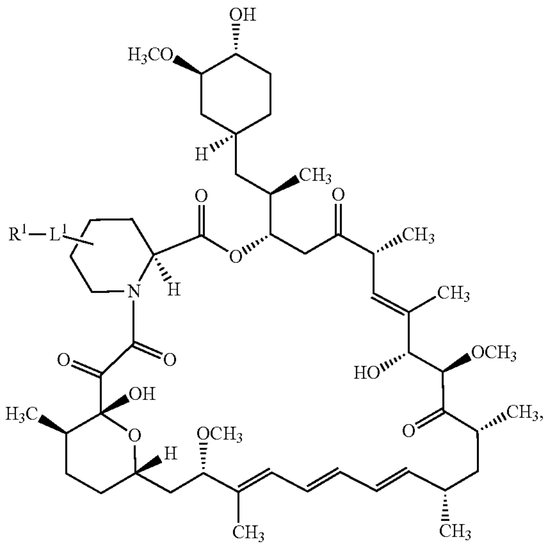

wherein $L^1$ is as described herein and may be bonded to any atom in the ring ($L^1$ is a floating substituent) and $R^1$ is as described herein.

In embodiments, the anti-CNS disease drug has the formula:

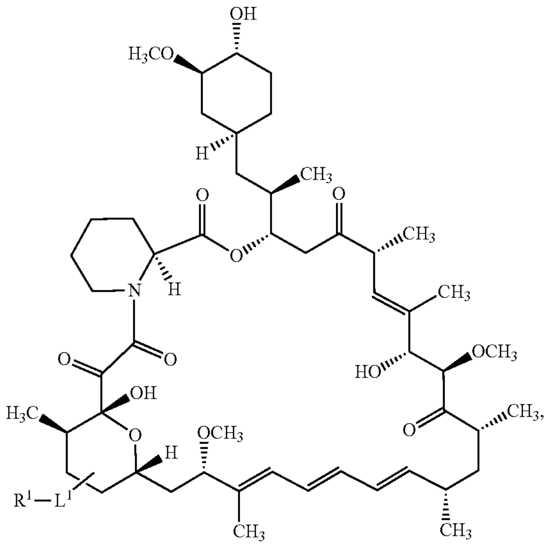

wherein $L^1$ is as described herein and may be bonded to any atom in the ring ($L^1$ is a floating substituent) and $R^1$ is as described herein.

In embodiments, the anti-CNS disease drug has the formula:

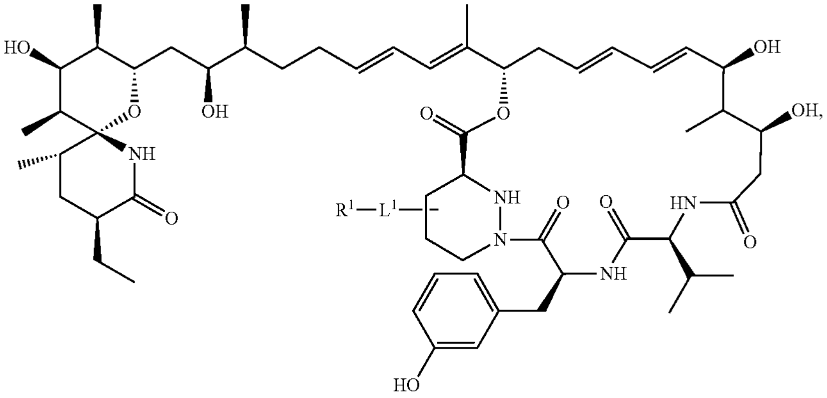

wherein $L^1$ is as described herein and may be bonded to any atom in the ring ($L^1$ is a floating substituent) and $R^1$ is as described herein.

In embodiments, the anti-CNS disease drug has the formula:

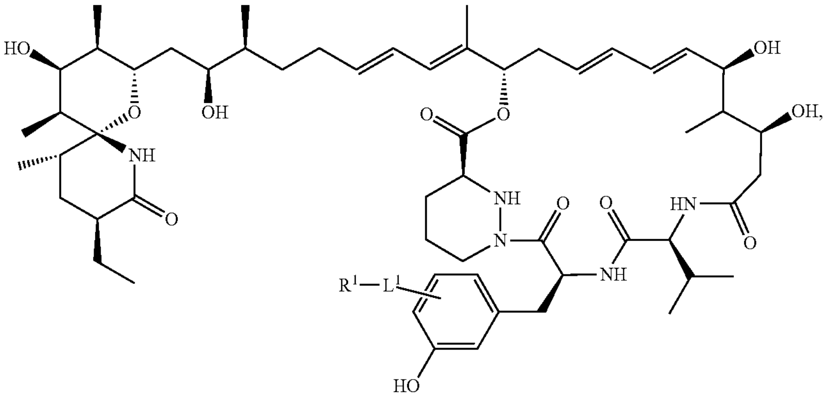

wherein $L^1$ is as described herein and may be bonded to any atom in the ring ($L^1$ is a floating substituent) and $R^1$ is as described herein.

In embodiments, the anti-CNS disease drug has the formula:

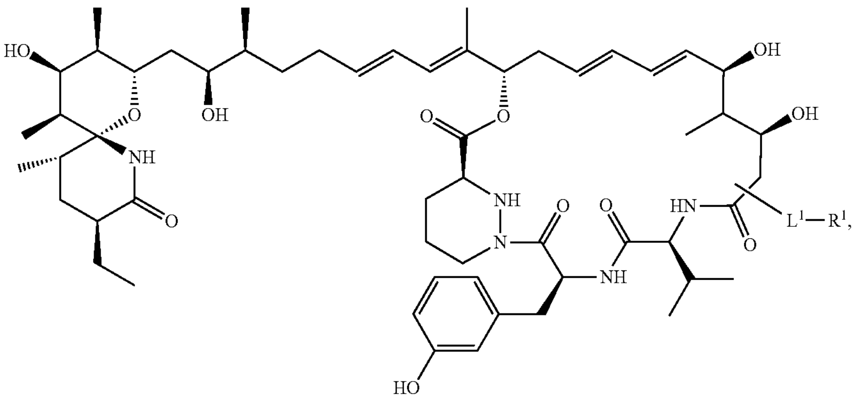

wherein $L^1$ is as described herein and may be bonded to any atom in the ring ($L^1$ is a floating substituent) and $R^1$ is as described herein.

In embodiments, $R^1$ is a kinase inhibitor moiety In embodiments, $R^1$ is a pseudokinase inhibitor moiety. In embodiments, $R^1$ is a GTPase inhibitor moiety. In embodiments, $R^1$ is a histone-modifying enzyme inhibitor moiety. In embodiments, $R^1$ is a monovalent anti-viral agent.

In embodiments, $R^1$ is a kinase inhibitor moiety. In embodiments, $R^1$ is a protein kinase inhibitor moiety, a lipid kinase inhibitor moiety, or a carbohydrate kinase inhibitor moiety. In embodiments, $R^1$ is a cyclin dependent kinase inhibitor moiety or a mitogen-activated protein kinase inhibitor moiety. In embodiments, $R^1$ is a phosphatidylinositol kinase inhibitor moiety or a sphingosine kinase inhibitor moiety. In embodiments, $R^1$ is a nucleoside-phosphate kinase inhibitor moiety or a nucleoside-diphosphate kinase inhibitor moiety. In embodiments, $R^1$ is a thymidine kinase inhibitor moiety or a riboflavin kinase inhibitor moiety.

In embodiments, $R^1$ is a protein kinase inhibitor moiety. In embodiments, $R^1$ is an AGC kinase inhibitor moiety, a CAM kinase inhibitor moiety, a CK1 kinase inhibitor moiety, a CMGC kinase inhibitor moiety, a STE kinase inhibitor moiety, a TK kinase inhibitor moiety or a TKL kinase inhibitor moiety. In embodiments, $R^1$ is PKA kinase inhibitor moiety, a PCK kinase inhibitor moiety, or a PKG kinase inhibitor moiety. In embodiments, $R^1$ is CDK kinase inhibitor moiety, a MAPK kinase inhibitor moiety, a GSK3 kinase inhibitor moiety, or a CLK kinase inhibitor moiety.

In embodiments, $R^1$ is a serine/threonine-specific protein kinase inhibitor moiety, a tyrosine-specific protein kinase inhibitor moiety, or a histidine-specific protein kinase inhibitor moiety.

In embodiments, $R^1$ is a serine/threonine-specific protein kinase inhibitor moiety. In embodiments, $R^1$ is a CK2 kinase inhibitor moiety, a protein kinase A inhibitor, a protein kinase C inhibitor, a Mos kinase inhibitor moiety, a Raf kinase inhibitor moiety, a mitogen-activated protein kinase (MAPK) inhibitor, a Ca2+/calmodulin-dependent (CaM) protein kinase inhibitor moiety, a phosphorylase kinase inhibitor moiety, a protein kinase B (AKT) inhibitor, or a leucine-rich repeat kinase (LRRK) inhibitor. In embodiments, $R^1$ is a Raf kinase inhibitor moiety. In embodiments, $R^1$ is a leucine-rich repeat kinase (LRRK) inhibitor.

In embodiments, $R^1$ is a MAP4K inhibitor moiety. In embodiments, $R^1$ is a MAP4K4 inhibitor moiety. In embodiments, $R^1$ is an HGK inhibitor moiety. In embodiments, $R^1$ is a MAP3K inhibitor moiety. In embodiments, $R^1$ is a MAP3K12 inhibitor moiety. In embodiments, $R^1$ is a DLK inhibitor moiety.

In embodiments, $R^1$ is a tyrosine-specific protein kinase inhibitor moiety. In embodiments, $R^1$ is a receptor tyrosine kinase inhibitor moiety or a non-receptor tyrosine kinase inhibitor moiety.

In embodiments, $R^1$ is a receptor tyrosine kinase inhibitor moiety. In embodiments, $R^1$ is a platelet-derived growth factor (PDGFR) kinase inhibitor moiety, an epidermal growth factor (EGFR) kinase inhibitor moiety, a HER2 kinase inhibitor moiety, an insulin receptor kinase inhibitor moiety, an insulin-like growth factor 1 (IGF1R) kinase inhibitor moiety, a vascular endothelial growth factor (VEGFR) inhibitor, a stem cell factor (SCF) kinase inhibitor moiety, a fibroblast growth factor (FGF) kinase inhibitor moiety, a colon carcinoma kinase 4 (CCK4) kinase inhibitor moiety, a NGF kinase inhibitor moiety, a c-KIT kinase inhibitor moiety, or a hepatocyte growth factor receptor (HGFR) kinase inhibitor moiety. In embodiments, $R^1$ is a platelet-derived growth factor (PDGFR) kinase inhibitor moiety. In embodiments, $R^1$ is an epidermal growth factor (EGFR) kinase inhibitor moiety. In embodiments, $R^1$ is a vascular endothelial growth factor (VEGFR) kinase inhibitor moiety. In embodiments, $R^1$ is a c-KIT kinase inhibitor moiety.

In embodiments, $R^1$ is a non-receptor tyrosine kinase inhibitor moiety. In embodiments, $R^1$ is an Abl kinase inhibitor moiety, an Ack kinase inhibitor moiety, a Csk kinase inhibitor moiety, a Fak kinase inhibitor moiety, a Fes kinase inhibitor moiety, a Frk kinase inhibitor moiety, a Jak kinase inhibitor moiety, a Src kinase inhibitor moiety, a Syk kinase inhibitor moiety, or a Tec kinase inhibitor moiety. In embodiments, $R^1$ is a Src kinase inhibitor moiety. In embodiments, $R^1$ is a PERK kinase inhibitor moiety. In embodiments, $R^1$ is a GSK3 kinase inhibitor moiety. In embodiments, $R^1$ is a p38α MAPK kinase inhibitor moiety.

In embodiments, $R^1$ is a pseudokinase inhibitor moiety (e.g., a HER3 inhibitor moiety).

In embodiments, $R^1$ is a GTPase inhibitor moiety (e.g., K-Ras inhibitor, K-RAs4A inhibitor, K-Ras4B inhibitor).

In embodiments, $R^1$ is a histone modifying enzyme inhibitor moiety (e.g., SET3D).

In embodiments, $R^1$ is a monovalent an anti-cancer agent (e.g., as described herein). In embodiments, $R^1$ is a monovalent a chemotherapeutic agent (e.g., as described herein). In embodiments, $R^1$ is a monovalent anti-neurodegenerative disease agent (e.g., as described herein). In embodiments, $R^1$ is a monovalent anti-viral agent (e.g., as described herein).

In embodiments, $R^1$ is a monovalent anti-viral agent. In embodiments, $R^1$ is not a monovalent anti-viral agent. In embodiments, $R^1$ is not an anti-HIV agent. In embodiments, $R^1$ is not an HIV inhibitor. In embodiments, $R^1$ is not an HIV protease inhibitor. In embodiments, $R^1$ is not a viral protease inhibitor.

In embodiments, $R^1$ is not a monovalent HIV inhibitor. In embodiments, $R^1$ is not a monovalent HIV protease inhibitor. In embodiments, $R^1$ is not a monovalent viral protease inhibitor. In embodiments, $R^1$ is not a monovalent amprenavir, or analog thereof. In embodiments, $R^1$ is not a monovalent amprenavir. In embodiments, $R^1$ is not a monovalent 4-methoxy amprenavir, or analog thereof. In embodiments, $R^1$ is not a monovalent 4-methoxy amprenavir.

In embodiments, $R^1$ is not an amyloid 3 aggregation inhibitor. In embodiments, $R^1$ is not a monovalent congo red, or analog thereof. In embodiments, $R^1$ is not a monovalent thioflavin T, or analog thereof. In embodiments, $R^1$ is not a monovalent curcumin, or analog thereof.

In embodiments, the monovalent Src kinase inhibitor is a monovalent dasatinib, monovalent saracatinib, monovalent bosutinib, or monovalent KX01, or an analog thereof.

In embodiments, the monovalent Raf, VEGFR, PDGFR, or c-Kit inhibitor is a monovalent sorafenib, monovalent imatinib, monovalent nilotinib, monovalent sunitinib, monovalent dasatinib, monovalent pazopanib, monovalent vandetanib, monovalent axitinib, monovalent lenvatinib, monovalent regorafenib, or an analog thereof.

In embodiments, the monovalent EGFR inhibitor is a monovalent lapatinib, monovalent erlotinib, monovalent gefitinib, monovalent vandetanib, monovalent osimertinib, monovalent regorafenib, monovalent AZD 9291, monovalent AG 1478, monovalent dacomitinib, monovalent afatinib, monovalent WZ 4002, monovalent CO-1686, monovalent neratinib, monovalent canertinib, monovalent AC-480, monovalent AZD 8931, monovalent AST 1306, or monovalent EKB 569, or an analog thereof.

In embodiments, the monovalent LRRK2 inhibitor is a monovalent staurosporine, monovalent K-252a, monovalent K-252b, monovalent G66976, monovalent GF109203X, monovalent Ro31-8220, monovalent 5-iodotubericidin, monovalent sorafenib, monovalent GW5074 (Raf-1 kinase inhibitor), monovalent indirubin-3'-monooxime, monovalent sunitinib, monovalent H-1152, monovalent Compound 4, monovalent Y-27632, monovalent SP600125, monovalent damnacanthal, monovalent LDN-73794, monovalent LDN-22684, monovalent CZC-25146, monovalent CZC-54252, monovalent LRRK2-IN-1, monovalent HG-10-102-1, monovalent GSK2578215A, monovalent JH-II-127, monovalent GNE-0877, monovalent GNE-9605, monovalent PF-06447475, monovalent MLi-2, or monovalent DNL201, or analog thereof.

In embodiments, the monovalent KRAS inhibitor is a monovalent KRAS G12C inhibitor, monovalent KRAS M72C inhibitor, monovalent AMG510, monovalent MRTX849, monovalent ARS-1620, or analog thereof.

In embodiments, the monovalent KRAS inhibitor is a monovalent KRAS G12C inhibitor, monovalent KRAS M72C inhibitor, monovalent MRTX849, monovalent ARS-1620, or analog thereof.

In embodiments, the monovalent PI4KIIIβ inhibitor is as described in *J. Med. Chem.*, 2016, 59 (5), 1830-1839.

In embodiments, the monovalent PI4KIIIβ inhibitor is a monovalent form of a PI4K inhibitor as shown in FIG. 64 (and as described in *J. Med. Chem.*, 2016, 59 (5), 1830-1839, which is herein incorporated by reference in its entirety for all purposes). In embodiments, the monovalent PI4KIIIβ inhibitor is

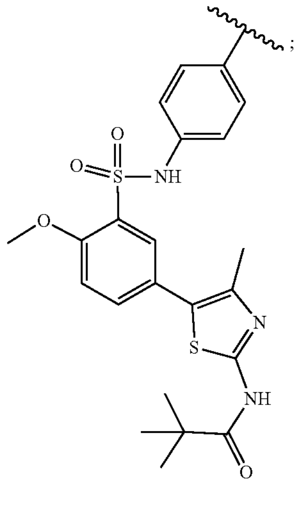 [SMILES: *c1ccc(NS(=O)(=O)c2cc(-c3sc(NC(=O)C(C)(C)C)nc3C)ccc2OC)cc1]

or an analog thereof.

In embodiments, $R^1$ is a monovalent MAP4K inhibitor. In embodiments, $R^1$ is a monovalent MAP4K4 inhibitor. In embodiments, $R^1$ is a monovalent HGK inhibitor. In embodiments, $R^1$ is a monovalent MAP3K inhibitor. In embodiments, $R^1$ is a monovalent MAP3K12 inhibitor. In embodiments, $R^1$ is a monovalent DLK inhibitor.

In embodiments, the monovalent HGK inhibitor is a monovalent compound 12k (as shown in FIG. 63 and as described in Cell Chemical Biology, 2019, 26, 1703-1715, which is herein incorporated by reference in its entirety and for all purposes). In embodiments, the monovalent HGK inhibitor is a monovalent URMC-099, a monovalent PF06260933, or a monovalent GNE-495.

In embodiments, the monovalent DLK inhibitor is a monovalent DLK inhibitor 8 (as shown in FIG. 63 and as described in *J. Med. Chem.,* 2018, 61, 8078-8087, which is herein incorporated by reference in its entirety and for all purposes). In embodiments, the monovalent DLK inhibitor is a monovalent sunitinib, monovalent tozasertib, monovalent GNE-8505, or monovalent GNE-3511.

In embodiments, $R^1$ is a monovalent form of an anti-cancer agent (e.g., as described herein).

In embodiments, $R^1$ is a monovalent form of

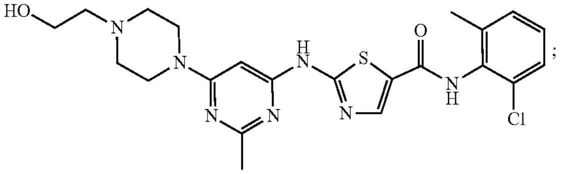 [SMILES: Cc1nc(Nc2ncc(C(=O)Nc3c(C)cccc3Cl)s2)cc(N2CCN(CCO)CC2)n1]

or an analog thereof.

In embodiments, $R^1$ is

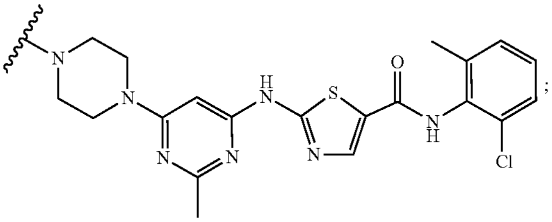 [SMILES: *N1CCN(c2cc(Nc3ncc(C(=O)Nc4c(C)cccc4Cl)s3)nc(C)n2)CC1]

or an analog thereof.

In embodiments, $R^1$ is

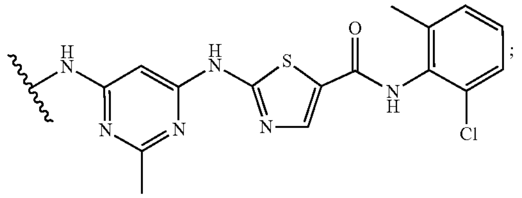 [SMILES: *Nc1cc(Nc2ncc(C(=O)Nc3c(C)cccc3Cl)s2)nc(C)n1]

or an analog thereof.

In embodiments, $R^1$ is

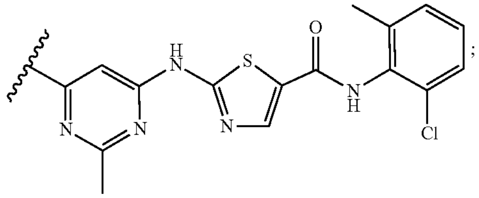 [SMILES: *c1cc(Nc2ncc(C(=O)Nc3c(C)cccc3Cl)s2)nc(C)n1]

or an analog thereof.

In embodiments, $R^1$ is

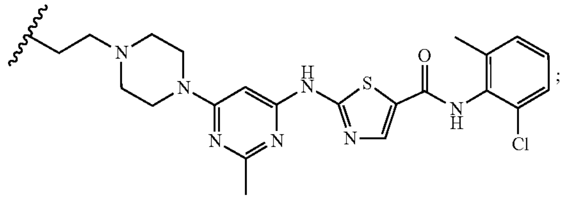 [SMILES: *CCN1CCN(c2cc(Nc3ncc(C(=O)Nc4c(C)cccc4Cl)s3)nc(C)n2)CC1]

or an analog thereof.

In embodiments, $R^1$ is

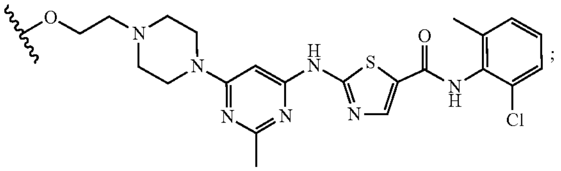 [SMILES: *OCCN1CCN(c2cc(Nc3ncc(C(=O)Nc4c(C)cccc4Cl)s3)nc(C)n2)CC1]

or an analog thereof.

In embodiments, $R^1$ is a monovalent form of

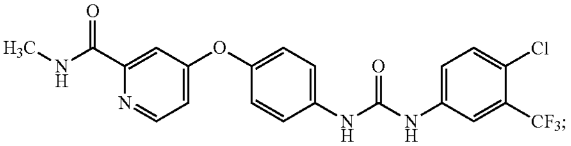 [SMILES: CNC(=O)c1cc(Oc2ccc(NC(=O)Nc3ccc(Cl)c(C(F)(F)F)c3)cc2)ccn1]

or an analog thereof.

In embodiments, $R^1$ is

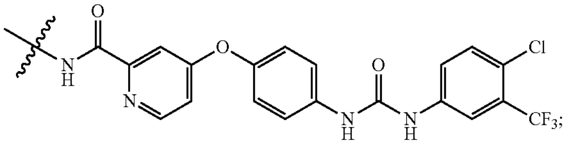 [SMILES: *NC(=O)c1cc(Oc2ccc(NC(=O)Nc3ccc(Cl)c(C(F)(F)F)c3)cc2)ccn1]

or an analog thereof.

In embodiments, $R^1$ is

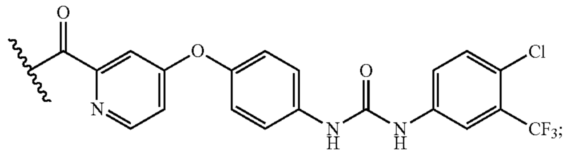 [SMILES: *C(=O)c1cc(Oc2ccc(NC(=O)Nc3ccc(Cl)c(C(F)(F)F)c3)cc2)ccn1]

or an analog thereof.

In embodiments, $R^1$ is

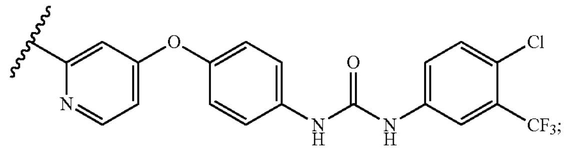 [SMILES: *c1cc(Oc2ccc(NC(=O)Nc3ccc(Cl)c(C(F)(F)F)c3)cc2)ccn1]

or an analog thereof.

In embodiments, $R^1$ is

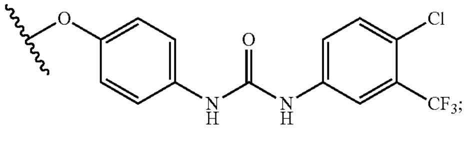 [SMILES: *Oc1ccc(NC(=O)Nc2ccc(Cl)c(C(F)(F)F)c2)cc1]

or an analog thereof.

In embodiments, $R^1$ is a monovalent form of

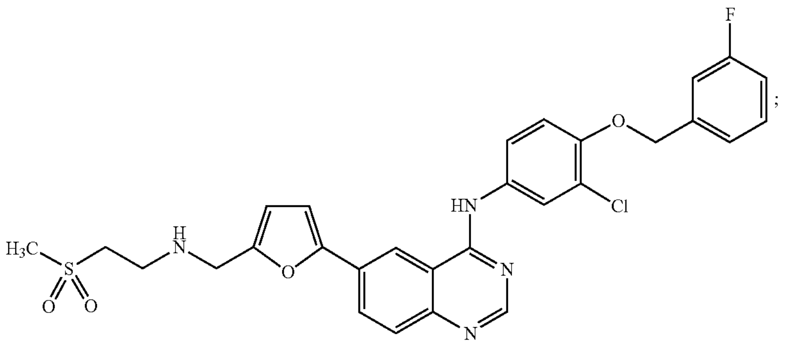 [SMILES: CS(=O)(=O)CCNCc1ccc(-c2ccc3ncnc(Nc4ccc(OCc5cccc(F)c5)c(Cl)c4)c3c2)o1]

or an analog thereof.

In embodiments, $R^1$ is

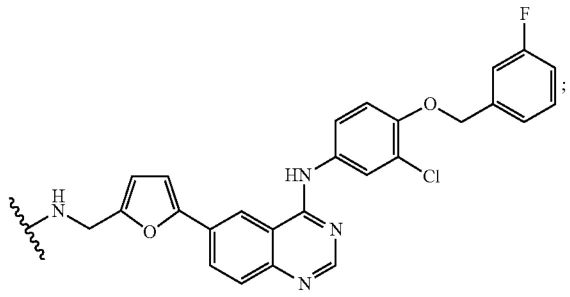 [SMILES: *NCc1ccc(-c2ccc3ncnc(Nc4ccc(OCc5cccc(F)c5)c(Cl)c4)c3c2)o1]

or an analog thereof.

In embodiments, $R^1$ is

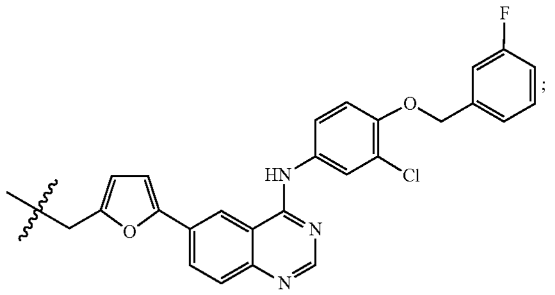 [SMILES: *Cc1ccc(-c2ccc3ncnc(Nc4ccc(OCc5cccc(F)c5)c(Cl)c4)c3c2)o1]

or an analog thereof.

In embodiments, $R^1$ is

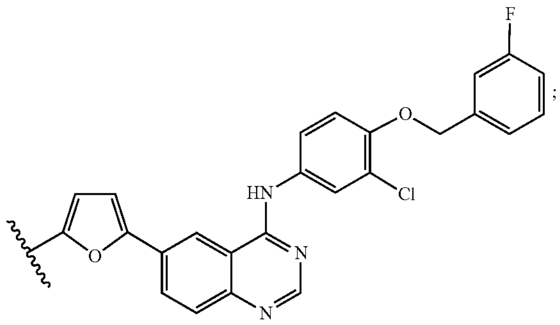 [SMILES: *c1ccc(-c2ccc3ncnc(Nc4ccc(OCc5cccc(F)c5)c(Cl)c4)c3c2)o1]

or an analog thereof.

In embodiments, $R^1$ is

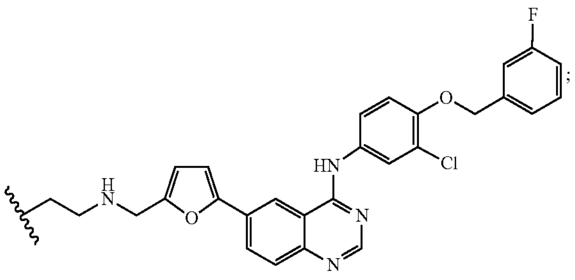 [SMILES: *CCNCc1ccc(-c2ccc3ncnc(Nc4ccc(OCc5cccc(F)c5)c(Cl)c4)c3c2)o1]

or an analog thereof.

In embodiments, $R^1$ is

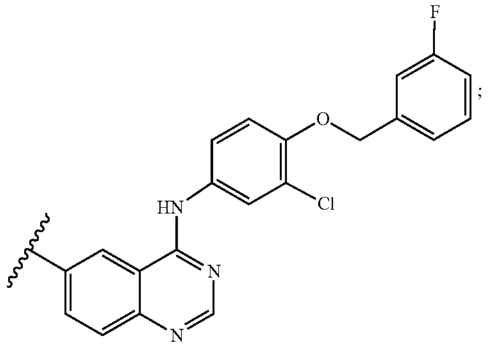 [SMILES: *c1ccc2ncnc(Nc3ccc(OCc4cccc(F)c4)c(Cl)c3)c2c1]

or an analog thereof.

In embodiments, $R^1$ is a monovalent form of

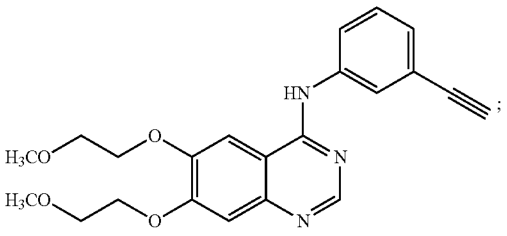 [SMILES: C#Cc1cccc(Nc2ncnc3cc(OCCOC)c(OCCOC)cc23)c1]

or an analog thereof.

In embodiments, $R^1$ is

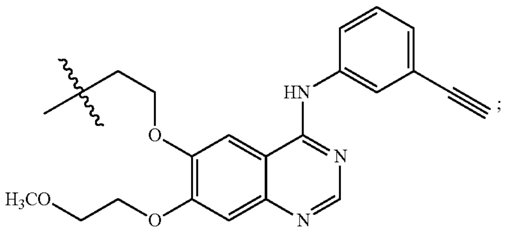 [SMILES: *CCOc1cc2c(Nc3cccc(C#C)c3)ncnc2cc1OCCOC]

or an analog thereof.

In embodiments, $R^1$ is

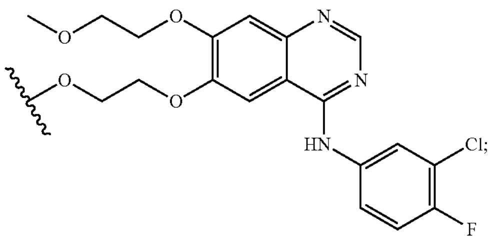 [SMILES: *OCCOc1cc2c(Nc3ccc(F)c(Cl)c3)ncnc2cc1OCCOC]

or an analog thereof.

In embodiments, $R^1$ is

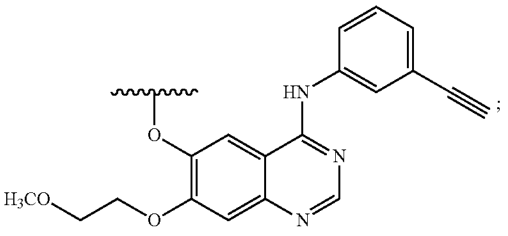 [SMILES: *Oc1cc2c(Nc3cccc(C#C)c3)ncnc2cc1OCCOC]

or an analog thereof.

In embodiments, $R^1$ is

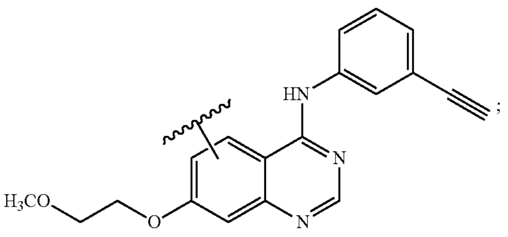

or an analog thereof.

In embodiments, $R^1$ is a monovalent form of

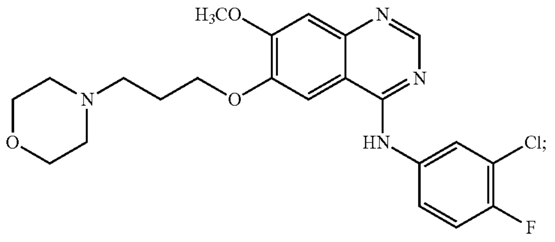 [SMILES: COc1cc2ncnc(Nc3ccc(F)c(Cl)c3)c2cc1OCCCN1CCOCC1]

or an analog thereof.

In embodiments, $R^1$ is

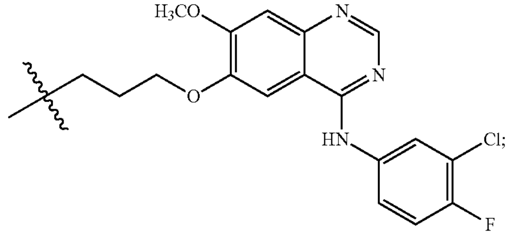 [SMILES: *CCCOc1cc2c(Nc3ccc(F)c(Cl)c3)ncnc2cc1OC]

or an analog thereof.

In embodiments, $R^1$ is

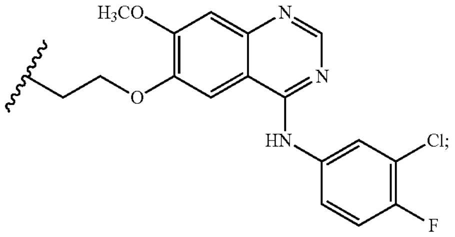 [SMILES: *CCOc1cc2c(Nc3ccc(F)c(Cl)c3)ncnc2cc1OC]

or an analog thereof.

In embodiments, $R^1$ is

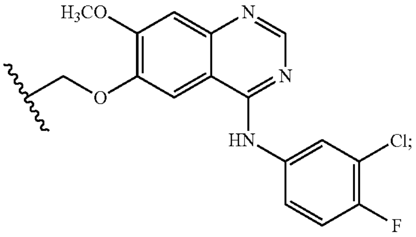 [SMILES: *COc1cc2c(Nc3ccc(F)c(Cl)c3)ncnc2cc1OC]

or an analog thereof.

In embodiments, $R^1$ is

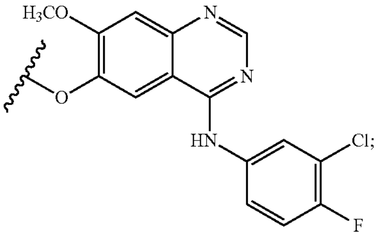 [SMILES: *Oc1cc2c(Nc3ccc(F)c(Cl)c3)ncnc2cc1OC]

or an analog thereof.

In embodiments, $R^1$ is

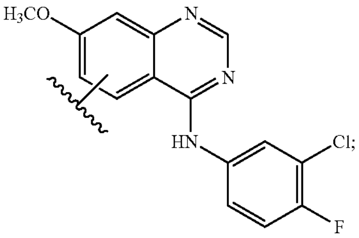

or an analog thereof.

In embodiments, $R^1$ is

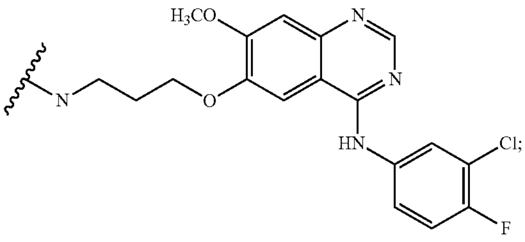 [SMILES: *NCCCOc1cc2c(Nc3ccc(F)c(Cl)c3)ncnc2cc1OC]

or an analog thereof.

In embodiments, $R^1$ is a monovalent form of

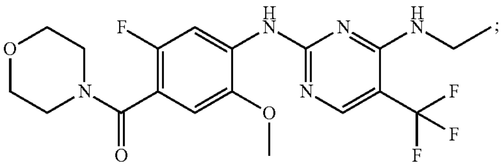 [SMILES: CCNc1nc(Nc2cc(F)c(C(=O)N3CCOCC3)cc2OC)ncc1C(F)(F)F]

or an analog thereof.

In embodiments, $R^1$ is

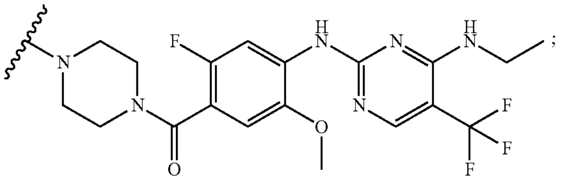 [SMILES: *N1CCN(C(=O)c2cc(OC)c(Nc3ncc(C(F)(F)F)c(NCC)n3)cc2F)CC1]

or an analog thereof.

In embodiments, $R^1$ is

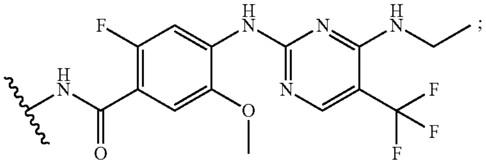 [SMILES: *NC(=O)c1cc(OC)c(Nc2ncc(C(F)(F)F)c(NCC)n2)cc1F]

or an analog thereof.

In embodiments, $R^1$ is

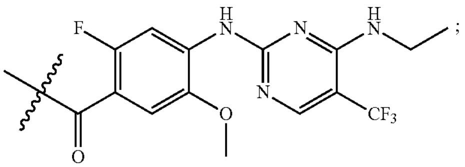 [SMILES: *C(=O)c1cc(OC)c(Nc2ncc(C(F)(F)F)c(NCC)n2)cc1F]

or an analog thereof.

In embodiments, $R^1$ is a monovalent form of

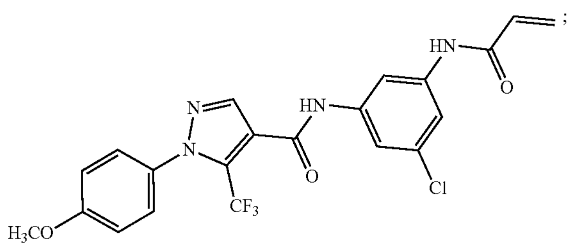 [SMILES: C=CC(=O)Nc1cc(Cl)cc(NC(=O)c2cnn(-c3ccc(OC)cc3)c2C(F)(F)F)c1]

an analog thereof.

In embodiments, $R^1$ is

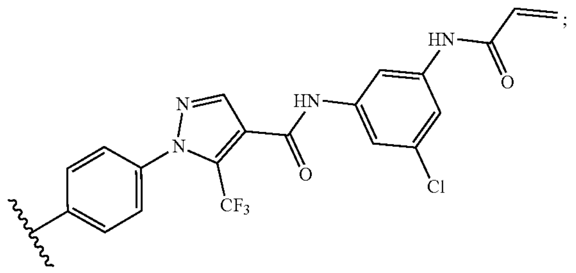 [SMILES: *c1ccc(-n2ncc(C(=O)Nc3cc(Cl)cc(NC(=O)C=C)c3)c2C(F)(F)F)cc1]

or an analog thereof.

In embodiments, $R^1$ is

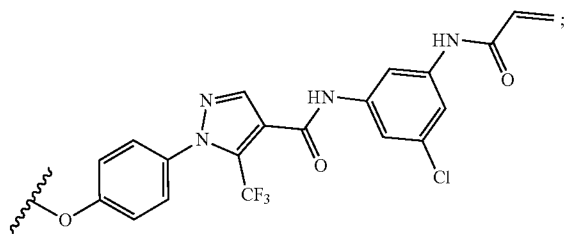 [SMILES: *Oc1ccc(-n2ncc(C(=O)Nc3cc(Cl)cc(NC(=O)C=C)c3)c2C(F)(F)F)cc1]

or an analog thereof.

In embodiments, $R^1$ is

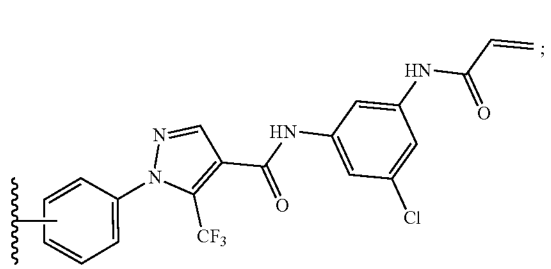

or an analog thereof.

In embodiments, $R^1$ is

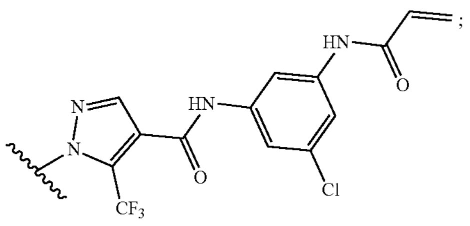 [SMILES: *n1ncc(C(=O)Nc2cc(Cl)cc(NC(=O)C=C)c2)c1C(F)(F)F]

or an analog thereof.

In embodiments, $R^1$ is

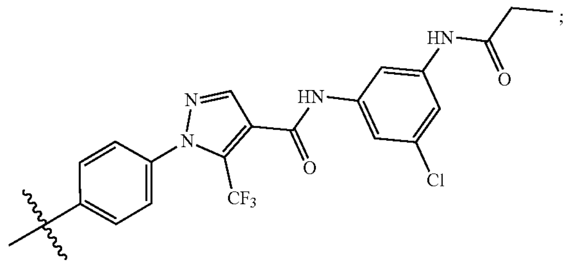 [SMILES: *c1ccc(-n2ncc(C(=O)Nc3cc(Cl)cc(NC(=O)CC)c3)c2C(F)(F)F)cc1]

or an analog thereof.

In embodiments, $R^1$ is

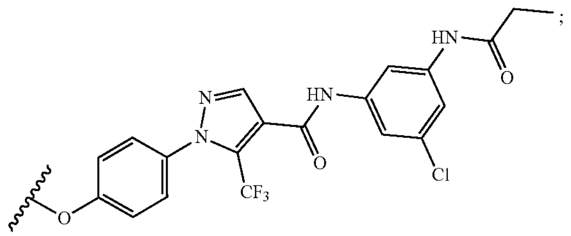 [SMILES: *Oc1ccc(-n2ncc(C(=O)Nc3cc(Cl)cc(NC(=O)CC)c3)c2C(F)(F)F)cc1]

or an analog thereof.

In embodiments, $R^1$ is

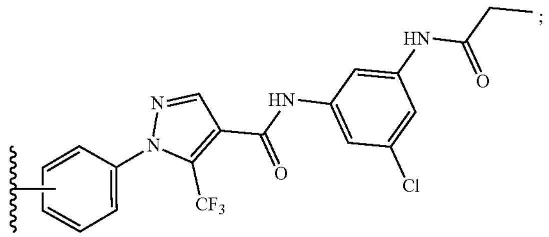

or an analog thereof.

In embodiments, $R^1$ is

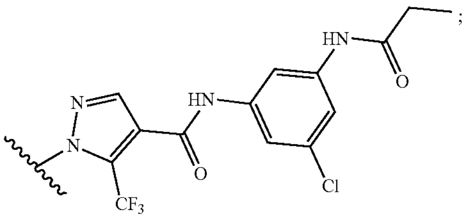 [SMILES: *n1ncc(C(=O)Nc2cc(Cl)cc(NC(=O)CC)c2)c1C(F)(F)F]

or an analog thereof.

In embodiments, $R^1$ is a monovalent form of

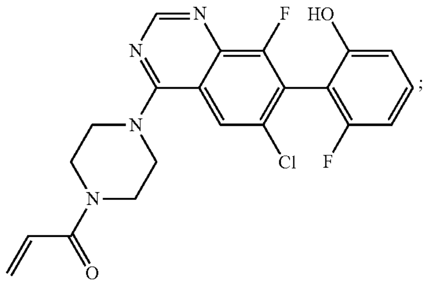 [SMILES: C=CC(=O)N1CCN(c2ncnc3c(F)c(-c4c(O)cccc4F)c(Cl)cc23)CC1]

or an analog thereof.

In embodiments, $R^1$ is

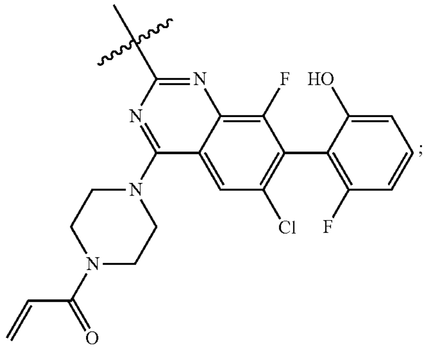 [SMILES: *c1nc(N2CCN(C(=O)C=C)CC2)c2cc(Cl)c(-c3c(O)cccc3F)c(F)c2n1]

or an analog thereof.

In embodiments, $R^1$ is

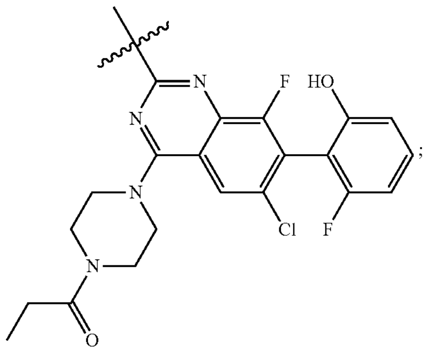 [SMILES: *c1nc(N2CCN(C(=O)CC)CC2)c2cc(Cl)c(-c3c(O)cccc3F)c(F)c2n1]

or an analog thereof.

In embodiments, $R^1$ is

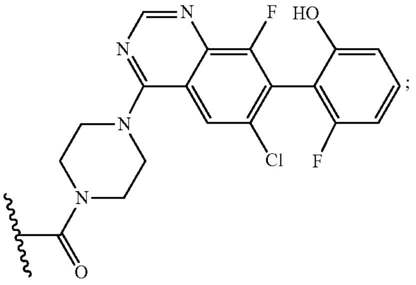 [SMILES: *C(=O)N1CCN(c2ncnc3c(F)c(-c4c(O)cccc4F)c(Cl)cc23)CC1]

or an analog thereof.

In embodiments, $R^1$ is

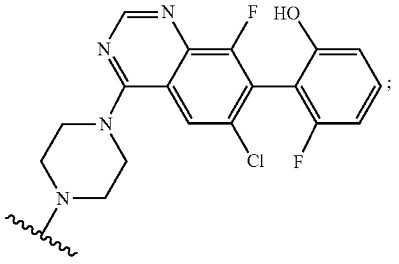 [SMILES: *N1CCN(c2ncnc3c(F)c(-c4c(O)cccc4F)c(Cl)cc23)CC1]

or an analog thereof.

In embodiments, $R^1$ is

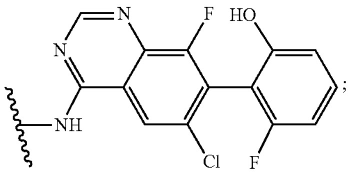 [SMILES: *Nc1ncnc2c(F)c(-c3c(O)cccc3F)c(Cl)cc12]

or an analog thereof.

In embodiments, $R^1$ is

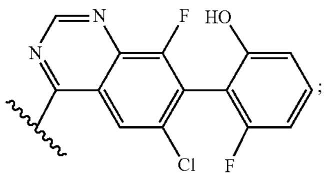 [SMILES: *c1ncnc2c(F)c(-c3c(O)cccc3F)c(Cl)cc12]

or an analog thereof.

In embodiments, $R^1$ is

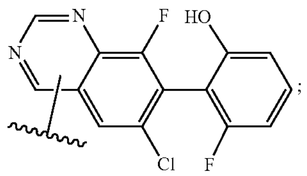

or an analog thereof.

In embodiments, $R^1$ is a monovalent form of

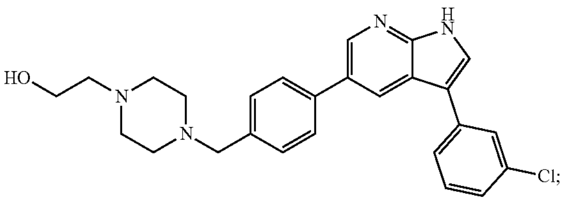 [SMILES: OCCN1CCN(Cc2ccc(-c3cnc4[nH]cc(-c5cccc(Cl)c5)c4c3)cc2)CC1]

or an analog thereof.

In embodiments, $R^1$ is

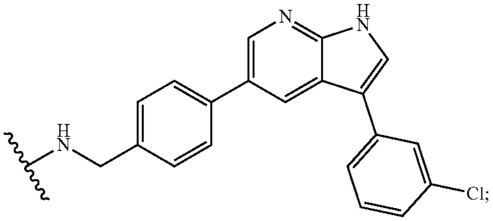 [SMILES: *NCc1ccc(-c2cnc3[nH]cc(-c4cccc(Cl)c4)c3c2)cc1]

or an analog thereof.

In embodiments, $R^1$ is

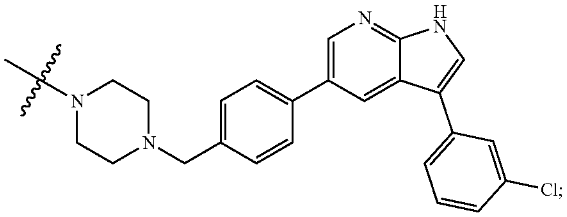 [SMILES: *N1CCN(Cc2ccc(-c3cnc4[nH]cc(-c5cccc(Cl)c5)c4c3)cc2)CC1]

or an analog thereof.

In embodiments, $R^1$ is

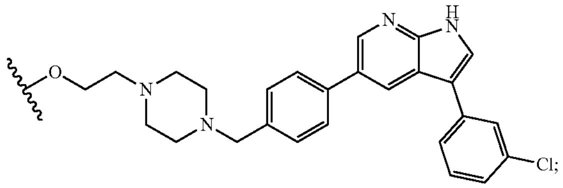 [SMILES: *OCCN1CCN(Cc2ccc(-c3cnc4[nH]cc(-c5cccc(Cl)c5)c4c3)cc2)CC1]

or an analog thereof.

In embodiments, $R^1$ is

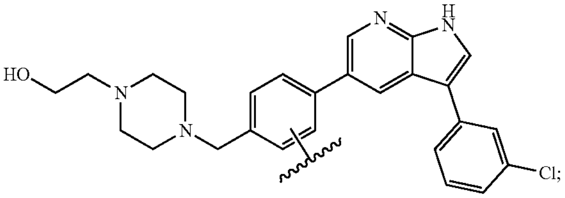

or an analog thereof.

In embodiments, $R^1$ is a monovalent form of

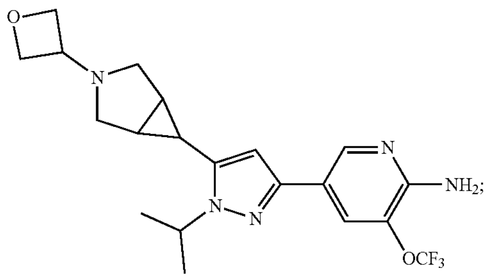 [SMILES: CC(C)n1nc(-c2cnc(N)c(OC(F)(F)F)c2)cc1C1C2CN(C3COC3)CC21]

or an analog thereof.

In embodiments, $R^1$ is

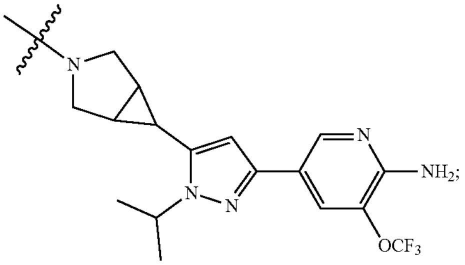 [SMILES: *N1CC2C(C1)C2c1cc(-c2cnc(N)c(OC(F)(F)F)c2)nn1C(C)C]

or an analog thereof.

In embodiments, $R^1$ is

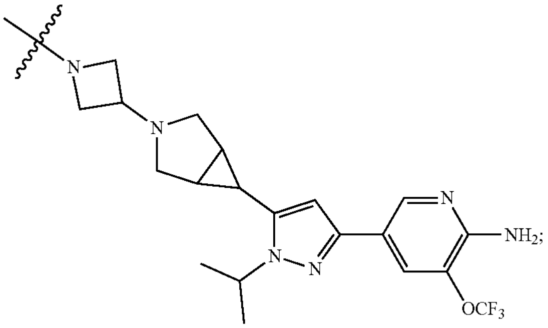 [SMILES: *N1CC(N2CC3C(C2)C3c2cc(-c3cnc(N)c(OC(F)(F)F)c3)nn2C(C)C)C1]

or an analog thereof.

In embodiments, $R^1$ is

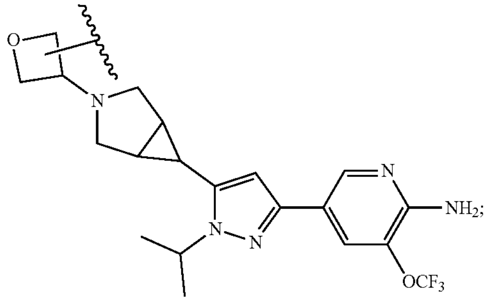

or an analog thereof.

In embodiments, $R^1$ is
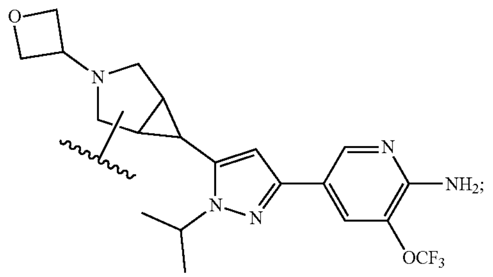
or an analog thereof.
In embodiments, $R^1$ is a monovalent form of
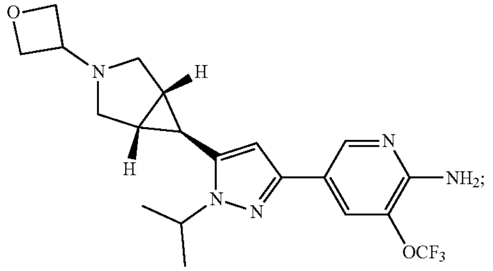 [SMILES: CC(C)n1nc(-c2cnc(N)c(OC(F)(F)F)c2)cc1[C@H]1[C@@H]2CN(C3COC3)C[C@@H]21]
or an analog thereof.
In embodiments, $R^1$ is
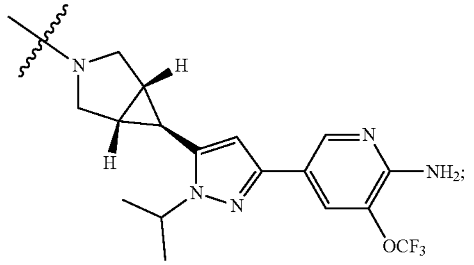 [SMILES: *N1C[C@@H]2[C@H](C1)[C@H]2c1cc(-c2cnc(N)c(OC(F)(F)F)c2)nn1C(C)C]
or an analog thereof.
In embodiments, $R^1$ is
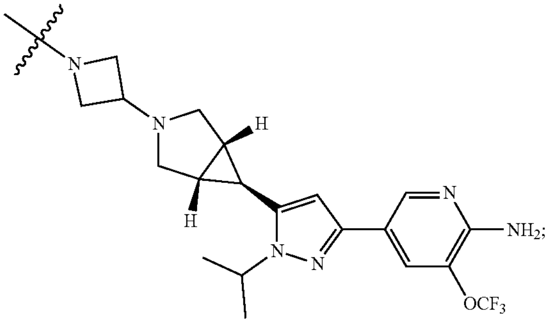 [SMILES: *N1CC(N2C[C@@H]3[C@H](C2)[C@H]3c2cc(-c3cnc(N)c(OC(F)(F)F)c3)nn2C(C)C)C1]
or an analog thereof.
In embodiments, $R^1$ is
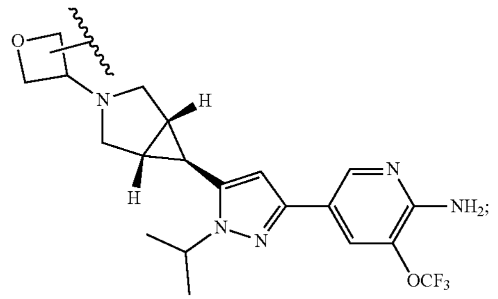
or an analog thereof.
In embodiments, $R^1$ is
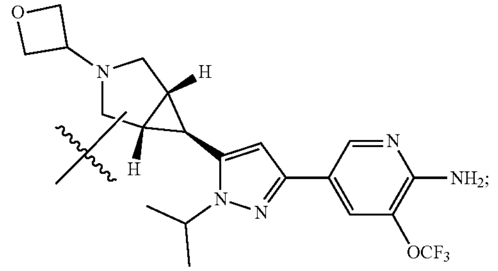
or an analog thereof.
In embodiments, $R^1$ is a monovalent form of
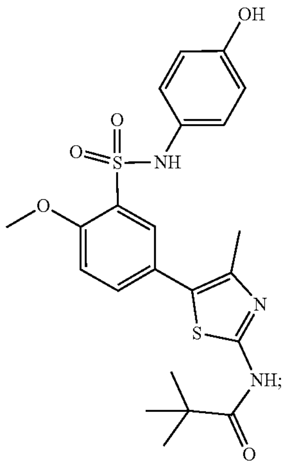 [SMILES: COc1ccc(-c2sc(NC(=O)C(C)(C)C)nc2C)cc1S(=O)(=O)Nc1ccc(O)cc1]
or an analog thereof.

In embodiments, $R^1$ is

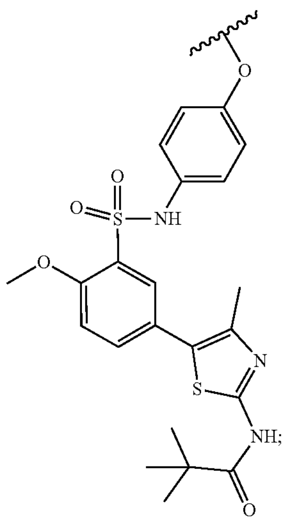 [SMILES: *Oc1ccc(NS(=O)(=O)c2cc(-c3sc(NC(=O)C(C)(C)C)nc3C)ccc2OC)cc1]

or an analog thereof.

In embodiments, $R^1$ is

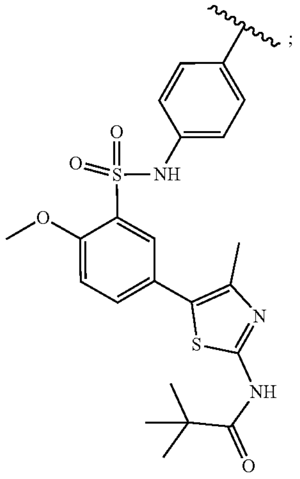 [SMILES: *c1ccc(NS(=O)(=O)c2cc(-c3sc(NC(=O)C(C)(C)C)nc3C)ccc2OC)cc1]

or an analog thereof.

In embodiments, $R^1$ is

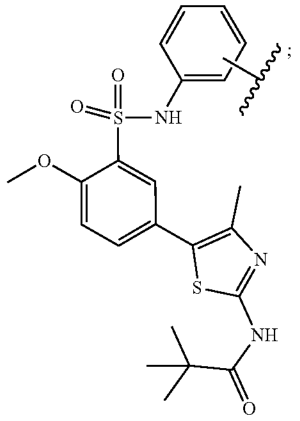

or an analog thereof.

In embodiments, $R^1$ is

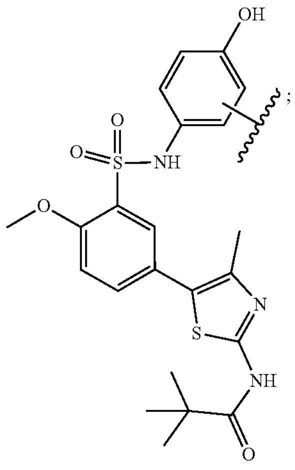

or an analog thereof.

In embodiments, $R^1$ is

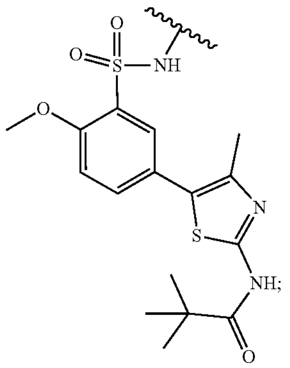 [SMILES: *NS(=O)(=O)c1cc(-c2sc(NC(=O)C(C)(C)C)nc2C)ccc1OC]

or an analog thereof.

In embodiments, $R^1$ is

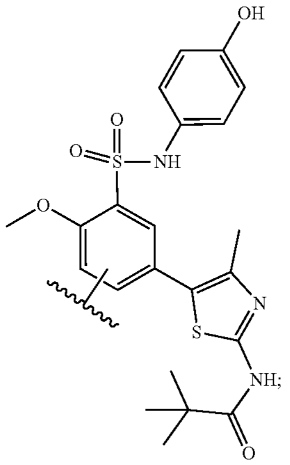

or an analog thereof.

In embodiments, $L^1$ is substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^1$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^1$ is substituted with a plurality of groups selected from substituent groups, size-limited substituent groups, and lower substituent groups; each substituent group, size-limited substituent group, and/or lower substituent group may optionally be different. In embodiments, when $L^1$ is substituted, it is substituted with at least one substituent group. In embodiments, when $L^1$ is substituted, it is substituted with at least one size-limited substituent group. In embodiments, when $L^1$ is substituted, it is substituted with at least one lower substituent group.

In embodiments, $L^1$ is substituted or unsubstituted alkylene, substituted or unsubstituted heteroalkylene, substituted or unsubstituted heterocycloalkylene.

In embodiments, $L^1$ is substituted or unsubstituted $C_1$-$C_{10}$ alkylene, substituted or unsubstituted 2 to 15 membered heteroalkylene, or substituted or unsubstituted 5 to 6 membered heterocycloalkylene.

In embodiments, $L^1$ is substituted or unsubstituted $C_1$-$C_{10}$ alkylene. In embodiments, $L^1$ is substituted or unsubstituted $C_1$-$C_8$ alkylene. In embodiments, $L^1$ is substituted or unsubstituted $C_1$-$C_3$ alkylene. In embodiments, $L^1$ is substituted or unsubstituted $C_1$-$C_2$ alkylene. In embodiments, $L^1$ is substituted or unsubstituted 2 to 15 membered heteroalkylene. In embodiments, $L^1$ is substituted or unsubstituted 2 to 10 membered heteroalkylene. In embodiments, $L^1$ is oxo substituted 2 to 5 membered heteroalkylene. In embodiments, $L^1$ is substituted or unsubstituted 2 to 5 membered heteroalkylene. In embodiments, $L^1$ is substituted or unsubstituted 2 to 3 membered heteroalkylene. In embodiments, $L^1$ is oxo substituted 2 to 3 membered heteroalkylene. In embodiments, $L^1$ is substituted or unsubstituted 5 to 6 membered heterocycloalkylene. In embodiments, $L^1$ is substituted or unsubstituted piperazinylene. In embodiments, $L^1$ is unsubstituted piperazinylene.

In embodiments, $L^2$ is —O—, substituted or unsubstituted alkylene, substituted or unsubstituted heteroalkylene, substituted or unsubstituted heterocycloalkylene.

In embodiments, $L^2$ is —O—. In embodiments, $L^2$ is —NH—. In embodiments, $L^2$ is substituted or unsubstituted $C_1$-$C_{10}$ alkylene. In embodiments, $L^2$ is substituted or unsubstituted $C_1$-$C_8$ alkylene. In embodiments, $L^2$ is substituted or unsubstituted $C_1$-$C_3$ alkylene. In embodiments, $L^2$ is substituted or unsubstituted $C_1$-$C_2$ alkylene. In embodiments, $L^2$ is substituted or unsubstituted $C_1$-$C_2$ alkylene. In embodiments, $L^2$ is oxo substituted $C_1$-$C_{10}$ alkylene. In embodiments, $L^2$ is oxo substituted $C_2$-$C_3$ alkylene. In embodiments, $L^2$ is substituted or unsubstituted 2 to 15 membered heteroalkylene. In embodiments, $L^2$ is substituted or unsubstituted 2 to 10 membered heteroalkylene. In embodiments, $L^2$ is substituted or unsubstituted 2 to 5 membered heteroalkylene. In embodiments, $L^2$ is substituted or unsubstituted 2 to 3 membered heteroalkylene. In embodiments, $L^2$ is oxo substituted 2 to 15 membered heteroalkylene. In embodiments, $L^2$ is oxo substituted 2 to 10 membered heteroalkylene. In embodiments, $L^2$ is oxo substituted 2 to 5 membered heteroalkylene. In embodiments, $L^2$ is oxo substituted 2 to 3 membered heteroalkylene. In embodiments, $L^2$ is substituted or unsubstituted 5 to 6 membered heterocycloalkylene. In embodiments, $L^2$ is substituted or unsubstituted piperazinylene. In embodiments, $L^2$ is unsubstituted piperazinylene.

In embodiments, $L^3$ is substituted or unsubstituted alkylene, substituted or unsubstituted heteroalkylene, substituted or unsubstituted heterocycloalkylene, substituted or unsubstituted arylene, or substituted or unsubstituted heteroarylene.

In embodiments, $L^3$ is substituted or unsubstituted $C_1$-$C_{10}$ alkylene. In embodiments, $L^3$ is substituted or unsubstituted $C_1$-$C_8$ alkylene. In embodiments, $L^3$ is substituted or unsubstituted $C_1$-$C_3$ alkylene. In embodiments, $L^3$ is substituted or unsubstituted $C_1$-$C_2$ alkylene. In embodiments, $L^3$ is substituted or unsubstituted $C_1$-$C_2$ alkylene. In embodiments, $L^3$ is substituted or unsubstituted $C_1$-$C_2$ alkylene. In embodiments, $L^3$ is oxo substituted $C_1$-$C_{10}$ alkylene. In embodiments, $L^3$ is oxo substituted $C_2$-$C_3$ alkylene. In embodiments, $L^3$ is substituted or unsubstituted 2 to 15 membered heteroalkylene. In embodiments, $L^3$ is substituted or unsubstituted 2 to 10 membered heteroalkylene In embodiments, $L^3$ is substituted or unsubstituted 2 to 5 membered heteroalkylene. In embodiments, $L^3$ is substituted or unsubstituted 2 to 3 membered heteroalkylene. In embodiments, $L^3$ is oxo substituted 2 to 15 membered heteroalkylene. In embodiments, $L^3$ is oxo substituted 2 to 10 membered heteroalkylene. In embodiments, $L^3$ is oxo substituted 2 to 5 membered heteroalkylene. In embodiments, $L^3$ is oxo substituted 2 to 3 membered heteroalkylene. In embodiments, $L^3$ is substituted or unsubstituted 5 to 6 membered heterocycloalkylene. In embodiments, $L^3$ is substituted or unsubstituted piperazinylene. In embodiments, $L^3$ is 5 to 6-membered substituted or unsubstituted arylene. In embodiments, $L^3$ is substituted or unsubstituted phenylene. In embodiments, $L^3$ is 5 to 6-membered substituted or unsubstituted heteroarylene. In embodiments, $L^3$ is substituted or unsubstituted pyridinylene. In embodiments, $L^3$ is substituted or unsubstituted furanylene. In embodiments, $L^3$ is unsubstituted pyridinylene. In embodiments, $L^3$ is unsubstituted furanylene.

In embodiments, $L^4$ is —O—. In embodiments, $L^4$ is —NH—. In embodiments, $L^4$ is substituted or unsubstituted $C_1$-$C_{10}$ alkylene. In embodiments, $L^4$ is substituted or unsubstituted $C_1$-$C_8$ alkylene. In embodiments, $L^4$ is substituted or unsubstituted $C_1$-$C_3$ alkylene. In embodiments, $L^4$ is substituted or unsubstituted $C_1$-$C_2$ alkylene. In embodiments, $L^4$ is substituted or unsubstituted $C_1$-$C_2$ alkylene. In embodiments, $L^4$ is oxo substituted $C_1$-$C_{10}$ alkylene. In embodiments, $L^4$ is oxo substituted $C_2$-$C_3$ alkylene. In embodiments, $L^4$ is substituted or unsubstituted 2 to 15 membered heteroalkylene. In embodiments, $L^4$ is substituted or unsubstituted 2 to 10 membered heteroalkylene. In embodiments, $L^4$ is substituted or unsubstituted 2 to 5 membered heteroalkylene. In embodiments, $L^4$ is substituted or unsubstituted 2 to 3 membered heteroalkylene. In embodiments, $L^4$ is oxo substituted 2 to 15 membered heteroalkylene. In embodiments, $L^4$ is oxo substituted 2 to 10 membered heteroalkylene. In embodiments, $L^4$ is oxo substituted 2 to 5 membered heteroalkylene. In embodiments, $L^4$ is oxo substituted 2 to 3 membered heteroalkylene. In embodiments, $L^4$ is substituted or unsubstituted 5 to 6 membered heterocycloalkylene. In embodiments, $L^4$ is substituted or unsubstituted piperazinylene.

In embodiments, $L^1$ is —NH—, —$NR^{23}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is $L^2$-$L^3$-$L^4$-$L^5$-$L^6$. In embodiments, $L^2$ is connected directly to a monovalent FK506 or a monovalent FK506 analog. In embodiments, $L^2$ is connected directly to a monovalent SLF or a monovalent SLF analog. In embodiments, $L^2$ is connected directly to a monovalent cyclosporin A or a monovalent cyclosporin A analog. In embodiments, $L^2$ is connected directly to a monovalent rapamycin or a monovalent rapamycin analog. In embodiments, $L^2$ is connected directly to a monovalent sangliferin A or a monovalent sangliferin A analog. In embodiments, $L^2$ is a bond, —NH—, —$NR^{26}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is a bond, —NH—, —$NR^{29}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bond, —NH—, —$NR^{32}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is a bond, —NH—, —$NR^{35}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^6$ is a bond, —NH—, —$NR^{38}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^6$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^1$ is a divalent linker including one or more amino acids. In embodiments, $L^1$ is a divalent linker consisting of amino acids. In embodiments, $L^1$ is a divalent linker including an amino acid analog. In embodiments, $L^1$ is a divalent linker including an amino acid mimetic. In embodiments, $L^1$ is a divalent linker consisting of amino acid analogs. In embodiments, $L^1$ is a divalent linker consisting of amino acid mimetics.

In embodiments, $L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, or —OC(O)—.

In embodiments, $L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —NHC(O) $N(R^3)$—, —C(O)O—, or —OC(O)—.

In embodiments, $L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —NHC(O) $N(R^4)$—, —C(O)O—, or —OC(O)—.

In embodiments, $L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —NHC(O) $N(R^5)$—, —C(O)O—, or —OC(O)—.

In embodiments, $L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —NHC(O) $N(R^6)$—, —C(O)O—, or —OC(O)—.

In embodiments, $L^2$ is a bond. In embodiments, $L^3$ is a bond. In embodiments, $L^4$ is a bond. In embodiments, $L^5$ is a bond. In embodiments, $L^6$ is a bond.

In embodiments, $L^2$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^2$ is substituted or unsubstituted 3 to 8 membered heteroalkylene. In embodiments, $L^2$ is —$CH_2CH_2OCH_2$—. In embodiments, $L^2$ is unsubstituted 3 to 8 membered heteroalkylene. In embodiments, $L^2$ is unsubstituted 3 to 6 membered heteroalkylene. In embodiments, $L^2$ is unsubstituted 3 to 5 membered heteroalkylene. In embodiments, $L^2$ is a divalent linker including one or more amino acids. In embodiments, $L^2$ is a divalent linker consisting of amino acids. In embodiments, $L^2$ is a divalent linker including an amino acid analog. In embodiments, $L^2$ is a divalent linker including an amino acid mimetic. In embodiments, $L^2$ is a divalent linker consisting of amino acid analogs. In embodiments, $L^2$ is a divalent linker consisting of amino acid mimetics. In embodiments, $L^2$ is a bioconjugate linker.

In embodiments, $L^3$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^3$ is a substituted or unsubstituted 5 to 10 membered heteroarylene. In embodiments, $L^3$ is a bond. In embodiments, $L^3$ is a substituted or unsubstituted 5 to 6 membered heteroarylene. In embodiments, $L^3$ is a unsubstituted 5 to 6 membered heteroarylene. In embodiments, $L^3$ is unsubstituted divalent triazole. In embodiments, $L^3$ is unsubstituted divalent 1H-1,2,3-triazole. In embodiments, $L^3$ is unsubstituted divalent 2H-1,2,3-triazole. In embodiments, $L^3$ is a divalent linker including one or more amino acids. In embodiments, $L^3$ is a divalent linker consisting of amino acids. In embodiments, $L^3$ is a divalent linker including an amino acid analog. In embodiments, $L^3$ is a divalent linker including an amino acid mimetic. In embodiments, $L^3$ is a divalent linker consisting of amino acid analogs. In embodiments, $L^3$ is a divalent linker consisting of amino acid mimetics. In embodiments, $L^3$ is a bioconjugate linker.

In embodiments, $L^4$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^4$ is a substituted or unsubstituted 2 to 12 membered heteroalkylene. In embodiments, $L^4$ is a substituted or unsubstituted 2 to 32 membered heteroalkylene. In embodiments, $L^4$ is a bond. In embodiments, $L^4$ is a divalent linker including one or more amino acids. In embodiments, $L^4$ is a divalent linker consisting of amino acids. In embodiments, $L^4$ is a divalent linker including an amino acid analog. In embodiments, $L^4$ is a divalent linker including an amino acid mimetic. In embodiments, $L^4$ is a divalent linker consisting of amino acid analogs. In embodiments, $L^4$ is a divalent linker consisting of amino acid mimetics. In embodiments, $L^4$ is a bioconjugate linker.

In embodiments, $L^5$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^5$ is a substituted or unsubstituted 2 to 12 membered heteroalkylene. In embodiments, $L^5$ is a substituted or unsubstituted 2 to 32 membered heteroalkylene. In embodiments, $L^5$ is a bond. In embodiments, $L^5$ is a divalent linker including one or more amino acids. In embodiments, $L^5$ is a divalent linker consisting of amino acids. In embodiments, $L^5$ is a divalent linker including an amino acid analog. In embodiments, $L^5$ is a divalent linker including an amino acid mimetic. In embodiments, $L^5$ is a divalent linker consisting of amino acid analogs. In embodiments, $L^5$ is a divalent linker consisting of amino acid mimetics. In embodiments, $L^5$ is a bioconjugate linker.

In embodiments, $L^6$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^6$ is a substituted or unsubstituted 2 to 12 membered heteroalkylene. In embodiments, $L^6$ is a substituted or unsubstituted 2 to 32 membered heteroalkylene. In embodiments, $L^6$ is a bond. In embodiments, $L^6$ is a divalent linker including one or more amino acids. In embodiments, $L^6$ is a divalent linker consisting of amino acids. In embodiments, $L^6$ is a divalent linker including an amino acid analog. In embodiments, $L^6$ is a divalent linker including an amino acid mimetic. In embodiments, $L^6$ is a divalent linker consisting of amino acid analogs. In embodiments, $L^6$ is a divalent linker consisting of amino acid mimetics. In embodiments, $L^6$ is a bioconjugate linker.

In embodiments, $L^5$ is a divalent oligomer of ethylene oxide. In embodiments, $L^5$ is a divalent polyethylene glycol. In embodiments, $L^5$ is a divalent oligomer of ethylene oxide having 2 to 30 linear atoms (carbon and oxygen) between the two termini connecting to the remainder of the compound. In embodiments, $L^5$ is a $-(CH_2)_4C(O)NH-$. In embodiments, $L^5$ is a 2 to 8 membered substituted heteroalkylene. In embodiments, $L^5$ is a 3 to 6 membered substituted heteroalkylene. In embodiments, $L^5$ is a 5 to 6 membered substituted heteroalkylene. In embodiments, $L^5$ is a 5 to 7 membered oxo substituted heteroalkylene. In embodiments, $L^5$ is an unsubstituted $C_1$-$C_6$ alkylene.

In embodiments, $L^4$ is a divalent oligomer of ethylene oxide. In embodiments, $L^4$ is a divalent polyethylene glycol. In embodiments, $L^4$ is a divalent oligomer of ethylene oxide having 2 to 30 linear atoms (carbon and oxygen) between the two termini connecting to the remainder of the compound. In embodiments, $L^4$ is $-(CH_2CH_2O)_bCH_2CH_2-$ and b is an integer from 1 to 16. In embodiments, $L^4$ is $-(CH_2CH_2O)_bCH_2-$ and b is an integer from 1 to 16. In embodiments, $L^4$ is $-(CH_2CH_2O)_b-$ and b is an integer from 1 to 16. In embodiments, b is an integer from 2 to 15. In embodiments, b is an integer from 3 to 14. In embodiments, b is an integer from 4 to 12. In embodiments, b is an integer from 5 to 10. In embodiments, b is an integer from 5 to 8. In embodiments, b is an integer from 6 to 7.

In embodiments, $L^4$-$L^5$ is a 2 to 36 membered substituted heteroalkylene. In embodiments, $L^4$-$L^5$ is a 2 to 34 membered substituted heteroalkylene. In embodiments, $L^4$-$L^5$ is a 2 to 32 membered substituted heteroalkylene. In embodiments, $L^4$-$L^5$ is a 2 to 30 membered substituted heteroalkylene. In embodiments, $L^4$-$L^5$ is a 2 to 28 membered substituted heteroalkylene. In embodiments, $L^4$-$L^5$ is a 2 to 24 membered substituted heteroalkylene. In embodiments, $L^4$-$L^5$ is a 2 to 30 membered substituted heteroalkylene. In embodiments, $L^4$-$L^5$ is a 2 to 22 membered substituted heteroalkylene. In embodiments, $L^4$-$L^5$ is a 2 to 20 membered substituted heteroalkylene. In embodiments, $L^4$-$L^5$ is a 2 to 18 membered substituted heteroalkylene. In embodiments, $L^4$-$L^5$ is a 2 to 16 membered substituted heteroalkylene. In embodiments, $L^4$-$L^5$ is a 2 to 14 membered substituted heteroalkylene. In embodiments, $L^4$-$L^5$ is a 2 to 12 membered substituted heteroalkylene. In embodiments, $L^4$-$L^5$ is a 4 to 36 membered substituted heteroalkylene. In embodiments, $L^4$-$L^5$ is a 6 to 36 membered substituted heteroalkylene. In embodiments, $L^4$-$L^5$ is a 8 to 36 membered substituted heteroalkylene. In embodiments, $L^4$-$L^5$ is a 10 to 36 membered substituted heteroalkylene. In embodiments, $L^4$-$L^5$ is a 12 to 36 membered substituted heteroalkylene. In embodiments, $L^4$-$L^5$ is a 14 to 36 membered substituted heteroalkylene. In embodiments, $L^4$-$L^5$ is a 16 to 36 membered substituted heteroalkylene. In embodiments, $L^4$-$L^5$ is a 18 to 36 membered substituted heteroalkylene. In embodiments, $L^4$-$L^5$ is a 20 to 36 membered substituted heteroalkylene. In embodiments, $L^4$-$L^5$ is a 22 to 36 membered substituted heteroalkylene. In embodiments, $L^4$-$L^5$ is a 24 to 36 membered substituted heteroalkylene. In embodiments, $L^4$-$L^5$ is a 4 to 32 membered substituted heteroalkylene. In embodiments, $L^4$-$L^5$ is a 4 to 28 membered substituted heteroalkylene. In embodiments, $L^4$-$L^5$ is a 8 to 26 membered substituted heteroalkylene. In embodiments, $L^4$-$L^5$ is a 12 to 26 membered substituted heteroalkylene. In embodiments, $L^4$-$L^5$ is a 16 to 26 membered substituted heteroalkylene. In embodiments, $L^4$-$L^5$ is a 20 to 26 membered substituted heteroalkylene. In embodiments, $L^4$-$L^5$ is a 22 to 26 membered substituted heteroalkylene.

In embodiments, $R^2$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^3$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^4$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^5$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^6$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, the linker is formed by a conjugation or bioconjugation reaction combining a first reactant moiety covalently bonded to the immunophilin binding moiety and a second reactant moiety covalently bonded to the $R^1$ moiety. In such embodiments, the anti-CNS disease drug formed by such conjugation or bioconjugation reaction (including anti-CNS disease drugs as described herein) may be referred to as a conjugate or bioconjugate or bioconjugate linker.

In some embodiments of the anti-CNS disease drugs provided herein, $L^1$ is independently $R^{23}$-substituted or unsubstituted alkylene, $R^{23}$-substituted or unsubstituted heteroalkylene, $R^{23}$-substituted or unsubstituted cycloalkylene, $R^{23}$-substituted or unsubstituted heterocycloalkylene, $R^{23}$-substituted or unsubstituted arylene, or $R^{23}$-substituted or unsubstituted heteroarylene.

In embodiments, $L^1$ is a bond, —NH—, $—NR^{23}—$, —S—, —O—, —C(O)—, —NHC(O)—, —C(O)NH—, —NHC(O)NH—, —NHC(NH)NH—, —C(S)—, $R^{23}$-substituted or unsubstituted $C_1$-$C_{20}$ alkylene, $R^{23}$-substituted or unsubstituted 2 to 20 membered heteroalkylene, $R^{23}$-substituted or unsubstituted $C_3$-$C_8$ cycloalkylene, $R^{23}$-substituted or unsubstituted 3 to 8 membered heterocycloalkylene, $R^{23}$-substituted or unsubstituted $C_6$-$C_{10}$ arylene, or $R^{23}$-substituted or unsubstituted 5 to 10 membered heteroarylene. In embodiments, $L^1$ is a bond. In embodiments, $L^1$ is —NH—. In embodiments, $L^1$ is —$NR^{23}$—. In embodiments, $L^1$ is —S—. In embodiments, $L^1$ is —O—. In embodiments, $L^1$ is —C(O)—. In embodiments, $L^1$ is —NHC(O)—. In embodiments, $L^1$ is —C(O)NH—. In embodiments, $L^1$ is —NHC(O)NH—. In embodiments, $L^1$ is —NHC(NH)NH—. In embodiments, $L^1$ is —C(S)—. In embodiments, $L^1$ is $R^{23}$-substituted or unsubstituted $C_1$-$C_{20}$ alkylene. In embodiments, $L^1$ is $R^{23}$-substituted or unsubstituted 2 to 20 membered heteroalkylene. In embodiments, $L^1$ is $R^{23}$-substituted or unsubstituted $C_3$-$C_8$ cycloalkylene. In embodiments, $L^1$ is $R^{23}$-substituted or unsubstituted 3 to 8 membered heterocycloalkylene. In embodiments, $L^1$ is $R^{23}$-substituted or unsubstituted $C_6$-$C_{10}$ arylene. In embodiments, $L^1$ is $R^{23}$-substituted or unsubstituted 5 to 10 membered heteroarylene. In embodiments, $L^1$ is $R^{23}$-substituted $C_1$-$C_{20}$ alkylene. In embodiments, $L^1$ is $R^{23}$-substituted 2 to 20 membered heteroalkylene. In embodiments, $L^1$ is $R^{23}$-substituted $C_3$-$C_8$ cycloalkylene. In embodiments, $L^1$ is $R^{23}$-substituted 3 to 8 membered heterocycloalkylene. In embodiments, $L^1$ is $R^{23}$-substituted $C_6$-$C_{10}$ arylene. In embodiments, $L^1$ is $R^{23}$-substituted 5 to 10 membered heteroarylene. In embodiments, $L^1$ is unsubstituted $C_1$-$C_{20}$ alkylene. In embodiments, $L^1$ is unsubstituted 2 to 20 membered heteroalkylene. In embodiments, $L^1$ is unsubstituted $C_3$-$C_8$ cycloalkylene. In embodiments, $L^1$ is unsubstituted 3 to 8 membered heterocycloalkylene. In embodiments, $L^1$ is unsubstituted $C_6$-$C_{10}$ arylene. In embodiments, $L^1$ is unsubstituted 5 to 10 membered heteroarylene. In embodiments, $L^1$ is $R^{23}$-substituted $C_1$-$C_{15}$ alkylene. In embodiments, $L^1$ is $R^{23}$-substituted 2 to 15 membered heteroalkylene. In embodiments, $L^1$ is $R^{23}$-substituted $C_3$-$C_6$ cycloalkylene. In embodiments, $L^1$ is $R^{23}$-substituted 3 to 6 membered heterocycloalkylene. In embodiments, $L^1$ is $R^{23}$-substituted phenylene. In embodiments, $L^1$ is $R^{23}$-substituted 5 to 6 membered heteroarylene. In embodiments, $L^1$ is unsubstituted $C_1$-$C_{15}$ alkylene. In embodiments, $L^1$ is unsubstituted 2 to 15 membered heteroalkylene. In embodiments, $L^1$ is unsubstituted $C_3$-$C_6$ cycloalkylene. In embodiments, $L^1$ is unsubstituted 3 to 6 membered heterocycloalkylene. In embodiments, $L^1$ is unsubstituted phenylene. In embodiments, $L^1$ is unsubstituted 5 to 6 membered heteroarylene. In embodiments, $L^1$ is $R^{23}$-substituted $C_1$-$C_{10}$ alkylene. In embodiments, $L^1$ is $R^{23}$-substituted 2 to 10 membered heteroalkylene. In embodiments, $L^1$ is $R^{23}$-substituted $C_4$-$C_6$ cycloalkylene. In embodiments, $L^1$ is $R^{23}$-substituted 4 to 6 membered heterocycloalkylene. In embodiments, $L^1$ is $R^{23}$-substituted phenylene. In embodiments, $L^1$ is $R^{23}$-substituted 5 membered heteroarylene. In embodiments, $L^1$ is $R^{23}$-substituted $C_1$-$C_8$ alkylene. In embodiments, $L^1$ is $R^{23}$-substituted 2 to 8 membered heteroalkylene. In embodiments, $L^1$ is $R^{23}$-substituted $C_5$-$C_6$ cycloalkylene. In embodiments, $L^1$ is $R^{23}$-substituted 5 to 6 membered heterocycloalkylene. In embodiments, $L^1$ is $R^{23}$-substituted 6 membered heteroarylene. In embodiments, $L^1$ is $R^{23}$-substituted $C_1$-$C_6$ alkylene. In embodiments, $L^1$ is $R^{23}$-substituted 2 to 6 membered heteroalkylene. In embodiments, $L^1$ is $R^{23}$-substituted $C_6$-$C_{20}$ alkylene. In embodiments, $L^1$ is $R^{23}$-substituted 6 to 20 membered heteroalkylene. In embodiments, $L^1$ is unsubstituted $C_1$-$C_{10}$ alkylene. In embodiments, $L^1$ is unsubstituted 2 to 10 membered heteroalkylene. In embodiments, $L^1$ is unsubstituted $C_4$-$C_6$ cycloalkylene. In embodiments, $L^1$ is unsubstituted 4 to 6 membered heterocycloalkylene. In embodiments, $L^1$ is unsubstituted phenylene. In embodiments, $L^1$ is unsubstituted 5 membered heteroarylene. In embodiments, $L^1$ is unsubstituted $C_1$-$C_8$ alkylene. In embodiments, $L^1$ is unsubstituted 2 to 8 membered heteroalkylene. In embodiments, $L^1$ is unsubstituted $C_5$-$C_6$ cycloalkylene. In embodiments, $L^1$ is unsubstituted 5 to 6 membered heterocycloalkylene. In embodiments, $L^1$ is unsubstituted 6 membered heteroarylene. In embodiments, $L^1$ is unsubstituted $C_1$-$C_6$ alkylene. In embodiments, $L^1$ is unsubstituted 2 to 6 membered heteroalkylene. In embodiments, $L^1$ is unsubstituted $C_6$-$C_{20}$ alkylene. In embodiments, $L^1$ is unsubstituted 6 to 20 membered heteroalkylene.

$R^{23}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In embodiments, $R^{23}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered).

In embodiments, $R^{23}$ is independently —$NH_2$. In embodiments, $R^{23}$ is independently —OH. In embodiments, $R^{23}$ is independently halogen. In embodiments, $R^{23}$ is independently —CN. In embodiments, $R^{23}$ is independently oxo. In embodiments, $R^{23}$ is independently —$CF_3$. In embodiments, $R^{23}$ is independently —COOH. In embodiments, $R^{23}$ is independently —$CONH_2$. In embodiments, $R^{23}$ is independently —$NO_2$. In embodiments, $R^{23}$ is independently —SH. In embodiments, $R^{23}$ is independently —$SO_3H$. In embodiments, $R^{23}$ is independently —$SO_4H$. In embodiments, $R^{23}$ is independently —$SO_2NH_2$. In embodiments, $R^{23}$ is independently —$NHNH_2$. In embodiments, $R^{23}$ is independently —$ONH_2$. In embodiments, $R^{23}$ is independently —NHC(O)$NHNH_2$. In embodiments, $R^{23}$ is independently —NHC(O)$NH_2$. In embodiments, $R^{23}$ is independently —$NHSO_2H$. In embodiments, $R^{23}$ is independently —NHC(O)H. In embodiments, $R^{23}$ is independently —NHC(O)OH. In embodiments, $R^{23}$ is independently —NHOH. In embodiments, $R^{23}$ is independently —$OCF_3$. In embodiments, $R^{23}$ is independently —$OCHF_2$. In embodiments, $R^{23}$ is independently —$CCl_3$. In embodiments, $R^{23}$ is independently —$CBr_3$. In embodiments, $R^{23}$ is independently —$CI_3$. In embodiments, $R^{23}$ is independently —F. In embodiments, $R^{23}$ is independently —Cl. In embodiments, $R^{23}$ is independently —Br. In embodiments, $R^{23}$ is independently —I. In embodiments, $R^{23}$ is independently $R^{24}$-substituted $C_1$-$C_4$ alkyl. In embodiments, $R^{23}$ is independently $R^{24}$-substituted 2 to 4 membered heteroalkyl. In embodiments, $R^{23}$ is independently $R^{24}$-substituted $C_3$-$C_6$ cycloalkyl. In embodiments, $R^{23}$ is independently $R^{24}$-substituted 3 to 6 membered heterocycloalkyl. In embodiments, $R^{23}$ is independently $R^{24}$-substituted phenyl. In embodiments, $R^{23}$ is independently $R^{24}$-substituted 5 to 6 membered heteroaryl. In embodiments, $R^{23}$ is independently unsubstituted $C_1$-$C_4$ alkyl. In embodiments, $R^{23}$ is independently unsubstituted 2 to 4 membered heteroalkyl. In embodiments, $R^{23}$ is independently unsubstituted $C_3$-$C_6$ cycloalkyl. In embodiments, $R^{23}$ is independently unsubstituted 3 to 6 membered heterocycloalkyl. In embodiments, $R^{23}$ is independently unsubstituted phenyl. In embodiments, $R^{23}$ is independently unsubstituted 5 to 6 membered heteroaryl.

$R^{24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In embodiments, $R^{24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 8 membered, 3 to 6 membered, 4 to 6 membered, 4 to 5 membered, or 5 to 6 membered), $R^{25}$-substituted or unsubstituted aryl (e.g., $C_6$—$C_{10}$ or phenyl), or $R^{25}$-substituted or unsubstituted heteroaryl (e.g., 5 to 10 membered, 5 to 9 membered, or 5 to 6 membered).

In embodiments, $R^{24}$ is independently —$NH_2$. In embodiments, $R^{24}$ is independently —OH. In embodiments, $R^{24}$ is independently halogen. In embodiments, $R^{24}$ is independently —CN. In embodiments, $R^{24}$ is independently oxo. In embodiments, $R^{24}$ is independently —$CF_3$. In embodiments, $R^{24}$ is independently —COOH. In embodiments, $R^{24}$ is independently —$CONH_2$. In embodiments, $R^{24}$ is independently —$NO_2$. In embodiments, $R^{24}$ is independently —SH. In embodiments, $R^{24}$ is independently —$SO_3H$. In embodiments, $R^{24}$ is independently —$SO_4H$. In embodiments, $R^{24}$ is independently —$SO_2NH_2$. In embodiments, $R^{24}$ is independently —$NHNH_2$. In embodiments, $R^{24}$ is independently —$ONH_2$. In embodiments, $R^{24}$ is independently —NHC(O)$NHNH_2$. In embodiments, $R^{24}$ is independently —NHC(O)$NH_2$. In embodiments, $R^{24}$ is independently —$NHSO_2H$. In embodiments, $R^{24}$ is independently —NHC(O)H. In embodiments, $R^{24}$ is independently —NHC(O)OH. In embodiments, $R^{24}$ is independently —NHOH. In embodiments, $R^{24}$ is independently —$OCF_3$. In embodiments, $R^{24}$ is independently —$OCHF_2$. In embodiments, $R^{24}$ is independently —$CCl_3$. In embodiments, $R^{24}$ is independently —$CBr_3$. In embodiments, $R^{24}$ is independently —$CI_3$. In embodiments, $R^{24}$ is independently —F. In embodiments, $R^{24}$ is independently —Cl. In embodiments, $R^{24}$ is independently —Br. In embodiments, $R^{24}$ is independently —I. In embodiments, $R^{24}$ is independently $R^{25}$-substituted $C_1$-$C_4$ alkyl. In embodiments, $R^{24}$ is independently $R^{25}$-substituted 2 to 4 membered heteroalkyl. In embodiments, $R^{24}$ is independently $R^{25}$-substituted $C_3$-$C_6$ cycloalkyl. In embodiments, $R^{24}$ is independently $R^{25}$-substituted 3 to 6 membered heterocycloalkyl. In embodiments, $R^{24}$ is independently $R^{25}$-substituted phenyl. In embodiments, $R^{24}$ is independently $R^{25}$-substituted 5 to 6 membered heteroaryl. In embodiments, $R^{24}$ is independently unsubstituted $C_1$-$C_4$ alkyl. In embodiments, $R^{24}$ is independently unsubstituted 2 to 4 membered heteroalkyl. In embodiments, $R^{24}$ is independently unsubstituted $C_3$-$C_6$ cycloalkyl. In embodiments, $R^{24}$ is independently unsubstituted 3 to 6 membered heterocycloalkyl. In embodiments, $R^{24}$ is independently unsubstituted phenyl. In embodiments, $R^{24}$ is independently unsubstituted 5 to 6 membered heteroaryl.

In embodiments, $L^2$ is independently a bond, $R^{26}$-substituted or unsubstituted alkylene, $R^{26}$-substituted or unsubstituted heteroalkylene, $R^{26}$-substituted or unsubstituted cycloalkylene, $R^{26}$-substituted or unsubstituted heterocycloalkylene, $R^{26}$-substituted or unsubstituted arylene, or $R^{26}$-substituted or unsubstituted heteroarylene.

In embodiments, $L^2$ is independently bond, $R^{26}$-substituted or unsubstituted alkylene, $R^{26}$-substituted or unsubstituted heteroalkylene, $R^{26}$-substituted or unsubstituted cycloalkylene, $R^{26}$-substituted or unsubstituted heterocycloalkylene, $R^{26}$-substituted or unsubstituted arylene, or $R^{26}$-substituted or unsubstituted heteroarylene.

In embodiments, $L^2$ is a bond, —NH—, —$NR^{26}$—, —S—, —O—, —C(O)—, —NHC(O)—, —C(O)NH—, —NHC(O)NH—, —NHC(NH)NH—, —C(S)—, $R^{26}$-substituted or unsubstituted $C_1$-$C_{20}$ alkylene, $R^{26}$-substituted or unsubstituted 2 to 20 membered heteroalkylene, $R^{26}$-substituted or unsubstituted $C_3$-$C_8$ cycloalkylene, $R^{26}$-substituted or unsubstituted 3 to 8 membered heterocycloalkylene, $R^{26}$-substituted or unsubstituted $C_6$-$C_{10}$ arylene, or $R^{26}$-substituted or unsubstituted 5 to 10 membered heteroarylene. In embodiments, $L^2$ is a bond. In embodiments, $L^2$ is —NH—. In embodiments, $L^2$ is —$NR^{26}$—. In embodiments, $L^2$ is —S—. In embodiments, $L^2$ is —O—. In embodiments, $L^2$ is —C(O)—. In embodiments, $L^2$ is —NHC(O)—. In embodiments, $L^2$ is —C(O)NH—. In embodiments, $L^2$ is —NHC(O)NH—. In embodiments, $L^2$ is —NHC(NH)NH—. In embodiments, $L^2$ is —C(S)—. In embodiments, $L^2$ is $R^{26}$-substituted or unsubstituted $C_1$-$C_{20}$ alkylene. In embodiments, $L^2$ is $R^{26}$-substituted or unsubstituted 2 to 20 membered heteroalkylene. In embodiments, $L^2$ is $R^{26}$-substituted or unsubstituted $C_3$-$C_8$ cycloalkylene. In embodiments, $L^2$ is $R^{26}$-substituted or unsubstituted 3 to 8 membered heterocycloalkylene. In embodiments, $L^2$ is $R^{26}$-substituted or unsubstituted $C_6$-$C_{10}$ arylene. In embodiments, $L^2$ is $R^{26}$-substituted or unsubstituted 5 to 10 membered heteroarylene. In embodiments, $L^2$ is $R^{26}$-substituted $C_1$-$C_{20}$ alkylene. In embodiments, $L^2$ is $R^{26}$-substituted 2 to 20 membered heteroalkylene. In embodiments, $L^2$ is $R^{26}$-substituted $C_3$-$C_8$ cycloalkylene. In embodiments, $L^2$ is $R^{26}$-substituted 3 to 8 membered heterocycloalkylene. In embodiments, $L^2$ is $R^{26}$-substituted $C_6$-$C_{10}$ arylene. In embodiments, $L^2$ is $R^{26}$-substituted 5 to 10 membered heteroarylene. In embodiments, $L^2$ is unsubstituted $C_1$-$C_{20}$ alkylene. In embodiments, $L^2$ is unsubstituted 2 to 20 membered heteroalkylene. In embodiments, $L^2$ is unsubstituted $C_3$-$C_8$ cycloalkylene. In embodiments, $L^2$ is unsubstituted 3 to 8 membered heterocycloalkylene. In embodiments, $L^2$ is unsubstituted $C_6$-$C_{10}$ arylene. In embodiments, $L^2$ is unsubstituted 5 to 10 membered heteroarylene. In embodiments, $L^2$ is $R^{26}$-substituted $C_1$-$C_{15}$ alkylene. In embodiments, $L^2$ is $R^{26}$-substituted 2 to 15 membered heteroalkylene. In embodiments, $L^2$ is $R^{26}$-substituted $C_3$-$C_6$ cycloalkylene. In embodiments, $L^2$ is $R^{26}$-substituted 3 to 6 membered heterocycloalkylene. In embodiments, $L^2$ is $R^{26}$-substituted phenylene. In embodiments, $L^2$ is $R^{26}$-substituted 5 to 6 membered heteroarylene. In embodiments, $L^2$ is unsubstituted $C_1$-$C_{15}$ alkylene. In embodiments, $L^2$ is unsubstituted 2 to 15 membered heteroalkylene. In embodiments, $L^2$ is unsubstituted $C_3$-$C_6$ cycloalkylene. In embodiments, $L^2$ is unsubstituted 3 to 6 membered heterocycloalkylene. In embodiments, $L^2$ is unsubstituted phenylene. In embodiments, $L^2$ is unsubstituted 5 to 6 membered heteroarylene. In embodiments, $L^2$ is $R^{26}$-substituted $C_1$-$C_{10}$ alkylene. In embodiments, $L^2$ is $R^{26}$-substituted 2 to 10 membered heteroalkylene. In embodiments, $L^2$ is $R^{26}$-substituted $C_4$-$C_6$ cycloalkylene. In embodiments, $L^2$ is $R^{26}$-substituted 4 to 6 membered heterocycloalkylene. In embodiments, $L^2$ is $R^{26}$-substituted phenylene. In embodiments, $L^2$ is $R^{26}$-substituted 5 membered heteroarylene. In embodiments, $L^2$ is $R^{26}$-substituted $C_1$-$C_8$ alkylene. In embodiments, $L^2$ is $R^{26}$-substituted 2 to 8 membered heteroalkylene. In embodiments, $L^2$ is $R^{26}$-substituted $C_5$-$C_6$ cycloalkylene. In embodiments, $L^2$ is $R^{26}$-substituted 5 to 6 membered heterocycloalkylene. In embodiments, $L^2$ is $R^{26}$-substituted 6 membered heteroarylene. In embodiments, $L^2$ is $R^{26}$-substituted $C_1$-$C_6$ alkylene. In embodiments, $L^2$ is $R^{26}$-substituted 2 to 6 membered heteroalkylene. In embodiments, $L^2$ is $R^{26}$-substituted $C_6$-$C_{20}$ alkylene. In embodiments, $L^2$ is $R^{26}$-substituted 6 to 20 membered heteroalkylene. In embodiments, $L^2$ is unsubstituted $C_1$-$C_{10}$ alkylene. In embodiments, $L^2$ is unsubstituted 2 to 10 membered heteroalkylene. In embodiments, $L^2$ is unsubstituted $C_4$-$C_6$ cycloalkylene. In embodiments, $L^2$ is unsubstituted 4 to 6 membered heterocycloalkylene. In embodiments, $L^2$ is unsubstituted phenylene. In embodiments, $L^2$ is unsubstituted 5 membered heteroarylene. In embodiments, $L^2$ is unsubstituted $C_1$-$C_8$ alkylene. In embodiments, $L^2$ is unsubstituted 2 to 8 membered heteroalkylene. In embodiments, $L^2$ is unsubstituted $C_5$-$C_6$ cycloalkylene. In embodiments, $L^2$ is unsubstituted 5 to 6 membered heterocycloalkylene. In embodiments, $L^2$ is unsubstituted 6 membered heteroarylene. In embodiments, $L^2$ is unsubstituted $C_1$-$C_6$ alkylene. In embodiments, $L^2$ is unsubstituted 2 to 6 membered heteroalkylene. In embodiments, $L^2$ is unsubstituted $C_6$-$C_{20}$ alkylene. In embodiments, $L^2$ is unsubstituted 6 to 20 membered heteroalkylene.

$R^{26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$ substituted or unsubstituted heterocycloalkyl, $R^{27}$-substituted or unsubstituted aryl, or $R^{27}$-substituted or unsubstituted heteroaryl.

In embodiments, $R^{26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, 2 to 3 membered, or 4 to 5 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 8 membered, 3 to 6 membered, 4 to 6 membered, 4 to 5 membered, or 5 to 6 membered), $R^{27}$-substituted or unsubstituted aryl (e.g., $C_6$-$C_{10}$ or phenyl), or $R^{27}$-substituted or unsubstituted heteroaryl (e.g., 5 to 10 membered, 5 to 9 membered, or 5 to 6 membered).

In embodiments, $R^{26}$ is independently —$NH_2$. In embodiments, $R^{26}$ is independently —OH. In embodiments, $R^{26}$ is independently halogen. In embodiments, $R^{26}$ is independently —CN. In embodiments, $R^{26}$ is independently oxo. In embodiments, $R^{26}$ is independently —$CF_3$. In embodiments, $R^{26}$ is independently —COOH. In embodiments, $R^{26}$ is independently —$CONH_2$. In embodiments, $R^{26}$ is independently —$NO_2$. In embodiments, $R^{26}$ is independently —SH. In embodiments, $R^{26}$ is independently —$SO_3H$. In embodiments, $R^{26}$ is independently —$SO_4H$. In embodiments, $R^{26}$ is independently —$SO_2NH_2$. In embodiments, $R^{26}$ is independently —$NHNH_2$. In embodiments, $R^{26}$ is independently —$ONH_2$. In embodiments, $R^{26}$ is independently —NHC(O)$NHNH_2$. In embodiments, $R^{26}$ is independently —NHC(O)$NH_2$. In embodiments, $R^{26}$ is independently —$NHSO_2H$. In embodiments, $R^{26}$ is independently —NHC(O)H. In embodiments, $R^{26}$ is independently —NHC(O)OH. In embodiments, $R^{26}$ is independently —NHOH. In embodiments, $R^{26}$ is independently —$OCF_3$. In embodiments, $R^{26}$ is independently —$OCHF_2$. In embodiments, $R^{26}$ is independently —$CCl_3$. In embodiments, $R^{26}$ is independently —$CBr_3$. In embodiments, $R^{26}$ is independently —$CI_3$. In embodiments, $R^{26}$ is independently —F. In embodiments, $R^{26}$ is independently —Cl. In embodiments, $R^{26}$ is independently —Br. In embodiments, $R^{26}$ is independently —I. In embodiments, $R^{26}$ is independently $R^{27}$-substituted $C_1$-$C_4$ alkyl. In embodiments, $R^{26}$ is independently $R^{27}$-substituted 2 to 4 membered heteroalkyl. In embodiments, $R^{26}$ is independently $R^{27}$-substituted $C_3$-$C_6$ cycloalkyl. In embodiments, $R^{26}$ is independently $R^{27}$-substituted 3 to 6 membered heterocycloalkyl. In embodiments, $R^{26}$ is independently $R^{27}$-substituted phenyl. In embodiments, $R^{26}$ is independently $R^{27}$-substituted 5 to 6 membered heteroaryl. In embodiments, $R^{26}$ is independently unsubstituted $C_1$-$C_4$ alkyl. In embodiments, $R^{26}$ is independently unsubstituted 2 to 4 membered heteroalkyl. In embodiments, $R^{26}$ is independently unsubstituted $C_3$-$C_6$ cycloalkyl. In embodiments, $R^{26}$ is independently unsubstituted 3 to 6 membered heterocycloalkyl. In embodiments, $R^{26}$ is independently unsubstituted phenyl. In embodiments, $R^{26}$ is independently unsubstituted 5 to 6 membered heteroaryl.

$R^{27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In embodiments, $R^{27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, 2 to 3 membered, or 4 to 5 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 8 membered, 3 to 6 membered, 4 to 6 membered, 4 to 5 membered, or 5 to 6 membered), $R^{28}$-substituted or unsubstituted aryl (e.g., $C_6$-$C_{10}$ or phenyl), or $R^{28}$-substituted or unsubstituted heteroaryl (e.g., 5 to 10 membered, 5 to 9 membered, or 5 to 6 membered).

In embodiments, R''' is independently —$NH_2$. In embodiments, $R^{27}$ is independently —OH. In embodiments, $R^{27}$ is independently halogen. In embodiments, $R^{27}$ is independently —CN. In embodiments, $R^{27}$ is independently oxo. In embodiments, $R^{27}$ is independently —$CF_3$. In embodiments, $R^{27}$ is independently —COOH. In embodiments, $R^{27}$ is independently —$CONH_2$. In embodiments, $R^{27}$ is independently —$NO_2$. In embodiments, $R^{27}$ is independently —SH. In embodiments, $R^{27}$ is independently —$SO_3H$. In embodiments, $R^{27}$ is independently —$SO_4H$. In embodiments, $R^{27}$ is independently —$SO_2NH_2$. In embodiments, $R^{27}$ is independently —$NHNH_2$. In embodiments, $R^{27}$ is independently —$ONH_2$. In embodiments, $R^{27}$ is independently —NHC(O)$NHNH_2$. In embodiments, $R^{27}$ is independently —NHC(O)$NH_2$. In embodiments, $R^{27}$ is independently —$NHSO_2H$. In embodiments, $R^{27}$ is independently —NHC(O)H. In embodiments, $R^{27}$ is independently —NHC(O)—OH. In embodiments, $R^{27}$ is independently —NHOH. In embodiments, $R^{27}$ is independently —$OCF_3$. In embodiments, $R^{27}$ is independently —$OCHF_2$. In embodiments, $R^{27}$ is independently —$CCl_3$. In embodiments, $R^{27}$ is independently —$CBr_3$. In embodiments, $R^{27}$ is independently —$CI_3$. In embodiments, $R^{27}$ is independently —F. In embodiments, $R^{27}$ is independently —Cl. In embodiments, $R^{27}$ is independently —Br. In embodiments, $R^{27}$ is independently —I. In embodiments, $R^{27}$ is independently $R^{28}$-substituted $C_1$-$C_4$ alkyl. In embodiments, $R^{27}$ is independently $R^{28}$-substituted 2 to 4 membered heteroalkyl. In embodiments, $R^{27}$ is independently $R^{28}$-substituted $C_3$-$C_6$ cycloalkyl. In embodiments, $R^{27}$ is independently $R^{28}$-substituted 3 to 6 membered heterocycloalkyl. In embodiments, $R^{27}$ is independently $R^{28}$-substituted phenyl. In embodiments, $R^{27}$ is independently $R^{28}$-substituted 5 to 6 membered heteroaryl. In embodiments, $R^{27}$ is independently unsubstituted $C_1$-$C_4$ alkyl. In embodiments, $R^{27}$ is independently unsubstituted 2 to 4 membered heteroalkyl. In embodiments, $R^{27}$ is independently unsubstituted $C_3$-$C_6$ cycloalkyl. In embodiments, $R^{27}$ is independently unsubstituted 3 to 6 membered heterocycloalkyl. In embodiments, $R^{27}$ is independently unsubstituted phenyl. In embodiments, $R^{27}$ is independently unsubstituted 5 to 6 membered heteroaryl.

In embodiments, $L^3$ is independently a bond, $R^{29}$-substituted or unsubstituted alkylene, $R^{29}$-substituted or unsubstituted heteroalkylene, $R^{29}$-substituted or unsubstituted cycloalkylene, $R^{29}$-substituted or unsubstituted heterocycloalkylene, $R^{29}$-substituted or unsubstituted arylene, or $R^{29}$-substituted or unsubstituted heteroarylene.

In embodiments, $L^3$ is a bond, —NH—, —$NR^{29}$—, —S—, —O—, —C(O)—, —NHC(O)—, —C(O)NH—, —NHC(O)NH—, —NHC(NH)NH—, —C(S)—, $R^{29}$-substituted or unsubstituted $C_1$-$C_{20}$ alkylene, $R^{29}$-substituted or unsubstituted 2 to 20 membered heteroalkylene, $R^{29}$-substituted or unsubstituted $C_3$-$C_8$ cycloalkylene, $R^{29}$-substituted or unsubstituted 3 to 8 membered heterocycloalkylene, $R^{29}$-substituted or unsubstituted $C_6$-$C_{10}$ arylene, or $R^{29}$-substituted or unsubstituted 5 to 10 membered heteroarylene. In embodiments, $L^3$ is a bond. In embodiments, $L^3$ is —NH—. In embodiments, $L^3$ is —$NR^{29}$—. In embodiments, $L^3$ is —S—. In embodiments, $L^3$ is —O—. In embodiments, $L^3$ is —C(O)—. In embodiments, $L^3$ is —NHC(O)—. In embodiments, $L^3$ is —C(O)NH—. In embodiments, $L^3$ is —NHC(O)NH—. In embodiments, $L^3$ is —NHC(NH)NH—. In embodiments, $L^3$ is —C(S)—. In embodiments, $L^3$ is $R^{29}$-substituted or unsubstituted $C_1$-$C_{20}$ alkylene. In embodiments, $L^3$ is $R^{29}$-substituted or unsubstituted 2 to 20 membered heteroalkylene. In embodiments, $L^3$ is $R^{29}$-substituted or unsubstituted $C_3$-$C_8$ cycloalkylene. In embodiments, $L^3$ is $R^{29}$-substituted or unsubstituted 3 to 8 membered heterocycloalkylene. In embodiments, $L^3$ is $R^{29}$-substituted or unsubstituted $C_6$-$C_{10}$ arylene. In embodiments, $L^3$ is $R^{29}$-substituted or unsubstituted 5 to 10 membered heteroarylene. In embodiments, $L^3$ is $R^{29}$-substituted $C_1$-$C_{20}$ alkylene. In embodiments, $L^3$ is $R^{29}$-substituted 2 to 20 membered heteroalkylene. In embodiments, $L^3$ is $R^{29}$-substituted $C_3$-$C_8$ cycloalkylene. In embodiments, $L^3$ is $R^{29}$-substituted 3 to 8 membered heterocycloalkylene. In embodiments, $L^3$ is $R^{29}$-substituted $C_6$-$C_{10}$ arylene. In embodiments, $L^3$ is $R^{29}$-substituted 5 to 10 membered heteroarylene. In embodiments, $L^3$ is unsubstituted $C_1$-$C_{20}$ alkylene. In embodiments, $L^3$ is unsubstituted 2 to 20 membered heteroalkylene. In embodiments, $L^3$ is unsubstituted $C_3$-$C_8$ cycloalkylene. In embodiments, $L^3$ is unsubstituted 3 to 8 membered heterocycloalkylene. In embodiments, $L^3$ is unsubstituted $C_6$-$C_{10}$ arylene. In embodiments, $L^3$ is unsubstituted 5 to 10 membered heteroarylene. In embodiments, $L^3$ is $R^{29}$-substituted $C_1$-$C_{15}$ alkylene. In embodiments, $L^3$ is $R^{29}$-substituted 2 to 15 membered heteroalkylene. In embodiments, $L^3$ is $R^{29}$-substituted $C_3$-$C_6$ cycloalkylene. In embodiments, $L^3$ is $R^{29}$-substituted 3 to 6 membered heterocycloalkylene. In embodiments, $L^3$ is $R^{29}$-substituted phenylene. In embodiments, $L^3$ is $R^{29}$-substituted 5 to 6 membered heteroarylene. In embodiments, $L^3$ is unsubstituted $C_1$-$C_{15}$ alkylene. In embodiments, $L^3$ is unsubstituted 2 to 15 membered heteroalkylene. In embodiments, $L^3$ is unsubstituted $C_3$-$C_6$ cycloalkylene. In embodiments, $L^3$ is unsubstituted 3 to 6 membered heterocycloalkylene. In embodiments, $L^3$ is unsubstituted phenylene. In embodiments, $L^3$ is unsubstituted 5 to 6 membered heteroarylene. In embodiments, $L^3$ is $R^{29}$-substituted $C_1$-$C_{10}$ alkylene. In embodiments, $L^3$ is $R^{29}$-substituted 2 to 10 membered heteroalkylene. In embodiments, $L^3$ is $R^{29}$-substituted $C_4$-$C_6$ cycloalkylene. In embodiments, $L^3$ is $R^{29}$-substituted 4 to 6 membered heterocycloalkylene. In embodiments, $L^3$ is $R^{29}$-substituted phenylene. In embodiments, $L^3$ is $R^{29}$-substituted 5 membered heteroarylene. In embodiments, $L^3$ is $R^{29}$-substituted $C_1$-$C_8$ alkylene. In embodiments, $L^3$ is $R^{29}$-substituted 2 to 8 membered heteroalkylene. In embodiments, $L^3$ is $R^{29}$-substituted $C_5$-$C_6$ cycloalkylene. In embodiments, $L^3$ is $R^{29}$-substituted 5 to 6 membered heterocycloalkylene. In embodiments, $L^3$ is $R^{29}$-substituted 6 membered heteroarylene. In embodiments, $L^3$ is $R^{29}$-substituted $C_1$-$C_6$ alkylene. In embodiments, $L^3$ is $R^{29}$-substituted 2 to 6 membered heteroalkylene. In embodiments, $L^3$ is $R^{29}$-substituted $C_6$-$C_{20}$ alkylene. In embodiments, $L^3$ is $R^{29}$-substituted 6 to 20 membered heteroalkylene. In embodiments, $L^3$ is unsubstituted $C_1$-$C_{10}$ alkylene. In embodiments, $L^3$ is unsubstituted 2 to 10 membered heteroalkylene. In embodiments, $L^3$ is unsubstituted $C_4$-$C_6$ cycloalkylene. In embodiments, $L^3$ is unsubstituted 4 to 6 membered heterocycloalkylene. In embodiments, $L^3$ is unsubstituted phenylene. In embodiments, $L^3$ is unsubstituted 5 membered heteroarylene. In embodiments, $L^3$ is unsubstituted $C_1$-$C_8$ alkylene. In embodiments, $L^3$ is unsubstituted 2 to 8 membered heteroalkylene. In embodiments, $L^3$ is unsubstituted $C_5$-$C_6$ cycloalkylene. In embodiments, $L^3$ is unsubstituted 5 to 6 membered heterocycloalkylene. In embodiments, $L^3$ is unsubstituted 6 membered heteroarylene. In embodiments, $L^3$ is unsubstituted $C_1$-$C_6$ alkylene. In embodiments, $L^3$ is unsubstituted 2 to 6 membered heteroalkylene. In embodiments, $L^3$ is unsubstituted $C_6$-$C_{20}$ alkylene. In embodiments, $L^3$ is unsubstituted 6 to 20 membered heteroalkylene.

$R^{29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

In embodiments, $R^{29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 8 membered, 3 to 6 membered, 4 to 6 membered, 4 to 5 membered, or 5 to 6 membered), $R^{30}$-substituted or unsubstituted aryl (e.g., $C_6$-$C_{10}$ or phenyl), or $R^{30}$-substituted or unsubstituted heteroaryl (e.g., 5 to 10 membered, 5 to 9 membered, or 5 to 6 membered).

In embodiments, $R^{29}$ is independently —$NH_2$. In embodiments, $R^{29}$ is independently —OH. In embodiments, $R^{29}$ is independently halogen. In embodiments, $R^{29}$ is independently —CN. In embodiments, $R^{29}$ is independently oxo. In embodiments, $R^{29}$ is independently —$CF_3$. In embodiments, $R^{29}$ is independently —COOH. In embodiments, $R^{29}$ is independently —$CONH_2$. In embodiments, $R^{29}$ is independently —$NO_2$. In embodiments, $R^{29}$ is independently —SH. In embodiments, $R^{29}$ is independently —$SO_3H$. In embodiments, $R^{29}$ is independently —$SO_4H$. In embodiments, $R^{29}$ is independently —$SO_2NH_2$. In embodiments, $R^{29}$ is independently —$NHNH_2$. In embodiments, $R^{29}$ is independently —$ONH_2$. In embodiments, $R^{29}$ is independently —NHC(O)$NHNH_2$. In embodiments, $R^{29}$ is independently —NHC(O)$NH_2$. In embodiments, $R^{29}$ is independently —$NHSO_2H$. In embodiments, $R^{29}$ is independently —NHC(O)H. In embodiments, $R^{29}$ is independently —NHC(O)OH. In embodiments, $R^{29}$ is independently —NHOH. In embodiments, $R^{29}$ is independently —$OCF_3$. In embodiments, $R^{29}$ is independently —$OCHF_2$. In embodiments, $R^{29}$ is independently —$CCl_3$. In embodiments, $R^{29}$ is independently —$CBr_3$. In embodiments, $R^{29}$ is independently —$CI_3$. In embodiments, $R^{29}$ is independently —F. In embodiments, $R^{29}$ is independently —Cl. In embodiments, $R^{29}$ is independently —Br. In embodiments, $R^{29}$ is independently —I. In embodiments, $R^{29}$ is independently $R^{30}$-substituted $C_1$-$C_4$ alkyl. In embodiments, $R^{29}$ is independently $R^{30}$-substituted 2 to 4 membered heteroalkyl. In embodiments, $R^{29}$ is independently $R^{30}$-substituted $C_3$-$C_6$ cycloalkyl. In embodiments, $R^{29}$ is independently $R^{30}$-substituted 3 to 6 membered heterocycloalkyl. In embodiments, $R^{29}$ is independently $R^{30}$-substituted phenyl. In embodiments, $R^{29}$ is independently $R^{30}$-substituted 5 to 6 membered heteroaryl. In embodiments, $R^{29}$ is independently unsubstituted $C_1$-$C_4$ alkyl. In embodiments, $R^{29}$ is independently unsubstituted 2 to 4 membered heteroalkyl. In embodiments, $R^{29}$ is independently unsubstituted $C_3$-$C_6$ cycloalkyl. In embodiments, $R^{29}$ is independently unsubstituted 3 to 6 membered heterocycloalkyl. In embodiments, $R^{29}$ is independently unsubstituted phenyl. In embodiments, $R^{29}$ is independently unsubstituted 5 to 6 membered heteroaryl.

$R^{30}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In embodiments, $R^{30}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{31}$-substituted or unsubstituted alkyl (e.g., $C_1$-$C_8$, $C_1$-$C_6$, $C_1$-$C_4$, or $C_1$-$C_2$), $R^{31}$-substituted or unsubstituted heteroalkyl (e.g., 2 to 8 membered, 2 to 6 membered, 4 to 6 membered, 2 to 3 membered, or 4 to 5 membered), $R^{31}$-substituted or unsubstituted cycloalkyl (e.g., $C_3$-$C_8$, $C_3$-$C_6$, $C_4$-$C_6$, or $C_5$-$C_6$), $R^{31}$-substituted or unsubstituted heterocycloalkyl (e.g., 3 to 8 membered, 3 to 6 membered, 4 to 6 membered, 4 to 5 membered, or 5 to 6 membered), $R^{31}$-substituted or unsubstituted aryl (e.g., $C_6$-$C_{10}$ or phenyl), or $R^{31}$-substituted or unsubstituted heteroaryl (e.g., 5 to 10 membered, 5 to 9 membered, or 5 to 6 membered).

In embodiments, $R^{30}$ is independently —$NH_2$. In embodiments, $R^{30}$ is independently —OH. In embodiments, $R^{30}$ is independently halogen. In embodiments, $R^{30}$ is independently —CN. In embodiments, $R^{30}$ is independently oxo. In embodiments, $R^{30}$ is independently —$CF_3$. In embodiments, $R^{30}$ is independently —COOH. In embodiments, $R^{30}$ is independently —$CONH_2$. In embodiments, $R^{30}$ is independently —$NO_2$. In embodiments, $R^{30}$ is independently —SH. In embodiments, $R^{30}$ is independently —$SO_3H$. In embodiments, $R^{30}$ is independently —$SO_4H$. In embodiments, $R^{30}$ is independently —$SO_2NH_2$. In embodiments, $R^{30}$ is independently —$NHNH_2$. In embodiments, $R^{30}$ is independently —$ONH_2$. In embodiments, $R^{30}$ is independently —NHC(O)$NHNH_2$. In embodiments, $R^{30}$ is independently —NHC(O)$NH_2$. In embodiments, $R^{30}$ is independently —$NHSO_2H$. In embodiments, $R^{30}$ is independently —NHC(O)H. In embodiments, $R^{30}$ is independently —NHC(O)OH. In embodiments, $R^{30}$ is independently —NHOH. In embodiments, $R^{30}$ is independently —$OCF_3$. In embodiments, $R^{30}$ is independently —$OCHF_2$. In embodiments, $R^{30}$ is independently —$CCl_3$. In embodiments, $R^{30}$ is independently —$CBr_3$. In embodiments, $R^{30}$ is independently —$CI_3$. In embodiments, $R^{30}$ is independently —F. In embodiments, $R^{30}$ is independently —Cl. In embodiments, $R^{30}$ is independently —Br. In embodiments, $R^{30}$ is independently —I. In embodiments, $R^{30}$ is independently $R^{31}$-substituted $C_1$-$C_4$ alkyl. In embodiments, $R^{30}$ is independently $R^{31}$-substituted 2 to 4 membered heteroalkyl. In embodiments, $R^{30}$ is independently $R^{31}$-substituted $C_3$-$C_6$ cycloalkyl. In embodiments, $R^{30}$ is independently $R^{31}$-substituted 3 to 6 membered heterocycloalkyl. In embodiments, $R^{30}$ is independently $R^{31}$-substituted phenyl. In embodiments, $R^{30}$ is independently $R^{31}$-substituted 5 to 6 membered heteroaryl. In embodiments, $R^{30}$ is independently unsubstituted $C_1$-$C_4$ alkyl. In embodiments, $R^{30}$ is independently unsubstituted 2 to 4 membered heteroalkyl. In embodiments, $R^{30}$ is independently unsubstituted $C_3$-$C_6$ cycloalkyl. In embodiments, $R^{30}$ is independently unsubstituted 3 to 6 membered heterocycloalkyl. In embodiments, $R^{30}$ is independently unsubstituted phenyl. In embodiments, $R^{30}$ is independently unsubstituted 5 to 6 membered heteroaryl.

In some embodiments of the compounds provided herein, $L^4$ is independently a bond, $R^{32}$-substituted or unsubstituted alkylene, $R^{32}$-substituted or unsubstituted heteroalkylene, $R^{32}$-substituted or unsubstituted cycloalkylene, $R^{32}$-substituted or unsubstituted heterocycloalkylene, $R^{32}$-substituted or unsubstituted arylene, or $R^{32}$-substituted or unsubstituted heteroarylene.

In embodiments, $L^4$ is a bond, —NH—, —$NR^{32}$—, —S—, —O—, —C(O)—, —NHC(O)—, —C(O)NH—, —NHC(O)NH—, —NHC(NH)NH—, —C(S)—, $R^{32}$-substituted or unsubstituted $C_1$-$C_{20}$ alkylene, $R^{32}$-substituted or unsubstituted 2 to 20 membered heteroalkylene, $R^{32}$-substituted or unsubstituted $C_3$-$C_8$ cycloalkylene, $R^{32}$-substituted or unsubstituted 3 to 8 membered heterocycloalkylene, $R^{32}$-substituted or unsubstituted $C_6$-$C_{10}$ arylene, or $R^{32}$-substituted or unsubstituted 5 to 10 membered heteroarylene. In embodiments, $L^4$ is a bond. In embodiments, $L^4$ is —NH—. In embodiments, $L^4$ is —$NR^{32}$—. In embodiments, $L^4$ is —S—. In embodiments, $L^4$ is —O—. In embodiments, $L^4$ is —C(O)—. In embodiments, $L^4$ is —NHC(O)—. In embodiments, $L^4$ is —C(O)NH—. In embodiments, $L^4$ is —NHC(O)NH—. In embodiments, $L^4$ is —NHC(NH)NH—. In embodiments, $L^4$ is —C(S)—. In embodiments, $L^4$ is $R^{32}$-substituted or unsubstituted $C_1$-$C_{20}$ alkylene. In embodiments, $L^4$ is $R^{32}$-substituted or unsubstituted 2 to 20 membered heteroalkylene. In embodiments, $L^4$ is $R^{32}$-substituted or unsubstituted $C_3$-$C_8$ cycloalkylene. In embodiments, $L^4$ is $R^{32}$-substituted or unsubstituted 3 to 8 membered heterocycloalkylene. In embodiments, $L^4$ is $R^{32}$-substituted or unsubstituted $C_6$-$C_{10}$ arylene. In embodiments, $L^4$ is $R^{32}$-substituted or unsubstituted 5 to 10 membered heteroarylene. In embodiments, $L^4$ is $R^{32}$-substituted $C_1$-$C_{20}$ alkylene. In embodiments, $L^4$ is $R^{32}$-substituted 2 to 20 membered heteroalkylene. In embodiments, $L^4$ is $R^{32}$-substituted $C_3$-$C_8$ cycloalkylene. In embodiments, $L^4$ is $R^{32}$-substituted 3 to 8 membered heterocycloalkylene. In embodiments, $L^4$ is $R^{32}$-substituted $C_6$-$C_{10}$ arylene. In embodiments, $L^4$ is $R^{32}$-substituted 5 to 10 membered heteroarylene. In embodiments, $L^4$ is unsubstituted $C_1$-$C_{20}$ alkylene. In embodiments, $L^4$ is unsubstituted 2 to 20 membered heteroalkylene. In embodiments, $L^4$ is unsubstituted $C_3$-$C_8$ cycloalkylene. In embodiments, $L^4$ is unsubstituted 3 to 8 membered heterocycloalkylene. In embodiments, $L^4$ is unsubstituted $C_6$-$C_{10}$ arylene. In embodiments, $L^4$ is unsubstituted 5 to 10 membered heteroarylene. In embodiments, $L^4$ is $R^{32}$-substituted $C_1$-$C_{15}$ alkylene. In embodiments, $L^4$ is $R^{32}$-substituted 2 to 15 membered heteroalkylene. In embodiments, $L^4$ is $R^{32}$-substituted $C_3$-$C_6$ cycloalkylene. In embodiments, $L^4$ is $R^{32}$-substituted 3 to 6 membered heterocycloalkylene. In embodiments, $L^4$ is $R^{32}$-substituted phenylene. In embodiments, $L^4$ is $R^{32}$-substituted 5 to 6 membered heteroarylene. In embodiments, $L^4$ is unsubstituted $C_1$-$C_{15}$ alkylene. In embodiments, $L^4$ is unsubstituted 2 to 15 membered heteroalkylene. In embodiments, $L^4$ is unsubstituted $C_3$-$C_6$ cycloalkylene. In embodiments, $L^4$ is unsubstituted 3 to 6 membered heterocycloalkylene. In embodiments, $L^4$ is unsubstituted phenylene. In embodiments, $L^4$ is unsubstituted 5 to 6 membered heteroarylene. In embodiments, $L^4$ is $R^{32}$-substituted $C_1$-$C_{10}$ alkylene. In embodiments, $L^4$ is $R^{32}$-substituted 2 to 10 membered heteroalkylene. In embodiments, $L^4$ is $R^{32}$-substituted $C_4$-$C_6$ cycloalkylene. In embodiments, $L^4$ is $R^{32}$-substituted 4 to 6 membered heterocycloalkylene. In embodiments, $L^4$ is $R^{32}$-substituted phenylene. In embodiments, $L^4$ is $R^{32}$-substituted 5 membered heteroarylene. In embodiments, $L^4$ is $R^{32}$-substituted $C_1$-$C_8$ alkylene. In embodiments, $L^4$ is $R^{32}$-substituted 2 to 8 membered heteroalkylene. In embodiments, $L^4$ is $R^{32}$-substituted $C_5$-$C_6$ cycloalkylene. In embodiments, $L^4$ is $R^{32}$-substituted 5 to 6 membered heterocycloalkylene. In embodiments, $L^4$ is $R^{32}$-substituted 6 membered heteroarylene. In embodiments, $L^4$ is $R^{32}$-substituted $C_1$-$C_6$ alkylene. In embodiments, $L^4$ is $R^{32}$-substituted 2 to 6 membered heteroalkylene. In embodiments, $L^4$ is $R^{32}$-substituted $C_6$-$C_{20}$ alkylene. In embodiments, $L^4$ is $R^{32}$-substituted 6 to 20 membered heteroalkylene. In embodiments, $L^4$ is unsubstituted $C_1$-$C_{10}$ alkylene. In embodiments, $L^4$ is unsubstituted 2 to 10 membered heteroalkylene. In embodiments, $L^4$ is unsubstituted $C_4$-$C_6$ cycloalkylene. In embodiments, $L^4$ is unsubstituted 4 to 6 membered heterocycloalkylene. In embodiments, $L^4$ is unsubstituted phenylene. In embodiments, $L^4$ is unsubstituted 5 membered heteroarylene. In embodiments, $L^4$ is unsubstituted $C_1$-$C_8$ alkylene. In embodiments, $L^4$ is unsubstituted 2 to 8 membered heteroalkylene. In embodiments, $L^4$ is unsubstituted $C_5$-$C_6$ cycloalkylene. In embodiments, $L^4$ is unsubstituted 5 to 6 membered heterocycloalkylene. In embodiments, $L^4$ is unsubstituted 6 membered heteroarylene. In embodiments, $L^4$ is unsubstituted $C_1$-$C_6$ alkylene. In embodiments, $L^4$ is unsubstituted 2 to 6 membered heteroalkylene. In embodiments, $L^4$ is unsubstituted $C_6$-$C_{20}$ alkylene. In embodiments, $L^4$ is unsubstituted 6 to 20 membered heteroalkylene.

$R^{32}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In embodiments, $R^{32}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, 2 to 3 membered, or 4 to 5 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 8 membered, 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered).

In embodiments, $R^{32}$ is independently —$NH_2$. In embodiments, $R^{32}$ is independently —OH. In embodiments, $R^{32}$ is independently halogen. In embodiments, $R^{32}$ is independently —CN. In embodiments, $R^{32}$ is independently oxo. In embodiments, $R^{32}$ is independently —$CF_3$. In embodiments, $R^{32}$ is independently —COOH. In embodiments, $R^{32}$ is independently —$CONH_2$. In embodiments, $R^{32}$ is independently —$NO_2$. In embodiments, $R^{32}$ is independently —SH. In embodiments, $R^{32}$ is independently —$SO_3$H. In embodiments, $R^{32}$ is independently —$SO_4$H. In embodiments, $R^{32}$ is independently $—SO_2NH_2$. In embodiments, $R^{32}$ is independently —NHNH$_2$. In embodiments, $R^{32}$ is independently $—ONH_2$. In embodiments, $R^{32}$ is independently —NHC(O)NHNH$_2$. In embodiments, $R^{32}$ is independently —NHC(O)NH$_2$. In embodiments, $R^{32}$ is independently $—NHSO_2H$. In embodiments, $R^{32}$ is independently —NHC(O)H. In embodiments, $R^{32}$ is independently —NHC(O)OH. In embodiments, $R^{32}$ is independently —NHOH. In embodiments, $R^{32}$ is independently $—OCF_3$. In embodiments, $R^{32}$ is independently $—OCHF_2$. In embodiments, $R^{32}$ is independently $—CCl_3$. In embodiments, $R^{32}$ is independently $—CBr_3$. In embodiments, $R^{32}$ is independently $—CI_3$. In embodiments, $R^{32}$ is independently —F. In embodiments, $R^{32}$ is independently —Cl. In embodiments, $R^{32}$ is independently —Br. In embodiments, $R^{32}$ is independently —I. In embodiments, $R^{32}$ is independently $R^{33}$-substituted $C_1$-$C_4$ alkyl. In embodiments, $R^{32}$ is independently $R^{33}$-substituted 2 to 4 membered heteroalkyl. In embodiments, $R^{32}$ is independently $R^{33}$-substituted $C_3$-$C_6$ cycloalkyl. In embodiments, $R^{32}$ is independently $R^{33}$-substituted 3 to 6 membered heterocycloalkyl. In embodiments, $R^{32}$ is independently $R^{33}$-substituted phenyl. In embodiments, $R^{32}$ is independently $R^{33}$-substituted 5 to 6 membered heteroaryl. In embodiments, $R^{32}$ is independently unsubstituted $C_1$-$C_4$ alkyl. In embodiments, $R^{32}$ is independently unsubstituted 2 to 4 membered heteroalkyl. In embodiments, $R^{32}$ is independently unsubstituted $C_3$-$C_6$ cycloalkyl. In embodiments, $R^{32}$ is independently unsubstituted 3 to 6 membered heterocycloalkyl. In embodiments, $R^{32}$ is independently unsubstituted phenyl. In embodiments, $R^{32}$ is independently unsubstituted 5 to 6 membered heteroaryl.

$R^{33}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)NHNH$_2$, —NHC(O)NH$_2$, $—NHSO_2H$, —NHC(O)H, —NHC(O)OH, —NHOH, $—OCF_3$, $—OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In embodiments, $R^{33}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)NHNH$_2$, —NHC(O)NH$_2$, $—NHSO_2H$, —NHC(O)H, —NHC(O)OH, —NHOH, $—OCF_3$, $—OCHF_2$, $R^{34}$-substituted or unsubstituted alkyl (e.g., $C_1$-$C_8$, $C_1$-$C_6$, $C_1$-$C_4$, or $C_1$-$C_2$), $R^{34}$-substituted or unsubstituted heteroalkyl (e.g., 2 to 8 membered, 2 to 6 membered, 4 to 6 membered, 2 to 3 membered, or 4 to 5 membered), $R^{34}$-substituted or unsubstituted cycloalkyl (e.g., $C_3$-$C_8$, $C_3$-$C_6$, $C_4$-$C_6$, or $C_5$-$C_6$), $R^{34}$-substituted or unsubstituted heterocycloalkyl (e.g., 3 to 8 membered, 3 to 6 membered, 4 to 6 membered, 4 to 5 membered, or 5 to 6 membered), $R^{34}$-substituted or unsubstituted aryl (e.g., $C_6$-$C_{10}$ or phenyl), or $R^{34}$-substituted or unsubstituted heteroaryl (e.g., 5 to 10 membered, 5 to 9 membered, or 5 to 6 membered).

In embodiments, $R^{33}$ is independently $—NH_2$. In embodiments, $R^{33}$ is independently —OH. In embodiments, $R^{33}$ is independently halogen. In embodiments, $R^{33}$ is independently —CN. In embodiments, $R^{33}$ is independently oxo. In embodiments, $R^{33}$ is independently $—CF_3$. In embodiments, $R^{33}$ is independently —COOH. In embodiments, $R^{33}$ is independently $—CONH_2$. In embodiments, $R^{33}$ is independently $—NO_2$. In embodiments, $R^{33}$ is independently —SH. In embodiments, $R^{33}$ is independently $—SO_3H$. In embodiments, $R^{33}$ is independently $—SO_4H$. In embodiments, $R^{33}$ is independently $—SO_2NH_2$. In embodiments, $R^{33}$ is independently $—NHNH_2$. In embodiments, $R^{33}$ is independently $—ONH_2$. In embodiments, $R^{33}$ is independently —NHC(O)NHNH$_2$. In embodiments, $R^{33}$ is independently —NHC(O)NH$_2$. In embodiments, $R^{33}$ is independently $—NHSO_2H$. In embodiments, $R^{33}$ is independently —NHC(O)H. In embodiments, $R^{33}$ is independently —NHC(O)OH. In embodiments, $R^{33}$ is independently —NHOH. In embodiments, $R^{33}$ is independently $—OCF_3$. In embodiments, $R^{33}$ is independently $—OCHF_2$. In embodiments, $R^{33}$ is independently $—CCl_3$. In embodiments, $R^{33}$ is independently $—CBr_3$. In embodiments, $R^{33}$ is independently $—CI_3$. In embodiments, $R^{33}$ is independently —F. In embodiments, $R^{33}$ is independently —Cl. In embodiments, $R^{33}$ is independently —Br. In embodiments, $R^{33}$ is independently —I. In embodiments, $R^{33}$ is independently $R^{34}$-substituted $C_1$-$C_4$ alkyl. In embodiments, $R^{33}$ is independently $R^{34}$-substituted 2 to 4 membered heteroalkyl. In embodiments, $R^{33}$ is independently $R^{34}$-substituted $C_3$-$C_6$ cycloalkyl. In embodiments, $R^{33}$ is independently $R^{34}$-substituted 3 to 6 membered heterocycloalkyl. In embodiments, $R^{33}$ is independently $R^{34}$-substituted phenyl. In embodiments, $R^{33}$ is independently $R^{34}$-substituted 5 to 6 membered heteroaryl. In embodiments, $R^{33}$ is independently unsubstituted $C_1$-$C_4$ alkyl. In embodiments, $R^{33}$ is independently unsubstituted 2 to 4 membered heteroalkyl. In embodiments, $R^{33}$ is independently unsubstituted $C_3$-$C_6$ cycloalkyl. In embodiments, $R^{33}$ is independently unsubstituted 3 to 6 membered heterocycloalkyl. In embodiments, $R^{33}$ is independently unsubstituted phenyl. In embodiments, $R^{33}$ is independently unsubstituted 5 to 6 membered heteroaryl.

In embodiments, $L^5$ is independently a bond, $R^{35}$-substituted or unsubstituted alkylene, $R^{35}$-substituted or unsubstituted heteroalkylene, $R^{35}$-substituted or unsubstituted cycloalkylene, $R^{35}$-substituted or unsubstituted heterocycloalkylene, $R^{35}$-substituted or unsubstituted arylene, or $R^{35}$-substituted or unsubstituted heteroarylene.

In embodiments, $L^5$ is a bond, —NH—, $—NR^{35}—$, —S—, —O—, —C(O)—, —NHC(O)—, —C(O)NH—, —NHC(O)NH—, —NHC(NH)NH—, —C(S)—, $R^{35}$-substituted or unsubstituted $C_1$-$C_{20}$ alkylene, $R^{35}$-substituted or unsubstituted 2 to 20 membered heteroalkylene, $R^{35}$-substituted or unsubstituted $C_3$-$C_8$ cycloalkylene, $R^{35}$-substituted or unsubstituted 3 to 8 membered heterocycloalkylene, $R^{35}$-substituted or unsubstituted $C_6$-$C_{10}$ arylene, or $R^{35}$-substituted or unsubstituted 5 to 10 membered heteroarylene. In embodiments, $L^5$ is a bond. In embodiments, $L^5$ is —NH—. In embodiments, $L^5$ is —NR'—. In embodiments, $L^5$ is —S—. In embodiments, $L^5$ is —O—. In embodiments, $L^5$ is —C(O)—. In embodiments, $L^5$ is —NHC(O)—. In embodiments, $L^5$ is —C(O)NH—. In embodiments, $L^5$ is —NHC(O)NH—. In embodiments, $L^5$ is —NHC(NH)NH—. In embodiments, $L^5$ is —C(S)—. In embodiments, $L^5$ is $R^{35}$-substituted or unsubstituted $C_1$-$C_{20}$ alkylene. In embodiments, $L^5$ is $R^{35}$-substituted or unsubstituted 2 to 20 membered heteroalkylene. In embodiments, $L^5$ is $R^{35}$-substituted or unsubstituted $C_3$-$C_8$ cycloalkylene. In embodiments, $L^5$ is $R^{35}$-substituted or unsubstituted 3 to 8 membered heterocycloalkylene. In embodiments, $L^5$ is $R^{35}$-substituted or unsubstituted $C_6$-$C_{10}$ arylene. In embodiments, $L^5$ is $R^{35}$-substituted or unsubstituted 5 to 10 membered heteroarylene. In embodiments, $L^5$ is $R^{35}$-substituted $C_1$-$C_{20}$ alkylene. In embodiments, $L^5$ is $R^{35}$-substituted 2 to 20 membered heteroalkylene. In embodiments, $L^5$ is $R^{35}$-substituted $C_3$-$C_8$ cycloalkylene. In embodiments, $L^5$ is $R^{35}$-substituted 3 to 8 membered heterocycloalkylene. In embodiments, $L^5$ is $R^{35}$-substituted $C_6$-$C_{10}$ arylene. In embodiments, $L^5$ is $R^{35}$-substituted 5 to 10 membered heteroarylene. In embodiments, $L^5$ is unsubstituted $C_1$-$C_{20}$ alkylene. In embodiments, $L^5$ is unsubstituted 2 to 20 membered heteroalkylene. In embodiments, $L^5$ is unsubstituted $C_3$-$C_8$ cycloalkylene. In embodiments, $L^5$ is unsubstituted 3 to 8 membered heterocycloalkylene. In embodiments, $L^5$ is unsubstituted $C_6$-$C_{10}$ arylene. In embodiments, $L^5$ is unsubstituted 5 to 10 membered heteroarylene. In embodiments, $L^5$ is $R^{35}$-substituted $C_1$-$C_{15}$ alkylene. In embodiments, $L^5$ is $R^{35}$-substituted 2 to 15 membered heteroalkylene. In embodiments, $L^5$ is $R^{35}$-substituted $C_3$-$C_6$ cycloalkylene. In embodiments, $L^5$ is $R^{35}$-substituted 3 to 6 membered heterocycloalkylene. In embodiments, $L^5$ is $R^{35}$-substituted phenylene. In embodiments, $L^5$ is $R^{35}$-substituted 5 to 6 membered heteroarylene. In embodiments, $L^5$ is unsubstituted $C_1$-$C_{15}$ alkylene. In embodiments, $L^5$ is unsubstituted 2 to 15 membered heteroalkylene. In embodiments, $L^5$ is unsubstituted $C_3$-$C_6$ cycloalkylene. In embodiments, $L^5$ is unsubstituted 3 to 6 membered heterocycloalkylene. In embodiments, $L^5$ is unsubstituted phenylene. In embodiments, $L^5$ is unsubstituted 5 to 6 membered heteroarylene. In embodiments, $L^5$ is $R^{35}$-substituted $C_1$-$C_{10}$ alkylene. In embodiments, $L^5$ is $R^{35}$-substituted 2 to 10 membered heteroalkylene. In embodiments, $L^5$ is $R^{35}$-substituted $C_4$-$C_6$ cycloalkylene. In embodiments, $L^5$ is $R^{35}$-substituted 4 to 6 membered heterocycloalkylene. In embodiments, $L^5$ is $R^{35}$-substituted phenylene. In embodiments, $L^5$ is $R^{35}$-substituted 5 membered heteroarylene. In embodiments, $L^5$ is $R^{35}$-substituted $C_1$-$C_8$ alkylene. In embodiments, $L^5$ is $R^{35}$-substituted 2 to 8 membered heteroalkylene. In embodiments, $L^5$ is $R^{35}$-substituted $C_5$-$C_6$ cycloalkylene. In embodiments, $L^5$ is $R^{35}$-substituted 5 to 6 membered heterocycloalkylene. In embodiments, $L^5$ is $R^{35}$-substituted 6 membered heteroarylene. In embodiments, $L^5$ is $R^{35}$-substituted $C_1$-$C_6$ alkylene. In embodiments, $L^5$ is $R^{35}$-substituted 2 to 6 membered heteroalkylene. In embodiments, $L^5$ is $R^{35}$-substituted $C_6$-$C_{20}$ alkylene. In embodiments, $L^5$ is $R^{35}$-substituted 6 to 20 membered heteroalkylene. In embodiments, $L^5$ is unsubstituted $C_1$-$C_{10}$ alkylene. In embodiments, $L^5$ is unsubstituted 2 to 10 membered heteroalkylene. In embodiments, $L^5$ is unsubstituted $C_4$-$C_6$ cycloalkylene. In embodiments, $L^5$ is unsubstituted 4 to 6 membered heterocycloalkylene. In embodiments, $L^5$ is unsubstituted phenylene. In embodiments, $L^5$ is unsubstituted 5 membered heteroarylene. In embodiments, $L^5$ is unsubstituted $C_1$-$C_8$ alkylene. In embodiments, $L^5$ is unsubstituted 2 to 8 membered heteroalkylene. In embodiments, $L^5$ is unsubstituted $C_5$-$C_6$ cycloalkylene. In embodiments, $L^5$ is unsubstituted 5 to 6 membered heterocycloalkylene. In embodiments, $L^5$ is unsubstituted 6 membered heteroarylene. In embodiments, $L^5$ is unsubstituted $C_1$-$C_6$ alkylene. In embodiments, $L^5$ is unsubstituted 2 to 6 membered heteroalkylene. In embodiments, $L^5$ is unsubstituted $C_6$-$C_{20}$ alkylene. In embodiments, $L^5$ is unsubstituted 6 to 20 membered heteroalkylene.

$R^{35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

In embodiments, $R^{35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, 2 to 3 membered, or 4 to 5 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 8 membered, 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered).

In embodiments, $R^{35}$ is independently —$NH_2$. In embodiments, $R^{35}$ is independently —OH. In embodiments, $R^{35}$ is independently halogen. In embodiments, $R^{35}$ is independently —CN. In embodiments, $R^{35}$ is independently oxo. In embodiments, $R^{35}$ is independently —$CF_3$. In embodiments, $R^{35}$ is independently —COOH. In embodiments, $R^{35}$ is independently —$CONH_2$. In embodiments, $R^{35}$ is independently —$NO_2$. In embodiments, $R^{35}$ is independently —SH. In embodiments, $R^{35}$ is independently —$SO_3H$. In embodiments, $R^{35}$ is independently —$SO_4H$. In embodiments, $R^{35}$ is independently —$SO_2NH_2$. In embodiments, $R^{35}$ is independently —$NHNH_2$. In embodiments, $R^{35}$ is independently —$ONH_2$. In embodiments, $R^{35}$ is independently —NHC═(O)$NHNH_2$. In embodiments, $R^{35}$ is independently —NHC═(O)$NH_2$. In embodiments, $R^{35}$ is independently —$NHSO_2H$. In embodiments, $R^{35}$ is independently —NHC═(O)H. In embodiments, $R^{35}$ is independently —NHC(O)—OH. In embodiments, $R^{35}$ is independently —NHOH. In embodiments, $R^{35}$ is independently —$OCF_3$. In embodiments, $R^{35}$ is independently —$OCHF_2$. In embodiments, $R^{35}$ is independently —$CCl_3$. In embodiments, $R^{35}$ is independently —$CBr_3$. In embodiments, $R^{35}$ is independently —$CI_3$. In embodiments, $R^{35}$ is independently —F. In embodiments, $R^{35}$ is independently —Cl. In embodiments, $R^{35}$ is independently —Br. In embodiments, $R^{35}$ is independently —I. In embodiments, $R^{35}$ is independently $R^{36}$-substituted $C_1$-$C_4$ alkyl. In embodiments, $R^{35}$ is independently $R^{36}$-substituted 2 to 4 membered heteroalkyl. In embodiments, $R^{35}$ is independently $R^{36}$-substituted $C_3$-$C_6$ cycloalkyl. In embodiments, $R^{35}$ is independently $R^{36}$-substituted 3 to 6 membered heterocycloalkyl. In embodiments, $R^{35}$ is independently $R^{36}$-substituted phenyl. In embodiments, $R^{35}$ is independently $R^{36}$-substituted 5 to 6 membered heteroaryl. In embodiments, $R^{35}$ is independently unsubstituted $C_1$-$C_4$ alkyl. In embodiments, $R^{35}$ is independently unsubstituted 2 to 4 membered heteroalkyl. In embodiments, $R^{35}$ is independently unsubstituted $C_3$-$C_6$ cycloalkyl. In embodiments, $R^{35}$ is independently unsubstituted 3 to 6 membered heterocycloalkyl. In embodiments, $R^{35}$ is independently unsubstituted phenyl. In embodiments, $R^{35}$ is independently unsubstituted 5 to 6 membered heteroaryl.

$R^{36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In embodiments, $R^{36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{37}$-substituted or unsubstituted alkyl (e.g., $C_1$-$C_8$, $C_1$-$C_6$, $C_1$-$C_4$, or $C_1$-$C_2$), $R^{37}$-substituted or unsubstituted heteroalkyl (e.g., 2 to 8 membered, 2 to 6 membered, 4 to 6 membered, 2 to 3 membered, or 4 to 5 membered), $R^{37}$-substituted or unsubstituted cycloalkyl (e.g., $C_3$-$C_8$, $C_3$-$C_6$, $C_4$-$C_6$, or $C_5$-$C_6$), $R^{37}$-substituted or unsubstituted heterocycloalkyl (e.g., 3 to 8 membered, 3 to 6 membered, 4 to 6 membered, 4 to 5 membered, or 5 to 6 membered), $R^{37}$-substituted or unsubstituted aryl (e.g., $C_6$-$C_{10}$ or phenyl), or $R^{37}$-substituted or unsubstituted heteroaryl (e.g., 5 to 10 membered, 5 to 9 membered, or 5 to 6 membered).

In embodiments, $R^{36}$ is independently —$NH_2$. In embodiments, $R^{36}$ is independently —OH. In embodiments, $R^{36}$ is independently halogen. In embodiments, $R^{36}$ is independently —CN. In embodiments, $R^{36}$ is independently oxo. In embodiments, $R^{36}$ is independently —$CF_3$. In embodiments, $R^{36}$ is independently —COOH. In embodiments, $R^{36}$ is independently —$CONH_2$. In embodiments, $R^{36}$ is independently —$NO_2$. In embodiments, $R^{36}$ is independently —SH. In embodiments, $R^{36}$ is independently —$SO_3H$. In embodiments, $R^{36}$ is independently —$SO_4H$. In embodiments, $R^{36}$ is independently —$SO_2NH_2$. In embodiments, $R^{36}$ is independently —$NHNH_2$. In embodiments, $R^{36}$ is independently —$ONH_2$. In embodiments, $R^{36}$ is independently —$NHC(O)NHNH_2$. In embodiments, $R^{36}$ is independently —$NHC(O)NH_2$. In embodiments, $R^{36}$ is independently —$NHSO_2H$. In embodiments, $R^{36}$ is independently —NHC(O)H. In embodiments, $R^{36}$ is independently —NHC(O)—OH. In embodiments, $R^{36}$ is independently —NHOH. In embodiments, $R^{36}$ is independently —$OCF_3$. In embodiments, $R^{36}$ is independently —$OCHF_2$. In embodiments, $R^{36}$ is independently —$CCl_3$. In embodiments, $R^{36}$ is independently —$CBr_3$. In embodiments, $R^{36}$ is independently —$CI_3$. In embodiments, $R^{36}$ is independently —F. In embodiments, $R^{36}$ is independently —Cl. In embodiments, $R^{36}$ is independently —Br. In embodiments, $R^{36}$ is independently —I. In embodiments, $R^{36}$ is independently $R^{37}$-substituted $C_1$-$C_4$ alkyl. In embodiments, $R^{36}$ is independently $R^{37}$-substituted 2 to 4 membered heteroalkyl. In embodiments, $R^{36}$ is independently $R^{37}$-substituted $C_3$-$C_6$ cycloalkyl. In embodiments, $R^{36}$ is independently $R^{37}$-substituted 3 to 6 membered heterocycloalkyl. In embodiments, $R^{36}$ is independently $R^{37}$-substituted phenyl. In embodiments, $R^{36}$ is independently $R^{37}$-substituted 5 to 6 membered heteroaryl. In embodiments, $R^{36}$ is independently unsubstituted $C_1$-$C_4$ alkyl. In embodiments, $R^{36}$ is independently unsubstituted 2 to 4 membered heteroalkyl. In embodiments, $R^{36}$ is independently unsubstituted $C_3$-$C_6$ cycloalkyl. In embodiments, $R^{36}$ is independently unsubstituted 3 to 6 membered heterocycloalkyl. In embodiments, $R^{36}$ is independently unsubstituted phenyl. In embodiments, $R^{36}$ is independently unsubstituted 5 to 6 membered heteroaryl.

In embodiments, $L^6$ is independently a bond, $R^{38}$-substituted or unsubstituted alkylene, $R^{38}$-substituted or unsubstituted heteroalkylene, $R^{38}$-substituted or unsubstituted cycloalkylene, $R^{38}$-substituted or unsubstituted heterocycloalkylene, $R^{38}$-substituted or unsubstituted arylene, or $R^{38}$-substituted or unsubstituted heteroarylene.

In embodiments, $L^6$ is a bond, —NH—, —$NR^{38}$—, —S—, —O—, —C(O)—, —NHC(O)—, —C(O)NH—, —NHC(O)NH—, —NHC(NH)NH—, —C(S)—, $R^{38}$-substituted or unsubstituted $C_1$-$C_{20}$ alkylene, $R^{38}$-substituted or unsubstituted 2 to 20 membered heteroalkylene, $R^{38}$-substituted or unsubstituted $C_3$-$C_8$ cycloalkylene, $R^{38}$-substituted or unsubstituted 3 to 8 membered heterocycloalkylene, $R^{38}$-substituted or unsubstituted $C_6$-$C_{10}$ arylene, or $R^{38}$-substituted or unsubstituted 5 to 10 membered heteroarylene. In embodiments, $L^6$ is a bond. In embodiments, $L^6$ is —NH—. In embodiments, $L^6$ is —$NR^{38}$—. In embodiments, $L^6$ is —S—. In embodiments, $L^6$ is —O—. In embodiments, $L^6$ is —C(O)—. In embodiments, $L^6$ is —NHC(O)—. In embodiments, $L^6$ is —C(O)NH—. In embodiments, $L^6$ is —NHC(O)NH—. In embodiments, $L^6$ is —NHC(NH)NH—. In embodiments, $L^6$ is —C(S)—. In embodiments, $L^6$ is $R^{38}$-substituted or unsubstituted $C_1$-$C_{20}$ alkylene. In embodiments, $L^6$ is $R^{38}$-substituted or unsubstituted 2 to 20 membered heteroalkylene. In embodiments, $L^6$ is $R^{38}$-substituted or unsubstituted $C_3$-$C_8$ cycloalkylene. In embodiments, $L^6$ is $R^{38}$-substituted or unsubstituted 3 to 8 membered heterocycloalkylene. In embodiments, $L^6$ is $R^{38}$-substituted or unsubstituted $C_6$-$C_{10}$ arylene. In embodiments, $L^6$ is $R^{38}$-substituted or unsubstituted 5 to 10 membered heteroarylene. In embodiments, $L^6$ is $R^{38}$-substituted $C_1$-$C_{20}$ alkylene. In embodiments, $L^6$ is $R^{38}$-substituted 2 to 20 membered heteroalkylene. In embodiments, $L^6$ is $R^{38}$-substituted $C_3$-$C_8$ cycloalkylene. In embodiments, $L^6$ is $R^{38}$-substituted 3 to 8 membered heterocycloalkylene. In embodiments, $L^6$ is $R^{38}$-substituted $C_6$-$C_{10}$ arylene. In embodiments, $L^6$ is $R^{38}$-substituted 5 to 10 membered heteroarylene. In embodiments, $L^6$ is unsubstituted $C_1$-$C_{20}$ alkylene. In embodiments, $L^6$ is unsubstituted 2 to 20 membered heteroalkylene. In embodiments, $L^6$ is unsubstituted $C_3$-$C_8$ cycloalkylene. In embodiments, $L^6$ is unsubstituted 3 to 8 membered heterocycloalkylene. In embodiments, $L^6$ is unsubstituted $C_6$-$C_{10}$ arylene. In embodiments, $L^6$ is unsubstituted 5 to 10 membered heteroarylene. In embodiments, $L^6$ is $R^{38}$-substituted $C_1$-$C_{15}$ alkylene. In embodiments, $L^6$ is $R^{38}$-substituted 2 to 15 membered heteroalkylene. In embodiments, $L^6$ is $R^{38}$-substituted $C_3$-$C_6$ cycloalkylene. In embodiments, $L^6$ is $R^{38}$-substituted 3 to 6 membered heterocycloalkylene. In embodiments, $L^6$ is $R^{38}$-substituted phenylene. In embodiments, $L^6$ is $R^{38}$-substituted 5 to 6 membered heteroarylene. In embodiments, $L^6$ is unsubstituted $C_1$-$C_{15}$ alkylene. In embodiments, $L^6$ is unsubstituted 2 to 15 membered heteroalkylene. In embodiments, $L^6$ is unsubstituted $C_3$-$C_6$ cycloalkylene. In embodiments, $L^6$ is unsubstituted 3 to 6 membered heterocycloalkylene. In embodiments, $L^6$ is unsubstituted phenylene. In embodiments, $L^6$ is unsubstituted 5 to 6 membered heteroarylene. In embodiments, $L^6$ is $R^{38}$-substituted $C_1$-$C_{10}$ alkylene. In embodiments, $L^6$ is $R^{38}$-substituted 2 to 10 membered heteroalkylene. In embodiments, $L^6$ is $R^{38}$-substituted $C_4$-$C_6$ cycloalkylene. In embodiments, $L^6$ is $R^{38}$-substituted 4 to 6 membered heterocycloalkylene. In embodiments, $L^6$ is $R^{38}$-substituted phenylene. In embodiments, $L^6$ is $R^{38}$-substituted 5 membered heteroarylene. In embodiments, $L^6$ is $R^{38}$-substituted $C_1$-$C_8$ alkylene. In embodiments, $L^6$ is $R^{38}$-substituted 2 to 8 membered heteroalkylene. In embodiments, $L^6$ is $R^{38}$-substituted $C_5$-$C_6$ cycloalkylene. In embodiments, $L^6$ is $R^{38}$-substituted 5 to 6 membered heterocycloalkylene. In embodiments, $L^6$ is $R^{38}$-substituted 6 membered heteroarylene. In embodiments, $L^6$ is $R^{38}$-substituted $C_1$-$C_6$ alkylene. In embodiments, $L^6$ is $R^{38}$-substituted 2 to 6 membered heteroalkylene. In embodiments, $L^6$ is $R^{38}$-substituted $C_6$-$C_{20}$ alkylene. In embodiments, $L^6$ is $R^{38}$-substituted 6 to 20 membered heteroalkylene. In embodiments, $L^6$ is unsubstituted $C_1$-$C_{10}$ alkylene. In embodiments, $L^6$ is unsubstituted 2 to 10 membered heteroalkylene. In embodiments, $L^6$ is unsubstituted $C_4$-$C_6$ cycloalkylene. In embodiments, $L^6$ is unsubstituted 4 to 6 membered heterocycloalkylene. In embodiments, $L^6$ is unsubstituted phenylene. In embodiments, $L^6$ is unsubstituted 5 membered heteroarylene. In embodiments, $L^6$ is unsubstituted $C_1$-$C_8$ alkylene. In embodiments, $L^6$ is unsubstituted 2 to 8 membered heteroalkylene. In embodiments, $L^6$ is unsubstituted $C_5$-$C_6$ cycloalkylene. In embodiments, $L^6$ is unsubstituted 5 to 6 membered heterocycloalkylene. In embodiments, $L^6$ is unsubstituted 6 membered heteroarylene. In embodiments, $L^6$ is unsubstituted $C_1$-$C_6$ alkylene. In embodiments, $L^6$ is unsubstituted 2 to 6 membered heteroalkylene. In embodiments, $L^6$ is unsubstituted $C_6$-$C_{20}$ alkylene. In embodiments, $L^6$ is unsubstituted 6 to 20 membered heteroalkylene.

$R^{38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl.

In embodiments, $R^{38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 8 membered, 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered).

In embodiments, $R^{38}$ is independently —$NH_2$. In embodiments, $R^{38}$ is independently —OH. In embodiments, $R^{38}$ is independently halogen. In embodiments, $R^{38}$ is independently —CN. In embodiments, $R^{38}$ is independently oxo. In embodiments, $R^{38}$ is independently —$CF_3$. In embodiments, $R^{38}$ is independently —COOH. In embodiments, $R^{38}$ is independently —$CONH_2$. In embodiments, $R^{38}$ is independently —$NO_2$. In embodiments, $R^{38}$ is independently —SH. In embodiments, $R^{38}$ is independently —$SO_3H$. In embodiments, $R^{38}$ is independently —$SO_4H$. In embodiments, $R^{38}$ is independently —$SO_2NH_2$. In embodiments, $R^{38}$ is independently —$NHNH_2$. In embodiments, $R^{38}$ is independently —$ONH_2$. In embodiments, $R^{38}$ is independently —NHC═(O)$NHNH_2$. In embodiments, $R^{38}$ is independently —NHC═(O) $NH_2$. In embodiments, $R^{38}$ is independently —$NHSO_2H$. In embodiments, $R^{38}$ is independently —NHC═(O)H. In embodiments, $R^{38}$ is independently —NHC(O)—OH. In embodiments, $R^{38}$ is independently —NHOH. In embodiments, $R^{38}$ is independently —$OCF_3$. In embodiments, $R^{38}$ is independently —$OCHF_2$. In embodiments, $R^{38}$ is independently —$CCl_3$. In embodiments, $R^{38}$ is independently —$CBr_3$. In embodiments, $R^{38}$ is independently —$CI_3$. In embodiments, $R^{38}$ is independently —F. In embodiments, $R^{38}$ is independently —Cl. In embodiments, $R^{38}$ is independently —Br. In embodiments, $R^{38}$ is independently —I. In embodiments, $R^{38}$ is independently $R^{39}$-substituted $C_1$-$C_4$ alkyl. In embodiments, $R^{38}$ is independently $R^{39}$-substituted 2 to 4 membered heteroalkyl. In embodiments, $R^{38}$ is independently $R^{39}$-substituted $C_3$-$C_6$ cycloalkyl. In embodiments, $R^{38}$ is independently $R^{39}$-substituted 3 to 6 membered heterocycloalkyl. In embodiments, $R^{38}$ is independently $R^{39}$-substituted phenyl. In embodiments, $R^{38}$ is independently $R^{39}$-substituted 5 to 6 membered heteroaryl. In embodiments, $R^{38}$ is independently unsubstituted $C_1$-$C_4$ alkyl. In embodiments, $R^{38}$ is independently unsubstituted 2 to 4 membered heteroalkyl. In embodiments, $R^{38}$ is independently unsubstituted $C_3$-$C_6$ cycloalkyl. In embodiments, $R^{38}$ is independently unsubstituted 3 to 6 membered heterocycloalkyl. In embodiments, $R^{38}$ is independently unsubstituted phenyl. In embodiments, $R^{38}$ is independently unsubstituted 5 to 6 membered heteroaryl.

$R^{39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^{39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 8 membered, 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered).

In embodiments, $R^{39}$ is independently —$NH_2$. In embodiments, $R^{39}$ is independently —OH. In embodiments, $R^{39}$ is independently halogen. In embodiments, $R^{39}$ is independently —CN. In embodiments, $R^{39}$ is independently oxo. In embodiments, $R^{39}$ is independently —$CF_3$. In embodiments, $R^{39}$ is independently —COOH. In embodiments, $R^{39}$ is independently —$CONH_2$. In embodiments, $R^{39}$ is independently —$NO_2$. In embodiments, $R^{39}$ is independently —SH. In embodiments, $R^{39}$ is independently —$SO_3H$. In embodiments, $R^{39}$ is independently —$SO_4H$. In embodiments, $R^{39}$ is independently —$SO_2NH_2$. In embodiments, $R^{39}$ is independently —$NHNH_2$. In embodiments, $R^{39}$ is independently —$ONH_2$. In embodiments, $R^{39}$ is independently —NHC═(O)$NHNH_2$. In embodiments, $R^{39}$ is independently —NHC═(O) $NH_2$. In embodiments, $R^{39}$ is independently —$NHSO_2H$. In embodiments, $R^{39}$ is independently —NHC═(O)H. In embodiments, $R^{39}$ is independently —NHC(O)—OH. In embodiments, $R^{39}$ is independently —NHOH. In embodiments, $R^{39}$ is independently —$OCF_3$. In embodiments, $R^{39}$ is independently —$OCHF_2$. In embodiments, $R^{39}$ is independently —$CCl_3$. In embodiments, $R^{39}$ is independently —$CBr_3$. In embodiments, $R^{39}$ is independently —$CI_3$. In embodiments, $R^{39}$ is independently —F. In embodiments, $R^{39}$ is independently —Cl. In embodiments, $R^{39}$ is independently —Br. In embodiments, $R^{39}$ is independently —I. In embodiments, $R^{39}$ is independently $R^{40}$-substituted $C_1$-$C_4$ alkyl. In embodiments, $R^{39}$ is independently $R^{40}$-substituted 2 to 4 membered heteroalkyl. In embodiments, $R^{39}$ is independently $R^{40}$-substituted $C_3$-$C_6$ cycloalkyl. In embodiments, $R^{39}$ is independently $R^{40}$-substituted 3 to 6 membered heterocycloalkyl. In embodiments, $R^{39}$ is independently $R^{40}$-substituted phenyl. In embodiments, $R^{39}$ is independently $R^{40}$-substituted 5 to 6 membered heteroaryl. In embodiments, $R^{39}$ is independently unsubstituted $C_1$-$C_4$ alkyl. In embodiments, $R^{39}$ is independently unsubstituted 2 to 4 membered heteroalkyl. In embodiments, $R^{39}$ is independently unsubstituted $C_3$-$C_6$ cycloalkyl. In embodiments, $R^{39}$ is independently unsubstituted 3 to 6 membered heterocycloalkyl. In embodiments, $R^{39}$ is independently unsubstituted phenyl. In embodiments, $R^{39}$ is independently unsubstituted 5 to 6 membered heteroaryl.

$R^{25}$, $R^{28}$, $R^{31}$, $R^{34}$, $R^{37}$, and $R^{40}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, the anti-CNS disease drug is

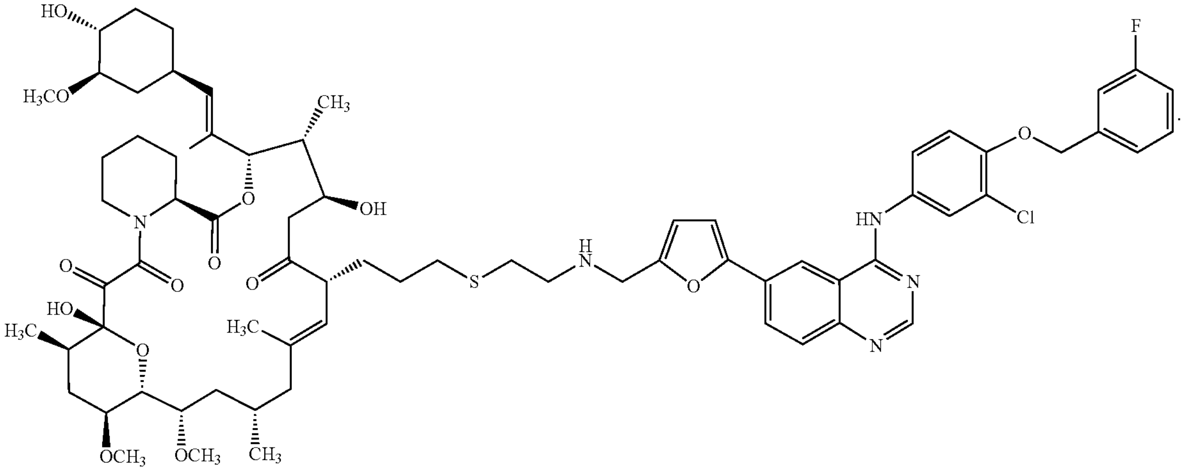 [SMILES: CO[C@H]1C[C@@H](C)C/C(C)=C/[C@@H](CCCSCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not

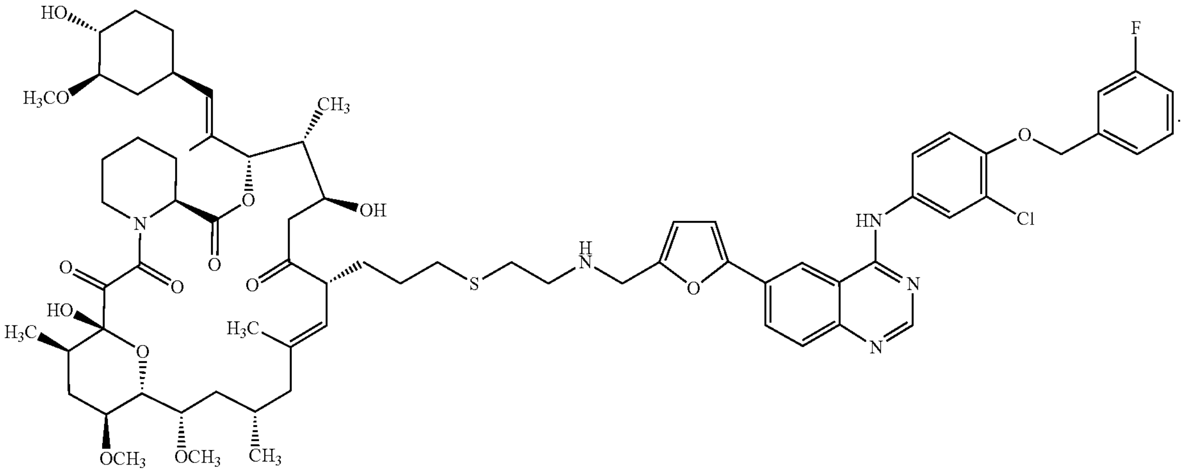 [SMILES: CO[C@H]1C[C@@H](C)C/C(C)=C/[C@@H](CCCSCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is
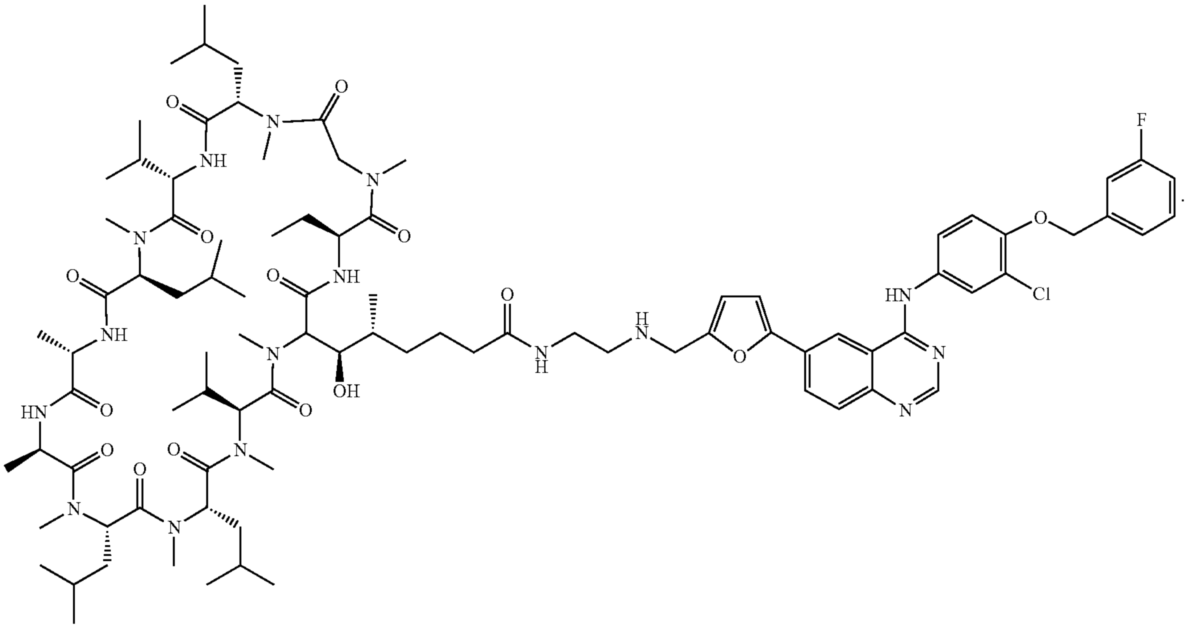 [SMILES: CC[C@@H]1NC(=O)C([C@H](O)[C@H](C)CCCC(=O)NCCNCc2ccc(-c3ccc4ncnc(Nc5ccc(OCc6cccc(F)c6)c(Cl)c5)c4c3)o2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]
In embodiments, the anti-CNS disease drug is not
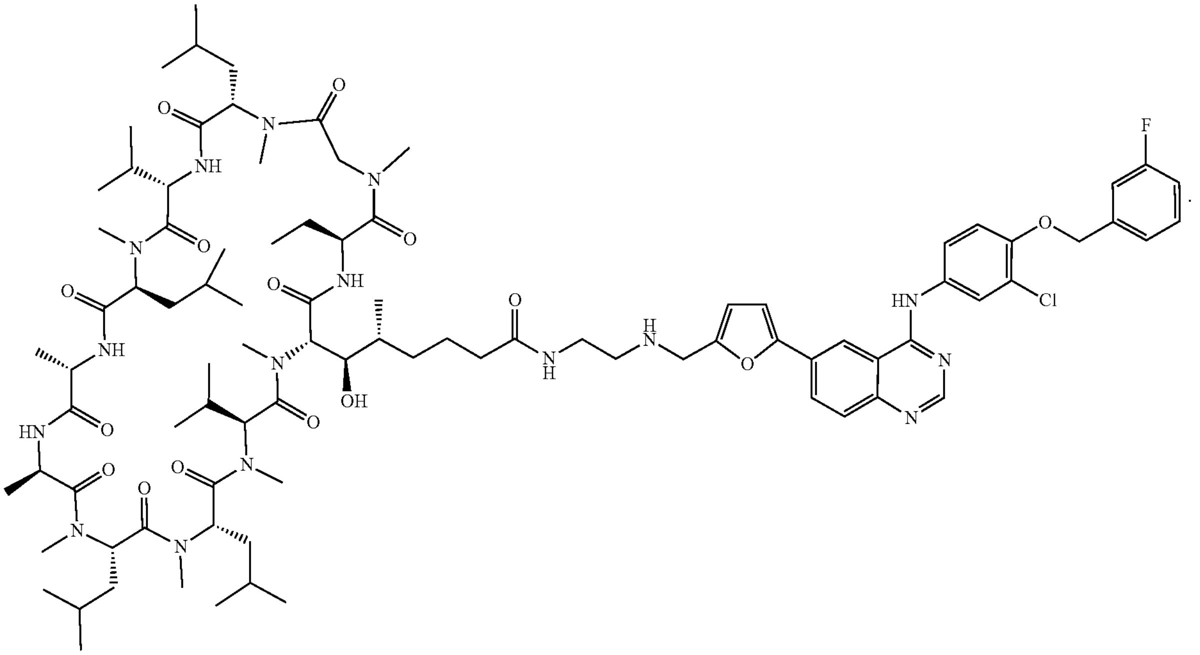 [SMILES: CC[C@@H]1NC(=O)[C@H]([C@H](O)[C@H](C)CCCC(=O)NCCNCc2ccc(-c3ccc4ncnc(Nc5ccc(OCc6cccc(F)c6)c(Cl)c5)c4c3)o2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]

In embodiments, the anti-CNS disease drug is
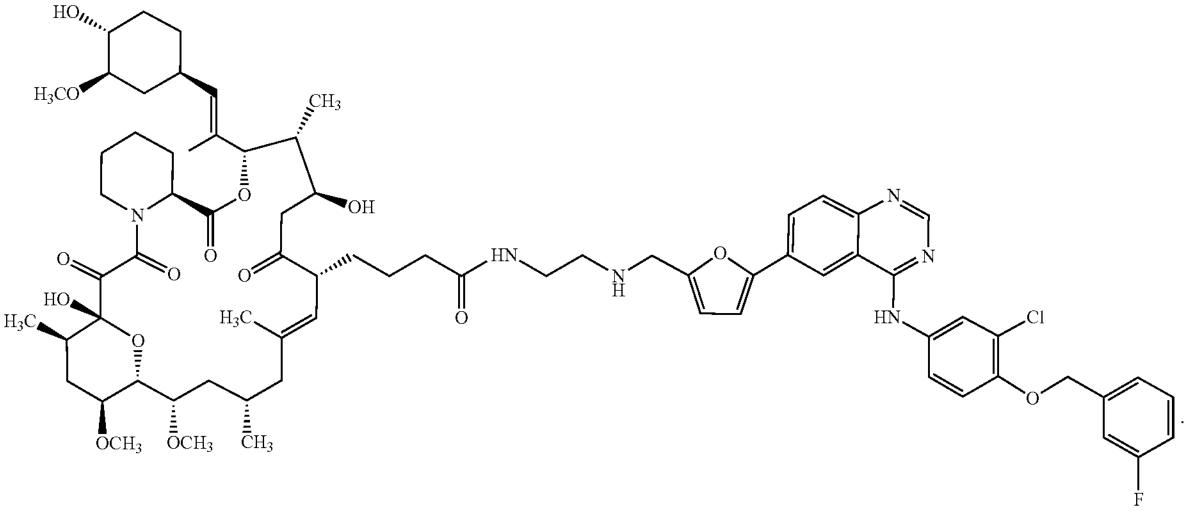 [SMILES: CO[C@H]1C[C@@H](C)C/C(C)=C/[C@@H](CCCC(=O)NCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
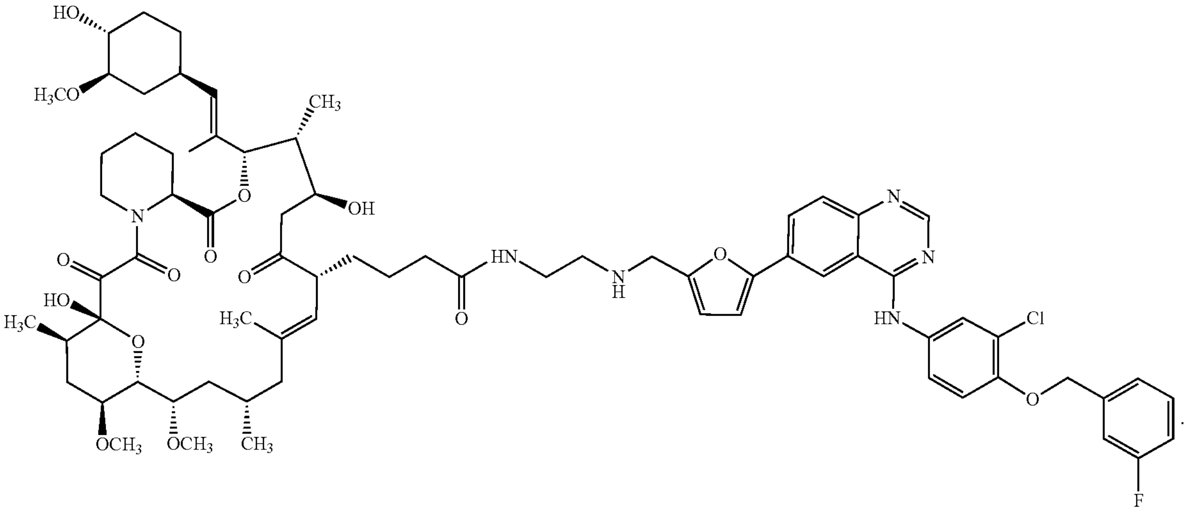 [SMILES: CO[C@H]1C[C@@H](C)C/C(C)=C/[C@@H](CCCC(=O)NCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is
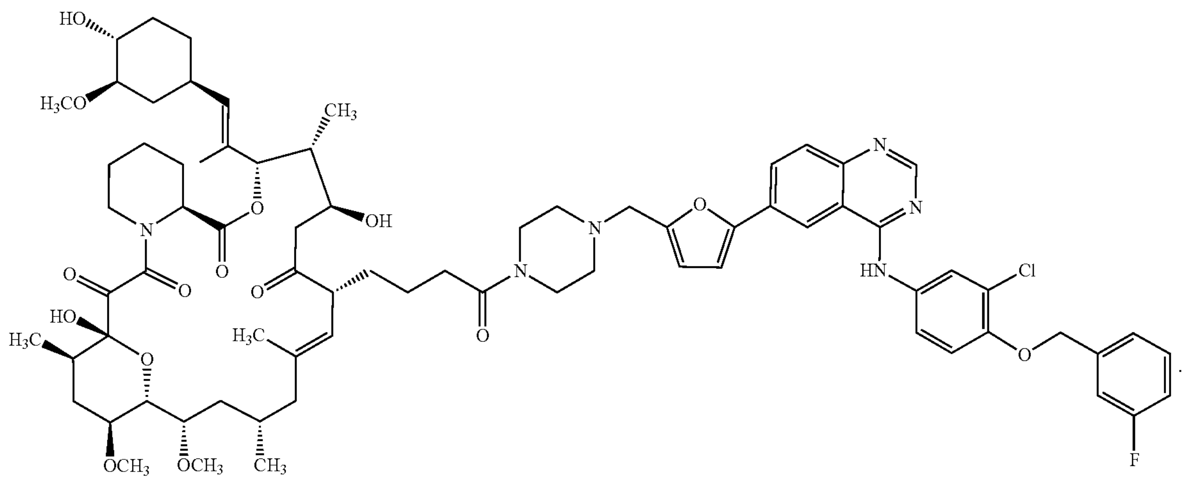 [SMILES: CO[C@H]1C[C@@H](C)C/C(C)=C/[C@@H](CCCC(=O)N2CCN(Cc3ccc(-c4ccc5ncnc(Nc6ccc(OCc7cccc(F)c7)c(Cl)c6)c5c4)o3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
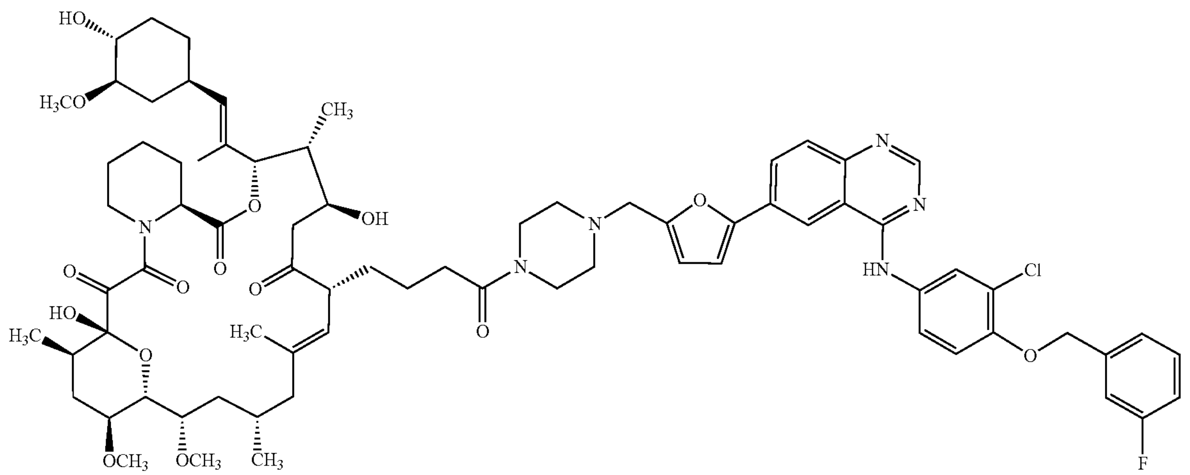 [SMILES: CO[C@H]1C[C@@H](C)C/C(C)=C/[C@@H](CCCC(=O)N2CCN(Cc3ccc(-c4ccc5ncnc(Nc6ccc(OCc7cccc(F)c7)c(Cl)c6)c5c4)o3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
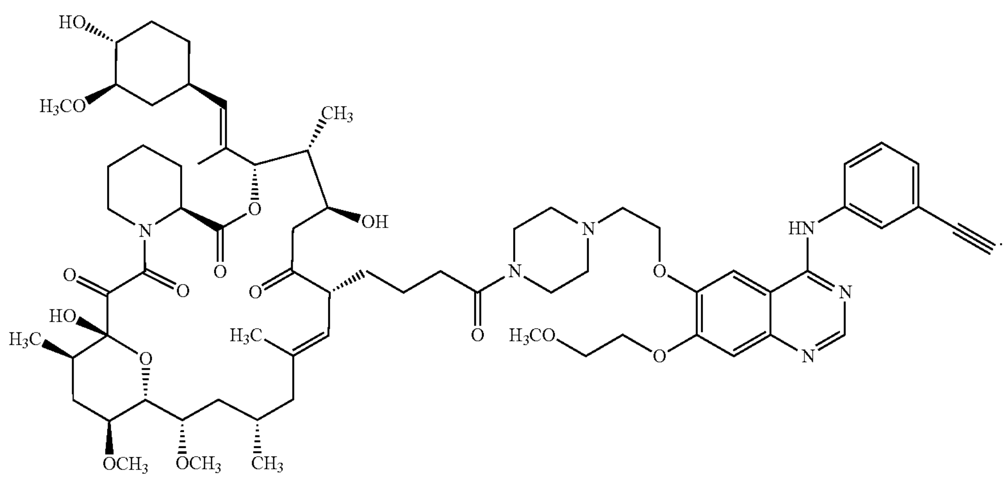 [SMILES: C#Cc1cccc(Nc2ncnc3cc(OCCOC)c(OCCN4CCN(C(=O)CCC[C@@H]5/C=C(\C)C[C@H](C)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc23)c1]

In embodiments, the anti-CNS disease drug is not
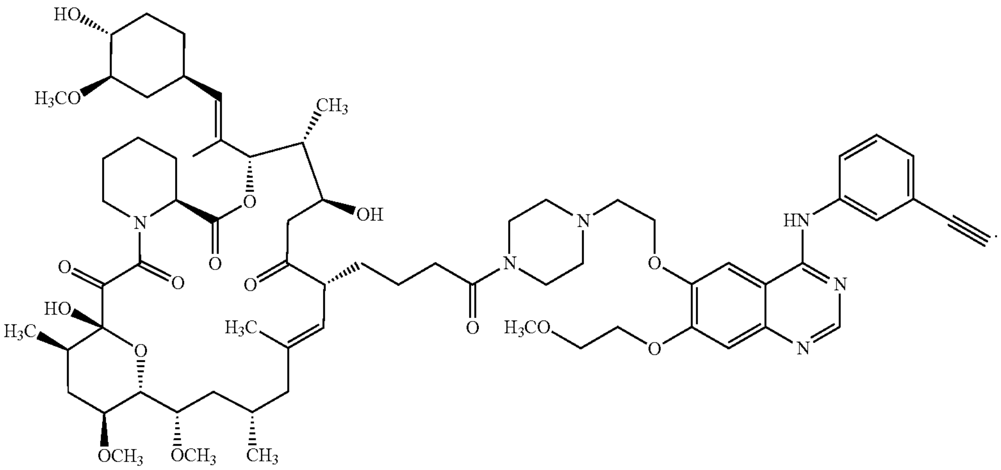 [SMILES: C#Cc1cccc(Nc2ncnc3cc(OCCOC)c(OCCN4CCN(C(=O)CCC[C@@H]5/C=C(\C)C[C@H](C)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc23)c1]
In embodiments, the anti-CNS disease drug is
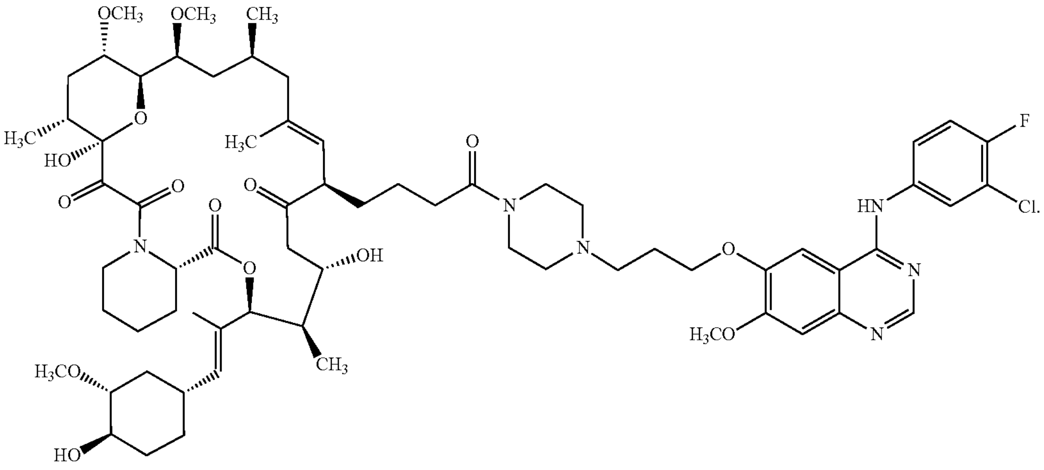 [SMILES: COc1cc2ncnc(Nc3ccc(F)c(Cl)c3)c2cc1OCCCN1CCN(C(=O)CCC[C@@H]2/C=C(\C)C[C@H](C)C[C@H](OC)[C@H]3O[C@@](O)(C(=O)C(=O)N4CCCC[C@H]4C(=O)O[C@H](/C(C)=C/[C@@H]4CC[C@@H](O)[C@H](OC)C4)[C@H](C)[C@@H](O)CC2=O)[C@H](C)C[C@@H]3OC)CC1]
In embodiments, the anti-CNS disease drug is not
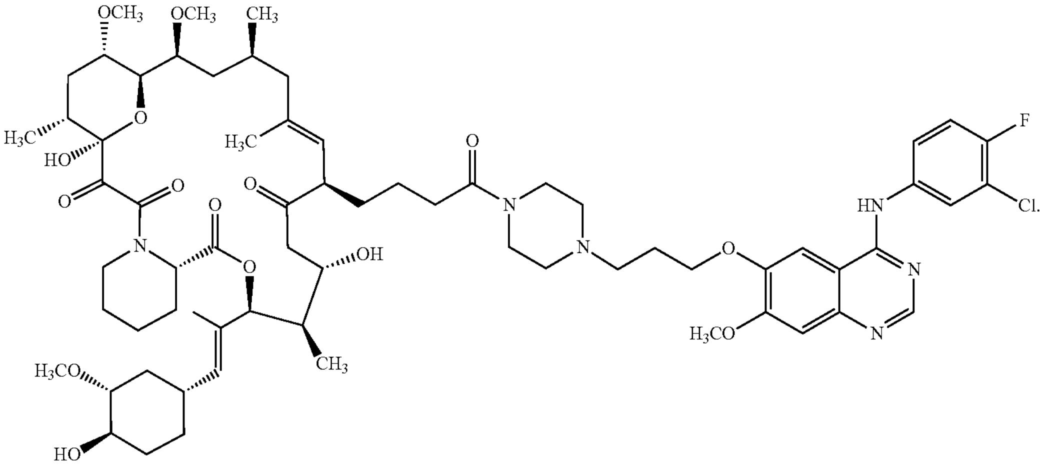 [SMILES: COc1cc2ncnc(Nc3ccc(F)c(Cl)c3)c2cc1OCCCN1CCN(C(=O)CCC[C@@H]2/C=C(\C)C[C@H](C)C[C@H](OC)[C@H]3O[C@@](O)(C(=O)C(=O)N4CCCC[C@H]4C(=O)O[C@H](/C(C)=C/[C@@H]4CC[C@@H](O)[C@H](OC)C4)[C@H](C)[C@@H](O)CC2=O)[C@H](C)C[C@@H]3OC)CC1]

In embodiments, the anti-CNS disease drug is
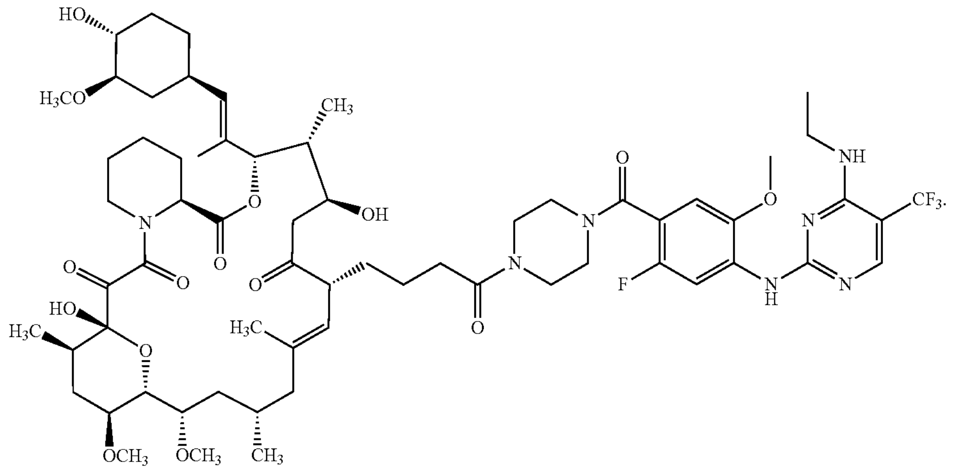 [SMILES: CCNc1nc(Nc2cc(F)c(C(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)cc2OC)ncc1C(F)(F)F]
In embodiments, the anti-CNS disease drug is not
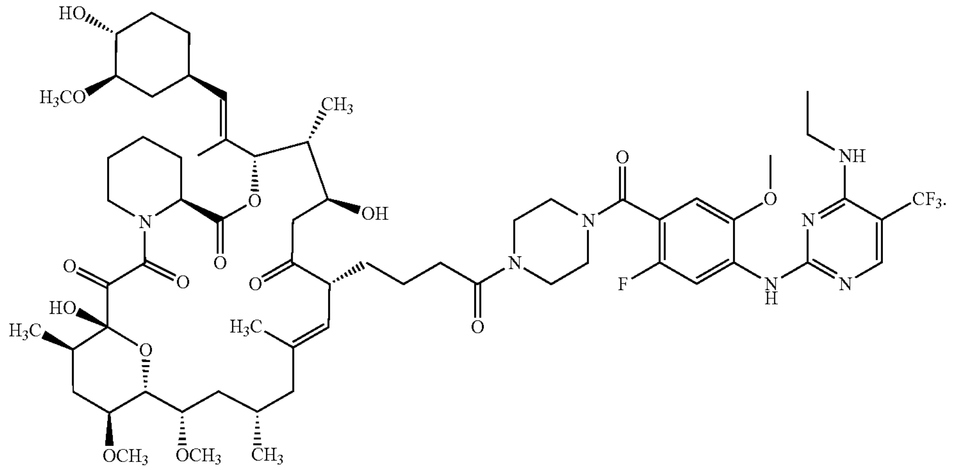 [SMILES: CCNc1nc(Nc2cc(F)c(C(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)cc2OC)ncc1C(F)(F)F]
In embodiments, the anti-CNS disease drug is
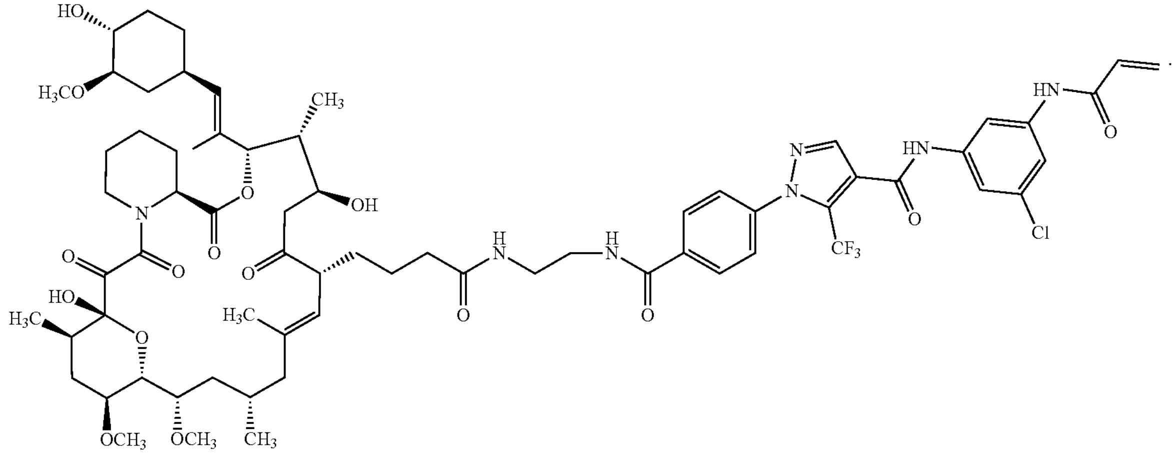 [SMILES: C=CC(=O)Nc1cc(Cl)cc(NC(=O)c2cnn(-c3ccc(C(=O)NCCNC(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]

In embodiments, the anti-CNS disease drug is not
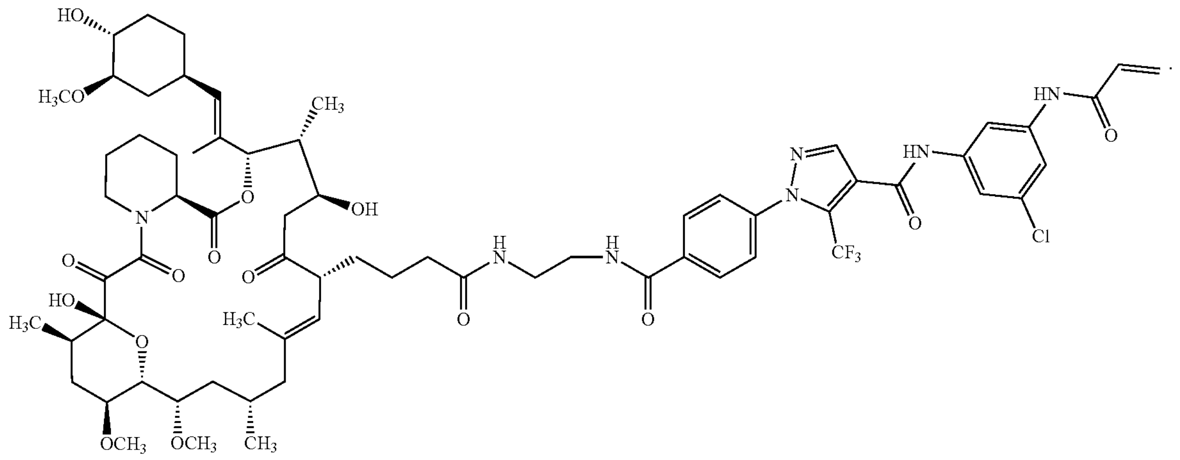 [SMILES: C=CC(=O)Nc1cc(Cl)cc(NC(=O)c2cnn(-c3ccc(C(=O)NCCNC(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]
In embodiments, the anti-CNS disease drug is
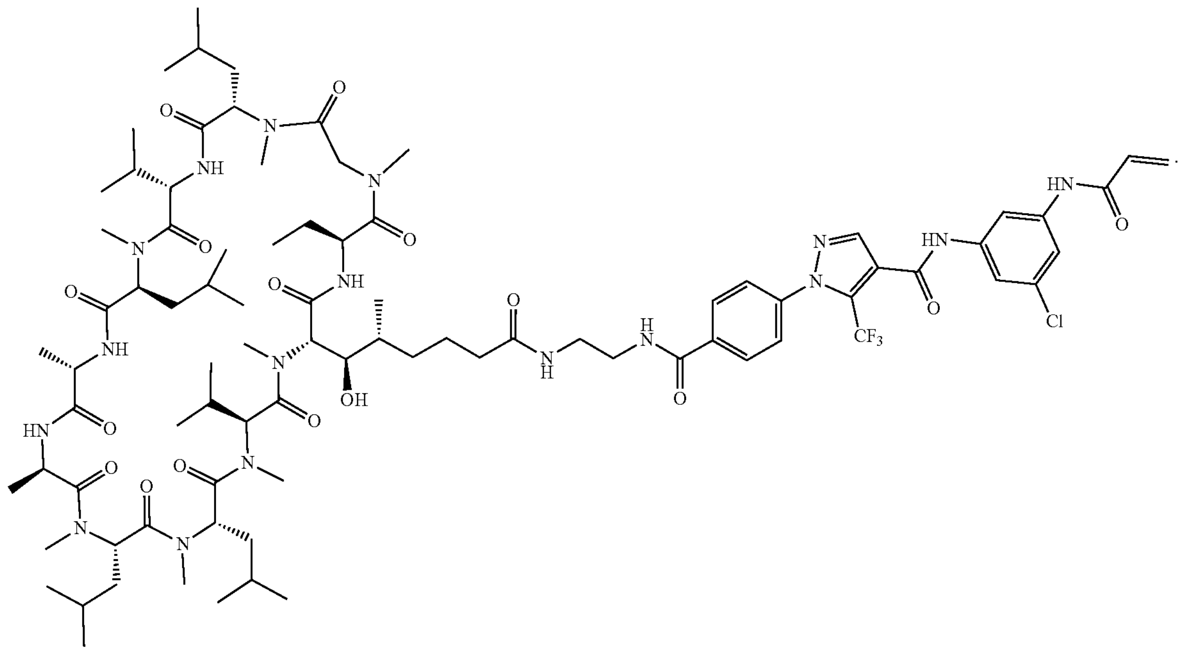 [SMILES: C=CC(=O)Nc1cc(Cl)cc(NC(=O)c2cnn(-c3ccc(C(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]

In embodiments, the anti-CNS disease drug is not
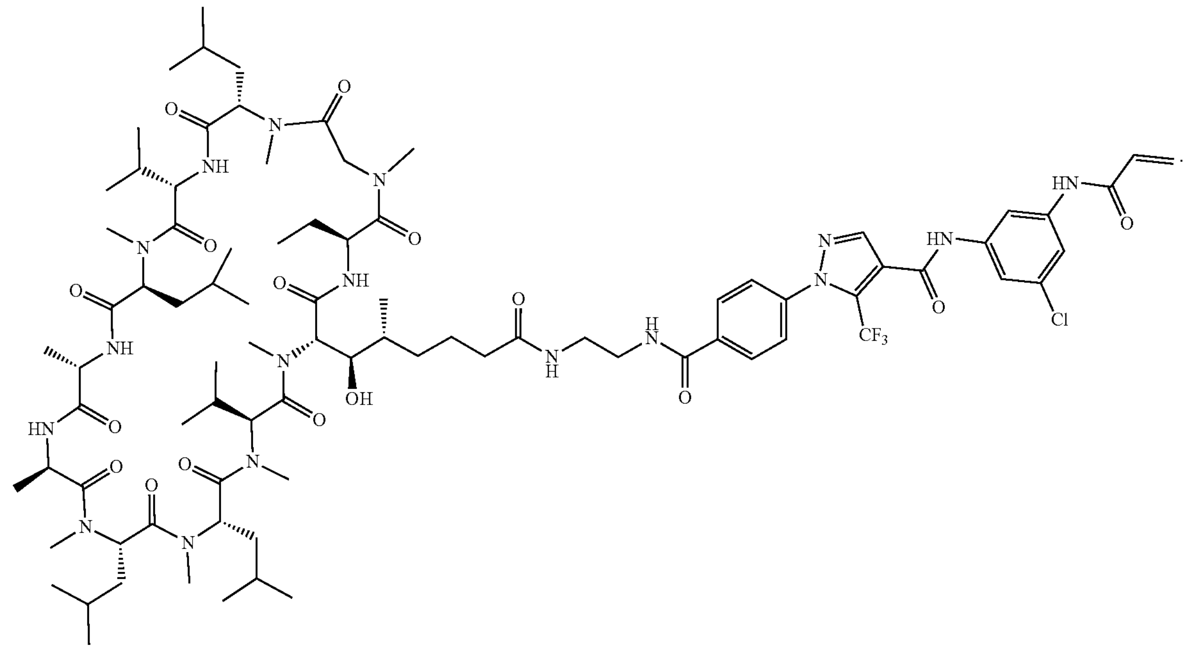 [SMILES: C=CC(=O)Nc1cc(Cl)cc(NC(=O)c2cnn(-c3ccc(C(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]
In embodiments, the anti-CNS disease drug is
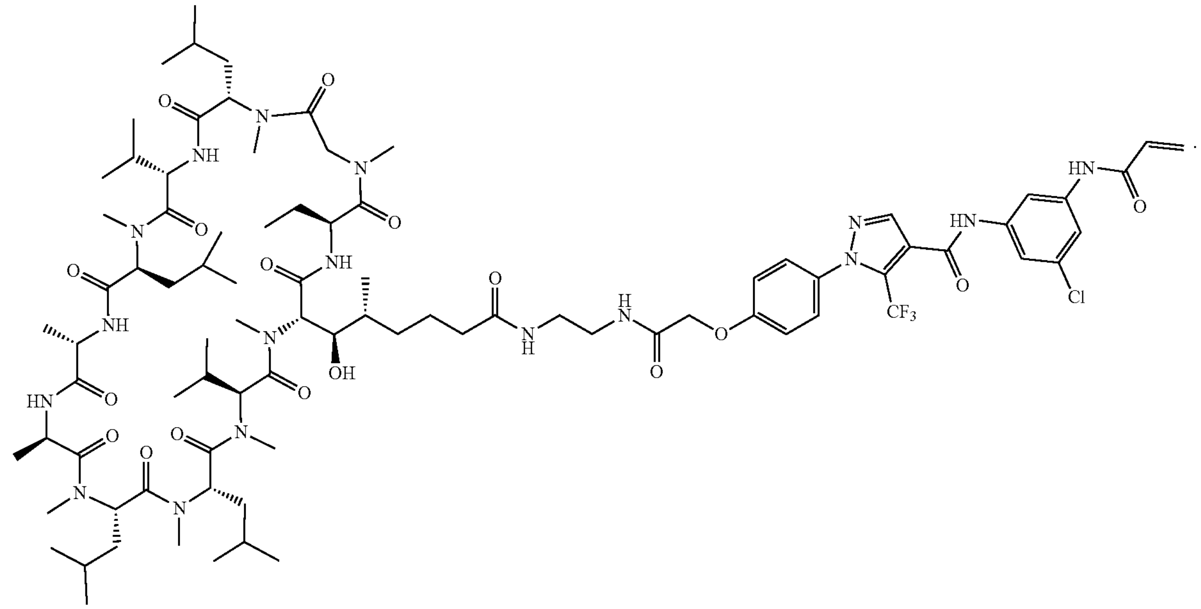 [SMILES: C=CC(=O)Nc1cc(Cl)cc(NC(=O)c2cnn(-c3ccc(OCC(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]

In embodiments, the anti-CNS disease drug is not
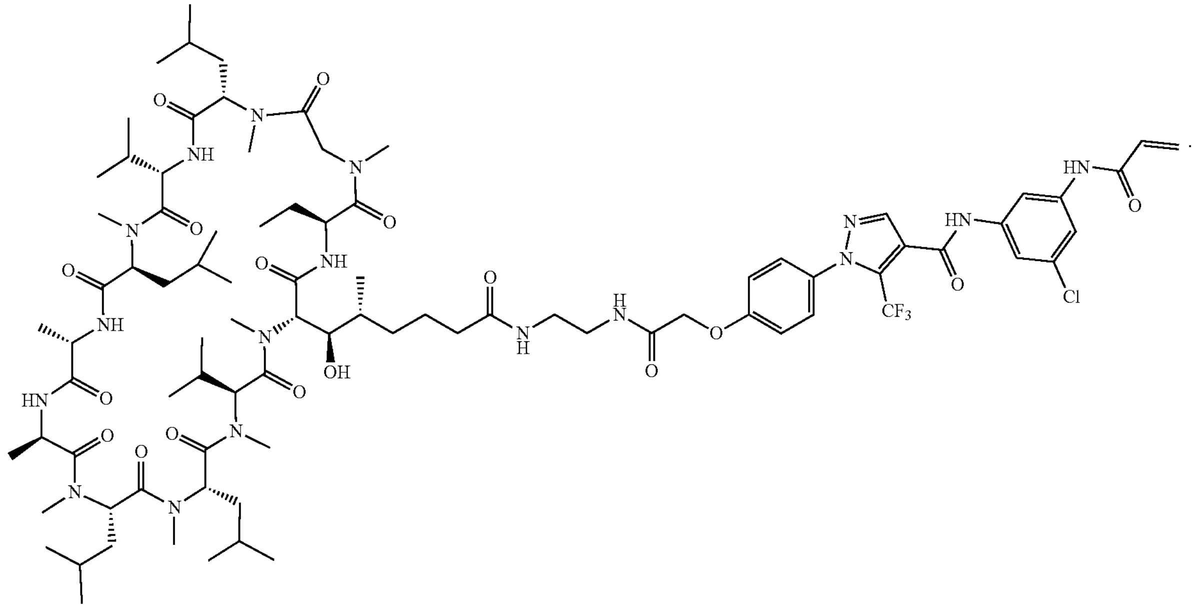 [SMILES: C=CC(=O)Nc1cc(Cl)cc(NC(=O)c2cnn(-c3ccc(OCC(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]
In embodiments, the anti-CNS disease drug is
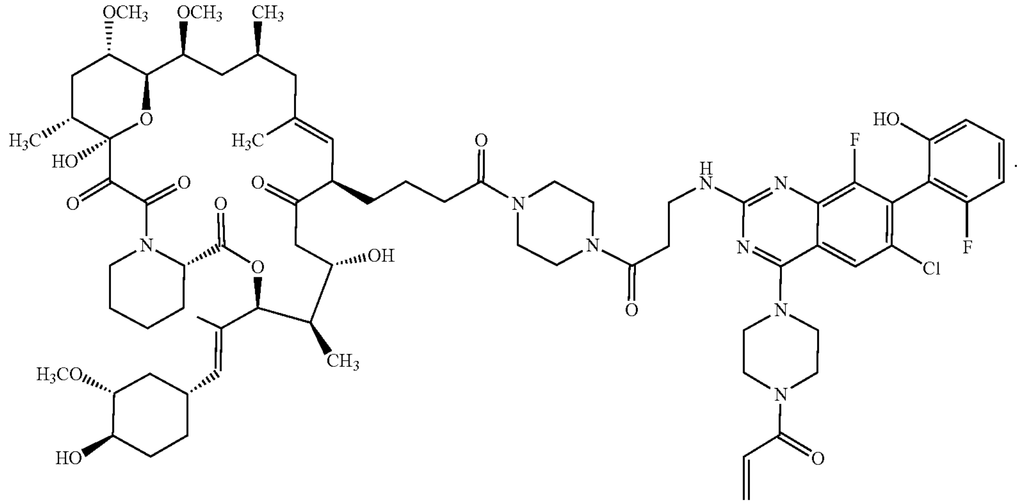 [SMILES: C=CC(=O)N1CCN(c2nc(NCCC(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)nc3c(F)c(-c4c(O)cccc4F)c(Cl)cc23)CC1]

In embodiments, the anti-CNS disease drug is not
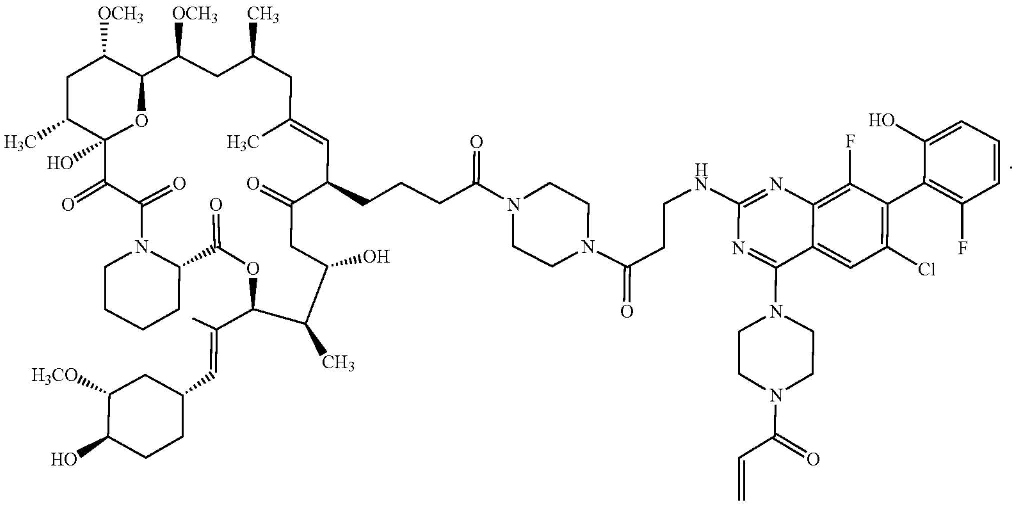 [SMILES: C=CC(=O)N1CCN(c2nc(NCCC(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)nc3c(F)c(-c4c(O)cccc4F)c(Cl)cc23)CC1]
In embodiments, the anti-CNS disease drug is
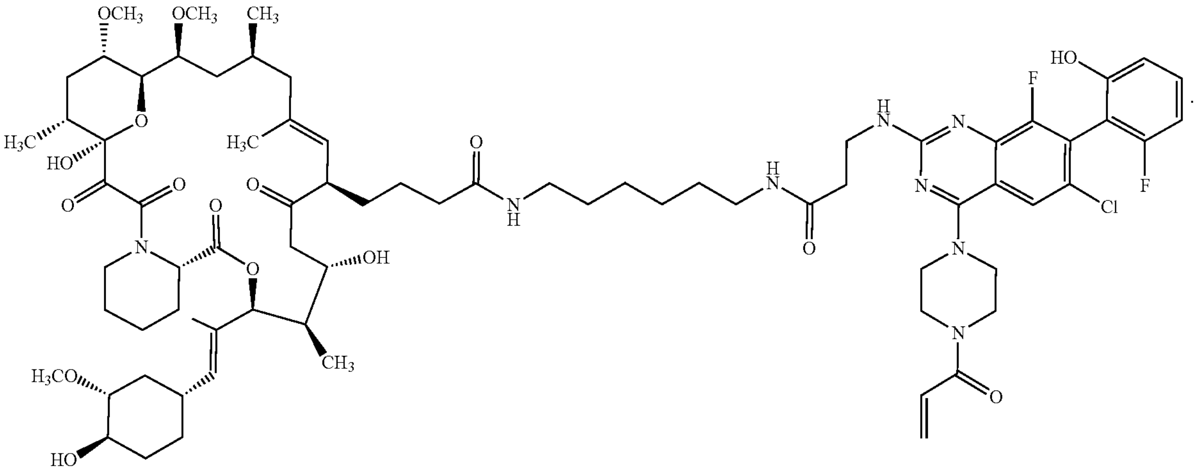 [SMILES: C=CC(=O)N1CCN(c2nc(NCCC(=O)NCCCCCCNC(=O)CCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]
In embodiments, the anti-CNS disease drug is not
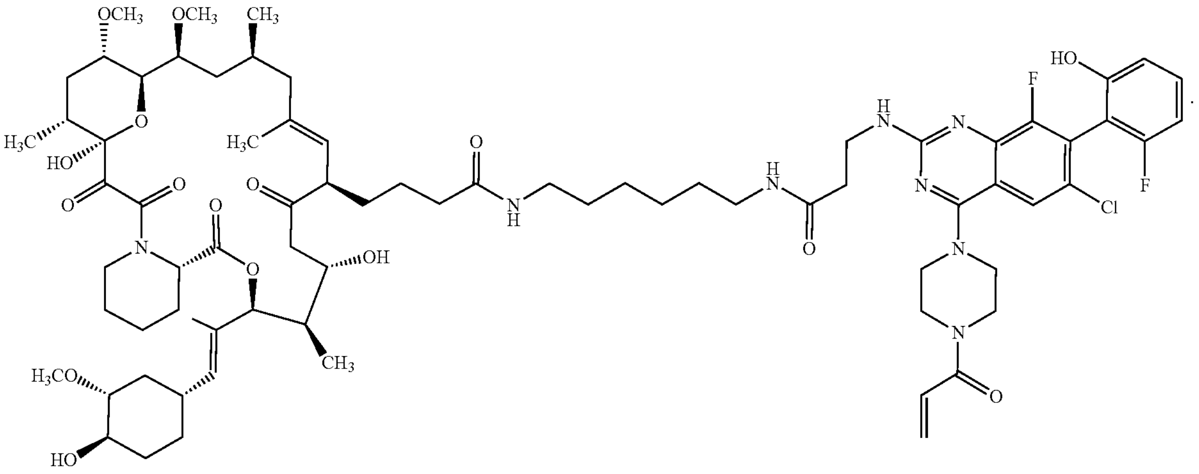 [SMILES: C=CC(=O)N1CCN(c2nc(NCCC(=O)NCCCCCCNC(=O)CCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]

In embodiments, the anti-CNS disease drug is
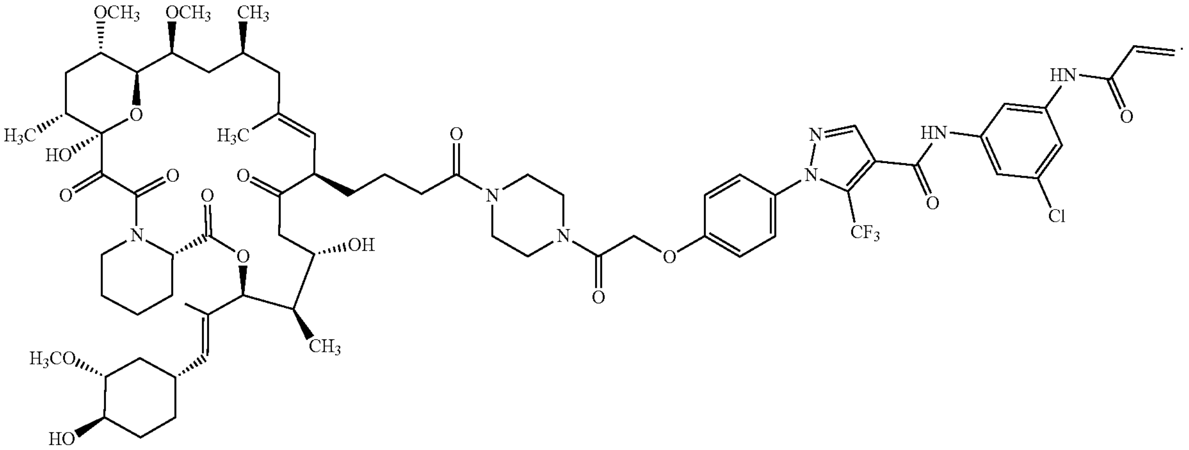 [SMILES: C=CC(=O)Nc1cc(Cl)cc(NC(=O)c2cnn(-c3ccc(OCC(=O)N4CCN(C(=O)CCC[C@@H]5/C=C(\C)C[C@H](C)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc3)c2C(F)(F)F)c1]
In embodiments, the anti-CNS disease drug is not
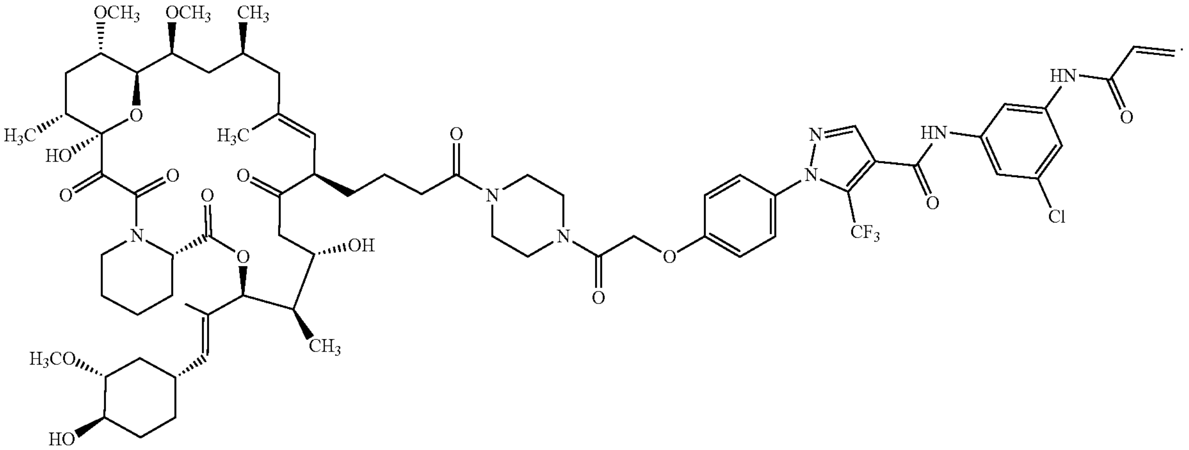 [SMILES: C=CC(=O)Nc1cc(Cl)cc(NC(=O)c2cnn(-c3ccc(OCC(=O)N4CCN(C(=O)CCC[C@@H]5/C=C(\C)C[C@H](C)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc3)c2C(F)(F)F)c1]

In embodiments, the anti-CNS disease drug is
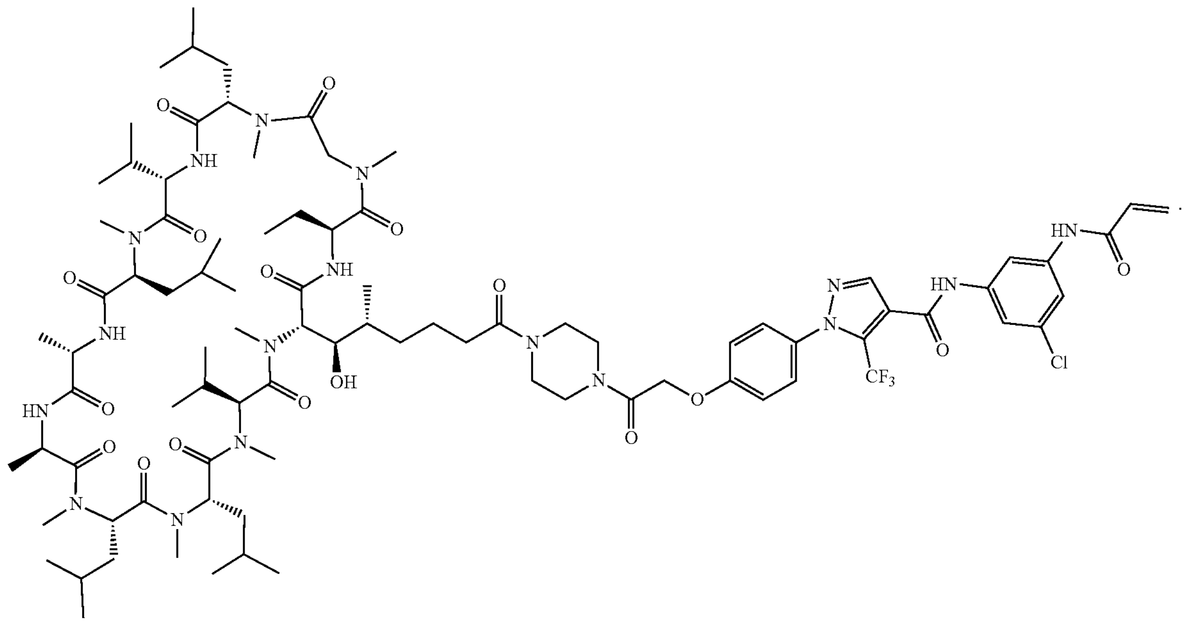 [SMILES: C=CC(=O)Nc1cc(Cl)cc(NC(=O)c2cnn(-c3ccc(OCC(=O)N4CCN(C(=O)CCC[C@@H](C)[C@@H](O)[C@H]5C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N5C)CC4)cc3)c2C(F)(F)F)c1]
In embodiments, the anti-CNS disease drug is not
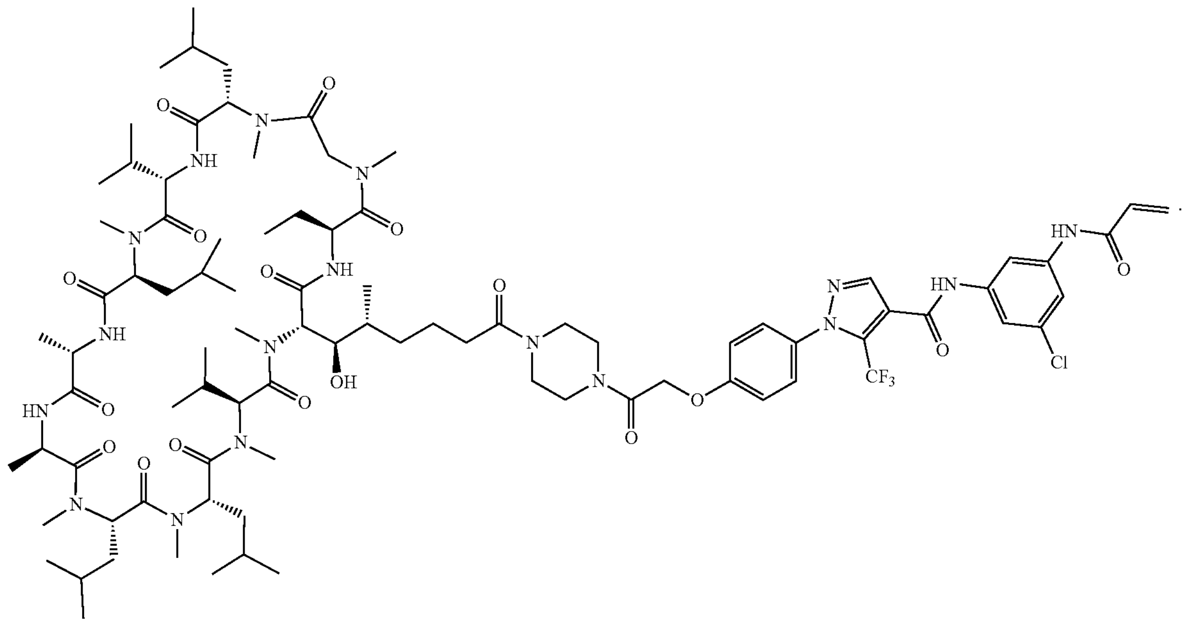 [SMILES: C=CC(=O)Nc1cc(Cl)cc(NC(=O)c2cnn(-c3ccc(OCC(=O)N4CCN(C(=O)CCC[C@@H](C)[C@@H](O)[C@H]5C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N5C)CC4)cc3)c2C(F)(F)F)c1]

In embodiments, the anti-CNS disease drug is
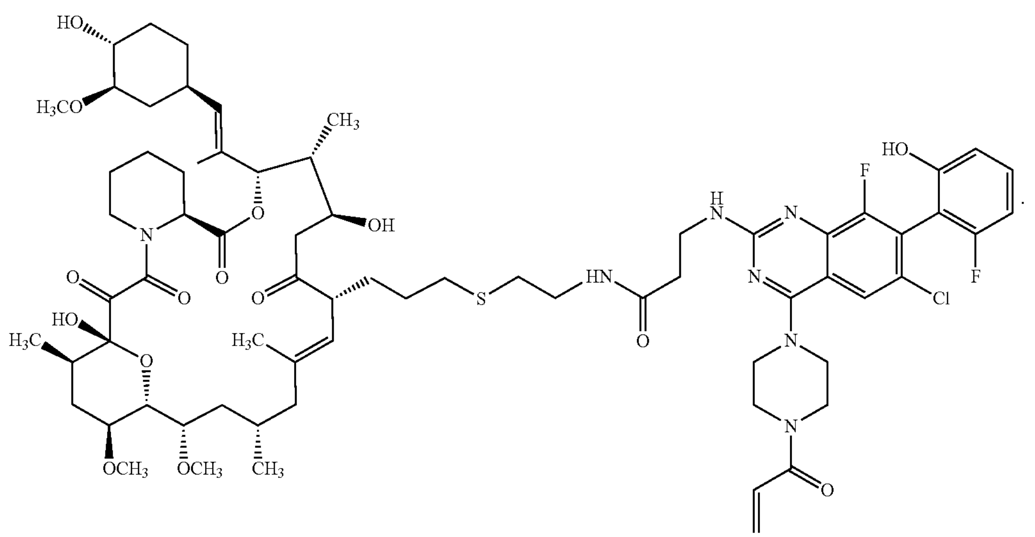 [SMILES: C=CC(=O)N1CCN(c2nc(NCCC(=O)NCCSCCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]
In embodiments, the anti-CNS disease drug is not
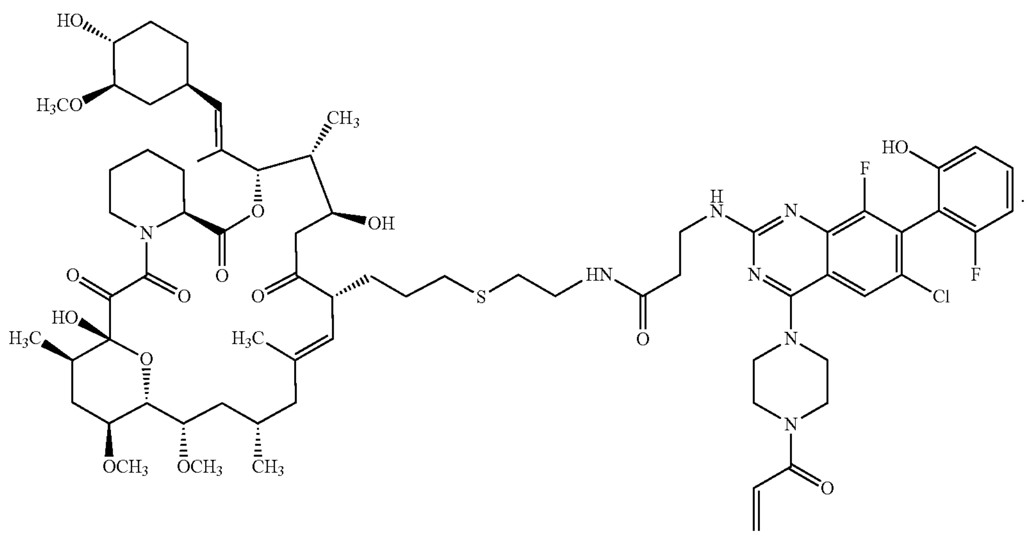 [SMILES: C=CC(=O)N1CCN(c2nc(NCCC(=O)NCCSCCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]

In embodiments, the anti-CNS disease drug is
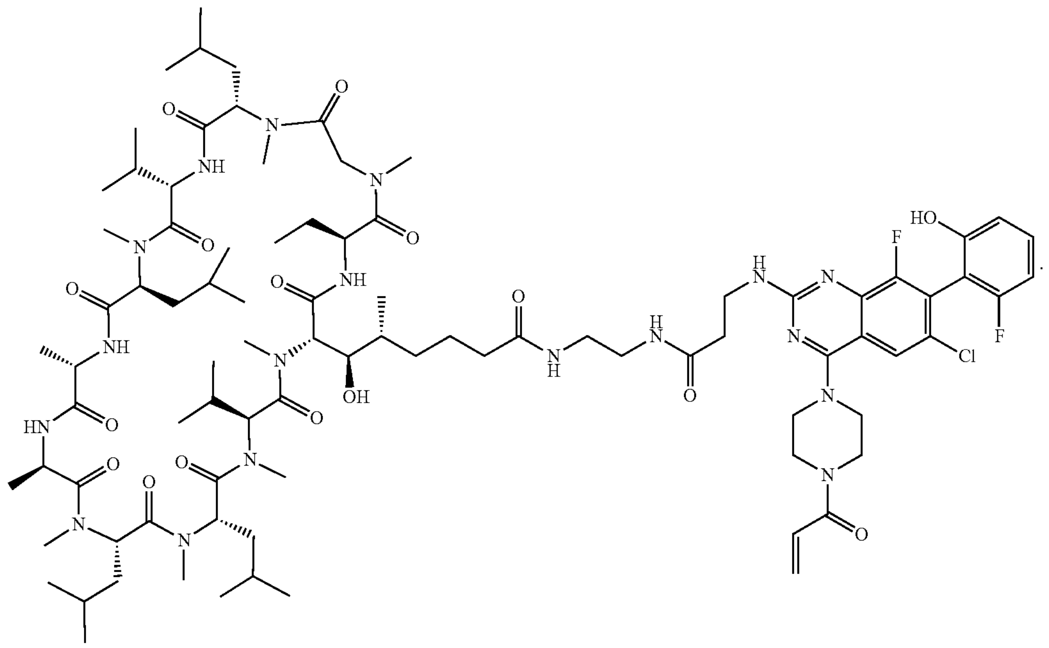 [SMILES: C=CC(=O)N1CCN(c2nc(NCCC(=O)NCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]
In embodiments, the anti-CNS disease drug is not
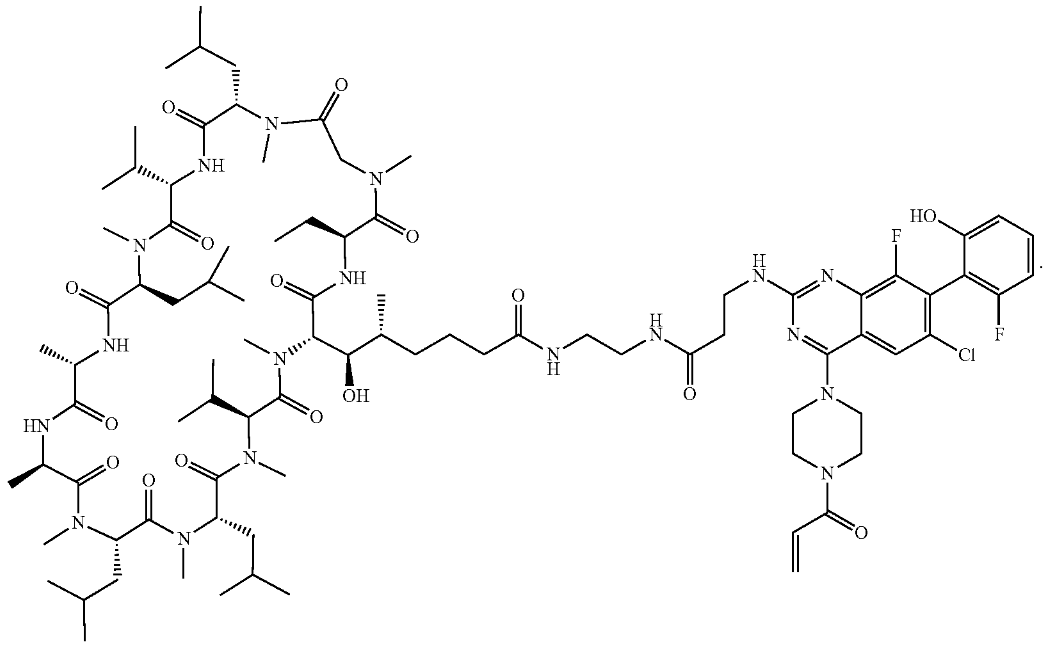 [SMILES: C=CC(=O)N1CCN(c2nc(NCCC(=O)NCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]

In embodiments, the anti-CNS disease drug is
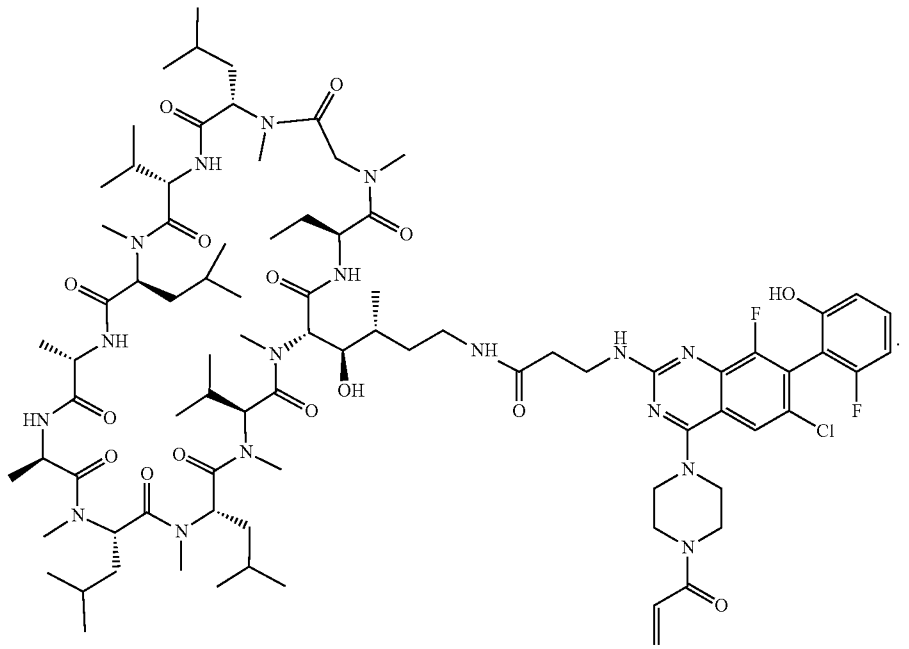 [SMILES: C=CC(=O)N1CCN(c2nc(NCCC(=O)NCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]
In embodiments, the anti-CNS disease drug is not
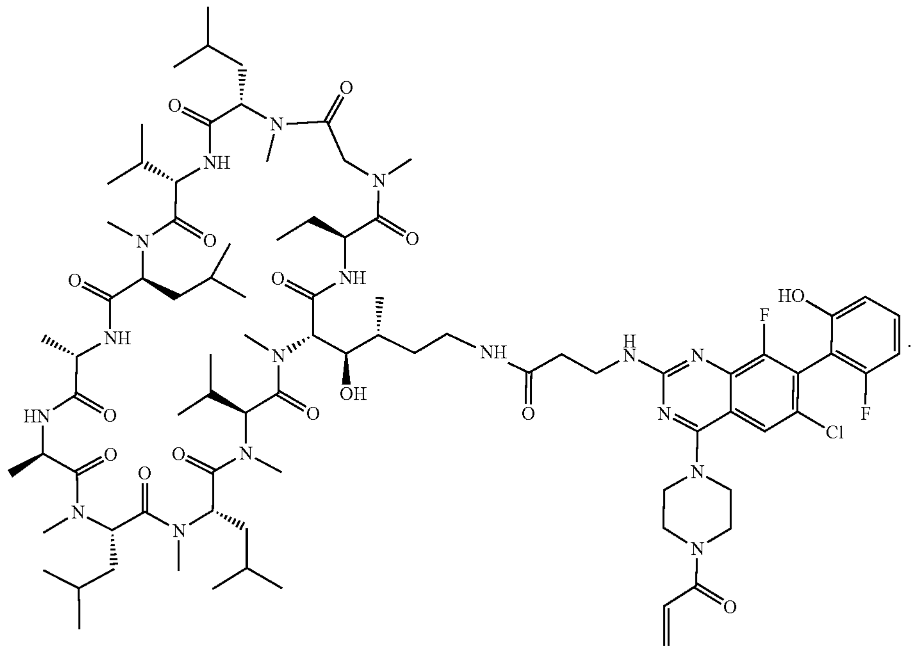 [SMILES: C=CC(=O)N1CCN(c2nc(NCCC(=O)NCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]

In embodiments, the anti-CNS disease drug is
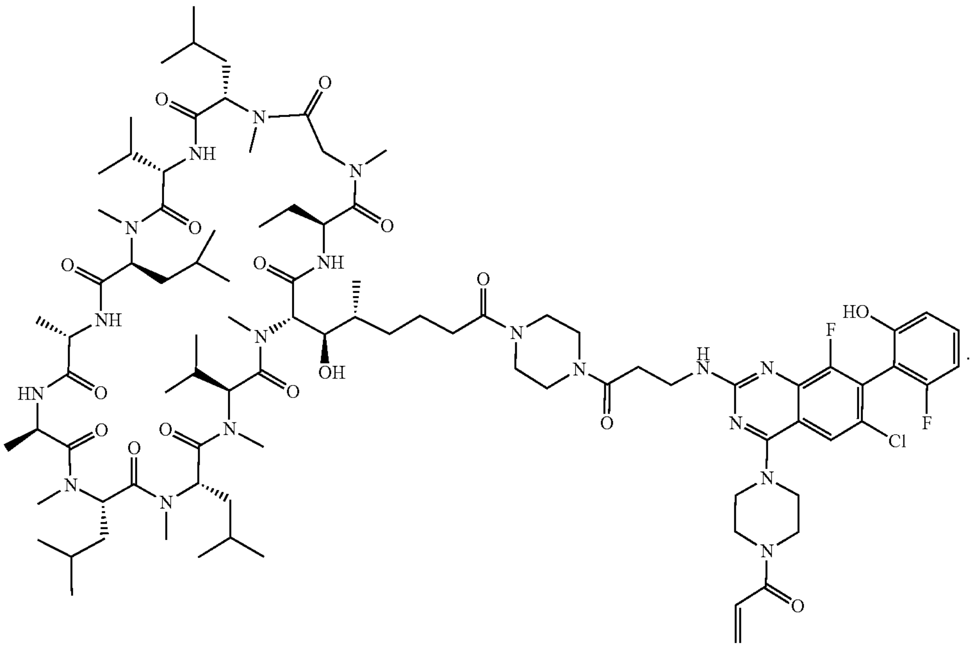 [SMILES: C=CC(=O)N1CCN(c2nc(NCCC(=O)N3CCN(C(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)CC3)nc3c(F)c(-c4c(O)cccc4F)c(Cl)cc23)CC1]
In embodiments, the anti-CNS disease drug is not
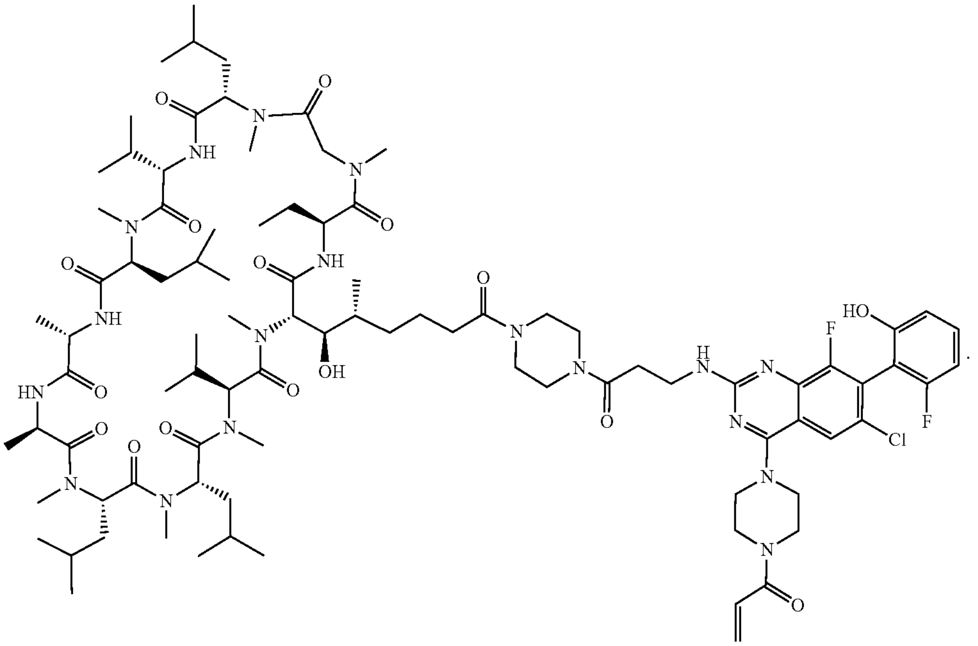 [SMILES: C=CC(=O)N1CCN(c2nc(NCCC(=O)N3CCN(C(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)CC3)nc3c(F)c(-c4c(O)cccc4F)c(Cl)cc23)CC1]

In embodiments, the anti-CNS disease drug is
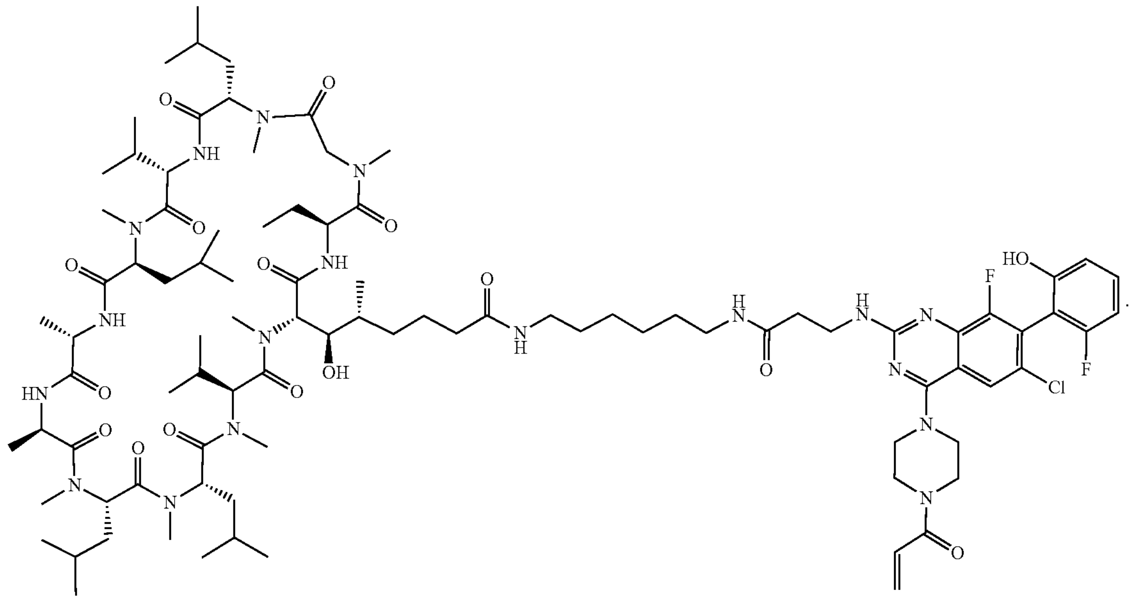 [SMILES: C=CC(=O)N1CCN(c2nc(NCCC(=O)NCCCCCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]
In embodiments, the anti-CNS disease drug is not
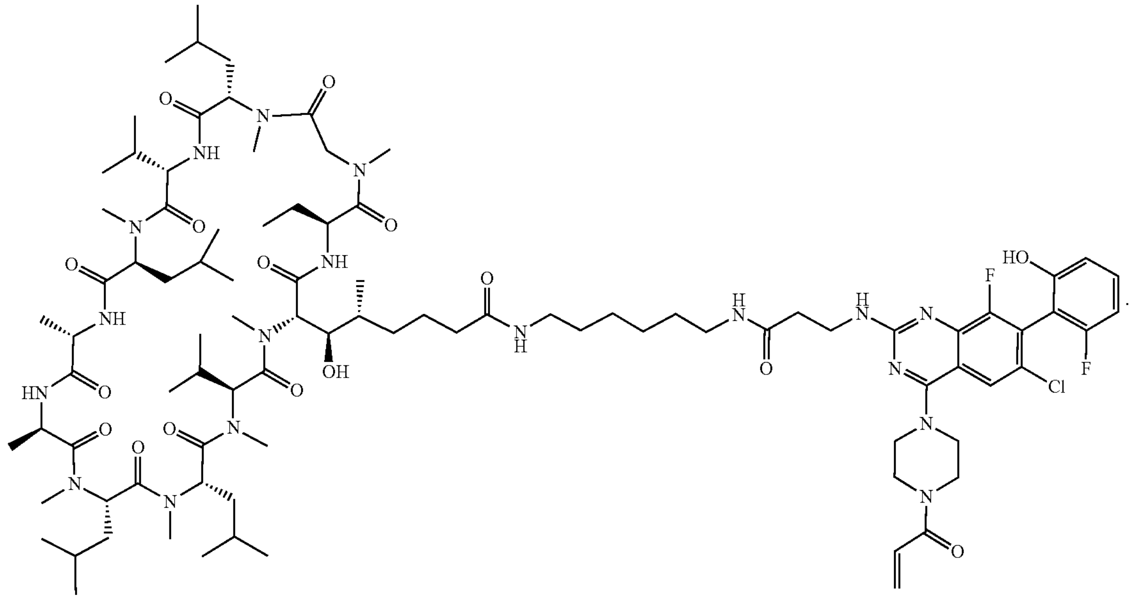 [SMILES: C=CC(=O)N1CCN(c2nc(NCCC(=O)NCCCCCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]

In embodiments, the anti-CNS disease drug is
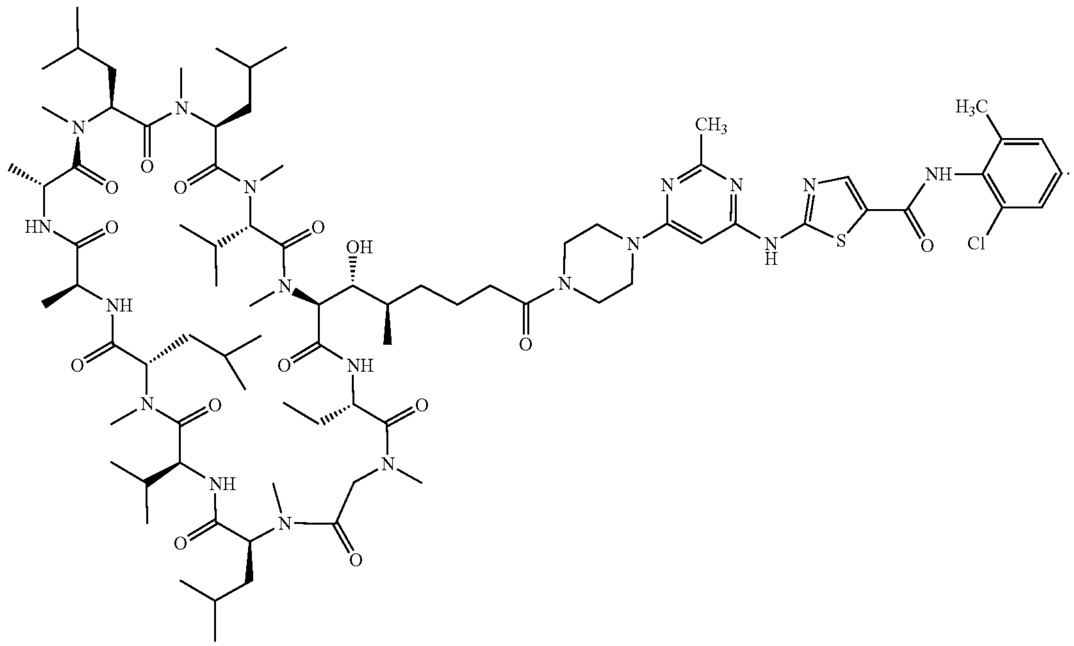
In embodiments, the anti-CNS disease drug is not
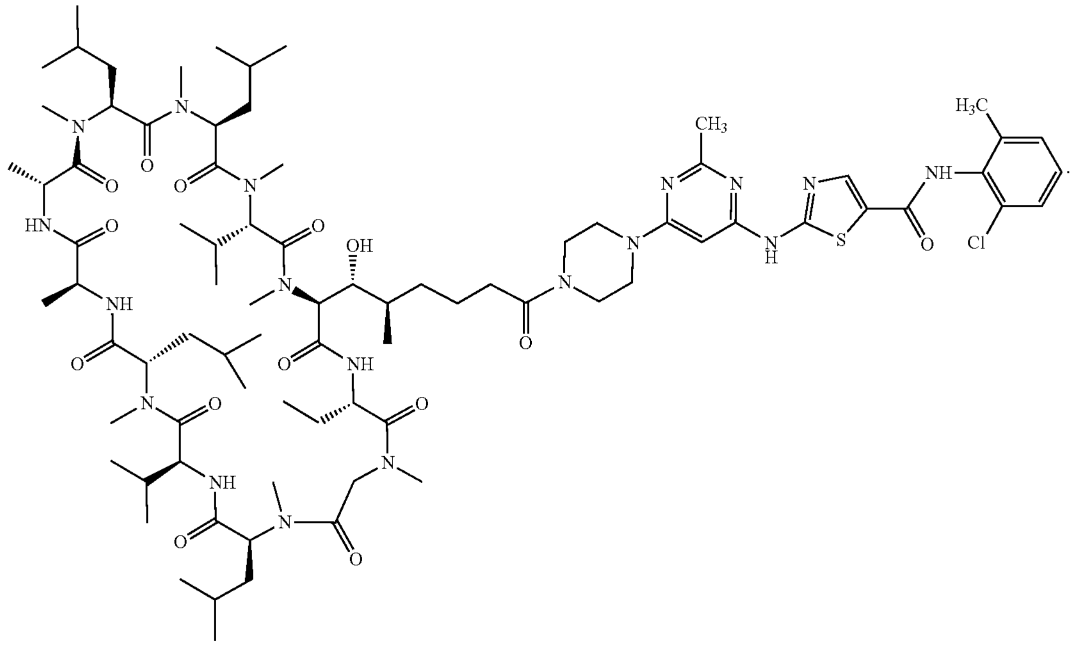

In embodiments, the anti-CNS disease drug is
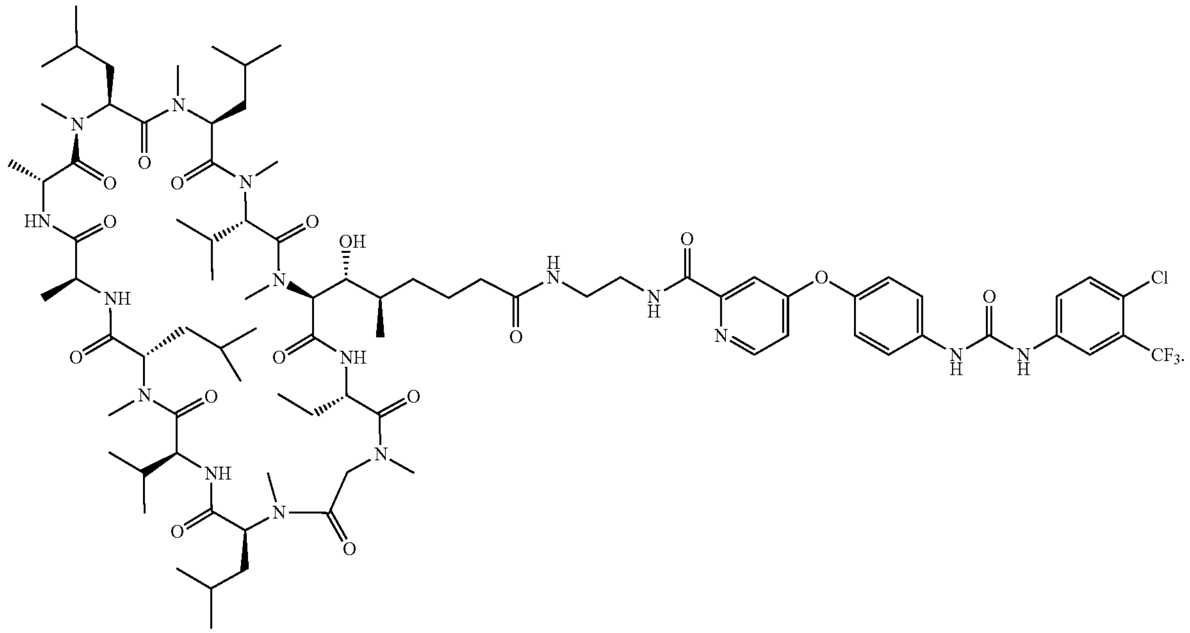
In embodiments, the anti-CNS disease drug is not
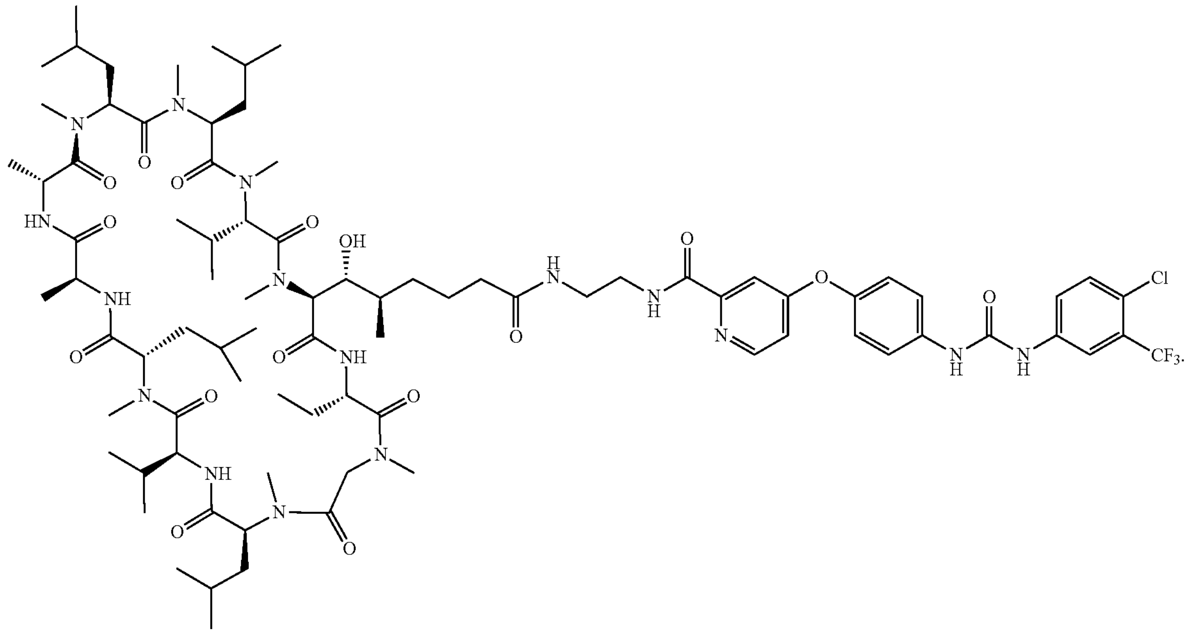

In embodiments, the anti-CNS disease drug is
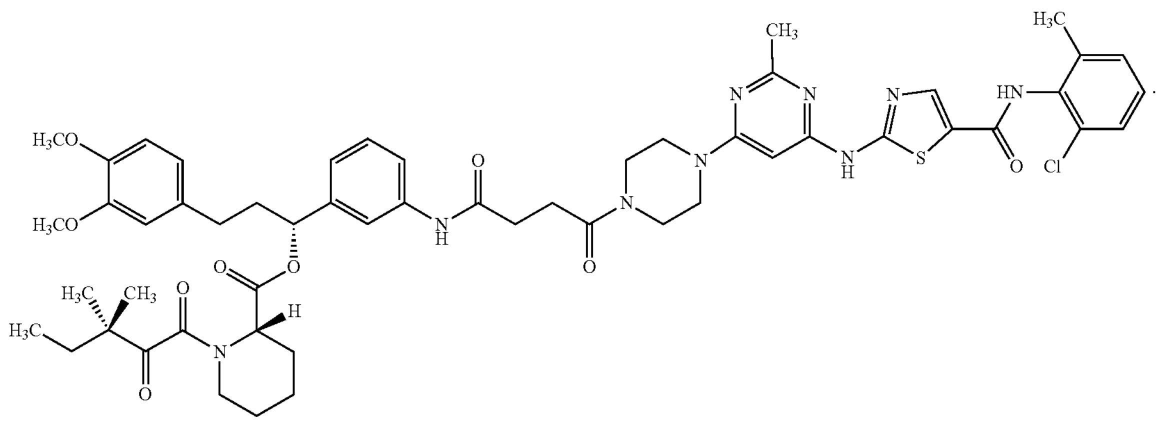
In embodiments, the anti-CNS disease drug is not
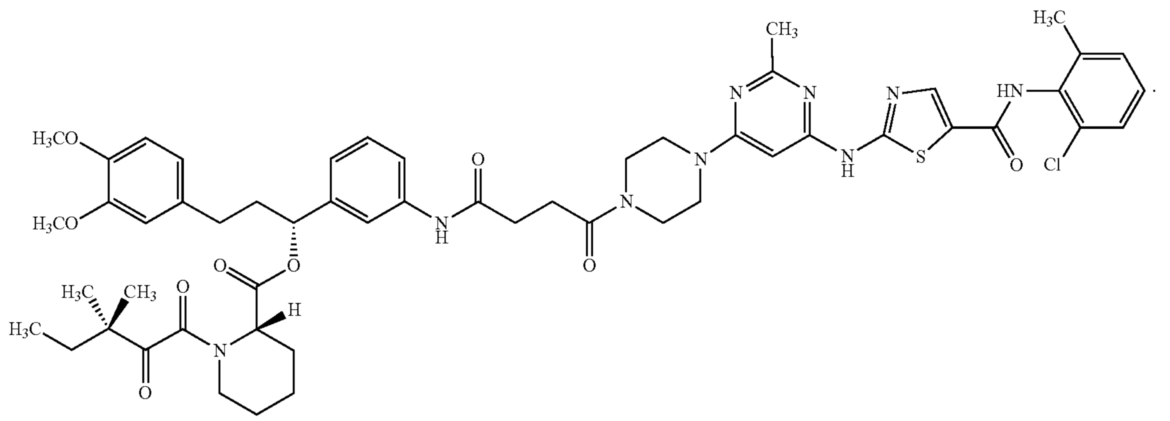
In embodiments, the anti-CNS disease drug is
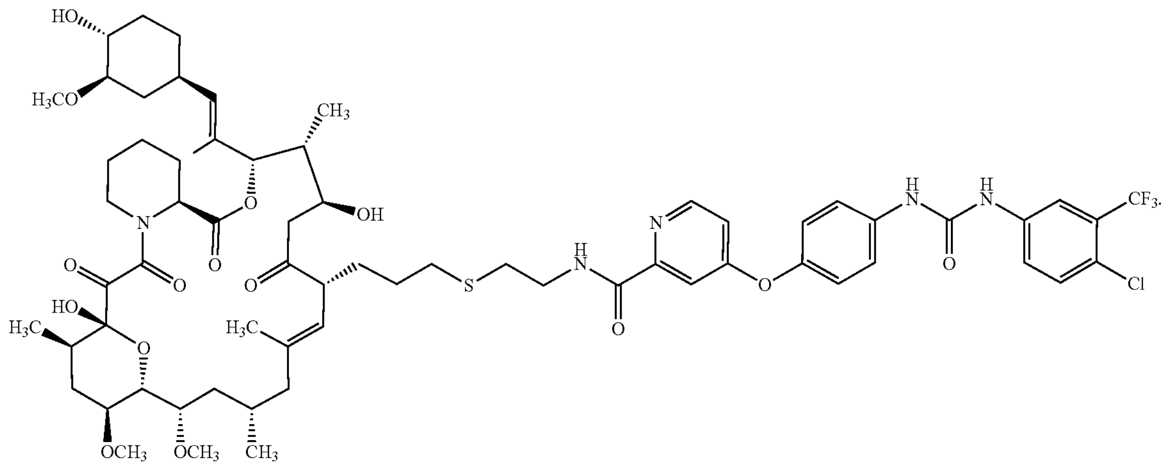 [SMILES: CO[C@H]1C[C@@H](C)C/C(C)=C/[C@@H](CCCSCCNC(=O)c2cc(Oc3ccc(NC(=O)Nc4ccc(Cl)c(C(F)(F)F)c4)cc3)ccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
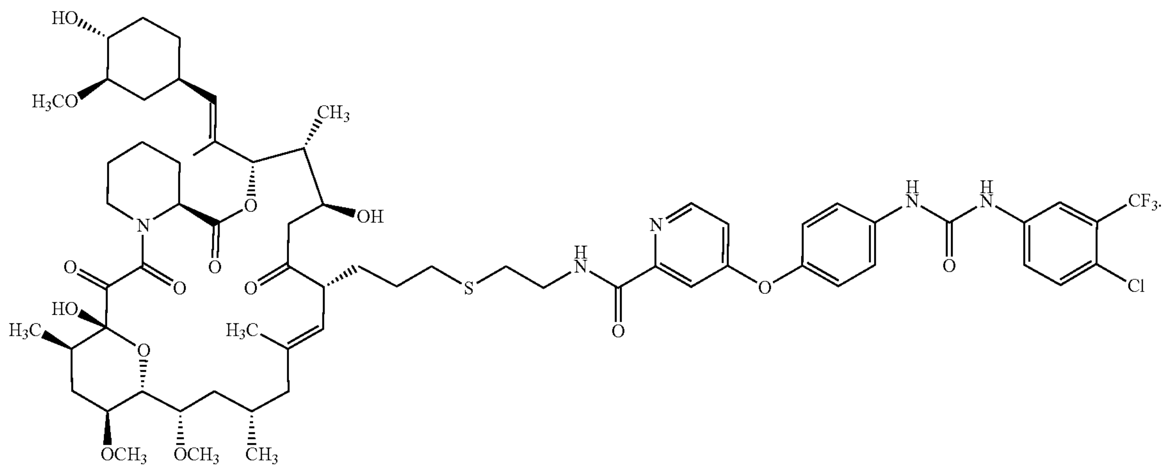 [SMILES: CO[C@H]1C[C@@H](C)C/C(C)=C/[C@@H](CCCSCCNC(=O)c2cc(Oc3ccc(NC(=O)Nc4ccc(Cl)c(C(F)(F)F)c4)cc3)ccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
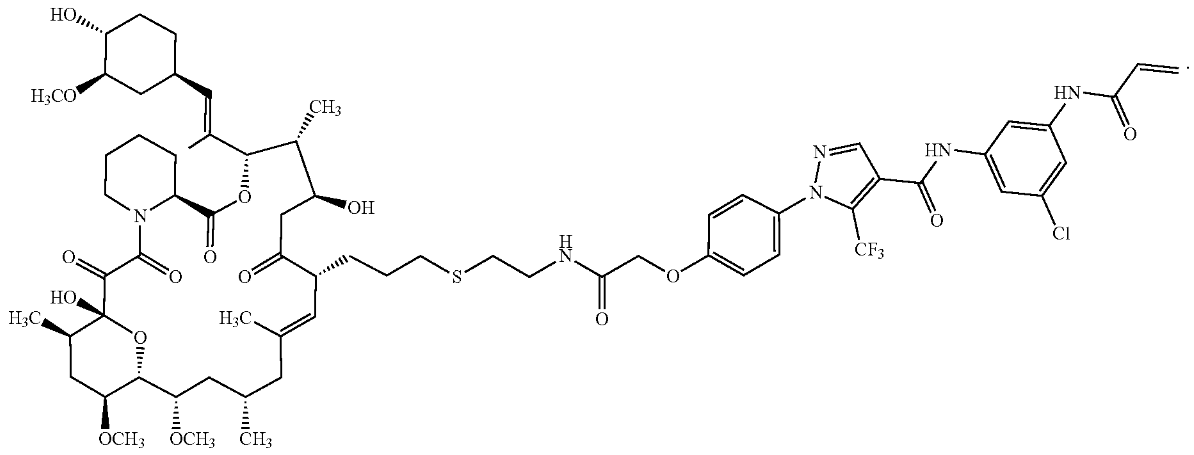 [SMILES: C=CC(=O)Nc1cc(Cl)cc(NC(=O)c2cnn(-c3ccc(OCC(=O)NCCSCCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]
In embodiments, the anti-CNS disease drug is not
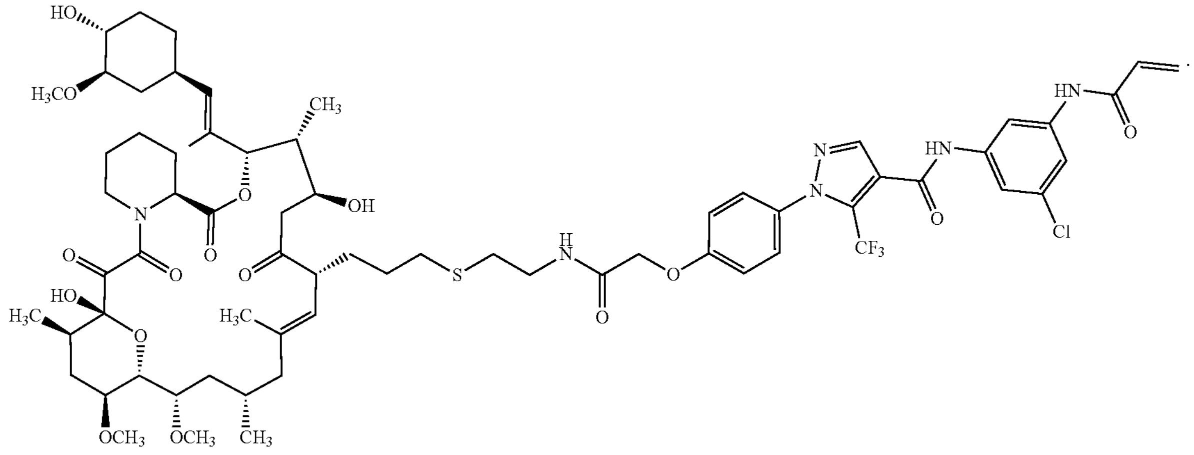 [SMILES: C=CC(=O)Nc1cc(Cl)cc(NC(=O)c2cnn(-c3ccc(OCC(=O)NCCSCCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]

In embodiments, the anti-CNS disease drug is
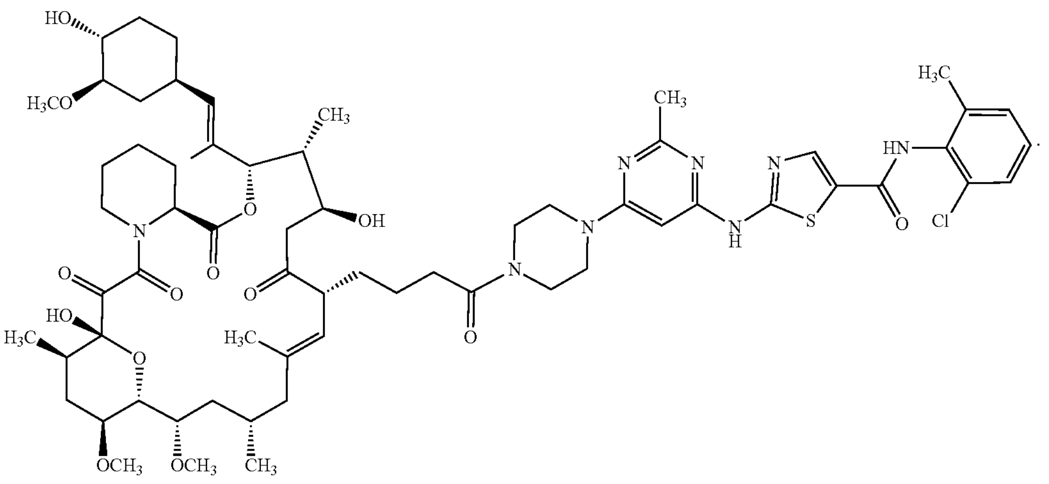 [SMILES: CO[C@H]1C[C@@H](C)C/C(C)=C/[C@@H](CCCC(=O)N2CCN(c3cc(Nc4ncc(C(=O)Nc5c(C)cccc5Cl)s4)nc(C)n3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
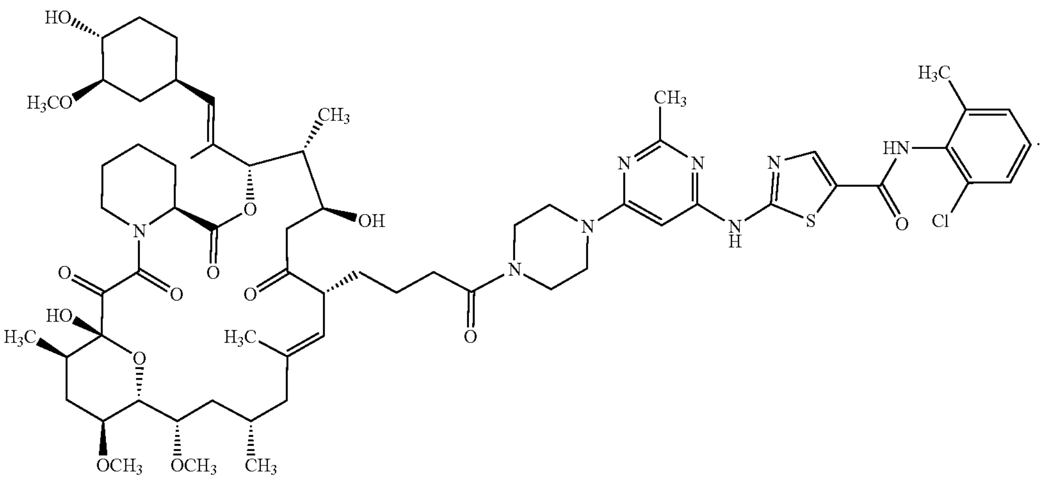 [SMILES: CO[C@H]1C[C@@H](C)C/C(C)=C/[C@@H](CCCC(=O)N2CCN(c3cc(Nc4ncc(C(=O)Nc5c(C)cccc5Cl)s4)nc(C)n3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
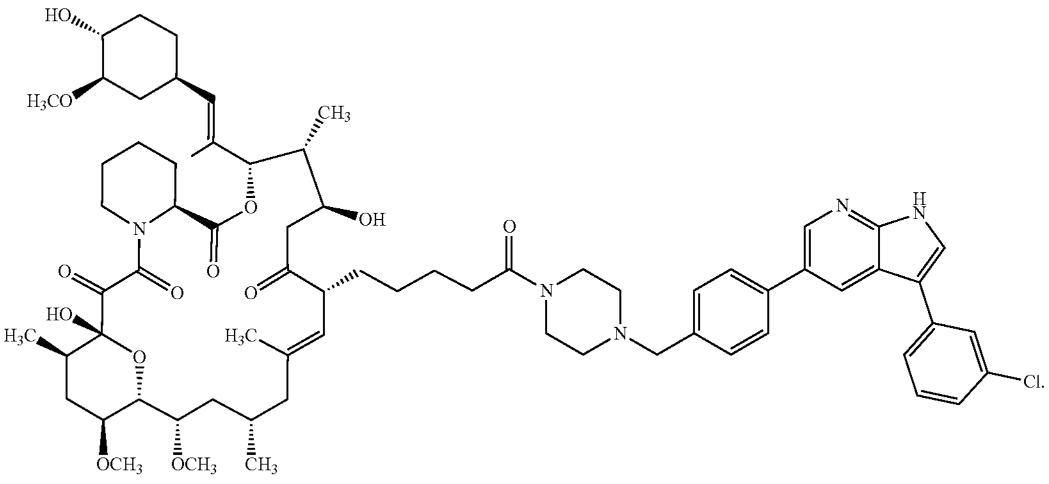 [SMILES: CO[C@H]1C[C@@H](C)C/C(C)=C/[C@@H](CCCCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
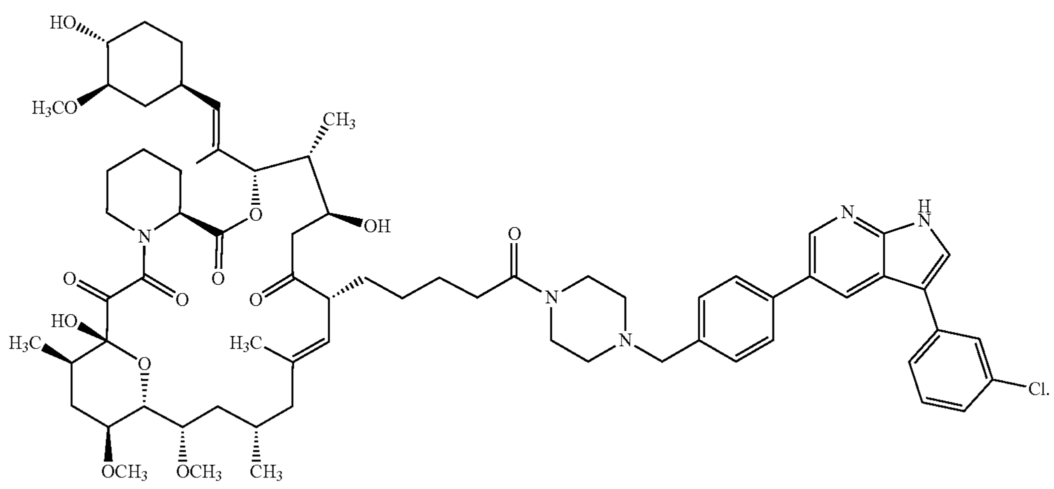 [SMILES: CO[C@H]1C[C@@H](C)C/C(C)=C/[C@@H](CCCCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
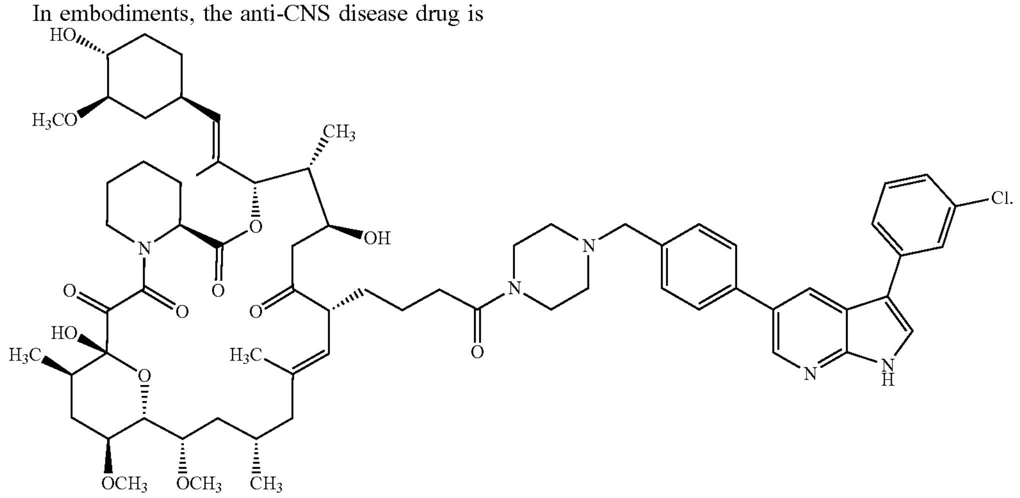
In embodiments, the anti-CNS disease drug is not
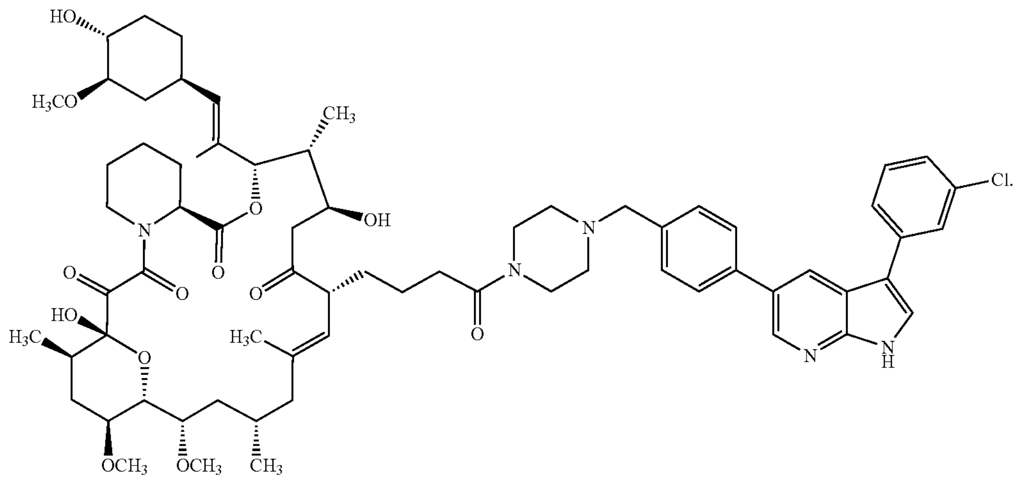 [SMILES: CO[C@H]1C[C@@H](C)C/C(C)=C/[C@@H](CCCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is
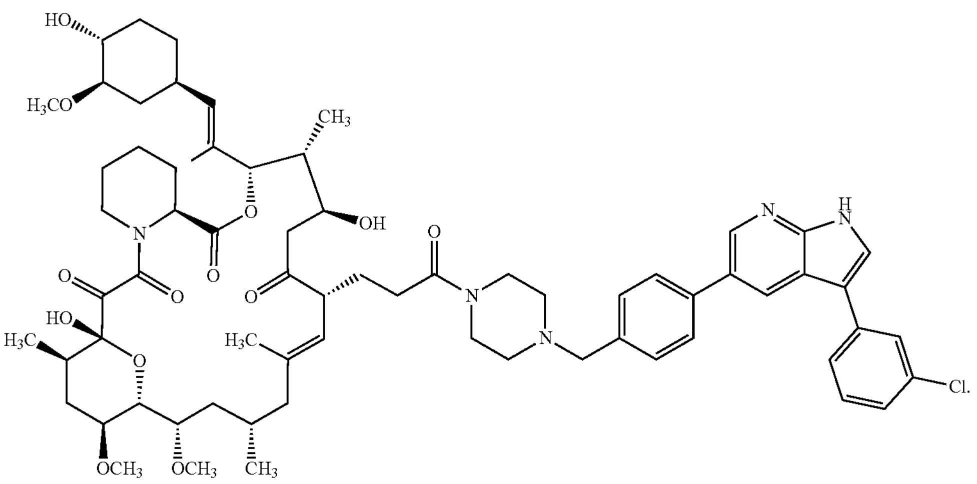 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
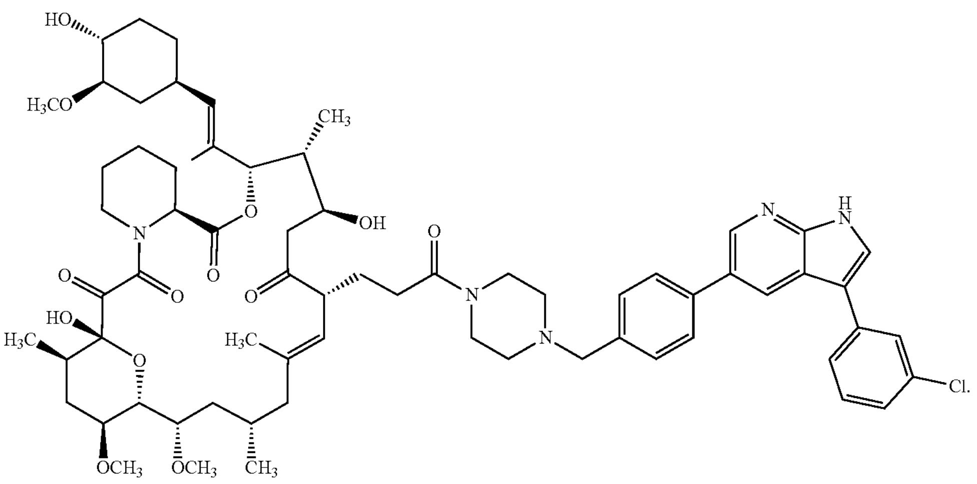 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
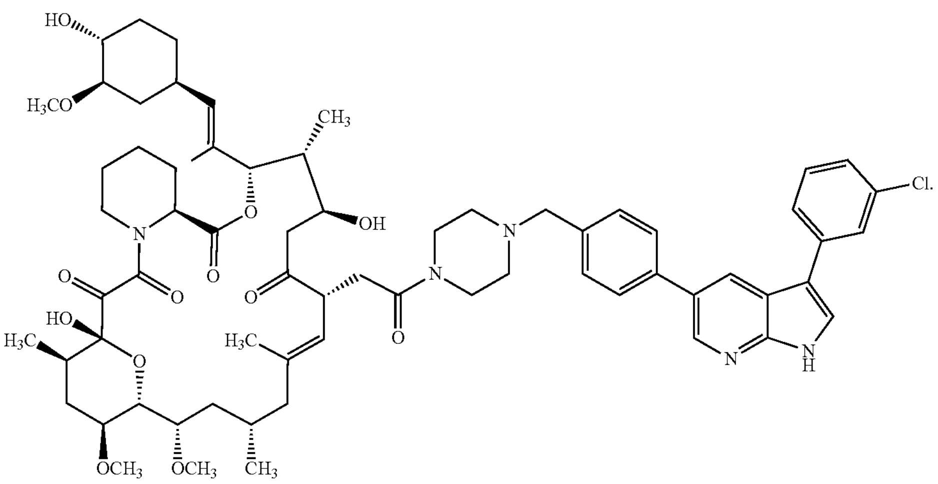 [SMILES: CO[C@H]1C[C@@H](C)C/C(C)=C/[C@@H](CC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
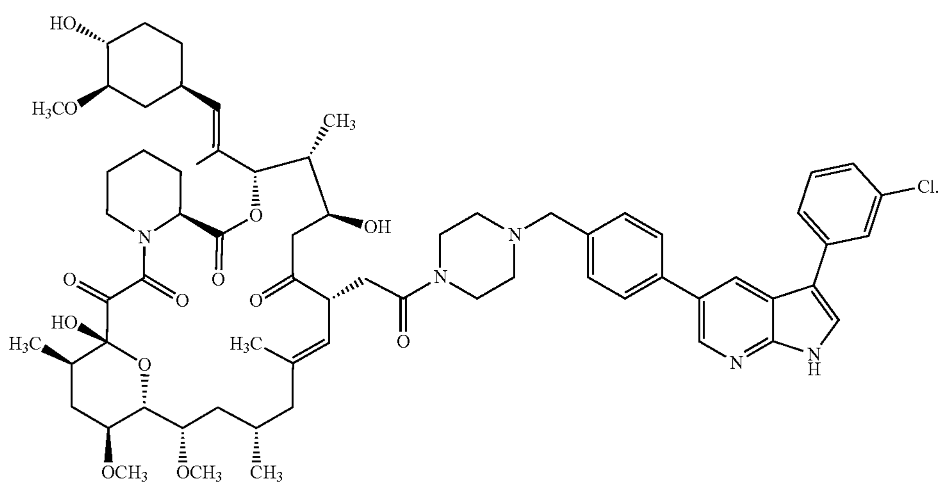 [SMILES: CO[C@H]1C[C@@H](C)C/C(C)=C/[C@@H](CC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
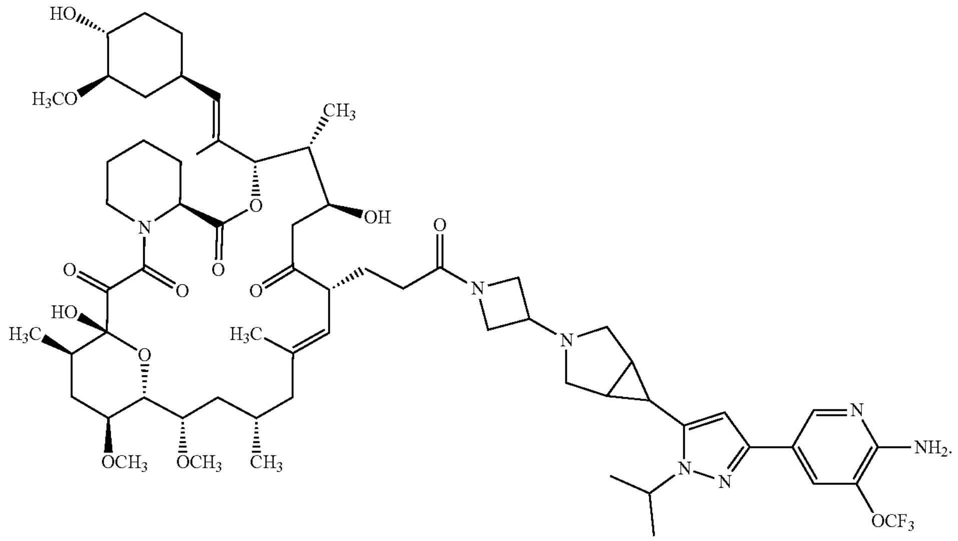 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
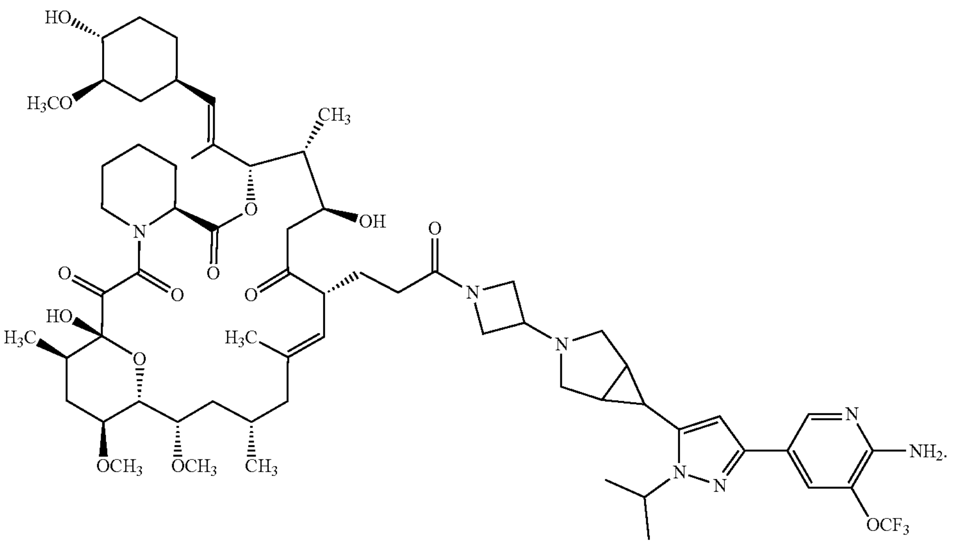 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
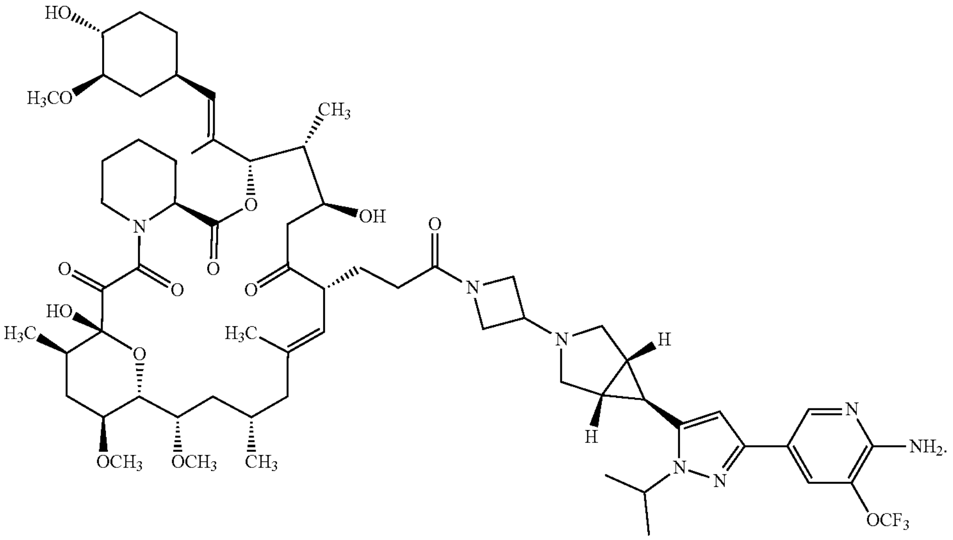 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
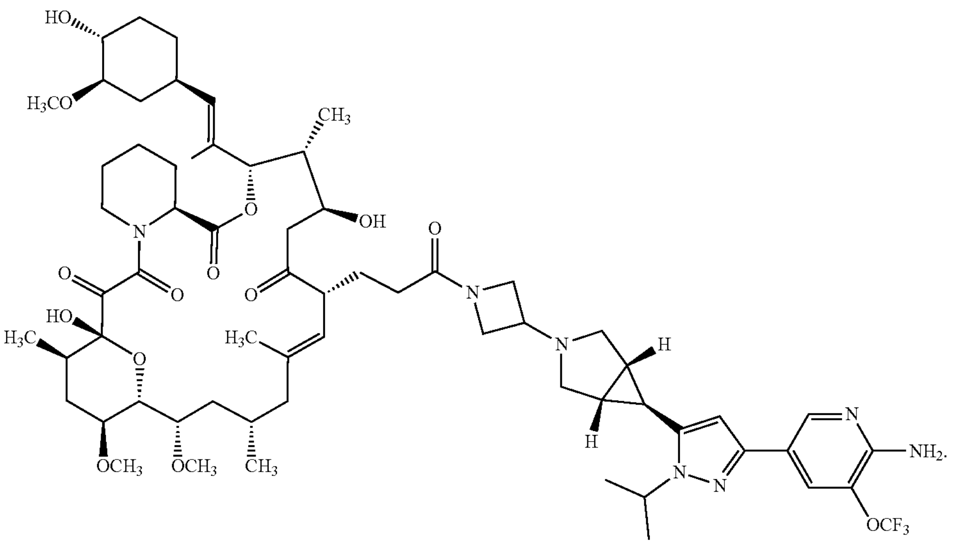 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
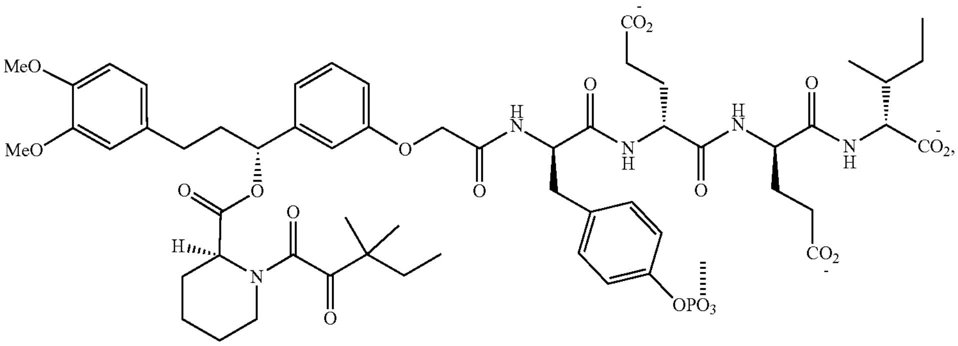
or an analog thereof.
In embodiments, the anti-CNS disease drug is not
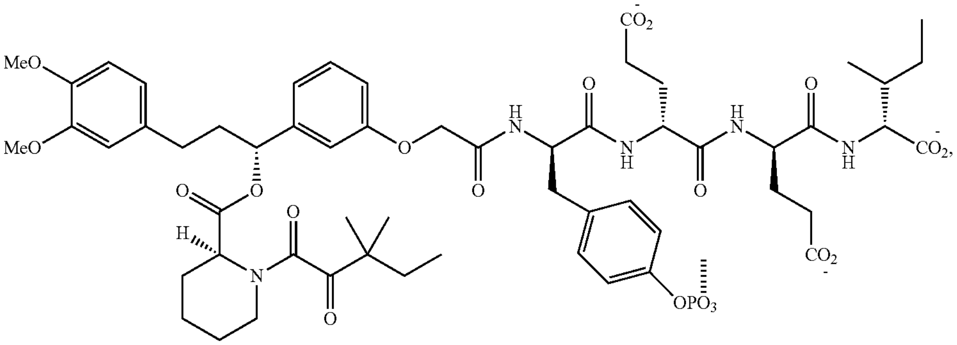
or an analog thereof.

In embodiments, the anti-CNS disease drug is
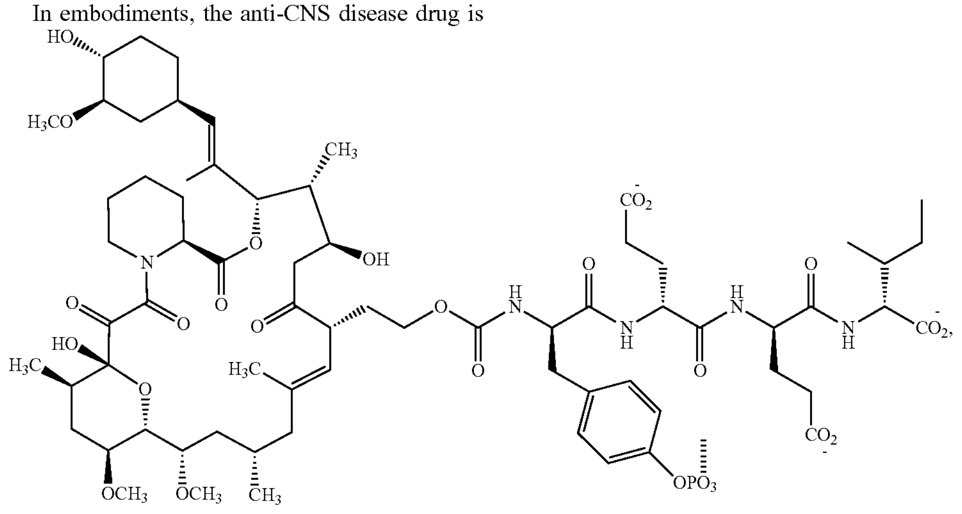
or an analog thereof.
In embodiments, the anti-CNS disease drug is not
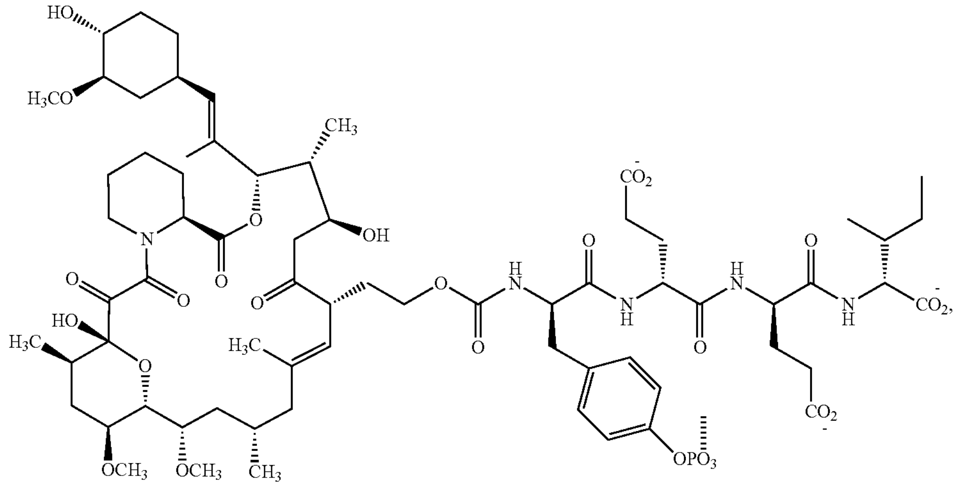
or an analog thereof.
In embodiments, the anti-CNS disease drug is
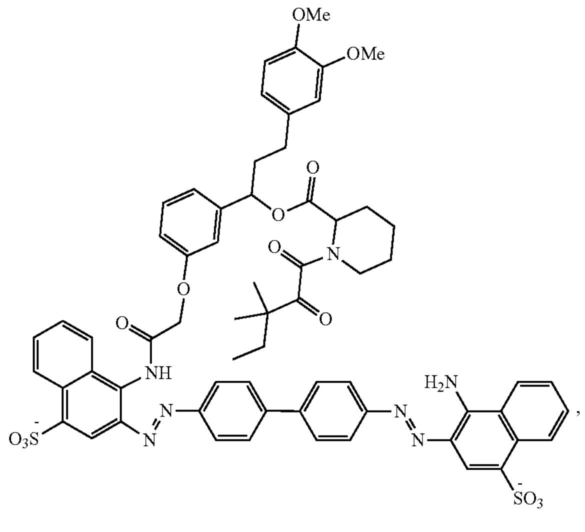
or an analog thereof.

In embodiments, the anti-CNS disease drug is not
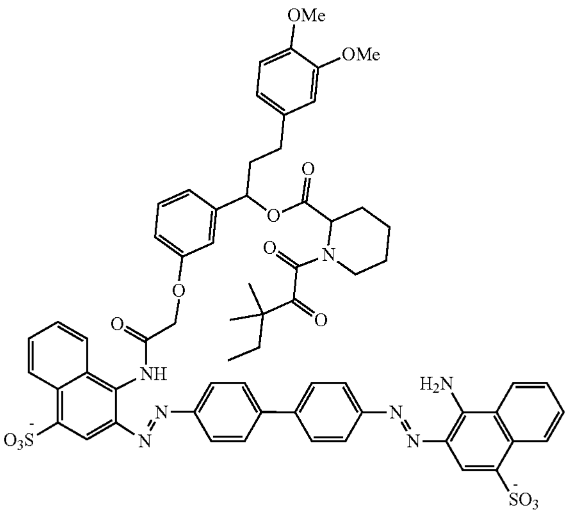
,
or an analog thereof.
In embodiments, the anti-CNS disease drug is
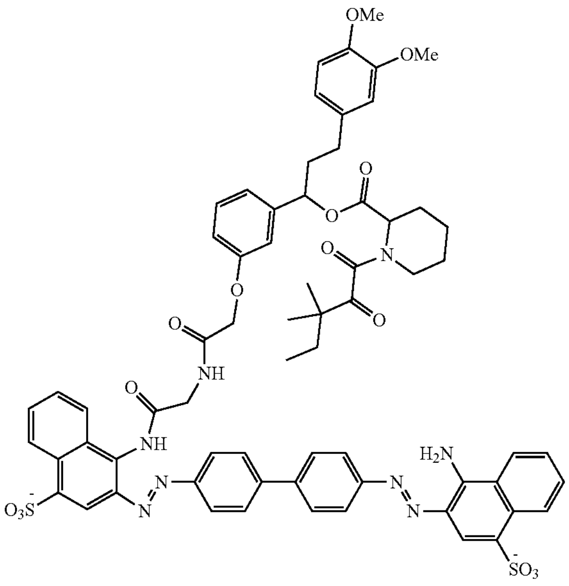
,
or an analog thereof.
In embodiments, the anti-CNS disease drug is not
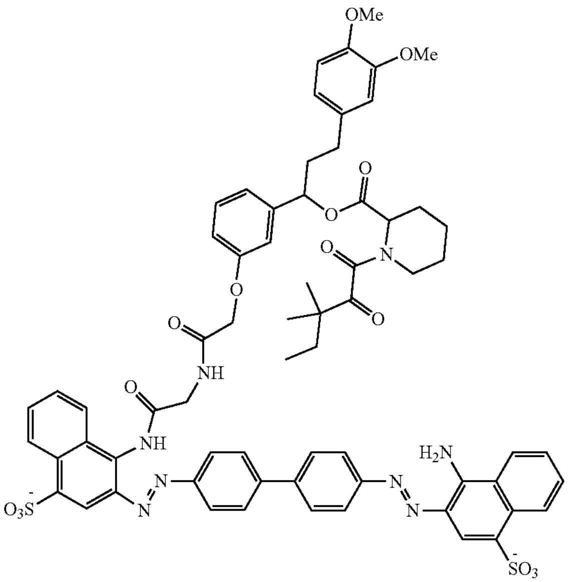
,
an analog thereof.
In embodiments, the anti-CNS disease drug is
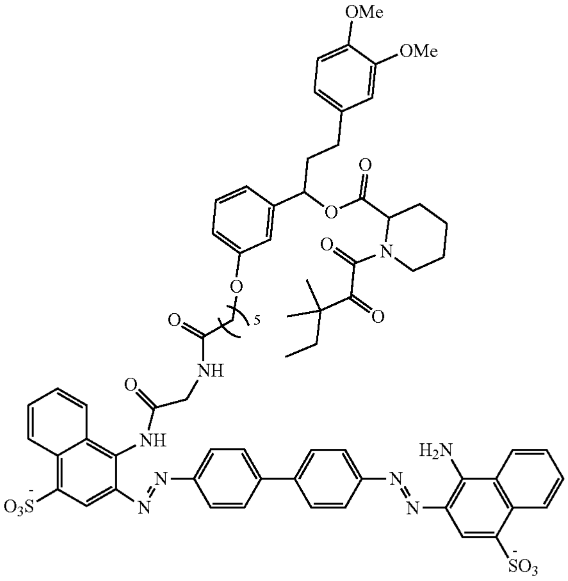
,
or an analog thereof.

In embodiments, the anti-CNS disease drug is not
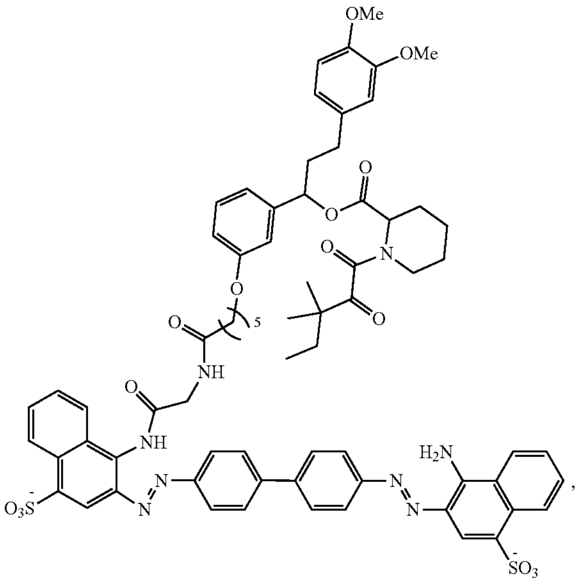
or an analog thereof.
In embodiments, the anti-CNS disease drug is
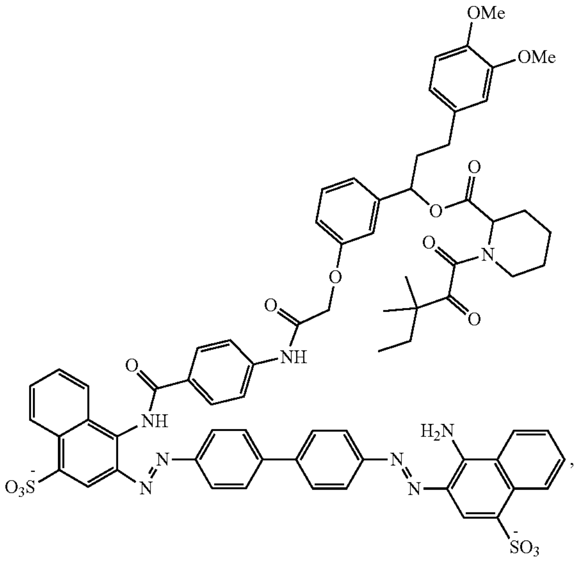
or an analog thereof.

In embodiments, the anti-CNS disease drug is not
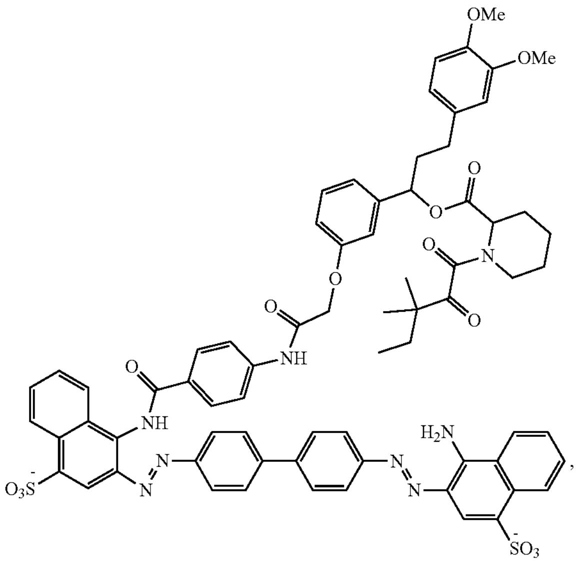
or an analog thereof.
In embodiments, the anti-CNS disease drug is
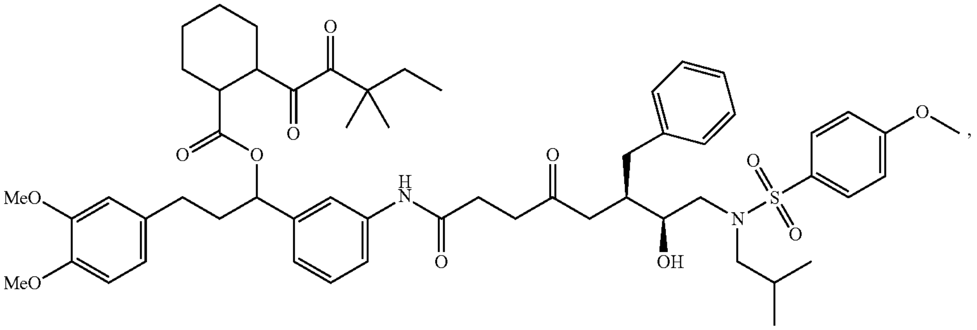 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc(OC)cc2)c1]
or an analog thereof.
In embodiments, the anti-CNS disease drug is not
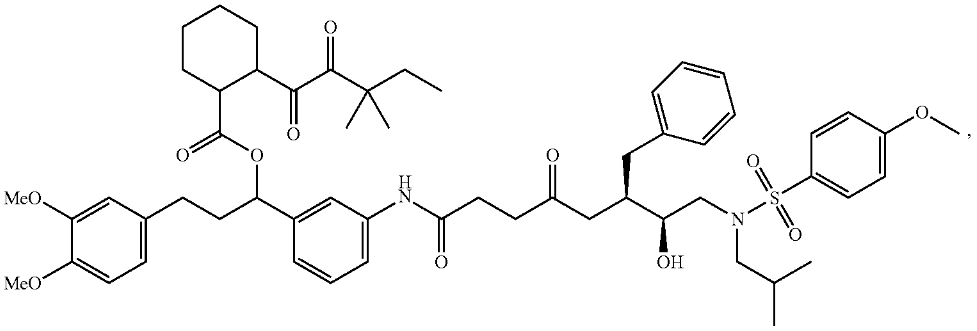 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc(OC)cc2)c1]
or an analog thereof.

In embodiments, the anti-CNS disease drug is
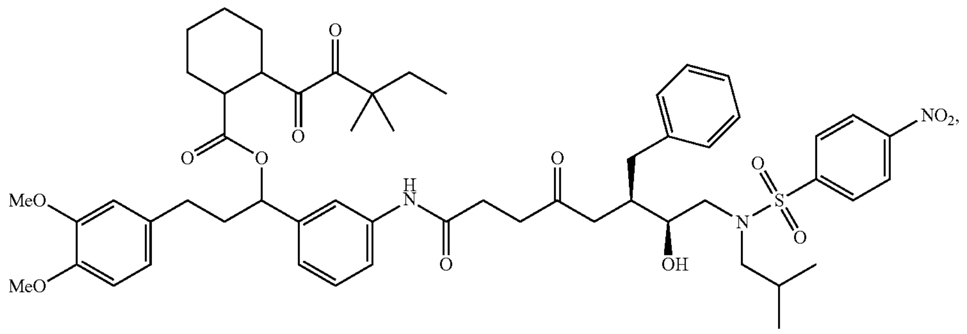 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc([N+](=O)[O-])cc2)c1]
or an analog thereof.
In embodiments, the anti-CNS disease drug is not
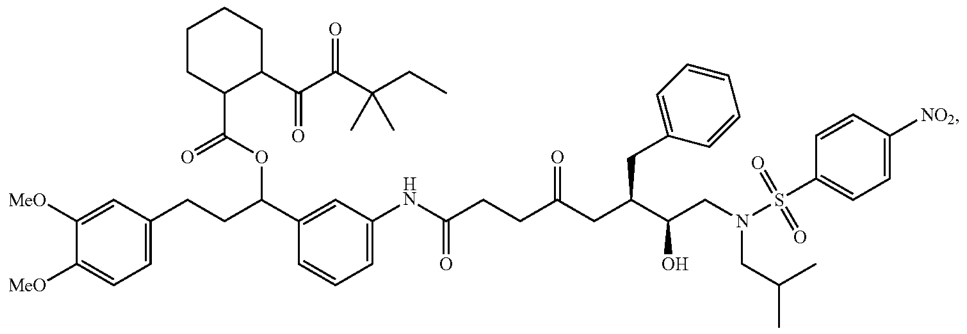 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc([N+](=O)[O-])cc2)c1]
or an analog thereof.
In embodiments, the anti-CNS disease drug is
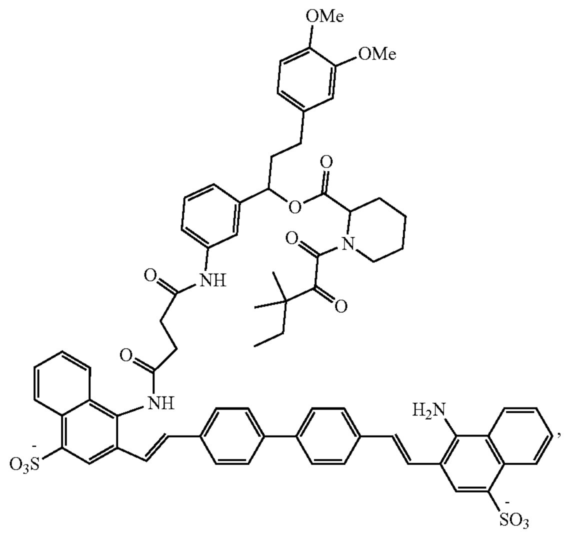
or an analog thereof.
In embodiments, the anti-CNS disease drug is not
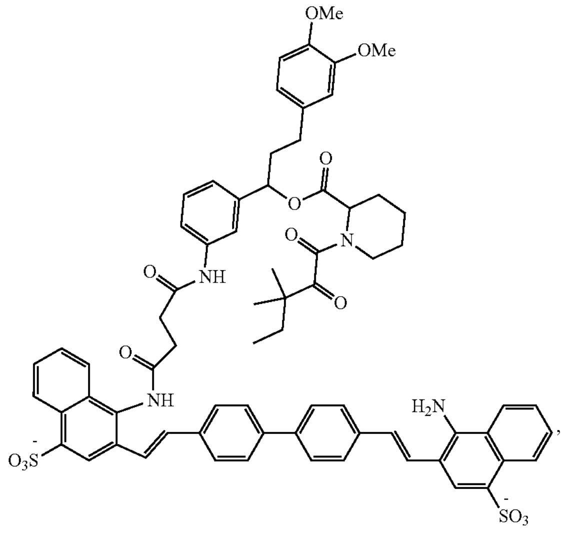
or an analog thereof.

In embodiments, the anti-CNS disease drug is
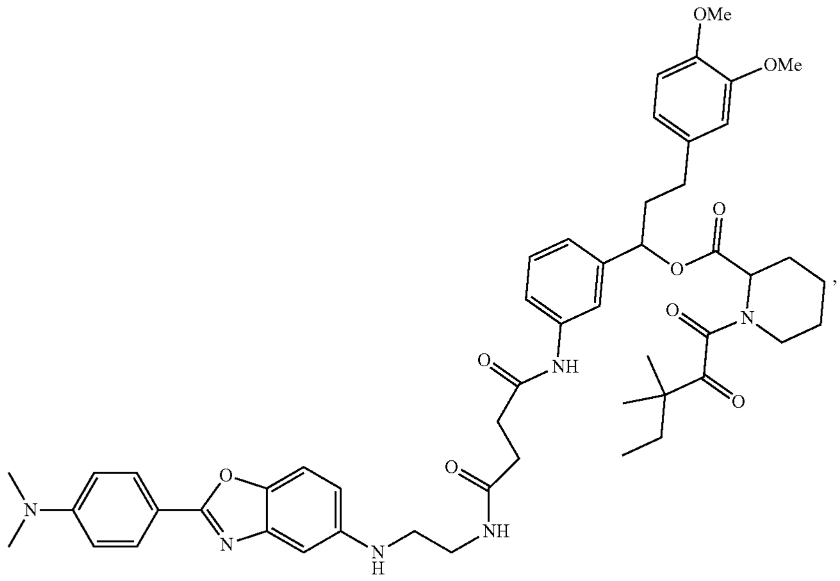 [SMILES: CCC(C)(C)C(=O)C(=O)N1CCCCC1C(=O)OC(CCc1ccc(OC)c(OC)c1)c1cccc(NC(=O)CCC(=O)NCCNc2ccc3oc(-c4ccc(N(C)C)cc4)nc3c2)c1]
,
or an analog thereof.
In embodiments, the anti-CNS disease drug is not
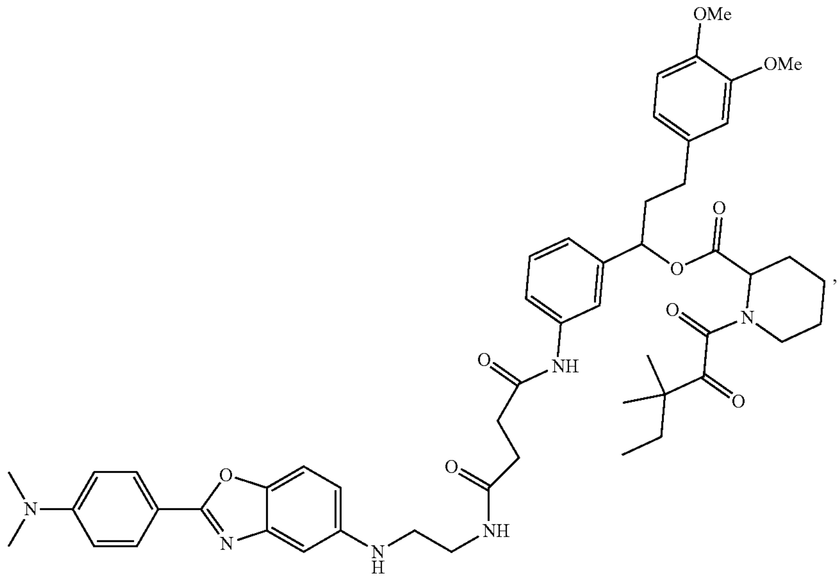 [SMILES: CCC(C)(C)C(=O)C(=O)N1CCCCC1C(=O)OC(CCc1ccc(OC)c(OC)c1)c1cccc(NC(=O)CCC(=O)NCCNc2ccc3oc(-c4ccc(N(C)C)cc4)nc3c2)c1]
,
or an analog thereof.

In embodiments, the anti-CNS disease drug is
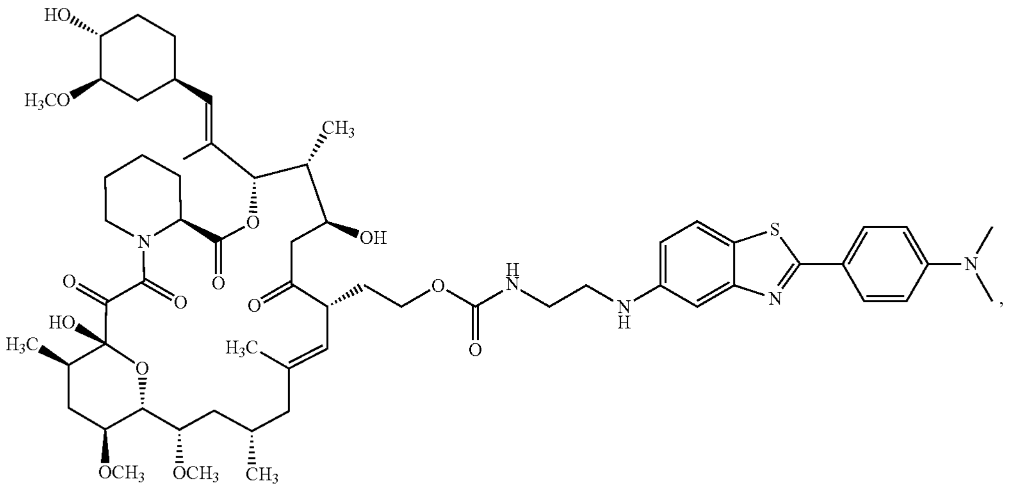
or an analog thereof.
In embodiments, the anti-CNS disease drug is not
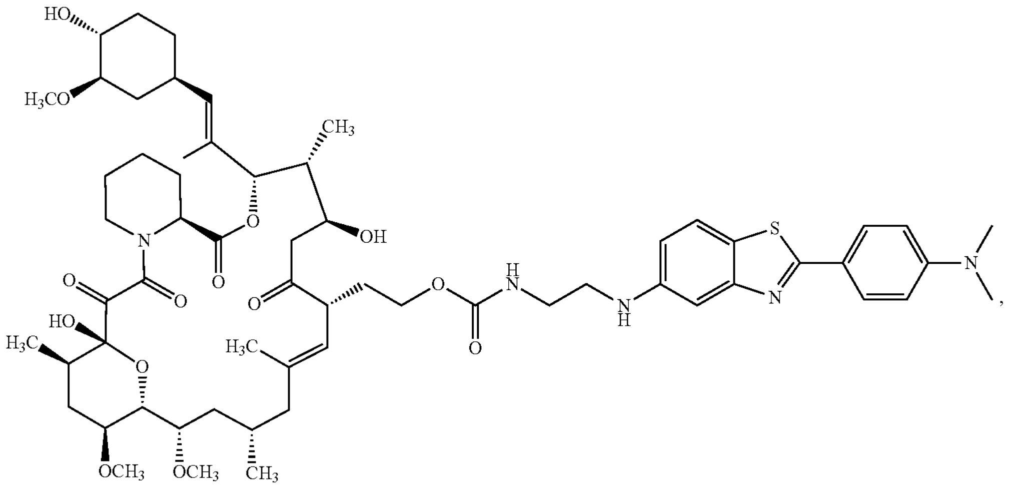
or an analog thereof.

In embodiments, the anti-CNS disease drug is
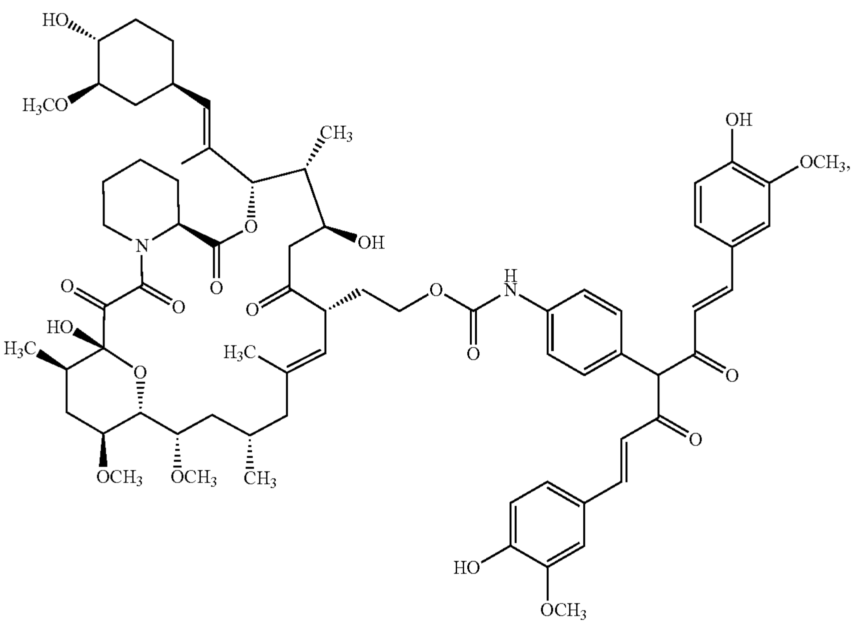 [SMILES: COc1cc(/C=C/C(=O)C(C(=O)/C=C/c2ccc(O)c(OC)c2)c2ccc(NC(=O)OCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)cc2)ccc1O]
or an analog thereof.
In embodiments, the anti-CNS disease drug is not
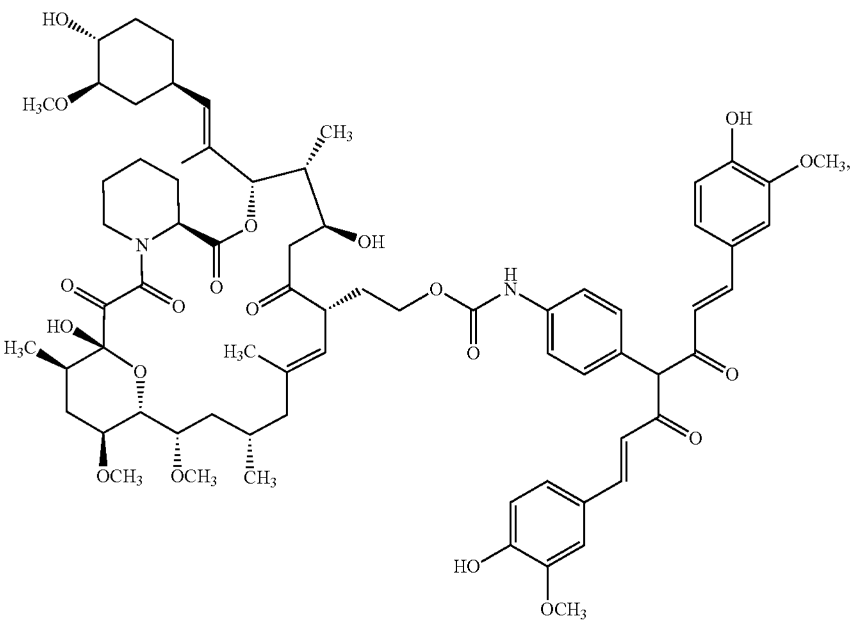 [SMILES: COc1cc(/C=C/C(=O)C(C(=O)/C=C/c2ccc(O)c(OC)c2)c2ccc(NC(=O)OCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)cc2)ccc1O]
or an analog thereof.

In embodiments, the anti-CNS disease drug is
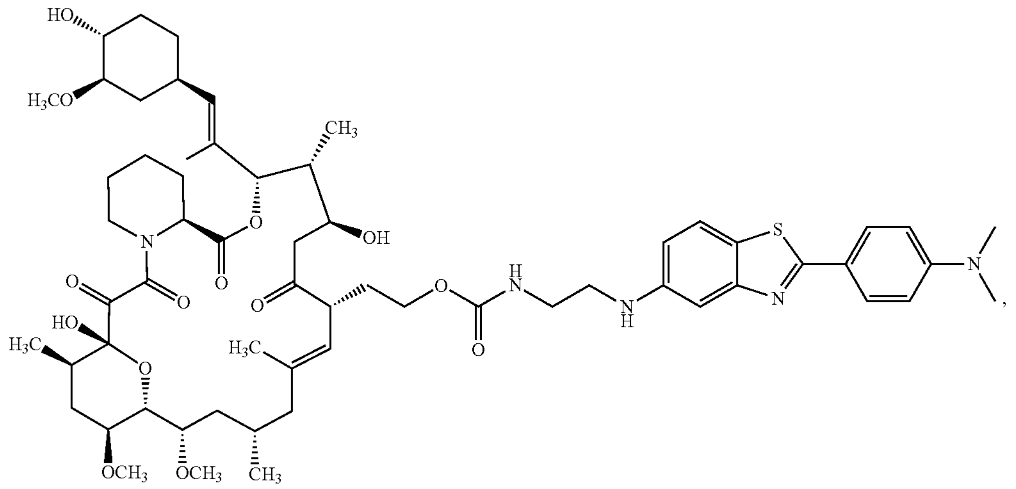
or an analog thereof.
In embodiments, the anti-CNS disease drug is not
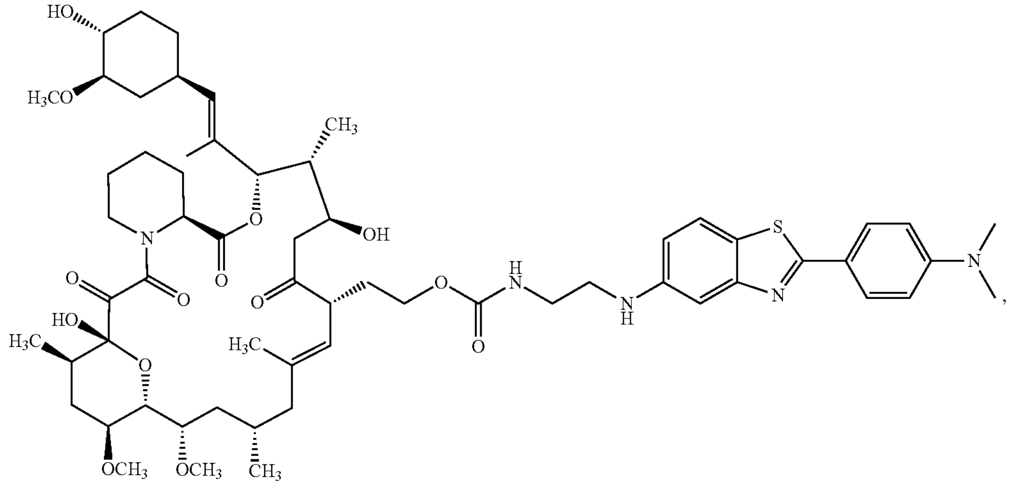
or an analog thereof.

In embodiments, the anti-CNS disease drug is
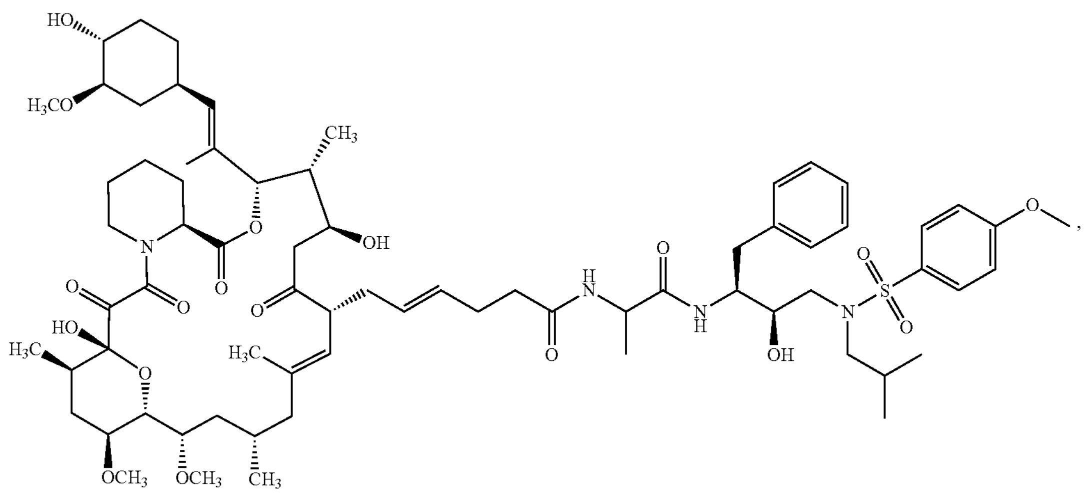
or an analog thereof.
In embodiments, the anti-CNS disease drug is not
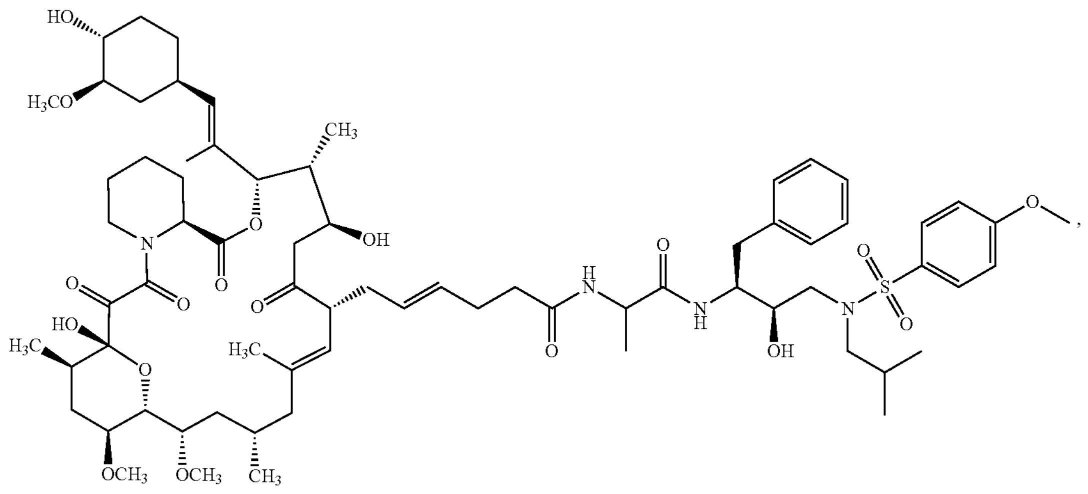
or an analog thereof.

In embodiments, the anti-CNS disease drug is
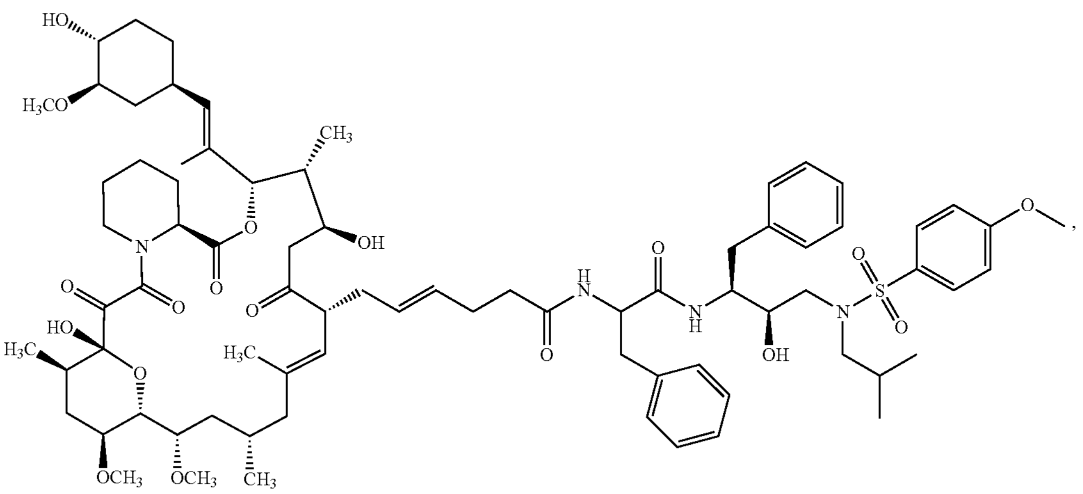
or an analog thereof.
In embodiments, the anti-CNS disease drug is not
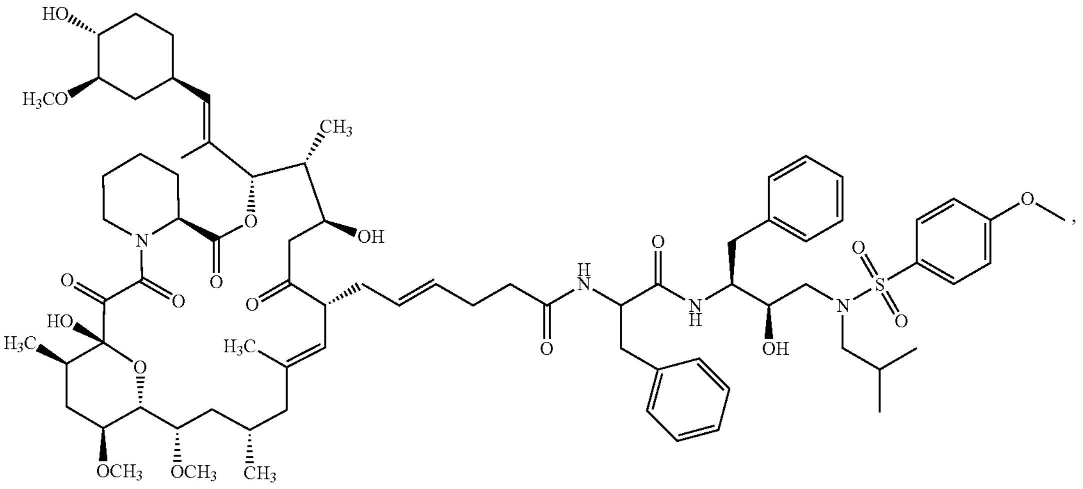
or an analog thereof.

In embodiments, the anti-CNS disease drug is
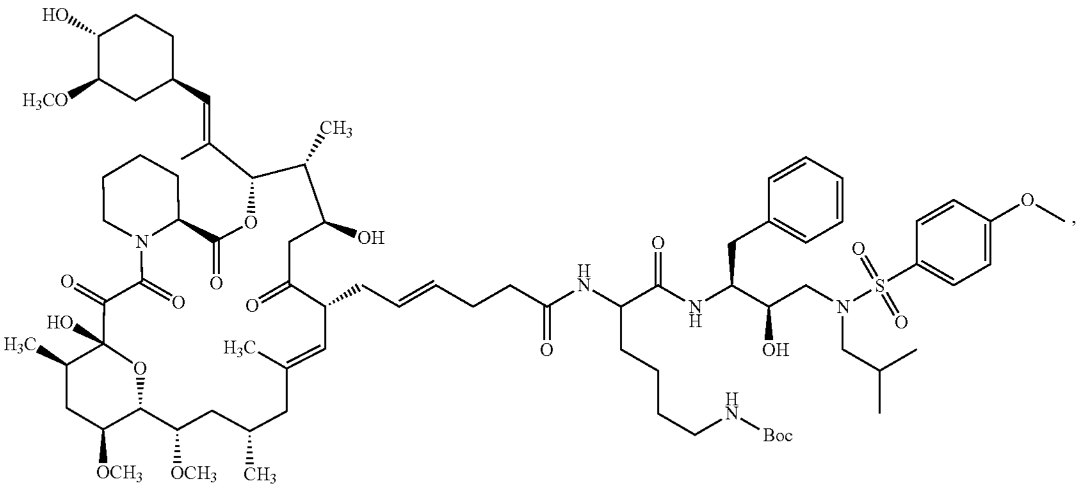
or an analog thereof.
In embodiments, the anti-CNS disease drug is not
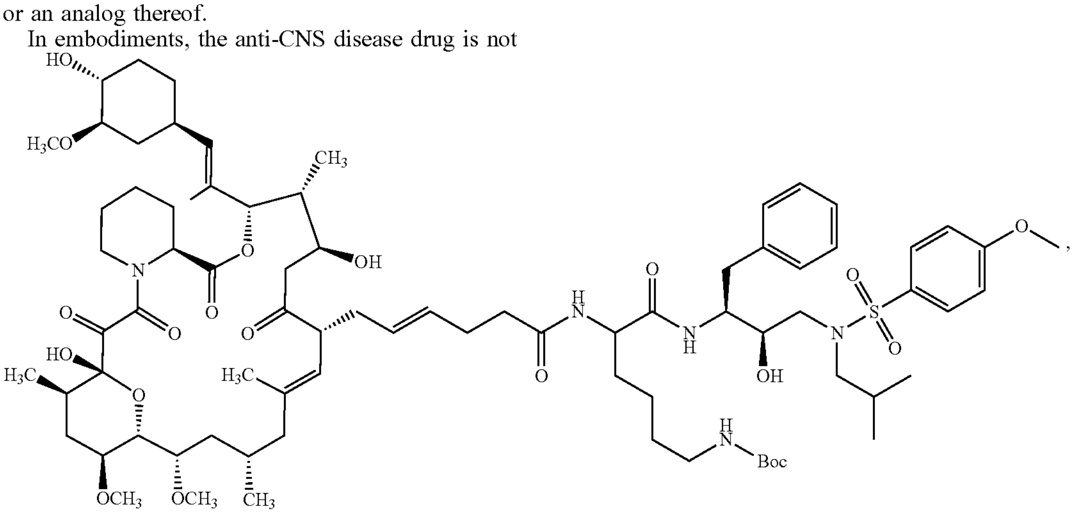
or an analog thereof.
In embodiments, the anti-CNS disease drug is
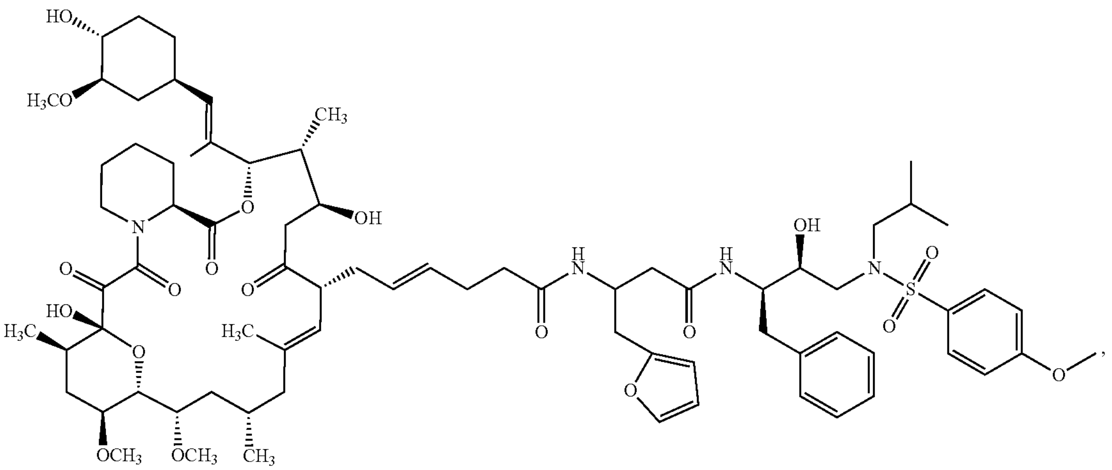
or an analog thereof.

In embodiments, the anti-CNS disease drug is not
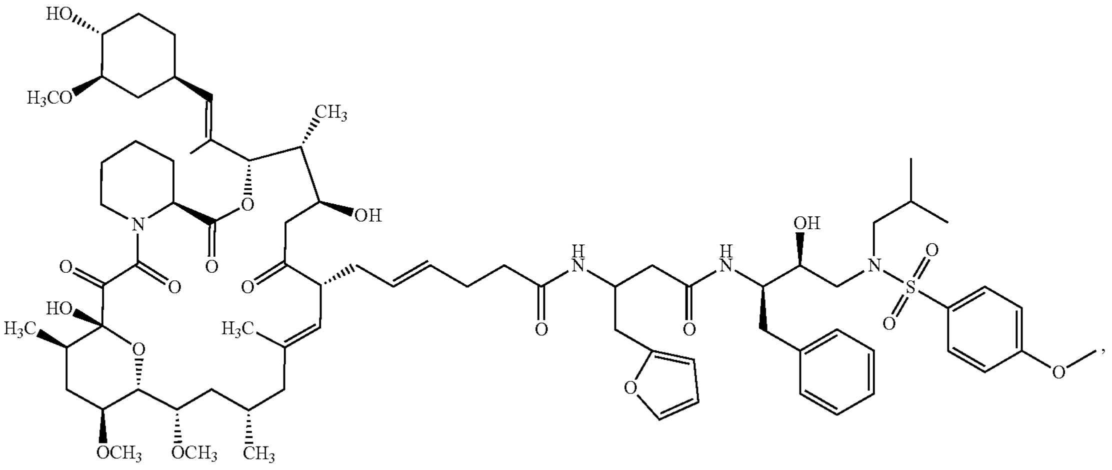
or an analog thereof.
In embodiments, the anti-CNS disease drug is
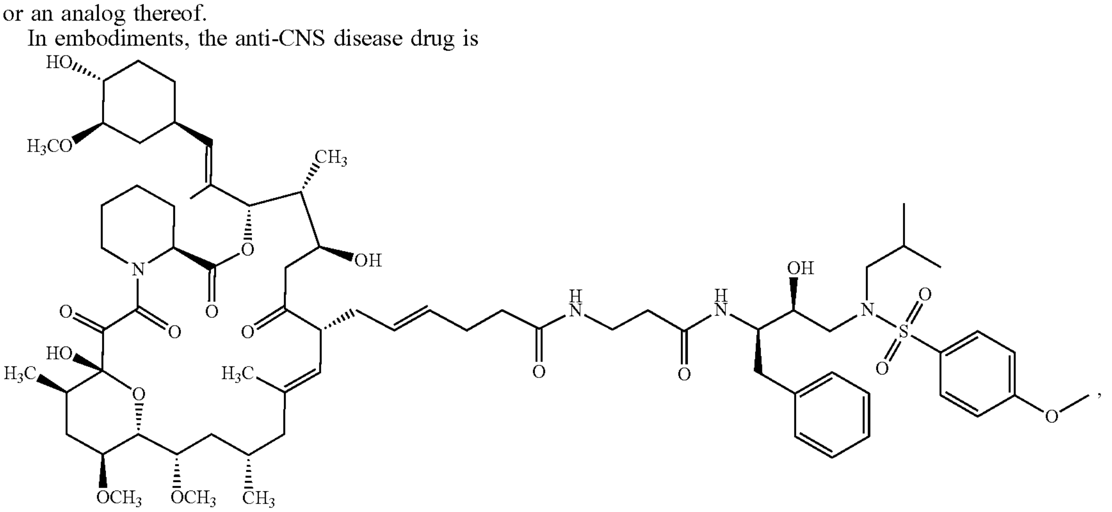
or an analog thereof.
In embodiments, the anti-CNS disease drug is not
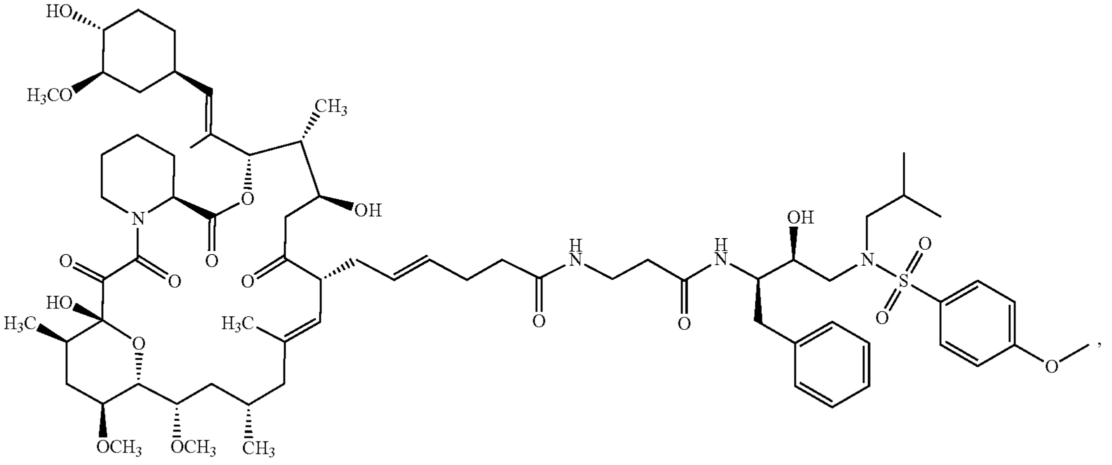
or an analog thereof.

In embodiments, the anti-CNS disease drug is
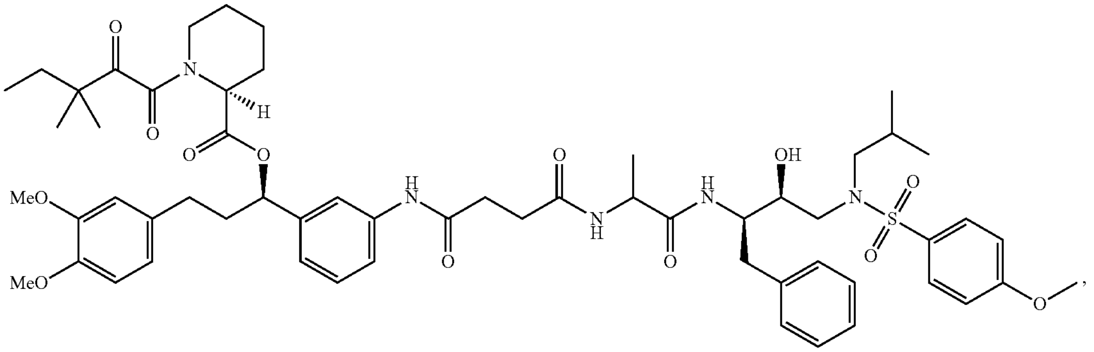 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(C)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is not
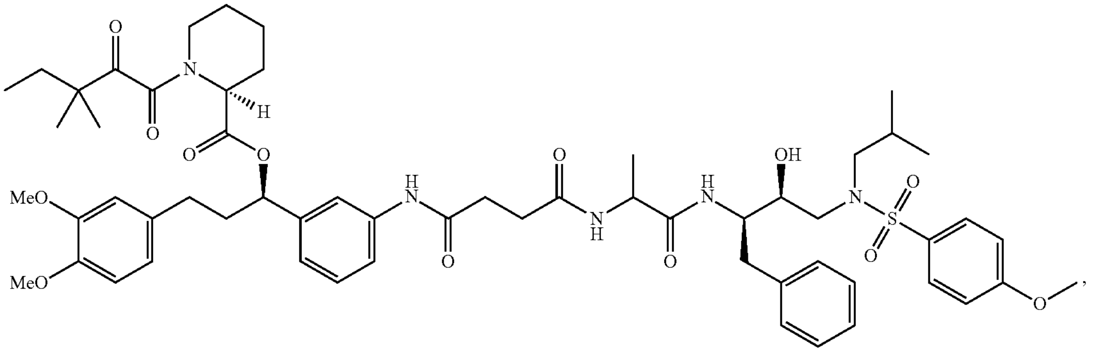 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(C)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is
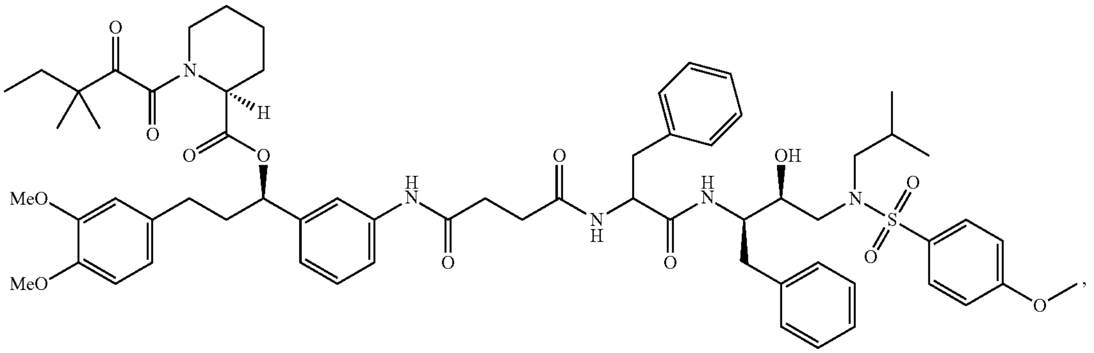 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(Cc2ccccc2)C(=O)N[C@H](Cc2ccccc2)[C@@H](O)CN(CC(C)C)S(=O)(=O)c2ccc(OC)cc2)c1]
or an analog thereof.

In embodiments, the anti-CNS disease drug is not
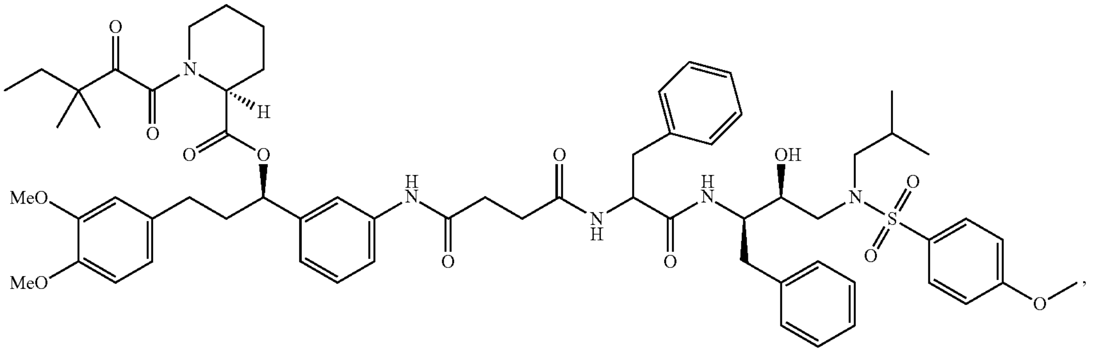 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(Cc2ccccc2)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is
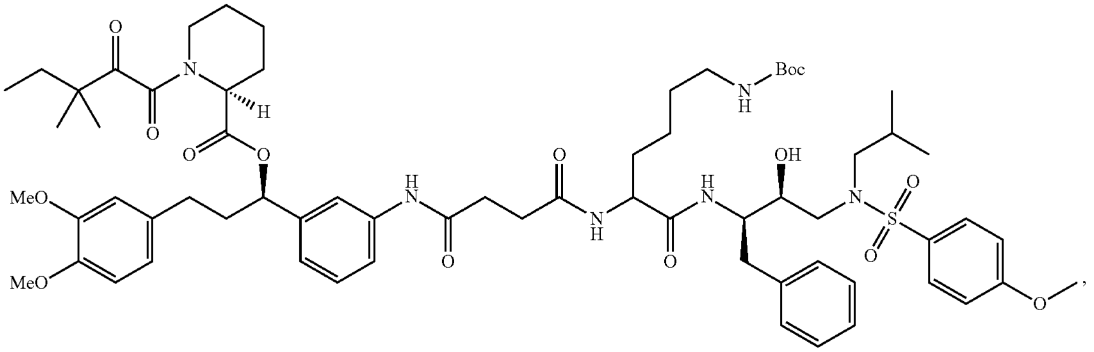 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CCCCNC(=O)OC(C)(C)C)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is not
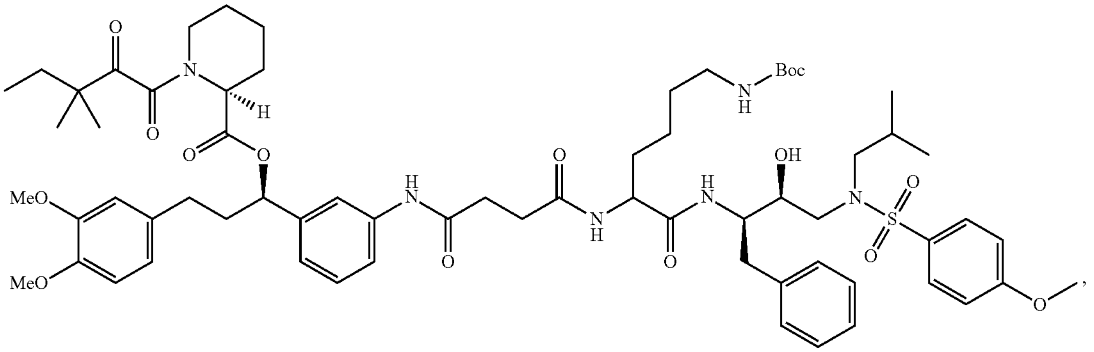 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CCCCNC(=O)OC(C)(C)C)C(=O)N[C@H](Cc2ccccc2)[C@@H](O)CN(CC(C)C)S(=O)(=O)c2ccc(OC)cc2)c1]
or an analog thereof.

In embodiments, the anti-CNS disease drug is
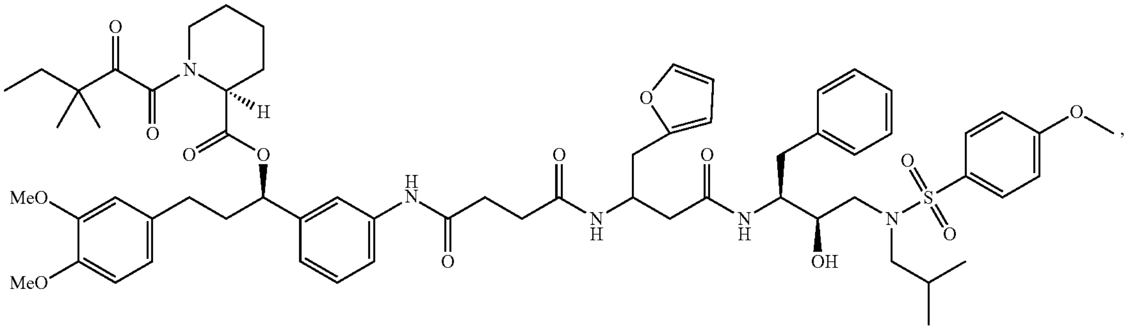 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CC(=O)N[C@@H](Cc2ccccc2)[C@H](O)CN(CC(C)C)S(=O)(=O)c2ccc(OC)cc2)Cc2ccco2)c1]
or an analog thereof.
In embodiments, the anti-CNS disease drug is not
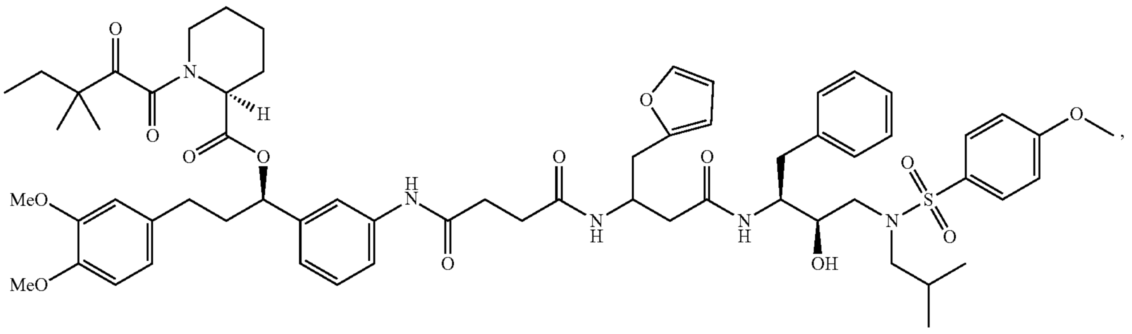 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CC(=O)N[C@@H](Cc2ccccc2)[C@H](O)CN(CC(C)C)S(=O)(=O)c2ccc(OC)cc2)Cc2ccco2)c1]
or an analog thereof.
In embodiments, the anti-CNS disease drug is
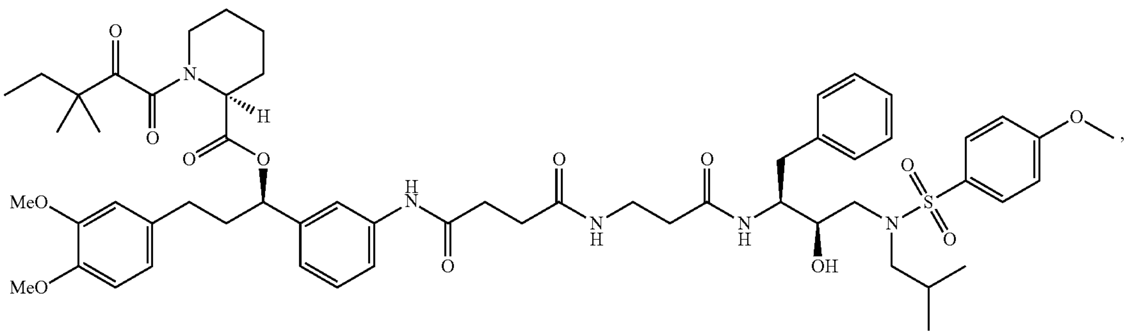 [SMILES: CCC(C)(C)C(=O)C(=O)N1CCCC[C@H]1C(=O)O[C@H](CCc1ccc(OC)c(OC)c1)c1cccc(NC(=O)CCC(=O)NCCC(=O)N[C@@H](Cc2ccccc2)[C@H](O)CN(CC(C)C)S(=O)(=O)c2ccc(OC)cc2)c1]
or an analog thereof.

In embodiments, the anti-CNS disease drug is not
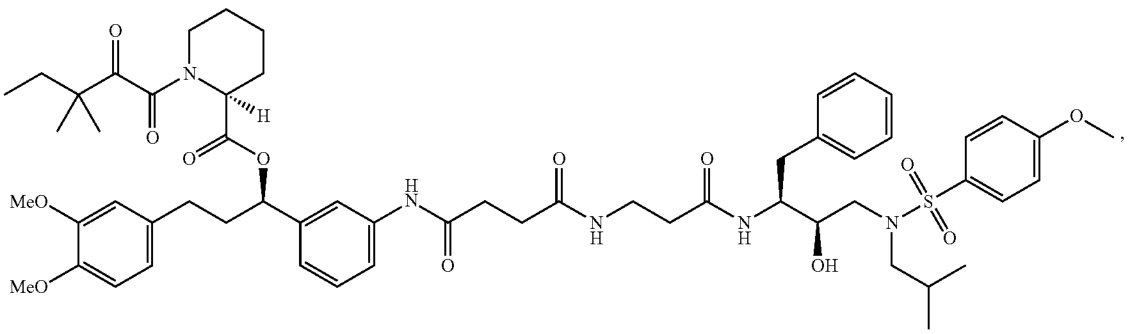 [SMILES: CCC(C)(C)C(=O)C(=O)N1CCCC[C@H]1C(=O)O[C@H](CCc1ccc(OC)c(OC)c1)c1cccc(NC(=O)CCC(=O)NCCC(=O)N[C@@H](Cc2ccccc2)[C@H](O)CN(CC(C)C)S(=O)(=O)c2ccc(OC)cc2)c1]
or an analog thereof.
In embodiments, the anti-CNS disease drug is
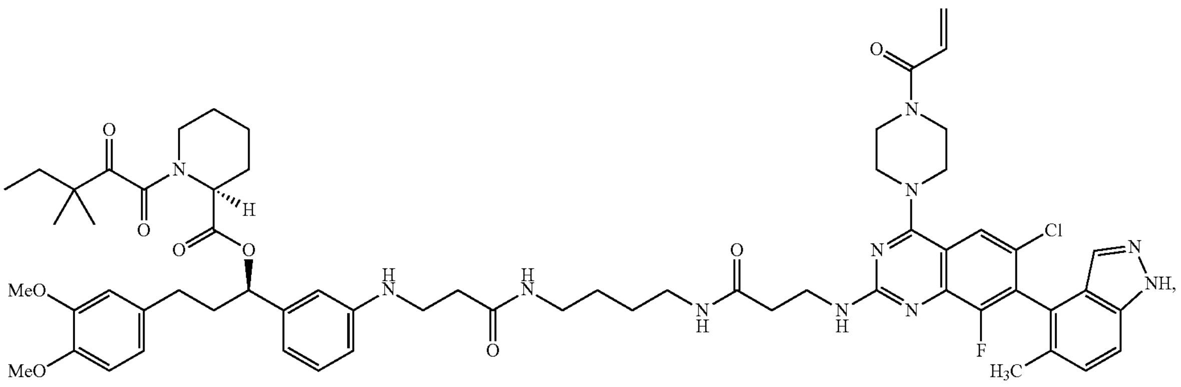 [SMILES: C=CC(=O)N1CCN(c2nc(NCCC(=O)NCCCCNC(=O)CCNc3cccc([C@@H](CCc4ccc(OC)c(OC)c4)OC(=O)[C@@H]4CCCCN4C(=O)C(=O)C(C)(C)CC)c3)nc3c(F)c(-c4c(C)ccc5[nH]ncc45)c(Cl)cc23)CC1]
or an analog thereof.
In embodiments, the anti-CNS disease drug is not
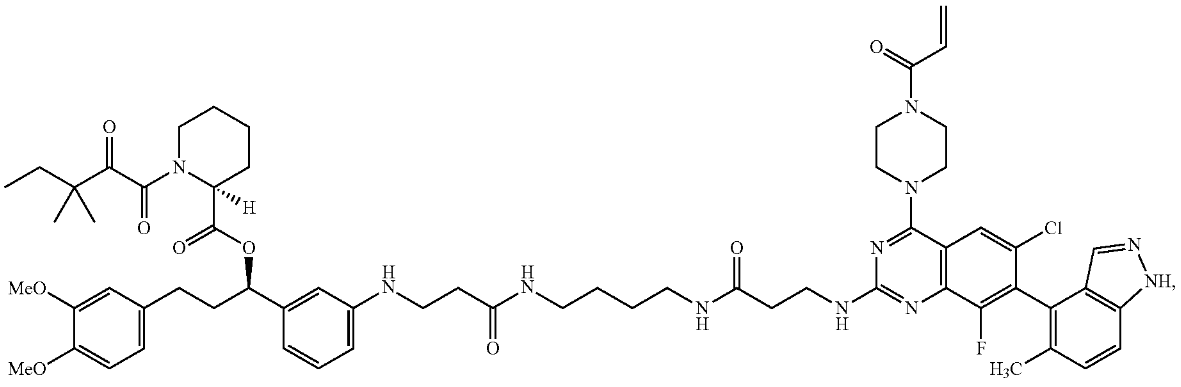 [SMILES: C=CC(=O)N1CCN(c2nc(NCCC(=O)NCCCCNC(=O)CCNc3cccc([C@@H](CCc4ccc(OC)c(OC)c4)OC(=O)[C@@H]4CCCCN4C(=O)C(=O)C(C)(C)CC)c3)nc3c(F)c(-c4c(C)ccc5[nH]ncc45)c(Cl)cc23)CC1]
or an analog thereof.

In embodiments, the anti-CNS disease drug is
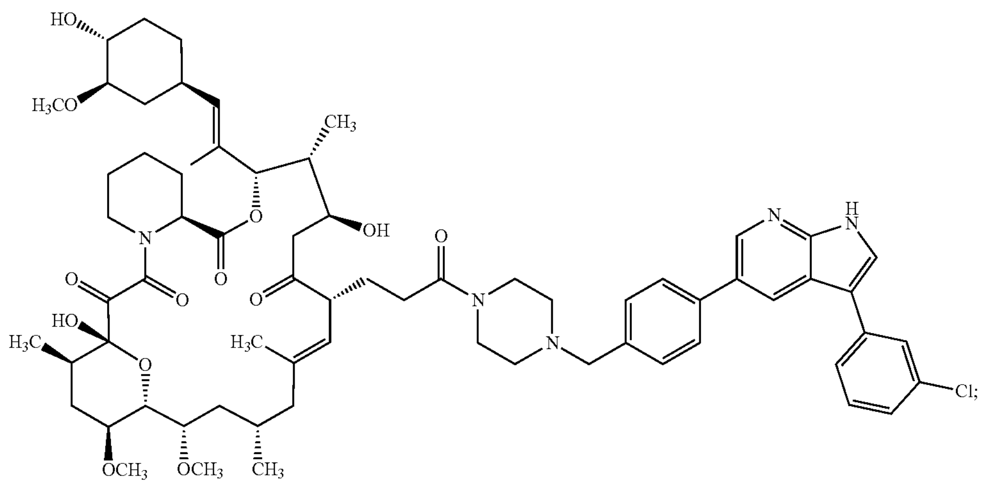 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.
In embodiments, the anti-CNS disease drug is not
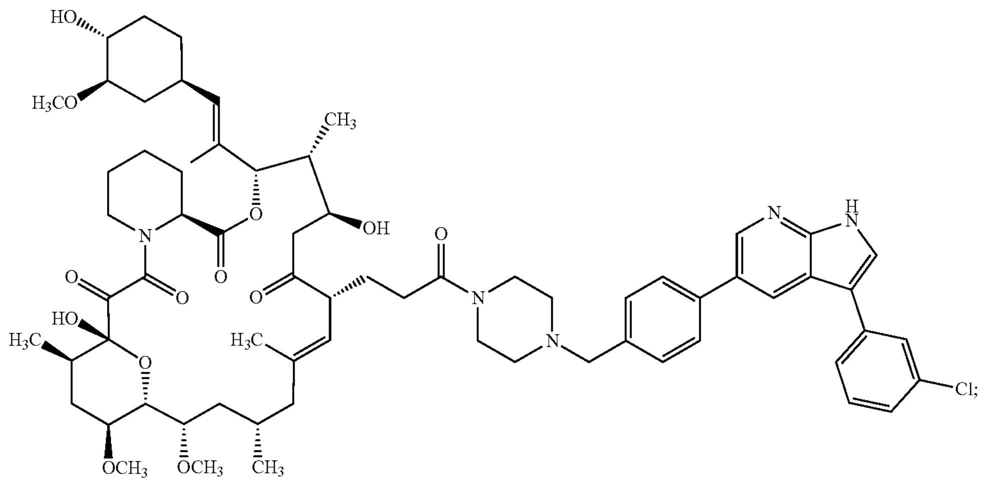 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.

In embodiments, the anti-CNS disease drug is
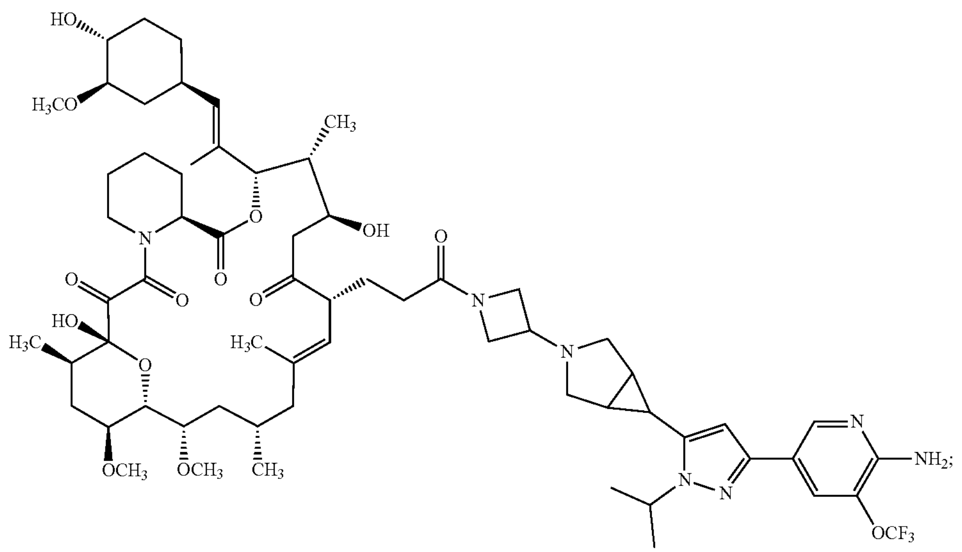 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.
In embodiments, the anti-CNS disease drug is not
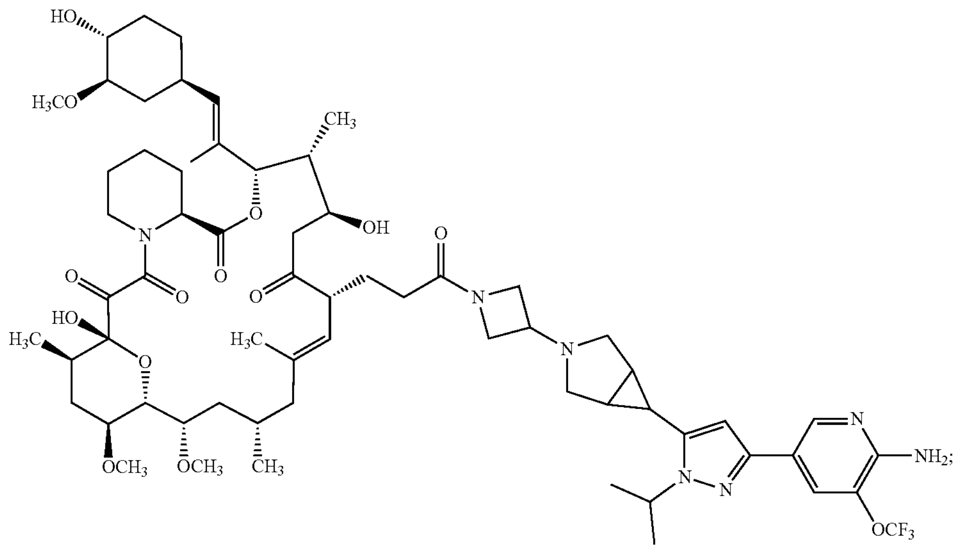 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.

In embodiments, the anti-CNS disease drug is
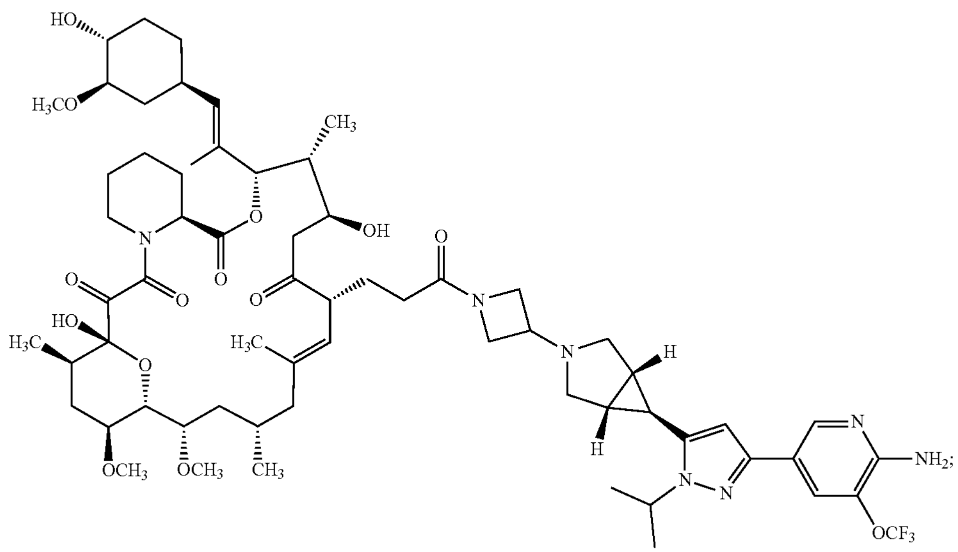 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.
In embodiments, the anti-CNS disease drug is not
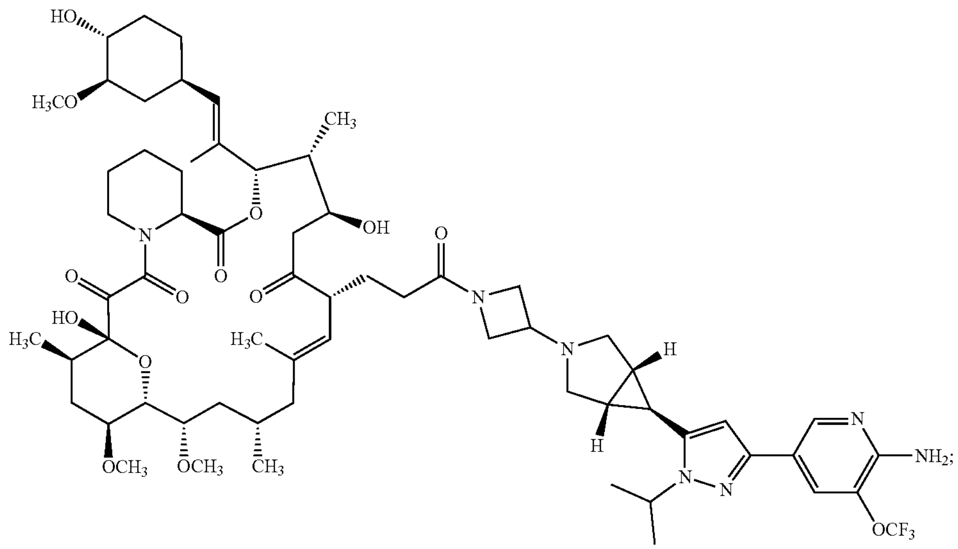 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.

In embodiments, the anti-CNS disease drug is

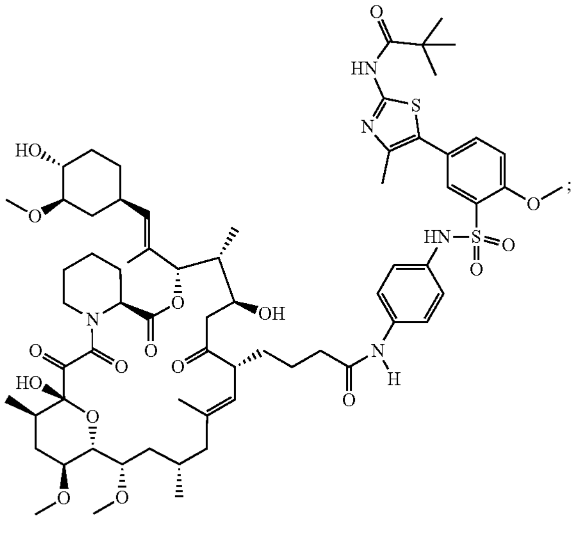

or an analog thereof.

In embodiments, the anti-CNS disease drug is not

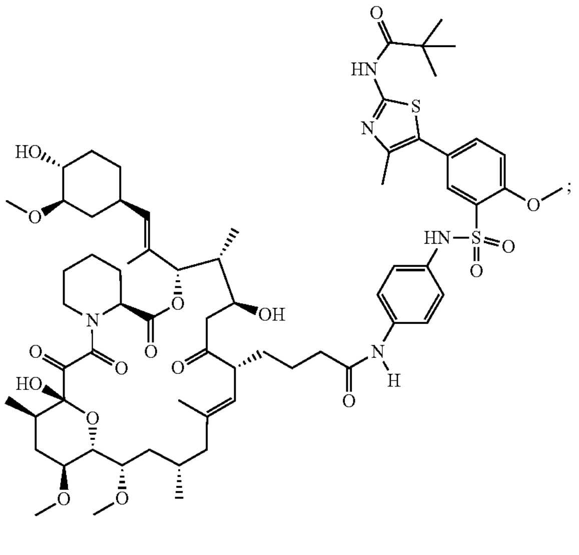

or an analog thereof.

In embodiments, the anti-CNS disease drug does not bind mTORC1. In embodiments, the anti-CNS disease drug does not bind mTOR. In embodiments, the immunophilin binding moiety is not rapamycin or an analog thereof. In embodiments, the immunophilin binding moiety is not rapamycin.

In embodiments, the anti-CNS disease drug residence time in cells is from 1 to 24 hours. In embodiments, the anti-CNS disease drug residence time in cells is from 1 to 12 hours. In embodiments, the anti-CNS disease drug residence time in cells is from 12 to 24 hours. In embodiments, the anti-CNS disease drug residence time in cells is 1, 2, 3, 4, 5, 6, 7, 8, 9, 10, 11, 12, 13, 14, 15, 16, 17, 18, 19, 20, 21, 22, 23, or 24 hours. In embodiments, the anti-CNS disease drug residence time in cells is about 1, 2, 3, 4, 5, 6, 7, 8, 9, 10, 11, 12, 13, 14, 15, 16, 17, 18, 19, 20, 21, 22, 23, or 24 hours. In embodiments, the anti-CNS disease drug residence time in cells is at least 1, 2, 3, 4, 5, 6, 7, 8, 9, 10, 11, 12, 13, 14, 15, 16, 17, 18, 19, 20, 21, 22, 23, or 24 hours. In embodiments, the anti-CNS disease drug including a monovalent kinase inhibitor, a monovalent pseudokinase inhibitor, a monovalent GTPase inhibitor, a monovalent histone-modifying enzyme inhibitor, or monovalent anti-viral agent has a residence time in cells that is at least 1.1 fold (e.g., at least 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 fold) greater than the residence time of the corresponding kinase inhibitor, a pseudokinase inhibitor, a GTPase inhibitor, a histone-modifying enzyme inhibitor, or anti-viral agent.

IV. Methods of Use

In an aspect is provided a method of treating a CNS disease in a subject in need of such treatment, including co-administering outside the CNS of the subject an anti-CNS disease drug (e.g., as described herein) and a compound described herein. Subsequent to administration (e.g., about 1, 2, 3, 4, 5, 6, 7, 8, 9, 10, 15, 20, 25, 30, 35, 40, 45, 50, 55, 60 minutes, 2, 3, 4, 5, 6, 7, 8, 9, 10, 11, 12, 13, 14, 15, 16, 17, 18, 19, 20, 21, 22, 23 or 24 hours following administration), the concentration of the compound in circulating blood of the subject is greater than the concentration of the compound in the CNS of the subject. Subsequent to administration (e.g., at least 1, 2, 3, 4, 5, 6, 7, 8, 9, 10, 15, 20, 25, 30, 35, 40, 45, 50, 55, 60 minutes, 2, 3, 4, 5, 6, 7, 8, 9, 10, 11, 12, 13, 14, 15, 16, 17, 18, 19, 20, 21, 22, 23 or 24 hours following administration), the concentration of the compound in circulating blood of the subject is greater than the concentration of the compound in the CNS of the subject.

In embodiments, the compound (e.g., as described herein) is co-administered with a second agent (e.g., an anti-CNS disease drug as described herein). In embodiments, the compound (e.g., as described herein) is co-administered simultaneously with the second agent (e.g., the anti-CNS disease drug as described herein). In embodiments, the compound (e.g., as described herein) and the second agent (e.g., the anti-CNS disease drug as described herein) are co-administered sequentially. In embodiments, the compound is co-administered after (e.g., after about 1, 5, 10, 15, 20, or about 30 minutes) the second agent (e.g., the anti-CNS disease drug as described herein). In embodiments, the compound is co-administered after (e.g., after 1, 5, 10, 15, 20, or 30 minutes) the second agent (e.g., the anti-CNS disease drug as described herein). In embodiments, the compound is co-administered after (e.g., after about 0.5, 1, 2, 4, 6, 8, 10, 12, 16, 20, or about 24 hours) the second agent (e.g., the anti-CNS disease drug as described herein). In embodiments, the compound is co-administered after (e.g., after 0.5, 1, 2, 4, 6, 8, 10, 12, 16, 20, or 24 hours) the second agent (e.g., the anti-CNS disease drug as described herein).

In embodiments, the concentration of the compound in circulating blood is greater than 3-fold (e.g., 4-, 5-, 6-, 7-, 8-, 9-, 10-, 15-, 20-fold) the concentration of the compound in the CNS. In embodiments, the concentration of the compound in circulating blood is greater than 20-fold the concentration of the compound in the CNS. In embodiments, the compound is unable to cross the blood-brain barrier.

In embodiments, the CNS disease is glioblastoma, epilepsy, tuberous sclerosis (TSC), or alcohol use disorders. In embodiments, the CNS disease is glioblastoma. In embodiments, the CNS disease is epilepsy. In embodiments, the CNS disease is tuberous sclerosis (TSC). In embodiments, the CNS disease is alcohol use disorders.

In embodiments, the CNS disease is amyotrophic lateral sclerosis (ALS), Parkinson's disease, or Alzheimer's disease. In embodiments, the CNS disease is amyotrophic lateral sclerosis (ALS). In embodiments, the CNS disease is Parkinson's disease. In embodiments, the CNS disease is Alzheimer's disease.

In embodiments, the compound is unable to enter the central nervous system of a subject following administration to the subject outside of the central nervous system. In embodiments, the anti-CNS disease drug is capable of entering the central nervous system and the compound is incapable of entering the central nervous system following co-administration outside of the central nervous system of the subject.

In embodiments, affinity of the compound for calcineurin is lower (e.g., about 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-, 1500-, 2000-, 2500-, 3000-, 3500-, 4000-, 4500-, or 5000-fold) compared to compounds of formulae (I), (II), (III), (IV), or (V). In embodiments, affinity of the compound for calcineurin is lower (e.g., at least 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-, 1500-, 2000-, 2500-, 3000-, 3500-, 4000-, 4500-, or 5000-fold) compared to compounds of formulae (I), (II), (III), (IV), or (V). In embodiments, the compound does not bind calcineurin.

In embodiments, compound inhibition of transcription of T cell activation genes (e.g., IL-2 mRNA, IL-3 mRNA, IL-4 mRNA, GM-CSF, TNF alpha, IFN-gamma, or c-myc) is lower (e.g., about 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-fold) compared to compounds of formulae (I), (II), (III), (IV), or (V). In embodiments, compound inhibition of transcription of T cell activation genes (e.g., IL-2 mRNA, IL-3 mRNA, IL-4 mRNA, GM-CSF, TNF alpha, IFN-gamma, or c-myc) is lower (e.g., at least 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-fold) compared to compounds of formulae (I), (II), (III), (IV), or (V). In embodiments, the compound does not inhibit development and/or proliferation of T cells.

In embodiments, the compound does not reduce the body's immune response. In embodiments, the immune response is the adaptive immune response. In embodiments, the method includes reduced side effects associated with the anti-CNS disease drug compared to absence of the compound. In embodiments, the anti-CNS disease drug binds an immunophilin. In embodiments, the anti-CNS disease drug includes an immunophilin-binding moiety (e.g., as described herein). In embodiments, the anti-CNS disease drug is as described herein, including in embodiments.

In embodiments of the method, the CNS disease is a disease associated with aberrant enzyme activity. In embodiments, the enzyme activity is a kinase activity (e.g., a kinase described herein). In embodiments, the kinase activity is in the CNS of the subject (e.g., brain).

In embodiments, the CNS disease is a cancer, a neurodegenerative disease, or a viral disease.

In embodiments, the CNS disease is cancer or a neurodegenerative disease. In embodiments, the CNS disease is cancer. In embodiments, the cancer is glioblastoma or glioma. In embodiments, the CNS disease is a neurodegenerative disease. In embodiments the neurodegenerative disease is Parkinson's disease.

In embodiments, the CNS disease is a neurodegenerative disease. In embodiments, the neurodegenerative disease is amyotrophic lateral sclerosis (ALS), Parkinson's disease, or Alzheimer's disease. In embodiments, the neurodegenerative disease is amyotrophic lateral sclerosis (ALS). In embodiments, the neurodegenerative disease is Parkinson's disease. In embodiments, the neurodegenerative disease is Alzheimer's disease.

In embodiments, the neurodegenerative disease is not Alzheimer's Disease. In embodiments, the anti-CNS disease drug is not an amyloid p aggregation inhibitor. In embodiments, the anti-CNS disease drug does not include a monovalent amyloid p aggregation inhibitor.

In embodiments, the disease is a viral disease. In embodiments, the viral disease is human immunodeficiency virus (HIV). In embodiments, the anti-CNS disease drug is an HIV inhibitor. In embodiments, the anti-CNS disease drug is an HIV protease inhibitor. In embodiments, the anti-CNS disease drug is a viral protease inhibitor. In embodiments, the anti-CNS disease drug includes an HIV inhibitor. In embodiments, the anti-CNS disease drug includes an HIV protease inhibitor. In embodiments, the anti-CNS disease drug includes a viral protease inhibitor. In embodiments, the viral disease is not human immunodeficiency virus (HIV). In embodiments, the anti-CNS disease drug is not an HIV inhibitor. In embodiments, the anti-CNS disease drug is not an HIV protease inhibitor. In embodiments, the anti-CNS disease drug is not a viral protease inhibitor. In embodiments, the anti-CNS disease drug does not include an HIV inhibitor. In embodiments, the anti-CNS disease drug does not include an HIV protease inhibitor. In embodiments, the anti-CNS disease drug does not include a viral protease inhibitor.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A method of treating a CNS disease in a subject in need of such treatment, comprising co-administering outside the CNS of said subject an anti-CNS disease drug and a compound having the formula:

$A^B$-$L^{B1}$-$R^{B1}$, or a pharmaceutically acceptable salt thereof, wherein $A^B$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, $—CX^{B1}_3$, $—CHX^{B1}_2$, $—CH_2X^{B1}$, $—OCX^{B1}_3$, $—OCH_2X^{B1}$, $—OCHX^{B1}_2$, —CN, $—SO_{nB1}R^{B1D}$, $—SO_{vB1}NR^{B1A}R^{B1B}$, $—NHC(O)NR^{B1A}R^{B1B}$, $—N(O)_{mB1}$, $—NR^{B1A}R^{B1B}$, $—C(O)R^{B1C}$, $—C(O)OR^{B1C}$, $—C(O)NR^{B1A}R^{B1B}$, $—OR^{B1D}$, $—NR^{B1A}SO_2R^{B1D}$, $—NR^{B1A}C(O)R^{B1C}$, $—NR^{B1A}C(O)OR^{B1C}$, $—NR^{B1A}OR^{B1C}$, $—NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$ and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently —F, —Cl, —Br, or —I;

when $L^{B1}$ is a bond, $R^{B1}$ is not H; and wherein, subsequent to administration, the concentration of the compound in circulating blood of said subject is greater than the concentration of the compound in the CNS of said subject.

Embodiment P2. The method of embodiment P1, wherein the immunophilin-binding moiety is a cyclophilin-binding moiety or an FKBP-binding moiety.

Embodiment P3. The method of one of embodiments P1 to P2, wherein the immunophilin-binding moiety is

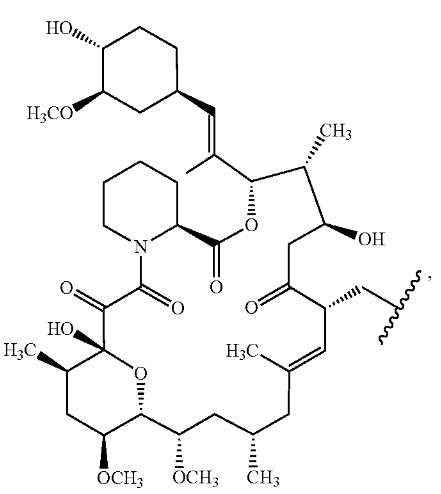 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

-continued

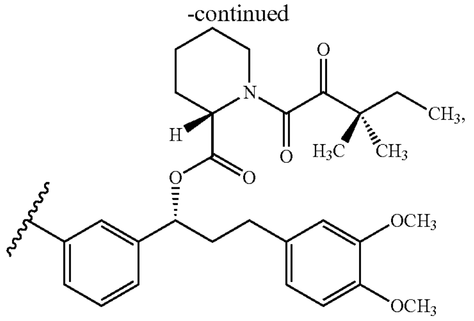

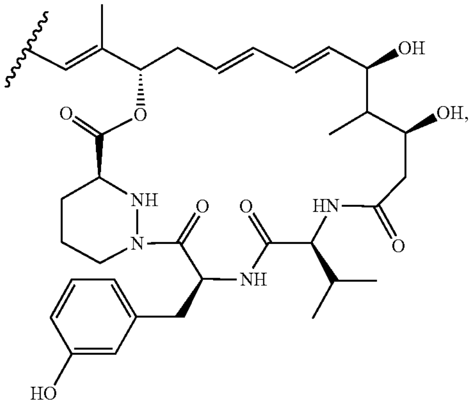

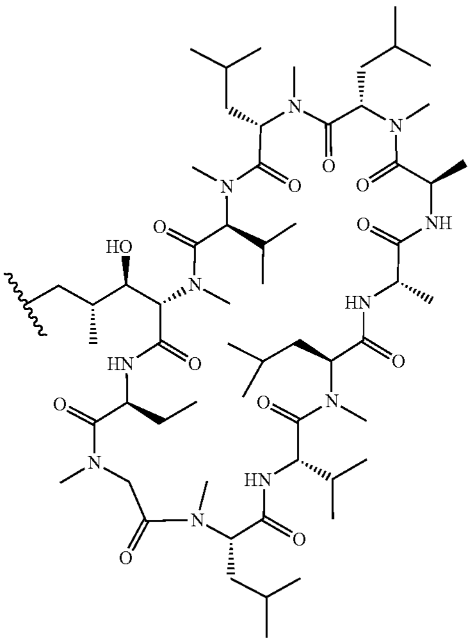

, or

-continued

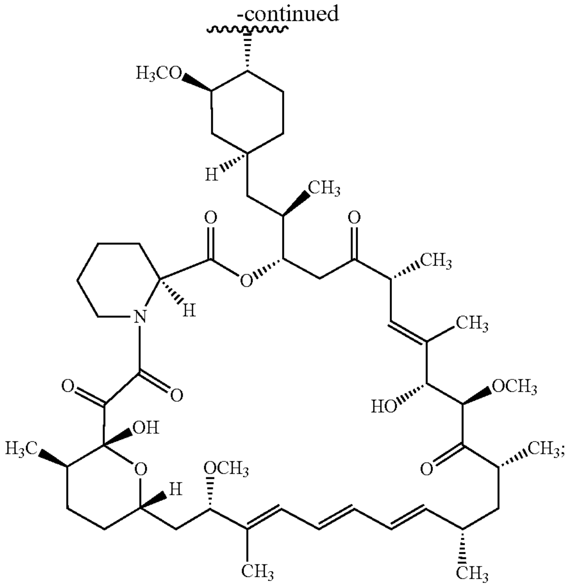

or an analog thereof.

Embodiment P4. The method of one of embodiments P1 to P3, wherein $L^{B1}$ is $L^{B2}$-$L^{B3}$-$L^{B4}$.

$L^{B2}$ is a bond, —$S(O)_2$—, —$N(R^{B2})$—, —O—, —S—, —C(O)—, —$C(O)N(R^{B2})$—, —$N(R^{B2})C(O)$, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{B3}$ is a bond, —$S(O)_2$—, —$N(R^{B3})$—, —O—, —S—, —C(O)—, —$C(O)N(R^{B3})$—, —$N(R^{B3})C(O)$, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{B4}$ is a bond, —$S(O)_2$—, —$N(R^{B4})$—, —O—, —S—, —C(O)—, —$C(O)N(R^{B4})$—, —$N(R^{B4})C(O)$, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P5. The method of one of embodiments P1 to P4, wherein $L^{B1}$ is

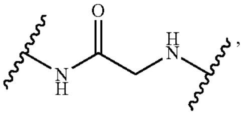, 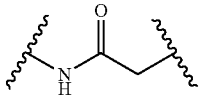,

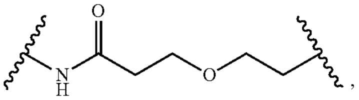,

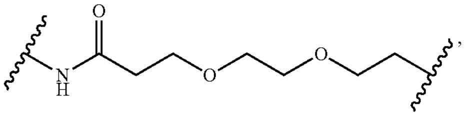,

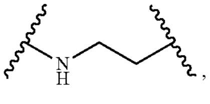, 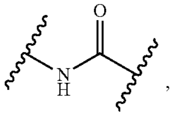,

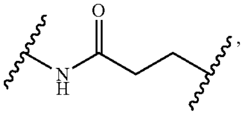, 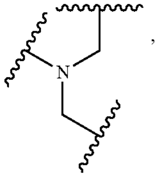,

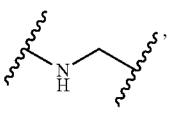, 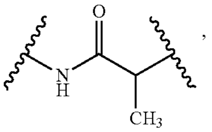,

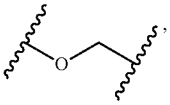, 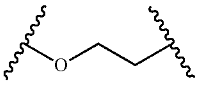,

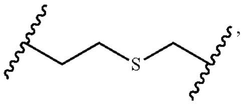, 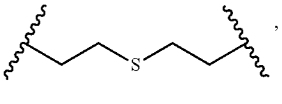,

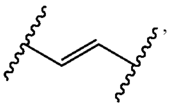, 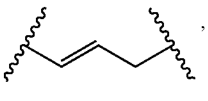,

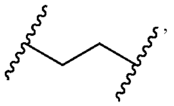,

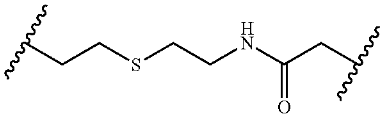,

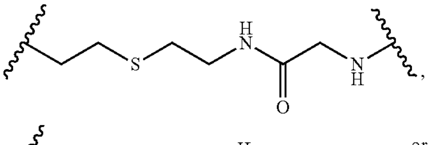,

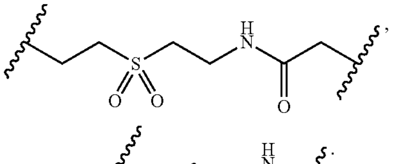, or

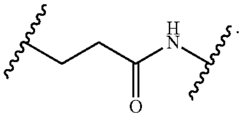.

Embodiment P6. The method of one of embodiments P1 to P5, wherein RB is halogen, —$NR^{B1A}R^{B1B}$, —$N_3$, —$SR^{B1D}$,

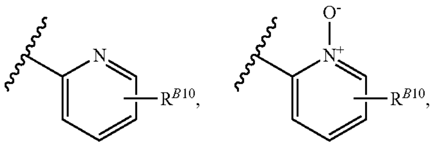

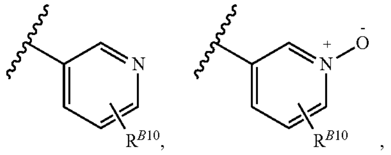

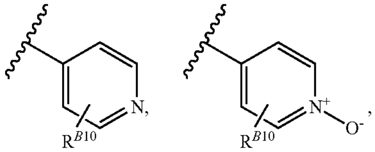

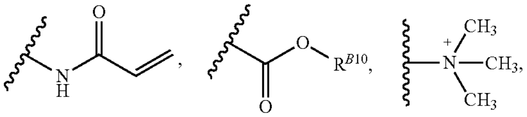

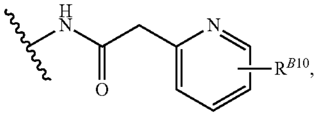

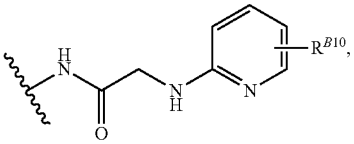

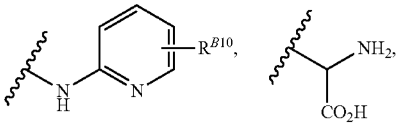

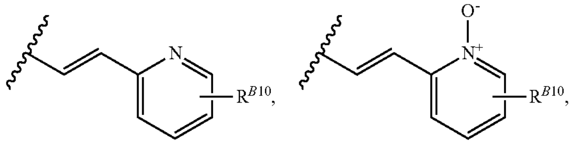

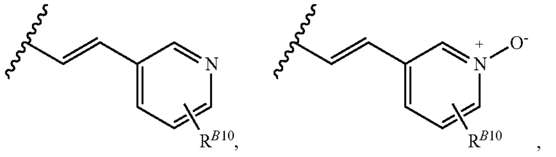

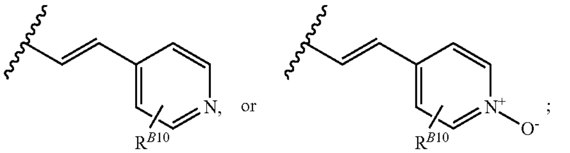

$R^{B10}$ is hydrogen, halogen, —$CX^{B10}_3$, —$CHX^{B10}_2$, —$CH_2X^{B10}$, —$OCX^{B10}_3$, —$OCH_2X^{B10}$, —$OCHX^{B10}_2$, —CN, —$SO_{nB10}R^{B10D}$, —$SO_{vB10}NR^{B10A}R^{B10B}$, —NHC(O)$NR^{B10A}R^{B10B}$, —$N(O)_{mB10}$, —$NR^{B10A}R^{B10B}$, —C(O)$R^{B10C}$, —C(O)$OR^{B10C}$, —C(O)$NR^{B10A}R^{B10B}$, —$OR^{B10D}$, —$NR^{B10A}SO_2R^{B10D}$, —$NR^{B10A}C(O)R^{B10C}$, —$NR^{B10A}C(O)OR^{B10C}$, —$NR^{B10A}OR^{B10C}$, —$NR^{B10A}C(NR^{B10C})R^{B10D}$, —$R^{B10A}C(NR^{B10C})NR^{B10A}R^{B10B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment P7. The method of one of embodiments P1 to P6, wherein $R^{B1}$ is —Cl, —$NH_2$, —$N_3$, —SH,

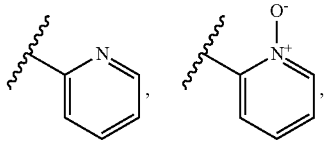

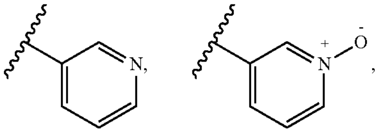

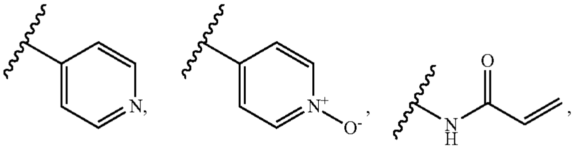

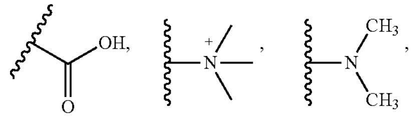

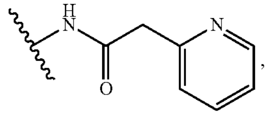

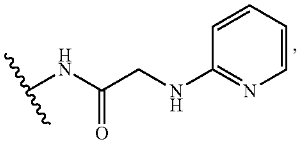

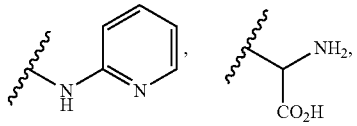

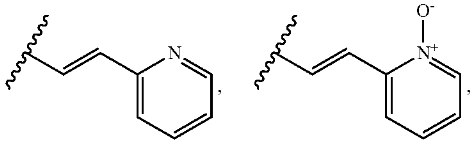

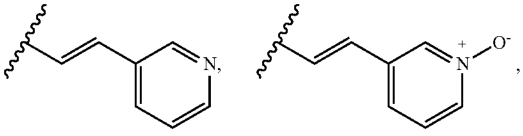

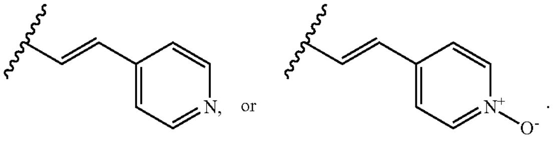

Embodiment P8. The method of one of embodiments P1 to P7, wherein $L^{B1}$-$R^{B1}$ is -continued
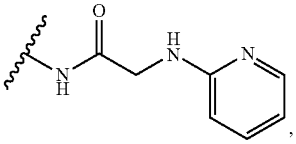,
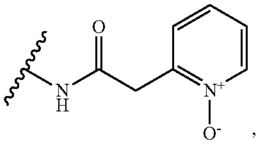,
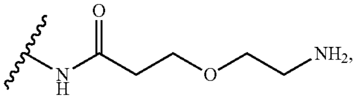
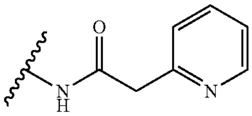,
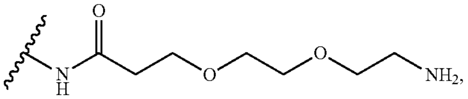
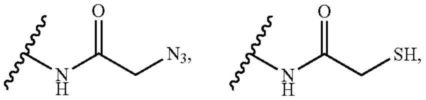
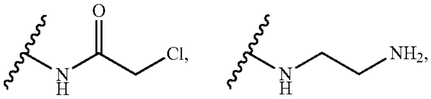
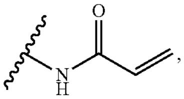
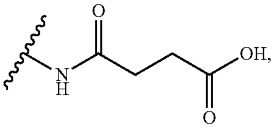
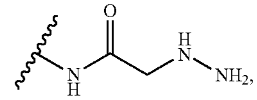
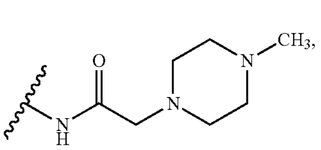
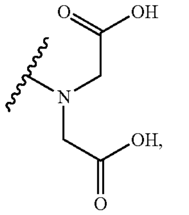
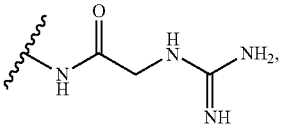
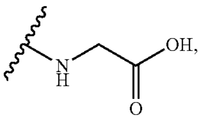
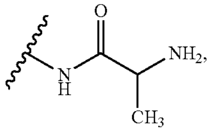
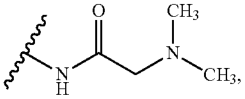
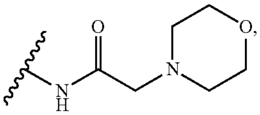
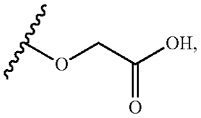
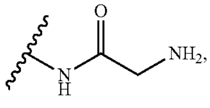
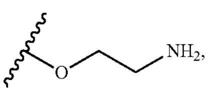
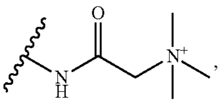,
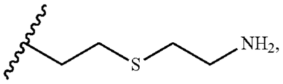
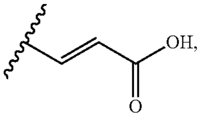
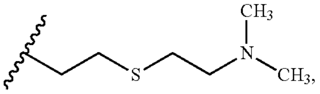
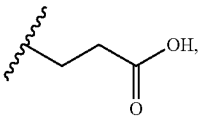
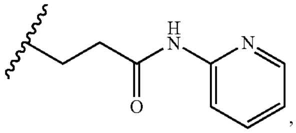,
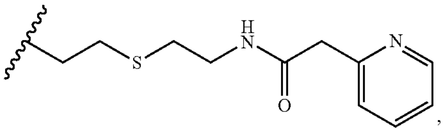,
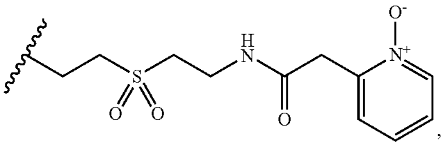,
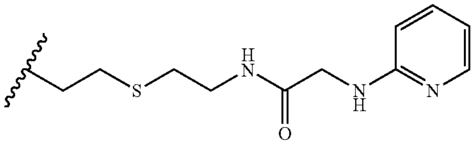,
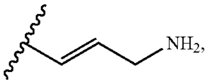
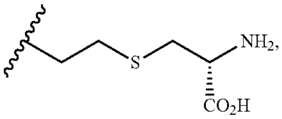
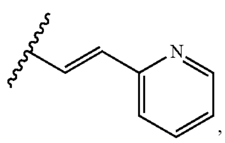,
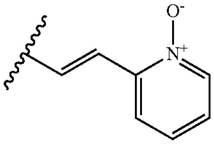,
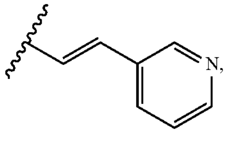
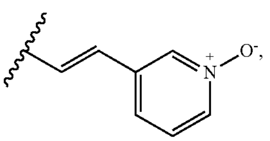
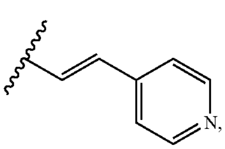
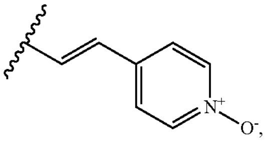
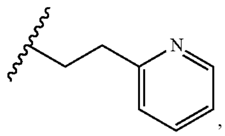,
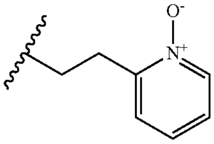,
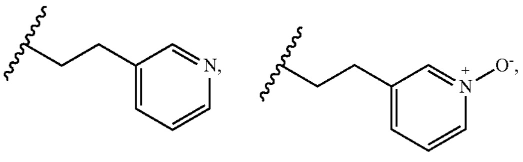

-continued

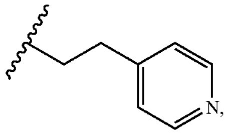

or

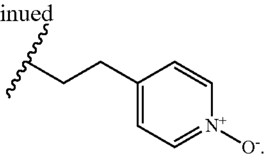

Embodiment P9. The method of one of embodiments P1 to P8, wherein the concentration of the compound in circulating blood is greater than 3-fold the concentration of the compound in the CNS.

Embodiment P10. The method of one of embodiments P1 to P9, wherein the concentration of the compound in circulating blood is greater than 20-fold the concentration of the compound in the CNS.

Embodiment P11. The method of one of embodiments P1 to P10, wherein the compound is unable to cross the blood-brain barrier.

Embodiment P12. The method of one of embodiments P1 to P11, wherein the compound is unable to enter the central nervous system of a subject following administration to the subject outside of the central nervous system.

Embodiment P13. The method of one of embodiments P1 to P12, wherein the anti-CNS disease drug is capable of entering the central nervous system and the compound is incapable of entering the central nervous system following co-administration outside of the central nervous system of the subject.

Embodiment P14. The method of one of embodiments P1 to P13, wherein the compound does not bind calcineurin.

Embodiment P15. The method of one of embodiments P1 to P14, wherein the compound does not inhibit development and/or proliferation of T cells.

Embodiment P16. The method of one of embodiments P1 to P15, wherein the compound does not reduce the body's immune response.

Embodiment P17. The method of one of embodiments P1 to P16, comprising reduced side effects associated with the anti-CNS disease drug compared to absence of the compound.

Embodiment P18. A compound having the formula:

$A^B$-$L^{B1}$-$R^{B1}$, or a pharmaceutically acceptable salt thereof, wherein $A^B$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —NHC(O)$NR^{B1A}R^{B1B}$, —$N(O)_{mB1}$, —$NR^{B1A}R^{B1B}$, —C(O)$R^{B1C}$, —C(O)$OR^{B1C}$, —C(O)$NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B1C}$, —$NR^{B1A}OR^{B1C}$, —$NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$ and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently —F, —Cl, —Br, or —I;

when $L^{B1}$ is a bond, $R^{B1}$ is not H; and $A^B$ is not

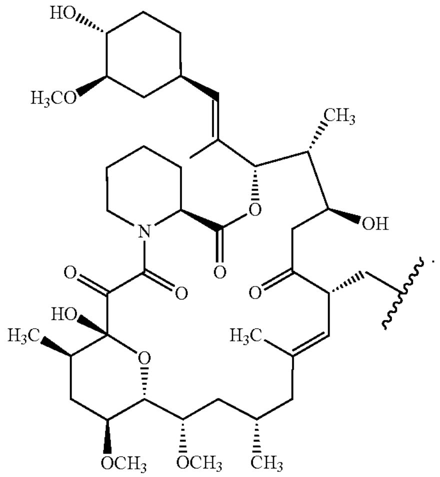 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

Embodiment P19. The compound of embodiment P18, wherein the immunophilin-binding moiety is

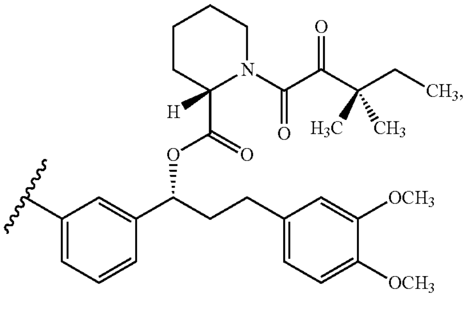

-continued

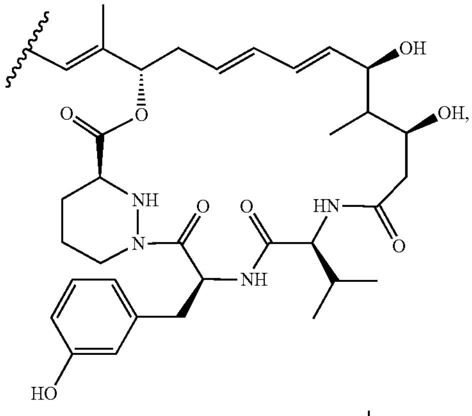

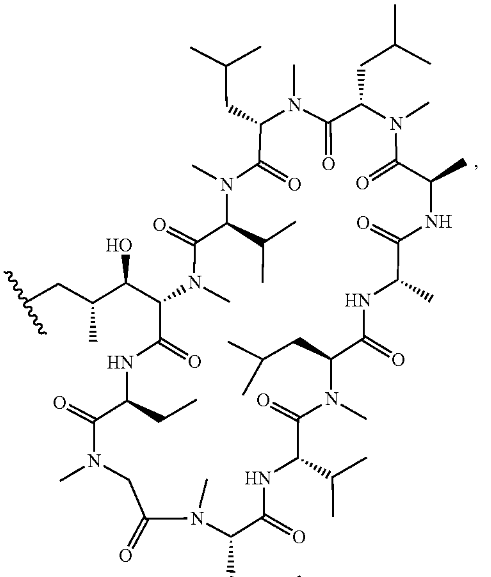

or

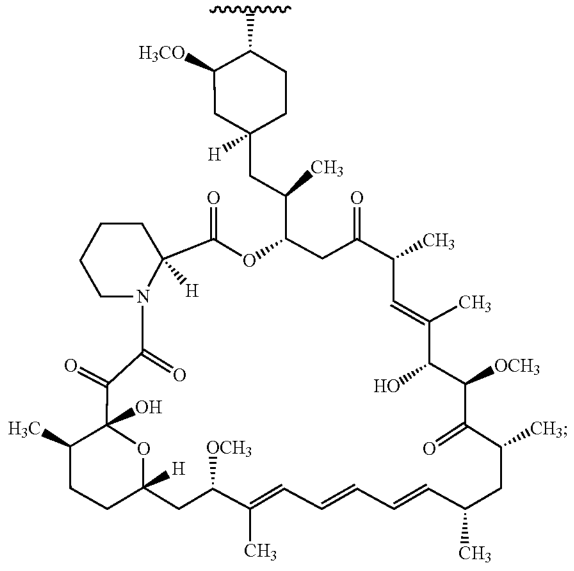

or an analog thereof.

Embodiment P20. The compound of one of embodiments P18 to P19, wherein $L^{B1}$ is $L^{B2}$-$L^{B3}$-$L^{B4}$.

$L^{B2}$ is a bond, —$S(O)_2$—, —$N(R^{B2})$—, —O—, —S—, —C(O)—, —$C(O)N(R^{B2})$—, —$N(R^{B2})C(O)$, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —$S(O)_2$—, —$N(R^{B3})$—, —O—, —S—, —C(O)—, —$C(O)N(R^{B3})$—, —$N(R^{B3})C(O)$, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P21. The compound of one of embodiments P18 to P20, wherein $L^{B1}$ is

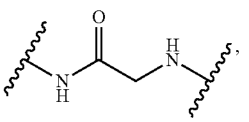,
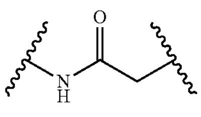,

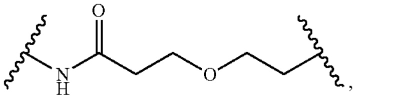,

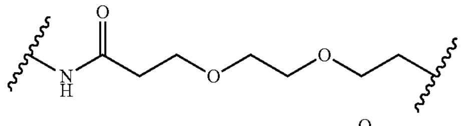,

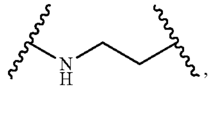,
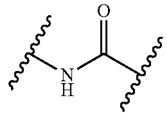,

-continued

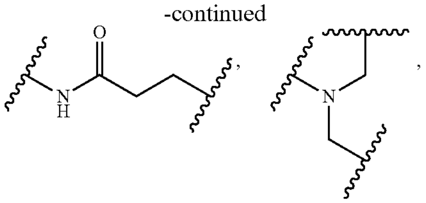

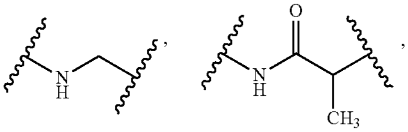

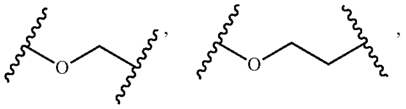

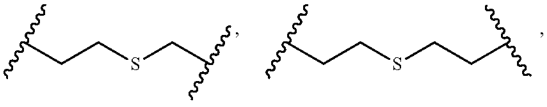

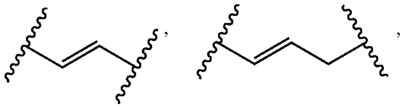

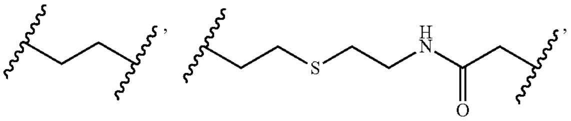

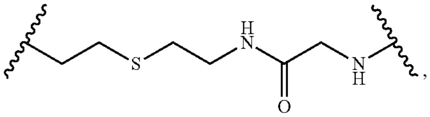

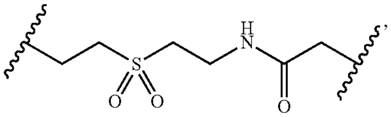

or

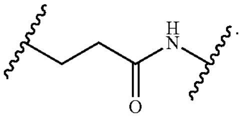

Embodiment P22. The compound of one of embodiments P18 to P21, wherein $R^{B1}$ is halogen, $-NR^{B1A}R^{B1B}$, $-N_3$, $-SR^{B1D}$,

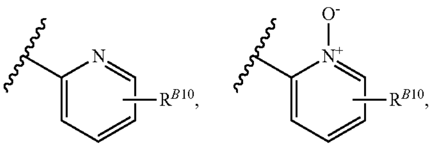

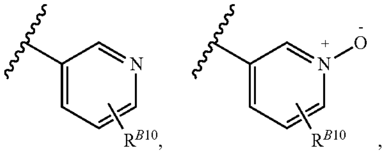

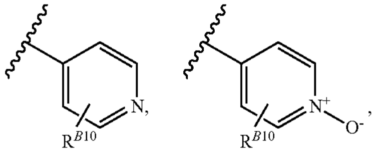

-continued

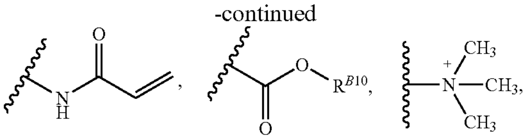

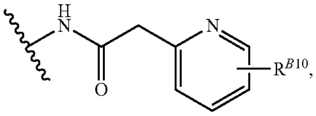

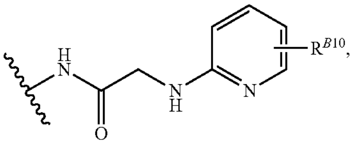

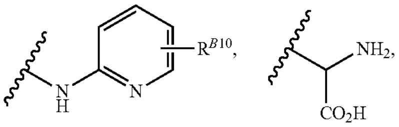

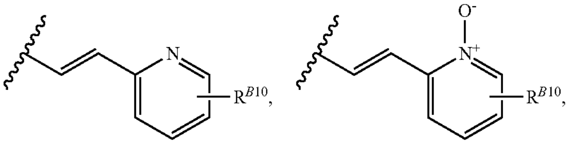

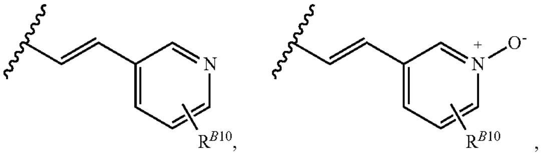

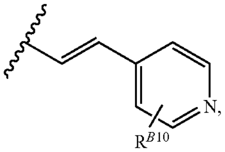

or

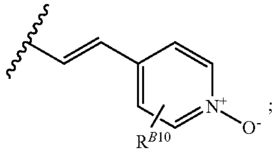

$R^{B10}$ is hydrogen, halogen, $-CX^{B10}_3$, $-CHX^{B10}_2$, $-CH_2X^{B10}$, $-OCX^{B10}_3$, $-OCH_2X^{B10}$, $-OCHX^{B10}_2$, $-CN$, $-SO_{nB10}R^{B10D}$, $-SO_{vB10}NR^{B10A}R^{B10B}$, $-NHC(O)NR^{B10A}R^{B10B}$, $-N(O)_{mB10}$, $-NR^{B10A}R^{B10B}$, $-C(O)R^{B10C}$, $-C(O)OR^{B10C}$, $-C(O)NR^{B10A}R^{B10B}$, $-OR^{B10D}$, $-NR^{B10A}SO_2R^{B10D}$, $-NR^{B10A}C(O)R^{B10C}$, $-NR^{B10A}C(O)OR^{B10C}$, $-NR^{B10A}OR^{B10C}$, $-NR^{B10A}C(NR^{B10C})R^{B10D}$, $-R^{B10A}C(NR^{B10C})NR^{B10A}R^{B10B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment P23. The compound of one of embodiments P18 to P22, wherein $R^{B1}$ is —Cl, $-NH_2$, $-N_3$, —SH,

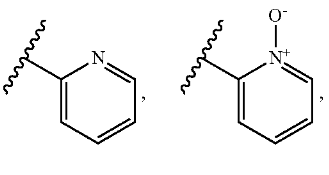

-continued
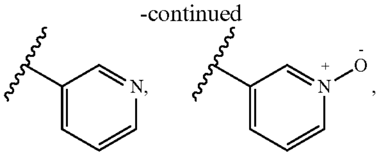
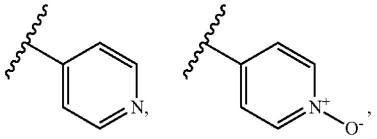
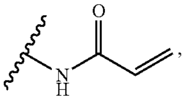
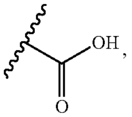
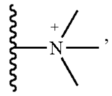
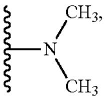
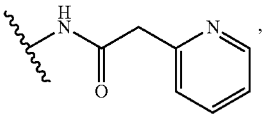
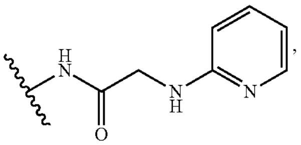
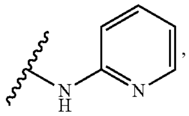
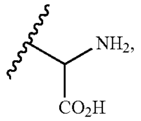
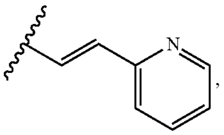
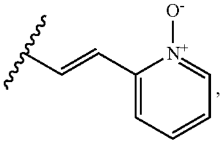
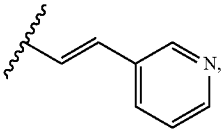
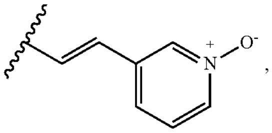
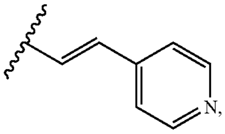
or
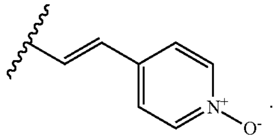
Embodiment P24. The compound of one of embodiments P18 to P23, wherein $L^{B1}$-$R^{B1}$ is
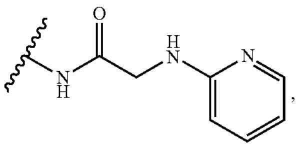
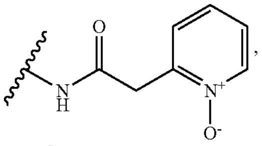
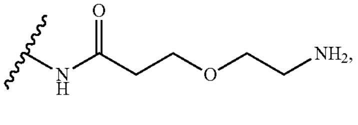
-continued
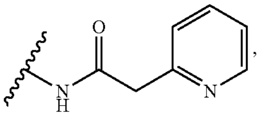
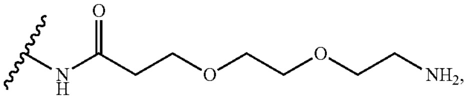
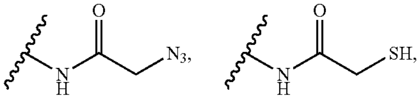
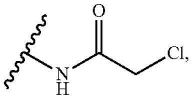
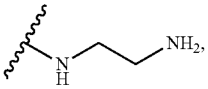
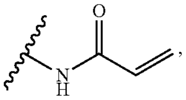
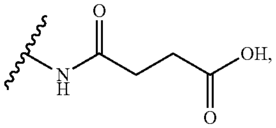
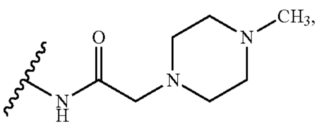
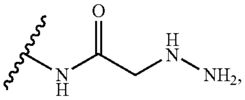
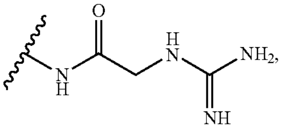
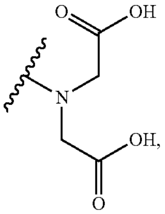
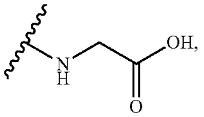
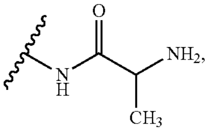
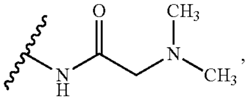
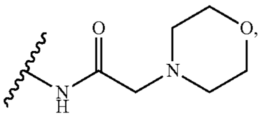
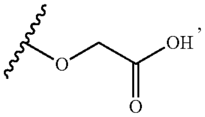
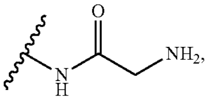
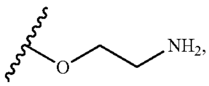
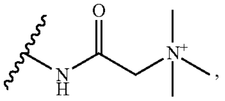
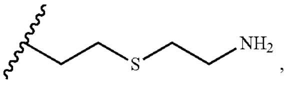
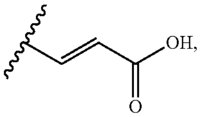

-continued
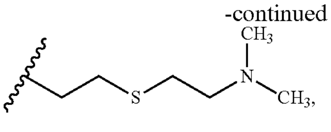, 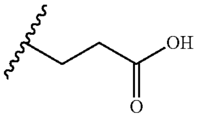,
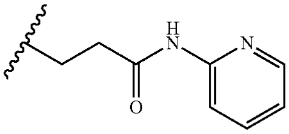,
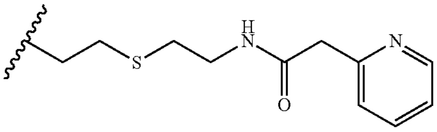,
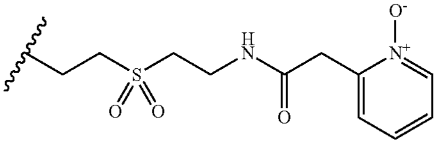,
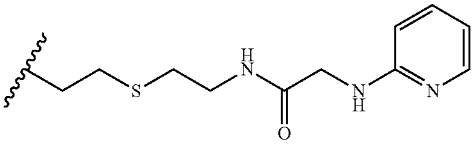,
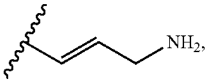,
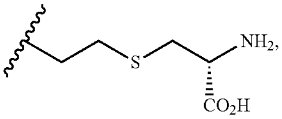,
-continued
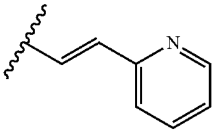, 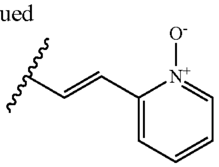,
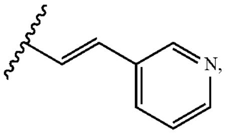, 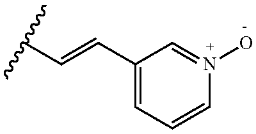,
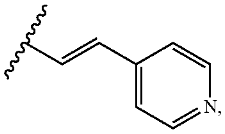, 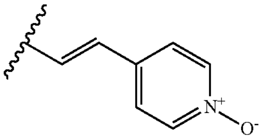,
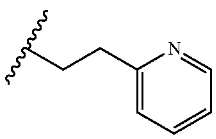, 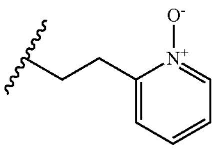,
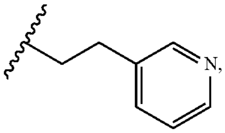, 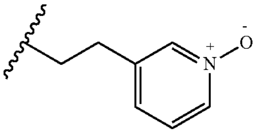,
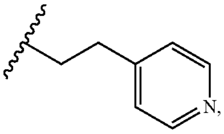 or 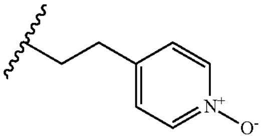.
Embodiment P25. The compound of one of embodiments P18 to P24, wherein the compound is not
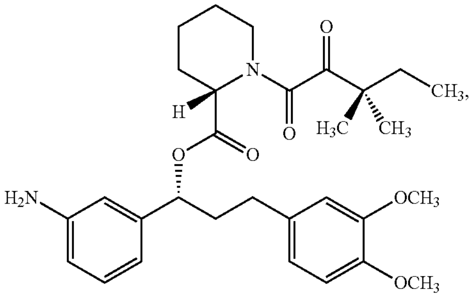
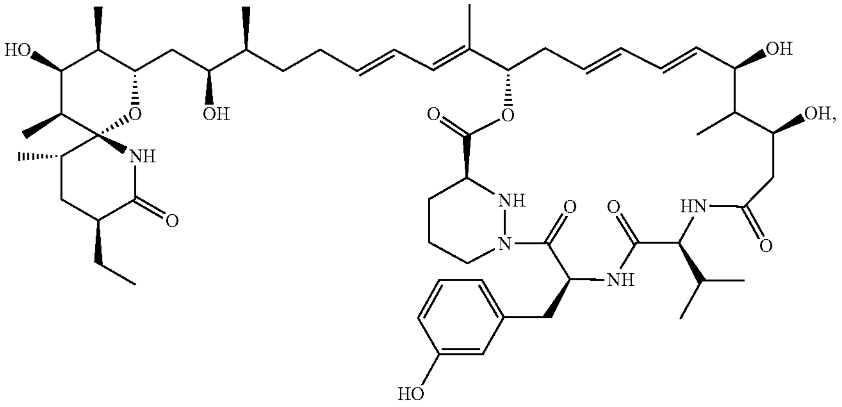

-continued

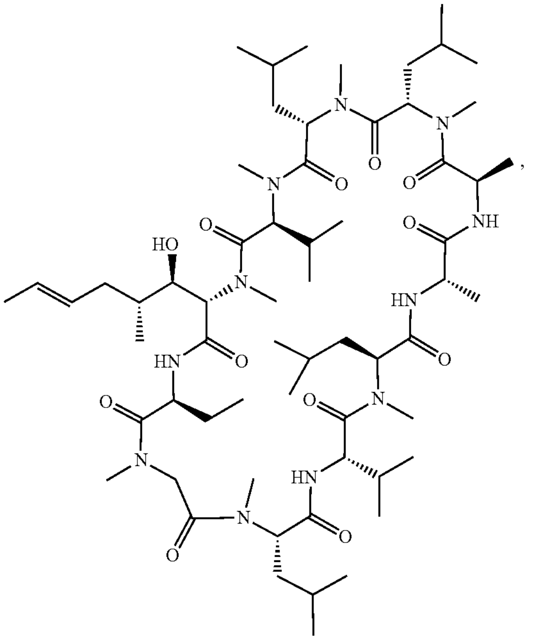

, or

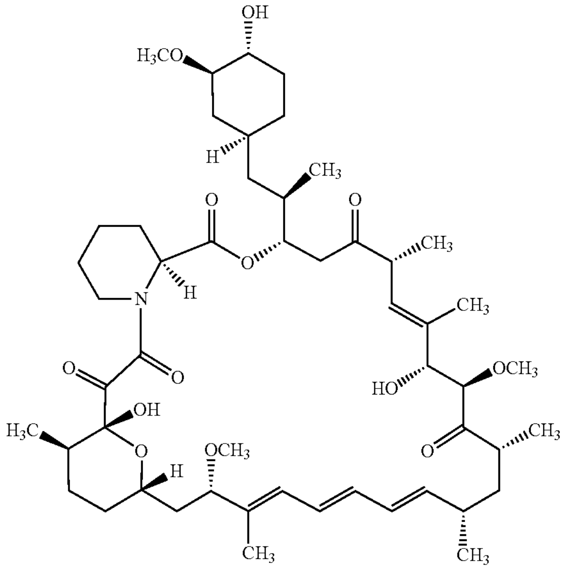

.

Embodiment P26. A compound having the formula:

$A^B$-$L^{B1}$-$R^{B1}$, or a pharmaceutically acceptable salt thereof, wherein $A^B$ is an immunophilin-binding moiety having the formula

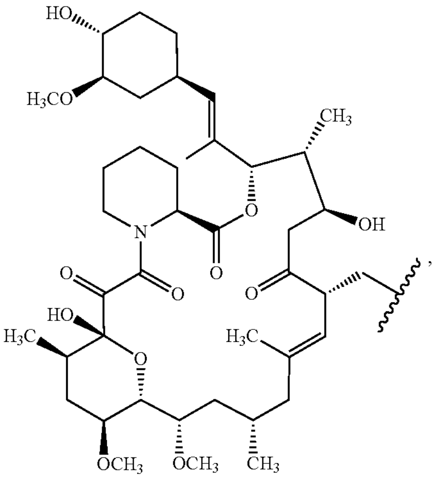

, $L^{B1}$-$R^{B1}$ is a polar moiety;

$L^{B1}$ is $L^{B2}$-$L^{B3}$-$L^{B4}$.

$L^{B2}$ is $S(O)_2$—, —$N(R^{B2})$—, —S—, —S—, —C(O)N($R^{B2}$)—, —$N(R^{B2})C(O)$—, —$N(R^{B2})C(O)NH$—, —$NHC(O)N(R^{B2})$—, —C(O)O—, —OC(O)—;

$L^{B3}$ is a bond, —$S(O)_2$—, —$N(R^{B3})$—, —O—, —S—, —C(O)—, —$C(O)N(R^{B3})$—, —$N(R^{B3})C(O)$, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —$NHC(O)NR^{B1A}R^{B1B}$, —$N(O)_{mB1}$, —$NR^{B1A}R^{B1B}$, —$C(O)R^{B1C}$, —$C(O)OR^{B1C}$, —$C(O)NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B15}C$, —$NR^{B1A}OR^{B1C}$, —$NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$ and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2; and $X^{B1}$ is independently —F, —Cl, —Br, or —I.

Embodiment P27. The compound of embodiment P26, wherein $L^{B1}$ is

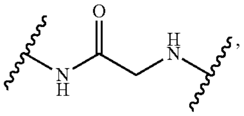
,
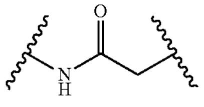
,
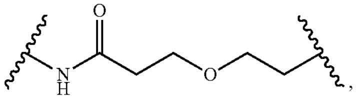
,
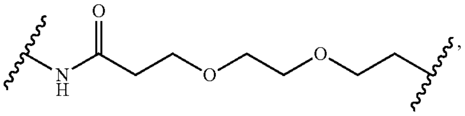
,
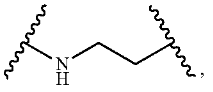
,
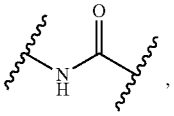
,
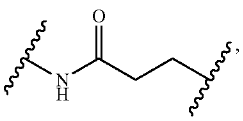
,
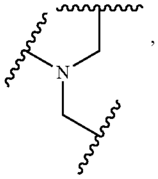
,
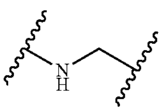
,
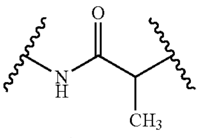
,
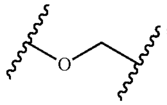
or
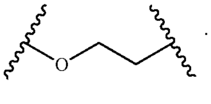
.

Embodiment P28. The compound of one of embodiments P26 to P27, wherein $R^{B1}$ is halogen, —$NR^{B1A}R^{B1B}$, —$N_3$, —$SR^{B1D}$,

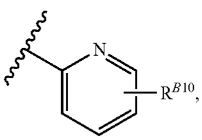
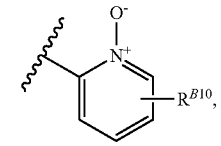
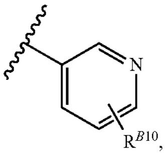
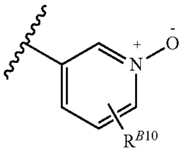
,
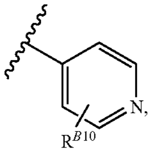
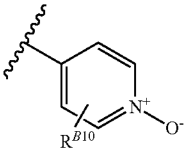
,
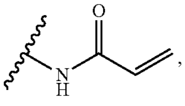
,
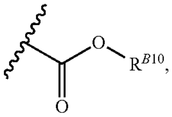
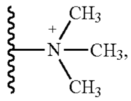
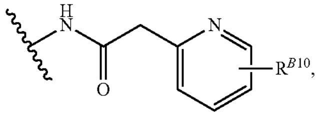
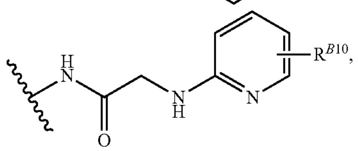
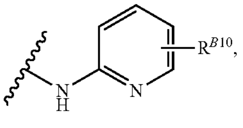
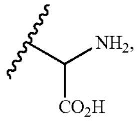
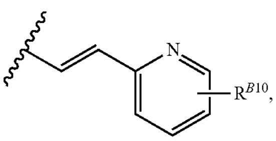
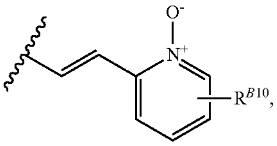
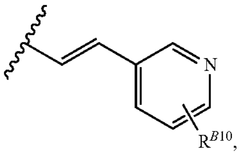
,
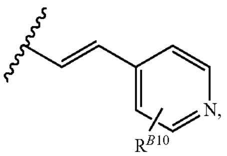
or
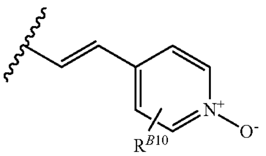
;

$R^{B10}$ is hydrogen, halogen, —$CX^{B10}_3$, —$CHX^{B10}_2$, —$CH_2X^{B10}$, —$OCX^{B10}_3$, —$OCH_2X^{B10}$, —$OCHX^{B10}_2$, —CN, —$SO_{nB10}R^{B10D}$, —$SO_{vB10}NR^{B10A}R^{B10B}$, —NHC(O)$NR^{B10A}R^{B10B}$, —$N(O)_{mB10}$, —$NR^{B10A}R^{B10B}$, —C(O)$R^{B10C}$, —C(O)$OR^{B10C}$, —C(O)$NR^{B10A}R^{B10B}$, —$OR^{B10D}$, —$NR^{B10A}SO_2R^{B10D}$, —$NR^{B10A}$C(O)$R^{B10C}$, —$NR^{B10A}$C(O)$OR^{B10C}$, —$NR^{B10A}OR^{B10C}$, —$NR^{B10A}C(NR^{B10C})R^{B10D}$, —$NR^{B10A}C(NR^{B10C})NR^{B10A}R^{B10B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment P29. The compound of one of embodiments P26 to P28, wherein $R^{B1}$ is —Cl, —$NH_2$, —$N_3$, —SH,

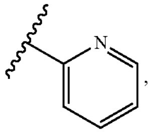
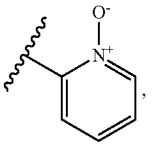
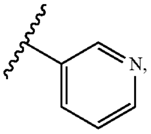
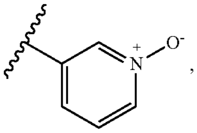
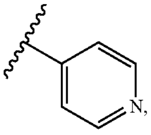
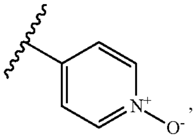
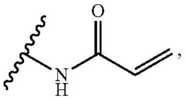
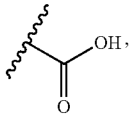
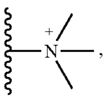
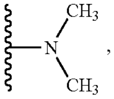
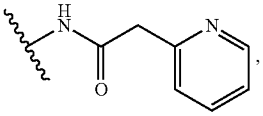
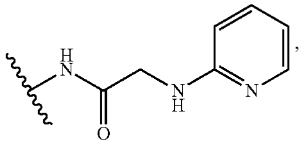
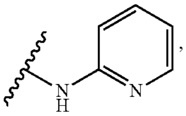
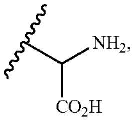
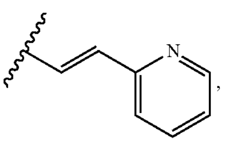
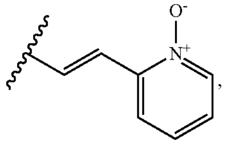
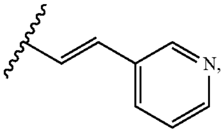
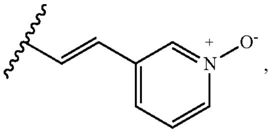
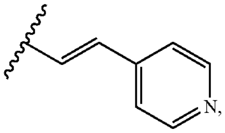 or 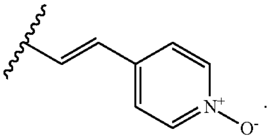

Embodiment P30. The compound of one of embodiments P26 to P29, wherein $L^{B1}$-$R^{B1}$ is

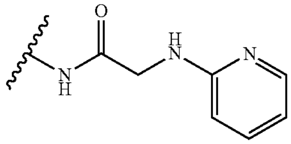
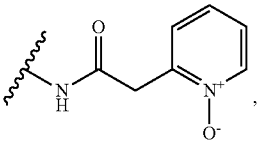
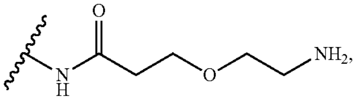
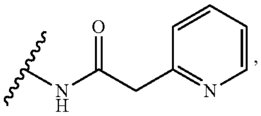
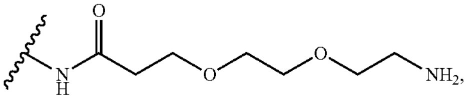
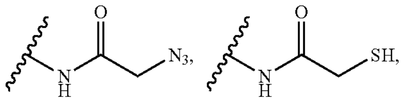
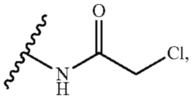
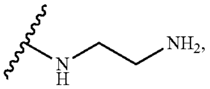
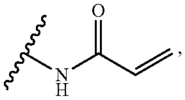
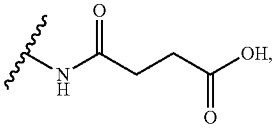
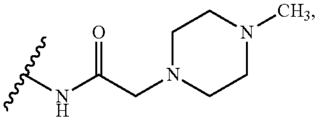
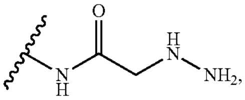
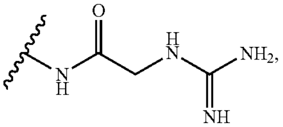
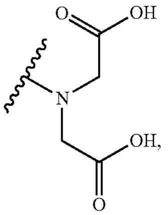
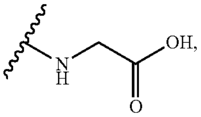
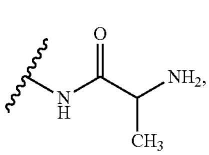
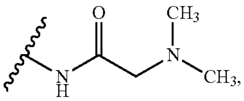
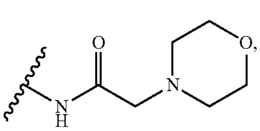
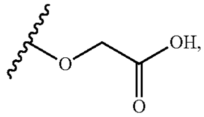
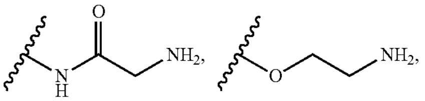 or -continued

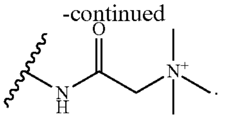

Embodiment P31. A compound having the formula:

$A^B$-$L^{B1}$-$R^{B1}$, or a pharmaceutically acceptable salt thereof, wherein $A^B$ is an immunophilin-binding moiety having the formula

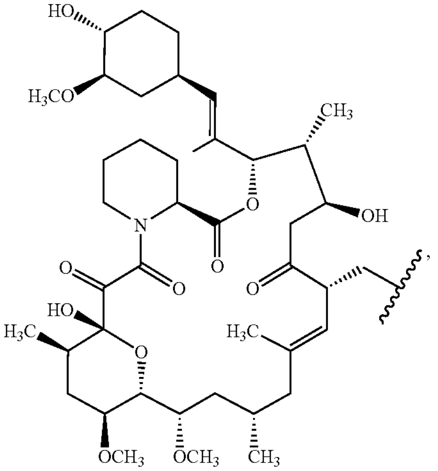 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof, $L^{B1}$-$R^{B1}$ is a polar moiety;

$L^{B1}$ is

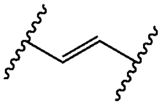

or

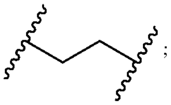

;

and $R^{B1}$ is substituted or unsubstituted heteroaryl.

Embodiment P32. The compound of embodiment P31, wherein $R^{B1}$ is substituted or unsubstituted pyridyl.

Embodiment P33. A compound having the formula:

$A^B$-$L^{B1}$-$R^{B1}$, or a pharmaceutically acceptable salt thereof, wherein $A^B$ is an immunophilin-binding moiety having the formula

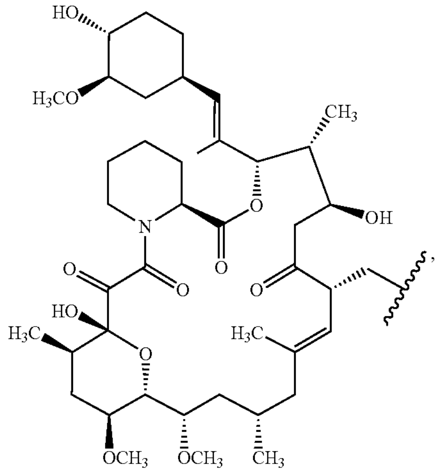 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof, $L^{B1}$-$R^{B1}$ is a polar moiety;

$L^{B1}$ is

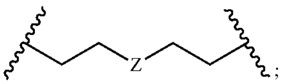

;

Z is —S— or —$SO_2$—;

$R^{B1}$ is —$NR^{B1A}R^{B1B}$ or —$NHC(O)CH_2R^{B1C}$;

$R^{B1A}$ and $R^{B1B}$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{B1C}$ is substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P34. The compound of embodiment P33, wherein $R^{B1A}$, $R^{B1B}$, or $R^{B1C}$ are independently substituted or unsubstituted pyridyl.

Embodiment P35. The compound of one of embodiments P18 to P34, wherein the immunophilin-binding moiety is a cyclophilin-binding moiety or an FKBP-binding moiety.

Embodiment P36. A pharmaceutical composition comprising a pharmaceutically acceptable excipient and a compound of one of embodiments P18 to P35.

Embodiment P37. The method of one of embodiments P1 to P17, wherein the anti-CNS disease drug has the formula:

A-$L^1$-$R^1$;

wherein

A is an immunophilin-binding moiety;

$L^1$ is a bond or a covalent linker; and $R^1$ is a kinase inhibitor, a pseudokinase inhibitor, a GTPase inhibitor, a histone-modifying enzyme inhibitor, or a monovalent anti-viral agent.

Embodiment P38. The method of embodiment P37, wherein the immunophilin-binding moiety of the anti-CNS disease drug is a cyclophilin-binding moiety or an FKBP-binding moiety.

Embodiment P39. The method of one of embodiments P37 to P38, wherein the immunophilin-binding moiety of the anti-CNS disease drug is

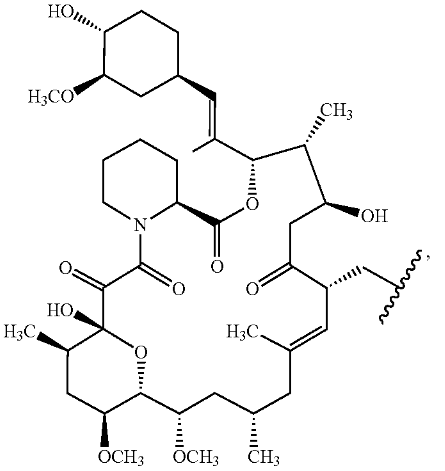

,

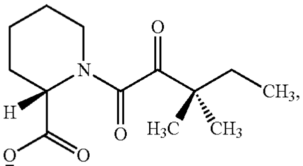

,

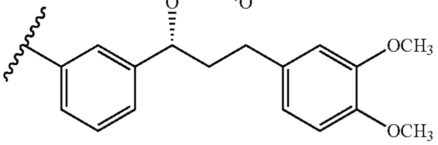

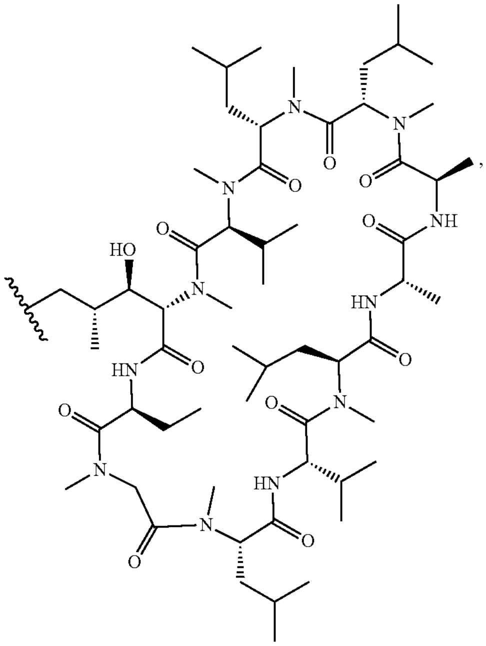

,

-continued

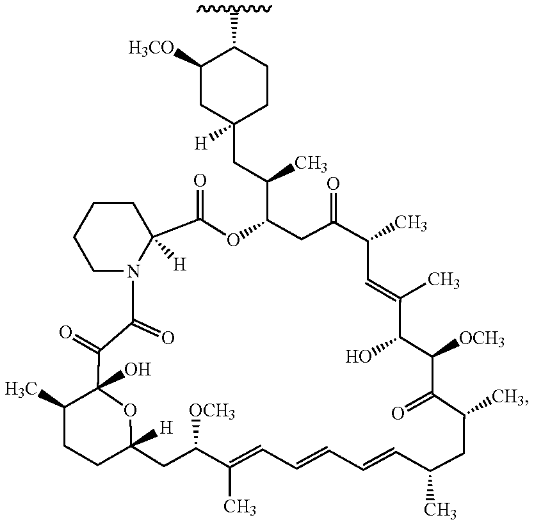

, or

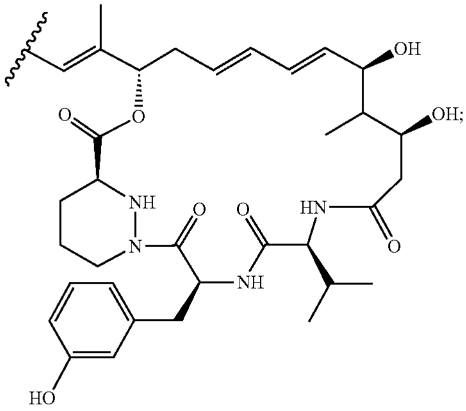

;

or an analog thereof.

Embodiment P40. The method of one of embodiments P37 to P38, wherein the immunophilin-binding moiety of the anti-CNS disease drug is

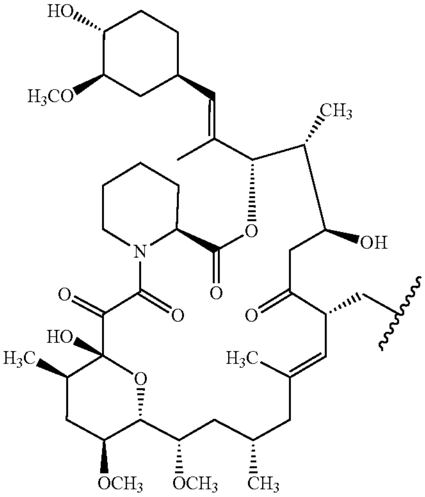

,

-continued

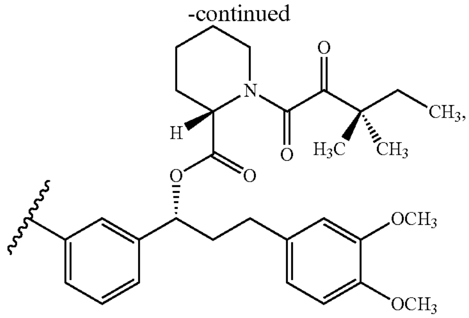

,

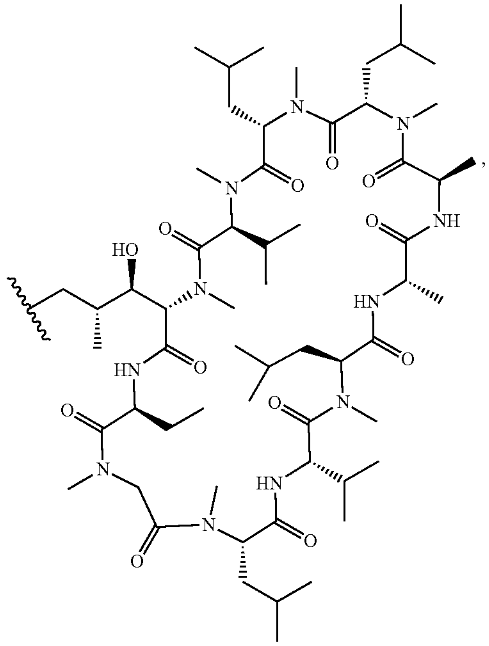

, or

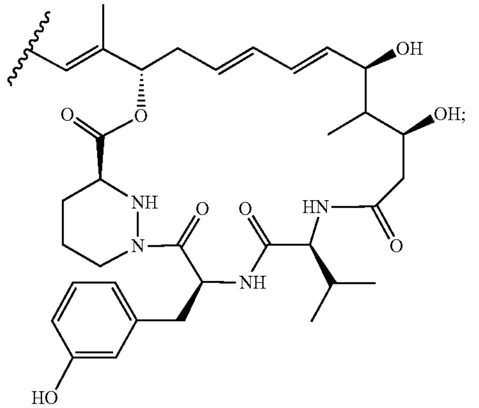

;

or an analog thereof.

Embodiment P41. The method of one of embodiments P37 to P39, wherein $L^1$ is $L^2$-$L^3$-$L^4$-$L^5$-$L^6$ $L^2$ is connected directly to the moiety of an immunophilin-binding compound;

$L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^2$, $R^3$, $R^4$, $R^5$, and $R^6$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P42. The method of embodiment P41, wherein $L^3$, $L^4$, $L^5$, and $L^6$ are a bond.

Embodiment P43. The method of embodiment P41, wherein $L^2$ is a substituted or unsubstituted alkylene, substituted or unsubstituted heteroalkylene, substituted or unsubstituted cycloalkylene, or substituted or unsubstituted heterocycloalkylene;

$L^3$ is a bond, substituted or unsubstituted alkylene, substituted or unsubstituted heteroalkylene, substituted or unsubstituted cycloalkylene, or substituted or unsubstituted heterocycloalkylene;

$L^4$ is a bond, substituted or unsubstituted alkylene, or substituted or unsubstituted heteroalkylene;

$L^5$ is a bond; and $L^6$ is a bond.

Embodiment P44. The method of embodiment P41, wherein $L^2$ is an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^3$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or an unsubstituted 5 to 6 membered heterocycloalkylene, and $L^4$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^5$ is a bond; and $L^6$ is a bond.

Embodiment P45. The method of one of embodiments P37 to P39, wherein $L^1$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

Embodiment P46. The method of one of embodiments P37 to P39, wherein $L^1$ is

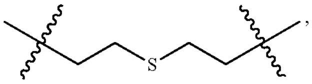,
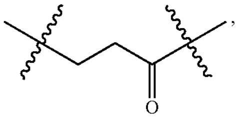,
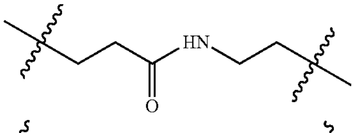,
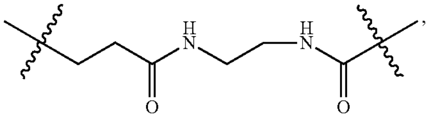,
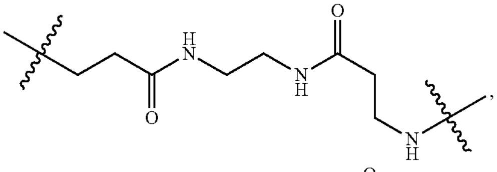,
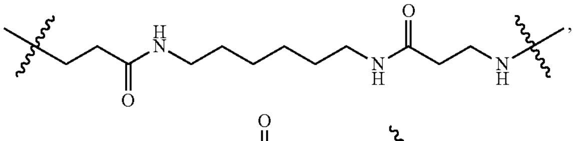,
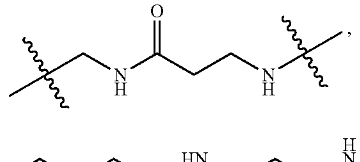,
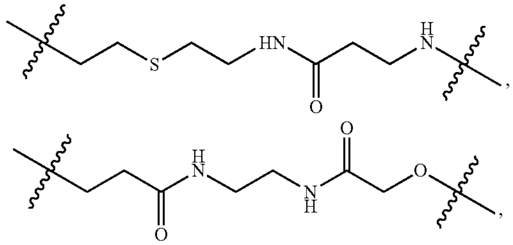,
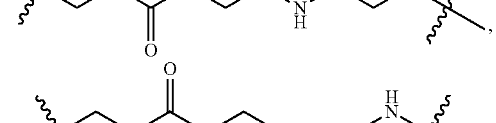,
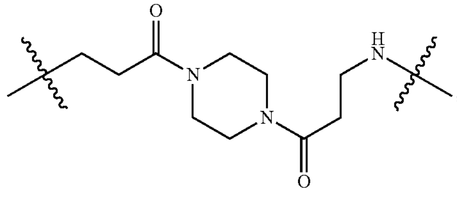, -continued

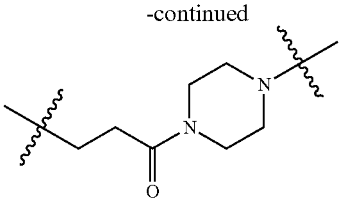, or

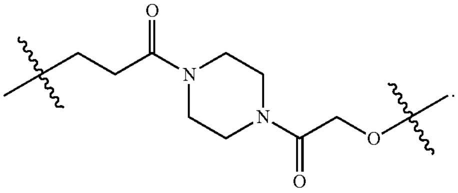.

Embodiment P47. The method of one of embodiments P37 to P39, wherein $L^1$ is a bond.

Embodiment P48. The method of one of embodiments P37 to P39, wherein $L^1$ is a substituted or unsubstituted alkylene or substituted or unsubstituted heteroalkylene.

Embodiment P49. The method of one of embodiments P37 to P48, wherein $R^1$ is a monovalent kinase inhibitor.

Embodiment P50. The method of embodiment P49, wherein the kinase is not mTOR.

Embodiment P51. The method of one of embodiments P49 to P50, wherein the monovalent kinase inhibitor is a monovalent Src kinase inhibitor.

Embodiment P52. The method of embodiments P49 to P50, wherein the monovalent Src kinase inhibitor is a monovalent dasatinib or monovalent dasatinib derivative.

Embodiment P53. The method of embodiment P52, wherein the monovalent dasatinib derivative has the formula:

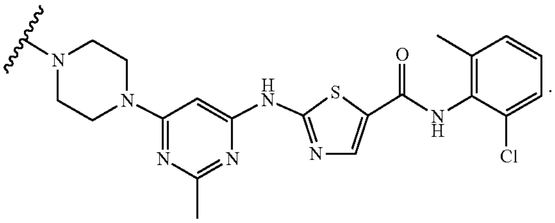 [SMILES: *N1CCN(c2cc(Nc3ncc(C(=O)Nc4c(C)cccc4Cl)s3)nc(C)n2)CC1].

Embodiment P54. The method of one of embodiments P49 to P50, wherein the monovalent kinase inhibitor is a monovalent Raf inhibitor, VEGFR inhibitor, PDGFR inhibitor, or c-Kit inhibitor.

Embodiment P55. The method of embodiment P54, wherein the monovalent Raf inhibitor, VEGFR inhibitor, PDGFR inhibitor, or c-Kit inhibitor is a monovalent sorafenib or monovalent sorafenib derivative.

Embodiment P56. The method of embodiment P55, wherein the monovalent sorafenib derivative has the formula:

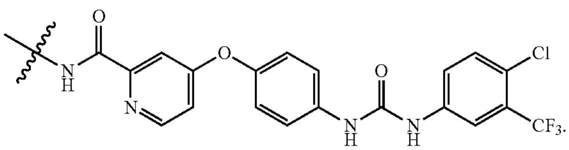 [SMILES: *NC(=O)c1cc(Oc2ccc(NC(=O)Nc3ccc(Cl)c(C(F)(F)F)c3)cc2)ccn1]

Embodiment P57. The method of one of embodiments P49 to P50, wherein the monovalent kinase inhibitor is a monovalent EGFR inhibitor.

Embodiment P58. The method of embodiment P57, wherein the monovalent EGFR inhibitor is a monovalent lapatinib, monovalent lapatinib derivative, monovalent erlotinib, monovalent erlotinib derivative, monovalent gefitinib, or monovalent gefitinib derivative.

Embodiment P59. The method of embodiment P58, wherein the monovalent EGFR inhibitor has the formula:

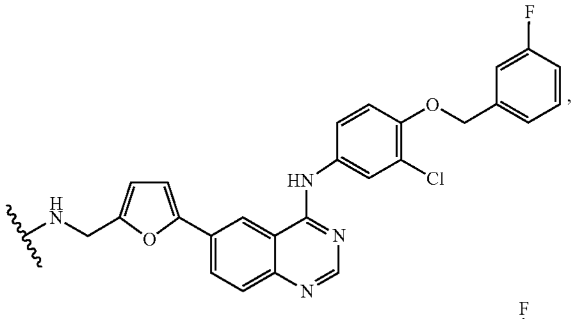
,

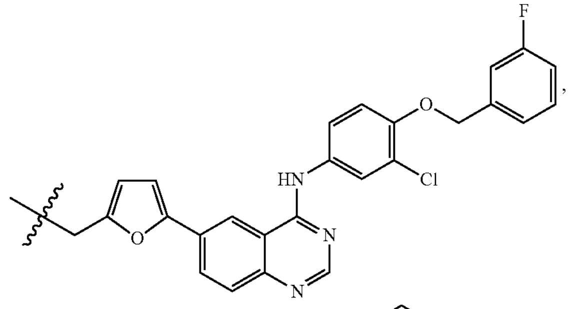
,

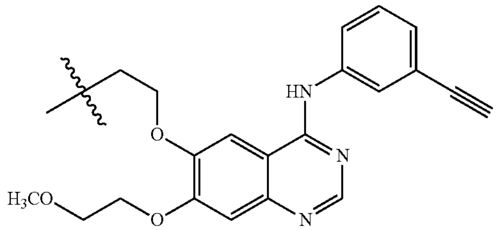
, or

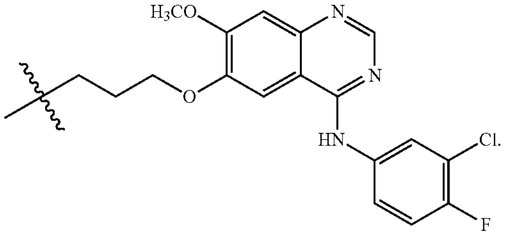
.

Embodiment P60. The method of one of embodiments P49 to P50, wherein the monovalent kinase inhibitor is a monovalent LRRK2 inhibitor.

Embodiment P61. The method of embodiment P60, wherein the monovalent LRRK2 inhibitor is a monovalent GNE-7915 or monovalent GNE-7915 derivative.

Embodiment P62. The method of embodiment P61, wherein the monovalent GNE-7915 derivative has the formula:

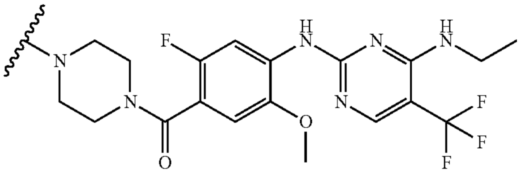
or

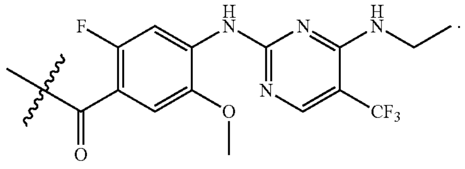
.

Embodiment P63. The method of one of embodiments P37 to P48, wherein $R^1$ is a monovalent KRAS inhibitor.

Embodiment P64. The method of embodiment P63, wherein the monovalent KRAS inhibitor is a monovalent KRAS G12C inhibitor or a monovalent KRAS M72C inhibitor.

Embodiment P65. The method of embodiment P44, wherein the monovalent KRAS inhibitor has the formula:

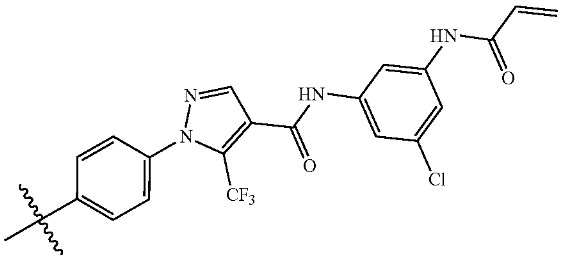
,

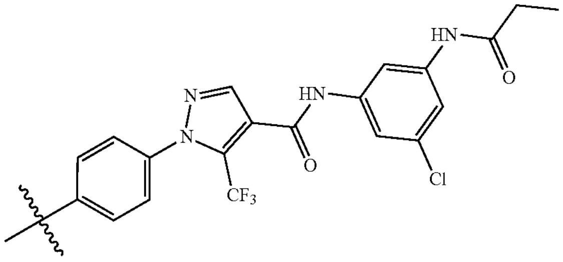
,

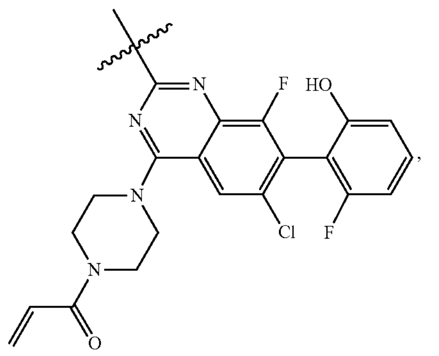
, or

-continued

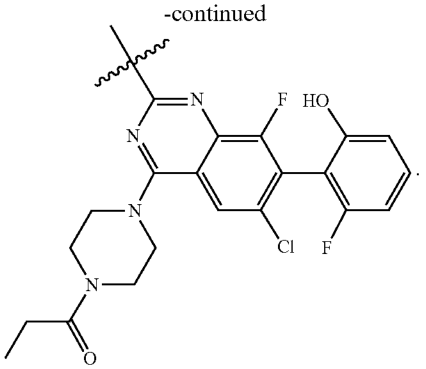

VI. Additional Embodiments

Embodiment 1. A method of treating a CNS disease in a subject in need of such treatment, comprising co-administering outside the CNS of said subject an anti-CNS disease drug and a compound having the formula:

$A^{B}$-$L^{B1}$-$R^{B1}$, or a pharmaceutically acceptable salt thereof, wherein $A^{B}$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, $-CX^{B1}_3$, $-CHX^{B1}_2$, $-CH_2X^{B1}$, $-OCX^{B1}_3$, $-OCH_2X^{B1}$, $-OCHX^{B1}_2$, —CN, $-SO_{nB1}R^{B1D}$, $-SO_{vB1}NR^{B1A}R^{B1B}$, $-NHC(O)NR^{B1A}R^{B1B}$, $-N(O)_{mB1}$, $-NR^{B1A}R^{B1B}$, $-C(O)R^{B1C}$, $-C(O)OR^{B1C}$, $-C(O)NR^{B1A}R^{B1B}$, $-OR^{B1D}$, $-NR^{B1A}SO_2R^{B1D}$, $-NR^{B1A}C(O)R^{B1C}$, $-NR^{B1A}C(O)OR^{B1C}$, $-NR^{B1A}OR^{B1C}$, $-NR^{B1A}C(NR^{B1C})R^{B1D}$, $-NR^{B1A}C(NR^{B1C})NR^{B1A}R^{B1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$ and $R^{B1D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHC(NH)H, $-NHC(NH)NH_2$, —NHOH, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently —F, —Cl, —Br, or —I;

when $L^{B1}$ is a bond, $R^{B1}$ is not H; and wherein, subsequent to administration, the concentration of the compound in circulating blood of said subject is greater than the concentration of the compound in the CNS of said subject.

Embodiment 2. The method of embodiment 1, wherein the immunophilin-binding moiety is a cyclophilin-binding moiety or an FKBP-binding moiety.

Embodiment 3. The method of one of embodiments 1 to 2, wherein the immunophilin-binding moiety is

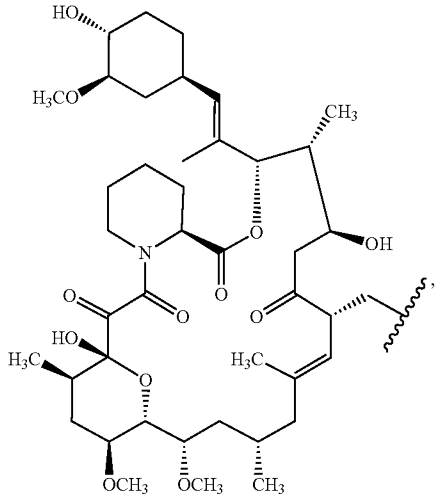

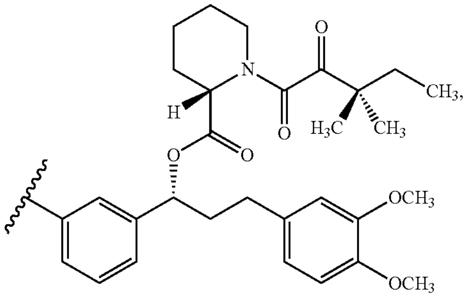

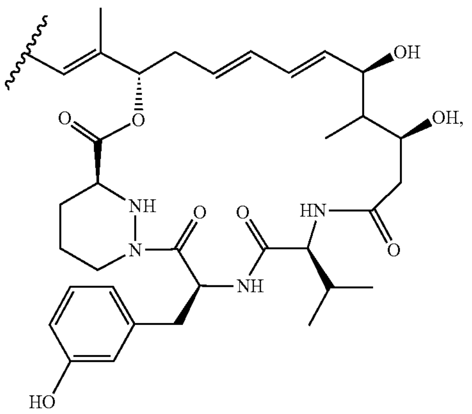

-continued

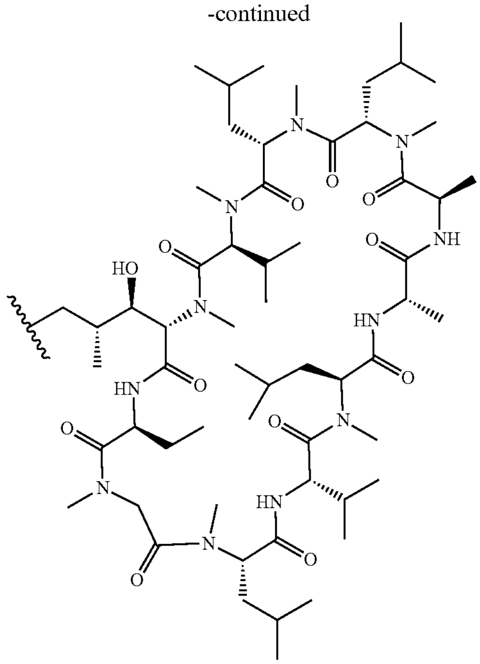

, or

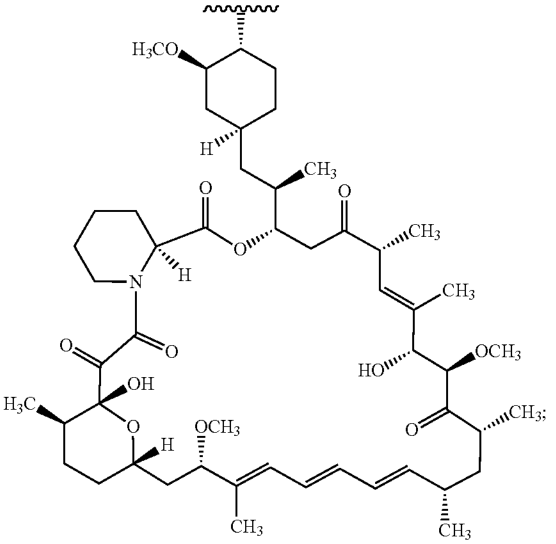

or an analog thereof.

Embodiment 4. The method of one of embodiments 1 to 3, wherein $L^{B1}$ is $L^{B2}$-$L^{B3}$-$L^{B4}$.

$L^{B2}$ is a bond, —$S(O)_2$—, —$N(R^{B2})$—, —O—, —S—, —C(O)—, —$C(O)N(R^{B2})$—, —$N(R^{B2})C(O)$—, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 5. The method of one of embodiments 1 to 4, wherein $L^{B1}$ is

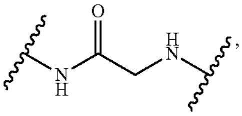, 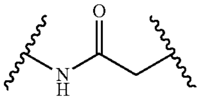,

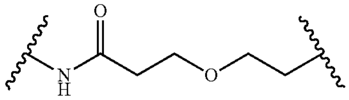,

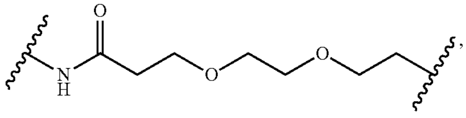,

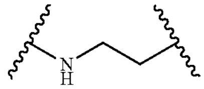, 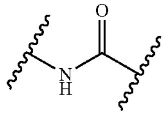,

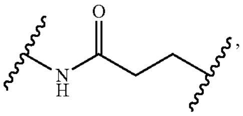, 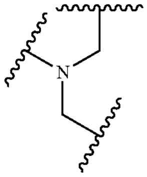,

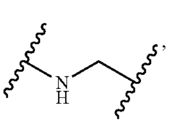, 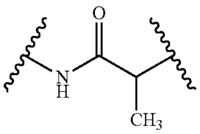, 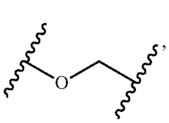,

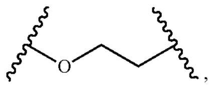, 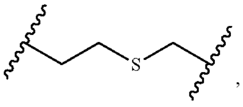,

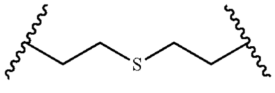, 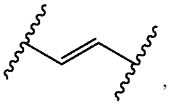,

-continued

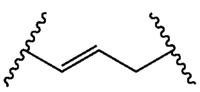, 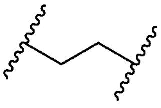,

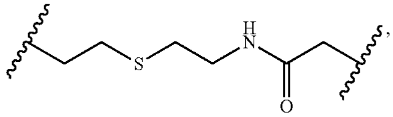,

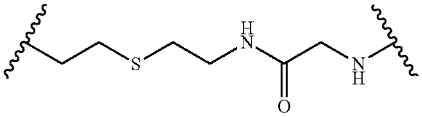,

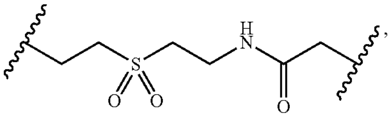, or

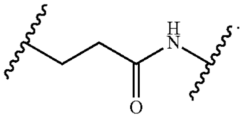.

Embodiment 6. The method of one of embodiments 1 to 5, wherein $R^{B1}$ is halogen, $—NR^{B1A}R^{B1B}$, $—N_3$, $—SR^{B1D}$,

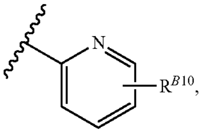, 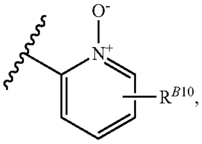,

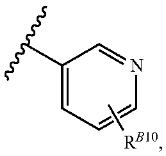, 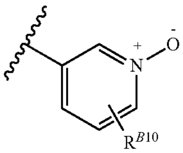,

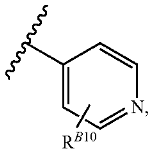, 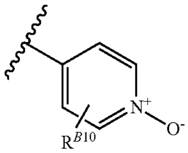,

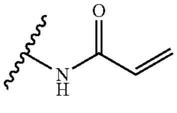, 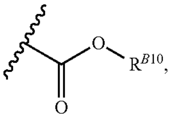, 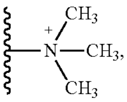,

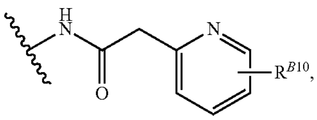,

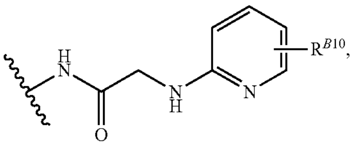,

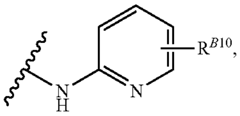, 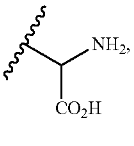

-continued

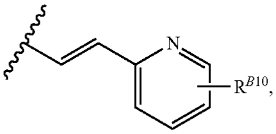, 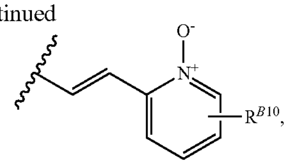,

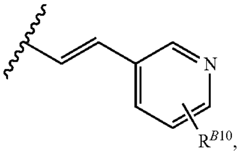, 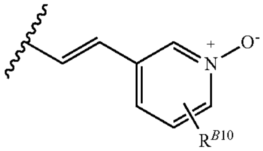,

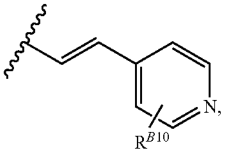 or 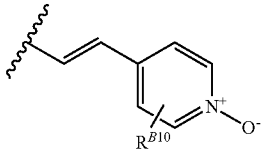;

$R^{B10}$ is hydrogen, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—N(O)_{mB10}$, $—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—NR^{B10A}C(NR^{B10C})R^{B10D}$, $—NR^{B10A}C(NR^{B10C})NR^{B10A}R^{B10B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment 7. The method of one of embodiments 1 to 6, wherein $R^{B1}$ is —Cl, $—NH_2$, $—N_3$, —SH,

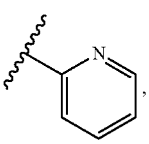, 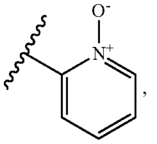,

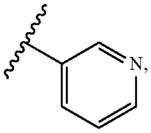, 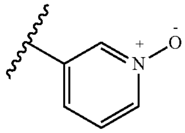,

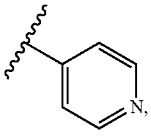, 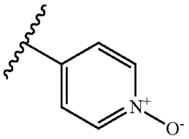,

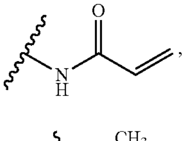, 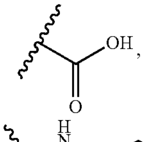, 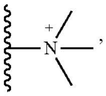,

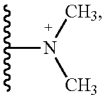, 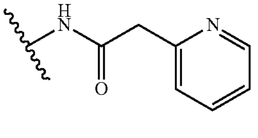,

-continued
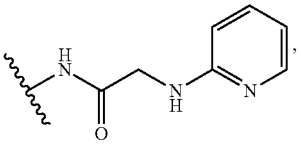
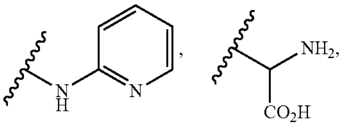
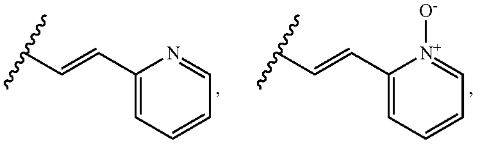
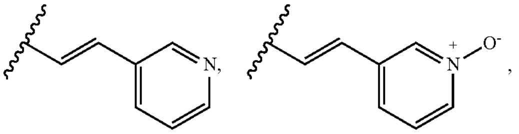
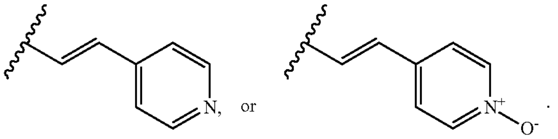
Embodiment 8. The method of one of embodiments 1 to 7, wherein $L^{B1}$-$R^{B1}$ is
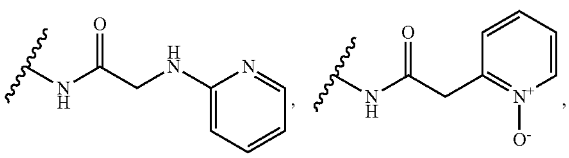
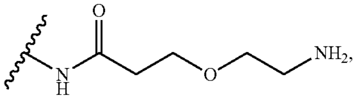
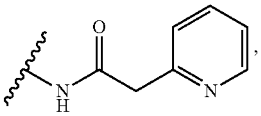
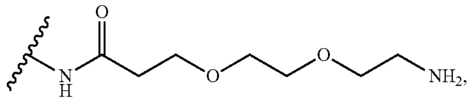
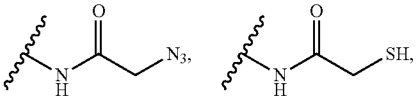
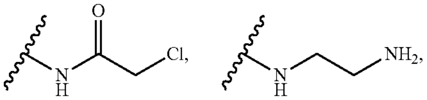
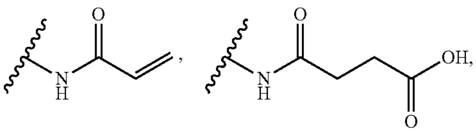
-continued
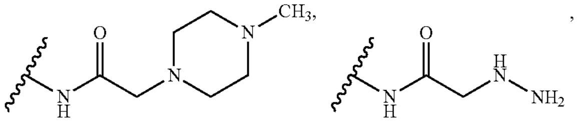
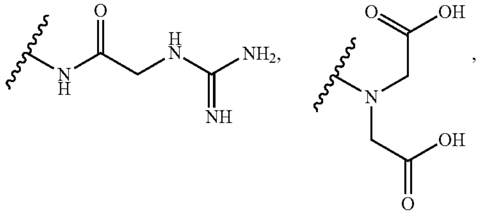
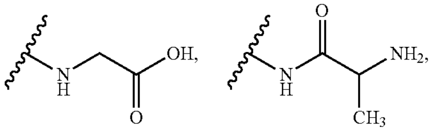
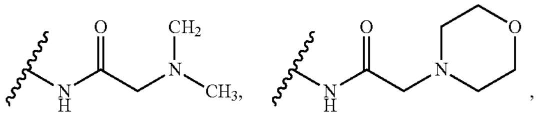
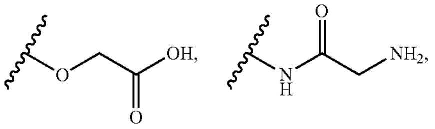
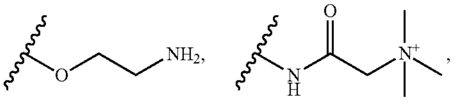
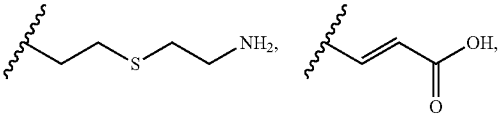
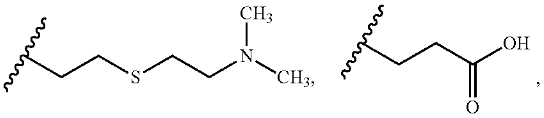
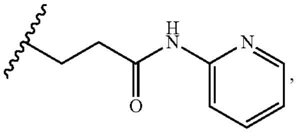
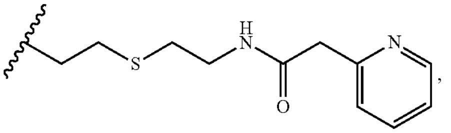
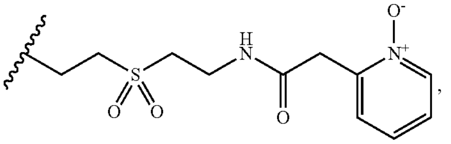
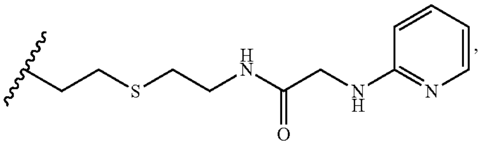
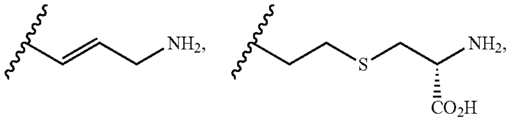

-continued

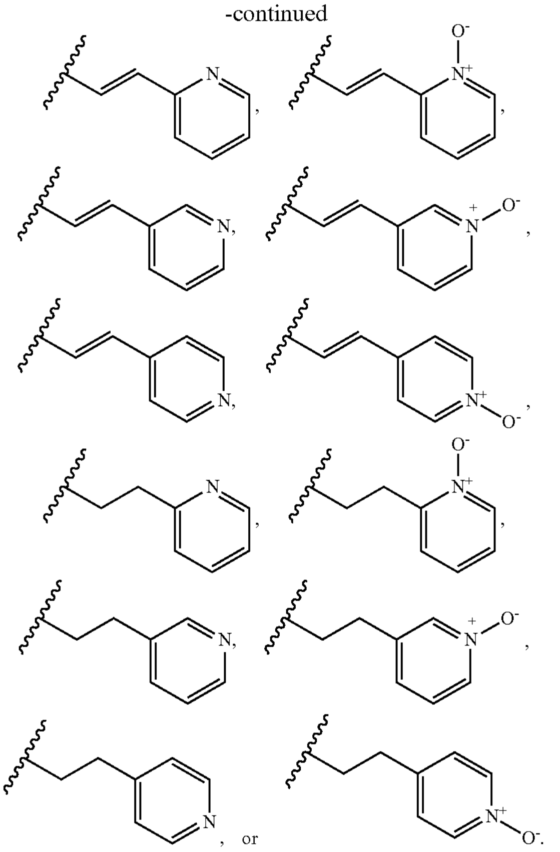

Embodiment 9. The method of one of embodiments 1 to 8, wherein the concentration of the compound in circulating blood is greater than 3-fold the concentration of the compound in the CNS.

Embodiment 10. The method of one of embodiments 1 to 9, wherein the concentration of the compound in circulating blood is greater than 20-fold the concentration of the compound in the CNS.

Embodiment 11. The method of one of embodiments 1 to 10, wherein the compound is unable to cross the blood-brain barrier.

Embodiment 12. The method of one of embodiments 1 to 11, wherein the compound is unable to enter the central nervous system of a subject following administration to the subject outside of the central nervous system.

Embodiment 13. The method of one of embodiments 1 to 12, wherein the anti-CNS disease drug is capable of entering the central nervous system and the compound is incapable of entering the central nervous system following co-administration outside of the central nervous system of the subject.

Embodiment 14. The method of one of embodiments 1 to 13, wherein the compound does not bind calcineurin.

Embodiment 15. The method of one of embodiments 1 to 14, wherein the compound does not inhibit development and/or proliferation of T cells.

Embodiment 16. The method of one of embodiments 1 to 15, wherein the compound does not reduce the body's immune response.

Embodiment 17. The method of one of embodiments 1 to 16, comprising reduced side effects associated with the anti-CNS disease drug compared to absence of the compound.

Embodiment 18. The method of one of embodiments 1 to 17, comprising enhanced therapeutic effects of the anti-CNS disease drug compared to absence of the compound.

Embodiment 19. The method of one of embodiments 1 to 18, wherein the anti-CNS disease drug has the formula:

$A-L^1-R^1$;

wherein

A is an immunophilin-binding moiety;

$L^1$ is a bond or a covalent linker; and $R^1$ is a kinase inhibitor, a pseudokinase inhibitor, a GTPase inhibitor, a histone-modifying enzyme inhibitor, or a monovalent anti-viral agent.

Embodiment 20. The method of embodiment 19, wherein the immunophilin-binding moiety of the anti-CNS disease drug is a cyclophilin-binding moiety or an FKBP-binding moiety.

Embodiment 21. The method of one of embodiments 19 to 20, wherein the immunophilin-binding moiety of the anti-CNS disease drug is

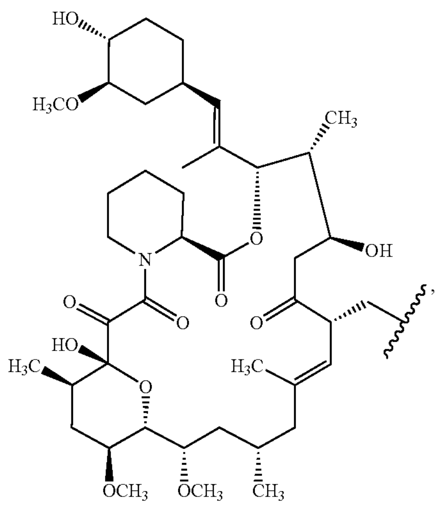

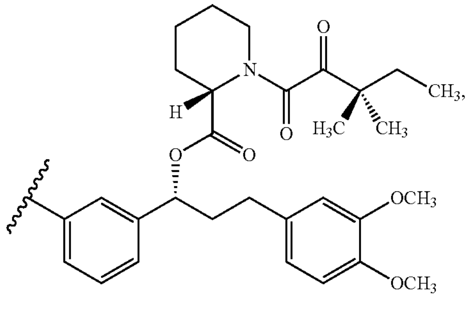

-continued
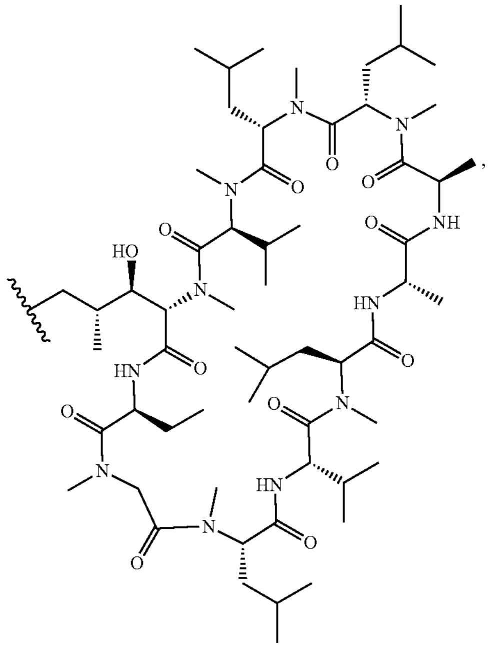
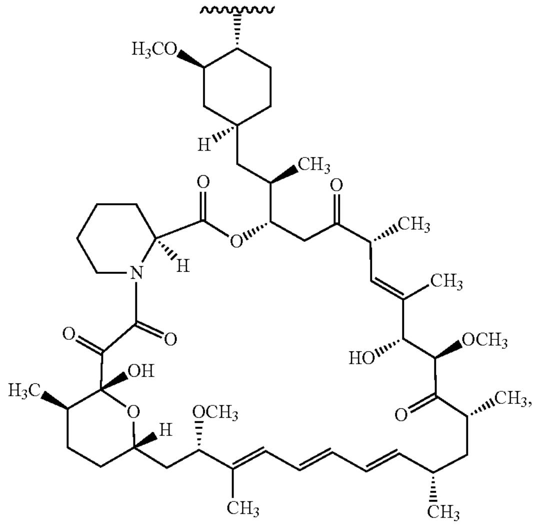 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
or
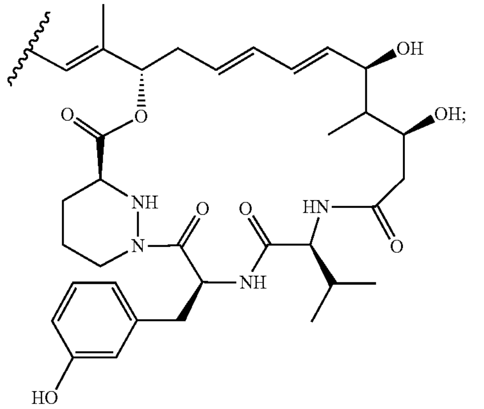
or an analog thereof.
Embodiment 22. The method of one of embodiments 19 to 20, wherein the immunophilin-binding moiety of the anti-CNS disease drug is
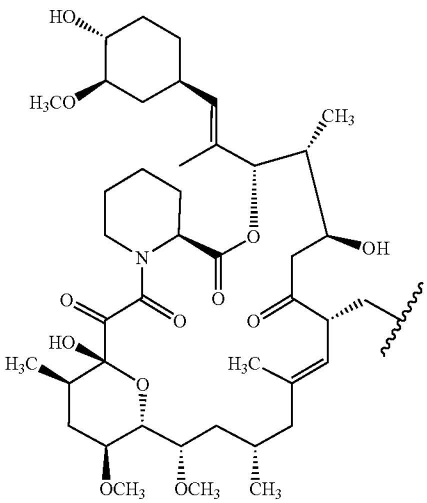
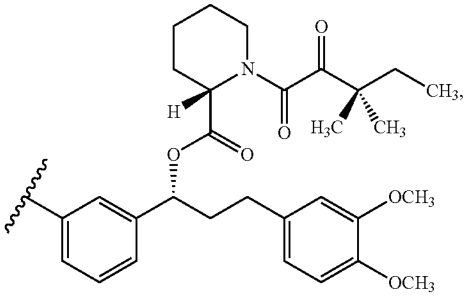
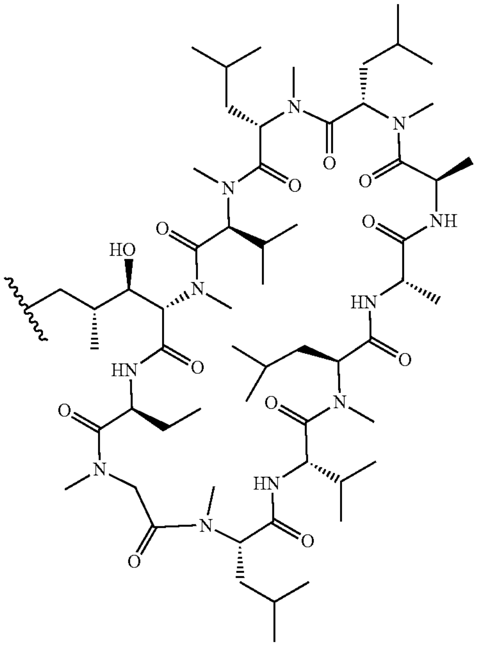
, or -continued

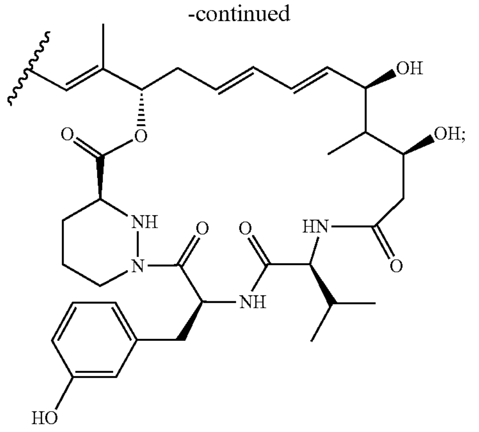

or an analog thereof.

Embodiment 23. The method of one of embodiments 19 to 21, wherein $L^1$ is $L^2$-$L^3$-$L^4$-$L^5$-$L^6$;

$L^2$ is connected directly to the moiety of an immunophilin-binding compound;

$L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^2$, $R^3$, $R^4$, $R^5$, and $R^6$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 24. The method of embodiment 23, wherein $L^3$, $L^4$, $L^5$, and $L^6$ are a bond.

Embodiment 25. The method of embodiment 23, wherein $L^2$ is a substituted or unsubstituted alkylene, substituted or unsubstituted heteroalkylene, substituted or unsubstituted cycloalkylene, or substituted or unsubstituted heterocycloalkylene;

$L^3$ is a bond, substituted or unsubstituted alkylene, substituted or unsubstituted heteroalkylene, substituted or unsubstituted cycloalkylene, or substituted or unsubstituted heterocycloalkylene;

$L^4$ is a bond, substituted or unsubstituted alkylene, or substituted or unsubstituted heteroalkylene;

$L^5$ is a bond; and $L^6$ is a bond.

Embodiment 26. The method of embodiment 23, wherein $L^2$ is an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^3$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or an unsubstituted 5 to 6 membered heterocycloalkylene, and $L^4$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^5$ is a bond; and $L^6$ is a bond.

Embodiment 27. The method of one of embodiments 19 to 21, wherein $L^1$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

Embodiment 28. The method of one of embodiments 19 to 21, wherein $L^1$ is

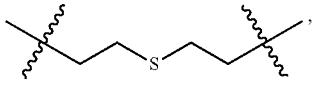,

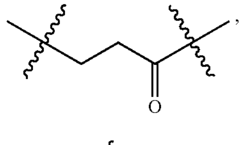,

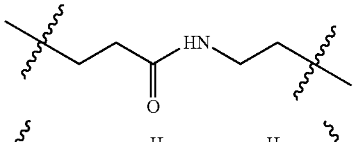,

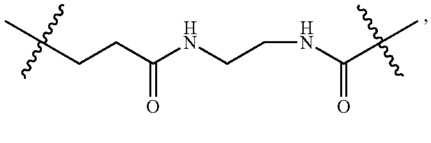,

-continued

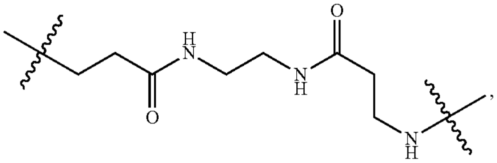

,

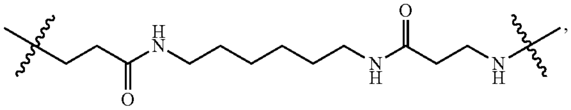

,

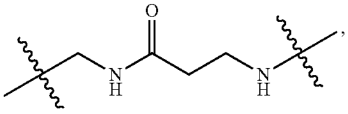

,

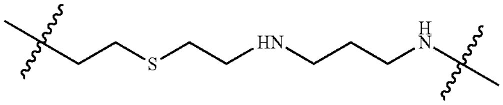

,

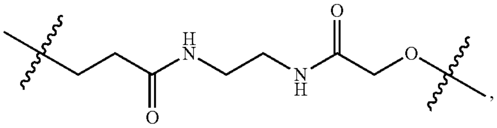

,

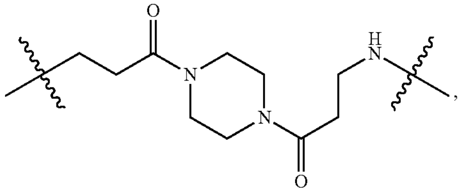

,

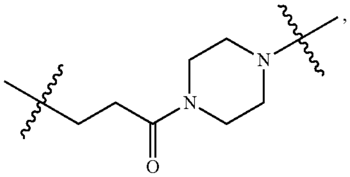

, or

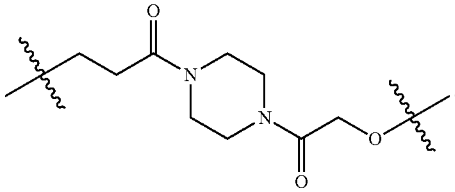

.

Embodiment 29. The method of one of embodiments 19 to 21, wherein $L^1$ is a bond.

Embodiment 30. The method of one of embodiments 19 to 21, wherein $L^1$ is a substituted or unsubstituted alkylene or substituted or unsubstituted heteroalkylene.

Embodiment 31. The method of one of embodiments 19 to 30, wherein $R^1$ is a monovalent kinase inhibitor.

Embodiment 32. The method of embodiment 31, wherein the kinase is not mTOR.

Embodiment 33. The method of one of embodiments 31 to 32, wherein the monovalent kinase inhibitor is a monovalent Src kinase inhibitor.

Embodiment 34. The method of one of embodiments 31 to 32, wherein the monovalent Src kinase inhibitor is a monovalent dasatinib or monovalent dasatinib derivative.

Embodiment 35. The method of embodiment 34, wherein the monovalent dasatinib derivative has the formula:

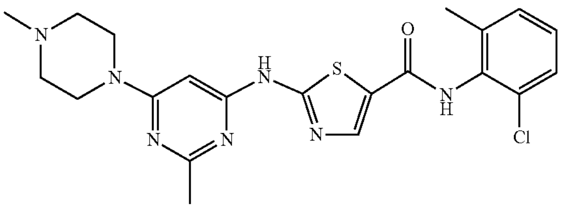

.

Embodiment 36. The method of one of embodiments 31 to 32, wherein the monovalent kinase inhibitor is a monovalent Raf inhibitor, VEGFR inhibitor, PDGFR inhibitor, or c-Kit inhibitor.

Embodiment 37. The method of embodiment 36, wherein the monovalent Raf inhibitor, VEGFR inhibitor, PDGFR inhibitor, or c-Kit inhibitor is a monovalent sorafenib or monovalent sorafenib derivative.

Embodiment 38. The method of embodiment 37, wherein the monovalent sorafenib derivative has the formula:

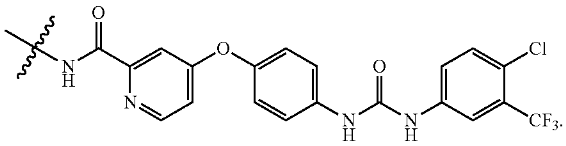 [SMILES: *NC(=O)c1cc(Oc2ccc(NC(=O)Nc3ccc(Cl)c(C(F)(F)F)c3)cc2)ccn1]

.

Embodiment 39. The method of one of embodiments 31 to 32, wherein the monovalent kinase inhibitor is a monovalent EGFR inhibitor.

Embodiment 40. The method of embodiment 39, wherein the monovalent EGFR inhibitor is a monovalent lapatinib, monovalent lapatinib derivative, monovalent erlotinib, monovalent erlotinib derivative, monovalent gefitinib, or monovalent gefitinib derivative.

Embodiment 41. The method of embodiment 40, wherein the monovalent EGFR inhibitor has the formula:

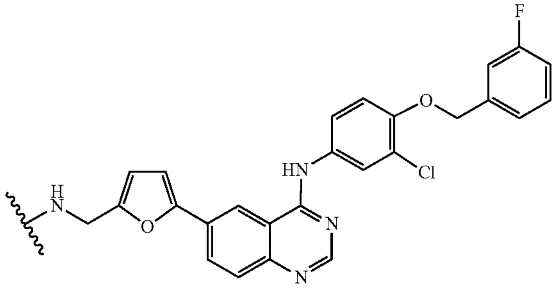

,

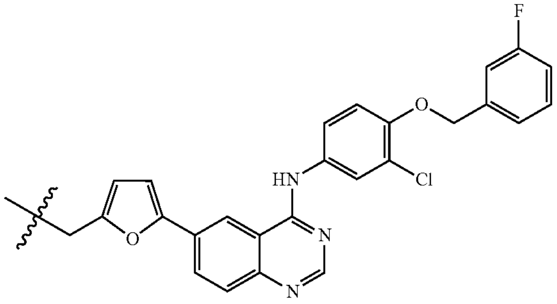

,

-continued

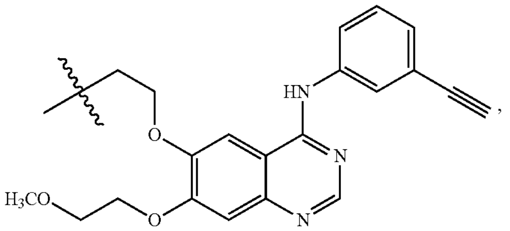

or

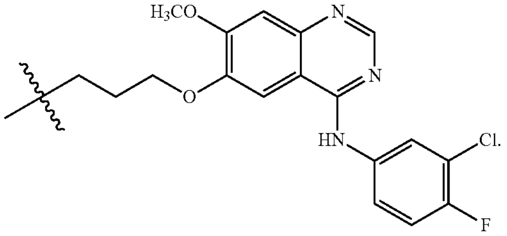

Embodiment 42. The method of one of embodiments 31 to 32, wherein the monovalent kinase inhibitor is a monovalent LRRK2 inhibitor.

Embodiment 43. The method of embodiment 42, wherein the monovalent LRRK2 inhibitor is a monovalent GNE-7915 or monovalent GNE-7915 derivative.

Embodiment 44. The method of embodiment 43, wherein the monovalent GNE-7915 derivative has the formula:

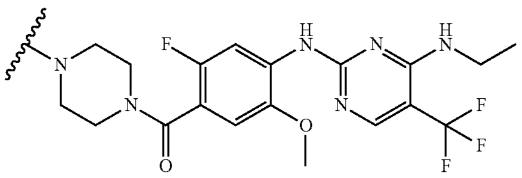

or

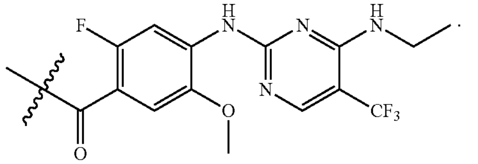

Embodiment 45. The method of one of embodiments 19 to 30, wherein $R^1$ is a monovalent KRAS inhibitor.

Embodiment 46. The method of embodiment 45, wherein the monovalent KRAS inhibitor is a monovalent KRAS G12C inhibitor or a monovalent KRAS M72C inhibitor.

Embodiment 47. The method of embodiment 26, wherein the monovalent KRAS inhibitor has the formula:

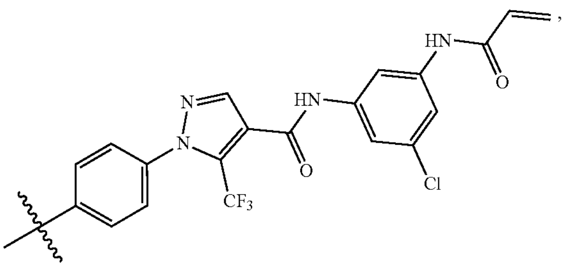

-continued

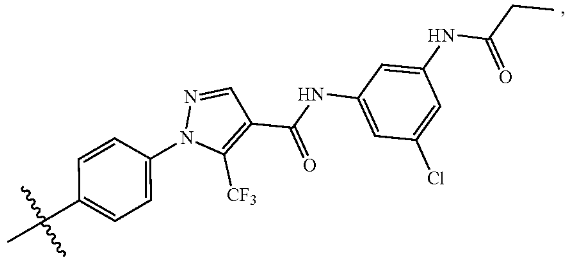

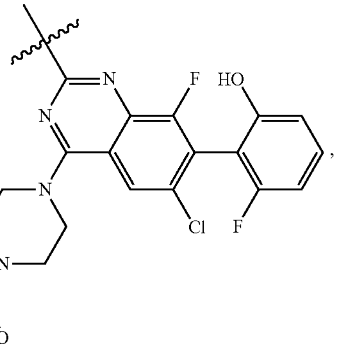

or

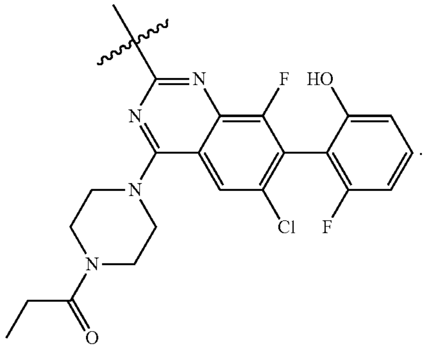

Embodiment 48. The method of one of embodiments 19 to 30, wherein $R^1$ is a monovalent MAP4K inhibitor.

Embodiment 49. The method of embodiment 48, wherein the monovalent MAP4K inhibitor is a monovalent HGK inhibitor.

Embodiment 50. The method of embodiment 49, wherein the monovalent HGK inhibitor has the formula:

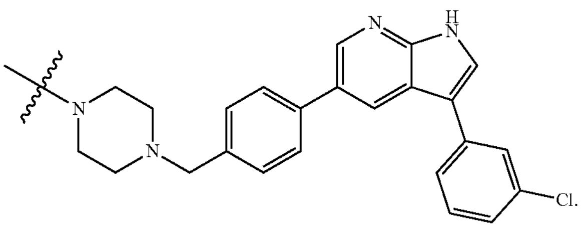 [SMILES: *N1CCN(Cc2ccc(-c3cnc4[nH]cc(-c5cccc(Cl)c5)c4c3)cc2)CC1]

Embodiment 51. The method of one of embodiments 19 to 30, wherein $R^1$ is a monovalent MAP3K inhibitor.

Embodiment 52. The method of embodiment 51, wherein the monovalent MAP3K inhibitor is a monovalent DLK inhibitor.

Embodiment 53. The method of embodiment 52, wherein the monovalent HGK inhibitor has the formula:

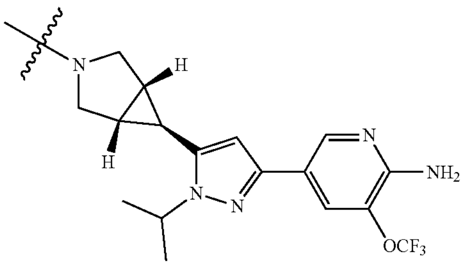

or

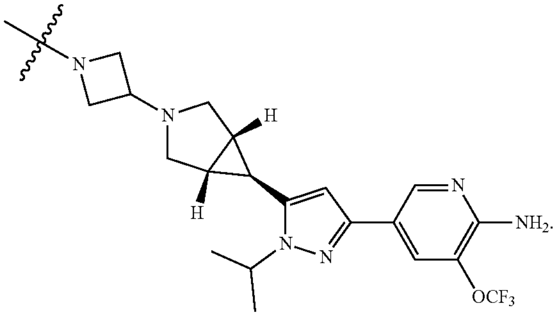

Embodiment 54. A compound having the formula: $A^{B}$-$L^{B1}$-$R^{B1}$, or a pharmaceutically acceptable salt thereof, wherein $A^{B}$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —NHC(O)$NR^{B1A}R^{B1B}$, —$N(O)_{mB1}$, —$NR^{B1A}R^{B1B}$, —C(O)$R^{B1C}$, —C(O)$OR^{B1C}$, —C(O)$NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B1C}$, —$NR^{B1A}OR^{B1C}$, —$NR^{B1A}C(NR^{B1C})R^{B1D}$, —$NR^{B1A}C(NR^{B1C})R^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$ and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently —F, —Cl, —Br, or —I;

when $L^{B1}$ is a bond, $R^{B1}$ is not H; and $A^{B}$ is not

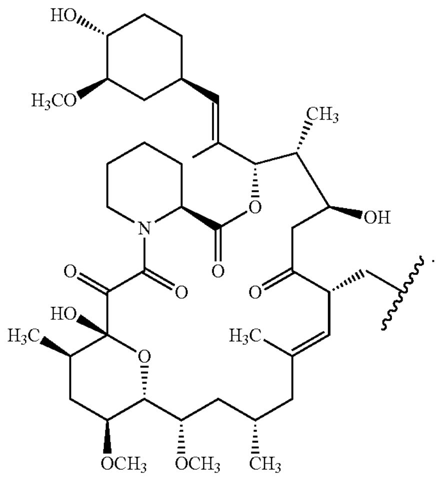 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

Embodiment 55. The compound of embodiment 54, wherein the immunophilin-binding moiety is

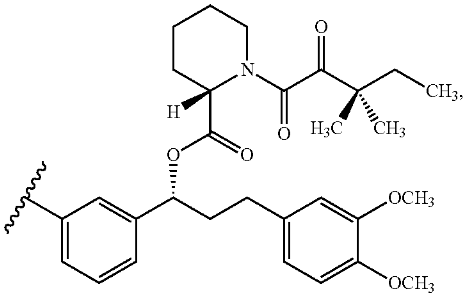

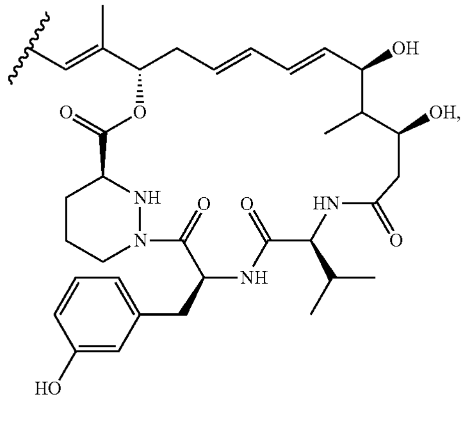

-continued

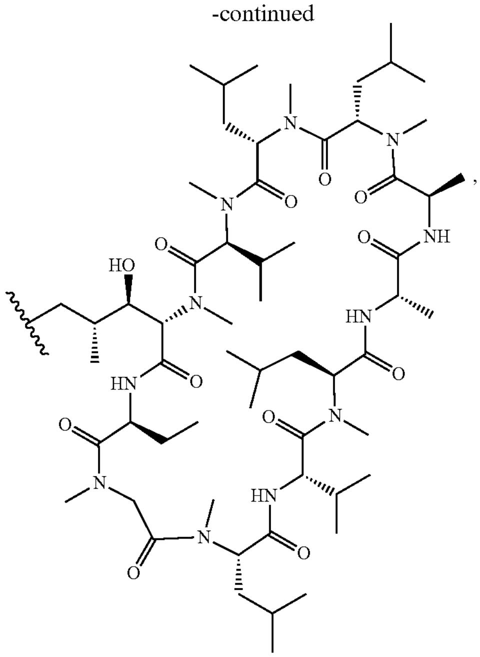

, or

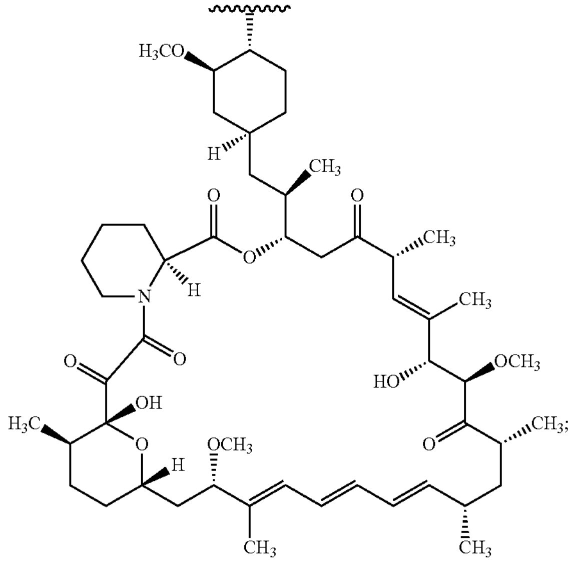 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

;

or an analog thereof.

Embodiment 56. The compound of one of embodiments 54 to 55, wherein $L^{B1}$ is $L^{B2}$-$L^{B3}$-$L^{B4}$.

$L^{B2}$ is a bond, —$S(O)_2$—, —$N(R^{B2})$—, —O—, —S—, —C(O)—, —$C(O)N(R^{B2})$—, —$N(R^{B2})C(O)$—, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 57. The compound of one of embodiments 54 to 56, wherein $L^{B1}$ is

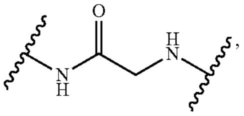
,
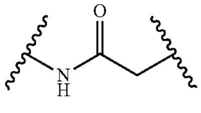
,
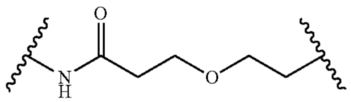
,
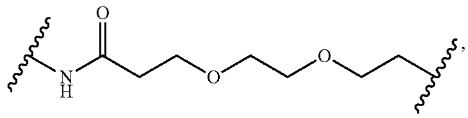
,
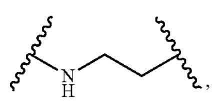
,
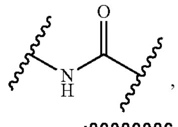
,
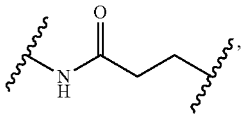
,
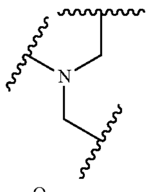
,
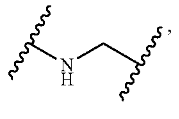
,
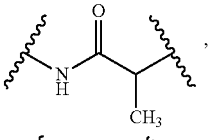
,
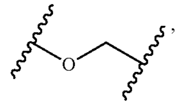
,
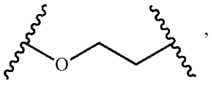
,
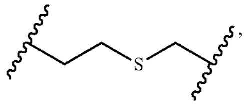
,
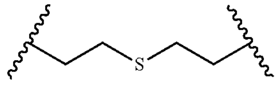
, -continued

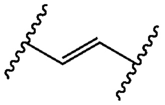, 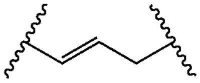,

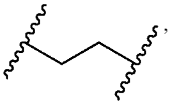, 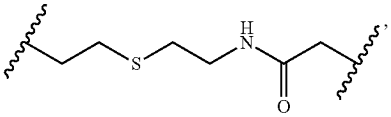,

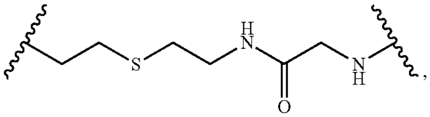,

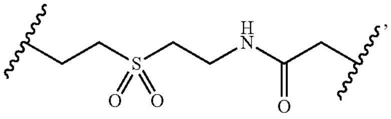, or

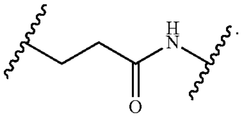.

Embodiment 58. The compound of one of embodiments 54 to 57, wherein $R^{B1}$ is halogen, $—NR^{B1A}R^{B1B}$, $—N_3$, $—SR^{B1D}$,

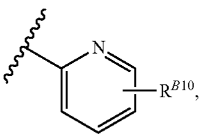, 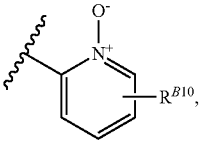,

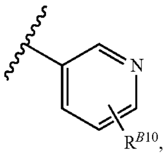, 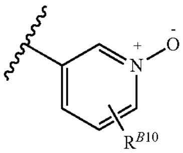,

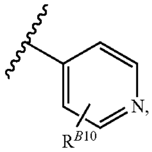, 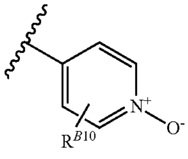,

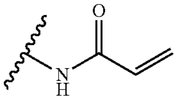, 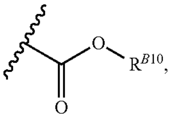, 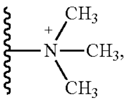,

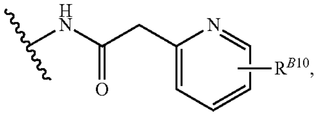,

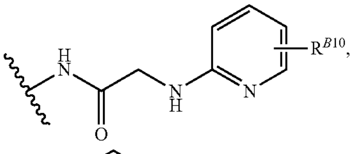,

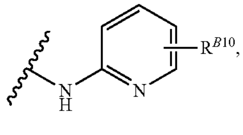, 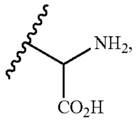

-continued

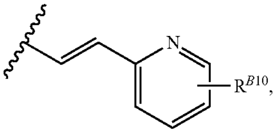, 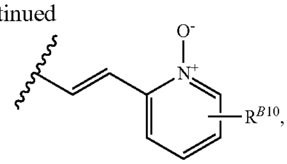,

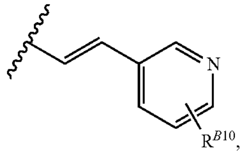, 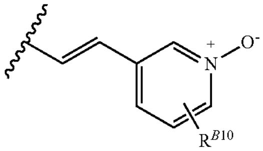,

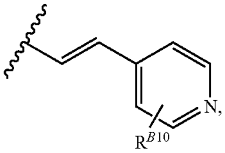 or 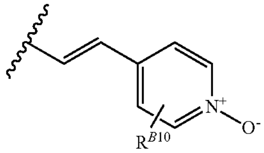;

$R^{B10}$ is hydrogen, halogen, $—CX^{B10}$, $—CHX^{B10}$, $—CH_2X^{B10}$, $—OCX^{B10}_3$, $—OCH_2X^{B1}$, $—OCHX^{B10}_2$, —CN, $—SO_{nB10}R^{B10D}$, $—SO_{vB10}NR^{B10A}R^{B10B}$, $—NH_1C(O)NR^{B10A}R^{B10}$, $—N(O)_{mB10}$, $—R^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—R^{B10A}C(NR^{B10C})R^{B10D}$, $—NR^{B10A}C(NR^{B10C})NR^{B10A}R^{B10B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment 59. The compound of one of embodiments 54 to 58, wherein $R^{B1}$ is —Cl, $—NH_2$, $—N_3$, —SH,

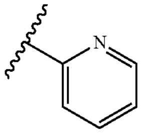, 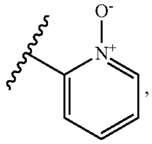,

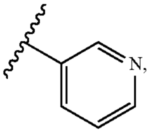, 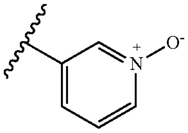,

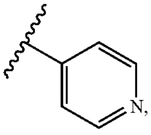, 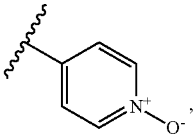,

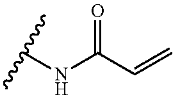, 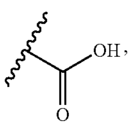,

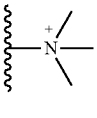, 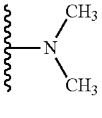, 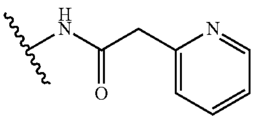,

-continued
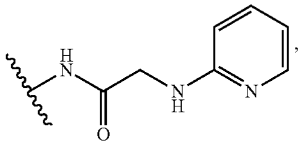 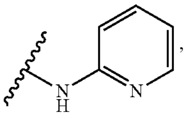
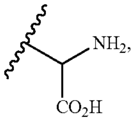
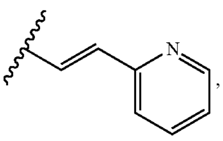 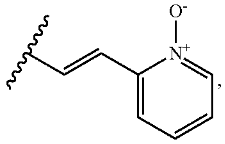
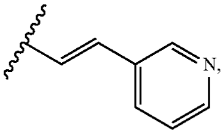 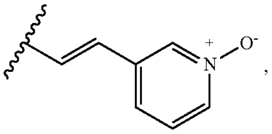
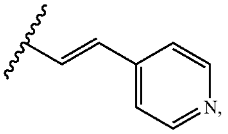 or 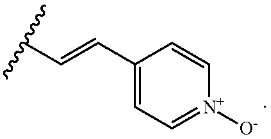
Embodiment 60. The compound of one of embodiments 54 to 59, wherein $L^{B1}$-$R^{B1}$ is
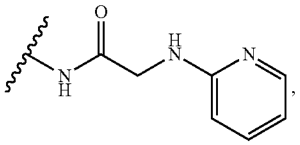 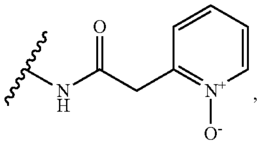
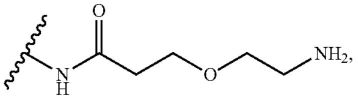
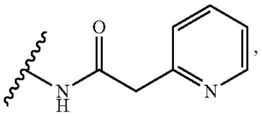
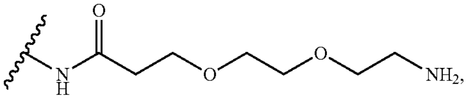
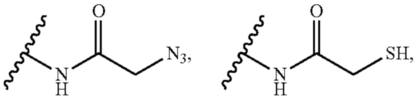
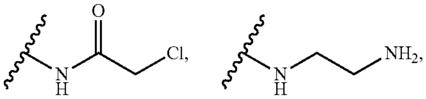
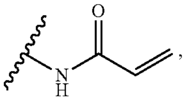 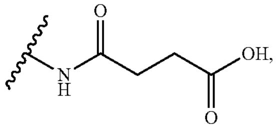
-continued
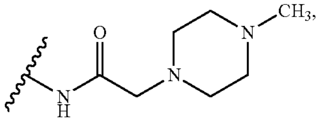 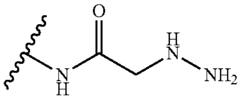
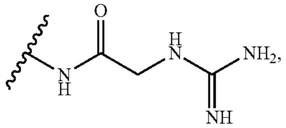 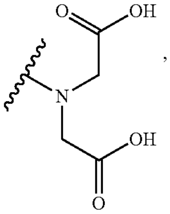
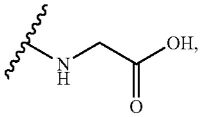 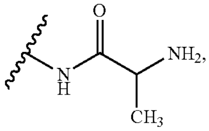
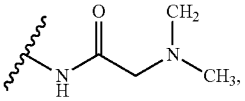 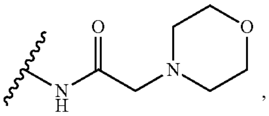
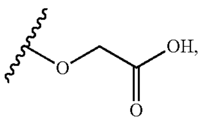 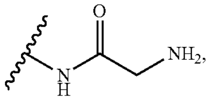
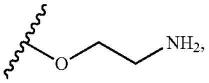 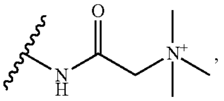
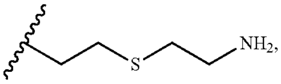 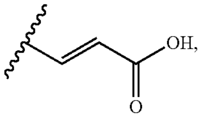
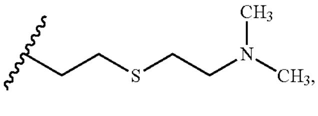 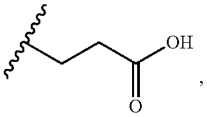
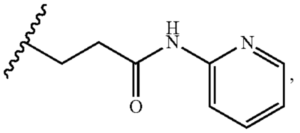
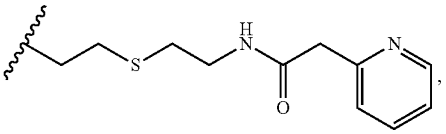
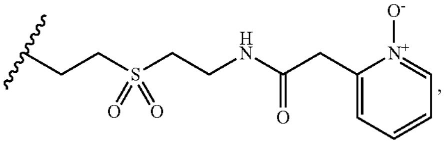
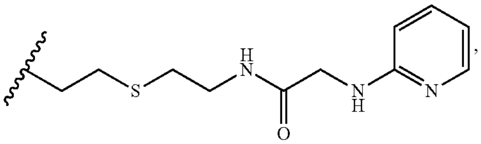
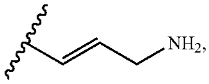 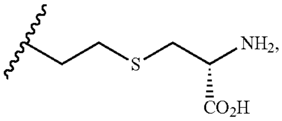

-continued
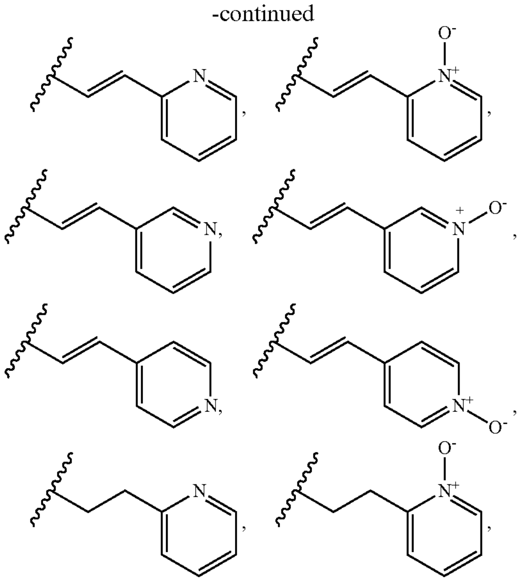
-continued
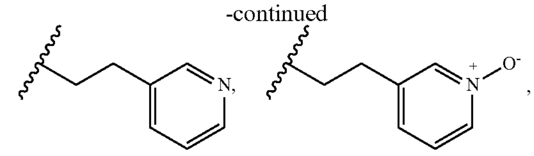
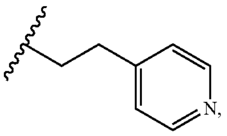
or
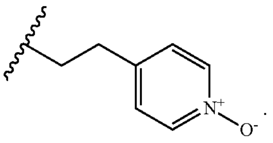
Embodiment 61. The compound of one of embodiments 54 to 60, wherein the compound is not
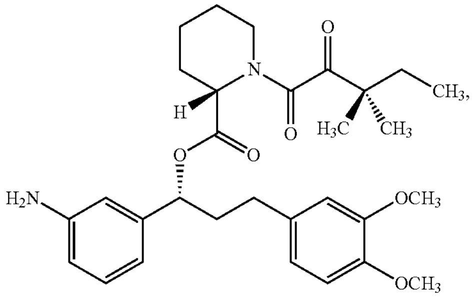
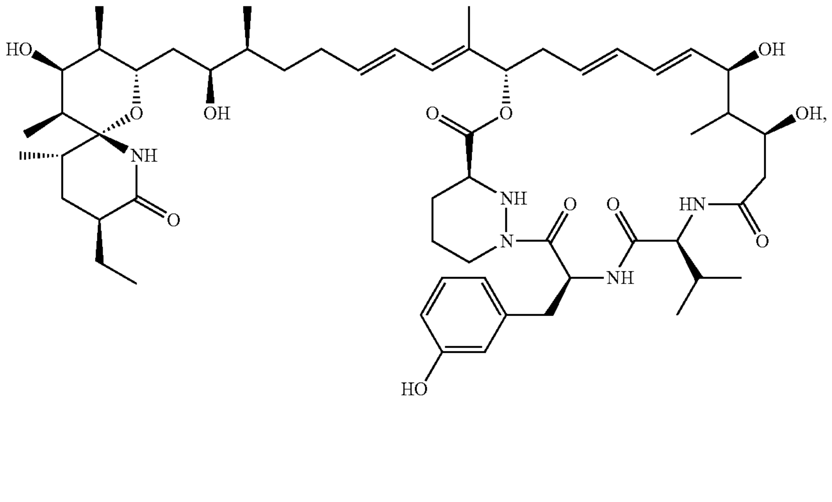

-continued

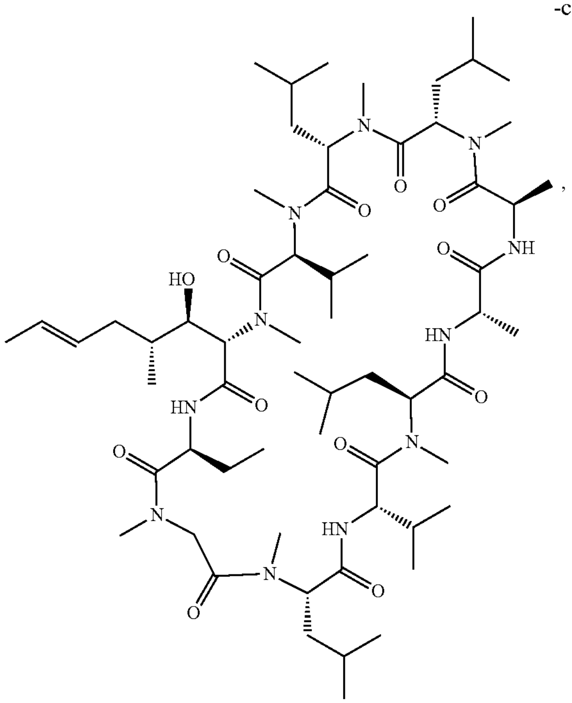

, or

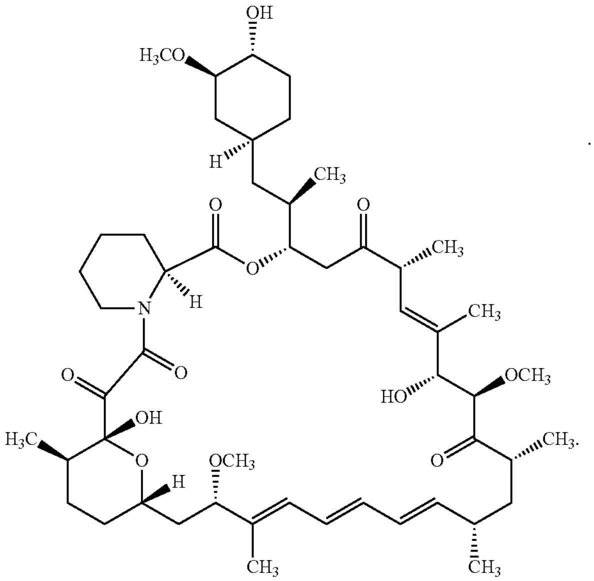

.

Embodiment 62. A compound having the formula: $A^{B}$-$L^{B1}$-$R^{B1}$, or a pharmaceutically acceptable salt thereof, wherein $A^{B}$ is an immunophilin-binding moiety having the formula

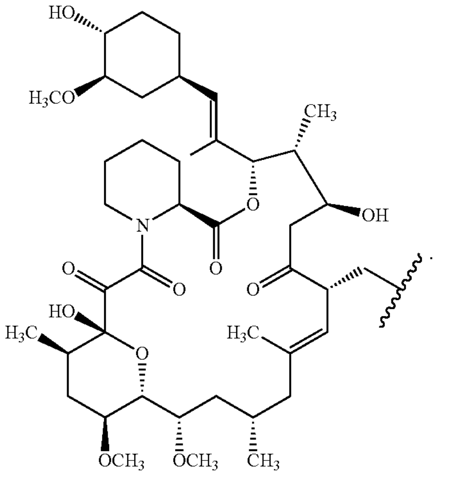 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof, $L^{B1}$-$R^{B1}$ is a polar moiety;

$L^{B1}$ is $L^{B2}$-$L^{B3}$-$L^{B4}$;

$L^{B2}$ is $S(O)_2$—, —N($R^{B2}$)—, —O—, —S—, —C(O)N($R^{B2}$)—, —N($R^{B2}$)C(O)—, —N($R^{B2}$)C(O)NH—, —NHC(O)N($R^{B2}$)—, —C(O)O—, —OC(O)—;

$L^{B3}$ is a bond, —$S(O)_2$—, —N($R^{B3}$)—, —O—, —S—, —C(O)—, —C(O)N($R^{B3}$)—, —N($R^{B3}$)C(O)—, —N($R^{B3}$)C(O)NH—, —NHC(O)N($R^{B3}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —N($R^{B4}$)—, —O—, —S—, —C(O)—, —C(O)N($R^{B4}$)—, —N($R^{B4}$)C(O)—, —N($R^{B4}$)C(O)NH—, —NHC(O)N($R^{B4}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —NHC(O)$NR^{B1A}R^{B1B}$, —$N(O)_{mB1}$, —$NR^{B1A}R^{B1B}$, —C(O)$R^{B1C}$, —C(O)$OR^{B1C}$, —C(O)$NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B15C}$, —$NR^{B1A}OR^{B1C}$, —$NR^{B1A}C(NR^{B1C})R^{B1D}$, —$NR^{B1A}C(NR^{B1C})R^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$ and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2; and $X^{B1}$ is independently —F, —Cl, —Br, or —I.

Embodiment 63. The compound of embodiment 62, wherein $L^{B1}$ is

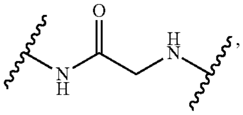,
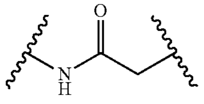,
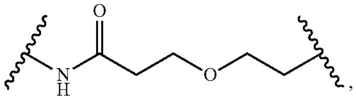,
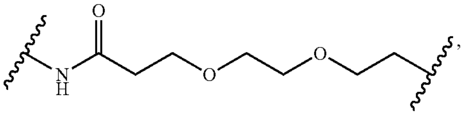,
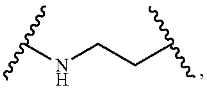,
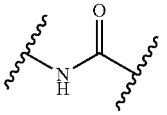,
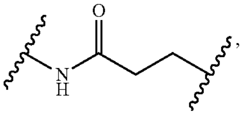,
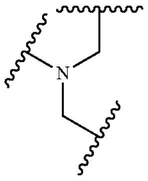,
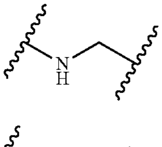,
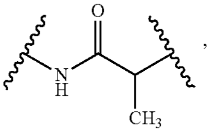,
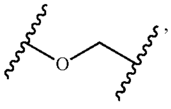 or
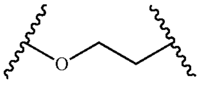.

Embodiment 64. The compound of one of embodiments 62 to 63, wherein $R^{B1}$ is halogen, —$NR^{B1A}R^{B1B}$, —$N_3$, —$SR^{B1D}$,

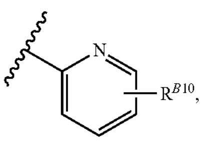,
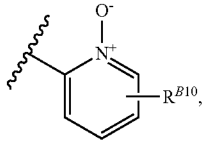,
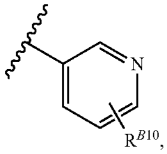,
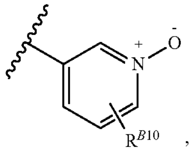,
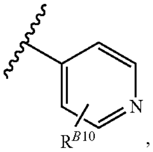,
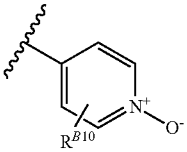,
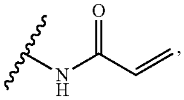,
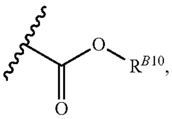,
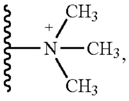,
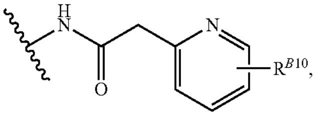,
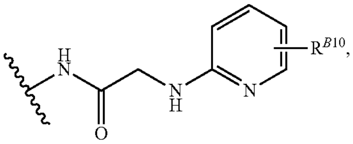,
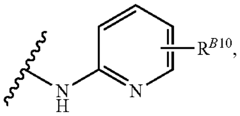,
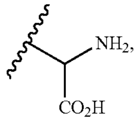,
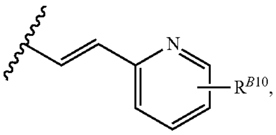,
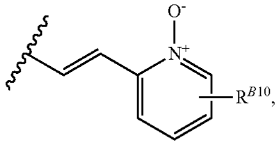,
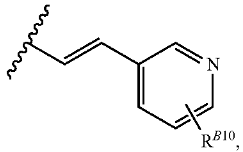,
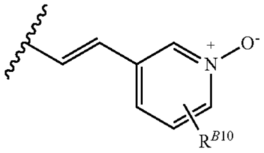,
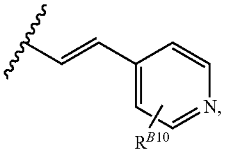, or
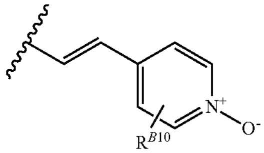;

$R^{B10}$ is hydrogen, halogen, —$CX^{B10}_3$, —$CHX^{B10}_2$, —$CH_2X^{B10}$, —$OCX^{B10}_3$, —$OCH_2X^{B10}$, —$OCHX^{B10}_2$, —CN, —$SO_{nB10}R^{B10D}$, —$SO_{vB10}NR^{B10A}R^{B10B}$, —NHC(O)$NR^{B10A}R^{B10B}$, —$N(O)_{mB10}$, —$NR^{B10A}R^{B10B}$, —C(O)$R^{B10C}$, —C(O)$OR^{B10C}$, —C(O)$NR^{B10A}R^{B10B}$, —$OR^{B10D}$, —$NR^{B10A}SO_2R^{B10D}$, —$NR^{B10A}C(O)R^{B10C}$, —$NR^{B10A}C(O)OR^{B10C}$, —$NR^{B10A}OR^{B10C}$, —$R^{B10A}C(NR^{B10C})R^{B10D}$, —$NR^{B10A}C(NR^{B10C})NR^{B10A}R^{B10B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment 65. The compound of one of embodiments 62 to 64, wherein $R^{B1}$ is —Cl, —$NH_2$, —$N_3$, —SH,

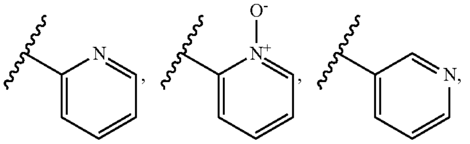

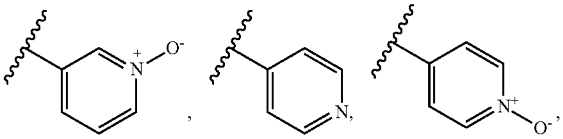

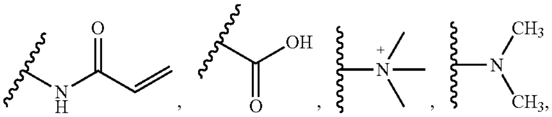

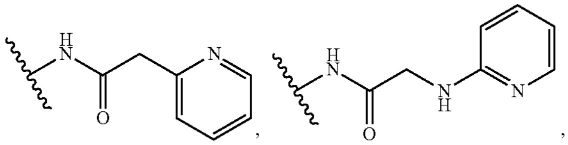

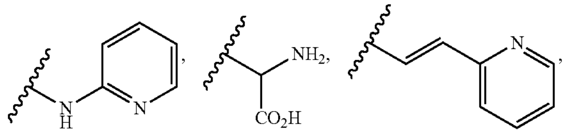

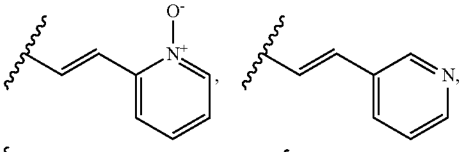

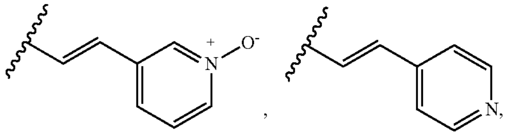 or

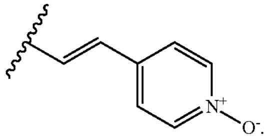

Embodiment 66. The compound of one of embodiments 62 to 65, wherein $L^{B1}$-$R^{B1}$ is

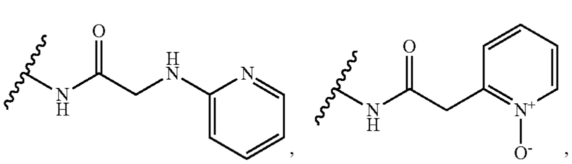

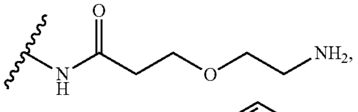

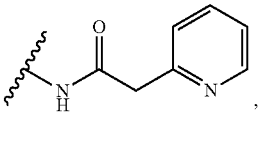

-continued

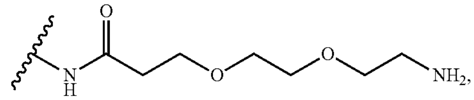

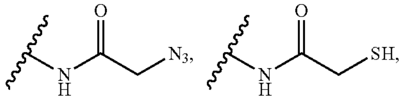

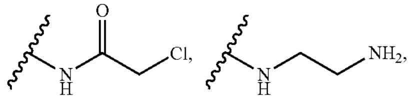

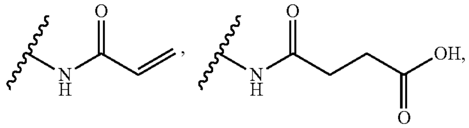

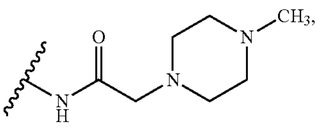

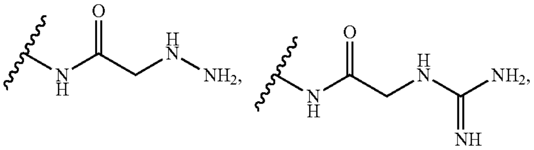

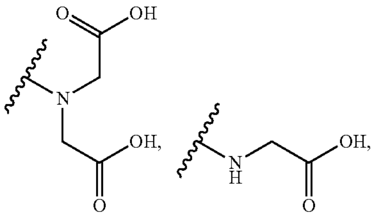

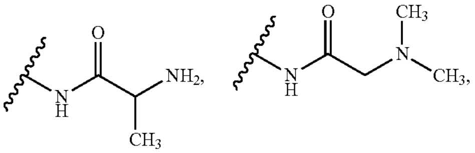

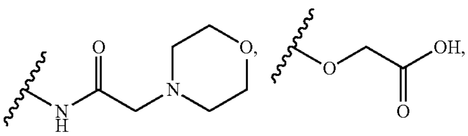

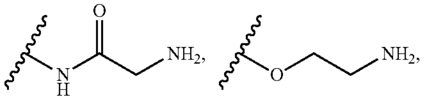 or

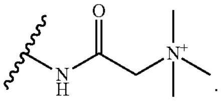

Embodiment 67. A compound having the formula:

$A^B$-$L^{B1}$-$R^{B1}$, or a pharmaceutically acceptable salt thereof, wherein $A^B$ is an immunophilin-binding moiety having the formula

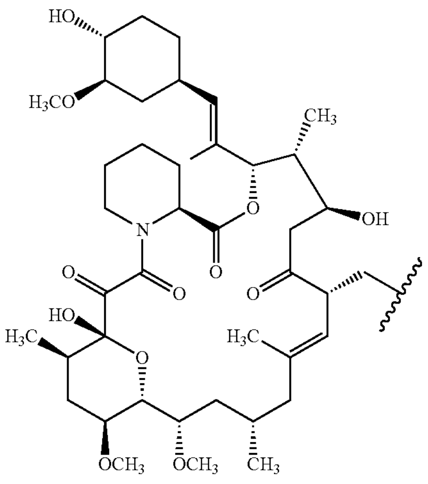, or an analog thereof, $L^{B1}$-$R^{B1}$ is a polar moiety;

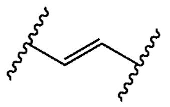 or 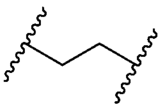;

and $R^{B1}$ is substituted or unsubstituted heteroaryl.

Embodiment 68. The compound of embodiment 67, wherein $R^{B1}$ is substituted or unsubstituted pyridyl.

Embodiment 69. A compound having the formula:

$A^{B}$-$L^{B1}$-$R^{B1}$, or a pharmaceutically acceptable salt thereof, wherein $A^{B}$ is an immunophilin-binding moiety having the formula

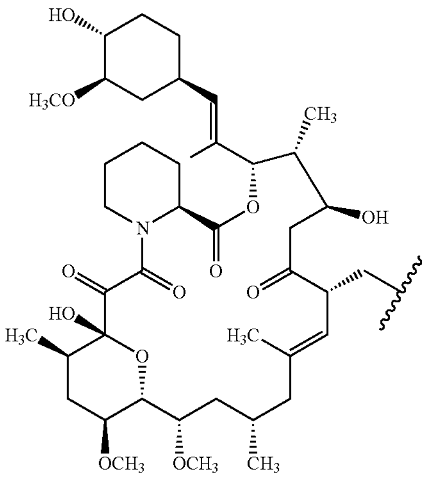, or an analog thereof, $L^{B1}$-$R^{B1}$ is a polar moiety;

$L^{B1}$ is

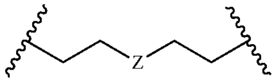;

Z is —S— or —$SO_2$—;

$R^{B1}$ is —$NR^{B1A}R^{B1B}$ or —$NHC(O)CH_2R^{B1C}$;

$R^{B1A}$ and $R^{B1B}$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{B1C}$ is substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 70. The compound of embodiment 69, wherein $R^{B1A}$, $R^{B1B}$, or $R^{B1C}$ are independently substituted or unsubstituted pyridyl.

Embodiment 71. The compound of one of embodiments 54 to 70, wherein the immunophilin-binding moiety is a cyclophilin-binding moiety or an FKBP-binding moiety.

Embodiment 72. A pharmaceutical composition comprising a pharmaceutically acceptable excipient and a compound of one of embodiments 54 to 71.

Embodiment 73. The pharmaceutical composition of embodiment 72, further comprising an anti-CNS disease drug.

EXAMPLES

Example 1: Brain-Specific Inhibition of mTOR to Mitigate Systemic Toxicity

We describe a novel method for inhibition of mTOR activity specific to the brain. mTOR is a protein kinase that plays a central role in regulating cell growth and proliferation, and is estimated to be overactivated in 30% of cancers. Therapeutic agents targeting mTOR have been widely pursued as potential therapies for cancer, as well as neurological disorders such as epilepsy. For example, a third-generation mTOR inhibitor, RapaLink-1, has been shown to be efficacious in driving glioblastoma regression in animal models (1). However, the success of these therapies is often hampered by insufficient amount of drug that can cross the blood-brain barrier. Even when this condition is met, the application of these drugs is confounded by the toxicity caused by system-wide inhibition of mTOR (e.g., immunosuppression, hyperglycemia, mucocytis in particular is a class specific effect of all mTOR inhibitors). Our disclosure provides a distinct solution to this problem through the combination of 1) a brain-permeable mTOR inhibitor and 2) a brain-impermeable ligand of another protein, FKBP (referred to as "blocker" hereafter). This "binary pharmacology" is enabled by the unique mechanism of action of RapaLink-1 and rapamycin that they require an auxiliary protein, FKBP, to exert its function. It represents a novel therapeutic modality to focus the pharmacological effects of RapaLink-1/rapamycin in the brain while minimizing systemic exposure.

Our invention is generally applicable in areas where brain-specific inhibition of mTOR can lead to a therapeutic advantage. A few examples include glioblastoma, epilepsy, tuberous sclerosis (TSC), and alcohol use disorders.

Glioblastoma is a particularly deadly type of cancer with poor prognosis, with more than 10,000 diagnoses each year in the US alone. Glioblastoma tumors are difficult to remove surgically and lack effective treatment options. Our invention may be directly applied to develop a new drug for the treatment of glioblastoma with high efficacy and low toxicity.

Epilepsy is the fourth most common neurological disorder—2015 statistics from the CDC show 1.2% of the US population (3.4 million) have active epilepsy. Despite the abundance of drugs approved for epilepsy, most current drugs are anticonvulsants and work by suppressing seizures as symptomatic therapy but do not address the rooting cause. One-third of patients do not respond to these drugs and are defined as "medically intractable." Treatment of epilepsy by mTOR inhibitors has shown promises as a new angle to tackle this disease.

Tuberous Sclerosis (TSC) affects as many as 25,000 to 40,000 individuals in the United States and about 1 to 2 million individuals worldwide, with an estimated prevalence of one in 6,000 newborns (according to NIH). It is a genetic disease that causes benign tumor to grow in the brain and results in seizures, behavioral problems, developmental delay, etc. mTOR inhibitors directly address the mechanistic cause of the disease (overactive mTOR), and everolimus (a rapamycin analog) has been approved as treatment for this disease. Our invention can be similarly adopted in this disease area to provide a safe and effective TSC drug.

Alcohol Use Disorder (AUD) affects approximately 15% of the world population and imposes significant medical and economical burdens. Recent research has shown the important role of mTOR signaling in the body's regulation of drinking behavior, and suggested pharmacological inhibition as a promising strategy to treat AUD. Our invention can be similarly adopted in this disease area to provide a safe and effective AUD drug.

TABLE 1 mTOR inhibition is an attractive strategy for treating many brain-related diseases (e.g., glioblastoma, epilepsy, tuberous sclerosis, alcohol addiction), yet systemic mTOR inhibition is known to cause multiple toxic side effects (e.g., hyperglycemia, immune suppression mucositis).

| Drug/ Candidate | Diphen-hydramine | GNE-7915 | GSK-2656157 | Rapamycin |
|---|---|---|---|---|
| Target | $H_1$ receptor | LRRK2 | PERK | mTOR |
| Application | Allergy | Parkinson's Disease | Parkinson's Disease | Glioblastoma, epilepsy, tuberous sclerosis, alcohol addiction |
| Adverse effects | CNS effects (drowsiness) | Lung toxicity | Pancreas toxicity | Hyperglycemia, immune suppression, mucositis |

Chronic mTOR inhibition and growth suppression in children. While mTOR inhibitors could be used in childhood diseases, this therapy has to be of limited duration, as chronic inhibition of mTOR is associated with growth failure (2,3). The fact that chronic use of mTOR inhibitors leads to short stature limits application of these agents in children who might need these agents chronically. Examples include children with tuberous sclerosis, neurofibromatosis, or similar disorders, where long-term delivery of mTOR inhibitors will likely increase IQ and behavior, but cannot be delivered chronically due to growth failure. Our ability to deliver mTOR inhibitors to the brain, while sparing exposure to the periphery, should allow use of these inhibitors chronically, in a broad range of developmental disorders in which chronic mTOR activation is associated with disease burden.

Unlike traditional methods that improve brain drug uptake by modifying the drug itself (e.g., increasing hydrophobicity, synthesizing prodrugs), our approach features a new therapeutic modality by the combination of a known brain-permeable mTOR inhibitor (RapaLink-1/rapamycin) with a brain-impermeable compound with no therapeutic effects itself. In doing so, we not only increase the distribution of the drug in the brain, but also eliminate its undesired effects in peripheral tissues. In addition, there is no need to change the nature of the "active component"—rapamycin is an approved drug and all the previously characterized molecular mechanism of actions will continue to apply.

Products developed with this technology will have augmented therapeutic effects in brain where the disease is but minimal systemic toxicity. Existing technologies (drugs) do not address this problem and system-wide mTOR inhibition is often associated with side effects.

Use of a combination of a brain-targeted drug and non-brain permeable auxiliary drug is precedented, but not to inhibit mTOR (Table 2).

TABLE 2

Known combinations of a blood-brain barrier (BBB)-permeable and a BBB-impermeable agent.

| Sinemet [Merck] (Levodopa + Carbidopa) | Duavee [Pfizer] (Estrone sulfate + Bazadoxifene) |
|---|---|
| Levodopa: BBB-permeable, precursor to dopamine (converted by dopamine decarboxylase) | Estrone sulfate: BBB-permeable, estrogen receptor agonist |
| Carbidopa: BBB-impermeable, dopamine decarboxylase inhibitor | Bazadoxifene: BBB-impermeable, estrogen receptor modulator |

We have designed and synthesized several "blocker" molecules and shown that they can potently bind FKBP and thus render RapaLink-1 ineffective in cell culture. Four of these molecules have been tested in mice in combination with RapaLink-1; mice treated with these combination therapies showed augmented inhibition of mTOR in the brain (compared to RapaLink-1 alone) but no detectable change in mTOR signaling in peripheral tissues (skeletal muscle).

Example 2: Building a Focused, Non-BBB Permeable FKBP Ligand Library

A focused, non-BBB permeable FKBP ligand library was generated using the following workflow: (1) compound synthesis; (2) FKBP12 binding assay; (3) compound screen by western blot (S6-phosphorylation); and (4) in vivo brain/periphery distribution in mouse model.

TABLE 3
| Compound structures of SLF-focused library. | |
|---|---|
| 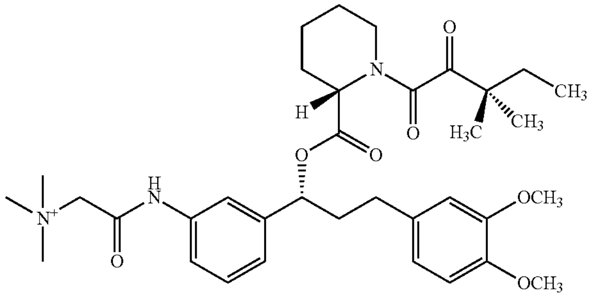 | ZZY01-025 |
| 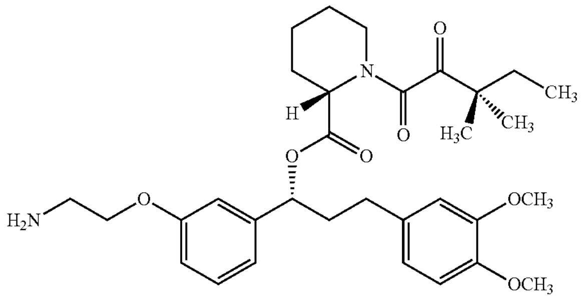 | ZZY01-038 |
| 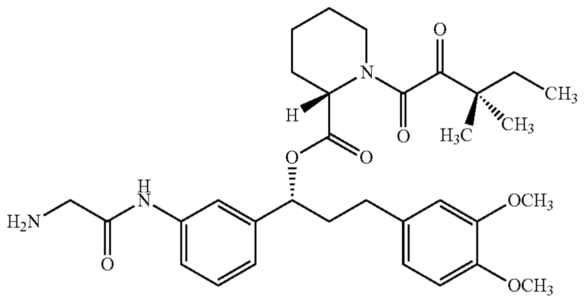 | ZZY01-040 |
| 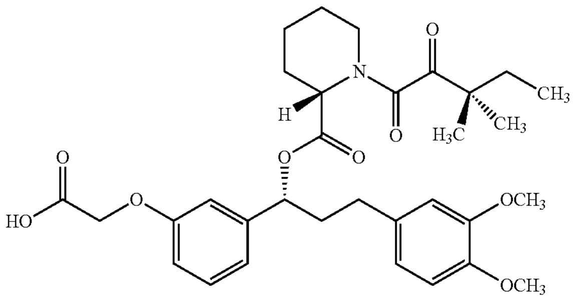 | ZZY01-041 |
| 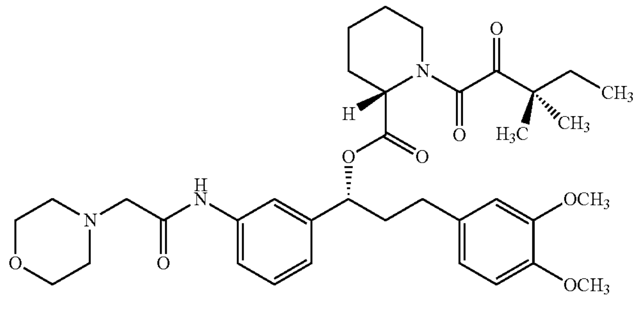 | ZZY01-043 |

TABLE 3-continued
| Compound structures of SLF-focused library. |
| --- |
| ZZY01-044 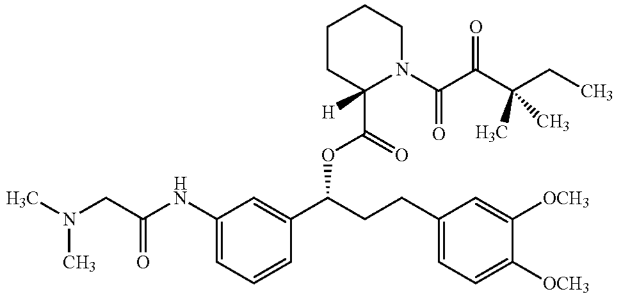 |
| ZZY01-059 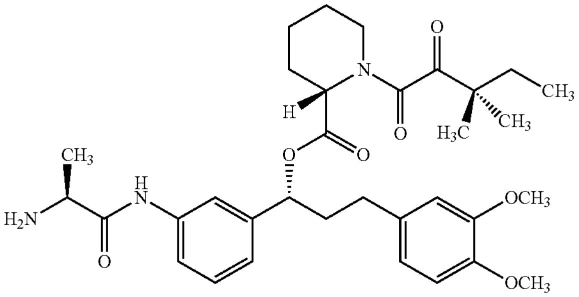 |
| ZZY01-060A 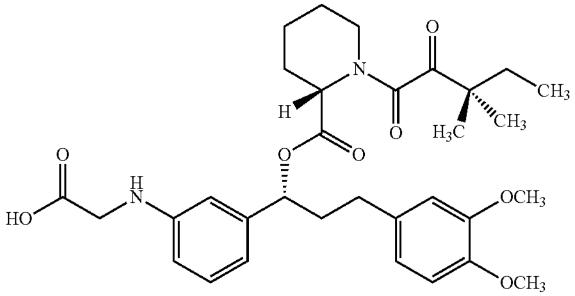 |
| ZZY01-060B 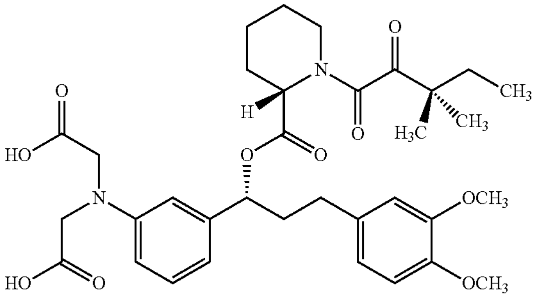 |
| ZZY01-065 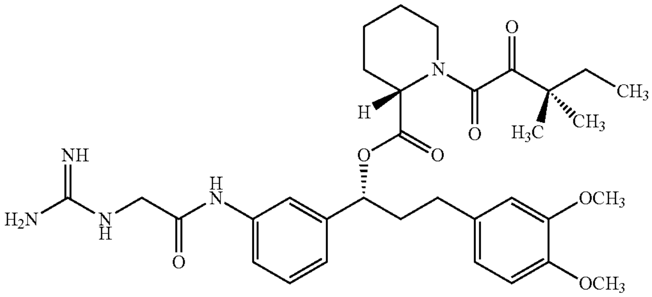 |

TABLE 3-continued
| Compound structures of SLF-focused library. |
| --- |
ZZY01-070
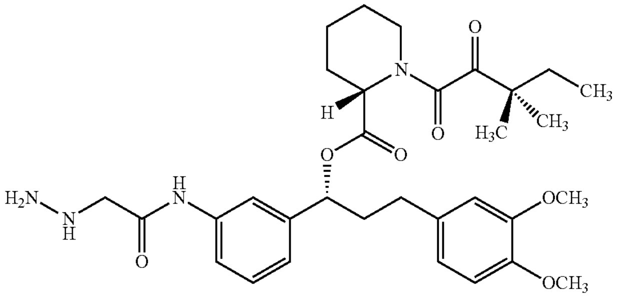
ZZY01-072
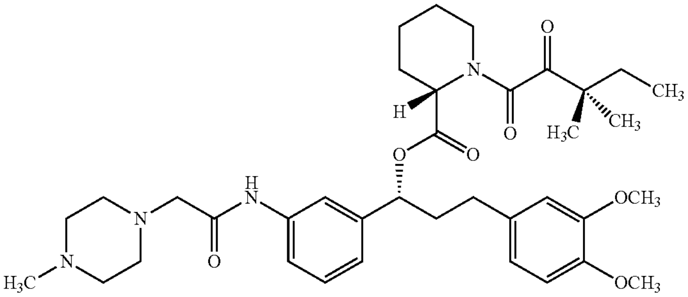
ZZY01-083
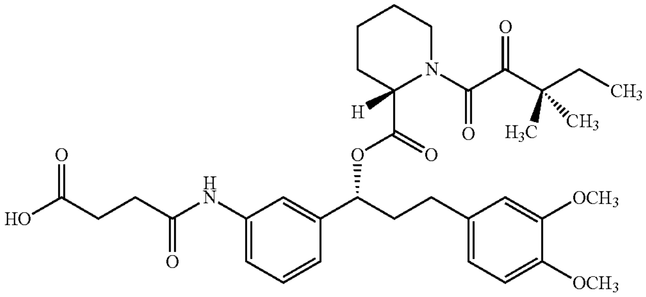
ZZY02-014
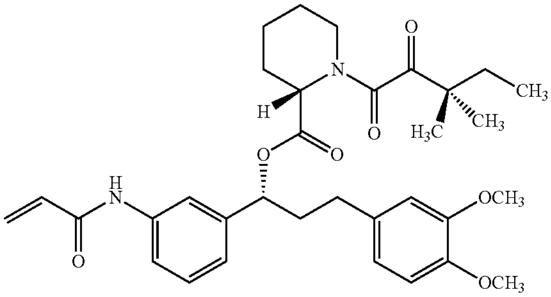
ZZY02-032
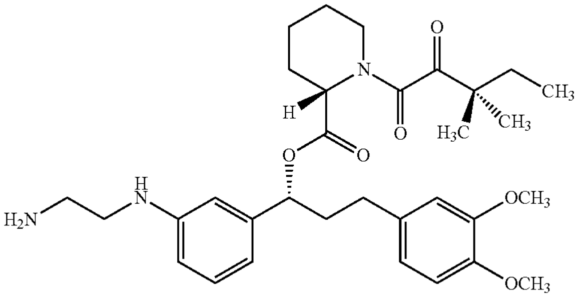

TABLE 3-continued
| Compound structures of SLF-focused library. |
| --- |
ZZY02-033
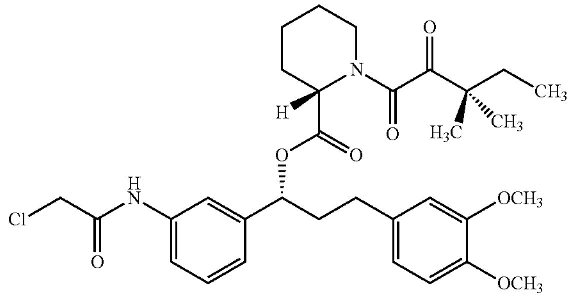
ZZY02-055
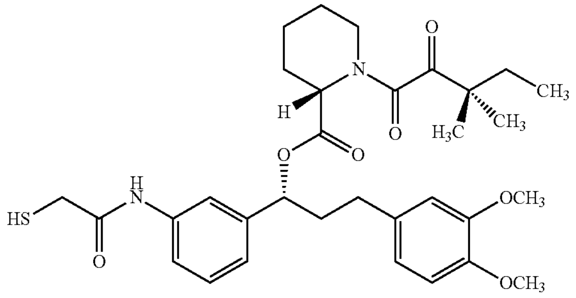
ZZY02-096
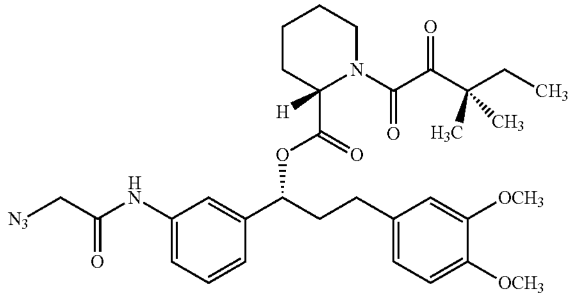
ZZY03-077
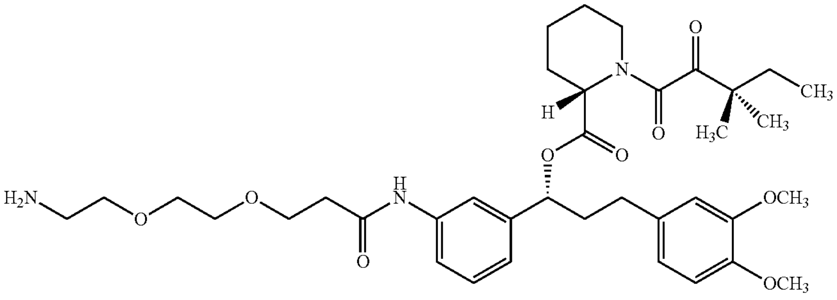
ZZY03-083
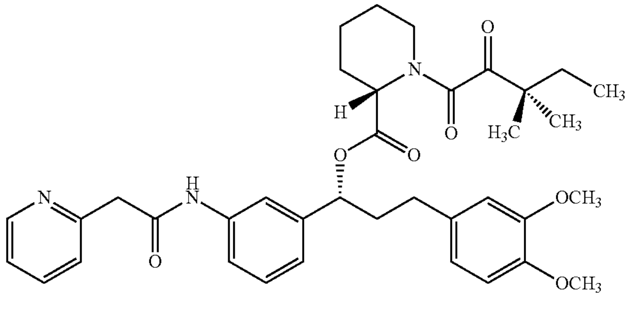

TABLE 3-continued
| Compound structures of SLF-focused library. | |
|---|---|
| 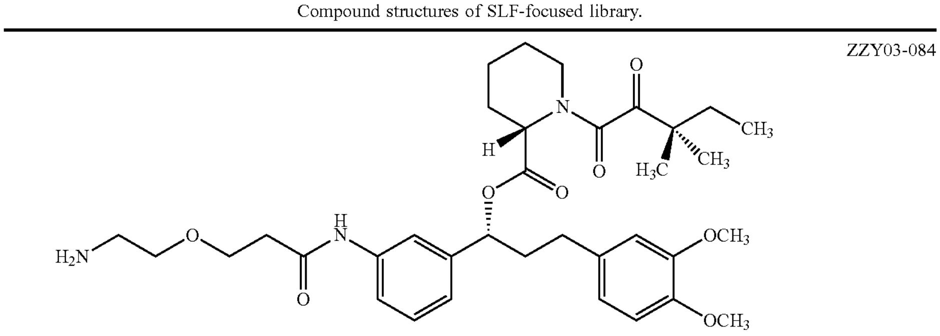 | ZZY03-084 |
| 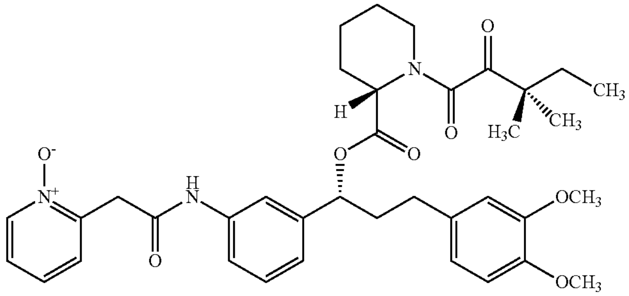 | ZZY03-087 |
| 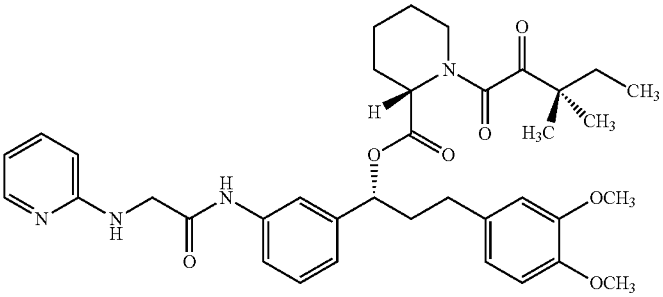 | ZZY03-091 |
TABLE 4
| Compound structures of FK506-focused library. | |
|---|---|
| 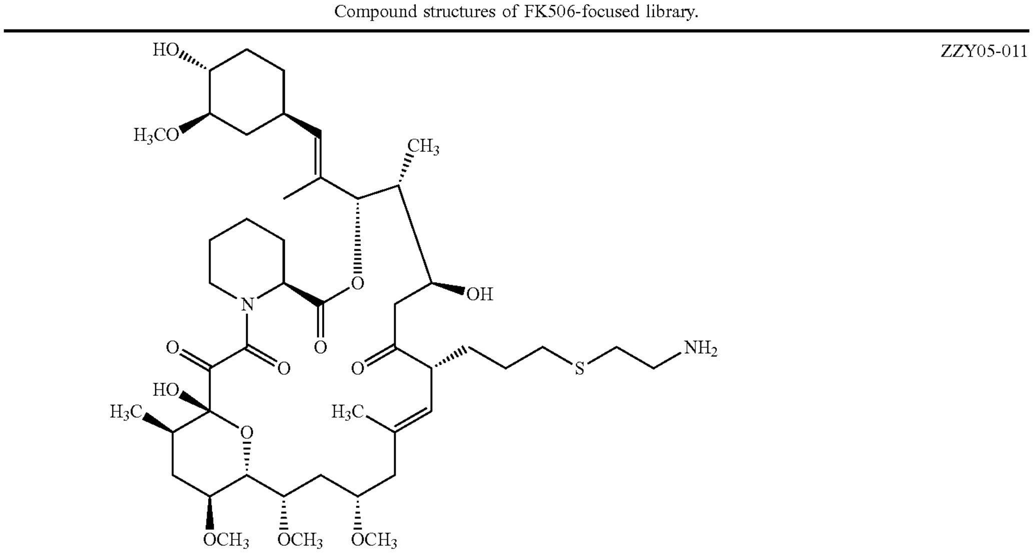 | ZZY05-011 |

TABLE 4-continued
Compound structures of FK506-focused library.
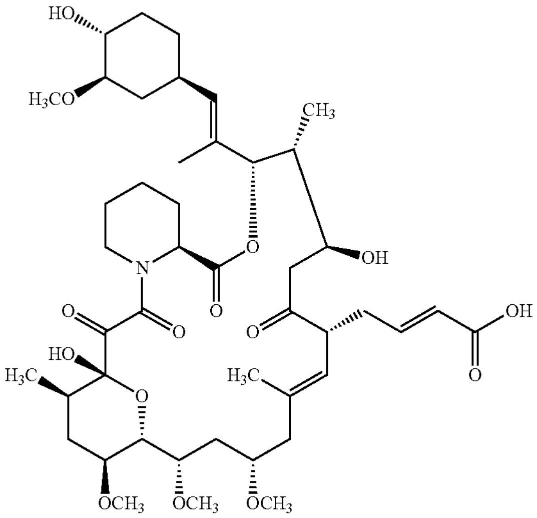 [SMILES: CO[C@H]1C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-012
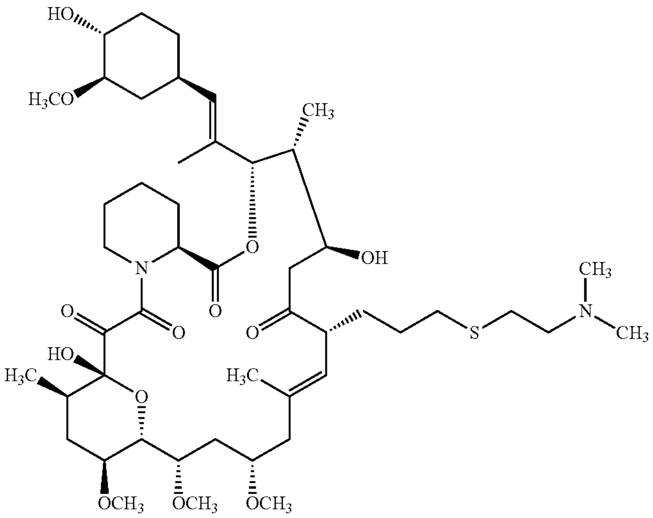
ZZY05-013
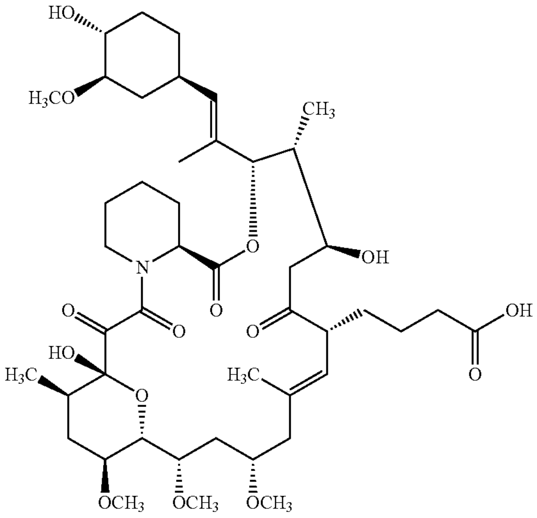
ZZY05-020

TABLE 4-continued
Compound structures of FK506-focused library.
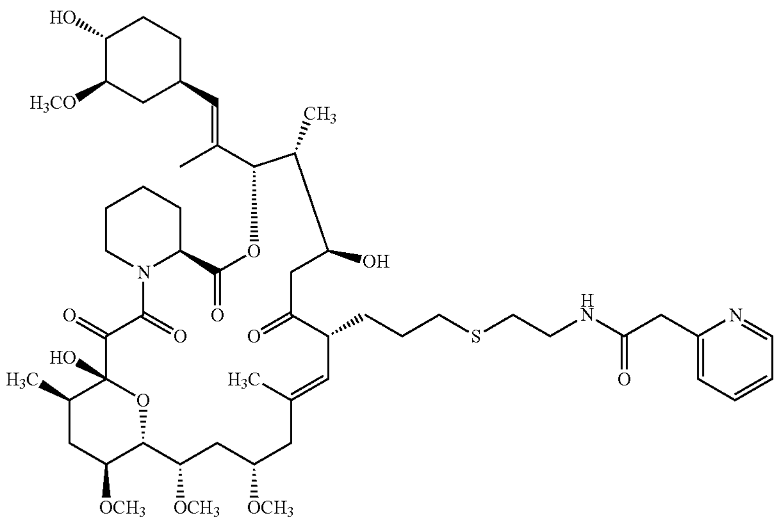 [SMILES: CO[C@H]1C/C(C)=C/[C@@H](CCCSCCNC(=O)Cc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-026
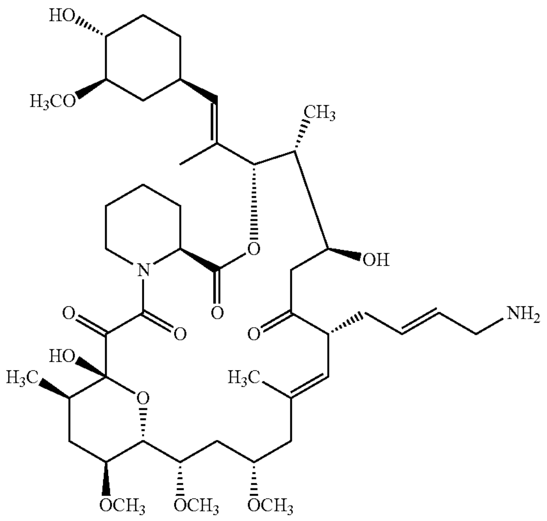 [SMILES: CO[C@H]1C/C(C)=C/[C@@H](C/C=C/CN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-027
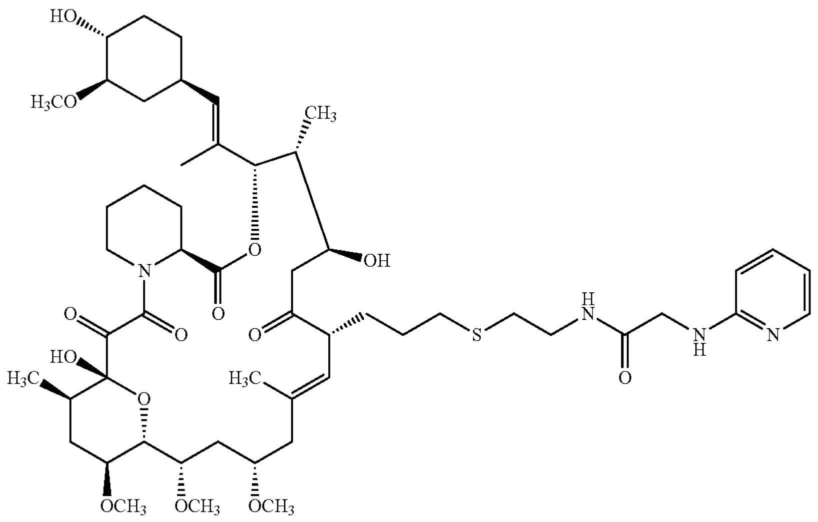 [SMILES: CO[C@H]1C/C(C)=C/[C@@H](CCCSCCNC(=O)CNc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-028

TABLE 4-continued
Compound structures of FK506-focused library.
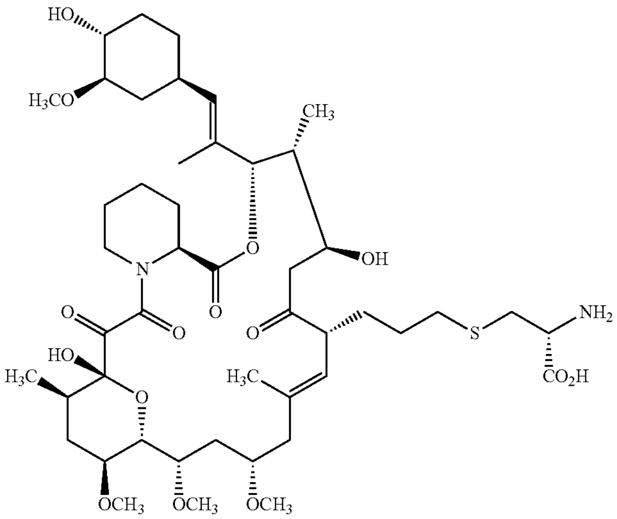 [SMILES: CO[C@H]1C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-037
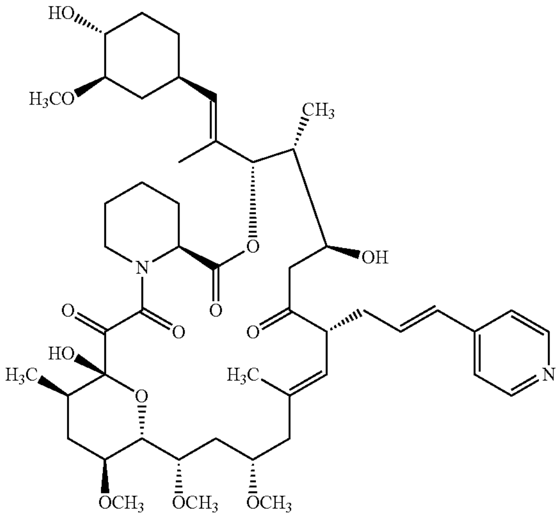 [SMILES: CO[C@H]1C/C(C)=C/[C@@H](C/C=C/c2ccncc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-050
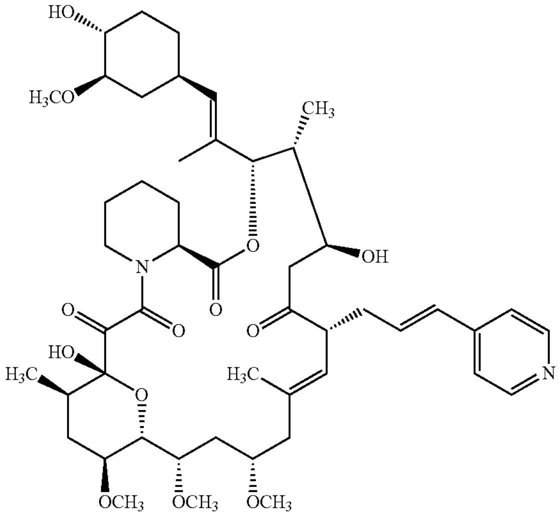 [SMILES: CO[C@H]1C/C(C)=C/[C@@H](C/C=C/c2ccncc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-051

TABLE 4-continued
Compound structures of FK506-focused library.
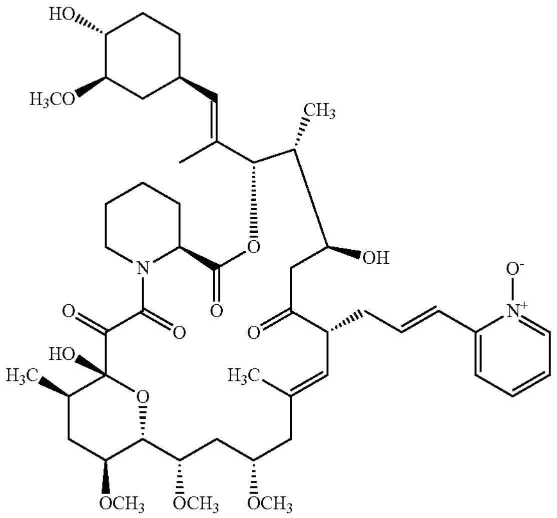 [SMILES: CO[C@H]1C/C(C)=C/[C@@H](C/C=C/c2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-060
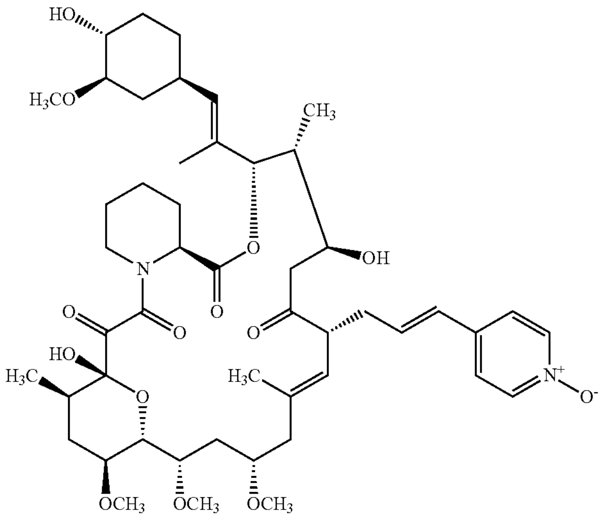 [SMILES: CO[C@H]1C/C(C)=C/[C@@H](C/C=C/c2cc[n+]([O-])cc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-061
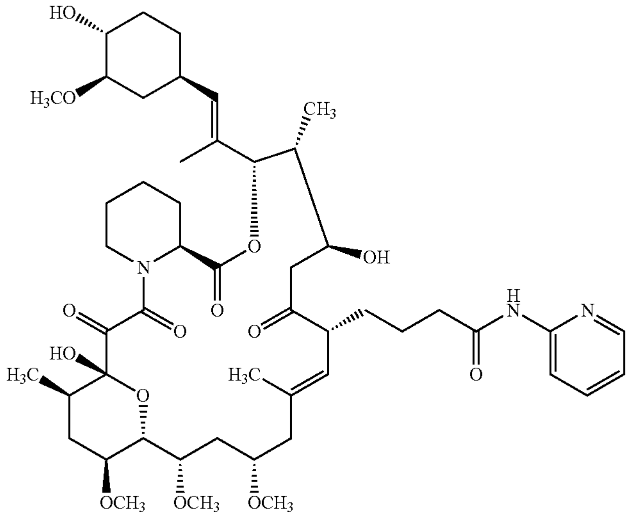 [SMILES: CO[C@H]1C/C(C)=C/[C@@H](CCCC(=O)Nc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-064

TABLE 4-continued
| Compound structures of FK506-focused library. |
| --- |
ZZY05-084/ZZY06-039
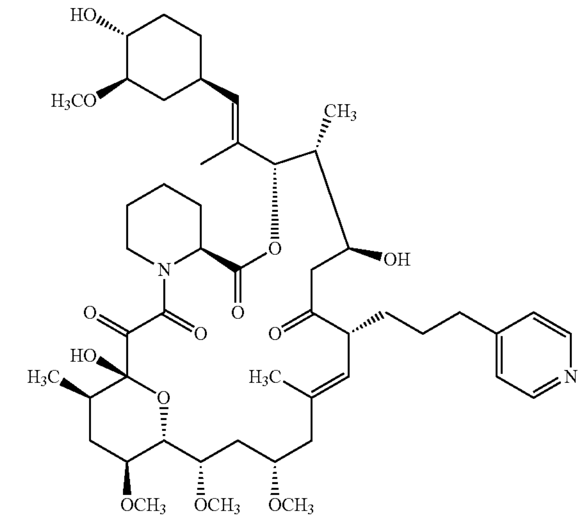 [SMILES: CO[C@H]1C/C(C)=C/[C@@H](CCCc2ccncc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-085
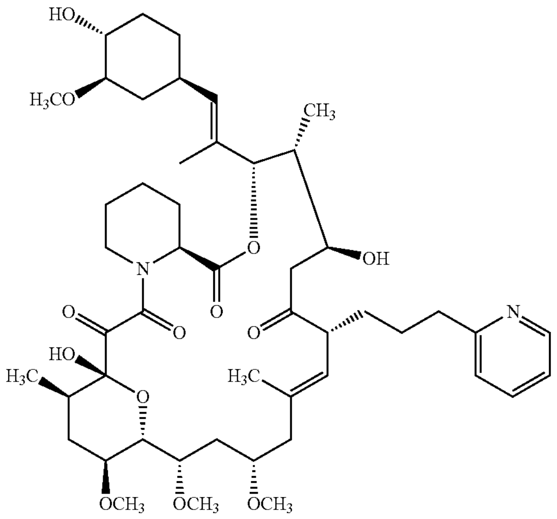 [SMILES: CO[C@H]1C/C(C)=C/[C@@H](CCCc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-086
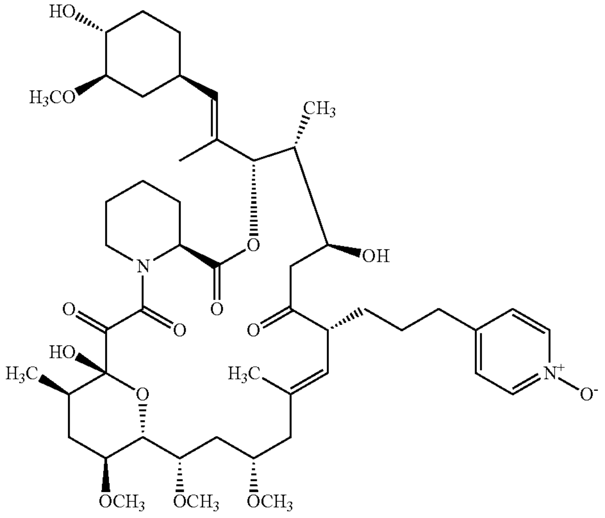 [SMILES: CO[C@H]1C/C(C)=C/[C@@H](CCCc2cc[n+]([O-])cc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]

TABLE 4-continued
| Compound structures of FK506-focused library. |
| --- |
ZZY-05-092/ZZY06-041
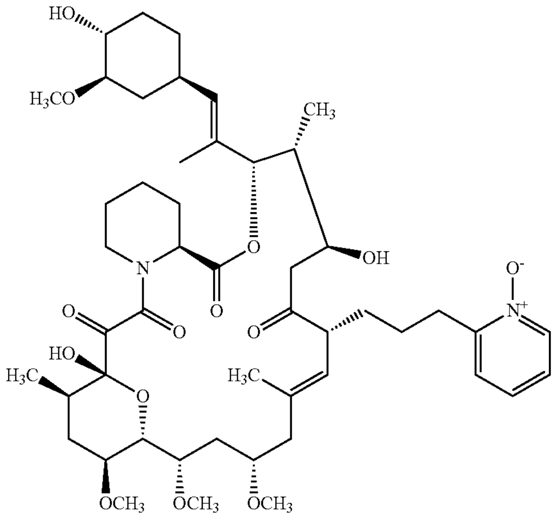 [SMILES: CO[C@H]1C/C(C)=C/[C@@H](CCCc2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-094
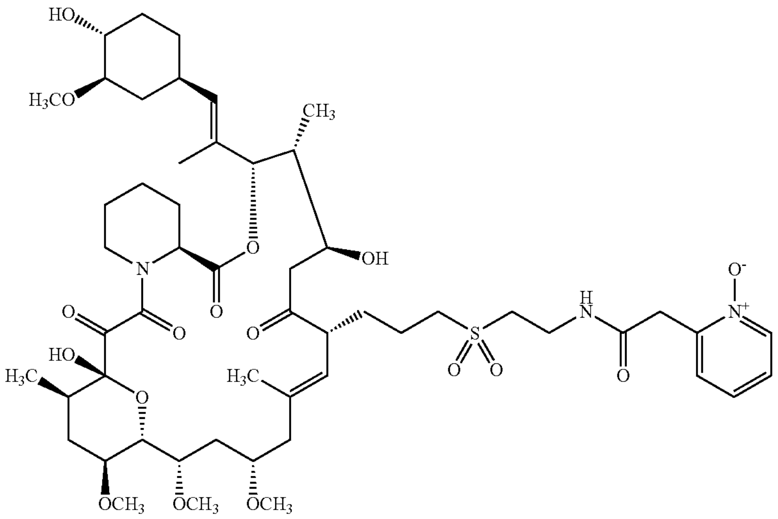 [SMILES: CO[C@H]1C/C(C)=C/[C@@H](CCCS(=O)(=O)CCNC(=O)Cc2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]

Example 3: Biological Data

TABLE 5

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| SLF | 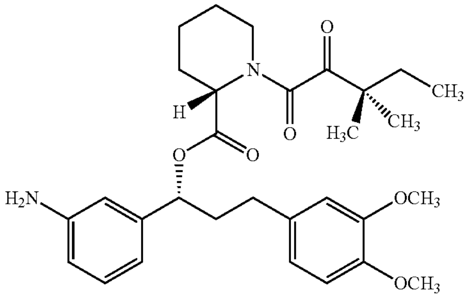 | 23 | 3 | 0 | | 4.71 |
| ZZY01-025 | 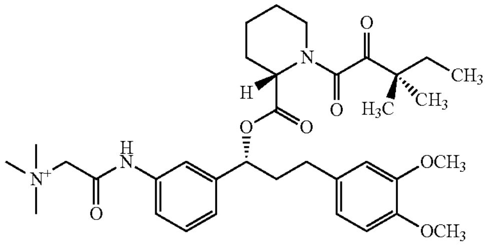 | 95 | 1 | ND | | 0.97 |
| ZZY01-038 | 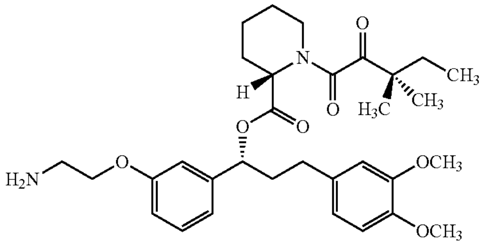 | 9.4 | 1 | ND | | 5.05 |
| ZZY01-040 | 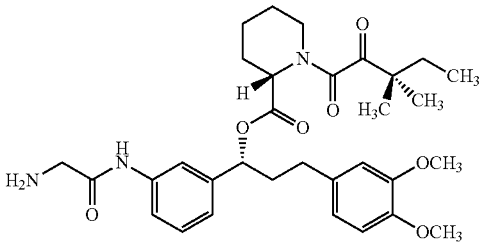 | 21.3 | 3 | ND | | 4.04 |
| ZZY01-041 | 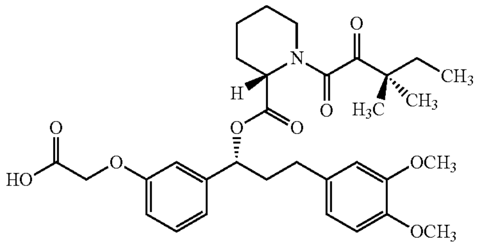 | 38 | 0 | ND | | 5.14 |

TABLE 5-continued

| RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%. | | | | | | |
|---|---|---|---|---|---|---|
| Compound | Structure | Kd FKBP12 (nM) | Rapamycin Blockade | RapaLink-1 Blockade | In Vivo | cLogP |
| ZZY01-043 | 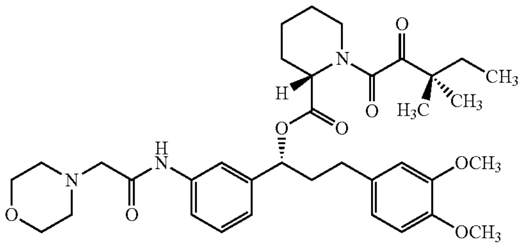 | 15 | 3 | ND | | 5.08 |
| ZZY01-044 | 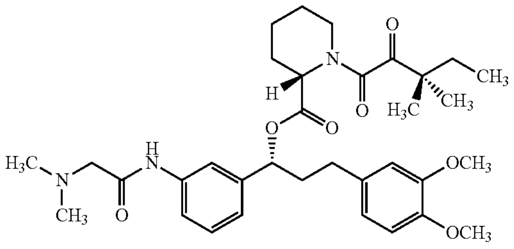 | 12.7 | 3 | ND | | 4.99 |
| ZZY01-059 | 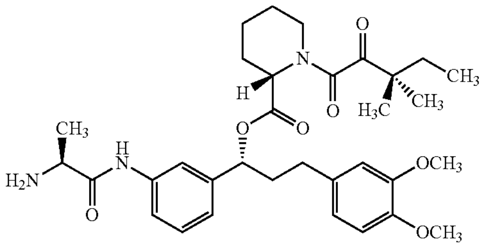 | 13.6 | 3 | ND | | 4.35 |
| ZZY01-060A | 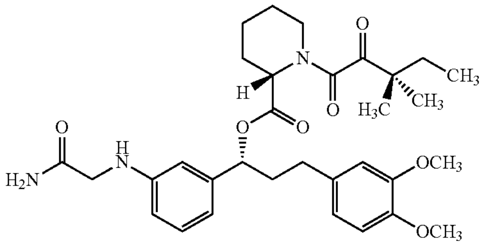 | 46.4 | 0 | ND | | 4.89 |
| ZZY01-060B | 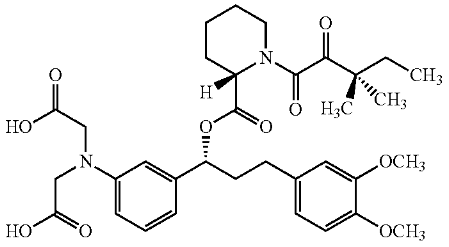 | 75.0 | 1 | ND | | 5.11 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY01-065 | 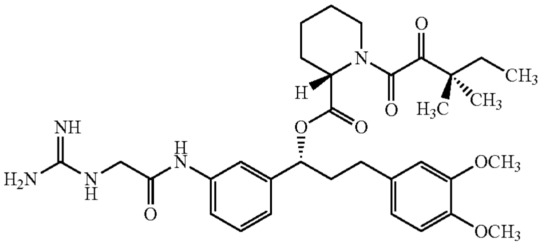 | 37.8 | 2 | ND | | 3.47 |
| ZZY01-070 | 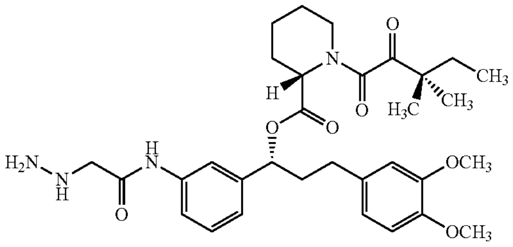 | 21.0 | 1 | ND | | 3.77 |
| ZZY01-072 | 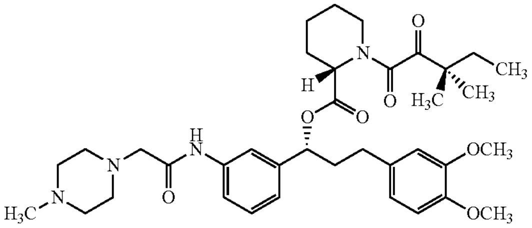 | 12.5 | 3 | ND | | 4.16 |
| ZZY01-083 | 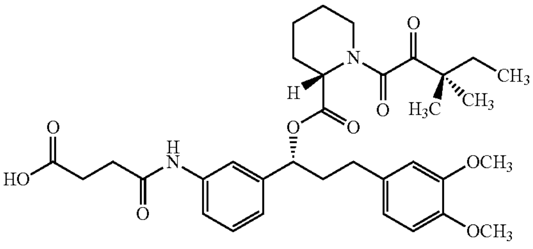 | 13.3 | 1 | ND | | 4.73 |
| ZZY02-014 | 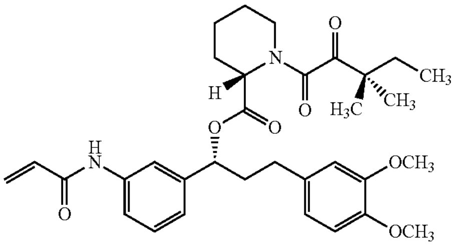 | 64.0 | 3 | ND | | 5.2 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
|---|---|---|---|---|---|---|
| ZZY02-032 | 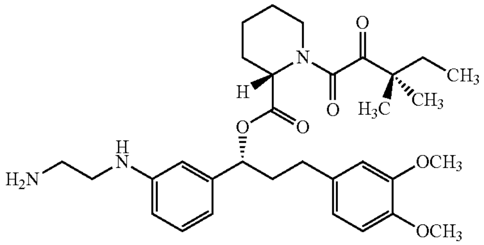 | 36.4 | 0 | ND | | 4.74 |
| ZZY02-033 | 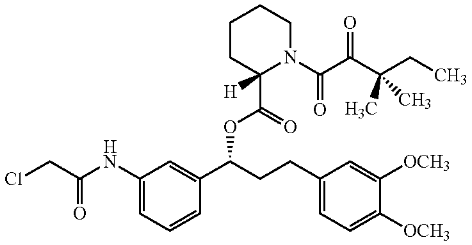 | 10.3 | 0 | ND | | 5.56 |
| ZZY02-055 | 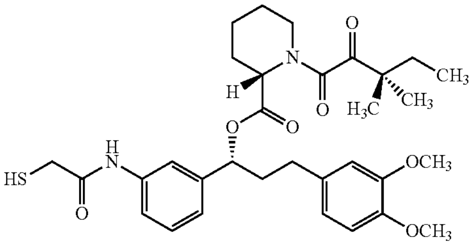 | 63.8 | 0 | ND | | 4.97 |
| ZZY02-096 | 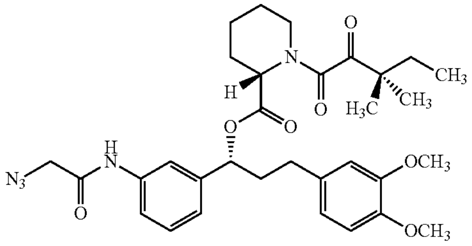 | 6.0 | 2 | ND | | 5.83 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
| --- | --- | --- | --- | --- | --- | --- |
| ZZY03-077 | 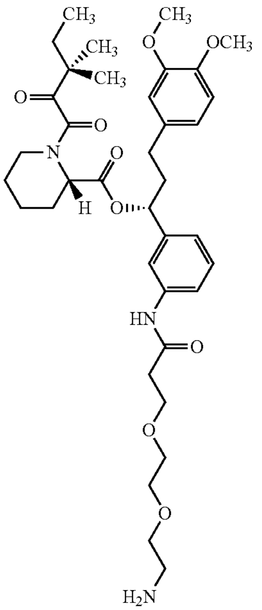 | 43.7 | 3 | ND | | 4.31 |
| ZZY03-083 | 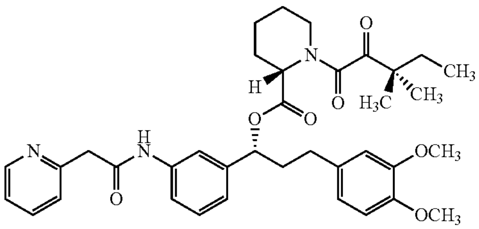 | 31.1 | 3 | 0 | | 4.99 |
| ZZY03-084 | 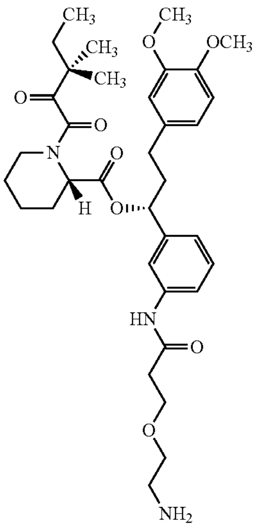 | 18.6 | 2 | ND | | 4.45 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY03-087 | 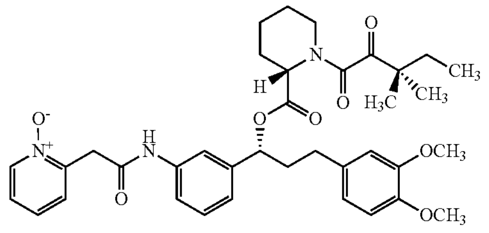 | 28.8 | 3 | 0 | Blocks rapamycin in muscle, potentiates rapamycin in brain | 3.11 |
| ZZY03-091 | 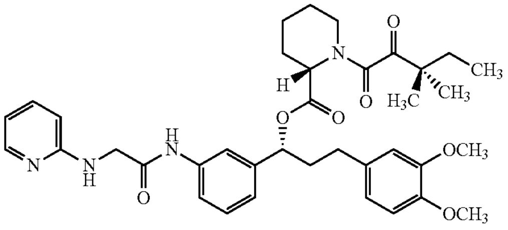 | 37.3 | 2 | ND | | 5.65 |
| FK506 | 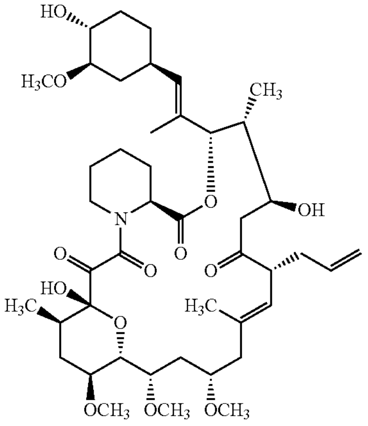 [SMILES: C=CC[C@@H]1/C=C(\C)C[C@H](OC)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC] | 0.8 | 3 | 3 | | 5.77 |
| ZZY05-011 | 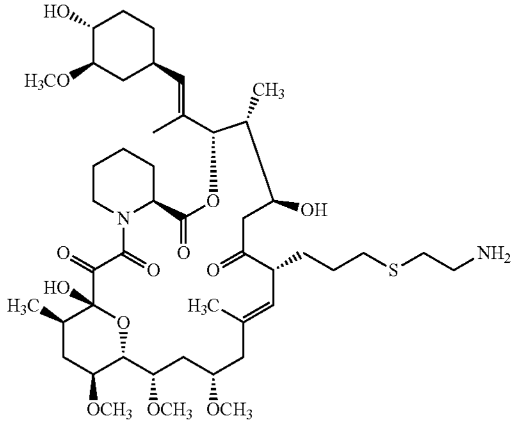 [SMILES: CO[C@H]1C/C(C)=C/[C@@H](CCCSCCN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.69 | 3 | 3 | | 5.12 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
|---|---|---|---|---|---|---|
| ZZY05-012 | 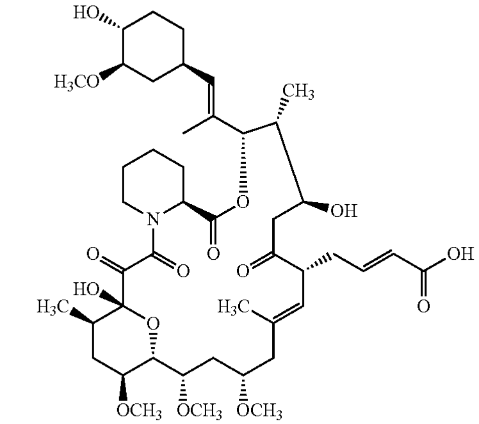 [SMILES: CO[C@H]1C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.39 | 0 | 0 | | 4.86 |
| ZZY05-013 | 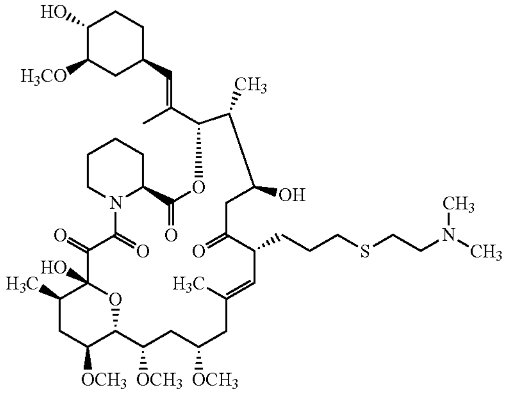 | 1.36 | 3 | 3 | | 6.02 |
| ZZY05-020 | 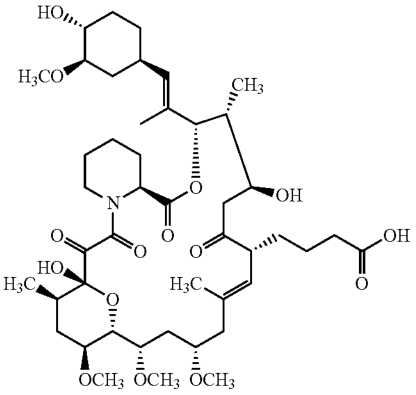 | 1.49 | 2 | 0 | | 4.84 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY05-026 | 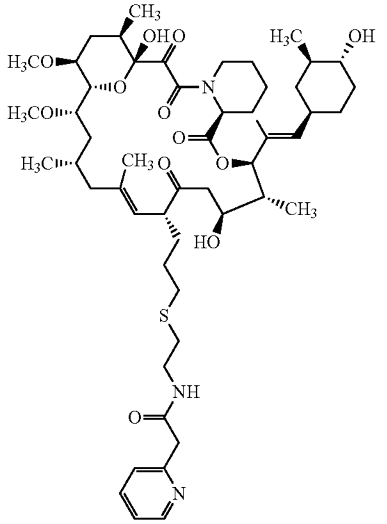 [SMILES: CO[C@H]1C[C@@H](C)C/C(C)=C/[C@@H](CCCSCCNC(=O)Cc2ccccn2)C(=O)C[C@H](O)[C@@H](C)[C@H](/C(C)=C/[C@@H]2CC[C@@H](O)[C@H](C)C2)OC(=O)[C@@H]2CCCCN2C(=O)C(=O)[C@]2(O)O[C@H]1[C@@H](OC)C[C@H]2C] | 3.7 | 3 | 3 | Dose: 1 mg/kg Rapalink-1 + 40 mg/kg ZZY05-026; Blocks Rapalink-1 in muscle, Potentiates RapaLink-1 in brain | 5.23 |
| ZZY05-028 | 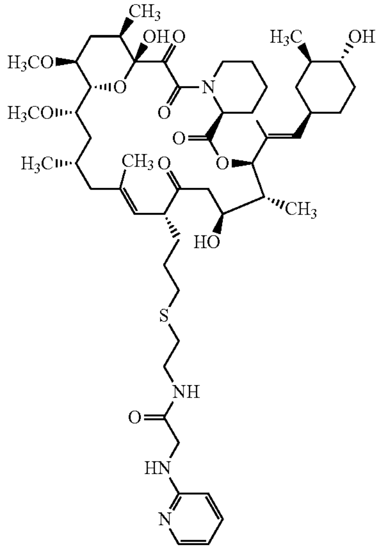 [SMILES: CO[C@H]1C[C@@H](C)C/C(C)=C/[C@@H](CCCSCCNC(=O)CNc2ccccn2)C(=O)C[C@H](O)[C@@H](C)[C@H](/C(C)=C/[C@@H]2CC[C@@H](O)[C@H](C)C2)OC(=O)[C@@H]2CCCCN2C(=O)C(=O)[C@]2(O)O[C@H]1[C@@H](OC)C[C@H]2C] | 2.5 | 3 | 3 | | 6.01 |
| ZZY05-037 | 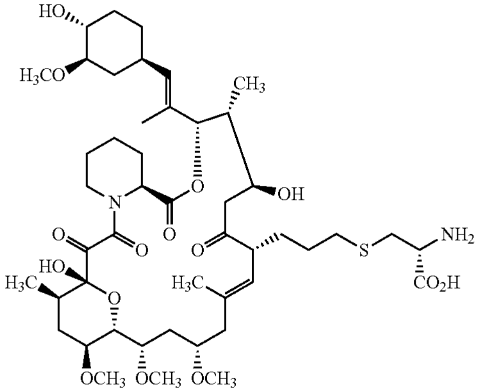 [SMILES: CO[C@H]1C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 8.7 | ND | 1 | | 3.04 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
|---|---|---|---|---|---|---|
| ZZY05-050 | 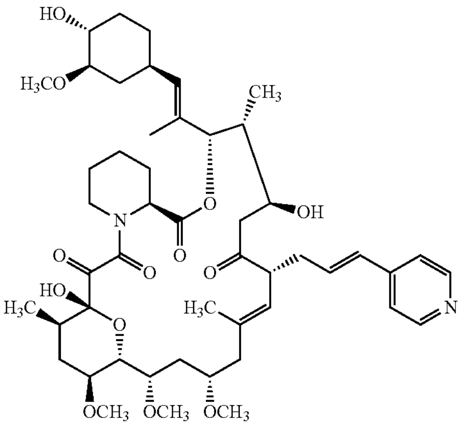 [SMILES: CO[C@H]1C/C(C)=C/[C@@H](C/C=C/c2ccncc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 3.6 | ND | 3 | | 5.87 |
| ZZY05-051 | 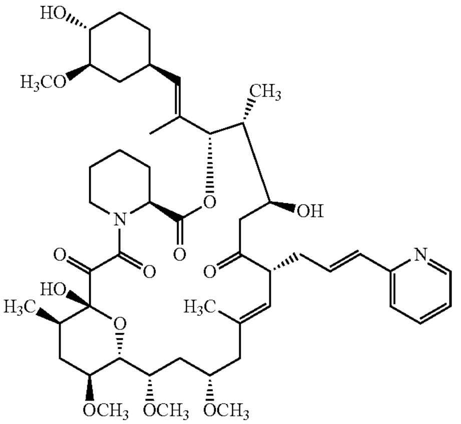 | 1.2 | ND | 3 | | 5.87 |
| ZZY05-060 | 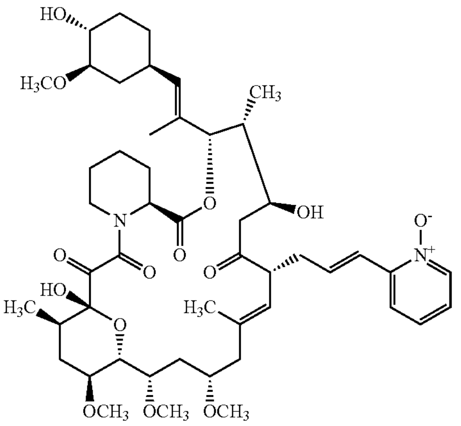 [SMILES: CO[C@H]1C/C(C)=C/[C@@H](C/C=C/c2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.62 | ND | 1 | | 4 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY05-061 | 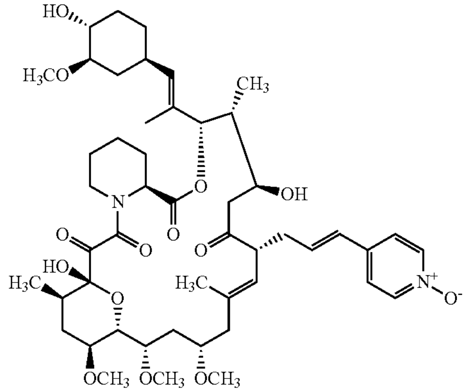 [SMILES: CO[C@H]1C/C(C)=C/[C@@H](C/C=C/c2cc[n+]([O-])cc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.21 | ND | 0 | | 4 |
| ZZY05-064 | 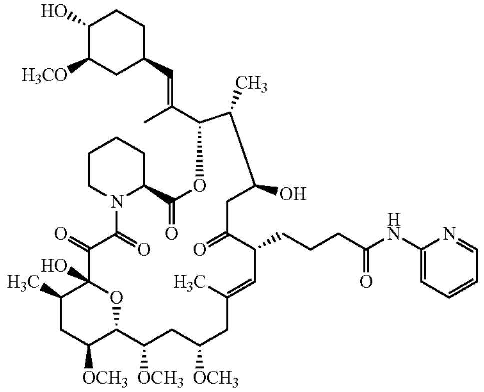 [SMILES: CO[C@H]1C/C(C)=C/[C@@H](CCCC(=O)Nc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.2 | ND | 3 | | 5.53 |
| ZZY05-085 | 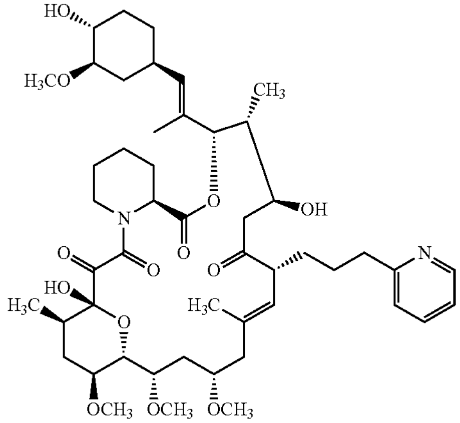 | 1.5 | ND | 3 | Appears to have blocked Rapalink-1 in brain | 4.3 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY05-086 | 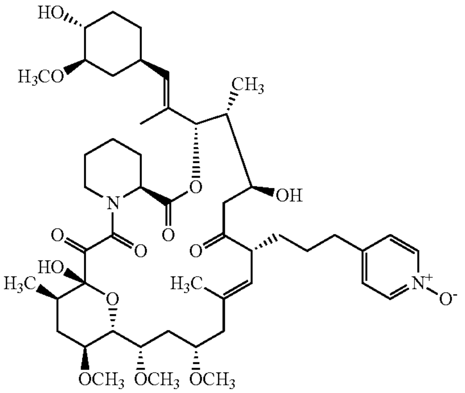 | 1.6 | ND | 3 | | 4.3 |
| ZZY05-092 / ZZY06-041 | 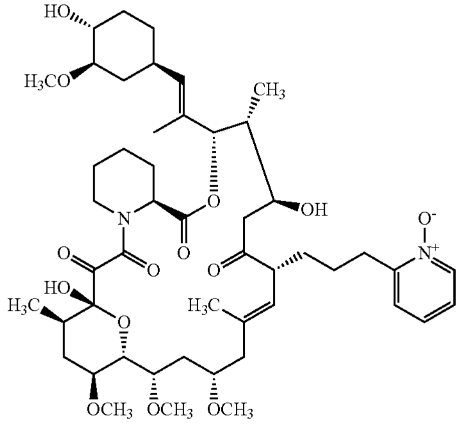 | 2.5 | ND | 3 | Dose: 1 mg/kg Rapalink-1 + 40 mg/kg ZZY05-092 Blocks Rapalink-1 in muscle; Potentiates Rapalink-1 in brain | 4.3 |

Example 4: Bispecific Chemical Ligands Allow Programmable Kinase Inhibition

Dysregulation of kinase activity underlies a variety of human diseases. While many small molecule kinase inhibitors have demonstrated remarkable success in precision medicine, the temporal (timing) and spatial (tissue distribution) control of their activity remains an intractable challenge. Here we present a strategy to build a new class of kinase inhibitors that overcome these limitations. Created by chemically linking kinase inhibitors and the immunosuppressant FK506, the resultant bispecific ligands show kinase inhibitory activity that depends on the endogenous protein FKBP12 and hence can be modulated by co-administration with an exogenous FKBP12 ligand. Using this approach, we successfully constructed highly potent, cell-permeable, programmable inhibitors of Src-family kinases, HER2 and LRRK2 based on dasatinib, lapatinib and GNE-7915, respectively. The method described here may be adapted for other kinases and even other classes of therapeutic targets.

Protein kinases orchestrate an intricate network of cellular signaling events, and their dysregulation are implicated in many human diseases including cancer, autoimmunity and neurodegenerative disorders. Inhibition of aberrant kinases by small molecule ligands proves to be a fruitful therapeutic strategy that remains widely pursued in various disease areas (48 FDA-approved kinase inhibitors as of December 2018). Nonetheless, methods are lacking to allow reversal of the effects of kinase inhibitors of or tissue-directed kinase inhibition. These features are highly desirable, as systemic kinase inhibition often is unnecessary and contributes to toxicity. Here we describe a method to construct bispecific chemical ligands that induce the association of protein kinases and a ubiquitously expressed protein, FKBP12, by chemically linking a kinase inhibitor to a high affinity ligand of FKBP, FK506. We show that these bispecific ligands are cell-permeable and effect potent, specific and long-lasting inhibition of their respective targets, and that their cellular activity is amenable to modulation with a separate ligand of FKBP12. We exemplify our approach with three case studies: an inhibitor of Src-family kinases based on dasatinib, an inhibitor of EGFR/HER2 based on lapatinib, and an inhibitor of LRRK2 based GNE7915.

It is important to point out that several other FKBP12-binding hybrids have been reported with diverse pharmacological properties. For example, Briesewtiz et al. discovered that linking an pYEEI peptide to FK506 or SLF led to an increase or decrease of its affinity for the SH2 domain of Fyn in the presence of FKBP12, respectively. Gestwicki et al. demonstrated that SLF-Congo Red is a bifunctional molecule that recruits FKBP12 to β-amyloids and uses the steric bulk of FKBP12 to inhibit β-amyloid aggregation. Marinec et al. reported that an amprenavir-SLF hybrid preferentially partitions into red blood cells which express high levels of FKBP12 protein, creating an intracellular reservoir of the HIV protease inhibitor and significantly increasing its serum half-life. Many properties observed with our bispecific kinase inhibitors are congruent with these precedents. However, a distinct advantage unique to our compounds is that their activity is highly dependent on the availability of FKBP12 protein; they are poor kinase inhibitors in the absence of FKBP12 and therefore their cellular activity can be conveniently modulated with another FKBP12 ligand (vide infra).

We chose dasatinib, an FDA-approved pan-Src family kinase inhibitor, for our model study as abundant literature on its pharmacological properties and structural information is available to aid our initial design and analysis. Inspection of the crystal structures of FKBP12-FK506 complex (PDB: 1FKJ) and dasatinib-Src complex (PDB: 3G5D) revealed that the allyl group at the C21 position of FK506 and the hydroxylethyl group in dasatinib on the piperazine ring are exposed to solvent and serve as suitable sites for chemical fusing. Previous structure-activity relationship studies on FK506 and dasatinib also indicate that chemical alterations at these two sites have minimal impact on their affinities for their respective targets. We envisioned that modifying the C21 allyl group confers an additional advantage: substituents larger than allyl at this position will ablate FK506's ability to inhibit its natural target calcineurin, an undesirable activity in our present application. To synthesize the bispecific ligand FK506-Dasatinib, we employed HATU-mediated amide coupling reaction to join a carboxylic acid derived from FK506 and a secondary amine derived from Dasatinib. The synthetic route used is amenable to incorporating linkers with various length and geometry for further optimization.

Figure 14B:
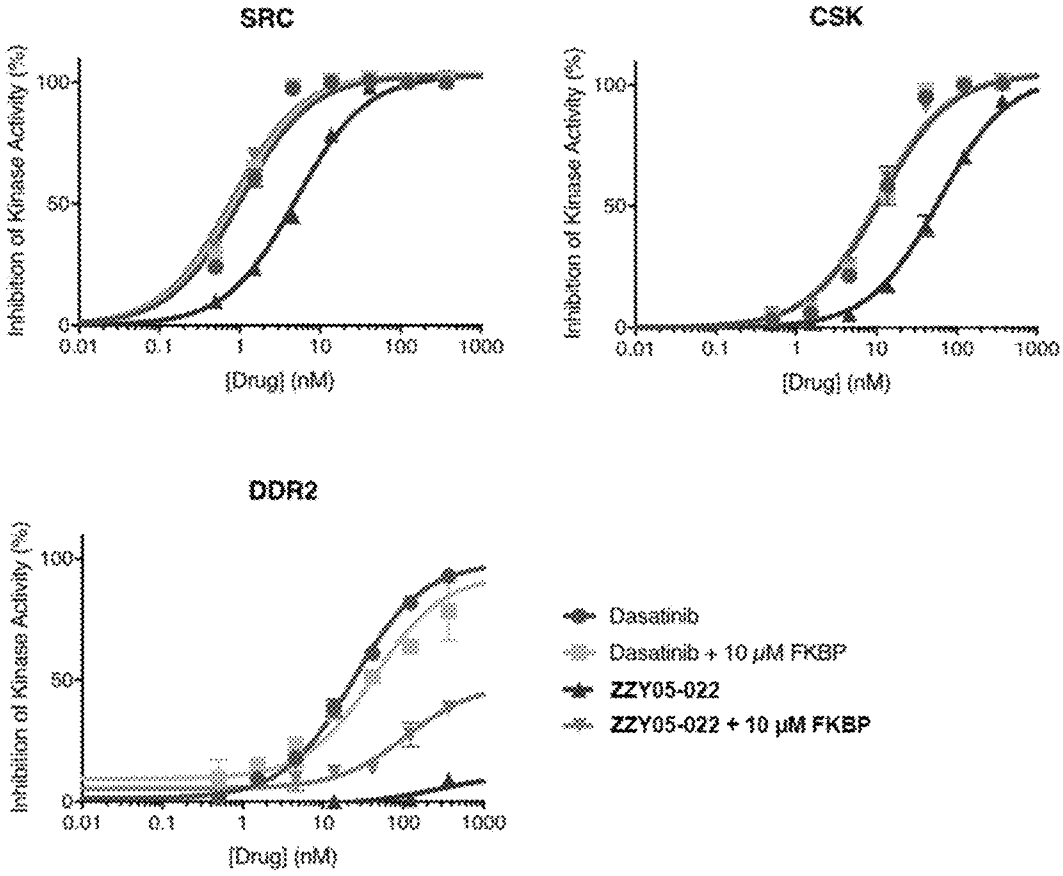
Figure 14C:
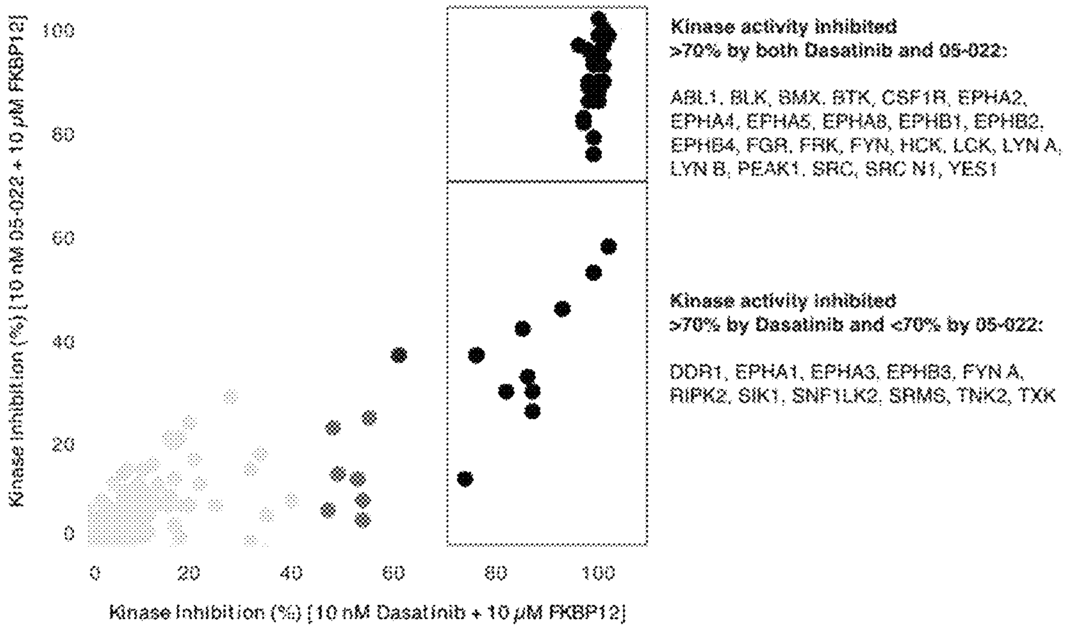
Figure 14D:

Using a fluorescence polarization assay, we found that FK506-Dasatinib maintained potent binding to FKBP12 ($K_d$=23 nM), consistent with our previous anticipation. To assess the kinase inhibition activity of FK506-Dasatinib, we performed in vitro kinase assays with ATP concentrations at the apparent Km values of each kinase. Three kinases were chosen in this preliminary investigation: Src, Csk and DDR2. Src and Csk are both Src-family tyrosine kinases but with opposite functions in cellular signal transduction, while DDR2 is a receptor tyrosine kinase also potently inhibited by dasatinib. Under standard assay conditions, FK506-Dasatinib showed weaker inhibitory activity toward all three kinases compared to dasatinib, with $IC_{50}$ values more than ten-fold greater those of the latter (FIG. 14B). To further mimic the cellular environment, we supplemented the assay buffer with 10 μM recombinant FKBP12, a concentration chosen to match the estimated intracellular concentration of FKBP proteins. At this FKBP concentration, we also ensured that >99.7% of the FK506-Dasatinib population would be in complex with FKBP12. Under the new assay conditions, we observed a significant left-shift of the inhibition curves for FK506-Dasatinib, whereas the potency of dasatinib remained unchanged. For Src and Csk, the two inhibitors achieved equipotent inhibition upon FKBP12 supplementation. Meanwhile, for DDR2, though enhancement of activity of FK506-Dasatinib was also observed, it was still inferior to dasatinib, failing to fully inhibit this kinase even at 1 μM concentration. This difference prompted us to investigate if linking FK506 to dasatinib had reshaped its selectivity for kinase targets. We profiled these two inhibitors against a panel of 485 protein kinases at 10 nM inhibitor concentration and with 10 μM supplemented FKBP12 protein (FIG. 14C). Of these 485 kinases, 23 were inhibited >70% by both inhibitors, and another 11 were inhibited >70% by dasatinib but not FK506-Dasatinib. Overall, FK506-Dasatinib did not achieve greater inhibition of any kinase tested than dasatinib at 10 nM, but certain kinases (for example, DDR1) appeared to be more disfavored by FK506-Dasatinib than others. This differential attenuation of inhibitory activity may be attributed to the favorable or unfavorable interactions with FKBP12 that the kinase must experience in order to bind the FK506-Dasatinib/FKBP12 complex. In this model, we envision that when FKBP12 binds FK506-dasatinib, a composite surface is formed that presents the dasatinib moiety and surveys various proteins for energetically favorable binding events (FIG. 14D).

Figure 15A:
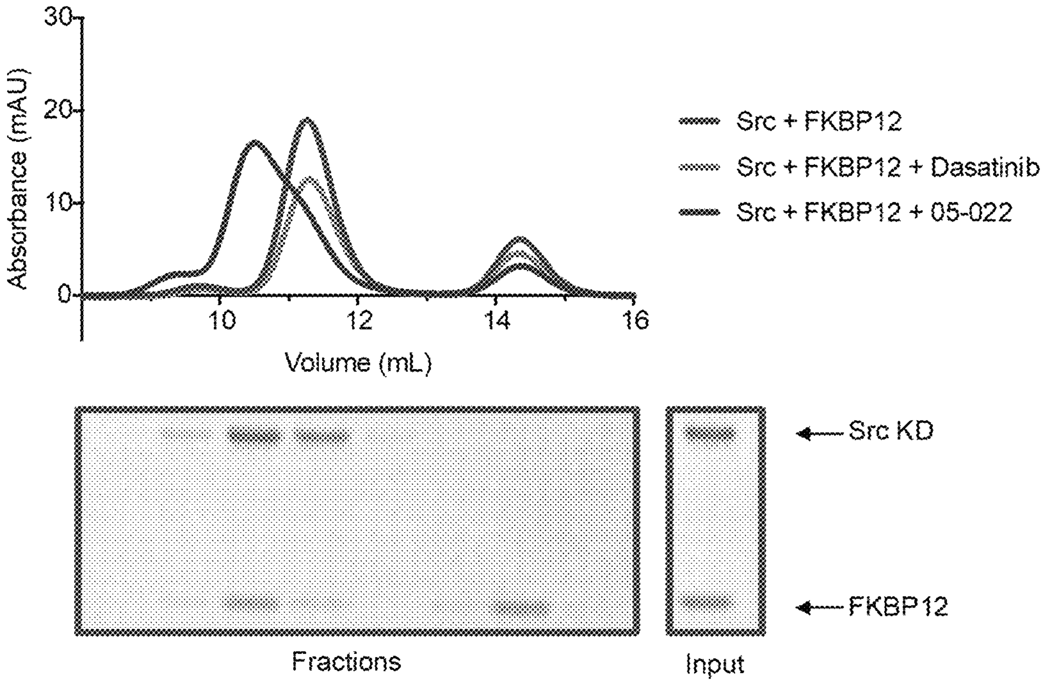
FIGS. 15A-15C. FK506-Dasatinib forms a stable ternary complex with Src and Dasatinib.
Figure 15B:
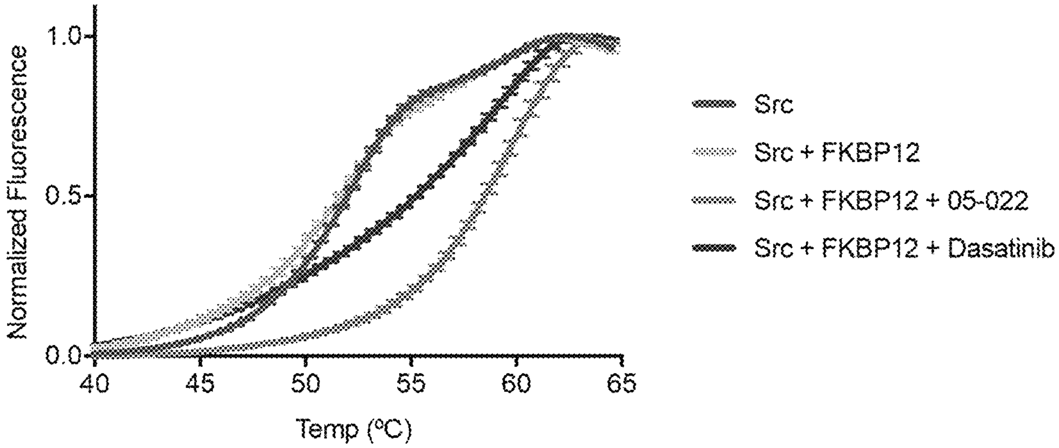
Figure 15C:
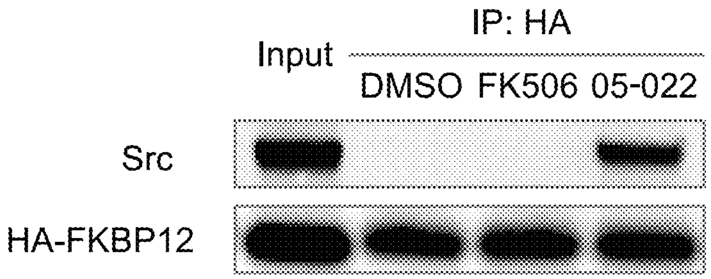

The participation of FKBP12 in the inhibition of kinases by FK506-dasatinib is further revealed by its ligand-dependent association with kinases. Addition of FK506-Dasatinib to a mixture of recombinant Src kinase domain (33 kDa) and FKBP12 (12 kDa) induced the formation of a stable complex (~50 kDa) that can be purified by size exclusion chromatography (FIG. 15A). The molecular weight of the complex suggests a 1:1:1 stoichiometry consistent with the anticipated binding mechanism of FK506-dasatinib. Differential scanning fluorimetry suggested that formation of this complex led to stabilization of both protein components toward thermal denaturation to a greater extent than dasatinib alone (FIG. 15B). Such tripartite interactions are preserved in more complex native environments—Src co-immunoprecipitated with HA-FKBP12 in Jurkat cell lysates treated with FK506-Dasatinib, but not FK506 (FIG. 15C).

Figure 16A:
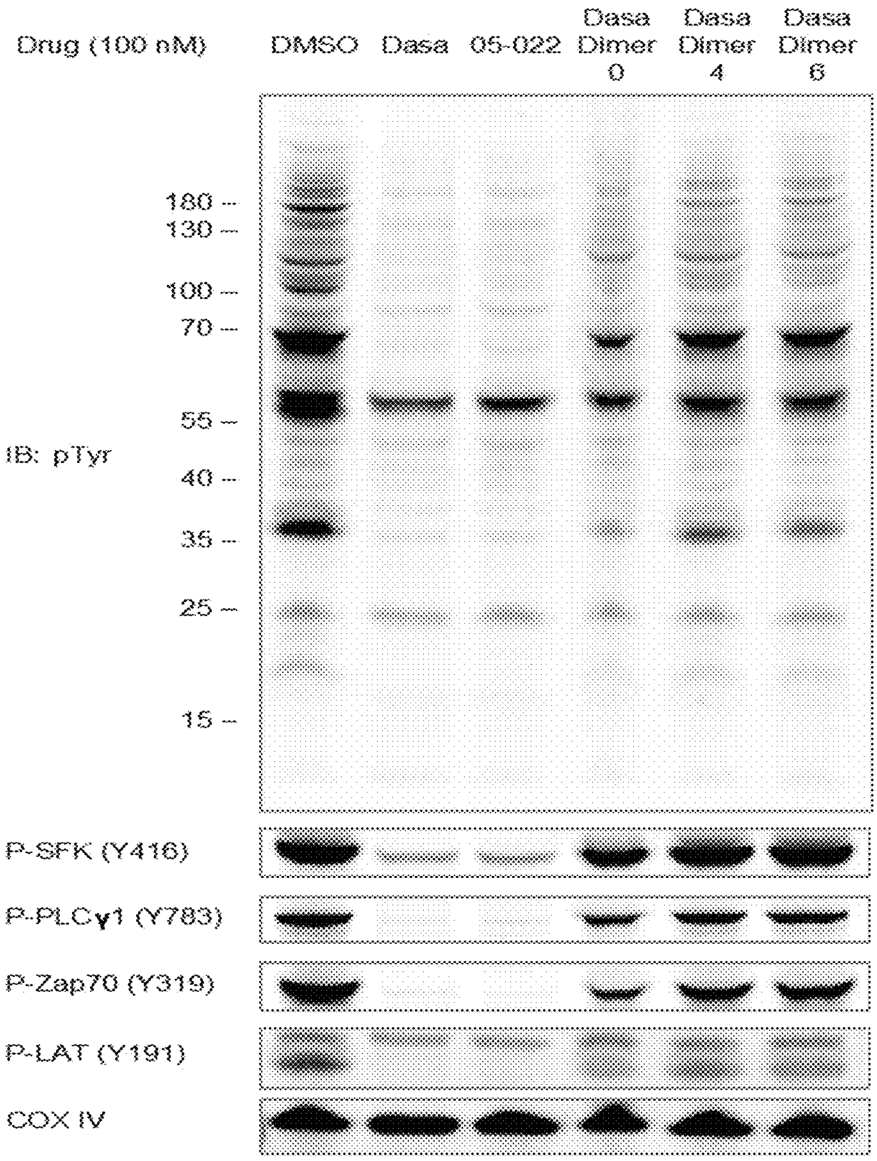
FIGS. 16A-16D. FK506-Dasatinib is a potent cell-permeable Src-family kinase inhibitor with long cellular retention time.

To evaluate the efficacy of FK506-Dasatinib in cells, we studied its effect on CD3 crosslinking-triggered T cell activation. Src family kinases, notably Lck and Fyn, are key regulators of T cell receptor (TCR) signal transduction, and dasatinib is known to block T cell activation by inhibiting these kinases. We stimulated Jurkat cells with an anti-CD3 monoclonal antibody (OKT3) in the presence of dasatinib or FK506-dasatinib and monitored their activation by Western blot. At 100 nM, both dasatinib and FK506-dasatinib dampened the of total phospho-tyrosine level and suppressed the phosphorylation of several proteins involved in TCR signaling including Src-family kinases, PLCgamma1, ZAP70 and LAT (FIG. 16A).

Figure 16B:
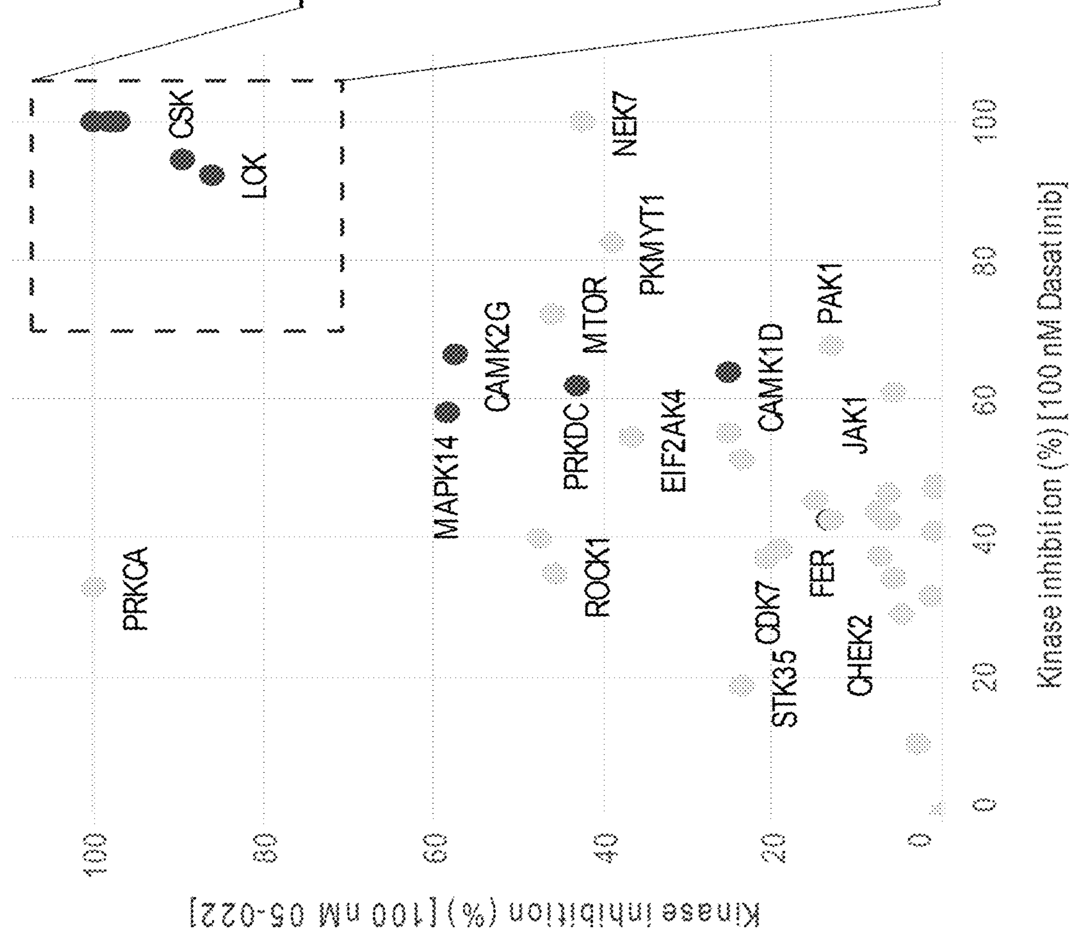
Figure 16C:
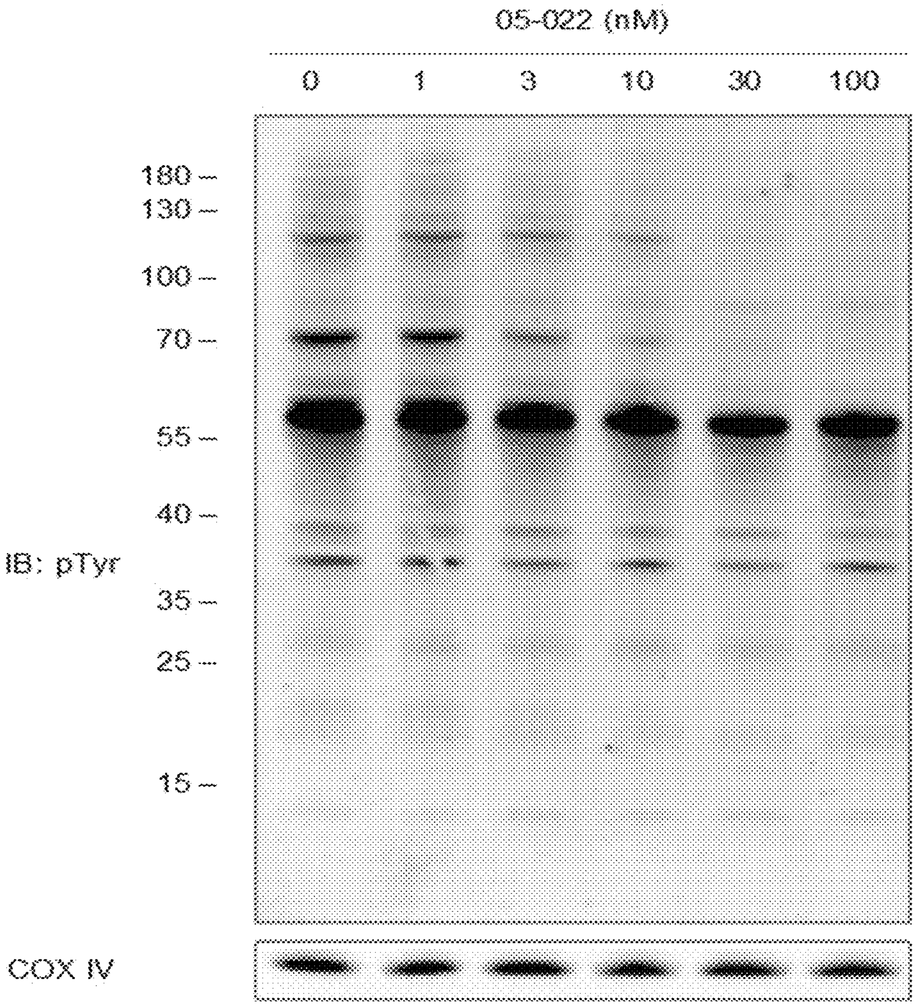
Figure 16D:
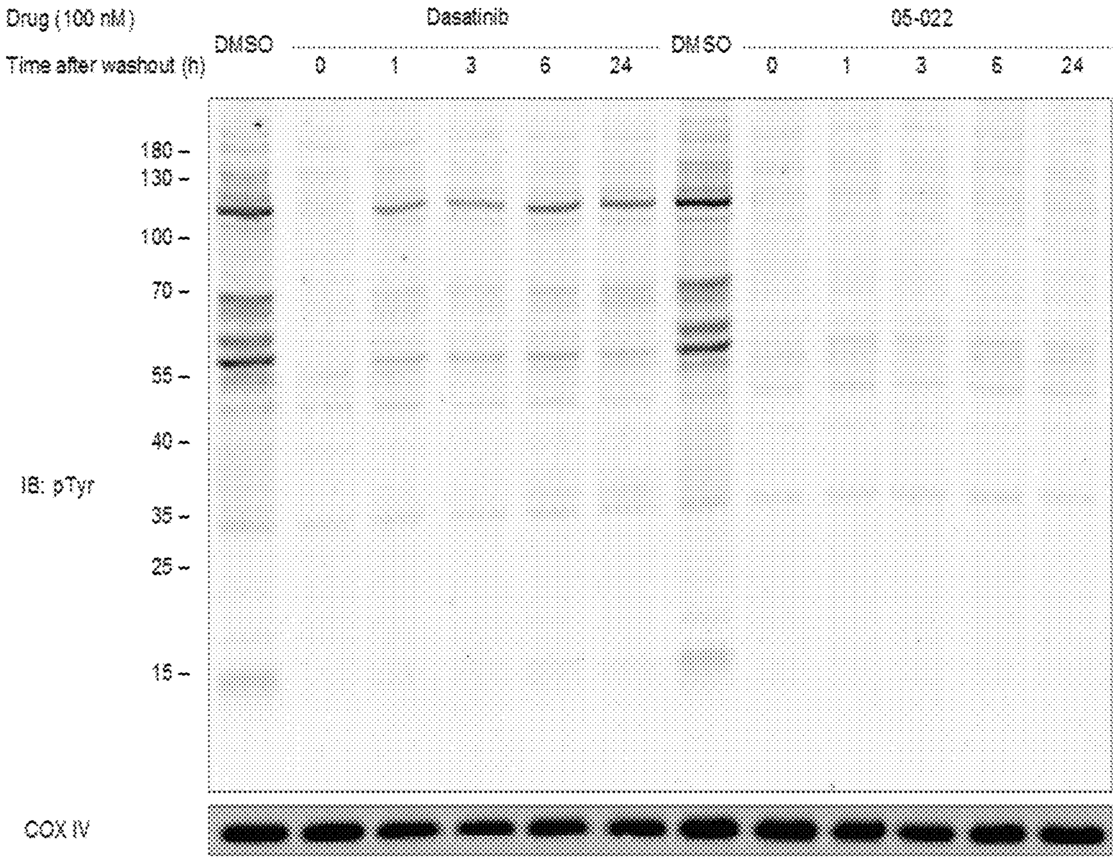
Figure 19B:
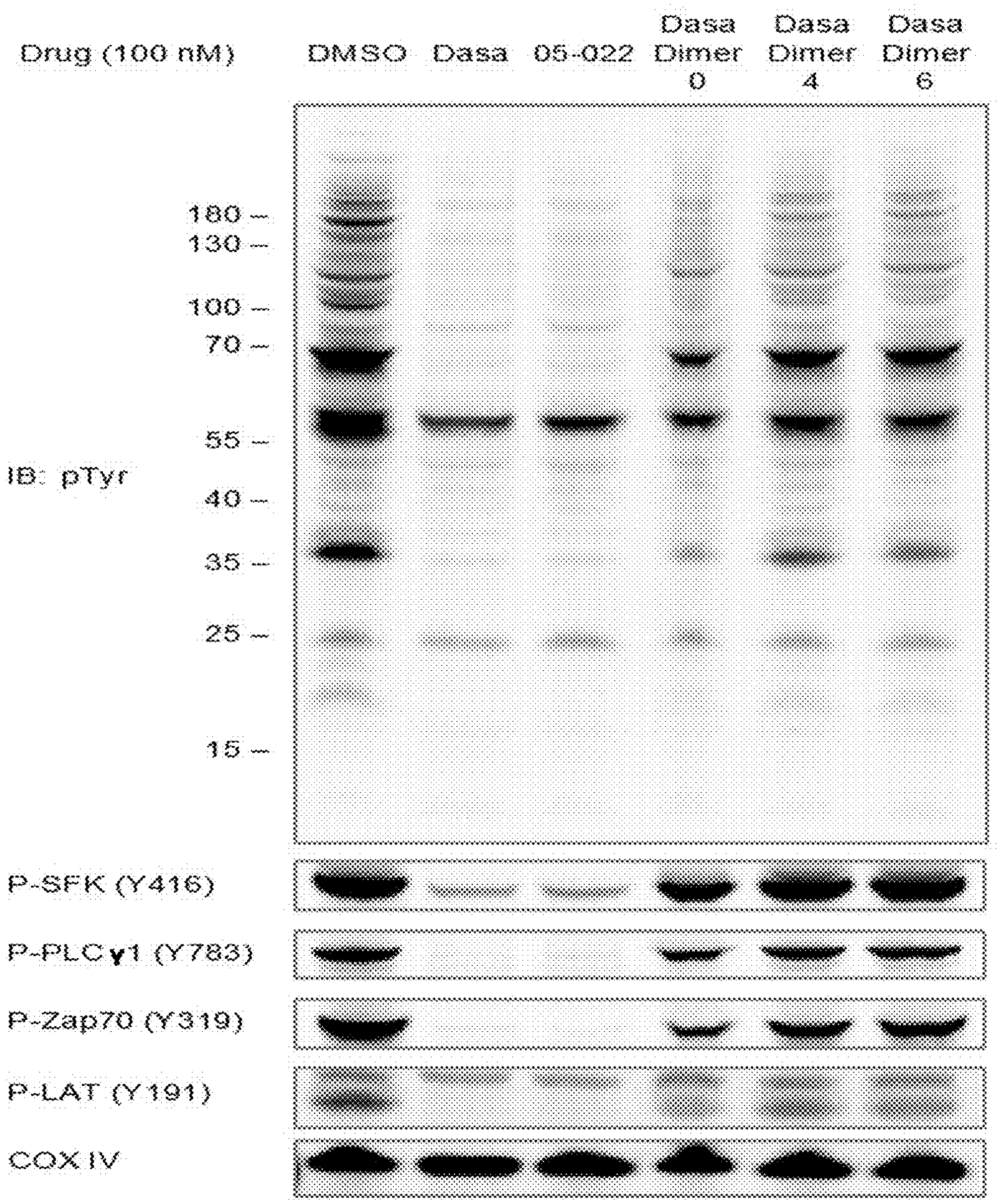
Figure 20:
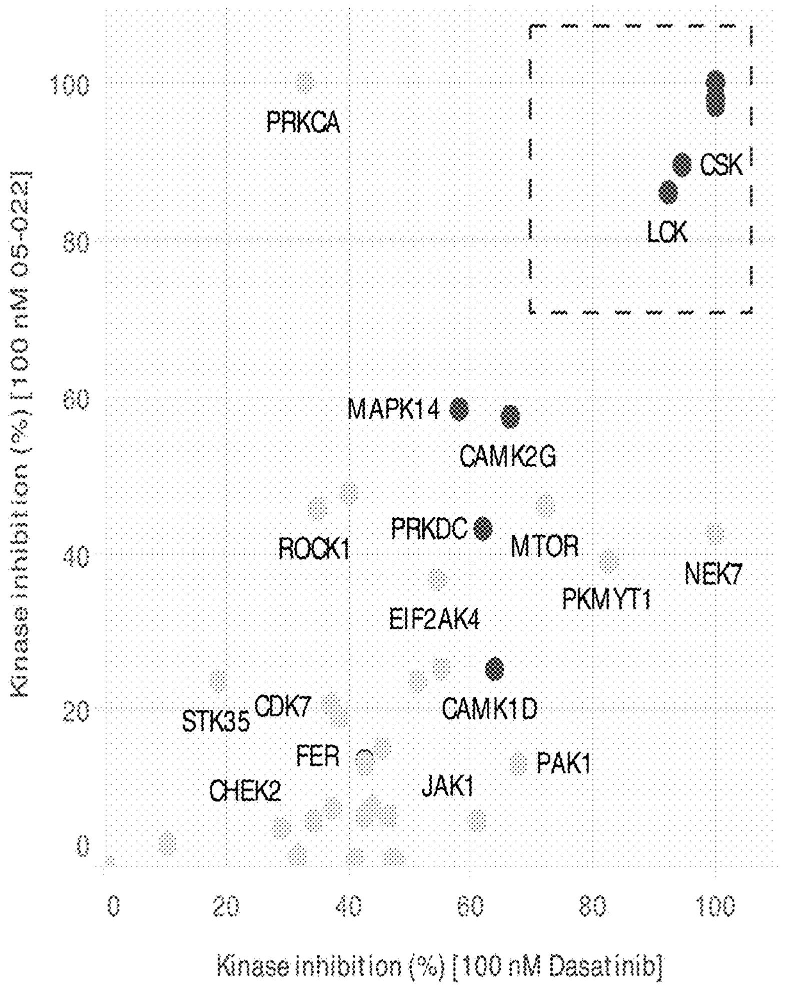
FIG. 20. In cell profiling of kinase inhibition by dasatinib and FK506-dasatinib using chemoproteomic probe XO44.
Figure 21A:
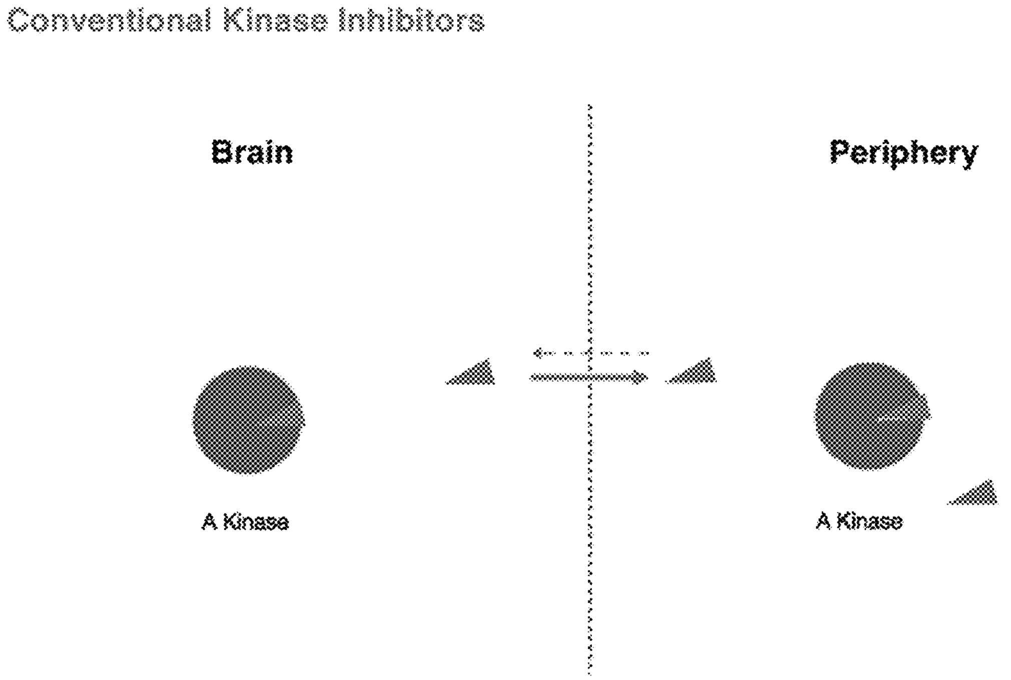
Figure 21B:
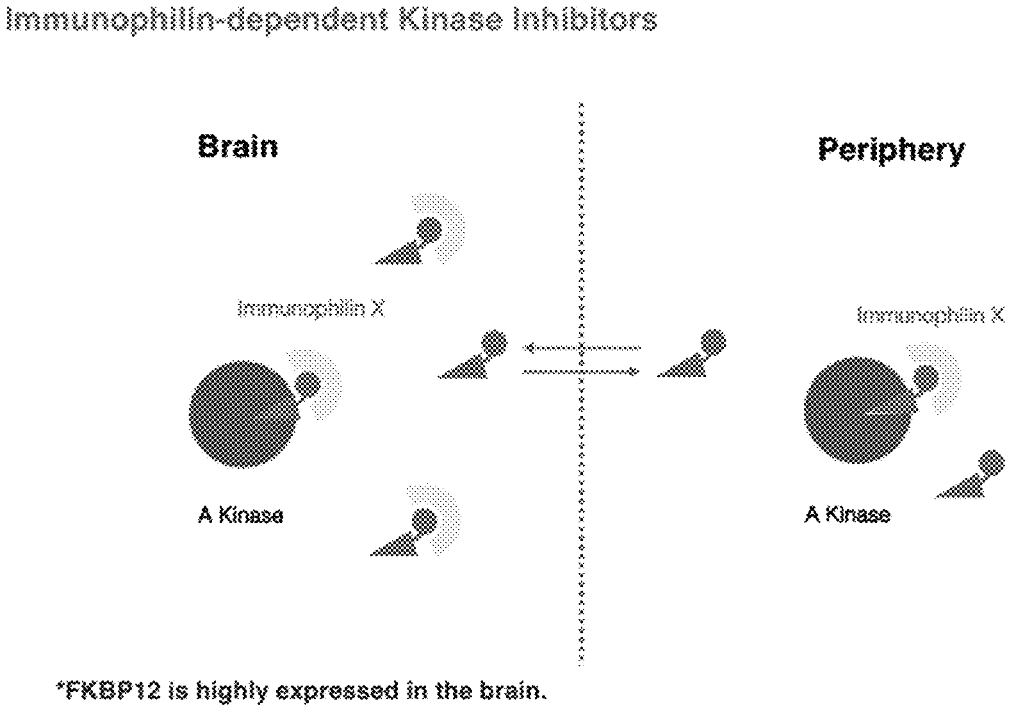
Figure 23A:
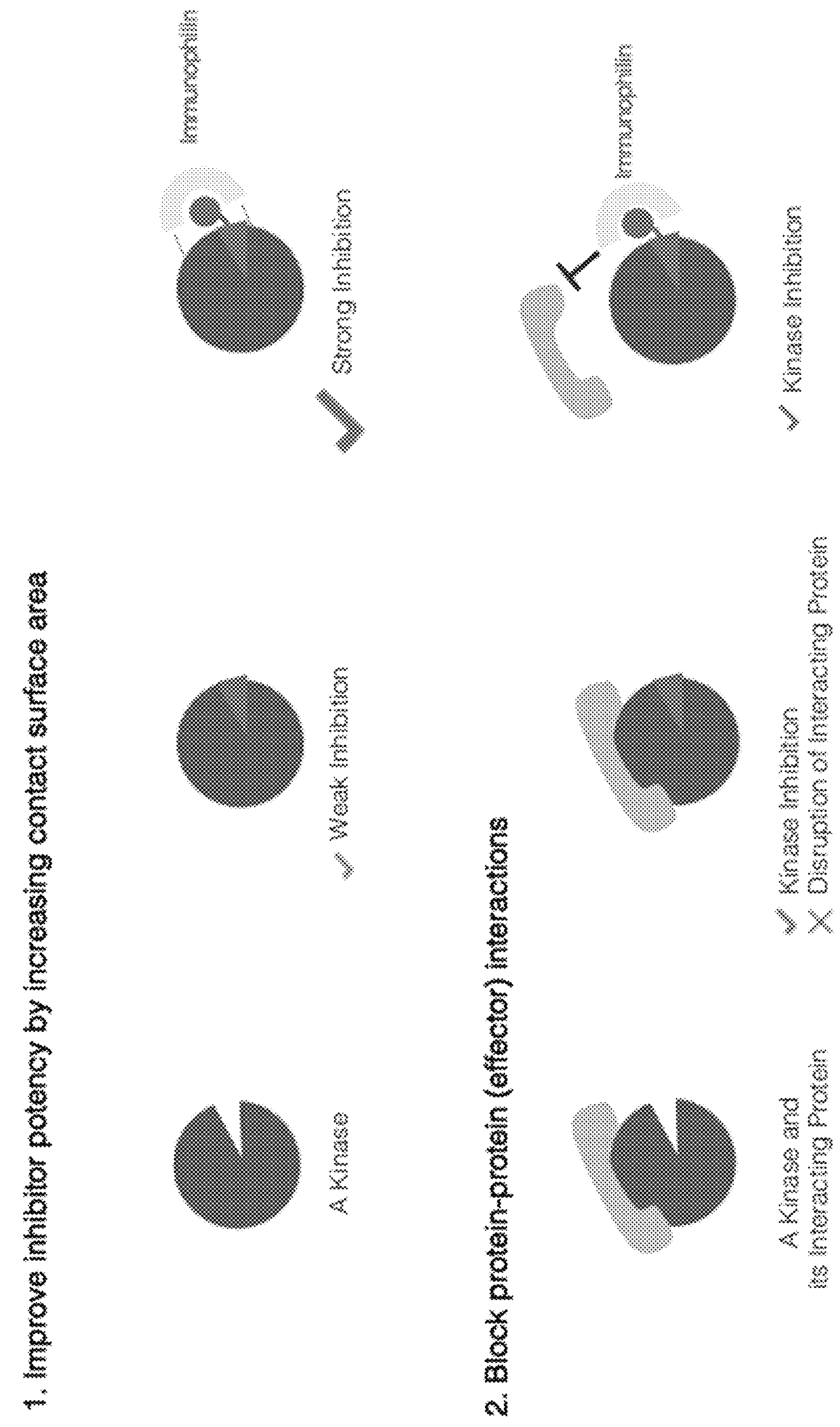
FIGS. 23A-23C. Potential advantages.
Figure 23B:
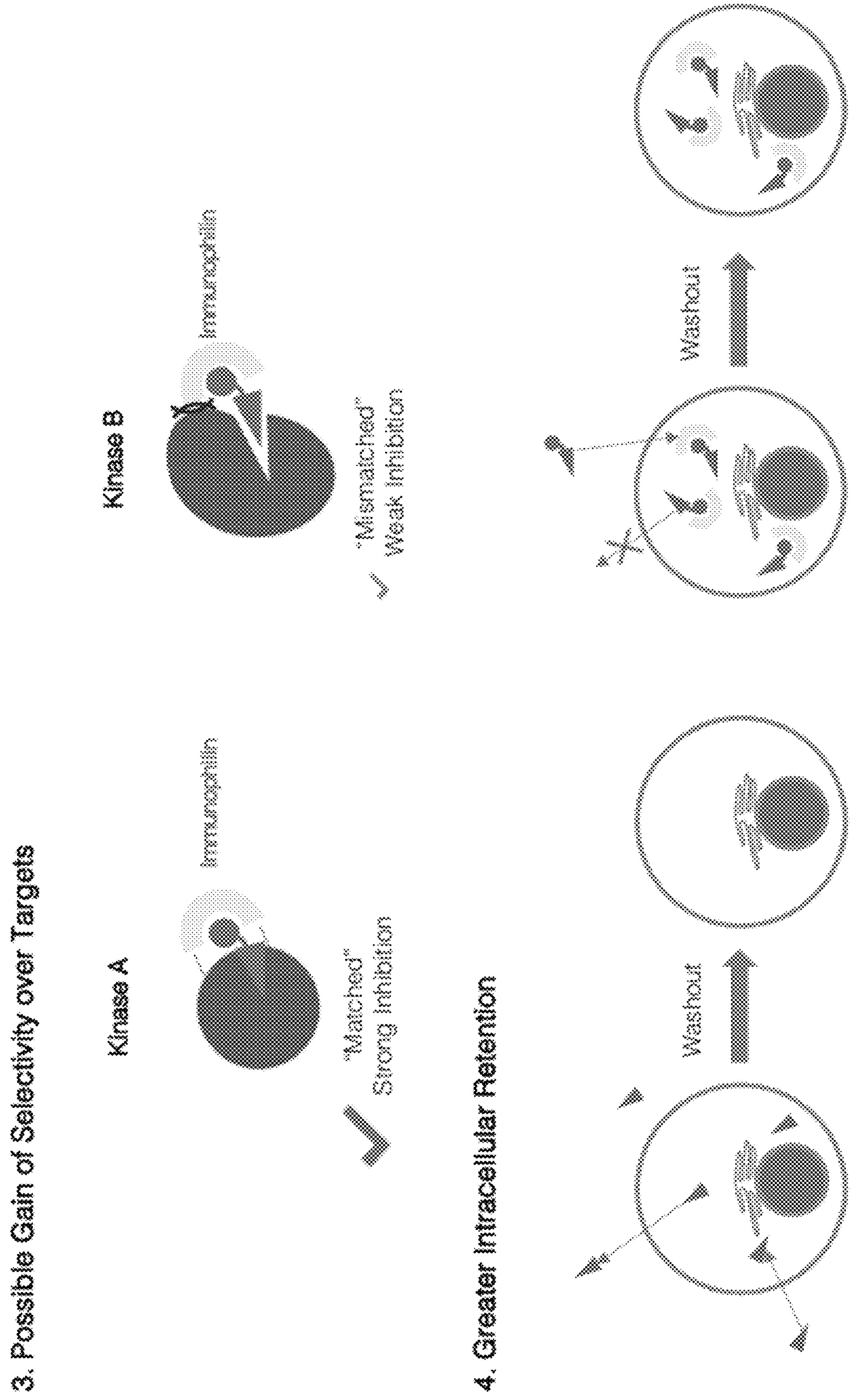
Figure 23C:
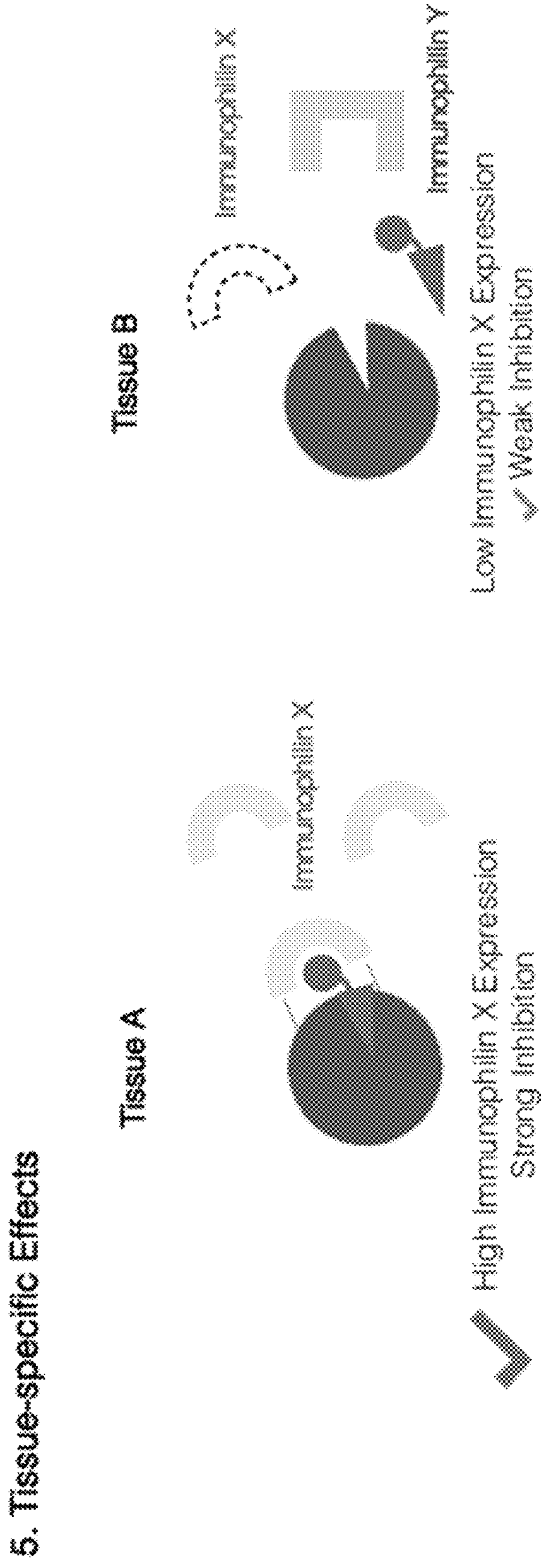
Figure 26:
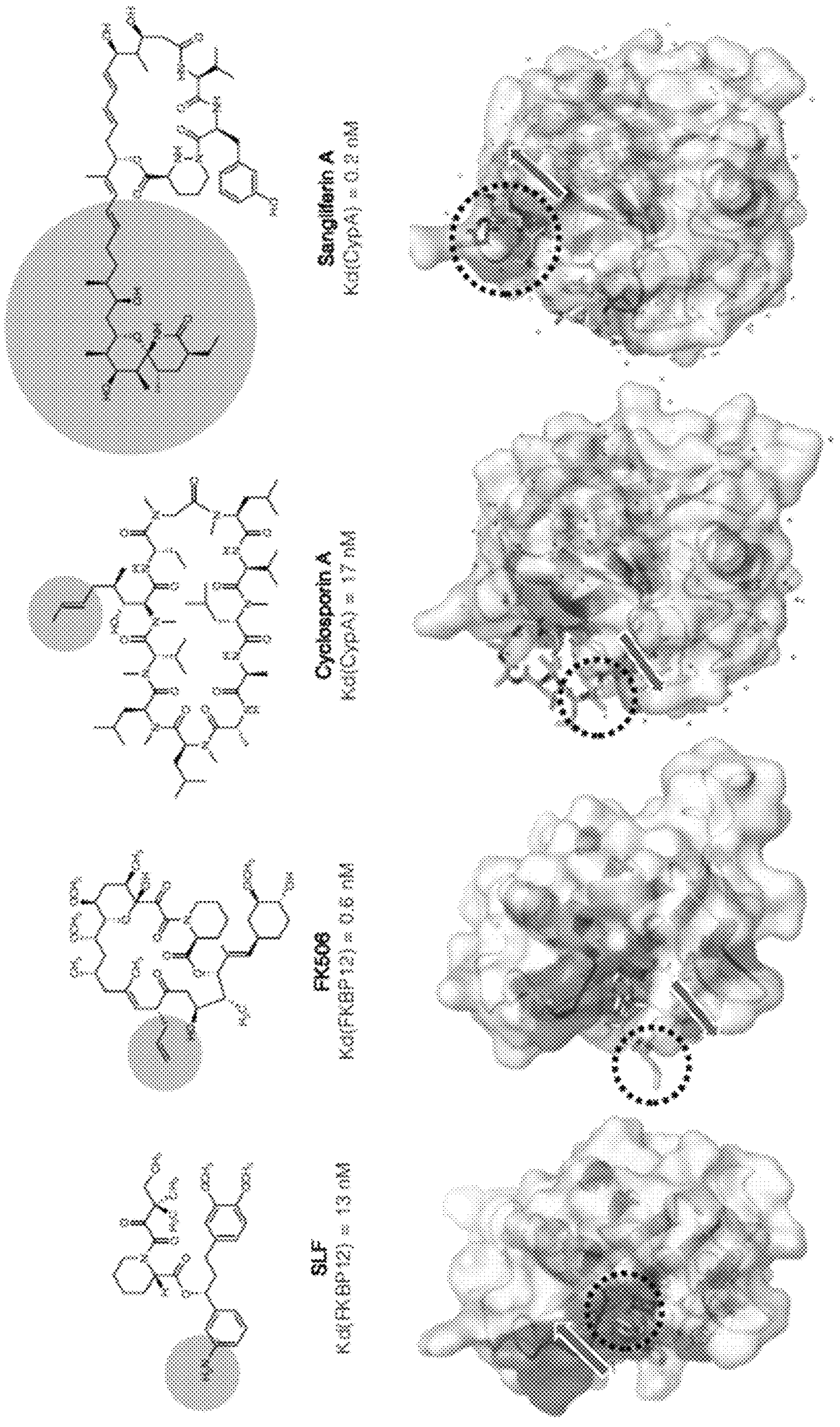
FIG. 26. Src kinase inhibitors. Proof of concept study and brain tumor applications. Immunophilin ligands.
Figure 29:
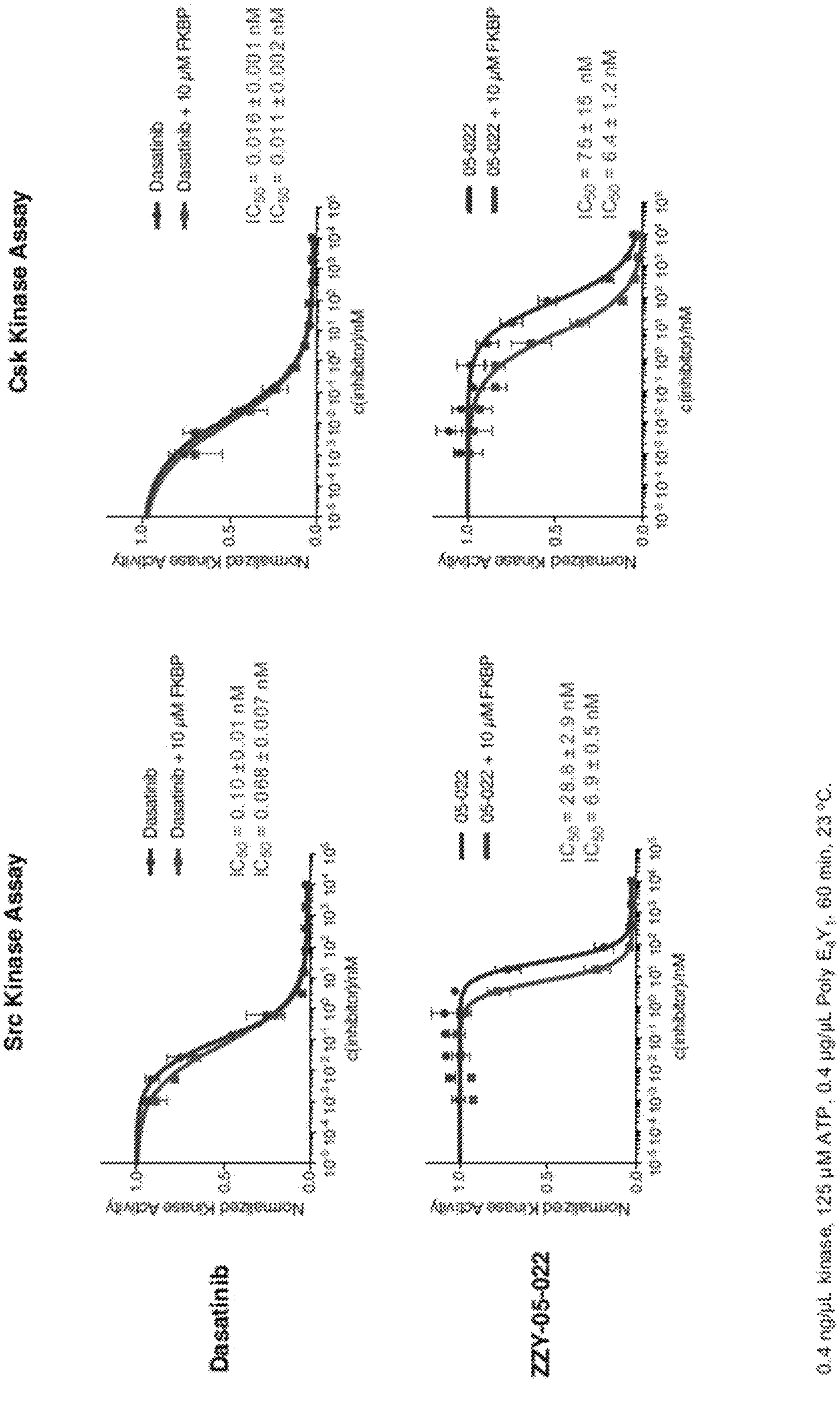
FIG. 29. Activity of ZZY05-022 is dependent on FKBP12.
Figure 30A:
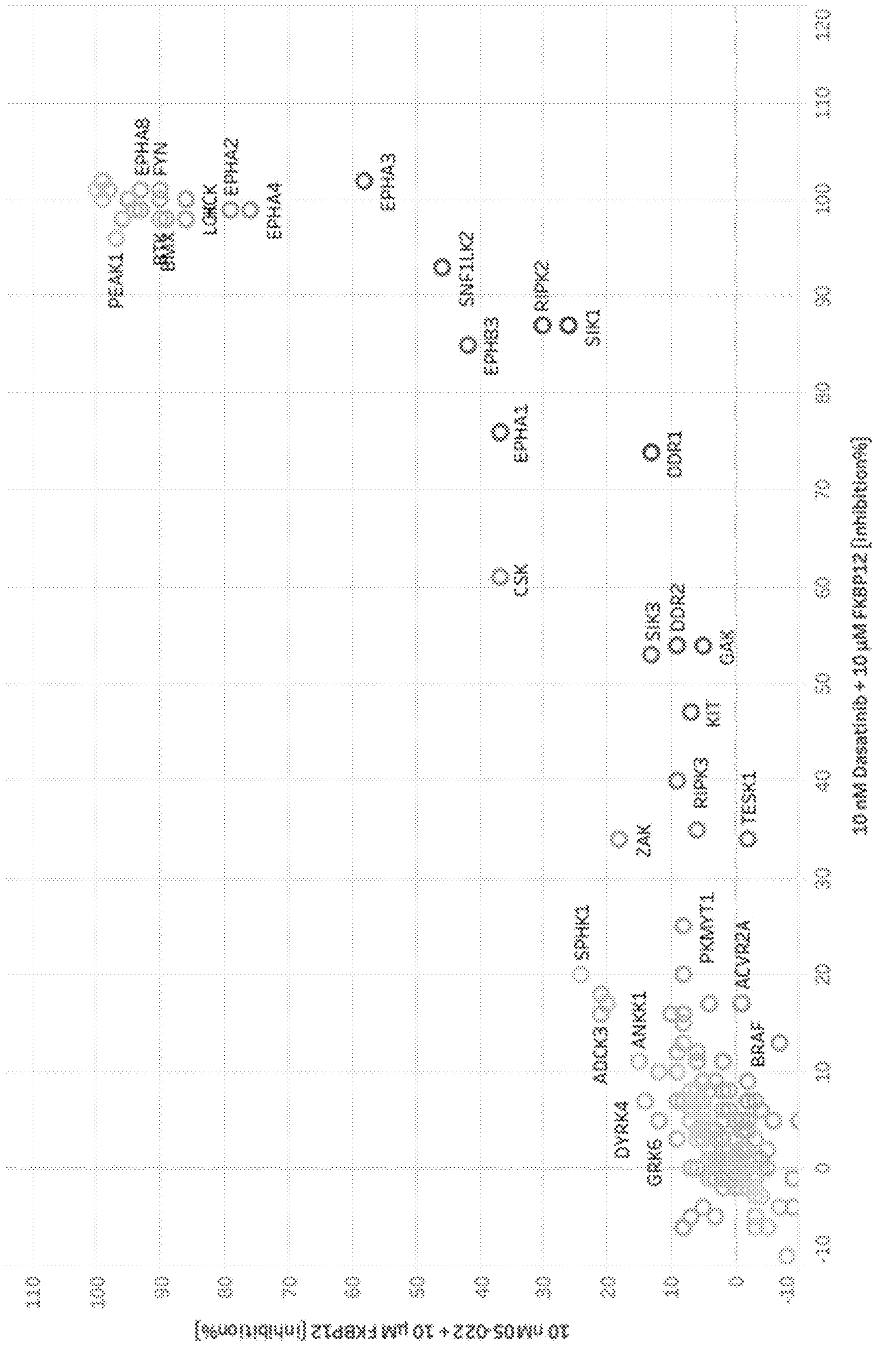
FIGS. 30A-30B. ZZY05-022 has similar target scope to dasatinib.
Figure 30B:
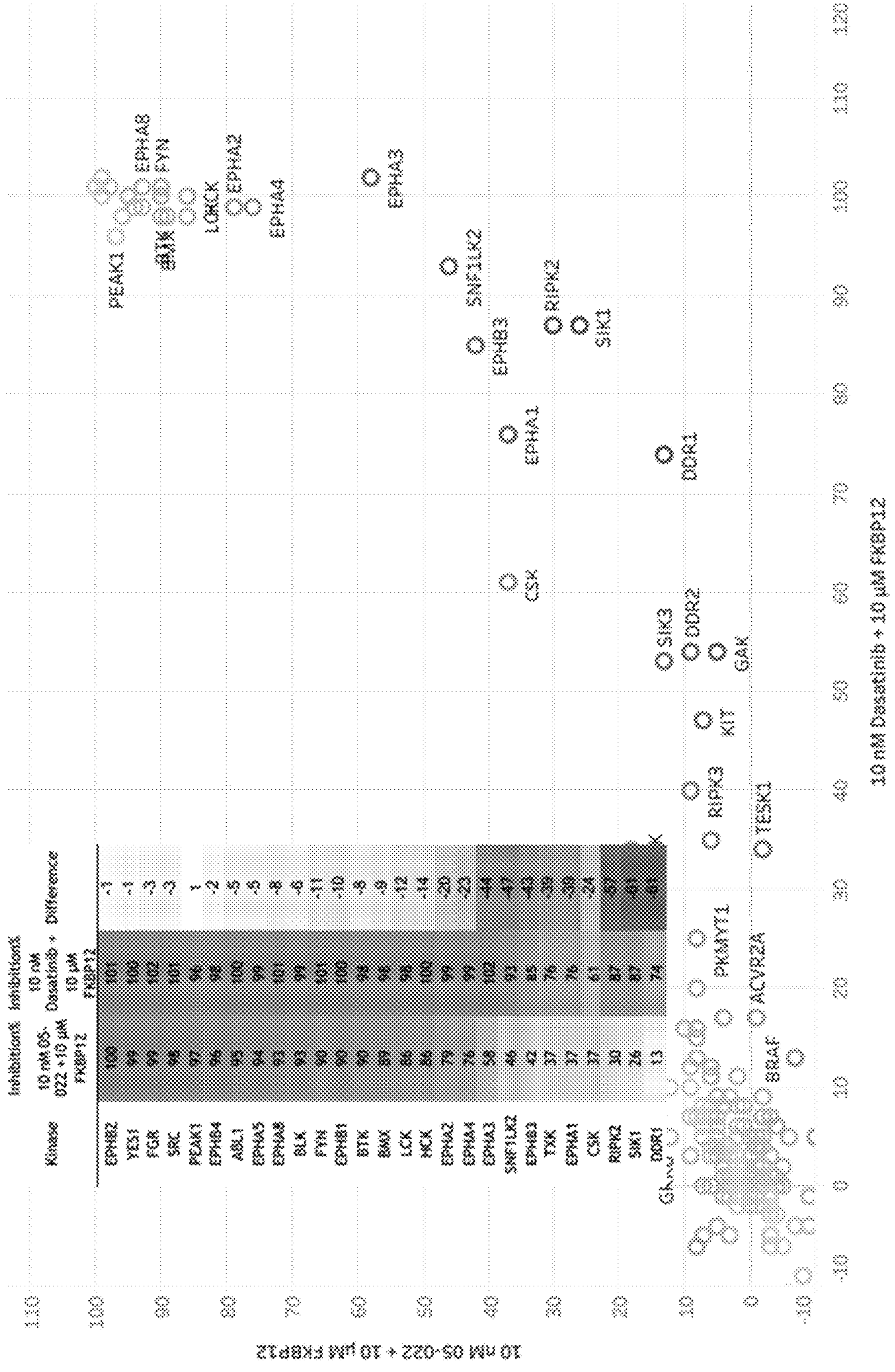
Figure 31:
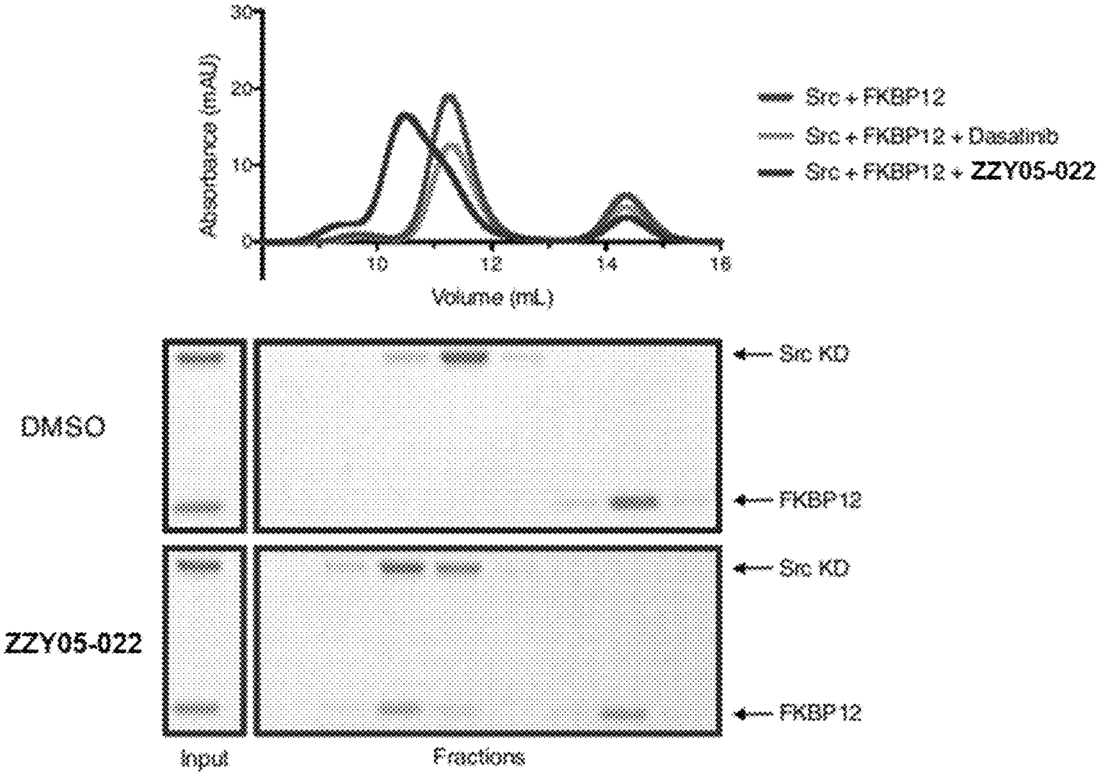
FIG. 31. Src, FKBP12, and ZZY05-022 form a stable ternary complex. Concentrations at injection: Src kinase domain (50 μM), FKBP12 (50 μM), dasatinib or ZZY05-022 (100 μM).
Figure 32:
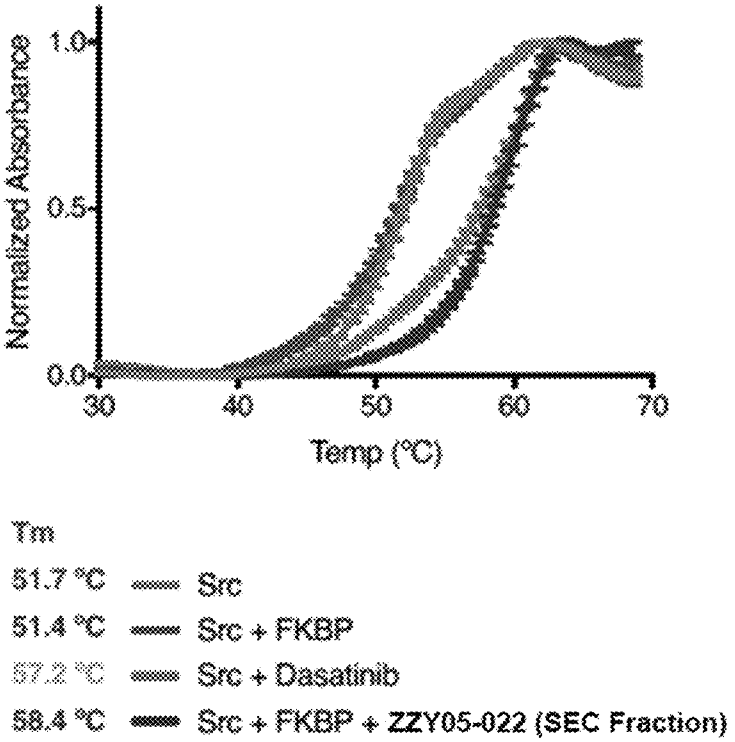
FIG. 32. Src, FKBP12, and ZZY05-022 form a stable ternary complex. Assay concentrations: Src kinase domain (1 μM), FKBP12 (0 or 1 μM), dasatinib (1 μM), ZZY05-022 (1 μM), SYPRO Orange (5×).
Figure 33:
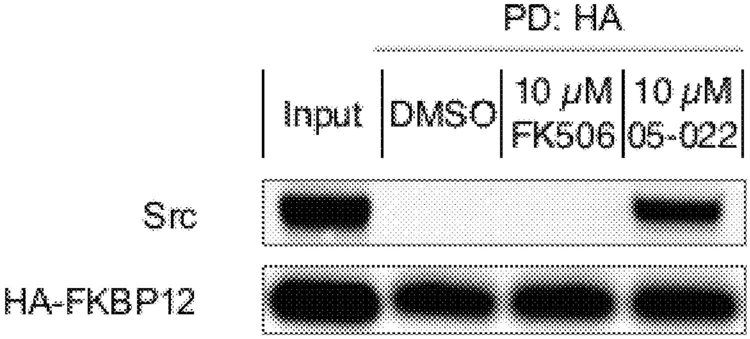
FIG. 33. Src, FKBP12, and ZZY05-022 form a stable ternary complex. Pulldown was performed with Jurkat cell lysate (1 mg/mL, 200 μL), supplemented with 2 μg HA-FKBP12. Pulldown/wash buffer: 50 mM Tris 7.4, 120 mM NaCl, 1% NP-40, 1 mM EDTA, phosphatase/protease inhibitors.
Figure 34A:
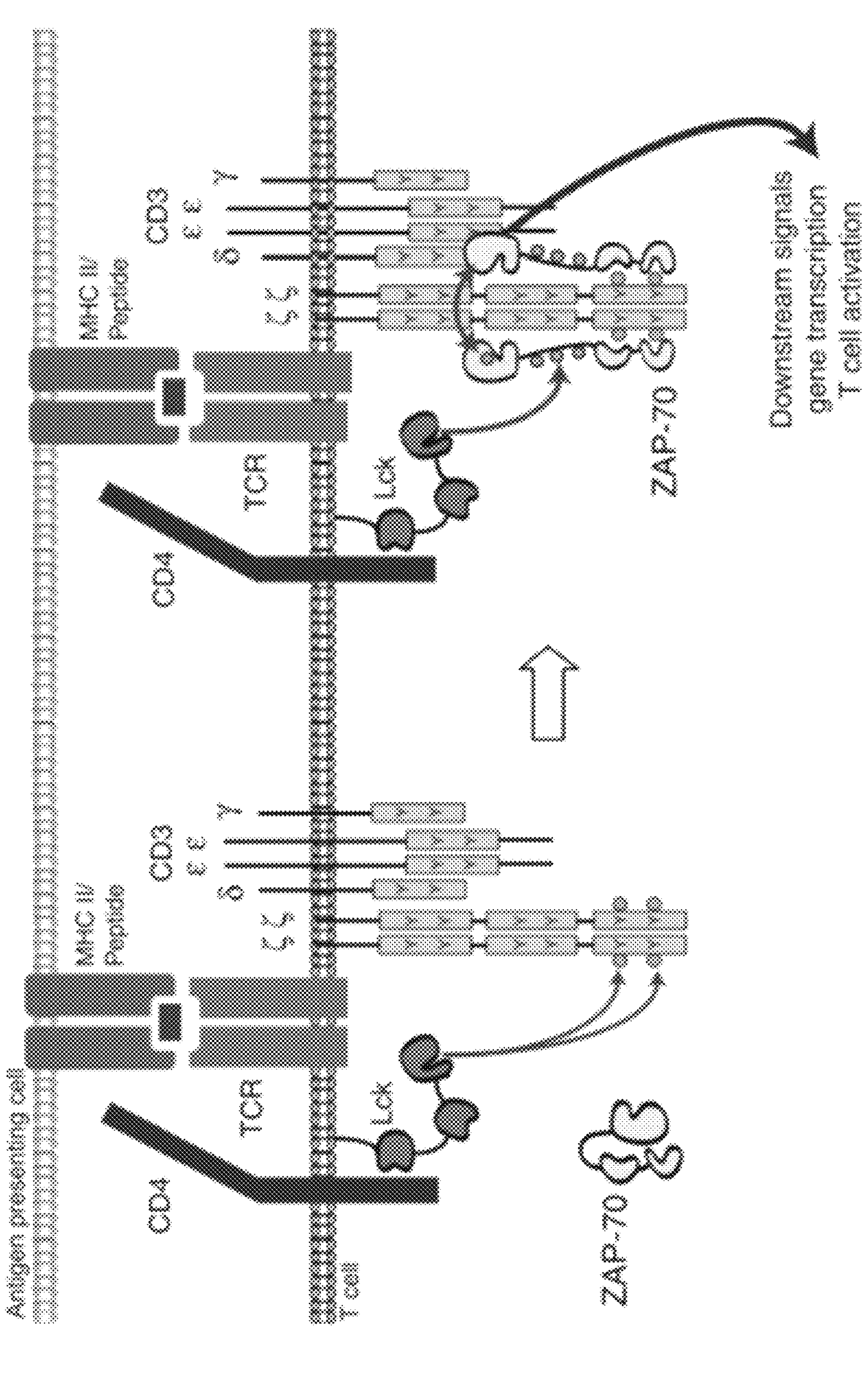
FIGS. 34A-34B. ZZY05-022 potently inhibits p-Tyr signaling in Jurkat cells.
Figure 34B:
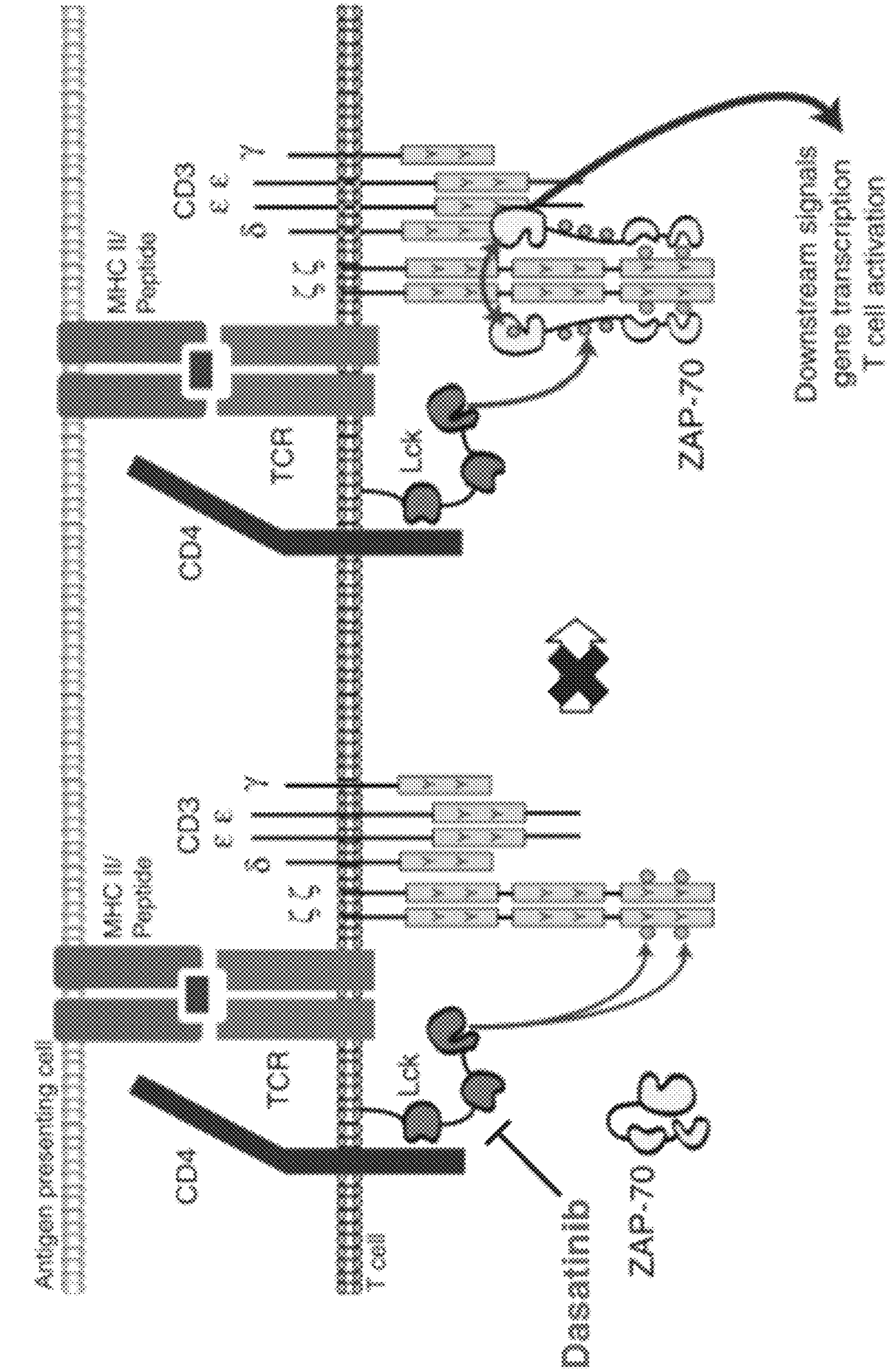
Figure 35:
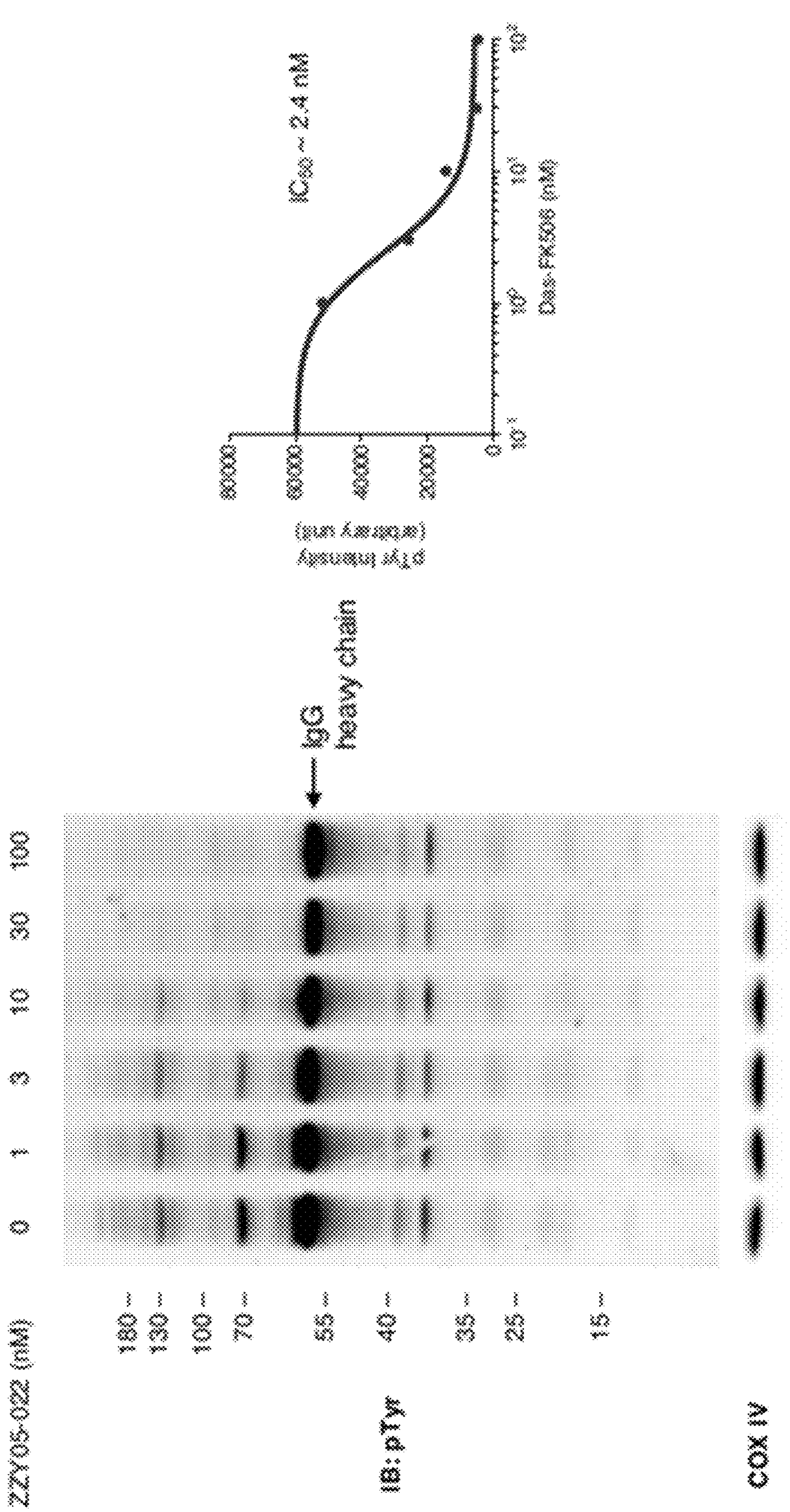
FIG. 35. ZZY05-022 potently inhibits p-Tyr signaling from CD3 crosslinking in Jurkat cells. Jurkat cells ($1\times10^6$/mL) were treated with the indicated drugs for 1 h, then stimulated with anti-CD3 mAb OKT3 (5 μg/mL) for 5 min. before lysis and analysis.
Figure 36:
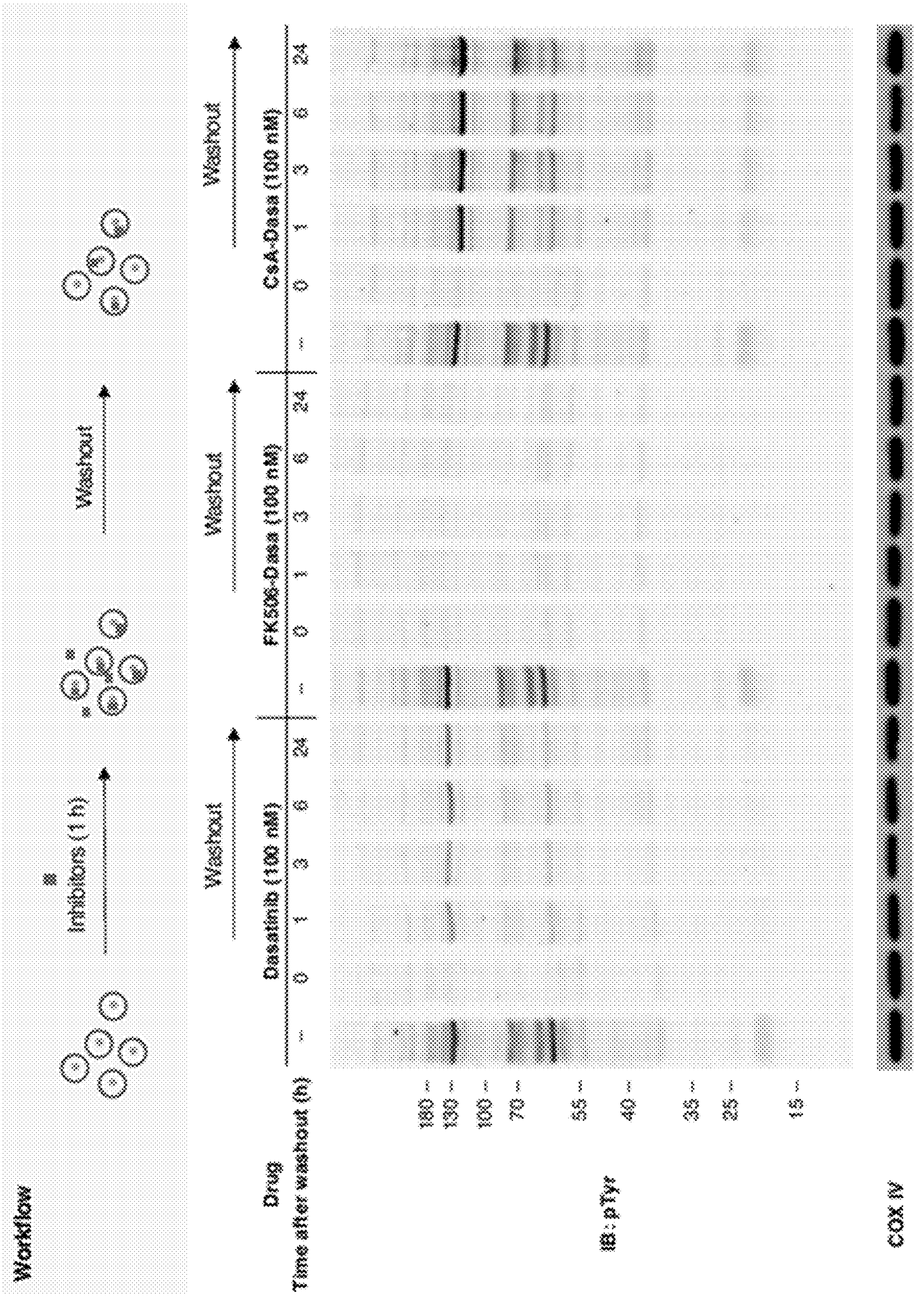
FIG. 36. Effect of ZZY05-022 is durable after washout. Jurkat cells ($1\times10^6$/mL) were treated with 100 nM of the indicated compounds for 1 h, then were washed 3 times with PBS and resuspended in culture media. Samples were taken at the indicated time points and lysed immediately.
Figure 37:
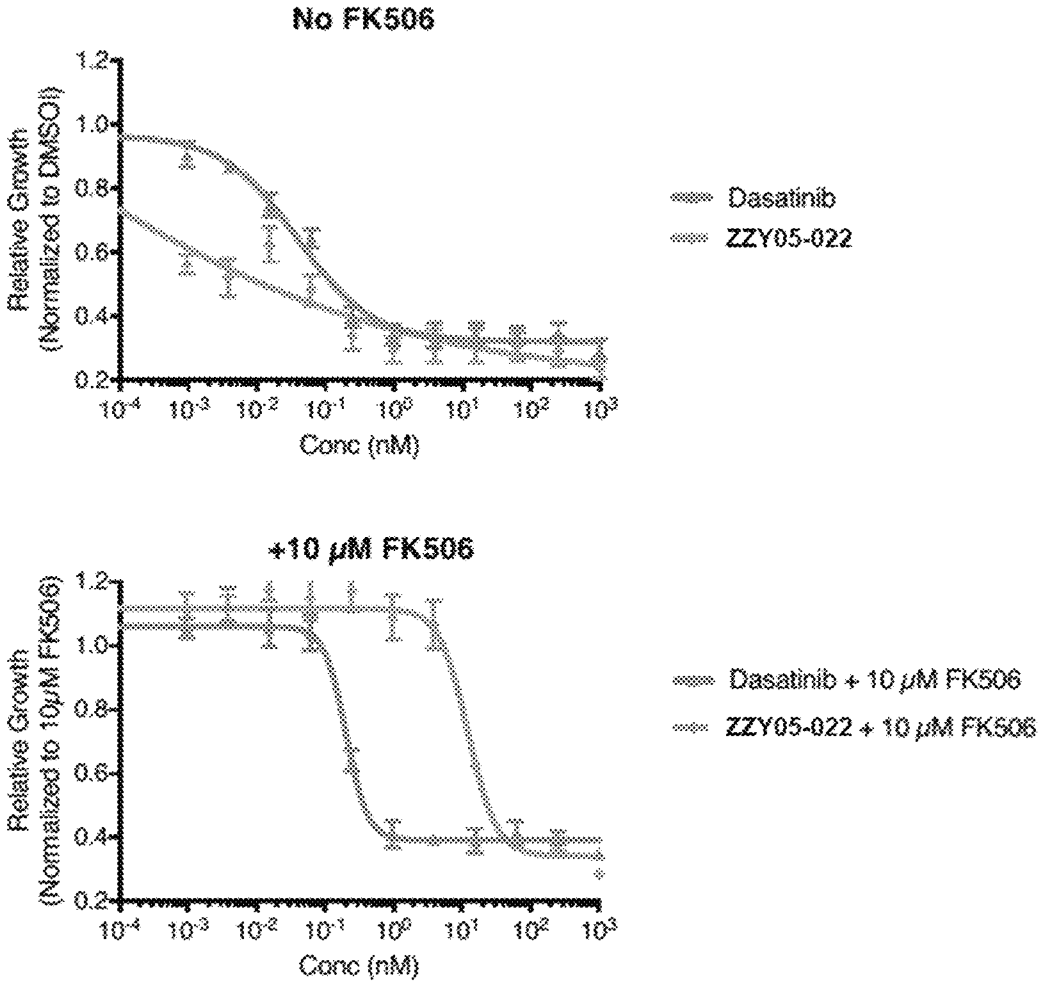
FIG. 37. ZZY05-022 shows FKBP-dependent growth inhibition of Bcr-Abl Cell Line. K562 (seeding density $5\times10^4$/mL) cells, 72h treatment.
Figure 39:
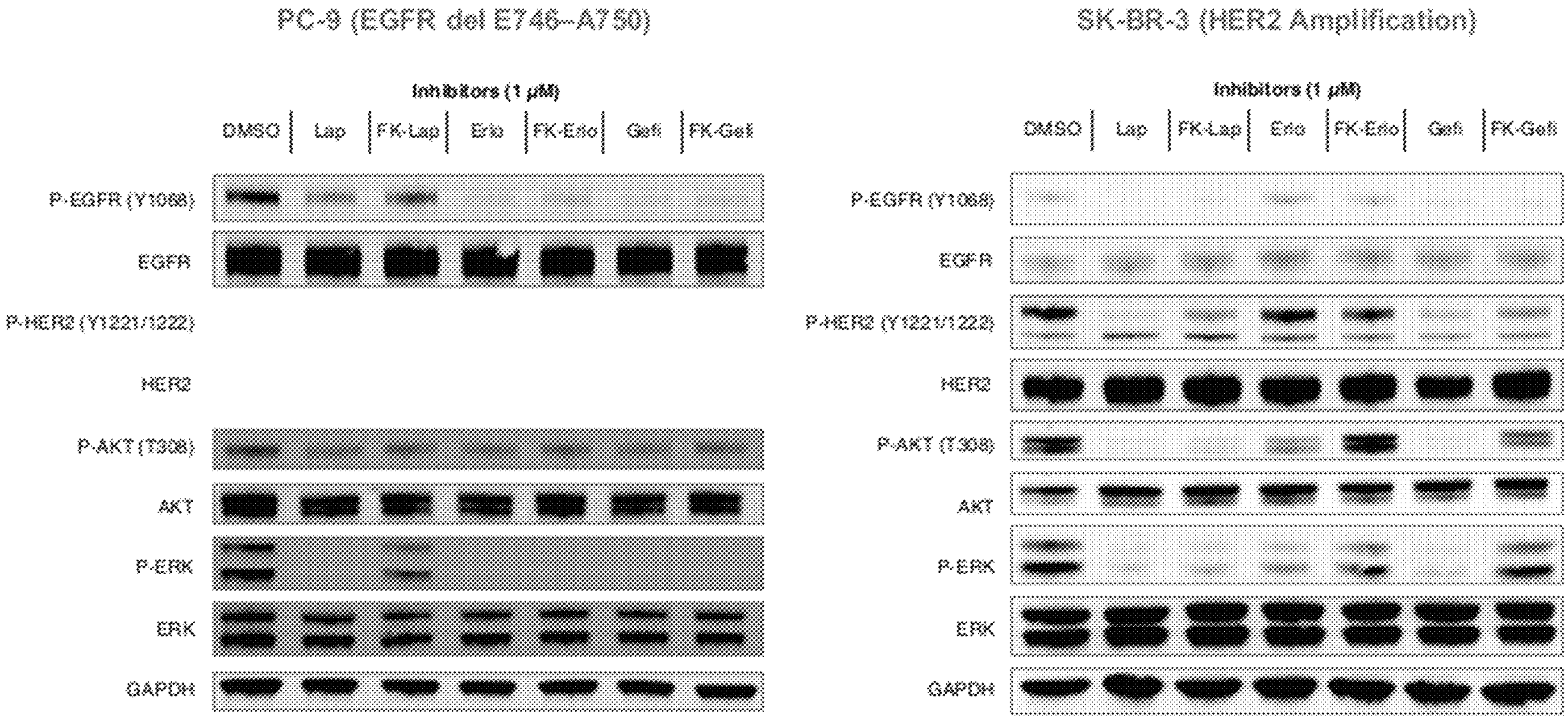
FIG. 39. FK506-EGFRi displays similar pharmacology to parent inhibitor, albeit slightly less polar. PC-9 or SK-BR-3 cells, 4 h treatment.
Figure 40:
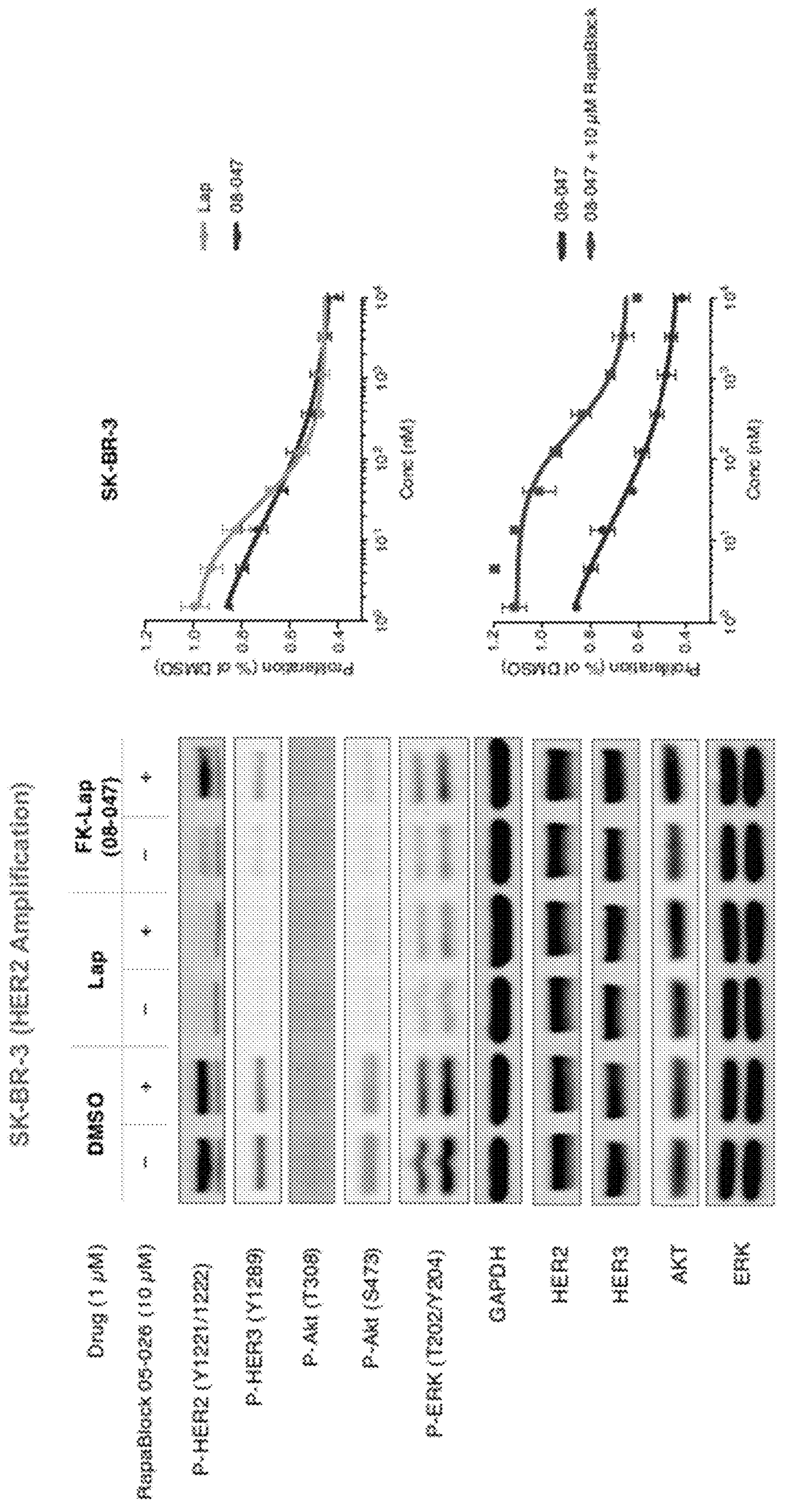
FIG. 40. The inhibitory effects of FK506-EGFRi is dependent on FKBP12, and is reversed by RapaBlock.
Figure 42:
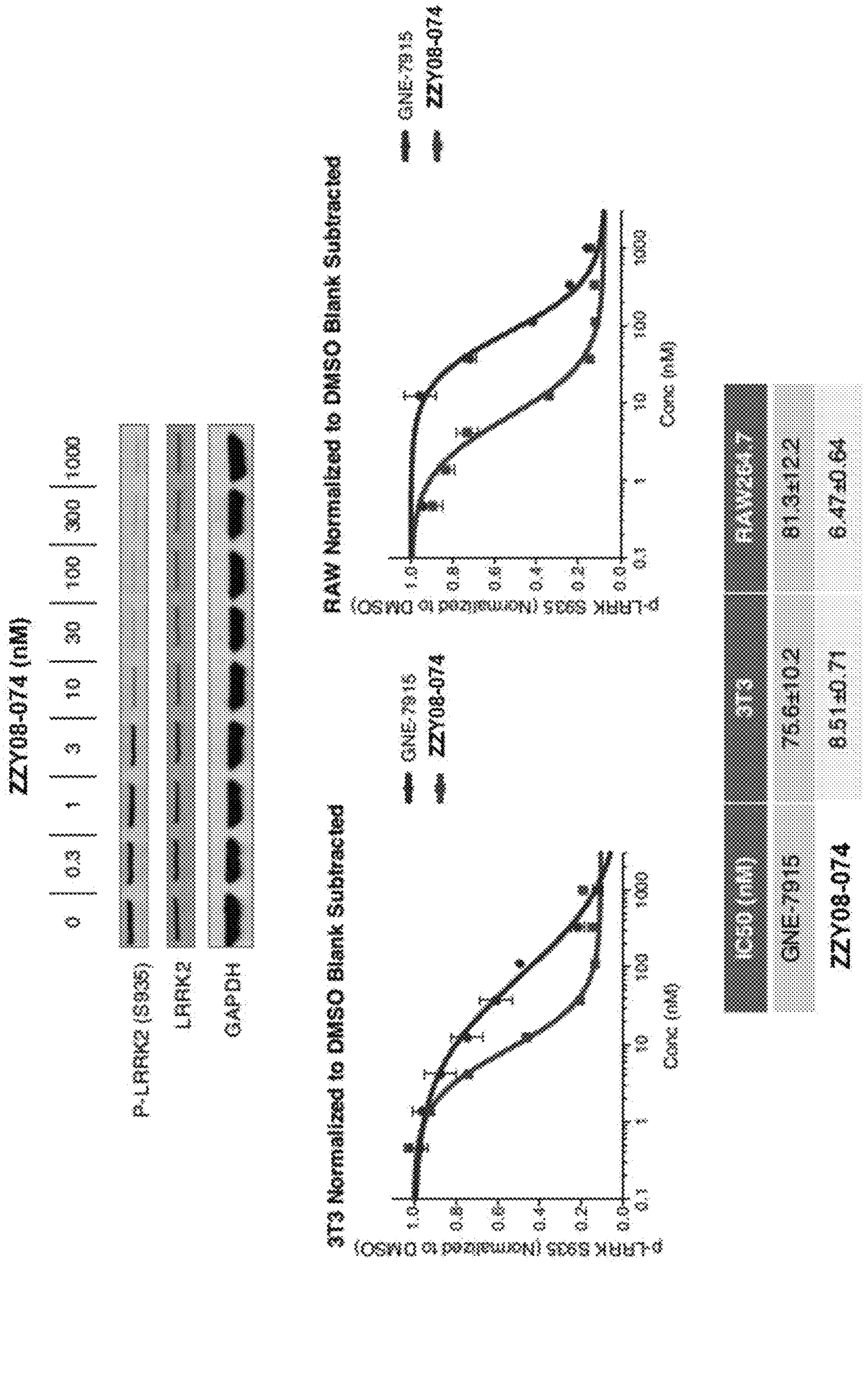
FIG. 42. Compound ZZY08-074 demonstrates more potent cellular activity than its parent compound GNE-7915. 3T3 or RAW264.7 cells (MJFF cell line), 2 h treatment.
Figure 45:
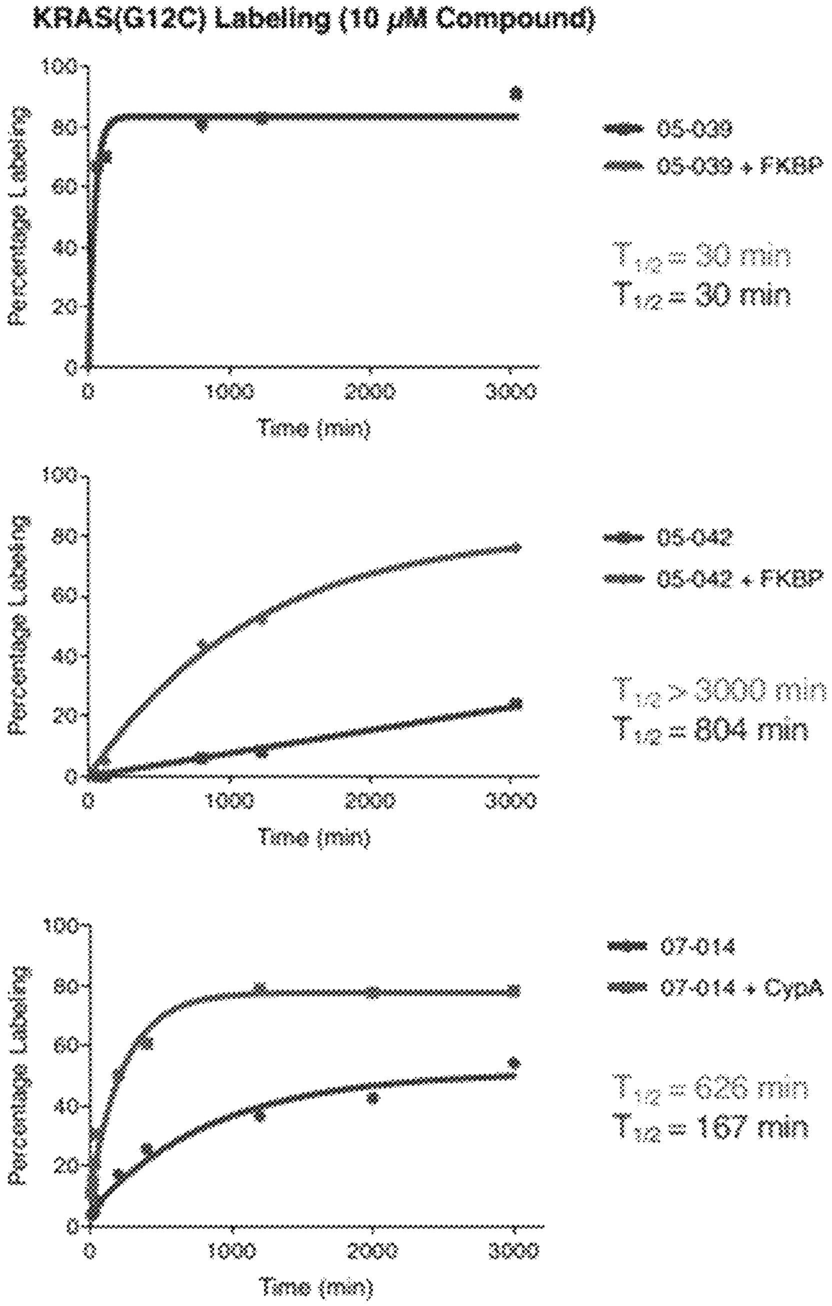
FIG. 45. Immunophilins accelerate the reaction between $KRAS^{G12C}$ and hybrid ligands. Assay conditions: 4 μM K-Ras+10 μM immunophilin (if indicated)+10 μM Compound; 20 nM HEPES 7.5, 150 mM NaCl, 1 mM $MgCl_2$, 23° C., 1% DMSO. Percentage labeled was measured by LC-MS analysis of the reaction mixture.
Figure 47:
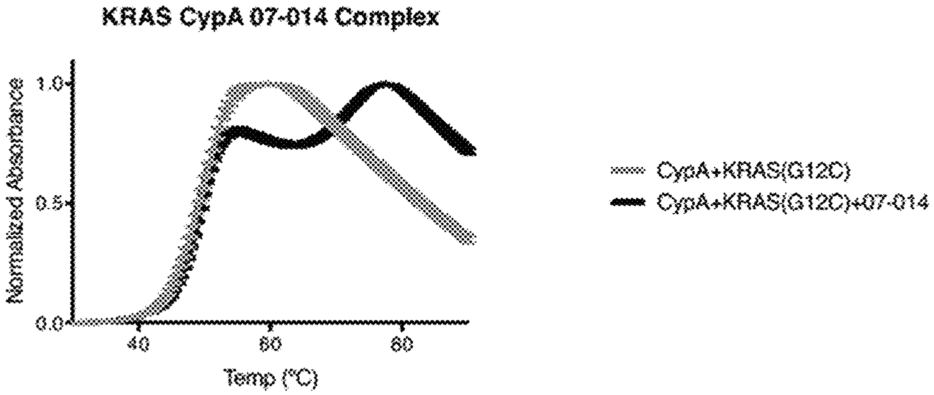
FIG. 47. The KRAS•CypA•ZZY07-014 complex displays 2-stage melting curve.
Figure 48:
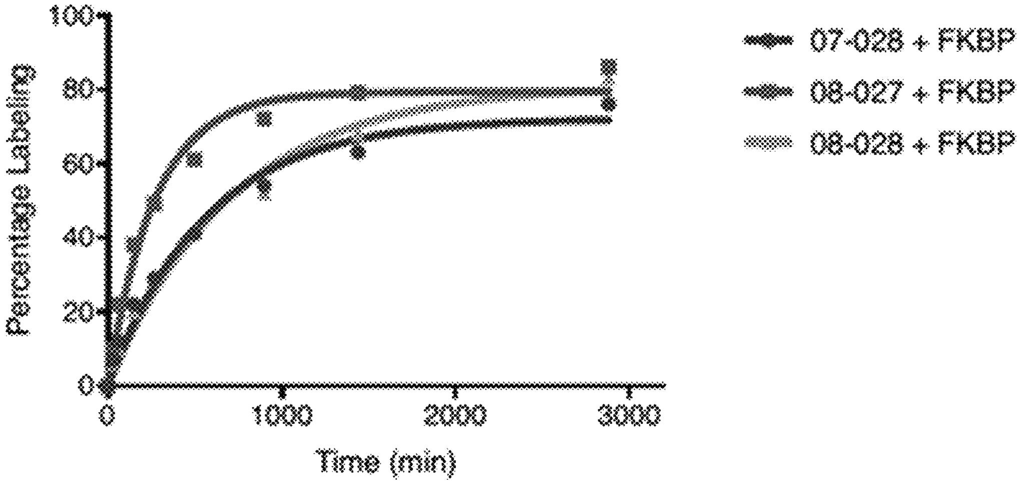
FIG. 48. Limited linker chemistry improves reaction kinetics. Assay conditions: 4 μM K-Ras+10 μM immunophilin (if indicated)+10 μM Compound; 20 nM HEPES 7.5, 150 mM NaCl, 1 mM $MgCl_2$, 23° C., 1% DMSO.
Figure 49:
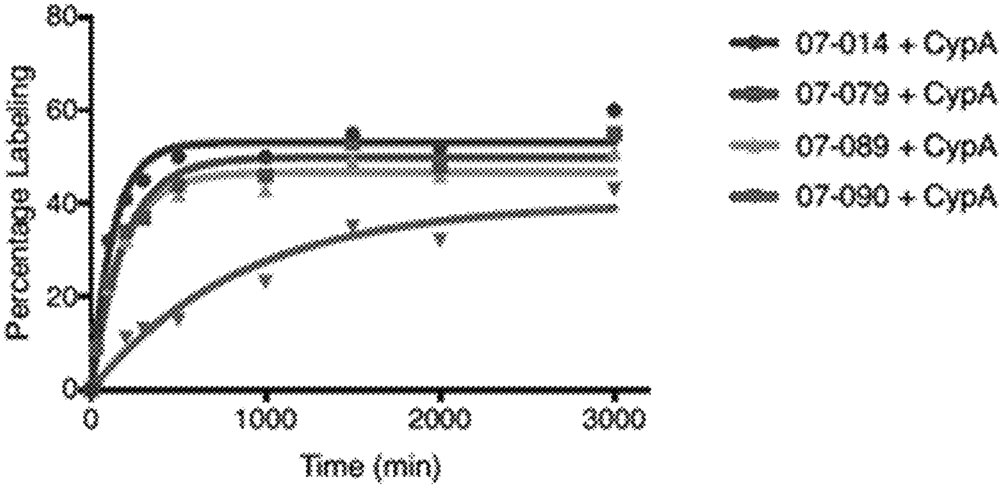
FIG. 49. Changing the linker. Assay conditions: 4 μM K-Ras+10 μM immunophilin (if indicated)+10 μM Compound; 20 nM HEPES 7.5, 150 mM NaCl, 1 mM $MgCl_2$, 23° C., 1% DMSO.
Figure 50:
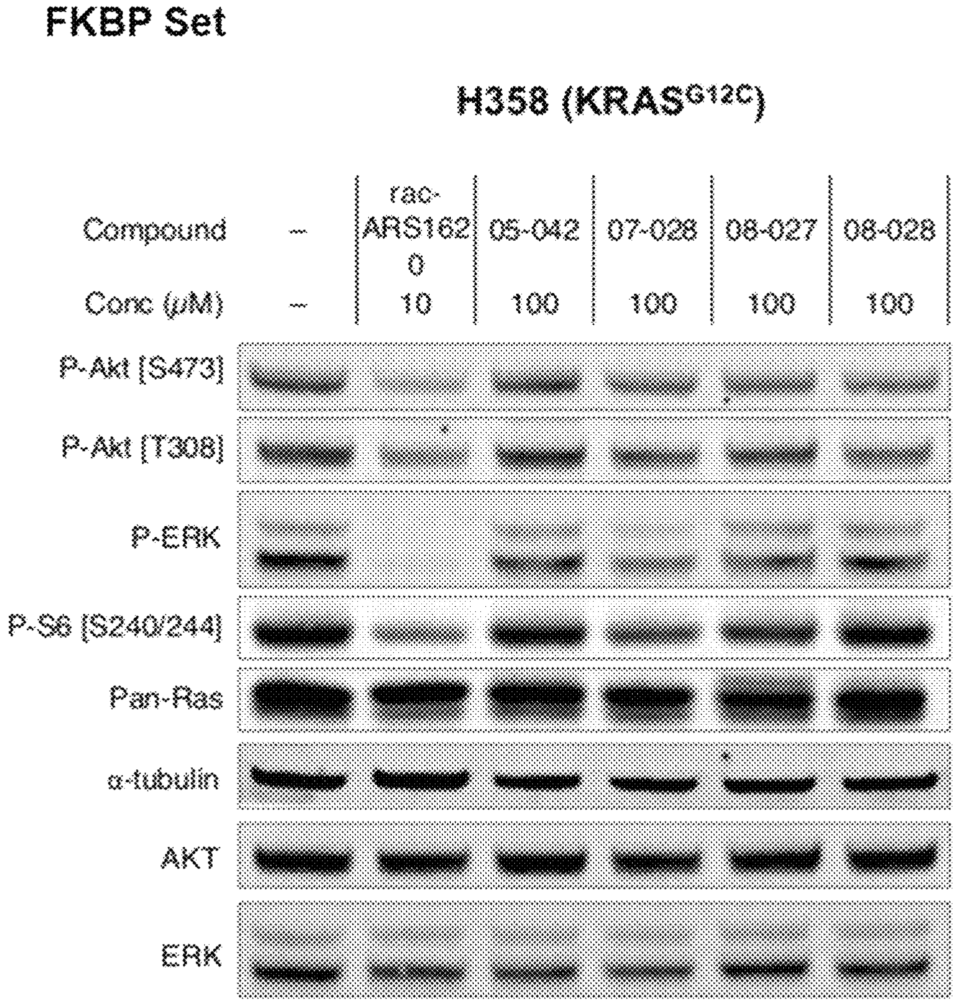
FIG. 50. Cellular efficacy, 24 h.
Figure 51:
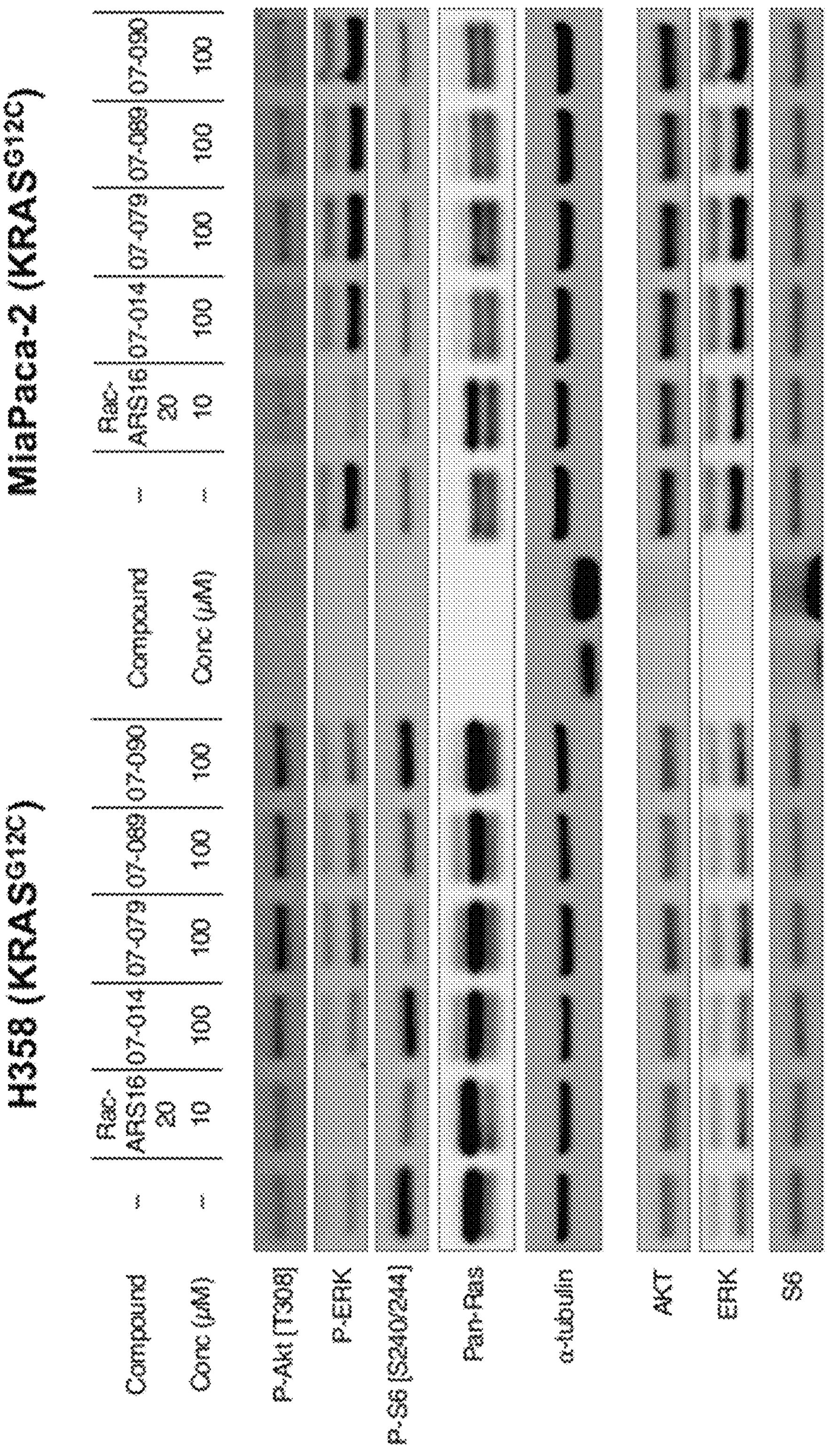
FIG. 51. Cellular efficacy, 24 h.
Figure 52:
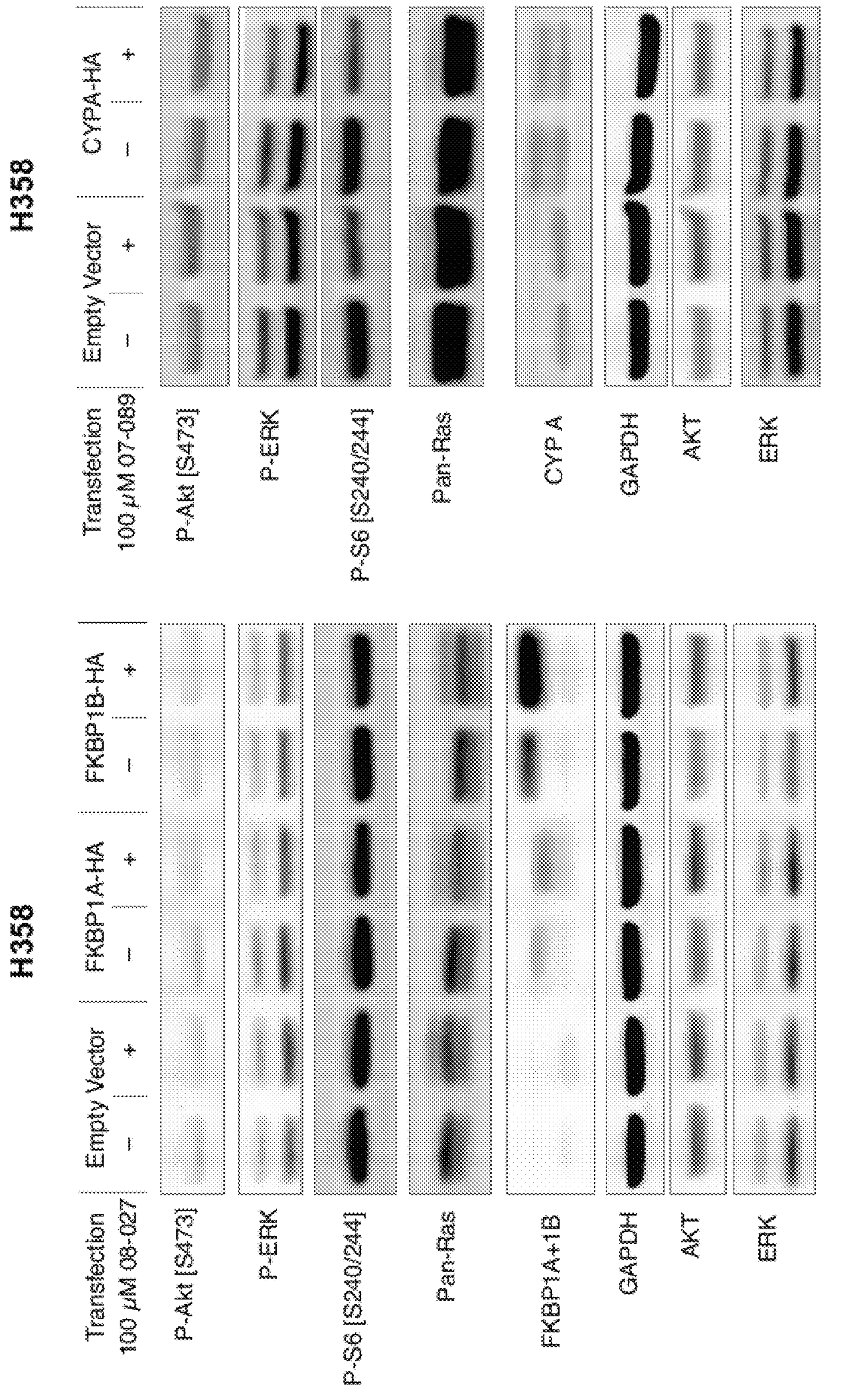
FIG. 52. Overexpression of either FKBP or CypA did not improve cellular efficacy. H358 cells, treated with inhibitors for another 24 h, 24 h post-transfection.
Figure 54:
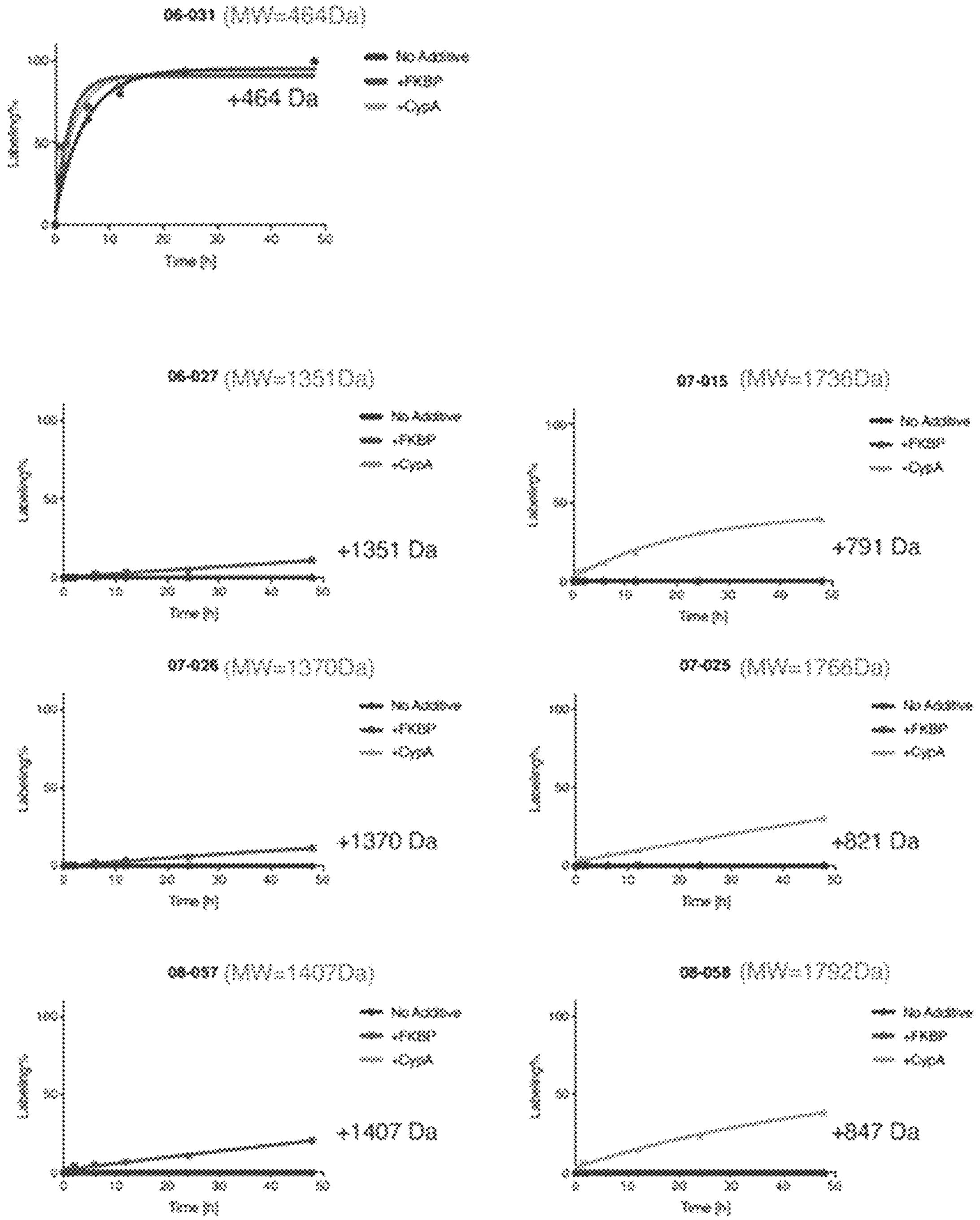
FIG. 54. Molecules built on the M72C inhibitor scaffold display similar dependence on immunophilins. Assay conditions: 4 μM H-Ras M72C (GDP)+10 μM immunophilin (if indicated)+10 μM Compound; 20 nM HEPES 7.5, 150 mM NaCl, 1 mM $MgCl_2$, 23° C., 1% DMSO.
Figure 56:
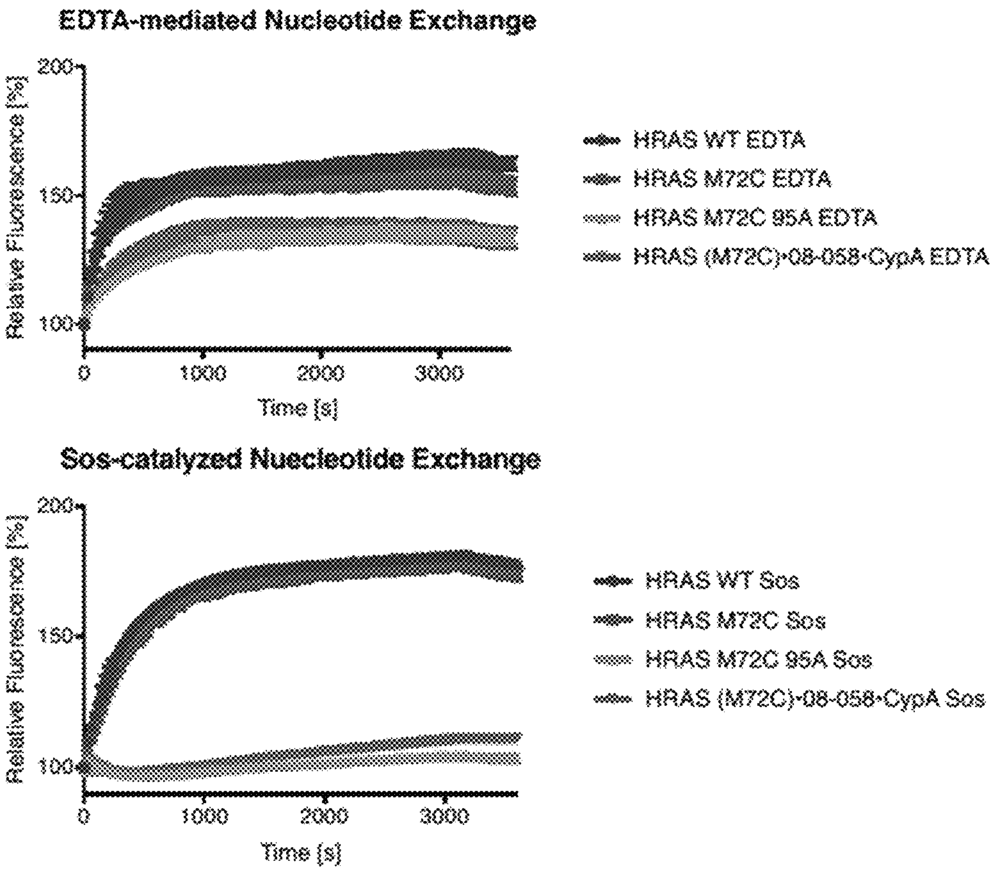
FIG. 56. HRAS•CypA•ZZY08-058 forms a ternary complex, and inhibits Sos-mediated nucleotide exchange. Assay conditions: 1 μM Ras•GDP, 1 μM Mant-GDP, 20 mM EPES 7.5, 150 mM NaCl, 10 mM EDTA or 1 μM Sos. 95A is synonymous to ZZY06-031.
Figure 57:
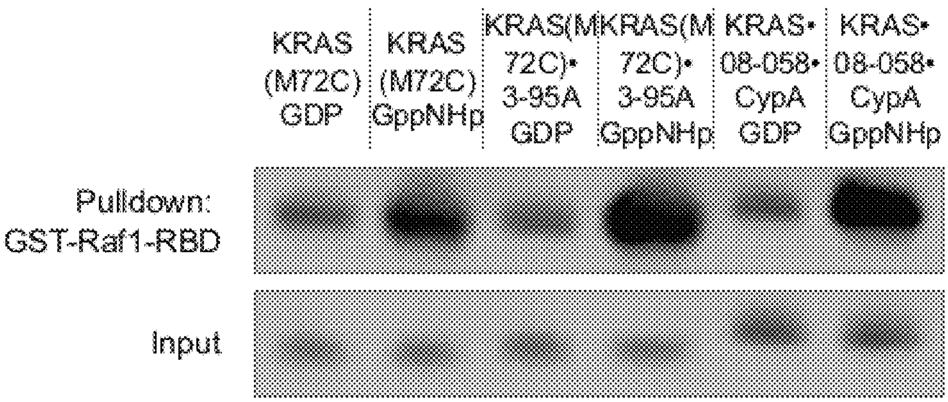
FIG. 57. HRAS•CypA•08-058 ternary complex does not seem to impair Ras•Raf binding. Pulldown conditions: 100 nM KRAS, 50 μg/mL BSA, 20 mM HEPES 7.5, 150 mM NaCl, 5 mM $MgCl_2$, 1 mM DDT, 1% NP-40. GppNHp loaded proteins were prepared by EDTA-mediated nucleotide exchange.
Figure 59:
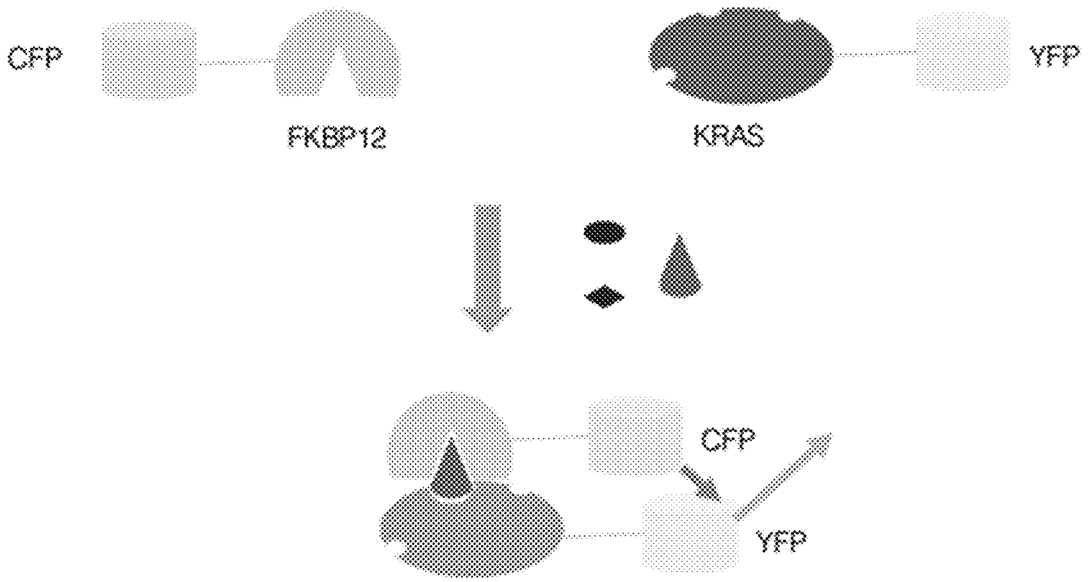
FIG. 59. Screening novel "dimerizers".

Interestingly, three homodimers of dasatinib containing linkers of various length (FIG. 19A) had no measurable inhibition of phosphotyrosine signal. FK506-dasatinib was effective at concentrations as low as 10 nM ($EC_{50}$=3.4 nM, FIG. 16C). To profile the target scope of FK506-dasatinib in live cells, we employed a lysine-targeted chemoproteomic probe XO44, which irreversibly reacts with a conserved lysine in the ATP pocket of kinases and allows the quantification of the occupancy of the intracellular kinome by inhibitors by label-free mass spectrometry. We found that with both dasatinib and FK506-dasatinib at 100 nM, an identical set of 9 kinases were inhibited >70% (FIG. 16B and FIG. 20) among the 139 kinases captured by the probe. This is consistent with previous knowledge of dasatinib as well as our findings in the biochemical profiling with purified kinases. That the selectivity of FK506-dasatinib was indistinguishable from dasatinib was not surprising—none of kinases displaying differential response to the two inhibitors in the biochemical assay (FIG. 14C) were highly expressed in Jurkat cells or detected by the XO44 probe. Notwithstanding, one remarkable distinction of FK506-dasatinib from dasatinib we observed was its prolonged residence time in cells. We measured the change of phosphotyrosine levels at various timepoints after treating Jurkat cells with 100 nM dasatinib or FK506-dasatinib for 1 h and removing the drug (FIG. 16D). Restored phosphotyrosine bands were seen at as early as 1 h in dasatinib-treated cells. By contrast, no increase in phosphotyrosine signals could be detected even at 24 h after the drug washout in FK506-dasatinib-treated cells, suggesting a mechanism that supports durable cellular retention of the drug. Unusually long cellular retention times have also been previously observed with other drugs that engage FKBP proteins. We believe that in these cases, the abundant intracellular FKBP proteins serve as a sink for these drugs, capturing them as in a FKBP-drug complex that cannot cross the plasma membrane to exit the cell and hence significantly lengthening their residence inside the cell.

The unique dependency of FK506-dasatinib on FKBP proteins implied that it may be exploited to modulate the function of these molecules. We reasoned that if FK506-dasatinib is co-administered with another ligand of FKBP ("blocker"), the latter would attenuate the activity FK506-dasatinib by competing for the intracellular pool of FKBP. We chose RapaBlock, a non-immunosuppressive FK506 analog developed in our lab that maintains potent binding to FKBP12 ($K_d$=3.7 nM), as the blocker molecule. When a combination of 100 nM FK506-dasatinib and 10 μM RapaBlock were used in the Jurkat cell activation assay, the inhibition of phosphotyrosine signaling by FK506-dasatinib was completely neutralized (FIG. 13A, lanes 3 and 6). Meanwhile, the blocker compound had no in dasatinib-treated samples (FIG. 13A, lanes 2 and 5). In a separate application, we measured growth inhibition of K562 cells, a Bcr-Abl-driven cell lines sensitive to dasatinib treatment (FIG. 13B). Absent ZZY05-026, dasatinib and FK506-dasatinib inhibited the growth of K562 cells with comparable potency ($IC_{50}$ of 0.063 nM and 0.053 nM, respectively). Addition of 10 μM RapaBlock caused a >200-fold increase of the $IC_{50}$ value for FK506-Dasatinib (10.2 nM), in contrast to the minute shift of $IC_{50}$ for dasatinib (0.16 nM).

Figure 17B:
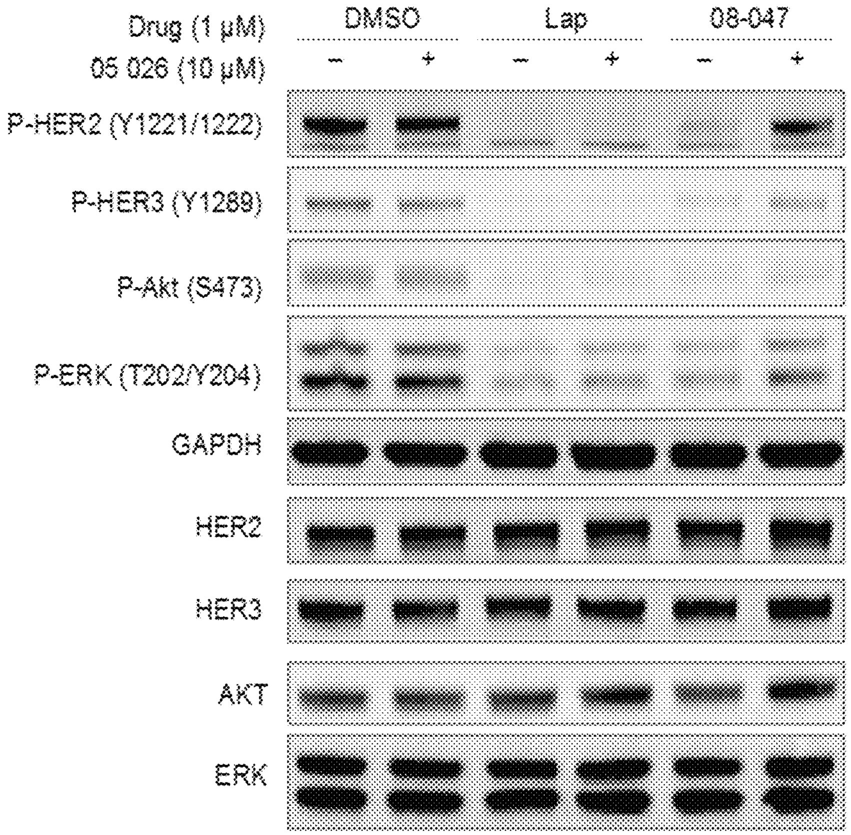
Figure 17C:
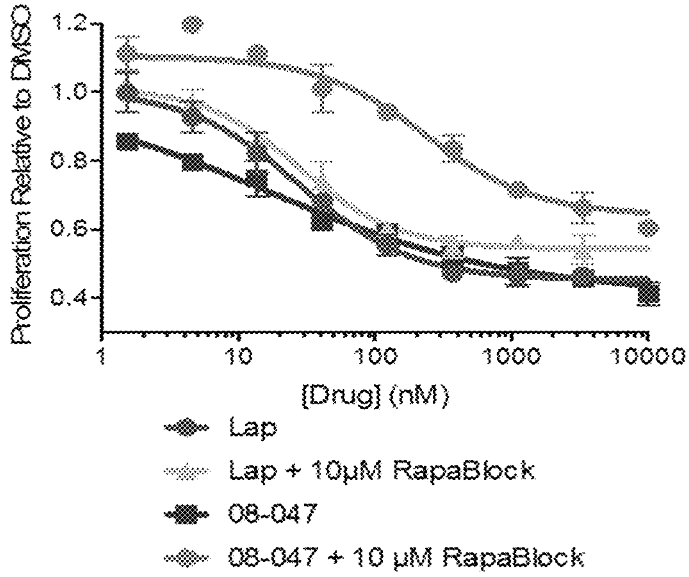
Figure 17F:
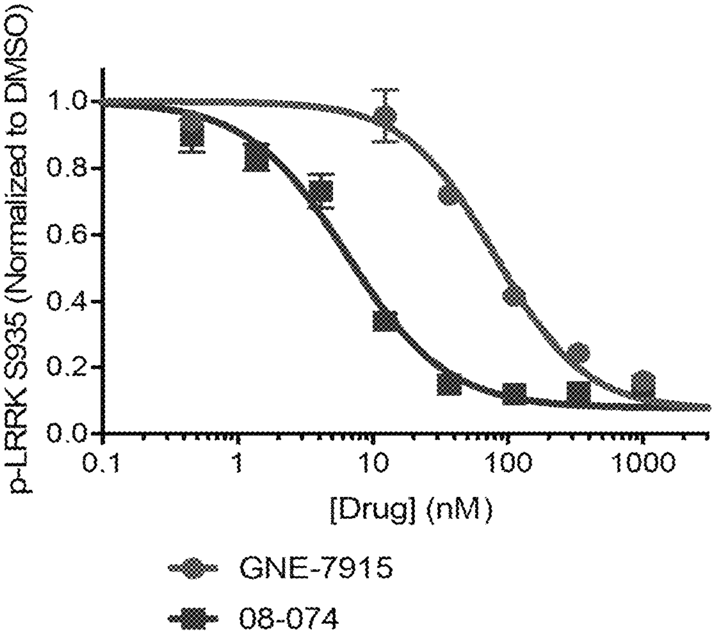
Figure 18:
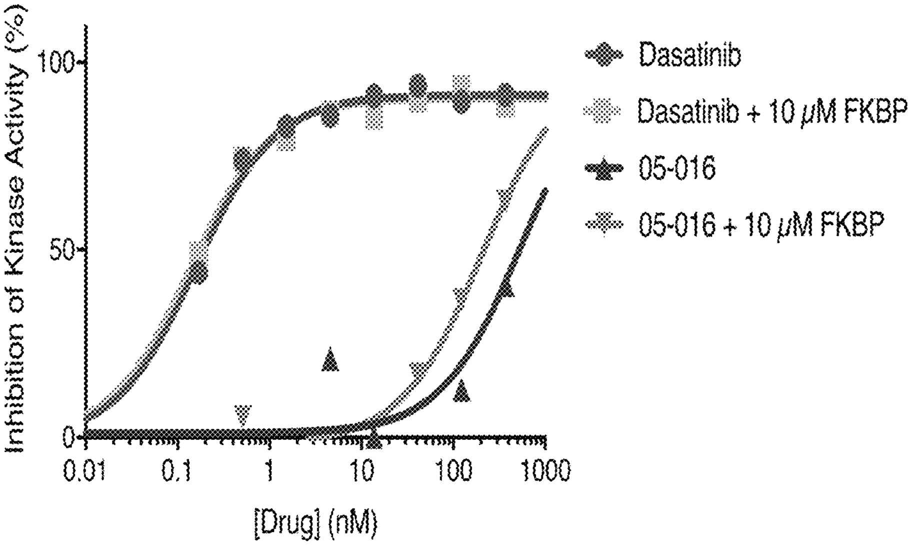
FIG. 18. A bispecific molecule built from Dasatinib and a different FKBP ligand (SLF) shows greatly diminished activity.

We extended our design strategy and prepared two other bispecific ligands based on the structures of an FDA-approved HER2/EGFR inhibitor (lapatinib) and an LRRK2 inhibitor in clinical development (GNE7915). FK506-lapatinib suppressed HER2 signaling in SK-BR-3 cells (a cell line with HER2-amplification) at 1 μM and inhibited the growth of this cell line with an $IC_{50}$ comparable to that of lapatinib (FIGS. 17A-17C). Both effects were attenuated by the addition of 10 μM RapaBlock. Interestingly, FK506-GNE7915 appeared to be more efficacious than its parent molecule GNE7915 at inhibiting the autophosphorylation of LRRK2, a kinase currently pursued as a promising therapeutic target for Parkinson's disease. Similar to the cases of FK506-dasatinib and FK506-lapatinib, RapaBlock rescued the inhibition of LRRK2 phosphorylation by FK506-GNE7915 to a near-baseline level. With the three case studies presented above, we anticipate that the same workflow could be applied to convert other kinase inhibitors into FKBP-dependent formats with similar if not better cellular activities, with the important recognition that exceptions may occur as in the case with FK506-Dasatinib/DDR2.

By chemically linking FK506 and ATP-site kinase inhibitors at their respective solvent-exposed sites, we have developed a method to build a new class of kinase inhibitors whose activity depends on an endogenous protein, FKBP12. These inhibitors are characterized by their ability to mediate the formation of a ternary complex of the drug, the target kinase and FKBP12, as well as their aptitude for activity modulation by another ligand of FKBP12. De novo complex formation has been exploited by nature as a strategy to create highly specific bioactive compounds, with notable examples including rapamycin (mTOR inhibitor), FK506 (calcineurin inhibitor), cyclosporin A (calcineurin inhibitor) and sanglifehrin (IMPDH2 inhibitor). Medicinal chemistry innovations have led to compounds with improved pharmaceutical property or efficacy (e.g., the third-generation mTOR inhibitor RapaLink-1), yet with the same target as the parent natural inhibitor. Our method expands the targetable space by this mode of action far beyond those addressed by known natural products. The amenability of these bispecific kinase inhibitors towards activity modulation by a second molecule is unique and offers an additional dimension of pharmacological control. In theory, timed administration of the blocker molecule or using blocker molecules that have defined tissue distribution will allow us to choreograph the temporal and spatial effects of the inhibitor and achieve programmable kinase inhibition. While we have focused on protein kinases in this study, it seems reasonable to expect that the approach is also applicable to other classes of therapeutic targets, such as GTPases and histone modification enzymes.

Example 5: Immunophilin-Dependent Inhibitor Compounds
TABLE 6
| Compound structures of EGFR analogs. | |
|---|---|
| Compound | Structure |
| ZZY07-057 | 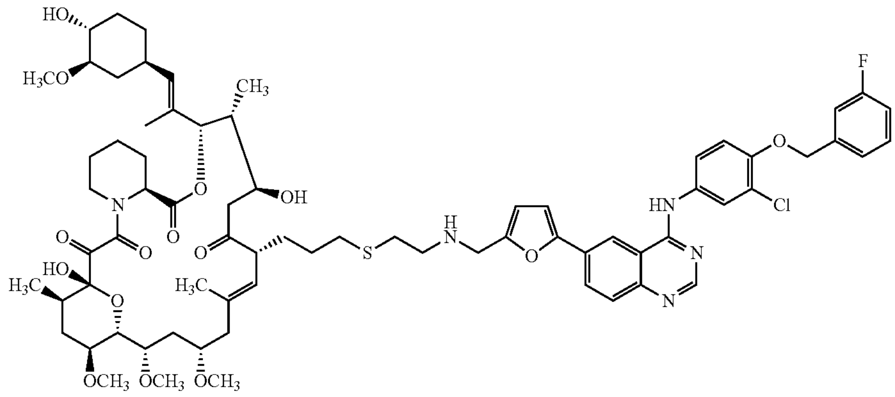 [SMILES: CO[C@H]1C/C(C)=C/[C@@H](CCCSCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |
| ZZY07-058 | 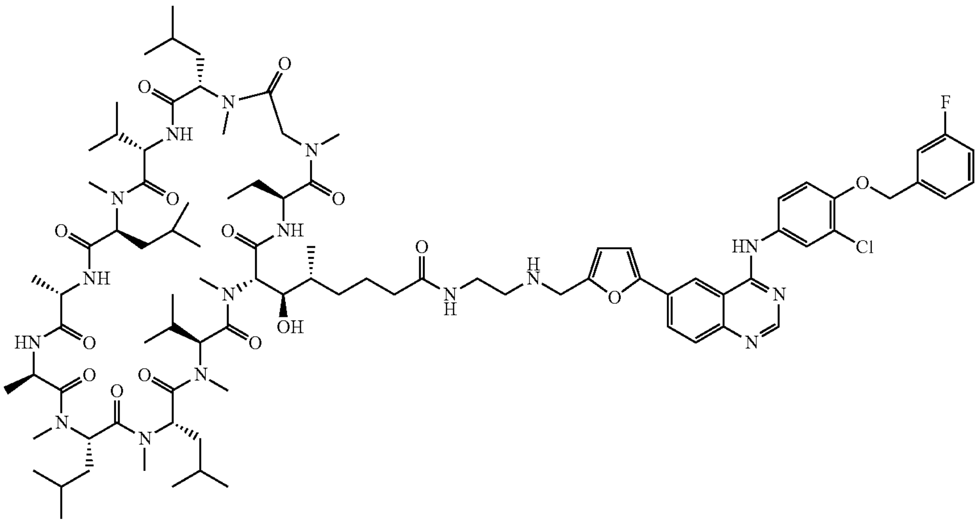 [SMILES: CC[C@@H]1NC(=O)[C@H]([C@H](O)[C@H](C)CCCC(=O)NCCNCc2ccc(-c3ccc4ncnc(Nc5ccc(OCc6cccc(F)c6)c(Cl)c5)c4c3)o2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O] |
| ZZY08-025 | 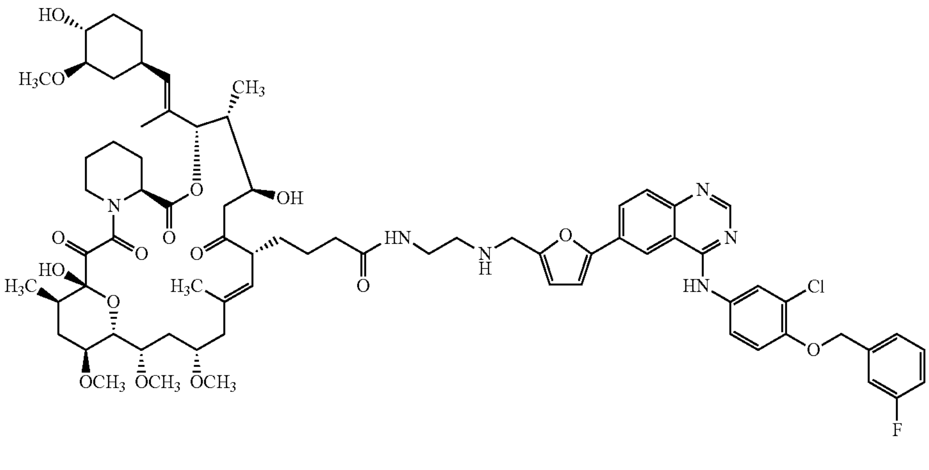 [SMILES: CO[C@H]1C/C(C)=C/[C@@H](CCCC(=O)NCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |

TABLE 6-continued
| Compound structures of EGFR analogs. | |
|---|---|
| Compound | Structure |
| ZZY08-047 | 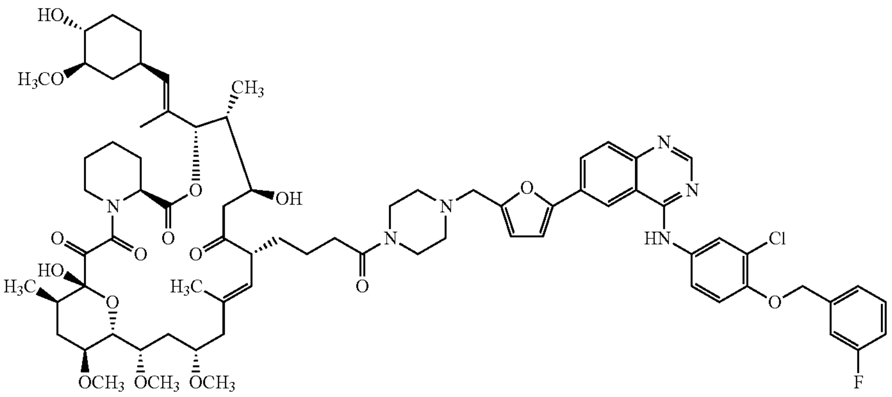 [SMILES: CO[C@H]1C/C(C)=C/[C@@H](CCCC(=O)N2CCN(Cc3ccc(-c4ccc5ncnc(Nc6ccc(OCc7cccc(F)c7)c(Cl)c6)c5c4)o3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |
| ZZY08-068 | 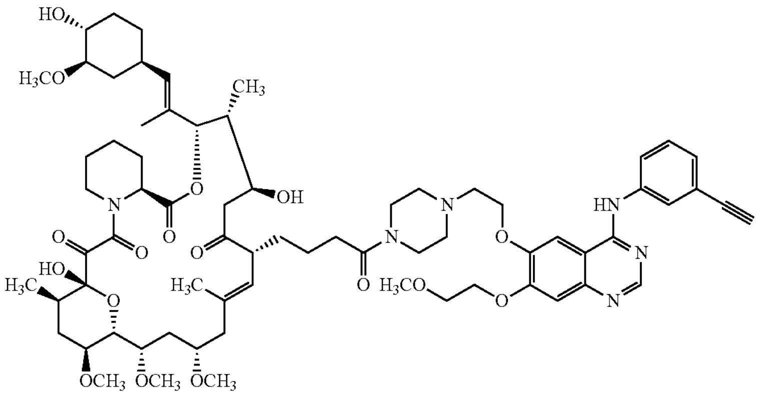 [SMILES: C#Cc1cccc(Nc2ncnc3cc(OCCOC)c(OCCN4CCN(C(=O)CCC[C@@H]5/C=C(\C)C[C@H](OC)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc23)c1] |
| ZZY08-069 | 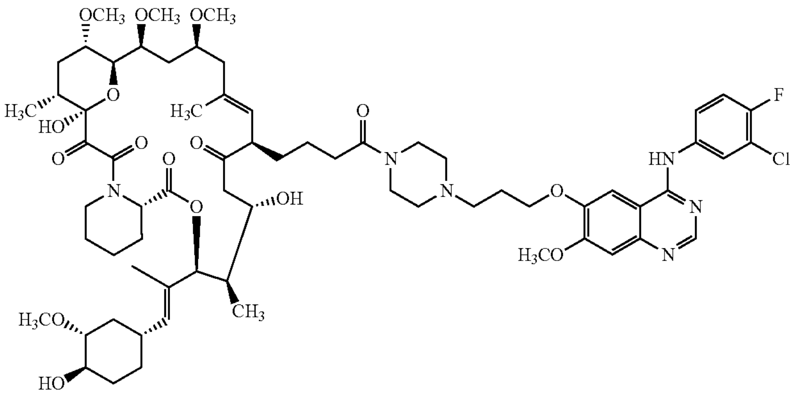 [SMILES: COc1cc2ncnc(Nc3ccc(F)c(Cl)c3)c2cc1OCCCN1CCN(C(=O)CCC[C@@H]2/C=C(\C)C[C@H](OC)C[C@H](OC)[C@H]3O[C@@](O)(C(=O)C(=O)N4CCCC[C@H]4C(=O)O[C@H](/C(C)=C/[C@@H]4CC[C@@H](O)[C@H](OC)C4)[C@H](C)[C@@H](O)CC2=O)[C@H](C)C[C@@H]3OC)CC1] |

TABLE 7
| Compound structures of LRRK analogs. | |
|---|---|
| Compound | Structure |
| ZZY08-074 | 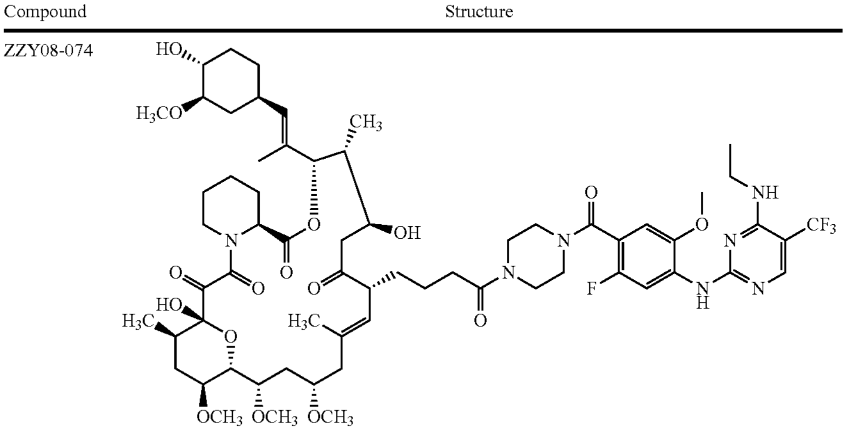 |
TABLE 8
| Compound structures of KRAS analogs. | |
|---|---|
| Compound | Structure |
| ZZY06-027 | 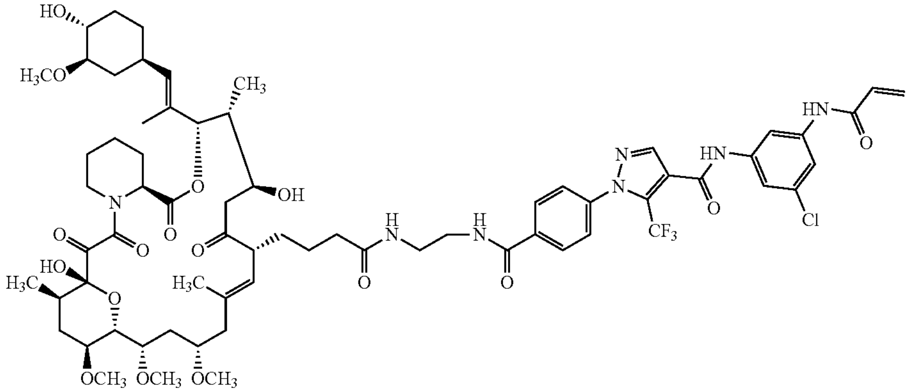 [SMILES: C=CC(=O)Nc1cc(Cl)cc(NC(=O)c2cnn(-c3ccc(C(=O)NCCNC(=O)CCC[C@@H]4/C=C(\C)C[C@H](OC)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1] |
| ZZY07-015 | 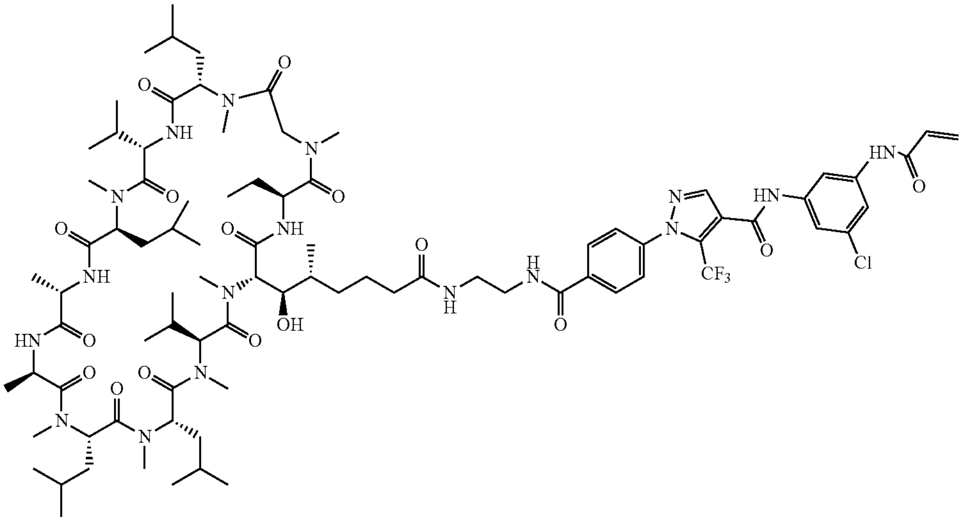 [SMILES: C=CC(=O)Nc1cc(Cl)cc(NC(=O)c2cnn(-c3ccc(C(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1] |

TABLE 8-continued
| Compound structures of KRAS analogs. | |
|---|---|
| Compound | Structure |
| ZZY07-025 | 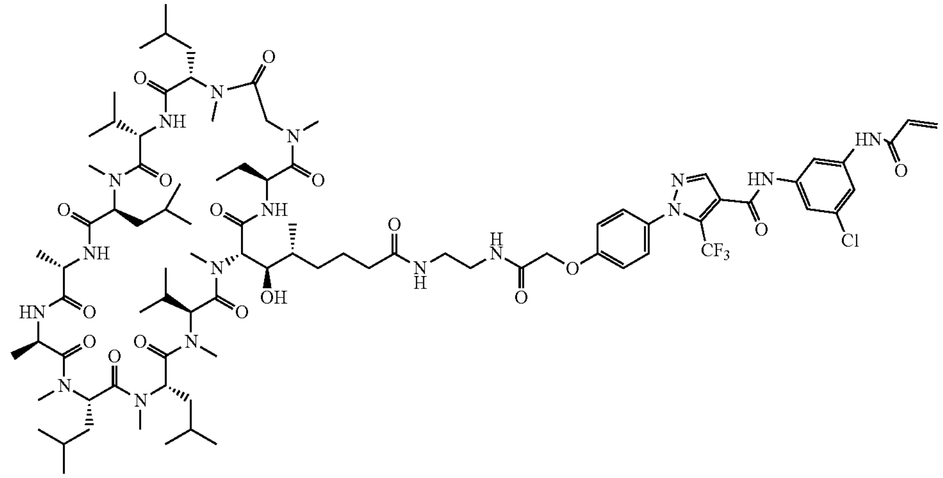 [SMILES: C=CC(=O)Nc1cc(Cl)cc(NC(=O)c2cnn(-c3ccc(OCC(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1] |
| ZZY08-027 | 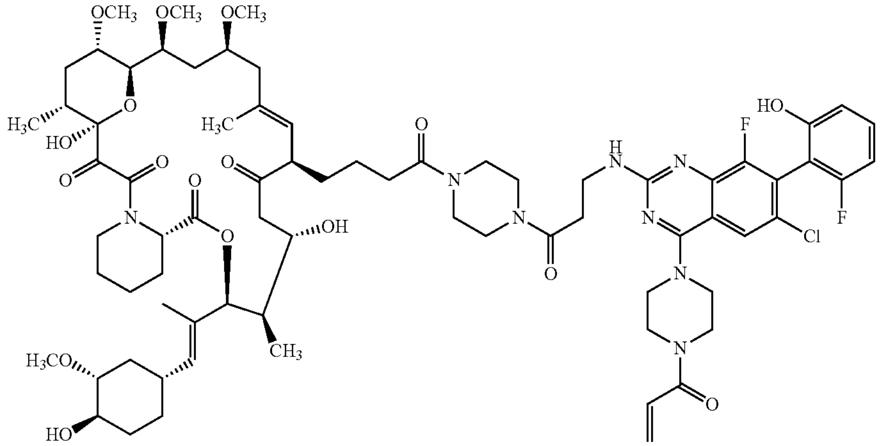 [SMILES: C=CC(=O)N1CCN(c2nc(NCCC(=O)N3CCN(C(=O)CCC[C@@H]4/C=C(\C)C[C@H](OC)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)nc3c(F)c(-c4c(O)cccc4F)c(Cl)cc23)CC1] |
| ZZY08-028 | 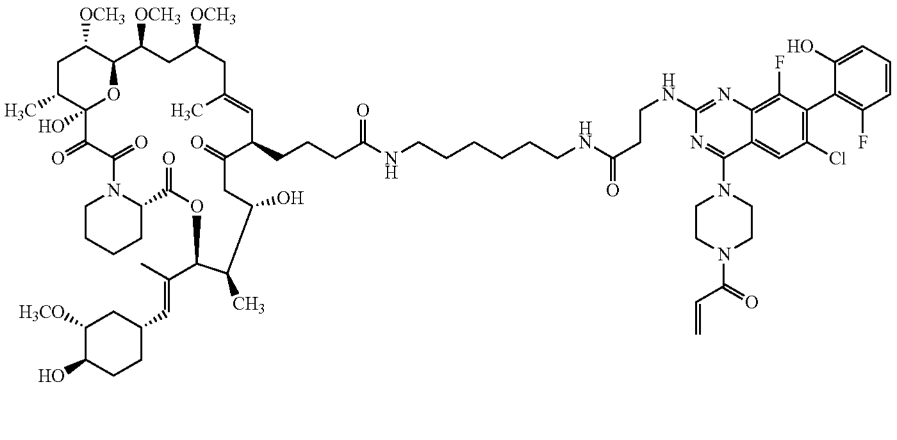 [SMILES: C=CC(=O)N1CCN(c2nc(NCCC(=O)NCCCCCCNC(=O)CCC[C@@H]3/C=C(\C)C[C@H](OC)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1] |

TABLE 8-continued
| Compound structures of KRAS analogs. | |
|---|---|
| Compound | Structure |
| ZZY08-057 | 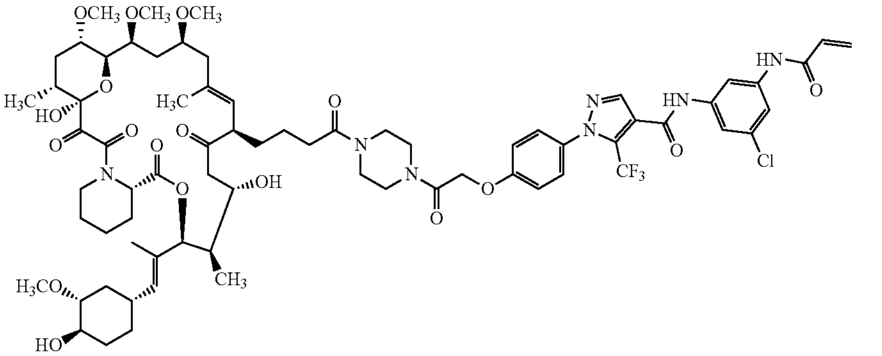 [SMILES: C=CC(=O)Nc1cc(Cl)cc(NC(=O)c2cnn(-c3ccc(OCC(=O)N4CCN(C(=O)CCC[C@@H]5/C=C(\C)C[C@H](OC)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc3)c2C(F)(F)F)c1] |
| ZZY08-058 | 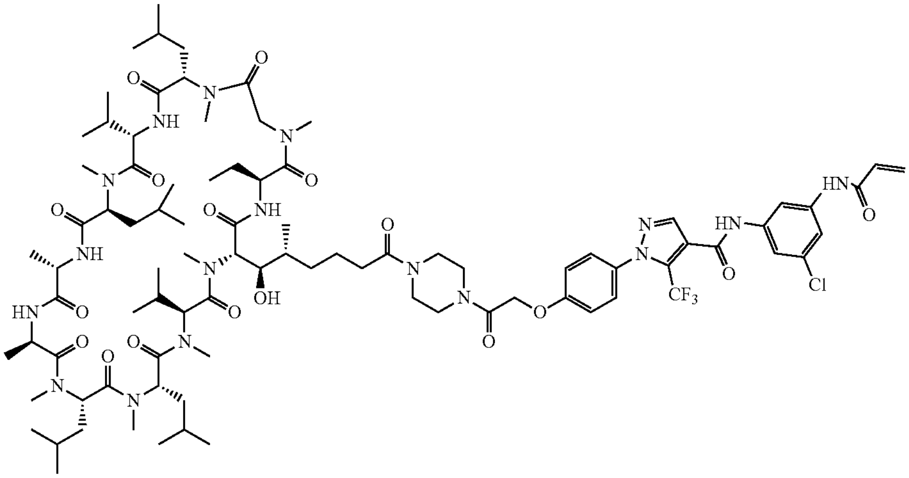 [SMILES: C=CC(=O)Nc1cc(Cl)cc(NC(=O)c2cnn(-c3ccc(OCC(=O)N4CCN(C(=O)CCC[C@@H](C)[C@@H](O)[C@H]5C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N5C)CC4)cc3)c2C(F)(F)F)c1] |
| ZZY05-042/ ZZY07-028 | 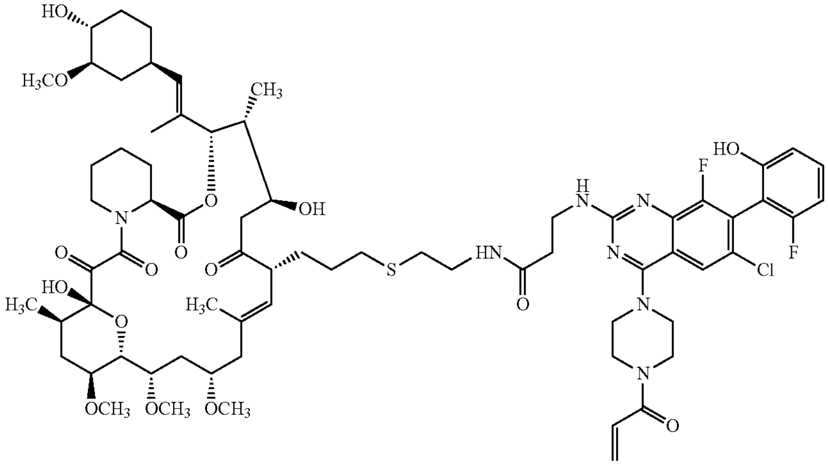 [SMILES: C=CC(=O)N1CCN(c2nc(NCCC(=O)NCCSCCC[C@@H]3/C=C(\C)C[C@H](OC)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1] |

TABLE 8-continued
| Compound structures of KRAS analogs. | |
|---|---|
| Compound | Structure |
| ZZY07-014 | 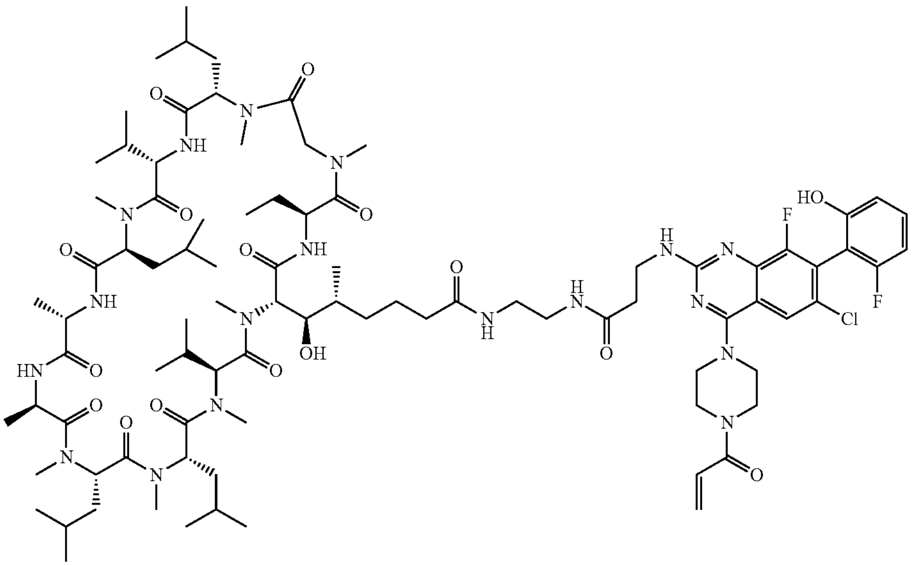 [SMILES: C=CC(=O)N1CCN(c2nc(NCCC(=O)NCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1] |
| ZZY07-079 | 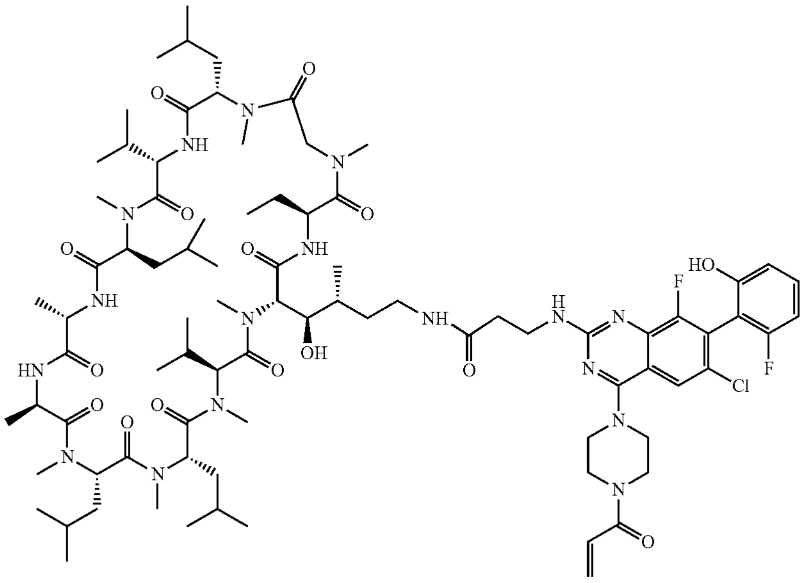 [SMILES: C=CC(=O)N1CCN(c2nc(NCCC(=O)NCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1] |

TABLE 8-continued
| Compound structures of KRAS analogs. | |
|---|---|
| Compound | Structure |
| ZZY07-089 | 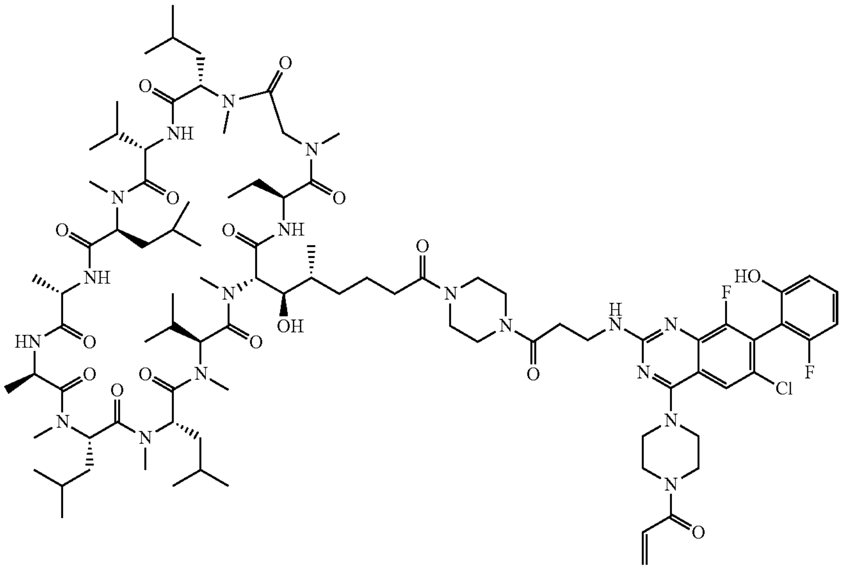 [SMILES: C=CC(=O)N1CCN(c2nc(NCCC(=O)N3CCN(C(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)CC3)nc3c(F)c(-c4c(O)cccc4F)c(Cl)cc23)CC1] |
| ZZY07-090 | 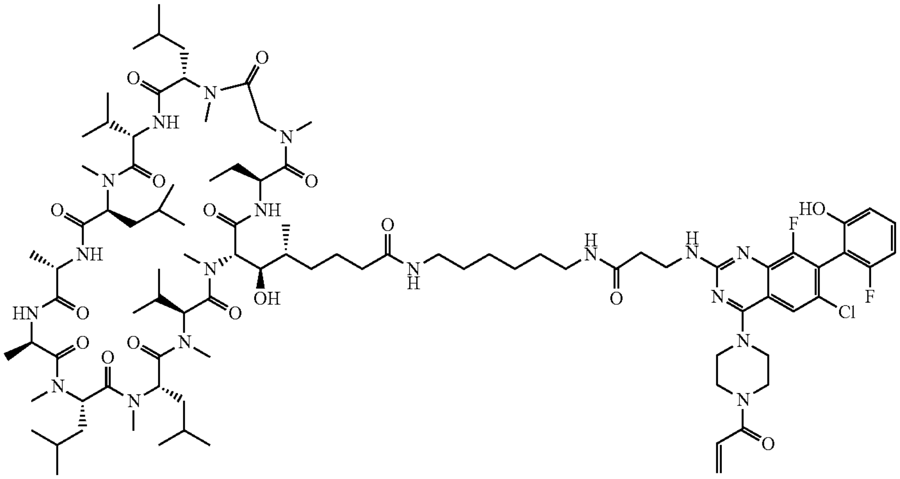 [SMILES: C=CC(=O)N1CCN(c2nc(NCCC(=O)NCCCCCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1] |

TABLE 9
| Compound structures of Cyclosporin analogs. | |
|---|---|
| Compound | Structure |
| ZZY06-082 | 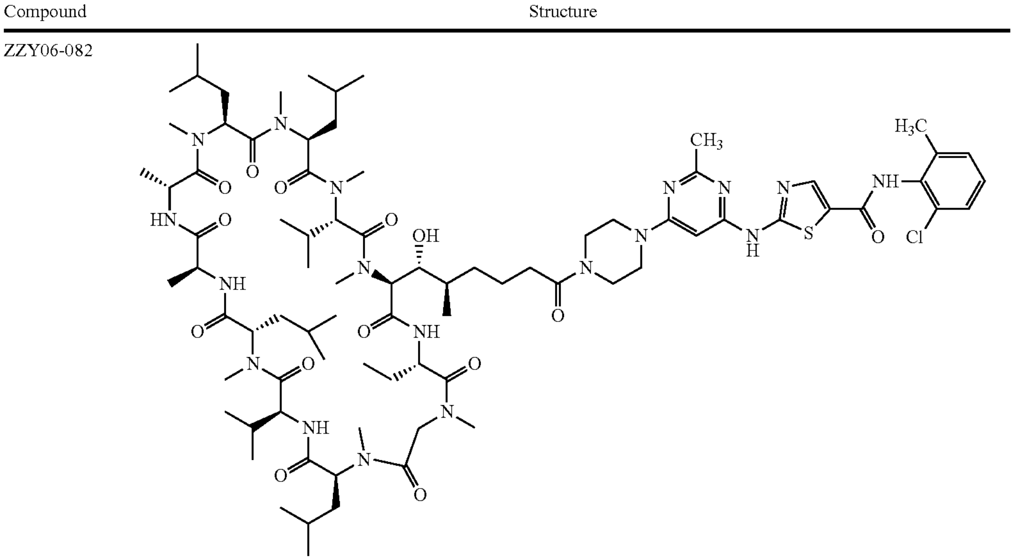 |
| ZZY06-083 | 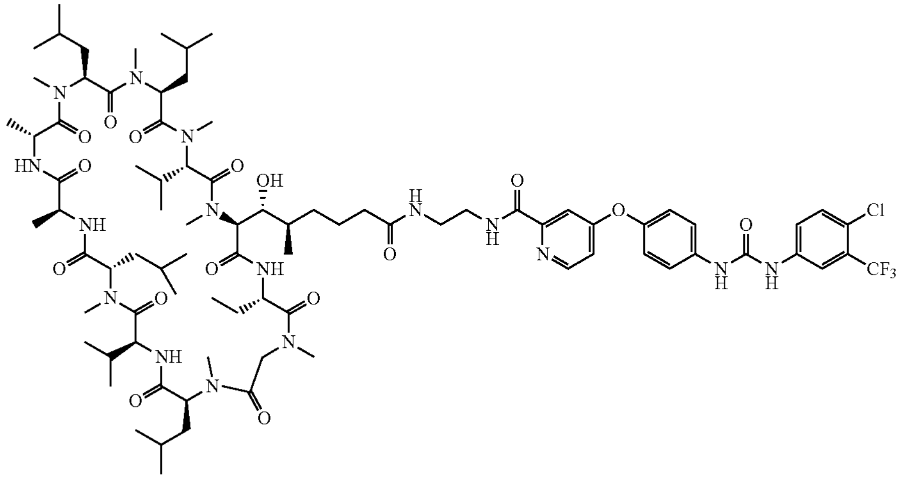 [SMILES: CC[C@@H]1NC(=O)[C@H]([C@H](O)[C@H](C)CCCC(=O)NCCNC(=O)c2cc(Oc3ccc(NC(=O)Nc4ccc(Cl)c(C(F)(F)F)c4)cc3)ccn2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O] |
TABLE 10
| Additional analogs. | |
|---|---|
| Compound | Structure |
| ZZY05-016 | 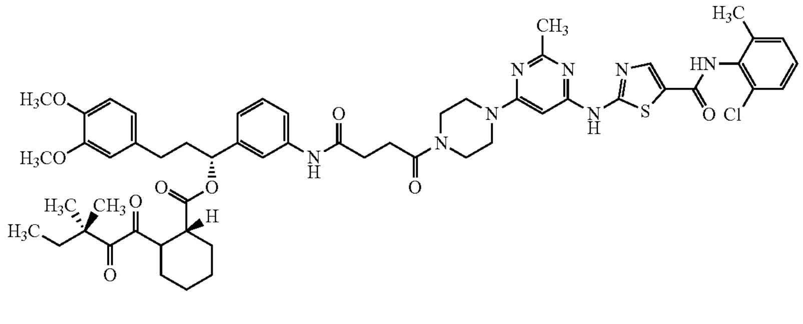 |

TABLE 10-continued

| Additional analogs. | |
|---|---|
| Compound | Structure |
| ZZY05-049 | 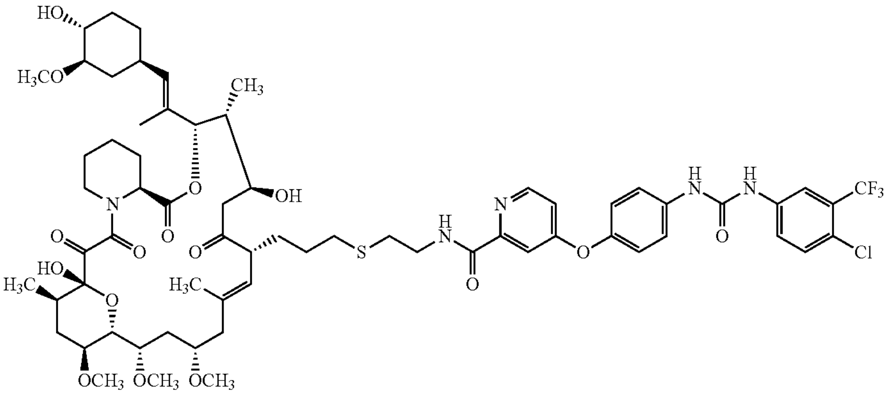 [SMILES: CO[C@H]1C/C(C)=C/[C@@H](CCCSCCNC(=O)c2cc(Oc3ccc(NC(=O)Nc4ccc(Cl)c(C(F)(F)F)c4)cc3)ccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |
| ZZY07-026 | 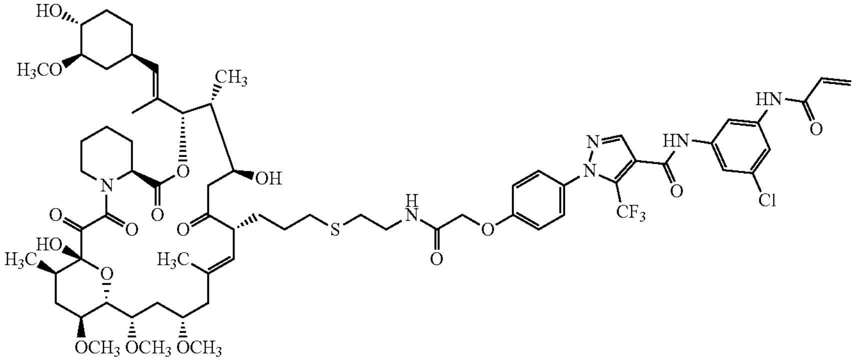 [SMILES: C=CC(=O)Nc1cc(Cl)cc(NC(=O)c2cnn(-c3ccc(OCC(=O)NCCSCCC[C@@H]4/C=C(\C)C[C@H](OC)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1] |
| ZZY05-022 | 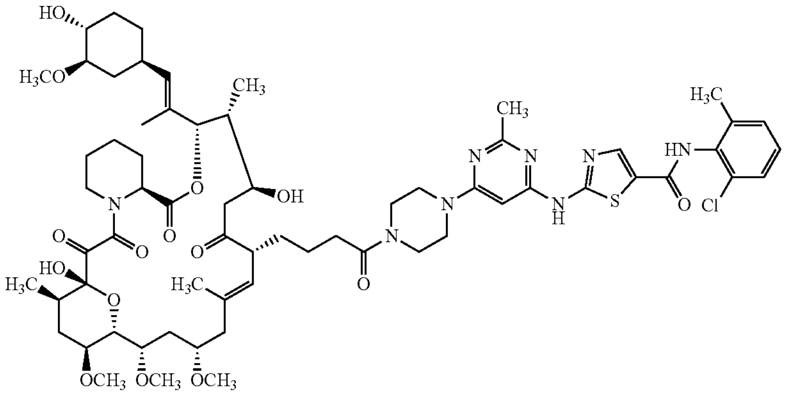 [SMILES: CO[C@H]1C/C(C)=C/[C@@H](CCCC(=O)N2CCN(c3cc(Nc4ncc(C(=O)Nc5c(C)cccc5Cl)s4)nc(C)n3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |

Example 6: Materials and Methods

Note on rotamers in $^1$H NMR data. All of the SLF analogs and FK506 analogs synthesized here exist as a mixture of two amide rotamers in $CDCl_3$ or $CD_3OD$. Due to extensive spectral overlap of the two, the coupling pattern of certain protons can be complicated even if they should display clear splitting patterns in theory. Sometimes, overlapping peaks prevent the identification of all peaks of the minor rotamer, and on occasion, of the major rotamer. In this document, only $^1$H NMR peaks of the major rotamer are reported in the best effort of resolving the peaks.

Cyclosporin analogs demonstrate more complicated conformational flexibility. In $CD_3OD$, most compounds exist as >6 conformational isomers (Ko, S. Y.; Dalvit, C. *Int. J. Pept. Protein Res.* 1992, 40, 380-382). In $CDCl_3$ the spectra are generally less complicated, and for certain compounds, only two conformational isomers are observed. For these compounds the $^1$H NMR spectra in $CDCl_3$ are resolvable, and peaks belonging to the major conformation are reported.

Mini-workup. When a mini-workup (A/B) is indicated in the procedure, it was performed as follows: an aliquot (5 μL) of the reaction mixture was retrieved with a glass pipet and added to a plastic vial containing 0.2 mL organic solvent A and 0.2 mL aqueous solution B. The vial was shaken vigorously and allowed to stand until the two layers partitioned. The organic layer was then used for TLC or LC-MS analysis as specified in the procedure.

Monitoring reaction progress by LC-MS. When analysis of the reaction mixture is indicated in the procedure, it was performed as follows. An aliquot (1 μL) of the reaction mixture (or the organic phase of a mini-workup mixture) was diluted with 100 μL 1:1 acetonitrile:water. 1 μL of the diluted solution was injected onto a Waters Acquity UPLC BEH C18 1.7 μm column and eluted with a linear gradient of 5-95% acetonitrile/water (+0.1% formic acid) over 3.0 min. Chromatograms were recorded with a UV detector set at 254 nm and a time-of-flight mass spectrometer (Waters Xevo G2-XS).

General experimental procedures. All reactions were performed in oven-dried glassware fitted with rubber septa under a positive pressure of argon, unless otherwise noted. Air- and moisture-sensitive liquids were transferred via syringe or stainless steel cannula. Solutions were concentrated by rotary evaporation at or below 40° C. Analytical thin-layer chromatography (TLC) was performed using glass plates pre-coated with silica gel (0.25-mm, 60-A pore size, 230-400 mesh, Merck KGA) impregnated with a fluorescent indicator (254 nm). TLC plates were visualized by exposure to ultraviolet light (UV), then were stained by submersion in a 10% solution of phosphomolybdic acid (PMA) in ethanol or an acidic ethanolic solution of p-anisaldehyde (this solution was prepared by sequential additions of concentrated sulfuric acid (5.0 mL), glacial acetic acid (1.5 mL) and p-anisaldehyde (3.7 mL) to absolute ethanol (135 mL) at 23° C. with efficient stirring), followed by brief heating on a hot plate. Flash column chromatography was performed with Teledyne ISCO CombiFlash EZ Prep chromatography system, employing pre-packed silica gel cartridges (Teledyne ISCO RediSep).

Solvents and reagents. Anhydrous solvents were purchased from Acros Organics. Except for those specified in the Starting Materials section, all chemical reagents were purchased from Sigma-Aldrich and AK Scientific. Commercial solvents and reagents were used as received.

Starting materials. SLF was purchased from Cayman Chemical and/or synthesized following the synthetic route reported by Holt et al. 3'-desamino-3'-hydroxy SLF was synthesized following the synthetic route reported by Holt et al. (Holt, D. A. et al. *J. Am. Chem. Soc.* 1993, 115, 9925-9938). Cyclosporin A and FK506 were purchased from LC Laboratories. Sorafenib acid [4-(4-(3-(4-chloro-3-(trifluoromethyl)phenyl)ureido)phenoxy)picolinic acid] was purchased from BOC Sciences. Des(hydroxyethyl)dasatinib [N-(2-chloro-6-methylphenyl)-2-((2-methyl-6-(piperazin-1-yl)pyrimidin-4-yl)amino)thiazole-5-carboxamide]was purchased from 5A Chemicals. Lapatinib aldehyde [5-(4-((3-chloro-4-((3-fluorobenzyl)oxy)phenyl)amino)quinazolin-6-yl)furan-2-carbaldehyde]was purchased from AK Scientific. Desmethoxychloro erlotinib [6-(2-chloroethoxy)-N-(3-ethynylphenyl)-7-(2-methoxyethoxy)quinazolin-4-amine]was purchased from AstaTech. Desmethoxychloro gefitinib [N-(3-chloro-4-fluorophenyl)-6-(3-chloropropoxy)-7-methoxyquinazolin-4-amine]was purchased from AstaTech. tert-Butyl 4-(7-bromo-6-chloro-2-((3-ethoxy-3-oxopropyl)amino)-8-fluoroquinazolin-4-yl)piperazine-1-carboxylate was purchased from Pharmaron Inc.

Instrumentation. Proton nuclear magnetic resonance ($^1$H NMR) spectra and carbon nuclear magnetic resonance ($^{13}$C NMR) spectra were recorded on Bruker AvanceIII HD 2-channel instrument (400 MHz/100 MHz) at 23° C. Proton chemical shifts are expressed in parts per million (ppm, 6 scale) and are referenced to residual protium in the NMR solvent ($CHCl_3$: δ 7.26, $D_2HCOD$: δ 3.31). Carbon chemical shifts are expressed in parts per million (ppm, δ scale) and are referenced to the carbon resonance of the NMR solvent ($CDCl_3$: δ 77.0, $CD_3OD$: δ 49.0). Data are represented as follows: chemical shift, multiplicity (s=singlet, d=doublet, t=triplet, q=quartet, dd=doublet of doublets, dt=doublet of triplets, m=multiplet, br=broad, app=apparent), integration, and coupling constant (J) in Hertz (Hz). High-resolution mass spectra were obtained using a Waters Xevo G2-XS time-of-flight mass spectrometer. Unless otherwise specified, diastereomeric ratios of products are reported as (major diastereomer): (sum of minor diastereomers).

Synthetic Procedures.

SLF Analogs.

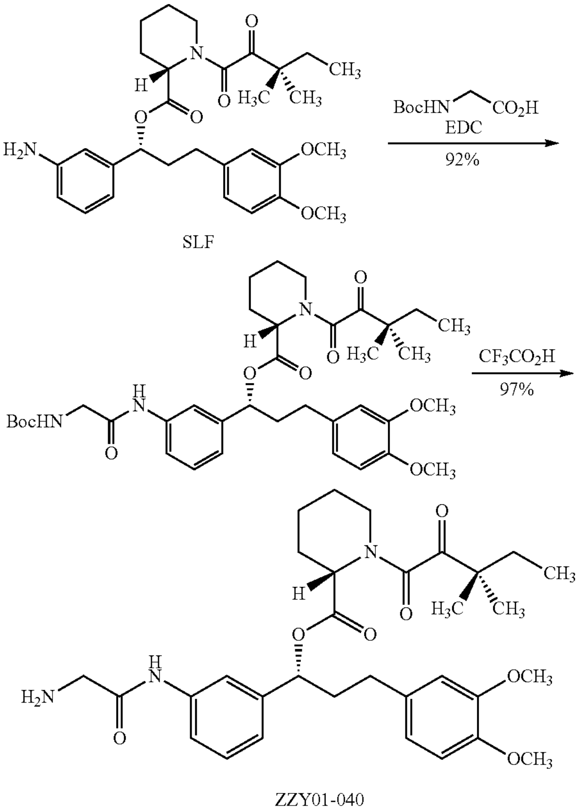

SLF

ZZY01-040

EDC (548.08 mg, 2.86 mmol) was added in one portion to a stirred solution of SLF (1.00 g, 1.91 mmol) and Boc-Gly-OH (500 mg, 2.86 mmol) in dichloromethane (9.5 mL) at 0° C. The resulting mixture was allowed to warm to 23° C. over 30 min, then was kept stirred at 23° C. After a total of 5 h, TLC analysis (50% ethyl acetate-hexanes) showed that the reaction was complete. The reaction mixture was directly concentrated under reduced pressure, and the residue was purified by column chromatography (20-50% ethyl acetate-hexanes, 40-g CombiFlash column) to afford the product as a white foam (1.20 g, 92%). The product exists as a 6:1 mixture of amide rotamers. $^1$H NMR (400 MHz, Chloroform-d) δ 8.33 (s, 1H), 7.62 (d, J=8.1 Hz, 1H), 7.51-7.45 (m, 1H), 7.30 (t, J=7.9 Hz, 1H), 7.03 (d, J=7.8 Hz, 1H), 6.77 (d, J=8.7 Hz, 1H), 6.73-6.63 (m, 2H), 5.80 (dd, J=7.7, 5.6 Hz, 1H), 5.34 (d, J=5.5 Hz, 1H), 5.27 (s, 1H), 3.98-3.89 (m, 2H), 3.86 (s, 3H), 3.84 (s, 3H), 3.34 (d, J=13.7 Hz, 1H), 3.07 (td, J=12.9, 3.0 Hz, 1H), 2.64-2.49 (m, 2H), 2.35 (d, J=13.6 Hz, 1H), 2.28-2.15 (m, 1H), 2.12-2.02 (m, 1H), 1.78-1.58 (m, 5H), 1.47 (s, 9H), 1.46-1.34 (m, 2H), 1.24 (s, 3H), 1.24 (s, 3H), 0.91 (t, J=7.5 Hz, 3H). HRMS (ESI): Calcd for $(C_{37}H_{51}N_3O_9+H)^+$: 682.3704. Found: 682.3699.

A solution of [(1R)-1-[3-[[2-(tert-butoxycarbonylamino) acetyl]amino]phenyl]-3-(3,4-dimethoxyphenyl)propyl] (2S)-1-(3,3-dimethyl-2-oxo-pentanoyl)piperidine-2-carboxylate (1.20 g, 1.76 mmol) in dichloromethane (8.4 mL) was cooled to 0° C., then trifluoroacetic acid (8.4 mL) was added dropwise. The resulting yellow solution was stirred at 0° C. until TLC analysis (50% ethyl acetate-hexanes, mini-workup with ether/aqueous sodium bicarbonate solution) showed full consumption of the starting material. The reaction solution was concentrated in vacuo, and the residue was partitioned between dichloromethane (10 mL) and saturated sodium bicarbonate solution (10 mL). The layers were separated, and the aqueous layer was extracted with dichlormethane (2×10 mL). The combined organic layers were dried over sodium sulfate, and the dried solution was concentrated in vacuo to afford the product as a white foam (997 mg, 97%). 6:1 mixture of rotamers. $^1H$ NMR (400 MHz, Chloroform-d) δ 7.30-7.22 (m, 1H), 7.00-6.88 (m, 2H), 6.88-6.80 (m, 2H), 6.80-6.74 (m, 1H), 6.70-6.65 (m, 2H), 5.77 (dd, J=7.8, 5.9 Hz, 1H), 5.31 (d, J=5.5 Hz, 1H), 4.53 (s, 2H), 3.86 (s, 3H), 3.85 (s, 3H), 3.36 (d, J=13.0 Hz, 1H), 3.14 (td, J=13.1, 3.2 Hz, 1H), 2.66-2.45 (m, 2H), 2.36 (d, J=13.7 Hz, 1H), 2.31-2.15 (m, 1H), 2.04 (s, 1H), 1.82-1.58 (m, 5H), 1.42-1.29 (m, 2H), 1.23 (s, 3H), 1.21 (s, 3H), 0.89 (t, J=7.5 Hz, 3H). HRMS (ESI): Calcd for $(C_{32}H_{43}N_3O_7+H)^+$: 582.3179. Found: 582.3176.

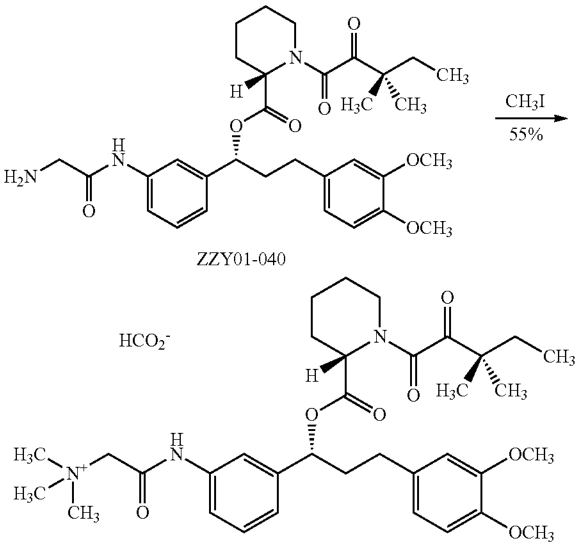

ZZY01-040

ZZY01-025

Sodium bicarbonate (36.5 mg, 0.430 mmol) and iodomethane (107 μL, 1.72 mmol) were added to a solution of ZZY01-040 (50 mg, 0.090 mmol) in THE (0.50 mL) at 23° C. The resulting suspension was stirred at 23° C., and the reaction progress was monitored by LC-MS. After 24 h, the bulk of the solvent was removed by rotary evaporation. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (29.5 mg, 55%). 6:1 mixture of rotamers. $^1H$ NMR (400 MHz, Methanol-$d_4$) δ 8.35 (s, 1H), 7.81-7.64 (m, 1H), 7.51-7.43 (m, 1H), 7.43-7.33 (m, 1H), 7.18 (app t, J=8.1 Hz, 1H), 6.92-6.85 (m, 1H), 6.85-6.79 (m, 1H), 6.79-6.70 (m, 1H), 5.83-5.70 (m, 1H), 5.29-5.22 (m, 1H), 4.31 (s, 2H), 3.83 (s, 3H), 3.82 (s, 3H), 3.41 (s, 10H), 3.30-3.19 (m, 1H), 2.75-2.55 (m, 2H), 2.37 (d, J=13.6 Hz, 1H), 2.34-2.19 (m, 1H), 2.17-2.02 (m, 1H), 1.86-1.58 (m, 5H), 1.58-1.29 (m, 2H), 1.25 (s, 3H), 1.23 (s, 3H), 0.90 (t, J=7.4 Hz, 3H). HRMS (ESI): Calcd for $(C_{35}H_5ON_3O_7)^+$: 624.3642. Found: 624.3636.

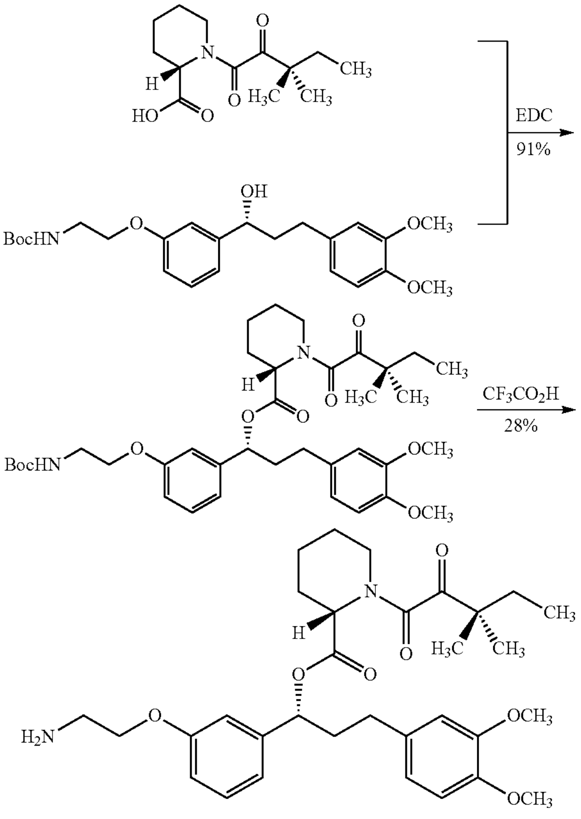

ZZY01-038 tert-Butyl N-[2-[3-[(1R)-3-(3,4-dimethoxyphenyl)-1-hydroxy-propyl]phenoxy]ethyl]carbamate (65 mg, 0.15 mmol) and (2S)-1-(3,3-dimethyl-2-oxo-pentanoyl)piperidine-2-carboxylic acid (42.3 mg, 0.17 mmol) were dissolved in dry dichloromethane (3.0 mL). The resulting solution was cooled to 0° C., then EDC (43.5 mg, 0.23 mmol) was added in one portion as a solid. The ice bath was removed and the reaction mixture was allowed to warm to 23° C. In 4 h, TLC analysis (50% ethyl acetate-hexanes) showed that the reaction was complete. The reaction mixture was directly concentrated, and the residue was purified by column chromatography (4-g CombiFlash column, 10-50% ethyl acetate-hexanes) to afford the product as a colorless film (92 mg, 91%).

50% Trifluoroacetic acid-dichloromethane (1 mL) was added to [(1R)-1-[3-[2-(tert-butoxycarbonylamino)ethoxy] phenyl]-3-(3,4-dimethoxyphenyl)propyl](2S)-1-(3,3-dimethyl-2-oxo-pentanoyl)piperidine-2-carboxylate (95 mg, 0.14 mmol) in a 20-mL scintillation vial at 0° C. The resulting solution was warmed to 23° C. over 5 min. TLC analysis (mini-workup with ether/sodium bicarbonate, 50% ethyl acetate-hexanes) showed complete consumption of the starting material. The product has an Rf of 0 in this solvent system. The reaction mixture was concentrated under reduced pressure. The residue was partitioned between dichloromethane (5 mL) and saturated sodium bicarbonate solution (5 mL). The layers were separated, and the aqueous layer was extracted with dichloromethane (2×5 mL). The combined organic layers were dried over sodium sulfate, and the dried solution was concentrated. The residue was purified by column chromatography (3-5% methanol-dichloromethane+0.3-0.5% saturated aqueous ammonium hydroxide solution, 4-g CombiFlash column) to afford the product as a colorless film (23 mg, 28%). 6:1 mixture of rotamers. $^1$H NMR (400 MHz, Chloroform-d) δ 7.29-7.22 (m, 1H), 6.95-6.88 (m, 2H), 6.85 (dd, J=8.2, 2.2 Hz, 1H), 6.78 (d, J=8.6 Hz, 1H), 6.72-6.65 (m, 2H), 5.77 (dd, J=7.9, 5.8 Hz, 1H), 5.35-5.28 (m, 1H), 4.05-3.94 (m, 2H), 3.86 (s, 3H), 3.85 (s, 3H), 3.35 (d, J=13.6 Hz, 1H), 3.20-3.06 (m, 3H), 2.67-2.43 (m, 2H), 2.42-2.32 (m, 1H), 2.31-2.17 (m, 1H), 2.13-1.97 (m, 1H), 1.76-1.57 (m, 5H), 1.57-1.27 (m, 2H), 1.22 (s, 3H), 1.20 (s, 3H), 0.88 (t, J=7.5 Hz, 3H). HRMS (ESI): Calcd for $(C_{32}H_{44}N_2O_7+H)^+$: 569.3227. Found: 569.3239.

-continued

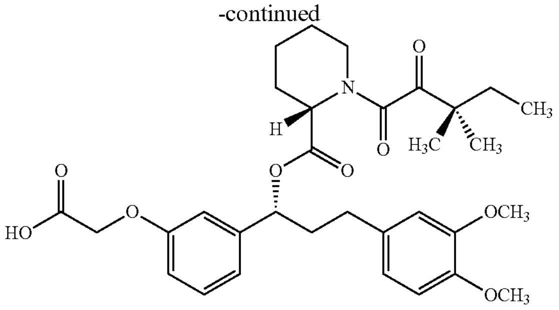

ZZY01-041

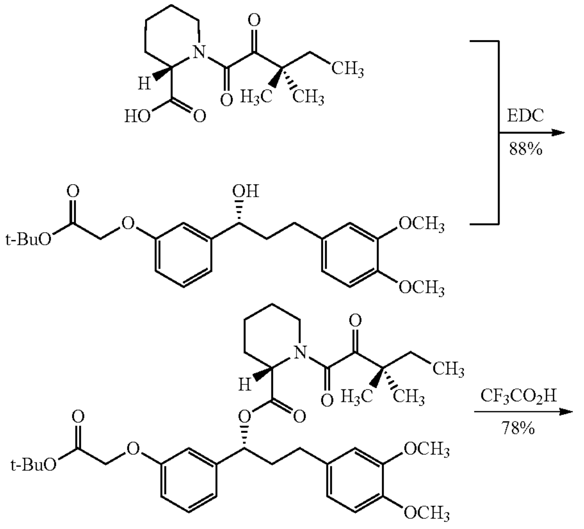

A solution of [(1R)-1-[3-(2-tert-butoxy-2-oxo-ethoxy)phenyl]-3-(3,4-dimethoxyphenyl)propyl](2S)-1-(3,3-dimethyl-2-oxo-pentanoyl)piperidine-2-carboxylate (453 mg, 0.71 mmol) in dichloromethane (1.42 mL) was cooled to 0° C., then trifluoroacetic acid (1.42 mL) was added dropwise. The resulting yellow solution was stirred at 0° C. until TLC analysis (50% ethyl acetate-hexanes) showed full consumption of the starting material (~2 h). The reaction solution was concentrated in vacuo to afford the product as a brown liquid. The liquid solidified slowly upon standing under vacuum, giving rise to an off-white powder. 6:1 mixture of rotamers. $^1$H NMR (400 MHz, Chloroform-d) δ 7.32-7.23 (m, 1H), 6.93 (d, J=7.7 Hz, 1H), 6.90-6.84 (m, 2H), 6.78 (d, J=7.9 Hz, 1H), 6.68 (d, J=7.7 Hz, 2H), 5.74 (dd, J=8.3, 5.3 Hz, 1H), 5.30 (d, J=7.8 Hz, 1H), 4.75-4.61 (m, 2H), 3.86 (s, 3H), 3.85 (s, 3H), 3.41-3.32 (m, 1H), 3.21 (td, J=13.0, 3.1 Hz, 1H), 2.70-2.48 (m, 2H), 2.39 (d, J=13.8 Hz, 1H), 2.31-2.17 (m, 1H), 2.13-2.03 (m, 1H), 1.86-1.58 (m, 5H), 1.58-1.31 (m, 2H), 1.20 (s, 3H), 1.18 (s, 3H), 0.87 (t, J=7.4 Hz, 3H). HRMS (ESI): Calcd for $(C_{32}H_{41}NO_9+H)^+$: 584.2859. Found: 584.2852.

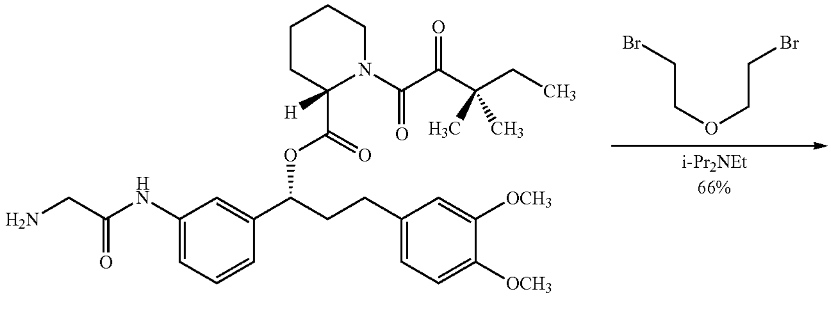

ZZY01-040

-continued

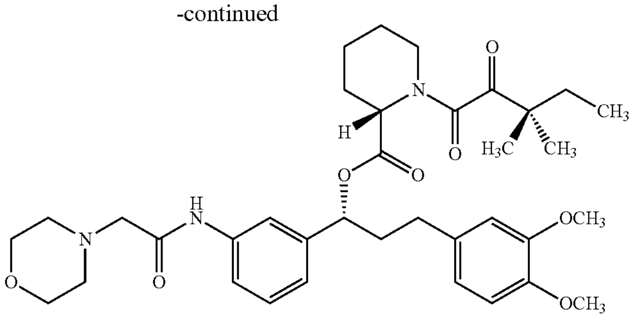

ZZY01-043

A 1-dram vial was charged with ZZY01-040 (50 mg, 0.090 mmol) and a stir bar. DMSO (0.2 mL) and N,N-Diisopropylethylamine (45 μL, 0.26 mmol) were added sequentially. 1-bromo-2-(2-bromoethoxy)ethane (30 mg, 0.13 mmol) was added via syringe. The resulting mixture was stirred at 23° C. and the reaction progress was monitored by TLC analysis (10% methanol-dichloromethane). After 5 h, the reaction mixture was warmed to 55° C. In a total of 22 h, TLC analysis showed full conversion. The reaction mixture was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid. 6:1 mixture of rotamers. $^1H$ NMR (400 MHz, Methanol-$d_4$) δ 8.16 (s, 1H), 7.75 (t, J=1.8 Hz, 1H), 7.53-7.46 (m, 1H), 7.35 (t, J=7.9 Hz, 1H), 7.14 (d, J=7.6 Hz, 1H), 6.87 (d, J=8.2 Hz, 1H), 6.84-6.78 (m, 1H), 6.74 (dd, J=8.1, 1.8 Hz, 1H), 5.75 (dd, J=8.6, 4.9 Hz, 1H), 5.24 (d, J=5.4 Hz, 1H), 3.83 (d, J=1.1 Hz, 3H), 3.81 (s, 3H), 3.46-3.38 (m, 1H), 3.27 (td, J=13.2, 3.1 Hz, 1H), 2.73 (s, 6H), 2.69-2.53 (m, 3H), 2.42-2.20 (m, 3H), 2.15-2.02 (m, 2H), 1.80-1.55 (m, 5H), 1.55-1.29 (m, 2H), 1.25 (s, 3H), 1.23 (s, 3H), 0.90 (t, J=7.4 Hz, 3H). HRMS (ESI): Calcd for $(C_{36}H_{49}N_3O_8+H)^+$: 652.3598. Found: 652.3613.

A 1-dram vial was charged with ZZY01-040 (50 mg, 0.0900 mmol), a stir bar, and 9:1 methanol:acetic acid (0.5 mL). Formaldehyde (37% aqueous solution, 24 μL, 0.86 mmol) was added via pipette. Sodium cyanoborohydride (11 mg, 0.17 mmol) was added in one portion, and the resulting solution was stirred at 23° C. In 3 h, TLC analysis (10% methanol-dichloromethane+1% 30% aqueous ammonium hydroxide solution) showed full consumption of starting material and formation of a less polar product. The reaction mixture was diluted with 50% acetonitrile-water to a final volume of 5 mL, and the resulting solution was purified by reverse-phase HPLC (5-95% acetonitrile-water with 0.1% formic acid, 50 min, 20 mL/min) to afford the product as a white foam. 6:1 mixture of rotamers. $^1H$ NMR (400 MHz, Methanol-$d_4$) δ 8.32 (s, 1H), 7.75 (t, J=1.8 Hz, 1H), 7.51-7.42 (m, 1H), 7.37 (t, J=7.9 Hz, 1H), 7.17 (d, J=7.6 Hz, 1H), 6.88 (d, J=7.4 Hz, 1H), 6.81 (d, J=1.9 Hz, 1H), 6.74 (dd, J=8.2, 1.9 Hz, 1H), 5.74 (dd, J=8.8, 5.0 Hz, 1H), 5.24 (d, J=5.5 Hz, 1H), 3.95 (br s, 2H), 3.83 (s, 3H), 3.82 (s, 3H), 3.47-3.38 (m, 1H), 3.31-3.20 (m, 1H), 2.89 (s, 6H), 2.75-2.53 (m, 2H), 2.41-2.19 (m, 2H), 2.09 (dddd, J=12.4, 9.1, 5.7, 3.7 Hz, 1H), 1.89-1.57 (m, 5H), 1.57-1.29 (m, 2H), 1.25 (s, 3H), 1.23 (s, 3H), 0.90 (t, J=7.4 Hz, 3H). HRMS (ESI): Calcd for $(C_{34}H_{47}N_3O_7+H)^+$: 610.3492. Found: 610.3473.

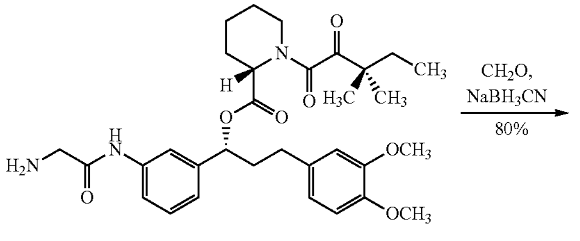

ZZY01-040

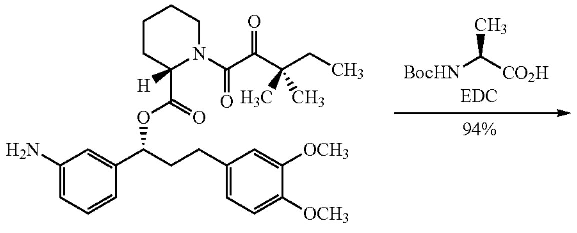

SLF $\cdot HCO_2H$

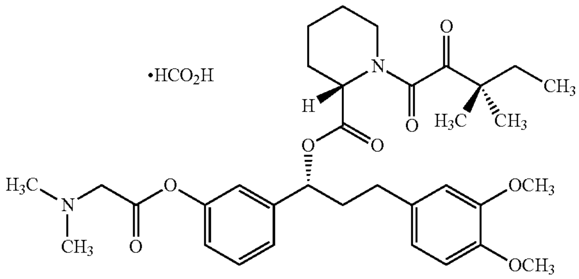

ZZY01-044

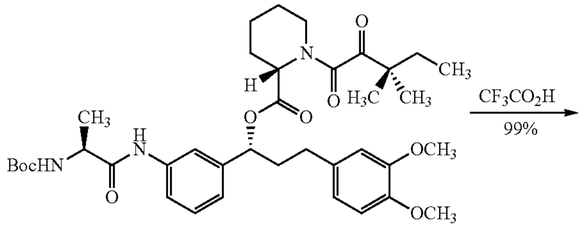

-continued

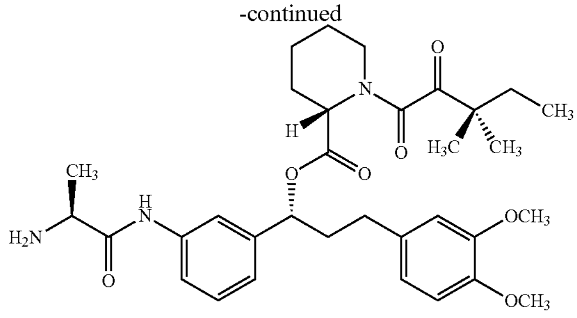

ZZY01-059

EDC (55 mg, 0.29 mmol) was added in one portion to a stirred solution of SLF (100 mg, 0.190 mmol) and D-Boc-Alanine (54 mg, 0.29 mmol) in dichloromethane (9.5 mL) at 0° C. The resulting mixture was allowed to warm to 23° C. over 30 min, then was kept stirred at 23° C. In 2 h, TLC analysis (50% ethyl acetate-hexanes) did not reveal any new spot but LC-MS analysis indicated that a new product with higher mass was being formed. In a total of 20 h, LC-MS analysis showed no detectable starting material. The reaction mixture was directly loaded onto a silica gel column and purified by column chromatography (20-50% ethyl acetate-hexanes) to afford the product as a colorless wax (125 mg, 94%).

Trifluoroacetic acid (0.5 mL) was added dropwise to a solution of [(1R)-1-[3-[[(2S)-2-(tert-butoxycarbonylamino)propanoyl]amino]phenyl]-3-(3,4-dimethoxyphenyl)propyl] (2S)-1-(3,3-dimethyl-2-oxo-pentanoyl)piperidine-2-carboxylate (125 mg, 0.18 mmol) in dichloromethane (0.5 mL) at 23° C. The resulting clear solution was allowed to stand at 23° C. for 1 h. The solution was concentrated in vacuo, and the residue was partitioned between 10 mL dichloromethane and 10 mL saturated sodium bicarbonate solution. The layers were separated, and the aqueous layer was extracted with dichloromethane (2×10 mL). The combined organic layers were dried over sodium sulfate, and the dried solution was concentrated to afford the product as a white foam (108 mg, 99%). 6:1 mixture of rotamers. $^1$H NMR (400 MHz, Chloroform-d) δ 9.52 (s, 1H), 7.71-7.44 (m, 2H), 7.30 (t, J=7.9 Hz, 1H), 7.11-6.99 (m, 1H), 6.84-6.72 (m, 1H), 6.72-6.64 (m, 2H), 5.79 (dd, J=8.0, 5.5 Hz, 1H), 5.38-5.30 (m, 1H), 3.86 (s, 3H), 3.85 (s, 3H), 3.70-3.56 (m, 1H), 3.36 (d, J=13.1 Hz, 1H), 3.16 (t, J=12.9 Hz, 1H), 2.69-2.48 (m, 2H), 2.37 (d, J=13.6 Hz, 1H), 2.24 (ddd, J=13.9, 10.4, 7.0 Hz, 1H), 2.14-2.02 (m, 1H), 1.81-1.51 (m, 5H), 1.52-1.35 (m, 5H), 1.23 (s, 3H), 1.22 (s, 3H), 0.89 (t, J=7.5 Hz, 3H). HRMS (ESI): Calcd for $(C_{33}H_{45}N_3O_7+H)^+$: 596.3336. Found: 596.3351.

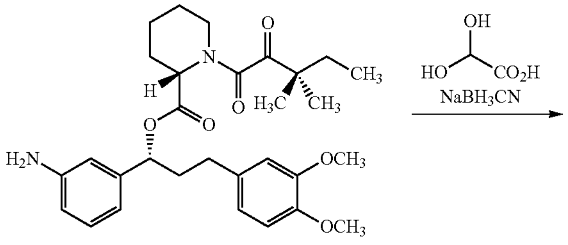

SLF

-continued

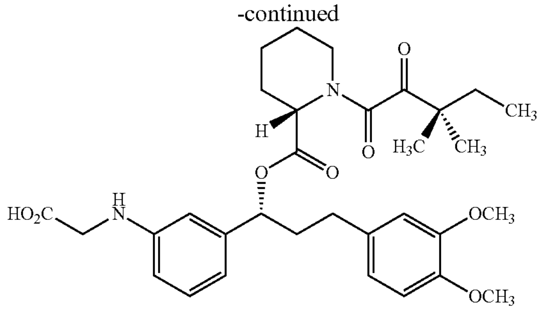

ZZY01-060A
38%

+

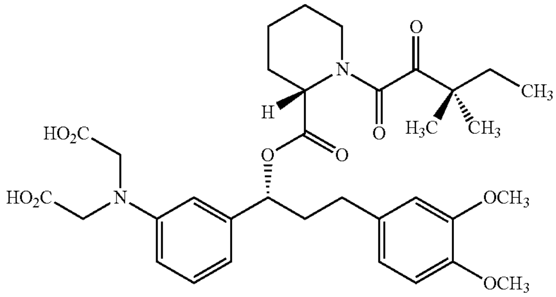

ZZY01-060B
43%

An oven-dried 1-dram vial was charged with SLF (50 mg, 0.10 mmol), glyoxylic acid (18 mg, 0.19 mmol) and a magnetic stir bar. 9:1 Methanol:acetic acid (0.5 mL) was added and the resulting solution was cooled to 0° C. Sodium cyanoborohydride (12 mg, 0.19 mmol) was added in one portion. The mixture was allowed to stir at 4° C. and the progress was monitored by LC-MS. In 1 h, LC-MS indicated that the starting material had been fully consumed and two products had formed in roughly 1:1 ratio. To avoid further bis-alkylation, the reaction mixture was immediately diluted with 50% acetonitrile-water to a volume of 5 mL. The resulting solution was purified by reverse-phase HPLC (5-95% acetonitrile-water+0.1% formic acid, 50 min) to afford the two products as two discrete peaks, both as white powders. 01-060B (26 mg, 43%) eluted faster; 01-060A (21 mg, 38%) eluted slower.

ZZY01-060A. 6:1 mixture of rotamers. $^1$H NMR (400 MHz, Methanol-$d_4$) δ 7.18-7.09 (m, 1H), 6.87 (d, J=8.2 Hz, 1H), 6.85-6.76 (m, 1H), 6.76-6.70 (m, 1H), 6.68 (d, J=7.9 Hz, 1H), 6.65-6.56 (m, 2H), 5.72-5.65 (m, 1H), 5.24 (d, J=5.4 Hz, 1H), 3.93-3.87 (m, 2H), 3.83 (s, 3H), 3.81 (s, 3H), 3.45-3.38 (m, 1H), 3.19 (td, J=13.1, 3.1 Hz, 1H), 2.69-2.52 (m, 2H), 2.35 (d, J=13.6 Hz, 1H), 2.31-2.15 (m, 1H), 2.13-1.97 (m, 1H), 1.87-1.59 (m, 5H), 1.59-1.28 (m, 2H), 1.26 (s, 3H), 1.24 (s, 3H), 0.91 (t, J=7.5 Hz, 3H). HRMS (ESI): Calcd for $(C_{32}H_{42}N_2O_8+H)^+$: 583.3019. Found: 583.3010.

ZZY01-060B. 6:1 mixture of rotamers. $^1$H NMR (400 MHz, Methanol-$d_4$) δ 7.23 (t, J=7.9 Hz, 1H), 6.87 (d, J=8.2 Hz, 1H), 6.85-6.69 (m, 3H), 6.65-6.56 (m, 2H), 5.71 (dd, J=8.4, 5.3 Hz, 1H), 5.23 (d, J=5.2 Hz, 1H), 4.26-4.19 (m, 4H), 3.83 (s, 3H), 3.82 (s, 3H), 3.42 (d, J=13.5 Hz, 1H), 3.19 (td, J=13.2, 3.0 Hz, 1H), 2.60 (h, J=6.7, 6.2 Hz, 2H), 2.35 (d, J=13.6 Hz, 1H), 2.30-2.17 (m, 1H), 2.14-2.01 (m, 1H), 1.72 (dtdd, J=16.2, 12.6, 8.4, 4.7 Hz, 5H), 1.57-1.29 (m, 2H), 1.26 (s, 3H), 1.24 (s, 3H), 0.91 (t, J=7.4 Hz, 3H). HRMS (ESI): Calcd for $(C_{33}H_{44}N_2O_{10}+H)^+$: 641.3074. Found: 641.3093.

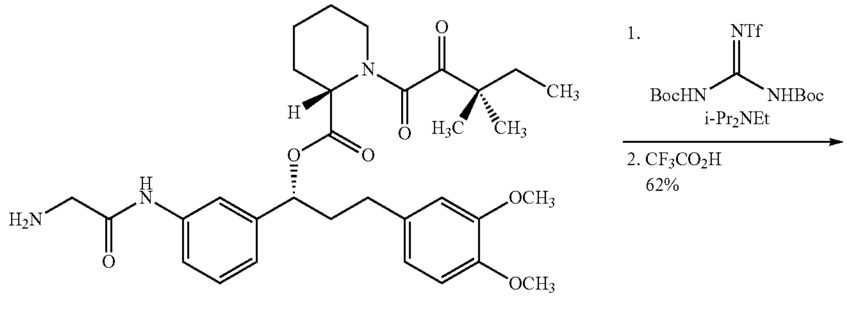

ZZY01-040

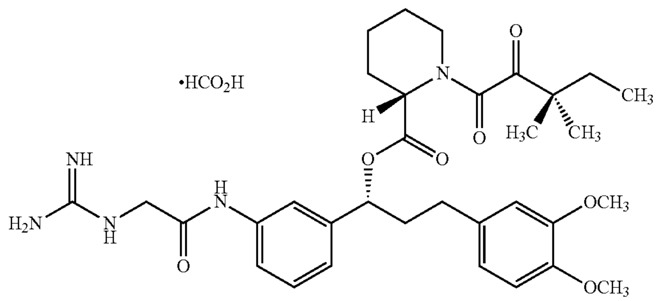

ZZY01-065

An oven-dried 2-mL vial was charged with ZZY01-040 (50 mg, 0.090 mmol), tert-butyl N—[N-tert-butoxycarbonyl-N'-(trifluoromethylsulfonyl)carbamimidoyl]carbamate (50 mg, 0.13 mmol), and a magnetic stir bar. Dichloromethane (0.50 mL) and N,N-diisopropylethylamine (30 μL, 0.17 mmol) were added sequentially via syringe. The resulting mixture was allowed to stir at 23° C. In 4 h, LC-MS showed full consumption of the starting material and formation of the desired product mass (Boc protected). Trifluoroacetic acid (0.5 mL) was added to the reaction mixture via syringe. After stirring for another 1 h, LC-MS analysis showed full deprotection of the Boc groups. The reaction mixture was concentrated under reduced pressure. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (33 mg, 62%). 6:1 mixture of rotamers. $^1$H NMR (400 MHz, Methanol-d$_4$) δ 8.35 (s, 1H), 7.78 (t, J=1.9 Hz, 1H), 7.44 (ddd, J=8.1, 2.2, 1.1 Hz, 1H), 7.35 (t, J=7.8 Hz, 1H), 7.18-7.11 (m, 1H), 6.87 (d, J=8.2 Hz, 1H), 6.81 (d, J=2.0 Hz, 1H), 6.74 (dd, J=8.2, 2.0 Hz, 1H), 5.74 (dd, J=8.8, 5.0 Hz, 1H), 5.26-5.21 (m, 1H), 4.11 (s, 2H), 3.83 (s, 3H), 3.82 (s, 3H), 3.42 (d, J=13.4 Hz, 1H), 3.27 (dd, J=13.2, 3.0 Hz, 1H), 2.74-2.54 (m, 2H), 2.36 (d, J=14.1 Hz, 1H), 2.32-2.18 (m, 1H), 2.15-2.01 (m, 1H), 1.83-1.55 (m, 5H), 1.55-1.28 (m, 2H), 1.25 (s, 3H), 1.23 (s, 3H), 0.90 (t, J=7.5 Hz, 3H). HRMS (ESI): Calcd for $(C_{33}H_{45}N_5O_7+H)^+$: 624.3397. Found: 624.3381.

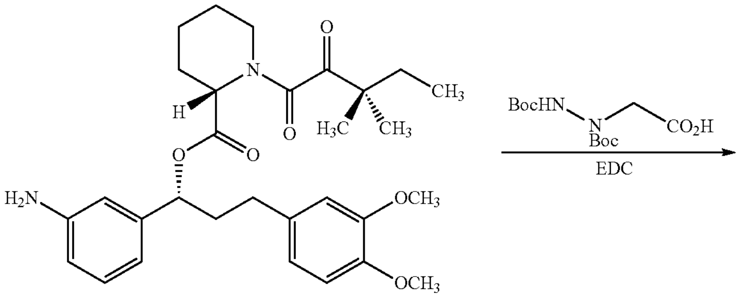

SLF

-continued

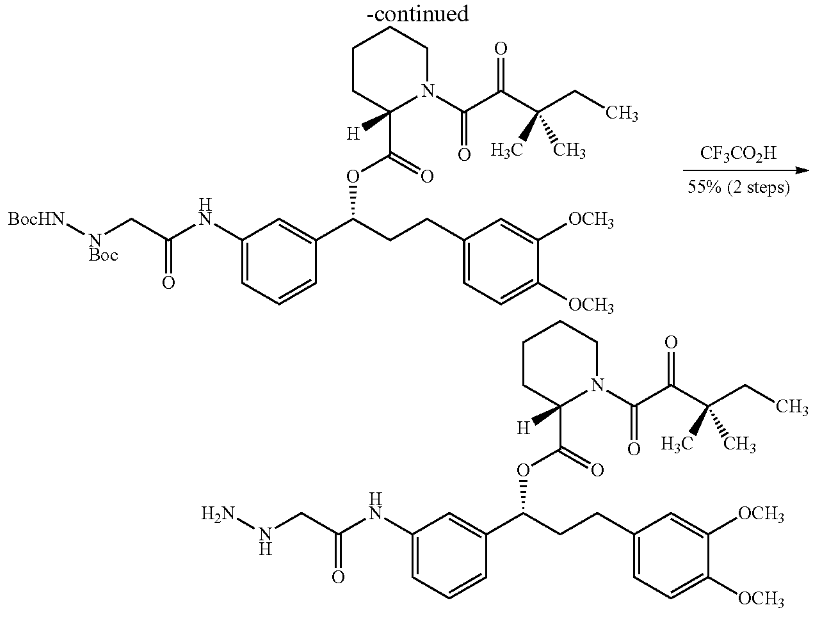

ZZY01-070

EDC (27.4 mg, 0.1400 mmol) was added in one portion to a stirred solution of SLF (50 mg, 0.10 mmol) and 2-[tert-butoxycarbonyl-(tert-butoxycarbonylamino)amino] acetic acid (42 mg, 0.14 mmol) in dichloromethane (0.19 mL) at 0° C. The resulting mixture was allowed to warm to 23° C. over 30 min, then was kept stirred at 23° C. In 3 h, TLC analysis (50% ethyl acetate-hexanes) showed that the reaction was complete. The reaction mixture was directly concentrated under reduced pressure, and the residue was purified by column chromatography (20-50% ethyl acetate-hexanes, 40-g CombiFlash column) to afford the intermediate as a white foam.

The intermediate product was dissolved in dichloromethane (0.5 mL) was cooled to 0° C., then trifluoroacetic acid (0.5 mL) was added dropwise. The resulting yellow solution was stirred at 0° C. until TLC analysis (50% ethyl acetate-hexanes, mini-workup with ether/sodium bicarbonate) showed full consumption of the starting material (~2 h). The reaction solution was concentrated in vacuo, and the residue was partitioned between dichloromethane (10 mL) and saturated sodium bicarbonate solution (10 mL). The layers were separated, and the aqueous layer was extracted with dichloromethane (2×10 mL). The combined organic layers were dried over sodium sulfate, and the dried solution was concentrated in vacuo to afford the product as a white foam (29 mg, 55%). 6:1 mixture of rotamers. $^1$H NMR (400 MHz, Chloroform-d) δ 7.65-7.46 (m, 2H), 7.33 (t, J=7.9 Hz, 1H), 7.08 (d, J=7.7 Hz, 1H), 6.80 (d, J=8.7 Hz, 1H), 6.75-6.68 (m, 2H), 5.84-5.74 (m, 1H), 5.35 (d, J=5.6 Hz, 1H), 3.93 (s, 2H), 3.88 (s, 3H), 3.87 (s, 3H), 3.38 (d, J=13.2 Hz, 1H), 3.17 (t, J=12.8 Hz, 1H), 2.72-2.47 (m, 2H), 2.38 (d, J=13.3 Hz, 1H), 2.26 (dt, J=16.2, 7.5 Hz, 1H), 2.16-2.03 (m, 1H), 1.83-1.49 (m, 5H), 1.49-1.33 (m, 2H), 1.26 (s, 3H), 1.24 (s, 3H), 0.92 (t, J=7.4 Hz, 3H). HRMS (ESI): Calcd for $(C_{32}H_{44}N_4O_7+H)^+$: 597.3288. Found: 597.3302.

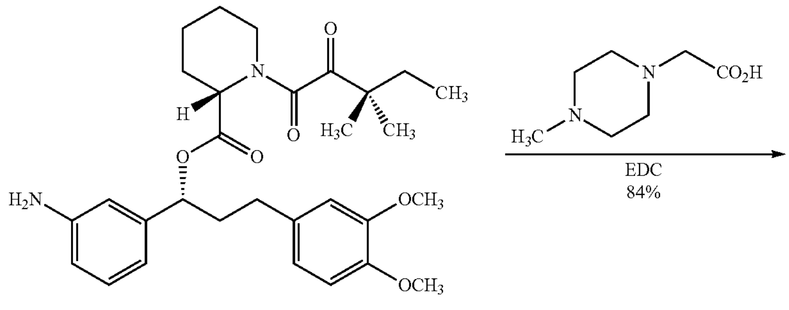

SLF

-continued

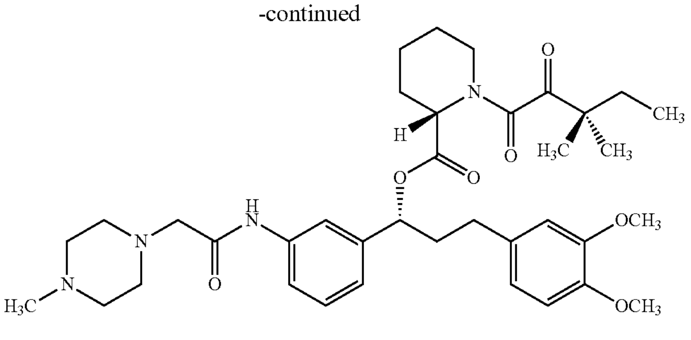

ZZY01-072

An oven-dried 1-dram vial was charged with 2-(4-methylpiperazin-1-yl)acetic acid (30 mg, 0.19 mmol), SLF (50 mg, 0.10 mmol), and a magnetic stir bar. Dichloromethane (0.48 mL) was added via syringe, and the resulting solution was cooled to 0° C. 3-(ethyliminomethyleneamino)-N,N-dimethyl-propan-1-amine hydrochloride (37 mg, 0.19 mmol) was added in one portion to the cooled solution, and the resulting mixture was allowed to warm to 23° C. over 30 min. In 2 h, LC-MS analysis showed full consumption of the starting material. The reaction mixture was directly loaded onto a silica gel column (4-g RediSep) and purified by column chromatography (2-10% methanol in dichloromethane with 0.2-1% saturated aqueous ammonium hydroxide solution) to afford the product as a white solid (53 mg, 84%). 6:1 mixture of rotamers. $^1$H NMR (400 MHz, Chloroform-d) δ 9.13 (s, 1H), 7.58 (d, J=1.8 Hz, 1H), 7.54-7.49 (m, 1H), 7.32 (t, J=7.9 Hz, 1H), 7.09 (d, J=7.9 Hz, 1H), 6.84-6.75 (m, 1H), 6.75-6.65 (m, 2H), 5.78 (dd, J=8.2, 5.4 Hz, 1H), 5.32 (d, J=5.4 Hz, 1H), 3.86 (s, 3H), 3.85 (s, 3H), 3.37 (d, J=13.3 Hz, 1H), 3.20 (td, J=13.1, 3.1 Hz, 1H), 2.71-2.44 (m, 10H), 2.41-2.36 (m, 1H), 2.34 (s, 3H), 2.27 (ddt, J=12.6, 8.6, 4.5 Hz, 1H), 2.16-2.00 (m, 1H), 1.80-1.55 (m, 5H), 1.54-1.29 (m, 2H), 1.23 (s, 3H), 1.21 (s, 3H), 0.89 (t, J=7.5 Hz, 3H). HRMS (ESI): Calcd for $(C_{37}H_{52}N_4O_7+H)^+$: 665.3914. Found: 665.3913.

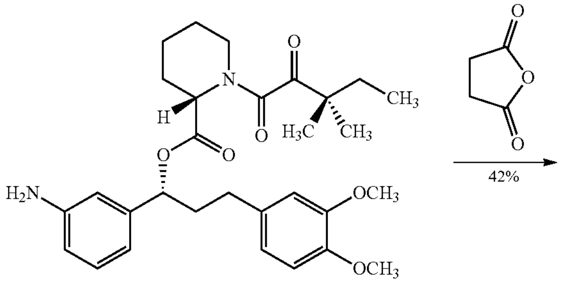

SLF

-continued

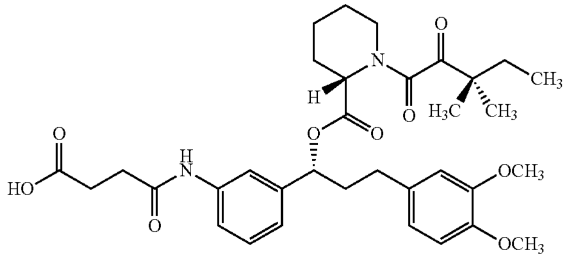

ZZY01-083

Succinic anhydride (14 mg, 0.14 mmol) was added to a solution of SLF (50 mg, 0.10 mmol) in DMF (0.48 mL) at 23° C. The resulting solution was stirred at 23° C. for 16 h. The reaction mixture was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (25 mg, 42%). 6:1 mixture of rotamers. Spectroscopic data was in agreement with that reported by Winter et al. (Winter, G. E. et al. Science 2015, 348, 1376-81). HRMS (ESI): Calcd for $(C_{33}H_{44}N_2O_9+H)^+$: 625.3125. Found: 625.3102.

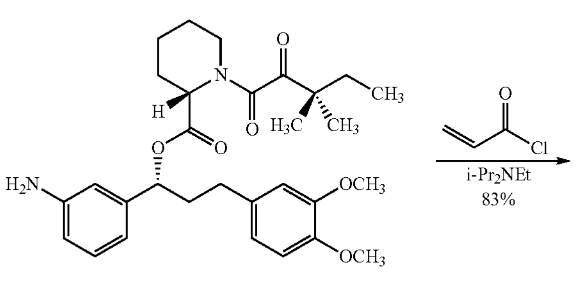

SLF

-continued

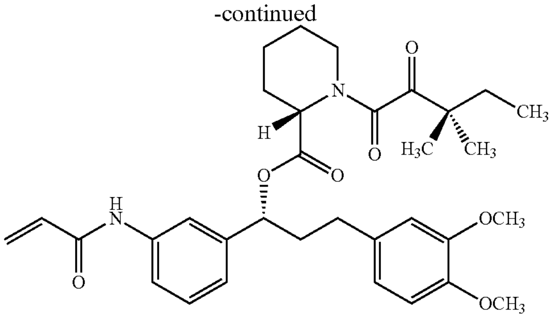

ZZY02-014

Acryloyl chloride (12 μL, 0.010 mmol) was added via pipet to a solution of SLF (5 mg, 0.010 mmol) and N,N-Diisopropylethylamine (17 μL, 0.010 mmol) in dichloromethane (0.10 mL) at 0° C. The resulting solution was stirred at 0° C. for 30 min. At this point, LC-MS analysis showed full consumption of starting material and formation of a single peak corresponding to the desired mass. The reaction mixture was concentrated with a stream of dry air. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (4.6 mg, 83%). 6:1 mixture of rotamers. $^1$H NMR (400 MHz, Chloroform-d) δ 8.14 (s, 1H), 7.97 (d, J=8.2 Hz, 1H), 7.47 (s, 1H), 7.35 (t, J=7.9 Hz, 1H), 7.01 (d, J=7.6 Hz, 1H), 6.79 (d, J=7.9 Hz, 1H), 6.75-6.64 (m, 2H), 6.49 (dd, J=16.9, 1.4 Hz, 1H), 6.35 (dd, J=16.9, 10.1 Hz, 1H), 5.86 (dd, J=7.3, 5.6 Hz, 1H), 5.80 (dd, J=10.1, 1.4 Hz, 1H), 5.39 (d, J=5.5 Hz, 1H), 3.88 (s, 3H), 3.87 (s, 3H), 3.32 (d, J=13.6 Hz, 1H), 3.10-2.97 (m, 1H), 2.64-2.52 (m, 2H), 2.38 (d, J=13.5 Hz, 1H), 2.34-2.17 (m, 1H), 2.17-2.00 (m, 1H), 1.87-1.61 (m, 5H), 1.55-1.38 (m, 2H), 1.29 (s, 3H), 1.27 (s, 3H), 0.94 (t, J=7.5 Hz, 3H). HRMS (ESI): Calcd for $(C_{33}H_{42}N_2O_7+H)^+$: 579.3070. Found: 579.3085.

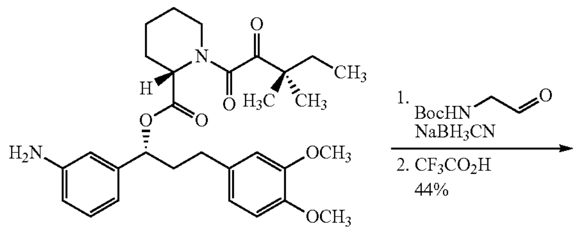

SLF

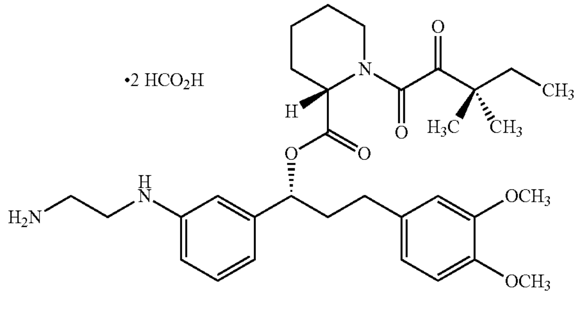

ZZY02-032 tert-Butyl N-(2-oxoethyl)carbamate (17 mg, 0.10 mmol) was added to a solution of SLF (50 mg, 0.10 mmol) in 9:1 methanol:acetic acid (0.5 mL). The resulting solution was stirred at 23° C. for 30 min, then sodium cyanoborohydride (9.0 mg, 0.14 mmol) was added in one portion. The resulting mixture was stirred at 23° C. for another 30 min, at which point LC-MS analysis showed full conversion to the mono-alkylation product. The reaction mixture was concentrated, and the residue was dissolved in trifluoroacetic acid (0.5 mL). After 30 min, LC-MS analysis showed full deprotection of the Boc group. The reaction mixture was concentrated in vacuo. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (24 mg, 44%). 6:1 mixture of rotamers. $^1$H NMR (400 MHz, Methanol-$d_4$) δ 8.43 (s, 2H), 7.18 (t, J=7.8 Hz, 1H), 6.88 (d, J=8.2 Hz, 1H), 6.79 (d, J=2.0 Hz, 1H), 6.78-6.70 (m, 2H), 6.69-6.60 (m, 2H), 5.69 (dd, J=8.7, 5.0 Hz, 1H), 5.23 (d, J=5.6 Hz, 1H), 3.83 (s, 3H), 3.82 (s, 3H), 3.48-3.37 (m, 4H), 3.24 (td, J=13.1, 3.2 Hz, 1H), 3.15 (td, J=6.0, 2.5 Hz, 2H), 2.72-2.47 (m, 2H), 2.37 (d, J=13.6 Hz, 1H), 2.33-2.18 (m, 1H), 2.18-1.96 (m, 1H), 1.85-1.63 (m, 5H), 1.60-1.29 (m, 2H), 1.24 (s, 3H), 1.23 (s, 3H), 0.91 (t, J=7.5 Hz, 3H). HRMS (ESI): Calcd for $(C_{32}H_{45}N_3O_6+H)^+$: 568.3386. Found: 568.3440.

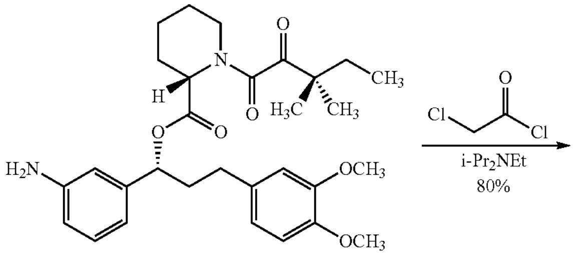

SLF

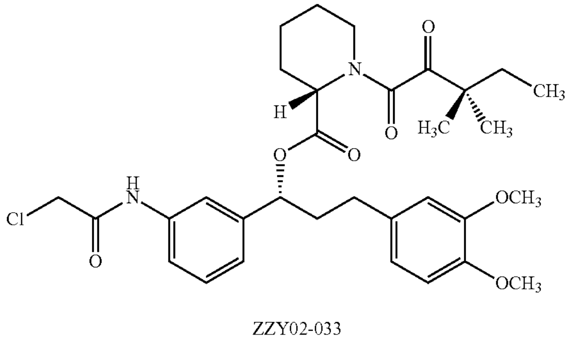

ZZY02-033

2-Chloroacetyl chloride (7.6 μL, 0.10 mmol) was added to a solution of SLF (50 mg, 0.10 mmol) and N,N-Diisopropylethylamine (50 μL, 0.29 mmol) in dichloromethane (0.20 mL) at 0° C. In 40 min, TLC (50% ethyl acetate-hexanes) showed full consumption of the starting material and formation of a just slightly less polar spot. LC-MS analysis confirmed the identity of the product. The reaction mixture was partitioned between dichloromethane (1 mL) and saturated sodium bicarbonate solution (1 mL). The aqueous layer was extracted with dichloromethane (2×1 mL). The combined organic layers were dried over sodium sulfate, and the dried solution was concentrated. The residue was purified by column chromatography (20-50% ethyl acetate-hexanes, 15 min, 4-g CombiFlash column) to afford the product as a white solid (46 mg, 80%). 6:1 mixture of rotamers. $^1$H NMR (400 MHz, Methanol-$d_4$) δ 7.76 (t, J=1.9 Hz, 1H), 7.46 (ddd, J=8.2, 2.2, 1.1 Hz, 1H), 7.34 (t, J=7.9 Hz, 1H), 7.14 (dt, J=7.7, 1.3 Hz, 1H), 6.86 (d, J=8.2 Hz, 1H), 6.80 (d, J=2.0 Hz, 1H), 6.73 (dd, J=8.2, 2.0 Hz, 1H), 5.75 (dd, J=8.8, 5.1 Hz, 1H), 5.24 (d, J=5.2 Hz, 1H), 4.19 (s, 2H), 3.82 (s, 3H), 3.81 (s, 3H), 3.46-3.39 (m, 1H), 3.26 (td, J=13.1, 3.0 Hz, 1H), 2.63 (tdd, J=15.4, 8.6, 5.2 Hz, 2H), 2.46-2.19 (m, 2H), 2.16-2.04 (m, 1H), 1.81-1.57 (m, 5H), 1.55-1.28 (m, 2H), 1.25 (s, 3H), 1.23 (s, 3H), 0.90 (t, J=7.5 Hz, 3H). HRMS (ESI): Calcd for $(C_{32}H_{41}ClN_2O_7+H)^+$: 601.2680. Found: 601.2688.

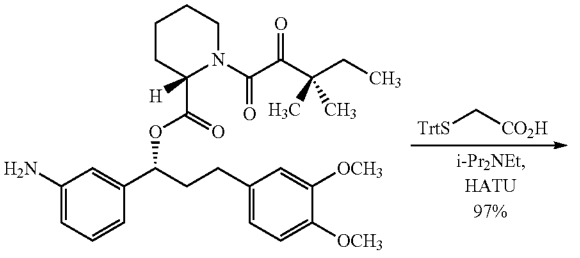

SLF

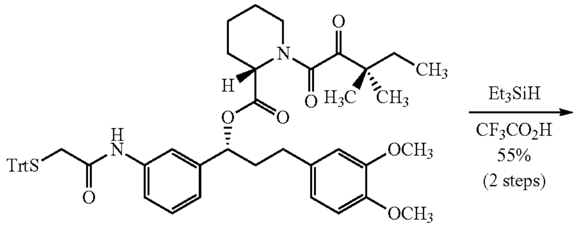

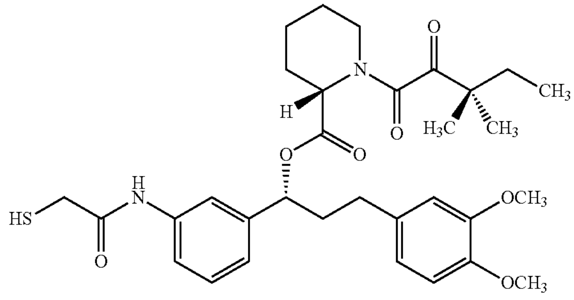

ZZY02-055

N,N-Diisopropylamine (50 μL, 0.29 mmol) and HATU (54 mg, 0.14 mmol) were added sequentially to a stirred solution of SLF (50 mg, 0.10 mmol) and S-trityl thioglycolic acid (38 mg, 0.11 mmol) in dichloromethane (0.19 mL). The resulting mixture was stirred at 23° C. No reaction was observed at 2 h, likely due to the insolubility of HATU in dichloromethane. DMF (0.2 mL) was added, and the resulting solution was stirred at 23° C. In 2 h, LC-MS analysis showed full conversion to the desired product. The reaction mixture was partitioned between ether (10 mL) and water (10 mL). The aqueous layer was extracted with ether (2×10 mL). The combined organic layers were washed with water (2×10 mL), then with brine (10 mL). The washed solution was dried over magnesium sulfate, and the dried solution was concentrated. The residue was purified by column chromatography (20-100% ethyl acetate-hexanes) to afford the product as a white solid (78 mg, 97%).

Triethylsilane (0.15 mL, 0.93 mmol) and trifluoroacetic acid (40 μL, 0.46 mmol) were sequentially added to a stirred solution of the intermediate (78 mg, 0.090 mmol) in dichloromethane (0.19 mL) at 23° C. The resulting yellow solution was stirred at 23° C. for 1 h, at which point the yellow color had completely faded. The reaction mixture was concentrated, and the residue was purified by column chromatography (50-100% ethyl acetate-hexanes) to afford the product as a white solid (49 mg, 86%). 6:1 mixture of rotamers. $^1$H NMR (400 MHz, Chloroform-d) δ 8.72 (s, 1H), 7.67 (ddd, J=8.1, 2.2, 1.0 Hz, 1H), 7.49 (d, J=2.0 Hz, 1H), 7.31 (t, J=7.9 Hz, 1H), 7.04 (dt, J=7.7, 1.2 Hz, 1H), 6.76 (d, J=8.7 Hz, 1H), 6.71-6.63 (m, 2H), 5.80 (dd, J=7.7, 5.6 Hz, 1H), 5.37-5.31 (m, 1H), 3.85 (s, 3H), 3.83 (s, 3H), 3.39 (d, J=9.0 Hz, 2H), 3.36-3.29 (m, 1H), 3.15-3.01 (m, 1H), 2.64-2.48 (m, 2H), 2.48-2.31 (m, 2H), 2.30-2.17 (m, 1H), 2.09 (t, J=9.0 Hz, 1H), 1.78-1.57 (m, 5H), 1.51-1.33 (m, 2H), 1.23 (s, 6H), 0.89 (t, J=7.5 Hz, 3H). HRMS (ESI): Calcd for $(C_{32}H_{42}N_2O_7S+H)^+$: 599.2791. Found: 599.2778.

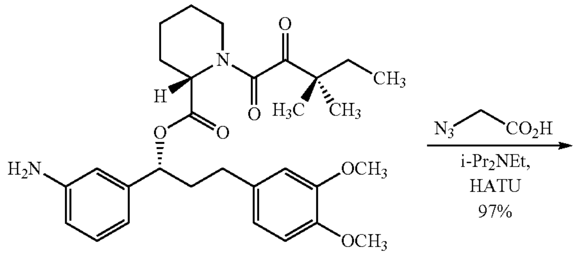

SLF

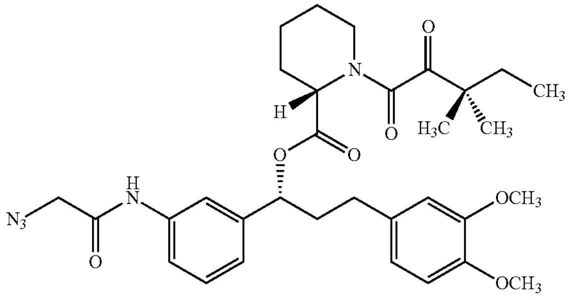

ZZY02-096

N,N-Diisopropylamine (50 μL, 0.29 mmol) and HATU (54 mg, 0.14 mmol) were added sequentially to a stirred solution of SLF (50 mg, 0.10 mmol), 2-azidoacetic acid (8.6 μL, 0.11 mmol) in 9:1 dichloromethane:DMF (0.19 mL). In 2 h, LC-MS analysis showed full conversion to the desired product. The reaction mixture was partitioned between ether (10 mL) and water (10 mL). The aqueous layer was extracted with ether (2×10 mL). The combined organic layers were washed with water (2×10 mL), then with brine (10 mL). The washed solution was dried over magnesium sulfate, and the dried solution was concentrated. The residue was purified by column chromatography (20-100% ethyl acetate-hexanes) to afford the product as a white solid (56 mg, 97%). 6:1 mixture of rotamers. $^1$H NMR (400 MHz, Chloroform-d) δ 8.29 (s, 1H), 7.71 (ddd, J=8.1, 2.3, 1.0 Hz, 1H), 7.50 (t, J=1.9 Hz, 1H), 7.34 (t, J=7.9 Hz, 1H), 7.07 (d, J=7.5 Hz, 1H), 6.82-6.74 (m, 1H), 6.74-6.57 (m, 2H), 5.81 (dd, J=7.7, 5.6 Hz, 1H), 5.34 (d, J=5.5 Hz, 1H), 4.17-4.10 (m, 2H), 3.86 (s, 3H), 3.85 (s, 3H), 3.33 (d, J=13.7 Hz, 1H), 3.15-3.01 (m, 1H), 2.66-2.41 (m, 2H), 2.36 (d, J=13.6 Hz, 1H), 2.31-2.16 (m, 1H), 2.11-1.99 (m, 1H), 1.78-1.59 (m, 5H), 1.51-1.33 (m, 2H), 1.24 (s, 6H), 0.91 (t, J=7.5 Hz, 3H). HRMS (ESI): Calcd for $(C_{32}H_{41}N_5O_7+H)^+$: 608.3084. Found: 608.3110.

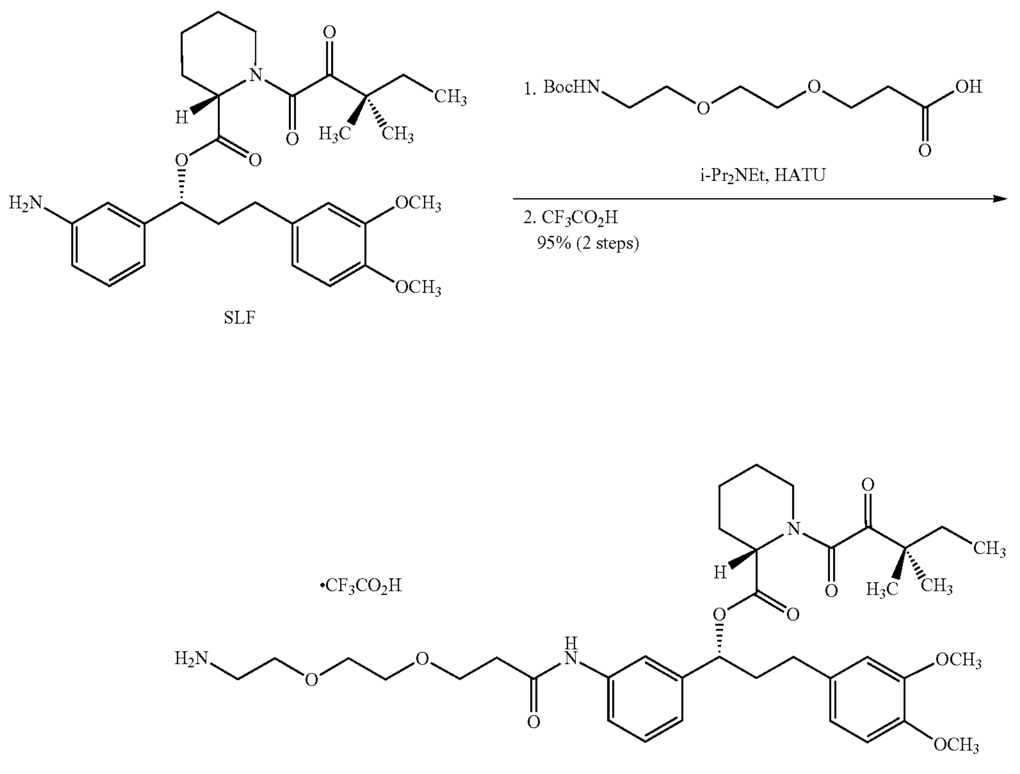

SLF

ZZY03-077

N,N-Diisopropylethylamine (16.6 μL, 0.10 mmol) and HATU (72 mg, 0.19 mmol) were added sequentially to a solution of SLF (50 mg, 0.10 mmol) and 3-[2-[2-(tert-butoxycarbonylamino)ethoxy]ethoxy]propanoic acid (40 mg, 0.14 mmol) in 9:1 dichloromethane:DMF (0.2 mL). The resulting mixture was stirred at 23° C. for 12 h, at which point LC-MS analysis showed full conversion to the desired product. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a yellow oil.

The intermediate product (70 mg, 0.090 mmol) was dissolved in 1:1 dichloromethane:trifluoroacetic acid (1.0 mL). The resulting solution was allowed to stand at 23° C. for 1 h, then was concentrated under reduced pressure to afford the product as a yellow foam (71 mg, 95%). 6:1 mixture of rotamers. $^1H$ NMR (400 MHz, Methanol-$d_4$) δ 7.70 (t, J=1.9 Hz, 1H), 7.52-7.44 (m, 1H), 7.34 (t, J=7.9 Hz, 1H), 7.14 (d, J=8.0 Hz, 1H), 6.88 (d, J=8.1 Hz, 1H), 6.81 (d, J=2.1 Hz, 1H), 6.75 (dd, J=8.2, 2.0 Hz, 1H), 5.73 (dd, J=8.8, 5.0 Hz, 1H), 5.24 (d, J=5.6 Hz, 1H), 3.86 (t, J=6.5 Hz, 2H), 3.84 (s, 3H), 3.82 (s, 4H), 3.71-3.64 (m, 8H), 3.42 (d, J=13.9 Hz, 1H), 3.26 (dd, J=13.4, 3.3 Hz, 1H), 3.09-2.99 (m, 2H), 2.70-2.54 (m, 4H), 2.37 (d, J=14.3 Hz, 1H), 2.34-2.22 (m, 1H), 2.15-2.03 (m, 1H), 1.84-1.59 (m, 5H), 1.59-1.29 (m, 2H), 1.25 (s, 3H), 1.24 (s, 3H), 0.90 (t, J=7.5 Hz, 3H). HRMS (ESI): Calcd for $(C_{37}H_{53}N_3O_9+H)^+$: 684.3860. Found: 684.3851.

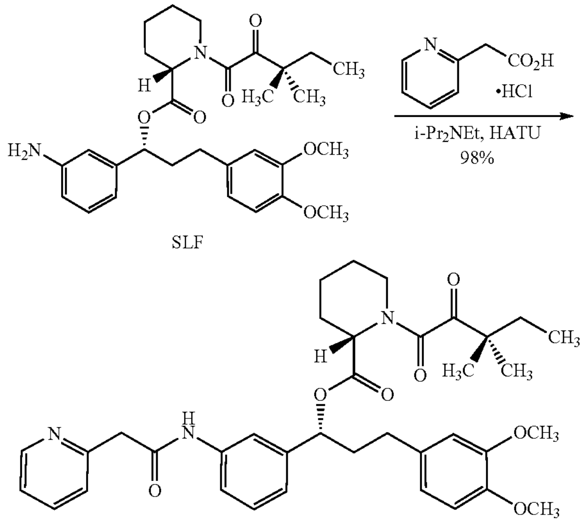

SLF

ZZY03-083

N,N-Diisopropylethylamine (16.6 μL, 0.10 mmol) and HATU (72 mg, 0.1900 mmol) were added sequentially to a solution of SLF (50 mg, 0.10 mmol) and 2-(2-pyridyl)acetic acid hydrochloride (25 mg, 0.14 mmol) in 9:1 dichloromethane:DMF (0.2 mL). The resulting mixture was stirred at 23° C. for 12 h, at which point LC-MS analysis showed full conversion to the desired product. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a white solid (60 mg, 98%). 6:1 mixture of rotamers. $^1$H NMR (400 MHz, Chloroform-d) δ 9.91 (s, 1H), 8.62 (dd, J=5.3, 1.7 Hz, 1H), 7.93 (t, J=7.6 Hz, 1H), 7.61 (s, 1H), 7.54 (t, J=7.5 Hz, 2H), 7.44 (t, J=6.5 Hz, 1H), 7.34-7.23 (m, 1H), 7.05 (d, J=7.7 Hz, 1H), 6.82-6.73 (m, 1H), 6.74-6.63 (m, 2H), 5.76 (dd, J=8.1, 5.4 Hz, 1H), 5.32 (d, J=5.4 Hz, 1H), 4.05 (s, 2H), 3.85 (s, 3H), 3.85 (s, 3H), 3.37 (d, J=13.3 Hz, 1H), 3.18 (td, J=13.0, 3.1 Hz, 1H), 2.69-2.46 (m, 2H), 2.36 (d, J=13.5 Hz, 1H), 2.33-2.19 (m, 1H), 2.19-1.99 (m, 1H), 1.79-1.57 (m, 5H), 1.57-1.29 (m, 2H), 1.23 (s, 3H), 1.21 (s, 3H), 0.88 (t, J=7.4 Hz, 3H). HRMS (ESI): Calcd for $(C_{37}H_{45}N_3O_7+H)^+$: 644.3336. Found: 644.3350.

1H), 2.17-2.04 (m, 1H), 1.84-1.56 (m, 5H), 1.55-1.33 (m, 2H), 1.21 (s, 3H), 1.20 (s, 3H), 0.87 (t, J=7.5 Hz, 3H). HRMS (ESI): Calcd for $(C_{35}H_{49}N_3O_8+H)^+$: 640.3598. Found: 640.3611.

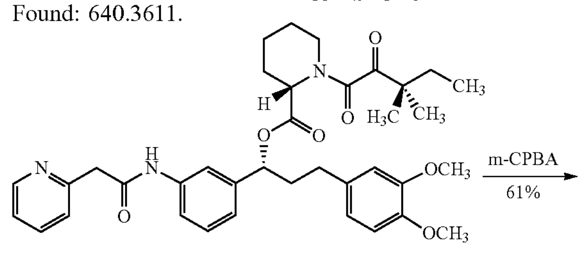

ZZY03-083

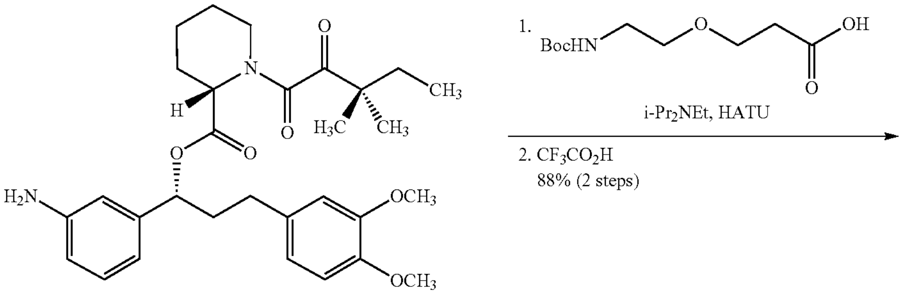

SLF

•$CF_3CO_2H$

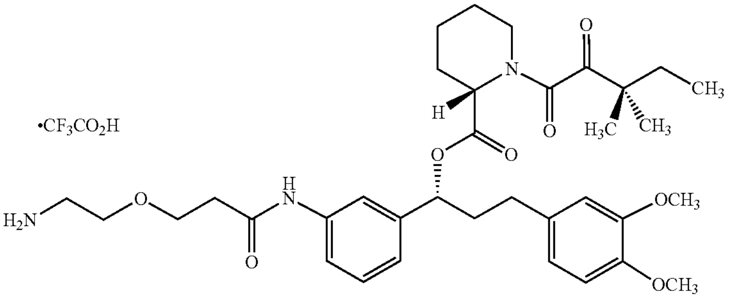

ZZY03-084

N,N-Diisopropylethylamine (16.6 μL, 0.10 mmol) and HATU (72 mg, 0.19 mmol) were added sequentially to a solution of SLF (50 mg, 0.10 mmol) and 3-[2-(tert-butoxycarbonylamino)ethoxy]propanoic acid (33 mg, 0.14 mmol) in 9:1 dichloromethane:DMF (0.2 mL). The resulting mixture was stirred at 23° C. for 12 h, at which point LC-MS analysis showed full conversion to the desired product. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a yellow oil. The oil was dissolved in 1:1 dichloromethane:trifluoroacetic acid (1.0 mL). The resulting colorless solution was allowed to stand at 23° C. for 1 h, then was concentrated in vacuo to afford the product as a white foam (62 mg, 88%). 6:1 mixture of rotamers. $^1$H NMR (400 MHz, Acetonitrile-d$_3$) δ 8.85 (s, 1H), 7.68 (s, 1H), 7.51 (d, J=8.1 Hz, 1H), 7.35 (t, J=7.9 Hz, 1H), 7.11 (d, J=7.6 Hz, 1H), 6.86 (d, J=8.2 Hz, 1H), 6.80 (d, J=2.0 Hz, 1H), 6.74 (dd, J=8.1, 2.0 Hz, 1H), 5.70 (dd, J=8.7, 4.8 Hz, 1H), 5.24 (d, J=5.6 Hz, 1H), 3.80 (s, 3H), 3.79 (s, 3H), 3.72 (dd, J=6.2, 4.1 Hz, 2H), 3.38 (d, J=14.0 Hz, 1H), 3.25 (dd, J=12.9, 3.1 Hz, 1H), 3.17 (s, 4H), 2.72-2.51 (m, 4H), 2.37 (d, J=13.9 Hz, 1H), 2.32-2.17 (m, -continued

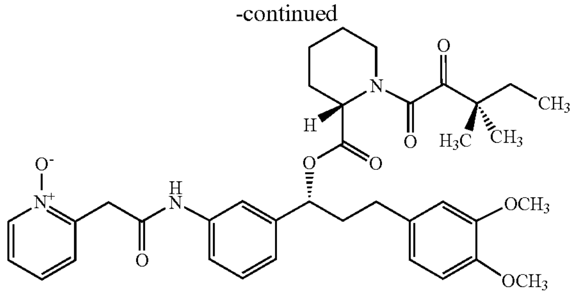

ZZY03-087

3-Chlorobenzenecarboperoxoic acid (5.4 mg, 0.020 mmol) was added to an ice-cold solution of ZZY03-083 (10 mg, 0.020 mmol) in dichloromethane (0.16 mL). The resulting pale yellow solution was stirred at 0° C. for 1 h. LC-MS analysis showed complete conversion to the desired m/z.

Triethylamine (10 μL) was added to consume the excess mCPBA. After warming to 23° C., the solution was concentrated under reduced pressure. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (6.3 mg, 61%). 6:1 mixture of rotamers. $^1$H NMR (400 MHz, Chloroform-d) δ 10.91 (s, 1H), 8.46-8.37 (m, 1H), 7.60-7.49 (m, 3H), 7.45 (t, J=7.7 Hz, 1H), 7.36 (t, J=7.0 Hz, 1H), 7.33-7.24 (m, 1H), 7.09-7.00 (m, 1H), 6.80 (d, J=8.8 Hz, 1H), 6.74-6.67 (m, 2H), 5.77 (dd, J=8.1, 5.6 Hz, 1H), 5.33 (d, J=5.4 Hz, 1H), 4.12 (s, 2H), 3.88 (s, 3H), 3.87 (s, 3H), 3.40 (d, J=13.4 Hz, 1H), 3.22 (td, J=13.0, 3.1 Hz, 1H), 2.68-2.48 (m, 2H), 2.38 (d, J=13.7 Hz, 1H), 2.33-2.17 (m, 1H), 2.14-2.02 (m, 1H), 1.84-1.58 (m, 5H), 1.58-1.30 (m, 2H), 1.26 (s, 3H), 1.23 (s, 3H), 0.90 (t, J=7.4 Hz, 3H). HRMS (ESI): Calcd for $(C_{37}H_{45}N_3O_8+H)^+$: 660.3285. Found: 660.3268.

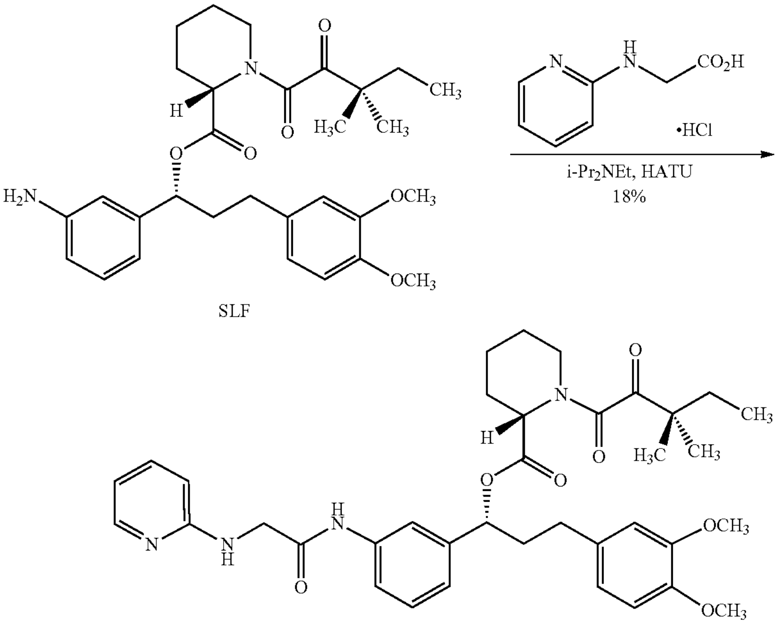

SLF

ZZY03-091

HATU (72 mg, 0.19 mmol) was added to a mixture of SLF (50 mg, 0.10 mmol), 2-(2-pyridylamino)acetic acid hydrochloride (27 mg, 0.14 mmol), N,N-Diisopropylethylamine (34 μL, 0.20 mmol) in 9:1 dichloromethane:DMF (0.2 mL). The resulting mixture was stirred at 23° C. for 12 h, at which point LC-MS analysis showed ~50% conversion to the desired product. Additional 2-(2-pyridylamino)acetic acid hydrochloride (27 mg, 0.14 mmol) and HATU (72 mg, 0.19 mmol) were added, and the mixture was stirred for another 1 h. LC-MS analysis showed no further progress. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a yellow solid (11.2 mg, 18%). 6:1 mixture of rotamers. $^1$H NMR (400 MHz, Chloroform-d) δ 7.92 (s, 1H), 7.83 (s, 1H), 7.65 (d, J=8.3 Hz, 1H), 7.59 (s, 1H), 7.36-7.28 (m, 1H), 7.20-6.99 (m, 3H), 6.87 (t, J=6.4 Hz, 1H), 6.85-6.75 (m, 1H), 6.75-6.64 (m, 2H), 5.81-5.74 (m, 1H), 5.33 (d, J=5.2 Hz, 1H), 4.54-4.35 (m, 2H), 3.86 (s, 3H), 3.85 (s, 3H), 3.37 (d, J=13.7 Hz, 1H), 3.26-2.99 (m, 2H), 2.66-2.46 (m, 2H), 2.37 (d, J=13.4 Hz, 1H), 2.33-2.18 (m, 1H), 2.14-2.02 (m, 1H), 1.80-1.64 (m, 5H), 1.51-1.32 (m, 2H), 1.23 (s, 3H), 1.21 (s, 3H), 0.88 (t, J=7.4 Hz, 3H). HRMS (ESI): Calcd for $(C_{37}H_{46}N_4O_7+H)^+$: 659.3444. Found: 659.3436.

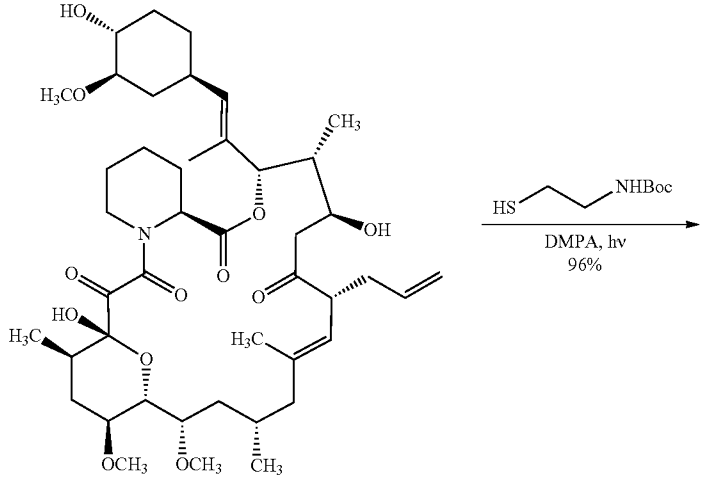

FK506

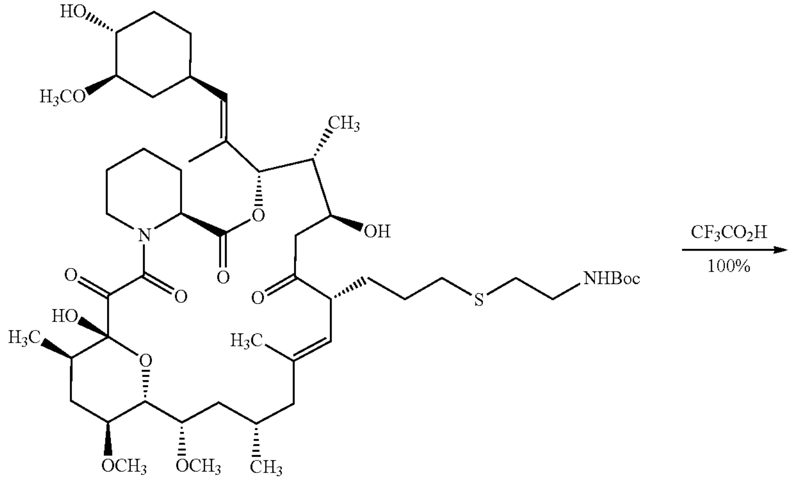

ZZY05-009

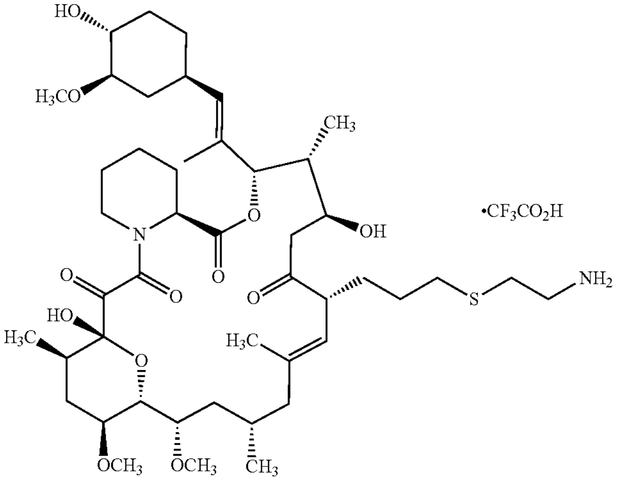

ZZY05-011 tert-Butyl N-(2-sulfanylethyl)carbamate (23 mg, 0.13 mmol) and dimethoxyphenylacetophenone (DMPA, 3.2 mg, 0.010 mmol) were added sequentially to a solution of FK506 (100 mg, 0.120 mmol) in dichloromethane (1.2 mL) at 23° C. After all reactants had dissolved, the vial was placed above a hand-held UV-light operating at 365 nm wavelength (the light was placed upside-down so that the contents of vial were directly irradiated). The irradiation was maintained for 15 min, at which point TLC analysis (100% ethyl acetate) showed full consumption of FK506 and formation of a slightly more polar product. The reaction solution was directly loaded onto a 12-g silica gel column. Purification by column chromatography (50-100% ethyl acetate-hexanes, 12-g RediSep® Rf column, Teledyne ISCO, Lincoln, NE) afforded the product as a white foam (117 mg, 96%).

Trifluoroacetic acid (0.5 mL) was added dropwise to a solution of ZZY05-009 (117 mg, 0.120 mmol) in dichloromethane (0.5 mL) at 0° C. The resulting mixture was stirred at 0° C. for 1 h, at which point LC-MS analysis showed full deprotection of the Boc group. The reaction solution was concentrated under reduced pressure and the product was dried azeotropically by rotary evaporation of its suspension in toluene to afford the product as an off-white powder (119 mg, 100%). NMR: 3:2 mixture of rotamers. $^1$H NMR (400 MHz, Methanol-$d_4$) δ 5.29-5.07 (m, 2H), 4.95 (d, J=11.7 Hz, 1H), 4.64 (s, 1H), 4.37 (d, J=13.4 Hz, 1H), 4.13-3.93 (m, 2H), 3.78-3.70 (m, 2H), 3.69-3.54 (m, 2H), 3.44 (s, 3H), 3.42 (s, 3H), 3.41-3.39 (m, 3H), 3.36 (s, 3H), 3.19-3.09 (m, 2H), 3.09-2.96 (m, 2H), 2.84-2.75 (m, 2H), 2.60 (t, J=6.9 Hz, 2H), 2.43-2.26 (m, 4H), 2.27-2.10 (m, 4H), 2.10-1.89 (m, 4H), 1.84-1.73 (m, 6H), 1.73-1.60 (m, 6H), 1.61-1.29 (m, 8H), 1.04-0.98 (m, 2H), 0.98-0.87 (m, 9H). HRMS (ESI): Calcd for $(C_{46}H_{76}N_2O_{12}S+H)^+$: 881.5197. Found: 881.5207.

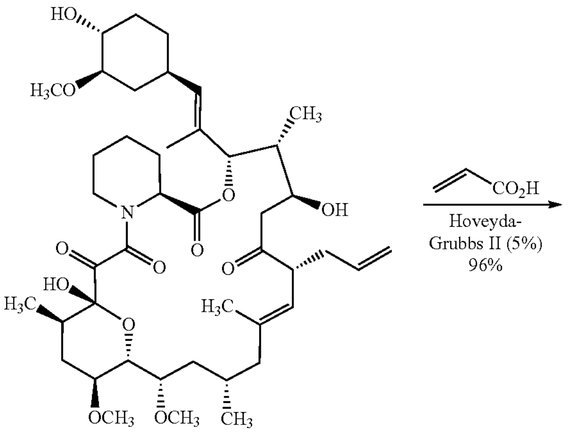

FK506

-continued

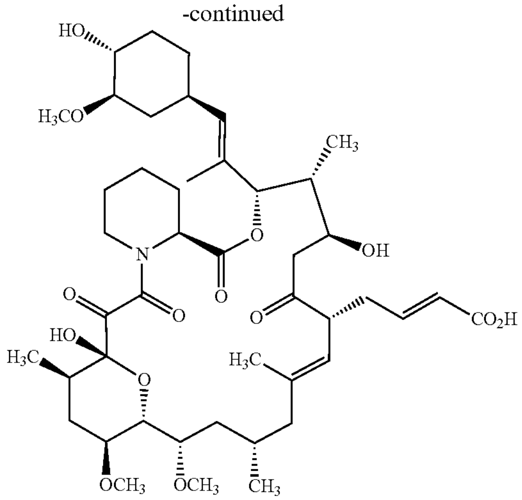

ZZY05-012

A flame-dried 10-mL microwave vial was flushed with dry argon, and then was charged with FK506 (100 mg, 0.120 mmol), DCE (1.20 mL), and a magnetic stir bar. Acrylic acid (170 mg, 2.49 mmol) and Grubbs Catalyst 2nd Gen (5.3 mg, 0.010 mmol) were added sequentially. The vial was flushed with argon again and sealed with a rubber cap. The reaction mixture was heated at 85° C. for 1 h in a CEM Discover SP microwave reactor. After cooling to 23° C., TLC analysis (100% ethyl acetate) of the reaction mixture showed full disappearance of the starting material and formation of a highly polar new spot. The reaction solution was concentrated in vacuo. The residue was purified by column chromatography (20-100% ethyl acetate-hexanes, 12-g RediSep® Rf column, Teledyne ISCO, Lincoln, NE) to afford the product as a yellow powder (101 mg, 96%). NMR: 3:2 mixture of rotamers. $^1$H NMR (400 MHz, Chloroform-d) δ 7.01-6.88 (m, 1H), 5.86 (d, J=15.5 Hz, 1H), 5.34 (s, 1H), 5.11 (app t, J=8.8 Hz, 1H), 5.03 (app d, J=8.4 Hz, 1H), 4.68 (d, J=5.2 Hz, 1H), 4.46 (d, J=13.9 Hz, 1H), 3.96-3.84 (m, 1H), 3.72 (d, J=9.3 Hz, 1H), 3.68-3.54 (m, 1H), 3.55-3.41 (m, 3H), 3.43 (s, 3H), 3.41 (s, 3H), 3.32 (s, 3H), 3.08-2.96 (m, 3H), 2.86-2.78 (m, 1H), 2.74-2.62 (m, 1H), 2.49-2.26 (m, 3H), 2.24-2.08 (m, 3H), 2.06-1.98 (m, 2H), 1.98-1.86 (m, 2H), 1.86-1.71 (m, 4H), 1.71-1.60 (m, 6H), 1.59-1.32 (m, 8H), 1.14-1.05 (m, 2H), 1.03 (d, J=6.3 Hz, 3H), 0.96 (d, J=6.4 Hz, 3H), 0.90 (d, J=7.1 Hz, 3H). HRMS (ESI): Calcd for $(C_{45}H_{69}NO_{14}—H)^-$: 846.4640. Found: 846.4601.

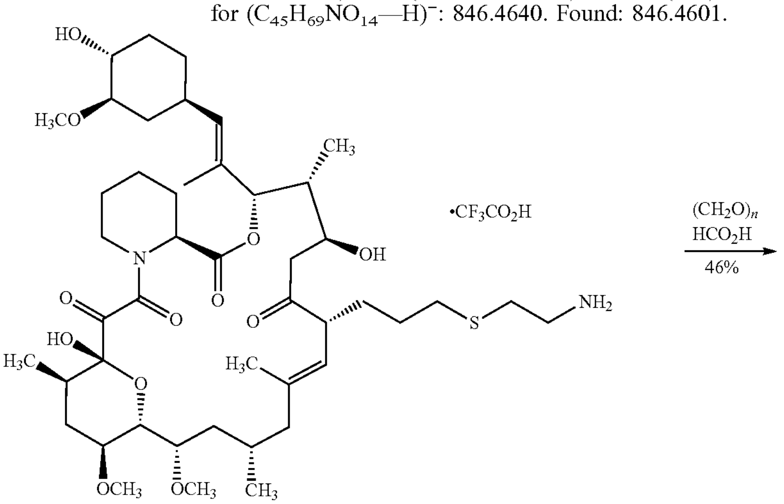

ZZY05-011

-continued

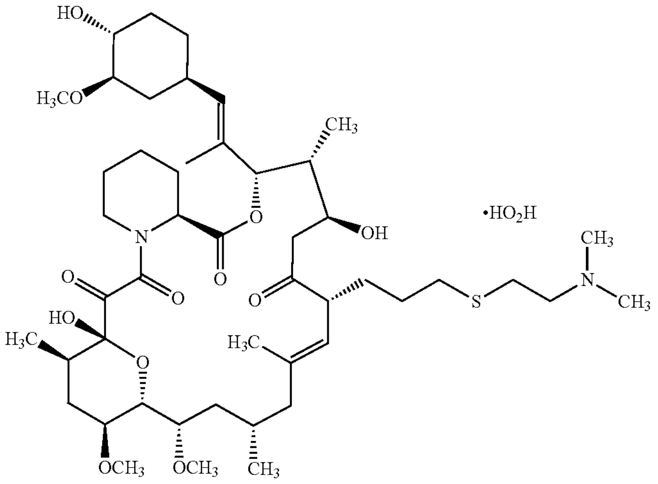

ZZY05-013

Paraformaldehyde (3.0 mg, 0.10 mmol) and formic acid (4.6 mg, 0.10 mmol) were added sequentially to a solution of ZZY05-011 (10 mg, 0.010 mmol) in chloroform (0.2 mL). The suspension was heated to 70° C. for 1 h. In 1 h, LC-MS analysis showed formation of two peaks, both of which had the desired mass. The reaction mixture was cooled to 23° C. The reaction mixture was partitioned between saturated aqueous sodium bicarbonate solution (1 mL) and dichloromethane (1 mL). The layers were separated, and the aqueous layer was extracted with dichloromethane (2×1 mL). The combined organic layers were dried over sodium sulfate. The dried solution was filtered, and the filtrate was concentrated. The residue was diluted with 50% acetonitrile-water to a volume of 4.7 mL, and the solution was filtered through a 0.45 μM PTFE syringe filter. The filtrate was purified by reverse-phase HPLC (Waters XBridge $C_{18}$ column 5 μm particle size 30×250 mm, 5-95% acetonitrile-water+0.1% formic acid, 40 min, 20 mL/min) to afford the product as a white solid (4.2 mg, 46%). 3:2 mixture of rotamers. $^1$H NMR (400 MHz, Methanol-$d_4$) δ 5.31-5.09 (m, 2H), 4.97 (d, J=9.9 Hz, 1H), 4.65 (s, 1H), 4.37 (d, J=13.5 Hz, 1H), 4.12-3.89 (m, 2H), 3.80-3.70 (m, 1H), 3.70-3.59 (m, 2H), 3.59-3.47 (m, 2H), 3.44 (s, 3H), 3.42 (s, 3H), 3.40-3.37 (m, 3H), 3.36 (s, 3H), 3.09-2.98 (m, 2H), 2.90 (s, 6H), 2.89-2.84 (m, 2H), 2.68-2.60 (m, 2H), 2.42-2.27 (m, 4H), 2.27-2.13 (m, 4H), 2.13-1.76 (m, 6H), 1.76-1.67 (m, 6H), 1.68-1.29 (m, 8H), 1.16-1.03 (m, 2H), 1.01-0.87 (m, 9H). HRMS (ESI): Calcd for $(C_{48}H_{80}N_2O_{12}S+H)^+$: 909.5510. Found: 909.5502.

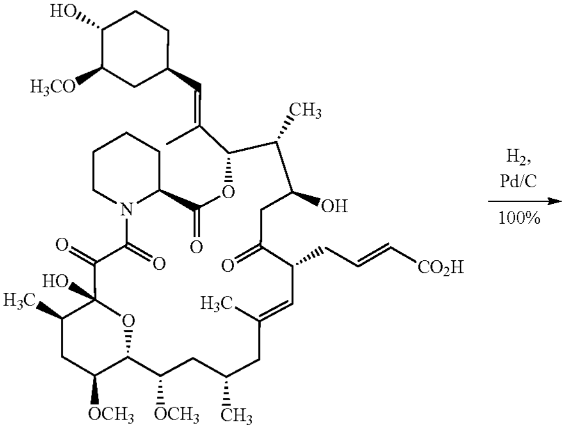

ZZY05-012

-continued

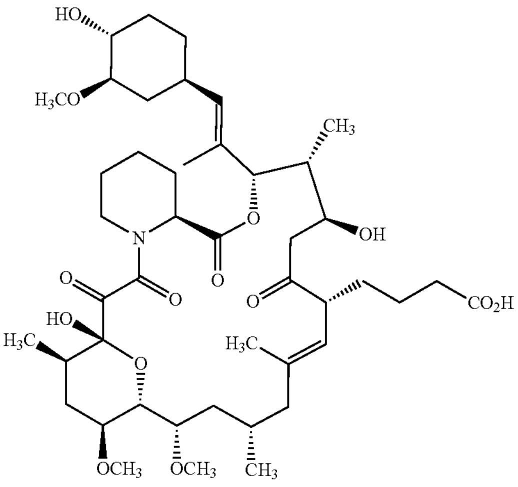

ZZY05-020

10 wt % Palladium on carbon (13 mg, 0.010 mmol) was added to a solution of ZZY05-012 (50 mg, 0.060 mmol) in methanol (5 mL) at 23° C. under an atmosphere of argon. The reaction flask was evacuated until effervescence occurred, then flushed with hydrogen gas. The process was repeated three times. The resulting suspension was stirred at 23° C. for 16 h under an atmosphere of hydrogen. The reaction flask was purged with argon, and the reaction suspension was filtered through a pad of Celite. The filter cake was rinsed with ethyl acetate (20 mL). The combined filtrate was concentrated in vacuo, and the residue was purified by column chromatography (0-10% methanol-dichloromethane+0.1% acetic acid) to afford the product as a white solid (50 mg, 100%). 3:2 mixture of rotamers. $^1$H NMR (400 MHz, Chloroform-d) δ 5.35-5.31 (m, 1H), 5.13-5.07 (m, 1H), 5.03 (d, J=10.3 Hz, 1H), 4.61 (d, J=5.4 Hz, 1H), 4.43 (d, J=13.8 Hz, 1H), 4.01-3.89 (m, 1H), 3.70 (d, J=9.6 Hz, 1H), 3.64-3.52 (m, 1H), 3.42 (s, 3H), 3.40 (s, 3H), 3.43-3.36 (m, 3H), 3.31 (s, 3H), 3.10-2.93 (m, 3H), 2.79 (dd, J=15.9, 3.0 Hz, 1H), 2.45-2.25 (m, 5H), 2.26-2.10 (m, 3H), 2.09-1.88 (m, 6H), 1.89-1.71 (m, 6H), 1.60 (s, 6H), 1.60-1.35 (m, 8H), 1.13-1.03 (m, 2H), 1.00 (d, J=6.3 Hz, 3H), 0.94 (d, J=6.4 Hz, 3H), 0.88 (d, J=7.1 Hz, 3H). HRMS (ESI): Calcd for $(C_{45}H_{71}NO_{14}—H)^-$: 848.4796. Found: 848.4809.

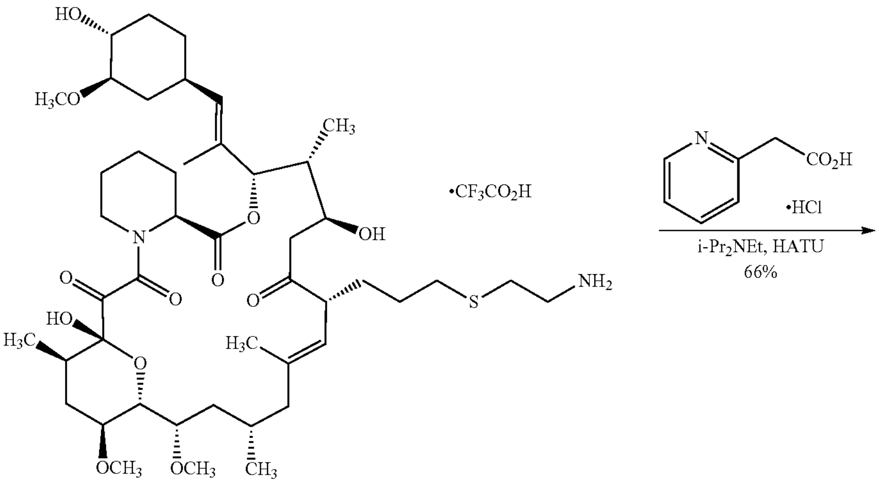

ZZY05-011

-continued

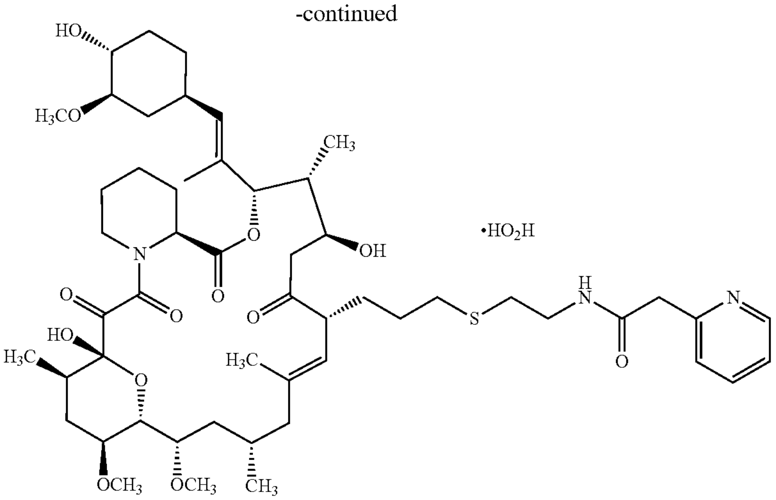

ZZY05-026

An oven-dried one-dram vial was charged with ZZY05-011 (15 mg, 0.020 mmol), 2-(2-pyridyl)acetic acid hydrochloride (4.4 mg, 0.030 mmol), DMF (0.17 mL), N,N-Diisopropylethylamine (15 µL, 0.090 mmol), and a magnetic stir bar. HATU (7.7 mg, 0.020 mmol) was added as a solid at 23° C., and the resulting mixture was stirred at 23° C. for 30 min. At this point, LC-MS analysis showed full consumption of the starting amine and formation of a single peak corresponding to the desired mass. The residue was diluted with 50% acetonitrile-water to a volume of 5.0 mL, and the solution was filtered through a 0.45 µM PTFE syringe filter. The filtrate was purified by reverse-phase HPLC (Waters XBridge C18 column 5 µm particle size 30×250 mm, 5-95% acetonitrile-water+0.1% formic acid, 40 min, 20 mL/min) to afford the product as a white solid (11.2 mg, 66%). 3:2 mixture of rotamers. $^1$H NMR (400 MHz, Methanol-$d_4$) δ 8.54-8.45 (m, 1H), 8.13 (br s, 1H), 7.88-7.74 (m, 2H), 7.44 (d, J=7.9 Hz, 1H), 7.37-7.31 (m, 1H), 5.29-5.08 (m, 2H), 4.93 (s, 1H), 4.63 (s, 1H), 4.36 (d, J=13.4 Hz, 1H), 4.12-3.92 (m, 2H), 3.79-3.71 (m, 2H), 3.70-3.45 (m, 4H), 3.43 (s, 3H), 3.42 (s, 3H), 3.41-3.38 (m, 3H), 3.36 (s, 3H), 3.09-2.98 (m, 1H), 2.85 (dd, J=14.4, 6.2 Hz, 1H), 2.64 (t, J=7.0 Hz, 2H), 2.54 (t, J=6.4 Hz, 2H), 2.44-2.27 (m, 4H), 2.27-2.08 (m, 4H), 2.08-1.74 (m, 6H), 1.74-1.64 (m, 6H), 1.64-1.33 (m, 8H), 1.18-1.01 (m, 2H), 0.99-0.86 (m, 9H). HRMS (ESI): Calcd for $(C_{53}H_{81}N_3O_{13}S+H)^+$: 1000.5568. Found: 1000.5567.

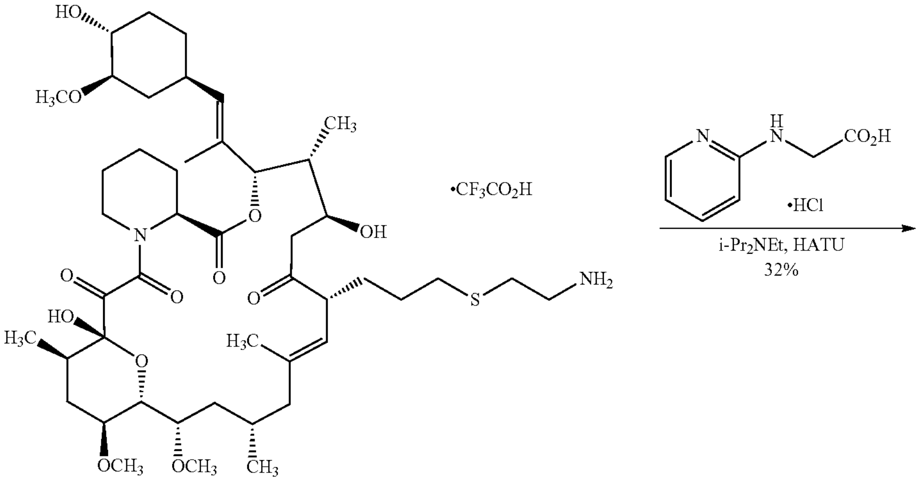

ZZY05-011

-continued

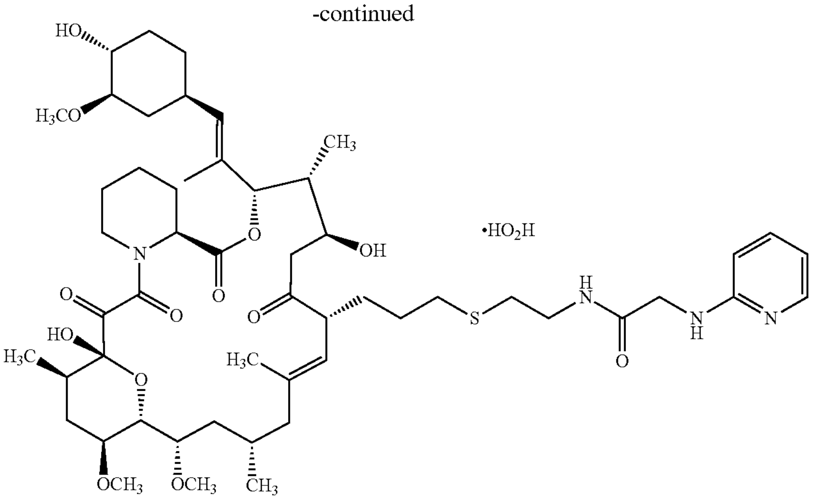

ZZY05-028

An oven-dried one-dram vial was charged with ZZY05-011 (15 mg, 0.020 mmol), 2-(2-pyridylamino)acetic acid hydrochloride (4.8 mg, 0.030 mmol), DMF (0.17 mL), N,N-Diisopropylethylamine (15 μL, 0.090 mmol), and a magnetic stir bar. HATU (7.8 mg, 0.020 mmol) was added as a solid at 23° C., and the resulting mixture was stirred at 23° C. for 30 min. At this point, LC-MS analysis showed full consumption of the starting amine and formation of a single peak corresponding to the desired mass. The residue was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.5 mg, 32%). 3:2 mixture of rotamers. HRMS (ESI): Calcd for $(C_{53}H_{82}N_4O_{13}S+H)^+$: 1015.5677. Found: 1015.5701.

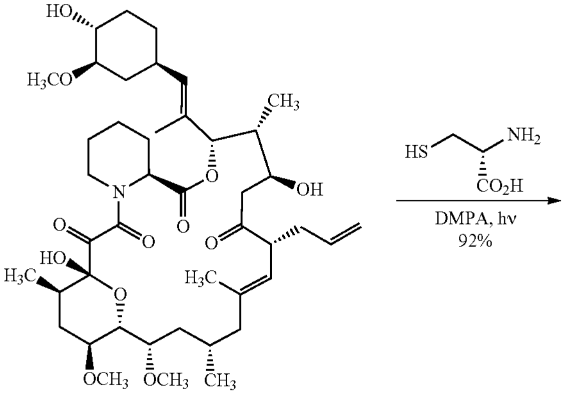

FK506

-continued

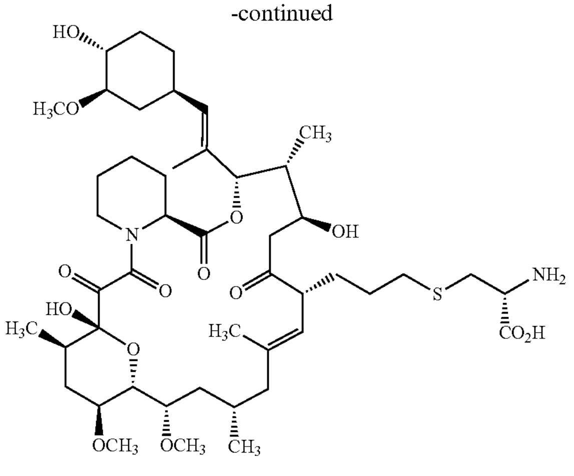

ZZY05-037

L-Cysteine (16 mg, 0.13 mmol) and DMPA (3.2 mg, 0.012 mmol) were added sequentially to a solution of FK506 (100 mg, 0.12 mmol) in 1:1 Methanol (0.25 mL): Water (0.25 mL) at 23° C. After all reactants had dissolved, the vial was placed above a hand-held UV-light operating at 365 nm wavelength (the light was placed upside-down so that the contents of vial were directly irradiated). The irradiation was maintained for 15 min, at which point TLC analysis showed full disappearance of the starting material. The reaction solution was directly diluted with 50% acetonitrile-water to a volume of 4.7 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (105 mg, 92%). 3:2 mixture of rotamers. $^1H$ NMR (400 MHz, Methanol-$d_4$) δ 5.31-5.10 (m, 2H), 4.94 (s, 1H), 4.63 (d, J=7.9 Hz, 1H), 4.37 (d, J=13.2 Hz, 1H), 4.10-3.94 (m, 1H), 3.78-3.69 (m, 1H), 3.67-3.45 (m, 3H), 3.43 (s, 3H), 3.42 (s, 3H), 3.41-3.39 (m, 3H), 3.36 (s, 3H), 3.15 (ddd, J=14.7, 3.8, 1.2 Hz, 1H), 3.11-2.97 (m, 1H), 2.97-2.71 (m, 4H), 2.62 (t, J=7.1 Hz, 1H), 2.43-2.28 (m, 4H), 2.28-2.11 (m, 4H), 2.09-1.75 (m, 6H), 1.75-1.68 (m, 6H), 1.68-1.28 (m, 8H), 1.21-1.00 (m, 2H), 1.00-0.86 (m, 9H). HRMS (ESI): Calcd for $(C_{47}H_{76}N_2O_{14}S+H)^+$: 925.5095. Found: 925.5092.

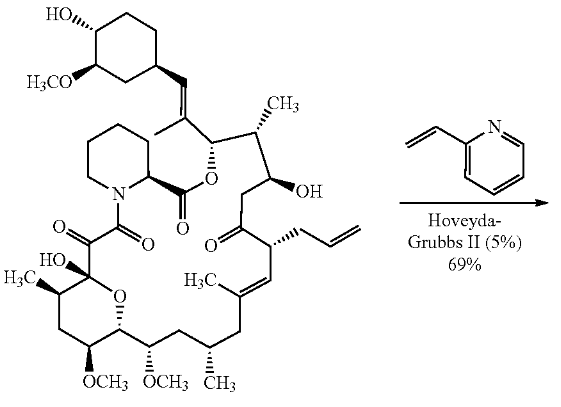

FK506

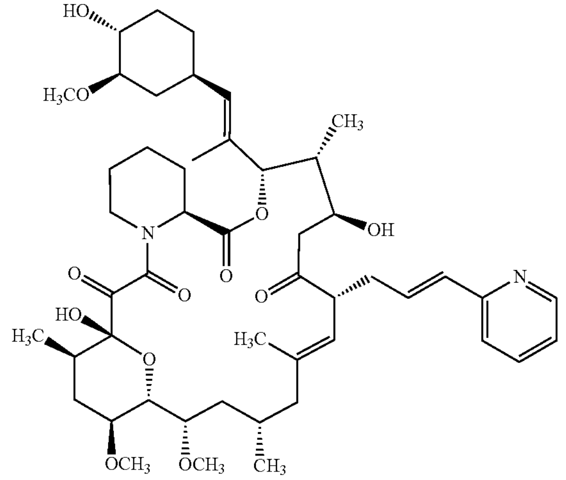

ZZY05-050

A 15-mi microwave vial was dried with gentle flame under vacuum. The vial was cooled to 23° C., flushed with argon, then charged with FK506 (50 mg, 0.062 mmol), DCE (0.62 mL) and a magnetic stir bar. Argon was bubbled through the resulting solution via a 19-gauge needle for 1 min. 2-Vinylpyridine (6.7 μL, 0.062 mmol) was added via pipette, and Grubbs-Hoveyda $2^{nd}$ Gen Catalyst (4.0 mg, 0.0062 mmol) was added in one portion as a solid. The mixture was stirred briefly (giving a bright green solution) before being loaded on a CEM DiscoverSP microwave reactor. Microwave reaction was performed at 100° C. for 30 min with 1 min pre-equilibration. After cooling to 23° C., the reaction mixture was analyzed by TLC (100% ethyl acetate), which showed formation of an UV-active, more polar spot. The reaction mixture was directly loaded onto a 4-g RediSep (Teledyne ISCO) column. Elution with 100% ethyl acetate gave the product as a yellow solid (38 mg, 69%). 3:2 mixture of rotamers. $^1$H NMR (400 MHz, Chloroform-d) δ 8.55-8.47 (m, 1H), 7.66-7.56 (m, 1H), 7.24 (tt, J=8.1, 1.1 Hz, 1H), 7.16-7.06 (m, 1H), 6.69-6.56 (m, 1H), 6.57-6.46 (m, 1H), 5.38-5.30 (m, 1H), 5.16-5.00 (m, 2H), 4.63 (d, J=5.3 Hz, 1H), 4.44 (d, J=14.1 Hz, 1H), 4.02-3.84 (m, 2H), 3.77-3.67 (m, 1H), 3.66-3.50 (m, 2H), 3.42 (s, 3H), 3.40 (s, 3H), 3.38-3.35 (m, 1H), 3.31 (s, 3H), 3.07-2.96 (m, 3H), 2.86-2.64 (m, 3H), 2.51-2.23 (m, 4H), 2.24-1.85 (m, 8H), 1.71-

1.60 (m, 6H), 1.60-1.31 (m, 8H), 1.14-1.03 (m, 2H), 1.01 (d, J=6.3 Hz, 3H), 0.94 (d, J=6.7 Hz, 3H), 0.89 (d, J=7.2 Hz, 3H). HRMS (ESI): Calcd for $(C_{49}H_{72}N_2O_{12}+H)^+$: 881.5163. Found: 881.5207.

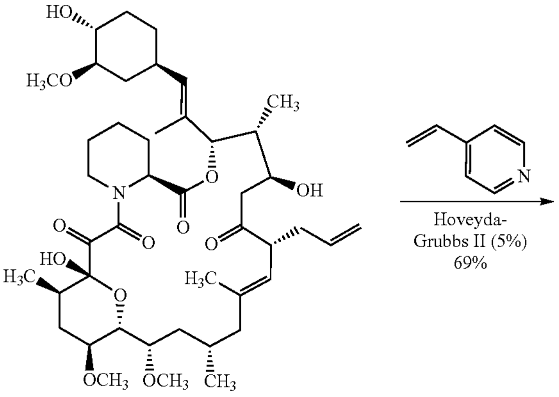

FK506

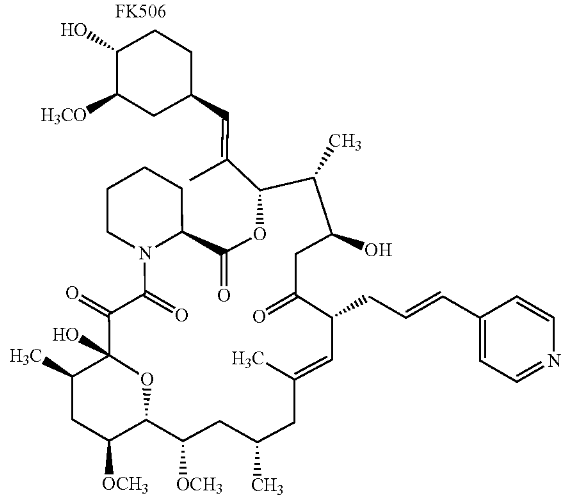

ZZY05-051

A 15-mi microwave vial was dried with gentle flame under vacuum. The vial was cooled to 23° C., flushed with argon, then charged with FK506 (50 mg, 0.060 mmol), DCE (0.62 mL) and a magnetic stir bar. Argon was bubbled through the resulting solution via a 19-gauge needle for 1 min. 4-Vinylpyridine (6.7 μL, 0.060 mmol) was added via pipette, and Grubbs-Hoveyda $2^{nd}$ Gen Catalyst (4.0 mg, 0.0062 mmol) was added in one portion as a solid. The mixture was stirred briefly (giving a bright green solution) before being loaded on a CEM DiscoverSP microwave reactor. Microwave reaction was performed at 100° C. for 30 min with 1 min pre-equilibration. After cooling to 23° C., the reaction mixture was analyzed by TLC (100% ethyl acetate), which showed formation of an UV-active, more polar spot. The reaction mixture was directly loaded onto a 4-g RediSep (Teledyne ISCO) column. Elution with 100% ethyl acetate gave the product as a yellow solid (38 mg, 69%). 3:2 mixture of rotamers. $^1$H NMR (400 MHz, Chloroform-d) δ 8.56-8.49 (m, 2H), 8.21 (br s, 1H), 7.27-7.18 (m, 2H), 6.49-6.32 (m, 2H), 5.35 (s, 1H), 5.17-5.05 (m, 2H), 4.67 (d, J=5.5 Hz, 1H), 4.46 (d, J=13.7 Hz, 1H), 4.04-3.86 (m, 1H), 3.72 (d, J=9.6 Hz, 1H), 3.61 (d, J=10.6 Hz, 1H), 3.56-3.45 (m, 1H), 3.43 (s, 3H), 3.41 (s, 3H), 3.39-3.36 (m, 2H), 3.32 (s, 3H), 3.08-2.98 (m, 3H), 2.84 (dd, J=16.3, 2.6 Hz, 1H), 2.80-2.60

(m, 2H), 2.55-2.25 (m, 4H), 2.26-1.88 (m, 6H), 1.88-1.71 (m, 4H), 1.71-1.61 (m, 6H), 1.61-1.26 (m, 8H), 1.14-1.04 (m, 2H), 1.01 (d, J=6.3 Hz, 3H), 0.96 (d, J=6.4 Hz, 3H), 0.90 (d, J=7.2 Hz, 3H). HRMS (ESI): Calcd for $(C_{49}H_{72}N_2O_{12}+H)^+$: 881.5163. Found: 881.5207.

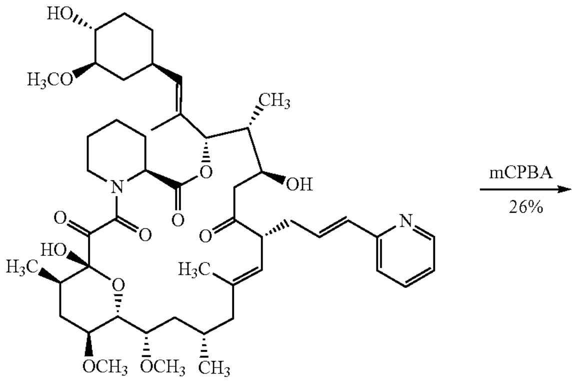

ZZY05-050

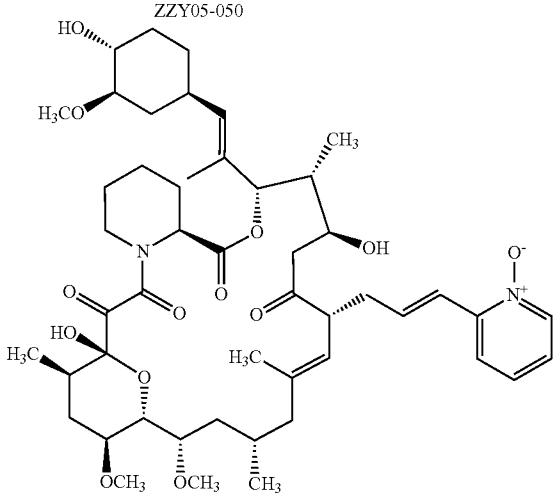

ZZY05-060

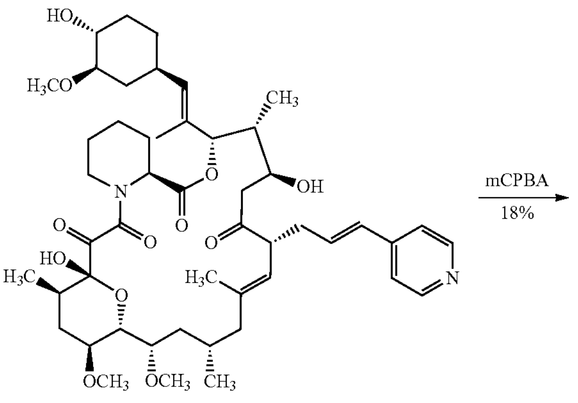

ZZY05-051

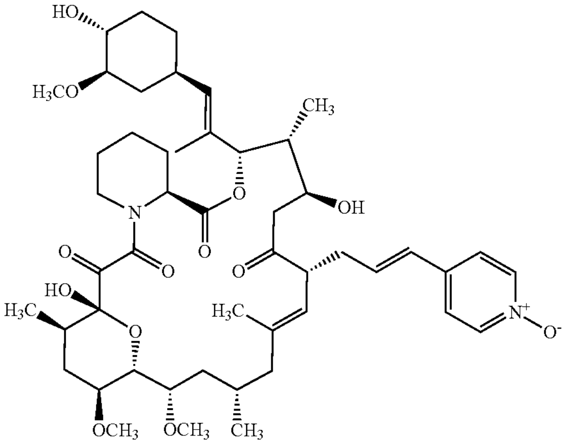

ZZY05-061 mCPBA (3.4 mg, 0.010 mmol) was added as a 10 wt % solution in dichloromethane (34 uL) to a solution of ZZY05-050 (10 mg, 0.010 mmol) in dichloromethane (0.11 mL) at 0° C. In 4 h, most of the starting material had been consumed judged by TLC analysis (100% ethyl acetate)—the product did not move in this solvent system. 10% Methanol-dichloromethane resolved the product spot (with streak). Attempted purification by column chromatography (0-10% methanol-dichloromethane) afforded a white solid. The material was further again by reverse-phase HPLC (5-95% acetonitrile-water+0.1% formic acid over 40 min). The product-containing fraction were pooled and concentrated in vacuo to afford the product as a while solid (2.6 mg, 26%). 3:2 mixture of rotamers. $^1$H NMR (400 MHz, Chloroform-d) δ 8.14-8.08 (m, 2H), 7.22-7.10 (m, 2H), 6.38-6.17 (m, 2H), 5.34 (s, 1H), 5.14-5.03 (m, 2H), 4.65 (d, J=6.0 Hz, 1H), 4.44 (d, J=13.4 Hz, 1H), 4.04-3.84 (m, 2H), 3.69 (d, J=9.6 Hz, 1H), 3.68-3.52 (m, 2H), 3.41 (s, 3H), 3.39 (s, 3H), 3.38-3.34 (m, 3H), 3.30 (s, 3H), 3.08-2.95 (m, 3H), 2.81 (d, J=16.1 Hz, 1H), 2.75-2.58 (m, 2H), 2.52-2.21 (m, 4H), 2.21-1.72 (m, 6H), 1.72-1.52 (m, 6H), 1.53-1.13 (m, 8H), 1.12-1.02 (m, 2H), 0.99 (d, J=6.3 Hz, 3H), 0.94 (d, J=6.4 Hz, 3H), 0.87 (d, J=7.2 Hz, 3H). HRMS (ESI): Calcd for $(C_{49}H_{72}N_2O_{13}+H)^+$: 897.5112. Found: 897.5134.

mCPBA (3.4 mg, 0.010 mmol) was added as a 10 wt % solution in dichloromethane (34 uL) to a solution of ZZY05-051 (10 mg, 0.010 mmol) in dichloromethane (0.11 mL) at 0° C. In 4 h, most of the starting material had been consumed judged by TLC analysis (100% ethyl acetate)—the product did not move in this solvent system. 10% Methanol-dichloromethane resolved the product spot (with streak). Attempted purification by column chromatography (0-10% methanol-dichloromethane) afforded a white solid. The material was further purified by reverse-phase HPLC (5-95% acetonitrile-water+0.1% formic acid over 40 min). The product-containing fraction were pooled and concentrated in vacuo to afford the product as a while solid (1.8 mg, 18%). 3:2 mixture of rotamers. $^1$H NMR (400 MHz, Chloroform-d) δ 8.19 (d, J=5.8 Hz, 1H), 7.47-7.37 (m, 1H), 7.26-7.08 (m, 2H), 7.08-6.93 (m, 1H), 6.54 (dd, J=15.7, 7.8 Hz, 1H), 5.29 (s, 1H), 5.17-5.07 (m, 2H), 4.55-4.27 (m, 2H), 4.27-4.13 (m, 1H), 3.80-3.49 (m, 3H), 3.41 (s, 3H), 3.38 (s, 3H), 3.37-3.32 (m, 3H), 3.29 (s, 3H), 3.10-2.93 (m, 3H), 2.84 (d, J=16.9 Hz, 1H), 2.75-2.55 (m, 2H), 2.50-2.23 (m, 4H), 2.25-1.79 (m, 6H), 1.75-1.64 (m, 6H), 1.54-1.27 (m, 8H), 1.07-0.98 (m, 2H), 0.96 (d, J=7.1 Hz, 3H), 0.92 (d, J=6.9 Hz, 3H), 0.89 (d, J=4.6 Hz, 3H). HRMS (ESI): Calcd for $(C_{49}H_{72}N_2O_{13}+H)^+$: 897.5112. Found: 897.5134.

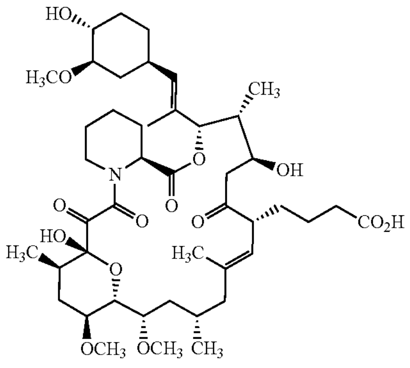

ZZY05-020

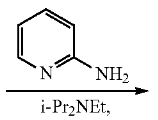

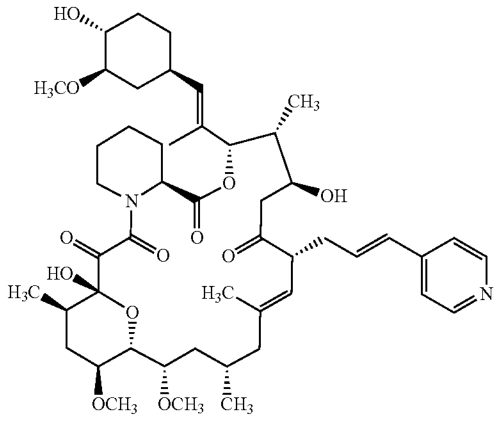

ZZY05-051

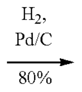

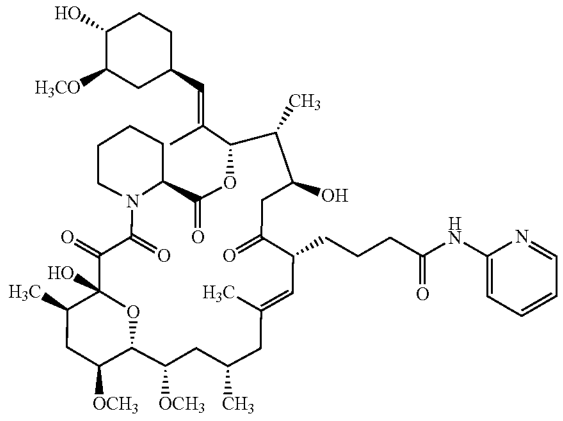

ZZY05-064

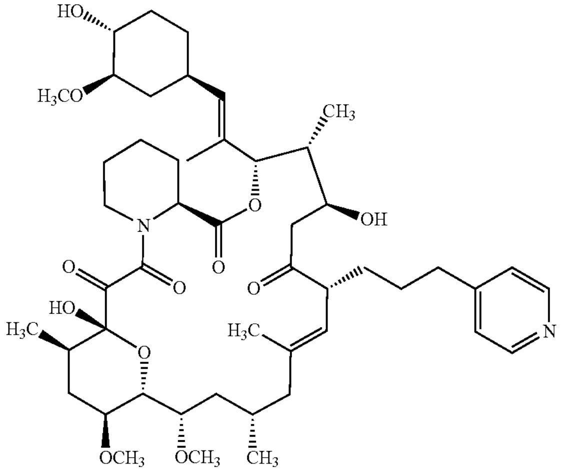

ZZY05-084

N,N-Diisopropylethylamine (12.3 μL, 0.071 mmol) and HATU (11 mg, 0.028 mmol) were added sequentially to a stirred solution of ZZY05-020 (20 mg, 0.024 mmol) and 2-aminopyridine (2.7 mg, 0.028 mmol) in DMF (0.24 mL) at 23° C. In 24 h, LC-MS analysis showed full consumption of the staring acid. The reaction mixture was diluted with 50% acetonitrile-water to a volume of 4.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (6.4 mg, 29%). 3:2 mixture of rotamers. $^1$H NMR (400 MHz, Chloroform-d) δ 9.18 (br s, 1H), 8.29 (d, J=8.6 Hz, 1H), 8.24-8.16 (m, 1H), 7.79-7.72 (m, 1H), 7.09-7.04 (m, 1H), 5.35 (d, J=2.5 Hz, 1H), 5.14-4.98 (m, 2H), 4.65 (d, J=5.4 Hz, 1H), 4.45 (d, J=13.8 Hz, 1H), 4.03-3.84 (m, 2H), 3.81-3.68 (m, 1H), 3.68-3.55 (m, 2H), 3.43 (s, 3H), 3.41 (s, 3H), 3.41-3.36 (m, 3H), 3.32 (s, 3H), 3.13-2.93 (m, 2H), 2.81 (dd, J=16.2, 2.2 Hz, 1H), 2.51-2.25 (m, 6H), 2.25-1.72 (m, 8H), 1.71-1.58 (m, 6H), 1.57-1.19 (m, 8H), 1.18-1.05 (m, 2H), 1.02 (d, J=6.2 Hz, 3H), 0.96 (d, J=6.4 Hz, 3H), 0.89 (d, J=7.2 Hz, 3H). HRMS (ESI): Calcd for $(C_{50}H_{75}N_3O_{13}+H)^+$: 926.5378. Found: 926.5380.

A 20-mL vial was charged with ZZY05-051 (20 mg, 0.020 mmol), Ethyl acetate (1.0 mL) and Palladium on carbon (10 wt %, 2.4 mg). The vial was briefly purged with argon, and then fitted with a rubber septum. Hydrogen was bubbled through the solution via a 19-gauge needle for 5 min, then the mixture was stirred under hydrogen atmosphere at 23° C. In a total of 3 h, LC-MS showed full conversion to the desired m/z. The reaction mixture was filtered through a pad of Celite, and the filter cake was rinsed with ethyl acetate (5 mL). The combined filtrate was concentrated to afford the product as a pale-yellow foam (16 mg, 80%). 3:2 mixture of rotamers. $^1$H NMR (400 MHz, Chloroform-d) δ 8.53-8.47 (m, 2H), 7.13-7.07 (m, 2H), 5.34 (d, J=2.7 Hz, 1H), 5.13-4.97 (m, 2H), 4.63 (d, J=5.4 Hz, 1H), 4.45 (d, J=13.7 Hz, 2H), 4.00-3.86 (m, 2H), 3.78-3.66 (m, 1H), 3.66-3.55 (m, 1H), 3.55-3.45 (m, 1H), 3.43 (s, 3H), 3.41 (s, 3H), 3.40-3.38 (m, 2H), 3.32 (s, 3H), 3.10-2.98 (m, 2H), 2.78 (dd, J=15.9, 2.9 Hz, 1H), 2.62 (app t, J=7.7 Hz, 2H), 2.40-2.24 (m, 3H), 2.24-2.13 (m, 3H), 2.06 (s, 6H), 1.86-1.71 (m, 4H), 1.71-1.57 (m, 6H), 1.57-1.33 (m, 8H), 1.15-1.05 (m, 2H), 1.02 (d, J=6.3 Hz, 3H), 0.95 (d, J=6.4 Hz, 3H), 0.87 (d, J=7.1 Hz, 3H). HRMS (ESI): Calcd for $(C_{49}H_{74}N_2O_{12}+H)^+$: 883.5320. Found: 883.5332.

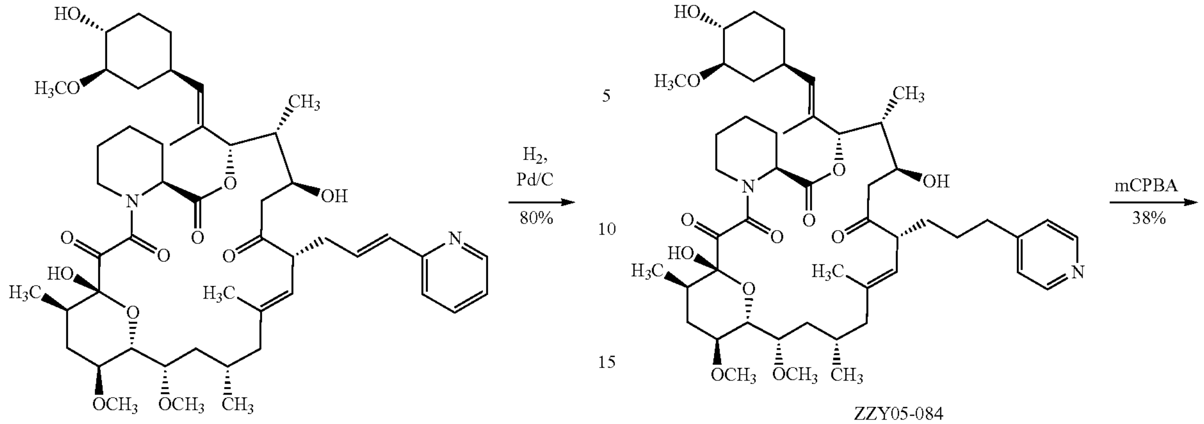

ZZY05-050

ZZY05-084

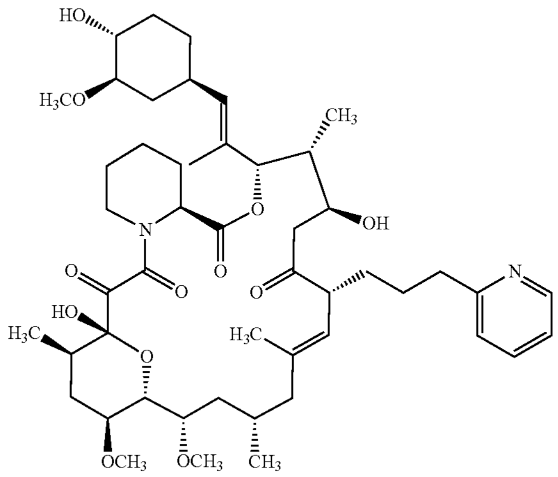

ZZY05-085

A 20-mL vial was charged with ZZY05-050 (20 mg, 0.020 mmol), Ethyl acetate (1.0 mL) and Palladium on carbon (10 wt %, 2.4 mg). The vial was briefly purged with argon, and then fitted with a rubber septum. Hydrogen was bubbled through the solution via a 19-gauge needle for 5 min, then the mixture was stirred under hydrogen atmosphere at 23° C. In a total of 3 h, LC-MS showed full conversion to the desired m/z. The reaction mixture was filtered through a pad of Celite, and the filter cake was rinsed with ethyl acetate (5 mL). The combined filtrate was concentrated to afford the product as a pale-yellow foam (20 mg, 99%). 3:2 mixture of rotamers. $^1$H NMR (400 MHz, Chloroform-d) δ 8.56-8.43 (m, 2H), 7.61 (tt, J=7.6, 2.3 Hz, 2H), 7.21-7.07 (m, 4H), 5.37 (s, 1H), 5.28-5.15 (m, 1H), 5.15-4.96 (m, 2H), 4.62 (d, J=5.0 Hz, 1H), 4.45 (d, J=13.5 Hz, 1H), 4.00-3.86 (m, 1H), 3.74 (d, J=9.8 Hz, 1H), 3.67-3.55 (m, 1H), 3.52-3.25 (m, 3H), 3.43 (s, 3H), 3.41 (s, 3H), 3.32 (s, 3H), 3.09-2.95 (m, 1H), 2.92-2.75 (m, 2H), 2.73-2.64 (m, 1H), 2.43-2.11 (m, 3H), 2.11-1.84 (m, 4H), 1.84-1.70 (m, 4H), 1.70-1.57 (m, 6H), 1.57-1.33 (m, 8H), 1.15-1.05 (m, 2H), 1.03 (d, J=6.5 Hz, 3H), 0.96 (d, J=6.1 Hz, 3H), 0.87 (d, J=7.2 Hz, 3H). HRMS (ESI): Calcd for $(C_{49}H_{74}N_2O_{12}+H)^+$: 883.5320. Found: 883.5332.

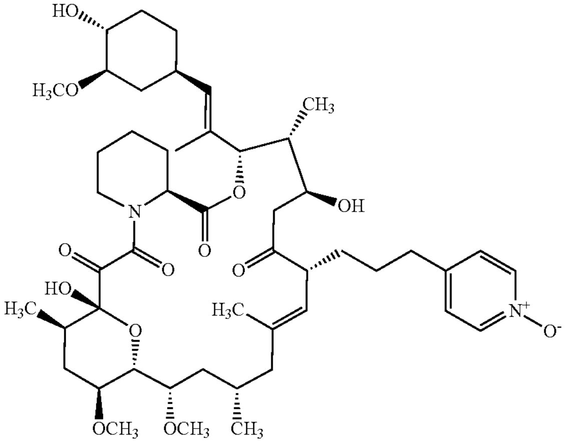

ZZY05-086 m-CPBA (4.8 mg, 0.018 mmol) was added as a 10 wt % solution in dichloromethane (48 μL) to a solution of ZZY05-084 (16 mg, 0.018 mmol) in dichloromethane at 0° C. The reaction progress was monitored by LC-MS. In a total of 6 h, LC-MS showed full conversion to the desired m/z. The reaction mixture was directly concentrated under reduced pressure. The residue was diluted with 50% acetonitrile-water to a volume of 3.0 mL, and the solution was filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) to afford the product as a white solid (6.2 mg, 38%). 3:2 mixture of rotamers. $^1$H NMR (400 MHz, Chloroform-d) δ 8.24-8.14 (m, 2H), 7.13 (t, J=6.8 Hz, 2H), 5.35 (s, 1H), 5.13-4.96 (m, 3H), 4.65 (d, J=5.4 Hz, 1H), 4.45 (d, J=13.6 Hz, 1H), 3.95-3.84 (m, 1H), 3.74-3.67 (m, 1H), 3.66-3.54 (m, 1H), 3.43 (s, 3H), 3.41 (s, 3H), 3.32 (s, 3H), 3.45-3.27 (m, 3H), 3.11-2.97 (m, 3H), 2.79 (dd, J=16.2, 2.7 Hz, 1H), 2.67-2.59 (m, 2H), 2.31 (d, J=9.4 Hz, 2H), 2.25-2.10 (m, 3H), 2.10-1.96 (m, 2H), 1.96-1.73 (m, 6H), 1.72-1.57 (m, 6H), 1.57-1.19 (m, 8H), 1.15-1.05 (m, 2H), 1.03 (d, J=6.3 Hz, 3H), 0.96 (d, J=6.3 Hz, 4H), 0.88 (d, J=7.2 Hz, 3H). HRMS (ESI): Calcd for $(C_{49}H_{74}N_2O_{13}+H-H_2O)^+$: 881.5164. Found: 881.5146.

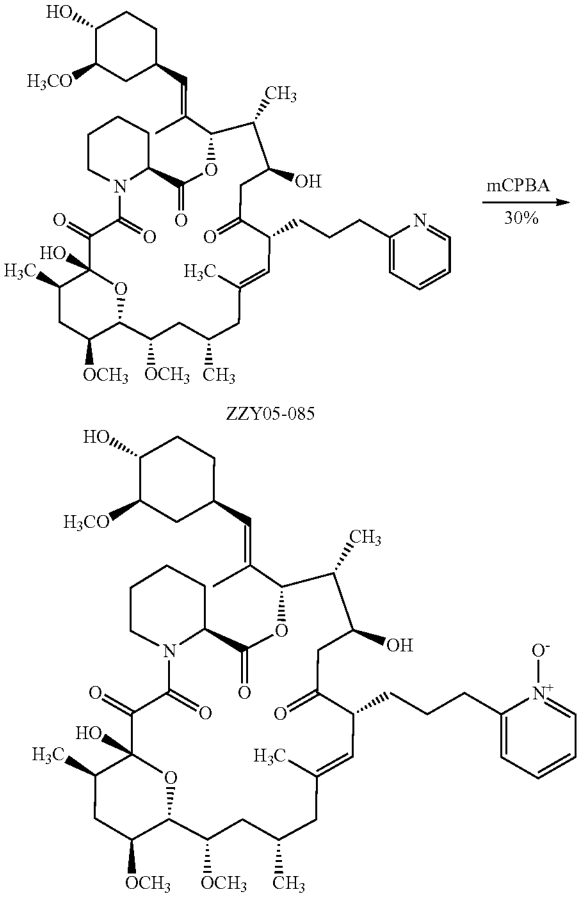

ZZY05-085

ZZY05-092 m-CPBA (6.6 mg, 0.025 mmol) was added as a 10 wt % solution in dichloromethane (66 μL) to a solution of ZZY05-085 (22 mg, 0.025 mmol) in dichloromethane at 0° C. The reaction progress was monitored by LC-MS. In a total of 6 h, LC-MS showed full conversion to the desired m/z. The reaction mixture was directly concentrated under reduced pressure. The residue was diluted with 50% acetonitrile-water to a volume of 3.0 mL, and the solution was filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) to afford the product as a white solid (6.6 mg, 30%). 3:2 mixture of rotamers. $^1$H NMR (400 MHz, Chloroform-d) δ 8.32-8.22 (m, 2H), 8.03 (s, 1H), 7.24-7.11 (m, 3H), 5.34 (s, 1H), 5.13 (d, J=9.6 Hz, 1H), 5.10-5.04 (m, 1H), 4.78-4.67 (m, 1H), 4.58 (d, J=3.3 Hz, 1H), 4.43 (d, J=13.8 Hz, 1H), 3.93 (t, J=10.2 Hz, 1H), 3.77-3.68 (m, 1H), 3.64-3.52 (m, 1H), 3.41 (s, 3H), 3.39 (s, 3H), 3.48-3.23 (m, 3H), 3.30 (s, 3H), 3.06-2.91 (m, 3H), 2.83-2.73 (m, 1H), 2.73-2.65 (m, 1H), 2.41-2.23 (m, 3H), 2.22-2.08 (m, 3H), 2.06-1.94 (m, 2H), 1.94-1.71 (m, 6H), 1.71-1.50 (m, 6H), 1.50-1.30 (m, 8H), 1.06 (d, J=13.4 Hz, 2H), 1.00 (d, J=6.5 Hz, 3H), 0.93 (d, J=5.8 Hz, 3H), 0.86 (d, J=7.2 Hz, 3H). HRMS (ESI): Calcd for $(C_{49}H_{74}N_2O_{13}+H-H_2O)^+$: 881.5164. Found: 881.5150.

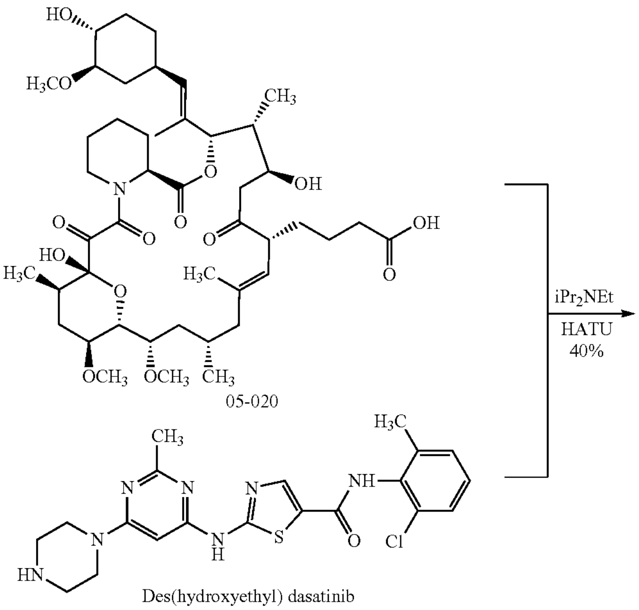

05-020

Des(hydroxyethyl) dasatinib

-continued

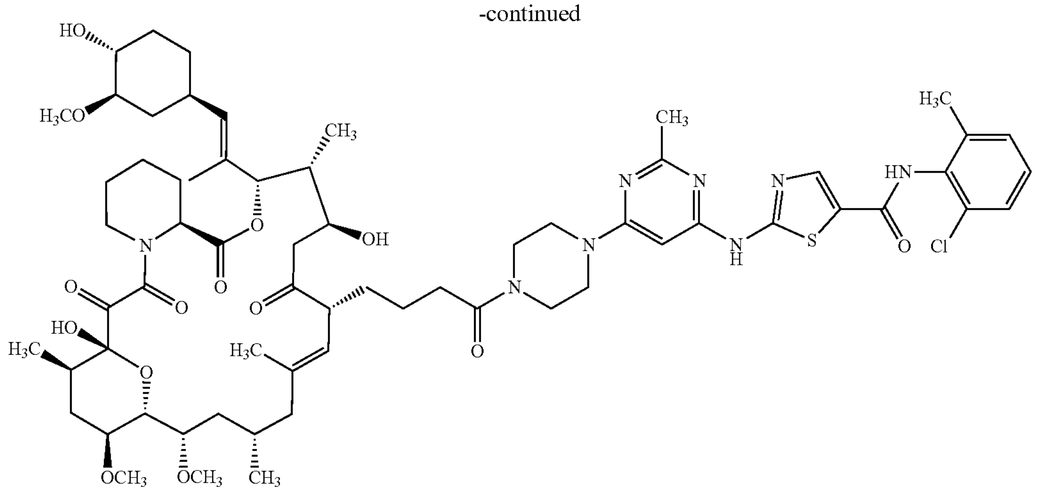

05-022

An oven-dried 1-dram vial was charged with 05-020 (10 mg, 0.012 mmol), des(hydroxyethyl)dasatinib (5.8 mg, 0.012 mmol), DMF (0.20 mL) and a magnetic stir bar. The solution was cooled to 0° C., then N,N-diisopropylethylamine (6.2 μL, 0.035 mmol) and HATU (5.4 mg, 0.010 mmol) were added sequentially. The resulting mixture was stirred at 0° C. and the reaction progress was monitored by LC-MS. In 30 min, LC-MS analysis indicated that the starting material had been fully consumed. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.9 mg, 40%). 3:2 mixture of rotamers. $^1$H NMR (400 MHz, Chloroform-d) δ 8.19 (s, 1H), 7.99 (br s, 1H), 7.42-7.31 (m, 2H), 7.26-7.10 (m, 2H), 5.89 (s, 1H), 5.39 (s, 1H), 5.16-5.06 (m, 1H), 4.66 (d, J=5.4 Hz, 1H), 4.48 (d, J=13.8 Hz, 1H), 3.99-3.94 (m, 1H), 3.81-3.68 (m, 5H), 3.68-3.53 (m, 5H), 3.44 (s, 3H), 3.41 (s, 3H), 3.46-3.33 (m, 3H), 3.32 (s, 3H), 3.10-2.98 (m, 3H), 2.79 (d, J=14.7 Hz, 1H), 2.55 (s, 3H), 2.43-2.38 (m, 1H), 2.37 (s, 3H), 2.35-2.25 (m, 2H), 2.24-1.98 (m, 5H), 1.97-1.72 (m, 6H), 1.71-1.62 (m, 6H), 1.62-1.32 (m, 8H), 1.12-1.04 (m, 2H), 1.02 (d, J=6.2 Hz, 3H), 0.95 (d, J=5.6 Hz, 3H), 0.89 (d, J=7.2 Hz, 3H). HRMS (ESI): Calcd for $(C_{65}H_{91}ClN_8O_{14}S+H)^+$: 1275.6142. Found: 1275.6085.

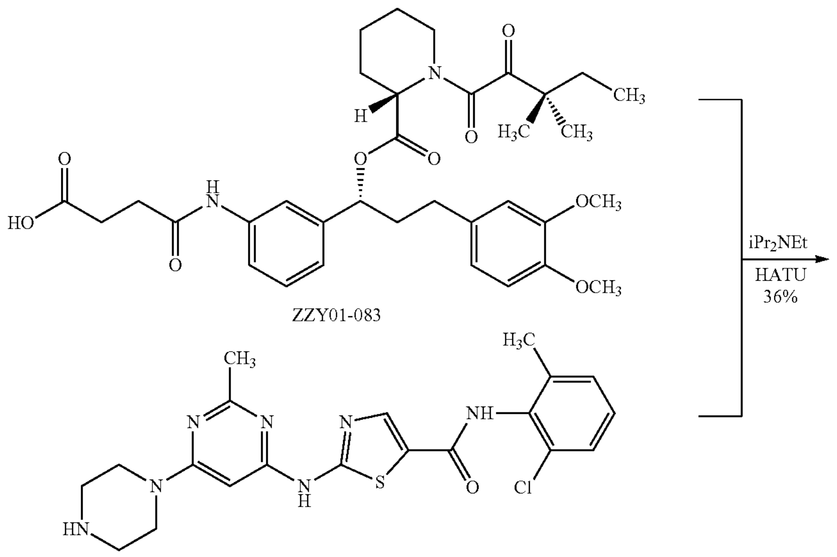

ZZY01-083

Des(hydroxyethyl) dasatinib

-continued

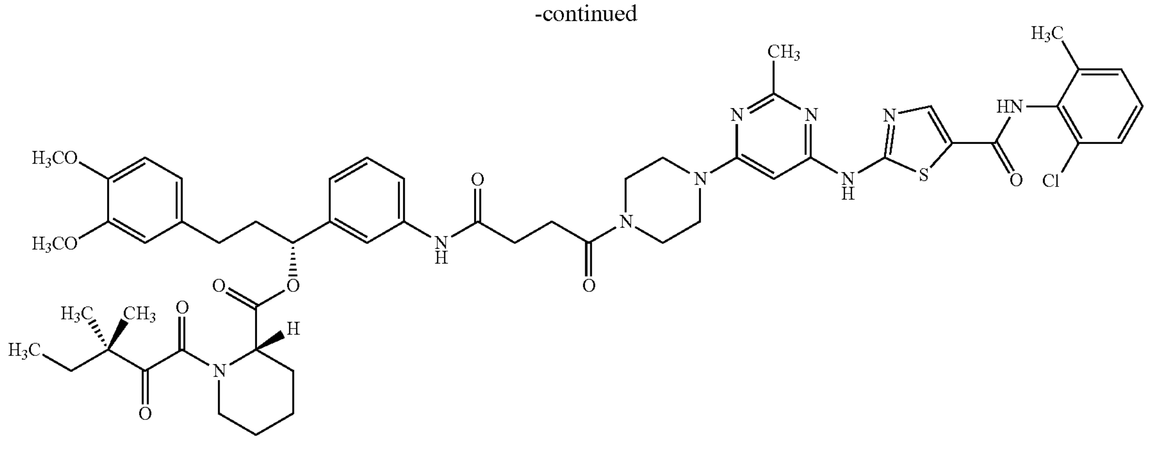

ZZY05-016

An oven-dried 1-dram vial was charged with des(hydroxyethyl)dasatinib (10 mg, 0.023 mmol), ZZY01-083 (14 mg, 0.023 mmol), DMF (0.11 mL), N,N-diisopropylethylamine (12 μL, 0.068 mmol) and a magnetic stir bar. The solution was cooled to 0° C., then HATU (12.8 mg, 0.034 mmol) was added as a solid. The resulting mixture was stirred at 0° C. and the reaction progress was monitored by LC-MS. In 30 min, LC-MS analysis indicated that the starting material had been fully consumed. The residue was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (8.5 mg, 36%). 6:1 mixture of rotamers. $^{1}H$ NMR (400 MHz, Chloroform-d) δ 9.80 (br s, 1H), 8.10 (br s, 1H), 7.86 (br s, 1H), 7.66 (d, J=8.1 Hz, 1H), 7.40-7.27 (m, 2H), 7.24-7.13 (m, 3H), 6.96 (d, J=7.8 Hz, 1H), 6.79-6.71 (m, 1H), 6.70-6.58 (m, 2H), 5.98 (s, 1H), 5.69 (t, J=6.8 Hz, 1H), 5.22 (d, J=5.6 Hz, 1H), 3.95-3.84 (m, 1H), 3.83 (s, 3H), 3.82 (s, 3H), 3.81-3.71 (m, 1H), 3.66 (d, 4H), 3.45-3.39 (m, 4H), 3.27 (d, J=13.6 Hz, 1H), 3.05 (t, J=13.1 Hz, 1H), 2.95-2.76 (m, 3H), 2.52 (q, 5H), 2.34 (s, 3H), 2.27-2.11 (m, 2H), 2.08-1.93 (m, 1H), 1.72-1.46 (m, 5H), 1.46-1.30 (m, 2H), 1.17 (s, 3H), 1.16 (s, 3H), 0.85 (t, J=7.4 Hz, 3H). HRMS (ESI): Calcd for $(C_{54}H_{64}ClN_9O_9S+H)^+$: 1050.4314. Found: 1050.4298.

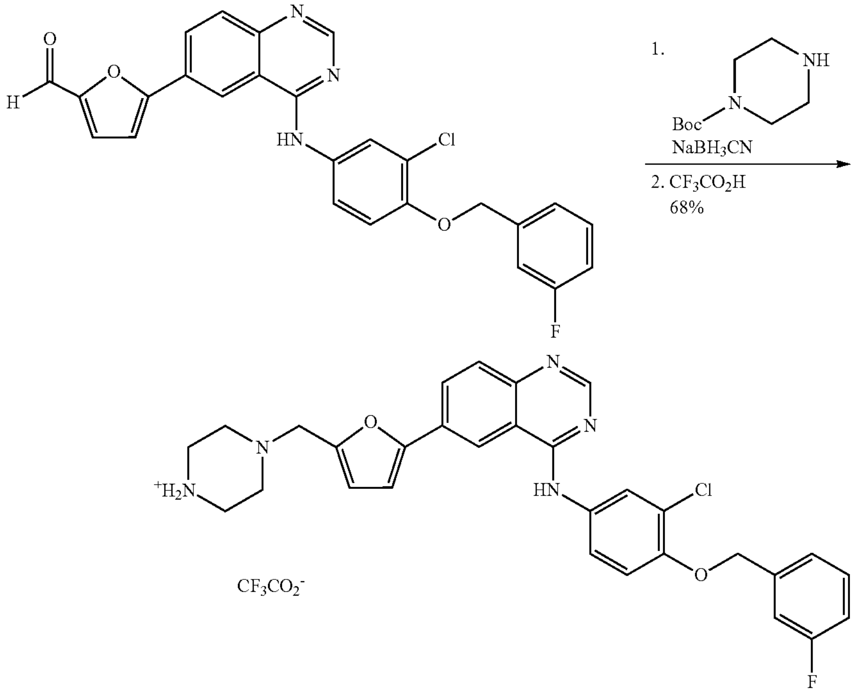

A suspension of 5-[4-[3-chloro-4-[(3-fluorophenyl) methoxy]anilino]quinazolin-6-yl]furan-2-carbaldehyde (100 mg, 0.211 mmol) in 9:1 methanol (1.8 mL):acetic acid (0.2 mL) was sonicated until a fine suspension was formed. 1-Boc-Piperazine (79 mg, 0.42 mmol) was added and the resulting mixture was stirred at 23° C. for 30 min. Sodium cyanoborohydride (20 mg, 0.32 mmol) was added in a single portion at 23° C. The precipitates dissolved over time to a point with a few speckles left in 1 h. At this point TLC analysis (100% ethyl acetate) showed full consumption of the aldehyde starting material. The reaction mixture was concentrated under reduced pressure. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-100% ethyl acetate-hexanes) to afford the product as a yellow powder. The yellow powder was resuspended in dichloromethane (2.0 mL), and trifluoroacetic acid (2.0 mL) was added dropwise, giving rise to a bright yellow solution. After standing at 23° C. for 1 h, the solution was concentrated under reduced pressure to afford the product as a yellow powder (93 mg, 68%). HRMS (ESI): Calcd for $(C_{30}H_{27}ClFN_5O_2+H)^+$: 544.1910. Found: 544.1882.

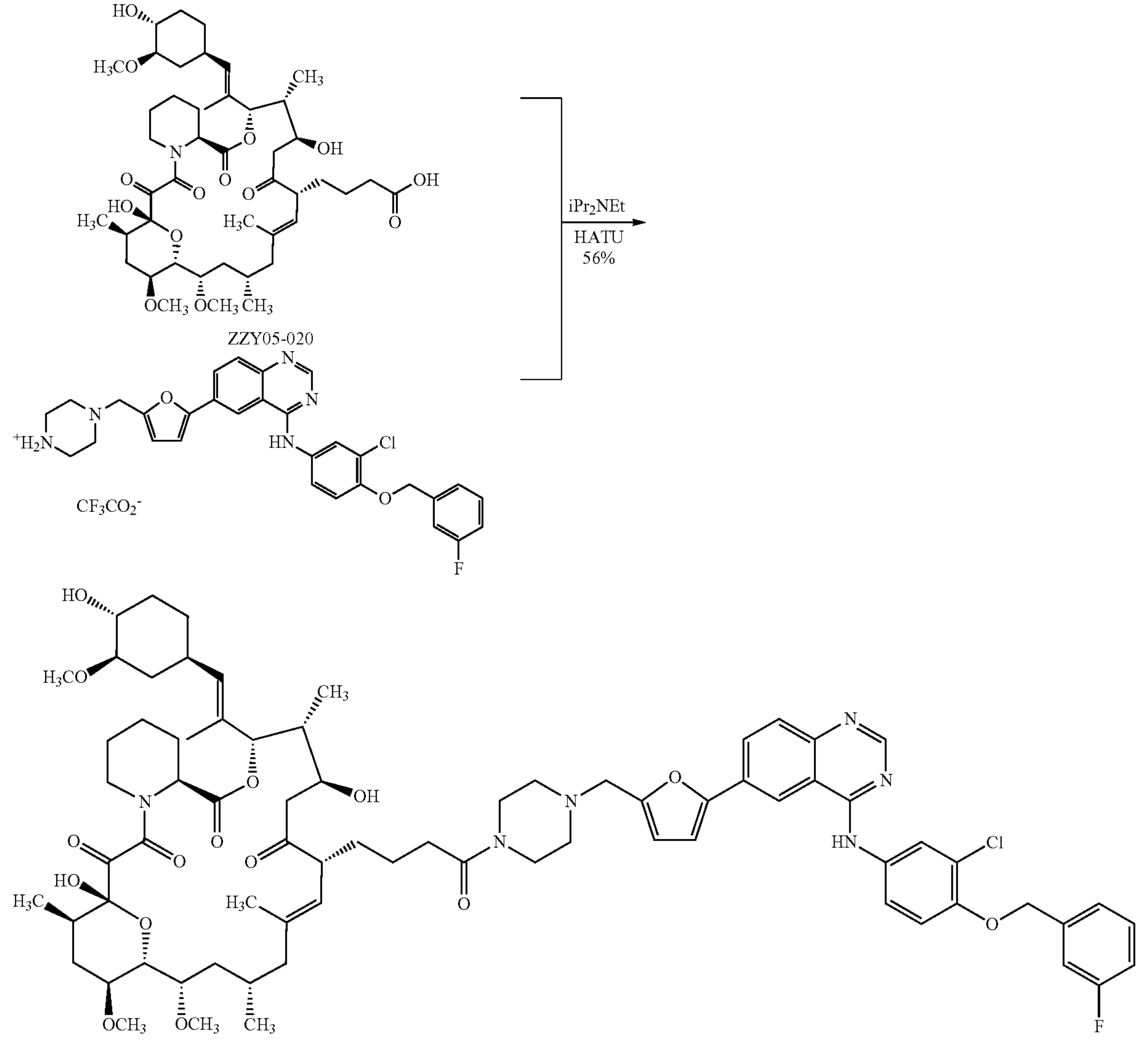

ZZY05-020

ZZY08-047
(FK506-Lapatinib)

N,N-Diisopropylethylamine (12.3 μL, 0.071 mmol) and HATU (9.8 mg, 0.026 mmol) were added sequentially to a stirred solution of ZZY05-020 (20 mg, 0.024 mmol) and Lapatinib-piperidine (17 mg, 0.026 mmol) in 9:1 dichloromethane (0.9 mL):DMF (0.1 mL). The resulting yellow solution was stirred at 23° C. for 1 h. At this point, LC-MS analysis showed full consumption of the acid starting material and formation of a new specie with the desired m/z. The reaction mixture was concentrated under reduced pressure to remove dichloromethane. The residue was diluted with 50% acetonitrile-water to a volume of 4.1 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (18.7 mg, 56%). 3:2 mixture of rotamers. $^1$H NMR (400 MHz, Chloroform-d) δ 8.71 (s, 1H), 8.07-7.94 (m, 2H), 7.90 (d, J=8.7 Hz, 2H), 7.72 (d, J=9.2 Hz, 1H), 7.43-7.34 (m, 1H), 7.27-7.19 (m, 3H), 7.09-6.97 (m, 2H), 6.76 (d, J=3.2 Hz, 1H), 6.55 (s, 1H), 5.42 (s, 1H), 5.18 (d, 3H), 5.12-5.04 (m, 2H), 4.70 (d, J=4.7 Hz, 1H), 4.43 (d, J=13.4 Hz, 1H), 4.07-3.92 (m, 2H), 3.92-3.80 (m, 1H), 3.80-3.66 (m, 2H), 3.61 (d, J=10.1 Hz, 1H), 3.52 (s, 2H), 3.43 (s, 3H), 3.41 (s, 3H), 3.45-3.36 (m, 3H), 3.32 (s, 3H), 3.09-2.95 (m, 2H), 2.95-2.69 (m, 2H), 2.44-2.22 (m, 3H), 2.22-2.09 (m, 3H), 2.05-1.70 (m, 8H), 1.69-1.60 (m, 6H), 1.62-1.32 (m, 8H), 1.11-1.04 (m, 2H), 1.02 (d, J=6.3 Hz, 3H), 0.96 (d, J=6.3 Hz, 3H), 0.86 (d, J=7.3 Hz, 3H). HRMS (ESI): Calcd for $(C_{75}H_{96}ClFN_6O_{15}+2H)^{2+}$: 688.3381. Found: 688.3373.

Ref: *J. Med. Chem.* 2012, 55, 9416.

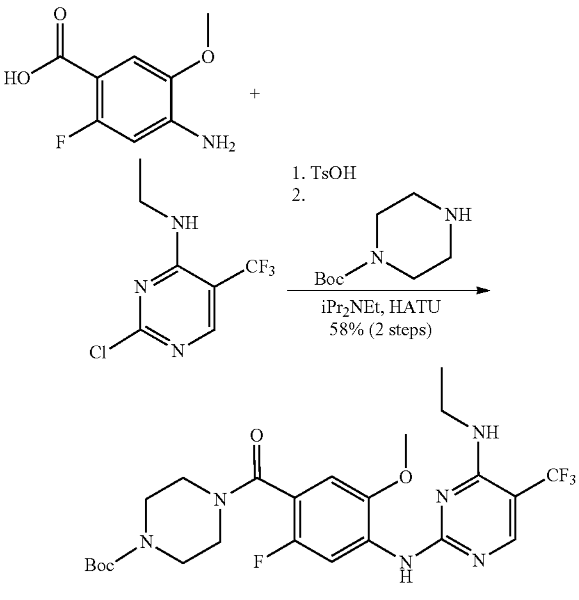

A 20-mL vial was charged with 4-amino-2-fluoro-5-methoxy-benzoic acid (100 mg, 0.54 mmol), 2-chloro-N-ethyl-5-(trifluoromethyl)pyrimidin-4-amine (146 mg, 0.650 mmol), p-toluenesulfonic acid monohydrate (51 mg, 0.27 mmol) and 1,4-dioxane (8.1 mL). The mixture was heated to 100° C. with constant stirring. Despite heating not all the solids dissolved. After 2 h, LC-MS analysis showed full conversion to the desired product. The reaction mixture was then cooled to room temperature. The insoluble solids were collected by filtration, washed with 1,4-dioxane (100 mL) and ethyl (50 mL), and air-dried for 12 h to afford the product as a white solid. The crude material was used in the next step without further purification. Dichloromethane (2.67 mL) and N,N-diisopropylamine (93 μL, 0.53 mmol) were added to the crude product from the last reaction. The resulting suspension was cooled to 0° C., and HATU (308 mg, 0.802 mmol) was added in one portion. The mixture was stirred at 0° C. for 15 min before warming to 23° C. and stirring for another 45 min. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-50% ethyl acetate-hexanes, 4-g RediSep® Rf column, Teledyne ISCO, Lincoln, NE) to afford the product as a white powder (151 mg, 58% over 2 steps). $^1$H NMR (400 MHz, Chloroform-d) δ 8.41 (br s, 1H), 8.18 (s, 1H), 6.91 (d, J=6.0 Hz, 1H), 3.92 (s, 3H), 3.76 (s, 2H), 3.68-3.58 (m, 2H), 3.58-3.47 (m, 2H), 3.49-3.35 (m, 4H), 1.48 (s, 9H), 1.34 (t, J=7.2 Hz, 3H). HRMS (ESI): Calcd for $(C_{24}H_{30}F_4N_6O_4+H)^+$: 543.2343. Found: 543.2389.

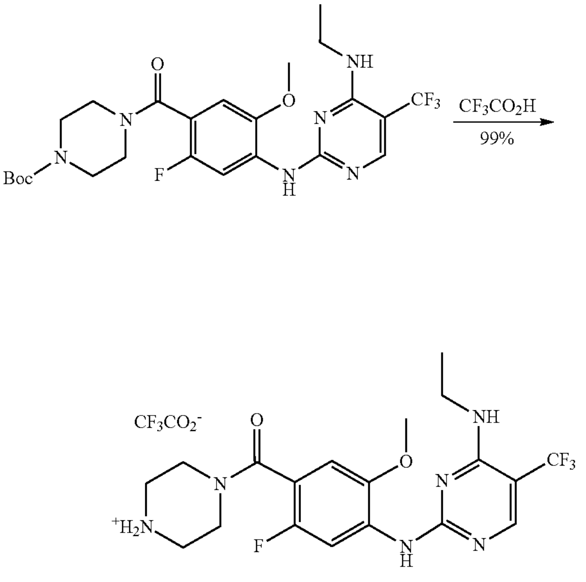

Trifluoroacetic acid (0.50 mL) was added dropwise to a solution of tert-butyl 4-[4-[[4-(ethylamino)-5-(trifluoromethyl)pyrimidin-2-yl]amino]-2-fluoro-5-methoxy-benzoyl] piperazine-1-carboxylate (151 mg, 0.28 mmol) in dichloromethane (0.50 mL) at 23° C. and the resulting solution was allowed to stand at 23° C. for 1 h. The reaction mixture was concentrated in vacuo to afford the product as a white solid. To assist removal of residual trifluoroacetic acid, the solids were triturated with ether (10 mL), and the supernatant was removed. The resulting solids were dried under vacuum over night to afford the product as a white powder (153 mg, 99%). $^1$H NMR (400 MHz, Methanol-d$_4$) δ 8.38 (d, J=11.9 Hz, 1H), 8.29 (d, J=1.1 Hz, 1H), 7.14 (d, J=6.1 Hz, 1H), 4.08-4.01 (m, 2H), 4.00 (s, 3H), 3.78-3.69 (m, 2H), 3.66 (q, J=7.2 Hz, 2H), 3.41-3.25 (m, 4H), 1.32 (t, J=7.1 Hz, 3H). HRMS (ESI): Calcd for $(C_{19}H_{21}F_4N_6O_2+H)^+$: 443.1813. Found: 443.1786.

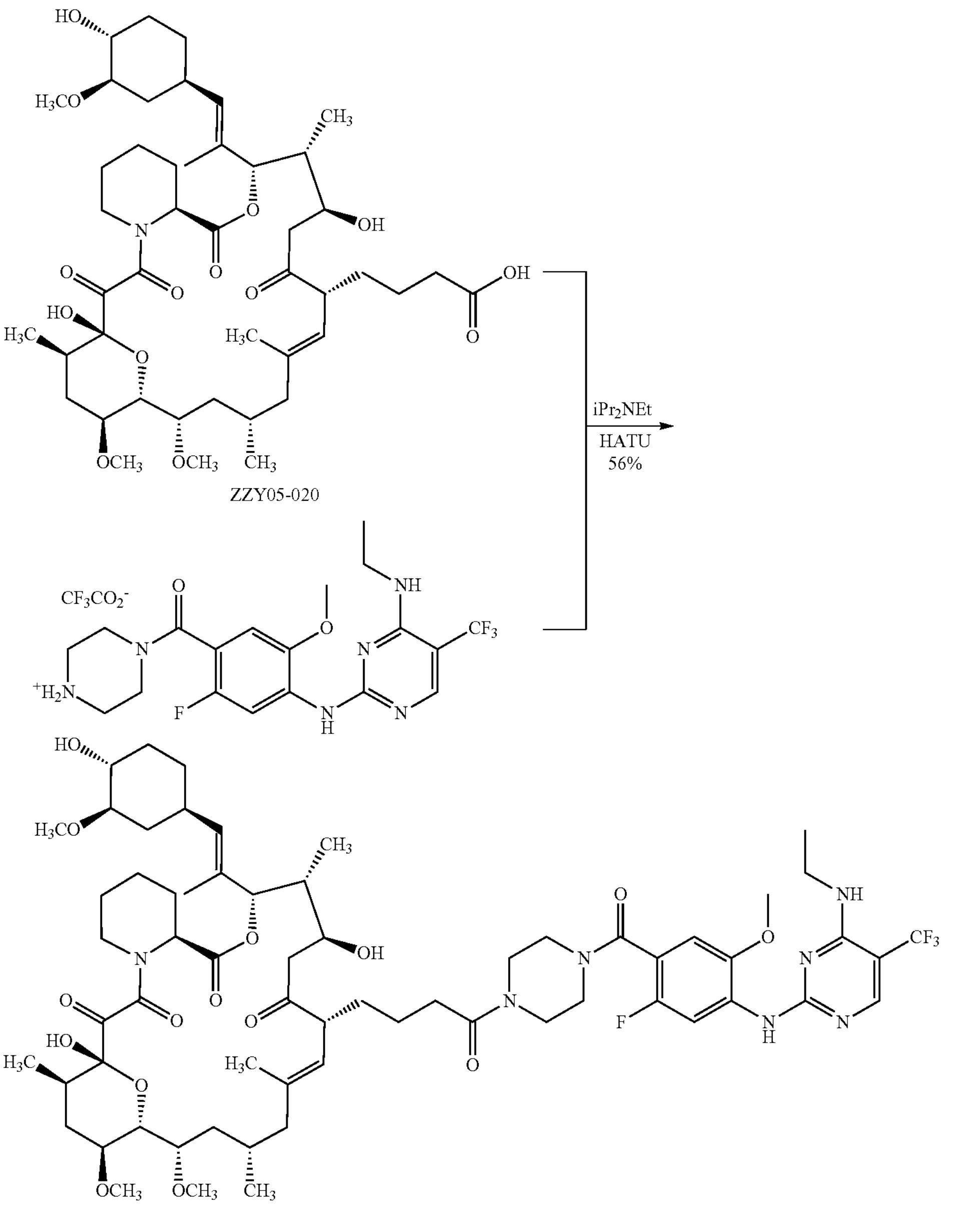

ZZY05-020

ZZY08-074

An oven-dried 1-dram vial was charged with ZZY05-020 (20 mg, 0.024 mmol), Pip-GNE7915 (13 mg, 0.023 mmol), DMF (0.12 mL) and a magnetic stir bar. N,N-Diisopropylethylamine (12 μL, 0.071 mmol) was added and the mixture was stirred until all reactants had dissolved. HATU (11 mg, 0.030 mmol) was added as a 10% (w/v) solution in DMF (110 μL), and the reaction progress was monitored by LC-MS. In 30 min, LC-MS analysis showed that the FK506-acid starting material had been fully consumed and a new product with desired m/z had formed. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (0-10% methanol-dichloromethane, 4-g RediSep® Rf column, Teledyne ISCO, Lincoln, NE) to afford the product as a white powder (16.7 mg, 56%). 3:2 mixture of rotamers. $^1$H NMR (400 MHz, Chloroform-d) δ 8.45 (d, J=12.4 Hz, 1H), 8.20 (s, 1H), 7.87 (s, 1H), 6.91 (s, 1H), 5.34 (s, 1H), 5.26-5.16 (m, 1H), 5.16-4.92 (m, 2H), 4.61 (d, J=5.4 Hz, 1H), 4.42 (d, J=13.4 Hz, 1H), 3.92 (s, 3H), 3.85-3.65 (m, 5H), 3.65-3.51 (m, 5H), 3.51-3.43 (m, 3H), 3.40 (s, 3H), 3.38 (s, 3H), 3.43-3.31 (m, 3H), 3.29 (s, 3H), 3.24-3.19 (m, 1H), 3.19-3.12 (m, 1H), 3.05-2.96 (m, 2H), 2.79 (dd, J=15.9, 2.4 Hz, 1H), 2.67 (br s, 1H), 2.43-2.22 (m, 5H), 2.22-1.94 (m, 5H), 1.94-1.69 (m, 6H), 1.69-1.60 (m, 6H), 1.60-1.40 (m, 8H), 1.33 (t, J=7.2 Hz, 3H), 1.10-1.02 (m, 2H), 0.99 (d, J=6.3 Hz, 3H), 0.93 (d, J=5.9 Hz, 3H), 0.85 (d, J=7.6 Hz, 3H). HRMIS (ESI): Calcd for $(C_{64}H_{91}F_4N_7O_{15}+H)^+$: 1274.6587. Found: 1274.6560.

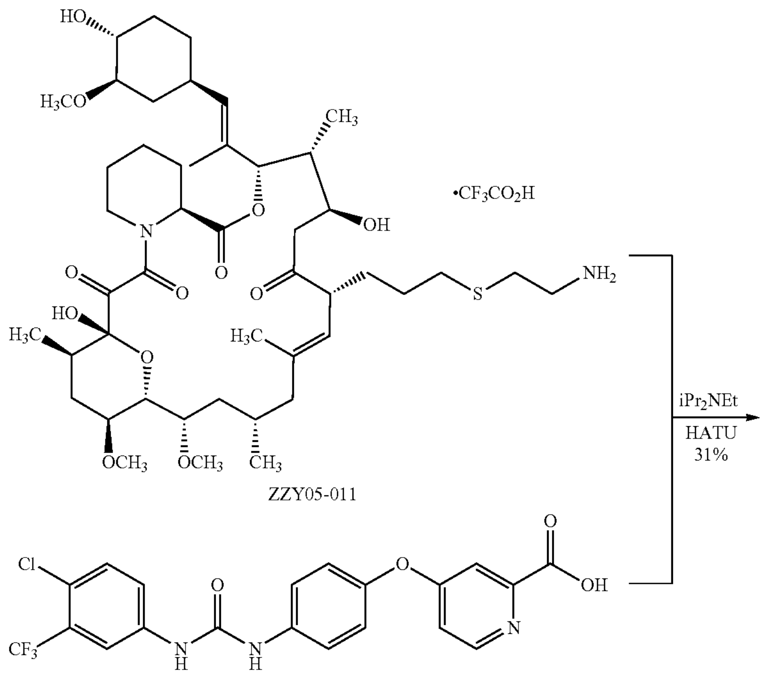

ZZY05-011

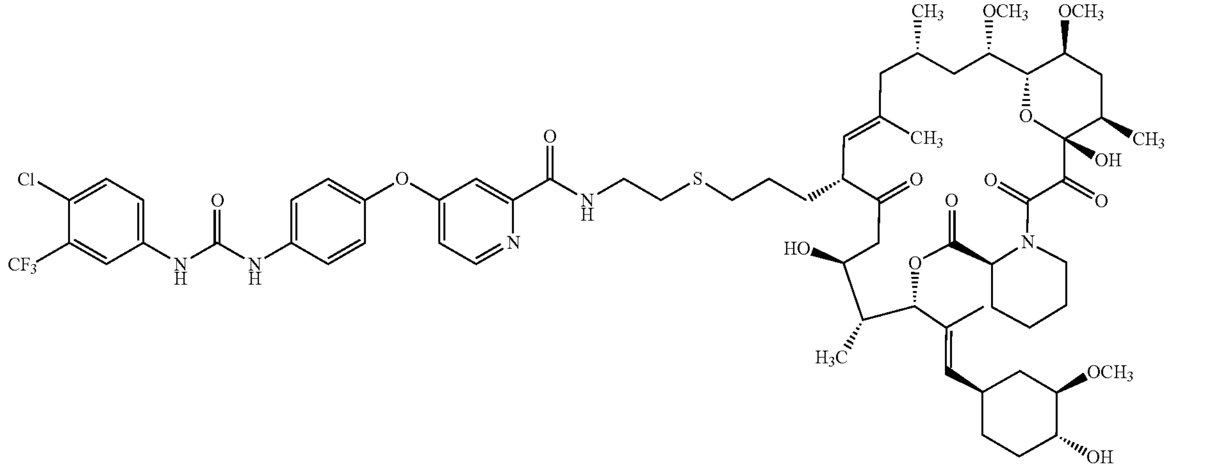

ZZY05-049
(FK506-Sorafenib)

A 1-dram vial was charged with ZZY05-011 (22 mg, 0.022 mmol), 4-[4-[[4-chloro-3-(trifluoromethyl)phenyl] carbamoylamino]phenoxy]pyridine-2-carboxylic acid (10 mg, 0.022 mmol), DMF (0.11 mL), and a magnetic stir bar. The resulting mixture was stirred until all reactants had dissolved. N,N-diisopropylamine (12 μL, 0.066 mmol) and HATU (10 mg, 0.026 mmol) were added sequentially at 23° C., and the resulting solution was stirred at 23° C. for 15 min. LC-MS analysis at this point showed full consumption of the starting material and formation of the desired product. The reaction mixture was diluted with 50% acetonitrile-water to a volume of 4.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (9.1 mg, 31%). 3:2 mixture of rotamers. $^1$H NMR (400 MHz, Chloroform-d) δ 8.51-8.37 (m, 2H), 7.93 (s, 1H), 7.82-7.68 (m, 2H), 7.60-7.49 (m, 2H), 7.49-7.35 (m, 1H), 7.18-7.12 (m, 1H), 7.12-7.00 (m, 2H), 5.36 (s, 1H), 5.12-4.99 (m, 2H), 4.62 (s, 1H), 4.43 (d, J=13.4 Hz, 1H), 4.34 (s, 1H), 4.04-3.97 (m, 1H), 3.73-3.63 (m, 2H), 3.63-3.48 (m, 2H), 3.42 (s, 3H), 3.41 (s, 3H), 3.40-3.36 (m, 3H), 3.33 (s, 3H), 3.09-2.99 (m, 1H), 2.94 (t, J=12.1 Hz, 1H), 2.85-2.66 (m, 4H), 2.54 (t, J=7.5 Hz, 2H), 2.40-2.24 (m, 2H), 2.23-1.94 (m, 5H), 1.94-1.60 (m, 6H), 1.57 (d, J=8.4 Hz, 6H), 1.55-1.26 (m, 8H), 1.12-0.99 (m, 2H), 0.96 (d, J=6.3 Hz, 3H), 0.88 (d, J=7.2 Hz, 3H). HRMS (ESI): Calcd for $(C_{66}H_{87}ClF_3N_5O_{15}S+H)^+$: 1314.5638. Found: 1314.5674.

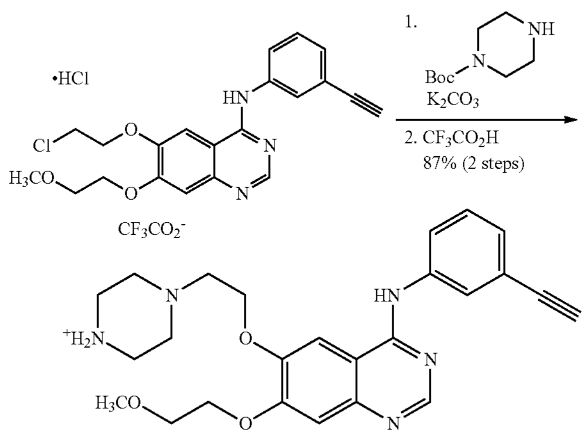

ZZY08-066

An oven-dried 1-dram vial was charged with 6-(2-chloroethoxy)-N-(3-ethynylphenyl)-7-(2-methoxyethoxy)quinazolin-4-amine hydrochloride (100 mg, 0.23 mmol), 1-Boc-piperazine (86 mg, 0.46 mmol), Potassium carbonate (95 mg, 0.69 mmol). DMF (1.15 mL) was added via syringe. The vial was flushed with argon and closed with a rubber septum fitted with a needle connected to an argon source. The mixture was warmed to 80° C. In 1 h, LC-MS analysis showed consumption of the starting material and formation of one single product with the desired m/z. The reaction mixture was partitioned between ethyl acetate (5 mL) and water (5 mL), and the layers were separated. The aqueous layer was extracted with ethyl acetate (3×5 mL). The combined organic layers were dried over sodium sulfate, and the dried solution was concentrated. The residue was purified by column chromatography (0-10% methanol-dichloromethane) to afford the product as a brown solid (112 mg, 88%). tert-butyl 4-[2-[4-(3-ethynylanilino)-7-(2-methoxyethoxy)quinazolin-6-yl]oxyethyl]piperazine-1-carboxylate (112 mg, 0.20 mmol) was dissolved in 1:1 dichloromethane (0.50 mL):Trifluroacetic Acid (0.50 mL) at 23° C. and the resulting solution was allowed to stand at 23° C. for 1 h. At this point, LC-MS analysis showed full consumption of the starting material and formation of one single product with desired m/z. The reaction mixture was concentrated in vacuo to give a syrup, which was triturated with ether (10 mL) to afford the product as a white powder (113 mg, 98%). $^1H$ NMR (400 MHz, Methanol-$d_4$) δ 8.69 (s, 1H), 8.01 (s, 1H), 7.84 (t, J=1.7 Hz, 1H), 7.70 (dt, J=7.7, 1.9 Hz, 1H), 7.49-7.36 (m, 2H), 7.26 (s, 1H), 4.45 (t, J=4.9 Hz, 2H), 4.41-4.33 (m, 2H), 3.88-3.79 (m, 2H), 3.57 (s, 1H), 3.43 (s, 3H), 3.37-3.29 (m, 4H), 3.22 (t, J=4.9 Hz, 2H), 3.17 (d, J=6.8, 3.8 Hz, 4H). HRMS (ESI): Calcd for $(C_{25}H_{29}N_5O_3+H)^+$: 448.2343. Found: 448.2350.

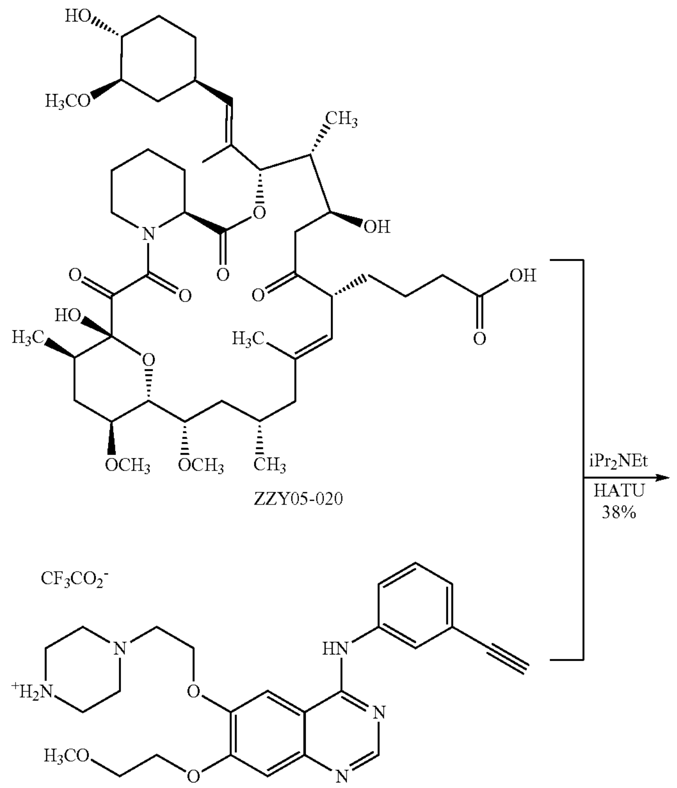

ZZY05-020

ZZY08-066

-continued

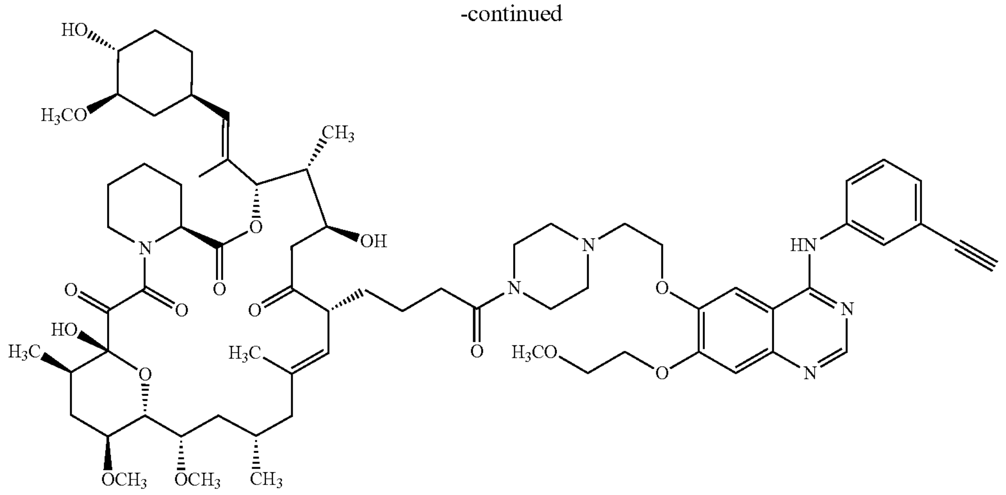

ZZY08-068

A 1-dram vial was charged with 05-020 (20 mg, 0.024 mmol), Pip-Erlotinib (13 mg, 0.024 mmol), DMF (0.12 mL) and a magnetic stir bar. N,N-Diisopropylethylamine (12 μL, 0.071 mmol) was added and the mixture was stirred until all reactants had gone into solution. HATU (10.7 mg, 0.0282 mmol) was added as a freshly made 10% w/v solution in DMF. The mixture was stirred at 23° C. while the reaction progress was monitored by LC-MS. In a total of 1 h, LC-MS analysis showed full consumption of the starting material. The reaction mixture was partitioned between ethyl acetate (5 mL) and water (5 mL), and the layers were separated. The aqueous layer was extracted with ethyl acetate (2x5 mL). The combined organic layers were dried over sodium sulfate, and the dried solution was concentrated. The residue was purified by column chromatography (0-10% methanol-dichloromethane) to afford the product as a pale-yellow solid (11.5 mg, 38%). 3:2 mixture of rotamers. $^1H$ NMR (400 MHz, Chloroform-d) δ 8.64 (s, 1H), 7.87 (dt, J=8.4, 1.4 Hz, 1H), 7.81-7.74 (m, 1H), 7.40-7.30 (m, 2H), 7.25-7.23 (m, 2H), 5.37 (s, 1H), 5.09-4.98 (m, 2H), 4.68 (d, J=4.8 Hz, 1H), 4.38 (d, J=12.9 Hz, 1H), 4.31-4.24 (m, 4H), 4.05-3.90 (m, 1H), 3.90-3.80 (m, 4H), 3.66-3.50 (m, 2H), 3.46 (s, 3H), 3.39 (s, 3H), 3.38 (s, 3H), 3.38-3.33 (m, 3H), 3.29 (s, 3H), 3.09 (s, 1H), 3.05-2.93 (m, 2H), 2.80-2.53 (m, 4H), 2.37-2.20 (m, 4H), 2.19-2.06 (m, 4H), 2.06-1.83 (m, 4H), 1.83-1.51 (m, 8H), 1.49-1.28 (m, 14H), 1.10-1.02 (m, 2H), 0.98 (d, J=6.2 Hz, 3H), 0.92 (d, J=5.6 Hz, 3H), 0.85 (d, J=7.2 Hz, 3H). HRMS (ESI): Calcd for $(C_{70}H_{98}N_6O_{16}+H)^+$: 1279.7117. Found: 1279.7131.

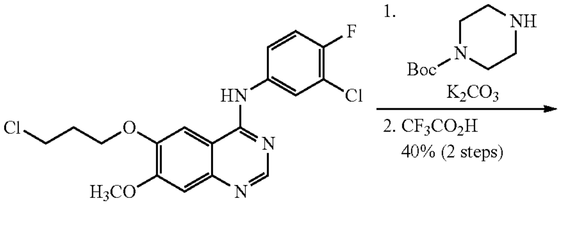

-continued

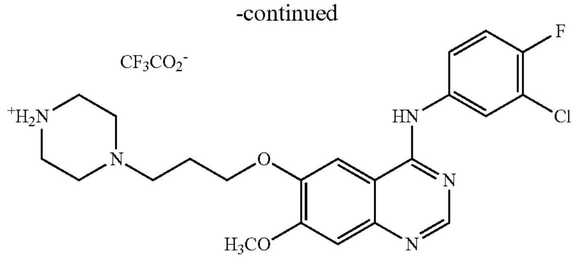

ZZY08-067

An oven-dried 1-dram vial was charged with N-(3-chloro-4-fluoro-phenyl)-6-(3-chloropropoxy)-7-methoxy-quinazolin-4-amine (100 mg, 0.25 mmol), 1-Boc-piperazine (94 mg, 0.50 mmol), Potassium carbonate (105 mg, 0.76 mmol) and a magnetic stir bar. DMF (2.00 mL) was added via syringe. The vial was flushed with argon and closed with a rubber septum fitted with a needle connected to an argon source. The mixture was warmed to 80° C. In 1 h, LC-MS analysis showed consumption of the starting material and formation of one single product with the desired m/z. The reaction mixture was partitioned between ethyl acetate (5 mL) and water (5 mL), and the layers were separated. The aqueous layer was extracted with ethyl acetate (3x5 mL). The combined organic layers were dried over sodium sulfate, and the dried solution was concentrated. The residue was purified by column chromatography (0-10% methanol-dichloromethane) to afford the product as a white solid (57 mg, 41%). tert-Butyl 4-[3-[4-(3-chloro-4-fluoro-anilino)-7-methoxy-quinazolin-6-yl]oxypropyl]piperazine-1-carboxylate (57 mg, 0.104 mmol) was dissolved in 1:1 dichloromethane (0.50 mL):trifluroacetic acid (0.50 mL), and the resulting solution was allowed to stand at 23° C. for 1 h. The solution was concentrated in vacuo to afford the product as a brown solid (58 mg, 99%). $^1H$ NMR (400 MHz, Methanol-$d_4$) δ 8.76 (s, 1H), 8.00 (s, 1H), 7.95 (dd, J=6.6, 2.6 Hz, 1H), 7.68 (ddd, J=8.9, 4.2, 2.6 Hz, 1H), 7.40 (t, J=8.9 Hz, 1H), 7.28 (s, 1H), 4.38 (t, J=5.7 Hz, 2H), 4.11 (s, 3H), 3.50 (t, J=5.3 Hz, 4H), 3.32-3.28 (m, 4H, this peak is covered by the $CD_2HOD$ solvent peak), 3.20 (t, J=7.1 Hz, 2H), 2.34 (p, J=6.4 Hz, 2H). HRMS (ESI): Calcd for $(C_{22}H_{25}ClN_5O_2+H)^+$: 446.1754. Found: 446.1748.

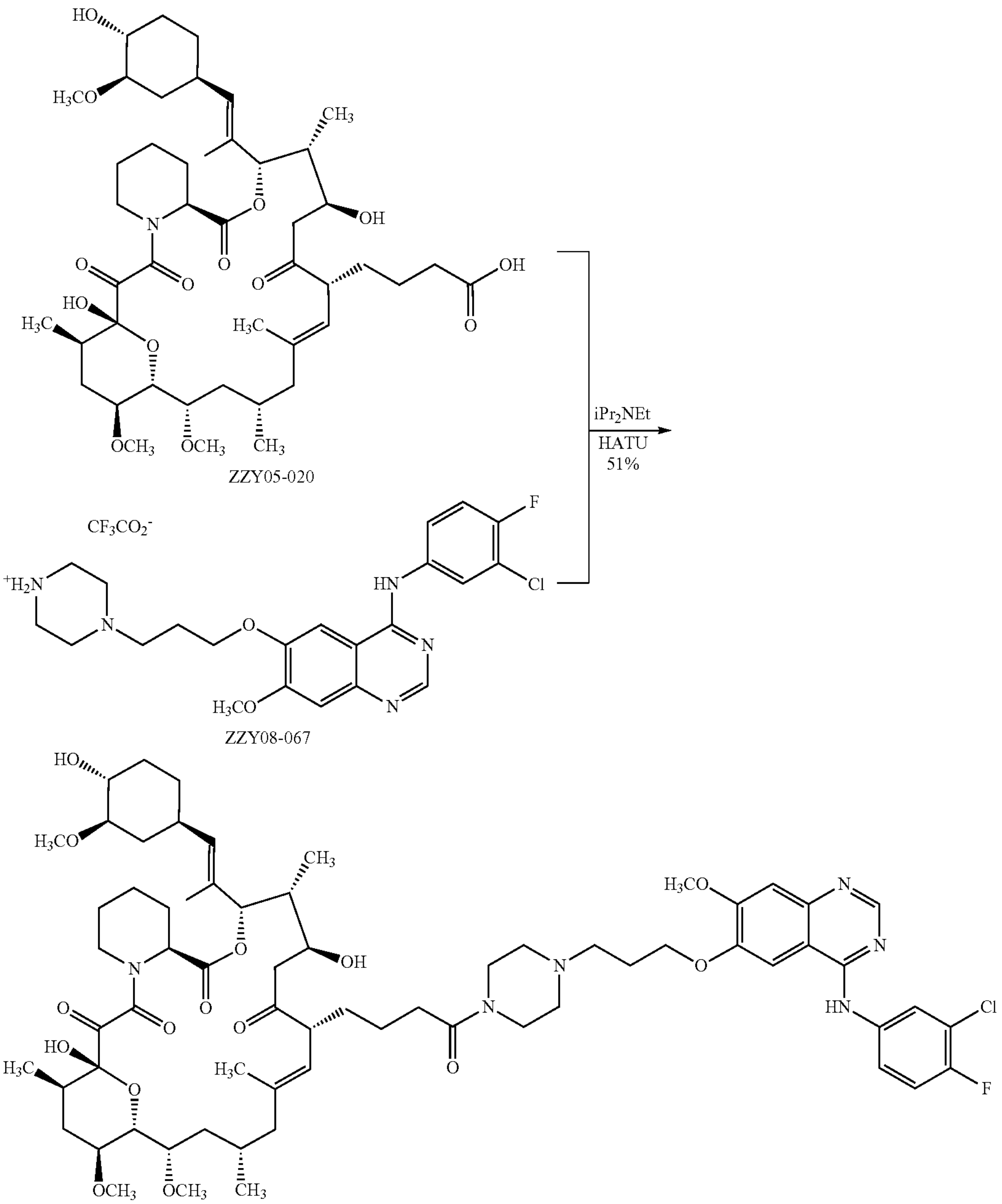

ZZY05-020

ZZY08-067

ZZY08-069

A 1-dram vial was charged with ZZY05-020 (20 mg, 0.024 mmol), Pip-gefetinib (13 mg, 0.024 mmol), DMF (0.12 mL) and a magnetic stir bar. N,N-Diisopropylethylamine (12 μL, 0.071 mmol) was added and the mixture was stirred until all reactants had gone into solution. HATU (10.7 mg, 0.0282 mmol) was added as a 10% w/v solution in DMF. The resulting solution was stirred at 23° C. and the reaction progress was monitored by LC-MS. In 15 min, LC-MS showed ~80% consumption of the amine starting material. Additional HATU (1.07 mg, as 10% solution in DMF) was added. In a total of 1 h, LC-MS analysis showed full consumption of the starting material. The reaction mixture was partitioned between ethyl acetate (5 mL) and water (5 mL), and the layers were separated. The aqueous layer was extracted with ethyl acetate (2×5 mL). The combined organic layers were dried over sodium sulfate, and the dried solution was concentrated. The residue was purified by column chromatography (0-10% methanol-dichloromethane) to afford the product as a pale-yellow solid (15.5 mg, 51%). 3:2 mixture of rotamers. $^1$H NMR (400 MHz, Chloroform-d) δ 8.63 (s, 1H), 8.03-7.87 (m, 1H), 7.70 (d, J=5.7 Hz, 1H), 7.50-7.38 (m, 1H), 7.24 (s, 1H), 7.20-7.12 (m, 2H), 5.40 (s, 1H), 5.21-5.02 (m, 3H), 4.73 (s, 1H), 4.39 (d, J=13.3 Hz, 1H), 4.29-4.14 (m, 4H), 4.14-4.03 (m, 2H), 3.99 (s, 3H), 3.83 (d, J=9.7 Hz, 1H), 3.80-3.56 (m, 4H), 3.51-3.47 (m, 3H), 3.42 (s, 3H), 3.39 (s, 3H), 3.35 (br s, 3H), 3.22 (s, 2H), 3.08-2.71 (m, 6H), 2.40-2.11 (m, 5H), 2.11-1.90 (m, 5H), 1.87-1.65 (m, 6H), 1.62-1.53 (m, 6H), 1.53-1.32 (m, 8H), 1.06-1.01 (m, 2H), 0.96 (d, J=6.0 Hz, 3H), 0.91 (d, J=6.6 Hz, 3H), 0.87 (d, J=6.5 Hz, 3H). HRMS (ESI): Calcd for $(C_{67}H_{94}ClFN_6O_{15}+H)^+$: 1277.6528. Found: 1277.6564.

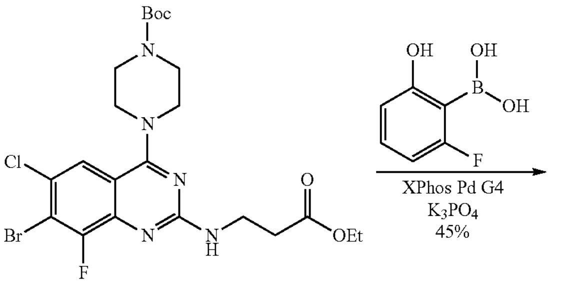

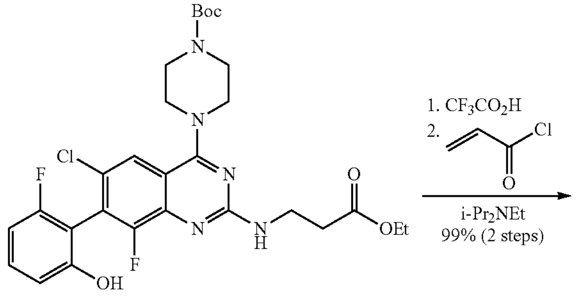

(±)-ZZY04-100

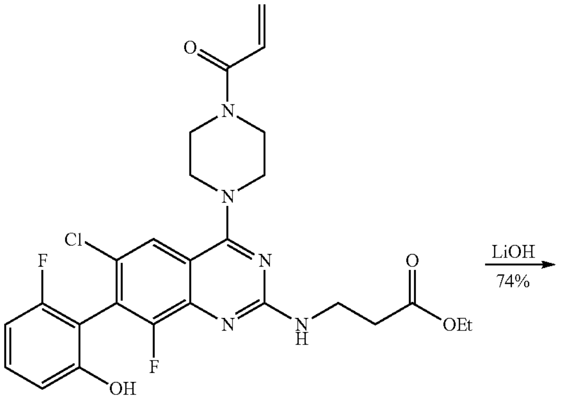

(±)-ZZY05-023

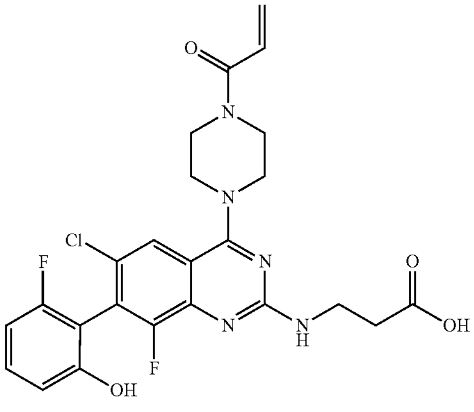

(±)-ZZY05-039

A 20-mL vial was charged with (2-fluoro-6-hydroxy-phenyl)boronic acid (278 mg, 1.78 mmol), tert-butyl 4-[7-bromo-6-chloro-2-[(3-ethoxy-3-oxo-propyl)amino]-8-fluoro-quinazolin-4-yl]piperazine-1-carboxylate (200 mg, 0.36 mmol), XPhos Pd G4 precatalyst (14.2 mg, 0.018 mmol), and 1:1 THF:water (4.0 mL). Argon was bubbled through the mixture for 5 min, then the vial was closed with a rubber septum fitted with a needle connected to an argon source. A 0.5 M aqueous solution of potassium phosphate (0.91 mL, 2.14 mmol) was added dropwise via syringe. After 16 h, both LC-MS and TLC analysis showed only ~50% conversion. Additional catalyst (14.2 mg) was added and the mixture was stirred at 50° C. for another 2 h. However, no further progress was detected after this second portion of catalyst. The reaction mixture was partitioned between ethyl acetate (10 mL) and 10% citric acid (10 mL). The layers were separated, and the aqueous layer was extracted with ethyl acetate (2×10 ml). The combined organic layers were dried over sodium sulfate, and the dried solution was concentrated. The residue was purified by column chromatography (20-50% ethyl acetate-hexanes, 4-g RediSep® Rf column, Teledyne ISCO, Lincoln, NE) to afford the product as a yellow powder (97 mg, 46%) and recovered bromide starting material (72 mg, 36%). $^1H$ NMR (400 MHz, Chloroform-d) δ 7.39 (s, 1H), 7.34-7.24 (m, 1H), 6.85 (d, J=8.3 Hz, 1H), 6.70 (t, J=8.5 Hz, 1H), 5.66 (s, 1H), 4.16 (q, J=7.1 Hz, 2H), 3.74 (app q, J=6.6 Hz, 2H), 3.71-3.51 (m, 8H), 2.65 (td, J=6.5, 1.4 Hz, 2H), 1.50 (s, 9H), 1.26 (t, J=7.1 Hz, 3H). HRMS (ESI): Calcd for $(C_{28}H_{32}ClF_2N_5O_5+H)^+$: 592.2138. Found: 592.2148.

tert-Butyl 4-[6-chloro-2-[(3-ethoxy-3-oxo-propyl)amino]-8-fluoro-7-(2-fluoro-6-hydroxy-phenyl)quinazolin-4-yl]piperazine-1-carboxylate (97 mg, 0.16 mmol) was dissolved in 1:1 trifluoroacetic acid (0.50 mL):dichloromethane (0.50 mL) and the resulting mixture was allowed to stand at 23° C. for 1 h. The solution was then concentrated under reduced pressure to afford the product as a yellow foam. Dichloromethane (1.45 mL) and N,N-diisopropylethylamine (43 μL, 0.25 mmol) were added sequentially to the foam. After stirring for 10 min, the material had fully dissolved. The solution was cooled to −78° C., and acryloyl chloride (14 μL, 0.170 mmol) was added dropwise via syringe. The resulting solution was warmed to 0° C., and the reaction progress was monitored by LC-MS. In 30 min, LC-MS analysis showed conversion to a single product with the desired m/z. The reaction mixture was partitioned between water (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-80% ethyl acetate-hexanes, 4-g RediSep® Rf column, Teledyne ISCO, Lincoln, NE) to afford the product as a yellow powder (100 mg, 99%). $^1H$ NMR (400 MHz, Methanol-$d_4$) δ 8.05 (s, 1H), 7.70 (dd, J=13.0, 5.9 Hz, 1H), 7.45-7.29 (m, 3H), 6.82 (dt, J=8.4, 0.8 Hz, 1H), 6.80-6.73 (m, 1H), 4.41 (s, 4H), 3.93-3.84 (m, 2H), 3.56-3.49 (m, 6H), 2.74 (t, J=6.3 Hz, 2H), 1.20 (t, J=7.0 Hz, 3H). HRMS (ESI): Calcd for $(C_{26}H_{26}ClF_2N_5O_4+H)^+$: 546.1719. Found: 546.1733.

Lithium hydroxide hydrate (1:1:1) (23 mg, 0.55 mmol) was added to a solution of ethyl 3-[[6-chloro-8-fluoro-7-(2-fluoro-6-hydroxy-phenyl)-4-(4-prop-2-enoylpiperazin-1-yl)quinazolin-2-yl]amino]propanoate (100 mg, 0.18 mmol) in 1:1 water (1.10 mL):THF (1.10 mL). The resulting mixture was stirred at 23° C., and the reaction progress was monitored by LC-MS. In 2 h, the ethyl ester had fully hydrolyzed. The volatile solvents were removed by rotary evaporation. The remaining aqueous suspension was acidified with 10% citric acid (2 mL), and then extracted with ethyl acetate (3×10 mL). The combined organic layers were dried over sodium sulfate, and the dried solution was concentrated to afford the product (71 mg, 74%). $^1H$ NMR (400 MHz, Methanol-$d_4$) δ 7.83 (s, 1H), 7.32 (td, J=8.3, 6.7 Hz, 1H), 6.91-6.77 (m, 2H), 6.73 (ddd, J=9.2, 8.3, 1.0 Hz, 1H), 6.29 (dd, J=16.8, 1.9 Hz, 1H), 5.82 (dd, J=10.6, 1.9 Hz, 1H), 4.11-3.84 (m, 8H), 3.78 (t, J=6.5 Hz, 2H), 2.68 (t, J=6.5 Hz, 2H). HRMS (ESI): Calcd for $(C_{24}H_{22}ClF_2N_5O_4+H)^+$: 518.1396. Found: 518.1397.

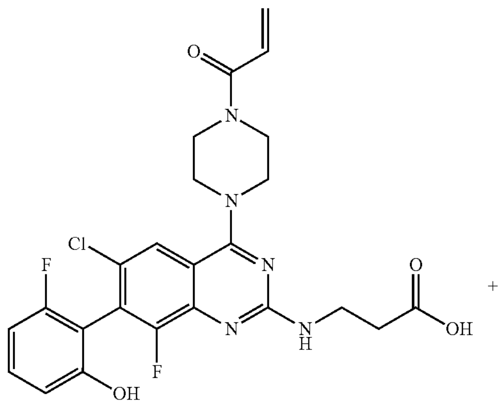

(±)-ZZY05-039

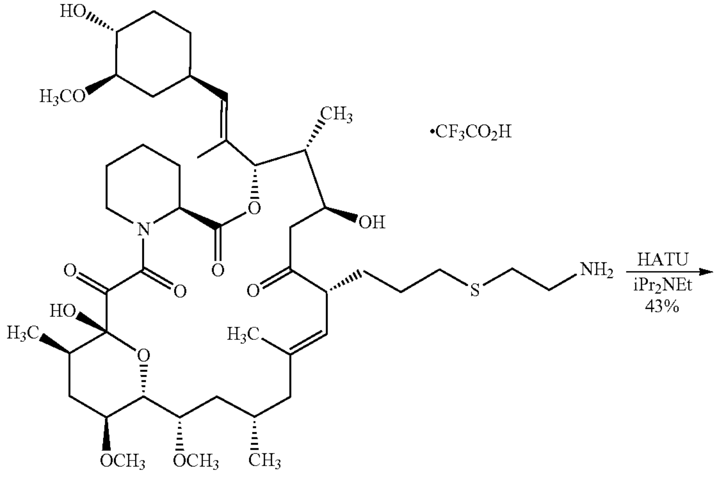

ZZY05-011

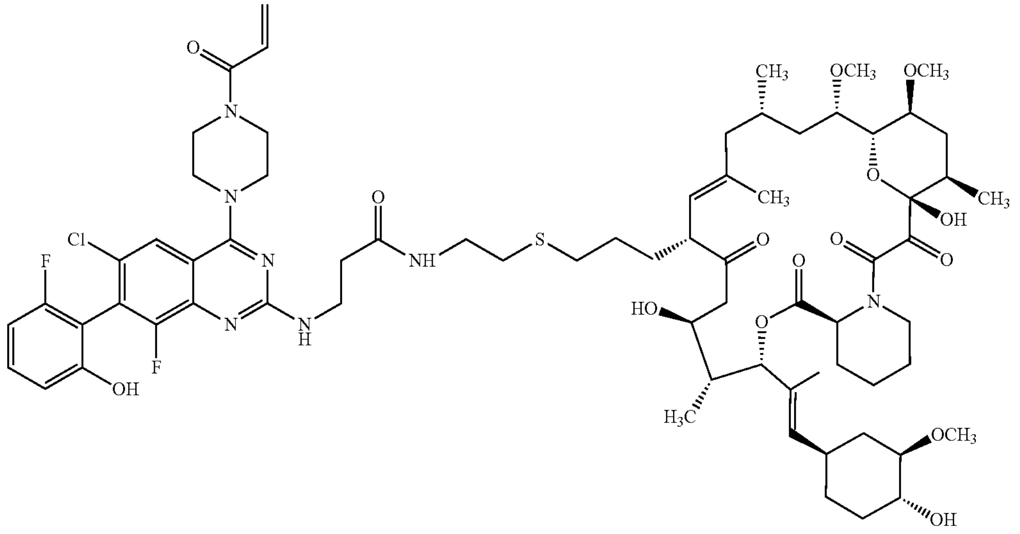

ZZY05-042

A 1-dram vial was charged with (±)-ZZY05-039 (5.0 mg, 0.010 mmol), ZZY05-011 (9.6 mg, 0.010 mmol), and DMF (0.30 mL). N,N-Diisopropylethylamine (5.0 μL, 0.030 mmol) and HATU (4.4 mg, 0.012 mmol) were added sequentially to the solution at 23° C., and the resulting mixture was stirred at 23° C. while the reaction progress was monitored by LC-MS. In 15 min, LC-MS showed full consumption of the amine starting material and formation of a new product with the expected m/z. The reaction mixture was diluted with 50% acetonitrile-water to a volume of 4.7 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.7 mg, 43%). 3:2 mixture of rotamers. $^1$H NMR (400 MHz, Chloroform-d) δ 8.28 (s, 1H), 7.77-7.62 (m, 1H), 6.90-6.72 (m, 2H), 6.64 (dd, J=16.9, 10.7 Hz, 1H), 6.39 (d, J=16.8 Hz, 1H), 5.80 (d, J=10.3 Hz, 1H), 5.35 (d, J=3.5 Hz, 1H), 5.11-4.96 (m, 2H), 4.61-4.32 (m, 2H), 4.07-3.73 (m, 6H), 3.72-3.53 (m, 2H), 3.42 (s, 3H), 3.42 (s, 3H), 3.41 (s, 3H), 3.40-3.37 (m, 3H), 3.17-2.86 (m, 6H), 2.68-2.52 (m, 4H), 2.49-2.24 (m, 6H), 2.24-1.86 (m, 8H), 1.86-1.70 (m, 6H), 1.70-1.61 (m, 6H), 1.61-1.24 (m, 8H), 1.14-1.05 (m, 2H), 1.05-0.81 (m, 9H). HRMS (ESI): Calcd for $(C_{70}H_{96}ClF_2N_7O_{15}S+H)^+$: 1380.6420. Found: 1380.6404.

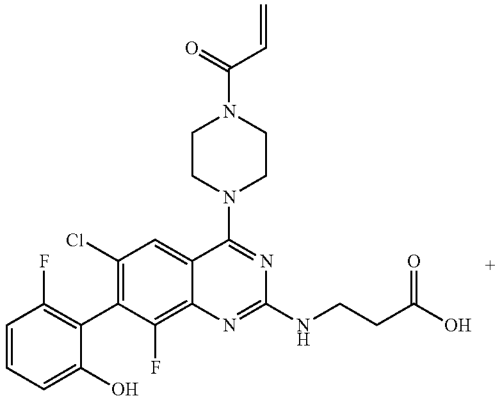

(±)-ZZY05-039

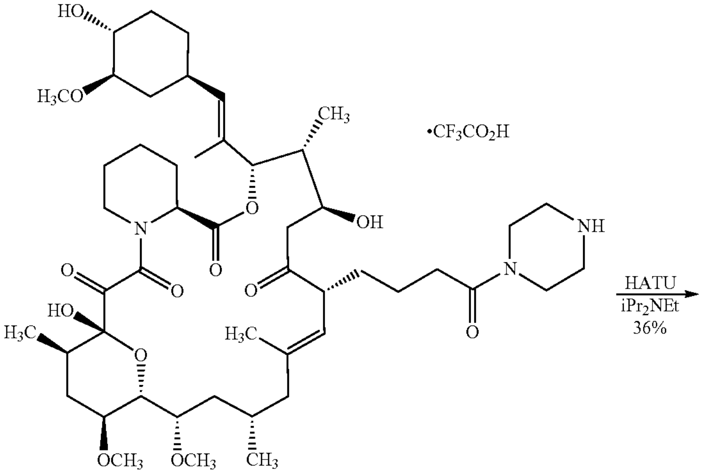

ZZY07-061

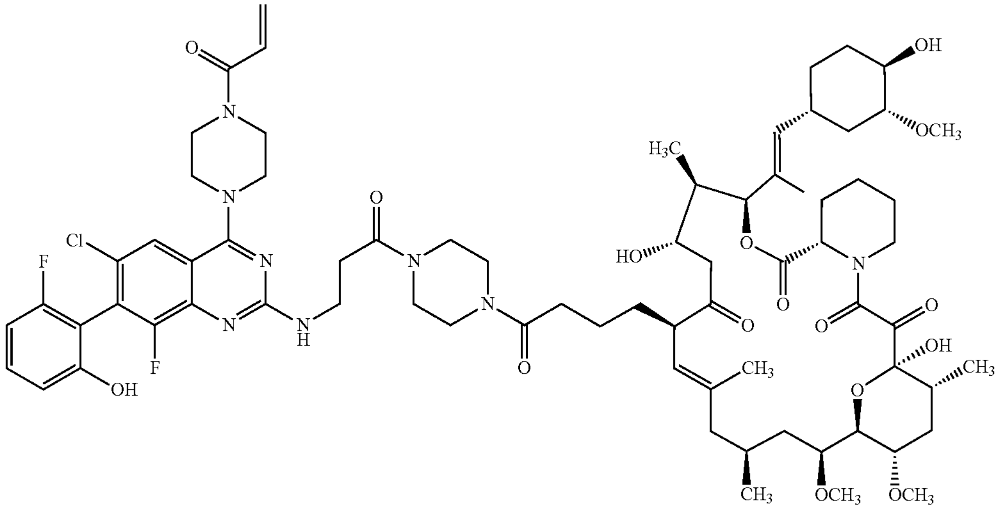

ZZY08-027

A 1-dram vial was charged with (±)-ZZY05-039 (5.5 mg, 0.011 mmol), ZZY08-019 (10.0 mg, 0.010 mmol), and DMF (0.30 mL). N,N-Diisopropylethylamine (5.0 μL, 0.030 mmol) and HATU (7.6 mg, 0.019 mmol) were added sequentially to the solution at 23° C., and the resulting mixture was stirred at 23° C. while the reaction progress was monitored by LC-MS. In 15 min, LC-MS showed full consumption of the amine starting material and formation of a new product with the expected m/z. The reaction mixture was diluted with 50% acetonitrile-water to a volume of 4.2 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (4.9 mg, 36%). 3:2 mixture of rotamers. $^1$H NMR (400 MHz, Methanol-$d_4$) δ 8.09 (s, 1H), 7.46-7.29 (m, 1H), 6.89-6.71 (m, 3H), 6.33 (d, J=16.6 Hz, 1H), 5.85 (d, J=10.6 Hz, 1H), 5.33-5.09 (m, 3H), 4.34 (br s, 4H), 4.06-3.83 (m, 4H), 3.77-3.52 (m, 10H), 3.43 (s, 3H), 3.42 (s, 3H), 3.41-3.38 (m, 2H), 3.35 (s, 3H), 3.09-2.94 (m, 2H), 2.94-2.75 (m, 4H), 2.50-2.27 (m, 6H), 2.27-1.87 (m, 6H), 1.88-1.72 (m, 4H), 1.72-1.52 (m, 6H), 1.52-1.28 (m, 8H), 1.15-1.02 (m, 2H), 1.02-0.86 (m, 9H). HRMS (ESI): Calcd for $(C_{73}H_{99}ClF_2N_8O_{16}+H)^+$: 1417.6914. Found: 1417.6904.

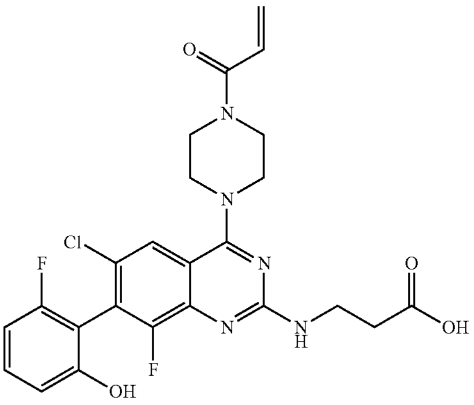

(±)-ZZY05-039

+

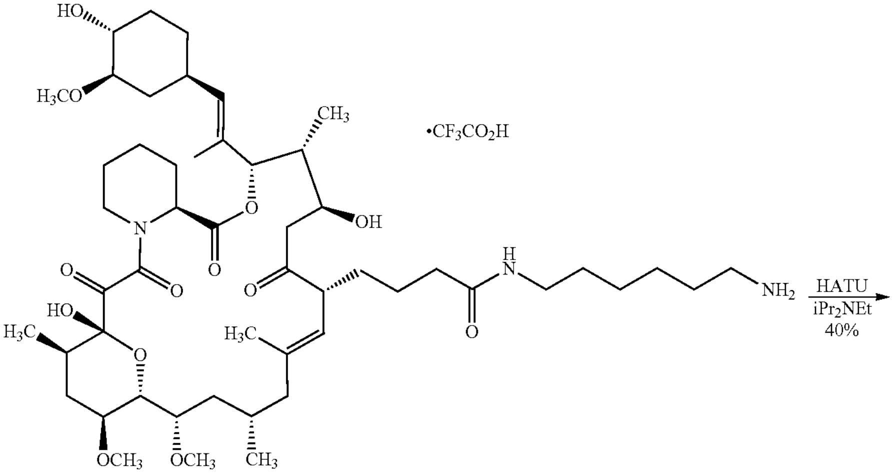

ZZY07-062

-continued

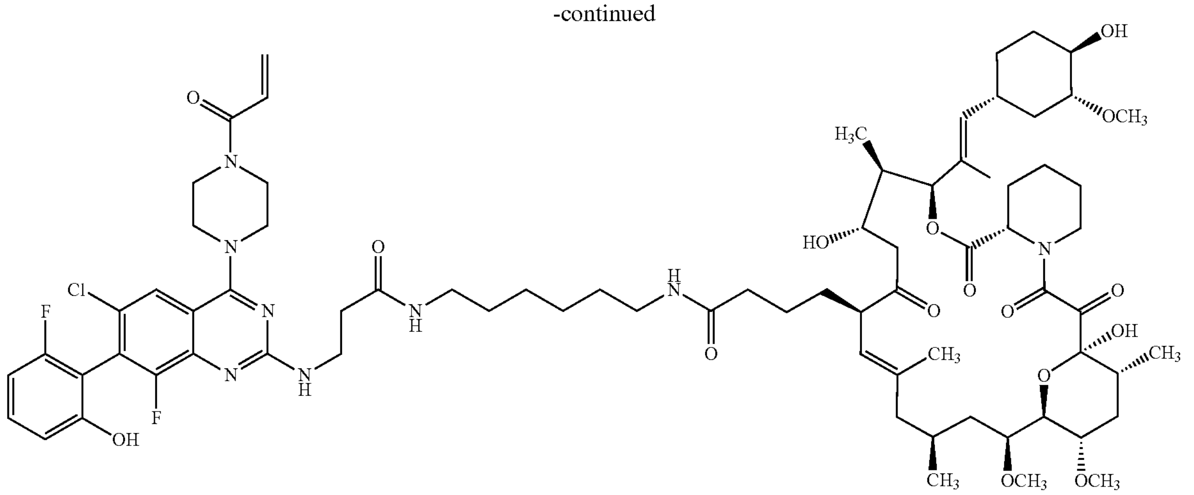

ZZY08-028

A 1-dram vial was charged with (±)-ZZY05-039 (5.5 mg, 0.011 mmol), ZZY08-062 (10.0 mg, 0.010 mmol), and DMF (0.30 mL). N,N-Diisopropylethylamine (5.0 μL, 0.030 mmol) and HATU (7.6 mg, 0.019 mmol) were added sequentially to the solution at 23° C., and the resulting mixture was stirred at 23° C. while the reaction progress was monitored by LC-MS. In 15 min, LC-MS showed full consumption of the amine starting material and formation of a new product with the expected m/z. The reaction mixture was diluted with 50% acetonitrile-water to a volume of 4.2 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.5 mg, 40%). 3:2 mixture of rotamers. $^1$H NMR (400 MHz, Methanol-$d_4$) δ 7.77 (s, 1H), 7.35-7.26 (m, 1H), 6.89-6.68 (m, 3H), 6.28 (d, J=16.1 Hz, 1H), 5.82 (d, J=12.3 Hz, 1H), 5.28-5.19 (m, 1H), 5.18-4.99 (m, 2H), 4.60 (s, 2H), 4.40-4.26 (m, 1H), 4.17-4.06 (m, 1H), 3.95-3.83 (m, 8H), 3.84-3.74 (m, 2H), 3.56-3.47 (m, 2H), 3.44 (s, 3H), 3.43 (s, 3H), 3.40 (s, 3H), 3.39-3.36 (m, 2H), 3.20-3.02 (m, 4H), 2.61-2.50 (m, 2H), 2.44-2.29 (m, 4H), 2.25-2.09 (m, 4H), 2.09-1.89 (m, 4H), 1.89-1.65 (m, 6H), 1.65-1.33 (m, 10H), 1.31-1.23 (m, 8H), 1.12-1.02 (m, 2H), 1.03-0.78 (m, 9H). HRMS (ESI): Calcd for $(C_{75}H_{105}ClF_2N_8O_{16}+H)^+$: 1447.7383. Found: 1447.7435.

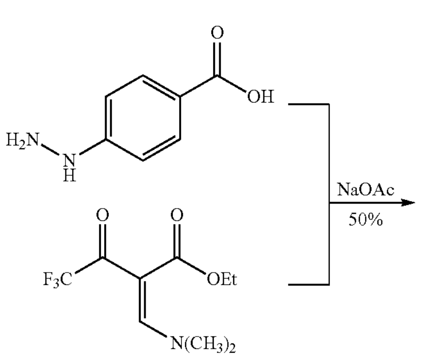

-continued

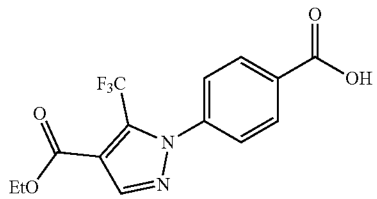

ZZY06-005

A 20-mL vial was charged with ethyl (2Z)-2-(dimethylaminomethylene)-4,4,4-trifluoro-3-oxo-butanoate (526 mg, 2.20 mmol), 4-hydrazinobenzoic acid (304 mg, 2.00 mmol), sodium acetate (180 mg, 2.2 mmol) and ethanol (5.0 mL). The mixture was warmed to 70° C. and kept stirred at that temperature. In 4 h, a large amount of precipitation had formed. TLC analysis (50% ethyl acetate-hexanes) showed full conversion of the starting material to a less polar compound. The reaction mixture was filtered through a sintered glass funnel. The collected solids were rinsed with cold ethanol (10 mL) and then ether (10 mL). The combined filtrate was concentrated under reduced pressure. The residue was purified by column chromatography (0-60% ethyl acetate-hexanes+0.1% acetic acid, 4-g RediSep® Rf column, Teledyne ISCO, Lincoln, NE) to afford the product as a yellow powder (332 mg, 50%). $^1$H NMR (400 MHz, Chloroform-d) δ 8.31-8.22 (m, 2H), 8.16 (d, J=0.7 Hz, 1H), 7.57 (d, J=8.5 Hz, 2H), 4.39 (q, J=7.1 Hz, 2H), 1.40 (t, J=7.2 Hz, 3H). HRMS (ESI): Calcd for $(C_{14}H_{11}F_3N_2O_4-H)^-$: 327.0593. Found: 327.0589.

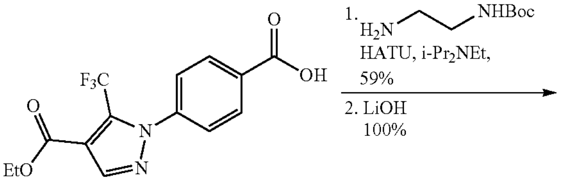

ZZY06-005

-continued

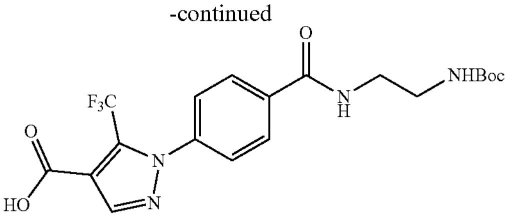

ZZY06-015

N,N-diisopropylethylamine (0.32 mL, 1.83 mmol) and HATU (278.01 mg, 0.730 mmol) were added sequentially to a mixed solution of N-tert-Boc-ethylenediamine (117.14 mg, 0.7300 mmol) and 4-[4-ethoxycarbonyl-3-(trifluoromethyl)pyrazol-1-yl]benzoic acid (200 mg, 0.6100 mmol) in 9:1 dichloromethane:DMF (1.2 mL). The resulting mixture was stirred at 23° C. for 30 min, at which point LC-MS analysis showed full consumption of the acid starting material and formation of a slightly less polar compound. The reaction mixture was concentrated under reduced pressure. The residue was purified by column chromatography (20-50% ethyl acetate-hexanes, 4-g RediSep® Rf column, Teledyne ISCO, Lincoln, NE) to afford the product as a yellow powder (170 mg, 59%). Lithium hydroxide hydrate (27 mg, 0.64 mmol) was added to a suspension of ethyl 1-[4-[2-(tert-butoxycarbonylamino)ethylcarbamoyl]phenyl]-3-(trifluoromethyl)pyrazole-4-carboxylate (100 mg, 0.21 mmol) in 1:1:1 methanol (0.50 mL):THF (0.50 mL):Water (0.50 mL) at 23° C. The resulting mixture turned into a clear solution immediately. In 30 min, LC-MS analysis showed full conversion to the carboxylic acid. 10% Aqueous citric acid (3 mL) was added, and the resulting mixture was extracted with ethyl acetate (3×10 mL). The combined organic layers were dried over sodium sulfate, and the dried solution was concentrated to afford the product as a white powder (99 mg, 100%). $^1H$ NMR (400 MHz, Chloroform-d) δ 8.21 (s, 1H), 8.01 (d, J=8.3 Hz, 2H), 7.53 (d, J=8.9 Hz, 2H), 3.66-3.58 (m, 2H), 3.54-3.41 (m, 2H), 1.45 (s, 9H). HRMS (ESI): Calcd for $(C_{19}H_{21}F_3N_4O_5-H)^-$: 441.1386. Found: 441.1370.

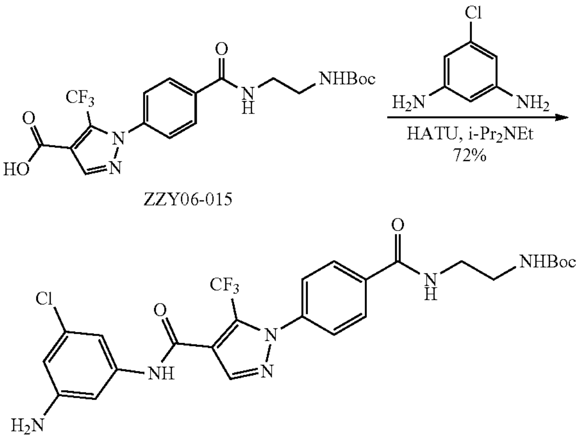

ZZY06-015

ZZY06-018

N,N-Diisopropylamine (87 μL, 0.50 mmol) and HATU (45 mg, 0.12 mmol) were added sequentially to a solution of 1-[4-[2-(tert-butoxycarbonylamino)ethylcarbamoyl]phenyl]-3-(trifluoromethyl)pyrazole-4-carboxylic acid (44 mg, 0.100 mmol) and 5-Chloro-1,3-benzenediamine (57 mg, 0.40 mmol) in 9:1 dichloromethane:DMF (0.5 mL) at 23° C. and the reaction progress was monitored by LC-MS. In 1 h, LC-MS analysis showed full consumption of the acid starting material and formation of a single, desired product. TLC analysis (100% ethyl acetate) showed that the excess diamine was easily separated from the product in this case. The reaction mixture was directly loaded onto a silica gel cartridge (~2 g). Purification by column chromatography (20-100% ethyl acetate-hexanes, 4-g RediSep Rf Column, Teledyne ISCO, Lincoln, NE) afforded the product as a white solid (51 mg, 72%). $^1H$ NMR (400 MHz, Methanol-$d_4$) δ 8.11 (s, 1H), 8.03 (d, J=8.5 Hz, 2H), 7.61 (d, J=8.6 Hz, 2H), 7.02 (s, 1H), 6.98 (s, 1H), 6.52 (t, J=1.9 Hz, 1H), 3.59-3.45 (m, 2H), 3.43-3.28 (m, 2H), 1.43 (s, 9H). HRMS (ESI): Calcd for $(C_{25}H_{27}ClF_3N_6O_4+H)^+$: 567.1734. Found: 567.1751.

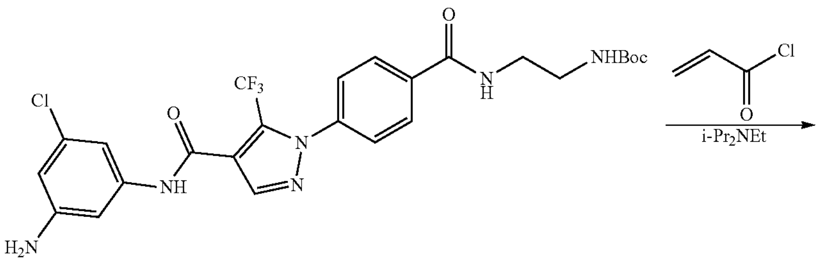

ZZY06-018

-continued

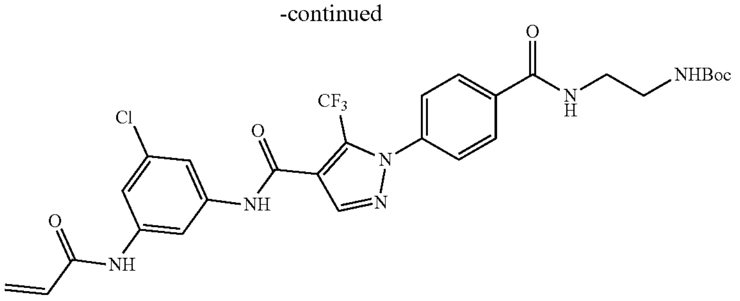

ZZY06-022

Acryloyl chloride (10.7 μL, 0.13 mmol) was added dropwise to an ice-cold solution of tert-butyl N-[2-[[4-[4-[(3-amino-5-chloro-phenyl)carbamoyl]-5-(trifluoromethyl)pyrazol-1-yl]benzoyl]amino]ethyl]carbamate (51 mg, 0.090 mmol) and triethylamine (37 μL, 0.27 mmol) in dichloromethane (1.0 mL) at 0° C. Upon addition the reaction mixture turned into a polymer-like gel. Nevertheless, TLC analysis (100% ethyl acetate) showed a new UV-active spot being formed. LC-MS analysis of an aliquot of filtered material showed full consumption of the starting material. The reaction mixture was partitioned between saturated aqueous sodium bicarbonate solution (5 mL) and dichloromethane (5 mL). The mixture was filtered to remove the polymeric material. The layers were separated, and the aqueous layer was extracted with dichloromethane (2×25 mL). The combined organic layers were dried over sodium sulfate. The dried solution was filtered, and the filtrate was concentrated. The residue was purified by column chromatography (20-100% ethyl acetate-hexanes, 4-g RediSep® Rf column, Teledyne ISCO, Lincoln, NE) to afford the product as a yellow solid (22 mg, 39%). $^1H$ NMR (400 MHz, Methanol-$d_4$) δ 8.18 (s, 1H), 8.05 (d, J=8.3 Hz, 2H), 8.02-7.96 (m, 1H), 7.68-7.61 (m, 3H), 7.56 (s, 1H), 6.47-6.40 (m, 2H), 5.82 (dd, J=8.9, 2.9 Hz, 1H), 3.54-3.45 (m, 4H), 1.44 (s, 9H). HRMS (ESI): Calcd for $(C_{28}H_{28}ClF_3N_6O_5+H)^+$: 621.1840. Found: 621.1855.

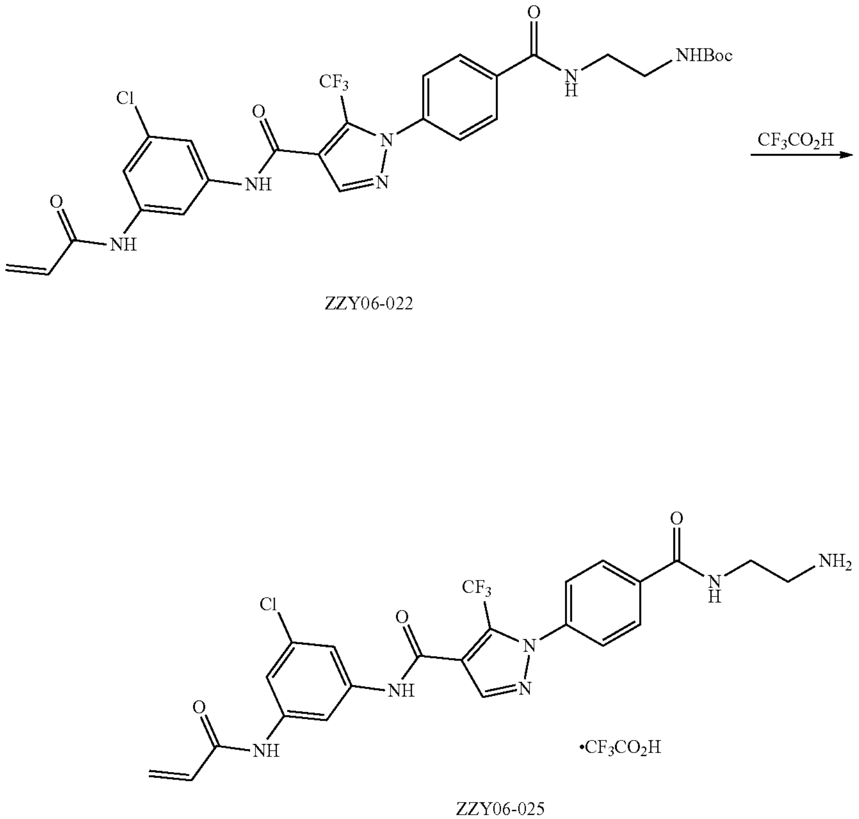

ZZY06-022

ZZY06-025 tert-Butyl N-[2-[[4-[4-[[3-chloro-5-(prop-2-enoylamino) phenyl]carbamoyl]-5-(trifluoromethyl)pyrazol-1-yl]benzoyl]amino]ethyl]carbamate (23 mg, 0.040 mmol) was dissolved in 50% trifluoroacetic acid-dichloromethane (1.0 mL). The resulting solution was allowed to stand at 23° C. for 1 h. LC-MS analysis at this point showed full conversion of the starting material to a single product. The reaction mixture was directly concentrated to afford the product as a white solid (23 mg, 98%). $^1$H NMR (400 MHz, Methanol-d$_4$) δ 8.22-8.19 (m, 1H), 8.10 (d, J=8.8 Hz, 2H), 8.00 (t, J=1.9 Hz, 1H), 7.68 (d, J=8.5 Hz, 2H), 7.61 (t, J=1.9 Hz, 1H), 7.56 (t, J=1.9 Hz, 1H), 6.46-6.36 (m, 2H), 5.82 (dd, J=9.0, 2.9 Hz, 1H), 3.77-3.69 (m, 2H), 3.22 (t, J=5.9 Hz, 2H). HRMS (ESI): Calcd for $(C_{23}H_{20}ClF_3N_6O_3+H)^+$: 521.1316, Found: 521.1319.

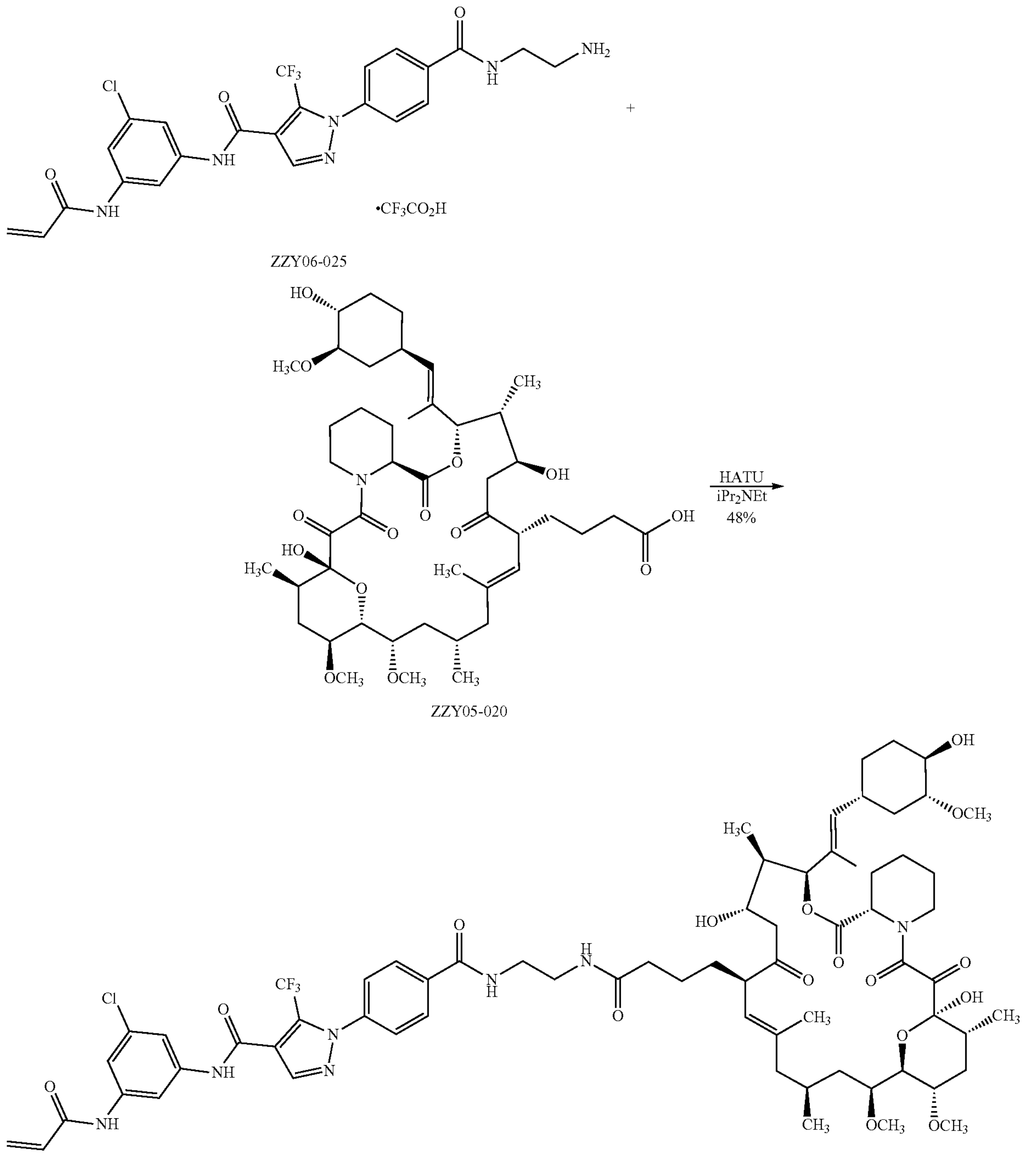

ZZY06-025

ZZY05-020

ZZY06-027

N,N-Diisopropylethylamine (8.2 μL, 0.047 mmol) and HATU (9.0 mg, 0.024 mmol) were added sequentially to a mixed solution of ZZY05-020 (14.7 mg, 0.017 mmol) and ZZY06-025 (10 mg, 0.016 mmol) in DMF (0.20 mL) at 23° C. The resulting mixture was stirred at 23° C., and the reaction progress was monitored by LC-MS. In 1 h, LC-MS analysis showed full consumption of the acid starting material. The residue was diluted with 50% acetonitrile-water to a volume of 3.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (10.2 mg, 48%). 3:2 mixture of rotamers. $^1$H NMR (400 MHz, Chloroform-d) δ 9.01 (s, 1H), 8.21 (s, 1H), 8.00 (s, 1H), 7.92 (d, J=8.5 Hz, 3H), 7.78 (s, 1H), 7.64 (d, J=13.4 Hz, 2H), 7.59-7.46 (m, 3H), 6.52-6.46 (m, 1H), 6.43 (d, J=17.1 Hz, 1H), 6.28 (dd, J=16.8, 10.2 Hz, 1H), 5.76 (d, J=11.1 Hz, 1H), 5.30 (s, 1H), 5.07-4.94 (m, 2H), 4.63 (d, J=4.3 Hz, 1H), 4.39 (d, J=13.5 Hz, 1H), 3.96-3.88 (m, 2H), 3.68-3.44 (m, 5H), 3.39 (s, 3H), 3.38 (s, 3H), 3.36-3.33 (m, 3H), 3.28 (s, 3H), 3.25-3.16 (m, 2H), 3.06-2.95 (m, 2H), 2.90 (t, J=12.7 Hz, 1H), 2.62 (d, J=15.6 Hz, 1H), 2.39-1.91 (m, 10H), 1.91-1.61 (m, 6H), 1.61-1.55 (m, 6H), 1.56-1.29 (m, 8H), 1.06-1.00 (m, 2H), 0.96 (d, J=6.3 Hz, 3H), 0.91 (d, J=5.7 Hz, 3H), 0.83 (d, J=7.2 Hz, 3H). HRMS (ESI): Calcd for $(C_{68}H_{89}ClF_3N_7O_{16}—H)^-$: 1350.5928. Found: 1350.5908

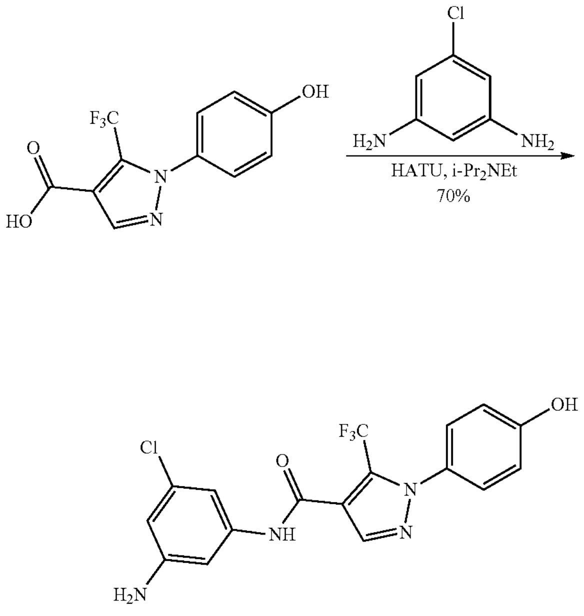

ZZY07-004

An oven-dried 20-mL vial was charged with 1-(4-hydroxyphenyl)-5-(trifluoromethyl)pyrazole-4-carboxylic acid (50 mg, 0.18 mmol), 5-Chloro-1,3-benzenediamine (131 mg, 0.92 mmol) and a magnetic stir bar. DMF (0.37 mL) was added and the mixture was stirred until all reactants had dissolved. N,N-Diisopropylethylamine (96 μL, 0.55 mmol) and HATU (91 mg, 0.24 mmol) were added sequentially. Stirring was continued and the reaction progress was monitored by LC-MS. In 8 h, LC-MS analysis showed full consumption of the starting material and formation of one major product and one minor product. The minor product had an m/z that matched a dimer (bis-acylation). The reaction mixture was diluted with 50% acetonitrile-water to a volume of 10.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (51 mg, 70%). $^1$H NMR (400 MHz, Methanol-$d_4$) δ 8.05 (s, 1H), 7.30 (d, J=8.8 Hz, 2H), 7.03-6.98 (m, 2H), 6.98-6.89 (m, 2H), 6.52 (t, J=1.9 Hz, 1H). HRMS (ESI): Calcd for $(C_{17}H_{12}ClF_3N_4O_2+H)^+$: 397.0679. Found: 397.0689.

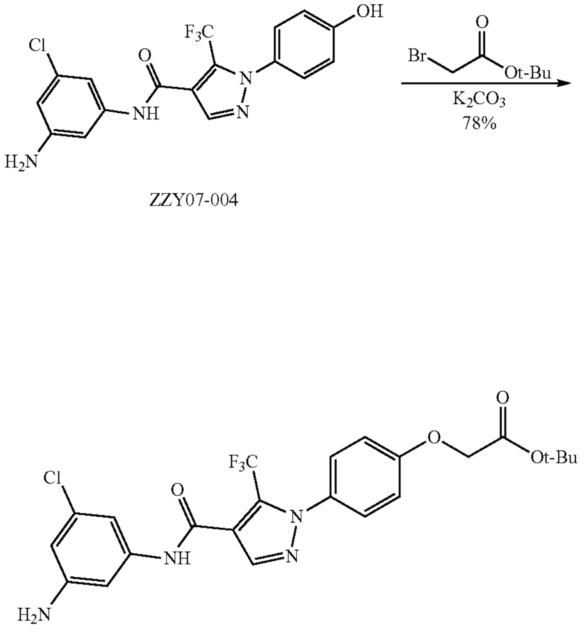

ZZY07-004

ZZY07-019

An oven-dried 1-dram vial was charged with N-(3-amino-5-chloro-phenyl)-1-(4-hydroxyphenyl)-5-(trifluoromethyl)pyrazole-4-carboxamide (30 mg, 0.076 mmol), Potassium carbonate (21 mg, 0.15 mmol), DMF (0.13 mL), and a magnetic stir bar. tert-Butyl bromoacetate (11 μL, 0.076 mmol) was added via pipette, and the resulting mixture was stirred at 23° C. In 16 h, LC-MS indicated that the starting material had been fully consumed and two products had formed. One had the desired m/z and the other seemed to be a bis-alkylation product. The reaction mixture was partitioned between saturated aqueous sodium bicarbonate solution (5 mL) and ethyl acetate (5 mL). The layers were separated, and the aqueous layer was extracted with ethyl acetate (2×5 mL). The combined organic layers were dried over sodium sulfate. The dried solution was filtered, and the filtrate was concentrated. The residue was purified by column chromatography (20-80% ethyl acetate-hexanes, 4-g RediSep® Rf column, Teledyne ISCO, Lincoln, NE) to afford the product as a yellow powder (30 mg, 78%). $^1$H NMR (400 MHz, Chloroform-d) δ 7.96 (s, 1H), 7.51 (s, 1H), 7.40-7.32 (m, 2H), 7.10 (d, J=2.3 Hz, 1H), 7.04-6.94 (m, 2H), 6.79 (t, J=1.8 Hz, 1H), 6.47 (t, J=1.9 Hz, 1H), 4.58 (s, 2H), 3.83 (s, 2H), 1.49 (s, 9H). HRMS (ESI): Calcd for $(C_{23}H_{22}ClF_3N_4O_4+H)^+$: 511.1360. Found: 511.1376.

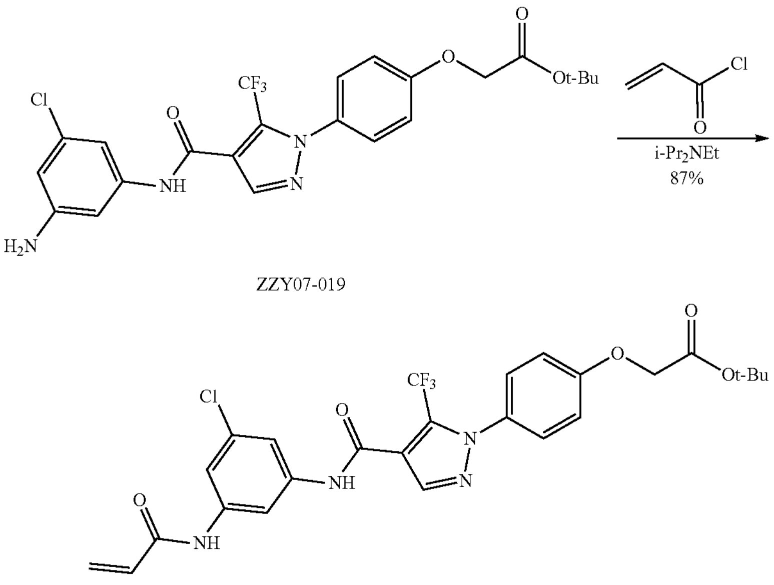

ZZY07-019

ZZY07-022

A solution of tert-butyl 2-[4-[4-[(3-amino-5-chloro-phenyl)carbamoyl]-5-(trifluoromethyl)pyrazol-1-yl]phenoxy] acetate (30 mg, 0.060 mmol) in dichloromethane (0.39 mL) was cooled to 0° C. Triethylamine (16.37 μL, 0.12 mmol) and Acryloyl chloride (5.7 μL, 0.071 mmol) were added sequentially via syringe. The resulting solution was stirred at 0° C. for 30 min, at which point TLC analysis (50% ethyl acetate-hexanes) indicated full conversion of the starting material to a slightly less polar spot. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-80% ethyl acetate-hexanes, 4-g RediSep® Rf column, Teledyne ISCO, Lincoln, NE) to afford the product as a yellow powder (29 mg, 87%). $^1$H NMR (400 MHz, Chloroform-d) δ 8.81 (s, 1H), 8.33 (s, 1H), 7.94 (s, 1H), 7.82-7.75 (m, 1H), 7.38 (dt, J=11.3, 1.8 Hz, 2H), 7.27 (d, J=7.1 Hz, 1H), 7.00-6.88 (m, 2H), 6.32 (dd, J=16.9, 1.4 Hz, 1H), 6.18 (dd, J=16.9, 10.2 Hz, 1H), 5.68 (dd, J=10.1, 1.4 Hz, 1H), 4.55 (s, 2H), 1.48 (s, 9H). HRMS (ESI): Calcd for $(C_{26}H_{24}ClF_3N_4O_5+H)^+$: 565.1466. Found: 565.1466.

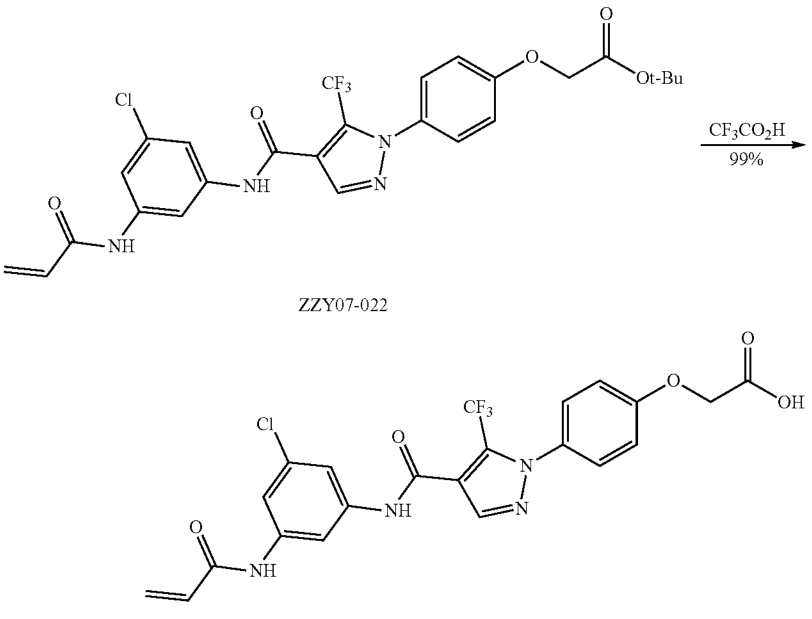

ZZY07-022

ZZY07-023 tert-Butyl 2-[4-[4-[[3-chloro-5-(prop-2-enoylamino)phenyl]carbamoyl]-5-(trifluoromethyl)pyrazol-1-yl]phenoxy] acetate (29 mg, 0.050 mmol) was dissolved in 1:1 dichloromethane (0.200 mL): trifluroacetic Acid (0.2000 mL) and the resulting solution was allowed to stand at 23° C. for 1 h. The solution was then concentrated to afford the product as a white solid (26 mg, 990%). HRMS (ESI): Calcd for $(C_{22}H_{16}ClF_3N_4O_5+H)$: 509.0840. Found: 509.0847.

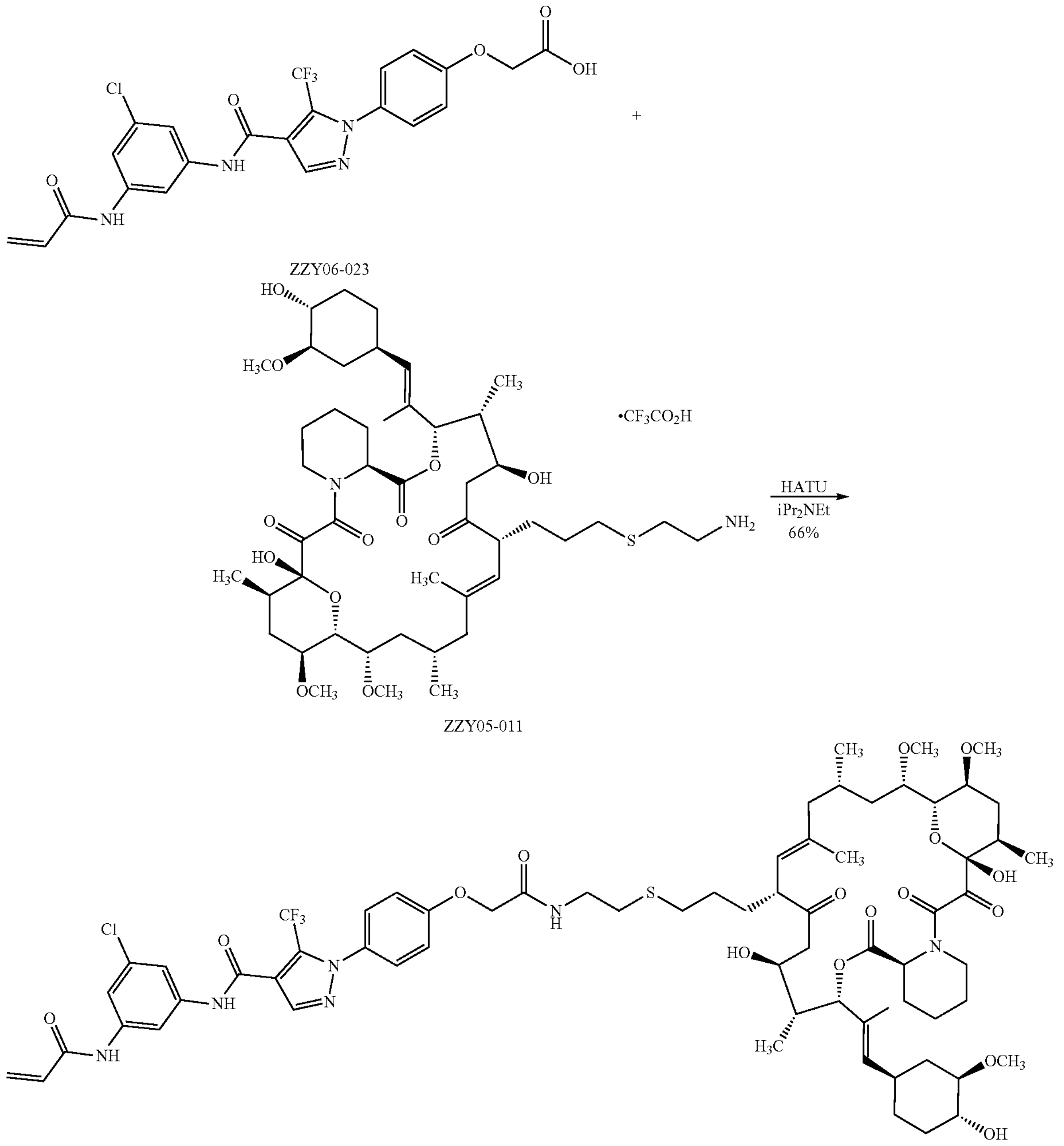

ZZY06-023

ZZY05-011

ZZY07-026

An oven-dried 1-dram vial was charged with ZZY06-023 (7.7 mg, 0.015 mmol), ZZY05-011 (15 mg, 0.015 mmol), DMF (0.11 mL), and a magnetic stir bar. N,N-Diisopropylethylamine (7.9 μL, 0.045 mmol) and HATU (6.9 mg, 0.018 mmol) were added sequentially, and the resulting solution was stirred at 23° C. Within 30 min, LC-MS analysis showed that the starting material (FK506-amine) was fully consumed. The residue was diluted with 1:1:1 methanol-acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (13.7 mg, 66%). $^1$H NMR (400 MHz, Chloroform-d) δ 8.37 (s, 1H), 8.07-7.99 (m, 1H), 7.65 (s, 1H), 7.59 (s, 1H), 7.45 (d, J=8.8 Hz, 2H), 7.09 (d, J=8.9 Hz, 2H), 6.47 (dd, J=16.8, 1.3 Hz, 1H), 6.28 (dd, J=16.8, 10.3 Hz, 1H), 5.81 (d, J=9.9 Hz, 1H), 5.32 (s, 1H), 5.11-4.97

(m, 2H), 4.66-4.62 (m, 3H), 4.43 (d, J=13.3 Hz, 1H), 4.22 (s, 1H), 3.95-3.85 (m, 2H), 3.68 (d, J=9.4 Hz, 1H), 3.64-3.51 (m, 4H), 3.42 (s, 3H), 3.41 (s, 3H), 3.41-3.37 (m, 3H), 3.32 (s, 3H), 3.08-2.98 (m, 2H), 2.70 (app t, J=6.4 Hz, 4H), 2.43 (d, J=7.0 Hz, 1H), 2.38-2.24 (m, 2H), 2.24-2.13 (m, 3H), 2.12-1.86 (m, 5H), 1.85-1.68 (m, 6H), 1.66-1.54 (m, 6H), 1.53-1.25 (m, 8H), 1.10-1.03 (m, 2H), 1.00 (d, J=6.3 Hz, 3H), 0.96 (d, J=6.2 Hz, 3H), 0.88 (d, J=7.1 Hz, 3H). HRMS (ESI): Calcd for $(C_{68}H_{90}ClF_3N_6O_{16}S-H)^-$: 1369.5697. Found: 1369.5664.

propylethylamine (8.4 μL, 0.048 mmol) and HATU (4.4 mg, 0.012 mmol) were added sequentially to the solution, and the mixture was stirred at 23° C. while the reaction progress was monitored by LC-MS. In 1 h, LC-MS analysis showed full consumption of the FK506 starting material. The residue was diluted with 50% acetonitrile-water to a volume of 4.4 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40

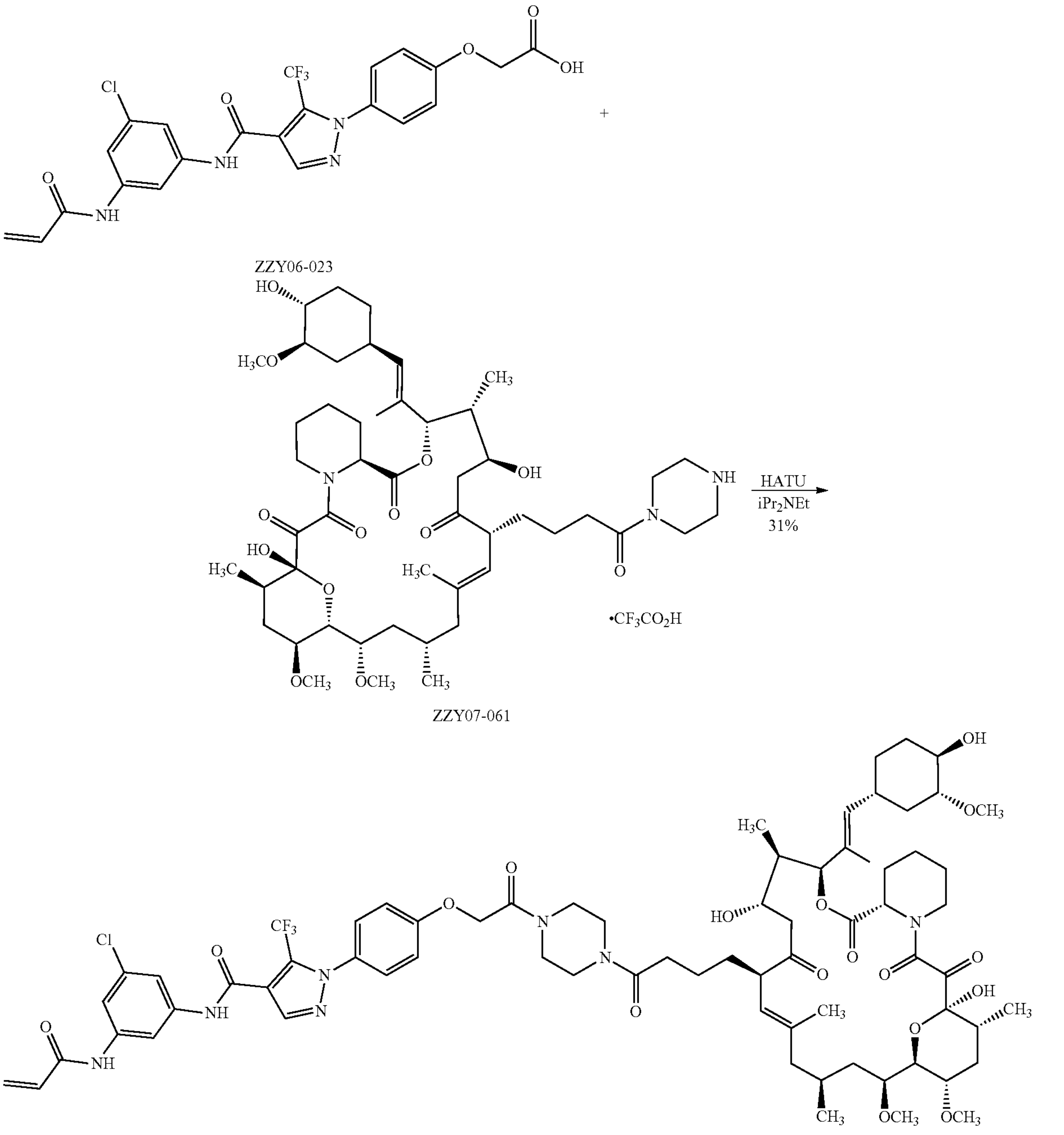

ZZY08-057

An oven-dried 1-dram vial was charged with ZZY06-023 (5.4 mg, 0.011 mmol) and ZZY07-061 (10 mg, 0.010 mmol), DMF (0.20 mL) and magnetic stir bar. N,N-Diisomin, 20 mL/min) to afford the product as a yellow solid (4.3 mg, 31%). $^1$H NMR (400 MHz, Chloroform-d) δ 7.99 (s, 1H), 7.94-7.80 (m, 1H), 7.61-7.47 (m, 2H), 7.43-7.34 (m, 2H), 7.12-7.04 (m, 2H), 6.45 (d, J=16.9 Hz, 1H), 6.29-6.18 (m, 1H), 5.81 (d, J=10.4 Hz, 1H), 5.35 (s, 1H), 5.15-4.94 (m, 2H), 4.84-4.77 (m, 3H), 4.45-4.31 (m, 1H), 3.99-3.77 (m, 2H), 3.72-3.53 (m, 10H), 3.41 (s, 3H), 3.37 (s, 3H), 3.35-3.31 (m, 3H), 3.30 (s, 3H), 3.05-2.97 (m, 2H), 2.84-2.63 (m, 1H), 2.42-2.20 (m, 5H), 2.01 (d, 5H), 1.67 (s, 6H), 1.61-1.52 (m, 6H), 1.51-1.26 (m, 8H), 1.10-1.01 (m, 2H), 1.00 (d, J=6.3 Hz, 3H), 0.93 (d, J=6.8 Hz, 3H), 0.85 (d, J=7.1 Hz, 3H). HRMS (ESI): Calcd for $(C_{71}H_{93}ClF_3N_7O_{17}+H)^+$: 1408.6347. Found: 1408.6415.

Cyclosporin Derivatives.

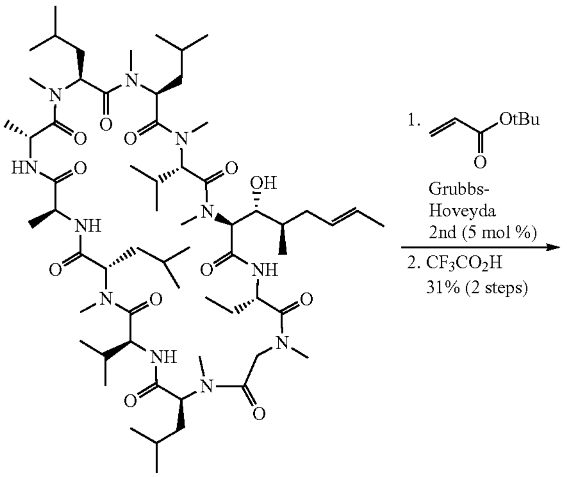

CsA

-continued

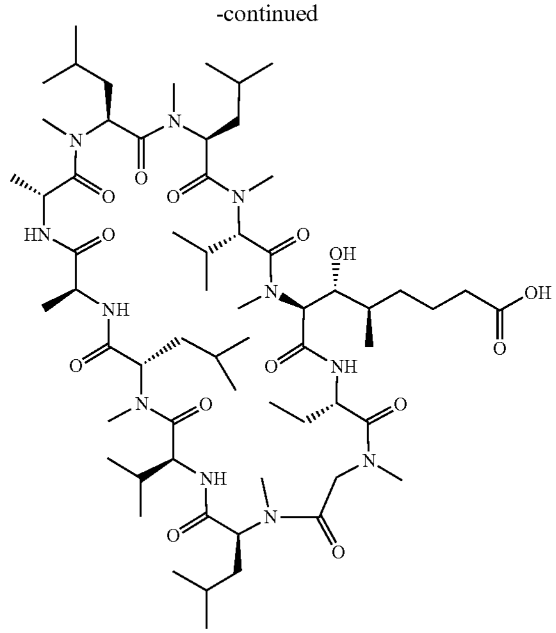

ZZY06-067

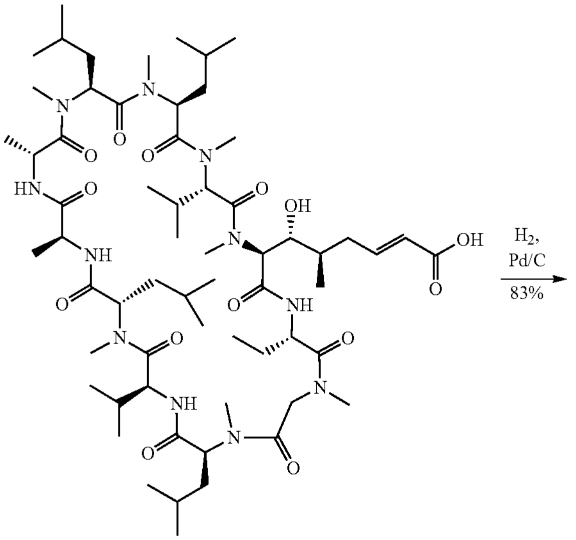

ZZY06-058

A flame-dried 10-mL microwave vial was flushed with dry argon, and then was charged with cyclosporin A (100 mg, 0.083 mmol), 1,2-dichloroethane (1.24 mL), and a magnetic stir bar. tert-Butyl acrylate (0.24 mL, 1.66 mmol) and Grubbs-Hoveyda Catalyst 2nd Gen (3.5 mg, 0.042 mmol) were added sequentially. The vial was flushed with argon again and sealed with a rubber cap. The reaction mixture was heated at 70° C. for 1 h in a CEM Discover SP microwave reactor with constant stirring. After cooling to 23° C., LC-MS analysis showed ~50% conversion to the desired product mass. The vial was returned to the microwave reactor and heated for an additional 3 h at 70° C. The reaction mixture was cooled to 23° C. and directly loaded onto a silica gel cartridge (~4 g). Purification by column chromatography (0-20% methanol-dichloromethane, 4-g RediSep Rf Column, Teledyne ISCO, Lincoln, NE) afforded the product as a brown solid. The purity of this material was ~80% by $^1$H NMR analysis.

Trifluoroacetic acid (0.5 mL) was added to a solution of the product from the cross-metathesis reaction in dichloromethane (0.5 mL). In 1 h, LC-MS analysis showed full consumption of the tert-butyl ester starting material (m/z=1288). The reaction mixture was concentrated under vacuum. The residue was diluted with 50% acetonitrile-water to a volume of 4.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (31 mg, 31% over 2 steps).

A 100-mL round bottom flask was charged with ZZY06-058 (412 mg, 0.33 mmol), 1:1 Ethyl acetate (6.6 mL): methanol (6.6 mL) and a magnetic stir bar. Argon was bubbled through the solution for 5 min, then Palladium on carbon (10 wt %, 71 mg, 0.033 mmol) was added. The vessel was fitted with a rubber septum and a hydrogen balloon was attached via a 19-gauge needle. An additional needle was attached to allow a gentle flow of hydrogen to bubble through the solution at a continuous rate. At 3 h, LC-MS could no longer detect any starting material. The hydrogen balloon was switched to one filled with argon, and bubbling was continued for 5 min. The reaction mixture was then filtered through a tightly packed plug of Celite (~2 g). Concentration of the filtrate afforded a colorless glass. The material was purified by reverse-phase HPLC in multiple batches with the following procedure. The residue was divided into batches and dissolved in 50% methanol-water (100 mg in 5 mL, 150 mg in 8 mL, then 150 mg in 8 mL), and the solutions were filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) in batches, and the product-containing fractions were pooled to afford the product as a white solid (343 mg, 83%). $^1$H NMR (400 MHz, Chloroform-d) δ 7.99 (d, J=9.2 Hz, 1H), 7.63 (d, J=7.5 Hz, 1H), 5.68 (dd, J=11.0, 4.1 Hz, 1H), 5.39 (d, J=7.3 Hz, 1H), 5.31-5.23 (m, 1H), 5.17-5.05 (m, 3H), 5.00 (q, J=7.5 Hz, 1H), 4.88-4.81 (m, 1H), 4.72 (d, J=14.3 Hz, 1H), 4.63 (t, J=8.8 Hz, 1H), 4.51 (dt, J=14.6, 7.5 Hz, 1H), 3.87 (t, J=6.3 Hz, 1H), 3.42 (s, 3H), 3.40-3.35 (m, 4H), 3.30 (d, J=11.8 Hz, 1H), 3.23 (s, 3H), 3.19 (s, 3H), 3.18 (d, J=17.2 Hz, 1H), 3.09 (s, 3H), 2.87 (d, J=17.6 Hz, 1H), 2.78-2.68 (m, 1H), 2.69 (s, 3H), 2.67 (s, 3H), 2.48-2.30 (m, 2H), 2.23 (t, J=6.9 Hz, 2H), 2.22-1.87 (m, 5H), 1.80-1.37 (m, 13H), 1.34 (d, J=7.3 Hz, 3H), 1.26 (d, J=6.9 Hz, 3H), 1.24-1.12 (m, 3H), 1.07-0.79 (m, 39H, 13 methyl doublets). HRMS (ESI): Calcd for $(C_{62}H_{111}N_{11}O_{14}-H)^+$: 1232.8234. Found: 1232.8215

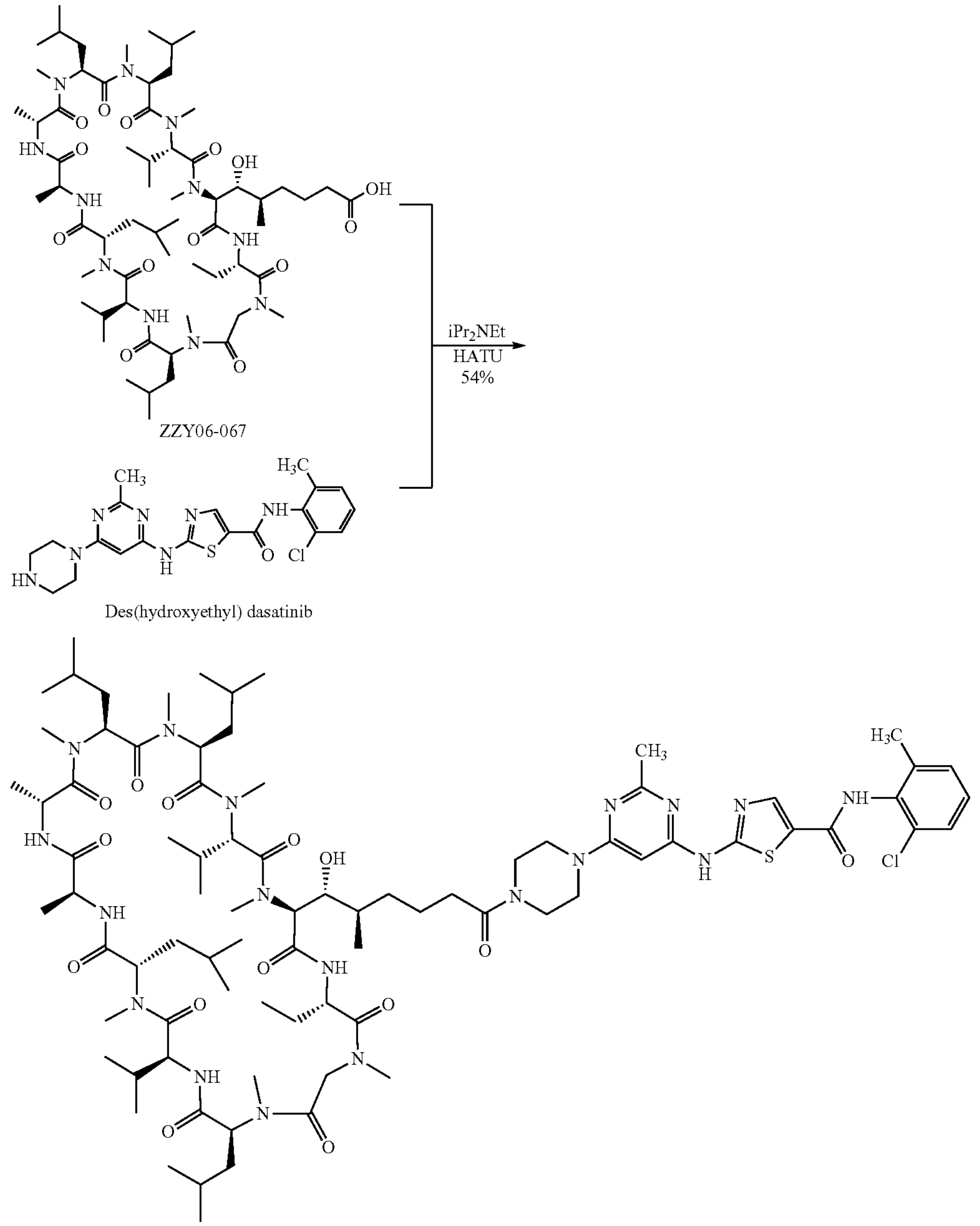

ZZY06-067

Des(hydroxyethyl) dasatinib

ZZY06-082

A 1-dram vial was charged with Cyclosporin C4 Acid (20 mg, 0.016 mmol), des(hydroxyethyl)dasatinib (7.9 mg, 0.018 mmol), DMF (0.20 mL), N,N-Diisopropylethylamine (8.5 μL, 0.049 mmol) and a magnetic stir bar. The solution was cooled to 0° C., then HATU (7.4 mg, 0.019 mmol) was added as a solid. The resulting mixture was stirred at 0° C. In 30 min, LC-MS analysis indicated that the starting material had been fully consumed. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (14.5 mg, 54%). $^1$H NMR spectrum of this compound contains at least three conformational isomers and cannot be resolved. HRMS (ESI): Calcd for $(C_{82}H_{131}ClN_{18}O_{14}S+2H)^{2+}$: 830.4789. Found: 830.4791.

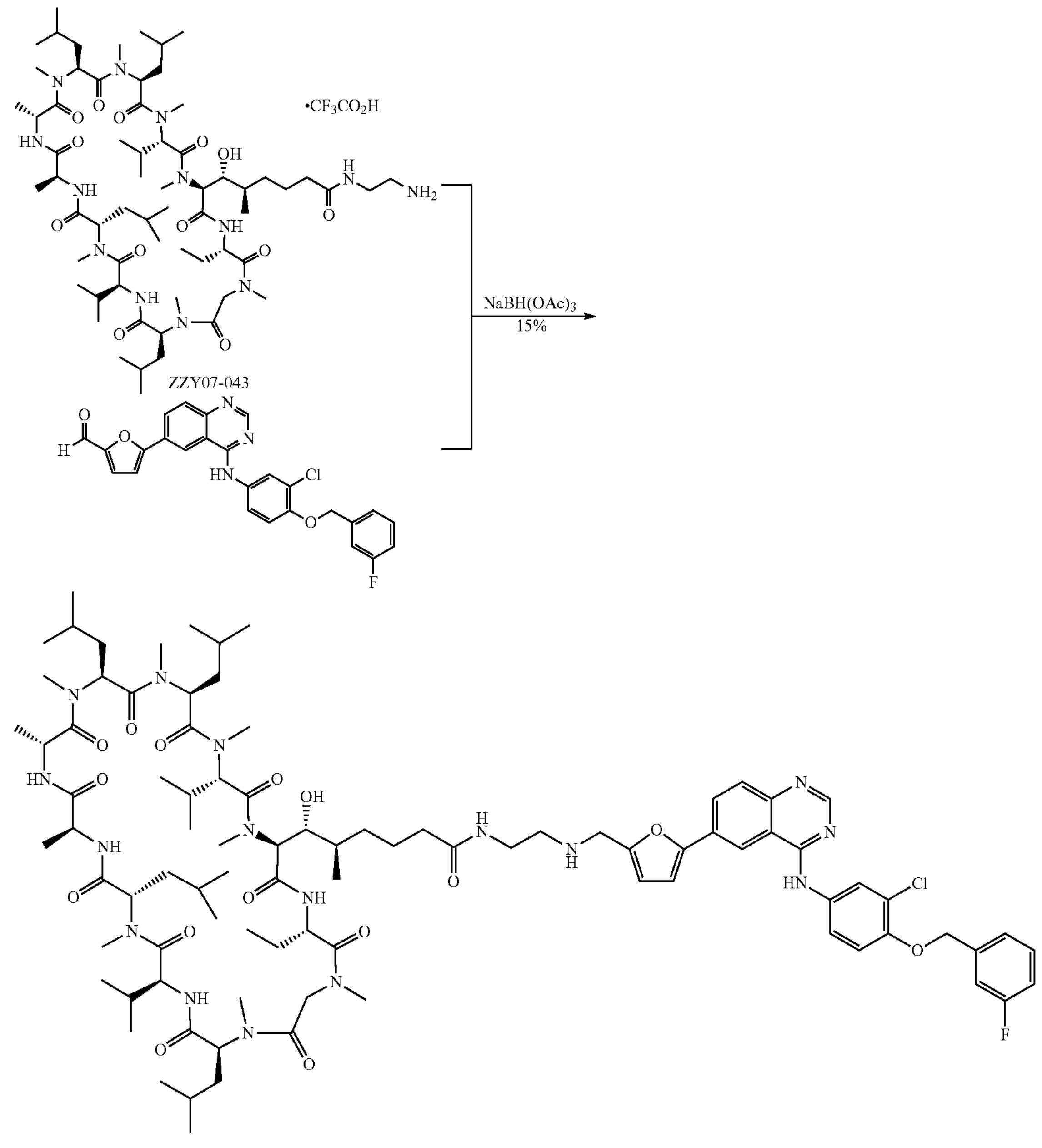

ZZY07-058

An oven-dried 1-dram vial was charged with ZZY07-043 (15 mg, 0.011 mmol), Lapatinib aldehyde (5.0 mg, 0.011 mmol), dichloromethane (0.11 mL) and a magnetic stir bar. Sodium triacetoxyborohydride (4.5 mg, 0.021 mmol) was added as a solid. In about 5 min, all the solids had gone into solution. The reaction mixture was kept stirred for a total of 2 h, at which point LC-MS still showed presence of both starting materials. Additional sodium triacetoxyborohydride (4.5 mg, 0.021 mmol) was added. In a total of 6 h, LC-MS showed full consumption of the amine starting material. The reaction solution was concentrated to dryness until vacuum. The residue was diluted with 50% acetonitrile-water to a volume of 3.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (2.7 mg, 15%). $^{1}$H NMR spectrum of this compound contains at least three conformational isomers and cannot be resolved. HRMS (ESI): Calcd for $(C_{90}H_{134}ClFN_{16}O_{15}+2H)^{2+}$: 867.5021. Found: 867.5022.

0° C., then HATU (7.4 mg, 0.019 mmol) was added as a solid. The resulting mixture was stirred at 0° C. and the reaction progress was monitored by LC-MS. In 30 min, LC-MS analysis indicated that the starting material had been fully consumed. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (16.2 mg, 58%). $^{1}$H NMR

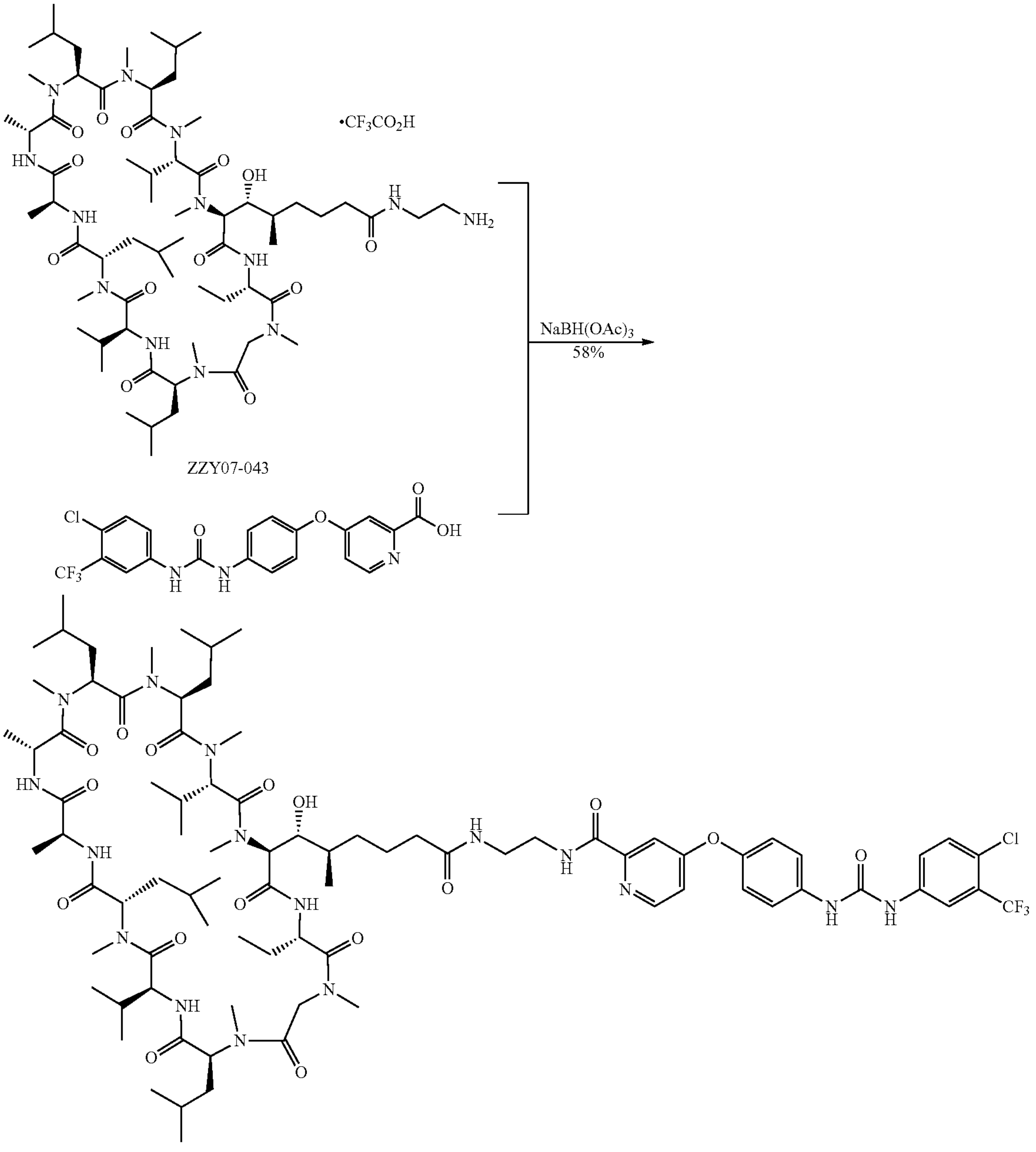

ZZY07-043

ZZY06-083

A 1-dram vial was charged with ZZY07-043 (20 mg, 0.016 mmol), sorafenib acid (11 mg, 0.018 mmol), DMF (0.20 mL), N,N-Diisopropylethylamine (8.5 μL, 0.048 mmol) and a magnetic stir bar. The solution was cooled to spectrum of this compound contains at least three conformational isomers and cannot be resolved. HRMS (ESI): Calcd for $(C_{84}H_{128}ClF_3N_{16}O_{16}+2H)^{+}$: 855.4746. Found: 855.4745.

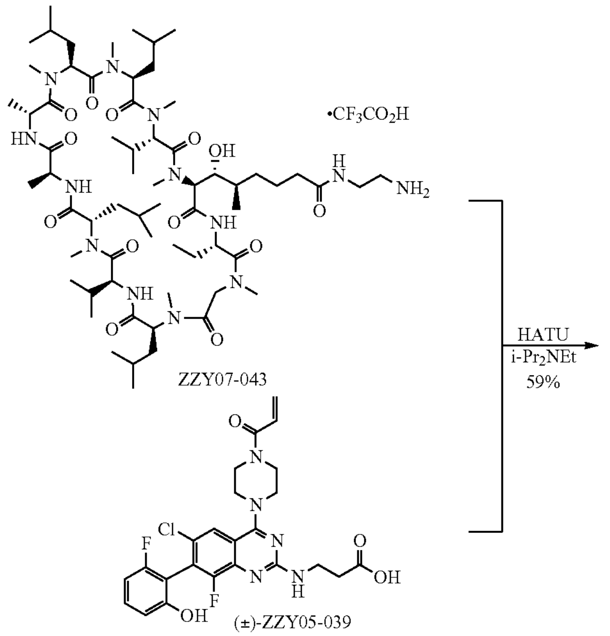

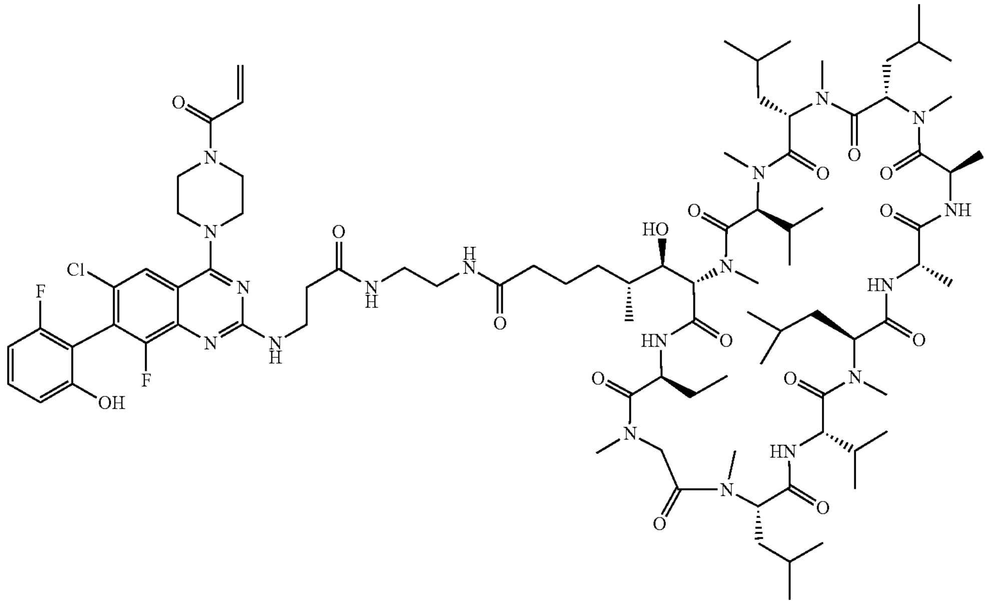

ZZY07-014

An oven dried one-dram vial was charged with ZZY07-043 (10 mg, 0.076 mmol), ZZY05-039 (4.3 mg, 0.083 mmol), DMF (0.10 mL), and a magnetic stir bar. N,N-Diisopropylethylamine (4.0 μL, 0.023 mmol) and HATU (4.3 mg, 0.011 mmol) were added sequentially to the reaction mixture at 23° C. In 40 min, LC-MS analysis showed 100% conversion. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white powder (7.9 mg, 58%). HRMS (ESI): Calcd for $(C_{88}H_{137}ClF_2N_{18}O_{16}+2H)^+$: 888.5136. Found: 888.5137.

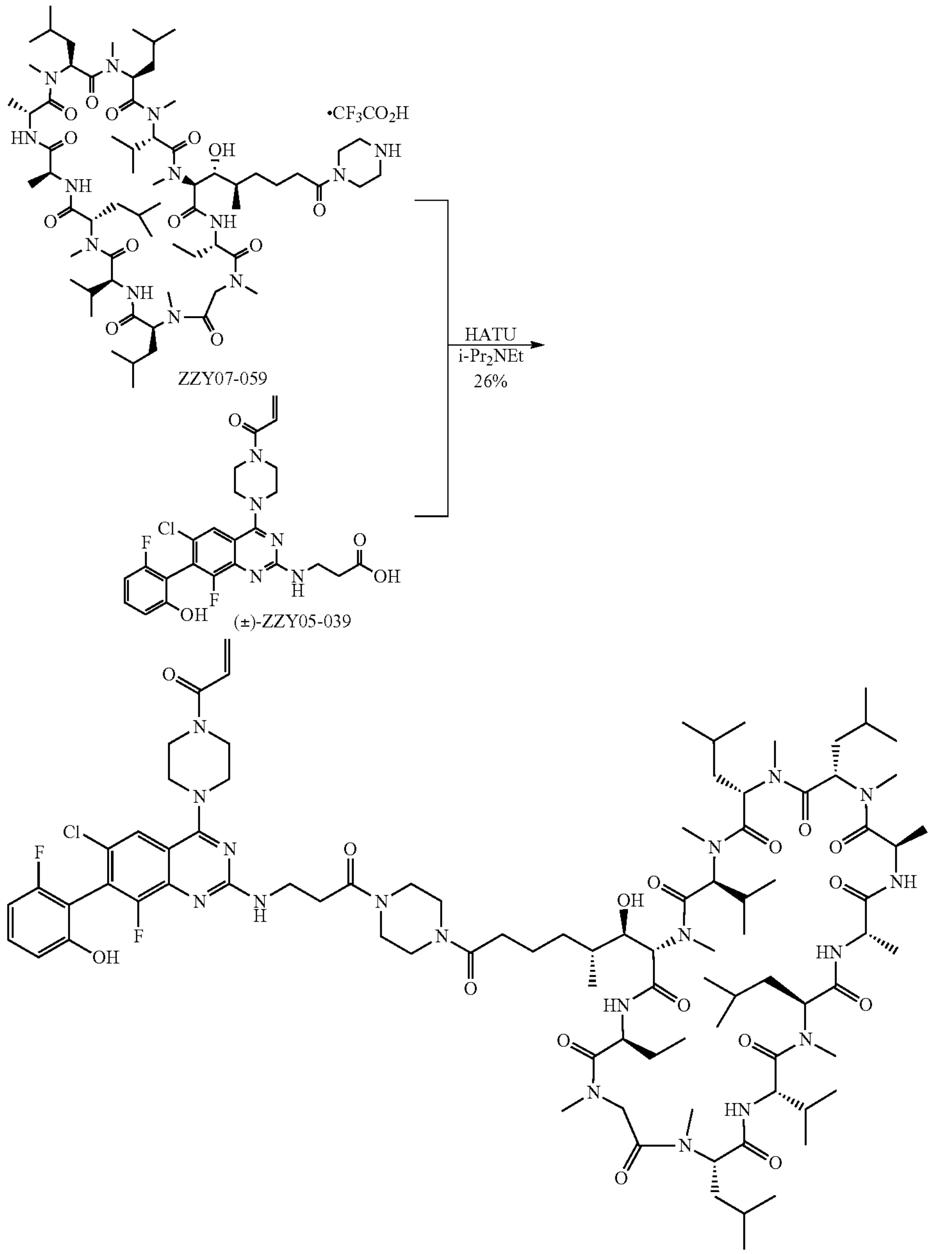

ZZY07-059

(±)-ZZY05-039

ZZY07-089

An oven dried one-dram vial was charged with ZZY07-059 (10 mg, 0.071 mmol), ZZY05-039 (4.0 mg, 0.078 mmol), DMF (0.10 mL), and a magnetic stir bar. N,N-Diisopropylethylamine (3.7 μL, 0.023 mmol) and HATU (3.0 mg, 0.011 mmol) were added sequentially to the reaction mixture at 23° C. In 1 h, LC-MS analysis showed full consumption of the starting material. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white powder (3.3 mg, 26%). HRMS (ESI): Calcd for $(C_{90}H_{139}ClF_2N_{18}O_{16}+2H)^+$: 901.5214. Found: 901.5244.

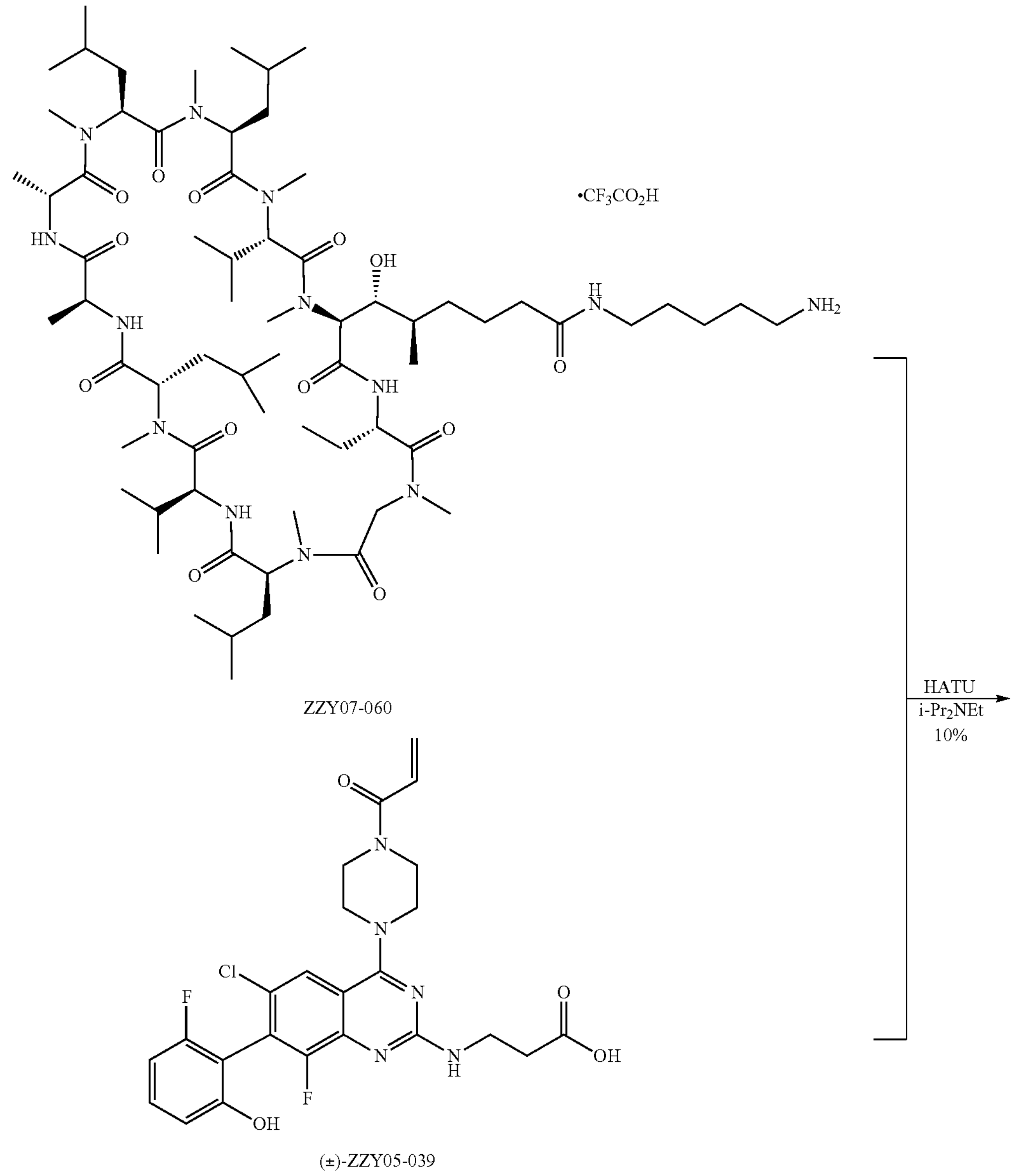
•CF3CO2H
ZZY07-060
(±)-ZZY05-039
HATU
i-Pr2NEt
10%

-continued

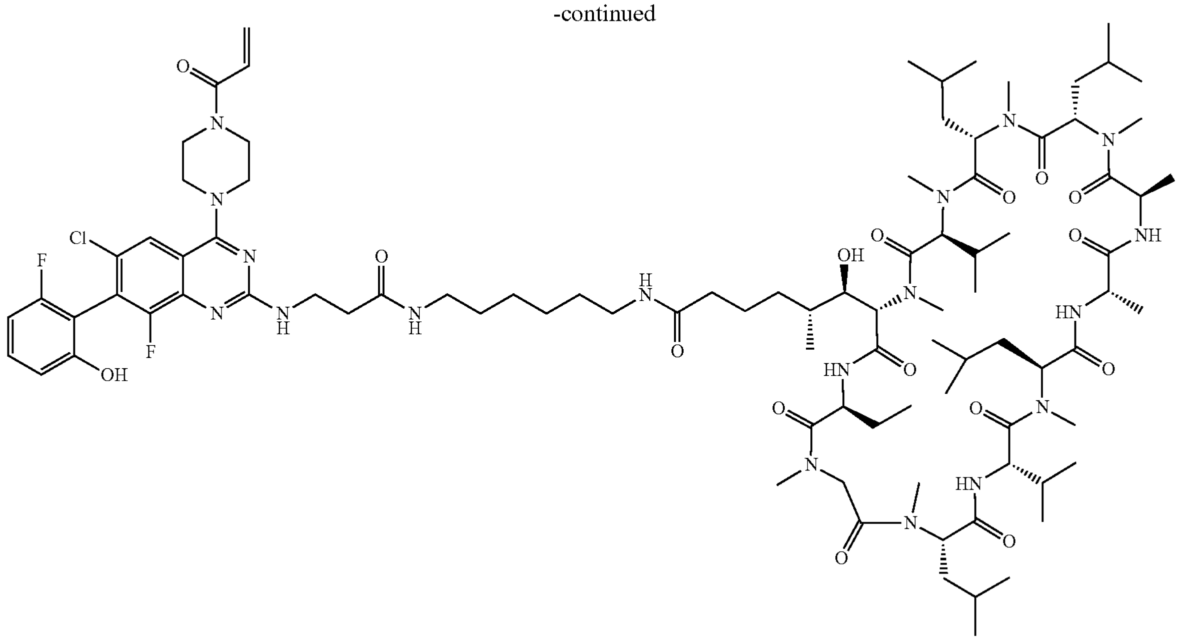

ZZY07-090

An oven dried one-dram vial was charged with ZZY07-060 (10 mg, 0.071 mmol), ZZY05-039 (4.0 mg, 0.078 mmol), DMF (0.10 mL), and a magnetic stir bar. N,N-Diisopropylethylamine (3.7 μL, 0.023 mmol) and HATU (3.0 mg, 0.011 mmol) were added sequentially to the reaction mixture at 23° C. In 1 h, LC-MS analysis showed full consumption of the starting material. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white powder (1.3 mg, 10%). HRMS (ESI): Calcd for $(C_{92}H_{145}ClF_2N_{18}O_{16}+2H)^+$: 916.5450. Found: 916.5455.

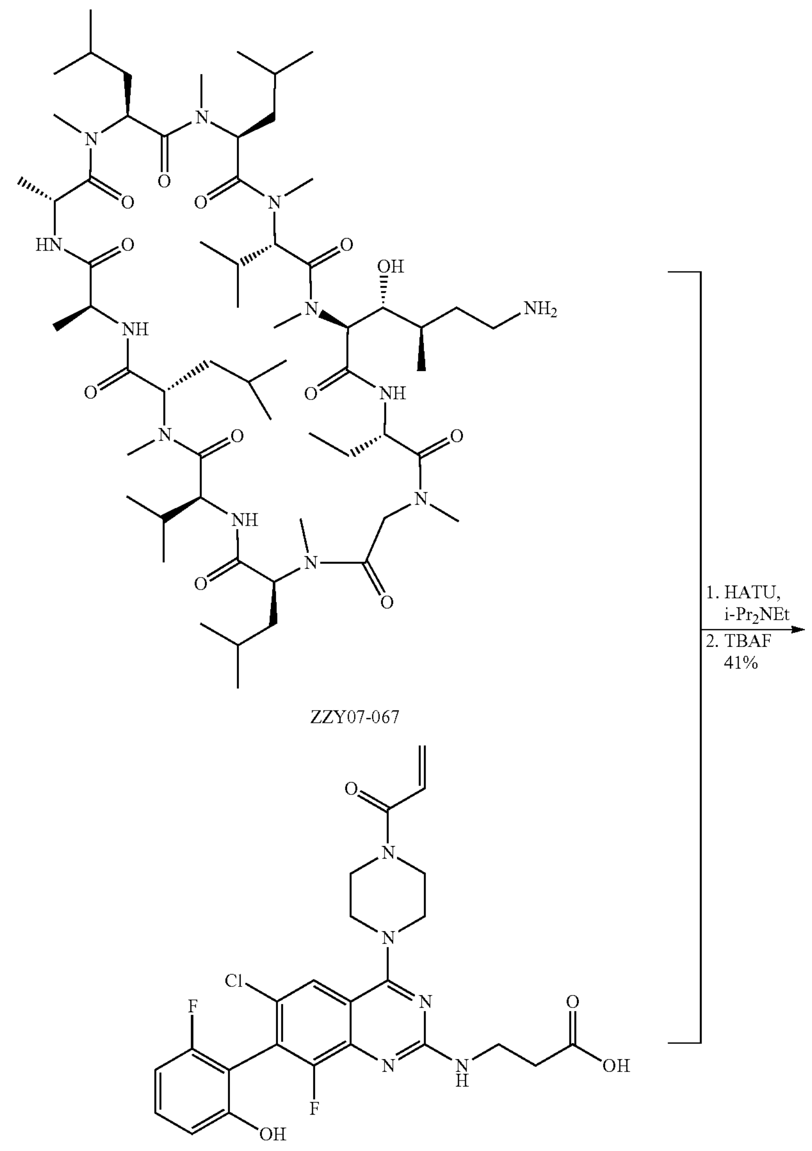
ZZY07-067
(±)-ZZY05-039

-continued

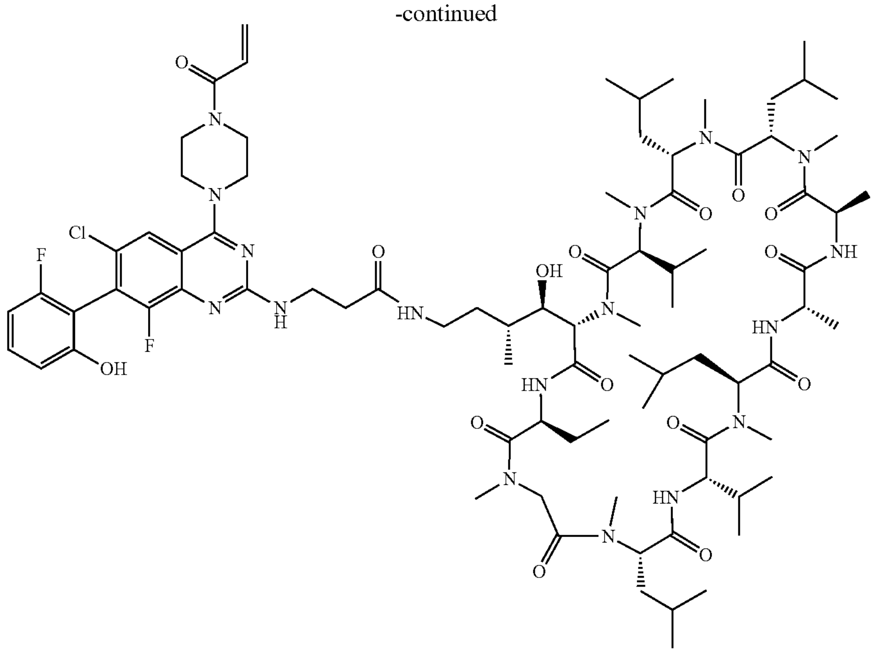

ZZY07-079

A 1-dram vial was charged with ZZY07-067 (7.0 mg, 0.0054 mmol), ZZY05-039 (3.3 mg, 0.0064 mmol) and a magnetic stir bar. DMF (0.10 mL) and N,N-Diisopropylethylamine (4.7 μL, 0.027 mmol) were added sequentially via pipette. HATU (2.5 mg, 0.0064 mmol) was added as a freshly prepared 10% w/v DMF solution via pipette. The resulting solution was stirred at 23° C. and the reaction progress was monitored by LC-MS. In 12 h, LC-MS analysis showed full consumption of the amine starting material and formation of a new species. The reaction mixture was diluted with 0.1 mL THF, and a 1.0 M solution of tetra-n-butylammonium fluoride in THE (27 μL, 0.027 mmol) was added dropwise via syringe. In 2 h, LC-MS showed full deprotection of the TBS group. The residue was diluted with 50% acetonitrile-water to a volume of 3.9 mL, and the solution was filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) to afford the product as a white solid (3.7 mg, 41%). HRMS (ESI): Calcd for $(C_{84}H_{130}ClF_2N_{17}O_{15}—H)^-$: 1688.9511. Found: 1688.9529.

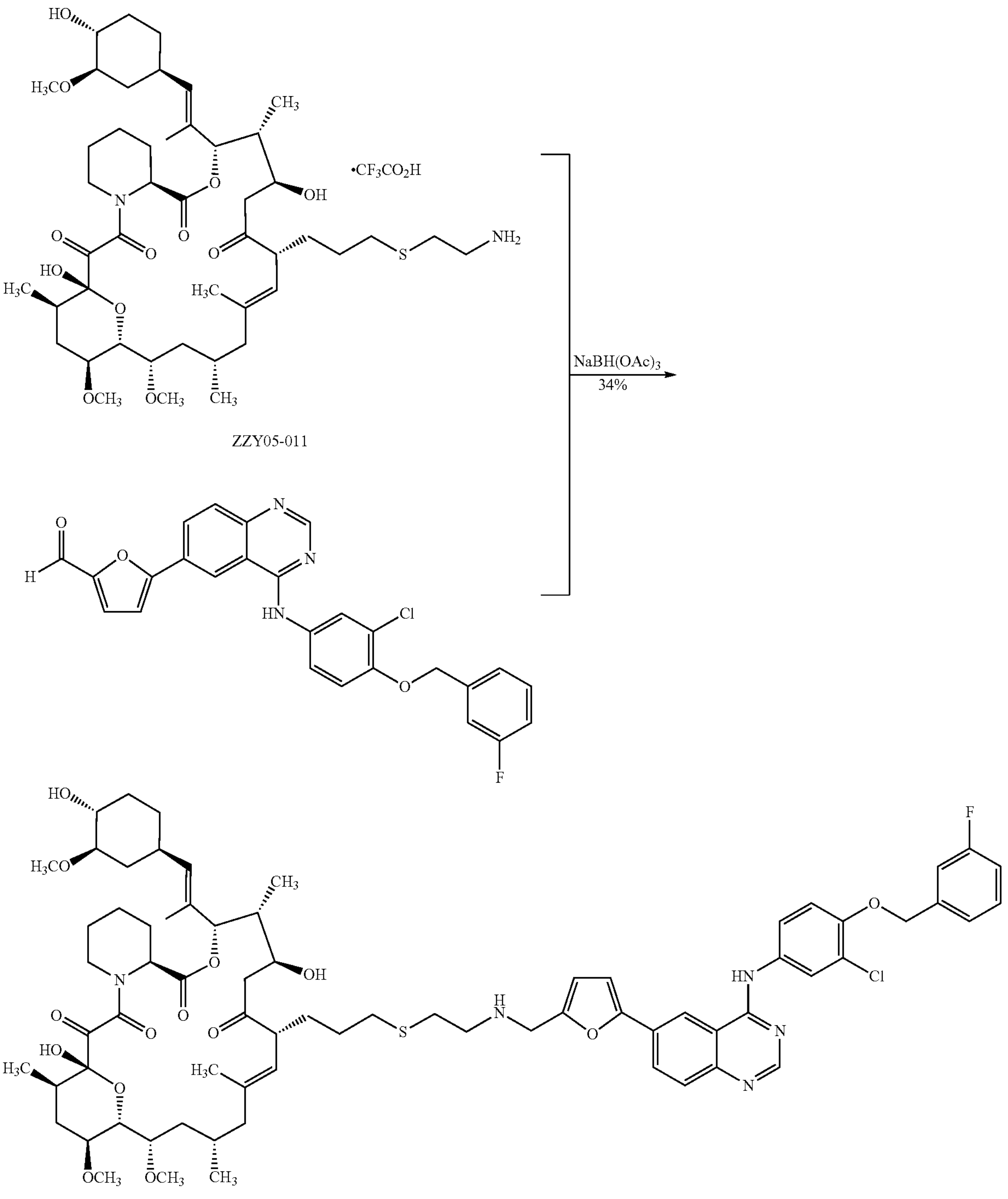

ZZY05-011

ZZY07-057

An oven-dried one-dram vial was charged with ZZY05-011 (10.5 mg, 0.0106 mmol), Lapatinib aldehyde (5.0 mg, 0.0106 mmol) and a magnetic stir bar. DCM (0.11 mL) was added via syringe. The resulting mixture was stirred at 23° C. for 10 min. The aldehyde reactant did not fully dissolve. Sodium triacetoxyborohydride (4.5 mg, 0.0211 mmol) was added as a solid. In about 5 min, all the solids had gone into solution. The reaction mixture was kept stirred for a total of 2 h, at which point no starting material amine could be detected. The reaction solution was concentrated to dryness under vacuum. The residue was diluted with 50% acetonitrile-water to a volume of 3.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (4.8 mg, 34%). HRMS (ESI): Calcd for $(C_{72}H_{93}ClFN_5O_{14}S+2H)^{2+}$: 669.8134. Found: 669.7951.

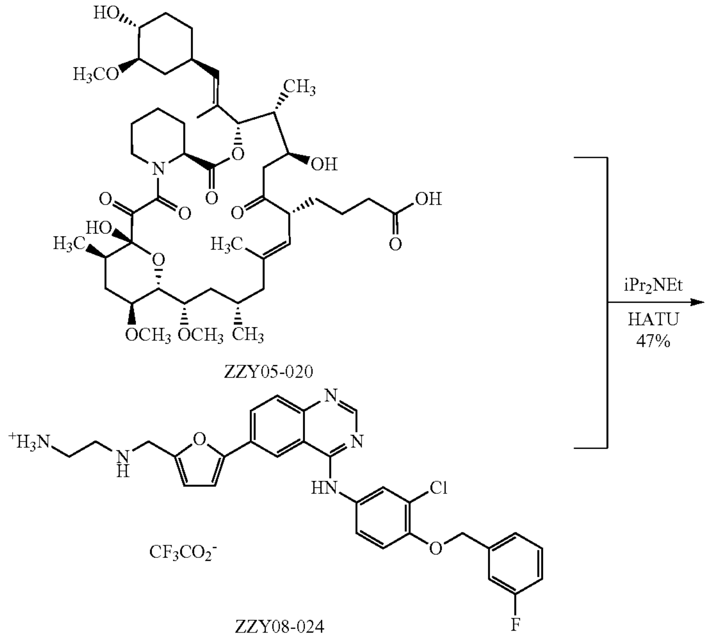

ZZY05-020

ZZY08-024

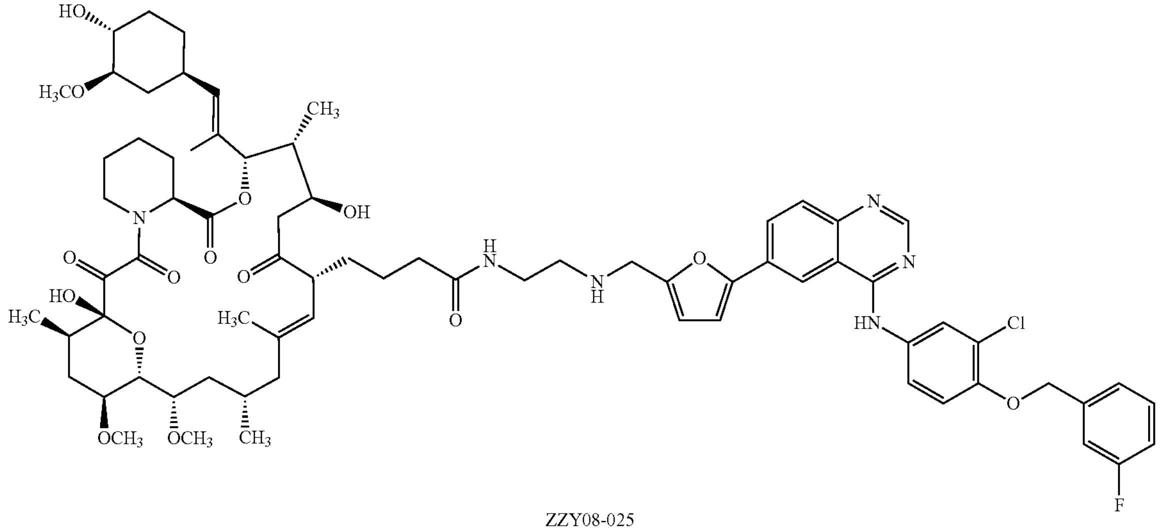

ZZY08-025

An oven-dried 1-dram vial was charged ZZY05-020 (20 mg, 0.024 mmol), ZZY08-024 (15 mg, 0.024 mmol), DMF (0.12 mL) and a magnetic stir bar. N,N-Diisopropylethylamine (12.3 μL, 0.071 mmol) was added and the mixture was stirred until all reactants had gone into solution. HATU (10.7 mg, 0.0282 mmol) was added as a 10% solution in DMF. The resulting solution was stirred at 23° C. and the reaction progress was monitored by LC-MS. In 15 min, LC-MS showed full consumption of the amine starting material. The reaction mixture was diluted with 50% acetonitrile-water to a volume of 4.2 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (15 mg, 47%). HRMS (ESI): Calcd for $(C_{73}H_{94}ClFN_6O_{15}+2H)^{2+}$: 675.3303. Found: 675.3334.

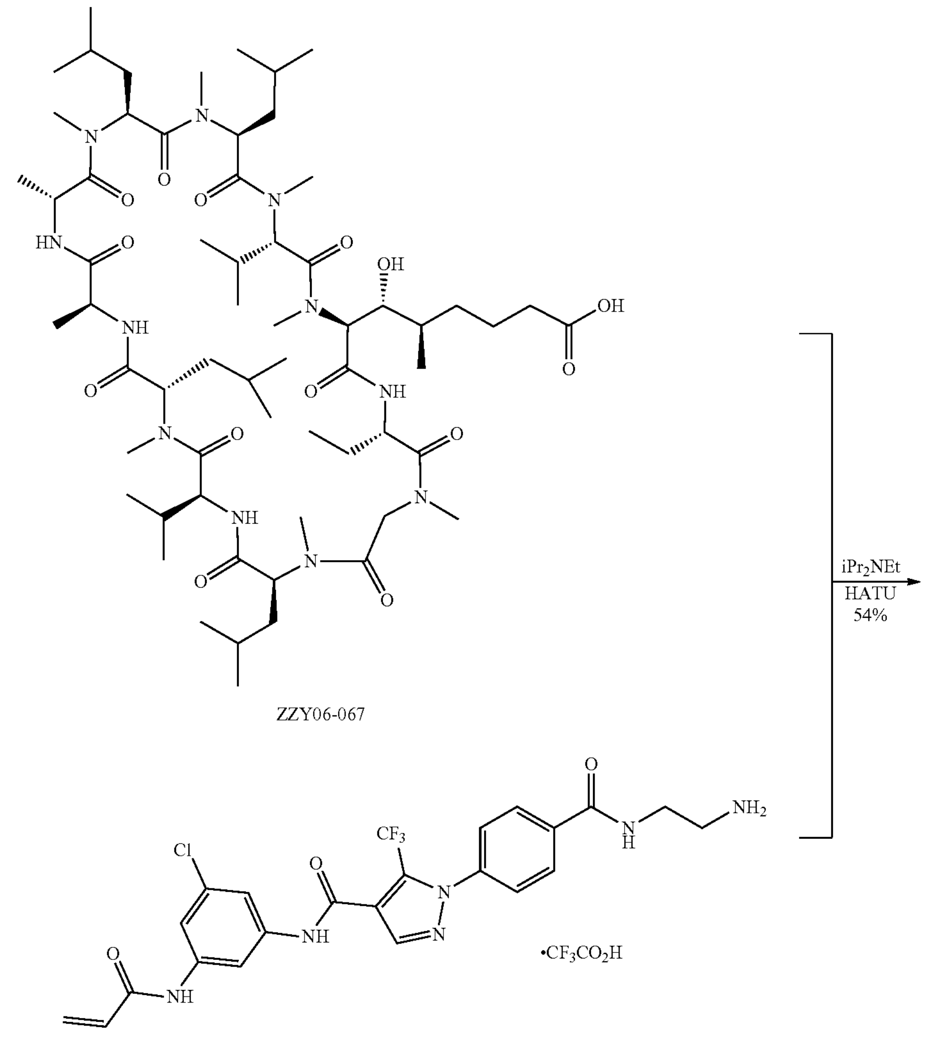
iPr2NEt
HATU
54%
ZZY06-067
ZZY06-025

-continued

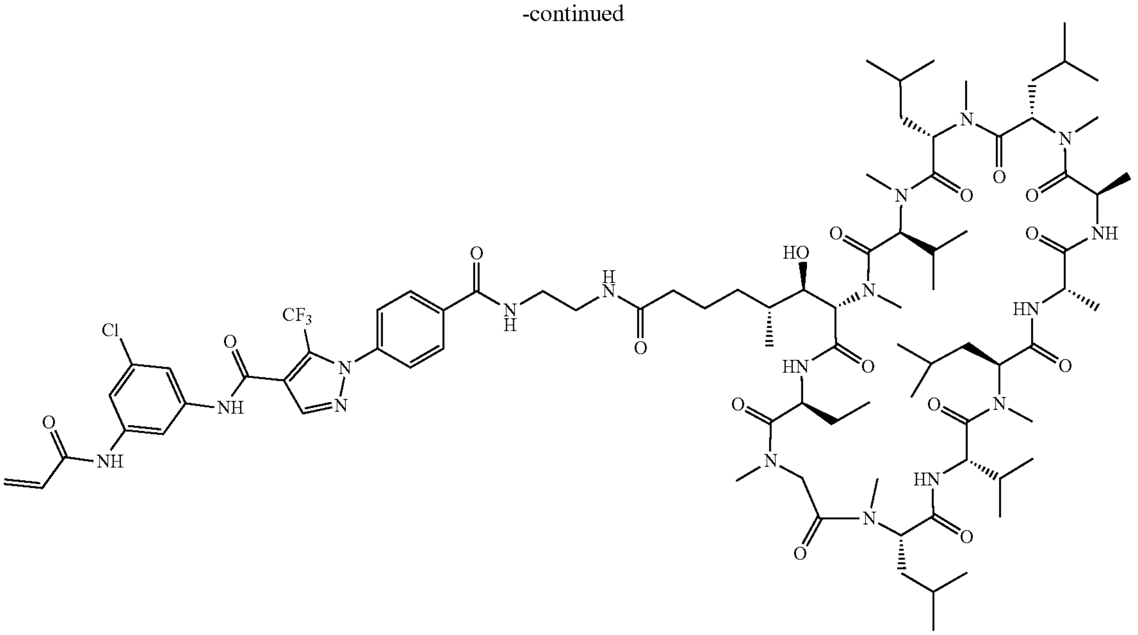

ZZY07-015

An oven-dried 1-dram vial was charged ZZY06-067 (19.5 mg, 0.016 mmol), ZZY06-025 (10 mg, 0.016 mmol), DMF (0.10 mL) and a magnetic stir bar. N,N-Diisopropylethylamine (8.2 μL, 0.047 mmol) and HATU (7.8 mg, 0.020 mmol) were added sequentially to the reaction mixture at 23° C. In 2 h, LC-MS showed full conversion of the starting material. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (13.6 mg, 54%). HRMS (ESI): Calcd for ($C_{85}H_{129}ClF_3N_{17}O_{16}$—H)$^-$: 1734.9366. Found: 1734.9539.

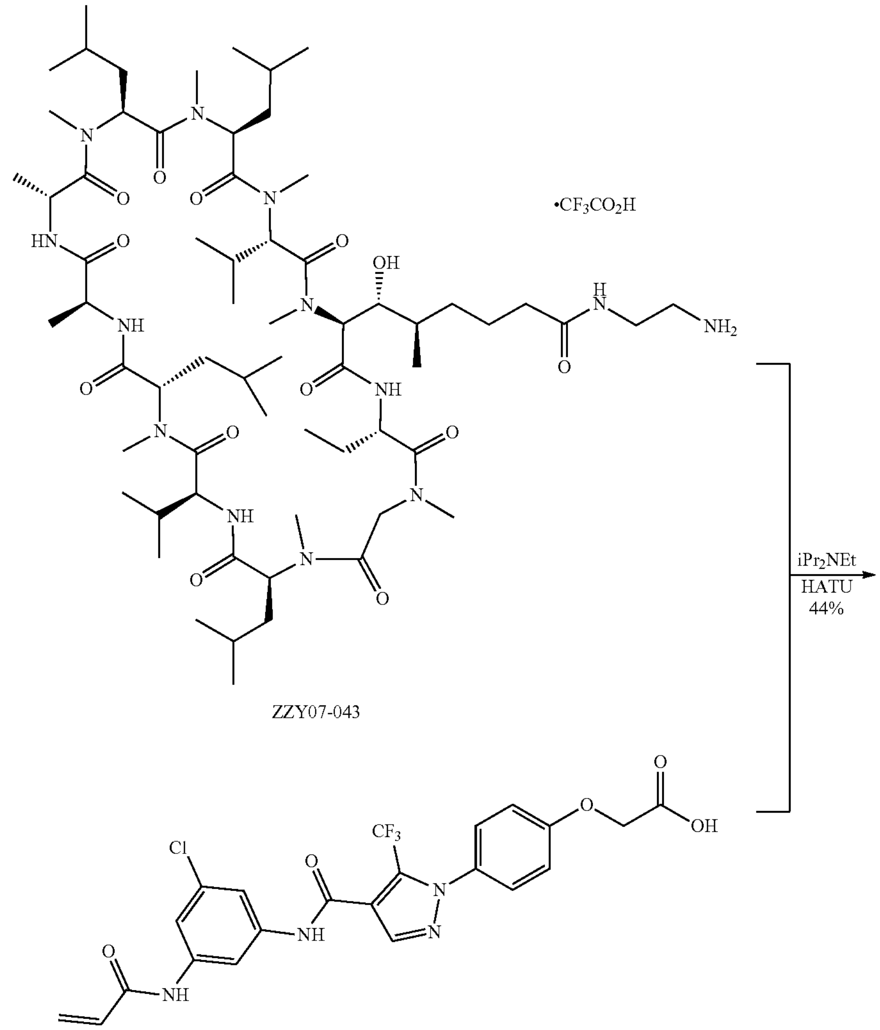
ZZY07-043
ZZY07-023

-continued

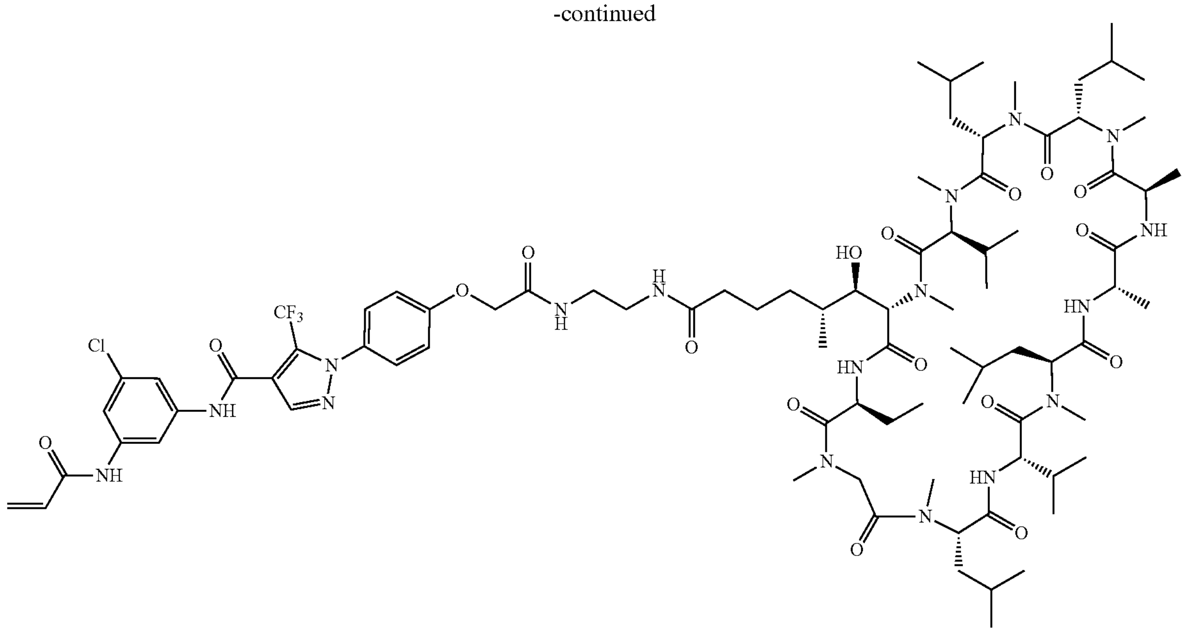

ZZY07-025

An oven-dried 1-dram vial was charged ZZY07-043 (15 mg, 0.011 mmol), ZZY07-023 (5.7 mg, 0.011 mmol), DMF (0.11 mL) and a magnetic stir bar. N,N-Diisopropylethylamine (5.9 μL, 0.034 mmol) and HATU (5.2 mg, 0.014 mmol) were added sequentially to the reaction mixture at 23° C. In 2 h, LC-MS showed full conversion of the starting material. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (8.9 mg, 44%). HRMS (ESI): Calcd for $(C_{86}H_{131}ClF_3N_{17}O_{17}—H)^-$: 1764.9471. Found: 1764.9409.

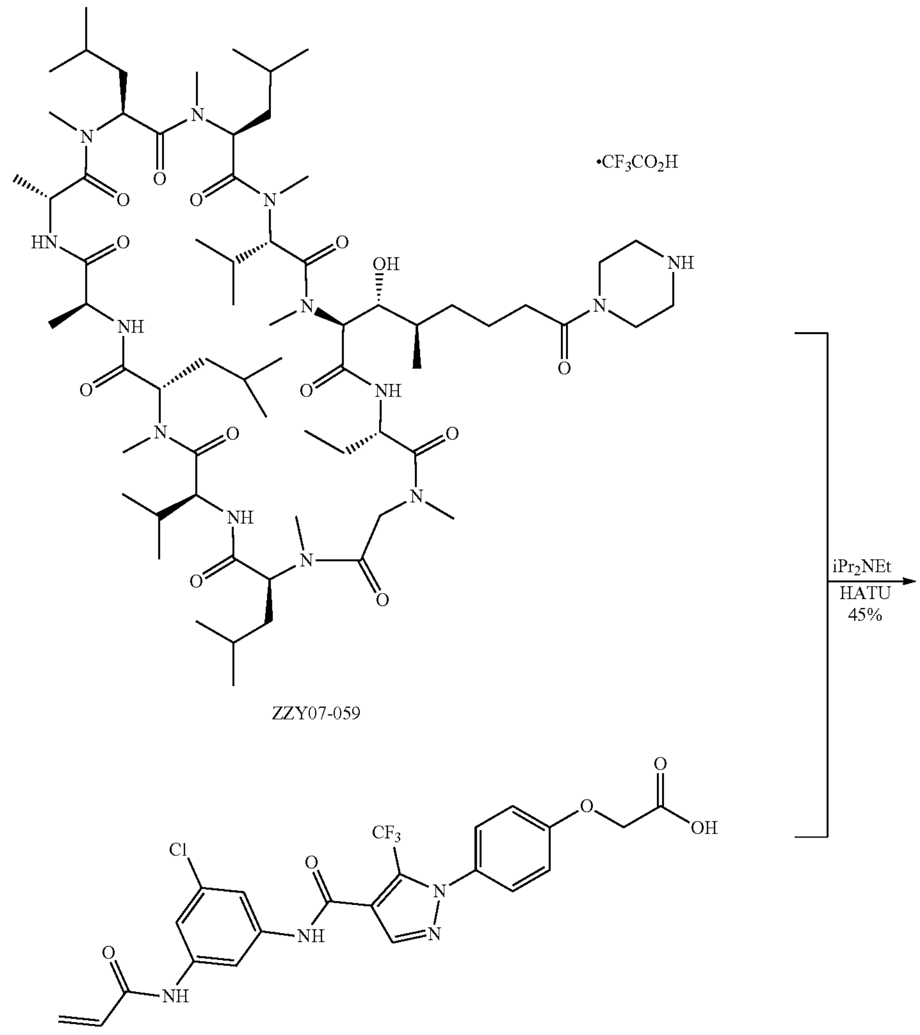
ZZY07-023

-continued

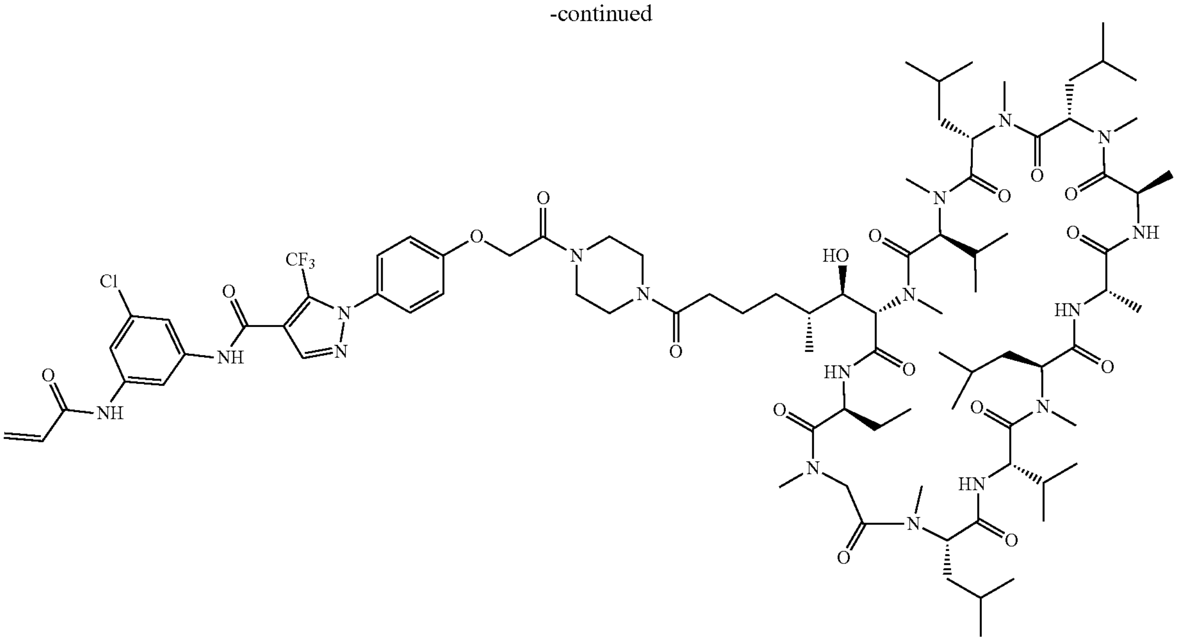

ZZY08-058

A mixture of ZZY07-059 (12 mg, 0.0085 mmol) and ZZY07-023 (4.7 mg, 0.0093 mmol) was dried by azeotropic evaporation of their suspension in benzene (1 mL). The residue was dissolved in DMF (0.20 mL). N,N-Diisopropylethylamine (8.4 μL, 0.048 mmol) and HATU (3.5 mg, 0.0093 mmol) were added sequentially to the solution, and the mixture was stirred at 23° C. while the reaction progress was monitored by LC-MS. In 1 h, LC-MS showed full consumption of the 07-059 starting material. The residue was diluted with 50% acetonitrile-water to a volume of 4.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (6.9 mg, 45%). HRMS (ESI): Calcd for $(C_{88}H_{133}ClF_3N_{17}O_{17}+2H)^{2+}$: 896.9931. Found: 896.9883.

Example 7: Blocker Compounds in Combination with mTOR Inhibitors

Figure 61A:
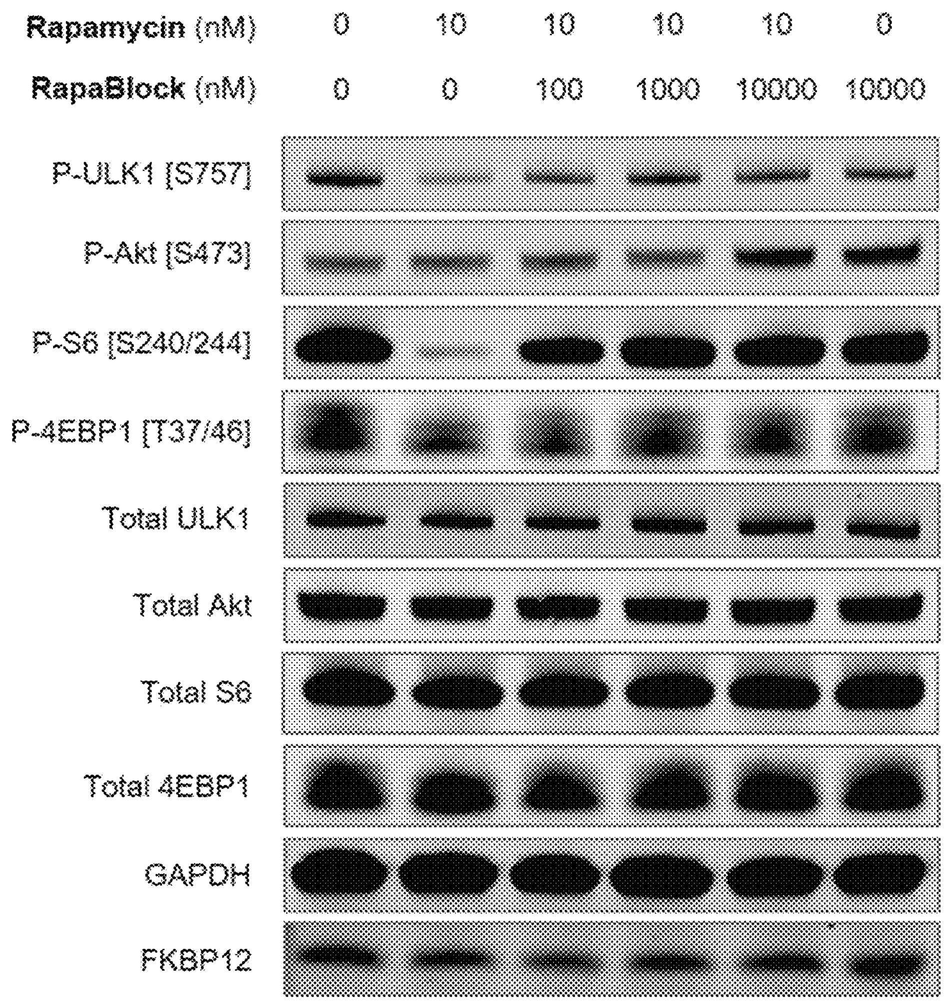
FIGS. 61A-61B. RapaBlock rescues mTOR inhibition by Rapamycin (FIG. 61A) or RapaLink-1 (FIG. 61B) in cells.
Figure 61B:
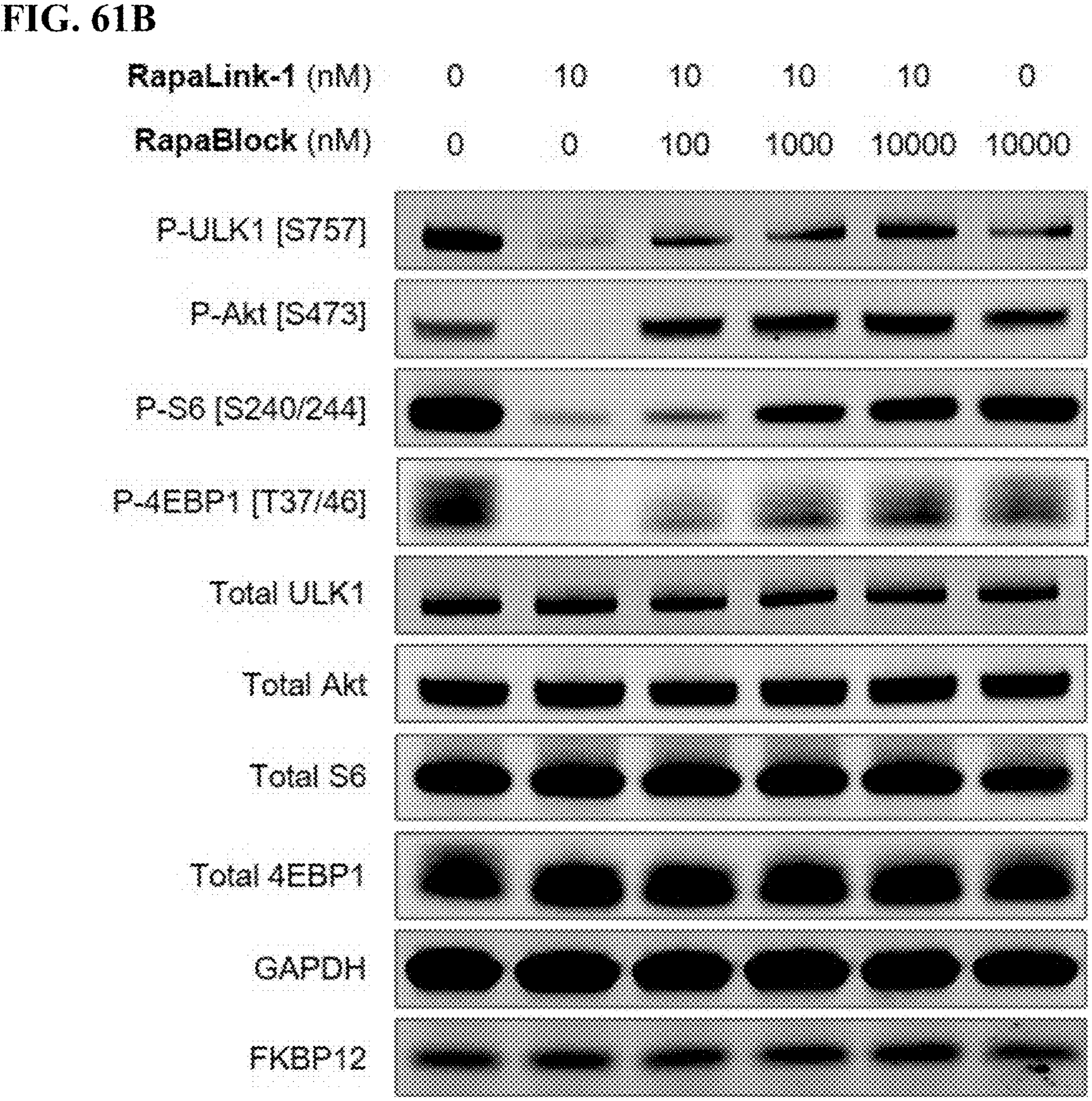

RapaBlock rescues mTOR inhibition by Rapamycin or RapaLink-1 in cells (FIGS. 61A-61B).

Experimental procedure. MCF7 cells were grown in 6-well tissue culture plates (2 plates total) to ~80% confluence (10% FBS in DMEM, 5% $CO_2$, 37° C.). Cells were treated with the following drug combinations with a fixed final DMSO concentration of 1%. The cells were incubated at 37° C. for 4 h. The media was removed by aspiration and the cells were washed twice with ice-cold PBS (1 mL/well). Cells were scraped in the presence of 0.5 mL PBS/well, collected in microfuge vials and pelleted by centrifugation at 7,000 g for 1 min. The supernatant was removed by aspiration and the cell pellet was resuspended in 30 μL ice-cold RIPA Buffer supplemented with complete protease inhibitors and PhosStop phosphotase inhibitors (Roche). Lysis was performed by incubating the suspension on ice for 10 min, and the resulting lysates were clarified by centrifugation at 14,000 g for 10 min. The clarified lysates were transferred into new microfuge tubes. Protein concentrations were determined with BCA assay and normalized to 2.0 mg/mL by dilution with RIPA buffer. Concentration-normalized lysates (30 μL/sample) were mixed with 7.5 μL 5×SDS Sample Buffer and boiled at 95° C. for 5 min. Proteins were resolved by electrophoresis on a 4-12% Novex Bis-Tris gel (200 V, 35 min, MES Running Buffer) and the bands were transferred onto a 0.45 μM nitrocellulose membrane (75 V, 30 min). Western blot analysis was performed following the standard protocol with the antibodies in Table 11.

TABLE 11

Antibodies used in Western blot analysis.

| MW | Antibody 1 | Source | Species | Dilution | Antibody 2 | Source | Species | Dilution |
|---|---|---|---|---|---|---|---|---|
| 100-55 | P-AKT[S473] | CST-4060 | Rabbit | 1:1000 | AKT | CST-2020 | Mouse | 1:1000 |
| 55-25 | P-S6[S240/244] | CST-5364 | Rabbit | 1:2000 | S6 | CST-2317 | Mouse | 1:1000 |
| 100+ | P-ULK1[S757] | | Rabbit | 1:1000 | | | | |
| 25– | P-4EBP1[T37/46] | CST-2855 | Rabbit | 1:1000 | FKBP12 | Ab58072 | Mouse | 1:500 |
| 55-25 | GAPDH | 60004-1-Ig | Mouse | 1:50000 | S6 | CST-2217 | Rabbit | 1:1000 |

TABLE 11-continued

| Antibodies used in Western blot analysis. | | | | | | | | |
|---|---|---|---|---|---|---|---|---|
| MW | Antibody 1 | Source | Species | Dilution | Antibody 2 | Source | Species | Dilution |
| 100+ | ULK1 | | Rabbit | 1:1000 | | | | |
| 25- | 4EBP1 | CST-9644 | Rabbit | 1:1000 | | | | |

Primary antibodies were added as solutions in 5% BSA-TBST, and the membranes were incubated at 4° C. overnight (16 h). The membranes were washed with TBST for three times (5 mL and 5 min for each wash). Secondary antibody binding was performed with LICOR IRDye 680RD Goat Anti-Mouse IgG or IRDye 800RD Goat Anti-Rabbit IgG in 5% non-fat milk-TBST (1:5000) at 23° C. for 1 h. Membranes were washed three times with TBST (5 mL and 5 min for each wash) before being imaged on a LICOR CLx Imaging System.

Figure 62A:
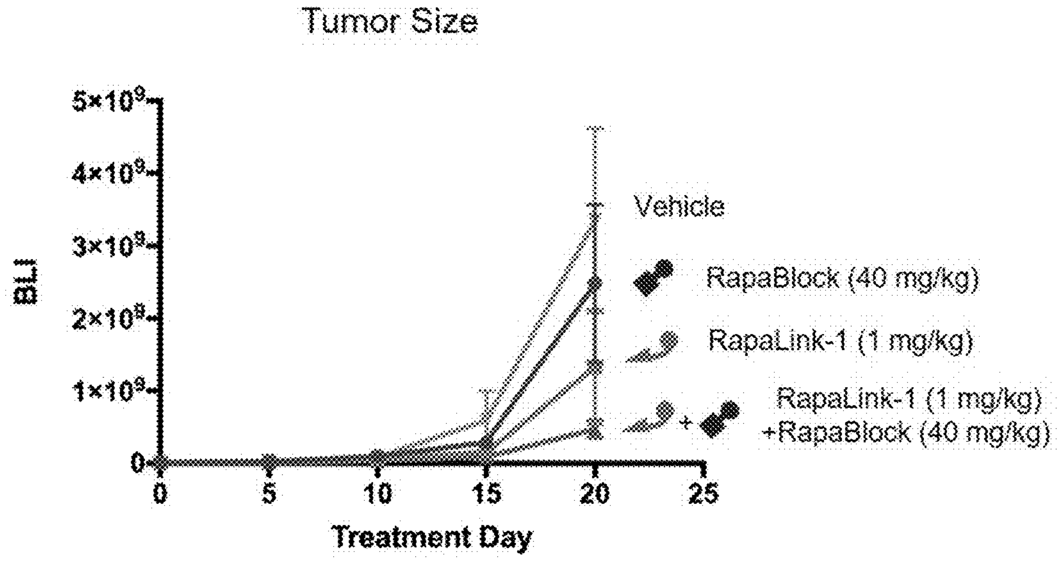
FIGS. 62A-62B. Combination of RapaBlock and RapaLink-1 is efficacious against glioblastoma xenograft in vivo. U87MG cells expressing luciferase were implanted intracranially. Treatment was started on day 0. Drugs were administered every 5 days intraperitoneally: RapaLink-1 (1 mg/kg); RapaBlock (40 mg/kg). BLI—Bioluminescence Imaging.
Figure 62B:
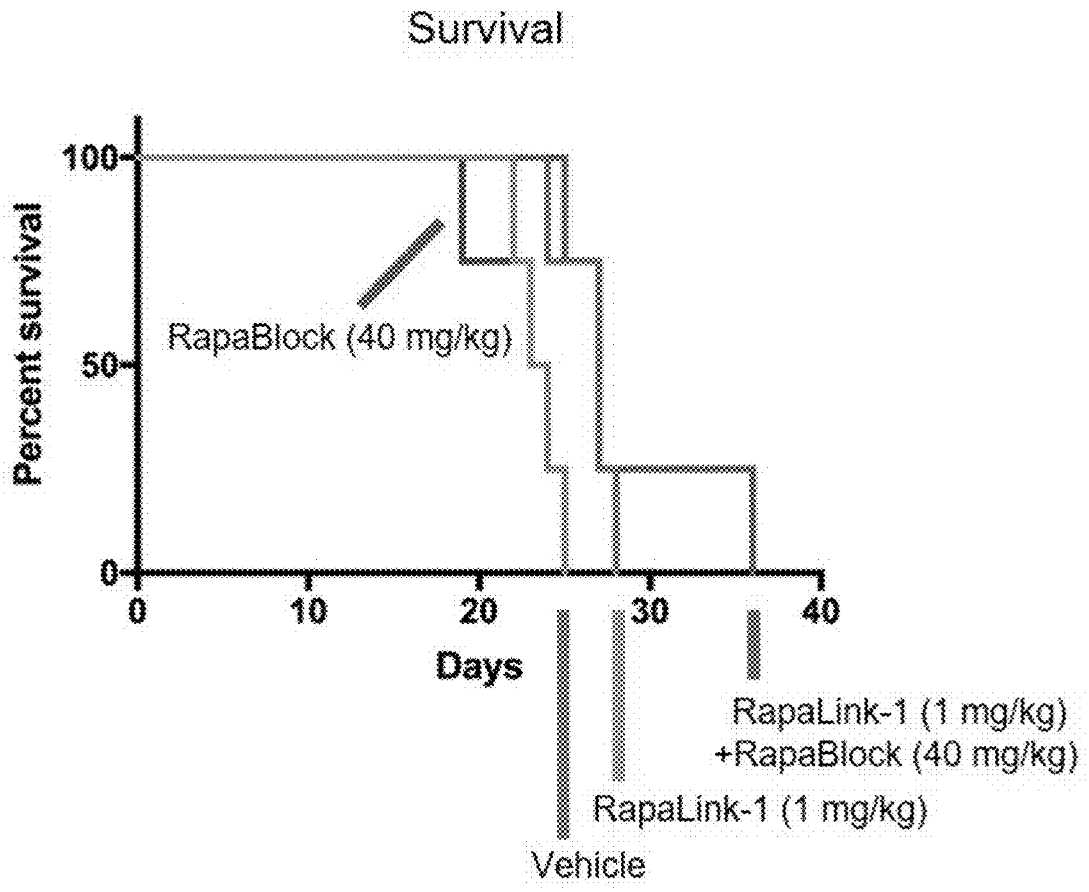

Combination of RapaBlock and RapaLink-1 is efficacious against glioblastoma xenograft in vivo (FIGS. 62A-62B).

Experimental procedure. Orthotopic injections and treatment studies: female BALB/Cnu/nu, mice (4 to 6 weeks old) were anesthetized using ketamine and xylazine. U87MG ($3\times10^5$) cells expressing firefly luciferase were injected intracranially (Hamilton syringe) at coordinates 2 mm anterior and 1.5 mm lateral of the right hemisphere relative to bregma, at a depth of 3 mm. Whole-brain bioluminescence was measured for each mouse every 3 to 5 days. When bioluminescence reached 107 photons/s (U87MG), mice were sorted into four groups of equal mean bioluminescent signal, and therapy initiated. Mice were treated with i.p. injection of vehicle (20% DMSO, 40% PEG-300, and 40% PBS [v/v], daily), RapaLink-1 (1 mg/kg, every 5 days), RapaBlock (40 mg/kg, every 5 days) or a combination of RapaLink-1 (1 mg/kg) and RapaBlock (40 mg/kg, every 5 days). Mice were monitored daily and euthanized when they exhibited neurological deficits or 15% reduction from initial body weight.

Example 8: HGK Inhibitors

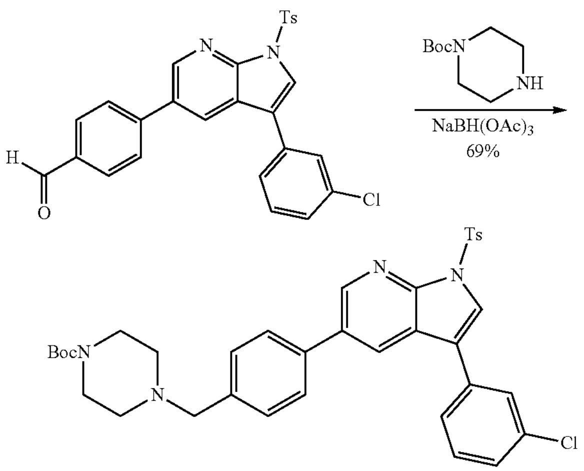

N-Boc-Piperazine (229 mg, 1.23 mmol) and sodium triacetoxyborohydride (196 mg, 0.924 mmol) were added sequentially to a stirred solution of 4-[3-(3-chlorophenyl)-1-(p-tolylsulfonyl)pyrrolo[2,3-b]pyridin-5-yl]benzaldehyde (44) (300 mg, 0.6161 mmol) in DCM (3.0803 mL) at 23° C. The resulting mixture was stirred at 23° C. and the reaction progress was monitored by LC-MS. In 18 h, LC-MS analysis showed full consumption of the aldehyde starting material. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-50% ethyl acetate-hexanes, 4-g RediSep® Rf column, Teledyne ISCO, Lincoln, NE) to afford the product as a yellow powder (279 mg, 69%). $^1H$ NMR (400 MHz, $CDCl_3$) δ 8.72 (d, J=2.1 Hz, 1H), 8.23-8.13 (m, 3H), 7.94 (s, 1H), 7.62 (t, J=1.8 Hz, 1H), 7.59-7.49 (m, 3H), 7.47-7.42 (m, 2H), 7.43-7.30 (m, 4H), 3.58 (s, 2H), 3.55-3.43 (m, 4H), 2.50-2.34 (m, 7H), 1.48 (s, 9H). HRMS (ESI): Calcd for $(C_{36}H_{37}ClN_4O_4S+H)^+$: 657.2302. Found: 657.2278.

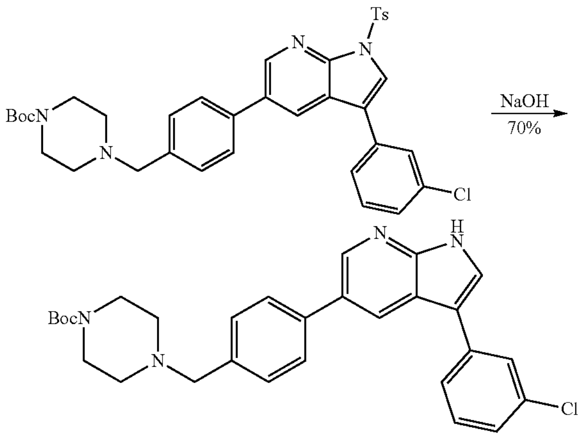

tert-butyl 4-[[4-[3-(3-chlorophenyl)-1-(p-tolylsulfonyl)pyrrolo[2,3-b]pyridin-5-yl]phenyl]methyl]piperazine-1-carboxylate (279 mg, 0.43 mmol) was dissolved in a 1:1:1 mixture of acetone (2 mL):methanol (2 mL): 2 M aqueous NaOH (2 mL). The mixture was heated to 65° C. In 1 h, LC-MS analysis showed full deprotection of the tosyl group. The reaction mixture was partitioned between ethyl acetate (10 mL) and 1 N NaOH (10 mL). The aqueous layer was extracted with ethyl acetate (2×10 mL). The combined organic layers were dried over sodium sulfate, and the dried solution was concentrated. The residue was purified by column chromatography (20-50% ethyl acetate-hexanes, 4-g RediSep® Rf column, Teledyne ISCO, Lincoln, NE) to afford the product as a yellow powder (150 mg, 70%). $^1H$ NMR (400 MHz, $CDCl_3$) δ 9.43 (s, 1H), 8.64 (d, J=2.1 Hz, 1H), 8.38 (d, J=2.0 Hz, 1H), 7.70-7.55 (m, 5H), 7.50-7.37 (m, 3H), 7.32 (ddd, J=8.0, 2.1, 1.1 Hz, 1H), 3.61 (s, 2H), 3.48 (t, J=5.1 Hz, 4H), 2.46 (t, J=5.1 Hz, 4H), 1.49 (s, 9H). HRMS (ESI): Calcd for $(C_{29}H_{31}ClN_4O_2+H)^+$: 503.2214. Found: 503.2233.

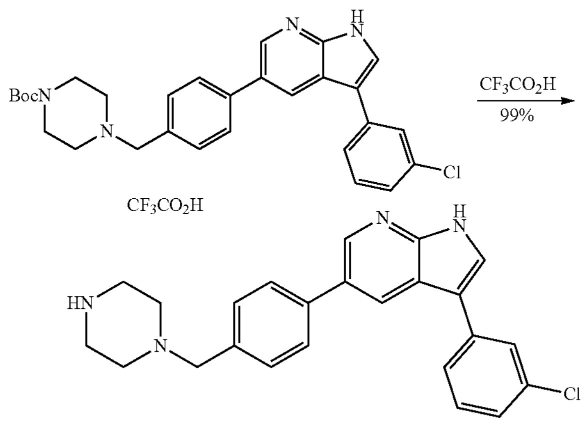

tert-butyl 4-[[4-[3-(3-chlorophenyl)-1H-pyrrolo[2,3-b]pyridin-5-yl]phenyl]methyl]piperazine-1-carboxylate (150 mg, 0.299 mmol) was dissolved in 50% trifluoroacetic acid-dichloromethane (2.0 mL) and the resulting solution was allowed to stand at 23° C. for 1 h. At this point, LC-MS analysis showed full consumption of the starting material and formation of the desired product. The reaction mixture was concentrated under reduced pressure and the residue was triturated with ether and dried under vacuum to afford the product as a yellow solid (151 mg, 99%). $^1H$ NMR (400 MHz, $CDCl_3$) δ 9.43 (s, 1H), 8.64 (d, J=2.1 Hz, 1H), 8.38 (d, J=2.0 Hz, 1H), 7.70-7.55 (m, 5H), 7.50-7.37 (m, 3H), 7.32 (ddd, J=8.0, 2.1, 1.1 Hz, 1H), 3.61 (s, 2H), 3.48 (t, J=5.1 Hz, 4H), 2.46 (t, J=5.1 Hz, 4H), 1.49 (s, 9H). HRMS (ESI): Calcd for $(C_{24}H_{23}ClN_4+H)^+$: 403.1689. Found: 403.1698.

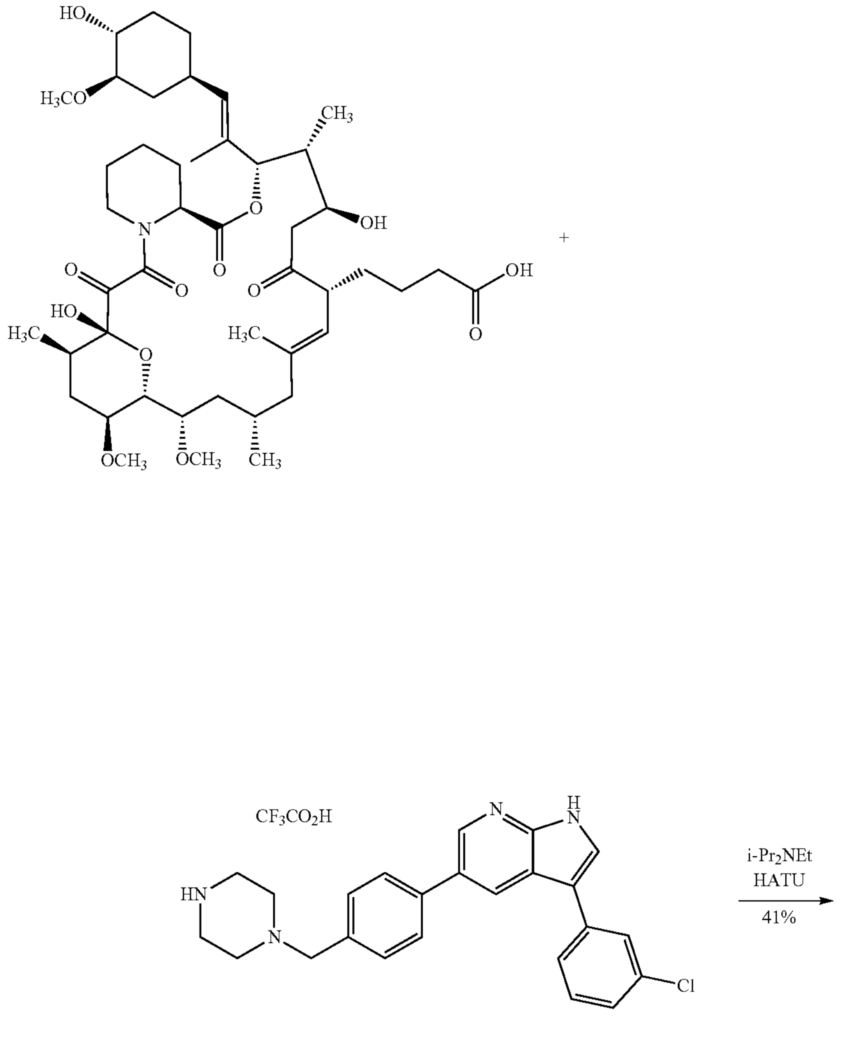

-continued

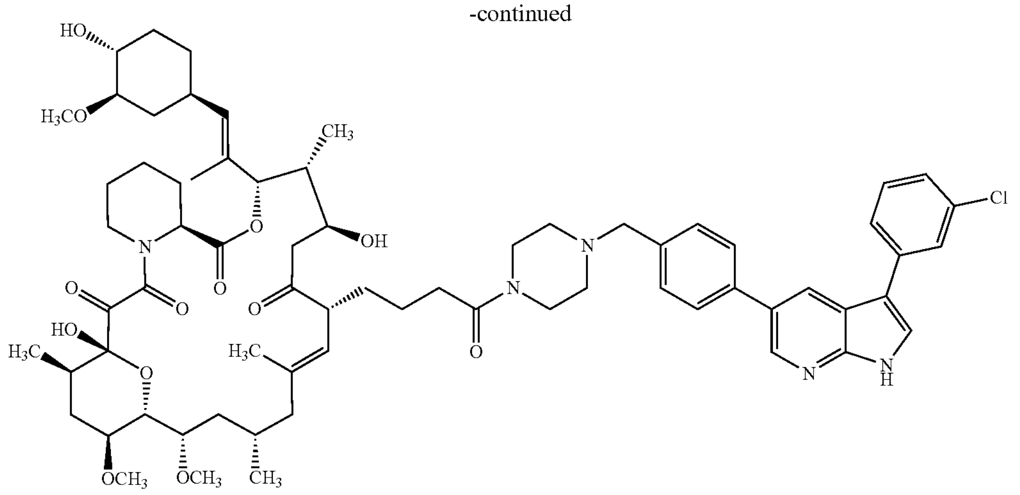

N,N-Diisopropylethylamine (6.2 μL, 0.035 mmol) and HATU (4.5 mg, 0.012 mmol) were added sequentially to a stirred solution of 3-(3-chlorophenyl)-5-[4-(piperazin-1-yl-methyl)phenyl]-1H-pyrrolo[2,3-b]pyridine trifluoroacetic acid salt (6.1 mg, 0.012 mmol) and FK506-$C_4$-Acid (10 mg, 0.012 mmol) in DMF (0.2 mL) at 23° C. The resulting mixture quickly turned yellow, and LC-MS analysis at 15 min showed full consumption of the FK506 acid starting material. The reaction mixture was diluted with 50% acetonitrile-water to a volume of 3.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.9 mg, 41%). HRMS (ESI): Calcd for $(C_{69}H_{92}ClN_5O_{13}+2H)^{2+}$: 617.8268. Found: 617.8257.

REFERENCES

1. Fan, Q. W. et al. A Kinase Inhibitor Targeted to mTORC1 Drives Regression in Glioblastoma. Cancer Cell 31, 424-435 (2017). 2. González, D. et al. Growth of kidney-transplanted pediatric patients treated with sirolimus. Pediatr Nephrol 26, 961-966 (2011). 3. Alvarez-Garcia, O. et al. Rapamycin induces growth retardation by disrupting angiogenesis in the growth plate. Kidney Int. 78, 561-568 (2010). 4. Briesewitz, R., Ray, G. T., Wandless, T. J. & Crabtree, G. R. Affinity modulation of small-molecule ligands by borrowing endogenous protein surfaces. Proc. Natl. Acad. Sci. U.S.A. 96, 1953-8 (1999). 5. Modulating a pharmacokinetic property of a drug by administering a bifunctional molecule containing the drug. US 20050209265, U.S. Pat. No. 6,887,842. 6. Administering bifunctional molecules containing a drug moiety and presenter protein ligand for therapy. US20050209146. 7. Bifunctional molecules and therapies based thereon. US20020147133. 8. Targeted bifunctional molecules and therapies based thereon U.S. Pat. No. 7,498,025. 9. Small Molecule Composite Surfaces As Inhibitors Of Protein-Protein Interactions. US 20160333054. 10. Gestwicki, J. E. Harnessing Chaperones to Generate Small-Molecule Inhibitors of Amyloid. Aggregation. 865, 865-870 (2011). 11. Neurodegenerative protein aggregation inhibition methods and compounds. US20050209173. 12. Marinec, P. S. et al. FK506-binding protein (FKBP) partitions a modified HIV protease inhibitor into blood cells and prolongs its lifetime in vivo. Proc. Natl. Acad. Sci. U.S.A. 106, 1336-1341 (2009). 13. Marinec, P. S., Lancia, J. K. & Gestwicki, J. E. Bifunctional molecules evade cytochrome P450 metabolism by forming protective complexes with FK506-binding protein. *Mol. Biosyst.* 4, 571-578 (2008). 14. Dunyak, B. M., Nakamura, R. L., Frankel, A. D. & Gestwicki, J. E. Selective Targeting of Cells via Bispecific Molecules That Exploit Coexpression of Two Intracellular Proteins. *ACS Chem. Biol.* 10, 2441-2447 (2015). 15. Methods of screening bifunctional molecules for modulated pharmacokinetic properties US 20070054348. 16. Pharmacokinetics of protease inhibitors and other drugs. US 20080306098. 17. Braun, P. D. et al. A bifunctional molecule that displays context-dependent cellular activity. J. Am. Chem. Soc. 125, 7575-7580 (2003). 18. Sellmyer, M. A., Stankunas, K., Briesewitz, R., Crabtree, G. R. & Wandless, T. J. Engineering small molecule specificity in nearly identical cellular environments. Bioorganic Med. Chem. Lett. 17, 2703-2705 (2007). 19. Wu, X. et al. Creating diverse target-binding surfaces on FKBP12: Synthesis and evaluation of a rapamycin analogue library. ACS Comb. Sci. 13, 486-495 (2011). 20. Small Molecule Composite Surfaces As Inhibitors Of Protein-Protein Interactions. U.S. Pat. No. 9,260,484. US20160333054. US 20140200186. 21. Guo, Z. et al. Rapamycin-inspired macrocycles with new target specificity. Nat. Chem. (2018). doi:10.1038/s41557-018-0187-4. 22. Synthesis and composition of rapafucin libraries. WO2017136708A1. 23. Guo, Z.-F., Zhang, R. & Liang, F.-S. Facile functionalization of FK506 for biological studies by the thiol-ene 'click' reaction. RSC Adv. 4, 11400 (2014). 24. Marinec, P. S. et al. Synthesis of orthogonally reactive FK506 derivatives via olefin cross metathesis. *Bioorganic Med. Chem.* 17, 5763-5768 (2009). 25. Nambu, M. et al. A calcineurin antifungal strategy with analogs of FK506. Bioorganic Med. Chem. Lett. 27, 2465-2471 (2017). 26. Preparation of cyclosporin A analogs as Cyclophilin A inhibitors for treating dry eye and other conditions. PCT Int. Appl., 2013181339. 27. Synthesis of cyclosporin derivatives for use in diagnosis or treatment of disease, plant protection, or pest control. PCT Int. Appl., 2013030208. 28. Preparation of non-immunosuppressive cyclosporin A analogs modified on the (4R)-4-[(E)-2-butenyl]-4-methyl-L-threonine side chain by heterocyclic rings as potent cyclophilin A inhibitors for treating dry eye and other conditions. PCT Int. Appl., 2016160362. 29. Preparation of non-immunosuppressive analogs of cyclosporin A derivatives possessing a (4R)-4-[(E)-2-butenyl]-4-methyl-L-threonine cyclized side-chain as potent inhibitors of cyclophilin D. PCT Int. Appl., 2016112321. 30. Preparation of cyclosporins for the treatment of immune disorders. U.S. Pat. Appl. Publ., 20040110666. 31. Preparation of cyclosporins for the treatment of immune disorders. U.S. Pat. Appl. Publ., 20040157768. 32. Preparation of cyclosporin alkyne analogs for preventing or treating viral-induced disorders. U.S., 7696165. 33. Preparation of cyclosporin alkene analogues for preventing or treating viral-induced disorders. PCT Int. Appl., 2007112345. 34. Preparation of cyclosporin alkyne/alkene analogues for preventing or treating viral-induced disorders. PCT Int. Appl., 2007112352. 35. Preparation of cyclosporin alkynes as pharmaceutical agents. U.S. Pat. Appl. Publ., 20060074015. 36. Preparation of cyclosporin alkyne analogues for preventing or treating viral-induced disorders. PCT Int. Appl., 2007112357. 37. Preparation of cyclosporin analogues for pharmaceutical use. U.S. Pat. Appl. Publ., 20060069015. 38. Preparation of novel cyclosporins. PCT Int. Appl., 200408262. 39. Preparation of cyclosporin A analogs modified at amino acid 1 and 3 as cyclophilin ligands with reduced immunosuppressivity for treating cyclophilin mediated diseases. PCT Int. Appl., 2012079172. 40. A semisynthetic approach to olefinic analogs of amino acid one (MeBMT) in cyclosporin A. Tetrahedron Letters, 30(32), 4215-18; 1989. 41. Semisynthetic di- and tri-functionalized non-immunosuppressive cyclosporin A derivatives as potential anti-HIV 1 drugs. Synlett, (2), 316-320; 2004. 42. Preparation of novel cyclosporin A derivatives. Bioconjugate Chemistry, 3(1), 32-6; 1992. 43. Rutaganira, F. U. et al. Design and Structural Characterization of Potent and Selective Inhibitors of Phosphatidylinositol 4 Kinase III β. (2016). doi:10.1021/acs.jmedchem.5b01311. 44. Bos, P. H. et al. Development of MAP4 Kinase Inhibitors as Motor Neuron-Protecting Agents. *Cell Chem. Biol.* 26, 1703-1715.e37 (2019).

What is claimed is:

1. A compound having the formula:

$A^B$-$L^{B1}$-$R^{B1}$, or a pharmaceutically acceptable salt thereof;

wherein $A^B$ is an immunophilin-binding moiety having the formula

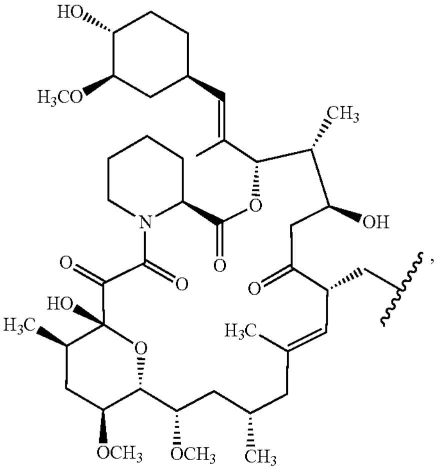 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or a stereoisomeric form thereof;

$L^{B1}$-$R^{B1}$ is $L^{B4}$-$L^{B3}$-$L^{B2}$-$R^{B1}$;

$L^{B2}$ is $—S(O)_2—$;

$L^{B3}$ is a bond;

$L^{B4}$ is unsubstituted, fully saturated or mono-unsaturated, $C_3$-$C_6$ alkylene;

$R^{B1}$ is $—NR^{B1A}R^{B1B}$; and $R^{B1A}$ and $R^{B1B}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{B1A}$ and $R^{B1B}$ substituents bonded to the same nitrogen atom are joined to form a substituted or unsubstituted heterocycloalkyl or substituted or unsubstituted heteroaryl.

2. The compound of claim 1, or a pharmaceutically acceptable salt thereof, wherein each of $R^{B1A}$ and $R^{B1B}$ is independently hydrogen or substituted or unsubstituted, $C_1$-$C_4$ alkyl.

3. A pharmaceutical composition comprising a pharmaceutically acceptable excipient and a compound of claim 1, or a pharmaceutically acceptable salt thereof.

4. A compound having the formula:

$A^B$-$L^{B1}$-$R^{B1}$, or a pharmaceutically acceptable salt thereof;

wherein $A^B$ is an immunophilin-binding moiety having the formula

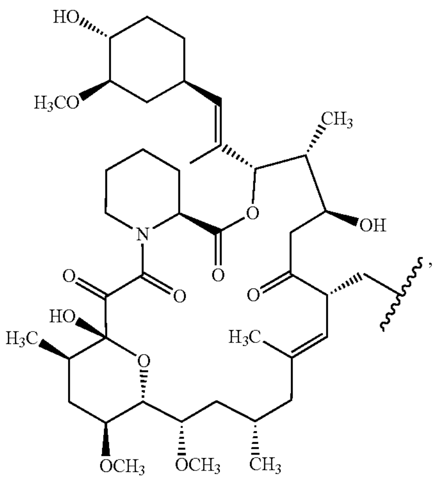 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or a stereoisomeric form thereof;

$L^{B1}$ is

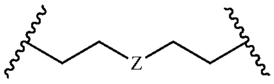

;

Z is —S— or —$SO_2$—;

$R^{B1}$ is —$NR^{B1A}R^{B1B}$ or —$NHC(O)CH_2R^{B1C}$; and each of $R^{B1A}$, $R^{B1B}$, and $R^{B1C}$ is independently substituted or unsubstituted pyridyl.

5. A pharmaceutical composition comprising a pharmaceutically acceptable excipient and a compound of claim 4, or a pharmaceutically acceptable salt thereof.

6. A compound of the formula:

$A^B$-$L^{B1}$-$R^{B1}$, or a pharmaceutically acceptable salt thereof, wherein $A^B$ is an immunophilin-binding moiety having the formula

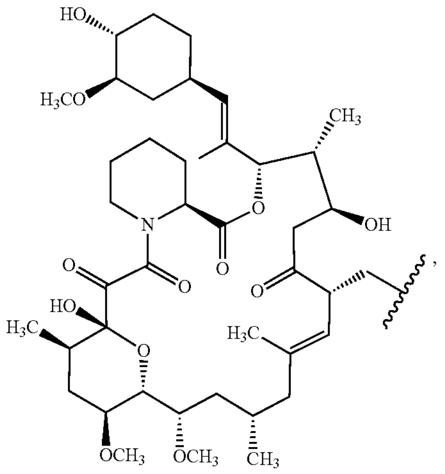 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

, or a stereoisomeric form thereof;

$L^{B1}$-$R^{B1}$ is $L^{B4}$-$L^{B3}$-$L^{B2}$-$R^{B1}$;

$L^{B2}$ is —$N(R^{B2})$—;

$L^{B3}$ is a bond;

$L^{B4}$ is unsubstituted, fully saturated or mono-unsaturated, $C_3$-$C_6$ alkylene;

$R^{B2}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1}$ is —$SO_{nB1}R^{B1D}$;

$R^{B1D}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and nB1 is an integer from 0 to 4.

7. A pharmaceutical composition comprising a pharmaceutically acceptable excipient and a compound of claim 6, or a pharmaceutically acceptable salt thereof.

8. A compound, or a pharmaceutically acceptable salt thereof, wherein the compound is of the formula:

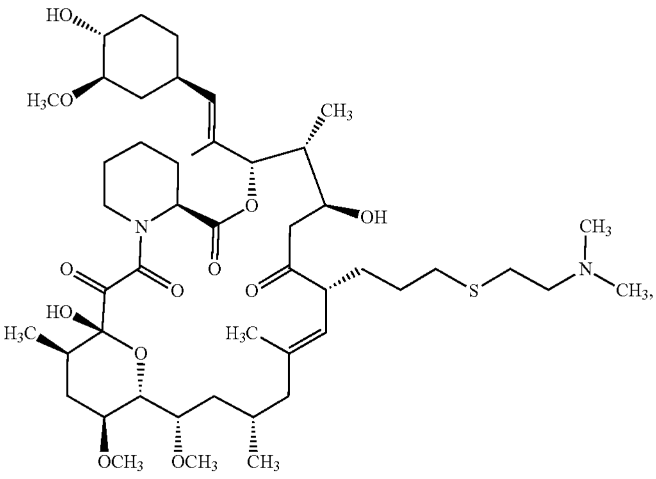
,
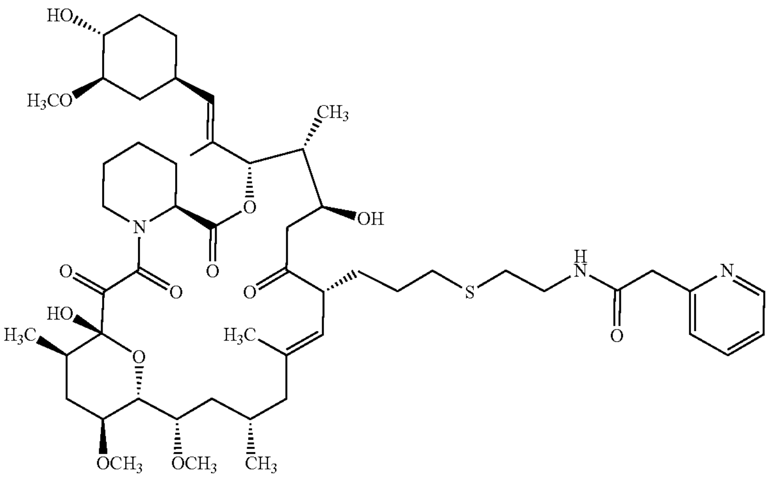
,
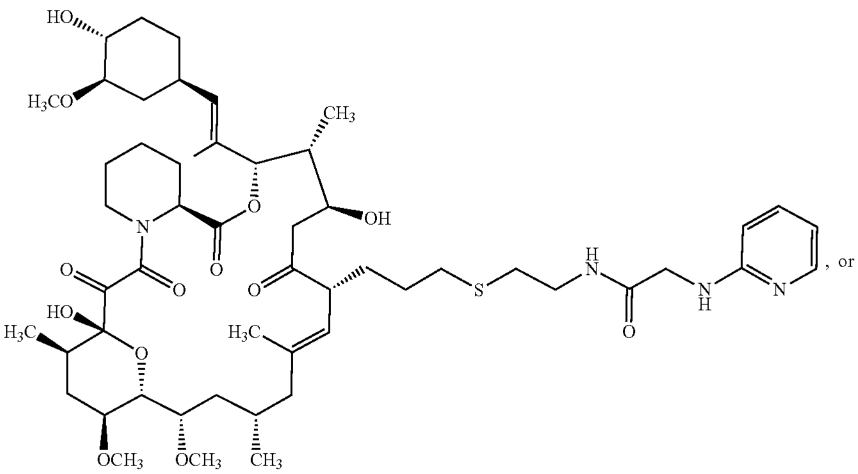
, or

-continued
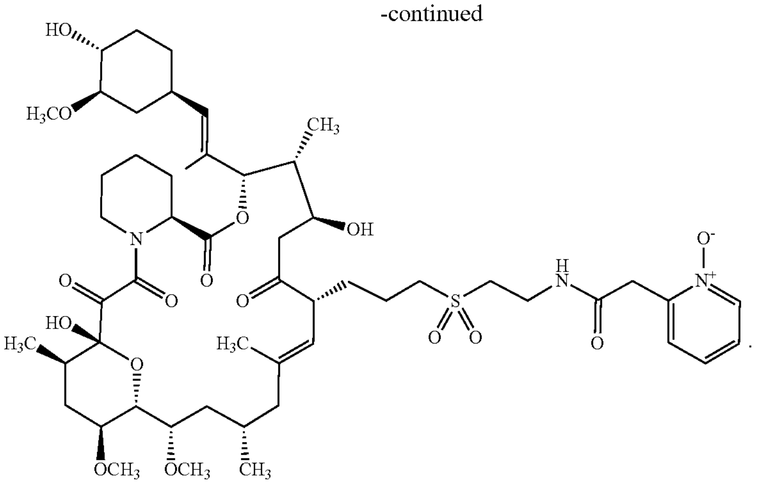
9. A pharmaceutical composition comprising a pharmaceutically acceptable excipient and a compound of claim 8, or a pharmaceutically acceptable salt thereof.
* * * * *

SEQUENCE LISTING

```
Sequence total quantity: 12
SEQ ID NO: 1          moltype = AA  length = 2549
FEATURE               Location/Qualifiers
REGION                1..2549
                      note = Synthetic polypeptide
source                1..2549
                      mol_type = protein
                      organism = synthetic construct
SEQUENCE: 1
MLGTGPAAAT TAATTSSNVS VLQQFASGLK SRNEETRAKA AKELQHYVTM ELREMSQEES  60
TRFYDQLNHH IFELVSSSDA NERKGGILAI ASLIGVEGGN ATRIGRFANY LRNLLPSNDP  120
VVMEMASKAI GRLAMAGDTF TAEYVEFEVK RALEWLGADR NEGRRHAAVL VLRELAISVP  180
TFFFQQVQPF FDNIFVAVWD PKQAIREGAV AALRACLILT TQREPKEMQK PQWYRHTFEE  240
AEKGFDETLA KEKGMNRDDR IHGALLILNE LVRISSMEGE RLREEMEEIT QQQLVHDKYC  300
KDLMGFGTKP RHITPFTSFQ AVQPQQSNAL VGLLGYSSHQ GLMGFGTSPS PAKSTLVESR  360
CCRDLMEEKF DQVCQWVLKC RNSKNSLIQM TILNLLPRLA AFRPSAFTDT QYLQDTMNHV  420
LSCVKKEKER TAAFQALGLL SVAVRSEFKV YLPRVLDIIR AALPPKDFAH KRQKAMQVDA  480
TVFTCISMLA RAMGPGIQQD IKELLEPMLA VGLSPALTAV LYDLSRQIPQ LKKDIQDGLL  540
KMLSLVLMHK PLRHPGMPKG LAHQLASPGL TTLPEASDVG SITLALRTLG SFEFEGHSLT  600
QFVRHCADHF LNSEHKEIRM EAARTCSRLL TPSIHLISGH AHVVSQTAVQ VVADVLSKLL  660
VVGITDPDPD IRYCVLASLD ERFDAHLAQA ENLQALFVAL NDQVFEIREL AICTVGRLSS  720
MNPAFVMPFL RKMLIQILTE LEHSGIGRIK EQSARMLGHL VSNAPRLIRP YMEPILKALI  780
LKLKDPDPDP NPGVINNVLA TIGELAQVSG LEMRKWVDEL FIIIMDMLQD SSLLAKRQVA  840
LWTLGQLVAS TGYVVEPYRK YPTLLEVLLN FLKTEQNQGT RREAIRVLGL LGALDPYKHK  900
VNIGMIDQSR DASAVSLSES KSSQDSSDYS TSEMLVNMGN LPLDEFYPAV SMVALMRIFR  960
DQSLSHHHTM VVQAITFIFK SLGLKCVQFL PQVMPTFLNV IRVCDGAIRE FLFQQLGMLV  1020
SFVKSHIRPY MDEIVTLMRE FWVMNTSIQS TIILLIEQIV VALGGEFKLY LPQLIPHMLR  1080
VFMHDNSPGR IVSIKLLAAI QLFGANLDDY LHLLLPPIVK LFDAPEAPLP SRKAALETVD  1140
RLTESLDFTD YASRIIHPIV RTLDQSPELR STAMDTLSSL VFQLGKKYQI FIPMVNKVLV  1200
RHRINHQRYD VLICRIVKGY TLADEEEDPL IYQHRMLRSG QGDALASGPV ETGPMKKLHV  1260
STINLQKAWG AARRVSKDDW LEWLRRLSLE LLKDSSSPSL RSCWALAQAY NPMARDLFNA  1320
AFVSCWSELN EDQQDELIRS IELALTSQDI AEVTQTLLNL AEFMEHSDKG PLPLRDDNGI  1380
VLLGERAAKC RAYAKALHYK ELEFQKGPTP AILESLISIN NKLQQPEAAA GVLEYAMKHF  1440
GELEIQATWY EKLHEWEDAL VAYDKKMDTN KDDPELMLGR MRCLEALGEW GQLHQQCCEK  1500
WTLVNDETQA KMARMAAAAA WGLGQWDSME EYTCMIPRDT HDGAFYRAVL ALHQDLFSLA  1560
QQCIDKARDL LDAELTAMAG ESYSRAYGAM VSCHMLSELE EVIQYKLVPE RREIIRQIWW  1620
ERLQGCQRIV EDWQKILMVR SLVVSPHEDM RTWLKYASLC GKSGRLALAH KTLVLLLGVD  1680
PSRQLDHPLP TVHPQVTYAY MKNMWKSARK IDAFQHMQHF VQTMQQQAQH AIATEDQQHK  1740
QELHKLMARC FLKLGEWQLN LQGINESTIP KVLQYYSAAT EHDRSWYKAW HAWAVMNFEA  1800
VLHYKHQNQA RDEKKKLRHA SGANITNATT AATTAATATT TASTEGSNSE SEAESTENSP  1860
TPSPLQKKVT EDLSKTLLMY TVPAVQGFFR SISLSRGNNL QDTLRVLTLW FDYGHWPDVN  1920
EALVEGVKAI QIDTWLQVIP QLIARIDTPR PLVGRLIHQL LTDIGRYHPQ ALIYPLTVAS  1980
KSTTTARHNA ANKILKNMCE HSNTLVQQAM MVSEELIRVA ILWHEMWHEG LEEASRLYFG  2040
ERNVKGMFEV LEPLHAMMER GPQTLKETSF NQAYGRDLME AQEWCRKYMK SGNVKDLTQA  2100
WDLYYHVFRR ISKQLPQLTS LELQYVSPKL LMCRDLELAV PGTYDPNQPI IRIQSIAPSL  2160
QVITSKQRPR KLTLMGSNGH EFVFLLKGHE DLRQDERVMQ LFGLVNTLLA NDPTSLRKNL  2220
SIQRYAVIPL STNSGLIGWV PHCDTLHALI RDYREKKKIL LNIEHRIMLR MAPDYDHLTL  2280
MQKVEVFEHA VNNTAGDDLA KLLWLKSPSS EVWFDRRTNY TRSLAVMSMV GYILGLGDRH  2340
PSNLMLDRLS GKILHIDFGD CFEVAMTREK FPEKIPFRLT RMLTNAMEVT GLDGNYRITC  2400
HTVMEVLREH KDSVMAVLEA FVYDPLLNWR LMDTNTKGNK RSRTRTDSYS AGQSVEILDG  2460
VELGEPAHKK TGTTVPESIH SFIGDGLVKP EALNKKAIQI INRVRDKLTG RDFSHDDTLD  2520
VPTQVELLIK QATSHENLCQ CYIGWCPFW                                  2549
```

```
SEQ ID NO: 2           moltype = AA  length = 1210
FEATURE                Location/Qualifiers
REGION                 1..1210
                       note = Synthetic polypeptide
source                 1..1210
                       mol_type = protein
                       organism = synthetic construct
SEQUENCE: 2
MRPSGTAGAA LLALLAALCP ASRALEEKKV CQGTSNKLTQ LGTFEDHFLS LQRMFNNCEV  60
VLGNLEITYV QRNYDLSFLK TIQEVAGYVL IALNTVERIP LENLQIIRGN MYYENSYALA  120
VLSNYDANKT GLKELPMRNL QEILHGAVRF SNNPALCNVE SIQWRDIVSS DFLSNMSMDF  180
QNHLGSCQKC DPSCPNGSCW GAGEENCQKL TKIICAQQCS GRCRGKSPSD CCHNQCAAGC  240
TGPRESDCLV CRKFRDEATC KDTCPPLMLY NPTTYQMDVN PEGKYSFGAT CVKKCPRNYV  300
VTDHGSCVRA CGADSYEMEE DGVRKCKKCE GPCRKVCNGI GIGEFKDSLS INATNIKHFK  360
NCTSISGDLH ILPVAFRGDS FTHTPPLDPQ ELDILKTVKE ITGFLLIQAW PENRTDLHAF  420
ENLEIIRGRT KQHGQFSLAV VSLNITSLGL RSLKEISDGD VIISGNKNLC YANTINWKKL  480
FGTSGQKTKI ISNRGENSCK ATGQVCHALC SPEGCWGPEP RDCVSCRNVS RGRECVDKCN  540
LLEGEPREFV ENSECIQCHP ECLPQAMNIT CTGRGPDNCI QCAHYIDGPH CVKTCPAGVM  600
GENNTLVWKY ADAGHVCHLC HPNCTYGCTG PGLEGCPTNG PKIPSIATGM VGALLLLLVV  660
ALGIGLFMRR RHIVRKRTLR RLLQERELVE PLTPSGEAPN QALLRILKET EFKKIKVLGS  720
GAFGTVYKGL WIPEGEKVKI PVAIKELREA TSPKANKEIL DEAYVMASVD NPHVCRLLGI  780
CLTSTVQLIT QLMPFGCLLD YVREHKDNIG SQYLLNWCVQ IAKGMNYLED RRLVHRDLAA  840
RNVLVKTPQH VKITDFGLAK LLGAEEKEYH AEGGKVPIKW MALESILHRI YTHQSDVWSY  900
GVTVWELMTF GSKPYDGIPA SEISSILEKG ERLPQPPICT IDVYMIMVKC WMIDADSRPK  960
FRELIIEFSK MARDPQRYLV IQGDERMHLP SPTDSNFYRA LMDEEDMDDV VDADEYLIPQ  1020
QGFFSSPSTS RTPLLSSLSA TSNNSTVACI DRNGLQSCPI KEDSFLQRYS SDPTGALTED  1080
SIDDTFLPVP EYINQSVPKR PAGSVQNPVY HNQPLNPAPS RDPHYQDPHS TAVGNPEYLN  1140
TVQPTCVNST FDSPAHWAQK GSHQISLDNP DYQQDFFPKE AKPNGIFKGS TAENAEYLRV  1200
APQSSEFIGA                                                        1210

SEQ ID NO: 3           moltype = AA  length = 1255
FEATURE                Location/Qualifiers
REGION                 1..1255
                       note = Synthetic polypeptide
source                 1..1255
                       mol_type = protein
                       organism = synthetic construct
SEQUENCE: 3
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERP KTLSPGKNGV VKDVFAFGGA VENPEYLTPQ  1200
GGAAPQPHPP PAFSPAFDNL YYWDQDPPER GAPPSTFKGT PTAENPEYLG LDVPV       1255

SEQ ID NO: 4           moltype = AA  length = 2527
FEATURE                Location/Qualifiers
REGION                 1..2527
                       note = Synthetic polypeptide
source                 1..2527
                       mol_type = protein
                       organism = synthetic construct
SEQUENCE: 4
MASGSCQGCE EDEETLKKLI VRLNNVQEGK QIETLVQILE DLLVFTYSER ASKLFQGKNI  60
HVPLLIVLDS YMRVASVQQV GWSLLCKLIE VCPGTMQSLM GPQDVGNDWE VLGVHQLILK  120
MLTVHNASVN LSVIGLKTLD LLLTSGKITL LILDEESDIF MLIFDAMHSF PANDEVQKLG  180
CKALHVLFER VSEEQLTEFV ENKDYMILLS ALTNFKDEEE IVLHVLHCLH SLAIPCNNVE  240
VLMSGNVRCY NIVVEAMKAF PMSERIQEVS CCLLHRLTLG NFFNILVLNE VHEFVVKAVQ  300
QYPENAALQI SALSCLALLT ETIFLNQDLE EKNENQENDD EGEEDKLFWL EACYKALTWH  360
RKNKHVQEAA CWALNNLLMY QNSLHEKIGD EDGHFPAHRE VMLSMLMHSS SKEVFQASAN  420
ALSTLLEQNV NFRKILLSKG IHLNVLELMQ KHIHSPEVAE SGCKMLNHLF EGSNTSLDIM  480
AAVVPKILTV MKRHETSLPV QLEALRAILH FIVPGMPEES REDTEFHHKL NMVKKQCFKN  540
DIHKLVLAAL NRFIGNPGIQ KCGLKVISSI VHFPDALEML SLEGAMDSVL HTLQMYPDDQ  600
EIQCLGLSLI GYLITKKNVF IGTGHLLAKI LVSSLYRFKD VAEIQTKGFQ TILAILKLSA  660
```

-continued

```
SFSKLLVHHS FDLVIFHQMS SNIMEQKDQQ FLNLCCKCFA KVAMDDYLKN VMLERACDQN  720
NSIMVECLLL LGADANQAKE GSSLICQVCE KESSPKLVEL LLNSGSREQD VRKALTISIG  780
KGDSQIISLL LRRLALDVAN NSICLGGFCI GKVEPSWLGP LFPDKTSNLR KQTNIASTLA  840
RMVIRYQMKS AVEEGTASGS DGNFSEDVLS KFDEWTFIPD SSMDSVFAQS DDLDSEGSEG  900
SFLVKKKSNS ISVGEFYRDA VLQRCSPNLQ RHSNSLGPIF DHEDLLKRKR KILSSDDSLR  960
SSKLQSHMRH SDSISSLASE REYITSLDLS ANELRDIDAL SQKCCISVHL EHLEKLELHQ  1020
NALTSFPQQL CETLKSLTHL DLHSNKFTSF PSYLLKMSCI ANLDVSRNDI GPSVVLDPTV  1080
KCPTLKQFNL SYNQLSFVPE NLTDVVEKLE QLILEGNKIS GICSPLRLKE LKILNLSKNH  1140
ISSLSENFLE ACPKVESFSA RMNFLAAMPF LPPSMTILKL SQNKFSCIPE AILNLPHLRS  1200
LDMSSNDIQY LPGPAHWKSL NLRELLFSHN QISILDLSEK AYLWSRVEKL HLSHNKLKEI  1260
PPEIGCLENL TSLDVSYNLE LRSFPNEMGK LSKIWDLPLD ELHLNFDFKH IGCKAKDIIR  1320
FLQQRLKKAV PYNRMKLMIV GNTGSGKTTL LQQLMKTKKS DLGMQSATVG IDVKDWPIQI  1380
RDKRKRDLVL NVWDFAGREE FYSTHPHFMT QRALYLAVYD LSKGQAEVDA MKPWLFNIKA  1440
RASSSPVILV GTHLDVSDEK QRKACMSKIT KELLNKRGFP AIRDYHFVNA TEESDALAKL  1500
RKTIINESLN FKIRDQLVVG QLIPDCYVEL EKIILSERKN VPIEFPVIDR KRLLQLVREN  1560
QLQLDENELP HAVHFLNESG VLLHFQDPAL QLSDLYFVEP KWLCKIMAQI LTVKVEGCPK  1620
HPKGIISRRD VEKFLSKKRK FPKNYMSQYF KLLEKFQIAL PIGEEYLLVP SSLSDHRPVI  1680
ELPHCENSEI IIRLYEMPYF PMGFWSRLIN RLLEISPYML SGRERALRPN RMYWRQGIYL  1740
NWSPEAYCLV GSEVLDNHPE SFLKITVPSC RKGCILLGQV VDHIDSLMEE WFPGLLEIDI  1800
CGEGETLLKK WALYSFNDGE EHQKILLDDL MKKAEEGDLL VNPDQPRLTI PISQIAPDLI  1860
LADLPRNIML NNDELEFEQA PEFLLGDGSF GSVYRAAYEG EEVAVKIFNK HTSLRLLRQE  1920
LVVLCHLHHP SLISLLAAGI RPRMLVMELA SKGSLDRLLQ QDKASLTRTL QHRIALHVAD  1980
GLRYLHSAMI IYRDLKPHNV LLFTLYPNAA IIAKIADYGI AQYCCRMGIK TSEGTPGFRA  2040
PEVARGNVIY NQQADVYSFG LLLYDILTTG GRIVEGLKFP NEFDELEIQG KLPDPVKEYG  2100
CAPWPMVEKL IKQCLKENPQ ERPTSAQVFD ILNSAELVCL TRRILLPKNV IVECMVATHH  2160
NSRNASIWLG CGHTDRGQLS FLDLNTEGYT SEEVADSRIL CLALVHLPVE KESWIVSGTQ  2220
SGTLLVINTE DGKKRHTLEK MTDSVTCLYC NSFSKQSKQK NFLLVGTADG KLAIFEDKTV  2280
KLKGAAPLKI LNIGNVSTPL MCLSESTNST ERNVMWGGCG TKIFSFSNDF TIQKLIETRT  2340
SQLFSYAAFS DSNIITVVVD TALYIAKQNS PVVEVWDKKT EKLCGLIDCV HFLREVMVKE  2400
NKESKHKMSY SGRVKTLCLQ KNTALWIGTG GGHILLLDLS TRRLIRVIYN FCNSVRVMMT  2460
AQLGSLKNVM LVLGYNRKNT EGTQKQKEIQ SCLTVWDINL PHEVQNLEKH IEVRKELAEK  2520
MRRTSVE                                                           2527

SEQ ID NO: 5           moltype = AA  length = 189
FEATURE                Location/Qualifiers
REGION                 1..189
                       note = Synthetic polypeptide
source                 1..189
                       mol_type = protein
                       organism = synthetic construct
SEQUENCE: 5
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ RVEDAFYTLV REIRQYRLKK ISKEEKTPGC  180
VKIKKCIIM                                                         189

SEQ ID NO: 6           moltype = AA  length = 188
FEATURE                Location/Qualifiers
REGION                 1..188
                       note = Synthetic polypeptide
source                 1..188
                       mol_type = protein
                       organism = synthetic construct
SEQUENCE: 6
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 7           moltype = AA  length = 2102
FEATURE                Location/Qualifiers
REGION                 1..2102
                       note = Synthetic polypeptide
source                 1..2102
                       mol_type = protein
                       organism = synthetic construct
SEQUENCE: 7
MAAAPARGGG GGGGGGGGCS GSGSSASRGF YFNTVLSLAR SLAVQRPASL EKVQKLLCMC  60
PVDFHGIFQL DERRRDAVIA LGIFLIESDL QHKDCVVPYL LRLLKGLPKV YWVEESTARK  120
GRGALPVAES FSFCLVTLLS DVAYRDPSLR DEILEVLLQV LHVLLGMCQA LEIQDKEYLC  180
KYAIPCLIGI SRAFGRYSNM EESLLSKLFP KIPPHSLRVL EELEGVRRRS FNDFRSILPS  240
NLLTVCQEGT LKRKTSSVSS ISQVSPERGM PPPSSPGGSA FHYFEASCLP DGTALEPEYY  300
FSTISSSFSV SPLFNGVTYK EFNIPLEMLR ELLNLVKKIV EEAVLKSLDA IVASVMEANP  360
SADLYYTSFS DPLYLTMFKM LRDTLYYMKD LPTSFVKEIH DFVLEQFNTS QGELQKILHD  420
ADRIHNELSP LKLRCQANAA CVDLMVWAVK DEQGAENLCI KLSEKLQSKT SSKVIIAHLP  480
LLICCLQGLG RLCERFPVVV HSVTPSLRDF LVIPSPVLVK LYKYHSQYHT VAGNDIKISV  540
TNEHSESTLN VMSGKKSQPS MYEQLRDIAI DNICRCLKAG LTVDPVIVEA FLASLSNRLY  600
ISQESDKDAH LIPDHTIRAL GHIAVALRDT PKVMEPILQI LQQKFCQPPS PLDVLIIDQL  660
GCLVITGNQY IYQEVWNLFQ QISVKASSVV YSATKDYKDH GYRHCSLAVI NALANIAANI  720
```

-continued

```
QDEHLVDELL MNLLELFVQL GLEGKRASER ASEKGPALKA SSSAGNLGVL IPVIAVLTRR  780
LPPIKEAKPR LQKLFRDFWL YSVLMGFAVE GSGLWPEEWY EGVCEIATKS PLLTFPSKEP  840
LRSVLQYNSA MKNDTVTPAE LSELRSTIIN LLDPPPEVSA LINKLDFAMS TYLLSVYRLE  900
YMRVLRSTDP DRFQVMFCYF EDKAIQKDKS GMMQCVIAVA DKVFDAFLNM MADKAKTKEN  960
EEELERHAQF LLVNFNHIHK RIRRVADKYL SGLVDKFPHL LWSGTVLKTM LDILQTLSLS  1020
LSADIHKDQP YYDIPDAPYR ITVPDTYEAR ESIVKDFAAR CGMILQEAMK WAPTVTKSHL  1080
QEYLNKHQNW VSGLSQHTGL AMATESILHF AGYNKQNTTL GATQLSERPA CVKKDYSNFM  1140
ASLNLRNRYA GEVYGMIRFS GTTGQMSDLN KMMVQDLHSA LDRSHPQHYT QAMFKLTAML  1200
ISSKDCDPQL LHHLCWGPLR MFNEHGMETA LACWEWLLAG KDGVEVPFMR EMAGAWHMTV  1260
EQKFGLFSAE IKEADPLAAS EASQPKPCPP EVTPHYIWID FLVQRFEIAK YCSSDQVEIF  1320
SSLLQRSMSL NIGGAKGSMN RHVAAIGPRF KLLTLGLSLL HADVVPNATI RNVLREKIYS  1380
TAFDYFSCPP KFPTQGEKRL REDISIMIKF WTAMFSDKKY LTASQLVPPD NQDTRSNLDI  1440
TVGSRQQATQ GWINTYPLSS GMSTISKKSG MSKKTNRGSQ LHKYYMKRRT LLLSLLATEI  1500
ERLITWYNPL SAPELELDQA GENSVANWRS KYISLSEKQW KDNVNLAWSI SPYLAVQLPA  1560
RFKNTEAIGN EVTRLVRLDP GAVSDVPEAI KFLVTWHTID ADAPELSHVL CWAPTDPPTG  1620
LSYFSSMYPP HPLTAQYGVK VLRSFPPDAI LFYIPQIVQA LRYDKMGYVR EYILWAASKS  1680
QLLAHQFIWN MKTNIYLDEE GHQKDPDIGD LLDQLVEEIT GSLSGPAKDF YQREFDFFNK  1740
ITNVSAIIKP YPKGDERKKA CLSALSEVKV QPGCYLPSNP EAIVLDIDYK SGTPMQSAAK  1800
APYLAKFKVK RCGVSELEKE GLRCRSDSED ECSTQEADGQ KISWQAAIFK VGDDCRQDML  1860
ALQIIDLFKN IFQLVGLDLF VFPYRVVATA PGCGVIECIP DCTSRDQLGR QTDFGMYDYF  1920
TRQYGDESTL AFQQARYNFI RSMAAYSLLL FLLQIKDRHN GNIMLDKKGH IIHIDFGFMF  1980
ESSPGGNLGW EPDIKLTDEM VMIMGGKMEA TPFKWFMEMC VRGYLAVRPY MDAVVSLVTL  2040
MLDTGLPCFR GQTIKLLKHR FSPNMTEREA ANFIMKVIQS CFLSNRSRTY DMIQYYQNDI  2100
PY                                                                2102

SEQ ID NO: 8            moltype = AA  length = 562
FEATURE                 Location/Qualifiers
REGION                  1..562
                        note = Synthetic polypeptide
source                  1..562
                        mol_type = protein
                        organism = synthetic construct
SEQUENCE: 8
MASASSGPSS SVGFSSFDPA VPSCTLSSAA SGIKRPMASE VLEARQDSYI SLVPYASGMP  60
IKKIGHRSVD SSGETTYKKT TSSALKGAIQ LGITHTVGSL STKPERDVLM QDFYVVESIF  120
FPSEGSNLTP AHHYNDFRFK TYAPVAFRYF RELFGIRPDD YLYSLCSEPL IELCSSGASG  180
SLFYVSSDDE FIIKTVQHKE AEFLQKLLPG YYMNLNQNPR TLLPKFYGLY CVQAGGKNIR  240
IVVMNNLLPR SVKMHIKYDL KGSTYKRRAS QKEREKPLPT FKDLDFLQDI PDGLFLDADM  300
YNALCKTLQR DCLVLQSFKI MDYSLLMSIH NIDHAQREPL SSETQYSVDT RRPAPQKALY  360
STAMESIQGE ARRGGTMETD DHMGGIPARN SKGERLLLYI GIIDILQSYR FVKKLEHSWK  420
ALVHDGDTVS VHRPGFYAER FQRFMCNTVF KKIPLKPSPS KKFRSGSSFS RRAGSSGNSC  480
ITYQPSVSGE HKAQVTTKAE VEPGVHLGRP DVLPQTPPLE EISEGSPIPD PSFSPLVGET  540
LQMLTTSTTL EKLEVAESEF TH                                          562

SEQ ID NO: 9            moltype = AA  length = 594
FEATURE                 Location/Qualifiers
REGION                  1..594
                        note = Synthetic polypeptide
source                  1..594
                        mol_type = protein
                        organism = synthetic construct
SEQUENCE: 9
MGKKSRVKTQ KSGTGATATV SPKEILNLTS ELLQKCSSPA PGPGKEWEEY VQIRTLVEKI  60
RKKQKGLSVT FDGKREDYFP DLMKWASENG ASVEGFEMVN FKEEGFGLRA TRDIKAEELF  120
LWVPRKLLMT VESAKNSVLG PLYSQDRILQ AMGNIALAFH LLCERASPNS FWQPYIQTLP  180
SEYDTPLYFE EDEVRYLQST QAIHDVFSQY KNTARQYAYF YKVIQTHPHA NKLPLKDSFT  240
YEDYRWAVSS VMTRQNQIPT EDGSRVTLAL IPLWDMCNHT NGLITTGYNL EDDRCECVAL  300
QDFRAGEQIY IFYGTRSNAE FVIHSGFFFD NNSHDRVKIK LGVSKSDRLY AMKAEVLARA  360
GIPTSSVFAL HFTEPPISAQ LLAFLRVFCM TEEELKEHLL GDSAIDRIFT LGNSEFPVSW  420
DNEVKLWTFL EDRASLLLKT YKTTIEEDKS VLKNHDLSVR AKMAIKLRLG EKEILEKAVK  480
SAAVNREYYR QQMEEKAPLP KYEESNLGLL ESSVGDSRLP LVLRNLEEEA GVQDALNIRE  540
AISKAKATEN GLVNGENSIP NGTRSENESL NQESKRAVED AKGSSSDSTA GVKE        594

SEQ ID NO: 10           moltype = AA  length = 3859
FEATURE                 Location/Qualifiers
REGION                  1..3859
                        note = Synthetic polypeptide
source                  1..3859
                        mol_type = protein
                        organism = synthetic construct
SEQUENCE: 10
MAFVATQGAT VVDQTTLMKK YLQFVAALTD VNTPDETKLK MMQEVSENFE NVTSSPQYST  60
FLEHIIPRFL TFLQDGEVQF LQEKPAQQLR KLVLEIIHRI PTNEHLRPHT KNVLSVMFRF  120
LETENEENVL ICLRIIIELH KQFRPPITQE IHHFLDFVKQ IYKELPKVVN RYFENPQVIP  180
ENTVPPPEMV GMITTIAVKV NPEREDSETR THSIIPRGSL SLKVLAELPI IVVLMYQLYK  240
LNIHNVVAEF VPLIMNTIAI QVSAQARQHK LYNKELYADF IAAQIKTLSF LAYIIRIYQE  300
LVTKYSQQMV KGMLQLLSNC PAETAHLRKE LLIAAKHILT TELRNQFIPC MDKLFDESIL  360
IGSGYTARET LRPLAYSTLA DLVHHVRQHL PLSDLSLAVQ LFAKNIDDES LPSSIQTMSC  420
KLLLNLVDCI RSKSEQESGN GRDVLMRMLE VFVLKFHTIA RYQLSAIFKK CKPQSELGAV  480
```

-continued

```
EAALPGVPTA PAAPGPAPSP APVPAPPPPP PPPPPATPVT PAPVPPFEKQ GEKDKEDKQT  540
FQVTDCRSLV KTLVCGVKTI TWGITSCKAP GEAQFIPNKQ LQPKETQIYI KLVKYAMQAL  600
DIYQVQIAGN GQTYIRVANC QTVRMKEEKE VLEHFAGVFT MMNPLTFKEI FQTTVPYMVE  660
RISKNYALQI VANSFLANPT TSALFATILV EYLLDRLPEM GSNVELSNLY LKLFKLVFGS  720
VSLFAAENEQ MLKPHLHKIV NSSMELAQTA KEPYNYFLLL RALFRSIGGG SHDLLYQEFL  780
PLLPNLLQGL NMLQSGLHKQ HMKDLFVELC LTVPVRLSSL LPYLPMLMDP LVSALNGSQT  840
LVSQGLRTLE LCVDNLQPDF LYDHIQPVRA ELMQALWRTL RNPADSISHV AYRVLGKFGG  900
SNRKMLKESQ KLHYVVTEVQ GPSITVEFSD CKASLQLPME KAIETALDCL KSANTEPYYR  960
RQAWEVIKCF LVAMMSLEDN KHALYQLLAH PNFTEKTIPN VIISHRYKAQ DTPARKTFEQ  1020
ALTGAFMSAV IKDLRPSALP FVASLIRHYT MVAVAQQCGP FLLPCYQVGS QPSTAMFHSE  1080
ENGSKGMDPL VLIDAIAICM AYEEKELCKI GEVALAVIFD VASIILGSKE RACQLPLFSY  1140
IVERLCACCY EQAWYAKLGG VVSIKFLMER LPLTWVLQNQ QTFLKALLFV MMDLTGEVSN  1200
GAVAMAKTTL EQLLMRCATP LKDEERAEEI VAAQEKSFHH VTHDLVREVT SPNSTVRKQA  1260
MHSLQVLAQV TGKSVTVIME PHKEVLQDMV PPKKHLLRHQ PANAQIGLME GNTFCTTLQP  1320
RLFTMDLNVV EHKVFYTELL NLCEAEDSAL TKLPCYKSLP SLVPLRIAAL NALAACNYLP  1380
QSREKIIAAL FKALNSTNSE LQEAGEACMR KFLEGATIEV DQIHTHMRPL LMMLGDYRSL  1440
TLNVVNRLTS VTRLFPNSFN DKFCDQMMQH LRKWMEVVVI THKGGQRSDG NESISECGRC  1500
PLSPFCQFEE MKICSAIINL FHLIPAAPQT LVKPLLEVVM KTERAMLIEA GSPFREPLIK  1560
FLTRHPSQTV ELFMMEATLN DPQWSRMFMS FLKHKDARPL RDVLAANPNR FITLLLPGGA  1620
QTAVRPGSPS TSTMRLDLQF QAIKIISIIV KNDDSWLASQ HSLVSQLRRV WVSENFQERH  1680
RKENMAATNW KEPKLLAYCL LNYCKRNYGD IELLFQLLRA FTGRFLCNMT FLKEYMEEEI  1740
PKNYSIAQKR ALFFRFVDFN DPNFGDELKA KVLQHILNPA FLYSFEKGEG EQLLGPPNPE  1800
GDNPESITSV FITKVLDPEK QADMLDSLRI YLLQYATLLV EHAPHHIHDN NKNRNSKLRR  1860
LMTFAWPCLL SKACVDPACK YSGHLLLAHI IAKFAIHKKI VLQVFHSLLK AHAMEARAIV  1920
RQAMAILTPA VPARMEDGHQ MLTHWTRKII VEEGHTVPQL VHILHLIVQH FKVYYPVRHH  1980
LVQHMVSAMQ RLGFTPSVTI EQRRLAVDLS EVVIKWELQR IKDQQPDSDM DPNSSGEGVN  2040
SVSSSIKRGL SVDSAQEVKR FRTATGAISA VFGRSQSLPG ADSLLAKPID KQHTDTVVNF  2100
LIRVACQVND NTNTAGSPGE VLSRRCVNLL KTALRPDMWP KSELKLQWFD KLLMTVEQPN  2160
QVNYGNICTG LEVLSFLLTV LQSPAILSSF KPLQRGIAAC MTCGNTKVLR AVHSLLSRLM  2220
SIFPTEPSTS SVASKYEELE CLYAAVGKVI YEGLTNYEKA TNANPSQLFG TLMILKSACS  2280
NNPSYIDRLI SVFMRSLQKM VREHLNPQAA SGSTEATSGT SELVMLSLEL VKTRLAVMSM  2340
EMRKNFIQAI LTSLIEKSPD AKILRAVVKI VEEWVKNNSP MAANQTPTLR EKSILLVKMM  2400
TYIEKRFPED LELNAQFLDL VNYVYRDETL SGSELTAKLE PAFLSGLRCA QPLIRAKFFE  2460
VFDNSMKRRV YERLLYVTCS QNWEAMGNHF WIKQCIELLL AVCEKSTPIG TSCQGAMLPS  2520
ITNVINLADS HDRAAFAMVT HVKQEPRERE NSESKEEDVE IDIELAPGDQ TSTPKTKELS  2580
EKDIGNQLHM LTNRHDKFLD TLREVKTGAL LSAFVQLCHI STTLAEKTWV QLFPRLWKIL  2640
SDRQQHALAG EISPFLCSGS HQVQRDCQPS ALNCFVEAMS QCVPPIPIRP CVLKYLGKTH  2700
NLWFRSTLML EHQAFEKGLS LQIKPKQTTE FYEQESITPP QQEILDSLAE LYSLLQEEDM  2760
WAGLWQKRCK YSETATAIAY EQHGFFEQAQ ESYEKAMDKA KKEHERSNAS PAIFPEYQLW  2820
EDHWIRCSKE LNQWEALTEY GQSKGHINPY LVLECAWRVS NWTAMKEALV QVEVSCPKEM  2880
AWKVNMYRGY LAICHPEEQQ LSFIERLVEM ASSLAIREWR RLPHVVSHVH TPLLQAAQQI  2940
IELQEAAQIN AGLQPTNLGR NNSLHDMKTV VKTWRNRLPI VSDDLSHWSS IFMWRQHHYQ  3000
GKPTWSGMHS SSIVTAYENS SQHDPSSNNA MLGVHASASA IIQYGKIARK QGLVNVALDI  3060
LSRIHTIPTV PIVDCFQKIR QQVKCYLQLA GVMGKNECMQ GLEVIESTNL KYFTKEMTAE  3120
FYALKGMFLA QINKSEEANK AFSAAVQMHD VLVKAWAMWG DYLENIFVKE RQLHLGVSAI  3180
TCYLHACRHQ NESKSRKYLA KVLWLLSFDD DKNTLADAVD KYCIGVPPIQ WLAWIPQLLT  3240
CLVGSEGKLL LNLISQVGRV YPQAVYFPIR TLYLTLKIEQ RERYKSDPGP IRATAPMWRC  3300
SRIMHMQREL HPTLLSSLEG IVDQMVWFRE NWHEEVLRQL QQGLAKCYSV AFEKSGAVSD  3360
AKITPHTLNF VKKLVSTFGV GLENVSNVST MFSSAASESL ARRAQATAQD PVFQKLKGQF  3420
TTDFDFSVPG SMKLHNLISK LKKWIKILEA KTKQLPKFFL IEEKCRFLSN FSAQTAEVEI  3480
PGEFLMPKPT HYYIKIARFM PRVEIVQKHN TAARRLYIRG HNGKIYPYLV MNDACLTESR  3540
REERVLQLLR LLNPCLEKRK ETTKRHLFFT VPRVVAVSPQ MRLVEDNPSS LSLVEIYKQR  3600
CAKKGIEHDN PISRYYDRLA TVQARGTQAS HQVLRDILKE VQSNMVPRSM LKEWALHTFP  3660
NATDYWTFRK MFTIQLALIG FAEFVLHLNR LNPEMLQIAQ DTGKLNVAYF RFDINDATGD  3720
LDANRPVPFR LTPNISEFLT TIGVSGPLTA SMIAVARCFA QPNFKVDGIL KTVLRDEIIA  3780
WHKKTQEDTS SPLSAAGQPE NMDSQQLVSL VQKAVTAIMT RLHNLAQFEG GESKVNTLVA  3840
AANSLDNLCR MDPAWHPWL                                              3859
```

```
SEQ ID NO: 11           moltype = AA  length = 1239
FEATURE                 Location/Qualifiers
REGION                  1..1239
                        note = Synthetic polypeptide
source                  1..1239
                        mol_type = protein
                        organism = synthetic construct
SEQUENCE: 11
MANDSPAKSL VDIDLSSLRD PAGIFELVEV VGNGTYGQVY KGRHVKTGQL AAIKVMDVTE  60
DEEEEIKLEI NMLKKYSHHR NIATYYGAFI KKSPPGHDDQ LWLVMEFCGA GSITDLVKNT  120
KGNTLKEDWI AYISREILRG LAHLHIHHVI HRDIKGQNVL LTENAEVKLV DFGVSAQLDR  180
TVGRRNTFIG TPYWMAPEVI ACDENPDATY DYRSDLWSCG ITAIEMAEGA PPLCDMHPMR  240
```

-continued

```
ALFLIPRNPP PRLKSKKWSK KFFSFIEGCL VKNYMQRPST EQLLKHPFIR DQPNERQVRI  300
QLKDHIDRTR KKRGEKDETE YEYSGSEEEE EEVPEQEGEP SSIVNVPGES TLRRDFLRLQ  360
QENKERSEAL RRQQLLQEQQ LREQEEYKRQ LLAERQKRIE QQKEQRRRLE EQQRREREAR  420
RQQEREQRRR EQEEKRRLEE LERRRKEEEE RRRAEEEKRR VEREQEYIRR QLEEEQRHLE  480
VLQQQLLQEQ AMLLECRWRE MEEHRQAERL QRQLQQEQAY LLSLQHDHRR PHPQHSQQPP  540
PPQQERSKPS FHAPEPKAHY EPADRAREVE DRFRKTNHSS PEAQSKQTGR VLEPPVPSRS  600
ESFSNGNSES VHPALQRPAE PQVPVRTTSR SPVLSRRDSP LQGSGQQNSQ AGQRNSTSIE  660
PRLLWERVEK LVPRPGSGSS SGSSNSGSQP GSHPGSQSGS GERFRVRSSS KSEGSPSQRL  720
ENAVKKPEDK KEVFRPLKPA DLTALAKELR AVEDVRPPHK VTDYSSSSEE SGTTDEEDDD  780
VEQEGADEST SGPEDTRAAS SLNLSNGETE SVKTMIVHDD VESEPAMTPS KEGTLIVRQT  840
QSASSTLQKH KSSSSFTPFI DPRLLQISPS SGTTVTSVVG FSCDGMRPEA IRQDPTRKGS  900
VVNVNPTNTR PQSDTPEIRK YKKRFNSEIL CAALWGVNLL VGTESGLMLL DRSGQGKVYP  960
LINRRRFQQM DVLEGLNVLV TISGKKDKLR VYYLSWLRNK ILHNDPEVEK KQGWTTVGDL  1020
EGCVHYKVVK YERIKFLVIA LKSSVEVYAW APKPYHKFMA FKSFGELVHK PLLVDLTVEE  1080
GQRLKVIYGS CAGFHAVDVD SGSVYDIYLP THIQCSIKPH AIIILPNTDG MELLVCYEDE  1140
GVYVNTYGRI TKDVVLQWGE MPTSVAYIRS NQTMGWGEKA IEIRSVETGH LDGVFMHKRA  1200
QRLKFLCERN DKVFFASVRS GGSSQVYFMT LGRTSLLSW                         1239

SEQ ID NO: 12          moltype = AA  length = 859
FEATURE                Location/Qualifiers
REGION                 1..859
                       note = Synthetic polypeptide
source                 1..859
                       mol_type = protein
                       organism = synthetic construct
SEQUENCE: 12
MACLHETRTP SPSFGGFVST LSEASMRKLD PDTSDCTPEK DLTPTHVLQL HEQDAGGPGG  60
AAGSPESRAS RVRADEVRLQ CQSGSGFLEG LFGCLRPVWT MIGKAYSTEH KQQQEDLWEV  120
PFEEILDLQW VGSGAQGAVF LGRFHGEEVA VKKVRDLKET DIKHLRKLKH PNIITFKGVC  180
TQAPCYCILM EFCAQGQLYE VLRAGRPVTP SLLVDWSMGI AGGMNYLHLH KIIHRDLKSP  240
NMLITYDDVV KISDFGTSKE LSDKSTKMSF AGTVAWMAPE VIRNEPVSEK VDIWSFGVVL  300
WELLTGEIPY KDVDSSAIIW GVGSNSLHLP VPSSCPDGFK ILLRQCWNSK PRNRPSFRQI  360
LLHLDIASAD VLSTPQETYF KSQAEWREEV KLHFEKIKSE GTCLHRLEEE LVMRRREELR  420
HALDIREHYE RKLERANNLY MELNALMLQL ELKERELLRR EQALERRCPG LLKPHPSRGL  480
LHGNTMEKLI KKRNVPQKLS PHSKRPDILK TESLLPKLDA ALSGVGLPGC PKGPPSPGRS  540
RRGKTRHRKA SAKGSCGDLP GLRTAVPPHE PGGPGSPGGL GGGPSAWEAC PPALRGLHHD  600
LLLRKMSSSS PDLLSAALGS RGRGATGGAG DPGSPPPARG DTPPSEGSAP GSTSPDSPGG  660
AKGEPPPPVG PGEGVGLLGT GREGTSGRGG SRAGSQHLTP AALLYRAAVT RSQKRGISSE  720
EEEGEVDSEV ELTSSQRWPQ SLNMRQSLST FSSENPSDGE EGTASEPSPS GTPEVGSTNT  780
DERPDERSDD MCSQGSEIPL DPPPSEVIPG PEPSSLPIPH QELLRERGPP NSEDSDCDST  840
ELDNSNSVDA LRPPASLPP                                                859
```